US008575156B2

(12) United States Patent
Claremon et al.

(10) Patent No.: US 8,575,156 B2
(45) Date of Patent: Nov. 5, 2013

(54) CYCLIC INHIBITORS OF 11β-HYDROXYSTEROID DEHYDROGENASE 1

(75) Inventors: David A. Claremon, Maple Glen, PA (US); Wei He, Audubon, PA (US); Gerard McGeehan, Garnet Valley, PA (US); Suresh B. Singh, Kendall Park, NJ (US); Colin M. Tice, Ambler, PA (US); Zhenrong Xu, Horsham, PA (US); Yuanjie Ye, Ambler, PA (US); Wei Zhao, Eagleville, PA (US); Linghang Zhuang, Chalfont, PA (US); Salvacion Cacatian, Blue Bell, PA (US); Katerina Leftheris, Skillman, NJ (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 302 days.

(21) Appl. No.: 12/670,205

(22) PCT Filed: Jul. 25, 2008

(86) PCT No.: PCT/US2008/009017
§ 371 (c)(1),
(2), (4) Date: Sep. 3, 2010

(87) PCT Pub. No.: WO2009/017664
PCT Pub. Date: Feb. 5, 2009

(65) Prior Publication Data
US 2011/0015157 A1    Jan. 20, 2011

Related U.S. Application Data

(60) Provisional application No. 60/962,058, filed on Jul. 26, 2007, provisional application No. 61/001,253, filed on Oct. 31, 2007, provisional application No. 61/049,650, filed on May 1, 2008.

(51) Int. Cl.
*C07D 413/10* (2006.01)
*C07D 413/04* (2006.01)
*C07D 241/04* (2006.01)
*A61K 31/675* (2006.01)
*A61K 31/5377* (2006.01)
*A61K 31/541* (2006.01)

(52) U.S. Cl.
USPC ............................ 514/228.8; 544/96; 544/97

(58) Field of Classification Search
USPC .................................. 544/96, 97; 514/228.8
See application file for complete search history.

(56) References Cited

U.S. PATENT DOCUMENTS

| 3,341,538 A | 9/1967 | Block et al. |
|---|---|---|
| 3,378,587 A | 4/1968 | Reinhardt |
| 3,681,349 A | 8/1972 | Schwan et al. |
| 3,703,529 A | 11/1972 | Frederick et al. |
| 3,919,047 A | 11/1975 | Vidic et al. |
| 4,009,171 A | 2/1977 | Albertson |
| 4,043,927 A | 8/1977 | Duling et al. |
| 4,108,857 A | 8/1978 | Albertson |
| 4,136,145 A | 1/1979 | Fuchs et al. |
| 4,136,162 A | 1/1979 | Fuchs et al. |
| 4,268,673 A | 5/1981 | Akkerman et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |

(Continued)

FOREIGN PATENT DOCUMENTS

| DE | 1801556 A1 | 5/1970 |
|---|---|---|
| DE | 2 105 743 A1 | 8/1972 |

(Continued)

OTHER PUBLICATIONS

Chalmers (TiPS vol. 17, pp. 166-172 Apr. 1996.*

(Continued)

*Primary Examiner* — Kahsay Habte
(74) *Attorney, Agent, or Firm* — McCarter & English, LLP; Steven G. Davis; Michael J. DeGrazia

(57) ABSTRACT

Disclosed are compounds represented by Formula (I):

$$\text{R}^3 \cdots \underset{\underset{\text{R}^2}{|}}{\text{E}} \cdots \overset{\text{O}}{\underset{\text{N}}{\overset{||}{\text{C}}}} \cdots \text{A}^1 \cdots \text{Cy}^1 \cdots \text{A}^2 \cdots \text{Cy}^2;$$

$$(Y)_n$$

I or pharmaceutically acceptable salts, enantiomers or diastereomers thereof. Also disclosed are pharmaceutical compositions comprising the compounds of Formula (I) or pharmaceutically acceptable salts, enantiomers or diastereomers thereof and methods of inhibiting 11β-HSD1 activity comprising the step of administering to a mammal in need of such treatment an effective amount of a compound of Formula (I), or a pharmaceutically acceptable salt, enantiomer or diastereomer thereof. Values for the variables in Formula (I) are defined herein.

20 Claims, No Drawings

(56) References Cited

U.S. PATENT DOCUMENTS

| | | |
|---|---|---|
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,368,816 B2 | 4/2002 | Walker et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,838,253 B2 | 1/2005 | Walker et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 6,946,487 B2 | 9/2005 | Walker et al. |
| 7,026,310 B2 | 4/2006 | Emig et al. |
| 7,056,912 B2 | 6/2006 | Emig et al. |
| 7,087,400 B2 | 8/2006 | Walker et al. |
| 7,122,531 B2 | 10/2006 | Walker et al. |
| 7,122,532 B2 | 10/2006 | Walker et al. |
| 7,129,231 B2 | 10/2006 | Walker et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 7,652,049 B2 | 1/2010 | Ali et al. |
| 7,897,773 B2 | 3/2011 | Aletru et al. |
| 8,114,868 B2 | 2/2012 | Himmelsbach |
| 8,138,178 B2 | 3/2012 | Claremon et al. |
| 8,202,857 B2 | 6/2012 | Claremon et al. |
| 8,242,111 B2 | 8/2012 | Claremon et al. |
| 8,329,897 B2 | 12/2012 | Xu |
| 8,440,658 B2 | 5/2013 | Claremon et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0170894 A1 | 7/2009 | Aletru et al. |
| 2009/0264650 A1 | 10/2009 | Cho et al. |
| 2010/0016164 A1 | 1/2010 | Hino et al. |
| 2010/0025636 A1 | 2/2010 | Gelbin et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2010/0331320 A1 | 12/2010 | Renz et al. |
| 2011/0009402 A1 | 1/2011 | Himmelsbach |
| 2011/0019643 A1 | 1/2011 | Kim et al. |
| 2011/0021512 A1 | 1/2011 | Claremon et al. |
| 2011/0028445 A1 | 2/2011 | Eckhardt et al. |
| 2011/0034455 A1 | 2/2011 | Claremon et al. |
| 2011/0039286 A1 | 2/2011 | Wu et al. |
| 2011/0053943 A1 | 3/2011 | Claremon et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112062 A1 | 5/2011 | Claremon et al. |
| 2011/0112082 A1 | 5/2011 | Claremon et al. |
| 2011/0124635 A1 | 5/2011 | Claremon et al. |
| 2011/0136800 A1 | 6/2011 | Eckhardt et al. |
| 2011/0136821 A1 | 6/2011 | Claremon et al. |
| 2011/0190262 A1 | 8/2011 | Himmelsbach et al. |
| 2011/0224242 A1 | 9/2011 | Giethlen et al. |
| 2011/0263582 A1 | 10/2011 | Claremon et al. |
| 2011/0263583 A1 | 10/2011 | Claremon et al. |
| 2011/0263584 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |
| 2011/0312950 A1 | 12/2011 | Eckhardt et al. |
| 2012/0040973 A1 | 2/2012 | Claremon et al. |
| 2012/0108578 A1 | 5/2012 | Himmelsbach et al. |
| 2012/0108579 A1 | 5/2012 | Renz et al. |
| 2012/0115853 A1 | 5/2012 | Eckhardt et al. |
| 2012/0172357 A1 | 7/2012 | Himmelsbach |
| 2012/0178746 A1 | 7/2012 | Claremon et al. |
| 2012/0184549 A1 | 7/2012 | Himmelsbach |
| 2012/0190675 A1 | 7/2012 | Himmelsbach |
| 2012/0208804 A1 | 8/2012 | Claremon et al. |
| 2012/0232050 A1 | 9/2012 | Claremon et al. |
| 2012/0277149 A1 | 11/2012 | Hamilton et al. |
| 2012/0277455 A1 | 11/2012 | Qu et al. |

FOREIGN PATENT DOCUMENTS

| | | |
|---|---|---|
| DE | 2 108 954 A1 | 9/1972 |
| DE | 2 229 695 A1 | 1/1974 |
| DE | 23 38 369 A1 | 2/1975 |
| DE | 23 54 002 A1 | 5/1975 |
| DE | 2 411 382 A1 | 9/1975 |
| DE | 2 437 610 A1 | 2/1976 |
| DE | 2 828 039 A1 | 1/1980 |
| DE | 19918725 A1 | 10/2000 |
| DE | 19929348 A1 | 12/2000 |
| DE | 100 34 623 | 1/2002 |
| DE | 10034623 | 1/2002 |
| EP | 0415642 A1 | 3/1991 |
| EP | 0454444 A1 | 10/1991 |
| EP | 0640594 A1 | 3/1995 |
| EP | 0645387 A | 3/1995 |
| EP | 0471591 B1 | 5/1995 |
| EP | 0 847 275 A1 | 6/1998 |
| EP | 0928789 A1 | 7/1999 |
| EP | 1156049 A | 11/2001 |
| EP | 1270724 A2 | 1/2003 |
| EP | 1801098 A1 | 6/2007 |
| EP | 1852425 A | 11/2007 |
| EP | 1864971 A | 12/2007 |
| EP | 1935420 | 6/2008 |
| GB | 1077711 | 8/1967 |
| JP | 6092945 A | 4/1994 |
| JP | 7157681 | 6/1995 |
| JP | 2009110842 A2 | 4/1997 |
| JP | 09151179 | 6/1997 |
| JP | 09151179 A * | 6/1997 |

(56) References Cited

FOREIGN PATENT DOCUMENTS

| | | |
|---|---|---|
| JP | 2002179572 A2 | 6/2002 |
| JP | 2003096058 | 4/2003 |
| JP | 2003300884 A2 | 10/2003 |
| JP | 2005-206503 A | 8/2005 |
| JP | 2005239670 | 9/2005 |
| JP | 2005272321 A | 10/2005 |
| JP | 2007 254409 | 10/2007 |
| JP | 2007 140188 | 6/2008 |
| JP | 2011519374 A | 7/2011 |
| WO | WO 92/07838 | 5/1992 |
| WO | WO 93/07128 | 4/1993 |
| WO | WO 93/13103 | 7/1993 |
| WO | WO 95/31440 | 11/1995 |
| WO | WO 96/14297 A | 5/1996 |
| WO | WO 96/023787 | 8/1996 |
| WO | 96/37494 A1 | 11/1996 |
| WO | 97/07789 A1 | 3/1997 |
| WO | WO 97/36605 | 10/1997 |
| WO | 98/22462 A1 | 5/1998 |
| WO | WO 98/57940 | 12/1998 |
| WO | WO 99/05125 | 2/1999 |
| WO | WO 99/06395 | 2/1999 |
| WO | 0009107 A2 | 2/2000 |
| WO | WO 01/00595 A1 | 1/2001 |
| WO | 0113917 A1 | 3/2001 |
| WO | WO 01/44200 A2 | 6/2001 |
| WO | WO 2001/055063 | 8/2001 |
| WO | WO 02/06244 A1 | 1/2002 |
| WO | WO 02/06277 A1 | 1/2002 |
| WO | WO 02/22572 A2 | 3/2002 |
| WO | WO 03/043988 A1 | 5/2003 |
| WO | WO 03/057673 A | 7/2003 |
| WO | 03/097608 A2 | 11/2003 |
| WO | WO 03/093261 A1 | 11/2003 |
| WO | WO 2004/004722 A | 1/2004 |
| WO | WO 2004/009559 A2 | 1/2004 |
| WO | WO 2004/014859 A2 | 2/2004 |
| WO | 2004/046137 A1 | 6/2004 |
| WO | 2004056745 A2 | 7/2004 |
| WO | 2004/089896 A1 | 10/2004 |
| WO | WO 2004/094375 A | 11/2004 |
| WO | WO 2005/000845 | 1/2005 |
| WO | WO 2005/113525 A1 | 2/2005 |
| WO | WO 2005/086700 A2 | 9/2005 |
| WO | 2005108360 A1 | 11/2005 |
| WO | WO 2005/108361 | 11/2005 |
| WO | WO 2005/108361 A | 11/2005 |
| WO | 2005116002 A2 | 12/2005 |
| WO | 2006002349 A1 | 1/2006 |
| WO | WO 2006/003494 A2 | 1/2006 |
| WO | 2006017443 | 2/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | WO 2006/090792 A1 | 8/2006 |
| WO | 2006/109056 A1 | 10/2006 |
| WO | WO 2006/104280 A | 10/2006 |
| WO | WO 2007/008529 A2 | 1/2007 |
| WO | 2007/022371 A2 | 2/2007 |
| WO | 2007/048595 A1 | 5/2007 |
| WO | WO 2007/051810 | 5/2007 |
| WO | WO 2007/061661 A2 | 5/2007 |
| WO | WO 2007/068330 A1 | 6/2007 |
| WO | 2007/076055 A2 | 7/2007 |
| WO | WO 2007/079186 A2 | 7/2007 |
| WO | WO 2007/081569 A2 | 7/2007 |
| WO | WO 2007/081570 A | 7/2007 |
| WO | WO 2007/081571 A2 | 7/2007 |
| WO | WO 2007/084314 A2 | 7/2007 |
| WO | 2007101270 A1 | 9/2007 |
| WO | 2007103719 A2 | 9/2007 |
| WO | WO 2007/109456 A2 | 9/2007 |
| WO | WO 2007/118185 A2 | 10/2007 |
| WO | 2007/124337 A1 | 11/2007 |
| WO | 2007/127763 A2 | 11/2007 |
| WO | 2007123853 A2 | 11/2007 |
| WO | Wo 2007/124254 | 11/2007 |
| WO | WO 2007/124329 A | 11/2007 |
| WO | WO 2007/124337 | 11/2007 |
| WO | WO 2007/127693 A | 11/2007 |
| WO | WO 2008/031227 A1 | 11/2007 |
| WO | WO 2008/000951 | 1/2008 |
| WO | 2008024497 A2 | 2/2008 |
| WO | WO 2008/03671 A1 | 3/2008 |
| WO | 2008/046578 A2 | 4/2008 |
| WO | WO 2008/046758 A | 4/2008 |
| WO | WO 2008/059948 A | 5/2008 |
| WO | WO 2008/106128 | 9/2008 |
| WO | WO 2008/106128 A | 9/2008 |
| WO | WO 2008/18332 A2 | 10/2008 |
| WO | 2009020140 A1 | 2/2009 |
| WO | WO 2009/017664 | 2/2009 |
| WO | WO 2009/017664 A1 | 2/2009 |
| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |
| WO | WO 2009/102428 | 8/2009 |
| WO | WO 2009/102460 | 8/2009 |
| WO | 2009/107664 A1 | 9/2009 |
| WO | 2009108332 A1 | 9/2009 |
| WO | WO 2009/117109 | 9/2009 |
| WO | 2009131669 A2 | 10/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | 2010/010150 A1 | 1/2010 |
| WO | WO 2010/010149 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | 2010089303 A1 | 8/2010 |
| WO | WO 2010/091067 | 8/2010 |
| WO | 2010104830 A1 | 9/2010 |
| WO | WO 2010/127237 | 11/2010 |
| WO | 2010/139673 A1 | 12/2010 |
| WO | 2010141424 A1 | 12/2010 |
| WO | 2011002910 A1 | 1/2011 |
| WO | 2011011123 A1 | 1/2011 |
| WO | 2011031979 A1 | 3/2011 |
| WO | 2011/057054 A1 | 5/2011 |
| WO | 2011056737 A1 | 5/2011 |
| WO | 2011159760 A1 | 12/2011 |
| WO | 2011161128 A1 | 12/2011 |
| WO | 2012059416 A1 | 5/2012 |

OTHER PUBLICATIONS

U.S. Appl. No. 12/670,209, filed Jul. 25, 2008, Vitae Pharmaceuticals, Inc.
U.S. Appl. No. 12/741,522, filed Apr. 30, 2009, Vitae Pharmaceuticals, Inc.
U.S. Appl. No. 12/990,309, filed Apr. 30, 2009, Vitae Pharmaceuticals, Inc.
U.S. Appl. No. 12/990,296, filed Apr. 30, 2009, Vitae Pharmaceuticals, Inc.
U.S. Appl. No. 12/745,663, filed Nov. 7, 2008, Vitae Pharmaceuticals, Inc.
U.S. Appl. No. 12/811,577, filed Jan. 7, 2009, Vitae Pharmaceuticals, Inc.

(56) References Cited

OTHER PUBLICATIONS

U.S. Appl. No. 12/747,391, filed Dec. 10, 2008, Vitae Pharmaceuticals, Inc.
U.S. Appl. No. 12/863,634, filed Jan. 21, 2009, Vitae Pharmaceuticals, Inc.
U.S. Appl. No. 12/867,374, filed Feb. 13, 2009, Vitae Pharmaceuticals, Inc.
U.S. Appl. No. 12/933,027, filed Mar. 18, 2009, Vitae Pharmaceuticals, Inc.
U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
International Search Report and Written Opinion—(PCT/US2008/009048) Date of mailing Dec. 4, 2008.
International Search Report—(PCT/US2009/004261) Date of Mailing Oct. 21, 2009.
Shibata, et al,, "Cycloaddition of Oxetanes with Heterocumulenes Catalysed by Organo tin Iodine-Lewis Base Complex", Journal of Heterocyclic Chemistry, vol. 24, 1987, pp. 361-363.
MS Bitar, "Glucocorticoid Dynamics and Impaired Wound Healing in Diabetes Mellitus", Am J Pathol., 1998, vol. 152, pp. 547-554.
MS Bitar, et al,, "Heat-Shock Protein 72/73 and Impaired Wound Healing in Diabetic and Hypercortisolemic States", Sugery, 1999, vol. 125, pp. 594-601.
MS Bitar, et al., "Glucocorticoid-Dependent Impairment of Wound Healing in Experimental Diabetes: Amelioration by Adrenalectomy and Ru 486", J Surg Res., 1999, vol. 82, pp. 234-243.
MS Bitar, "Insulin and Glucocorticoid-Dependent Suppression of the IGF-I System in Diabetic Wounds". Sugery, 2000, vol. 127, pp. 687-695.
Ho-Jane Shue et al., "Cyclic Urea Derivaives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists, Part II: Effects of Fluoro and Benzylic Methyl Substitutions", Bioorganic & Medicinal Chemistry Letters, 2006, vol. 16, pp. 1065-1069.
Kashima, et al., "Preparation of N-Aryl-2,4-diaminopentanes by the Ring Opening Reaction of 1-Aryl- 3,4,5,6-tetrahydro-2-(1H)pyrimidinones", Journal of Heterocyclic Chemistry, vol. 18, 1981, pp. 1595- 1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Warnil and Jonathan R, Seckl, "Inhibition of 11β-hydroxysteroid Dehydrogenase Type 1 as a Promising Therapeutic Target", Drug Discovery Today, 2007, vol. 12, pp. 504-520.
Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.
Schoellkopf, et al,, "Umsetzungen Alphametallierterlsocyanide Mit Einigen 1,3-Dipolen/Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.
Suga, Seiji et al., "N-Acyliminium Ion Pool" as a Heterodiene in [4+2] Cycioaddition Reaction, Organic Letters, 2003, vol. 5, pp. 945-947.
Suga, Seiji et al., "Cycloaddition of"N-Acyiiminium Ion Pools" with Carbon-Carbon Multiple Bonds", Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Pailadiurri(2+)-Catalyzed Cyclization of Unsaturated Amines", Journal of the American Chemical Society, 1988, vol, 110, pp. 3994-4002.
Yoshida, Masaaki et al., "Selective synthesis of five-and six-membered cyclic carbamates by the reation of 2-(1-haloalkl)oxiranes with carbon dioxide and aliphatic primary amines", Heterocycles, Elsevier Science Ltd., 1993, vol. 35 (2), pp. 623-626.

Yoshinao Tamaru, "Palladium(2+)-Catalyzed Intramolecular Aminocarbonyiation of 3-Hydroxy-4- pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
international Search Report—(PCT/US2009/002653) Date of Mailing Jul. 3, 2009.
International Search Report—(PCT/US2009/002641 ) Date of Mailing Jul. 3, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2008/012618) Date of Mailing Dec. 3, 2009.
International Search Report—(PCT/US2009/000057) Date of Mailing Mar. 25, 2009.
international Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No, 958700-63-5, Abstract, XP002556893.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-14-6, Abstract, XP002556898.
Database File Registry [Online], Chemical Abstracts Service, Columbus, Ohio, US, 2007, Database accession No. 958625-83-7, Abstract, XP002556899.
Database File Registry [Online], Chemical Abstracts Service, Columbus, Ohio, US, 2007, Database accession No. 958599-31-0, Abstract, XP002556900.
Chimica Therapeutica, 1968, vol. 3(5), pp. 321-324, 1968.
Zhumal Organicheskoi Khimii, 1978, vol. 14(5), pp. 1092-1094.
"Khimilia Elementoorganicheskikh Soedineni", 1982, vol. 1982 pp. 22-26.
"Zhurnal Organicheskoi Khimii", 1982, vol. 18, PT 11, p. 2468.
Chemical Abstracts, vol. 98, No. 11, 1983, Columbus, Ohio, US; abstract no.: 89280k, Lapkin, et al., "Synthesis of 1,3-oxazin-2,4-diones", p. 552 col. 1, XP002504063 abstract.
Chemical Abstracts, vol. 99, No. 23, 1983, Columbus, Ohio, US; abstract no.: 195067b, Saitkulova, et al., "Synthesis involving bromozinc alcoholates of carboxylic acid esters", p. 764 col. 1. XP002504064 abstract.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37 pp. 7727-7730.
Anderson, (Chem and Biol 10:787-797, 2003).
Bosch et al.: Heterocycles 1980, 14, p. 1983-1988.
CA 1267843-31-1, (Aug. 10, 2009).
CA 154:284276, (Mar . 17, 2011).
Caplus-133:4656—Anantanarayan, A. el. al., "Preparation of heteroarylpyrazoles as P38 kinase inhibitors". 2000.

(56) References Cited

OTHER PUBLICATIONS

Caplus-147:134403, Hembrough, TA, et al., Composition and methods comprising proteinase activated receptor 2 antagonists for treatment of angiogenesis and inflammatory disorders and cancer. 2007.
Caplus-77:5360, Helsley, G. C. "Antispasmodic 8-carbamoyl-3-phenylnortropanes". 1972.
Chemical Abstracts, Registry Number: 351443-37-3 (Available on Aug. 15, 2001.).
Claremon et al. CAS: 150:214405, 2009.
DeMarinis R.M. et.al. Journal of Medicinal Chemistry 1981, vol. 24, No. 12, pp. 1432-1437.
Examiner Interview Summary dated May 2, 2011, in U.S. Appl. No. 12/741,522 (U.S. Patent No. 8,138,178).
Gutkowska et al.: Acta Polonaie Pharmaceutica 1987, 39, p. 411-414.
Gutkowska et al.: Acta Poloniae Pharmaceutica 1986, 43, p. 403-405.
Gutkowska et al.: Acta Poloniae Pharmaceutica, 1982, vol. 39, p. 61-64.
Harno et. al. Trends in Endocrinology and Metabolism, Elsevier Science Publishing, New York 2010, vol. 21, No. 10, pp. 619-627.
Hughes, K.A. et al., "11-beta-hydroxysteroid dehydrogenase type 1 (11b-HSD1) inhibitors in Type 2 diabetes mellitus and obesity". Expert Opinion, Investig. Drugs, 17(4), 2008, pp. 481-496.
International Search Report & Written Opinion—(PCT/US2008/002517) Date of Mailing Dec. 29, 2008.
International Search Report and Written Opinion for PCT/EP2009/059509, mailed Feb. 9, 2009.
International Search Report and Written Opinion for PCT/US2012/050679 mailed Oct. 31, 2012.
International Search Report for PCT/EP2009/063913 mailed May 6, 2010.
Ma et al.: Synthesis 2007, p. 161-163.
Ma et al.: Tetrahedron 2007, 63, p. 7523-7531.
Morissette et al. Advanced Drug Deliery Reviews 2004, 56, 275-300.
Office Action dated Apr. 3, 2012 for corresponding U.S. Appl. No. 13/318,271.
Office Action dated Jun. 14, 2012 for corresponding U.S. Appl. No. 13/347,784.
Office Action dated May 3, 2012 for corresponding U.S. Appl. No. 13/347,799.
Office Action for U.S. Appl. No. 12/741,522 (U.S. Patent No. 8,138,178), date of mailing Dec. 15, 2010.
Office Action for U.S. Appl. No. 12/741,532 (US Patent No. 8,114,868), date of mailing Dec. 15, 2010.
Office Action for U.S. Appl. No. 12/771,499, date of mailing Dec. 21, 2010.
Olesen et al.: Current Opin Drug Dis Dev, 2001, vol. 4, No. 4, p. 471-478.
Rosenstock et.al. Diabetes Care Jul. 2010, LNKDPUBMED: 20413513, vol. 33, No. 7, pp. 1516-1522.
Souillac et al., Characterization of Delivery Systems, Differential Scanning Calorimetry, pp. 217-218 (in Encyclopedia of Controlled Drug Delivery, 1999, John Wiley & Sons, pp. 212-227).
Sullivan, John M. and Efner, Howard F., "The Preparation of 6-Aryltetrahydro-1,3-oxazin-2-ones and Their Hydrolysis to 3-Substituted Propylamines," The Journal of Organic Chemistry, 33 (5): 2134-2136 (1968).
Taddayon et.al. Expert opinion on Investigational Drugs, Ashley Publication Ltd. 2003, vol. 12, No. 3, pp. 307-324.
Thiel (Nature Biotechnol 2:513-519, 2004).
Thornber et al.: Chem Soc Rev, 1979, vol. 8, p. 563-580.
Vidic et al.: Chem. Ber. 1976, 109, p. 2657-2669.
Wolfling, Janos et al., "Neighboring Group Participation Part 15. Stereoselective Synthesis of Some Steroidal Tetrahydrooxaziin-2-ones, as Novel Presumed Inhibitors of Human 5?-Reductase," Steroids, 69: 451-460 (2004).
Yokoyama et al.: J. Med. Chem. 1979, 22, p. 537-553.
Database CA [Online], Chemical Abstracts Service, Fukushima et al., "Preparation of Imidazolidinone Derivatives as 11.beta.-HSD1 Inhibitors", 2007, XP 002531878.

Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CASRN: 20057-45-8 abstract, (1969).
Database Caplus [Online] Chemical Abstracts Service, Slyusarenko et al., "Synthesis based on Thionylamides.IV. 2Alkoxy-5,6-Dihydro-1,3-Oxazines", XP002516522, retrieved from STN Database accession No. 1978:563520 CASRN: 67868-26-2 abstract,(1978).
Gavezzotti, "Are Crystal Structures Predictable?", Accounts of Chemical Research, 1994, vol. 27, pp. 309-314.
International Search Report—(PCT/US2010/023021) Date of Mailing Aug. 5, 2010.
Vippagunta, et al., "Crystalline Solids", Advanced Drug Deliver Reviews, 2001, vol. 48, pp. 3-26.
Donohoe, T.J. et al., "Stereoselectivity in the double reductive alkylation of pyrroles: synthesis of cis-3,4- disubstituted pyrrolidines". Chemical Communications, vol. 1999, No. 2, Feb. 1, 1999, p141-142.
Evans, B.E. et al., "Orally active, nonpeptide osytocin antagonists". Journal of Medicinal Chemistry, American Chem. Soc., Vo. 35, No. 21, Oct. 15, 1992, p3919-3927.
Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, p5731-5741.
Aluri. B.R. et al., "Bulky n-Substituted 1,3-Benzazaphospholes: Access via Pd-Catalyzed C-N And C-P Cross Coupling, Lithiation, and Conversion to Novel P=C PtBu2 Hybrid Ligands". Inorganic Chemistry, 2008, 47, p6900-6912.
Aluri, B.R. et al., "Sterically and Polarity-Controlled Reactions of tBuLi with P=CH-NR Heterocycles: Novel Heterocyclic P-and P,O-Ligands and Preliminary Tests in Transition-Metal Catalysis", Chem. Eur. Journal, vol. 14, 2008, p4328-4335.
Fandrick, Dr. et al., "Copper Catalyzed Asymmetric Propargylation of Aldehydes". JACS Communications, Published on Web May 18, 2010, J. Am. Chem. Soc., vol. 132, No. 22, 2010, p7600,7601.
International Search Report and Written Opinion for PCT/EP/2009/059496 mailed Nov. 17, 2009.
International Search Report and Written Opinion for PCT/EP2010/051262 mailed May 3, 2010.
International Search Report and Written Opinion for PCT/EP2011/060386 mailed Sep. 16, 2011.
International Search Report and Written Opinion for PCT/US2010/054912 mailed Mar. 16, 2011.
International Search Report for PCT/EP2011/068938 mailed Mar. 27, 2012.
Lightburn, T.E. et al., "Catalytic Scaffolding Ligands: an Efficient Strategy for Direction Reactions". JACS Communications, Published on Web May 25, 2008, Journal American Chem. Soc., vol. 130, No. 29, 2008, p9210-9211.
Senanayake, C. Presentation: "Timely Chemical Process Research is a Critical Part for Efficient Drug Development". 4th Siegfried Symposium, Sep. 23, 2010, p1-91, Retrieved from internet: URL: http://www.siegfried/ch/fileadmin/User2/Bilder/Fotogalerien/Symposium_2010/Award_Talk_Senanayake.pdf. Retrieved on Feb. 23, 2010.
Tang, W. et al., "Novel and Efficient Chiral Bisphosphorus Ligands for Rhodium-Catalyzed Asymmetric Hydrogenation". Organic Letters, 2010, vol. 12, No. 5, p1104-1107.
Tang, W. et al., "Novel, Tunable, and Efficient Chiral Bisdihydrobenzooxaphosphole Ligands for Asymmetric Hydrogenation". Organic Letters, 2010, vol. 12, No. 1., p176-179.
Worthy, Ad. et al., "Regioselective Hydroformylation of Sulfonamides using a Scaffolding Ligand". Organic Letters, 2009, vol. 11, No. 13—p2764-2767.
Kametani et al. Chem Pharma Bull, 1965 vol. 13, No. 3, p. 295-299.
Patani et al. Chem Rev, 1996 p. 3147-3176.
Stewart et al. Vitam Horm. 1999;57:249-324.

* cited by examiner

CYCLIC INHIBITORS OF 11β-HYDROXYSTEROID DEHYDROGENASE 1

RELATED APPLICATIONS

The present application is a U.S. national stage application claiming the benefit of International Application No. PCT/US2008/009017, filed on Jul. 25, 2008, which claims the benefit of U.S. Provisional Application No. 60/962,058, filed on Jul. 26, 2007, U.S. Provisional Application No. 61/001,253, filed Oct. 31, 2007 and U.S. Provisional Application No. 61/049,650, filed May 1, 2008. The entire teachings of the above applications are incorporated herein by reference.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), $4^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Opthalmol. Vis. Sci. 41: 1629-1683; Rauz et al. (2001) Invest. Opthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula I or pharmaceutically acceptable salts or prodrugs thereof, are effective inhibitors of 11β-HSD1. The invention is a compound represented by Formula I:

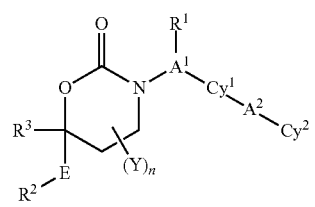

In a first embodiment of the invention, Formula I and its constituent members are defined herein as follows:

$R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkyl-sulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl. In one aspect, the heterocyclyl represented by $Cy^2$ is other than optionally substituted thiazolidine-2,4-dionyl;

Y is $(C_1-C_6)$alkyl, halo$(C_1-C_6)$alkyl or oxo;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

$R^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

or a pharmaceutically acceptable salt, enantiomer or diastereomer thereof.

In a second embodiment, Formula I and its constituent members are defined herein as follows:

$R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4OS(=O)_2NHC(=O)$—, $R^4OS(=O)_2NHC(=O)O$—, $R^4OS(=O)_2NHC(=O)N(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkyl-sulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

Y is $(C_1-C_6)$alkyl, halo$(C_1-C_6)$alkyl or oxo;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl;

$R^3$ is selected from $(C_1-C_6)$alkyl, $(C_2-C_6)$alkenyl, $(C_2-C_6)$alkynyl, $(C_1-C_3)$alkoxy$(C_1-C_3)$alkoxy or $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl (which in turn may be optionally substituted with alkyl, haloalkyl or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

or a pharmaceutically acceptable salt, enantiomer or diastereomer thereof.

In a third embodiment, Formula I and its constituent members are defined herein as follows:

$R^1$ is absent or is selected from $(C_1-C_6)$alkyl or $(C_2-C_6)$alkenyl, $(C_2-C_6)$alkynyl or $(C_1-C_3)$alkoxy$(C_1-C_3)$alkoxy and is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino;

$A^1$ is (a) a bond, or (b) $(C_1-C_3)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl each optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3$-

$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl and oxo;

$A^2$ is (a) a bond, O, S or $NR^4$; or (b) ($C_1$-$C_3$)alkylene, ($C_1$-$C_2$)alkyleneoxy, each of which is optionally substituted with 1 to 4 groups independently selected from methyl, ethyl, trifluoromethyl or oxo;

$Cy^2$ is (a) hydrogen or (b) aryl, heteroaryl, cycloalkyl or heterocyclyl each optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl and oxo;

Y is ($C_1$-$C_6$)alkyl, halo($C_1$-$C_6$)alkyl or oxo;

n is 0, 1 or 2;

E is (a) a bond or (b) ($C_1$-$C_3$)alkylene, ($C_1$-$C_2$)alkylenyloxy, wherein the O is attached to $R^2$, each of which is optionally substituted with 1 to 4 groups independently selected from methyl, ethyl, trifluoromethyl or oxo;

$R^2$ is ($C_1$-$C_6$)alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl or oxo;

$R^3$ is selected from ($C_1$-$C_6$)alkyl, ($C_2$-$C_6$)alkenyl, ($C_2$-$C_6$)alkynyl or ($C_1$-$C_3$)alkoxy($C_1$-$C_3$)alkoxy and is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl (which in turn may be optionally substituted with alkyl, haloalkyl or oxo), heteroaryl which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl;

or a pharmaceutically acceptable salt, enantiomer or diastereomer thereof.

In a fourth embodiment, $R^1$ is (a) absent or (b) is selected from $(C_1-C_6)$alkyl, $(C_2-C_6)$alkenyl, $(C_2-C_6)$alkynyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino;

$A^1$ is (a) a bond, or (b) $(C_1)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl, each optionally substituted with 1 to 4 groups independently selected from nitro, amino, hydroxy, carboxy, $(C_1-C_6)$alkyl, hydroxy$(C_1-C_6)$alkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl; or if the substitution is either meta or para to $A^1$, the substituents may also include optionally substituted cycloalkyl, optionally substituted halo cycloalkyl or optionally substituted heteroaryl.

$A^2$ is (a) a bond, O, S or $NR^4$; or (b) $(C_1-C_3)$alkylene or $(C_1-C_2)$alkyleneoxy, each of which is optionally substituted with 1 to 4 groups independently selected from methyl, ethyl, trifluoromethyl or oxo;

$Cy^2$ is meta or para to $A_1$ and is (a) hydrogen or (b) aryl, heteroaryl, cycloalkyl, pyrrolidine, pyrrolidin-2-one, 1-methylpyrrolidin-2-one, piperidine, piperidin-2-one, dihydropyridine, tetrahydropyridine, piperazine, 1-(2,2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1,6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl optionally substituted with 1 to 4 groups independently selected from fluorine, chlorine, bromine, iodine, cyano, nitro, hydroxy$(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkyl-alkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_8)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

Y is $(C_1-C_6)$alkyl, halo$(C_1-C_6)$alkyl or oxo;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$ alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

$R^3$ is selected from $(C_1-C_6)$alkyl, $(C_2-C_6)$alkenyl, $(C_2-C_6)$alkynyl, $(C_3-C_6)$cycloalkyl$(C_1-C_4)$alkyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O—$, $(R^4)_2N—$, $R^4O_2C—$, $R^4C(=O)O—$, $R^4S$, $R^4S(=O)—$, $R^4S(=O)_2—$, $R^4C(=O)NR^4$, $(R^4)_2NC(=O)—$, $(R^4)_2NC(=O)O—$, $(R^4)_2NC(=O)NR^4—$, $R^4OC(=O)NR^4—$, $(R^4)_2NC(=NCN)NR^4—$, $(R^4O)_2P(=O)O—$, $(R^4O)_2P(=O)NR^4—$, $R^4OS(=O)_2NR^4—$, $(R^4)_2NS(=O)_2O—$, $(R^4)_2NS(=O)_2NR^4—$, $R^4S(=O)_2NR^4—$, $R^4S(=O)_2NHC(=O)—$, $R^4S(=O)_2NHC(=O)O—$, $R^4S(=O)_2NHC(=O)NR^4—$, $R^4OS(=O)_2NHC(=O)—$, $R^4OS(=O)_2NHC(=O)O—$, $R^4OS(=O)_2NHC(=O)NR^4—$, $(R^4)_2NS(=O)_2NHC(=O)—$, $(R^4)_2NS(=O)_2NHC(=O)O—$, $(R^4)_2NS(=O)_2NHC(=O)NR^4—$, $R^4C(=O)NHS(=O)_2—$, $R^4C(=O)NHS(=O)_2O—$, $R^4C(=O)NHS(=O)_2NR^4—$, $R^4OC(=O)NHS(=O)_2—$, $R^4OC(=O)NHS(=O)_2O—$, $R^4OC(=O)NHS(=O)_2NR^4—$, $(R^4)_2NC(=O)NHS(=O)_2—$, $(R^4)_2NC(=O)NHS(=O)_2O—$, $(R^4)_2NC(=O)NHS(=O)_2NR^4—$, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

or a pharmaceutically acceptable salt, enantiomer or diastereomer thereof; and the remainder of the variables are as defined as for the first, second or third embodiments.

In a fifth embodiment,
n is 0;
$A^1$ is (a) a bond, or (b) $(C_1)$alkylene, $CH_2CH_2O$, wherein the oxygen is attached to $Cy^1$, or $CH_2C(=O)$, wherein the carbonyl carbon is attached to $Cy^1$;

$Cy^1$ is aryl, heteroaryl, monocyclic cycloalkyl or monocyclic heterocyclyl, each optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkyl-sulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl; or if the substitution is either meta or para to $A^1$, the substituents may also include optionally substituted cycloalkyl, optionally substituted halo cycloalkyl or optionally substituted heteroaryl.

$Cy^2$ is meta or para to $A_1$ and is (a) hydrogen or (b) aryl, heteroaryl, cycloalkyl pyrrolidine, pyrrolidin-2-one, 1-methylpyrrolidin-2-one, piperidine, piperidin-2-one, dihydropyridine, tetrahydropyridine, piperazine, 1-(2,2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1,6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

or a pharmaceutically acceptable salt, enantiomer or diastereomer thereof; and the remainder of the variables are as defined as for the first, second, third or fourth embodiments.

In a sixth embodiment, $R^3$ is selected from $(C_1-C_6)$alkyl, $(C_2-C_6)$alkenyl, $(C_2-C_6)$alkynyl, $(C_1-C_3)$alkoxy$(C_1-C_3)$alkoxy or $(C_1-C_3)$alkoxy$(C_1-C_3)$alkyl and is substituted with one to four groups independently selected from cyano, oxo, $R^4O—$, $(R^4)_2N—$, $R^4O_2C—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4C(=O)NR^4—$, $(R^4)_2NC(=NCN)NR^4—$, $(R^4O)_2P(=O)O—$, $(R^4O)_2P(=O)NR^4—$, $R^4OS(=O)_2NR^4—$, $(R^4)_2NS(=O)_2O—$, $(R^4)_2NS(=O)_2NR^4—$, $R^4S(=O)_2NR^4—$, $R^4SO_2NR^4—$, $R^4S(=O)_2NHC(=O)—$, $R^4S(=O)_2NHC(=O)O—$, $R^4S(=O)_2NHC(=O)NR^4—$, $R^4OS(=O)_2NHC(=O)—$, $R^4OS(=O)_2NHC(=O)O—$, $R^4OS(=O)_2NHC(=O)NR^4—$, $(R^4)_2NS(=O)_2NHC(=O)—$, $(R^4)_2NS(=O)_2NHC(=O)O—$, $(R^4)_2NS(=O)_2NHC(=O)NR^4—$, $R^4C(=O)NHS(=O)_2—$, $R^4C(=O)NHS(=O)_2O—$, $R^4C(=O)NHS(=O)_2NR^4—$, $R^4OC(=O)NHS(=O)_2—$, $R^4OC(=O)NHS(=O)_2O—$, $R^4OC(=O)NHS(=O)_2NR^4—$, $(R^4)_2NC(=O)NHS(=O)_2—$, $(R^4)_2NC(=O)NHS(=O)_2O—$ and $(R^4)_2NC(=O)NHS(=O)_2NR^4—$;

or a pharmaceutically acceptable salt, enantiomer or diastereomer thereof; and the remainder of the variables are as defined as for the first, second, third, fourth or fifth embodiments.

In a seventh embodiment, the variables in Formula (I) are as defined in the first or second embodiment, provided that the substituents for the aryl, heteroaryl, monocyclic cycloalkyl and monocyclic heterocyclyl group represented by $Cy^1$ can additionally be selected from $(C_3-C_6)$cycloalkylcarbonyl, $(C_3-C_6)$cycloalkylaminocarbonyl, $\{(C_3-C_6)$cycloalkyl$\}$ $\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}$ $\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}$ $\{(C_1-C_6)$alkyl$\}$aminocarbonyl$(C_1-C_6)$alkyl and di$(C_3-C_6)$cycloalkylaminocarbonyl$(C_1-C_6)$alkyl;

the substituents for the aryl, heteroaryl, cycloalkyl and heterocyclyl group represented by $Cy^2$ can additionally be selected from $(C_3-C_6)$cycloalkylcarbonyl, $(C_3-C_6)$cycloalkylaminocarbonyl, $\{(C_3-C_6)$cycloalkyl$\}$ $\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}$ $\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}$ $\{(C_1-C_6)$alkyl$\}$aminocarbonyl$(C_1-C_6)$alkyl and di$(C_3-C_6)$cycloalkylaminocarbonyl$(C_1-C_6)$alkyl; and the substituents for the aryl, heteroaryl, cycloalkyl and heterocyclyl group represented by $R^2$ can additionally be selected from $(C_3-C_6)$cycloalkylcarbonyl, $(C_3-C_6)$cycloalkylaminocarbonyl, $\{(C_3-C_6)$cycloalkyl$\}$ $\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}$ $\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}$ $\{(C_1-C_6)$alkyl$\}$aminocarbonyl$(C_1-C_6)$alkyl and di$(C_3-C_6)$cycloalkylaminocarbonyl$(C_1-C_6)$alkyl.

Another embodiment of the invention is a method of inhibiting 11β-HSD1 activity comprising the step of administering to a mammal in need of such treatment an effective amount of a compound of Formulas I, Ia, Ib, Ic, Id, Ie, If, Ig, Ih Ii, Ij, Ik, Il or, $Im^{1-12}$, $In^{1-12}$, $Io^{1-12}$, $Ip^{1-7}$, $Iq^{1-21}$, $Ir^{1-21}$, $Is^{1-21}$, $It^{1-7}$, $Iu^{1-20}$, $Iv^{1-20}$, $Iw^{1-20}$ or $Ix^{1-7}$ or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of a compound of Formulas I, Ia, Ib, Ic, Id, Ie, If, Ig, Ih Ii, Ij, Ik, Il, $Im^{1-12}$, $In^{1-12}$, $Io^{1-12}$, $Ip^{1-7}$, $Iq^{1-21}$, $Ir^{1-21}$, $Is^{1-21}$, $It^{1-7}$, $Iu^{1-20}$, $Iv^{1-20}$, $Iw^{1-20}$ or $Ix^{1-7}$ or a pharmaceutically acceptable salt, enantiomer or diastereomer thereof.

Another embodiment of the invention is the use of a compound of Formulas I, Ia, Ib, Ic, Id, Ie, If, Ig, Ih Ii, Ij, Ik, Il or, $Im^{1-12}$, $In^{1-12}$, $Io^{1-12}$, $Ip^{1-7}$, $Iq^{1-21}$, $Ir^{1-21}$, $Is^{1-21}$, $It^{1-7}$, $Iu^{1-20}$, $Iv^{1-20}$, $Iw^{1-20}$ or $Ix^{1-7}$ or a diastereomer thereof for the manufacture of a medicament for inhibiting 11β-HSD1 activity in a mammal in need of such treatment.

Another embodiment of the invention is the use of a compound of Formulas I, Ia, Ib, Ic, Id, Ie, If, Ig, Ih Ii, Ij, Ik, Il, $Im^{1-12}$, $In^{1-12}$, $Io^{1-12}$, $Ip^{1-7}$, $Iq^{1-21}$, $Ir^{1-21}$, $Is^{1-21}$, $It^{1-7}$, $Iu^{1-20}$, $Iv^{1-20}$, $Iw^{1-20}$ or $Ix^{1-7}$ or a or a pharmaceutically acceptable salt, enantiomer or diastereomer thereof for the manufacture of a medicament for treating a subject with a disease associated with the activity or expression of 11β-HSD1.

Another embodiment of the invention is a compound of Formulas I, Ia, Ib, Ic, Id, Ie, If, Ig, Ih Ii, Ij, Ik, Il, $Im^{1-12}$, $In^{1-12}$, $Io^{1-12}$, $Ip^{1-7}$, $Iq^{1-21}$, $Ir^{1-21}$, $Is^{1-21}$, $It^{1-7}$, $Iu^{1-20}$, $Iv^{1-20}$, $Iw^{1-20}$ or $Ix^{1-7}$ or a or a pharmaceutically acceptable salt, enantiomer or diastereomer thereof for use in inhibiting 11β-HSD1 activity in a mammal in need of such treatment.

Another embodiment of the invention is a compound of Formulas I, Ia, Ib, Ic, Id, Ie, If, Ig, Ih Ii, Ij, Ik, Il, Im$^{1-12}$, In$^{1-12}$, Io$^{1-12}$, Ip$^{1-7}$, Iq$^{1-21}$, Ir$^{1-21}$, Is$^{1-21}$, It$^{1-7}$, Iu$^{1-20}$, Iv$^{1-20}$, Iw$^{1-20}$ or Ix$^{1-7}$ or a or a pharmaceutically acceptable salt, enantiomer or diastereomer thereof for use in for treating a subject with a disease associated with the activity or expression of 11β-HSD1.

DETAILED DESCRIPTION OF THE INVENTION

In an eighth embodiment, the variables in Formula I or any one of Formulas Ia-Il are as defined in the following paragraphs:

$R^1$ is (a) absent or (b) ($C_1$-$C_6$)alkyl is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—;

$A^1$ is (a) a bond, or (b) ($C_1$-$C_2$)alkylene;

$Cy^1$ is aryl, heteroaryl, monocyclic cycloalkyl or monocyclic heterocyclyl and is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, halo($C_1$-$C_6$)alkyl, ($C_1$-$C_6$)alkoxy, ($C_3$-$C_6$)cycloalkoxy, halo($C_1$-$C_6$)alkoxy, ($C_1$-$C_6$)alkanesulfonyl, halo($C_1$-$C_6$)alkanesulfonyl, halo($C_3$-$C_6$)cycloalkanesulfonyl, $H_2NCO$, $H_2NSO_2$, ($C_1$-$C_6$)alkylaminocarbonyl, di($C_1$-$C_6$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, oxo, cyano($C_1$-$C_6$)alkyl, aminocarbonyl($C_1$-$C_6$)alkyl, ($C_1$-$C_6$)alkylaminocarbonyl($C_1$-$C_6$)alkyl and di($C_1$-$C_6$)alkylaminocarbonyl($C_1$-$C_6$)alkyl;

$A^2$ is a bond;

$Cy^2$ is (a) hydrogen or (b) aryl, heteroaryl, cycloalkyl or heterocyclyl and is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl $C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl and di($C_3$-$C_6$)cycloalkylaminosulfonyl; In one aspect, the heterocyclyl represented by $Cy^2$ is other than optionally substituted thiazolidine-2,4-dionyl;

n is 0;

E is a bond;

$R^2$ is ($C_1$-$C_6$)alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, halo($C_1$-$C_6$)alkyl, ($C_1$-$C_6$)alkoxy, ($C_3$-$C_6$)cycloalkoxy, halo($C_1$-$C_6$)alkoxy, ($C_1$-$C_6$)alkanesulfonyl, halo ($C_1$-$C_6$)alkanesulfonyl, halo($C_3$-$C_6$)cycloalkanesulfonyl, $H_2NCO$, $H_2NSO_2$, ($C_1$-$C_6$)alkylaminocarbonyl, di($C_1$-$C_6$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino and oxo;

$R^3$ is selected from ($C_1$-$C_6$)alkyl, ($C_2$-$C_6$)alkenyl, ($C_2$-$C_6$)alkynyl, ($C_3$-$C_5$)cycloalkyl($C_1$-$C_4$)alkyl, ($C_1$-$C_3$)alkoxy($C_1$-$C_3$)alkoxy, or ($C_1$-$C_3$)alkoxy($C_1$-$C_3$)alkyl and is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—; and $R^4$ is independently selected from H, ($C_1$-$C_6$)alkyl and halo ($C_1$-$C_6$)alkyl;

or a pharmaceutically acceptable salt, enantiomer or diastereomer thereof.

In a ninth embodiment, the variables in Formula I or in any one of Formulas Ia-Il are defined in the following paragraphs:

$R^1$ (for Formulas I, Id, Ig and Ih) is absent or is methyl or ethyl;

$A^1$ (for Formulas I, Id, Ig and Ih) is a bond or $CH_2$ or CH when $R^1$ is present;

$Cy^1$ (for Formulas I, Id, Ig, Ih) is phenyl, cyclohexyl, pyridyl, N-oxo-pyridyl, thiazolyl or pyrimidinyl each optionally substituted with 1 to 4 groups independently selected from halo, methyl, trifluoromethyl, hydroxy, methoxy, methoxycarbonyl, carboxy, ethoxycarbonylmethoxy and 2-hydroxy-2-methylpropoxy;

$A^2$ (for Formulas I, Ia-e, Ig and Ih) is a bond, O or $OCH_2CO$;

$Cy^2$ (for Formulas I, Ia-e, Ig and Ih) is (a) hydrogen or (b) phenyl, thienyl, pyridyl, N-oxo-pyridyl, cyclopropyl, piperidinyl or piperazinyl each optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl or tetrazolyl;

n (for Formulas I, Ig and Ih) is 0;
E (for Formulas I, Ia-c and Ie-i) is a bond or $CH_2$;
$R^2$ (for Formulas I, Ia-c and Ie-i) is phenyl, thienyl or pyridyl each optionally substituted with halo, methyl, methylthio or (4-morpholino)methyl; and
$R^3$ (for Formulas I and Ia-i) is methyl, ethyl, propyl, vinyl or allyl each optionally substituted with up to two groups independently selected from HO—, MeO—, $H_2N$—, $MeC(=O)NH$—, $MeS(=O)_2NH$—, $H_2NC(=O)$—, $MeNHC(=O)$—, $HO_2C$—, $(HO)_2P(=O)O$—, $H_2NS(=O)_2O$—, $H_2NS(=O)_2NH$—, $MeNHC(=O)NH$—, $MeNHC(=O)O$— oxo, cyano, $HO_2C$—, $HOCH_2CH_2NH$—, 4-morpholino, $HOCH_2C(=O)NH$—, $H_2NCH_2C(=O)NH$—, $EtNHC(=O)NH$, $MeOC(=O)NH$—, $MeNHC(=NC\equiv N)NH$—, or oxo;
or a pharmaceutically acceptable salt, enantiomer or diastereomer thereof.

In a tenth embodiment, the variables in Formula I or in any one of Formulas Ia-Il are as defined in the following paragraphs:
$R^1$ is absent or is methyl or ethyl;
$A^1$ is a bond, $CH_2$, $CH_2CH_2$, or CH when $R^1$ is present;
$Cy^1$ is phenyl, cyclopropyl, cyclohexyl, pyrrolidinyl, pyridyl, N-oxo-pyridyl, thiazolyl or pyrimidinyl each optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino;
$A^2$ is a bond, O, $OCH_2CO$ or $C=O$;
$Cy^2$ is (a) hydrogen or (b) phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl each optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;
n is 0;
E is a bond or $CH_2$;
$R^2$ is phenyl, thienyl, pyridyl or isopropyl each optionally substituted with halo, methyl, methylthio or (4-morpholino)methyl; and
$R^3$ is methyl, ethyl, propyl, butyl, vinyl, allyl or ethoxyethyl each optionally substituted with up to two groups independently selected from Methyl, HO—, MeO—, $H_2N$—, $MeC(=O)NH$—, $MeS(=O)_2NH$—, $H_2NC(=O)$—, $MeNHC(=O)$—, $HO_2C$—, $(HO)_2P(=O)O$—, $H_2NS(=O)_2O$—, $H_2NS(=O)_2NH$—, $MeNHC(=O)NH$—, $MeNHC(=O)O$—, oxo, cyano, $HO_2C$—, $HOCH_2CH_2NH$—, 4-morpholino, $HOCH_2C(=O)NH$—, $H_2NCH_2C(=O)NH$—, $EtNHC(=O)NH$, $MeOC(=O)NH$—, $MeNHC(=NC\equiv N)NH$—, Me-, MeS—, $MeSO_2$-$MeSO_2N(Me)$-, $MeS(=O)_2NHC(=O)$—, imidazolylamino-, imidazolyl, tetrazolyl, $H_2NCONH$—, $H_2NCO_2$—, $HOCH_2CH_2O$—, MeNH—, $Me_2N$— and MeCONMe;
or a pharmaceutically acceptable salt, enantiomer or diastereomer thereof.

In an eleventh embodiment, the variables in Formula I or any one of Formulas Ia-Il are as defined in the following paragraphs:

$R^1$ (for Formulas I, Id, Ig and Ih) is absent or is methyl or ethyl;
$R^{1a}$ (for Formulas Ij and Ik) is methyl or ethyl;
$A^1$ (for Formulas I, Id, Ig and Ih) is a bond, $CH_2$ or $CH_2CH_2$ or CH when $R^1$ is present;
$Cy^1$ (for Formulas I, Id, Ig, Ih) is phenyl, cyclopropyl, cyclohexyl, pyrrolidinyl, pyridyl, N-oxo-pyridyl, thiazolyl, piperidinyl or pyrimidinyl each optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl;
$A^2$ (for Formulas I, Ia-e, Ig and Ih) is a bond, $CH_2$, O, $OCH_2CO$ or $C=O$;
$Cy^2$ (for Formulas I, Ia-e, Ig, Ih, Ik and Il) is (a) hydrogen or (b) phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl each optionally substituted by 1 to 4 groups independently selected from halo, hydroxy, methoxy, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;
n (for Formulas I, Ig and Ih) is 0;
E (for Formulas I, Ia-c and Ie-i) is a bond or $CH_2$;
$R^2$ (for Formulas I, Ia-c and Ie-l) is phenyl, thienyl, pyridyl, t-butyl or isopropyl each optionally substituted with halo, methyl, methylthio, hydroxymethyl or (4-morpholino)methyl; and
$R^3$ (for Formulas I and Ia-l) is methyl, ethyl, propyl, butyl, vinyl, allyl or ethoxyethyl each optionally substituted with up to two groups independently selected from methyl, HO—, MeO—, $H_2N$—, $MeC(=O)NH$—, $MeS(=O)_2NH$—, $H_2NC(=O)$—, $MeNHC(=O)$—, $HO_2C$—, $(HO)_2P(=O)O$—, $H_2NS(=O)_2O$—, $H_2NS(=O)_2NH$—, $MeNHC(=O)NH$—, $MeNHC(=O)O$—, oxo, cyano, $HO_2C$—, $HOCH_2CH_2NH$—, 4-morpholino, $HOCH_2C(=O)NH$—, $H_2NCH_2C(=O)NH$—, $EtNHC(=O)NH$, $MeOC(=O)NH$—, $MeNHC(=NC\equiv N)NH$—, Me-, MeS—, $MeSO_2$—$MeSO_2N(Me)$-, $MeS(=O)_2NHC(=O)$—, imidazolylamino-, imidazolyl, tetrazolyl, spirocyclopropyl, $FCH_2CH_2NH$, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2NCONH$—, $H_2NCO_2$—, $HOCH_2CH_2O$—, MeNH—, $Me_2N$— and MeCONMe;
G (for Formulas Ia, Ie, Ii and Ij) is alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido;
r (for Formulas Ia, Ie, Ii and Ij) is 0, 1 or 2;
$G^1$ and $G^2$ (for Formula If) are independently alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido;
r (for Formulas Ia, Ie, If, Ii and Ij) is 0, 1 or 2;
s (for Formula If) is 0, 1 or 2;
t (for Formula Il) is 1 or 2;
or a pharmaceutically acceptable salt, enantiomer or diastereomer thereof.

In a twelfth embodiment, the variables in formula I or in any one or Formulas Ia-Il are as defined in the following paragraphs:

$R^1$ is absent or is methyl or ethyl;

$A^1$ is a bond, $CH_2$, $CH_2CH_2$, or CH when $R^1$ is present;

$Cy^1$ is phenyl, cyclopropyl, cyclohexyl, pyrrolidinyl, pyridyl, N-oxo-pyridyl, thiazolyl, pyrimidinyl, piperidinyl, each optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl, methylsulfonylamino, trifluoromethoxy, 2,2,2-trifluoroethoxy and benzyloxycarbonyl;

$A^2$ is a bond, O, $OCH_2CO$, C=O or $CH_2$;

$Cy^2$ is (a) hydrogen or (b) phenyl, thienyl, pyridyl, N-oxopyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl, pyridazinyl, pyrimidinyl, pyrazinyl, 3-oxo-2,3-dihydropyridazinyl, 4-oxo-3,4-dihydropyrimidinyl or 2-oxo-1,2-dihydropyrimidinyl each optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl, 1-aminoethyl, ethyl, isopropyl, 2,2,2-trifluoroethyl, cyano, ethoxy, cyclopropylcarbamoyl and t-butylcarbamoyl;

n is 0;

E is a bond or $CH_2$;

$R^2$ is phenyl, thienyl, pyridyl or isopropyl, t-butyl each optionally substituted with halo, methyl, methylthio or (4-morpholino)methyl; and $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2NC$(=O)—, MeNHC(=O)—, $HO_2C$—, $(HO)_2P$(=O)O—, $H_2NS$(=O)$_2$O—, $H_2NS$(=O)$_2$NH—, MeNHC(=O)NH—, MeNHC(=O)O—, oxo, cyano, $HO_2C$—, $HOCH_2CH_2NH$—, 4-morpholino, $HOCH_2C$(=O)NH—, $H_2NCH_2C$(=O)NH—, EtNHC(=O)NH, MeOC(=O)NH—, MeNHC(=NC≡N)NH—, Me-, MeS—, $MeSO_2$— $MeSO_2N$(Me)-, MeS(=O)$_2$NHC(=O)—, imidazolylamino-, imidazolyl, tetrazolyl, $H_2NCONH$—, $H_2NCO_2$—, $HOCH_2CH_2O$—, MeNH—, $Me_2N$—, MeCON(Me)-, 2-fluoroethylamino, azetidinyl, pyrrolidinyl, 3-fluoropyrrolidinyl, 3-oxopiperazinyl, 1,1-dioxoisothiazolidin-2-yl, methyl-1H-imidazol-2-yl, 5-methyl-1,3,4-oxadiazol-2-yl, 5-methyl-1,3,4-thiadiazol-2-yl, EtOC(=O)NH—, and fluoro;

alternatively $R^3$ is (1-hydroxycyclopropyl)methyl;

or a pharmaceutically acceptable salt, enantiomer or diastereomer thereof.

Another embodiment is a compound of Formula Ia:

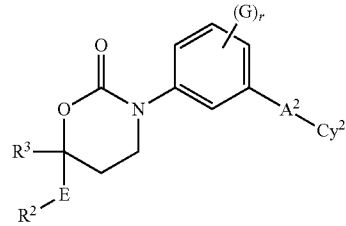

Ia wherein $A^2$, $Cy^2$, E, $R^2$, and $R^3$ are as defined for the first embodiment described for Formula I above, r is 0, 1, 2, 3 or 4 and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkylthio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkane-sulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

or a pharmaceutically acceptable salt, enantiomer or diastereomer thereof.

Alternatively for Formula Ia, $A^2$, $Cy^2$, E, $R^2$, and $R^3$ are as defined for the second embodiment described for Formula I above, and r is 0, 1, 2, 3 or 4 and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-$ $C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl and oxo;
or a pharmaceutically acceptable salt, enantiomer or diastereomer thereof.

In another alternative for Formulas Ia, $A^2$, $Cy^2$, E, $R^2$, and $R^3$ are as defined for the second embodiment described for Formula I above, and r is 0, 1, 2, 3 or 4 and substituents G are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkyl-sulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;
or a pharmaceutically acceptable salt, enantiomer or diastereomer thereof.

Another embodiment is a compound of Formula Ib:

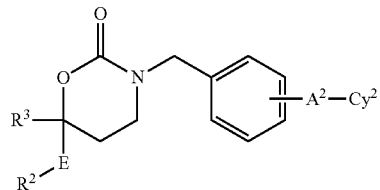

Ib wherein $A^2$, $Cy^2$, E, $R^2$, and $R^3$ are as defined for the first or second embodiments described for Formula I above;
or a pharmaceutically acceptable salt, enantiomer or diastereomer thereof.

Another embodiment is a compound of Formula Ic:

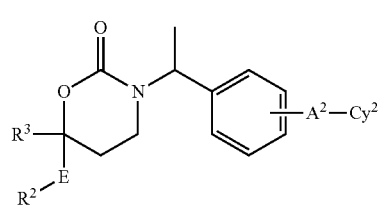

Ic wherein $A^2$, $Cy^2$, E, $R^2$, and $R^3$ are as defined for the first or second embodiments described for Formula I above;
or a pharmaceutically acceptable salt, enantiomer or diastereomer thereof.

Another embodiment is a compound of Formula Id:

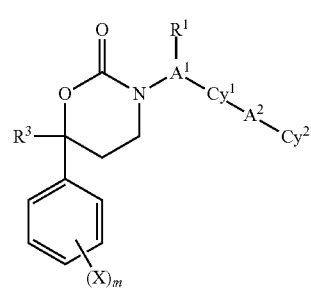

Id wherein, $Cy^1$, $A^1$, $R^1$, $A^2$, $Cy^2$, and $R^3$ are as defined for the first embodiment described for Formula I above, m is 0, 1, 2, 3 or 4 and substituents X are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkyl-alkanesulfinyl, ($C_1$-$C_6$)alkanesulfonyl, ($C_3$-

$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

or a pharmaceutically acceptable salt, enantiomer or diastereomer thereof.

Alternatively for Formula Id, $Cy^1$, $A^1$, $R^1$, $A^2$, $Cy^2$, and $R^3$ are as defined for the second embodiment described for Formula I above, m is 0, 1, 2, 3 or 4 and substituents X are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy and heteroaryl;

or a pharmaceutically acceptable salt, enantiomer or diastereomer thereof.

In another alternative for Formula Id, $Cy^1$, $A^1$, $R^1$, $A^2$, $Cy^2$, and $R^3$ are as defined for the second embodiment described for Formula I above, m is 0, 1, 2, 3 or 4 and substituents X are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkyl-sulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

or a pharmaceutically acceptable salt, enantiomer or diastereomer thereof.

Another embodiment is a compound of Formula Ie:

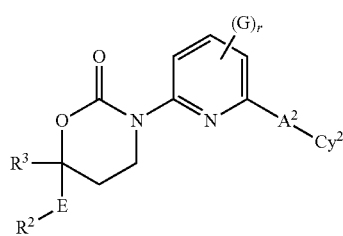

wherein $A^2$, $Cy^2$, E, $R^2$, and $R^3$ are as defined for the first embodiment described for Formula I above; r is 0, 1, 2, 3 or 4 and substituents G are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)

alkanesulfinyl, halo($C_3$-$C_6$)cycloalkanesulfinyl, halo($C_4$-$C_7$)cycloalkyl-alkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

or a pharmaceutically acceptable salt, enantiomer or diastereomer thereof.

Another embodiment is a compound of Formula If:

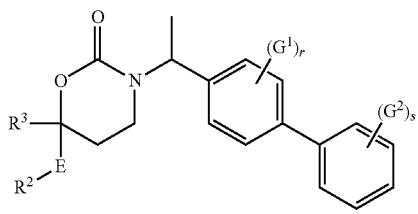

If wherein E, $R^2$, and $R^3$ are as defined for the first embodiment described for Formula I above; r and s are independently 0, 1, 2, 3 or 4, and $G^1$ and $G^2$ are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkyl-alkanesulfinyl, ($C_1$-$C_6$)alkanesulfonyl, ($C_3$-$C_6$)cycloalkanesulfonyl, ($C_4$-$C_7$)cycloalkyl-alkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

or a pharmaceutically acceptable salt, enantiomer or diastereomer thereof.

In one alternative for Formula If E, $R^2$, and $R^3$ are as defined for the first embodiment described for Formula I above; r and s are independently 0, 1, 2, 3 or 4, and $G^1$ and $G^2$ are independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkyl-sulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

or a pharmaceutically acceptable salt, enantiomer or diastereomer thereof.

Another embodiment is a compound of Formula Ig:

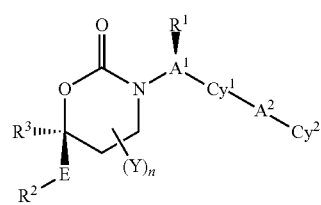

Ig wherein, $Cy^1$, $A^1$, $R^1$, $A^2$, $Cy^2$, $R^2$, E, $R^3$, Y, and n are as defined for the first or second embodiments described for Formula I above and at least one and preferably both stereocenters are in the configuration depicted. Pharmaceutically acceptable salts, enantiomers or diastereomers thereof are also included.

Another embodiment is a compound of Formula Ih:

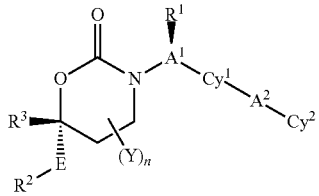

Ih wherein, $Cy^1$, $A^1$, $R^1$, $A^2$, $Cy^2$, $R^2$, E, $R^3$, Y, and n are as defined for the first or second embodiments described for Formula I above and at least one and preferably both stereocenters are in the configuration depicted. Pharmaceutically acceptable salts, enantiomers or diastereomers thereof are also included.

Another embodiment is a compound of Formula Ii:

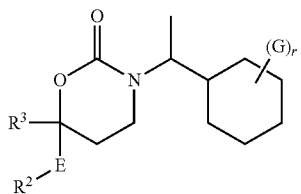

Ii wherein E, $R^2$ and $R^3$ are as defined for the first or second embodiments described for Formula I above, r is 0, 1, 2, 3 or 4, and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkyl-alkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkyl-sulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;

or a pharmaceutically acceptable salt, enantiomer or diastereomer thereof.

Alternatively, for Formula Ii:

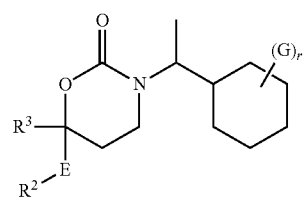

Ii

E, $R^2$ and $R^3$ are as defined for the first or second embodiments described for Formula I above, r is 0, 1, 2, 3 or 4, and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkyl-sulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl;

or a pharmaceutically acceptable salt, enantiomer or diastereomer thereof.

Another embodiment is a compound of Formula Ij:

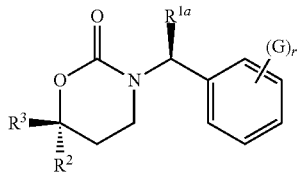

Ij wherein $R^2$ and $R^3$ are as defined for the first or second embodiments described for Formula I above, $R^{1a}$ is methyl or ethyl, r is 0, 1, 2, 3 or 4, and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkyl-alkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy and $(C_1-C_6)$alkylcarbonyl;
or a pharmaceutically acceptable salt, enantiomer or diastereomer thereof.

Alternatively for Formula Ij:
$R^2$ and $R^3$ are as defined for the first or second embodiments described for Formula I above, $R^{1a}$ is methyl or ethyl, r is 0, 1, 2, 3 or 4, and substituents G are independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkyl-sulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl;
or a pharmaceutically acceptable salt, enantiomer or diastereomer thereof.

Another embodiment is a compound of Formula Ik:

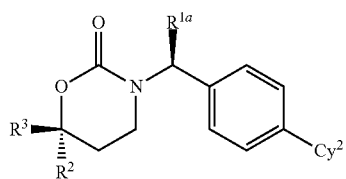

Ik wherein $Cy^2$, $R^2$ and $R^3$ are as defined for the first or second embodiments described for Formula I above, and $R^{1a}$ is methyl or ethyl;
or a pharmaceutically acceptable salt, enantiomer or diastereomer thereof.

Another embodiment is a compound of Formula Ik wherein $R^{1a}$ is methyl or ethyl, $R^2$ is phenyl optionally substituted with up to 2 groups selected from halogen, methyl, trifluoromethyl and cyano, $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl and $Cy^2$ is heterocyclyl optionally substituted with up to 3 groups independently selected from those described for $G^2$ in Formula If and oxo;
or a pharmaceutically acceptable salt, enantiomer or diastereomer thereof.

Another embodiment is a compound of Formula Ik wherein $R^{1a}$ is methyl or ethyl, $R^2$ is phenyl optionally substituted with up to 2 groups selected from halogen, methyl, trifluoromethyl and cyano, R³ is MeSO₂NHCH₂CH₂CH₂, H₂NC(=O)CH₂CH₂, H₂NC(=O)CMe₂CH₂, 3-hydroxypropyl, 3-hydroxy-3-methylbutyl, 2-hydroxyethyl, 2-hydroxy-2-methylpropyl or 2-cyano-2-methylpropyl and Cy² is 5-oxo-4,5-dihydro-1H-pyrazolyl, 3-oxo-2,3-dihydro-1H-pyrazolyl, 5-oxo-4,5-dihydro-1H-imidazolyl, 2-oxo-2,3-dihydro-1H-imidazolyl, 5-oxo-4,5-dihydro-1H-1,2,4-triazol-3-yl, 5-oxo-4,5-dihydro-1,3,4-thiadiazolyl, 1,2-dihydro-2-oxopyridyl, 2,3-dihydro-3-oxopyridazinyl, 1,2-dihydro-2-oxopyrimidinyl, 3,4-dihydro-4-oxopyrimidinyl or 1,2-dihydro-2-oxopyrazinyl optionally substituted with up to 3 groups independently selected from fluorine, chlorine, cyano, hydroxy, amino, (C₁-C₄)alkyl, (C₃-C₄)cycloalkyl, (C₃-C₄)cycloalkyl(C₁-C₂)alkyl, halo(C₁-C₄)alkyl, (C₁-C₄)alkoxy, (C₁-C₄)haloalkoxy, CONH₂, (C₁-C₄)alkylaminocarbonyl, di(C₁-C₄)alkylaminocarbonyl, and (C₁-C₄)alkylcarbonylamino;
or a pharmaceutically acceptable salt, enantiomer or diastereomer thereof. In one alternative, the embodiments described in this paragraph exclude the compound exemplified in Examples 221 or 313 or a pharmaceutically acceptable salt, enantiomer or diastereomer thereof.

Another embodiment is a compound of Formula Ik wherein R¹ᵃ is methyl or ethyl, R² is phenyl optionally substituted with up to 2 groups selected from halogen, methyl, trifluoromethyl and cyano, R³ is 2-hydroxy-2-methylpropyl or 2-cyano-2-methylpropyl and Cy² is 1,2-dihydro-2-oxopyridyl, 2,3-dihydro-3-oxopyridazinyl, 1,2-dihydro-2-oxopyrimidinyl, 3,4-dihydro-4-oxopyrimidinyl or 1,2-dihydro-2-oxopyrazinyl optionally substituted with up to 2 groups independently selected from (C₁-C₄)alkyl, (C₃-C₄)cycloalkyl, halo(C₁-C₄)alkyl and halogen;
or a pharmaceutically acceptable salt, enantiomer or diastereomer thereof.

Another embodiment is a compound of Formula Ik wherein R¹ᵃ is methyl or ethyl, R² is phenyl optionally substituted with up to 2 groups selected from halogen, methyl, trifluoromethyl and cyano, R³ is 2-hydroxy-2-methylpropyl or 2-cyano-2-methylpropyl and Cy² is heteroaryl optionally substituted with up 2 groups selected from (C₁-C₄)alkyl, halo(C₁-C₄)alkyl, halogen, cyano, CONH₂, (C₁-C₄)alkylaminocarbonyl, di(C₁-C₄)alkylaminocarbonyl and (C₃-C₅)cycloalkylaminocarbonyl or a pharmaceutically acceptable salt, enantiomer or diastereomer thereof. In another embodiment, Cy² is heteroaryl optionally substituted with one group selected from (C₁-C₄)alkyl, halo(C₁-C₄)alkyl, halogen, cyano, CONHMe and CONMe₂; or a pharmaceutically acceptable salt, enantiomer or diastereomer thereof. In an alternative embodiment CONH₂ is excluded as a permissible substituent when Cy² is pyridine or thiazole. In yet another embodiment, Cy² is heteroaryl optionally substituted with one group selected from (C₁-C₄)alkyl, halo(C₁-C₄)alkyl, halogen, cyano;
or a pharmaceutically acceptable salt, enantiomer or diastereomer thereof.

Another embodiment is a compound of Formula Ik wherein R¹ᵃ is methyl or ethyl, R² is phenyl or fluorophenyl, R³ is 2-hydroxy-2-methylpropyl or 2-cyano-2-methylpropyl and Cy² is pyridine, pyridine N-oxide, pyridazine, pyrimidine, pyrazine, thiazole, pyrazole or thiadiazole optionally substituted with methyl, fluorine, chlorine, cyano, CONH₂, CONHMe, CONMe₂, CONHt-Bu or CONHc-Pr;
or a pharmaceutically acceptable salt, enantiomer or diastereomer thereof. In an alternative embodiment CONH₂ is excluded as a permissible substituent when Cy² is pyridine or thiazole.

Another embodiment is a compound of Formula Il:

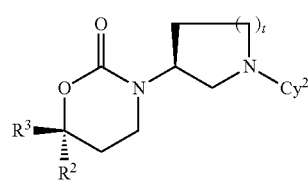

wherein Cy², R² and R³ are as defined for the first or second embodiments described for Formula I above, and t is 1, 2 or 3;
or a pharmaceutically acceptable salt, enantiomer or diastereomer thereof.

Another embodiment is a compound of Formula Il wherein t is 1, 2 or 3; R² is phenyl or fluorophenyl, R³ is MeSO₂NHCH₂CH₂CH₂, H₂NC(=O)CH₂CH₂, H₂NC(=O)CMe₂CH₂, 3-hydroxypropyl, 3-hydroxy-3-methylbutyl, 2-hydroxyethyl, 2-hydroxy-2-methylpropyl or 2-cyano-2-methylpropyl and Cy² is heterocyclyl optionally substituted with up to 3 groups independently selected from oxo, fluorine, chlorine, cyano, hydroxy, amino, (C₁-C₄)alkyl, (C₃-C₄)cycloalkyl, (C₃-C₄)cycloalkyl(C₁-C₂)alkyl, halo(C₁-C₄)alkyl, (C₁-C₄)alkoxy, (C₁-C₄)haloalkoxy, CONH₂, (C₁-C₄)alkylaminocarbonyl, di(C₁-C₄)alkylaminocarbonyl and (C₁-C₄)alkylcarbonylamino;
or a pharmaceutically acceptable salt, enantiomer or diastereomer thereof.

Another embodiment is a compound of Formula Il wherein t is 1, 2 or 3; R² is phenyl or fluorophenyl, R³ is MeSO₂NHCH₂CH₂CH₂, H₂NC(=O)CH₂CH₂, H₂NC(=O)CMe₂CH₂, 3-hydroxypropyl, 3-hydroxy-3-methylbutyl, 2-hydroxyethyl, 2-hydroxy-2-methylpropyl or 2-cyano-2-methylpropyl and Cy² is heteroaryl optionally substituted with up to 3 groups independently selected from oxo, fluorine, chlorine, cyano, hydroxy, amino, (C₁-C₄)alkyl, (C₃-C₄)cycloalkyl, (C₃-C₄)cycloalkyl(C₁-C₂)alkyl, halo(C₁-C₄)alkyl, (C₁-C₄)alkoxy, (C₁-C₄)haloalkoxy, CONH₂, (C₁-C₄)alkylaminocarbonyl, di(C₁-C₄)alkylaminocarbonyl and (C₁-C₄)alkylcarbonylamino;
or a pharmaceutically acceptable salt, enantiomer or diastereomer thereof.

Another embodiment is a compound of Formula Il wherein t is 1, 2 or 3; R² is phenyl or fluorophenyl, R³ is MeSO₂NHCH₂CH₂CH₂, H₂NC(=O)CH₂CH₂, H₂NC(=O)CMe₂CH₂, 3-hydroxypropyl, 3-hydroxy-3-methylbutyl, 2-hydroxyethyl, 2-hydroxy-2-methylpropyl or 2-cyano-2-methylpropyl and Cy² is pyridine, pyridazine, pyrimidine, pyrazine, thiadiazole, pyrazole or thiazole optionally substituted with up to 2 groups independently selected from methyl, fluorine, chlorine, cyano, CF₃, CONH₂, CONHMe or CONMe₂; or a pharmaceutically acceptable salt, enantiomer or diastereomer thereof.

Another embodiment is a compound of Formula Il wherein R² is phenyl or fluorophenyl, R³ is 2-hydroxy-2-methylpropyl or 2-cyano-2-methylpropyl and Cy² is pyridine, pyridazine, pyrimidine, pyrazine, thiadiazole, pyrazole or thiazole optionally substituted with up to 2 groups independently selected from methyl, fluorine, chlorine, cyano, CF₃, CONH₂, CONHMe or CONMe₂;
or a pharmaceutically acceptable salt, enantiomer or diastereomer thereof.

Another embodiment of the invention is a compound of any one of Formulas Im¹⁻¹² or a pharmaceutically acceptable salt, enantiomer or diastereomer thereof:

Im¹
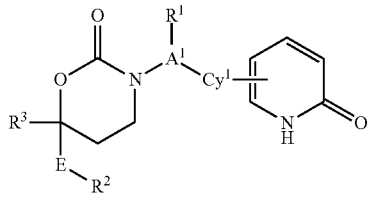

Im²
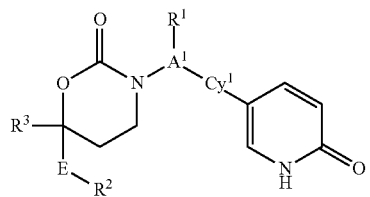

Im³
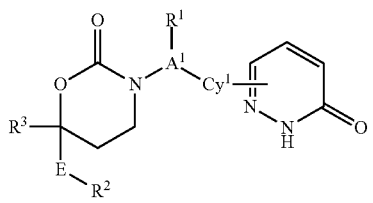

Im⁴
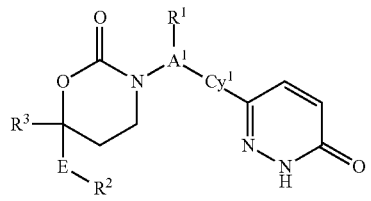

Im⁵
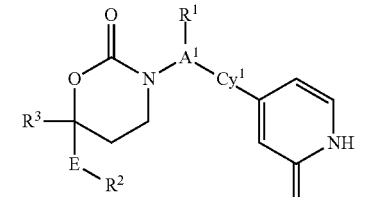

Im⁶
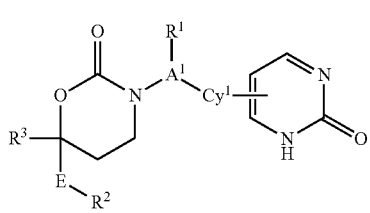

Im⁷
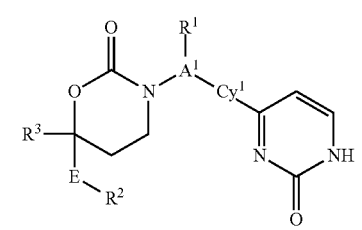

-continued

Im⁸
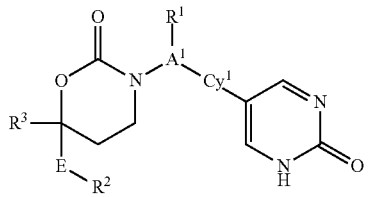

Im⁹
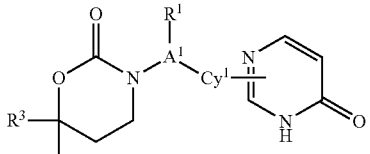

Im¹⁰
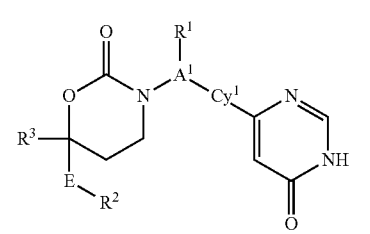

Im¹¹
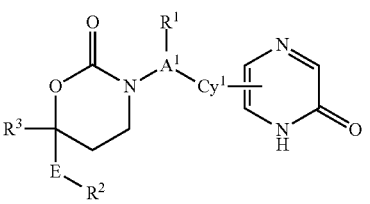

Im¹²
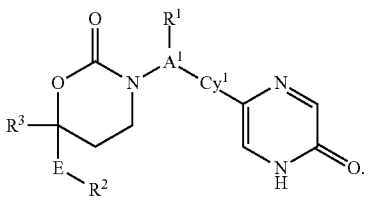

In Formulas $Im^{1-12}$, the oxodihydropyridyl, oxodihydropyridazinyl, oxodihydropyrimidinyl and oxodihydropyrazinyl rings in Formulas $Im^{1-12}$ are optionally substituted (substitution at ring carbons bonded to hydrogen and ring nitrogen atoms bonded to hydrogen atoms are encompassed, i.e., a "substitutable ring nitrogen atom") with up to four substituents as described above for $Cy^2$. Suitable substituents for $Cy^2$ and suitable values for $R^1$, $R^2$, $R^3$, $A^1$, $Cy^1$ and E are as defined in any one of the first, second, third, fourth, fifth, sixth, seventh, eighth, ninth, tenth, eleventh or twelfth embodiments. Alternatively, suitable substituents for $Cy^1$ and the oxodihydropyridyl, oxodihydropyridazinyl, oxodihydropyrimidinyl and oxodihydropyrazinyl rings in Formulas $Im^{1-12}$ are as described for $G^1$ and $G^2$, respectively, in Formula If, and values for $R^1$, $R^2$, $R^3$, $A^1$, $Cy^1$ and E are as defined in any one of the first, second, third, fourth, fifth, sixth, seventh, eighth, ninth, tenth, eleventh or twelfth embodiments. Alternatively, suitable substituents for $Cy^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a substitutable ring nitrogen atom in the oxodihydropyridyl, oxodihydropyridazinyl, oxodihydropyrimidinyl and oxodihydropyrazinyl rings in Formulas $Im^{1-12}$ include $(C_1-C_4)$alkyl, $(C_3-C_4)$cycloalkyl, $(C_3-C_4)$cycloalkyl$(C_1-C_2)$alkyl, and $(C_1-C_4)$haloalkyl; suitable substituents for a ring carbon atom in the oxodihydropyridyl, oxodihydropyridazinyl, oxodihydropyrimidinyl and oxodihydropyrazinyl rings in Formulas $Im^{1-12}$ include fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl and $(C_1-C_4)$alkylcarbonylamino; and suitable values for $R^1$, $R^2$, $R^3$, $A^1$, $Cy^1$ and E are as defined in any one of the first, second, third, fourth, fifth, sixth, seventh, eighth, ninth, tenth, eleventh or twelfth embodiments. In another alternative, the embodiments in this paragraph exclude the compound exemplified in Example 221 and Example 313 or a pharmaceutically acceptable salt, enantiomer or diastereomer thereof.

For each of the embodiments described in the previous paragraph, $R^1$ is preferably methyl or ethyl.

For each of the embodiments described in the paragraph immediately following Formulas $Im^{1-12}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Im^{1-12}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Im^{1-12}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl, and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Im^{1-12}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl, and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Im^{1-12}$, $R^1$ is preferably methyl or ethyl; and $R^3$ is 2-hydroxy-2-methylpropyl or 2-cyano-2-methylpropyl.

For each of the embodiments described in the paragraph immediately following Formulas $Im^{1-12}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas $Im^{1-12}$, $R^1$ is preferably methyl or ethyl; $R^2$ is phenyl or fluorophenyl; $R^3$ is 2-hydroxy-2-methylpropyl or 2-cyano-2-methylpropyl; the substituent on the substitutable ring nitrogen atom in the oxodihydropyridyl, oxodihydropyridazinyl, oxodihydropyrimidinyl and oxodihydropyrazinyl rings in Formulas $Im^{1-12}$ is $(C_1-C_4)$alkyl, $(C_3-C_4)$cycloalkyl, $(C_3-C_4)$cycloalkyl$(C_1-C_2)$alkyl, or $(C_1-C_2)$haloalkyl; and one or two ring carbon atoms in the oxodihydropyridyl, oxodihydropyridazinyl, oxodihydropyrimidinyl and oxodihydropyrazinyl rings in Formulas $Im^{1-12}$ are optionally substituted with methyl or ethyl.

Another embodiment of the invention is a compound of any one of Formulas $Im^{1-12}$, or a pharmaceutically acceptable salt, enantiomer or diastereomer thereof:

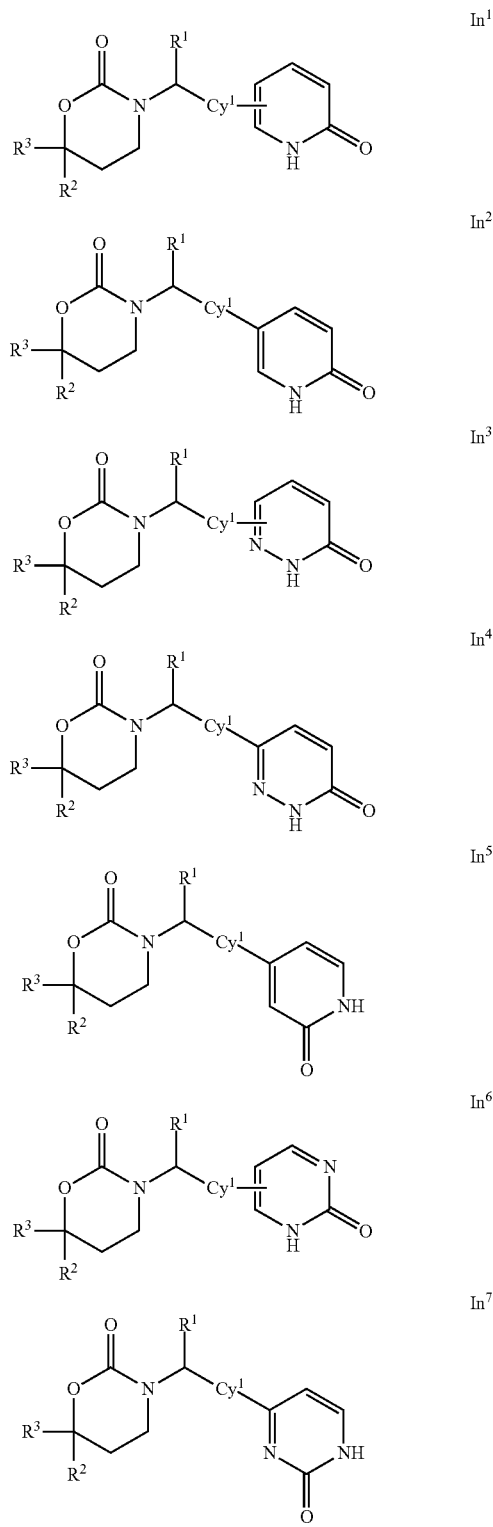

-continued

In⁸
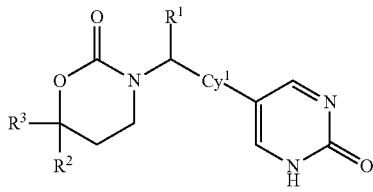

In⁹
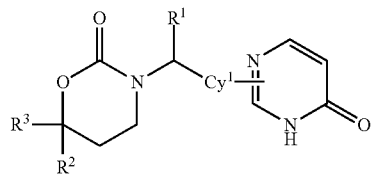

In¹⁰
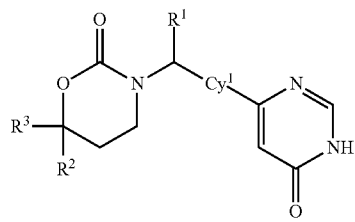

In¹¹
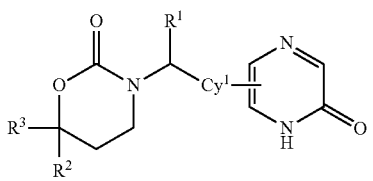

In¹²
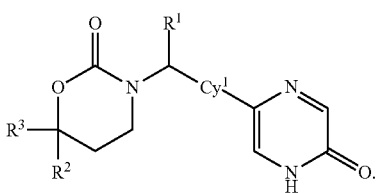

In Formulas $In^{1-12}$, the oxodihydropyridyl, oxodihydropyridazinyl, oxodihydropyrimidinyl and oxodihydropyrazinyl rings are optionally substituted (substitution at ring carbons bonded to hydrogen and at nitrogen atoms bonded to hydrogen atoms are encompassed, i.e., a "substitutable ring nitrogen atom") with up to four substituents as described above for $Cy^2$. Suitable substituents for $Cy^2$ and suitable values for $R^1$, $R^2$, $R^3$ and $Cy^1$ are as defined in any one of the first, second, third, fourth, fifth, sixth, seventh, eighth, ninth, tenth, eleventh or twelfth embodiments. Alternatively, suitable substituents for $Cy^1$ and the oxodihydropyridyl, oxodihydropyridazinyl, oxodihydropyrimidinyl and oxodihydropyrazinyl rings in Formulas $In^{1-12}$ are as described for $G^1$ and $G^2$, respectively, in Formula If, and values for $R^1$, $R^2$, $R^3$ and $Cy^1$ are as defined in any one of the first, second, third, fourth, fifth, sixth, seventh, eighth, ninth, tenth, eleventh or twelfth embodiments. Alternatively, suitable substituents for $Cy^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a substitutable ring nitrogen atom in the oxodihydropyridyl, oxodihydropyridazinyl, oxodihydropyrimidinyl and oxodihydropyrazinyl rings in Formulas $In^{1-12}$ include $(C_1-C_4)$alkyl, $(C_3-C_4)$cycloalkyl, $(C_3-C_4)$cycloalkyl$(C_1-C_2)$alkyl and $(C_1-C_4)$haloalkyl; suitable substituents for a ring carbon atom in the oxodihydropyridyl, oxodihydropyridazinyl, oxodihydropyrimidinyl and oxodihydropyrazinyl rings in Formulas $In^{1-12}$ include fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl and $(C_1-C_4)$alkylcarbonylamino; and suitable values for $R^1$, $R^2$, $R^3$, and $Cy^1$ are as defined in any one of the first, second, third, fourth, fifth, sixth, seventh, eighth, ninth, tenth, eleventh or twelfth embodiments. In another alternative, the embodiments described in this paragraph exclude the compound exemplified in Example 221 and Example 313 or a pharmaceutically acceptable salt, enantiomer or diastereomer thereof.

For each of the embodiments described in the previous paragraph, $R^1$ is preferably methyl or ethyl.

For each of the embodiments described in the paragraph immediately following Formulas $In^{1-12}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $In^{1-12}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $In^{1-12}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $In^{1-12}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $In^{1-12}$, $R^1$ is preferably methyl or ethyl; and $R^3$ is 2-hydroxy-2-methylpropyl or 2-cyano-2-methylpropyl.

For each of the embodiments described in the paragraph immediately following Formulas $In^{1-12}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas $In^{1-12}$, $R^1$ is preferably methyl or ethyl; $R^2$ is phenyl or fluorophenyl; $R^3$ is 2-hydroxy-2-methylpropyl or 2-cyano-2-methylpropyl; the substituent on the substitutable ring nitrogen atom in the oxodihydropyridyl, oxodihydropyridazinyl, oxodihydropyrimidinyl and oxodihydropyrazinyl rings in Formulas $In^{1-12}$ is $(C_1-C_4)$alkyl, $(C_3-C_4)$cycloalkyl, $(C_3-C_4)$cycloalkyl$(C_1-C_2)$alkyl, or $(C_1-C_2)$haloalkyl; and one or two ring carbon atoms in the oxodihydropyridyl, oxodihydropyridazinyl, oxodihydropyrimidinyl and oxodihydropyrazinyl rings in Formulas $In^{1-12}$ are optionally substituted with methyl or ethyl.

Another embodiment of the invention is a compound of any one for Formulas $Io^{1-12}$, or a pharmaceutically acceptable salt thereof:

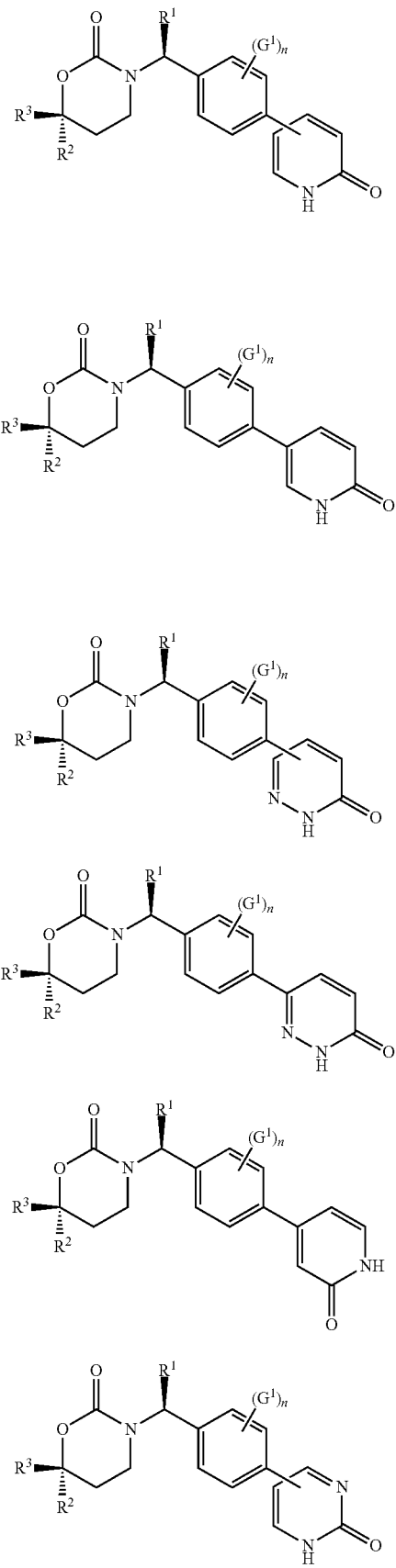
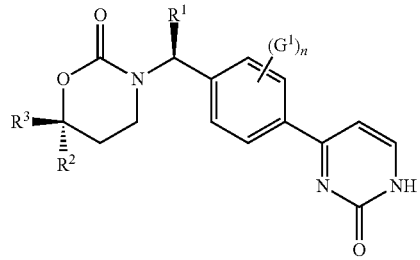
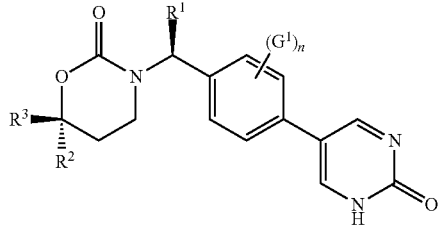
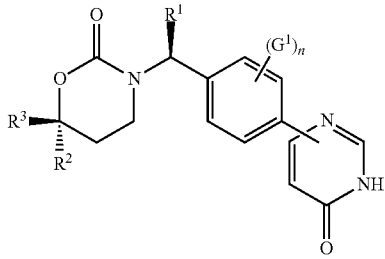
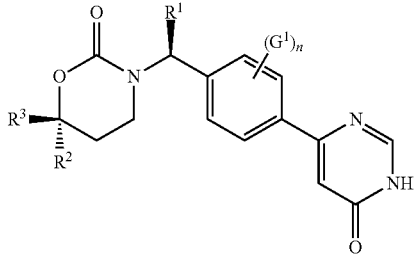
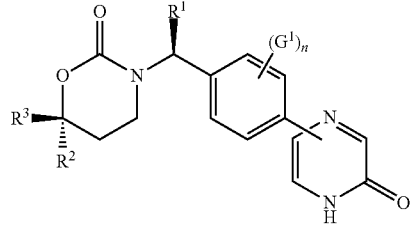
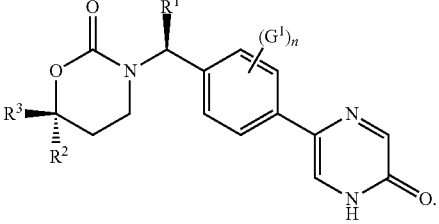
In Formulas $Io^{1-12}$, the oxodihydropyridyl, oxodihydropyridazinyl, oxodihydropyrimidinyl and oxodihydropyrazinyl rings in Formulas $Io^{1-12}$ are optionally substituted (substitution at ring carbons bonded to hydrogen and at nitrogen atoms bonded to hydrogen atoms are encompassed, i.e., a "substitutable ring nitrogen atom") with up to four substituents as described above for $Cy^2$; suitable values for $G^1$ are as described for $G^1$ in Formula If; n is 0, 1, 2 or 3; and suitable substituents for $Cy^2$ and suitable values for $R^1$, $R^2$ and $R^3$ are as defined in any one of the first, second, third, fourth, fifth, sixth, seventh, eighth, ninth, tenth, eleventh or twelfth embodiments. Alternatively, n is 0, 1, 2 or 3; suitable values for $G^1$ and substituents for the oxodihydropyridyl, oxodihydropyridazinyl, oxodihydropyrimidinyl and oxodihydropyrazinyl rings in Formulas $Io^{1-12}$ are as described for $G^1$ and $G^2$, respectively, in Formula If, and values for $R^1$, $R^2$ and $R^3$ are as defined in any one of the first, second, third, fourth, fifth, sixth, seventh, eighth, ninth, tenth, eleventh or twelfth embodiments. Alternatively, n is 0, 1, 2 or 3; suitable values for $G^1$ include $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a substitutable ring nitrogen atom in the oxodihydropyridyl, oxodihydropyridazinyl, oxodihydropyrimidinyl and oxodihydropyrazinyl rings in Formulas $Io^{1-12}$ include $C_1-C_4$ alkyl, $(C_3-C_4)$cycloalkyl, $(C_3-C_4)$cycloalkyl$(C_1-C_2)$alkyl and $C_1-C_4$ haloalkyl; suitable substituents for a ring carbon atom in the oxopyridyl, oxopyridazinyl, oxopyrimidinyl and oxopyrazinyl rings in Formulas $Io^{1-12}$ include fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl and $(C_1-C_4)$alkylcarbonylamino; and suitable values for $R^1$, $R^2$ and $R^3$ are as defined in any one of the first, second, third, fourth, fifth, sixth, seventh, eighth, ninth, tenth, eleventh or twelfth embodiments. In another alternative, the embodiments described in this paragraph exclude the compound exemplified in Example 221 and Example 313 or a pharmaceutically acceptable salt, enantiomer or diastereomer thereof.

For each of the embodiments described in the previous paragraph, $R^1$ is preferably methyl or ethyl.

For each of the embodiments described in the paragraph immediately following Formulas $Io^{1-12}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Io^{1-12}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Io^{1-12}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas $Io^{1-12}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Io^{1-12}$, $R^1$ is preferably methyl or ethyl; and $R^3$ is 2-hydroxy-2-methylpropyl or 2-cyano-2-methylpropyl.

For each of the embodiments described in the paragraph immediately following Formulas $Io^{1-12}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiments described in the paragraph immediately following Formulas $Io^{1-12}$, $R^1$ is preferably methyl or ethyl; $R^2$ is phenyl or fluorophenyl; $R^3$ is 2-hydroxy-2-methylpropyl or 2-cyano-2-methylpropyl; the substituent on the substitutable ring nitrogen atom in the oxodihydropyridyl, oxodihydropyridazinyl, oxodihydropyrimidinyl and oxodihydropyrazinyl rings in Formulas $Io^{1-12}$ is $(C_1-C_4)$alkyl, $(C_3-C_4)$cycloalkyl, $(C_3-C_4)$cycloalkyl$(C_1-C_2)$alkyl, or $(C_1-C_2)$haloalkyl; and one or two ring carbon atoms in the oxodihydropyridyl, oxodihydropyridazinyl, oxodihydropyrimidinyl and oxodihydropyrazinyl rings in Formulas $Io^{1-12}$ are optionally substituted with methyl or ethyl.

Another embodiment of the invention is a compound represented by any one of Formulas $Ip^{1-7}$, or a pharmaceutically acceptable salt thereof:

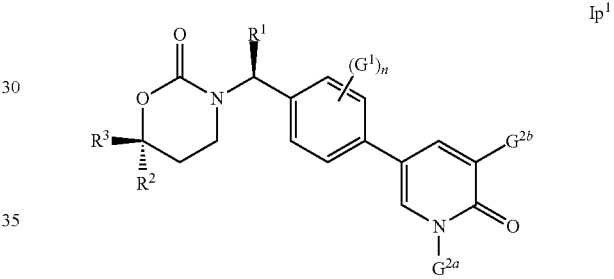

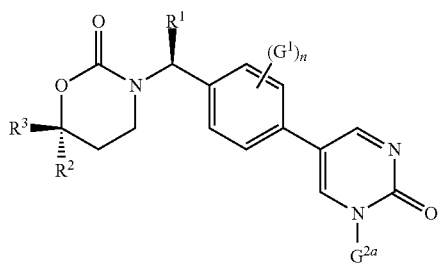

In Formulas Ip$^{1-7}$, G$^1$ is (C$_1$-C$_4$)alkyl, (C$_1$-C$_4$)alkoxy, (C$_1$-C$_4$)haloalkyl, (C$_1$-C$_4$)haloalkoxy, halogen, cyano or nitro; n is 0, 1 or 2; G$^{2a}$ is (C$_1$-C$_4$)alkyl, (C$_3$-C$_4$)cycloalkyl or (C$_1$-C$_4$)haloalkyl; G$^{2b}$ is hydrogen, fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl or (C$_1$-C$_4$)alkylcarbonylamino; and suitable values for R$^1$, R$^2$ and R$^3$ are as defined in any one of the first, second, third, fourth, fifth, sixth, seventh, eighth, ninth, tenth, eleventh or twelfth embodiments. In another alternative, the embodiments in this paragraph exclude the compound exemplified in Example 221 and Example 313 or a pharmaceutically acceptable salt, enantiomer or diastereomer thereof.

For each of the embodiments described in the previous paragraph, R$^1$ is preferably methyl or ethyl.

For each of the embodiments described in the paragraph immediately following Formulas Ip$^{1-7}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Ip$^{1-7}$, R$^1$ is preferably methyl or ethyl; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Ip$^{1-7}$, R$^1$ is preferably methyl or ethyl; R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Ip$^{1-7}$, R$^1$ is preferably methyl or ethyl; R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Ip$^{1-7}$, R$^1$ is preferably methyl or ethyl; and R$^3$ is 2-hydroxy-2-methylpropyl or 2-cyano-2-methylpropyl.

For each of the embodiments described in the paragraph immediately following Formulas Ip$^{1-7}$, R$^1$ is preferably methyl or ethyl; R$^2$ is phenyl or fluorophenyl; and R$^3$ is 2-hydroxy-2-methylpropyl or 2-cyano-2-methylpropyl.

For each of the embodiment described in the paragraph immediately following Formulas Ip$^{1-7}$, R$^1$ is preferably methyl or ethyl; R$^2$ is phenyl or fluorophenyl; R$^3$ is 2-hydroxy-2-methylpropyl or 2-cyano-2-methylpropyl; the substituent G$^{2a}$ is selected from (C$_1$-C$_4$)alkyl, (C$_3$-C$_4$)cycloalkyl, (C$_3$-C$_4$)cycloalkyl(C$_1$-C$_2$)alkyl, and (C$_1$-C$_2$)haloalkyl; and G$^{2b}$ is optionally selected from hydrogen, methyl or ethyl.

Another embodiment of the invention is a compound of any one of Formulas Iq$^{1-20}$ or a pharmaceutically acceptable salt, enantiomer or diastereomer thereof:

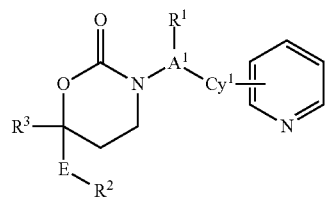

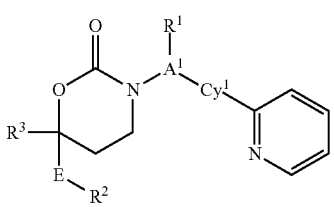

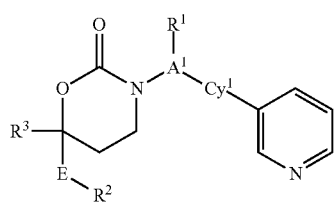
Iq³
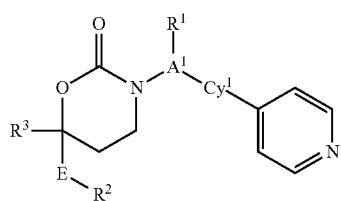
Iq⁴
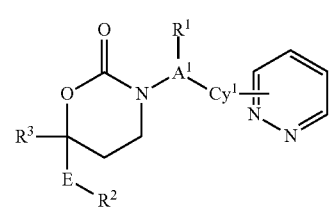
Iq⁵
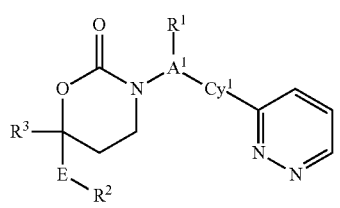
Iq⁶
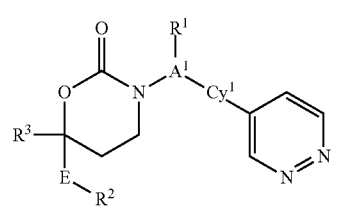
Iq⁷
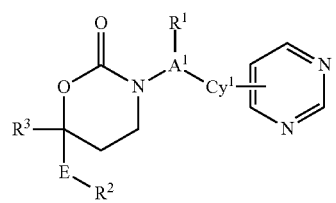
Iq⁸
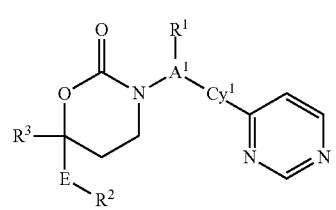
Iq⁹
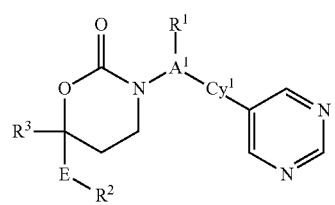
Iq¹⁰
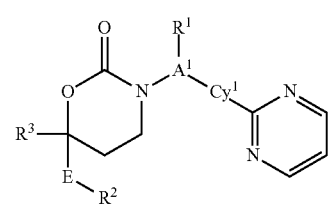
Iq¹¹
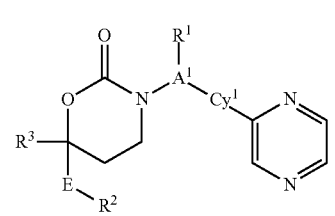
Iq¹²
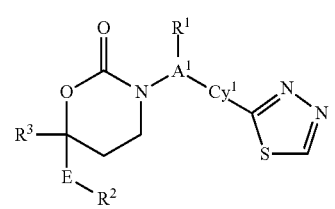
Iq¹³
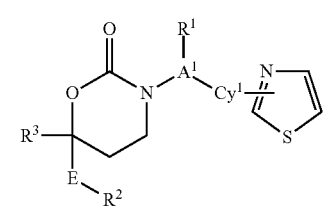
Iq¹⁴
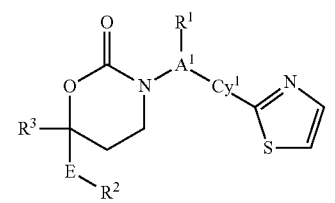
Iq¹⁵
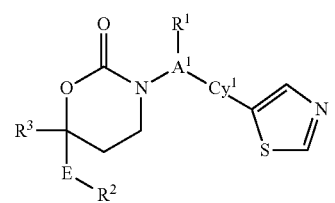
Iq¹⁶

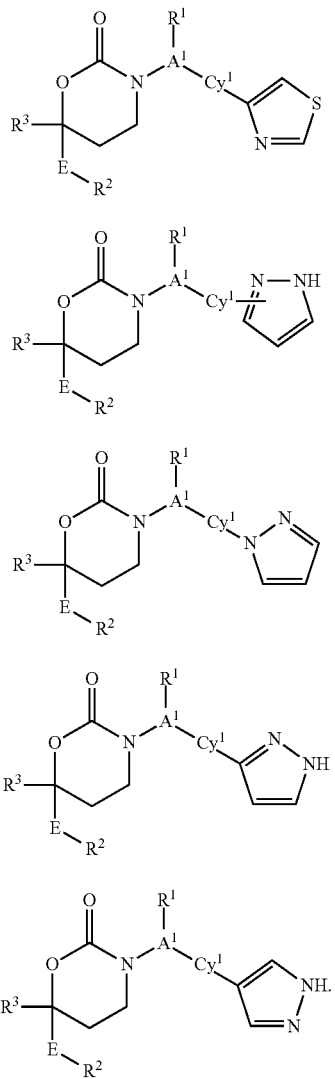

In Formulas Iq$^{1-21}$, the pyridine, pyridazine, pyrimidine, pyrazine, pyrazole, thiazole and thiadiazole rings in Formulas Iq$^{1-21}$ are optionally substituted (substitution at ring carbons bonded to hydrogen and ring nitrogen atoms bonded to hydrogen atoms are encompassed, i.e., a "substitutable ring nitrogen atom") with up to four substituents as described above for Cy$^2$. Suitable substituents for Cy$^2$ and suitable values for R$^1$, R$^2$, R$^3$, A$^1$, Cy$^1$ and E are as defined in any one of the first, second, third, fourth, fifth, sixth, seventh, eighth, ninth, tenth, eleventh or twelfth embodiments. Alternatively, suitable substituents for Cy$^1$ and the pyridine, pyridazine, pyrimidine, pyrazine, pyrazole, thiazole and thiadiazole rings in Formulas Iq$^{1-21}$ are as described for G$^1$ and G$^2$, respectively, in Formula If, and values for R$^1$, R$^2$, R$^3$, A$^1$, Cy$^1$ and E are as defined in any one of the first, second, third, fourth, fifth, sixth, seventh, eighth, ninth, tenth, eleventh or twelfth embodiments. Alternatively, suitable substituents for Cy$^1$ include (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; suitable substituents for a substitutable ring nitrogen atom in the pyrazole rings in Formulas Iq$^{18}$, Iq$^{20}$ and Iq$^{21}$ include (C$_1$-C$_4$)alkyl, (C$_3$-C$_4$)cycloalkyl, (C$_3$-C$_4$)cycloalkyl(C$_1$-C$_2$)alkyl, and (C$_1$-C$_4$)haloalkyl; suitable substituents for a ring carbon atom in the pyridine, pyridazine, pyrimidine, pyrazine, pyrazole, thiazole and thiadiazole rings in Formulas Iq$^{1-21}$ include fluorine, chlorine, cyano, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$)alkyl}{(C$_3$-C$_4$)cycloalkyl}aminocarbonyl and (C$_1$-C$_4$)alkylcarbonylamino; the ring nitrogen in the pyridine rings in Formulas Iq$^{1-4}$ is optionally substituted by oxo; and suitable values for R$^1$, R$^2$, R$^3$, A$^1$, Cy$^1$ and E are as defined in any one of the first, second, third, fourth, fifth, sixth, seventh, eighth, ninth, tenth, eleventh or twelfth embodiments. In another alternative, the embodiments in this paragraph exclude the compound exemplified in Example 205, Example 211, Example 214, Example 222, Example 226, Example 235, Example 236, Example 281, Example 292, Example 295, Example 298, Example 300, Example 302, Example 305, Example 304, Example 306, Example 307, Example 210, Example 296, Example 311, Example 230, Example 244, Example 258 and Example 291 or a pharmaceutically acceptable salt, enantiomer or diastereomer thereof.

For each of the embodiments described in the previous paragraph, R$^1$ is preferably methyl or ethyl.

For each of the embodiments described in the paragraph immediately following Formulas Iq$^{1-21}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Iq$^{1-21}$, R$^1$ is preferably methyl or ethyl; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Iq$^{1-21}$, R$^1$ is preferably methyl or ethyl; R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Iq$^{1-21}$, R$^1$ is preferably methyl or ethyl; R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Iq$^{1-21}$, R$^1$ is preferably methyl or ethyl; and R$^3$ is 2-hydroxy-2-methylpropyl or 2-cyano-2-methylpropyl.

For each of the embodiments described in the paragraph immediately following Formulas Iq$^{1-21}$, R$^1$ is preferably methyl or ethyl; R$^2$ is phenyl or fluorophenyl; and R$^3$ is 2-hydroxy-2-methylpropyl or 2-cyano-2-methylpropyl.

For each of the embodiments described in the paragraph immediately following Formulas Iq$^{1-21}$, R$^1$ is preferably methyl or ethyl; R$^2$ is phenyl or fluorophenyl; R$^3$ is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas Iq$^{1-21}$ are optionally substituted with fluoro, chloro, cyano, CONH$_2$, CONHMe, CONMe$_2$, CONHc-Pr, methoxy, ethoxy, methyl, ethyl or CF$_3$. the substitutable ring nitrogen atom in the pyrazole rings in Formulas Iq$^{18}$, Iq$^{20}$ and Iq$^{21}$ are optionally substituted with (C$_1$-C$_4$)alkyl, (C$_3$-C$_4$)cycloalkyl, (C$_3$-C$_4$)cycloalkyl(C$_1$-C$_2$)alkyl, or (C$_1$-C$_2$)haloalkyl, the ring nitrogen in the pyridine rings in Formulas Iq$^{1-4}$ is optionally substituted by oxo.

Another embodiment of the invention is a compound of any one of Formulas Ir$^{1-21}$, or a pharmaceutically acceptable salt, enantiomer or diastereomer thereof:

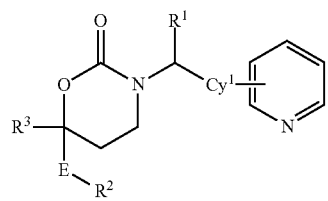
Ir$^1$

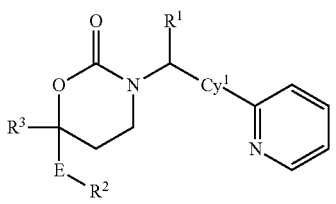
Ir$^2$

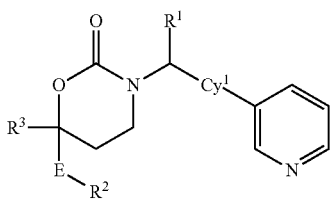
Ir$^3$

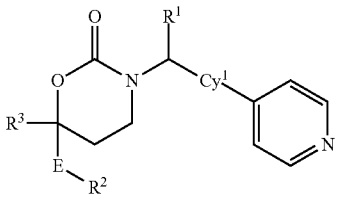
Ir$^4$

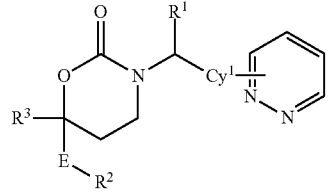
Ir$^5$

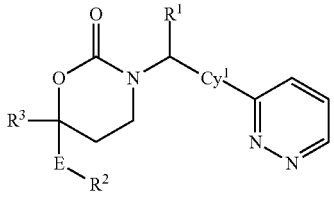
Ir$^6$

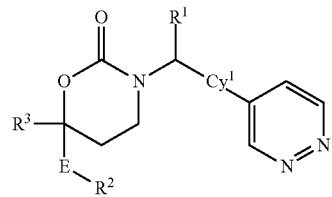
Ir$^7$

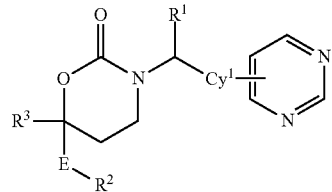
Ir$^8$

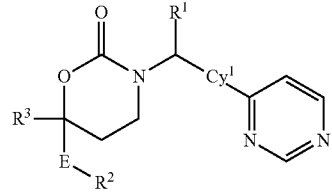
Ir$^9$

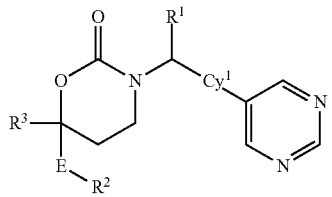
Ir$^{10}$

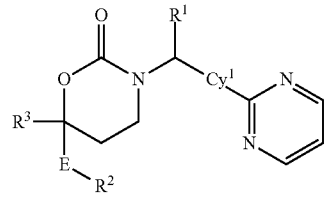
Ir$^{11}$

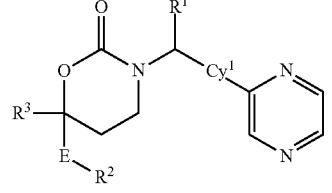
Ir$^{12}$

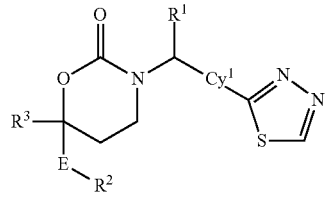
Ir$^{13}$

-continued

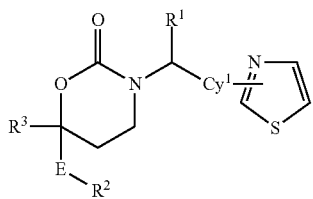
Ir¹⁴

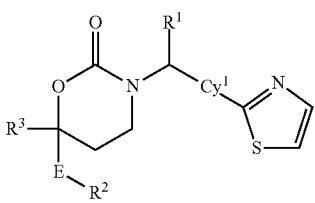
Ir¹⁵

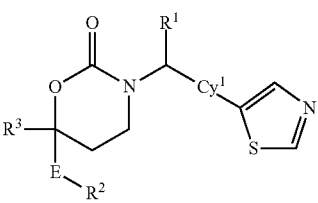
Ir¹⁶

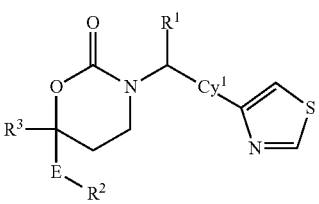
Ir¹⁷

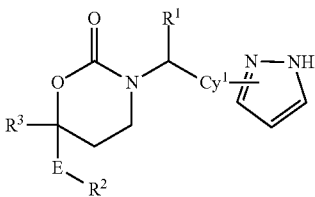
Ir¹⁸

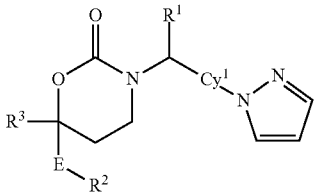
Ir¹⁹

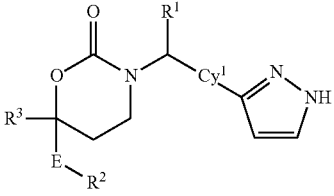
Ir²⁰

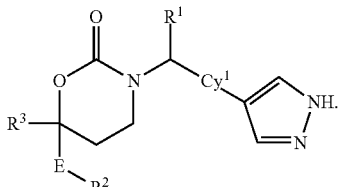
Ir²¹

In Formulas Ir$^{1-21}$, the pyridine, pyridazine, pyrimidine, pyrazine, pyrazole, thiazole and thiadiazole rings in Formulas Ir$^{1-21}$ are optionally substituted (substitution at ring carbons bonded to hydrogen and ring nitrogen atoms bonded to hydrogen atoms are encompassed, i.e., a "substitutable ring nitrogen atom") with up to four substituents as described above for Cy². Suitable substituents for Cy² and suitable values for R¹, R², R³, Cy¹ and E are as defined in any one of the first, second, third, fourth, fifth, sixth, seventh, eighth, ninth, tenth, eleventh or twelfth embodiments. Alternatively, suitable substituents for Cy¹ and the pyridine, pyridazine, pyrimidine, pyrazine, pyrazole, thiazole and thiadiazole rings in Formulas Ir$^{1-21}$ are as described for G¹ and G², respectively, in Formula If, and values for R¹, R², R³, Cy¹ and E are as defined in any one of the first, second, third, fourth, fifth, sixth, seventh, eighth, ninth, tenth, eleventh or twelfth embodiments. Alternatively, suitable substituents for Cy¹ include (C₁-C₄)alkyl, (C₁-C₄)alkoxy, (C₁-C₄)haloalkyl, (C₁-C₄)haloalkoxy, halogen, cyano and nitro; suitable substituents for a substitutable ring nitrogen atom in the pyrazole rings in Formulas Ir¹⁸, Ir²⁰ and Ir²¹ include (C₁-C₄)alkyl, (C₃-C₄)cycloalkyl, (C₃-C₄)cycloalkyl(C₁-C₂)alkyl, and (C₁-C₄)haloalkyl; suitable substituents for a ring carbon atom in the pyridine, pyridazine, pyrimidine, pyrazine, pyrazole, thiazole and thiadiazole rings in Formulas Ir$^{1-21}$ include fluorine, chlorine, cyano, hydroxy, amino, (C₁-C₄)alkyl, (C₃-C₄)cycloalkyl, (C₃-C₄)cycloalkyl (C₁-C₂)alkyl, halo(C₁-C₄)alkyl, (C₁-C₄)alkoxy, (C₁-C₄)haloalkoxy, CONH₂, (C₁-C₄)alkylaminocarbonyl, di(C₁-C₄)alkylaminocarbonyl, (C₃-C₄)cycloalkylaminocarbonyl, {(C₁-C₄)alkyl}{(C₃-C₄)cycloalkyl}aminocarbonyl and (C₁-C₄)alkylcarbonylamino; the ring nitrogen in pyridines Ir$^{1-4}$ is optionally substituted by oxo; and suitable values for R¹, R², R³, Cy¹ and E are as defined in any one of the first, second, third, fourth, fifth, sixth, seventh, eighth, ninth, tenth, eleventh or twelfth embodiments. In another alternative, the embodiments described in this paragraph exclude the compound exemplified in Example 205, Example 211, Example 214, Example 222, Example 226, Example 235, Example 236, Example 281, Example 292, Example 295, Example 298, Example 300, Example 302, Example 305, Example 304, Example 306, Example 307, Example 210, Example 296, Example 311, Example 230, Example 244, Example 258 and Example 291 or a pharmaceutically acceptable salt, enantiomer or diastereomer thereof.

For each of the embodiment described in the previous paragraph, R¹ is preferably methyl or ethyl.

For each of the embodiment described in the paragraph immediately following Formulas Ir$^{1-21}$, R¹ is preferably methyl or ethyl; and R³ is MeSO₂NHCH₂CH₂CH₂, H₂NC(=O)CH₂CH₂, H₂NC(=O)CMe₂CH₂, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas Ir$^{1-21}$, R¹ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $Ir^{1-21}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Ir^{1-21}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $Ir^{1-21}$, $R^1$ is preferably methyl or ethyl; and $R^3$ is 2-hydroxy-2-methylpropyl or 2-cyano-2-methylpropyl.

For each of the embodiment described in the paragraph immediately following Formulas $Ir^{1-21}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiment described in the paragraph immediately following Formulas $Ir^{1-21}$, $R^1$ is preferably methyl or ethyl; $R^2$ is phenyl or fluorophenyl; $R^3$ is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas $Ir^{1-21}$ are optionally substituted with fluoro, chloro, cyano, $CONH_2$, $CONHMe$, $CONMe_2$, $CONHc$-Pr, methoxy, ethoxy, methyl, ethyl or $CF_3$. the substitutable ring nitrogen atom in the pyrazole rings in Formulas $Ir^{18}$, $Ir^{20}$ and $Ir^{21}$ are optionally substituted with $(C_1-C_4)$alkyl, $(C_3-C_4)$cycloalkyl, $(C_3-C_4)$cycloalkyl$(C_1-C_2)$alkyl, or $(C_1-C_2)$haloalkyl, the ring nitrogen in the pyridine rings in Formulas $Ir^{1-4}$ is optionally substituted by oxo.

Another embodiment of the invention is a compound of any one of Formulas $Is^{1-21}$, or a pharmaceutically acceptable salt, enantiomer or diastereomer thereof:

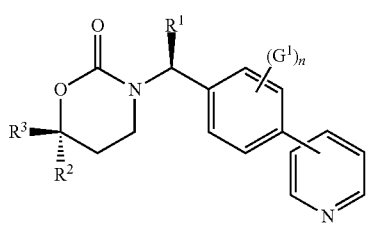

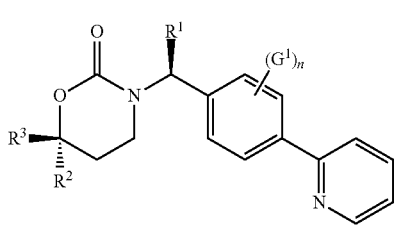

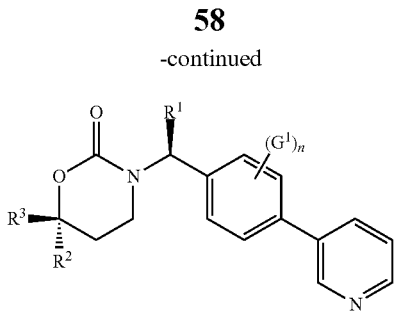

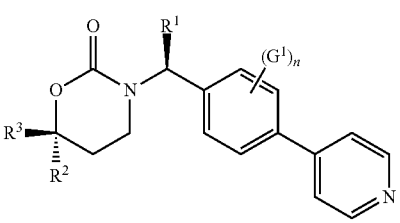

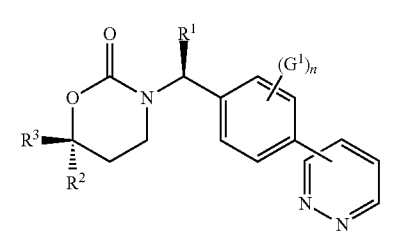

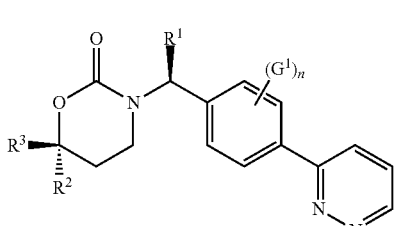

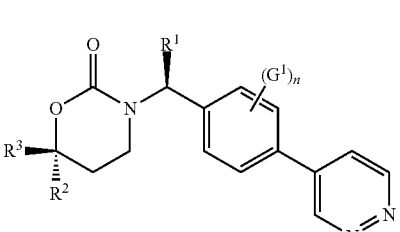

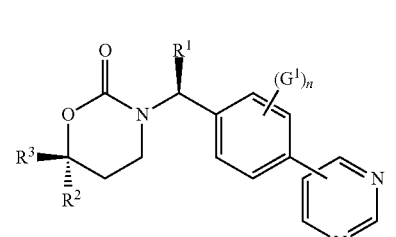

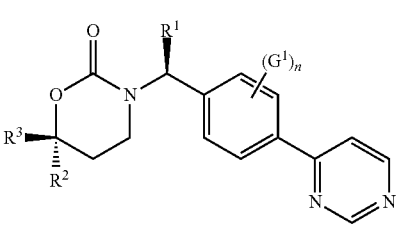

Is¹⁰ 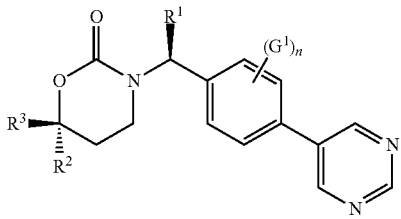

Is¹¹ 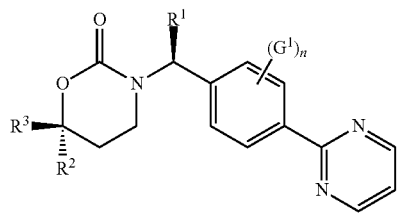

Is¹² 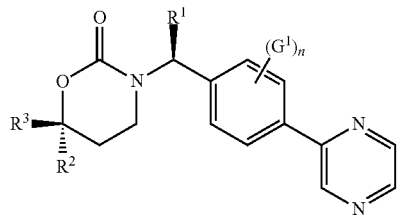

Is¹³ 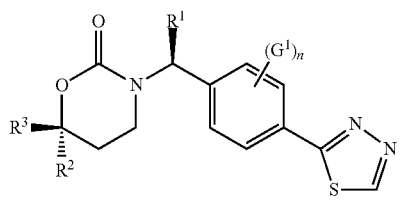

Is¹⁴ 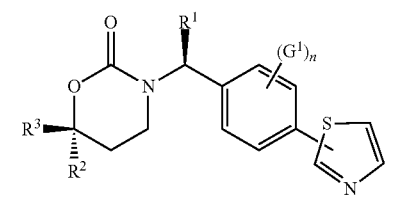

Is¹⁵ 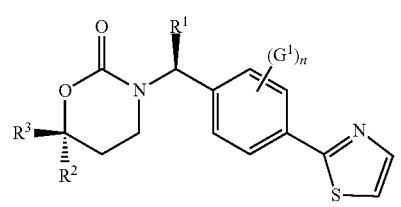

Is¹⁶ 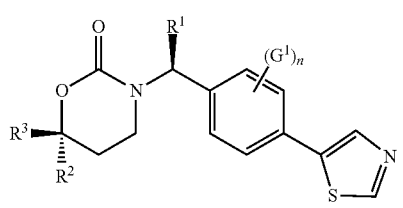

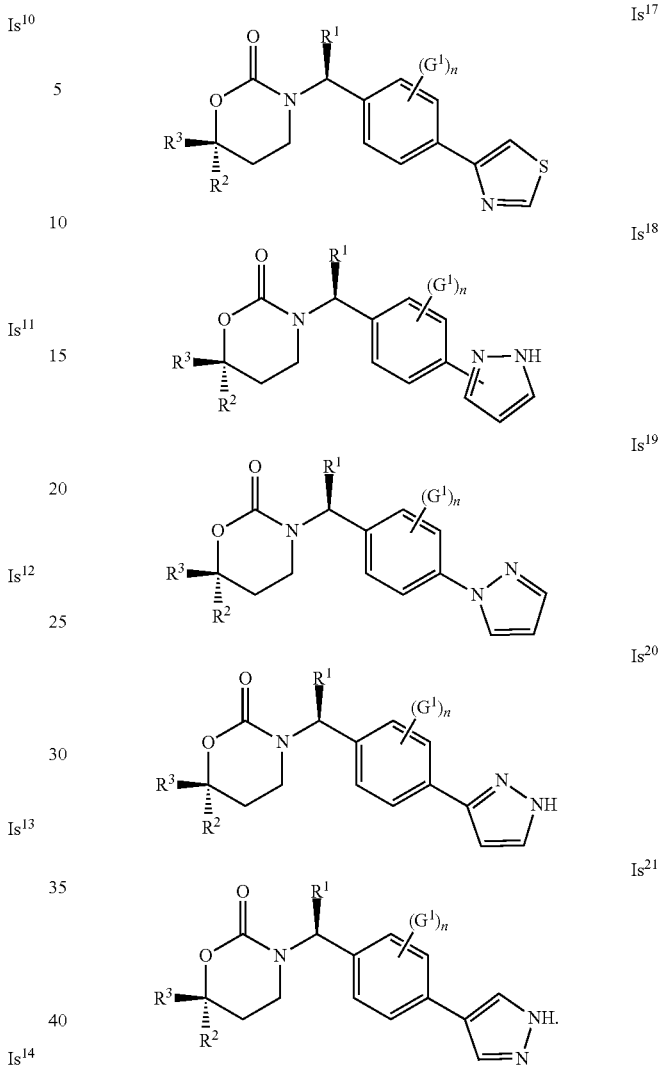

In Formulas Is$^{1-21}$, the pyridine, pyridazine, pyrimidine, pyrazine, pyrazole, thiazole and thiadiazole rings in Formulas Is$^{1-21}$ are optionally substituted (substitution at ring carbons bonded to hydrogen and ring nitrogen atoms bonded to hydrogen atoms are encompassed, i.e., a "substitutable ring nitrogen atom") with up to four substituents as described above for Cy². Suitable values for G¹ are as described in Formula If; n is 0, 1 or 2; substituents for Cy² and suitable values for R¹, R² and R³ are as defined in any one of the first, second, third, fourth, fifth, sixth, seventh, eighth, ninth, tenth, eleventh or twelfth embodiments. Alternatively, n is 0, 1 or 2, suitable values for G¹ in Formulas Is$^{1-21}$ and suitable substituents for the pyridine, pyridazine, pyrimidine, pyrazine, pyrazole, thiazole and thiadiazole rings in Formulas Is$^{1-21}$ are as described for G¹ and G², respectively, in Formula If, and values for R¹, R², R³ and E are as defined in any one of the first, second, third, fourth, fifth, sixth, seventh, eighth, ninth, tenth, eleventh or twelfth embodiments. Alternatively, n is 0, 1 or 2; suitable values for G¹ include $(C_1$-$C_4)$alkyl, $(C_1$-$C_4)$alkoxy, $(C_1$-$C_4)$haloalkyl, $(C_1$-$C_4)$haloalkoxy, halogen, cyano and nitro; suitable substituents for a substitutable ring nitrogen atom in the pyrazole rings in Formulas Is¹⁸, Is²⁰ and Is²¹ include $(C_1$-$C_4)$alkyl, $(C_3$-$C_4)$cycloalkyl, $(C_3$-$C_4)$cycloalkyl $(C_1$-$C_2)$alkyl, and $(C_1$-$C_4)$haloalkyl; suitable substituents for a ring carbon atom in the pyridine, pyridazine, pyrimidine, pyrazine, pyrazole, thiazole and thiadiazole rings in Formulas $Is^{1-21}$ include fluorine, chlorine, cyano, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl, $(C_3-C_4)$cycloalkylaminocarbonyl, $\{(C_1-C_4)$alkyl$\}\{(C_3-C_4)$cycloalkyl$\}$aminocarbonyl and $(C_1-C_4)$alkylcarbonylamino; the ring nitrogen in pyridines $Is^{1-4}$ is optionally substituted by oxo; and suitable values for $R^1$, $R^2$ and $R^3$ are as defined in any one of the first, second, third, fourth, fifth, sixth, seventh, eighth, ninth, tenth, eleventh or twelfth embodiments. In another alternative, the embodiments described in this paragraph exclude the compound exemplified in Example 205, Example 211, Example 214, Example 222, Example 226, Example 235, Example 236, Example 281, Example 292, Example 295, Example 298, Example 300, Example 302, Example 305, Example 304, Example 306, Example 307, Example 210, Example 296, Example 311, Example 230, Example 244, Example 258 and Example 291, or a pharmaceutically acceptable salt, enantiomer or diastereomer thereof.

For each of the embodiment described in the previous paragraph, $R^1$ is preferably methyl or ethyl.

For each of the embodiment described in the paragraph immediately following Formulas $Is^{1-21}$, $R^1$ is preferably methyl or ethyl; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Is^{1-21}$, $R^1$ is preferably methyl or ethyl; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $Is^{1-21}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas $Is^{1-21}$, $R^1$ is preferably methyl or ethyl; $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(=O)CMe_2CH_2$, 3-hydroxy-3-methylbutyl, 2-hydroxy-2-methylpropyl or 2-cyano-2-methylpropyl.

For each of the embodiment described in the paragraph immediately following Formulas $Is^{1-21}$, $R^1$ is preferably methyl or ethyl; and $R^3$ is 2-hydroxy-2-methylpropyl or 2-cyano-2-methylpropyl.

For each of the embodiment described in the paragraph immediately following Formulas $Is^{1-21}$, $R^1$ is preferably methyl or ethyl; $R^2$ is phenyl or fluorophenyl; and $R^3$ is 2-hydroxy-2-methylpropyl or 2-cyano-2-methylpropyl.

For each of the embodiment described in the paragraph immediately following Formulas $Is^{1-21}$, $R^1$ is preferably methyl or ethyl; $R^2$ is phenyl or fluorophenyl; $R^3$ is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas $Is^{1-21}$ are optionally substituted with fluoro, chloro, cyano, $CONH_2$, $CONHMe$, $CONMe_2$, $CONHc$-$Pr$, methyl, ethyl or $CF_3$; the substitutable ring nitrogen atom in the pyrazole rings in Formulas $Is^{18}$, $Is^{20}$ and $Is^{21}$ is optionally substituted with $(C_1-C_4)$alkyl, $(C_3-C_4)$cycloalkyl, $(C_3-C_4)$cycloalkyl$(C_1-C_2)$alkyl, or $(C_1-C_2)$haloalkyl, the ring nitrogen in the pyridine rings in Formulas $Is^{1-4}$ is optionally substituted by oxo.

Another embodiment of the invention is a compound represented by any one of Formulas $It^{1-6}$, or a pharmaceutically acceptable salt thereof:

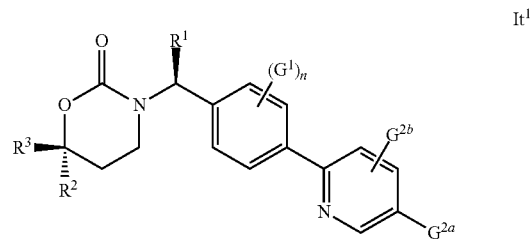

$It^1$

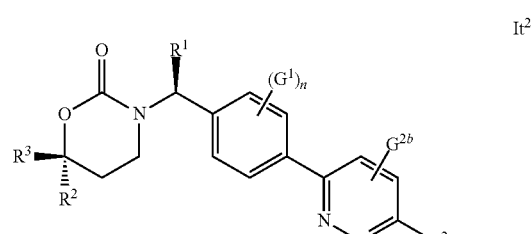

$It^2$

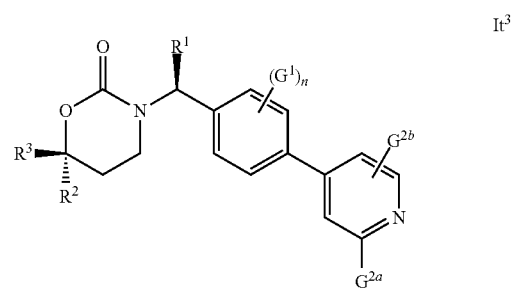

$It^3$

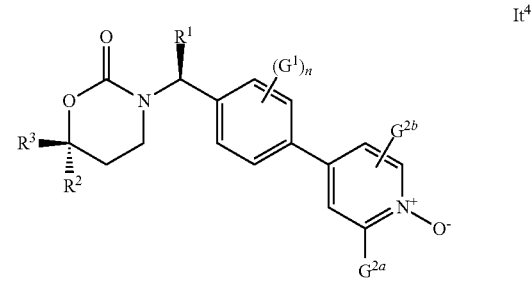

$It^4$

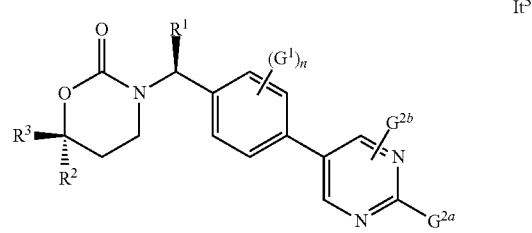

$It^5$

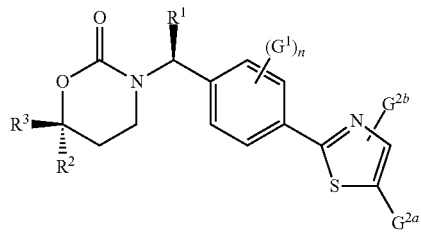

It⁶

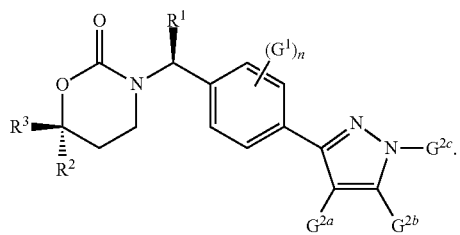

It⁷

In Formulas It$^{1-7}$, G$^1$ is (C$_1$-C$_4$)alkyl, (C$_1$-C$_4$)alkoxy, (C$_1$-C$_4$) haloalkyl, (C$_1$-C$_4$) haloalkoxy, halogen, cyano and nitro; n is 0 1 or 2; G$^{2a}$ and G$^{2b}$ are independently selected from hydrogen, fluorine, chlorine, cyano, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$) alkyl, (C$_1$-C$_4$)alkoxy, (C$_1$-C$_4$)haloalkoxy, CONH$_2$, (C$_1$-C$_4$) alkylaminocarbonyl, di(C$_1$-C$_4$)alkylaminocarbonyl, (C$_1$-C$_4$) cycloalkylaminocarbonyl, {(C$_1$-C$_4$)alkyl}{(C$_3$-C$_4$) cycloalkyl}aminocarbonyl and (C$_1$-C$_4$)alkylcarbonylamino; G$^{2c}$ is (C$_1$-C$_4$)alkyl, (C$_3$-C$_4$)cycloalkyl or (C$_1$-C$_4$)haloalkyl; and suitable values for R$^2$ and R$^3$ are as defined in any one of the first, second, third, fourth, fifth, sixth, seventh, eighth, ninth, tenth, eleventh or twelfth embodiments. In another alternative, the embodiments in the this paragraph exclude the compound exemplified in Example 205, Example 211, Example 214, Example 222, Example 226, Example 235, Example 236, Example 281, Example 292, Example 295, Example 298, Example 300, Example 302, Example 305, Example 304, Example 306, Example 307, Example 210, Example 296, Example 311, Example 230, Example 244, Example 258, and Example 291, or a pharmaceutically acceptable salt, enantiomer or diastereomer thereof.

For each of the embodiment described in the previous paragraph, R$^1$ is preferably methyl or ethyl.

For each of the embodiment described in the paragraph immediately following Formulas It$^{1-7}$, R$^1$ is preferably methyl or ethyl; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas It$^{1-7}$, R$^1$ is preferably methyl or ethyl; and R$^3$ is H$_2$NC(=O)CMe$_2$CH$_2$, 3-hydroxy-3-methylbutyl, 2-hydroxy-2-methylpropyl or 2-cyano-2-methylpropyl.

For each of the embodiment described in the paragraph immediately following Formulas It$^{1-7}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O) CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiment described in the paragraph immediately following Formulas It$^{1-7}$, R$^1$ is preferably methyl or ethyl; R$^2$ is phenyl optionally substituted with 1, 2 or 3 substituents selected from halo, cyano, CONH$_2$, (C$_1$-C$_4$) alkyl, (C$_1$-C$_4$)haloalkyl and SO$_2$Me; and R$^3$ is H$_2$NC(=O) CMe$_2$CH$_2$, 3-hydroxy-3-methylbutyl, 2-hydroxyethyl, 2-hydroxy-2-methylpropyl or 2-cyano-2-methylpropyl.

For each of the embodiment described in the paragraph immediately following Formulas It$^{1-7}$, R$^1$ is preferably methyl or ethyl; and R$^3$ is 2-hydroxy-2-methylpropyl or 2-cyano-2-methylpropyl.

For each of the embodiment described in the paragraph immediately following Formulas It$^{1-7}$, R$^1$ is preferably methyl or ethyl; R$^2$ is phenyl or fluorophenyl; and R$^3$ is 2-hydroxy-2-methylpropyl or 2-cyano-2-methylpropyl.

Alternatively, —CHO, NH$_2$—SO$_2$NH$_2$, —COOH, and —CONH$_2$ are excluded as permissible substituents for the pyridine and thiazole rings at the position corresponding to Cy$^1$ for all of the specific embodiments described above for Formulas Iq$^{1-21}$, Ip$^{1-21}$, Ir$^{1-21}$, Is$^{1-21}$ and It$^{1-7}$.

Another embodiment of the invention is a compound of any one of Formulas Iu$^{1-20}$ or a pharmaceutically acceptable salt, enantiomer or diastereomer thereof:

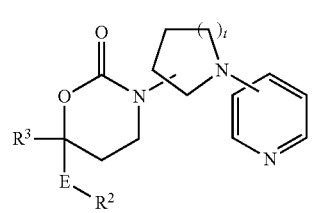

Iu$^1$

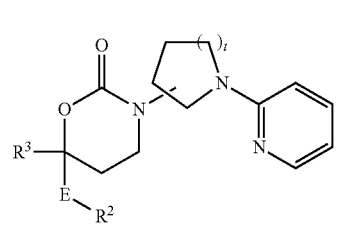

Iu$^2$

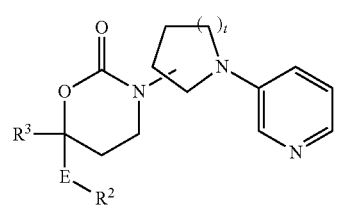

Iu$^3$

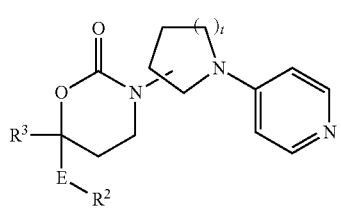

Iu$^4$

Iu⁵
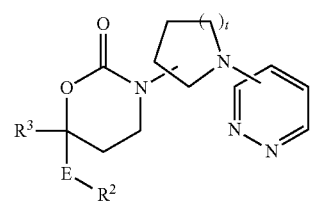
Iu⁶
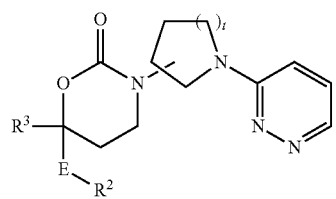
Iu⁷
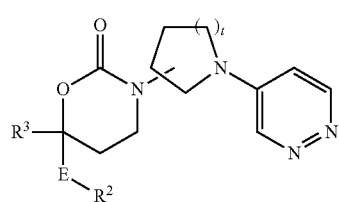
Iu⁸
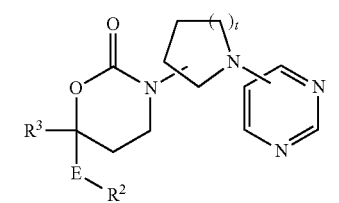
Iu⁹
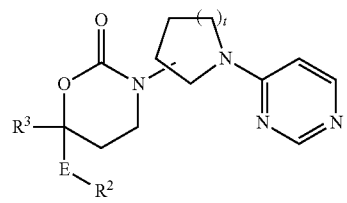
Iu¹⁰
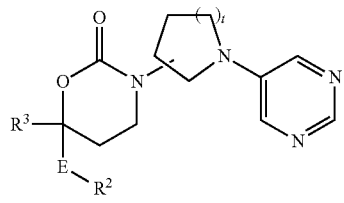
Iu¹¹
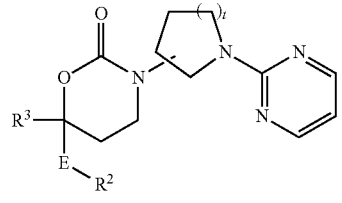
Iu¹²
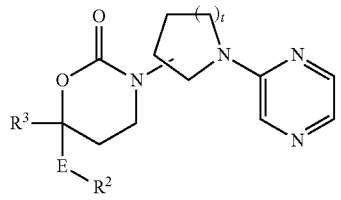
Iu¹³
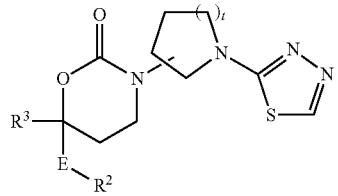
Iu¹⁴
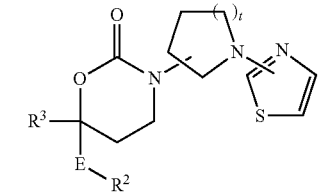
Iu¹⁵
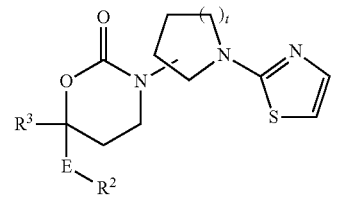
Iu¹⁶
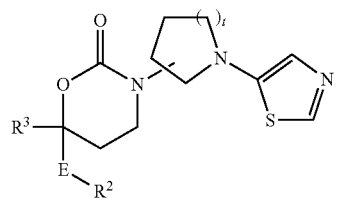
Iu¹⁷
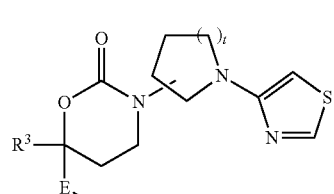
Iu¹⁸
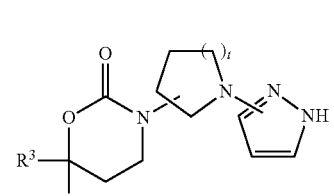

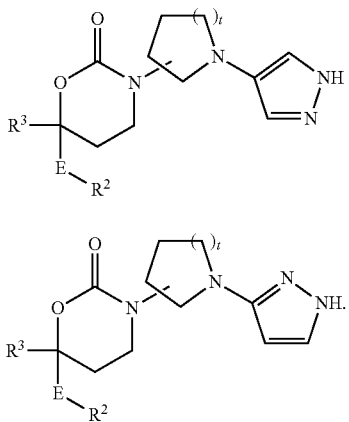

In Formulas Iu$^{1-20}$, the pyridine, pyridazine, pyrimidine, pyrazine, pyrazole, thiazole and thiadiazole rings in Formulas Iu$^{1-20}$ are optionally substituted (substitution at ring carbons bonded to hydrogen and ring nitrogen atoms bonded to hydrogen atoms are encompassed, i.e., a "substitutable ring nitrogen atom") with up to four substituents as described above for Cy$^2$; and the pyrrolidine, piperidine and azepane rings are optionally substituted with 0, 1 or 2 substituents as described above for Cy$^1$. Suitable substituents for Cy$^1$ and Cy$^2$ and suitable values for R$^2$, R$^3$ and E are as defined in any one of the first, second, third, fourth, fifth, sixth, seventh, eighth, ninth, tenth, eleventh or twelfth embodiments; and t is 1, 2 or 3. Alternatively, suitable substituents for the pyrrolidine, piperidine and azepane rings and the pyridine, pyridazine, pyrimidine, pyrazine, pyrazole, thiazole and thiadiazole rings in Formulas Iu$^{1-20}$ are as described for G$^1$ and G$^2$, respectively, in Formula If; values for R$^2$, R$^3$ and E are as defined in any one of the first, second, third, fourth, fifth, sixth, seventh, eighth, ninth, tenth, eleventh or twelfth embodiments; and t is 1, 2 or 3. Alternatively, suitable substituents for the pyrrolidine, piperidine and azepane rings include oxo, (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; suitable substituents for a substitutable ring nitrogen atom in the pyrazole rings in Formulas Iu$^{18-20}$ include (C$_1$-C$_4$)alkyl, (C$_3$-C$_4$)cycloalkyl, (C$_3$-C$_4$)cycloalkyl(C$_1$-C$_2$)alkyl, and (C$_1$-C$_4$)haloalkyl; suitable substituents for a ring carbon atom in the pyridine, pyridazine, pyrimidine, pyrazine, pyrazole, thiazole and thiadiazole rings in Formulas Iu$^{1-20}$ include fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$)alkyl}{(C$_3$-C$_4$)cycloalkyl}aminocarbonyl and (C$_1$-C$_4$)alkylcarbonylamino; the ring nitrogen in the pyridine rings in Formulas Iu$^{1-4}$ is optionally substituted by oxo; t is 1, 2 or 3; and suitable values for R$^2$, R$^3$ and E are as defined in any one of the first, second, third, fourth, fifth, sixth, seventh, eighth, ninth, tenth, eleventh or twelfth embodiments.

Alternatively, for each of the embodiments described in the paragraph immediately following Formulas Iu$^{1-20}$, R$^3$ is preferably MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Iu$^{1-20}$, R$^3$ is preferably H$_2$NC(=O)CMe$_2$CH$_2$, 3-hydroxy-3-methylbutyl, 2-hydroxy-2-methylpropyl or 2-cyano-2-methylpropyl.

Alternatively, for each of the embodiments described in the paragraph immediately following Formulas Iu$^{1-20}$, R$^2$ is preferably phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is preferably MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Iu$^{1-20}$, R$^2$ is preferably phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is preferably H$_2$NC(=O)CMe$_2$CH$_2$, 3-hydroxy-3-methylbutyl, 2-hydroxy-2-methylpropyl or 2-cyano-2-methylpropyl.

Alternatively, for each of the embodiments described in the paragraph immediately following Formulas Iu$^{1-20}$, t is preferably 2; R$^2$ is preferably phenyl or fluorophenyl; and R$^3$ is preferably 2-hydroxy-2-methylpropyl or 2-cyano-2-methylpropyl.

Alternatively, for each of the embodiment described in the paragraph immediately following Formulas Iu$^{1-20}$, wherein t is 2; R$^2$ is preferably phenyl or fluorophenyl; R$^3$ preferably is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas Iu$^{1-20}$ are optionally substituted with fluoro, chloro, cyano, CONH$_2$, CONHMe, CONMe$_2$, CONHc-Pr, methyl, ethyl or CF$_3$; the substitutable ring nitrogen atom in the pyrazole rings in Formulas Iu$^{18-20}$ are optionally substituted with (C$_1$-C$_4$)alkyl, (C$_3$-C$_4$)cycloalkyl, (C$_3$-C$_4$)cycloalkyl(C$_1$-C$_2$)alkyl, and (C$_1$C$_2$)haloalkyl; the ring nitrogen in the pyridine rings in Formulas Iu$^{1-4}$ are optionally substituted by oxo.

Another embodiment of the invention is a compound of any one of Formulas Iv$^{1-20}$, or a pharmaceutically acceptable salt, enantiomer or diastereomer thereof:

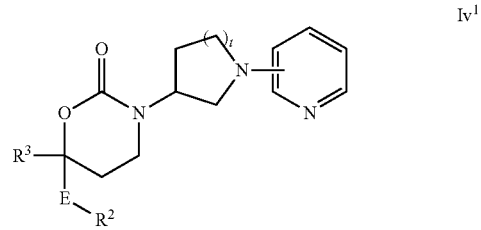

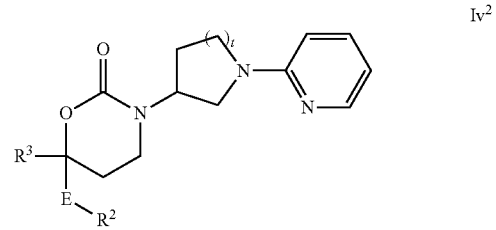

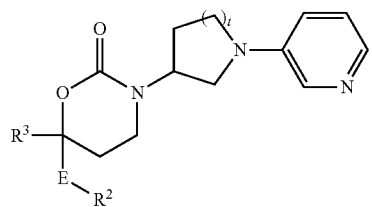 Iv³
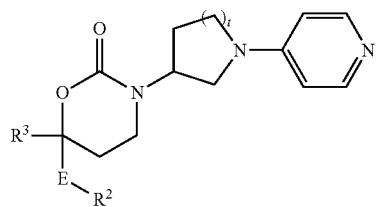 Iv⁴
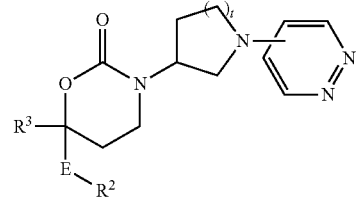 Iv⁵
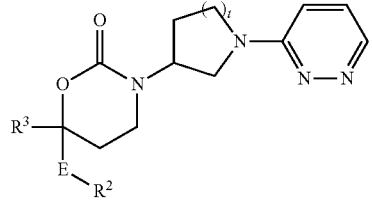 Iv⁶
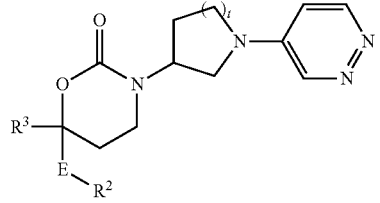 Iv⁷
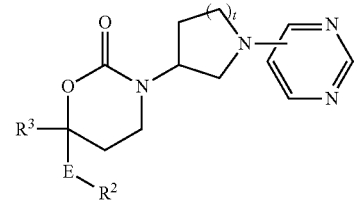 Iv⁸
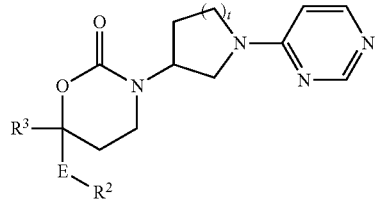 Iv⁹
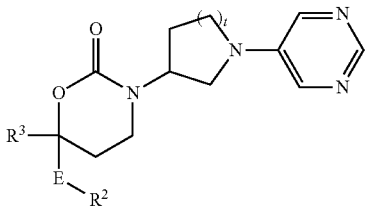 Iv¹⁰
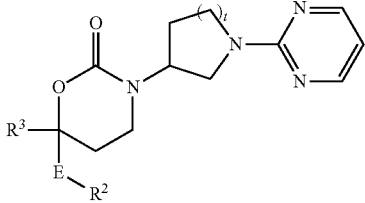 Iv¹¹
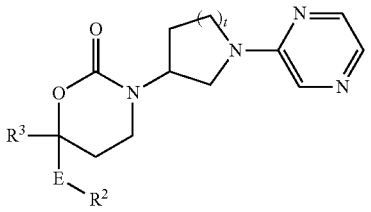 Iv¹²
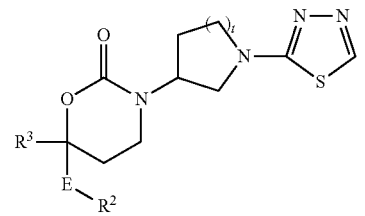 Iv¹³
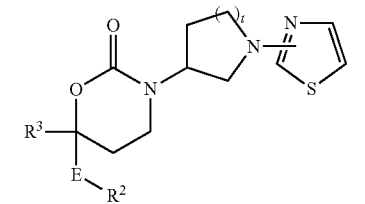 Iv¹⁴
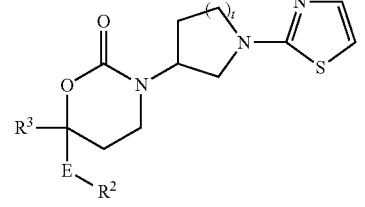 Iv¹⁵
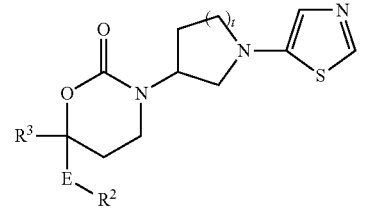 Iv¹⁶

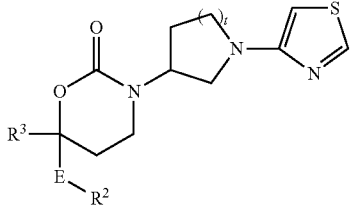

Iv¹⁷

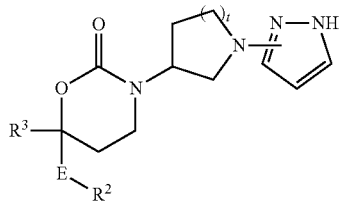

Iv¹⁸

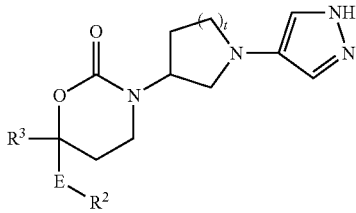

Iv¹⁹

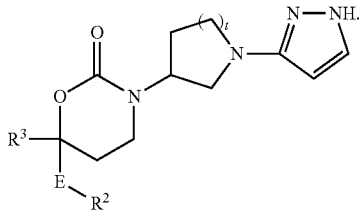

Iv²⁰

In Formulas Iv$^{1-20}$, the pyridine, pyridazine, pyrimidine, pyrazine, pyrazole, thiazole and thiadiazole rings in Formulas Iv$^{1-20}$ are optionally substituted (substitution at ring carbons bonded to hydrogen and ring nitrogen atoms bonded to hydrogen atoms are encompassed, i.e., a "substitutable ring nitrogen atom") with up to four substituents as described above for Cy². Suitable substituents for Cy² and suitable values for R², R³ and E are as defined in any one of the first, second, third, fourth, fifth, sixth, seventh, eighth, ninth, tenth, eleventh or twelfth embodiments. t is 1, 2 or 3. Alternatively, suitable substituents for the pyrrolidine, piperidine and azepane rings and the pyridine, pyridazine, pyrimidine, pyrazine, pyrazole, thiazole and thiadiazole rings in Formulas Iv$^{1-20}$ are as described for G¹ and G², respectively, in Formula If, t is 1, 2 or 3 and values for R², R³ and E are as defined in any one of the first, second, third, fourth, fifth, sixth, seventh, eighth, ninth, tenth, eleventh or twelfth embodiments. Alternatively, suitable substituents for the pyrrolidine, piperidine and azepane rings include oxo, (C$_1$-C$_4$)alkyl, (C$_1$-C$_4$)alkoxy, (C$_1$-C$_4$)haloalkyl, (C$_1$-C$_4$) haloalkoxy, halogen, cyano and nitro; suitable substituents for a substitutable ring nitrogen atom in the pyrazole rings in Formulas Iv$^{18-20}$ include (C$_1$-C$_4$)alkyl, (C$_3$-C$_4$)cycloalkyl, (C$_3$-C$_4$)cycloalkyl(C$_1$-C$_2$)alkyl, and (C$_1$-C$_4$)haloalkyl; suitable substituents for a ring carbon atom in the pyridine, pyridazine, pyrimidine, pyrazine, pyrazole, thiazole and thiadiazole rings in Formulas Iv$^{1-20}$ include fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$)alkyl}{(C$_3$-C$_4$)cycloalkyl}aminocarbonyl and (C$_1$-C$_4$)alkylcarbonylamino; the ring nitrogen in the pyridine rings in Formulas Iv$^{1-4}$ is optionally substituted by oxo; t is 1, 2 or 3; and suitable values for R², R³ and E are as defined in any one of the first, second, third, fourth, fifth, sixth, seventh, eighth, ninth, tenth, eleventh or twelfth embodiments.

For each of the embodiments described in the paragraph immediately following Formulas Iv$^{1-20}$, R³ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Iv$^{1-20}$, R³ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Iv$^{1-20}$, R² is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R³ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Iv$^{1-20}$, R² is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R³ is H$_2$NC(=O)CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Iv$^{1-20}$, t is preferably 2; R² is phenyl or fluorophenyl; and R³ is 2-hydroxy-2-methylpropyl or 2-cyano-2-methylpropyl.

For each of the embodiments described in the paragraph immediately following Formulas Iv$^{1-20}$, t is preferably 2; R² is phenyl or fluorophenyl; R³ is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas Iv$^{1-20}$ are optionally substituted with fluoro, chloro, cyano, CONH$_2$, CONHMe, CONMe$_2$, CONHc-Pr, methyl, ethyl or CF$_3$; the substitutable ring nitrogen atom in the pyrazole rings in Formulas Iv$^{18-20}$ is optionally substituted with (C$_1$-C$_4$) alkyl, (C$_3$-C$_4$)cycloalkyl, (C$_3$-C$_4$)cycloalkyl(C$_1$-C$_2$)alkyl, and (C$_1$-C$_2$)haloalkyl; the ring nitrogen in the pyridine rings in Formulas Iv$^{1-4}$ is optionally substituted by oxo.

Another embodiment of the invention is a compound of any one of Formulas Iw$^{1-20}$ or a pharmaceutically acceptable salt thereof:

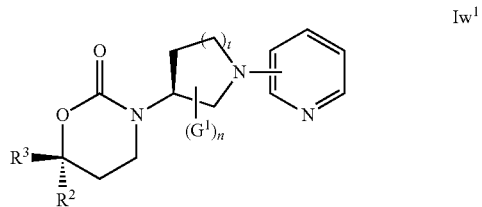

Iw¹

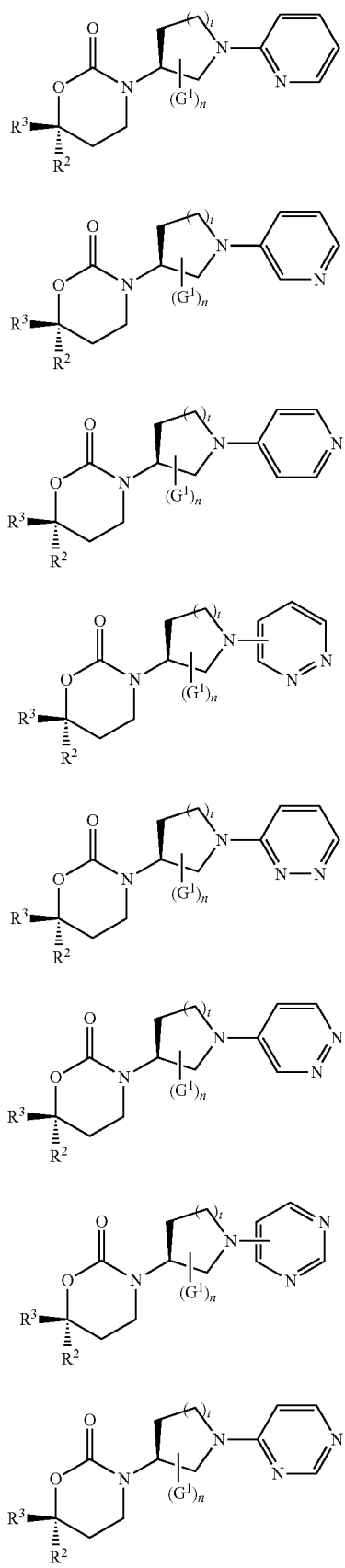
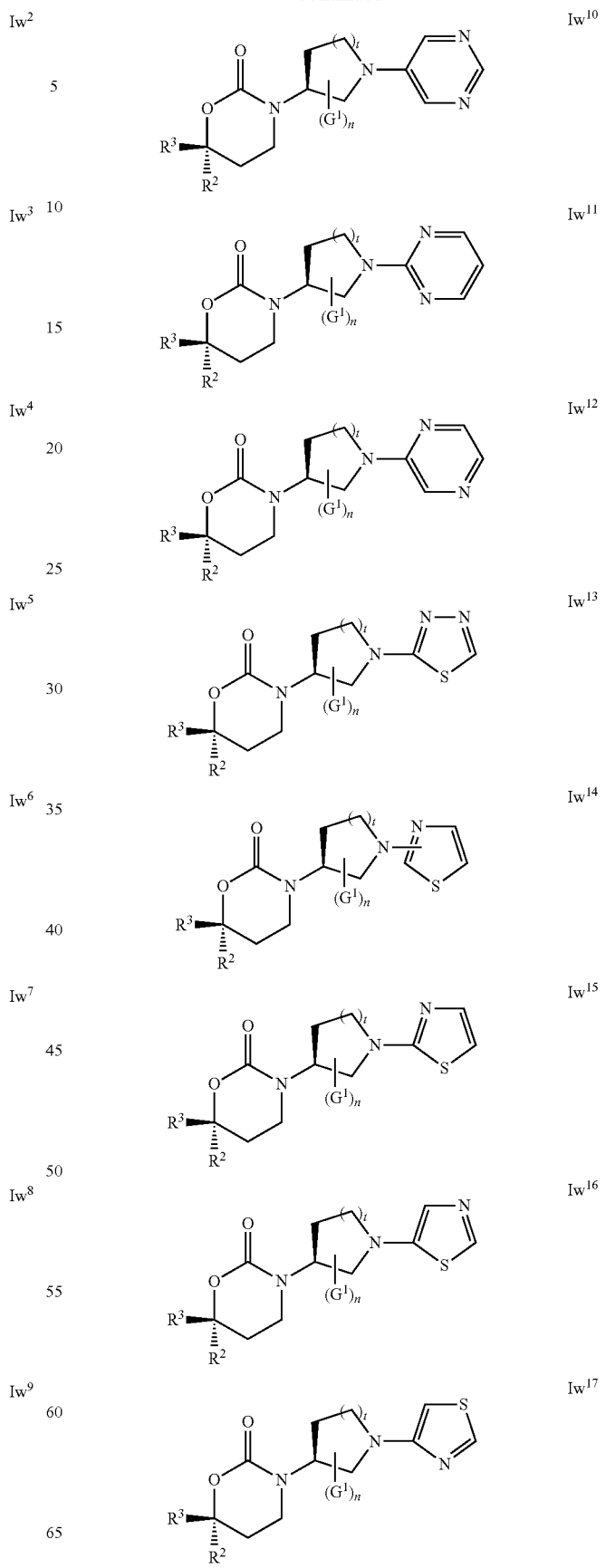

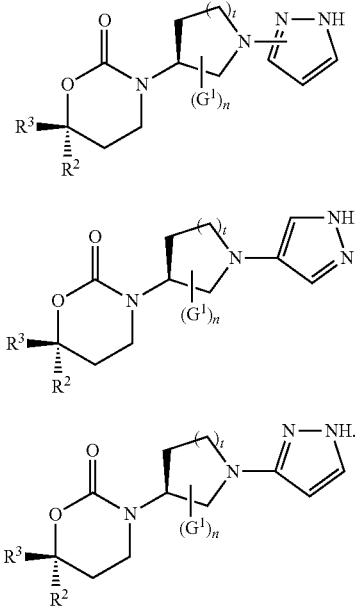

In Formulas Iw$^{1-20}$, the pyridine, pyridazine, pyrimidine, pyrazine, pyrazole, thiazole and thiadiazole rings in Formulas Iw$^{1-20}$ are optionally substituted (substitution at ring carbons bonded to hydrogen and ring nitrogen atoms bonded to hydrogen atoms are encompassed, i.e., a "substitutable ring nitrogen atom") with up to four substituents as described above for Cy$^2$. Suitable substituents for Cy$^2$ and suitable values for R$^2$ and R$^3$ are as defined in any one of the first, second, third, fourth, fifth, sixth, seventh, eighth, ninth, tenth, eleventh or twelfth embodiments; suitable values for G$^1$ is as described for Formula If, n is 0, 1 or 2; and t is 1, 2 or 3. Alternatively, suitable values for G$^1$ are as described for Formula If; substituents for the pyridine, pyridazine, pyrimidine, pyrazine, pyrazole, thiazole and thiadiazole rings in Formulas Iw$^{1-20}$ are as described for G$^2$ in Formula If; n is 0, 1 or 2; t is 1, 2 or 3; and values for R$^2$ and R$^3$ are as defined in any one of the first, second, third, fourth, fifth, sixth, seventh, eighth, ninth, tenth, eleventh or twelfth embodiments. Alternatively, suitable values for G$^1$ include oxo, (C$_1$-C$_4$)alkyl, (C$_1$-C$_4$)alkoxy, (C$_1$-C$_4$)haloalkyl, (C$_1$-C$_4$) haloalkoxy, halogen, cyano and nitro; suitable substituents for a substitutable ring nitrogen atom in the pyrazole rings in Formulas Iw$^{18-20}$ include (C$_1$-C$_4$)alkyl, (C$_3$-C$_4$)cycloalkyl, (C$_3$-C$_4$)cycloalkyl(C$_1$-C$_2$)alkyl, and (C$_1$-C$_4$)haloalkyl; suitable substituents for a ring carbon atom in the pyridine, pyridazine, pyrimidine, pyrazine, pyrazole, thiazole and thiadiazole rings in Formulas Iw$^{1-20}$ include fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$) alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$) alkyl}{(C$_3$-C$_4$)cycloalkyl}aminocarbonyl and (C$_1$-C$_4$)alkylcarbonylamino; the ring nitrogen in the pyridine rings in Formulas Iw$^{1-4}$ is optionally substituted by oxo; n is 0, 1 or 2; t is 1, 2 or 3; and suitable values for R$^2$ and R$^3$ are as defined in any one of the first, second, third, fourth, fifth, sixth, seventh, eighth, ninth, tenth, eleventh or twelfth embodiments.

Alternatively, for each of the embodiments described in the paragraph immediately following Formulas Iw$^{1-20}$, R$^3$ is preferably MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Iw$^{1-20}$, R$^3$ is preferably H$_2$NC(=O)CMe$_2$CH$_2$, 3-hydroxy-3-methylbutyl, 2-hydroxy-2-methylpropyl or 2-cyano-2-methylpropyl.

Alternatively, for each of the embodiments described in the paragraph immediately following Formulas Iw$^{1-20}$, R$^2$ is preferably phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is preferably MeSO$_2$NHCH$_2$CH$_2$CH$_2$, H$_2$NC(=O)CH$_2$CH$_2$, H$_2$NC(=O) CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Iw$^{1-20}$, R$^2$ is preferably phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is preferably H$_2$NC(=O)CMe$_2$CH$_2$, 3-hydroxy-3-methylbutyl, 2-hydroxy-2-methylpropyl or 2-cyano-2-methylpropyl.

Alternatively, for each of the embodiments described in the paragraph immediately following Formulas Iw$^{1-20}$, t is preferably 2; R$^2$ is preferably phenyl or fluorophenyl; and R$^3$ is preferably 2-hydroxy-2-methylpropyl or 2-cyano-2-methylpropyl.

Alternatively, for each of the embodiments described in the paragraph immediately following Formulas Iw$^{1-20}$ or a pharmaceutically acceptable salt thereof: wherein t is 2; R$^2$ is phenyl or fluorophenyl; R$^3$ is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas Iw$^{1-20}$ are optionally substituted with fluoro, chloro, cyano, CONH$_2$, CONHMe, CONMe$_2$, CONHc-Pr, methyl, ethyl or CF$_3$; the substitutable ring nitrogen atom in the pyrazole rings in Formulas Iw$^{18-20}$ is optionally substituted with (C$_1$-C$_4$)alkyl, (C$_3$-C$_4$)cycloalkyl, (C$_3$-C$_4$)cycloalkyl(C$_1$-C$_2$)alkyl, and (C$_1$-C$_2$)haloalkyl; the ring nitrogen in the pyridine rings in Formulas Iw$^{1-4}$ is optionally substituted by oxo.

Another embodiment of the invention is a compound represented by any one of Formulas It$^{1-6}$, or a pharmaceutically acceptable salt thereof:

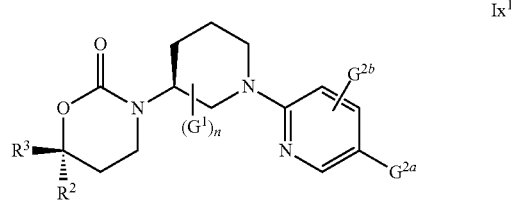

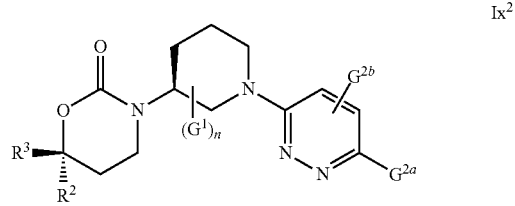

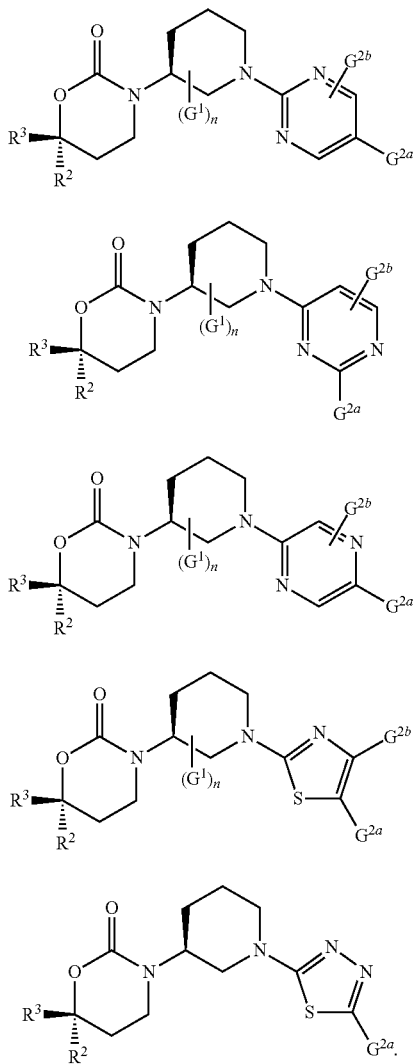

In Formulas Ix$^{1-7}$, G$^1$ is oxo, (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; n is 0, 1 or 2; G$^{2a}$ and G$^{2b}$ are independently selected from hydrogen, fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$)alkyl}{(C$_3$-C$_4$)cycloalkyl}aminocarbonyl and (C$_1$-C$_4$)alkylcarbonylamino; and suitable values for R$^2$ and R$^3$ are as defined in any one of the first, second, third, fourth, fifth, sixth, seventh, eighth, ninth, tenth, eleventh or twelfth embodiments.

Alternatively, for each of the embodiments described in the paragraph immediately following Formulas Ix$^{1-7}$, R$^3$ is preferably MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Ix$^{1-7}$, R$^3$ is preferably H$_2$NC(=O)CMe$_2$CH$_2$, 3-hydroxy-3-methylbutyl, 2-hydroxy-2-methylpropyl or 2-cyano-2-methylpropyl.

Alternatively, for each of the embodiments described in the paragraph immediately following Formulas Ix$^{1-7}$, R$^2$ is preferably phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is preferably MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Ix$^{1-7}$, R$^2$ is preferably phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is preferably H$_2$NC(=O)CMe$_2$CH$_2$, 3-hydroxy-3-methylbutyl, 2-hydroxy-2-methylpropyl or 2-cyano-2-methylpropyl.

In another alternative for each of the embodiments described in the paragraph immediately following Formulas Ix$^{1-7}$, R$^2$ is preferably phenyl or fluorophenyl; and R$^3$ preferably is 2-hydroxy-2-methylpropyl or 2-cyano-2-methylpropyl.

Compounds of the invention are also disclosed in INHIBITORS OF 11β-HYDROXYSTEROID DEHYDOGENASE I, U.S. Provisional Application No. 61/135,933, filed Jul. 25, 2008, the entire teachings of which are incorporated herein by reference.

The present invention further provides methods of inhibiting 11β-HSD1 by contacting 11β-HSD1 with a compound of Formula I, Ia, Ib, Ic, Id, Ie, If, Ig, Ih, Ii, Ij, Ik, Il, Im$^{1-12}$, In$^{1-12}$, Io$^{1-12}$, Ip$^{1-7}$, Iq$^{1-21}$, Ir$^{1-21}$, Is$^{1-21}$, It$^{1-7}$, Iu$^{1-20}$, Iv$^{1-20}$, Iw$^{1-20}$ or Ix$^{1-7}$ of the invention.

The present invention further provides methods of inhibiting or reducing the conversion of cortisone to cortisol in a cell using a compound of Formula I, Ia, Ib, Ic, Id, Ie, If, Ig, Ih, Ii, Ij, Ik, Il, Im$^{1-12}$, In$^{1-12}$, Io$^{1-12}$, Ip$^{1-7}$, Iq$^{1-21}$, Ir$^{1-21}$, Is$^{1-21}$, It$^{1-7}$, Iu$^{1-20}$, Iv$^{1-20}$, Iw$^{1-20}$ or Ix$^{1-7}$ of the invention.

The present invention further provides methods of inhibiting or reducing production of cortisol in a cell using a compound of Formula I, Ia, Ib, Ic, Id, Ie, If, Ig, Ih, Ii, Ij, Ik, Il, Im$^{1-12}$, In$^{1-12}$, Io$^{1-12}$, Ip$^{1-7}$, Iq$^{1-21}$, Ir$^{1-21}$, Is$^{1-21}$, It$^{1-7}$, Iu$^{1-20}$, Iv$^{1-20}$, Iw$^{1-20}$ or Ix$^{1-7}$ of the invention.

The present invention further provides methods of increasing insulin sensitivity in a subject in need thereof using a compound of Formula I, Ia, Ib, Ic, Id, Ie, If, Ig, Ih, Ii, Ij, Ik, Il, Im$^{1-12}$, In$^{1-12}$, Io$^{1-12}$, Ip$^{1-7}$, Iq$^{1-21}$, Ir$^{1-21}$, Is$^{1-21}$, It$^{1-7}$, Iu$^{1-20}$, Iv$^{1-20}$, Iw$^{1-20}$ or Ix$^{1-7}$ of the invention.

The present invention further provides methods of treating a subject with a disease associated with activity of expression of 11β-HSD1 using a compound of Formula I, Ia, Ib, Ic, Id, Ie, If, Ig, Ih, Ii, Ij, Ik, Il, Im$^{1-12}$, In$^{1-12}$, Io$^{1-12}$, Ip$^{1-7}$, Iq$^{1-21}$, Ir$^{1-21}$, Is$^{1-21}$, It$^{1-7}$, Iu$^{1-20}$, Iv$^{1-20}$, Iw$^{1-20}$ or Ix$^{1-7}$ of the invention.

Preferred values for the variables in the above-described structural formulas I, Ia, Ib, Ic, Id, Ie, If, Ig, Ih, Ii, Ij, Ik, Il Im$^{1-12}$, In$^{1-12}$, Io$^{1-12}$, Ip$^{1-7}$, Iq$^{1-21}$, Ir$^{1-21}$, Is$^{1-21}$, It$^{1-7}$, Iu$^{1-20}$, Iv$^{1-20}$, Iw$^{1-20}$ or Ix$^{1-7}$ are provided below:

A$^1$ is a bond. Alternatively, A$^1$ is (C$_1$-C$_3$)alkylene. In another specific embodiment, A$^1$ is methylene. In another specific embodiment, A$^1$ is CH when R$^1$ is present.

R$^1$ is (C$_1$-C$_6$)alkyl. Alternatively, R$^1$ is methyl or ethyl.

Cy$^1$ is optionally substituted aryl or optionally substituted heteroaryl.

Alternatively, Cy$^1$ is optionally substituted phenyl or optionally substituted pyridyl. In another alternative, Cy$^1$ is optionally substituted phenyl. In yet another specific embodiment, Cy$^1$ is substituted with fluorine or bromine. In another embodiment A$^2$ is a bond, Cy$^2$ is H and Cy$^1$ is optionally substituted monocyclic cycloalkyl. In another embodiment $A^2$ is a bond, $Cy^2$ is H and $Cy^1$ is optionally substituted cyclohexyl. In another embodiment $A^2$ is a bond, $Cy^2$ is H and $Cy^1$ is phenyl substituted with fluorine, chlorine, bromine, methyl, methoxy, trifluoromethyl, hydroxymethyl or 2-hydroxy-2-propyl. In another embodiment $Cy^1$ is phenyl substituted with trifluoromethoxy or 2,2,2-trifluoroethoxy. Alternatively $Cy^1$ is optionally substituted heterocyclyl. In another embodiment $Cy^1$ is optionally substituted pyrrolidinyl, piperidinyl or azepanyl.

$A^2$ is a bond and $Cy^2$ is hydrogen. Alternatively, $A^2$ is a bond and $Cy^2$ is cyclopropyl. Alternatively, $A^2$ is a bond and $Cy^2$ is $(C_3-C_7)$cycloalkyl. Alternatively, $A^2$ is a bond and $Cy^2$ is optionally substituted aryl or optionally substituted heteroaryl. In another specific embodiment, $A^2$ is a bond and $Cy^2$ is optionally substituted phenyl or optionally substituted pyridyl. In yet another specific embodiment, $A^2$ is a bond and $Cy^2$ is optionally substituted phenyl. In yet another specific embodiment, $A^2$ is a bond and $Cy^2$ is substituted with 1 to 4 groups independently selected from chlorine or fluorine. In yet another specific embodiment, $A^2$ is a bond and $Cy^2$ is difluorophenyl. In yet another specific embodiment, $A^2$ is a bond and $Cy^2$ is fluorophenyl. In yet another specific embodiment $A^2$ is a bond and $Cy^2$ is optionally substituted 2-thienyl, 1-pyrazolyl, 3-pyrazolyl, 1,2,4-thiadiazol-3-yl, thiazolyl or 2-oxo-1,2-dihydro-5-pyridyl. In yet another specific embodiment, $A^2$ is a bond and $Cy^2$ is phenyl or thienyl substituted with amino($C_1-C_6$)alkyl. In another embodiment $A^2$ is a bond and $Cy^2$ is optionally substituted pyridazinyl, pyrimidinyl, pyrazinyl, 1,2-dihydro-2-oxopyridyl, 2,3-dihydro-3-oxopyridazinyl, 1,2-dihydro-2-oxopyrimidinyl, 3,4-dihydro-4-oxopyrimidinyl or 1,2-dihydro-2-oxopyrazinyl. In yet another embodiment $A^2$ is a bond and $Cy^2$ is unsubstituted, methyl substituted or ethyl substituted pyridazinyl, pyrimidinyl, pyrazinyl, 1,2-dihydro-2-oxopyridyl, 2,3-dihydro-3-oxopyridazinyl, 1,2-dihydro-2-oxopyrimidinyl, 3,4-dihydro-4-oxopyrimidinyl or 1,2-dihydro-2-oxopyrazinyl. In yet another specific embodiment $A^2$ is a bond and $Cy^2$ is 6-oxo-1,6-dihydropyridin-3-yl, 1-methyl-6-oxo-1,6-dihydropyridin-3-yl, 1-methyl-2-oxo-1,2-dihydropyridin-4-yl, 1-ethyl-6-oxo-1,6-dihydropyridin-3-yl or 1-methyl-6-oxo-1,6-dihydropyridazin-3-yl. In another embodiment $A^2$ is a bond and $Cy^2$ is optionally substituted heterocyclyl. In another embodiment $A^2$ is a bond and $Cy^2$ is heterocylyl substituted by one oxo group and up 3 groups independently selected from amino, fluoro, chloro, cyano, $CONH_2$, CONHMe, $CONMe_2$, CONHc-Pr, methyl, ethyl, isopropyl, t-butyl, cyclopropyl, methoxy, ethoxy or trifluoromethyl. In yet another specific embodiment $A^2$ is a bond and $Cy^2$ is 1,5-dimethyl-6-oxo-1,6-dihydropyridin-3-yl, 1-isopropyl-6-oxo-1,6-dihydropyridin-3-yl, 6-oxo-1-(2,2,2-trifluoroethyl)-1,6-dihydropyridin-3-yl, 1,6-dimethyl-2-oxo-1,2-dihydropyridin-4-yl, 1-ethyl-2-oxo-1,2-dihydropyridin-4-yl, 1-isopropyl-2-oxo-1,2-dihydropyridin-4-yl, 2-oxo-1-(2,2,2-trifluoroethyl)-1,2-dihydropyridin-4-yl, 1-isopropyl-6-oxo-1,6-dihydropyridazin-3-yl, 1-ethyl-6-oxo-1,6-dihydropyridazin-3-yl, 1-ethyl-5-methyl-6-oxo-1,6-dihydropyridin-3-yl or 6-oxo-1-(2,2,2-trifluoroethyl)-1,6-dihydropyridazin-3-yl. In another specific embodiment, $A^2$ is a bond and $Cy^2$ is heteroaryl optionally substituted with by up to 2 groups independently selected from amino, halo, cyano, $CONH_2$, $(C_1-C_4)$alkylaminocarbonyl, di$(C_1-C_4)$alkylaminocarbonyl, cyclo$(C_3-C_5)$alkylaminocarbonyl, $(C_1-C_4)$alkyl, $(C_1-C_4)$alkoxy or $(C_1-C_2)$haloalkyl, $(C_1-C_2)$haloalkoxy. In yet another embodiment $A^2$ is a bond and $Cy^2$ is pyridinyl, N-oxo-pyridinyl, pyridazinyl, pyrimidinyl, pyrazinyl, thiadiazolyl or thiazolyl optionally substituted by up to 2 groups independently selected from amino, halo, cyano, $CONH_2$, $(C_1-C_4)$alkylaminocarbonyl, di$(C_1-C_4)$alkylaminocarbonyl, cyclo$(C_3-C_5)$alkylaminocarbonyl, $(C_1-C_4)$alkyl, $(C_1-C_4)$alkoxy or $(C_1-C_2)$haloalkyl, $(C_1-C_2)$haloalkoxy. In yet another embodiment $A^2$ is a bond and $Cy^2$ is pyridinyl, N-oxo-pyridinyl, pyridazinyl, pyrimidinyl, pyrazinyl, thiadiazolyl or thiazolyl optionally substituted by up to 2 groups independently selected from amino, fluoro, chloro, cyano, $CONH_2$, CONHMe, $CONMe_2$, CONHc-Pr, CONHt-Bu, methyl, ethyl, methoxy, ethoxy or trifluoromethyl. In yet another embodiment $A^2$ is a bond and $Cy^2$ is pyridin-2-yl, pyridin-3-yl, pyridin-4-yl, pyridazin-3-yl, pyrimidin-2-yl, pyrimidin-4-yl, pyrimidin-5-yl, pyrazin-3-yl, 1,3,4-thiadiazol-2-yl, thiazol-2-yl or thiazol-5-yl optionally substituted by up to 2 groups independently selected from amino, fluoro, chloro, cyano, $CONH_2$, CONHMe, $CONMe_2$, CONHc-Pr, methyl, ethyl, methoxy, ethoxy or trifluoromethyl. In yet another embodiment $A^2$ is a bond and $Cy^2$ is pyridinyl or thiazolyl optionally substituted by up to 2 groups independently selected from fluoro, chloro, cyano, CONHMe, $CONMe_2$, CONHc-Pr, methyl, ethyl, methoxy, ethoxy or trifluoromethyl. In yet another specific embodiment $A^2$ is a bond and $Cy^2$ is 5-fluoropyridin-2-yl, 5-(trifluoromethyl)pyridin-2-yl, 5-cyanopyridin-2-yl, 5-carbamoylpyridin-2-yl, 5-(methylcarbamoyl)pyridin-2-yl, 5-(dimethylcarbamoyl)pyridin-2-yl, 6-methoxypyridin-3-yl, 5-fluoropyridin-3-yl, 5-chloropyridin-3-yl, 2-methylpyridin-4-yl, 2,6-dimethylpyridin-4-yl, 6-methylpyridazin-3-yl, 2-methylpyrimidin-5-yl, 2-methylpyrimidin-4-yl, 5-methylpyrazin-2-yl, 5-cyanopyrazin-2-yl, 6-cyanopyrazin-2-yl, 5-(dimethylcarbamoyl)thiazol-2-yl, 6-carbamoylpyrazin-2-yl, 6-ethoxy-5-methylpyridin-3-yl, or 5-(cyclopropylcarbamoyl)pyridin-2-yl.

$R^3$ is hydroxy$(C_2-C_4)$alkyl. Alternatively, $R^3$ is dihydroxy$(C_3-C_4)$alkyl. In another specific embodiment, $R^3$ is $\omega$-$H_2NCO(C_1-C_3)$alkyl. In yet another specific embodiment, $R^3$ is $(C_1-C_2)$alkoxy$(C_1-C_3)$alkyl. In yet another specific embodiment, $R^3$ is $H_2NSO_2O(C_2-C_4)$alkyl. In yet another specific embodiment, $R^3$ is $H_2NSO_2NH(C_2-C_4)$alkyl. In yet another specific embodiment, $R^3$ is oxo$(C_2-C_4)$alkyl. In yet another specific embodiment, $R^3$ is alkenyl. In yet another specific embodiment, $R^3$ is allyl. In yet another specific embodiment, $R^3$ is MeC(=O)NH$(C_2-C_4)$alkyl. In yet another specific embodiment $R^3$ is 2-hydroxy-2-methylpropyl, 3-hydroxypropyl, 2-hydroxypropyl or 2-hydroxyethyl. In yet another specific embodiment $R^3$ is 2,3-dihydroxypropyl. In yet another specific embodiment $R^3$ is $H_2NC(=O)CH_2CH_2$—. In yet another specific embodiment $R^3$ is 2-(4-morpholino)ethyl. In yet another embodiment $R^3$ is $MeSO_2NH(C_2-C_4)$alkyl. In yet another specific embodiment $R^3$ is $MeSO_2NHCH_2CH_2CH_2$.

$R^3$ is $(HO)_2P(=O)(C_1-C_4)$alkyl. $R^3$ is hydroxy$(C_2-C_5)$alkyl. In yet another specific embodiment $R^3$ is 3-hydroxybutyl, 3-hydroxy-3-methylbutyl, 3-hydroxypropyl, 2-hydroxypropyl, 2-hydroxy-2-methylpropyl, or 2-hydroxyethyl. Alternatively, $R^3$ is dihydroxy$(C_3-C_4)$alkyl. In yet another specific embodiment $R^3$ is 2,3-dihydroxypropyl. $R^3$ is amino$(C_2-C_5)$alkyl or methylamino$(C_2-C_5)$alkyl, each optionally substituted with hydroxy. In another specific embodiment, $R^3$ is $\omega$-$H_2NCO(C_1-C_3)$alkyl. In another specific embodiment, $R^3$ is $H_2NCONH(C_1-C_3)$alkyl, optionally substituted with hydroxy. In another specific embodiment, $R^3$ is $H_2NCH_2CONH(C_1-C_3)$alkyl, optionally substituted with hydroxy. In another specific embodiment, $R^3$ is $(C_1-C_3)$alkylHNCONH$(C_1-C_3)$alkyl. In yet another specific embodiment, $R^3$ is $H_2NC(=O)C_1-C_4$ alkyl. In yet another specific embodiment, $R^3$ is MeC(=O)NH$C_1-C_4$ alkyl. In yet another specific embodiment, $R^3$ is MeOC(=O)NH$C_1-C_4$ alkyl. In yet another specific embodiment, $R^3$ is MeNHC(=O)$C_1-C_4$ alkyl. In yet another specific embodiment R³ is H₂NC(=O)OC₁-C₄ alkyl. In yet another specific embodiment, R³ is MeHNC(=O)OC₁-C₄ alkyl. In yet another specific embodiment, R³ is (C₁-C₂)alkoxy(C₁-C₃)alkyl, optionally substituted with hydroxy. In yet another specific embodiment, R³ is (C₁-C₂)alkylthio(C₁-C₃)alkyl, optionally substituted with hydroxy. In yet another specific embodiment, R³ is H₂NSO₂O(C₂-C₄)alkyl. In yet another specific embodiment, R³ is H₂NSO₂NH(C₂-C₄)alkyl. In yet another specific embodiment, R³ is oxo(C₂-C₄)alkyl. In yet another specific embodiment, R³ is MeCO(C₁-C₂alkyl). In yet another specific embodiment, R³ is HOCO(C₁-C₂alkyl). In yet another specific embodiment, R³ is alkenyl. In yet another specific embodiment, R³ is alkyl. In yet another specific embodiment, R³ is allyl. In yet another specific embodiment, R³ is MeC(=O)NH(C₂-C₄)alkyl. In yet another specific embodiment, R³ is MeOC(=O)NH(C₂-C₄)alkyl. In yet another specific embodiment, R³ is cyanoalkyl. In yet another specific embodiment, R³ is alkylsulfonylaminoalkyl. In yet another specific embodiment, R³ is alkylsulfonylalkyl. In yet another specific embodiment R³ is MeSO₂NH(C₂-C₄)alkyl, optionally substituted with hydroxy. In yet another specific embodiment, R³ is aminocarbonylaminoalkyl. In yet another specific embodiment, R³ is aminocarboxyalkyl. In yet another specific embodiment R³ is 2-(4-morpholino)ethyl. In yet another specific embodiment R³ is 2-(1-imidazolyl)ethyl. In yet another specific embodiment R³ is 2-(1-aminoimidazolyl)ethyl.

In another embodiment R³ is (C₃-C₄)cycloalkyl(C₁-C₂)alkyl. In another specific embodiment R³ is (1-hydroxycyclopropyl)methyl. In another specific embodiment R³ is 1-(hydroxymethyl)cyclopropyl)methyl. In another specific embodiment R³ is (1-carbamoylcyclopropyl)methyl. In another specific embodiment R³ is 2-(1-azetidinyl)ethyl, 2-(1-pyrrolidinyl)ethyl, 2-(3-fluoro-1pyrrolidinyl)ethyl, 2-(2-oxo-1-pyrrolidinyl)ethyl, 2-(1,1-dioxo-2-isothiazolidinyl)ethyl, 2-(3-oxo-1-piperazinyl)ethyl, (5-methyl-1,3,4-thiadiazol-2-yl)methyl, 2-(5-methyl-1,3,4-thiadiazol-2-yl)ethyl, (5-methyl-1,3,4-oxadiazol-2-yl)methyl or 2-(5-methyl-1,3,4-oxadiazol-2-yl)ethyl. In another embodiment R³ is heterocyclyl(C₁-C₃)alkyl.

In another specific embodiment R³ is H₂NCOCHMeCH₂—, H₂NCOC(Me)₂CH₂—, NCCHMeCH₂—, NCC(Me)₂CH₂—, H₂NCH₂C(Me)₂CH₂—, MeCONHCH₂C(Me)₂CH₂—, MeOCONHCH₂C(Me)₂CH₂—, MeSO₂NHCH₂C(Me)₂CH₂—, HOCH₂CHMeCH₂—, HOCH₂C(Me)₂CH₂—, MeSO₂NMeCH₂CH₂— or MeSO₂NMeCH₂CH₂CH₂—. In another specific embodiment R³ is methyl, ethyl, FCMe₂CH₂—, MeC(=O)NHCMe₂CH₂—, MeOC(=O)NHCMe₂CH₂— or MeS(=O)₂NHCMe₂CH₂—.

E is a bond.

R² is optionally substituted aryl, optionally substituted heteroaryl or cycloalkyl. In one specific embodiment, R² is optionally substituted phenyl or optionally substituted pyridyl. In another specific embodiment, R² is optionally substituted phenyl. In yet another specific embodiment, R² is fluorophenyl. R² is (C₃-C₅)alkyl. In one specific embodiment R² is isopropyl. In another specific embodiment R² is optionally substituted thienyl. In another specific embodiment R² is t-butyl.

In another embodiment of the invention, the provisos applied to pharmaceutical compositions comprising compounds of Formula I or Ia-Il or Im¹⁻¹², In¹⁻¹², Io¹⁻¹², Ip¹⁻⁷, Iq¹⁻²¹, Ir¹⁻²¹, Is¹⁻²¹, It¹⁻⁷, Iu¹⁻²⁰, Iv¹⁻²⁰, Iw¹⁻²⁰ or Ix¹⁻⁷ also apply to methods of treatment utilizing any one of the compounds of Formula I or Formulas Ia-Il or Im¹⁻¹², In¹⁻¹², Io¹⁻¹², Ip¹⁻⁷, Iq¹⁻²¹, Ir¹⁻²¹, Is¹⁻²¹, It¹⁻⁷, Iu¹⁻²⁰, Iv¹⁻²⁰, Iw¹⁻²⁰ or Ix¹⁻⁷.

Another embodiment of the invention is a compound of Formulas I, Ia, Ib, Ic, Id, Ie, If, Ig, Ih, Ii, Ij, Ik, Il Im¹⁻¹², In¹⁻¹², Io¹⁻¹², Ip¹⁻⁷, Iq¹⁻²¹, Ir¹⁻²¹, Is¹⁻²¹, It¹⁻⁷, Iu¹⁻²⁰, Iv¹⁻²⁰, Iw¹⁻²⁰ or Ix¹⁻⁷, or a pharmaceutically acceptable salt, enantiomer or diastereomer thereof, wherein any one of the following provisos apply or any combination thereof:

Proviso 1: If (a) either R³ or E-R² is (C₁-C₄)alkyl or benzyl substituted with halogen or (C₁-C₂)alkoxy, and (b) n is not zero, then Y cannot be either oxo or (C₁-C₃)alkyl at the position β to the nitrogen atom in the ring.

Proviso 2: If A₁ is a C₂-C₃ alkylene, then -Cy¹-A₂-Cy₂ cannot be

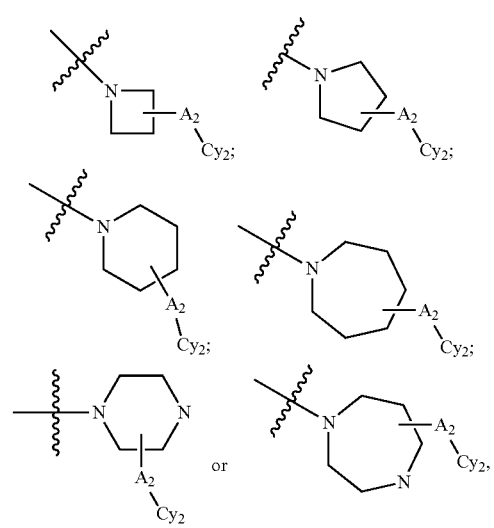

wherein the nitrogen-containing heterocycle represented by Cy¹ is optionally substituted.

Proviso 3: If (a) A¹ and A² are both bonds, (b) R³ is an alkyl optionally substituted with amino, alkyl, alkoxy, oxo, carboxy, hydroxy, fluorine, or sulfonyl, or an unsubstituted alkynyl (c) E-R² is (i) a optionally substituted alkyl or an optionally substituted carbocyclic aromatic group wherein the substituent is an amino, alkyl, alkenyl, alkynyl, alkoxy, carboxy, hydroxy, halogen or sulfonyl, or (ii) an unsubstituted cycloalkyl, and (d) Cy² is H, then Cy₁ is not (i) an unsubstituted monocyclic cycloalkyl or (ii) a substituted or unsubstituted carbocyclic aromatic group.

Proviso 4: If (a) A¹ and A² are both bonds, (b) R³ is an alkyl optionally substituted with amino, alkyl, alkoxy, oxo, carboxy, hydroxy, fluorine, or sulfonyl, or an unsubstituted alkynyl (c) E-R² is (i) a optionally substituted alkyl or an optionally substituted carbocyclic aromatic group wherein the substituent is an amino, alkyl, alkenyl, alkynyl, alkoxy, carboxy, hydroxy, halogen or sulfonyl, or (ii) an unsubstituted cycloalkyl, and (d) Cy¹ is an optionally substituted carbocyclic aromatic group, then Cy² is not an unsubstituted carbocyclic aromatic group.

Proviso 5: If (a) A¹ is alkyl optionally substituted with amino, alkyl, alkoxy, oxo, carboxy, hydroxy, fluorine, or sulfonyl, (b) R³ is an alkyl substituted with amino, alkyl, alkoxy, oxo, carboxy, hydroxy, fluorine, or sulfonyl, or an unsubstituted alkynyl (c) E-R² is (i) a optionally substituted alkyl or an optionally substituted carbocyclic aromatic group wherein the substituent is an amino, alkyl, alkenyl, alkynyl, alkoxy, carboxy, hydroxy, halogen or sulfonyl, or (ii) an unsubstituted cycloalkyl, then Cy¹ is a carbocyclic aromatic group optionally substituted with C₁C₄ alkoxy or halogen.

Proviso 6: If (a) $A^1$ is a bond or alkylene, (b) $Cy^1$ is ($C_3$-$C_7$) cycloalkyl, aryl or heteroaryl, and (c) E is a bond, then $R^2$ is not 3,4-dialkoxyphenyl optionally substituted with halogen or hydroxy, or 3,4-dicycloalkoxyphenyl optionally substituted with halogen or 3,4-dialkoxyalkoxyphenyl optionally substituted with halogen.

Proviso 7: If (a) $A^1$ is a bond, (b) $Cy^1$ is phenyl, (c) $A^2$ is unsubstituted methylene, (d) $Cy^2$ is H, and (e) n is 1, then Y is not oxo adjacent to the nitrogen in the oxazinone ring.

Proviso 8: If E is a bond or $C_1$alkylene, $R_2$ is aryl, heteroaryl or heterocyclyl, $A^1$ is ($C_1$)alkylene, $R^3$ is optionally fluorinated ($C_1$-$C_5$)alkyl, ($C_2$-$C_5$)alkenyl or ($C_2$-$C_6$)alkynyl and $Cy^1$ is optionally substituted phenyl, then $Cy^1$ is not substituted at the ortho position by optionally substituted aryl, heteroaryl, heterocyclyl or cycloalkyl.

Another embodiment of the present invention is a compound of Formulas I, Ia, Ib, Ic, Id, Ie, If, Ig, Ih, Ii, Ij, Ik, or Il or a pharmaceutically acceptable salt, enantiomer of diastereomer thereof, wherein all of the above Provisos apply. Yet another embodiment of the present invention is a compound of Formula I or a pharmaceutically acceptable salt, enantiomer of diastereomer thereof, wherein the above Provisos 3-8 apply.

Another embodiment of the present invention is a pharmaceutical composition comprising: i) a pharmaceutically acceptable carrier or diluent; and ii) a compound of Formula I, Ia, Ib, Ic, Id, Ie, If, Ig, Ih Ii, Ij, Ik, or Il or a pharmaceutically acceptable salt, enantiomer of diastereomer thereof, wherein the above Provisos 1, 2, 6 and 8 apply.

Another embodiment of the present invention is a pharmaceutical composition comprising a pharmaceutically acceptable carrier or diluent; and ii) a compound of Formulas I, Ia, Ib, Ic, Id, Ie, If, Ig, Ih Ii, Ij, Ik, or Il or a pharmaceutically acceptable salt, enantiomer of diastereomer thereof, wherein Provisos 6 and 8 apply.

In one embodiment, Proviso 2 applies when the subject is being treated to lower intraocular pressure.

In one embodiment, Proviso 2 applies when the subject is being treated for cardiovascular disorders.

In one embodiment, Proviso 2 applies when the subject is being treated for dyslipidemia or hypertension.

In one embodiment, Proviso 8 applies when the subject is being treated for atherosclerosis, dyslipidemia, or cardiovascular disorders.

In one embodiment, Proviso 8 applies when the subject is being treated for diabetes, atherosclerosis, dyslipidemia, hypertension, obesity or cardiovascular disorders.

In another embodiment, Provisos 2 and 8 apply to methods of treatment utilizing any one of the compounds of Formula I or Formulas Ia-Il.

DEFINITIONS

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "carbocyclic aromatic group" shall have the same meaning as the term "aryl" is used in U.S. Pat. No. 7,186,844, which is incorporated by reference herein in its entirety. For further clarity, the term "carbocyclic aromatic group," as used in U.S. Pat. No. 7,186,844, means is an all carbon, monocyclic or polycyclic ring system which obeys Huckel's 4n+2 rule (M. B. Smith and J. March, "March's Advanced Organic Chemistry" 5th Edition, p 57, Wiley-Interscience, 2001) and includes, for example, benzene and naphthalene.

The term "cycloalkyl" means a monocyclic, bicyclic or tricyclic, saturated hydrocarbon ring having 3-10 carbon atoms and includes, for example, cyclopropyl (c-Pr), cyclobutyl, cyclopentyl, cyclohexyl, cycloheptyl, cyclooctyl, bicyclo[2.2.2]octyl, bicyclo[2.2.1]heptyl, Spiro[4.4]nonane, adamantyl and the like.

The term "aryl" means an aromatic radical which is a phenyl group, a naphthyl group, an indanyl group or a tetrahydronaphthalene group. An aryl group is optionally substituted with 1-4 substituents. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A heteroaryl is optionally substituted. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, dihydropyridine, tetrahydropyridine, piperazine, 1-(2,2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1,6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl. A heterocyclyl can be optionally substituted with 1-4 substituents. Exemplary substituents include alkyl, haloalkyl, halogen and oxo.

The term "spirocycloalkyl" means a cycloalkyl group which shares one ring carbon with another alkyl or cycloalkyl group.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

The following abbreviations have the indicated meanings:

| Abbreviation | Meaning |
|---|---|
| A % | Area percentage |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| c-Pr | cyclopropyl |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIBAL-H | diisobutylaluminum hydride |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenylhydrazine |
| DPTBS | Diphenyl-t-butylsilyl |
| dr | diastereomer ratio |
| EDC•HCl, EDCl | 1-[3-(dimethylamino)propyl]-3-ethylcarbodiimide hydrochloride |
| Equiv | equivalents |
| EtOAc | ethyl acetate |
| Fmoc | 1-[[(9H-fluoren-9-ylmethoxy)carbonyl]oxy]- |
| Fmoc—OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |

| Abbreviation | Meaning |
| --- | --- |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| m-CPBA | meta-chloroperoxybenzoic acid |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| rt | room temperature |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| T$_{ext}$ | External temperature |
| T$_{int}$ | Internal temperature |
| TFA | trifluoroacetic acid |
| Tlc, TLC | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

General Description of Synthetic Methods

Compounds of Formula I can be prepared by several processes. In the discussion below, A$^1$, A$^2$, Cy$^1$, Cy$^2$, E, R$^1$, R$^2$, R$^3$, Y and n have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process a compound of Formula I, wherein can be prepared by reaction of an aminoalcohol intermediate of Formula II with a reagent of Formula III, wherein Z$^1$ and Z$^2$ are leaving groups such as chloride, 1-imidazolyl or aryloxide in an inert solvent such as THF, CH$_2$Cl$_2$, toluene or MeCN, usually in the presence of an organic or inorganic base such as triethylamine or NaHCO$_3$ respectively, at −10° C. to 120° C.:

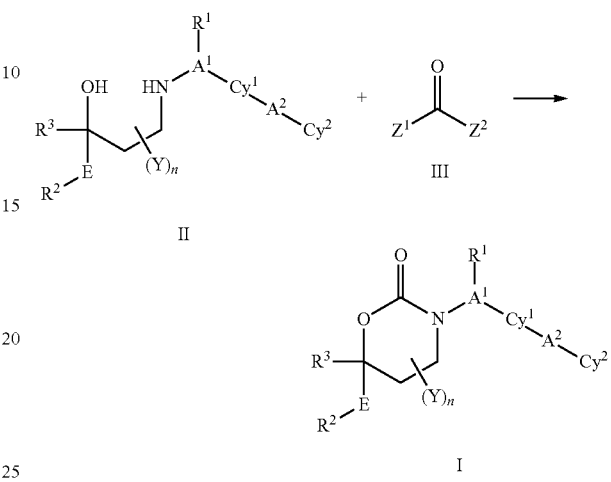

Certain instances of reagent III are especially convenient because they are commercially available. For example when Z$^1$ and Z$^2$ are both chloride, III is phosgene. When Z$^1$ and Z$^2$ are both 1-imidazolyl, III is carbonyl diimidazole. When Z$^1$ is chloride and Z$^2$ is p-nitrophenoxide, III is p-nitrophenyl chloroformate. When Z$^1$ and Z$^2$ are both OCCl$_3$, III is triphosgene and as little as one third of molar equivalent can be used.

Aminoalcohol intermediates of Formula II can be prepared by reduction of amides of Formula IV using a hydride reagent such as BH$_3$.THF solution, BH$_3$.Me$_2$S or LiAlH$_4$ in an inert solvent ethereal such as THF or DME at 20° C. to 100° C. for between 1 h and 48 h:

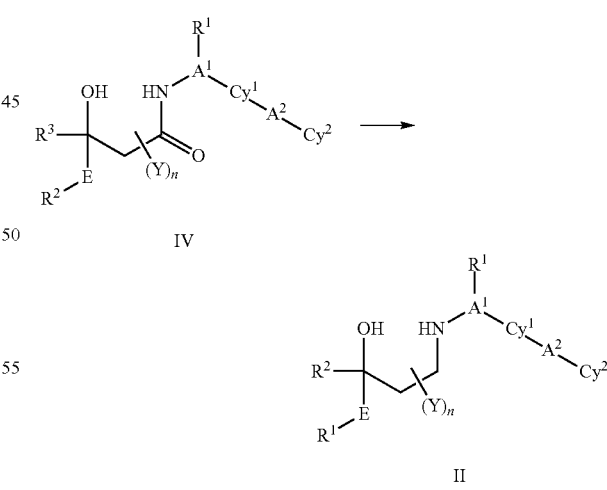

Intermediates of Formula IV can be prepared by coupling of a β-hydroxyacid of Formula V with an amine of Formula VI using standard peptide coupling reagents such as EDC in the presence of HOBt and N,N-diisopropylethylamine in an inert solvent such as CH$_2$Cl$_2$ at 0-30° C. for between 1 h and 24 h:

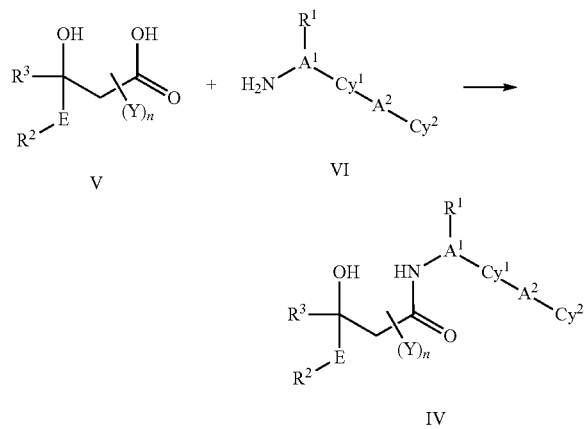

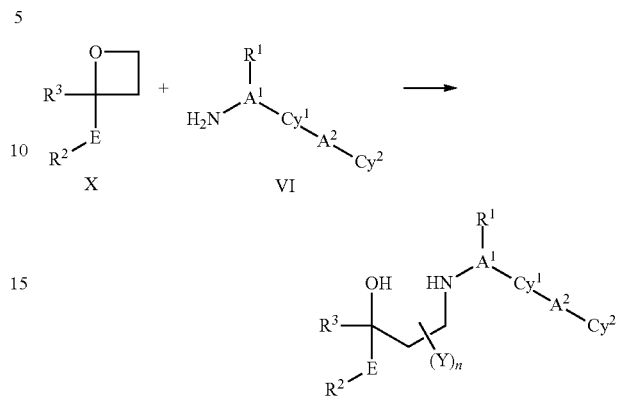

Amine intermediates of Formula VI, wherein $A^1=CH_2$ and $R^1$ is absent, can be prepared by reduction of amides of Formula VII using a hydride reagent such as $BH_3.THF$ solution, $BH_3.Me_2S$ or $LiAlH_4$ in an inert solvent ethereal such as THF or DME at 20° C. to 100° C. for between 1 h and 48 h:

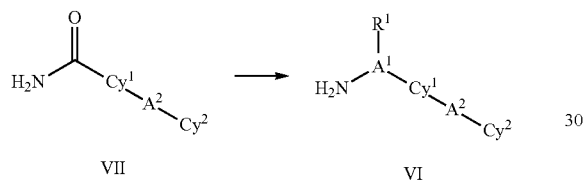

Amine intermediates of Formula VI, wherein $A^1$ is a bond, $R^1$ is absent and $Cy^1$ is not an aromatic or heteroaromatic ring, can be prepared from ketones of formula VIII via oximes of Formula IX or by reductive amination of a ketone of Formula VIII with ammonia:

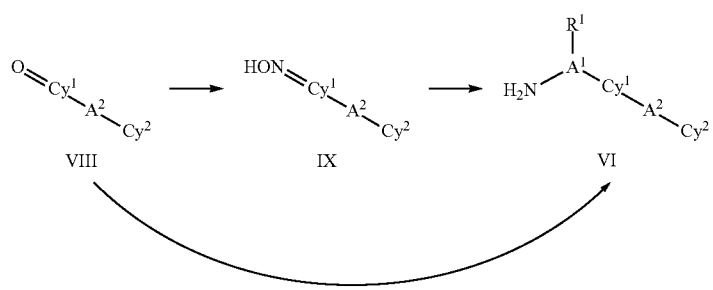

Methods for the conversion of ketones to oximes are described in Smith, M. B. and March, J. "March's Advanced Organic Chemistry" pp 1194-1195, 5th Edition, Wiley, New York, N.Y., 2001. Methods for the reduction of oximes to primary amines are described in Smith, M. B. and March, J. "March's Advanced Organic Chemistry" p 1555, 5th Edition, Wiley, New York, N.Y., 2001. Methods for the reductive amination of ketones are described in Baxter, E. W. and Reitz, A. B. "Organic Reactions" Volume 59, Ed. Overman, L. E., Wiley Interscience, 2002.

Intermediates of Formula II, wherein n=0, can be prepared by reaction of oxetanes of Formula X with amines of Formula VI as described in Smith, M. B. and March, J. "March's Advanced Organic Chemistry" p 505, 5th Edition, Wiley, New York, N.Y., 2001:

Intermediates of Formula II can also be prepared by reductive amination of β-hydroxyaldehydes of Formula Xa with amines of Formula VI. Methods for the reductive amination of aldehydes are described in Baxter, E. W. and Reitz, A. B. "Organic Reactions" Volume 59, Ed. Overman, L. E., Wiley Interscience, 2002.

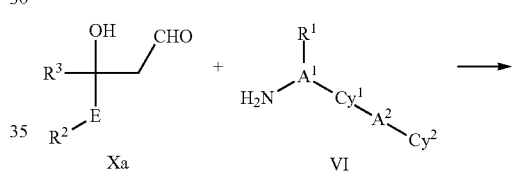

-continued

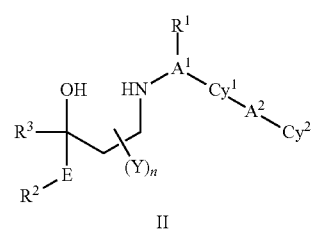

Aldehydes of Formula Xa can be prepared from homoallylic alcohols of Formula XXI by treatment with $OsO_4$ and $NaIO_4$.

Intermediates of Formula II, wherein $A^1$=$CH_2$ and $R^1$ is absent, can be prepared by reduction of amide intermediates of formula XI using a hydride reagent such as $BH_3$.THF solution, $BH_3.Me_2S$ or $LiAlH_4$ in an inert solvent ethereal such as THF or DME at 20° C. to 100° C. for between 1 h and 48 h:

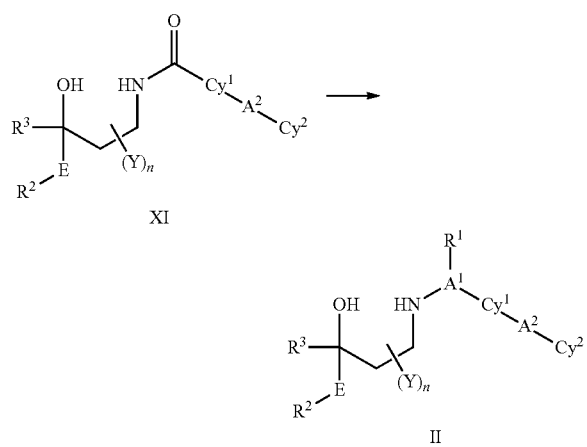

Amide intermediates of Formula XI can be prepared by reaction of an aminoalcohol intermediate of Formula XII with activated carboxylic acid of Formula XIII wherein $Z^3$=chloride or an activated ester, such as an N-hydroxysuccinimide ester:

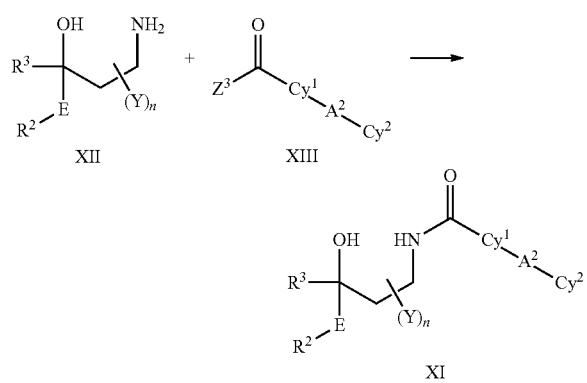

Amino-alcohol intermediates of Formula XII, wherein n=0, can be prepared by reaction of an epoxide of Formula XIV with cyanide ion followed by reduction of the resulting hydroxynitrile of Formula XV with hydrogen gas in the presence of a catalyst or with a hydride source such as $LiAlH_4$:

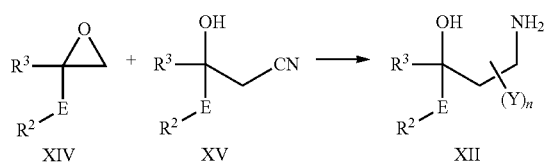

Epoxide compounds of formula XIV can, in turn, be prepared in a number of ways including, as described in Aube, J. "Epoxidation and Related Processes" Chapter 3.2 in Volume 1 of "Comprehensive Organic Synthesis" Edited by B. M. Trost, I. Fleming and Stuart L. Schreiber, Pergamon Press, New York, 1992.

Hydroxynitrile intermediates of Formula XV can be prepared by treatment of ketones of Formula XVI with acetonitrile anion, formed by treatment of acetonitrile with n-BuLi or LDA, in an inert, anhydrous solvent such as THF at low temperature:

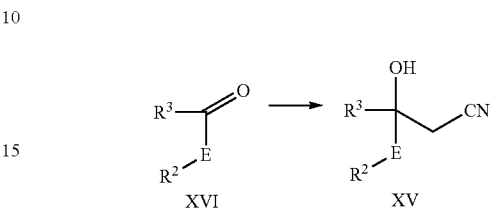

Amino-alcohol intermediates of Formula XII, wherein n is 0, can be prepared by treatment of sulfonate intermediates of Formula XVII, wherein $R^4$ is for example methyl, trifluoromethyl or p-methylphenyl, with ammonia:

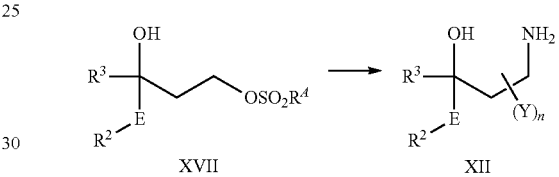

Amino-alcohol intermediates of Formula XII can be prepared by treatment of sulfonate intermediates of Formula XVII with sodium azide to give an azide intermediate of Formula XVIII, followed by catalytic hydrogenation or by Staudinger reduction with $PPh_3$ in wet THF:

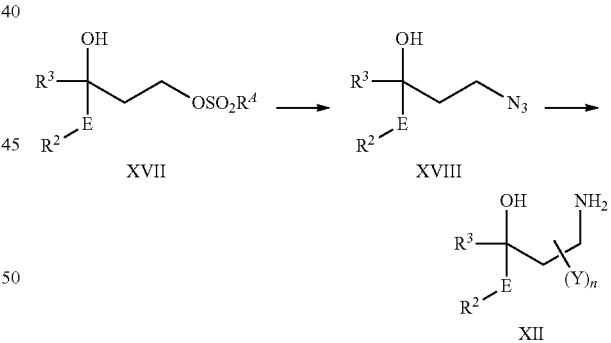

Sulfonate intermediates of Formula XVII can be prepared from diol intermediates of Formula XIX with a sulfonyl chloride $R^4SO_2Cl$:

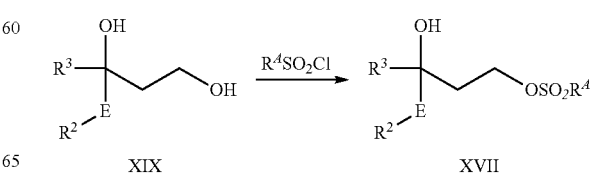

Diol intermediates of Formula XIX can be prepared by hydroboration of allyl alcohols of Formula XX:

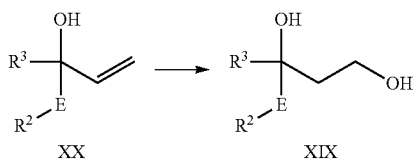

Diol intermediates of Formula XIX can be prepared by ozonolysis and reduction of homoallyl alcohols of Formula XXI:

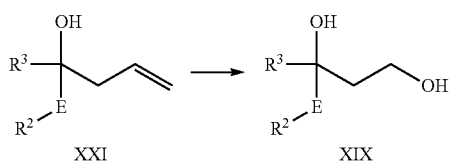

Aminoalcohol intermediates of Formula II, wherein $A^1$ is a bond, $R^1$ is absent, and $Cy^1$ is a heteroaryl group or an aryl group bearing at least one strongly electron withdrawing group such as $CF_3$, can be prepared by reaction of an aminoalcohol intermediate of Formula XII with a compound of Formula XXII, wherein $Cy^1$ is a heteroaryl group or an aryl group bearing at least one strongly electron withdrawing group such as $CF_3$ and $R^B$ is a leaving group such a fluoro, chloro, bromo or iodo:

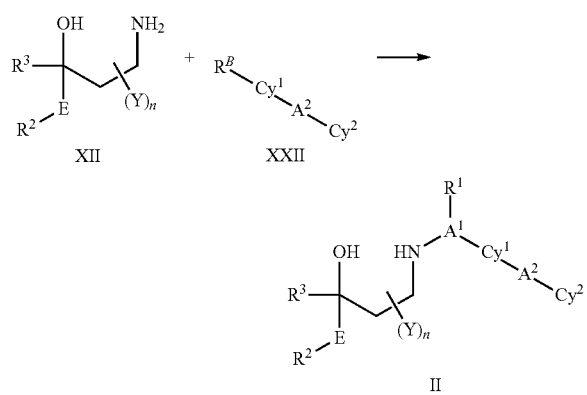

Aminoalcohol intermediates of Formula II, wherein $A^1$ is $(C_1)$alkylene can be prepared by reaction of an aminoalcohol of Formula XII with an aldehyde or methyl ketone of Formula XII in the presence of a reducing agent such as $NaCNBH_3$ or $Na(OAc)_3BH$:

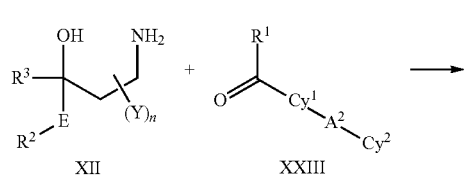

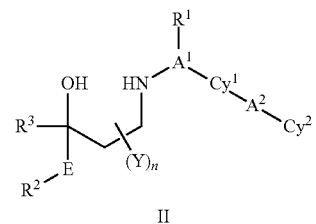

Methods for the reductive amination of aldehydes and ketones are described in Baxter, E. W. and Reitz, A. B. "Organic Reactions" Volume 59, Ed. Overman, L. E., Wiley Interscience, 2002.

In a second process a compound of Formula I can be prepared by reaction of a ketocarbamate of Formula XXIV, wherein $R^D$ is alkyl or arylalkyl group such as methyl, t-butyl or benzyl, with an organometallic reagent of Formula XXV wherein M includes, but is not limited to, MgCl, MgBr, MgI or Li:

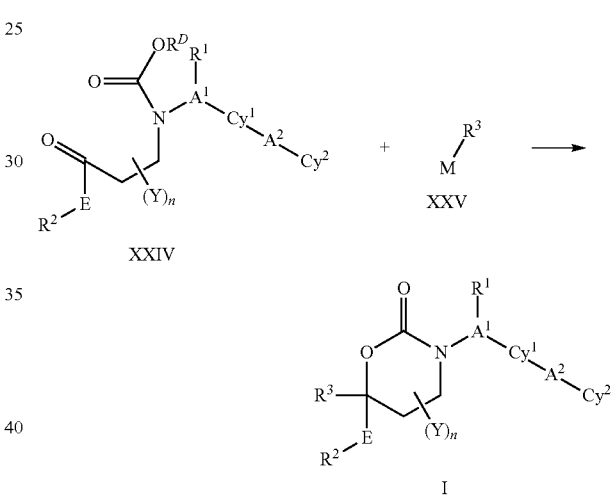

In specific examples, organometallic reagent XXV is allylmagnesium bromide, allylzinc(II) bromide, (2-methylallyl) magnesium chloride or (2-methoxy-2-oxoethyl)zinc(III) bromide. In certain cases when M is MgCl, MgBr or MgI, it is advantageous to add $CeCl_3$ to the reaction mixture.

Ketocarbamates of Formula XXIV can be prepared by reaction of aminoketones of Formula XXVI with intermediates of Formula XXVII wherein $R^E$ is a leaving group such as chloride, succinyloxy, imidazolyl or t-butoxycarboxycarbonyl:

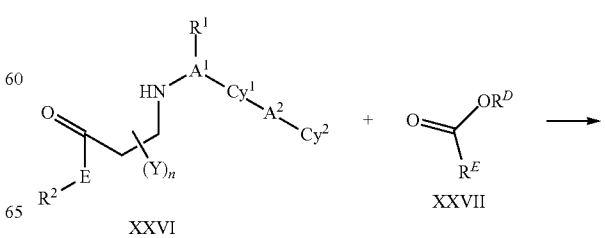

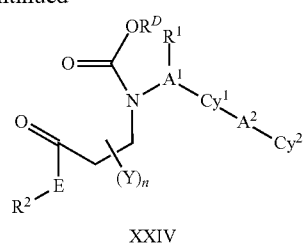

XXIV

Aminoketones of Formula XXVI, wherein n=0, can be prepared by reaction of α,β-unsaturated ketones of Formula XXVIII with amines of Formula VI:

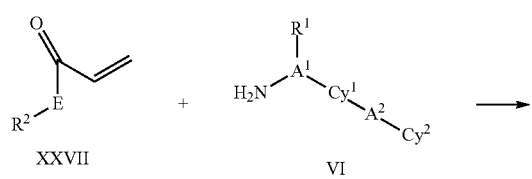

XXVII  VI

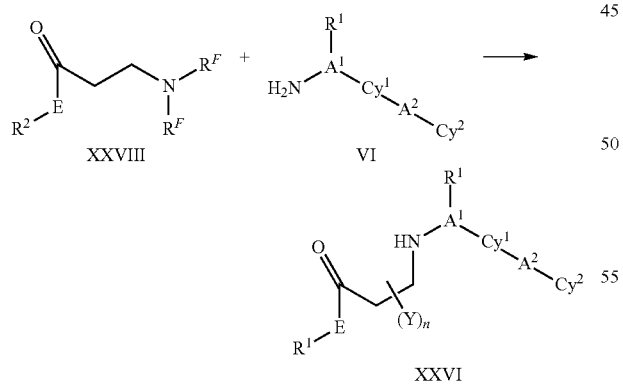

XXVI

Aminoketones of Formula XXVI, wherein n=0, can be prepared by reaction of β-dialkylaminoketones of Formula XXVIII, wherein $R^F$ is lower alkyl especially methyl, with amines of Formula VI:

XXVIII  VI

XXVI

β-Dialkylaminoketones of Formula XXVIII are in turn derived from α,β-unsaturated ketones of Formula XXVII with dialkylamines of Formula $R^F NHR^F$.

In a third process a compound of Formula I, can be prepared by reaction of a compound of Formula XVII with an isocyanate of Formula XXIX in the presence of a base:

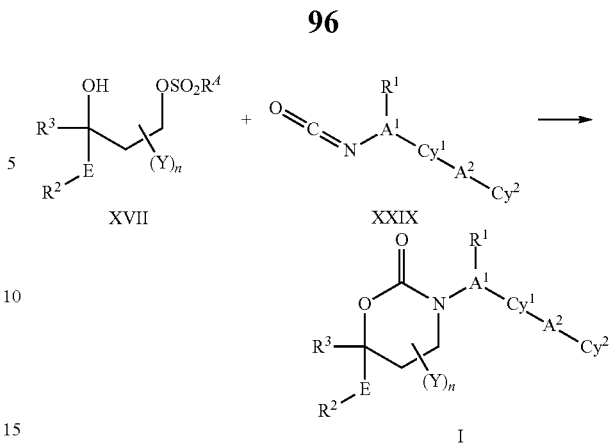

XVII  XXIX

I

Isocyanates of Formula XXIX can be prepared from amines of Formula VI by treatment with phosgene, diphosgene or triphosgene. This third process is described in greater detail in U.S. Provisional Application Ser. No. 61/137,013, filed Jul. 25, 2008 entitled SYNTHESIS OF INHIBITORS OF 11β-HYDROXYSTEROID DEHYDROGENASE TYPE 1, the entire teachings of which are incorporated herein by reference.

In a fourth process a compound of Formula I can be prepared by reaction of a halo compound of Formula, wherein Hal is chlorine or bromine, with an isocyanate of Formula XXIX in the presence of a base:

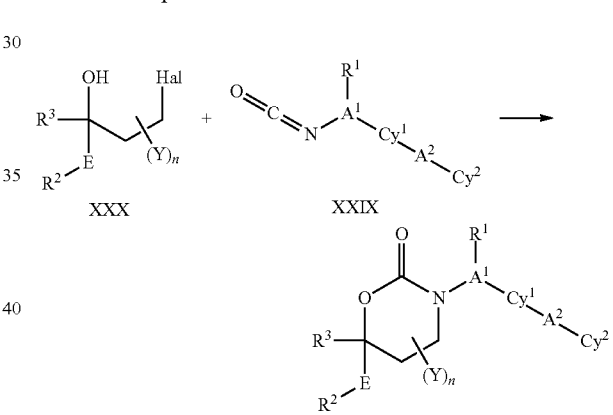

XXX  XXIX

I

Halo compounds of Formula XXX can be prepared by reaction of β-haloketones of Formula XXXI with organometallic reagents of Formula XXV wherein M is a metal containing radical including MgCl, MgBr, MgI or Li. The reaction is optionally carried out in the presence of anhydrous cerium trichloride:

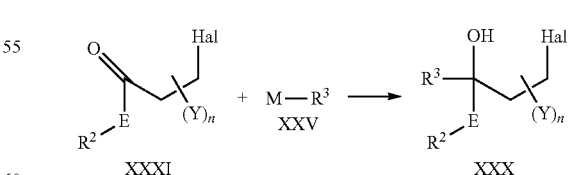

XXXI  XXV  XXX

In a fifth process a compound of Formula I, wherein $A^1$ is $CH_2$ or $CH_2CH_2$ and $R^1$ is absent, can be prepared by reaction of a compound of Formula XXXII, with a compound of Formula XXXIII, wherein $A^1$ is $CH_2$ or $CH_2CH_2$ and $R^G$ is a leaving group such as Br, I, $OSO_2Me$, $OSO_2CF_3$ or $OSO_2Ph$, in the presence of a base such as NaH or $K_2CO_3$:

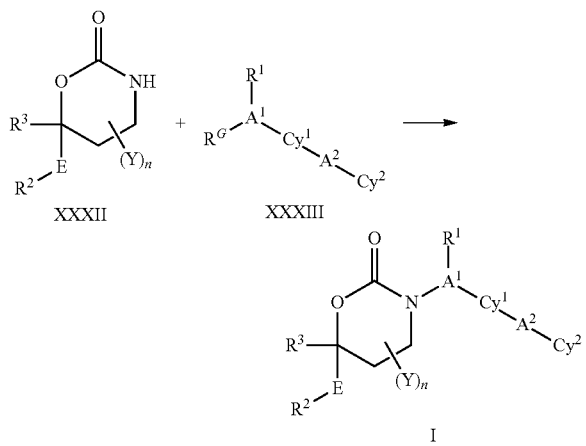

Compounds of Formula XXXII can be prepared by treatment of compounds of Formula XII with various reagents of Formula III, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at −10° C. to 120° C.:

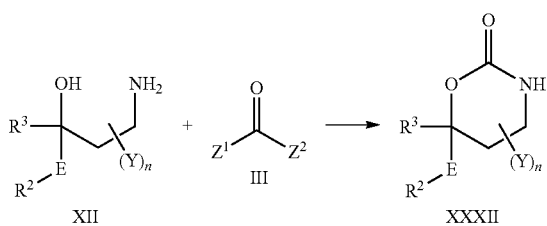

In a sixth process a compound of Formula I, wherein A is a bond can be prepared by reaction of a compound of Formula XXXII, with a compound of Formula XXII, wherein $R^B$ is a leaving group such as chloro, bromo, iodo or $OSO_2CF_3$, in the presence of a base such as $K_2CO_3$ and a copper or palladium catalyst in an inert solvent such as dioxane, DMF or NMP at elevated temperature:

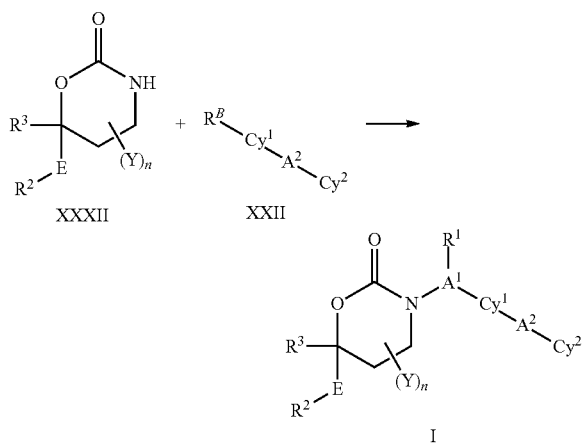

In a seventh process a compound of Formula I can be prepared from another compound of Formula I. For example:

(1) a compound of Formula I wherein $Cy^1$ is substituted with bromine or iodine, $A^2$ is a bond and $Cy^2$ is hydrogen can be reacted with an optionally substituted aryl or heteroarylboronic acid or ester in the presence of a palladium catalyst to give a compound of Formula I wherein $A^2$ is a bond and $Cy^2$ is optionally substituted aryl or heteroaryl.

(2) a compound of Formula I wherein $R^1$ or $R^3$ is ω-hydroxy($C_2$-$C_6$)alkyl can be oxidized to a compound of Formula I wherein $R^1$ or $R^3$ is ω-carboxy($C_1$-$C_5$)alkyl using Jones reagent.

(3) a compound of Formula I wherein $R^1$ or $R^3$ is ω-carboxy($C_1$-$C_6$)alkyl can be coupled with ammonia or a ($C_1$-$C_6$) alkylamine using a standard peptide coupling reagent such as EDC to afford a compound of Formula I wherein $R^1$ or $R^3$ is ω-$H_2$NC(=O)($C_1$-$C_6$)alkyl or ω-{($C_1$-$C_6$)alkylNHC(=O)} ($C_1$-$C_6$)alkyl.

(4) a compound of Formula I wherein $R^1$ or $R^3$ is ω-hydroxy($C_1$-$C_6$)alkyl can be converted to its methanesulfonate or trifluoromethanesulfonate, treated with sodium azide and reduced to give a compound of Formula I, wherein $R^1$ or $R^3$ is ω-amino($C_1$-$C_6$)alkyl.

(5) a compound of Formula I wherein $R^1$ or $R^3$ is amino ($C_1$-$C_6$)alkyl can be reacted with acetic anhydride or acetyl chloride to give a compound of Formula I wherein $R^1$ or $R^3$ is {acetylamino}($C_1$-$C_6$)alkyl.

(6) a compound of Formula I wherein $R^1$ or $R^3$ is amino ($C_1$-$C_6$)alkyl can be reacted with methanesulfonyl chloride to give a compound of Formula I wherein $R^1$ or $R^3$ is {methanesulfonylamino}($C_1$-$C_6$)alkyl.

(7) a compound of Formula I, wherein $R^1$ is ($C_2$-$C_6$)alkenyl is hydroborated to afford a compound of Formula I wherein $R^1$ is hydroxy($C_2$-$C_6$)alkyl.

(8) a compound of Formula I, wherein $R^3$ is ($C_2$-$C_6$)alkenyl, is hydroborated to afford a compound of Formula I wherein $R^3$ is hydroxy($C_2$-$C_6$)alkyl.

(9) a compound of Formula I, wherein $R^1$ is ($C_2$-$C_6$)alkenyl, can be reacted with osmium tetroxide and N-methylmorpholine-N-oxide to afford a compound of Formula I wherein $R^1$ is vicinal dihydroxy($C_2$-$C_6$)alkyl,

(10) a compound of Formula I, wherein $R^3$ is ($C_2$-$C_6$) alkenyl, can be reacted with osmium tetroxide and N-methylmorpholine-N-oxide to afford a vicinal diol compound of Formula I wherein $R^3$ is vicinal dihydroxy($C_2$-$C_6$)alkyl,

(11) a compound of Formula I, wherein $R^1$ is ($C_2$-$C_6$) alkenyl, can be reacted with ozone followed by $NaBH_4$ to give a compound of Formula I wherein $R^1$ is ω-hydroxy($C_1$-$C_5$) alkyl.

(12) a compound of Formula I, wherein $R^3$ is ($C_2$-$C_6$) alkenyl, can be reacted with ozone followed by $NaBH_4$ to give a compound of Formula I wherein $R^3$ is ω-hydroxy($C_1$-$C_5$) alkyl.

(13) a compound of Formula I wherein $R^1$ or $R^3$ is amino ($C_1$-$C_6$)alkyl can be reacted with an ($C_1$-$C_6$)alkyl isocyanate to give a compound of Formula I wherein $R^1$ or $R^3$ is ($C_1$-$C_6$) alkylaminocarbonylamino($C_1$-$C_6$)alkyl.

(14) a compound of Formula I wherein $R^1$ or $R^3$ is amino ($C_1$-$C_6$)alkyl can be reacted with an ($C_1$-$C_6$)alkyl chloroformate to give a compound of Formula I wherein $R^1$ or $R^3$ is ($C_1$-$C_6$)alkoxycarbonylamino($C_1$-$C_6$)alkyl.

(15) a compound of Formula I wherein $R^1$ or $R^3$ is amino ($C_1$-$C_6$)alkyl can be reacted with chlorosulfonyl isocyanate or sulfamide to give a compound of Formula I wherein $R^1$ or $R^3$ is aminosulfonylamino($C_1$-$C_6$)alkyl.

(16) a compound of Formula I wherein $R^1$ or $R^3$ is amino ($C_1$-$C_6$)alkyl can be reacted with a ($C_1$-$C_6$)alkylsulfamoyl chloride to give a compound of Formula I wherein $R^1$ or $R^3$ is ($C_1$-$C_6$)alkylaminosulfonylamino($C_1$-$C_6$)alkyl.

(17) a compound of Formula I wherein $R^1$ or $R^3$ is hydroxy ($C_1$-$C_6$)alkyl can be reacted with chlorosulfonyl isocyanate to give a compound of Formula I wherein $R^1$ or $R^3$ is aminosulfonyloxy($C_1$-$C_6$)alkyl.

(18) a compound of Formula I wherein $R^1$ or $R^3$ is hydroxy ($C_1$-$C_6$)alkyl can be reacted with p-nitrophenyl chloroformate, pentafluorophenyl chloroformate or carbonyl diimidazole, followed by ammonia, a ($C_1$-$C_6$)alkylamine or a di($C_1$-$C_6$)alkylamine to give a compound of Formula I wherein $R^1$ or $R^3$ is aminocarboxy($C_1$-$C_6$)alkyl, ($C_1$-$C_6$)alkyl aminocarboxy($C_1$-$C_6$)alkyl or di($C_1$-$C_6$)alkyl aminocarboxy($C_1$-$C_6$)alkyl.

(19) a compound of Formula I wherein $R^1$ or $R^3$ is hydroxy ($C_1$-$C_6$)alkyl can be reacted with $POCl_3$ to give a compound of Formula I wherein $R^1$ or $R^3$ is $(HO)_2P(\!=\!O)O(C_1$-$C_6)$alkyl.

(20) a compound of Formula I wherein $Cy^1$ is substituted with bromine or iodine, $A^2$ is a bond and $Cy^2$ is hydrogen can be reacted with a cyclic amine in the presence of a palladium catalyst to give a compound of Formula I wherein $A^2$ is a bond and $Cy^2$ is a cyclic amino moiety attached through its nitrogen atom.

(21) a compound of Formula I wherein $Cy^1$ is aryl or heteroaryl substituted with bromine or iodine, $A^2$ is a bond and $Cy^2$ is hydrogen can be reacted with bis(pinacolato)diboron in the presence of a palladium catalyst to give a boronate ester which can be further reacted with (a) an aryl, heteroaryl or heterocyclyl halide again in the presence of a palladium catalyst to give a compound of Formula I wherein $A^2$ is a bond and $Cy^2$ is aryl, heteroaryl or heterocyclyl.

(22) a compound of Formula I, wherein $R^3$ is allyl or homoallyl can be reacted with oxygen in the presence of $PdCl_2$ and CuCl to afford a compound of Formula I, wherein $R^3$ is 2-oxopropyl or 3-oxobutyl respectively.

(23) a compound of Formula I, wherein $R^3$ is 2-oxopropyl or 3-oxobutyl can be reacted with MeMgX, wherein X is Cl, Br or I, to give a compound of Formula I, wherein $R^3$ is 2-hydroxy-2-methylpropyl or 3-hydroxy-3-methylpropyl respectively.

(24) a compound of Formula I, wherein $R^3$ is —$CH_2CO_2Me$ can be treated with MeMgX, wherein X is Cl, Br or I, to give a compound of Formula I, wherein $R^3$ is 2-hydroxy-2-methylpropyl.

(25) a compound of Formula I, wherein $R^3$ is allyl or —$CH_2C(Me)\!=\!CH_2$ can be hydrocyanated with TsCN in the presence of triphenylsilane and various cobalt catalysts to afford compounds of Formula I, wherein $R^3$ is —$CH_2CH(CN)Me$ or —$CH_2CMe_2CN$ respectively.

(26) a compound of Formula I, wherein $R^3$ is $CH_2C(Me)_2CN$, can be treated with acetamide in the presence of $PdCl_2$ to give a compound of Formula I, wherein $R^3$ is $CH_2CMe_2CONH_2$.

(27) a compound of Formula I, wherein $R^3$ is —$CH_2C(Me)\!=\!CH_2$ can be treated with m-CPBA followed by lithium triethylborohydride to afford a compound of Formula I, wherein $R^3$ is 2-hydroxy-2-methylpropyl.

In an eighth process, compounds of the invention as prepared as follows:

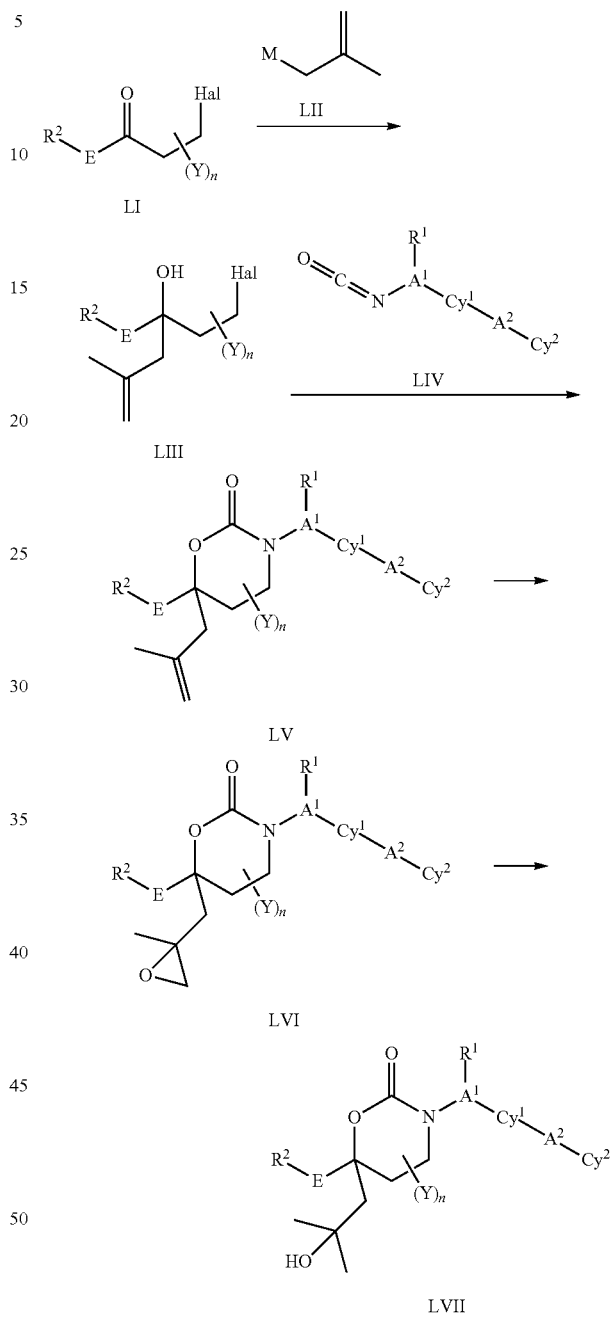

Halo compounds of Formula LIII can be formed by the treatment of β-haloketones of Formula LI with organometallic reagents of Formula LII, wherein M denotes MgCl, and the reaction is performed in the presence of anhydrous cerium trichloride in an inert anhydrous solvent, such as tetrahydrofuran, at about −25 to 0° C. for about 0.5 h.

Cyclic carbamates of Formula LV can be prepared from the reaction between β-haloalcohols of Formula LIII where Hal is a chloride and Isocyanates of Formula LIV in the presence of a base, such as but not limited to DBU (1,8-diazabicyclo [5.4.0]undec-7-ene), in a refluxing inert solvent, such as but not limited to tetrahydrofuran.

Tertiary alcohols of Formula LVII can be derived from trisubstituted alkenes of Formula LV by first epoxidizing the alkene with an epoxidation reagent, such as m-CPBA (3-chloroperbenzoic acid), in an inert solvent, such as dichloromethane to produce the corresponding epoxides of Formula LVI. The resulting epoxide is then reductively ring opened to provide the corresponding tertiary alcohol LVII via treatment with a strong hydride reagent, such as triethylborohydride, in an anhydrous inert solvent, such as tetrahydrofuran.

This eighth process is described in greater detail in U.S. Provisional Application Ser. No. 61/137,013, filed Jul. 25, 2008 entitled SYNTHESIS OF INHIBITORS OF 11β-HYDROXYSTEROID DEHYDROGENASE TYPE 1, the entire teachings of which are incorporated herein by reference.

In another variation, Id is prepared from Ia' by using a "Suzuki" coupling reaction with $Cy^2$-$B(OH)_2$ and $(PH_3P)_2PdCl_2$ as described in, for example, Example 111:

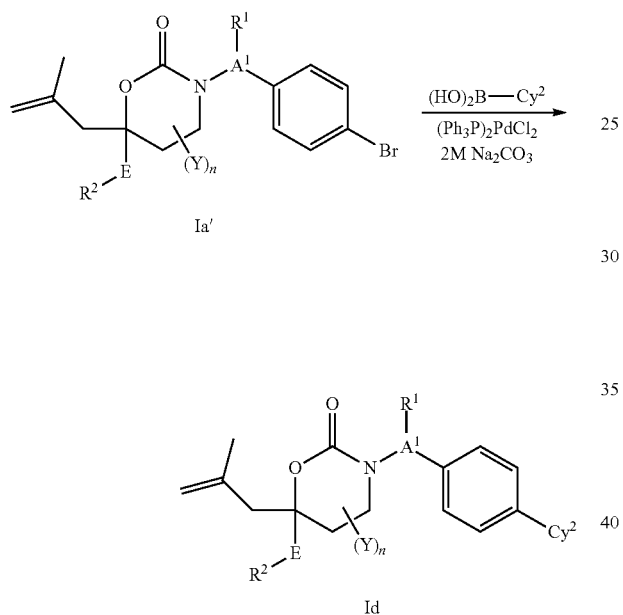

The 2-methyl-2-hydroxypropyl group is introduced via epoxidation and hydride ring opening as described above.

In a ninth process, compounds of Formula $Ie^1$ can be prepared according to the following scheme:

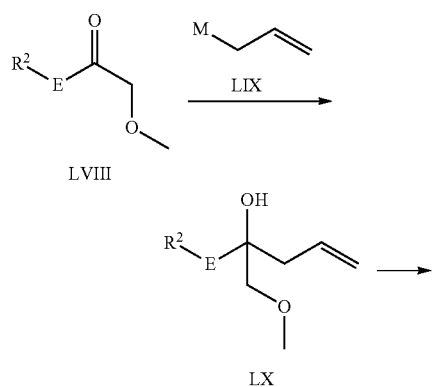

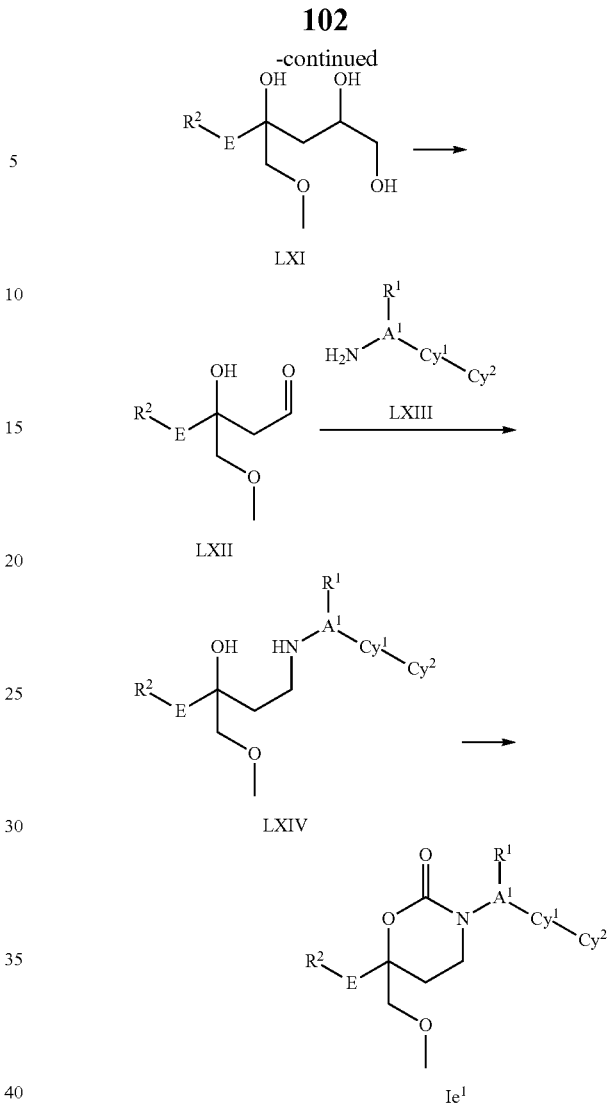

A methoxymethyl ketone of Formula LVIII is reacted with an organometallic allyl reagent of Formula LIX wherein M includes, but is not limited to, MgCl, MgBr, MgI or Li to yield an allyl compound of Formula LX. In specific examples, organometallic reagent LIX is allylmagnesium chloride, allylmagnesium bromide or allylzinc(II) bromide. In certain cases when M is MgCl, MgBr or MgI, it is advantageous to add $CeCl_3$ to the reaction mixture.

Allyl compound of Formula LX is converted to the aldehyde of Formula LXII by ozonolysis or by $OsO_4$ catalysed dihydroxylation followed by cleavage of the glycol of Formula LXI by periodates like sodium periodate. Aminocarbinol of Formula LXIV can be prepared by reductive amination with an amine of Formula LXIII using sodium cyanoborohydride or sodium triacetoxyborohydride as reducing agent. Cyclisation of the aminocarbinol of Formula LXIV to the compounds of Formula $Ie^1$ can be achieved by reacting with activated carbonic acid derivates such as phosgene, diphosgene, triphosgene or 1,1'-carbonyl-diimidazol.

Purification Methods

Compounds of the invention can be purified by high pressure liquid chromatography (prep HPLC). Unless otherwise specified, prep HPLC refers to preparative reverse phase HPLC on a C-18 column eluted with a water/acetonitrile gradient containing 0.01% TFA run on a Gilson 215 system.

LC-MS Methods

Method 1 [LC-MS (3 min)]

Column: Chromolith SpeedRod, RP-18e, 50×4.6 mm; Mobil phase: A: 0.01% TFA/water, B: 0.01% TFA/CH$_3$CN; Flow rate: 1 mL/min; Gradient:

| Time (min) | A % | B % |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

Method 2 (10-80)

| Column | YMC-PACK ODS-AQ, 50 × 2.0 mm 5 µm | | |
|---|---|---|---|
| Mobile Phase | A: water (4 L) + TFA (1.5 mL)) | | |
| | B: acetonitrile (4 L) + TFA (0.75 mL)) | | |
| | TIME (min) | A % | B % |
| | 0 | 90 | 10 |
| | 2.2 | 20 | 80 |
| | 2.5 | 20 | 80 |
| Flow Rate | 1 mL/min | | |
| Wavelength | UV 220 nm | | |
| Oven Temp | 50° C. | | |
| MS ionization | ESI | | |

Method 3 (30-90)

| Column | YMC-PACK ODS-AQ, 50 × 2.0 mm 5 µm | | |
|---|---|---|---|
| Mobile Phase | A: water (4 L) + TFA (1.5 mL)) | | |
| | B: acetonitrile (4 L) + TFA (0.75 mL)) | | |
| | TIME (min) | A % | B % |
| | 0 | 70 | 30 |
| | 2.2 | 10 | 90 |
| | 2.5 | 10 | 90 |
| Flow Rate | 1 mL/min | | |
| Wavelength | UV220 | | |
| Oven Temp | 50° C. | | |
| MS ionization | ESI | | |

Method 4 [50-100]

Example 1

6-methyl-6-phenyl-3-m-tolyl-1,3-oxazinan-2-one

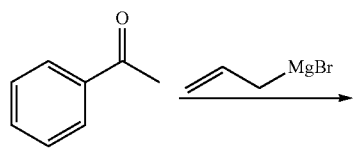

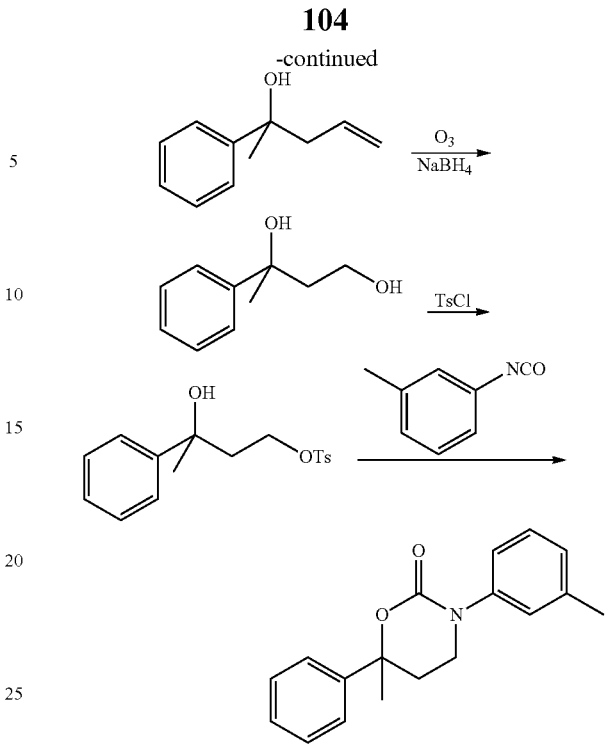

Step 1. 2-Phenylpent-4-en-2-ol

To a solution of acetophenone (30 g, 0.25 mol) in dry THF (250 mL) at −78° C. was added dropwise 1M allylmagnesium bromide (1.25 L, 1.25 mol). After addition was complete, the mixture was allowed to stir at rt for 3 h. The reaction was quenched with satd aq NH$_4$Cl solution (30 mL). The mixture was extracted with EtOAc (200 mL). The organic layer was washed with brine (30 mL), dried over anhydrous Na$_2$SO$_4$ and concentrated to give 2-phenylpent-4-en-2-ol (40.2 g), which was used for the next step without purification.

Step 2. 3-Phenylbutane-1,3-diol

A solution of 2-phenylpent-4-en-2-ol (74 g, 0.457 mol) in dry CH$_2$Cl$_2$ (1 L) was treated with ozone at −78° C. until the mixture turned blue. The system was then flushed with oxygen to remove excess ozone. NaBH$_4$ (42.8 g, 1.143 mol) was added to the mixture in portions at −20° C. The mixture was stirred overnight at rt. The mixture was quenched with water and the layers were separated. The aqueous layer was extracted with CH$_2$Cl$_2$ (2×). The organic layers were combined, washed with brine, dried over anhydrous Na$_2$SO$_4$ and concentrated to give 3-phenylbutane-1,3-diol (67.8 g), which was used for the next step without purification.

Step 3. 3-Hydroxy-3-phenylbutyl 4-methylbenzenesulfonate

To a solution of 3-phenylbutane-1,3-diol (68 g, 0.41 mol) in dry CH$_2$Cl$_2$ (500 mL) was added dropwise a solution of TsCl (78 g, 0.41 mol) and triethylamine (71 mL, 0.45 mol) in dry CH$_2$Cl$_2$ (500 mL) at 0° C. The mixture was stirred overnight. The mixture was poured into water and separated. The aqueous layer was extracted with CH$_2$Cl$_2$ (200 mL) twice. The organic layer was combined, washed with brine, dried over anhydrous Na$_2$SO$_4$ and concentrated to give the crude product. The crude product was purified by column chromatography to give 3-hydroxy-3-phenylbutyl 4-methylbenzenesulfonate (62 g, 42%). $^1$H NMR (400 MHz, CDCl$_3$): δ=1.55 (s, 3H), 1.93 (w, 1H), 2.19~2.24 (q, 2H), 2.45 (s, 3H), 3.87~4.01 (m, 1H), 4.09~4.16 (m, 1H), 7.19~7.34 (m, 7H), 7.68~7.76 (d, 2H).

Step 4.
6-methyl-6-phenyl-3-m-tolyl-1,3-oxazinan-2-one

To a solution of 3-hydroxy-3-phenylbutyl 4-methylbenzenesulfonate (1 g, 3.12 mmol) and DBU (1.4 g, 9.26 mmol) in CH$_2$Cl$_2$ (15 mL) was added a solution of 3-methylphenyl isocyanate (623 mg, 4.68 mmol) in CH$_2$Cl$_2$ (5 mL) at 0° C. over 0.5 h. The mixture was stirred at rt overnight. The mixture was concentrated to give the crude product, which was purified by column chromatography and then by preparative HPLC to afford 6-methyl-6-phenyl-3-m-tolyl-1,3-oxazinan-2-one. LC-MS Method 2, t$_R$=2.706 min, m/z=282. $^1$H NMR (CDCl$_3$) 1.75 (s, 3H), 2.30 (s, 3H), 2.35-2.50 (m, 2H), 3.30 (m, 1H), 3.50 (m, 1H), 6.95 (m, 2H), 7.05 (m, 1H), 7.20-7.30 (m, 1H), 7.35 (m, 1H), 7.42-7.50 (m, 4H).

Step 5. Enantiomers of
6-methyl-6-phenyl-3-m-tolyl-1,3-oxazinan-2-one

Chiral preparative SFC using a ChiralPak-AD, 400×25 mm I.D, 20 μm (Daicel Chemical Industries, Ltd) column maintained at 35 C eluted with 70:30 supercritical CO$_2$/0.1% diethylamine in MeOH at a flow rate of 70 mL min$^{-1}$ and a nozzle pressure of 100 bar afforded two isomers.

Isomer 1 (90 mg) gave the following spectral data: $^1$H NMR (400 MHz, CDCl$_3$): δ=1.62 (m, 1H), 1.76 (s, 3H), 2.31 (s, 3H), 2.48 (m, 2H), 3.28 (m, 1H), 3.50 (m, 1H), 6.95 (m, 1H), 7.04 (m, 1H), 7.23 (t, 1H), 7.35 (m, 1H), 7.44 (m, 4H);

Isomer 2 (100 mg) gave the following spectral data: (400 MHz, CDCl$_3$): δ=1.62 (m, 1H), 1.76 (s, 3H), 2.31 (s, 3H), 2.48 (m, 2H), 3.28 (m, 1H), 3.50 (m, 1H), 6.95 (m, 1H), 7.04 (m, 1H), 7.23 (t, 1H), 7.35 (m, 1H), 7.44 (m, 4H).

Example 2

3-(4-chlorophenyl)-6-methyl-6-phenyl-1,3-oxazinan-2-one

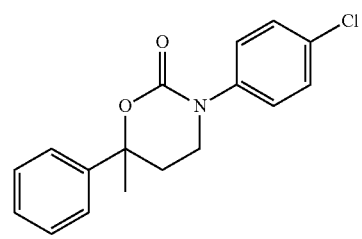 [SMILES: CC1(c2ccccc2)CCN(c2ccc(Cl)cc2)C(=O)O1]

The title compound was prepared following procedures analogous to those described in Example 1 Steps 1-4 using 4-chlorophenyl isocyanate in Step 4. LC-MS Method 2, t$_R$=2.798 min, m/z=324. $^1$H NMR (CD$_3$OD) 1.75 (s, 3H), 2.45 (m, 1H), 2.65 (m, 1H), 3.27 (m, 1H), 3.60 (m, 1H), 7.15 (d, 2H), 7.35 (dd, 3H), 7.47 (m, 4H).

Example 3

3-(2-chlorophenyl)-6-methyl-6-phenyl-1,3-oxazinan-2-one

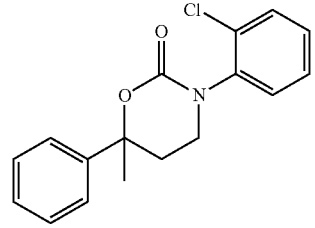 [SMILES: CC1(c2ccccc2)CCN(c2ccccc2Cl)C(=O)O1]

The title compound was prepared following procedures analogous to those described in Example 1 Steps 1-4 using 2-chlorophenyl isocyanate in Step 4. LC-MS Method 3, t$_R$=1.14 min, m/z=625.1. $^1$H NMR (CD$_3$OD) 1.80 (d, 3H), 2.50 (m, 1H), 2.62 (m, 1H), 3.20-3.30 (m, 1H), 3.42 (m, 1H), 3.50-3.60 (m, 2H), 7.03 (d, 1H), 7.30-7.50 (m, 5H), 7.50-7.60 (m, 4H).

Example 4

3-(3-chlorophenyl)-6-methyl-6-phenyl-1,3-oxazinan-2-one

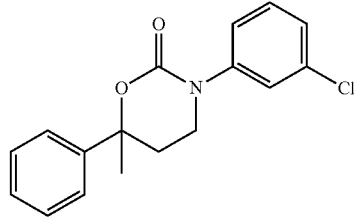 [SMILES: CC1(c2ccccc2)CCN(c2cccc(Cl)c2)C(=O)O1]

The title compound was prepared following procedures analogous to those described in Example 1 Steps 1-4 using 3-chlorophenyl isocyanate in Step 4. LC-MS Method 2, t$_R$=2.291 min, m/z=301. $^1$H NMR (CD$_3$OD) 1.75 (s, 3H), 2.50 (m, 1H), 2.70 (m, 1H), 3.30 (m, 1H), 3.68 (m, 1H), 7.12 (d, 1H), 7.30-7.45 (m, 4H), 7.50 (d, 4H).

Example 5

6-methyl-6-phenyl-3-(4-(trifluoromethyl)phenyl)-1,3-oxazinan-2-one

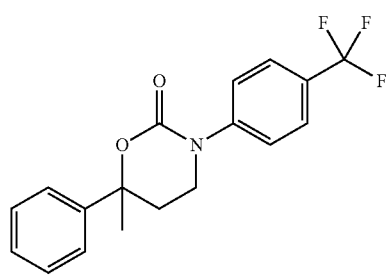 [SMILES: CC1(c2ccccc2)CCN(c2ccc(C(F)(F)F)cc2)C(=O)O1]

The title compound was prepared following procedures analogous to those described in Example 1 Steps 1-4 using 4-(trifluoromethyl)phenyl isocyanate in Step 4. LC-MS Method 2, $t_R$=2.903 min, m/z=336. $^1$H NMR (CD$_3$OD) 1.75 (s, 3H), 2.50 (m, 1H), 2.70 (m, 1H), 3.40 (m, 1H), 3.70 (m, 1H), 7.32-7.42 (m, 3H), 7.45-7.50 (m, 4H), 7.70 (d, 2H).

Example 6

3-(3-bromophenyl)-6-methyl-6-phenyl-1,3-oxazinan-2-one

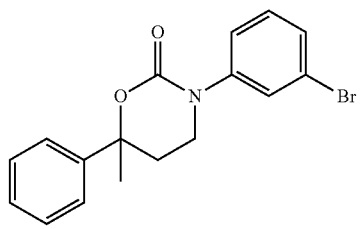 [SMILES: CC1(c2ccccc2)CCN(c2cccc(Br)c2)C(=O)O1]

The title compound was prepared following procedures analogous to those described in Example 1 Steps 1-4 using 3-bromophenyl isocyanate in Step 4. LC-MS Method 3, $t_R$=1.232 min, m/z=367.9. $^1$H NMR (CDCl$_3$) 1.70 (s, 2H), 2.30-2.40 (m, 1H), 3.45 (m, 1H), 7.07 (d, 1H), 7.12 (t, 1H), 7.22-7.30 (m, 3H), 7.35-7.40 (m, 4H).

Example 7

6-methyl-3,6-diphenyl-1,3-oxazinan-2-one

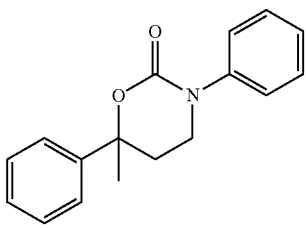 [SMILES: CC1(c2ccccc2)CCN(c2ccccc2)C(=O)O1]

The title compound was prepared following procedures analogous to those described in Example 1 Steps 1-4 using phenyl isocyanate in Step 4. LC-MS Method 2, $t_R$=1.99 min, m/z=268. $^1$H NMR (CD$_3$OD) 1.75 (s, 3H), 2.45 (m, 1H), 2.65 (m, 1H), 3.25 (m, 1H), 3.60 (m, 1H), 7.12 (d, 2H), 7.25 (t, 1H), 7.35 (m, 3H), 7.45-7.53 (m, 4H).

Example 8

3-cyclohexyl-6-methyl-6-phenyl-1,3-oxazinan-2-one

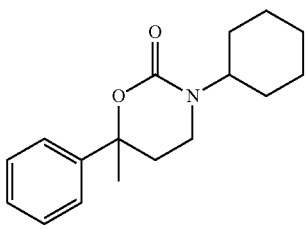 [SMILES: CC1(c2ccccc2)CCN(C2CCCCC2)C(=O)O1]

The title compound was prepared following procedures analogous to those described in Example 1 Steps 1-4 using cyclohexyl isocyanate in Step 4. LC-MS Method 3, $t_R$=1.529 min, m/z=274.1. $^1$H NMR (CDCl$_3$) 0.97-1.15 (m, 3H), 1.20-1.37 (m, 2H), 1.55 (d, 1H), 1.65 (m, 2H), 1.80-1.90 (m, 2H), 2.05 (s, 1H), 2.75 (m, 2H), 3.40 (b, 1H), 4.10 (t, 2H), 5.08 (s, 1H), 7.18 (m, 1H), 7.25 (m, 2H), 7.34 (dd, 2H).

Example 9

3-(biphenyl-3-yl)-6-methyl-6-phenyl-1,3-oxazinan-2-one

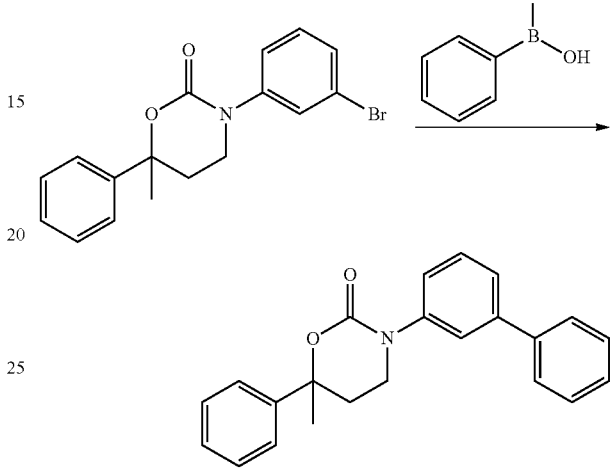

To a solution of 3-(3-bromophenyl)-6-methyl-6-phenyl-1,3-oxazinan-2-one (50 mg, 0.14 mmol) and phenylboronic acid (35 mg, 0.29 mmol) in THF (2 mL) was added a solution of NaHCO$_3$ (31 mg, 0.29 mmol) in H$_2$O (2 mL) followed by Pd(PPh$_3$)Cl$_2$ (9 mg, 0.01 mmol). The mixture was refluxed overnight. The mixture was concentrated to give the crude product, which was purified by column chromatography, followed by preparative HPLC to afford 3-(biphenyl-3-yl)-6-methyl-6-phenyl-1,3-oxazinan-2-one (10 mg, 20%). $^1$H NMR: (400 MHz, CDCl$_3$): δ 1.71 (s, 3H), 2.40 (m, 1H), 2.48 (m, 1H), 3.31 (m, 1H), 3.54 (m, 1H), 7.08 (m, 1H), 7.30 (m, 3H), 7.7.32-7.42 (m, 8H), 7.46 (m, 2H). LC-MS Method 3, $t_R$=1.362 min, m/z=344. $^1$H NMR (CDCl$_3$) 1.75 (s, 3H), 2.32-2.43 (m, 1H), 2.50 (m, 1H), 3.20 (m, 1H), 3.52 (m, 1H), 7.10 (d, 1H), 7.25-7.45 (m, 11H), 7.50 (d, 2H).

Example 10

3-(2'-chlorobiphenyl-3-yl)-6-methyl-6-phenyl-1,3-oxazinan-2-one

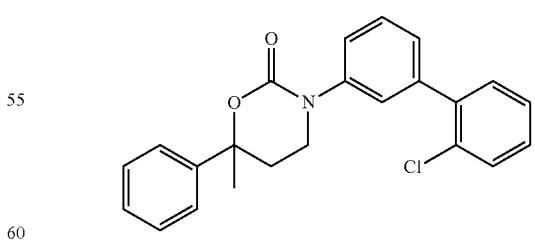

The title compound was prepared following procedures analogous to those in Example 9 using 2-chlorophenylboronic acid. LC-MS Method 3, $t_R$=1.479 min, m/z=378.1. $^1$H NMR (CDCl$_3$) 1.63 (s, 3H), 2.38 (m, 1H), 2.67 (m, 1H), 3.18-3.26 (m, 1H), 3.59 (m, 1H), 7.09 (m, 2H), 7.24 (m, 5H), 7.38 (m, 6H).

Example 11

3-(4'-Methanesulfonyl-biphenyl-3-yl)-6-methyl-6-phenyl-[1,3]oxazinan-2-one

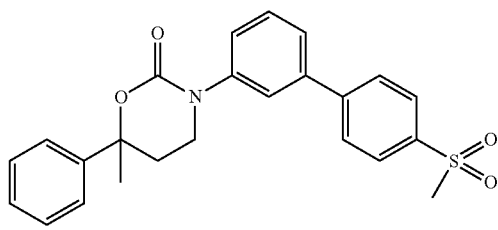 [SMILES: CC1(c2ccccc2)CCN(c2cccc(-c3ccc(S(C)(=O)=O)cc3)c2)C(=O)O1]

The title compound was prepared following procedures analogous to those in Example 9 using 4-(methylsulfonyl)phenylboronic acid. LC-MS Method 3, $t_R$=2.042 min, m/z=422.1. $^1$H NMR (CD$_3$OD) 1.69 (s, 3H), 2.40-2.50 (m, 1H), 2.50-2.60 (m, 1H), 3.20 (s, 1H), 3.51-3.60 (m, 1H), 4.5 (m, 1H), 7.05-7.11 (m, 2H), 7.20-7.30 (m, 5H), 7.30-7.45 (m, 6H).

Example 12

3'-(6-Methyl-2-oxo-6-phenyl-[1,3]oxazinan-3-yl)-biphenyl-2-carbonitrile

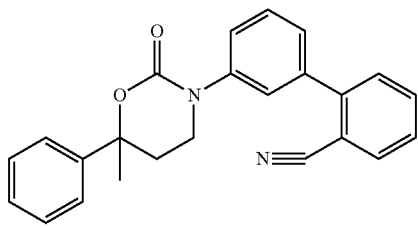 [SMILES: CC1(c2ccccc2)CCN(c2cccc(-c3ccccc3C#N)c2)C(=O)O1]

The title compound was prepared following procedures analogous to those in Example 9 using 2-cyanophenylboronic acid. LC-MS Method 3, $t_R$=1.376 min, m/z=369.1. $^1$H NMR (CD$_3$OD) 1.73 (s, 3H), 2.38-2.60 (m, 1H), 2.62-2.78 (m, 1H), 3.38-3.52 (m, 1H), 3.65-3.78 (m, 1H), 7.22-7.28 (m, 1H), 7.32-7.39 (m, 2H), 7.40-7.52 (m, 6H), 7.53-7.62 (m, 2H), 7.68-7.85 (m, 2H).

Example 13

N-isopropyl-3'-(6-methyl-2-oxo-6-phenyl-1,3-oxazinan-3-yl)biphenyl-4-sulfonamide

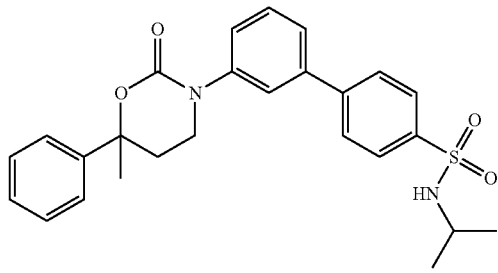 [SMILES: CC(C)NS(=O)(=O)c1ccc(-c2cccc(N3CCC(C)(c4ccccc4)OC3=O)c2)cc1]

The title compound was prepared following procedures analogous to those in Example 9 using 4-(isopropylaminosulfonyl)phenylboronic acid. LC-MS Method 3, $t_R$=1.566 min, m/z=465.1. $^1$H NMR (CDCl$_3$) 1.11-1.15 (m, 6H), 1.79 (s, 3H), 2.40-2.50 (m, 1H), 2.50-2.60 (m, 1H), 3.40 (s, 4H), 3.45-3.62 (m, 2H), 7.15-7.20 (m, 1H), 7.32-7.55 (m, 8H), 7.60-7.68 (m, 2H), 7.92-7.96 (m, 2H).

Example 14

N,N-dimethyl-3'-(6-methyl-2-oxo-6-phenyl-1,3-oxazinan-3-yl)biphenyl-3-sulfonamide

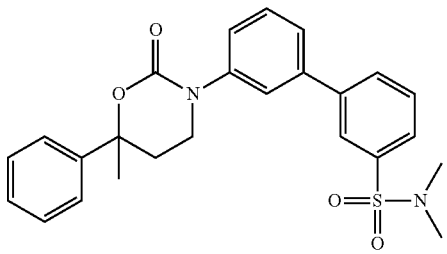 [SMILES: CN(C)S(=O)(=O)c1cccc(-c2cccc(N3CCC(C)(c4ccccc4)OC3=O)c2)c1]

The title compound was prepared following procedures analogous to those in Example 9 using 3-(dimethylaminosulfonyl)phenylboronic acid. LC-MS Method 3, $t_R$=1.459 min, m/z=451.1. $^1$H NMR (CDCl$_3$) 1.71 (s, 3H), 2.40-2.50 (m, 1H), 2.50-2.58 (m, 1H), 3.25-3.35 (m, 1H), 3.51-3.65 (m, 1H), 7.10-7.12 (m, 1H), 7.25-7.40 (m, 8H), 7.50-7.60 (m, 1H), 7.65-7.70 (m, 2H), 7.80-7.85 (m, 1H).

Example 15

6-methyl-3-(2'-(methylsulfonyl)biphenyl-3-yl)-6-phenyl-1,3-oxazinan-2-one

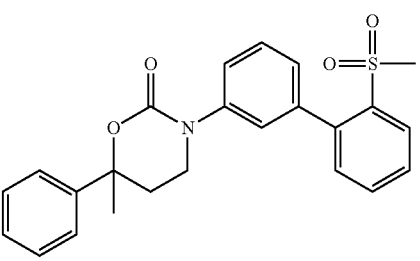 [SMILES: CC1(c2ccccc2)CCN(c2cccc(-c3ccccc3S(C)(=O)=O)c2)C(=O)O1]

The title compound was prepared following procedures analogous to those in Example 9 using 2-(methylsulfonyl)phenylboronic acid. LC-MS Method 3, $t_R$=1.464 min, m/z=422. $^1$H NMR (CDCl$_3$) 1.77 (s, 3H), 2.40-2.50 (m, 1H), 2.50-2.60 (m, 1H), 2.60-2.68 (m, 3H), 3.38-3.48 (m, 1H), 3.62-3.70 (m, 1H), 4.90-5.02 (s, 2H), 7.30-7.45 (m, 5H), 7.45-7.50 (m, 5H), 7.52-7.70 (m, 2H), 8.20-8.25 (m, 1H).

Example 16

6-methyl-6-phenyl-3-(4'-(pyrrolidin-1-ylsulfonyl)biphenyl-3-yl)-1,3-oxazinan-2-one

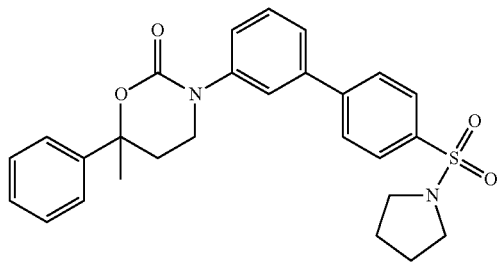 [SMILES: CC1(c2ccccc2)CCN(c2cccc(-c3ccc(S(=O)(=O)N4CCCC4)cc3)c2)C(=O)O1]

The title compound was prepared following procedures analogous to those in Example 9 using 4-(pyrrolidin-1-ylsulfonyl)phenylboronic acid. LC-MS Method 3, $t_R$=1.504 min, m/z=477.2. $^1$H NMR (CDCl$_3$) 1.72-1.75 (m, 7H), 2.35-2.42 (m, 1H), 2.45-2.52 (m, 1H), 3.20-3.28 (m, 6H), 3.30-3.35 (m, 1H), 3.50-3.58 (m, 1H), 7.10-7.15 (m, 1H), 7.26-7.40 (m, 4H), 7.52-7.60 (m, 2H), 7.60-7.70 (m, 2H), 7.80-7.90 (m, 3H).

Example 17

3'-(6-methyl-2-oxo-6-phenyl-1,3-oxazinan-3-yl)biphenyl-3-carbonitrile

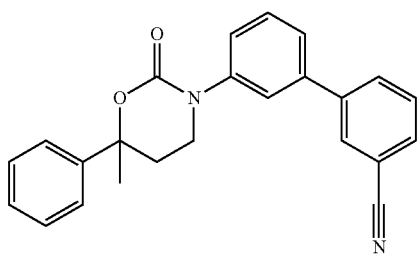 [SMILES: CC1(c2ccccc2)CCN(c2cccc(-c3cccc(C#N)c3)c2)C(=O)O1]

The title compound was prepared following procedures analogous to those in Example 9 using 3-cyanophenylboronic acid. LC-MS Method 3, $t_R$=1.487 min, m/z=369.1. $^1$H NMR (CDCl$_3$) 1.72 (s, 3H), 2.32-2.58 (m, 2H), 3.25-3.38 (m, 1H), 3.45-3.57 (m, 1H), 7.12-7.18 (m, 1H), 7.25-7.32 (m, 2H), 7.33-7.42 (m, 6H), 7.42-7.50 (m, 1H), 7.52-7.58 (m, 1H), 7.66-7.75 (m, 2H).

Example 18

N-(2-methoxyethyl)-3'-(6-methyl-2-oxo-6-phenyl-1,3-oxazinan-3-yl)biphenyl-3-carboxamide

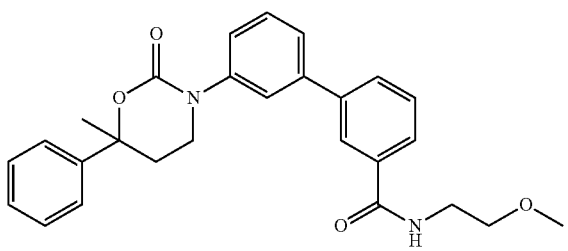 [SMILES: COCCNC(=O)c1cccc(-c2cccc(N3CCC(C)(c4ccccc4)OC3=O)c2)c1]

The title compound was prepared following procedures analogous to those in Example 9 using 3-(2-methoxyethylcarbamoyl)phenylboronic acid. LC-MS Method 3, $t_R$=1.328 min, m/z=445.2. $^1$H NMR (CDCl$_3$) 1.70 (s, 3H), 2.45 (m, 2H), 3.27 (m, 1H), 3.33 (s, 3H), 3.50 (m, 3H), 3.65 (m, 2H), 6.52 (m, 1H), 7.10 (m, 1H), 7.30-7.47 (m, 10H), 7.60 (m, 1H), 7.68 (m, 1H), 7.90 (s, 1H).

Example 19

N-((3'-(6-methyl-2-oxo-6-phenyl-1,3-oxazinan-3-yl)biphenyl-4-yl)methyl)methanesulfonamide

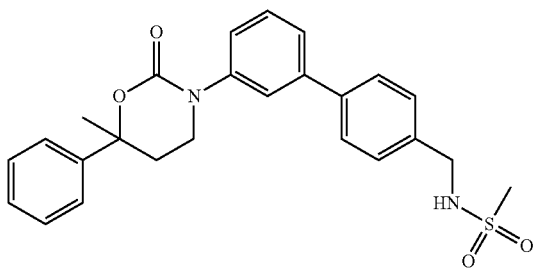 [SMILES: CC1(c2ccccc2)CCN(c2cccc(-c3ccc(CNS(C)(=O)=O)cc3)c2)C(=O)O1]

The title compound was prepared following procedures analogous to those in Example 9 using 4-(methylsulfonamidomethyl)phenylboronic acid. LC-MS Method 3, $t_R$=1.19 min, m/z=450.9. $^1$H NMR (CDCl$_3$) 1.70 (s, 3H), 2.35-2.60 (m, 2H), 2.95 (s, 3H), 3.35 (m, 1H), 3.60 (m, 1H), 4.40 (m, 2H), 4.65 (b, 1H), 6.95-7.20 (m, 3H), 7.30-7.60 (m, 11H).

Example 20

6-methyl-6-phenyl-3-(3-(pyridin-3-yl)phenyl)-1,3-oxazinan-2-one

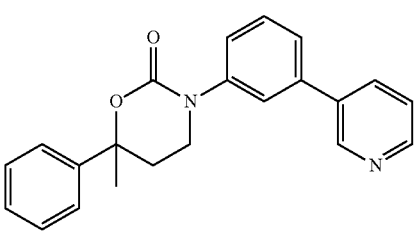 [SMILES: CC1(c2ccccc2)CCN(c2cccc(-c3cccnc3)c2)C(=O)O1]

The title compound was prepared following procedures analogous to those in Example 9 using 3-pyridylboronic acid. LC-MS Method 2, $t_R$=1.819 min, m/z=345.1. $^1$H NMR (CDCl$_3$) 1.80 (s, 3H), 2.45-2.65 (m, 2H), 3.40 (m, 1H), 3.62 (m, 1H), 7.30-7.60 (m, 8H), 7.85 (m, 1H), 8.40 (m, 1H), 8.75 (m, 1H), 9.00 (m, 1H), 9.30-9.50 (b, 2H).

Example 21

3-(2'-methoxybiphenyl-3-yl)-6-methyl-6-phenyl-1,3-oxazinan-2-one

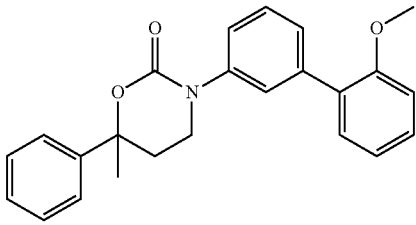 [SMILES: COc1ccccc1-c1cccc(N2CCC(C)(c3ccccc3)OC2=O)c1]

The title compound was prepared following procedures analogous to those in Example 9 using 2-methoxyphenylboronic acid. LC-MS Method 3, $t_R$=1.55 min, m/z=374.1. 1H NMR (CDCl3) 1.69 (s, 3H), 2.36 (m, 1H), 2.46 (m, 1H), 3.31 (m, 1H), 3.52 (m, 1H), 4.5 (m, 1H), 5.17 (m, 1H), 7.06 (m, 1H), 7.12 (m, 1H), 7.18 (m, 1H), 7.28 (m, 3H), 7.33 (m, 2H), 7.38 (m, 4H), 7.45 (m, 1H).

Example 22

3-(2',6'-dichlorobiphenyl-3-yl)-6-methyl-6-phenyl-1,3-oxazinan-2-one

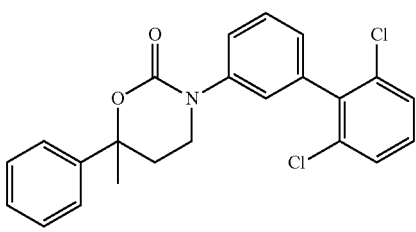 [SMILES: CC1(c2ccccc2)CCN(c2cccc(-c3c(Cl)cccc3Cl)c2)C(=O)O1]

The title compound was prepared following procedures analogous to those in Example 9 using 2,6-dichlorophenylboronic acid. LC-MS Method 3, $t_R$=1.676 min, m/z=412. 1H NMR (CDCl3) 1.69 (s, 3H), 2.36 (m, 1H), 2.45 (m, 1H), 3.30 (m, 1H), 3.50 (m, 1H), 7.05 (m, 2H), 7.16 (m, 1H), 7.25 (m, 2H), 7.30 (m, 1H), 7.32 (m, 1H), 7.40 (m, 5H).

Example 23

3-(2',4'-difluorobiphenyl-3-yl)-6-methyl-6-phenyl-1,3-oxazinan-2-one

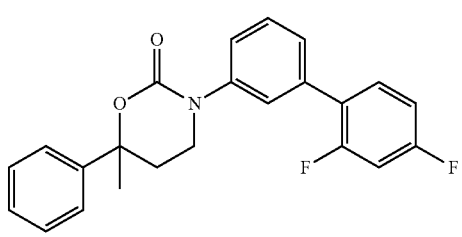 [SMILES: CC1(c2ccccc2)CCN(c2cccc(-c3ccc(F)cc3F)c2)C(=O)O1]

The title compound was prepared following procedures analogous to those in Example 9 using 2,4-difluorophenylboronic acid. LC-MS Method 3, $t_R$=1.595 min, m/z=380.1. 1H NMR (CDCl$_3$) 1.69 (s, 3H), 2.30-2.50 (m, 2H), 3.28 (m, 1H), 3.50 (m, 1H), 6.86 (m, 2H), 7.13 (m, 1H), 7.21 (m, 1H), 7.28 (m, 3H), 7.35 (m, 5H).

Example 24

3-(3'-chlorobiphenyl-3-yl)-6-methyl-6-phenyl-1,3-oxazinan-2-one

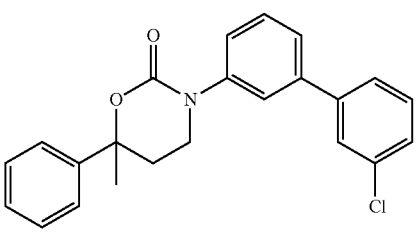 [SMILES: CC1(c2ccccc2)CCN(c2cccc(-c3cccc(Cl)c3)c2)C(=O)O1]

The title compound was prepared following procedures analogous to those in Example 9 using 3-chlorophenylboronic acid. LC-MS Method 3, $t_R$=1.67 min, m/z=378. 1H NMR (CDCl$_3$) (s, 3H), 2.36 (m, 1H), 2.48 (m, 1H), 3.28 (m, 1H), 3.49 (m, 1H), 7.12 (m, 1H), 7.27 (m, 4H), 7.32 (m, 3H), 7.38 (m, 4H), 7.42 (m, 1H).

Example 25

3-(3'-fluorobiphenyl-3-yl)-6-methyl-6-phenyl-1,3-oxazinan-2-one

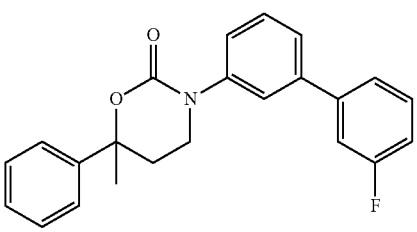 [SMILES: CC1(c2ccccc2)CCN(c2cccc(-c3cccc(F)c3)c2)C(=O)O1]

The title compound was prepared following procedures analogous to those in Example 9 using 3-fluorophenylboronic acid. LC-MS Method 3, $t_R$=1.69 min, m/z=362.1. 1H NMR (CDCl3) 1.68 (s, 3H), 2.46 (m, 1H), 2.57 (m, 1H), 3.38 (m, 1H), 3.62 (m, 1H), 7.06 (m, 1H), 7.17 (m, 1H), 7.23 (m, 1H), 7.32 (m, 2H), 7.38 (m, 2H), 7.48 (m, 6H).

Example 26

3-(2',5'-difluorobiphenyl-3-yl)-6-methyl-6-phenyl-1,3-oxazinan-2-one

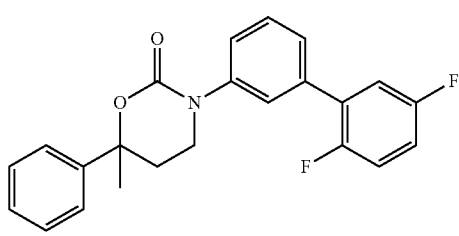 [SMILES: CC1(c2ccccc2)CCN(c2cccc(-c3cc(F)ccc3F)c2)C(=O)O1]

The title compound was prepared following procedures analogous to those in Example 9 using 2,5-difluorophenylboronic acid. LC-MS Method 3, $t_R$=1.686 min, m/z=380.1. 1H NMR (CDCl3) 1.77 (s, 3H), 2.42 (m, 1H), 2.55 (m, 1H), 3.35 (m, 1H), 3.58 (m, 1H), 6.98 (m, 1H), 7.08 (m, 2H), 7.23 (m, 1H), 7.35 (m, 2H), 7.43 (m, 6H).

Example 27

3-(3',5'-difluorobiphenyl-3-yl)-6-methyl-6-phenyl-1,3-oxazinan-2-one

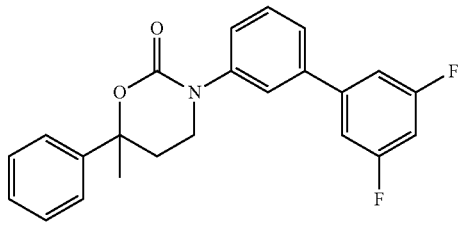 [SMILES: CC1(c2ccccc2)CCN(c2cccc(-c3cc(F)cc(F)c3)c2)C(=O)O1]

The title compound was prepared following procedures analogous to those in Example 9 using 3,5-difluorophenylboronic acid. LC-MS Method 3, $t_R$=1.468 min, m/z=379.9. 1H NMR (CDCl3) 1.78 (s, 3H), 2.42 (m, 1H), 2.56 (m, 1H), 3.37 (m, 1H), 3.58 (m, 1H), 6.78 (m, 1H), 7.03 (m, 2H), 7.23 (m, 1H), 7.32 (m, 1H), 7.38 (m, 1H), 7.42 (m, 2H), 7.48 (m, 4H).

Example 28

3-(4'-fluorobiphenyl-3-yl)-6-methyl-6-phenyl-1,3-oxazinan-2-one

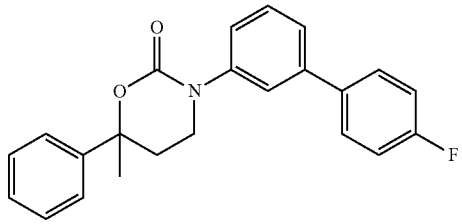 [SMILES: CC1(c2ccccc2)CCN(c2cccc(-c3ccc(F)cc3)c2)C(=O)O1]

The title compound was prepared following procedures analogous to those in Example 9 using 4-fluorophenylboronic acid. LC-MS Method 3, $t_R$=1.38 min, m/z=362.1. $^1$H NMR (CDCl$_3$) 1.77 (s, 3H), 2.42 (m, 1H), 2.55 (m, 1H), 3.35 (m, 1H), 3.58 (m, 1H), 7.13 (m, 3H), 7.32 (m, 1H), 7.36 (m, 1H), 7.39 (m, 2H), 7.48 (m, 6H).

Chiral preparative SFC using a ChiralCel-AS, 400×25 mm I.D, 20 μm (Daicel Chemical Industries, Ltd) column maintained at 35 C eluted with 60:40 supercritical CO$_2$/0.1% diethylamine in MeOH at a flow rate of 70 mL min$^{-1}$ and a nozzle pressure of 100 bar afforded the two enantiomers.

Isomer 1: LC-MS Method 3, $t_R$=1.38 min, m/z=362.1. 1H NMR (CDCl3) 1.81 (s, 3H), 2.41-2.50 (m, 2H), 3.35 (m, 1H), 3.51 (m, 1H), 7.15 (m, 3H), 7.33-7.52 (m, 10H).

Isomer 2: LC-MS Method 3, $t_R$=1.392 min, m/z=362.1. 1H NMR (CDCl3) 1.70 (s, 3H), 2.32-2.50 (m, 2H), 3.28 (m, 1H), 3.51 (m, 1H), 7.05 (m, 3H), 7.22-7.45 (m, 10H).

Example 29

N-(3'-(6-methyl-2-oxo-6-phenyl-1,3-oxazinan-3-yl)biphenyl-3-yl)methanesulfonamide

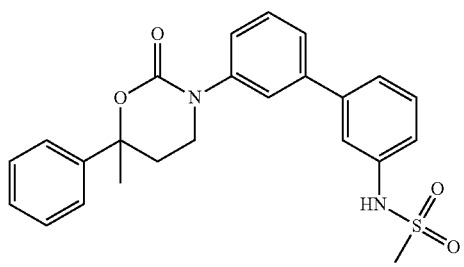 [SMILES: CC1(c2ccccc2)CCN(c2cccc(-c3cccc(NS(C)(=O)=O)c3)c2)C(=O)O1]

The title compound was prepared following procedures analogous to those in Example 9 using 3-(methylsulfonylamino)phenylboronic acid. LC-MS Method 3, $t_R$=1.626 min, m/z=437.1. 1H NMR (CDCl3) 1.70 (s, 3H), 2.34-2.50 (m, 2H), 2.98 (s, 3H), 3.21 (m, 1H), 3.51 (m, 1H), 6.48 (m, 1H), 7.05 (m, 1H), 7.18 (m, 1H), 7.25-7.40 (m, 11H).

Example 30

N-methyl-3'-(6-methyl-2-oxo-6-phenyl-1,3-oxazinan-3-yl)biphenyl-3-sulfonamide

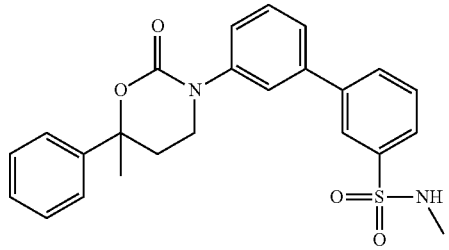 [SMILES: CNS(=O)(=O)c1cccc(-c2cccc(N3CCC(C)(c4ccccc4)OC3=O)c2)c1]

The title compound was prepared following procedures analogous to those in Example 9 using 3-(methylaminosulfonyl)phenylboronic acid. LC-MS Method 3, $t_R$=1.184 min, m/z=437.1. $^1$H NMR (CDCl$_3$) 1.11-1.13 (m, 6H), 1.70 (m, 3H), 2.40-2.50 (m, 1H), 2.50-2.60 (m, 1H), 3.20-3.49 (s, 4H), 3.49-3.65 (m, 2H), 7.15-7.21 (m, 1H), 7.31-7.56 (m, 8H), 7.62-7.68 (m, 2H), 7.90-7.96 (m, 2H).

Example 31

N-methyl-3'-(6-methyl-2-oxo-6-phenyl-1,3-oxazinan-3-yl)biphenyl-3-carboxamide

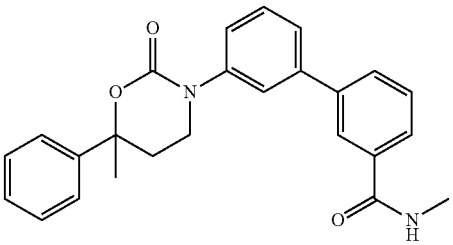 [SMILES: CNC(=O)c1cccc(-c2cccc(N3CCC(C)(c4ccccc4)OC3=O)c2)c1]

The title compound was prepared following procedures analogous to those in Example 9 using 3-(methylcarbamoyl)phenylboronic acid. LC-MS Method 3, $t_R$=1.11 min, m/z=401.1. $^1$H NMR (CDCl$_3$) 1.70 (s, 3H), 2.35 (m, 1H), 2.46 (m, 1H), 2.95 (s, 3H), 3.30 (m, 1H), 3.50 (m, 1H), 6.45 (m, 1H), 7.17 (m, 1H), 7.30 (m, 2H), 7.38 (m, 6H), 7.55 (m, 1H), 7.65 (m, 1H), 7.80 (s, 1H).

Example 32

3-(3'-aminobiphenyl-3-yl)-6-methyl-6-phenyl-1,3-oxazinan-2-one

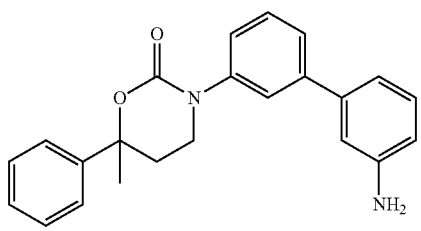 [SMILES: CC1(c2ccccc2)CCN(c2cccc(-c3cccc(N)c3)c2)C(=O)O1]

The title compound was prepared following procedures analogous to those in Example 9 using 3-aminophenylboronic acid. LC-MS Method 2, $t_R$=1.761 min, m/z=359.1. $^1$H NMR (CDCl$_3$) 1.70 (s, 3H), 2.30-2.50 (m, 2H), 3.30 (m, 1H), 3.50 (m, 1H), 6.62 (m, 1H), 6.80-6.90 (m, 2H), 7.05-7.47 (m, 10H).

Example 33

6-methyl-6-phenyl-3-(3-(pyridin-4-yl)phenyl)-1,3-oxazinan-2-one

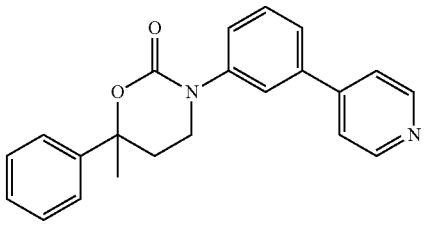 [SMILES: CC1(c2ccccc2)CCN(c2cccc(-c3ccncc3)c2)C(=O)O1]

The title compound was prepared following procedures analogous to those in Example 9 using 4-pyridylboronic acid. LC-MS Method 2, $t_R$=1.329 min, m/z=345.1. $^1$H NMR (CDCl$_3$) 1.70 (s, 3H), 2.30-2.50 (m, 2H), 3.30 (m, 1H), 3.50 (m, 1H), 4.10 (m, 2H), 7.27-7.50 (m, 9H), 8.60 (b, 1H).

Example 34

3-(3'-methoxybiphenyl-3-yl)-6-methyl-6-phenyl-1,3-oxazinan-2-one

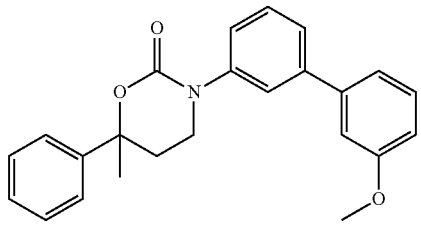 [SMILES: COc1cccc(-c2cccc(N3CCC(C)(c4ccccc4)OC3=O)c2)c1]

The title compound was prepared following procedures analogous to those in Example 9 using 3-methoxyphenylboronic acid. LC-MS Method 3, $t_R$=1.392 min, m/z=374.1. $^1$H NMR (CDCl$_3$) 1.70 (s, 3H), 2.30-2.50 (m, 2H), 3.30 (m, 1H), 3.50 (m, 1H), 3.80 (s, 3H), 6.85 (m, 1H), 7.00-7.45 (m, 12H).

Example 35

3-(2'-(hydroxymethyl)biphenyl-3-yl)-6-methyl-6-phenyl-1,3-oxazinan-2-one

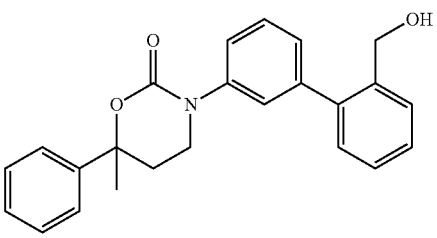 [SMILES: CC1(c2ccccc2)CCN(c2cccc(-c3ccccc3CO)c2)C(=O)O1]

The title compound was prepared following procedures analogous to those in Example 9 using 2-hydroxymethylphenylboronic acid. LC-MS Method 3, $t_R$=1.375 min, m/z=769.3. 1H NMR (CDCl3) 1.69 (s, 3H), 2.36 (m, 1H), 2.46 (m, 1H), 3.31 (m, 1H), 3.52 (m, 1H), 4.5 (m, 1H), 5.17 (m, 1H), 7.06 (m, 1H), 7.12 (m, 1H), 7.18 (m, 1H), 7.28 (m, 3H), 7.33 (m, 2H), 7.38 (m, 4H), 7.45 (m, 1H).

Example 36

6-methyl-6-phenyl-3-(3-(thiophen-2-yl)phenyl)-1,3-oxazinan-2-one

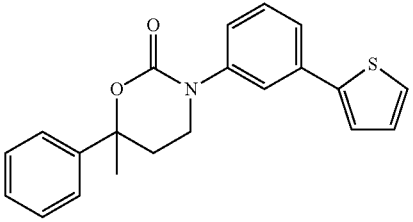 [SMILES: CC1(c2ccccc2)CCN(c2cccc(-c3cccs3)c2)C(=O)O1]

The title compound was prepared following procedures analogous to those in Example 9 using 2-thienylboronic acid. LC-MS Method 3, $t_R$=1.721 min, m/z=350. 1H NMR (CDCl3) 1.69 (s, 3H), 2.33-2.50 (m, 2H), 3.27 (m, 1H), 3.52 (m, 1H), 3.71 (S, 3H), 6.94 (m, 1H), 7.09 (m, 1H), 7.21-7.40 (m, 11H).

Example 37

3-(2'-fluorobiphenyl-3-yl)-6-methyl-6-phenyl-1,3-oxazinan-2-one

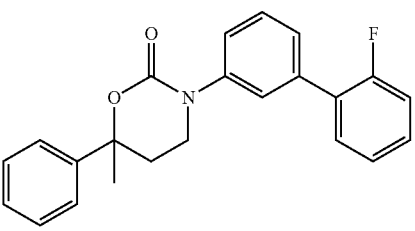 [SMILES: CC1(c2ccccc2)CCN(c2cccc(-c3ccccc3F)c2)C(=O)O1]

The title compound was prepared following procedures analogous to those in Example 9 using 2-fluorophenylboronic acid. LC-MS Method 3, $t_R$=1.772 min, m/z=362.1. $^1$H NMR (CDCl$_3$) 1.15 (s, 3H), 2.30-2.53 (m, 2H), 3.30 (m, 1H), 3.50 (m, 1H), 7.08 (m, 3H), 7.25 (m, 2H), 7.32 (m, 3H), 7.38 (m, 5H).

Example 38 methyl 3'-(6-methyl-2-oxo-6-phenyl-1,3-oxazinan-3-yl)biphenyl-3-carboxylate

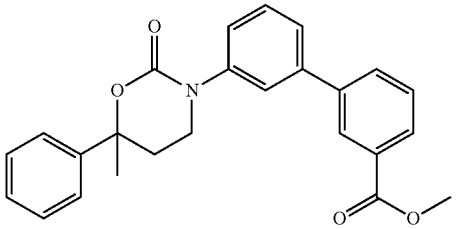 [SMILES: COC(=O)c1cccc(-c2cccc(N3CCC(C)(c4ccccc4)OC3=O)c2)c1]

The title compound was prepared following procedures analogous to those in Example 9 using 3-methoxycarbonylphenylboronic acid. LC-MS Method 3, $t_R$=1.745 min, m/z=402.1. $^1$H NMR (CDCl$_3$) 1.20 (s, 3H), 2.32-2.50 (m, 2H), 3.30 (m, 1H), 3.55 (m, 1H), 3.89 (s, 3H), 7.10 (m, 1H), 7.30-7.47 (m, 9H), 7.65 (m, 1H), 7.95 (m, 1H), 8.12 (m, 1H).

Example 39

3-(3'-(hydroxymethyl)biphenyl-3-yl)-6-methyl-6-phenyl-1,3-oxazinan-2-one

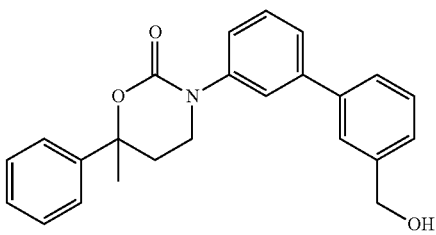 [SMILES: CC1(c2ccccc2)CCN(c2cccc(-c3cccc(CO)c3)c2)C(=O)O1]

The title compound was prepared following procedures analogous to those in Example 9 using 3-hydroxymethylphenylboronic acid. LC-MS Method 3, $t_R$=1.35 min, m/z=374.1. $^1$H NMR (CDCl$_3$) 1.70 (s, 3H), 2.30-2.50 (m, 2H), 3.30 (m, 1H), 4.70 (d, 2H), 7.05 (m, 1H), 7.27-7.55 (m, 13H).

Example 40

6-methyl-3-(3'-(methylsulfonyl)biphenyl-3-yl)-6-phenyl-1,3-oxazinan-2-one

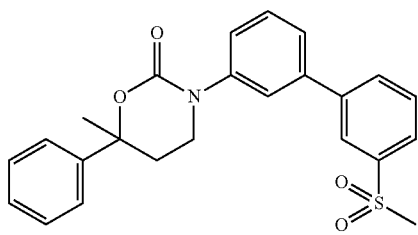 [SMILES: CC1(c2ccccc2)CCN(c2cccc(-c3cccc(S(C)(=O)=O)c3)c2)C(=O)O1]

The title compound was prepared following procedures analogous to those in Example 9 using 3-(methylsulfonyl)phenylboronic acid. LC-MS Method 3, $t_R$=1.172 min, m/z=422.1. $^1$H NMR (CDCl$_3$) 1.71 (s, 3H), 2.37-2.44 (m, 1H), 2.46-2.52 (m, 1H), 3.02 (s, 3H), 3.27-3.35 (m, 1H), 3.51-3.58 (m, 1H), 7.11 (d, 1H), 7.26 (m, 1H), 7.35-7.42 (m, 6H), 7.52-7.58 (t, 2H), 7.75 (d, 1H), 7.88 (d, 1H), 8.01 (s, 1H).

Example 41

N-((3'-(6-methyl-2-oxo-6-phenyl-1,3-oxazinan-3-yl)biphenyl-3-yl)methyl)acetamide

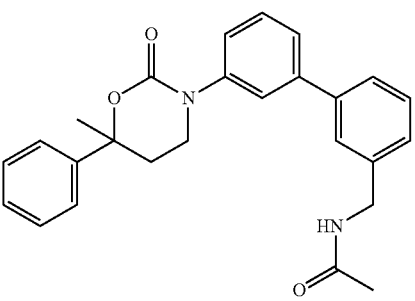 [SMILES: CC(=O)NCc1cccc(-c2cccc(N3CCC(C)(c4ccccc4)OC3=O)c2)c1]

The title compound was prepared following procedures analogous to those in Example 9 using 3-(acetamidomethyl)phenylboronic acid. LC-MS Method 3, $t_R$=1.329 min, m/z=415.2. 1H NMR (CDCl3) 1.70 (s, 3H), 2.00 (s, 3H), 2.38 (m, 1H), 2.50 (m, 1H), 3.30 (m, 1H), 3.52 (m, 1H), 4.40 (m, 2H), 6.35 (m, 1H), 7.27-7.62 (m, 19H).

Example 42

N,N-dimethyl-3'-(6-methyl-2-oxo-6-phenyl-1,3-oxazinan-3-yl)biphenyl-4-carboxamide

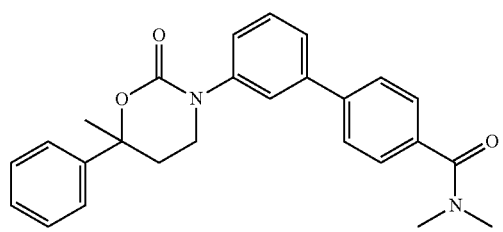 [SMILES: CN(C)C(=O)c1ccc(-c2cccc(N3CCC(C)(c4ccccc4)OC3=O)c2)cc1]

The title compound was prepared following procedures analogous to those in Example 9 using 4-(dimethylcarbamoyl)phenylboronic acid. LC-MS Method 3, $t_R$=1.157 min, m/z=415.1. 1H NMR (CDCl3) 1.70 (s, 2H), 2.30-2.50 (m, 2H), 2.85 (m, 1H), 2.97 (s, 3H), 3.10 (s, 3H), 3.30 (m, 1H), 3.50 (m, 1H), 7.00-7.60 (m, 14H).

Example 43

3-(4'-hydroxybiphenyl-3-yl)-6-methyl-6-phenyl-1,3-oxazinan-2-one

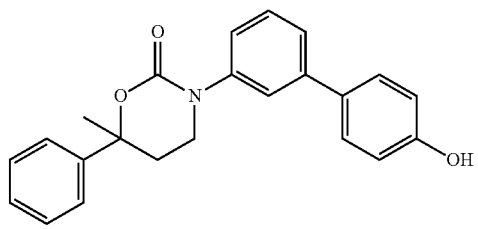 [SMILES: CC1(c2ccccc2)CCN(c2cccc(-c3ccc(O)cc3)c2)C(=O)O1]

The title compound was prepared following procedures analogous to those in Example 9 using 4-hydroxyphenylboronic acid. LC-MS Method 3, $t_R$=1.381 min, m/z=360.1. 1H NMR (CDCl3) 1.70 (s, 3H), 2.35-2.50 (m, 2H), 3.30 (m, 1H), 3.50 (m, 1H), 6.80 (m, 2H), 7.0 (m, 1H), 7.20-7.65 (m, 12H).

Example 44

3'-(6-methyl-2-oxo-6-phenyl-1,3-oxazinan-3-yl)biphenyl-4-carboxamide

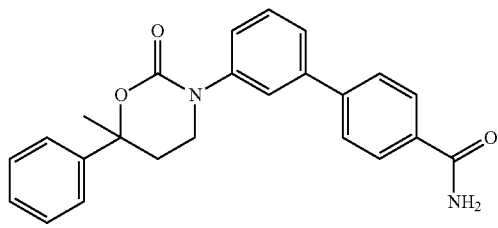 [SMILES: CC1(c2ccccc2)CCN(c2cccc(-c3ccc(C(N)=O)cc3)c2)C(=O)O1]

The title compound was prepared following procedures analogous to those in Example 9 using 4-(carbamoyl)phenylboronic acid. LC-MS Method 2, $t_R$=1.999 min, m/z=386.9. $^1$H NMR (CDCl$_3$) 1.79 (s, 3H), 1.930 (s, 3H), 2.46 (m, 1H), 2.52 (m, 1H), 3.38 (m, 1H), 3.62 (m, 1H), 6.46 (m, 1H), 7.26 (m, 1H), 7.2 (m, 1H), 7.38 (m, 2H), 7.43 (m, 5H), 7.48 (m, 1H), 7.13 (m, 2H), 7.17 (m, 1H), 7.88 (m, 1H).

Example 45

N-(3'-(6-methyl-2-oxo-6-phenyl-1,3-oxazinan-3-yl)biphenyl-2-yl)methanesulfonamide

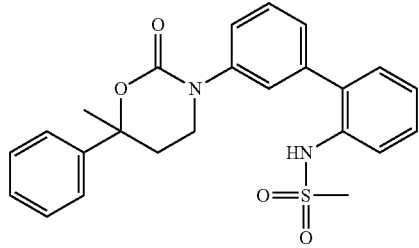 [SMILES: CC1(c2ccccc2)CCN(c2cccc(-c3ccccc3NS(C)(=O)=O)c2)C(=O)O1]

The title compound was prepared following procedures analogous to those in Example 9 using 2-(methylsulfonylamino)phenylboronic acid. LC-MS Method 3, $t_R$=1.167 min, m/z=437.1. $^1$H NMR (CDCl$_3$) 1.69 (s, 3H), 2.32-2.41 (m, 1H), 2.46-2.52 (m, 1H), 2.86 (s, 2H), 3.30-3.40 (m, 1H), 3.40-3.60 (m, 1H), 6.50 (s, 1H), 7.10-7.18 (m, 4H), 7.20-7.40 (m, 8H), 7.51-7.59 (m, 1H).

Example 46 methyl 3'-(6-methyl-2-oxo-6-phenyl-1,3-oxazinan-3-yl)biphenyl-4-carboxylate

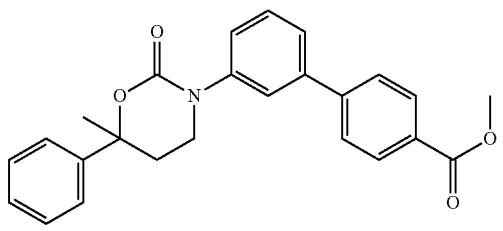 [SMILES: COC(=O)c1ccc(-c2cccc(N3CCC(C)(c4ccccc4)OC3=O)c2)cc1]

The title compound was prepared following procedures analogous to those in Example 9 using 4-(methoxycarbonyl)phenylboronic acid. LC-MS Method 3, $t_R$=1.359 min, m/z=402.1. 1H NMR (CDCl3) 1.80 (s, 3H), 2.42-2.62 (m, 2H), 3.38-3.44 (m, 1H), 3.60 (m, 1H), 3.95 (s, 3H), 7.19 (d, 1H), 7.34-7.53 (m, 8H), 7.60 (d, 2H), 8.10 (d, 2H).

Example 47

N-methyl-3'-(6-methyl-2-oxo-6-phenyl-1,3-oxazinan-3-yl)biphenyl-4-sulfonamide

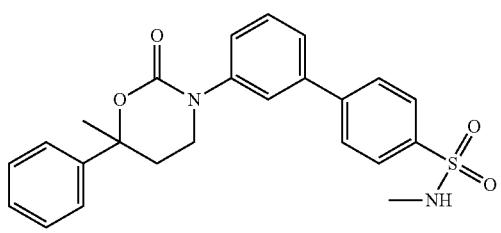 [SMILES: CNS(=O)(=O)c1ccc(-c2cccc(N3CCC(C)(c4ccccc4)OC3=O)c2)cc1]

The title compound was prepared following procedures analogous to those in Example 9 using 4-(methylaminosulfonyl)phenylboronic acid. LC-MS Method 3, $t_R$=1.403 min, m/z=437.1. 1H NMR (CDCl3) 1.70 (s, 3H), 2.40-2.50 (m, 1H), 2.50-2.60 (m, 1H), 3.20 (s, 3H), 3.32-3.42 (m, 1H), 3.52-3.62 (m, 1H), 7.15-7.20 (m, 1H), 7.30-7.50 (m, 8H), 7.60-7.70 (m, 2H), 7.86-7.95 (m, 2H).

Example 48

3-(4'-(hydroxymethyl)biphenyl-3-yl)-6-methyl-6-phenyl-1,3-oxazinan-2-one

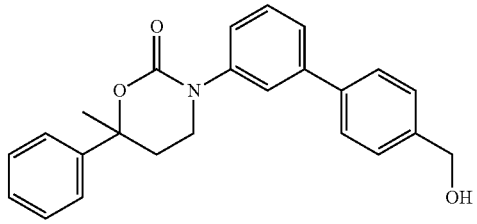 [SMILES: CC1(c2ccccc2)CCN(c2cccc(-c3ccc(CO)cc3)c2)C(=O)O1]

The title compound was prepared following procedures analogous to those in Example 9 using 4-(hydroxmethyl) phenylboronic acid. LC-MS Method 3, $t_R$=1.123 min, m/z=374.1. 1H NMR (CDCl3) 1.80 (s, 3H), 2.40-2.60 (m, 2H), 3.35 (m, 1H), 3.60 (m, 1H), 4.75 (d, 2H), 7.15 (m, 1H), 7.34-7.62 (m, 13H).

Example 49

3-(3'-(1H-tetrazol-5-yl)biphenyl-3-yl)-6-methyl-6-phenyl-1,3-oxazinan-2-one

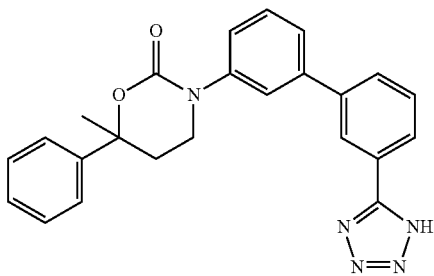 [SMILES: CC1(c2ccccc2)CCN(c2cccc(-c3cccc(-c4nnn[nH]4)c3)c2)C(=O)O1]

The title compound was prepared following procedures analogous to those in Example 9 using 3-(2H-tetrazol-5-yl) phenylboronic acid. LC-MS Method 3, $t_R$=1.341 min, m/z=412.2. $^1$H NMR (CDCl$_3$) 1.85 (s, 3H), 2.50-2.70 (m, 2H), 3.40 (m, 1H), 3.65 (m, 1H), 7.05 (d, 1H), 7.20-7.35 (m, 3H), 7.40-7.50 (m, 3H), 7.52 (m, 4H), 7.80 (s, 1H), 7.90 (d, 1H).

Example 50

3-(6-(2-chloro-4-fluorophenyl)pyridin-2-yl)-6-(2-fluorophenyl)-6-(2-hydroxyethyl)-1,3-oxazinan-2-one

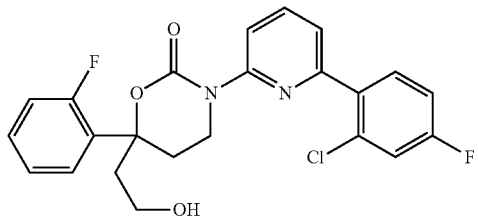 [SMILES: O=C1OC(CCO)(c2ccccc2F)CCN1c1cccc(-c2ccc(F)cc2Cl)n1]

The title compound was prepared by application of procedures analogous to those described in Example 63 using o-fluoroacetophenone in Step 1 and 2-amino-6-bromopyridine in Step 2, followed by Example 74 and Example 75 Step 1 using 2-chloro-4-fluorophenylboronic acid. LC-MS Method 3, $t_R$=1.381 min, m/z=444.11. $^1$H NMR (CD$_3$OD) δ=2.20-2.60 (m, 3H), 2.75 (dd, 1H), 3.42 (m, 2H), 3.72 (m, 1H), 4.15 (m, 1H), 7.03-7.30 (m, 4H), 7.42 (m, 3H), 7.55 (m, 1H), 7.75 (m, 2H).

Example 51

2-(3-((1S)-1-(2',4'-difluorobiphenyl-4-yl)ethyl)-6-(4-fluorophenyl)-2-oxo-1,3-oxazinan-6-yl)acetamide

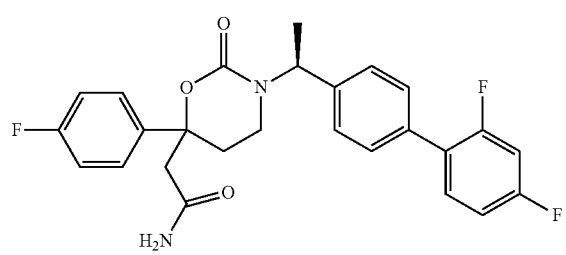 [SMILES: C[C@@H](c1ccc(-c2ccc(F)cc2F)cc1)N1CCC(CC(N)=O)(c2ccc(F)cc2)OC1=O]

The title compound was prepared from 3-((S)-1-(2',4'-difluorobiphenyl-4-yl)ethyl)-6-(4-fluorophenyl)-6-(2-hydroxyethyl)-1,3-oxazinan-2-one by application of procedures analogous to those described in Example 70 followed by Example 76. Two isomers were isolated.

Isomer 1: 2-((S)-3-((S)-1-(2',4'-difluorobiphenyl-4-yl)ethyl)-6-(4-fluorophenyl)-2-oxo-1,3-oxazinan-6-yl)acetamide LC-MS Method 1, $t_R$=1.71 min, m/z=469. $^1$H NMR (CDCl$_3$) 7.25-7.33 (m, 5H), 6.86-7.06 (m, 6H), 5.66 (q, 1H), 2.95-2.99 (m, 1H), 2.83 (d, 1H), 2.72 (d, 1H), 2.30-2.50 (m, 3H), 2.55 (d, 3H).

Isomer 2: 2-((R)-3-((S)-1-(2',4'-difluorobiphenyl-4-yl)ethyl)-6-(4-fluorophenyl)-2-oxo-1,3-oxazinan-6-yl)acetamide LC-MS Method 1 $t_R$=1.75 min, m/z=469 (M+1); $^1$H NMR (CDCl$_3$) 7.49-6.88 (m, 11H), 6.19 (br s, 1H), 5.75 (q, J=6.8 Hz, 1H), 5.46 (br s, 1H), 2.85-2.69 (m, 4H), 2.43-2.38 (m, 1H), 2.29-2.21 (m, 1H), 1.33 (d, J=6.8 Hz, 3H).

Example 52

(6S)-3-((S)-1-(2',4'-difluorobiphenyl-4-yl)ethyl)-6-(2,3-dihydroxypropyl)-6-(4-fluorophenyl)-1,3-oxazinan-2-one

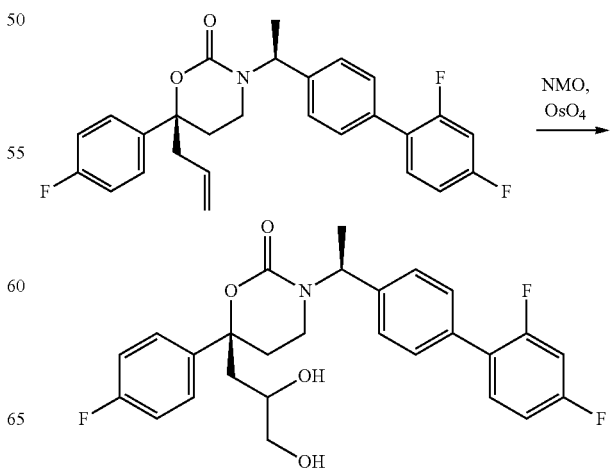

A mixture of (R)-6-allyl-3-((S)-1-(2',4'-difluorobiphenyl-4-yl)ethyl)-6-(4-fluorophenyl)-1,3-oxazinan-2-one (1.2722 g, 2.82 mmol), 4-methylmorpholine N-oxide monohydrate (0.8926 g, 6.60 mmol), and OsO$_4$ (2.5 wt. % solution in t-BuOH, 0.2800 g, 0.0275 mmol) in CH$_2$Cl$_2$ (25 mL) was stirred at rt for 16 h. The mixture was treated with EtOAc and washed with 0.5 N HCl, brine, dried (Na$_2$SO$_4$), filtered, and concentrated under reduced pressure to give 1.3462 g of the crude diol as a foam. The crude diol was directly used in the next step without further purification. LC-MS $t_R$=1.71 min in 3 min chromatography, m/z 486 (MH$^+$).

Analytical samples were purified by reversed-phase HPLC (SunFire™ Prep C$_{18}$ OBD™ 5 μm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford two diastereoisomers.

Isomer 1: (6S)-3-((S)-1-(2',4'-difluorobiphenyl-4-yl)ethyl)-6-(2,3-dihydroxypropyl)-6-(4-fluorophenyl)-1,3-oxazinan-2-one. LC-MS Method 1, $t_R$=1.7 min, m/z=486. $^1$H NMR (CD$_3$OD) 7.35-7.29 (m, 3H), 7.18 (d, J=7.0 Hz, 2H), 7.04-6.88 (m, 6H), 5.48 (q, J=7.0 Hz, 1H), 3.36-3.27 (m, 3H), 3.09-3.04 (m, 1H), 2.67-2.61 (m, 1H), 2.37-2.30 (m, 1H), 2.23-2.15 (m, 1H), 2.02-1.91 (m, 2H), 1.47 (d, J=7.0 Hz, 3H).

Isomer 2: (6S)-3-((S)-1-(2',4'-difluorobiphenyl-4-yl)ethyl)-6-(2,3-dihydroxypropyl)-6-(4-fluorophenyl)-1,3-oxazinan-2-one. LC-MS Method 1, $t_R$=1.71 min, m/z=486. $^1$H NMR (CD$_3$OD) 7.36-7.19 (m, 5H), 7.04-6.91 (m, 6H), 5.51 (q, J=7.0 Hz, 1H), 3.76-3.71 (m, 1H), 3.06-3.01 (m, 1H), 2.44-2.37 (m, 2H), 2.25-2.18 (m, 1H), 1.98 (dd, J=14.9, 2.6 Hz, 1H), 1.84 (dd, J=15.2, 7.9 Hz, 1H), 1.48 (d, J=7.0 Hz, 3H).

Example 53

6-(3-chlorophenyl)-6-methyl-3-(6-(piperidin-1-yl)pyridin-2-yl)-1,3-oxazinan-2-one

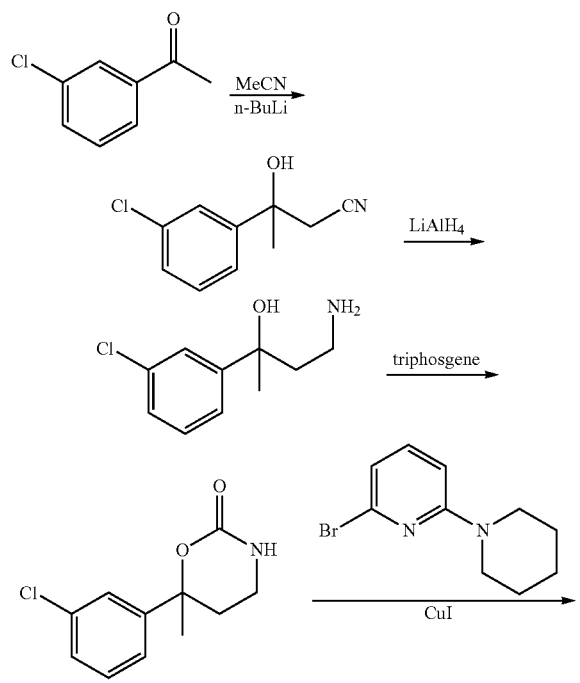

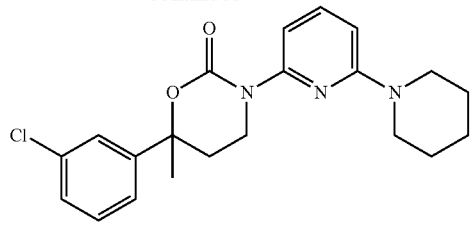

Step 1. 3-(3-chlorophenyl)-3-hydroxybutanenitrile

Dry THF (15 mL) was cooled to −78° C. and 2.5M n-BuLi (5.18 mL, 2.0 equiv.) was added. A solution of acetonitrile (680 μL, 2.0 equiv.) in dry THF (2 mL) was added dropwise over 2 min. The mixture was stirred at −78° C. for 1 h. A solution of 3-chloroacetophenone (835 μL, 6.468 mmol) in dry THF (2 mL) was added dropwise over 2 min. 30 min. The mixture was stirred at −78° C. for 30 min. and was warmed to rt slowly. After being stirred at rt for 15 min., the mixture was quenched with water (10 mL), diluted by ether (20 mL), washed with 2% aq HCl (15 mL). The aqueous layer was extracted with ether (2×10 mL). The combined organic layers were washed with satd aq NaHCO$_3$ (5 mL) and brine (10 mL), and dried over Na$_2$SO$_4$. After filtration and concentration, the crude product (1.4 g, quant. yield) was used for next step without further purification. LC-MS Method 1 $t_R$=1.40 min., m/z=219, 221 (M+Na).

Step 2. 4-amino-2-(3-chlorophenyl)butan-2-ol

A solution of 3-(3-chlorophenyl)-3-hydroxybutanenitrile (400 mg, 2.04 mmol) in dry THF (10 mL) was cooled to 0° C. LiAlH$_4$ powder (155 mg, 2 equiv.) was added. After 5 min, the mixture was warmed to rt and stirred for 4 h. The mixture was then heated to reflux for 6 h. The mixture was diluted with 1 M aq NaOH (30 mL) and extracted with CH$_2$Cl$_2$ (2×100 mL). The combined CH$_2$Cl$_2$ extracts were washed with brine, dried over Na2SO4 and concentrated to afford crude 4-amino-2-(3-chlorophenyl)butan-2-ol (550 mg, quant) which was used without purification. LC-MS Method 1, $t_R$=0.88 min, m/z=200, 202.

Step 3.
6-(3-chlorophenyl)-6-methyl-1,3-oxazinan-2-one

A stirred solution of crude 4-amino-2-(3-chlorophenyl)butan-2-ol (550 mg) and i-Pr$_2$NEt (1 mL, 5.5 mmol) in CH$_2$Cl$_2$ was cooled in an ice bath and solid triphosgene (286 mg, 0.96 mmol) was added. The ice bath was allowed to melt and the mixture was stirred overnight at rt. The mixture was diluted with ether (150 mL), washed with 5% aq HCl (50 mL) and satd aq NaHCO3 (50 mL) and dried over MgSO$_4$. Removal of the solvent left a brown oil (590 mg) which was purified by chromatography on a 12-g silica cartridge eluted with a 0-100% EtOAc in hexanes gradient to afford 6-(3-chlorophenyl)-6-methyl-1,3-oxazinan-2-one (57 mg).

Step 4. 6-(3-chlorophenyl)-6-methyl-3-(6-(piperidin-1-yl)pyridin-2-yl)-1,3-oxazinan-2-one A mixture of 6-(3-chlorophenyl)-6-methyl-1,3-oxazinan-2-one (28 mg, 0.12 mmol), 2-bromo-6-piperidinopyridine (33 mg, 0.14 mmol), CuI (7 mg, 0.037 mmol), powdered K2CO3 (19 mg, 0.14 mmol) and CH$_2$Cl$_2$ (0.25 mL) was heated to 130 C under a stream of N₂ such that the CH₂Cl₂ evaporated. The vessel was sealed and the mixture was heated at 130° C. for 1 h under N₂. The residue was dissolved in MeCN (0.5 mL) and DMSO (0.5 mL) and purified by prep HPLC to afford 6-(3-chlorophenyl)-6-methyl-3-(6-(piperidin-1-yl)pyridin-2-yl)-1,3-oxazinan-2-one (20 mg) as a brown oil. LC-MS Method 1, $t_R$=2.08 min, m/z=386, 388. $^1$H NMR (CDCl₃) 1.62 (6H), 1.73 (s, 3H), 2.35 (m, 1H), 2.48 (m, 1H), 3.43 (5H), 4.11 (m, 1H), 6.50 (d, 1H), 7.20-7.60 (6H).

Example 54

3-(2-(3-chlorophenyl)pyrimidin-4-yl)-6-methyl-6-phenyl-1,3-oxazinan-2-one

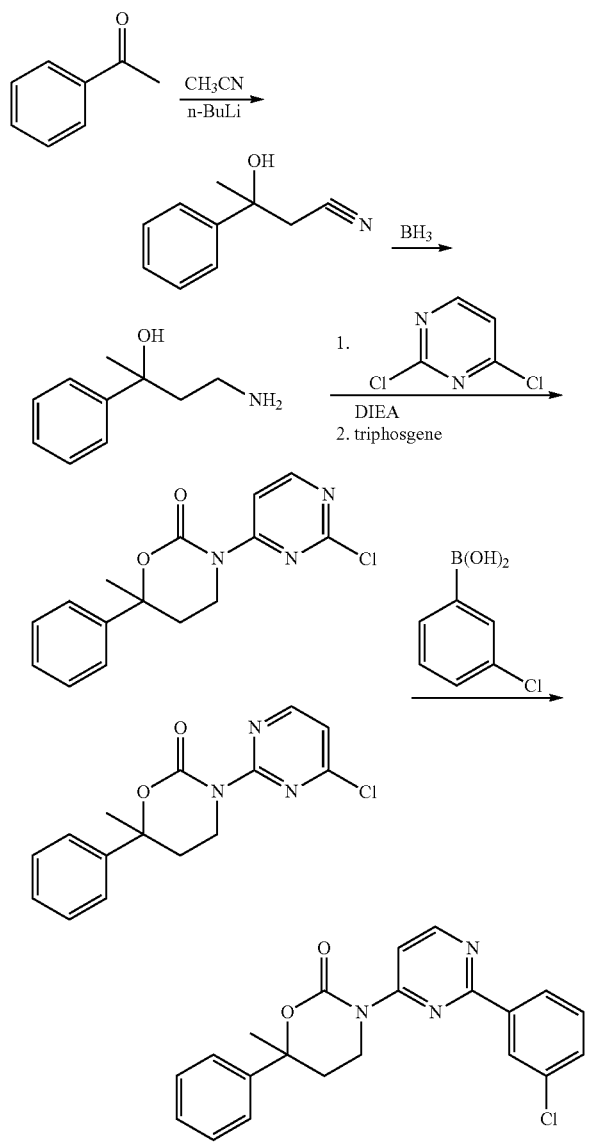

Step 1. 3-hydroxy-3-phenylbutanenitrile

Dry THF was cooled to −20° C. and 2.5 M n-BuLi (100 mL, 0.25 mol) was added. A solution of CH₃CN (11.25 g, 0.25 mol) in dry THF was added dropwise over 10 min. Then the mixture was stirred for 1 h at −20° C. and a solution of acetophenone (30 g, 0.25 mol) in THF was added dropwise over 10 min. The mixture was stirred at −20° C. for 15 min and warmed to rt over 15 min. Aq NH₄Cl was added to quench the reaction. The solution was extract with EtOAc. The organic layer washed with brine, dried over anhydrous Na₂SO₄ and concentrated to give 3-hydroxy-3-phenylbutanenitrile (30 g, yield 75%). $^1$H NMR (CDCl₃, 400 MH$_Z$): δ=1.76 (s, 3H), 2.83 (s, 2H), 7.34 (m, 1H), 7.41 (m, 2H), 7.5 (m, 2H).

Step 2. 4-amino-2-phenylbutan-2-ol

To a solution of 3-hydroxy-3-phenylbutanenitrile (1 g, 6.2 mmol) in THF (10 mL) was added dropwise BH₃.Me₂S (32 mL, 62 mmol) under a N₂ atmosphere. The mixture was stirred at rt overnight. The reaction was quenched with MeOH (10 mL). The mixture was concentrated to give crude 4-amino-2-phenylbutan-2-ol (1.2 g, crude), which was used in the next step without further purification.

Step 3. 4-(2-chloropyrimidin-4-ylamino)-2-phenylbutan-2-ol

To a solution of 4-amino-2-phenyl-butan-2-ol (1.2 g, 0.0072 mmol) and DIEA in CH₂Cl₂ (15 ml) was added dropwise a solution of 2,4-dichloro-pyrimidine (980 mg, 0.0072 mmol) in CH₂Cl₂ slowly at 0° C. under N₂. The mixture was stirred at rt overnight. The mixture was concentrated to give the crude product, which was purified by preparative TLC to afford a mixture of 4-(2-chloro-pyrimidin-4-ylamino)-2-phenyl-butan-2-ol and 4-(4-chloropyrimidin-2-ylamino)-2-phenylbutan-2-ol (450 mg, 23%). $^1$H NMR (CDCl₃, 400 MH$_Z$): δ=1.55 (s, 3H), 2.05 (m, 2H), 3.03 (m, 2H), 3.6 (m, 1H), 6.02 (m, 2H), 7.28 (m, 1H), 7.28 (m, 2H), 7.28 (m, 2H).

Step 4. 3-(2-chloropyrimidin-4-yl)-6-methyl-6-phenyl-1,3-oxazinan-2-one

To a solution of 4-(4-chloro-pyrimidin-2-ylamino)-2-phenyl-butan-2-ol (450 mg, 1.6 mmol) and Et₃N (508 mg, 4.8 mmol) in CH₂Cl₂ (2 ml) was added dropwise a solution of triphosgene (159 mg, 0.54 mmol) in CH₂Cl₂ slowly at 0° C. under nitrogen atmosphere. The mixture was stirred at rt overnight. The mixture was concentrated to give the crude product, which was purified by TLC and preparative HPLC to afford 3-(2-chloropyrimidin-4-yl)-6-methyl-6-phenyl-1,3-oxazinan-2-one (250 mg, 52%) $^1$H NMR (CDCl₃, 400 MH$_Z$): δ=1.73 (s, 3H), 2.38 (m, 1H), 2.63 (m, 1H), 3.49 (m, 1H), 4.2 (m, 1H), 7.36 (m, 5H), 8.28 (m, 1H), 8.52 (m, 1H) and 3-(4-chloropyrimidin-2-yl)-6-methyl-6-phenyl-1,3-oxazinan-2-one (20 mg, 9%) [Example 57]. $^1$H NMR (CDCl₃, 400 MH$_Z$): δ=1.73 (s, 3H), 2.4 (m, 1H), 2.58 (m, 1H), 3.47 (m, 1H), 4.13 (m, 1H), 7.06 (m, 5H), 7.16-7.55 (m, 5H), 8.54 (m, 1H).

Step 5. 3-(2-chloropyrimidin-4-yl)-6-methyl-6-phenyl-1,3-oxazinan-2-one

To a solution of 3-(2-chloropyrimidin-4-yl)-6-methyl-6-phenyl-1,3-oxazinan-2-one (100 mg, 0.33 mmol) and 3-chlorophenylboronic acid (0.53 mmol) in 2M aq K₂CO₃ (1 mL, 2 mmol) and 1,4-dioxane (3 mL) was slowly added Pd(Ph₃)₂Cl₂ (20 mg, 10%) at 0° C. under N₂. The mixture was refluxed overnight. The mixture was concentrated to give crude product, which was purified by TLC and preparative HPLC to afford 3-(2-chloropyrimidin-4-yl)-6-methyl-6-phenyl-1,3-oxazinan-2-one (13 mg). $^1$H NMR (CDCl₃, 400

MH$_Z$): δ=1.78 (s, 3H), 2.43 (m, 1H), 2.57 (m, 1H), 3.6 (m, 1H), 4.4 (m, 1H), 7.3-7.5 (m, 6H), 8.2-8.4 (m, 3H), 8.65 (m, 1H). LC-MS Method 3, t$_R$=1.655 min, m/z=380.

Example 55

3-(2-(4-fluorophenyl)pyrimidin-4-yl)-6-methyl-6-phenyl-1,3-oxazinan-2-one

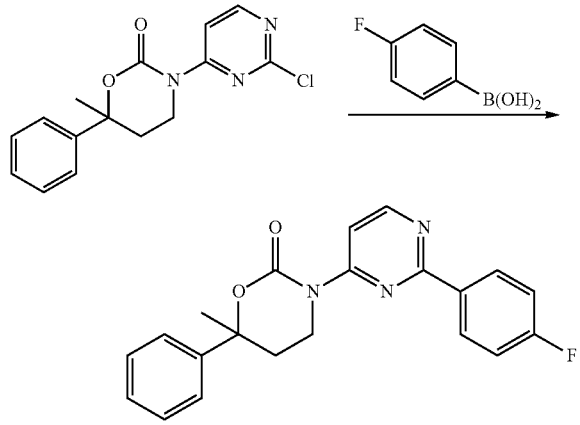

To a solution of 3-(2-chloropyrimidin-4-yl)-6-methyl-6-phenyl-1,3-oxazinan-2-one (50 mg, 0.165 mmol) and 4-fluorophenylboronic acid (32 mg, 0.33 mmol), K$_2$CO$_3$ (0.5 mL, 2 M) in 1,4-dioxane (1.5 ml) at 0° C. under N$_2$ was slowly added Pd(Ph$_3$)$_2$Cl$_2$ (10 mg, 20%). The mixture was refluxed overnight. The mixture was concentrated to give the crude product, which was purified by TLC and preparative HPLC to afford 3-(2-(4-fluorophenyl)pyrimidin-4-yl)-6-methyl-6-phenyl-1,3-oxazinan-2-one (15 mg, yield 25%). $^1$H NMR (CDCl$_3$, 400 MH$_Z$): δ=1.75 (s, 3H), 2.4 (m, 1H), 2.54 (m, 1H), 3.6 (m, 1H), 4.4 (m, 1H), 7.1 (m, 2H), 7.25-7.4 (m, 5H), 8.08 (m, 1H), 8.34 (m, 2H), 8.62 (m, 1H). LC-MS Method 3, t$_R$=1.519 min, m/z=364.1. $^1$H NMR (CDCl3) 1.80 (s, 3H), 2.40 (m, 1H), 2.60-2.70 (d, 1H), 3.60 (m, 1H), 4.40 (t, 1H), 7.10 (t, 2H), 7.20-7.45 (m, 5H), 8.17 (d, 1H), 8.35 (t, 2H), 8.65 (d, 1H).

Example 56

3-(2-(3-fluorophenyl)pyrimidin-4-yl)-6-methyl-6-phenyl-1,3-oxazinan-2-one

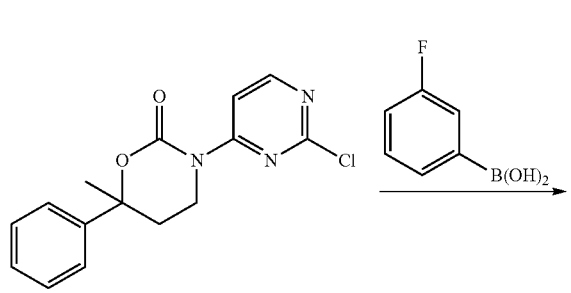

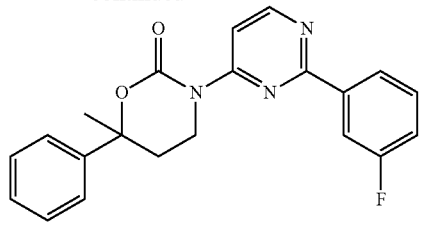

To a solution of 3-(2-chloropyrimidin-4-yl)-6-methyl-6-phenyl-1,3-oxazinan-2-one (100 mg, 0.33 mmol) and 3-fluorophenylboronic acid (80 mg, 0.53 mmol), K$_2$CO$_3$ (1 mL, 2 M) in 1,4-dioxane (3 ml) at 0° C. under N$_2$ was slowly added Pd(Ph$_3$)$_2$Cl$_2$ (20 mg, 20%). The mixture was refluxed overnight. The mixture was concentrated to give the crude product, which was purified by TLC and preparative HPLC to afford 3-(2-(3-fluorophenyl)pyrimidin-4-yl)-6-methyl-6-phenyl-1,3-oxazinan-2-one (20 mg, yield 17%). $^1$H NMR (CDCl$_3$, 400 MH$_Z$): δ=1.71 (s, 3H), 2.37 (m, 1H), 2.6 (m, 1H), 3.54 (m, 1H), 4.34 (m, 1H), 7.08 (m, 1H), 7.25 (m, 1H), 7.34 (m, 5H), 7.96 (m, 1H), 8.09 (m, 1H), 8.16 (m, 1H), 8.6 (m, 1H). LC-MS Method 3, t$_R$=1.46 min, m/z=364.

Example 57

3-(4-chloropyrimidin-2-yl)-6-methyl-6-phenyl-1,3-oxazinan-2-one

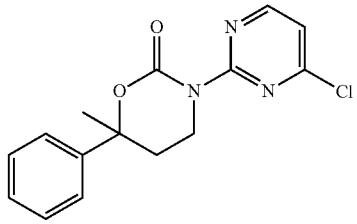 [SMILES: CC1(c2ccccc2)CCN(c2nccc(Cl)n2)C(=O)O1]

The title compound was isolated as described in Example 54 Step 3. LC-MS Method 3, t$_R$=1.007 min, m/z=304. $^1$H NMR (CDCl$_3$) 1.73 (s, 3H), 2.4 (m, 1H), 2.58 (m, 1H), 3.47 (m, 1H), 4.13 (m, 1H), 7.06 (m, 5H), 7.16-7.55 (m, 5H), 8.54 (m, 1H).

Example 58

3-(4-(3-chlorophenyl)pyrimidin-2-yl)-6-methyl-6-phenyl-1,3-oxazinan-2-one

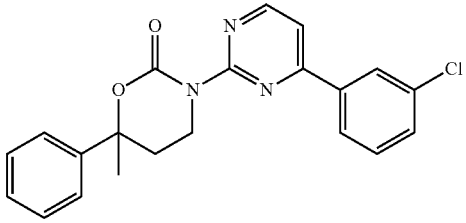 [SMILES: CC1(c2ccccc2)CCN(c2nccc(-c3cccc(Cl)c3)n2)C(=O)O1]

The title compound was prepared following procedures analogous to those in Example 56 using 3-(4-chloropyrimidin-2-yl)-6-methyl-6-phenyl-1,3-oxazinan-2-one and 3-chlorophenylboronic acid. LC-MS Method 3, $t_R$=1.354 min, m/z=781.1. $^1$H NMR (CDCl$_3$) 1.80 (s, 3H), 2.48-2.53 (m, 1H), 2.62-2.71 (m, 1H), 3.55-3.67 (m, 1H), 4.30-4.40 (m, 1H), 7.30-7.60 (m, 8H), 7.90-7.95 (m, 1H), 8.05 (s, 1H), 8.80-8.85 (m, 1H).

Example 59

3-(4-(2,4-difluorophenyl)pyrimidin-2-yl)-6-methyl-6-phenyl-1,3-oxazinan-2-one

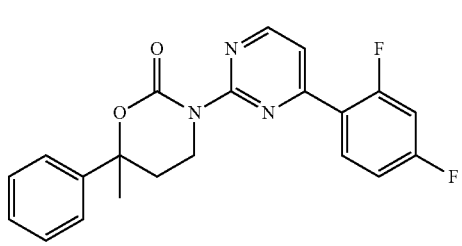 [SMILES: CC1(c2ccccc2)CCN(c2nccc(-c3ccc(F)cc3F)n2)C(=O)O1]

The title compound was prepared following procedures analogous to those in Example 56 using 3-(4-chloropyrimidin-2-yl)-6-methyl-6-phenyl-1,3-oxazinan-2-one and 2,4-difluorophenylboronic acid. LC-MS Method 3, $t_R$=1.238 min, m/z=785. $^1$H NMR (CDCl$_3$) 1.80 (s, 3H), 2.48-2.53 (m, 1H), 2.62-2.71 (m, 1H), 3.58-3.67 (m, 1H), 4.35-4.45 (m, 1H), 6.93-7.08 (m, 2H), 7.30-7.48 (m, 5H), 7.62-7.65 (m, 1H), 8.15-8.23 (m, 1H), 8.78-8.81 (m, 1H).

Example 60

3-(4-(2,6-dichlorophenyl)pyrimidin-2-yl)-6-methyl-6-phenyl-1,3-oxazinan-2-one

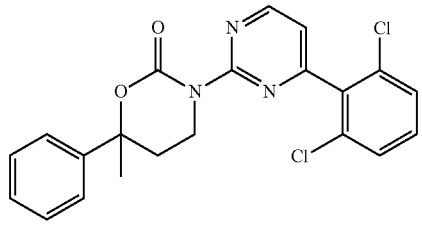

The title compound was prepared following procedures analogous to those in Example 56 using 3-(4-chloropyrimidin-2-yl)-6-methyl-6-phenyl-1,3-oxazinan-2-one and 2,6-dichlorophenylboronic acid. LC-MS Method 3, $t_R$=1.317 min, m/z=414. $^1$H NMR (CDCl$_3$) 1.70 (s, 3H), 2.30-2.40 (m, 1H), 2.48-2.52 (m, 1H), 3.47-3.51 (m, 1H), 4.10-4.15 (m, 1H), 7.10-7.40 (m, 10H), 8.78-8.79 (m, 1H).

Example 61

3-(4-(4-fluorophenyl)pyrimidin-2-yl)-6-methyl-6-phenyl-1,3-oxazinan-2-one

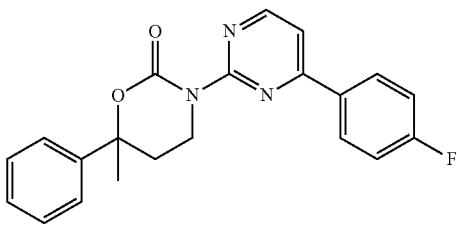 [SMILES: CC1(c2ccccc2)CCN(c2nccc(-c3ccc(F)cc3)n2)C(=O)O1]

The title compound was prepared following procedures analogous to those in Example 56 using 3-(4-chloropyrimidin-2-yl)-6-methyl-6-phenyl-1,3-oxazinan-2-one and 4-fluorophenylboronic acid. LC-MS Method 3, $t_R$=1.193 min, m/z=363.9. $^1$H NMR (CDCl$_3$) 1.60 (s, 1H), 1.80 (s, 3H), 2.48-2.53 (m, 1H), 2.62-2.71 (m, 1H), 3.60-3.67 (m, 1H), 4.30-4.40 (m, 1H), 7.20-7.55 (m, 10H), 7.60-7.62 (m, 1H), 8.05-8.15 (m, 3H), 8.80-8.85 (m, 1H).

Example 62

3-(4-(3-fluorophenyl)pyrimidin-2-yl)-6-methyl-6-phenyl-1,3-oxazinan-2-one

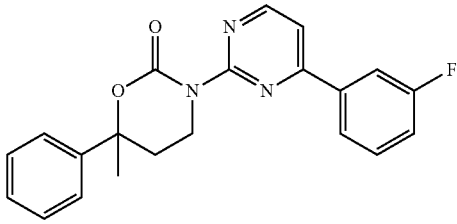 [SMILES: CC1(c2ccccc2)CCN(c2nccc(-c3cccc(F)c3)n2)C(=O)O1]

The title compound was prepared following procedures analogous to those in Example 56 using 3-(4-chloropyrimidin-2-yl)-6-methyl-6-phenyl-1,3-oxazinan-2-one and 3-fluorophenylboronic acid. LC-MS Method 3, $t_R$=1.215 min, m/z=749. $^1$H NMR (CDCl$_3$) 1.80 (s, 3H), 2.48-2.53 (m, 1H), 2.62-2.71 (m, 1H), 3.58-3.67 (m, 1H), 4.30-4.40 (m, 1H), 7.30-7.65 (m, 10H), 7.80-7.90 (m, 2H), 8.90-8.95 (m, 1H).

Example 63

6-allyl-3-(3-bromophenyl)-6-phenyl-1,3-oxazinan-2-one

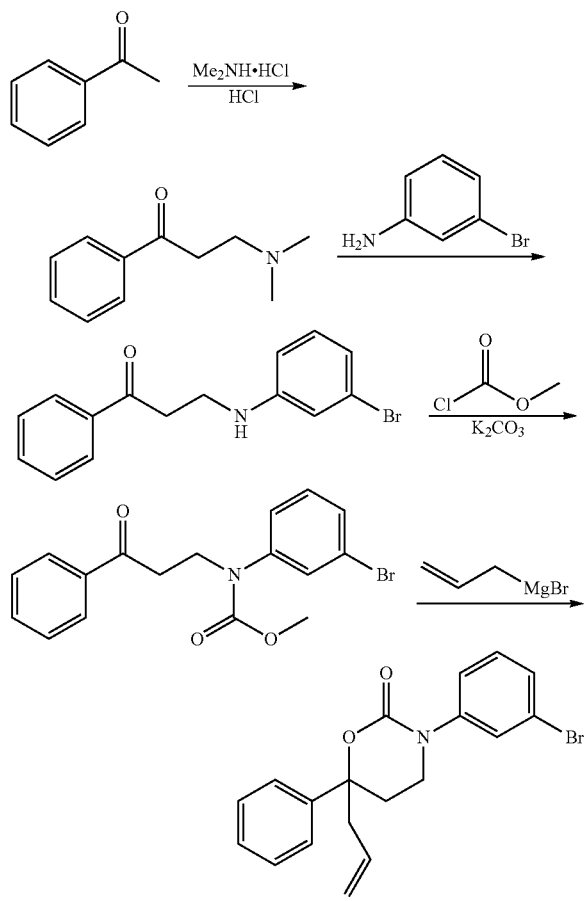

Step 1. 3-(dimethylamino)-1-phenylpropan-1-one

The solution of acetophenone (30 g, 0.25 mol) and Me₂NH.HCl (0.28 mol) in EtOH (400 mL) was heated at 70° C. overnight. The resulting mixture was concentrated and the residue was washed with EtOAc to give 3-(dimethylamino)-1-phenylpropan-1-one (17.7 g, 40%). ¹H NMR (400 MHz, CDCl₃): δ=2.36 (m, 6H), 2.74 (m, 2H), 3.14 (m, 2H), 7.43 (m, 2H), 7.52 (m, 1H), 7.94 (m, 2H).

Step 2. 3-(3-bromophenylamino)-1-phenylpropan-1-one

A mixture of 3-(dimethylamino)-1-phenylpropan-1-one (0.1 mol) and 3-bromoaniline (0.1 mol) in 1:1 EtOH/H₂O (100 mL) was heated at 80° C. overnight. The resulting mixture was concentrated and the residue was washed with H₂O and then EtOH several times to give to give 3-(3-bromophenylamino)-1-phenylpropan-1-one (27 g, 90%). ¹H NMR (400 MHz, CDCl₃): δ=3.52 (m, 2H), 4.33 (m, 2H), 4.51 (m, 1H), 6.8 (m, 1H), 7.05 (m, 2H), 7.28 (m, 1H), 7.72 (m, 2H), 7.80 (m, 1H), 8.2 (m, 2H).

Step 3. Methyl 3-bromophenyl(3-oxo-3-phenylpropyl)carbamate

To the solution of 3-(3-bromophenylamino)-1-phenylpropan-1-one (0.03 mol) in anhydrous THF (30 mL) was added K₂CO₃ (0.06 mol) and methyl chloroformate (0.033 mol) at 0° C. under N₂ atmosphere. Then the reaction mixture was stirred at rt for 2 h. The resulting mixture was filtered and the filtrate was concentrated. The residue was washed with H₂O, 1N HCl and brine and then extracted with EtOAc. The combined organic layers were concentrated to give crude product, which was purified by column chromatography to afford methyl 3-bromophenyl(3-oxo-3-phenylpropyl)carbamate (30.5 g, 95%). ¹H NMR (400 MHz, CDCl₃): δ=3.22 (m, 2H), 3.62 (s, 3H), 4.02 (m, 2H), 7.05-7.20 (m, 2H), 7.3-7.5 (m, 4H), 7.8 (m, 1H).

Step 4. 6-allyl-3-(3-bromophenyl)-6-phenyl-1,3-oxazinan-2-one

To a solution of methyl 3-bromophenyl(3-oxo-3-phenylpropyl)carbamate (250 mg, 0.69 mmol) in dry THF (2 mL) was added dropwise 1 M allylmagnesium bromide (10 mL) −78° C. The reaction mixture was stirred at rt for 3 h. The resulting mixture was quenched with sattd aq NH₄Cl and extracted with EtOAc. The combined organic layers were washed with brine, dried over anhydrous Na₂SO₄ and concentrated to give 6-allyl-3-(3-bromophenyl)-6-phenyl-1,3-oxazinan-2-one (120 mg, 47%). ¹H NMR (400 MHz, CDCl₃): δ=2.48 (m, 2H), 2.55-2.7 (m, 2H), 3.23 (m, 1H), 3.51 (m, 1H), 5.04 (m, 2H), 5.72 (m, 1H), 7.01 (m, 1H), 7.11 (m, 1H), 7.23 (m, 1H), 7.3 (m, 1H), 7.35 (m, 6H).

Example 64

6-allyl-3-(2',4'-difluorobiphenyl-3-yl)-6-phenyl-1,3-oxazinan-2-one

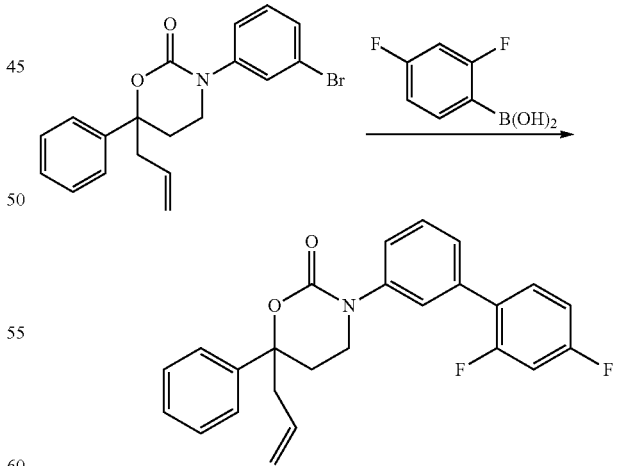

Step 1. 6-allyl-3-(2',4'-difluorobiphenyl-3-yl)-6-phenyl-1,3-oxazinan-2-one

To a solution of 6-allyl-3-(3-bromophenyl)-6-phenyl-1,3-oxazinan-2-one (50 mg, 0.134 mmol) and 2,4-difluorophenylboronic acid (40 mg, 0.215 mmol), K$_2$CO$_3$ (0.5 mL, 2 M) in 1,4-dioxane (1.5 ml) was slowly added Pd(Ph$_3$)$_2$Cl$_2$ (10 mg, 20%) at 0° C. under N$_2$. The mixture was refluxed overnight. The mixture was concentrated to give the crude product, which was purified by TLC and preparative HPLC to afford 6-allyl-3-(2',4'-difluorobiphenyl-3-yl)-6-phenyl-1,3-oxazinan-2-one (10 mg, 18%). $^1$H NMR (400 MHz, CDCl$_3$): δ=2.40 (m, 2H), 2.55-2.72 (m, 2H), 3.26 (m, 1H), 3.47 (m, 1H), 5.05 (m, 2H), 5.76 (m, 1H), 6.76-6.90 (m, 2H), 7.04 (m, 1H), 7.28 (m, 4H), 7.36 (m, 2H).

Example 65

3-(2',4'-difluorobiphenyl-3-yl)-6-(2-hydroxyethyl)-6-phenyl-1,3-oxazinan-2-one

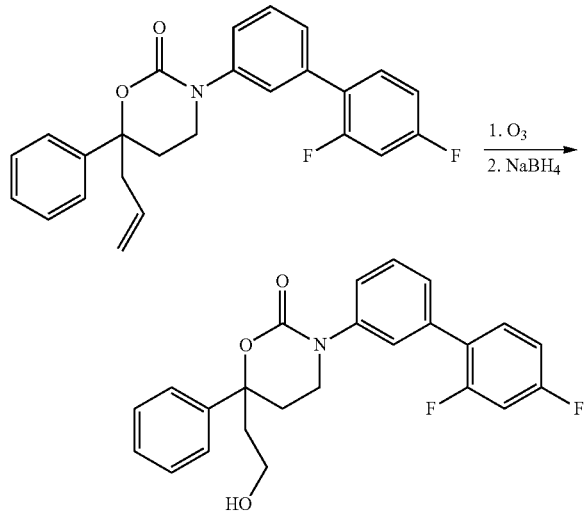

Step 1. 3-(2',4'-difluorobiphenyl-3-yl)-6-(2-hydroxyethyl)-6-phenyl-1,3-oxazinan-2-one A solution of 6-allyl-3-(2',4'-difluorobiphenyl-3-yl)-6-phenyl-1,3-oxazinan-2-one (600 mg, 1.47 mmol) in dry CH$_2$Cl$_2$ (10 mL) was treated with ozone at −78° C. until the mixture turned blue. The system was then flushed with oxygen to remove excess ozone. NaBH$_4$ (450 mg, 11.7 mmol) was added to the mixture in portions at −20° C. The mixture was stirred overnight at rt. The mixture was quenched with water and the layers were separated. The aqueous layer was extracted with CH$_2$Cl$_2$ (2×). The organic layers were combined, washed with brine, dried over anhydrous Na$_2$SO$_4$ and concentrated to give 3-(2',4'-difluorobiphenyl-3-yl)-6-(2-hydroxyethyl)-6-phenyl-1,3-oxazinan-2-one (150 mg, 25%). $^1$H NMR (400 MHz, CDCl$_3$): δ=2.12-2.35 (m, 2H), 2.51 (m, 2H), 3.26 (m, 1H), 3.47-3.6 (m, 2H), 4.25 (m, 1H), 6.83 (m, 2H), 7.06 (m, 1H), 7.26-7.51 (m, 8H).

Preparative HPLC on a Chiralpak IA, 4.6×250 mm, 5 micron column eluted with 10% EtOH in hexanes at a flow rate of 1 mL min$^{-1}$ afforded two isomers.

Isomer 1: LC-MS Method 1, t$_R$=min, m/z=410 (M+1). $^1$H NMR (CDCl$_3$) 7.47-7.33 (m, 8H), 7.27-7.26 (m, 1H), 7.16-7.13 (m, 1H), 6.96-6.86 (m, 2H), 3.86-3.80 (m, 1H), 3.64-3.61 (m, 1H), 3.58-3.53 (m, 1H), 3.35-3.28 (m, 1H), 2.58-2.52 (m, 2H), 2.37-2.23 (m, 2H).

Isomer 2 was not characterized.

Example 66

3-(4',6-difluorobiphenyl-3-yl)-6-(2-fluorophenyl)-6-(2-hydroxyethyl)-1,3-oxazinan-2-one

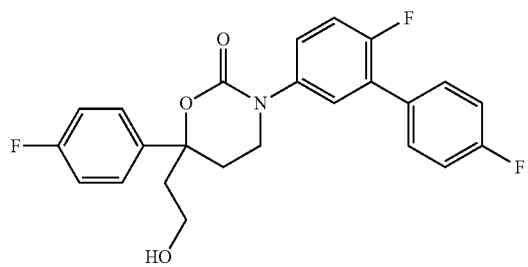 [SMILES: O=C1OC(CCO)(c2ccc(F)cc2)CCN1c1ccc(F)c(-c2ccc(F)cc2)c1]

The title compound was prepared by application of procedures analogous to those described in Example 63 using p-fluoroacetophenone in Step 1 and 3-bromo-4-fluoroaniline in Step 2 followed by procedures analogous to those described in Example 64 using 4-fluorophenylboronic acid followed by procedures analogous to those described in Example 65. LC-MS Method 3, t$_R$=1.234 min, m/z=428. $^1$H NMR (CDCl$_3$) 1.62-1.70 (m, 1H), 2.2-2.38 (m, 2H), 2.5-2.6 (m, 2H), 3.22-3.35 (m, 1H), 3.50-3.65 (m, 2H), 3.80-3.90 (m, 1H), 7.05-7.2 (m, 7H), 7.5-7.6 (m, 4H).

Example 67

3-(4',6-difluorobiphenyl-3-yl)-6-(2-fluorophenyl)-6-(2-hydroxyethyl)-1,3-oxazinan-2-one

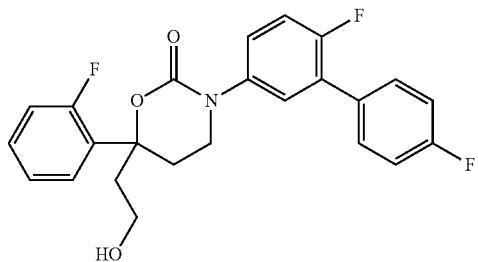 [SMILES: O=C1OC(CCO)(c2ccccc2F)CCN1c1ccc(F)c(-c2ccc(F)cc2)c1]

The title compound was prepared by application of procedures analogous to those described in Example 63 using o-fluoroacetophenone in Step 1 and 3-bromo-4-fluoroaniline in Step 2 followed by procedures analogous to those described in Example 64 using 4-fluorophenylboronic acid followed by procedures analogous to those described in Example 65. LC-MS Method 3, t$_R$=1.263 min, m/z=428.1. $^1$H NMR (CDCl$_3$) 2.35-2.6 (m, 3H), 2.79-2.85 (m, 1H), 3.28-

3.40 (m, 2H), 3.52-3.60 (m, 1H), 3.63-3.72 (m, 1H), 3.80-3.88 (m, 1H), 7.05-7.20 (m, 6H), 7.22-7.3 (m, 1H), 7.38-7.50 (m, 3H), 7.52-7.61 (m, 1H).

Example 68

3-(2'-chloro-4'-fluorobiphenyl-3-yl)-6-(2-hydroxyethyl)-6-phenyl-1,3-oxazinan-2-one

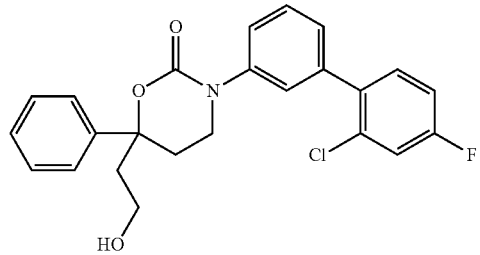 [SMILES: O=C1OC(CCO)(c2ccccc2)CCN1c1cccc(-c2ccc(F)cc2Cl)c1]

The title compound was prepared by application of procedures analogous to those described in Example 64 using 2-chloro-4-fluorophenylboronic acid in Step 1 followed by procedures analogous to those described in Example 65. LC-MS Method 3, $t_R$=1.268 min, m/z=426. $^1$H NMR (CD3OD) 2.2-2.30 (m, 2H), 2.45-2.60 (m, 1H), 2.60-2.70 (m, 1H), 3.15-3.25 (m, 1H), 3.3-3.40 (m, 1H), 3.5-3.65 (m, 1H), 3.65-3.77 (m, 1H), 7.0-7.2 (m, 3H), 7.3-7.48 (m, 9H).

Example 69

3-(2',6'-dichlorobiphenyl-3-yl)-6-(2-hydroxyethyl)-6-phenyl-1,3-oxazinan-2-one

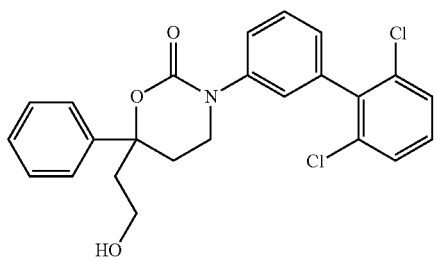 [SMILES: O=C1OC(CCO)(c2ccccc2)CCN1c1cccc(-c2c(Cl)cccc2Cl)c1]

The title compound was prepared by application of procedures analogous to those described in Example 64 using 2,6-dichlorophenylboronic acid in Step 1 followed by procedures analogous to those described in Example 65. LC-MS Method 3, $t_R$=1.28 min, m/z=441.9. $^1$H NMR (CDCl$_3$) 2.26-2.44 (m, 2H), 2.60 (m, 2H), 3.37-3.48 (m, 1H), 3.60-3.70 (m, 1H), 3.88 (m, 1H), 7.11 (m, 1H), 7.19 (m, 1H), 7.29 (m, 1H), 7.45 (m, 4H), 7.50 (m, 4H).

Example 70

2-(3-(2',4'-difluorobiphenyl-3-yl)-2-oxo-6-phenyl-1,3-oxazinan-6-yl)acetic acid

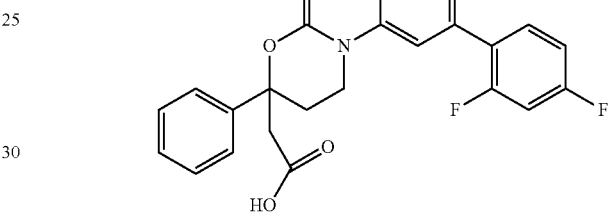

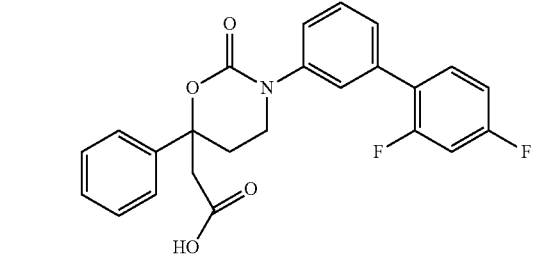

Step 1. 2-(3-(2',4'-difluorobiphenyl-3-yl)-2-oxo-6-phenyl-1,3-oxazinan-6-yl)acetic acid Jones reagent was prepared by addition of CrO$_3$ (1 g) to H$_2$SO$_4$ (1 mL) and addition of water to bring the total volume to 4 mL. 3-(2',4'-difluorobiphenyl-3-yl)-6-(2-hydroxyethyl)-6-phenyl-1,3-oxazinan-2-one (100 mg, 0.24 mmol) was dissolved in acetone (2 mL), and cooled in an ice bath. Jones reagent (0.2 mL) was slowly added to the mixture and the reaction mixture was stirred overnight. Solvent was removed in vacuo and the obtained residue was purified by preparative HPLC to afford 2-(3-(2',4'-difluorobiphenyl-3-yl)-2-oxo-6-phenyl-1,3-oxazinan-6-yl)acetic acid (20 mg, yield 19%). $^1$H NMR (400 MHz, CDCl$_3$): δ=2.7-2.9 (m, 4H), 3.55 (m, 2H), 6.86 (m, 2H), 7.05 (m, 1H), 7.19 (m, 1H), 7.33 (m, 5H), 7.44 (m, 3H).

Example 71

3-(3-bromobenzyl)-6-methyl-6-phenyl-1,3-oxazinan-2-one

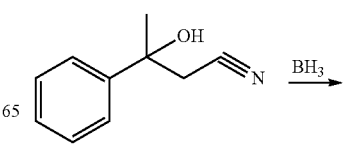

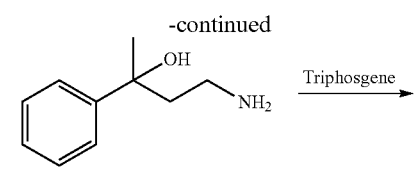

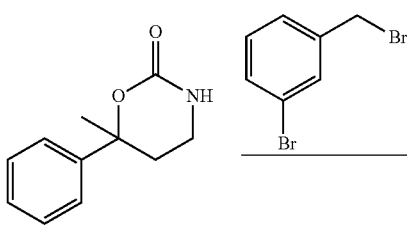

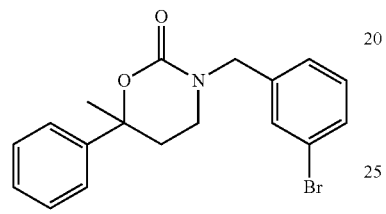

Step 1. 4-amino-2-phenylbutan-2-ol

To a solution of 3-hydroxy-3-phenylbutanenitrile (13 g, 0.081 mol) in THF (150 mL) was added $BH_3.Me_2S$ (2 M, 122 mL) at 0° C. The mixture was refluxed overnight. The reaction mixture was quenched with MeOH and extracted with EtOAc. The organic layer was washed with brine, dried over $Na_2SO_4$ and concentrated to obtain crude. 4-amino-2-phenylbutan-2-ol (15 g, 100%). $^1$H NMR ($CDCl_3$): 1.60 (s, 3H), 1.60 (s, 3H), 2.10-2.20 (m, 1H), 2.30-2.40 (m, 1H), 2.90-3.00 (m, 1H), 3.65-3.85 (m, 1H), 7.20-7.40 (m, 5H).

Step 2. 6-methyl-6-phenyl-1,3-oxazinan-2-one

A solution of 4-amino-2-phenylbutan-2-ol (5.0 g, 0.03 mol) in $CH_2Cl_2$ (50 mL) was added triphosgene (2.97 g, 0.01 mol) and $Et_3N$ (9.09 g, 0.09 mol) at 0° C. After stirring for 1 h, the mixture was diluted with water and extracted with $CH_2Cl_2$. The organic layer was washed with brine, dried over $Na_2SO_4$, concentrated and purified by chromatography to afford 6-methyl-6-phenyl-1,3-oxazinan-2-one (1.14 g, 20%). $^1$H NMR ($CDCl_3$): 1.60 (s, 3H), 1.80-2.00 (m, 1H), 2.30-2.40 (m, 1H), 3.15-3.21 (m, 1H), 6.00 (s, 1H), 7.30-7.45 (m, 5H), 8.90-9.01 (m, 1H).

Step 3. 3-(3-bromobenzyl)-6-methyl-6-phenyl-1,3-oxazinan-2-one

A solution of 6-methyl-6-phenyl-1,3-oxazinan-2-one (500 mg, 2.62 mmol) and NaH (189 mg, 7.86 mmol) in dry THF (10 mL) was stirred for 1 h. A solution of m-bromobenzyl bromide (1.31 g, 5.24 mmol) in dry THF (3 mL) was added. The mixture was stirred overnight at rt. The reaction mixture was quenched water and extracted with EtOAc. The organic layer was washed with brine, dried over $Na_2SO_4$, concentrated and purified by preparative TLC to afford 3-(3-bromobenzyl)-6-methyl-6-phenyl-1,3-oxazinan-2-one (300 mg, 32%). $^1$H NMR ($CDCl_3$): 1.60-1.70 (s, 3H), 2.15-2.30 (m, 1H), 2.35-2.48 (m, 1H), 2.79-2.90 (m, 1H), 3.00-3.10 (m, 1H), 4.30-4.40 (m, 1H), 4.50-4.60 (m, 1H), 6.90-7.00 (m, 1H), 7.00-7.10 (m, 1H), 7.20-7.45 (m, 7H).

Example 72

3-(2-bromobenzyl)-6-methyl-6-phenyl-1,3-oxazinan-2-one

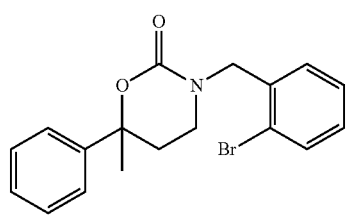 [SMILES: CC1(c2ccccc2)CCN(Cc2ccccc2Br)C(=O)O1]

The title compound was prepared following procedures analogous to those described in Example 71 using o-bromobenzyl bromide in Step 3. LC-MS Method 3, $t_R$=1.305 min, m/z=362. $^1$H NMR (CDCl3) 1.60-1.65 (s, 3H), 2.15-2.26 (m, 1H), 2.30-2.40 (m, 1H), 2.81-2.92 (m, 1H), 3.00-3.08 (m, 1H), 4.45-4.65 (m, 2H), 6.80-6.90 (m, 1H), 7.00-7.10 (m, 1H), 7.21-7.38 (m, 5H), 7.40-7.45 (m, 1H).

Example 73

3-(4-bromobenzyl)-6-methyl-6-phenyl-1,3-oxazinan-2-one

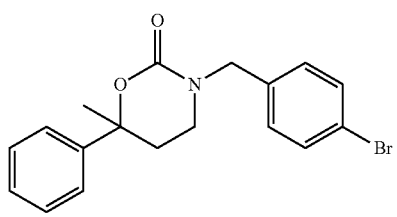 [SMILES: CC1(c2ccccc2)CCN(Cc2ccc(Br)cc2)C(=O)O1]

The title compound was prepared following procedures analogous to those described in Example 71 using p-bromobenzyl bromide in Step 3. LC-MS Method 3, $t_R$=1.317 min, m/z=361.8. $^1$H NMR ($CDCl_3$) 1.55-1.65 (s, 3H), 2.10-

2.20 (m, 1H), 2.30-2.40 (m, 1H), 2.79-2.80 (m, 1H), 2.90-3.00 (m, 1H), 4.25-4.50 (m, 2H), 6.80-6.90 (m, 1H), 7.21-7.38 (m, 7H).

Example 74

3-(3-bromophenyl)-6-(2-hydroxyethyl)-6-phenyl-1,3-oxazinan-2-one

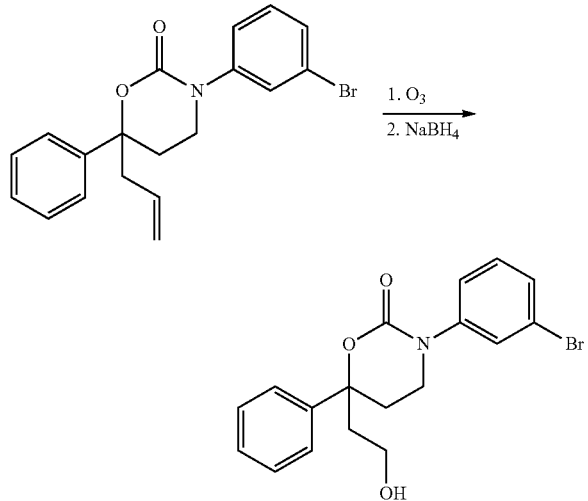

A solution of 6-allyl-3-(3-bromophenyl)-6-phenyl-1,3-oxazinan-2-one (200 mg, 0.54 mmol) in dry CH$_2$Cl$_2$ (10 mL) was treated with ozone at −78° C. until the mixture turned blue. The system was then flushed with oxygen to remove excess ozone. NaBH$_4$ (207 mg, 5.4 mmol) was added to the mixture in portions at −20° C. The mixture was stirred overnight at rt. The mixture was quenched with water and the layers were separated. The aqueous layer was extracted with CH$_2$Cl$_2$ (2×). The organic layers were combined, washed with brine, dried over anhydrous Na$_2$SO$_4$ and concentrated to give 3-(3-bromophenyl)-6-(2-hydroxyethyl)-6-phenyl-1,3-oxazinan-2-one (75 mg, 37%). $^1$H NMR (400 MHz, CDCl$_3$): δ=2.12-2.30 (m, 2H), 2.47 (m, 2H), 3.19 (m, 1H), 3.40 (m, 1H), 3.53 (m, 1H), 3.76 (m, 1H), 7.06 (m, 1H), 7.13 (m, 1H), 7.22 (m, 1H), 7.25-7.40 (m, 6H).

Example 75

6-(2-aminoethyl)-3-(2',4'-difluorobiphenyl-3-yl)-6-phenyl-1,3-oxazinan-2-one

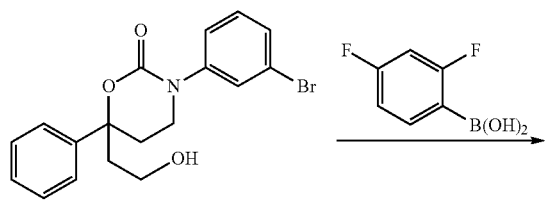

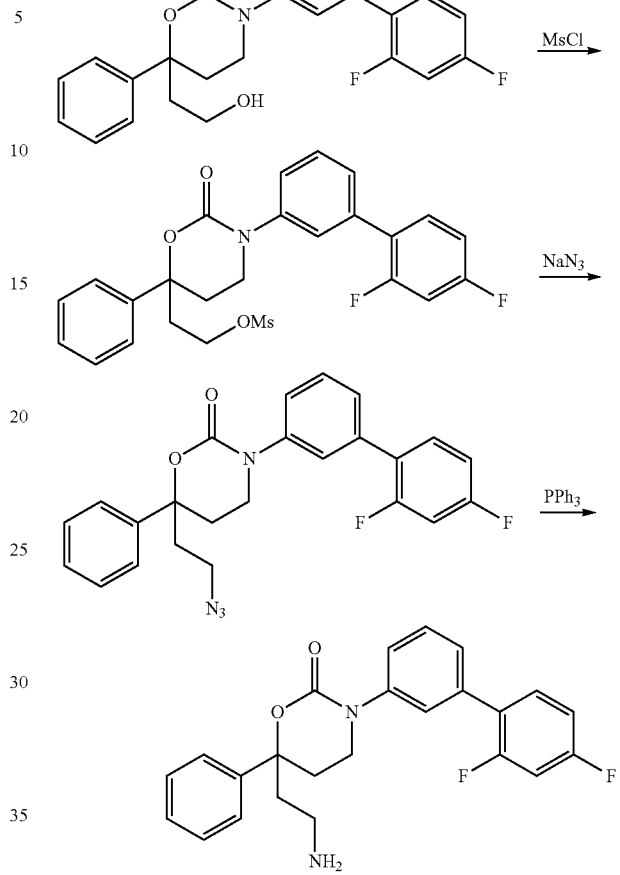

Step 1. 3-(2',4'-difluorobiphenyl-3-yl)-6-(2-hydroxyethyl)-6-phenyl-1,3-oxazinan-2-one To a solution of 3-(3-bromophenyl)-6-(2-hydroxyethyl)-6-phenyl-1,3-oxazinan-2-one (200 mg, 0.538 mmol), 4-fluorophenylboronic acid (128 mg, 0.806 mmol), and aq. K$_2$CO$_3$ (1 mL, 2 M) in 1,4-dioxane (3 ml) was slowly added Pd(Ph$_3$)$_2$Cl$_2$ (20 mg, 10%) at 0° C. under N$_2$. The mixture was refluxed overnight. The mixture was concentrated to give the crude product, which was purified by TLC and preparative HPLC to afford 3-(2',4'-difluorobiphenyl-3-yl)-6-(2-hydroxyethyl)-6-phenyl-1,3-oxazinan-2-one (200 mg, 91%). $^1$H-NMR (400 MHz, CDCl$_3$): δ=2.12-2.35 (m, 2H), 2.51 (m, 2H), 3.26 (m, 1H), 3.47-3.6 (m, 2H), 4.25 (m, 1H), 6.83 (m, 2H), 7.06 (m, 1H), 7.26-7.51 (m, 8H).

Step 2. 2-(3-(2',4'-difluorobiphenyl-3-yl)-2-oxo-6-phenyl-1,3-oxazinan-6-yl)ethyl methanesulfonate To a solution of 3-(2',4'-difluorobiphenyl-3-yl)-6-(2-hydroxyethyl)-6-phenyl-1,3-oxazinan-2-one (200 mg, 0.49 mmol) in dry CH$_2$Cl$_2$ (4 mL) was added Et$_3$N (0.234 mL, 1.46 mmol) at 0~5° C. A solution of methanesulfonyl chloride (67 mg, 0.59 mmol) in dry CH$_2$Cl$_2$ (1 mL) was added dropwise at the same temperature. After addition, the mixture was allowed to warm to it gradually. When the reaction was complete, water (10 mL) was added and the mixture was extracted with CH$_2$Cl$_2$ (3×10 mL). The combined organic layers were washed with 10% aq citric acid, satd aq NaHCO$_3$ and brine, then dried over Na$_2$SO$_4$, filtered and concentrated to give 2-(3-(2',4'-difluorobiphenyl-3-yl)-2-oxo-6-phenyl-1,3-oxazinan-6-yl)ethyl methanesulfonate (230 mg, 97%), which was used in the next step without purification.

Step 3. 6-(2-azidoethyl)-3-(2',4'-difluorobiphenyl-3-yl)-6-phenyl-1,3-oxazinan-2-one To a solution of 2-(3-(2',4'-difluorobiphenyl-3-yl)-2-oxo-6-phenyl-1,3-oxazinan-6-yl)ethyl methanesulfonate (230 mg, 0.47 mmol) in anhydrous DMF (5 mL) was added NaN$_3$ (92 mg, 1.42 mmol). The reaction mixture was heated to 70° C. overnight. The reaction mixture was cooled to rt and diluted with EtOAc (30 mL), and water (20 ml). The organic phase was washed with water (3×20 mL), dried over Na$_2$SO$_4$ and evaporated to give 6-(2-azidoethyl)-3-(2',4'-difluorobiphenyl-3-yl)-6-phenyl-1,3-oxazinan-2-one (100 mg, 49%).

Step 4. 3-(2',4'-difluorobiphenyl-3-yl)-6-(2-hydroxyethyl)-6-phenyl-1,3-oxazinan-2-one To a solution of 6-(2-azidoethyl)-3-(2',4'-difluorobiphenyl-3-yl)-6-phenyl-1,3-oxazinan-2-one (100 mg, 0.23 mmol) in 20:1 THF/H$_2$O (3 mL) was added PPh$_3$ (72 mg, 0.28 mmol). The reaction mixture was stirred at rt overnight. The solvent was removed under reduced pressure, and the residue was purified by column chromatography on silica gel to afford 6-(2-aminoethyl)-3-(2',4'-difluorobiphenyl-3-yl)-6-phenyl-1,3-oxazinan-2-one (30 mg, 31%). $^1$H NMR (400 MHz, CDCl$_3$): δ=2.20-2.51 (m, 2H), 2.51-2.60 (m, 2H), 2.72 (m, 1H), 3.00 (m, 1H), 3.24 (m, 1H), 3.53 (m, 1H), 6.85-6.99 (m, 2H), 7.14 (m, 1H), 7.31-7.50 (m, 8H).

Example 76

2-(3-(2',4'-difluorobiphenyl-3-yl)-2-oxo-6-phenyl-1,3-oxazinan-6-yl)acetamide

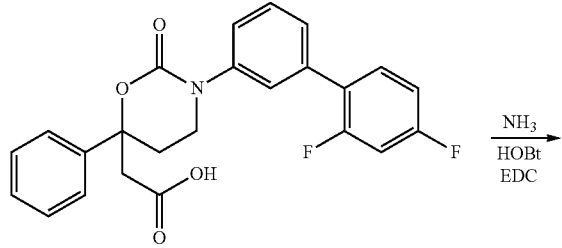

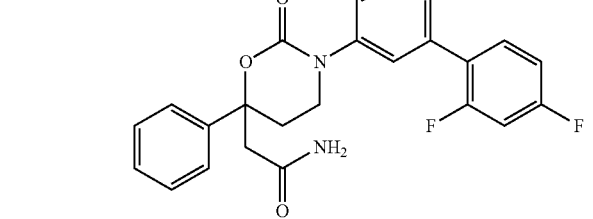

A solution of 2-(3-(2',4'-difluorobiphenyl-3-yl)-2-oxo-6-phenyl-1,3-oxazinan-6-yl)acetic acid (30 mg, 0.072 mmol), HOBt (18 mg, 0.144 mmol), EDCl (30 mg, 0.144 mmol) and DIEA (0.2 ML) in anhydrous CH$_2$Cl$_2$ (3 mL) was stirred at 0° C. under NH$_3$. Then the solution was stirred at rt overnight. Solvent was removed in vacuo, the residue was purified by HPLC to get 2-(3-(2',4'-difluorobiphenyl-3-yl)-2-oxo-6-phenyl-1,3-oxazinan-6-yl)acetamide (1.68 mg, 6%). $^1$H-NMR (400 MHz, CDCl$_3$): δ=2.58 (m, 2H), 2.80-3.00 (m, 2H), 3.27 (m, 1H), 3.50 (m, 1H), 6.00 (s, 1H), 6.36 (s, 1H), 6.78-6.90 (m, 2H), 7.05 (m, 1H), 7.23-7.55 (m, 9H).

Example 77

3-(2',4'-difluorobiphenyl-3-yl)-6-(2,3-dihydroxypropyl)-6-phenyl-1,3-oxazinan-2-one

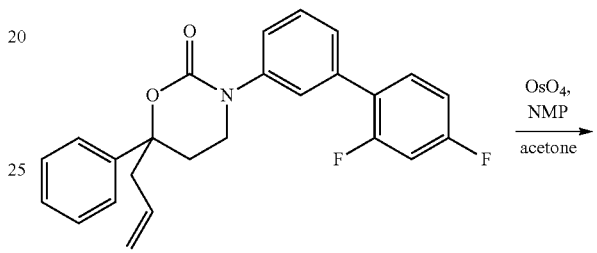

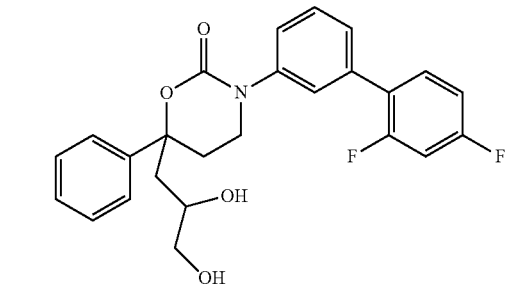

Step 1. 3-(2',4'-difluorobiphenyl-3-yl)-6-(2,3-dihydroxypropyl)-6-phenyl-1,3-oxazinan-2-one To a solution of 6-allyl-3-(2',4'-difluorobiphenyl-3-yl)-6-phenyl-1,3-oxazinan-2-one (7.1 mg, 0.018 mmol) in acetone (0.5 mL) was added NMO.H$_2$O (6 mg, 0.044 mmol), then OsO$_4$ (10 µL, 2.5 wt % in 2-Me-2-propanol). The reaction was stirred overnight at rt. The solvent was evaporated and the residue was redissolved in EtOAc. The organic layer was washed with 10% aq Na$_2$S$_2$O$_3$ (2×), 1M aq HCl (2×) and brine (1×). The organic layer was dried over Na$_2$SO$_4$, filtered, evaporated, and purified by prep HPLC to afford 3-(2',4'-difluorobiphenyl-3-yl)-6-(2,3-dihydroxypropyl)-6-phenyl-1,3-oxazinan-2-one (6.53 mg). LC-MS Method 1, m/z=440 (M+H)$^+$. $^1$H NMR (CDCl$_3$) 7.47-7.33 (m), 7.15-7.12 (m), 6.96-6.86 (m), 3.51 (br m), 3.37-3.26 (m), 2.69 (br m), 2.58-2.48 (m), 2.29-2.23 (m), 2.14 (d), 2.06 (d).

Example 78

3-(2',4'-difluorobiphenyl-3-yl)-6-(3-hydroxypropyl)-6-phenyl-1,3-oxazinan-2-one

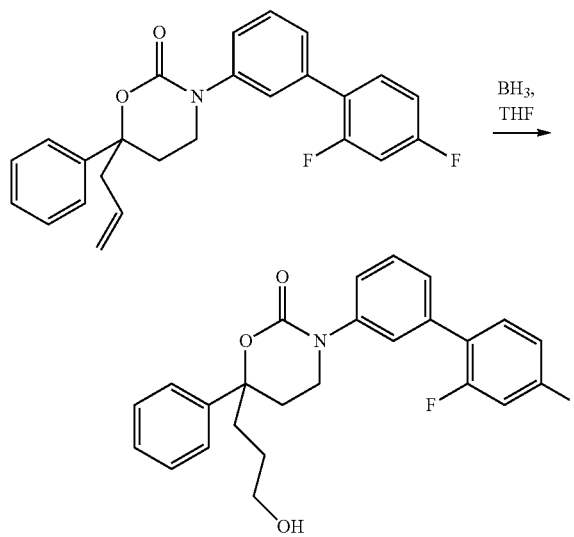

Step 1. 3-(2',4'-difluorobiphenyl-3-yl)-6-(3-hydroxypropyl)-6-phenyl-1,3-oxazinan-2-one To a 0° C. solution of 6-allyl-3-(2',4'-difluorobiphenyl-3-yl)-6-phenyl-1,3-oxazinan-2-one (18 mg, 0.045 mmol) in THF (1 mL) was added $BH_3$.THF (60 μL, 1M THF solution) and the mixture was stirred overnight at rt. The reaction was cooled to 0° C. and $NaBO_3$.$H_2O$ (19 mg, 0.20 mmol) was added and stirred for 2 h warming to rt. The solvent was removed in vacuo and the residue was redissolved in $CH_3CN$ (4 mL). The solution was filtered and purified by prep HPLC to afford 3-(2',4'-difluorobiphenyl-3-yl)-6-(3-hydroxypropyl)-6-phenyl-1,3-oxazinan-2-one (4.44 mg). LC-MS Method 1, $t_R$=1.97 min, m/z=424 (M+H). $^1$H NMR ($CDCl_3$) 7.47-7.33 (m), 7.32-7.26 (m), 7.16-7.12 (m), 6.96-6.85 (m), 4.28 (t), 3.52-3.13 (m), 3.36-3.27 (m), 2.5-2.47 (m), 2.15-1.99 (m).

Example 79

3-(biphenyl-3-yl)-6-(3-chlorophenyl)-6-methyl-1,3-oxazinan-2-one

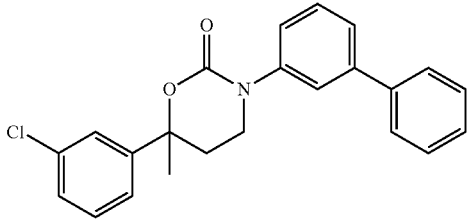 [SMILES: CC1(c2cccc(Cl)c2)CCN(c2cccc(-c3ccccc3)c2)C(=O)O1]

The title compound was prepared following procedures analogous to those described in Example 53 using 3-bromobiphenyl in Step 4. LC-MS Method 1, $t_R$=1.99 min, m/z=378, 380. $^1$H NMR ($CDCl_3$) 1.78 (s, 3H), 2.43 (m, 2H), 3.38 (m, 1H), 3.61 (m, 1H), 7.10-7.60 (13H).

Example 80

3-(2',4'-difluorobiphenyl-3-yl)-6-methyl-6-(pyridin-2-yl)-1,3-oxazinan-2-one

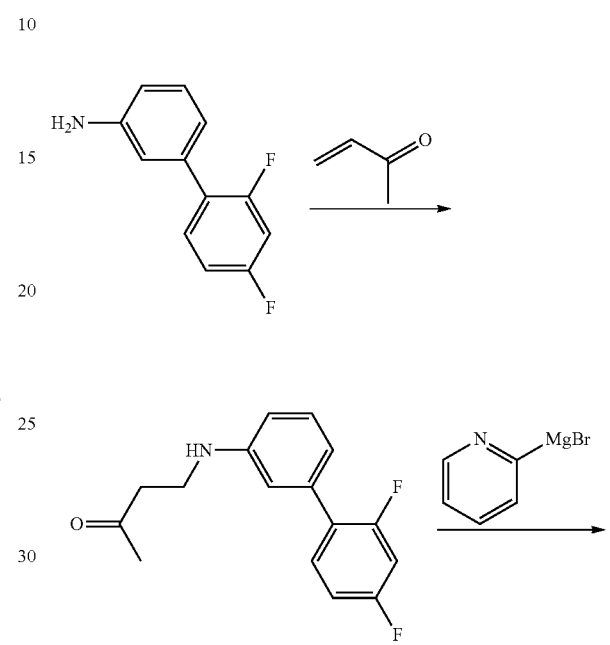

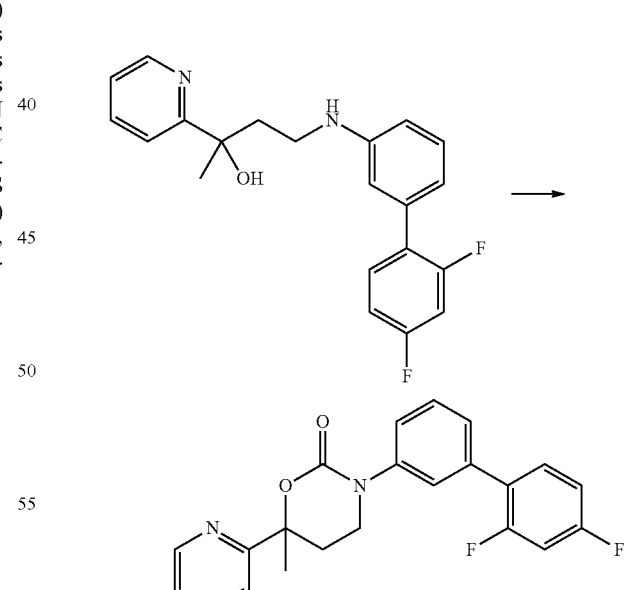

The title compound was prepared following procedures analogous to those described in Example 82 using 2',4'-difluorobiphenyl-3-amine in Step 1 and 2-pyridylmagnesium bromide in Step 2. LC-MS Method 1, $t_R$=1.72 min, m/z=381 (M+1). $^1$H NMR ($CD_3OD$) 8.55-8.54 (m, 1H), 7.91-7.87 (m, 1H), 7.62-7.60 (m, 1H), 7.44-7.32 (m, 4H), 7.26-7.25 (m, 1H), 7.14-7.11 (m, 1H), 7.00-6.94 (m, 2H), 3.66-3.60 (m, 1H), 3.25-3.18 (m, 1H), 2.78-2.72 (m, 1H), 2.43-2.35 (m, 1H), 1.69 (s, 3H).

Example 81

6-methyl-3-(3-phenoxyphenyl)-6-phenyl-1,3-oxazinan-2-one

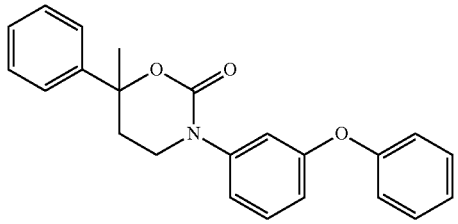 [SMILES: CC1(c2ccccc2)CCN(c2cccc(Oc3ccccc3)c2)C(=O)O1]

The title compound was prepared following procedures analogous to those described in Example 82 using 3-phenoxyaniline in Step 1. LC-MS Method 1, $t_R$=1.9 min, m/z=360 (M+1). $^1$H NMR (CD$_3$OD) 7.37-7.22 (m, 8H), 7.08-7.04 (m, 1H), 6.92-6.90 (m, 2H), 6.81-6.78 (m, 2H), 6.68-6.67 (m, 1H), 3.55-3.50 (m, 1H), 3.18-3.11 (m, 1H), 2.58-2.53 (m, 1H), 2.39-2.31 (m, 1H), 1.63 (s, 3H).

Example 82

6-methyl-6-phenyl-3-((S)-1-phenylethyl)-1,3-oxazinan-2-one

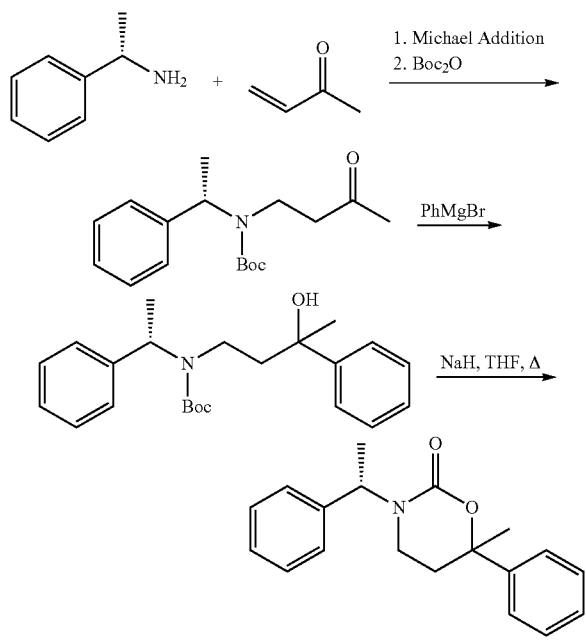

Step 1. (S)-tert-Butyl 3-oxobutyl(1-phenylethyl)carbamate

A solution of (S)-1-phenylethanamine (0.1901 g, 1.57 mmol, 1.0 equiv) and methyl vinyl ketone (0.1117 g, 1.59 mmol, 1.02 equiv) in THF (5 mL) was allowed to stand in a refrigerator (ca. 3.3° C.) for 2 d. Boc$_2$O (0.6700 g, 3.07 mmol, 1.95 equiv) was added to the solution at rt. The solution was stirred for 2 h and the solvent was removed under reduced pressure. The residue was purified by chromatography on silica gel eluted with hexanes/EtOAc to give (S)-tert-butyl 3-oxobutyl(1-phenylethyl)carbamate (0.3235 g, 71% over two steps) as a colorless oil.

Step 2. tert-Butyl 3-hydroxy-3-phenylbutyl((S)-1-phenylethyl)carbamate

A solution of phenylmagnesium bromide (1.0 M in THF, 1.0 mL) was added dropwise to a solution of (S)-tert-butyl 3-oxobutyl(1-phenylethyl)carbamate (0.0421 g, 0.144 mmol in THF (4 mL) under N$_2$ at rt. After the solution was stirred for 14 h, the reaction was quenched with 10% aq Na$_2$CO$_3$ (0.5 mL) and diluted with CH$_2$Cl$_2$. The organic layer was dried over Na$_2$SO$_4$. After the solvents were evaporated, the crude product was directly used in the next step without further purification.

Step 3. 6-Methyl-6-phenyl-3-((S)-1-phenylethyl)-1,3-oxazinan-2-one

A mixture of crude tert-butyl 3-hydroxy-3-phenylbutyl ((S)-1-phenylethyl)carbamate, obtained as described above, 60% NaH in oil (0.320 g) and THF (5 mL) was heated to reflux for 21 h. The reaction was then quenched with H$_2$O (1.5 mL) and diluted with CH$_2$Cl$_2$. The organic layer was dried over Na$_2$SO$_4$. After the solvents were evaporated, the residue was purified by reversed-phase HPLC to afford 6-methyl-6-phenyl-3-((S)-1-phenylethyl)-1,3-oxazinan-2-one. After the solvents were evaporated, the residue was purified by reversed-phase HPLC (Phenomenex® Luna 5μ C18(2) 100 A, 250×21.20 mm, 5 micron, 10%→90% CH$_3$CN/H$_2$O, 0.1% CF$_3$COOH over 13 min and then 90% CH$_3$CN/H$_2$O, 0.1% CF$_3$COOH over 4 min, flow rate 25 mL/min) to afford 6-methyl-6-phenyl-3-((S)-1-phenylethyl)-1,3-oxazinan-2-one as a mixture of diastereomers. LC-MS Method 1 $t_R$=1.71, 1.75 min, m/z=296 (MW); $^1$H NMR (400 MHz, CD$_3$OD) δ 7.36-7.18 (m), 7.06-7.02 (m), 6.89-6.85 (m), 5.54 (q, J=7.1 Hz), 5.47 (q, J=7.0 Hz), 3.00-2.95 (m), 2.73-2.69 (m), 2.40-2.34 (m), 2.26-2.19 (m), 2.13-2.05 (m), 2.00-1.92 (m), 1.53 (s), 1.52 (s), 1.45 (d, J=7.0 Hz), 1.23 (d, J=7.0 Hz). A fraction containing on the less polar diastereomer was also isolated (Isomer 1). LC-MS Method 1 $t_R$=1.75 min, m/z=296 (MH$^+$); $^1$H NMR (400 MHz, CD$_3$OD) δ 7.35-7.18 (m, 10H), 5.54 (q, J=7.0 Hz, 1H), 2.72-2.69 (m, 2H), 2.39-2.33 (m, 1H), 1.99-1.92 (m, 1H), 1.52 (s, 3H), 1.23 (d, J=7.0 Hz, 3H).

Example 83

6-methyl-6-phenyl-3-((R)-1-phenylethyl)-1,3-oxazinan-2-one

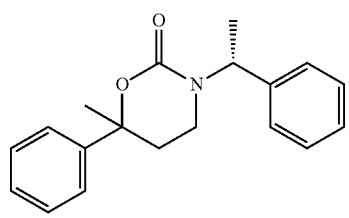 [SMILES: C[C@H](c1ccccc1)N1CCC(C)(c2ccccc2)OC1=O]

The two diastereomers of the title compound were prepared and separated following procedures analogous to those described in Example 82 using (R)-1-phenylethanamine in Step 1.

Isomer 1: LC-MS Method 1, $t_R$=1.75 min, m/z=296 (M+1). $^1$H NMR (CD$_3$OD) 7.35-7.18 (m, 10H), 5.54 (q, J=7.1 Hz, 1H), 2.72-2.69 (m, 2H), 2.39-2.34 (m, 1H), 2.00-1.92 (m, 1H), 1.52 (s, 3H), 1.23 (d, J=7.0 Hz, 3H).

Isomer 2: LC-MS Method 1, tR==1.71 min, m/z=296 (M+1). $^1$H NMR (CD$_3$OD) 7.37-7.18 (m), 7.06-7.01 (m), 6.89-6.85 (m), 5.54 (q, J=7.2 Hz), 5.47 (q, J=7.0 Hz), 3.00-2.95 (m), 2.72-2.69 (m), 2.40-2.34 (m), 2.25-2.18 (m), 2.13-2.05 (m), 2.00-1.92 (m), 1.53 (s), 1.52 (s), 1.45 (d, J=7.0 Hz), 1.23 (d, J=7.0 Hz).

Example 84

3-((S)-1-(3-methoxyphenyl)ethyl)-6-methyl-6-phenyl-1,3-oxazinan-2-one

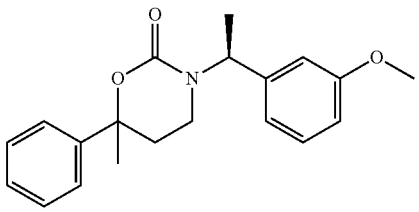 [SMILES: COc1cccc([C@H](C)N2CCC(C)(c3ccccc3)OC2=O)c1]

The two diastereomers of the title compound were prepared and separated following procedures analogous to those described in Example 82 using (S)-1-(3-methoxyphenyl)ethanamine in Step 1.

Isomer 1: LC-MS Method 1, $t_R$=1.72 min, m/z=326 (M+1). $^1$H NMR (CDCl$_3$) 7.40-7.23 (m, 6H), 6.91-6.80 (m, 3H), 5.78 (q, J=7.0 Hz, 1H), 3.80 (s, 3H), 2.70-2.67 (m, 2H), 2.29-2.23 (m, 1H), 2.06-1.98 (m, 1H), 1.64 (s, 3H), 1.27 (d, J=7.3 Hz, 3H).

Isomer 2: LC-MS Method 1, $t_R$=1.68 min, m/z=326 (M+1). $^1$H NMR (CDCl$_3$) 7.34-7.25 (m, 5H), 7.06-7.02 (m, 1H), 6.70-6.67 (m, 1H), 6.57-6.54 (m, 2H), 5.68 (q, J=7.0 Hz, 1H), 3.63 (s, 3H), 2.92-2.87 (m, 1H), 2.39-2.26 (m, 2H), 2.17-2.10 (m, 1H), 1.64 (s, 3H), 1.52 (d, J=7.0 Hz, 3H).

Example 85

3-((S)-1-(4-methoxyphenyl)ethyl)-6-methyl-6-phenyl-1,3-oxazinan-2-one

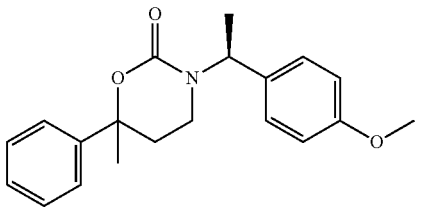 [SMILES: COc1ccc([C@H](C)N2CCC(C)(c3ccccc3)OC2=O)cc1]

The two diastereomers of the title compound were prepared and separated following procedures analogous to those described in Example 82 (S)-1-(4-methoxyphenyl)ethanamine in Step 1.

Isomer 1: LC-MS Method 1, $t_R$=1.72 min, m/z=326 (M+1). $^1$H NMR (CDCl$_3$) 7.40-7.21 (m, 7H), 6.88-6.84 (m, 2H), 5.76 (q, J=7.1 Hz, 1H), 3.80 (s, 3H), 2.68-2.65 (m, 2H), 2.27-2.22 (m, 1H), 2.02-1.95 (m, 1H), 1.62 (s, 3H), 1.26 (d, J=7.3 Hz, 3H).

Isomer 2: LC-MS Method 1, $t_R$=1.68 min, m/z=326 (M+1). $^1$H NMR (CDCl$_3$) 7.37-7.27 (m, 5H), 6.88-6.84 (m, 2H), 6.66-6.62 (m, 2H), 5.65 (q, J=7.1 Hz, 1H), 3.73 (s, 3H), 2.90-2.85 (m, 1H), 2.32-2.25 (m, 2H), 2.16-2.09 (m, 1H), 1.64 (s, 3H), 1.50 (d, J=7.0 Hz, 3H).

Example 86

6-methyl-3-((S)-1-phenylethyl)-6-o-tolyl-1,3-oxazinan-2-one

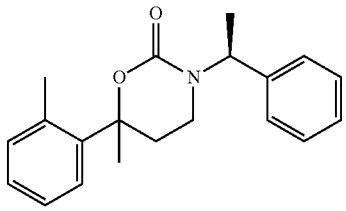 [SMILES: Cc1ccccc1C1(C)CCN([C@@H](C)c2ccccc2)C(=O)O1]

The two diastereomers of the title compound were prepared and separated following procedures analogous to those described in Example 82 using o-tolylmagnesium bromide in Step 2.

Isomer 1: LC-MS Method 1, $t_R$=1.83 min, m/z=310 (M+1). $^1$H NMR (CDCl$_3$) 7.42-7.16 (m, 9H), 5.77 (q, J=7.1 Hz, 1H), 2.79-2.66 (m, 2H), 2.61-2.55 (m, 1H), 2.47 (s, 3H), 2.03-1.95 (m, 1H), 1.70 (s, 3H), 1.27 (d, J=7.3 Hz, 3H).

Isomer 2: LC-MS Method 1, $t_R$=1.79 min, m/z=310 (M+1). $^1$H NMR (CDCl$_3$) 7.35-7.33 (m, 1H), 7.23-7.06 (m, 6H), 6.86-6.84 (m, 2H), 5.66 (q, J=7.0 Hz, 1H), 2.96-2.91 (m, 1H), 2.62-2.56 (m, 1H), 2.48 (s, 3H), 2.43-2.36 (m, 1H), 2.16-2.08 (m, 1H), 1.71 (s, 3H), 1.53 (d, J=7.0 Hz, 3H).

Example 87

6-methyl-3-((S)-1-phenylethyl)-6-m-tolyl-1,3-oxazinan-2-one

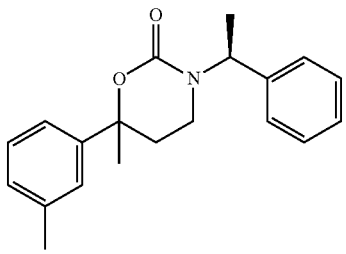 [SMILES: Cc1cccc(C2(C)CCN([C@@H](C)c3ccccc3)C(=O)O2)c1]

The two diastereomers of the title compound were prepared and separated following procedures analogous to those described in Example 82 using m-tolylmagnesium bromide in Step 2.

Isomer 1: LC-MS Method 1, $t_R$=1.84 min, m/z=310 (M+1). $^1$H NMR (CDCl$_3$) 7.36-7.24 (m, 6H), 7.16-7.10 (m, 3H), 5.81 (q, J=7.1 Hz, 1H), 2.74-2.63 (m, 2H), 2.37 (s, 3H), 2.26-2.21 (m, 1H), 2.03-1.95 (m, 1H), 1.62 (s, 3H), 1.31 (d, J=7.0 Hz, 3H).

Isomer 2: LC-MS Method 1, $t_R$=1.80 min, m/z=310 (M+1). $^1$H NMR (CDCl$_3$) 7.24-7.20 (m, 1H), 7.14-7.09 (m, 6H), 6.98-6.95 (m, 2H), 5.73 (q, J=7.0 Hz, 1H), 2.93-2.87 (m, 1H), 2.35 (s, 3H), 2.34-2.23 (m, 2H), 2.17-2.09 (m, 1H), 1.64 (s, 3H), 1.53 (d, J=7.0 Hz, 3H).

Example 88

6-methyl-3-((S)-1-phenylethyl)-6-p-tolyl-1,3-oxazinan-2-one

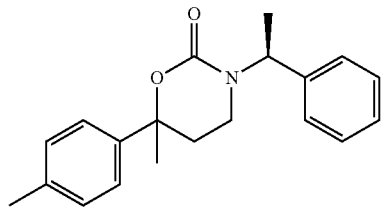 [SMILES: Cc1ccc(C2(C)CCN([C@@H](C)c3ccccc3)C(=O)O2)cc1]

The two diastereomers of the title compound were prepared and separated following procedures analogous to those described in Example 82 using p-tolylmagnesium bromide in Step 2.

Isomer 1: LC-MS Method 1, $t_R$=1.86 min, m/z=310 (M+1). $^1$H NMR (CDCl$_3$) 7.36-7.17 (m, 9H), 5.81 (q, J=7.2 Hz, 1H), 2.74-2.63 (m, 2H), 2.35 (s, 3H), 2.25-2.20 (m, 1H), 2.03-1.95 (m, 1H), 1.61 (s, 3H), 1.31 (d, J=7.3 Hz, 3H).

Isomer 2: LC-MS Method 1, $t_R$=1.80 min, m/z=310 (M+1). $^1$H NMR (CDCl$_3$) 7.22-7.19 (m, 2H), 7.16-7.08 (m, 5H), 6.96-6.93 (m, 2H), 5.71 (q, J=7.0 Hz, 1H), 2.92-2.87 (m, 1H), 2.36 (s, 3H), 2.35-2.23 (m, 2H), 2.16-2.08 (m, 1H), 1.62 (s, 3H), 1.53 (d, J=7.0 Hz, 3H).

Example 89

3-((S)-1-(3-hydroxyphenyl)ethyl)-6-methyl-6-phenyl-1,3-oxazinan-2-one

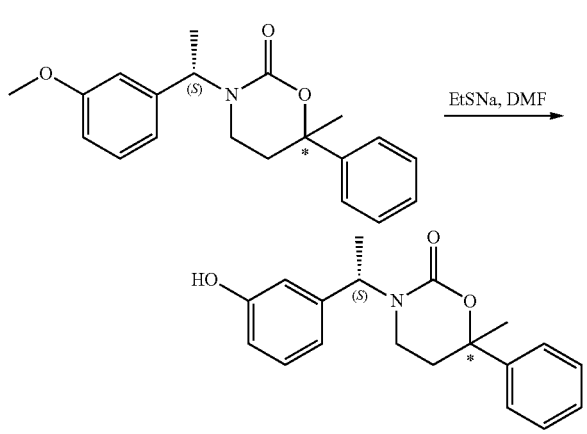

A mixture of 3-((S)-1-(3-methoxyphenyl)ethyl)-6-methyl-6-phenyl-1,3-oxazinan-2-one Isomer 1 (0.1240 g, 0.381 mmol) and EtSNa (0.2115 g, 2.51 mmol) in DMF (2 mL) was heated at 170° C. for 2.5 h under nitrogen. The mixture was diluted with EtOAc, washed with 1 N aq HCl. The aqueous phase was extracted with EtOAc (2x). The combined organic phase was dried over Na$_2$SO$_4$. After the solvents were evaporated, the residue was purified by chromatography on silica gel eluted with hexanes/EtOAc to afford of 3-((S)-1-(3-hydroxyphenyl)ethyl)-6-methyl-6-phenyl-1,3-oxazinan-2-one (0.1036 g, 87%). LC-MS Method 1 $t_R$=1.49 min, m/z 312 (MH$^+$); $^1$H NMR (400 MHz, CDCl$_3$) δ 7.59-7.53 (m, 1H), 7.40-7.28 (m, 5H), 7.19-7.15 (m, 1H), 6.98 (m, 1H), 6.83-6.75 (m, 2H), 5.74 (q, J=7.1 Hz, 1H), 2.80-2.67 (m, 2H), 2.30-2.25 (m, 1H), 2.09-2.01 (m, 1H), 1.62 (s, 3H), 1.25 (d, J=7.0 Hz, 3H).

Example 90

6-methyl-6-(4-(methylthio)phenyl)-3-((S)-1-phenylethyl)-1,3-oxazinan-2-one

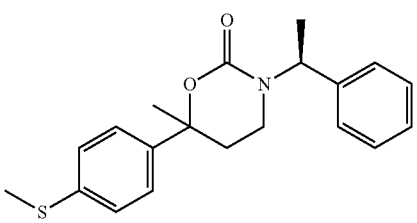 [SMILES: CSc1ccc(C2(C)CCN([C@@H](C)c3ccccc3)C(=O)O2)cc1]

The title compound was prepared following procedures analogous to those described in Example 82 using p-(methylthio)phenylmagnesium bromide in Step 2. LC-MS Method 1, $t_R$=1.84 min, m/z=342 (M+1). $^1$H NMR (CDCl$_3$) 7.37-7.24 (m, 9H), 5.81 (q, J=7.2 Hz, 1H), 2.75-2.65 (m, 2H), 2.50 (s, 3H), 2.25-2.19 (m, 1H), 2.04-1.96 (m, 1H), 1.61 (s, 3H), 1.33 (d, J=7.0 Hz, 3H).

Example 91 ethyl 2-(3-((1S)-1-(6-methyl-2-oxo-6-phenyl-1,3-oxazinan-3-yl)ethyl)phenoxy)acetate

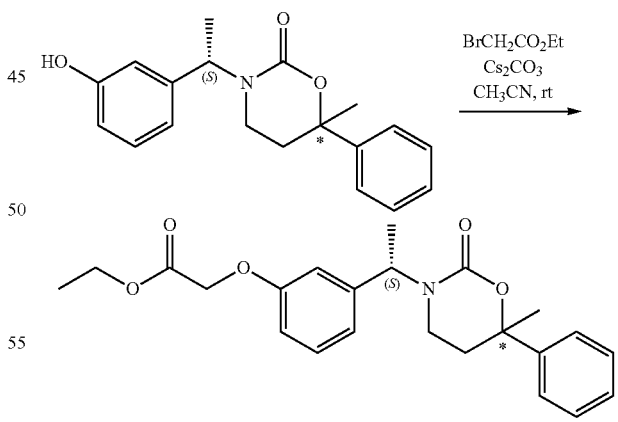

A mixture of (R/S)-3-((S)-1-(3-hydroxyphenyl)ethyl)-6-methyl-6-phenyl-1,3-oxazinan-2-one (0.0955 g, 0.31 mmol, 1.0 equiv), Cs$_2$CO$_3$ (0.3307 g, 1.01 mmol, 3.3 equiv), and ethyl bromoacetate (0.1468 g, 0.88 mmol, 2.8 equiv) in CH$_3$CN (1.5 mL) was stirred at rt for 3 d. The mixture was diluted with CH$_2$Cl$_2$, treated with H$_2$O (2 mL), dried over Na$_2$SO$_4$. After the solvents were evaporated, the residue was purified by chromatography on silica gel eluted with hexanes/

EtOAc to afford 0.1025 g (84%) of ethyl 2-(3-((S)-1-((R/S)-6-methyl-2-oxo-6-phenyl-1,3-oxazinan-3-yl)ethyl)phenoxy)acetate. LC-MS Method 1, $t_R$=1.75 min, m/z=398 (M+1). $^1$H NMR (CDCl$_3$) 7.40-7.23 (m, 6H), 6.95-6.93 (m, 1H), 6.88 (m, 1H), 6.81-6.78 (m, 1H), 5.76 (q, J=7.1 Hz, 1H), 4.61 (s, 2H), 4.27 (q, J=7.1 Hz, 2H), 2.68-2.65 (m, 2H), 2.28-2.23 (m, 1H), 2.06-1.98 (m, 1H), 1.63 (s, 3H), 1.30 (t, J=7.2 Hz, 3H), 1.26 (d, J=7.3 Hz, 3H).

Example 92

6-methyl-6-(4-(morpholinomethyl)phenyl)-3-((S)-1-phenylethyl)-1,3-oxazinan-2-one

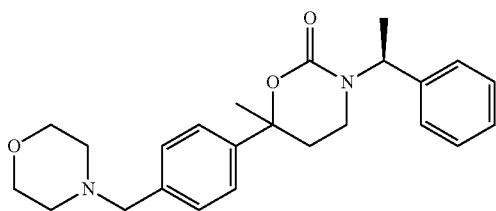 [SMILES: C[C@@H](c1ccccc1)N1CCC(C)(c2ccc(CN3CCOCC3)cc2)OC1=O]

The title compound was prepared following procedures analogous to those described in Example 82 using (4-(morpholinomethyl)phenyl)magnesium bromide in Step 2. LC-MS Method 1, $t_R$=1.12 min, m/z=395 (M+1). $^1$H NMR (CD$_3$OD) 7.48 (d, J=8.5 Hz, 2H), 7.42 (d, J=8.5 Hz, 2H), 7.27-7.16 (m, 5H), 5.51 (q, J=7.2 Hz, 1H), 4.28 (s, 2H), 3.95-3.92 (m, 2H), 3.66-3.60 (m, 2H), 3.28-3.25 (m, 2H), 3.13-3.08 (m, 2H), 2.72-2.69 (m, 2H), 2.36-2.30 (m, 1H), 2.02-1.94 (m, 1H), 1.49 (s, 3H), 1.22 (d, J=7.0 Hz, 3H).

Example 93

(R/S)-3-(S)-1-(3-(2-hydroxy-2-methylpropoxy)phenyl)ethyl)-6-methyl-6-phenyl-1,3-oxazinan-2-one

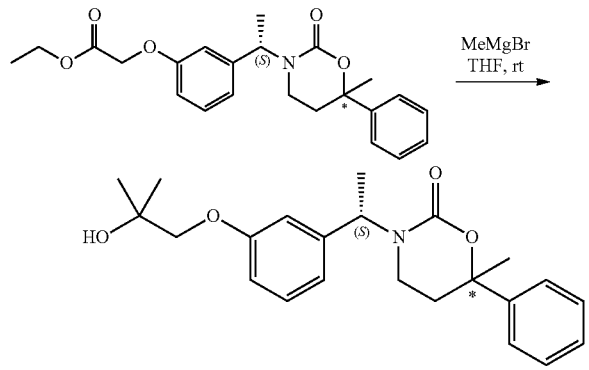

To a solution of ethyl 2-(3-((S)-1-((R/S)-6-methyl-2-oxo-6-phenyl-1,3-oxazinan-3-yl)ethyl)phenoxy)acetate (0.0369 g, 0.0928 mmol) in THF (5 mL) was added methylmagnesium bromide (1.4 M in toluene/THF, 1.0 mL, 1.4 mmol) at rt under nitrogen. After stirring for 1 h, the mixture was quenched with saturated NH$_4$Cl (1 mL), diluted with CH$_2$Cl$_2$, and dried over Na$_2$SO$_4$. After the solvents were evaporated, the residue was purified by chromatography on silica gel eluted with hexanes/EtOAc to afford 0.0268 g (75%) of (R/S)-3-((S)-1-(3-(2-hydroxy-2-methylpropoxy)phenyl) ethyl)-6-methyl-6-phenyl-1,3-oxazinan-2-one. LC-MS Method 1, $t_R$=1.64 min, m/z=384 (M+1). $^1$H NMR (CDCl$_3$) 7.41-7.23 (m, 6H), 6.92-6.88 (m, 2H), 6.84-6.81 (m, 1H), 5.77 (q, J=7.0 Hz, 1H), 3.78 (s, 2H), 2.70-2.67 (m, 2H), 2.29-2.24 (m, 1H), 2.23 (s, 1H), 2.06-1.98 (m, 1H), 1.64 (s, 3H), 1.35 (s, 6H), 1.27 (d, J=7.0 Hz, 3H).

Example 94

(R/S)-6-methyl-3-((S)-1-(3-(2-oxo-2-(piperazin-1-yl)ethoxy)phenyl)ethyl)-6-phenyl-1,3-oxazinan-2-one

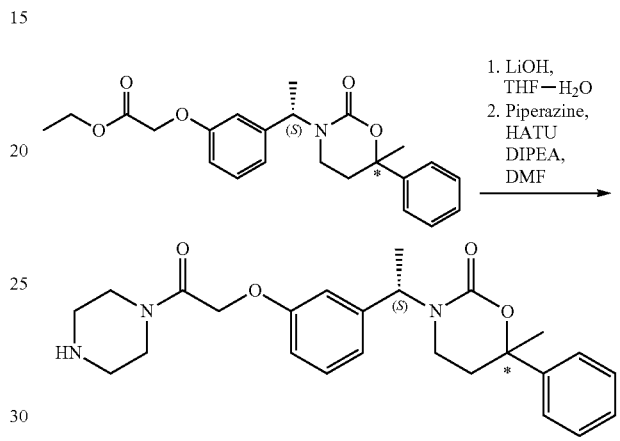

Step 1. 2-(3-((S)-1-((R/S)-6-methyl-2-oxo-6-phenyl-1,3-oxazinan-3-yl)ethyl)phenoxy)-acetic acid A mixture of ethyl 2-(3-((S)-1-((R/S)-6-methyl-2-oxo-6-phenyl-1,3-oxazinan-3-yl)ethyl)phenoxy)acetate (0.0587 g, 0.148 mmol) and lithium hydroxide monohydrate (0.4275 g, 10.2 mmol) in THF (10 mL) and H$_2$O (10 mL) was vigorously stirred at rt for 2 d. The mixture was treated with 1 N HCl (30 mL), extracted with EtOAc (3×), dried over Na$_2$SO$_4$. After the solvents were evaporated, the crude product was directly used in the next step without further purification. LC-MS $t_R$=1.48 min in 3 min chromatography, m/z 370 (MH$^+$).

Step 2. (R/S)-6-methyl-3-((S)-1-(3-(2-oxo-2-(piperazin-1-yl)ethoxy)phenyl)ethyl)-6-phenyl-1,3-oxazinan-2-one A mixture of 2-(3-((S)-1-((R/S)-6-methyl-2-oxo-6-phenyl-1,3-oxazinan-3-yl)ethyl)phenoxy)acetic acid (0.0178 g, 0.0481 mmol), piperazine (0.0575 g, 0.67 mmol), HATU (0.1136 g, 0.30 mmol), and i-Pr$_2$NEt (0.5 mL, 2.87 mmol) in DMF (1 mL) was stirred overnight at rt. After the solvents were removed in vacuo, the residue was purified by reversed-phase HPLC (Phenomenex® Luna 5µ C18(2) 100 A, 250× 21.20 mm, 5 micron, 10%→90% CH$_3$CN/H$_2$O, 0.1% CF$_3$COOH over 13 min, flow rate 25 mL/min) to give 0.0207 g of TFA salt of (R/S)-6-methyl-3-((S)-1-(3-(2-oxo-2-(piperazin-1-yl)ethoxy)phenyl)ethyl)-6-phenyl-1,3-oxazinan-2-one. LC-MS Method 1, $t_R$=1.17 min, m/z=438 (M+1). $^1$H NMR (CD$_3$OD) 7.34-7.17 (m, 6H), 6.84-6.80 (m, 3H), 5.47 (q, J=7.1 Hz, 1H), 4.78 (m, 2H), 3.78-3.75 (m, 4H), 3.18 (m, 4H), 2.72-2.69 (m, 2H), 2.40-2.34 (m, 1H), 2.01-1.93 (m, 1H), 1.52 (s, 3H), 1.20 (d, J=7.3 Hz, 3H).

Example 95

6-allyl-6-(4-fluorophenyl)-3-((S)-1-phenylethyl)-1,3-oxazinan-2-one

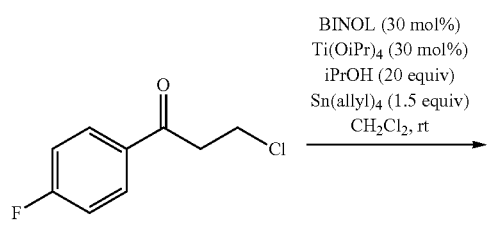

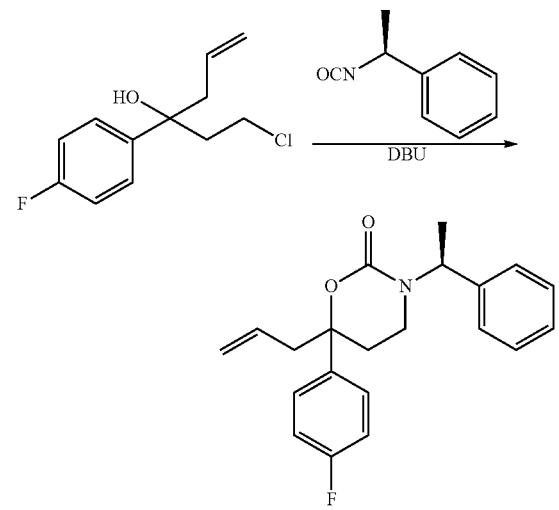

Step 1. 1-Chloro-3-(4-fluorophenyl)hex-5-en-3-ol

To a solution of 1,1'-bi-2-naphthol (0.2280 g, 0.80 mmol, 0.26 equiv), CH$_2$Cl$_2$ (5 mL) and titanium(IV) isopropoxide (0.2243 g, 0.79 mmol, 0.26 equiv) were added 2-propanol (3.1620 g, 52.6 mmol, 17 equiv), tetraallylstannane (1.2538 g, 4.43 mmol, 1.43 equiv), and 3-chloro-1-(4-fluorophenyl)propan-1-one (0.5760 g, 3.09 mmol, 1.0 equiv) successively. The reaction mixture was stirred at rt under nitrogen for 22 h. The reaction was quenched with satd aq NH$_4$Cl and extracted with EtOAc. The organic layer was dried over Na$_2$SO$_4$. After the solvents were evaporated, the residue was purified by chromatography on silica gel eluted with hexanes/EtOAc to afford 1-chloro-3-(4-fluorophenyl)hex-5-en-3-ol as an oil.

Step 2. 6-Allyl-6-(4-fluorophenyl)-3-((S)-1-phenylethyl)-1,3-oxazinan-2-one

A mixture of 1-chloro-3-(4-fluorophenyl)hex-5-en-3-ol (0.0889 g, 0.39 mmol, 1.0 equiv), (S)-(−)α-methylbenzyl isocyanate (0.0823 g, 0.56 mmol, 1.44 equiv), and DBU (0.1397 g, 0.92 mmol, 2.36 equiv) in THF (2 mL) was heated to reflux for 17 h. After the solvent was removed, the residue was purified by chromatography on silica gel eluted with hexanes/EtOAc to give 0.0990 g (75%) of the product as a mixture of diastereomers. Selected fractions contained the individual diastereomers.

Isomer 1: (R)-6-allyl-6-(4-fluorophenyl)-3-((S)-1-phenylethyl)-1,3-oxazinan-2-one. LC-MS Method 1, t$_R$=1.89 min, m/z=340 (M+1). $^1$H NMR (CDCl$_3$) 7.36-7.27 (m, 7H), 7.10-7.05 (m, 2H), 5.79-5.67 (m, 2H), 5.09-4.98 (m, 2H), 2.72-2.68 (m, 2H), 2.64-2.53 (m, 2H), 2.22-2.16 (m, 1H), 2.09-2.01 (m, 1H), 1.26 (d, J=7.3 Hz, 3H).

Isomer 2: (S)-6-allyl-6-(4-fluorophenyl)-3-((S)-1-phenylethyl)-1,3-oxazinan-2-one. LC-MS Method 1, t$_R$=1.86 min, m/z=340 (M+1). $^1$H NMR (CDCl$_3$) 7.29-7.24 (m, 2H), 7.14-7.08 (m, 3H), 7.05-7.00 (m, 2H), 6.88-6.85 (m, 2H), 5.77-5.63 (m, 2H), 5.10-5.00 (m, 2H), 2.93-2.88 (m, 1H), 2.65-2.52 (m, 2H), 2.32-2.17 (m, 3H), 1.51 (d, J=7.0 Hz, 3H).

Example 96

3-(4',6-difluorobiphenyl-3-yl)-6-(2-hydroxyethyl)-6-phenyl-1,3-oxazinan-2-one

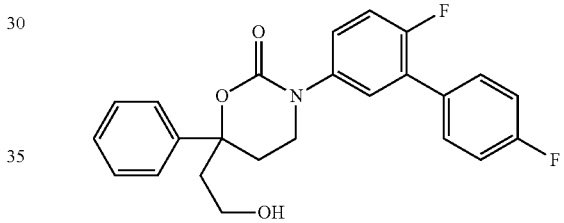

The title compound was prepared by application of procedures analogous to those described in Example 63 using 4',6-difluorobiphenyl-3-amine in Step 2 followed by Example 65. LC-MS Method 3, t$_R$=1.215 min, m/z=410. $^1$H NMR (CDCl$_3$) 2.12-2.30 (m, 2H), 2.47 (m, 2H), 3.21 (m, 1H), 3.42 (m, 1H), 3.54 (m, 1H), 3.75 (m, 2H), 7.06-7.11 (m, 5H), 7.26-7.40 (m, 7H).

Chiral preparative SFC using a ChiralCel-AS, 400×25 mm I.D, 20 µm (Daicel Chemical Industries, Ltd) column maintained at 35° C. eluted with 70:30 supercritical CO$_2$/0.1% diethylamine in MeOH at a flow rate of 70 mL min$^{-1}$ and a nozzle pressure of 100 bar afforded the two enantiomers.

Isomer 1: (S)-3-(4',6-difluorobiphenyl-3-yl)-6-(2-hydroxyethyl)-6-phenyl-1,3-oxazinan-2-one. LC-MS Method 3, t$_R$=1.214 min, m/z=410. $^1$H NMR (CDCl$_3$) δ=2.12-2.30 (m, 2H), 2.47 (m, 2H), 3.21 (m, 1H), 3.42 (m, 1H), 3.54 (m, 1H), 3.75 (m, 2H), 7.06-7.11 (m, 5H), 7.26-7.40 (m, 7H).

Isomer 2: (R)-3-(4',6-difluorobiphenyl-3-yl)-6-(2-hydroxyethyl)-6-phenyl-1,3-oxazinan-2-one. LC-MS Method 3, t$_R$=1.207 min, m/z=410. $^1$H NMR (CDCl$_3$) δ=2.20-2.40

(m, 2H), 2.57 (m, 2H), 3.30 (m, 1H), 3.53 (m, 2H), 3.64 (m, 1H), 3.84 (m, 1H), 7.06-7.20 (m, 5H), 7.39 (m, 1H), 7.45 (m, 6H).

Example 97

6-(4-fluorophenyl)-6-(2-hydroxyethyl)-3-((S)-1-phenylethyl)-1,3-oxazinan-2-one

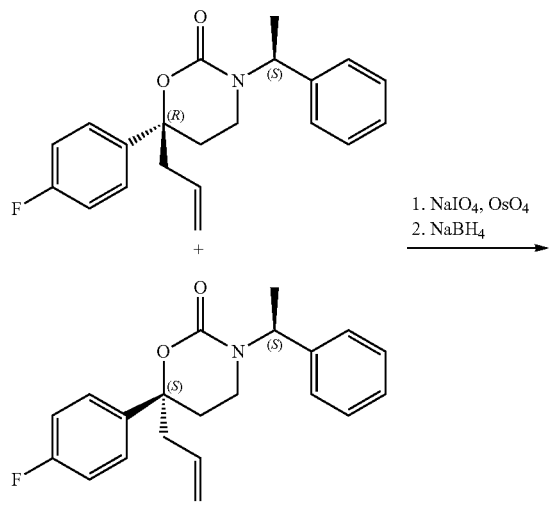

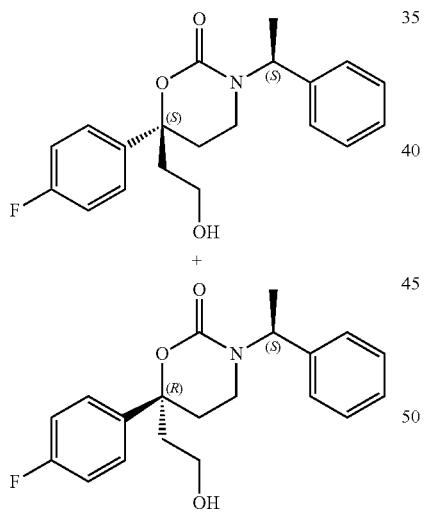

To a solution of 6-allyl-6-(4-fluorophenyl)-3-((S)-1-phenylethyl)-1,3-oxazinan-2-one (0.1016 g, 0.30 mmol, 1.0 equiv) in THF-H$_2$O (1:1, 6 mL) were added NaIO$_4$ (0.3240 g, 1.5 mmol, 5 equiv) and OsO$_4$ (2.5 wt. % solution in t-BuOH, 0.0507 g, 0.0049 mmol, 0.016 equiv), and the mixture was stirred at rt for 2 h. The mixture was diluted with EtOAc, dried over Na$_2$SO$_4$, and concentrated under reduced pressure. The residue was dissolved in MeOH (3 mL) and NaBH$_4$ (0.100 g) was added. After the mixture was stirred for 1.5 h at rt, acetone was added. The solvents were removed in vacuo, the residue was treated with saturated brine, extracted with CH$_2$Cl$_2$, and dried over Na$_2$SO$_4$. After the solvents were evaporated, the residue was purified by chromatography on silica gel eluted with hexanes/EtOAc to afford the two diastereomers of 6-(4-fluorophenyl)-6-(2-hydroxyethyl)-3-((S)-1-phenylethyl)-1,3-oxazinan-2-one.

Isomer 1: (R)-6-(4-fluorophenyl)-6-(2-hydroxyethyl)-3-((S)-1-phenylethyl)-1,3-oxazinan-2-one. LC-MS Method 1 $t_R$=1.51 min, m/z=344 (MH$^+$); $^1$H NMR (400 MHz, CDCl$_3$) δ 7.36-7.27 (m, 7H), 7.12-7.07 (m, 2H), 5.76 (q, J=7.1 Hz, 1H), 3.78-3.74 (m, 1H), 3.58-3.51 (m, 1H), 2.72-2.62 (m, 2H), 2.28-2.08 (m, 4H), 1.80 (br s, 1H), 1.28 (d, J=7.3 Hz, 3H); $^{19}$F NMR (376 MHz, CDCl$_3$) δ −114.84 (m).

Isomer 2: (S)-6-(4-fluorophenyl)-6-(2-hydroxyethyl)-3-((S)-1-phenylethyl)-1,3-oxazinan-2-one. LC-MS Method 1 $t_R$=1.48 min, m/z=344 (MH$^+$); $^1$H NMR (400 MHz, CDCl$_3$) δ 7.29-7.25 (m, 2H), 7.16-7.10 (m, 3H), 7.07-7.02 (m, 2H), 6.93-6.90 (m, 2H), 5.66 (q, J=7.0 Hz, 1H), 3.80-3.74 (m, 1H), 3.58-3.53 (m, 1H), 2.94-2.88 (m, 1H), 2.32-2.07 (m, 5H), 1.79 (br s, 1H), 1.52 (d, J=7.0 Hz, 3H); $^{19}$F NMR (376 MHz, CDCl$_3$) δ −115.03 (m).

Example 98

N-(2-(3-(2',4'-difluorobiphenyl-3-yl)-2-oxo-6-phenyl-1,3-oxazinan-6-yl)ethyl)acetamide

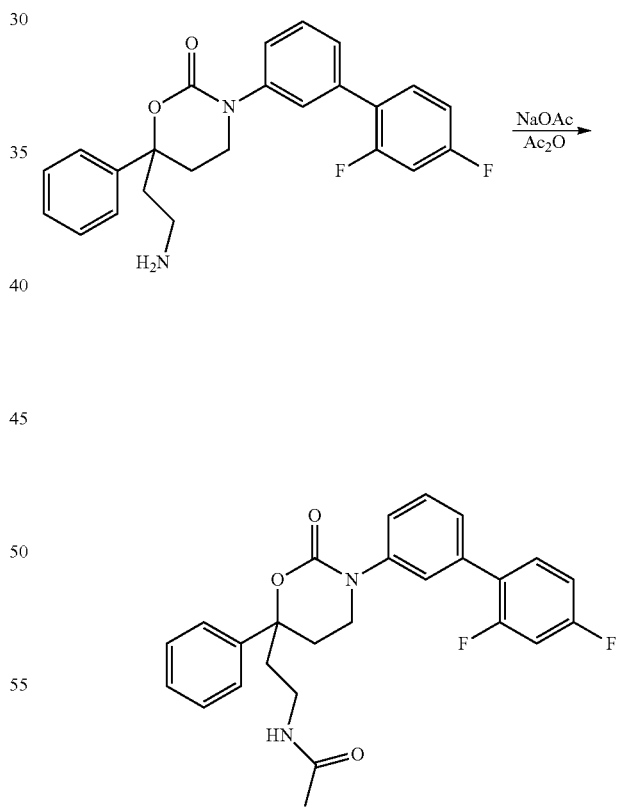

In a 5 dram vial, sodium acetate (3 mg, 0.04 mmol) was added to 6-(2-aminoethyl)-3-(2',4'-difluorobiphenyl-3-yl)-6-phenyl-1,3-oxazinan-2-one (5.13 mg, 0.013 mmol) in acetic anhydride (0.5 mL). The reaction was stirred for 2 h. The solvent was evaporated and the crude residue purified via prep HPLC to afford 1.88 mg of N-(2-(3-(2',4'-difluorobiphenyl- 3-yl)-2-oxo-6-phenyl-1,3-oxazinan-6-yl)ethyl)acetamide. LC-MS Method 1 m/z=451 (M+H)+.

Example 99

N-(2-(3-(2',4'-difluorobiphenyl-3-yl)-2-oxo-6-phenyl-1,3-oxazinan-6-yl)ethyl)methanesulfonamide

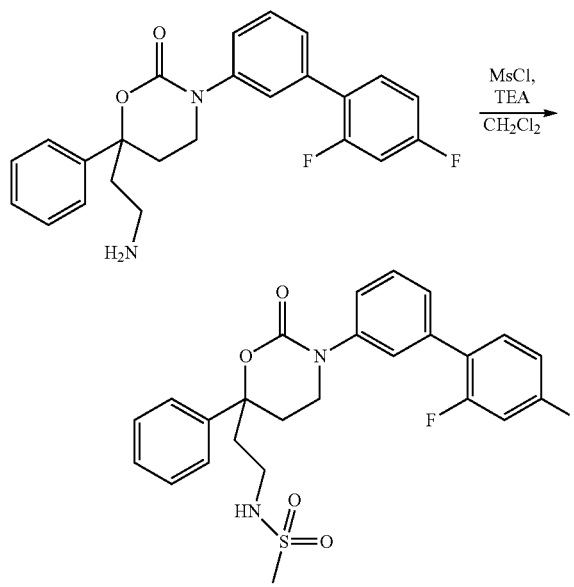

In a 5 dram vial, methanesulfonyl chloride (5 drops) was added to 6-(2-aminoethyl)-3-(2',4'-difluorobiphenyl-3-yl)-6-phenyl-1,3-oxazinan-2-one (5 mg, 0.012 mmol) and TEA (5 drops) dissolved in methylene chloride (0.5 mL). The reaction was stirred for 2 h. The solvent was evaporated and the crude residue purified via prep HPLC to afford 3.56 mg of N-(2-(3-(2',4'-difluorobiphenyl-3-yl)-2-oxo-6-phenyl-1,3-oxazinan-6-yl)ethyl)methanesulfonamide. LC-MS Method 1 m/z=487 (M+H)+.

Example 100

3-(2'-chloro-4',6-difluorobiphenyl-3-yl)-6-(4-fluorophenyl)-6-(2-hydroxyethyl)-1,3-oxazinan-2-one

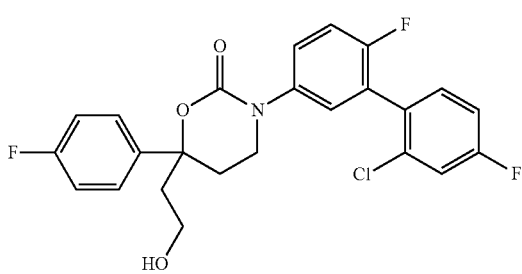 [SMILES: O=C1OC(CCO)(c2ccc(F)cc2)CCN1c1ccc(F)c(-c2ccc(F)cc2Cl)c1]

The title compound was prepared by sequential application of procedures analogous to those described in Example 63 using p-fluoroacetophenone in Step 1 and 3-bromo-4-fluoroaniline in Step 2, Example 74 and Example 75 Step 1 using 2-chloro-4-fluorophenylboronic acid. LC-MS Method 3, $t_R$=1.265 min, m/z=462. $^1$H NMR (CDCl$_3$) 2.10-2.30 (m, 2H), 2.45-2.51 (m, 2H), 3.20-3.31 (m, 1H), 3.55-3.60 (m, 2H), 3.70-3.80 (m, 1H), 6.90-7.16 (m, 6H), 7.20-7.40 (m, 4H).

Example 101

3-(2'-chloro-4',6-difluorobiphenyl-3-yl)-6-(2-hydroxyethyl)-6-phenyl-1,3-oxazinan-2-one

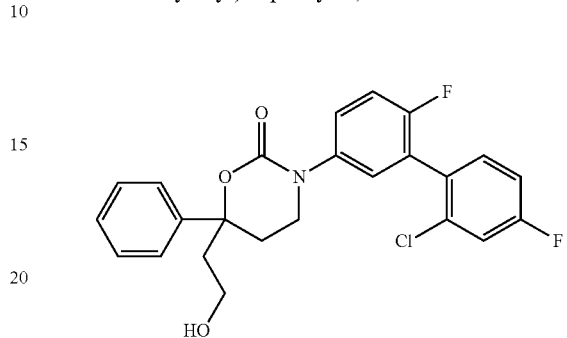

The title compound was prepared by sequential application of procedures analogous to those described in Example 63 using 3-bromo-4-fluoroaniline in Step 2, Example 74 and Example 75 Step 1 using 2-chloro-4-fluorophenylboronic acid. LC-MS Method 3, $t_R$=1.367 min, m/z=466.1. $^1$H NMR (CD$_3$OD) δ=2.17 (m, 2H), 2.47 (m, 1H), 2.58 (m, 1H), 3.16 (m, 1H), 3.25 (m, 1H), 3.54 (m, 1H), 3.63 (m, 1H), 6.98 (m, 1H), 7.08 (m, 3H), 7.26 (m, 3H), 7.37 (m, 4H).

Example 102

3-(6-(4-fluorophenyl)pyridin-2-yl)-6-(2-hydroxyethyl)-6-phenyl-1,3-oxazinan-2-one

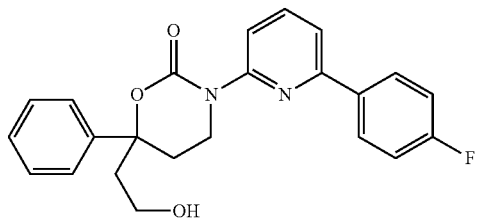 [SMILES: O=C1OC(CCO)(c2ccccc2)CCN1c1cccc(-c2ccc(F)cc2)n1]

The title compound was prepared by application of procedures analogous to those described in Example 63 using 2-amino-6-bromopyridine in Step 2, followed by Example 74 and Example 75 Step 1 using 4-fluorophenylboronic acid. LC-MS Method 3, $t_R$=1.217 min, m/z=393. $^1$H NMR (CD$_3$OD) δ=2.29 (m, 2H), 2.51 (m, 1H), 2.73 (m, 1H), 3.47 (m, 2H), 3.75 (m, 1H), 4.21 (m, 1H), 7.14 (m, 2H), 7.35 (m, 1H), 7.46 (m, 4H), 7.63 (m, 1H), 7.68 (m, 1H), 7.72 (m, 1H), 8.00 (m, 2H).

Chiral preparative SFC using a ChiralCel-AS, 400×25 mm I.D, 20 μm (Daicel Chemical Industries, Ltd) column maintained at 35° C. eluted with 65:35 supercritical CO$_2$/0.1% diethylamine in MeOH at a flow rate of 70 mL min$^{-1}$ and a nozzle pressure of 100 bar afforded the two enantiomers.

Isomer 1: (R)-3-(6-(4-fluorophenyl)pyridin-2-yl)-6-(2-hydroxyethyl)-6-phenyl-1,3-oxazinan-2-one. LC-MS Method 3, $t_R$=1.2 min, m/z=393. $^1$H NMR (CD$_3$OD) δ=2.29 (m, 2H), 2.51 (m, 1H), 2.68 (m, 1H), 3.42 (m, 2H), 3.75 (m, 1H), 4.16

(m, 1H), 7.11 (m, 2H), 7.33 (m, 1H), 7.46 (m, 4H), 7.53 (m, 1H), 7.72 (m, 2H), 7.98 (m, 2H).

Isomer 2: (S)-3-(6-(4-fluorophenyl)pyridin-2-yl)-6-(2-hydroxyethyl)-6-phenyl-1,3-oxazinan-2-one. LC-MS Method 3, $t_R$=1.183 min, m/z=393. $^1$H NMR (CD$_3$OD) δ=2.27 (m, 2H), 2.48 (m, 1H), 2.63 (m, 1H), 3.45 (m, 2H), 3.75 (m, 1H), 4.18 (m, 1H), 7.08 (m, 2H), 7.31 (m, 1H), 7.44 (m, 4H), 7.50 (m, 1H), 7.68 (m, 2H), 7.91 (m, 2H).

Example 103

6-(4-fluorophenyl)-3-(6-(4-fluorophenyl)pyridin-2-yl)-6-(2-hydroxyethyl)-1,3-oxazinan-2-one

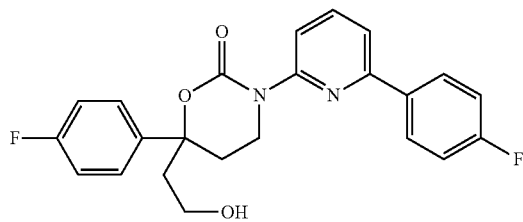 [SMILES: O=C1OC(CCO)(c2ccc(F)cc2)CCN1c1cccc(-c2ccc(F)cc2)n1]

The title compound was prepared by application of procedures analogous to those described in Example 63 using p-fluoroacetophenone in Step 1 and 2-amino-6-bromopyridine in Step 2, followed by Example 74 and Example 75 Step 1 using 4-fluorophenylboronic acid. LC-MS Method 2, $t_R$=2.25 min, m/z=411. $^1$H NMR (CD$_3$OD) 25 (m, 2H), 2.55 (m, 1H), 2.60 (m, 1H), 3.40 (m, 1H), 3.50 (m, 1H), 3.75 (m, 1H), 4.20 (m, 1H), 7.15 (m, 4H), 7.50 (m, 2H), 7.65 (m, 2H), 7.80 (m, 1H), 8.00 (m, 2H).

Example 104

6-(2-fluorophenyl)-3-(6-(4-fluorophenyl)pyridin-2-yl)-6-(2-hydroxyethyl)-1,3-oxazinan-2-one

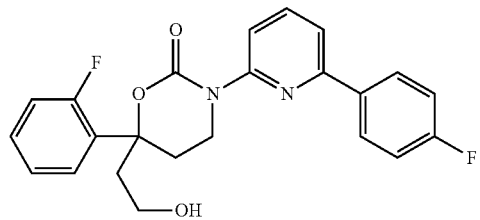 [SMILES: O=C1OC(CCO)(c2ccccc2F)CCN1c1cccc(-c2ccc(F)cc2)n1]

The title compound was prepared by application of procedures analogous to those described in Example 63 using o-fluoroacetophenone in Step 1 and 2-amino-6-bromopyridine in Step 2, followed by Example 74 and Example 75 Step 1 using 4-fluorophenylboronic acid. LC-MS Method 3, $t_R$=1.26 min, m/z=410.14. $^1$H NMR (CD$_3$OD) δ=2.20-2.40 (m, 2H), 2.45 (m, 1H), 2.75 (m, 1H), 3.42 (m, 2H), 3.72 (m, 1H), 4.15 (m, 1H), 7.03-7.20 (m, 4H), 7.35 (m, 2H), 7.55 (m, 1H), 7.65 (m, 1H), 7.75 (m, 1H), 7.95 (m, 2H).

Chiral preparative SFC using a ChiralCel-AS, 400×25 mm I.D, 20 μm (Daicel Chemical Industries, Ltd) column maintained at 35° C. eluted with 75:25 supercritical CO$_2$/0.1% diethylamine in MeOH at a flow rate of 70 mL min$^{-1}$ and a nozzle pressure of 100 bar afforded the two enantiomers.

Isomer 1: (R)-6-(2-fluorophenyl)-3-(6-(4-fluorophenyl)pyridin-2-yl)-6-(2-hydroxyethyl)-1,3-oxazinan-2-one.
LC-MS Method 3, $t_R$=1.255 min, m/z=410.14. $^1$H NMR (CD$_3$OD) δ=2.20-2.40 (m, 2H), 2.45 (m, 1H), 2.75 (m, 1H), 3.35 (m, 2H), 3.72 (m, 1H), 4.15 (m, 1H), 7.03-7.20 (m, 4H), 7.35 (m, 2H), 7.55 (m, 1H), 7.65 (m, 1H), 7.75 (m, 1H), 7.95 (m, 2H).

Isomer 2: (S)-6-(2-fluorophenyl)-3-(6-(4-fluorophenyl)pyridin-2-yl)-6-(2-hydroxyethyl)-1,3-oxazinan-2-one.
LC-MS Method 3, $t_R$=1.262 min, m/z=410.14. $^1$H NMR (CD$_3$OD) δ=2.20-2.40 (m, 2H), 2.45 (m, 1H), 2.75 (m, 1H), 3.42 (m, 2H), 3.72 (m, 1H), 4.15 (m, 1H), 7.03-7.20 (m, 4H), 7.45 (m, 2H), 7.55 (m, 1H), 7.65 (m, 1H), 7.75 (m, 1H), 7.95 (m, 2H).

Example 105

6-(4-fluorophenyl)-6-(2-hydroxyethyl)-3-(2',4',6-trifluorobiphenyl-3-yl)-1,3-oxazinan-2-one

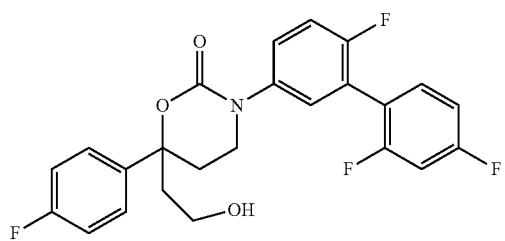 [SMILES: O=C1OC(CCO)(c2ccc(F)cc2)CCN1c1ccc(F)c(-c2ccc(F)cc2F)c1]

The title compound was prepared by sequential application of procedures analogous to those described in Example 63 using p-fluoroacetophenone in Step 1 and 3-bromo-4-fluoroaniline in Step 2, Example 74 and Example 75 Step 1 using 2,4-difluorophenylboronic acid. LC-MS Method 3, $t_R$=1.225 min, m/z=446. $^1$H NMR (CDCl$_3$) δ=2.15-2.30 (m, 2H), 2.50-2.60 (m, 2H), 3.22-3.37 (m, 1H), 3.50-3.65 (m, 2H), 3.75-3.85 (m, 1H), 6.89-6.92 (m, 2H), 7.10-7.20 (m, 5H), 7.30-7.40 (m, 3H).

Example 106

6-(2-fluorophenyl)-6-(2-hydroxyethyl)-3-(2',4',6-trifluorobiphenyl-3-yl)-1,3-oxazinan-2-one

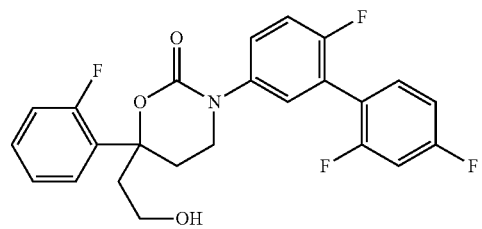 [SMILES: O=C1OC(CCO)(c2ccccc2F)CCN1c1ccc(F)c(-c2ccc(F)cc2F)c1]

The title compound was prepared by sequential application of procedures analogous to those described in Example 63 using o-fluoroacetophenone in Step 1 and 3-bromo-4-fluoroaniline in Step 2, Example 74 and Example 75 Step 1 using 2,4-difluorophenylboronic acid. LC-MS Method 3, $t_R$=1.237 min, m/z=446. $^1$H NMR (CDCl$_3$) δ=2.30-2.50 (m, 3H), 2.70-2.80 (m, 1H), 3.20-3.30 (m, 1H), 3.40-3.50 (m, 1H), 3.55-

3.65 (m, 1H), 3.70-3.80 (m, 1H), 6.85-6.90 (m, 2H), 7.00-7.10 (m, 4H), 7.20-7.38 (m, 3H), 7.45-7.52 (m, 1H).

Example 107

3-(6-(2,4-difluorophenyl)pyridin-2-yl)-6-(2-hydroxyethyl)-6-phenyl-1,3-oxazinan-2-one

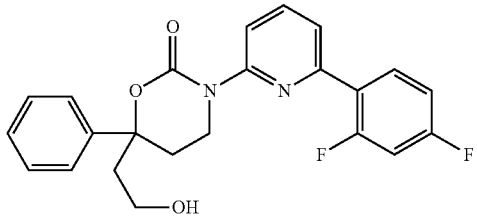 [SMILES: O=C1OC(CCO)(c2ccccc2)CCN1c1cccc(-c2ccc(F)cc2F)n1]

The title compound was prepared by application of procedures analogous to those described in Example 63 using 2-amino-6-bromopyridine in Step 2, followed by Example 74 and Example 75 Step 1 using 2,4-difluorophenylboronic acid. LC-MS Method 3, $t_R$=1.25 min, m/z=411. $^1$H NMR (CD$_3$OD) δ=2.27 (m, 2H), 2.53 (m, 1H), 2.72 (m, 1H), 3.38 (m, 2H), 3.74 (m, 1H), 4.15 (m, 1H), 7.02 (m, 2H), 7.32 (m, 1H), 7.42 (m, 4H), 7.55 (m, 1H), 7.71 (m, 1H), 7.78 (m, 1H), 7.91 (m, 1H).

Example 108

3-(6-(2,4-difluorophenyl)pyridin-2-yl)-6-(4-fluorophenyl)-6-(2-hydroxyethyl)-1,3-oxazinan-2-one

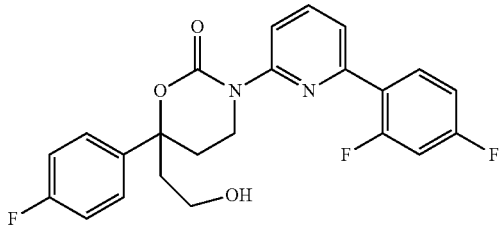 [SMILES: O=C1OC(CCO)(c2ccc(F)cc2)CCN1c1cccc(-c2ccc(F)cc2F)n1]

The title compound was prepared by application of procedures analogous to those described in Example 63 using p-fluoroacetophenone in Step 1 and 2-amino-6-bromopyridine in Step 2, followed by Example 74 and Example 75 Step 1 using 2,4-difluorophenylboronic acid. LC-MS Method 2, $t_R$=2.311 min, m/z=429.4. $^1$H NMR (CD$_3$OD) 2.25 (m, 2H), 2.55 (m, 1H), 2.60 (m, 1H), 3.40 (m, 2H), 3.50 (m, 1H), 3.75 (m, 1H), 7.15 (m, 3H), 7.30 (m, 1H), 7.45 (m, 3H), 7.75 (m, 1H), 7.80 (m, 1H).

Example 109

3-(6-(2,4-difluorophenyl)pyridin-2-yl)-6-(2-fluorophenyl)-6-(2-hydroxyethyl)-1,3-oxazinan-2-one

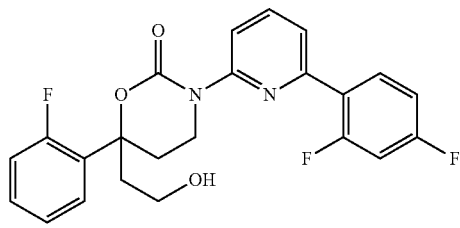 [SMILES: O=C1OC(CCO)(c2ccccc2F)CCN1c1cccc(-c2ccc(F)cc2F)n1]

The title compound was prepared by application of procedures analogous to those described in Example 63 using o-fluoroacetophenone in Step 1 and 2-amino-6-bromopyridine in Step 2, followed by Example 74 and Example 75 Step 1 using 2,4-difluorophenylboronic acid. LC-MS Method 2, $t_R$=2.311 min, m/z=429. $^1$H NMR (CD$_3$OD) 2.35 (m, 2H), 2.55 (m, 1H), 2.80 (m, 1H), 3.45 (m, 2H), 3.75 (m, 1H), 4.20 (m, 1H), 7.05 (m, 2H), 7.20 (m, 2H), 7.40 (m, 2H), 7.60 (m, 1H), 7.80 (m, 2H), 7.90 (m, 1H).

The isomers were separated by
Isomer 1: (R)-3-(6-(2,4-difluorophenyl)pyridin-2-yl)-6-(2-fluorophenyl)-6-(2-hydroxyethyl)-1,3-oxazinan-2-one.
Isomer 2: (S)-3-(6-(2,4-difluorophenyl)pyridin-2-yl)-6-(2-fluorophenyl)-6-(2-hydroxyethyl)-1,3-oxazinan-2-one.

Example 110

6-allyl-3-((S)-1-(4-bromophenyl)ethyl)-6-(4-fluorophenyl)-1,3-oxazinan-2-one

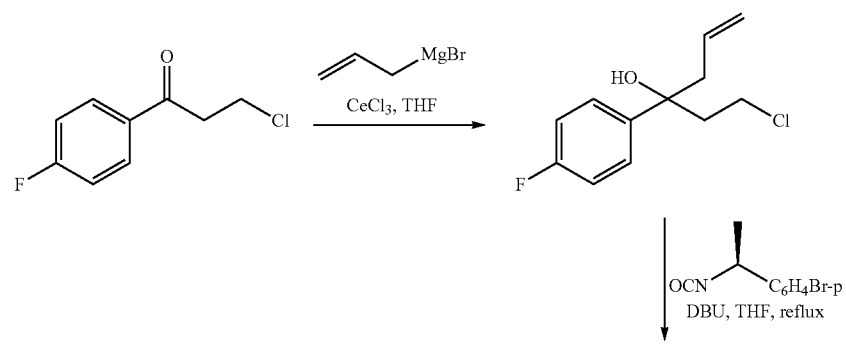

-continued

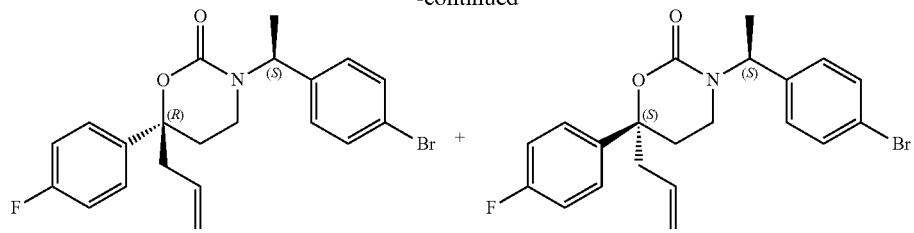

Step 1. 1-chloro-3-(4-fluorophenyl)hex-5-en-3-ol

A 250-mL flask was charged with anhydrous CeCl₃ (5.58 g, 22.6 mmol) and THF (40 mL). The mixture was vigorously stirred for 3.5 h at rt. The suspension was then cooled to −78° C. and a solution of allylmagnesium bromide (1.0 M in THF, 21 mL, 21.0 mmol) was added. After stirring for 2 h at −78° C., a solution of 3-chloro-1-(4-fluorophenyl)propan-1-one (2.522 g, 13.5 mmol) in THF (30 mL) was added via cannula. The reaction mixture was allowed to slowly warm to 8° C. while stirring overnight (18 h). The reaction was then quenched with satd aq NaHCO₃, extracted with EtOAc, and dried over Na₂SO₄. After the solvents were evaporated, the residue was purified by chromatography on silica gel eluted with hexanes/EtOAc to afford of 1-chloro-3-(4-fluorophenyl)hex-5-en-3-ol (3.0049 g, 97%) as an oil. LC-MS Method 1 $t_R$=1.79 min, m/z 213, 211 (M-OH)⁺; ¹H NMR (400 MHz, CDCl₃) δ 7.37-7.32 (m, 2H), 7.07-7.02 (m, 2H), 5.57-5.47 (m, 1H), 5.20-5.19 (m, 1H), 5.16 (m, 1H), 3.59-3.52 (m, 1H), 3.24-3.18 (m, 1H), 2.70 (dd, J=13.8, 5.9 Hz, 1H), 2.50 (dd, J=13.8, 8.5 Hz, 1H), 2.29 (t, J=7.9 Hz, 2H), 2.22 (s, 1H); ¹⁹F NMR (376 MHz, CDCl₃) δ −116.52 (m).

Step 2. (R)-6-allyl-3-((S)-1-(4-bromophenyl)ethyl)-6-(4-fluorophenyl)-1,3-oxazinan-2-one and (S)-6-allyl-3-((S)-1-(4-bromophenyl)ethyl)-6-(4-fluorophenyl)-1,3-oxazinan-2-one A mixture of 1-chloro-3-(4-fluorophenyl)hex-5-en-3-ol (0.4129 g, 1.8 mmol, 1.0 equiv), (S)-(−)-1-(4-bromophenyl)ethyl isocyanate (0.5005 g, 2.2 mmol, 1.2 equiv), and DBU (0.7375 g, 4.8 mmol, 2.7 equiv) in THF (10 mL) was heated to reflux for 25 h. The mixture was diluted with EtOAc and washed with 1 N aq HCl. The aqueous phase was extracted with EtOAc (2×). The combined organic phase was dried over Na₂SO₄. After the solvents were evaporated, the crude product was directly used in the next step without further purification.

An analytical sample was purified by chromatography on silica gel eluted with hexanes/EtOAc to afford the two diastereomers of 6-allyl-3-((S)-1-(4-bromo-phenyl)ethyl)-6-(4-fluorophenyl)-1,3-oxazinan-2-one.

Isomer 1: (S)-6-allyl-3-((S)-1-(4-bromophenyl)ethyl)-6-(4-fluorophenyl)-1,3-oxazinan-2-one. LC-MS Method 1 $t_R$=2.03 min, m/z 420, 418 (MH⁺); ¹H NMR (400 MHz, CDCl₃) δ 7.46 (d, J=8.2 Hz, 2H), 7.31-7.28 (m, 2H), 7.17 (d, J=8.2 Hz, 2H), 7.07 (t, J=8.5 Hz, 2H), 5.76-5.66 (m, 2H), 5.10-4.99 (m, 2H), 2.75-2.52 (m, 4H), 2.23-2.19 (m, 1H), 2.08-2.00 (m, 1H), 1.24 (d, J=7.0 Hz, 3H); ¹⁹F NMR (376 MHz, CDCl₃) δ −115.07 (m).

Isomer 2: (R)-6-allyl-3-((S)-1-(4-bromophenyl)ethyl)-6-(4-fluorophenyl)-1,3-oxazinan-2-one. LC-MS Method 1 $t_R$=1.98 min, m/z 420, 418 (MH⁺); ¹H NMR (400 MHz, CDCl₃) δ 7.25-7.20 (m, 4H), 7.05-7.01 (m, 2H), 6.71 (d, J=8.5 Hz, 2H), 5.74-5.64 (m, 1H), 5.58 (q, J=7.0 Hz, 1H), 5.09-4.99 (m, 2H), 2.92-2.87 (m, 1H), 2.63-2.50 (m, 2H), 2.33-2.16 (m, 3H), 1.47 (d, J=7.0 Hz, 3H); ¹⁹F NMR (376 MHz, CDCl₃) δ −114.91 (m).

(R)-6-allyl-3-((S)-1-(4-chlorophenyl)ethyl)-6-phenyl-1,3-oxazinan-2-one was prepared following procedures analogous to those described above using 3-chloro-1-phenylpropan-1-one in Step 1 and (S)-1-chloro-4-(1-isocyanatoethyl)benzene in Step 2.

Example 111

6-allyl-3-((S)-1-(2',4'-difluorobiphenyl-4-yl)ethyl)-6-(4-fluorophenyl)-1,3-oxazinan-2-one

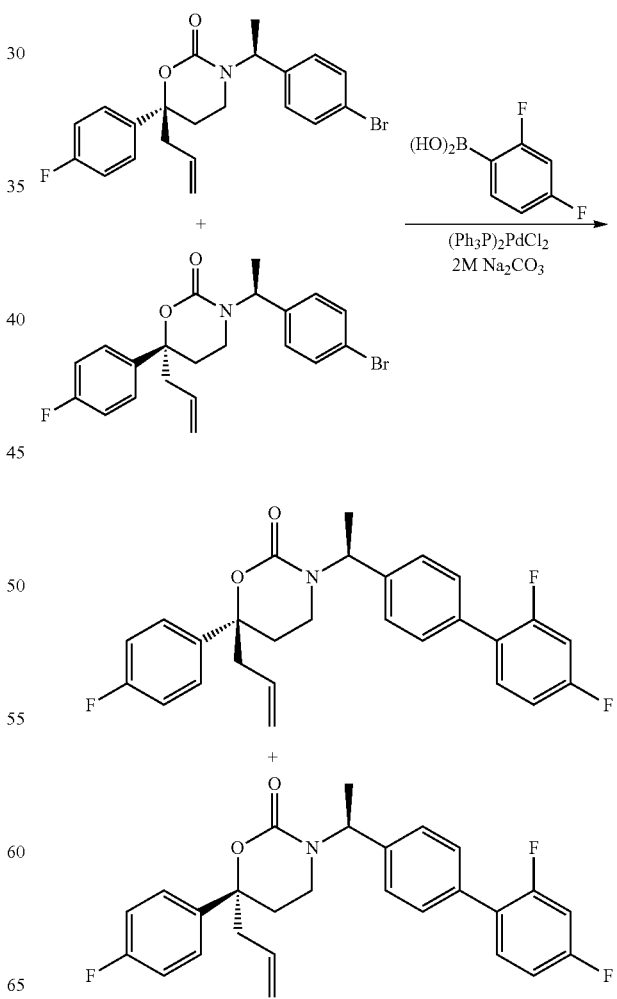

Step 1. 6-allyl-3-((S)-1-(2',4'-difluorobiphenyl-4-yl)ethyl)-6-(4-fluorophenyl)-1,3-oxazinan-2-one To a solution of 6-allyl-3-((S)-1-(4-bromophenyl)ethyl)-6-(4-fluorophenyl)-1,3-oxazinan-2-one (0.3860 g, 0.92 mmol, 1.0 equiv) in THF (10 mL) were added, under a nitrogen atmosphere, 2,4-difluorophenylboronic acid (0.2708 g, 1.71 mmol, 1.86 equiv), 2 M aq $Na_2CO_3$ (8 mL), and $(Ph_3P)_2PdCl_2$ (0.0308 g, 0.0438 mmol, 0.047 equiv). The mixture was stirred for 2 d at 100° C. Brine was then added, the mixture was extracted with $Et_2O$ (3×), and the combined ether extracts were dried over $Na_2SO_4$. After the solvents were evaporated, the crude product was directly used in the next step without further purification. LC-MS $t_R$=2.13, 2.17 min in 3 min chromatography, m/z 452 (MH+).

Analytical samples were separated by silica gel chromatography.

Isomer 1: (S)-6-allyl-3-((S)-1-(2',4'-difluorobiphenyl-4-yl)ethyl)-6-(4-fluorophenyl)-1,3-oxazinan-2-one. LC-MS Method 1, $t_R$=2.17 min, m/z=452. $^1$H NMR ($CDCl_3$) 7.47 (d, J=8.2 Hz, 2H), 7.42-7.30 (m, 5H), 7.08 (t, J=8.2 Hz, 2H), 6.98-6.88 (m, 2H), 5.82-5.68 (m, 2H), 5.08 (d, J=10.2 Hz, 1H), 5.02 (d, J=17.0 Hz, 1H), 2.78-2.71 (m, 2H), 2.66-2.54 (m, 2H), 2.25-2.20 (m, 1H), 2.13-2.05 (m, 1H), 1.30 (d, J=7.0 Hz, 3H).

Isomer 2: (R)-6-allyl-3-((S)-1-(2',4'-difluorobiphenyl-4-yl)ethyl)-6-(4-fluorophenyl)-1,3-oxazinan-2-one. LC-MS Method 1, $t_R$=2.13 min, m/z=452. $^1$H NMR ($CDCl_3$) 7.33-7.23 (m, 5H), 7.03 (t, J=8.2 Hz, 2H), 6.96-6.86 (m, 4H), 5.77-5.67 (m, 2H), 5.10 (d, J=10.3 Hz, 1H), 5.04 (d, J=17.3 Hz, 1H), 2.99-2.94 (m, 1H), 2.66-2.54 (m, 2H), 2.41-2.34 (m, 1H), 2.30-2.17 (m, 2H), 1.55 (d, J=7.0 Hz, 3H).

Example 112

3-((S)-1-(2',4'-difluorobiphenyl-4-yl)ethyl)-6-(4-fluorophenyl)-6-(2-hydroxyethyl)-1,3-oxazinan-2-one

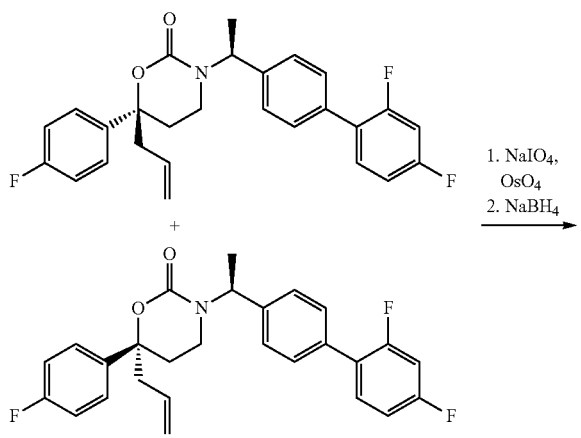

1. $NaIO_4$, $OsO_4$
2. $NaBH_4$

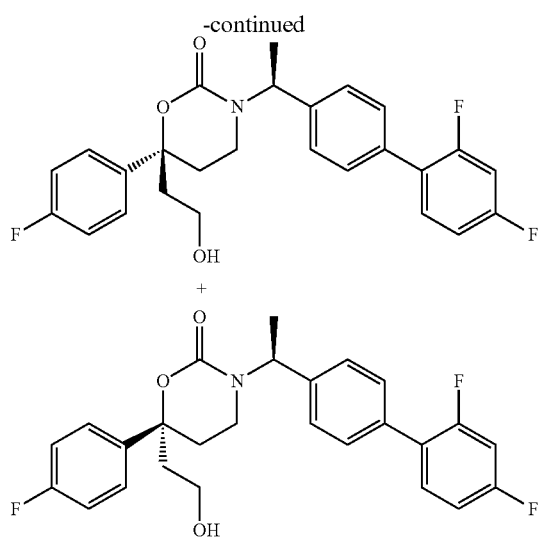

Step 1. (S)-3-((S)-1-(2',4'-difluorobiphenyl-4-yl)ethyl)-6-(4-fluorophenyl)-6-(2-hydroxyethyl)-1,3-oxazinan-2-one and (R)-3-((S)-1-(2',4'-difluorobiphenyl-4-yl)ethyl)-6-(4-fluorophenyl)-6-(2-hydroxyethyl)-1,3-oxazinan-2-one To a solution of 6-allyl-3-((S)-1-(2',4'-difluorobiphenyl-4-yl)ethyl)-6-(4-fluorophenyl)-1,3-oxazinan-2-one (obtained as described in Example 111) in THF-$H_2O$ (1:1, 20 mL) were added $NaIO_4$ (1.0148 g, 4.74 mmol, 5 equiv) and $OsO_4$ (2.5 wt. % solution in t-BuOH, 0.1708 g, 0.0167 mmol, 0.018 equiv), and the mixture was stirred at rt for 2 h. The mixture was diluted with EtOAc, dried over $Na_2SO_4$, and concentrated under reduced pressure. The residue was dissolved in MeOH (10 mL) and $NaBH_4$ (0.200 g) was added. After the mixture was stirred for 1 h at rt, acetone was added. The solvents were removed in vacuo, the residue was treated with saturated brine, extracted with $CH_2Cl_2$, and dried over $Na_2SO_4$. After the solvents were evaporated, the residue was purified by chromatography on silica gel eluted with hexanes/EtOAc to afford the two diastereomers of 3-((S)-1-(2',4'-difluorobiphenyl-4-yl)ethyl)-6-(4-fluorophenyl)-6-(2-hydroxyethyl)-1,3-oxazinan-2-one.

Isomer 1: (R)-3-((S)-1-(2',4'-difluorobiphenyl-4-yl)ethyl)-6-(4-fluorophenyl)-6-(2-hydroxyethyl)-1,3-oxazinan-2-one, less polar isomer, LC-MS Method 1 $t_R$=1.86 min, m/z 456 (MH+); $^1$H NMR (400 MHz, $CDCl_3$) δ 7.48-7.30 (m, 7H), 7.13-6.88 (m, 4H), 5.78 (q, J=7.0 Hz, 1H), 3.78-3.74 (m, 1H), 3.57-3.50 (m, 1H), 2.79-2.67 (m, 2H), 2.31-2.11 (m, 4H), 1.81 (br s, 1H), 1.31 (d, J=7.3 Hz, 3H); $^{19}$F NMR (376 MHz, $CDCl_3$) δ −111.48 (m), −113.88 (m), −114.67 (m).

Isomer 2: (S)-3-((S)-1-(2',4'-difluorobiphenyl-4-yl)ethyl)-6-(4-fluorophenyl)-6-(2-hydroxyethyl)-1,3-oxazinan-2-one, more polar isomer, LC-MS Method 1 $t_R$=1.80 min, m/z 456 (MH+); $^1$H NMR (400 MHz, $CDCl_3$) δ 7.24-7.17 (m, 5H), 7.00-6.79 (m, 6H), 5.62 (q, J=7.0 Hz, 1H), 3.74-3.68 (m, 1H), 3.51-3.45 (m, 1H), 2.91-2.88 (m, 1H), 2.30-2.01 (m, 5H), 1.96 (br s, 1H), 1.48 (d, J=7.0 Hz, 3H); $^{19}$F NMR (376 MHz, CDCl₃) δ −111.61 (m), −114.05 (m), −114.90 (m). The absolute configuration was determined by X-ray crystallography.

Example 113

6-(4-fluorophenyl)-3-((S)-1-phenylethyl)-6-vinyl-1,3-oxazinan-2-one

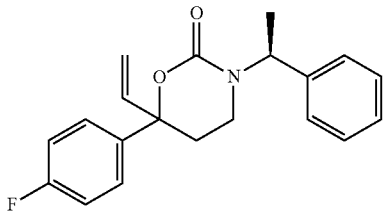 [SMILES: C=CC1(c2ccc(F)cc2)CCN([C@@H](C)c2ccccc2)C(=O)O1]

The title compound was prepared by application of procedures analogous to those described in Example 110 using vinylmagnesium bromide in Step 1 and (S)-(1-isocyanatoethyl)benzene in Step 2. The isomers were separated by chromatography on silica gel.

Isomer 1: LC-MS Method 1, $t_R$=1.8 min, m/z=348 (M+23), 326 (M+1). ¹H NMR (CDCl₃) 7.39-7.28 (m, 7H), 7.06 (t, J=8.6 Hz, 2H), 5.96 (dd, J=17.3, 10.8 Hz, 1H), 5.80 (q, J=7.0 Hz, 1H), 5.32 (d, J=17.3 Hz, 1H), 5.21 (d, J=10.8 Hz, 1H), 2.87-2.81 (m, 1H), 2.74-2.68 (m, 1H), 2.31-2.24 (m, 1H), 2.18-2.11 (m, 1H), 1.41 (d, J=7.3 Hz, 3H).

Isomer 2: LC-MS Method 1, $t_R$=1.79 min, m/z=348 (M+23), 326 (M+1). ¹H NMR (CDCl₃) 7.39-7.35 (m, 2H), 7.25-7.22 (m, 3H), 7.12-7.10 (m, 2H), 7.03 (t, J=8.6 Hz, 2H), 6.00 (dd, J=17.3, 10.8 Hz, 1H), 5.78 (q, J=7.0 Hz, 1H), 5.34 (d, J=17.3 Hz, 1H), 5.27 (d, J=10.5 Hz, 1H), 3.10-3.04 (m, 1H), 2.59-2.53 (m, 1H), 2.24-2.20 (m, 2H), 1.53 (d, J=7.3 Hz, 3H).

Example 114

6-(4-fluorophenyl)-6-(hydroxymethyl)-3-((S)-1-phenylethyl)-1,3-oxazinan-2-one

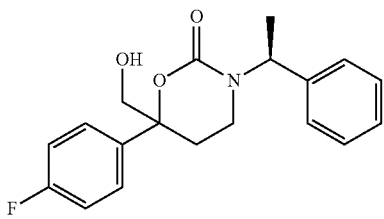 [SMILES: C[C@@H](c1ccccc1)N1CCC(CO)(c2ccc(F)cc2)OC1=O]

The title compound was prepared from 6-(4-fluorophenyl)-3-((S)-1-phenylethyl)-6-vinyl-1,3-oxazinan-2-one by application of procedures analogous to those described in Example 112. The isomers were separated by chromatography on silica gel.

Isomer 1 of 6-(4-fluorophenyl)-6-(hydroxymethyl)-3-((S)-1-phenylethyl)-1,3-oxazinan-2-one: LC-MS Method 1, $t_R$=1.5 min, m/z=330. ¹H NMR (CDCl₃) 7.34-7.25 (m, 7H), 7.07 (t, 2H), 7.73 (q, 1H), 3.76 (d, 1H), 3.62 (d, 1H), 2.75 (m, 2H), 2.39 (m, 1H), 2.13 (dt, 1H), 1.30 (d, 3H).

Isomer 2 of 6-(4-fluorophenyl)-6-(hydroxymethyl)-3-((S)-1-phenylethyl)-1,3-oxazinan-2-one: LC-MS Method 1, $t_R$=1.48 min, m/z=330. ¹H NMR (CDCl₃) 7.27 (m, 2H), 7.12 (m, 3H), 7.02 (t, 2H), 7.90 (m, 2H), 5.63 (q, 1H), 3.78 (d, 1H), 3.61 (d, 1H), 2.96 (m, 1H), 2.54 (m, 1H), 2.29 (m, 1H), 2.18 (m, 1H), 1.51 (d, 3H).

Example 115

3-((S)-1-(4-bromophenyl)ethyl)-6-(4-fluorophenyl)-6-(2-hydroxyethyl)-1,3-oxazinan-2-one

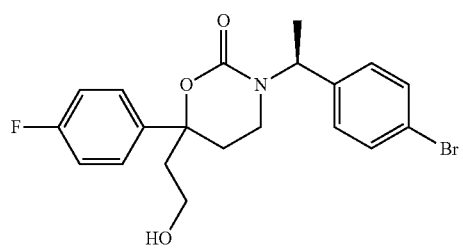 [SMILES: C[C@@H](c1ccc(Br)cc1)N1CCC(CCO)(c2ccc(F)cc2)OC1=O]

The title compound was prepared from 6-allyl-3-((S)-1-(4-bromophenyl)ethyl)-6-(4-fluorophenyl)-1,3-oxazinan-2-one by application of procedures analogous to those described in Example 112. The isomers were separated by chromatography on silica gel.

Isomer 1: (R)-3-((S)-1-(4-bromophenyl)ethyl)-6-(4-fluorophenyl)-6-(2-hydroxyethyl)-1,3-oxazinan-2-one: LC-MS Method 1, $t_R$=1.67 min, m/z=423. ¹H NMR (CDCl₃) 7.44-7.48 (ad, 2H), 7.28-7.32 (m, 2H), 7.16-7.19 (ad, 7.09 (at, 2H), 5.69 (q, 1H), 3.73-3.79 (m, 1H), 3.51-3.57 (m, 1H), 2.67 (dd, 2H), 2.28 (dt, 1H), 2.22-2.07 (m, 3H), 1.25 (d, 3H).

Isomer 2: (S)-3-((S)-1-(4-bromophenyl)ethyl)-6-(4-fluorophenyl)-6-(2-hydroxyethyl)-1,3-oxazinan-2-one: LC-MS Method 1, $t_R$=1.63 min, m/z=423. ¹H NMR (CDCl₃) 7.23-7.29 (m, 4H), 7.02-7.08 (m, 2H), 6.77 9d, 2H), 5.58 (q, 1H), 3.73-3.79 (m, 1H), 3.51-3.57 (m, 1H), 2.86-2.94 (m, 1H), 2.25-2.34 (m, 3H), 2.06-2.21 (m, 2H), 1.49 (d, 3H).

Example 116

3-(6-(2-chloro-4-fluorophenyl)pyridin-2-yl)-6-(2-hydroxyethyl)-6-phenyl-1,3-oxazinan-2-one

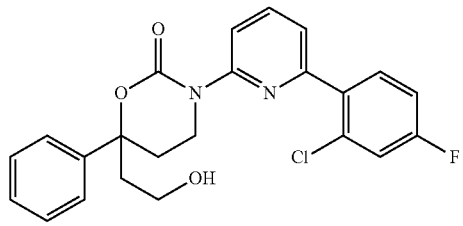 [SMILES: O=C1OC(CCO)(c2ccccc2)CCN1c1cccc(-c2ccc(F)cc2Cl)n1]

The title compound was prepared by application of procedures analogous to those described in Example 63 using acetophenone in Step 1 and 2-amino-6-bromopyridine in Step 2, followed by Example 74 and Example 75 Step 1 using 2-chloro-4-fluorophenylboronic acid. LC-MS Method 3, $t_R$=1.267 min, m/z=427. ¹H NMR (CD₃OD) δ=2.28 (m, 2H), 2.53 (m, 1H), 2.72 (m, 1H), 3.41 (m, 2H), 3.76 (m, 1H), 4.13

(m, 1H), 7.15 (m, 1H), 7.32 (m, 2H), 7.44 (m, 5H), 7.55 (m, 1H), 7.76 (m, 1H), 7.85 (m, 1H).

Example 117

3-(2',4'-difluorobiphenyl-3-yl)-6-(2-hydroxy-2-methylpropyl)-6-phenyl-1,3-oxazinan-2-one

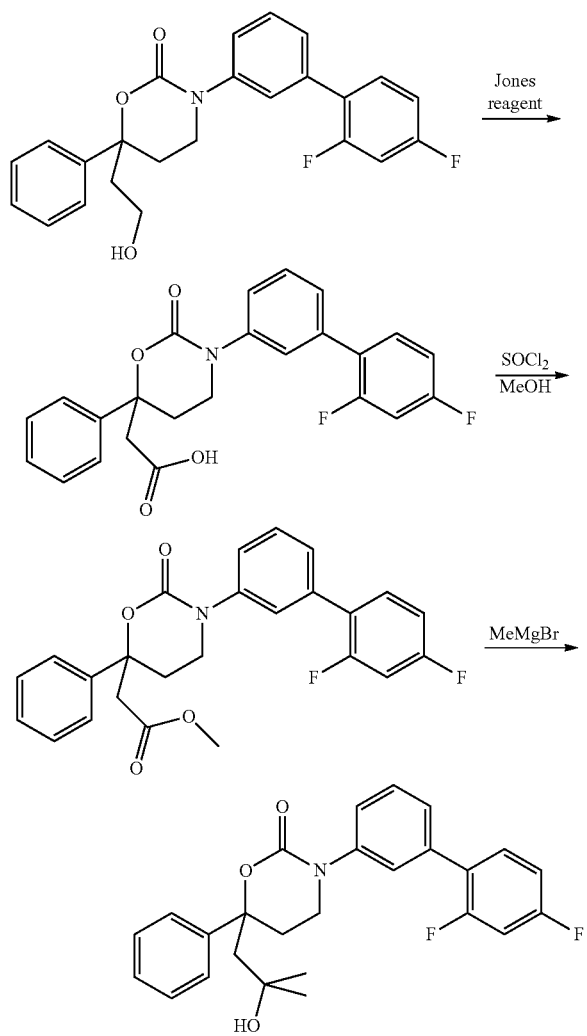

Step 1. 2-(3-(2',4'-difluorobiphenyl-3-yl)-2-oxo-6-phenyl-1,3-oxazinan-6-yl)acetic acid A 100-mL of flask was charged with 3-(2',4'-difluorobiphenyl-3-yl)-6-(2-hydroxyethyl)-6-phenyl-1,3-oxazinan-2-one (1 g, 2.4 mmol) dissolved in acetone (10 mL). Jones reagent ($CrO_3$: 1 g; $H_2SO_4$: 1 mL, $H_2O$: 4 mL) was added at 0° C. under $N_2$ protection. The mixture was stirred overnight at rt. Aqueous $K_2CO_3$ (5 mL) was added and the mixture was extracted with EtOAc (3×15 mL). The organic layers were combined, washed with brine, dried over $Na_2SO_4$, filtered and concentrated. The residue (1.03 g) was used directly for the next step.

Step 2. methyl 2-(3-(2',4'-difluorobiphenyl-3-yl)-2-oxo-6-phenyl-1,3-oxazinan-6-yl)acetate A 100-mL of flask was charged with 2-(3-(2',4'-difluorobiphenyl-3-yl)-2-oxo-6-phenyl-1,3-oxazinan-6-yl)acetic acid (1.02 g, 2.4 mmol) dissolved in MeOH (15 mL). Then thionyl chloride (418 mg, 3.5 mmol) was added dropwise slowly at 0° C. under $N_2$ protection. The mixture was stirred overnight under reflux. The mixture was concentrated to give the crude product, which was purified by chromatography to give the pure product (230 mg, 23%).

Step 3. 3-(2',4'-difluorobiphenyl-3-yl)-6-(2-hydroxy-2-methylpropyl)-6-phenyl-1,3-oxazinan-2-one A 25-mL of flask was charged with methyl 2-(3-(2',4'-difluorobiphenyl-3-yl)-2-oxo-6-phenyl-1,3-oxazinan-6-yl)acetate (100 mg, 0.23 mmol) dissolved in dry THF (3 mL) under $N_2$ protection at −78° C. Then methylmagnesium bromide (3.0 M, 1 mL, 3 mmol) was added dropwise slowly at −78° C. and stirred overnight. The mixture was quenched with water and extracted with EtOAc (3×5 mL). The organic layers were combined, washed with brine, dried over $Na_2SO_4$, filtered and concentrated. The residue was purified by preparative HPLC to give the pure product (2.38 mg, 2%). LC-MS Method 3, $t_R$=1.267 min, m/z=897.3. $^1$H NMR ($CD_3OD$): 1.0 (s, 3H), 1.30 (s, 3H), 2.30 (s, 2H), 2.60 (m, 1H), 2.80 (m, 1H), 3.17 (m, 1H), 3.60 (m, 1H), 7.02 (m, 2H), 7.10 (m, 1H), 7.23 (s, 1H), 7.30-7.50 (m, 6H).

Example 118

3-(6-(2-chloro-4-fluorophenyl)pyridin-2-yl)-6-(4-fluorophenyl)-6-(2-hydroxyethyl)-1,3-oxazinan-2-one

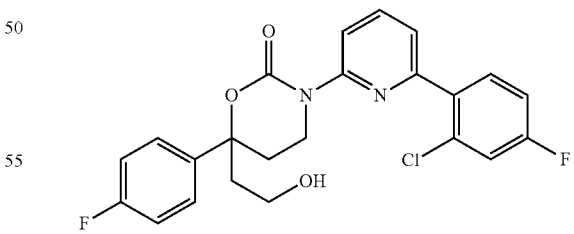

The title compound was prepared by application of procedures analogous to those described in Example 63 using p-fluoroacetophenone in Step 1 and 2-amino-6-bromopyridine in Step 2, followed by Example 74 and Example 75 Step 1 using 2-chloro-4-fluorophenylboronic acid. LC-MS Method 3, $t_R$=1.347 min, m/z=445.1. $^1$H NMR ($CD_3OD$) 2.25 (m, 2H), 2.55 (m, 1H), 2.60 (m, 1H), 3.40 (m, 2H), 3.50

(m, 1H), 3.75 (m, 1H), 7.15 (m, 3H), 7.30 (m, 1H), 7.45 (m, 3H), 7.75 (m, 1H), 7.80 (m, 1H).

Example 119

3-((S)-1-(4'-fluorobiphenyl-4-yl)ethyl)-6-(4-fluorophenyl)-6-(2-hydroxyethyl)-1,3-oxazinan-2-one

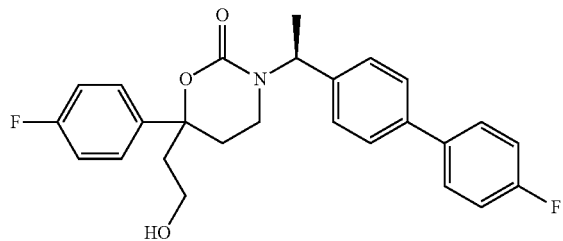 [SMILES: C[C@@H](c1ccc(-c2ccc(F)cc2)cc1)N1CCC(CCO)(c2ccc(F)cc2)OC1=O]

The title compound was prepared from 3-((S)-1-(4-bromophenyl)ethyl)-6-(4-fluorophenyl)-6-(2-hydroxyethyl)-1,3-oxazinan-2-one by application of procedures analogous to those described in Example 75 Step 1 using 4-fluorophenylboronic acid. The isomers were separated by chromatography on silica gel.

Isomer 1: (S)-3-((S)-1-(4'-fluorobiphenyl-4-yl)ethyl)-6-(4-fluorophenyl)-6-(2-hydroxyethyl)-1,3-oxazinan-2-one. LC-MS Method 1, $t_R$=1.79 min, m/z=438. $^1$H NMR (CDCl$_3$) 7.47-7.44 (m, 2H), 7.32-7.27 (m, 4H), 7.13-7.04 (m, 4H), 6.98 (d, J=7.9 Hz, 2H), 5.69 (q, J=7.0 Hz, 1H), 3.80-3.74 (m, 1H), 3.60-3.54 (m, 1H), 2.99-2.95 (m, 1H), 2.38-2.28 (m, 3H), 2.24-2.19 (m, 1H), 2.18-2.08 (m, 1H), 1.56 (d, J=7.0 Hz, 3H).

Isomer 2: (R)-3-((S)-1-(4'-fluorobiphenyl-4-yl)ethyl)-6-(4-fluorophenyl)-6-(2-hydroxyethyl)-1,3-oxazinan-2-one. LC-MS Method 1, $t_R$=1.84 min, m/z=438.

Example 120

6-allyl-3-((S)-1-cyclohexylethyl)-6-(4-fluorophenyl)-1,3-oxazinan-2-one

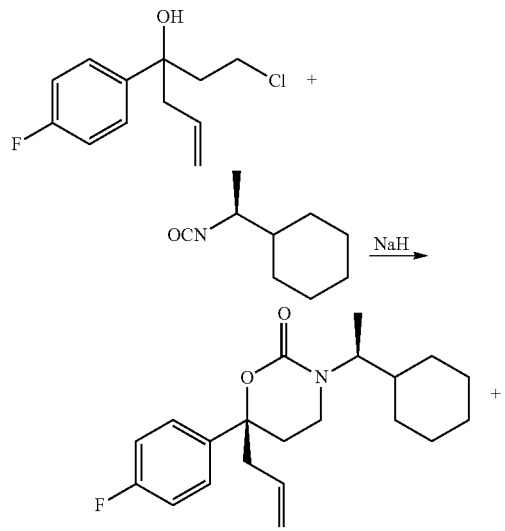

-continued

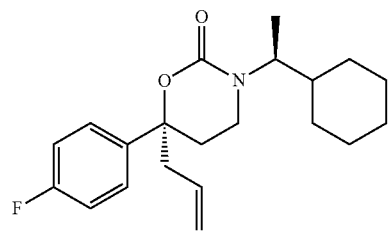

1-chloro-3-(4-fluorophenyl)hex-5-en-3-ol (126 mg, 0.55 mmol), (S)-(+)-1-cyclohexylethyl isocyanate (160 mg, 1.44 equiv.) and proton sponge (271 mg, 2.3 equiv.) were dissolved in dry THF (5 mL) and heated to reflux for 3 h. The mixture was then cooled to 0° C. and NaH (22 mg, 1.0 equiv.) was added slowly. After 5 min, the mixture was heated to reflux overnight. LC-MS showed the reaction was complete. The mixture was diluted with EtOAc (50 mL) and washed with 1% aq HCl (2×15 mL), satd aq NaHCO$_3$ (10 mL) and brine (10 mL), and dried over Na$_2$SO$_4$. After filtration and concentration, the residue was purified by chromatography on a 12-g silica cartridge eluted with a 10-45% EtOAc in hexanes gradient to afford two isomeric products.

Isomer 1: (R)-6-allyl-3-((S)-1-cyclohexylethyl)-6-(4-fluorophenyl)-1,3-oxazinan-2-one (57.5 mg, 30%). LC-MS Method 1, $t_R$=2.05 min, m/z=346. $^1$H NMR (CDCl$_3$) 7.29 (m, 2H), 7.02 (m, 2H), 5.70 (m, 1H), 5.05 (dd, 2H), 3.94 (m, 1H), 3.06 (m, 1H), 2.68-2.49 (m, 3H), 2.33 (m, 1H), 2.14 (m, 1H), 1.17 (d, 3H), 0.78 (m, 2H).

Isomer 2: (S)-6-allyl-3-((S)-1-cyclohexylethyl)-6-(4-fluorophenyl)-1,3-oxazinan-2-one (56 mg, 29%). LC-MS Method 1, $t_R$=2.06 min, m/z=346. $^1$H NMR (CDCl$_3$) 7.27 (m, 2H), 7.03 (t, 2H), 5.71 (m, 1H), 5.05 (dd, 2H), 3.95 (m, 1H), 2.92 (m, 1H), 2.72 (m, 1H), 2.57 (m, 2H), 2.22 (m, 2H), 1.49 (d, 1H), 1.32 (m, 1H), 0.86 (d, 3H).

Example 121

6-methyl-6-phenyl-3-(4-phenylthiazol-2-yl)-1,3-oxazinan-2-one

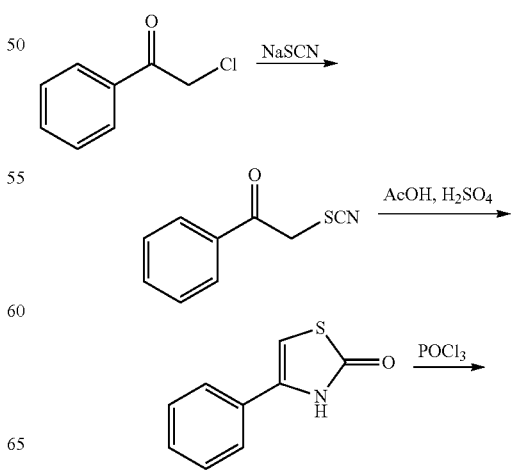

-continued

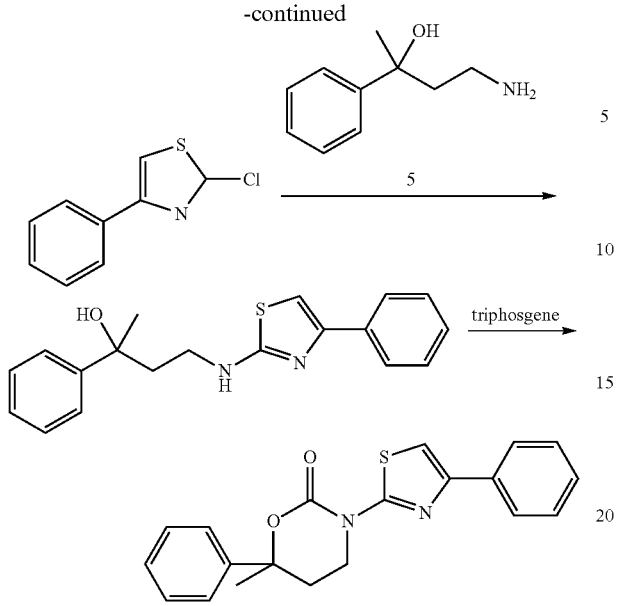

Step 1. 1-Phenyl-2-thiocyanatoethanone

To a solution of 2-bromo-1-phenylethanone (20 g, 0.1 mol) in acetone (170 mL) was added NaSCN (8.1 g, 0.1 mol). The mixture was stirred till the reaction was complete. The mixture was filtered, and the filtrate was concentrated to give the crude 1-phenyl-2-thiocyanato-ethanone (20 g), which was used for the next step without further purification.

Step 2. 4-Phenylthiazol-2(3H)-one

To a solution of 1-phenyl-2-thiocyanato-ethanone (20 g, 113 mmol) in HOAc (100 mL) was added 50% aqueous $H_2SO_4$ (20 mL). The mixture was refluxed for 10 min. The mixture was poured into water. The solid formed was collected by filtration to give crude 4-phenyl-3H-thiazol-2-one (20 g) which was used for the next step without further purification.

Step 3. 2-Chloro-4-phenylthiazole

4-Phenyl-3H-thiazol-2-one (5 g, 28.2 mmol) was dissolved in $POCl_3$ (30 mL), and the mixture was refluxed overnight. The mixture was concentrated in vacuum, and the residue was purified by column chromatography to give 2-chloro-4-phenylthiazole (3.1 g, 57%).

Step 4. 2-Phenyl-4-(4-phenylthiazol-2-ylamino)butan-2-ol

A mixture of 2-chloro-4-phenylthiazole (300 mg, 1.5 mmol), 4-amino-2-phenyl-butan-2-ol (294 mg, 1.5 mmol) and DBU (1.5 mL) was heated to 100° C. under $N_2$ in a microwave for 2 h. After the material was consumed, the mixture was neutralized with 1 N HCl solution (5 mL), extracted with $CH_2Cl_2$ (3×5 mL). The combined organic extracts were dried over $Na_2SO_4$ and concentrated to leave a residue, which was purified by column chromatography (1:2 petroleum ether/EtOAc) to afford 2-phenyl-4-(4-phenylthiazol-2-ylamino)butan-2-ol (100 mg, 20%).

Step 5. 6-methyl-6-phenyl-3-(4-phenylthiazol-2-yl)-1,3-oxazinan-2-one

To a solution of 2-phenyl-4-(4-phenylthiazol-2-ylamino) butan-2-ol (50 mg, 0.15 mmol) and $Et_3N$ (80 mg, 0.75 mmol) in $CH_2CH_2$ (5 mL) was added triphosgene (15 mg, 0.05 mmol) at 0° C. Then, the mixture was stirred at rt overnight. The reaction solution was concentrated to give an oil, which was purified by column chromatography (1:2 petroleum ether/EtOAc) to afford 6-methyl-6-phenyl-3-(4-phenylthiazol-2-yl)-1,3-oxazinan-2-one (20 mg, 37%). LC-MS Method 3, $t_R$=1.446 min, m/z=351. $^1$H NMR (CDCl$_3$, 400 Hz): 1.80 (s, 3H), 2.45 (m, 1H), 2.65 b (m, 1H), 3.70 (m, 1H), 4.42 (m, 1H), 7.18 (s, 1H), 7.20-7.40 (m, 8H), 7.80 (d, 2H).

Example 122

(R)-3-((S)-1-cyclohexylethyl)-6-(4-fluorophenyl)-6-(3-hydroxypropyl)-1,3-oxazinan-2-one

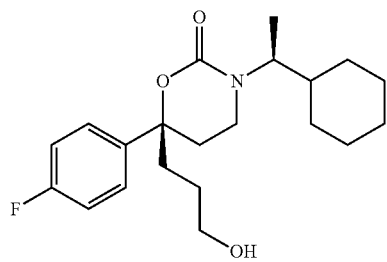 [SMILES: C[C@@H](C1CCCCC1)N1CC[C@](CCCO)(c2ccc(F)cc2)OC1=O]

The title compound was prepared from (R)-6-allyl-3-((S)-1-cyclohexylethyl)-6-(4-fluorophenyl)-1,3-oxazinan-2-one using a procedure analogous to that described in Example 78. LC-MS Method 1, $t_R$=1.72 min, m/z=364. $^1$H NMR (CDCl$_3$) 7.29 (m, 2H), 7.06 (m, 2H), 3.98 (m, 1H), 3.57 (t, 2H), 3.07 (m, 1H), 2.64 (m, 1H), 2.16 (m, 1H), 1.95 (m, 2H), 1.09 (d, 3H), 0.66 (m, 1H).

Example 123

(R)-6-allyl-3-((S)-1-(4-cyclopropylphenyl)ethyl)-6-(4-fluorophenyl)-1,3-oxazinan-2-one

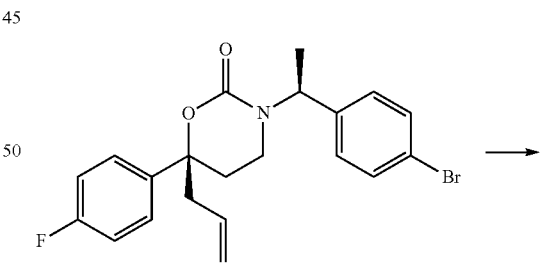

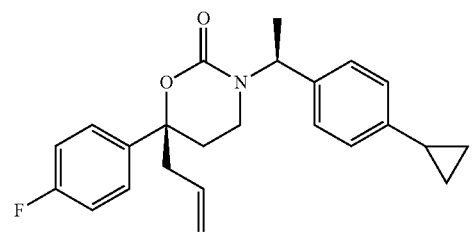

A mixture of (R)-6-allyl-3-((S)-1-(4-bromophenyl)ethyl)-6-(4-fluorophenyl)-1,3-oxazinan-2-one (15 mg, 0.036 mmol), cyclopropylboronic acid (5.5 mg, 1.78 equiv.), Pd(OAc)$_2$ (2 mg, 25% mol), tricyclohexylphosphine (5 mg, 50% mol), K$_3$PO$_4$ (20 mg, excess), water (1 mL) and DMF (1 mL) were heated in a microwave oven for 45 min at 100° C. The mixture was diluted with EtOAc (10 mL), washed with water (4 mL) and brine (5 mL), and dried over Na$_2$SO$_4$. After filtration and concentration, the residue was purified by preparative HPLC to afford (R)-6-allyl-3-((S)-1-(4-cyclopropylphenyl)ethyl)-6-(4-fluorophenyl)-1,3-oxazinan-2-one (6.2 mg, 45%). LC-MS Method 1, t$_R$=2.02 min, m/z=380. $^1$H NMR (CDCl$_3$) 7.24 (m, 2H), 7.02 (t, 2H), 6.76 (q, 4H), 5.75-5.56 (m, 2H), 5.10-4.98 (dd, 2H), 2.57 (m, 2H), 1.48 (d, 3H), 0.92 (m, 2H), 0.60 (m, 2H).

Example 124

Methyl 4-((S)-1-((R)-6-allyl-6-(4-fluorophenyl)-2-oxo-1,3-oxazinan-3-yl)ethyl)benzoate

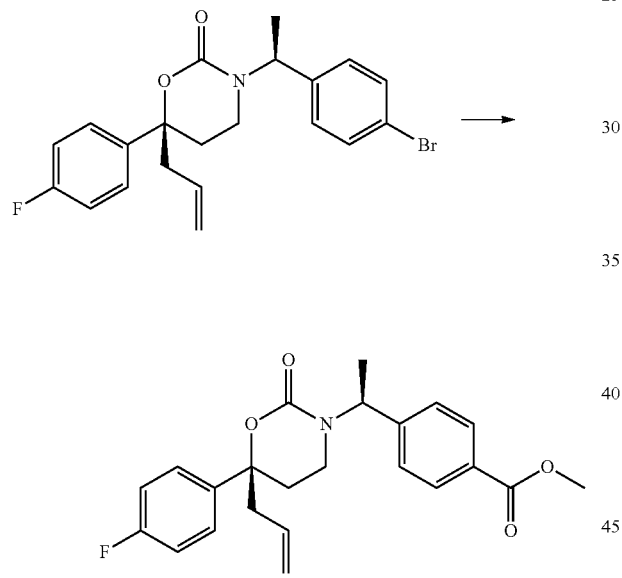

To a 16 mm culture tube with a Teflon-coated stirring bar, a solution of (R)-6-allyl-3-((S)-1-(4-bromophenyl)ethyl)-6-(4-fluorophenyl)-1,3-oxazinan-2-one (87 mg, 0.209 mmol) in dry DMSO (4 mL) and dry methanol (1.5 mL), triethylamine (60 μL, 2 equiv), Pd(OAc)$_2$ (10 mg, 0.2 equiv) and 1,3-bis(diphenylphosphino)propane (35 mg, 0.4 equiv) were added. The tube was sealed with a septum and Parafilm tape. The reaction mixture was purged with CO gas through a long needle for 1 min. A balloon filled with CO gas was attached to maintain a CO atmosphere. The reaction mixture was submerged in an oil bath preheated to 85° C. and stirred vigorously. After 12 h, LC-MS showed the reaction was complete. The mixture was filtered through a thin pad of Celite. The Celite was washed with EtOAc (35 mL). The filtrate was washed with 3% aq HCl (10 mL), water (2×8 mL) and brine (2×7 mL), and dried over Na$_2$SO$_4$. After filtration and concentration, the residue was purified by chromatography on a 12-g silica gel cartridge eluted with a 10-60% EtOAc in hexanes gradient to afford methyl 4-((S)-1-((R)-6-allyl-6-(4-fluorophenyl)-2-oxo-1,3-oxazinan-3-yl)ethyl)benzoate (68.4 mg, 83%). LC-MS Method 1, t$_R$=1.79 min, m/z=398. $^1$H NMR (CDCl$_3$) 7.79 (d, 2H), 7.26 (m, 2H), 7.04 (t, 2H), 6.94 (d, 2H), 5.69 (m, m, 2H), 5.07 (dd, 2H), 3.89 (s, 3H), 2.94 (m, 1H), 2.58 (m, 2H), 1.54 (d, 3H).

Example 125

(R)-3-((S)-1-(4-cyclopropylphenyl)ethyl)-6-(4-fluorophenyl)-6-(3-hydroxypropyl)-1,3-oxazinan-2-one

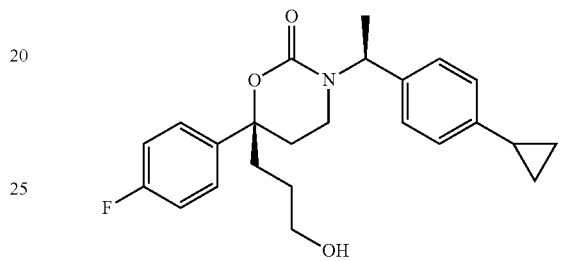

The title compound was prepared from (R)-6-allyl-3-((S)-1-(4-cyclopropyl-phenyl)ethyl)-6-(4-fluorophenyl)-1,3-oxazinan-2-one using a procedure analogous to that described in Example 78. LC-MS Method 1, t$_R$=1.71 min, m/z=420. $^1$H NMR (CDCl$_3$) 7.31 (m, 4H), 7.07 (m, 2H), 6.82 (d, 2H), 5.65 (m, 1H), 3.96 (m, 1H), 3.58 (t, 2H), 1.48 (t, 3H), 1.12 (d, 2H), 0.92 (d, 2H).

Example 126

(S)-2-(4-fluorophenyl)-6-(6-(2-hydroxyethyl)-2-oxo-6-phenyl-1,3-oxazinan-3-yl)pyridine 1-oxide

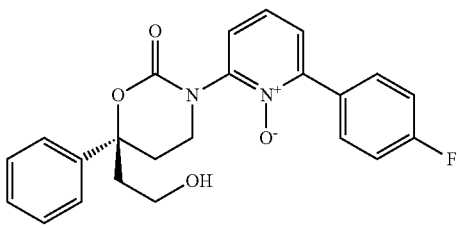 [SMILES: O=C1O[C@@](CCO)(c2ccccc2)CCN1c1cccc(-c2ccc(F)cc2)[n+]1[O-]]

The title compound was prepared from (S)-3-(6-(4-fluorophenyl)pyridin-2-yl)-6-(2-hydroxyethyl)-6-phenyl-1,3-oxazinan-2-one using a procedure analogous to that described in Example 129. LC-MS Method 2, t$_R$=1.637 min, m/z=409.1. $^1$H NMR (CD$_3$OD) 2.25-2.40 (m, 2H), 2.56-2.70

(m, 2H), 3.05-3.14 (m, 1H), 3.32-3.40 (m, 1H), 3.62-3.80 (m, 2H), 7.15-7.26 (m, 2H), 7.30-7.68 (m, 7H), 7.70-7.88 (m, 2H).

Example 127

Methyl 4-((S)-1-((R)-6-(4-fluorophenyl)-6-(3-hydroxypropyl)-2-oxo-1,3-oxazinan-3-yl)ethyl)benzoate

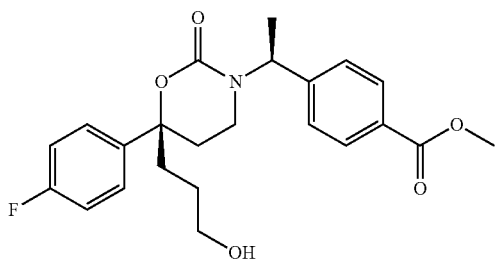 [SMILES: COC(=O)c1ccc([C@H](C)N2CC[C@](CCCO)(c3ccc(F)cc3)OC2=O)cc1]

The title compound was prepared from methyl 4-((S)-1-((R)-6-allyl-6-(4-fluorophenyl)-2-oxo-1,3-oxazinan-3-yl)ethyl)benzoate using a procedure analogous to that described in Example 78. LC-MS Method 1, $t_R$=1.49 min, m/z=416. $^1$H NMR (CDCl$_3$) 7.80 (d, 2H), 7.23 (m, 2H), 7.02 (m, 4H), 5.67 (m, 1H), 3.88 (s, 3H), 3.576 (t, 2H), 2.94 (m, 1H), 1.65 (m, 1H), 1.53 (d, 3H), 1.35 (m, 1H).

Example 128

6-allyl-3-((S)-1-(5-bromopyridin-2-yl)ethyl)-6-(4-fluorophenyl)-1,3-oxazinan-2-one

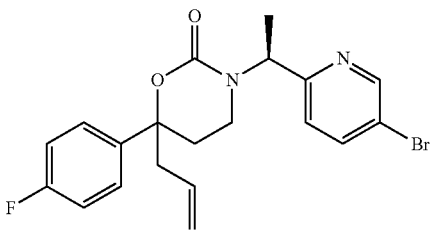 [SMILES: C=CCC1(c2ccc(F)cc2)CCN([C@@H](C)c2ccc(Br)cn2)C(=O)O1]

The title compound was prepared following using a procedure analogous to that described in Example 95 using (S)-5-bromo-2-(1-isocyanatoethyl)pyridine in Step 2.

Isomer 1: (R)-6-allyl-3-((S)-1-(5-bromopyridin-2-yl)ethyl)-6-(4-fluorophenyl)-1,3-oxazinan-2-one. LC-MS Method 3, $t_R$=1.281 min, m/z=419. $^1$H NMR (CDCl$_3$) 1.25 (s, 1H), 1.60 (m, 3H), 2.25-2.33 (m, 1H), 2.35 (s, 3H), 2.46-2.55 (m, 2H), 2.60-2.70 (m, 1H), 3.80 (s, 1H), 4.48-4.59 (m, 2H), 5.06-5.14 (m, 2H), 5.52-5.65 (m, 1H), 6.30 (d, 2H), 6.95 (m, 3H), 7.27 (m, 1H), 7.35 (m, 2H).

Isomer 2: (S)-6-allyl-3-((S)-1-(5-bromopyridin-2-yl)ethyl)-6-(4-fluorophenyl)-1,3-oxazinan-2-one. LC-MS Method 3, $t_R$=1.242 min, m/z=419. $^1$H NMR (CDCl$_3$) 2.05 (m, 1H), 2.13 (d, 3H), 2.24 (m, 1H), 2.36 (m, 3H), 2.52 (m, 1H), 3.63 (m, 1H), 3.85 (m, 1H), 4.09 (m, 1H), 4.99 (m, 2H), 5.55 (m, 1H), 6.13 (d, 1H), 6.48 (m, 1H), 6.83 (m, 1H), 6.98 (m, 1H), 7.22 (m, 2H), 7.33 (m, 1H).

Example 129

2-(4-fluorophenyl)-6-(6-(2-fluorophenyl)-6-(2-hydroxyethyl)-2-oxo-1,3-oxazinan-3-yl)pyridine 1-oxide

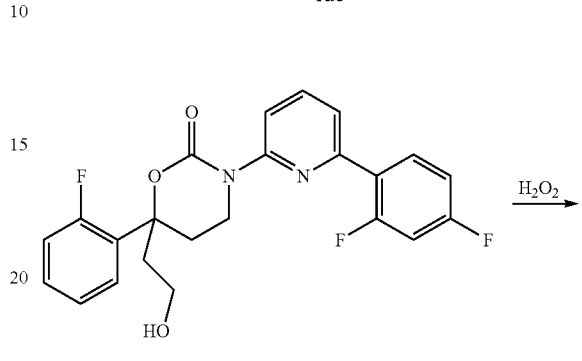

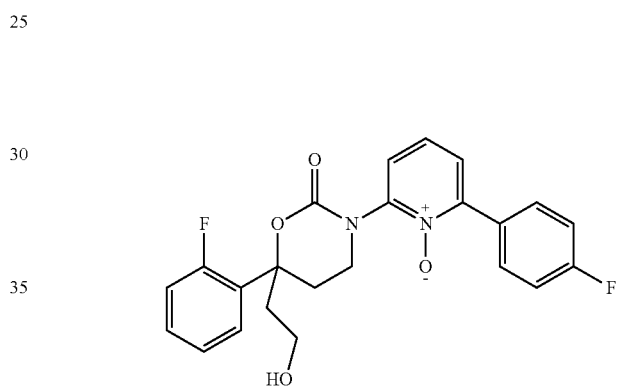

6-(2-fluorophenyl)-3-(6-(4-fluorophenyl)pyridin-2-yl)-6-(2-hydroxyethyl)-1,3-oxazinan-2-one (680 mg, 1.66 mmol) was added to acetic acid (20 mL), 30% aq hydrogen peroxide (50 mL) was added at rt and the reaction mixture was stirred for about 5 h at 80° C. The mixture was extracted with CH$_2$Cl$_2$ and the organic phase washed with Na$_2$SO$_3$ solution, then dried over Na$_2$SO$_4$. Removal of the solvent gave the crude product, which was purified by HPLC and give 2-(4-fluorophenyl)-6-(6-(2-fluorophenyl)-6-(2-hydroxyethyl)-2-oxo-1,3-oxazinan-3-yl)pyridine 1-oxide (80 mg, 11%). LC-MS Method 2, $t_R$=1.704 min, m/z=427.1. $^1$H NMR (CD$_3$OD) 2.33-2.50 (m, 2H), 2.60-2.77 (m, 2H), 3.08-3.20 (m, 1H), 3.32-3.40 (m, 1H), 3.40-3.52 (m, 1H), 3.70-3.85 (m, 1H), 7.08-7.37 (m, 5H), 7.40-7.69 (m, 4H), 7.70-7.86 (m, 2H). $^1$H NMR (400 MHz, CDCl$_3$): δ=2.5 (s, 2H), 2.6 (m, 2H), 3.05 (m, 1H), 3.3 (m, 1H), 3.35-3.6 (m, 1H), 3.75 (m, 1H), 7.0-7.8 (m, 11H).

The enantiomers were separated by chiral SFC.

Isomer 1: LC-MS Method 2, $t_R$=1.843 min, m/z=427.1. $^1$H NMR (CD$_3$OD) 2.40-2.52 (m, 2H), 2.62-2.80 (m, 2H), 3.12-3.23 (m, 1H), 3.35-3.45 (m, 1H), 3.58-3.65 (m, 1H), 3.72-3.88 (m, 1H), 7.12-7.49 (m, 5H), 7.50-7.70 (m, 4H), 7.72-7.90 (m, 2H).

Isomer 2: LC-MS Method 2, $t_R$=1.841 min, m/z=427.1. $^1$H NMR (CD$_3$OD) 2.26-2.40 (m, 2H), 2.50-2.70 (m, 2H), 3.06

(m, 1H), 3.23-3.32 (m, 1H), 3.23-3.58 (m, 1H), 3.62-3.75 (m, 1H), 6.98-7.30 (m, 1H), 7.30-7.60 (m, 4H), 7.62-7.78 (m, 2H).

Example 130

6-allyl-3-((S)-1-(4-bromophenyl)propyl)-6-(4-fluorophenyl)-1,3-oxazinan-2-one

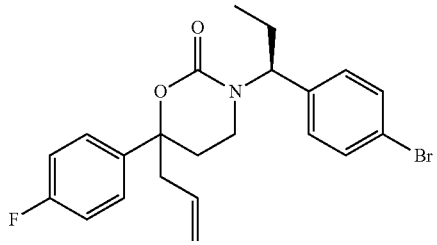 [SMILES: C=CCC1(c2ccc(F)cc2)CCN([C@@H](CC)c2ccc(Br)cc2)C(=O)O1]

The title compound was prepared following using a procedure analogous to that described in Example 95 using (S)-1-bromo-4-(1-isocyanatopropyl)benzene in Step 2.

Isomer 1: (R)-6-allyl-3-((S)-1-(4-bromophenyl)propyl)-6-(4-fluorophenyl)-1,3-oxazinan-2-one. LC-MS Method 3, $t_R$=1.415 min, m/z=432. $^1$H NMR (CD$_3$OD) 0.94 (t, 3H), 1.96 (m, 2H), 2.28 (m, 2H), 2.46 (m, 1H), 2.62 (m, 2H), 3.10 (m, 1H), 5.06 (m, 1H), 5.28 (m, 1H), 5.68 (m, 1H), 6.92 (m, 2H), 7.06 (m, 2H), 7.29 (m, 4H)

Isomer 2: (S)-6-allyl-3-((S)-1-(4-bromophenyl)propyl)-6-(4-fluorophenyl)-1,3-oxazinan-2-one. LC-MS Method 3, $t_R$=1.454 min, m/z=432. $^1$H NMR (CD$_3$OD) 0.56 (d, 3H), 1.65-1.75 (m, 1H), 1.76-1.88 (m, 1H), 1.98-2.08 (m, 1H), 2.46-2.55 (m, 1H), 2.60 (m, 2H), 2.72-2.86 (m, 2H), 4.98-5.08 (m, 2H), 5.30 (m, 1H), 5.62-5.72 (m, 1H), 7.11-7.18 (m, 1H), 7.25 (m, 2H), 7.39 (m, 2H), 7.50 (m, 2H).

(S)-1-bromo-4-(1-isocyanatopropyl)benzene was prepared as follows.

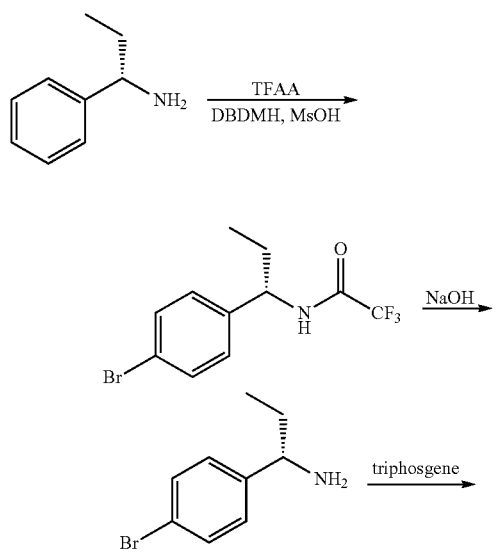

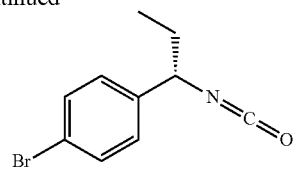

Step 1

TFAA (27 mL) was dissolved in methylene chloride (121 mL) and cooled in ice water bath. A solution of (S)-1-phenyl-propan-1-amine (25 g, 0.1851 mol) in methylene chloride (41 mL) was added and the ice water removed. The reaction mixture was stirred at rt for 3 h. The reaction mixture was cooled in ice water and MsOH (32.5 mL) was added followed by 1,3-dibromo-5,5-dimethylimidazolidine-2,4-dione (DBDMH) (26.16 g, 0.09255 mol). The mixture was stirred overnight. The mixture was quenched with water, and the precipitate was filtered to give (S)—N-(1-(4-bromophenyl)propyl)-2,2,2-trifluoroacetamide (45.24 g, 79%).

Step 2

To a solution of (S)—N-(1-(4-bromophenyl)propyl)-2,2,2-trifluoroacetamide (45.24 g, 0.1464 mol) in methanol (317 mL) was added a solution of NaOH (188 mL, 13%) at 0° C. The mixture was stirred for 2 h. The mixture was concentrated and extracted with methylene chloride. The solvent was removed to give (S)-1-(4-bromophenyl)propan-1-amine (29.65 g, 95%). $^1$H NMR (CDCl$_3$): 084 (t, 3H), 1.63 (m, 2H), 3.79 (m, 1H), 7.19 (m, 2H), 7.45 (m, 2H).

Step 3

(S)-1-(4-bromophenyl)propan-1-amine was used in a procedure analogous to that described in Example 392 Step 1 to afford (S)-1-bromo-4-(1-isocyanatopropyl)benzene.

Example 131

6-allyl-3-(1-(5-(2,4-difluorophenyl)pyridin-2-yl)ethyl)-6-(4-fluorophenyl)-1,3-oxazinan-2-one

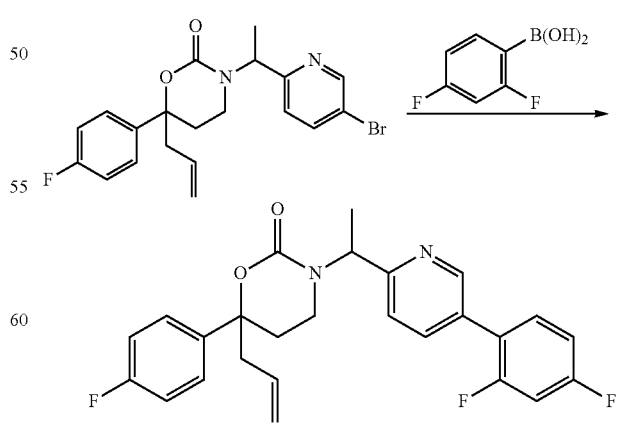

A solution of 6-allyl-3-(1-(5-bromopyridin-2-yl)ethyl)-6-(4-fluorophenyl)-1,3-oxazinan-2-one (100 mg, 0.24 mmol), 2,4-difluorophenylboronic acid (56.9 mg, 0.36 mmol), PdCl₂(PPh₃)₂ (10 mg, 10%) and aqueous solution of Cs₂CO₃ (2 M, 0.2 mL) in 1,4-dioxane (3 mL) was heated to reflux overnight. After the solvents were evaporated, the crude product was purified by preparative TLC to give 6-allyl-3-(1-(5-(2,4-difluorophenyl)pyridin-2-yl)ethyl)-6-(4-fluorophenyl)-1,3-oxazinan-2-one (50 mg, 46%). LC-MS Method 3, tR=1.336 min, m/z=453.1. ¹H NMR (CDCl₃): 2.30-2.40 (m, 1H), 2.39-2.42 (d, 3H), 2.50-2.60 (m, 2H), 2.60-2.70 (m, 2H), 4.10-4.20 (m, 1H), 4.50-4.65 (m, 2H), 5.55-5.70 (m, 2H), 6.40-6.50 (d, 1H), 6.80-7.00 (m, 4H), 7.10-7.15 (m, 1H), 7.22-7.30 (m, 2H), 7.30-7.40 (m, 3H).

Example 132

2-(2,4-difluorophenyl)-6-(6-(2-fluorophenyl)-6-(2-hydroxyethyl)-2-oxo-1,3-oxazinan-3-yl)pyridine 1-oxide

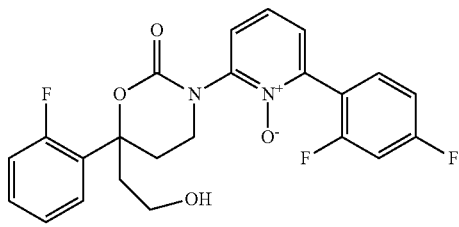 [SMILES: O=C1OC(CCO)(c2ccccc2F)CCN1c1cccc(-c2ccc(F)cc2F)[n+]1[O-]]

The title compound was prepared from 3-(6-(2,4-difluorophenyl)pyridin-2-yl)-6-(2-fluorophenyl)-6-(2-hydroxyethyl)-1,3-oxazinan-2-one following a procedure analogous to that described in Example 129. LC-MS Method 2, t$_R$=1.724 min, m/z=445. ¹H NMR (CD₃OD) 2.32-2.50 (m, 3H), 2.78-2.86 (m, 1H), 3.33-3.53 (m, 1H), 3.63 (m, 1H), 3.80 (m, 1H), 4.25 (m, 1H), 7.05-7.13 (m, 3H), 7.18 (m, 1H), 7.32 (m, 1H), 7.50 (m, 1H), 7.65-7.70 (m, 5H).

Example 133

3-(5-chloro-6-(4-fluorophenyl)pyridin-2-yl)-6-(2-fluorophenyl)-6-(2-hydroxyethyl)-1,3-oxazinan-2-one

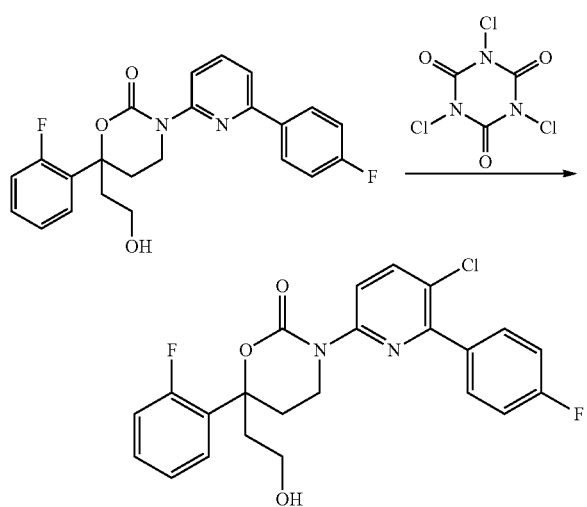

A mixture of 6-(2-fluorophenyl)-3-(6-(4-fluorophenyl)pyridin-2-yl)-6-(2-hydroxyethyl)-1,3-oxazinan-2-one (30 mg, 0.07 mmol), NaOAc (9 mg, 0.11 mmol) in HOAc (4 mg, 0.07 mmol), CH₃CN (2 mL), H₂O (0.1 mL) and CH₂Cl₂ (2 mL) was stirred at rt for 5 min. A solution of 1,3,5-trichloro-1,3,5-triazinane-2,4,6-trione (37 mg, 0.11 mmol) in CH₃CN (0.5 mL) was added slowly. The mixture was stirred for 20 min and heated to 40° C. for 2 h. The reaction was quenched with aq NaHSO₃ and extracted with CH₂Cl₂. The organic layer was dried with Na₂SO₄, concentrated to afford the crude product. Purification afforded 3-(5-chloro-6-(4-fluorophenyl)pyridin-2-yl)-6-(2-fluorophenyl)-6-(2-hydroxyethyl)-1,3-oxazinan-2-one (15 mg, 48%). LC-MS Method 3, t$_R$=1.331 min, m/z=445. ¹H NMR (CDCl₃, 400 Hz): 2.40 (m, 3H), 2.84 (m, 1H), 3.40 (m, 1H), 3.66 (m, 1H), 3.82 (m, 1H), 4.26 (m, 1H), 7.10 (m, 3H), 7.18 (m, 1H), 7.34 (m, 1H), 7.50 (m, 1H), 7.68 (m, 2H), 7.76 (m, 1H), 8.01 (m, 1H).

Example 134

(R)-6-(2-aminoethyl)-3-((S)-1-(2',4'-difluorobiphenyl-4-yl)ethyl)-6-(4-fluorophenyl)-1,3-oxazinan-2-one

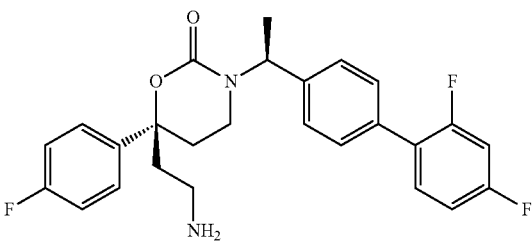 [SMILES: C[C@@H](c1ccc(-c2ccc(F)cc2F)cc1)N1CC[C@](CCN)(c2ccc(F)cc2)OC1=O]

The title compound was prepared from (S)-3-((S)-1-(2',4'-difluorobiphenyl-4-yl)ethyl)-6-(4-fluorophenyl)-6-(2-hydroxyethyl)-1,3-oxazinan-2-one following procedures analogous to those described in Example 75 Steps 2, 3 and 4. LC-MS Method 2, t$_R$=1.981 min, m/z=455.2. ¹H NMR (CDCl₃) 1.50 (m, 3H), 2.29 (m, 3H), 2.34-2.50 (m, 1H), 2.80-3.18 (m, 5H), 5.60 (m, 1H), 6.85-7.09 (m, 6H), 7.21 (m, 2H), 7.30 (m, 2H), 8.05-8.35 (m, 2H).

Example 135

3-(5-chloro-6-(2,4-difluorophenyl)pyridin-2-yl)-6-(2-fluorophenyl)-6-(2-hydroxyethyl)-1,3-oxazinan-2-one

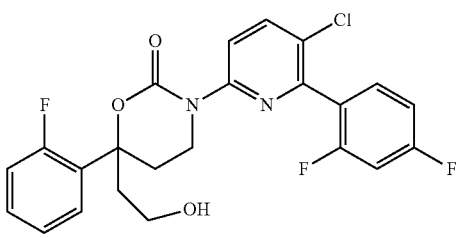 [SMILES: O=C1OC(CCO)(c2ccccc2F)CCN1c1ccc(Cl)c(-c2ccc(F)cc2F)n1]

The title compound was prepared from 3-(6-(2,4-difluorophenyl)pyridin-2-yl)-6-(2-fluorophenyl)-6-(2-hydroxyethyl)-1,3-oxazinan-2-one using a procedure analogous to that described in Example 133. LC-MS Method 3, $t_R$=1.314 min, m/z=463. $^1$H NMR (CDCl$_3$) 2.42-2.53 (m, 3H), 2.64-2.86 (m, 1H), 3.29-3.40 (m, 1H), 3.65 (m, 1H), 3.78 (m, 1H), 4.20 (m, 1H), 4.30-4.58 (m, 1H), 6.83-6.95 (m, 2H), 7.09 (m, 1H), 7.18 (m, 1H), 7.30-7.40 (m, 2H), 7.42-7.51 (m, 1H), 7.76 (m, 1H), 8.05 (m, 1H).

Example 136

(R)-3-((S)-1-(2',4'-difluorobiphenyl-4-yl)ethyl)-6-(4-fluorophenyl)-6-(3-hydroxypropyl)-1,3-oxazinan-2-one

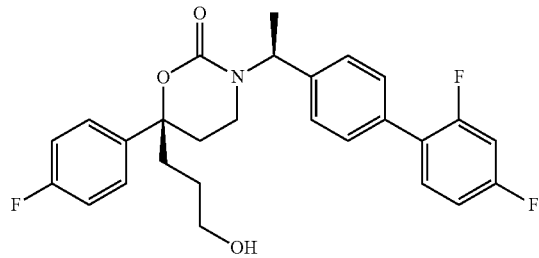 [SMILES: C[C@@H](c1ccc(-c2ccc(F)cc2F)cc1)N1CC[C@](CCCO)(c2ccc(F)cc2)OC1=O]

The title compound was prepared from (R)-6-allyl-3-((S)-1-(2',4'-difluorobiphenyl-4-yl)ethyl)-6-(4-fluorophenyl)-1,3-oxazinan-2-one using a procedure analogous to that described in Example 78. LC-MS Method 1, $t_R$=1.84 min, m/z=470. $^1$H NMR (CDCl$_3$) 7.34-7.22 (m, 4H), 7.07-6.98 (m, 4H), 6.96-6.85 (m, 3H), 5.69 (m, 1H), 3.58 (t, 1H), 1.56 (d, 3H).

Example 137

(6S)-3-((S)-1-(2',4'-difluorobiphenyl-4-yl)ethyl)-6-(4-fluorophenyl)-6-(2-hydroxypropyl)-1,3-oxazinan-2-one

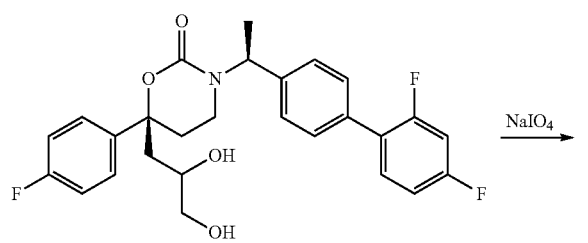

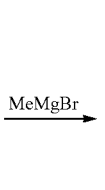

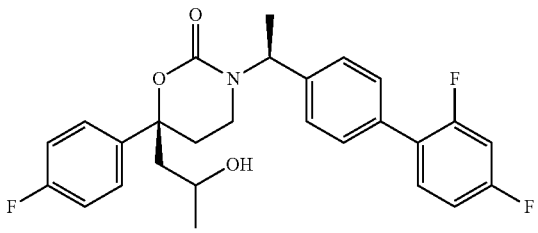

Step 1. 2-((S)-3-((S)-1-(2',4'-difluorobiphenyl-4-yl)ethyl)-6-(4-fluorophenyl)-2-oxo-1,3-oxazinan-6-yl)acetaldehyde To a stirred solution of crude (6S)-3-((S)-1-(2',4'-difluorobiphenyl-4-yl)ethyl)-6-(2,3-dihydroxypropyl)-6-(4-fluorophenyl)-1,3-oxazinan-2-one (0.2726 g, 0.56 mmol) in acetone/water (4:1, 5 mL) was added NaIO$_4$ (0.3070 g, 1.43 mmol) at rt. The white suspension was stirred for 1 h and treated with EtOAc, dried (Na$_2$SO$_4$), filtered, and concentrated under reduced pressure to give crude aldehyde (0.2669 g) as a foam. The crude aldehyde was directly used in the next step without further purification. LC-MS Method 1 $t_R$=1.93 min, m/z 454 (MH$^+$).

Step 2. (6S)-3-((S)-1-(2',4'-difluorobiphenyl-4-yl)ethyl)-6-(4-fluorophenyl)-6-(2-hydroxypropyl)-1,3-oxazinan-2-one To a stirred solution of 2-((S)-3-((S)-1-(2',4'-difluorobiphenyl-4-yl)ethyl)-6-(4-fluorophenyl)-2-oxo-1,3-oxazinan-6-yl)acetaldehyde in THF (3 mL) was added MeMgBr (1.4 M in toluene/THF, 3 mL, 4.2 mmol) at 0° C. The mixture was warmed up to rt and stirred for 1.5 h before quenching with satd aq NH$_4$Cl (3 mL). The mixture was diluted with CH$_2$Cl$_2$ and dried over Na$_2$SO$_4$. Removal of the solvent gave the crude alcohol as a mixture of diastereomers.

Analytical samples were purified by reversed-phase HPLC (SunFire™ Prep C$_{18}$ OBD™ 5 µm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford two diastereoisomers.

Isomer 1: (S)-3-((S)-1-(2',4'-difluorobiphenyl-4-yl)ethyl)-6-(4-fluorophenyl)-6-(2-hydroxypropyl)-1,3-oxazinan-2-one. LC-MS Method 1, $t_R$=1.87 min, m/z=470. $^1$H NMR (CD$_3$OD) 7.34-7.16 (m, 5H), 7.03-6.87 (m, 6H), 5.47 (q, J=7.0 Hz, 1H), 3.47-3.43 (m, 1H), 3.07-3.02 (m, 1H), 2.63-2.58 (m, 1H), 2.35-2.28 (m, 1H), 2.19-2.12 (m, 1H), 2.01 (dd, J=14.3, 7.6 Hz, 1H), 1.86 (dd, J=14.3, 4.4 Hz, 1H), 1.46 (d, J=7.0 Hz, 3H), 1.04 (d, J=6.4 Hz, 3H).

Isomer 2: (S)-3-((S)-1-(2',4'-difluorobiphenyl-4-yl)ethyl)-6-(4-fluorophenyl)-6-(2-hydroxypropyl)-1,3-oxazinan-2-one. LC-MS Method 1, $t_R$=1.88 min, m/z=470. $^1$H NMR (CD$_3$OD) 7.35-7.19 (m, 5H), 7.03-6.92 (m, 6H), 5.50 (q, J=7.0 Hz, 1H), 3.90-3.86 (m, 1H), 3.04-2.99 (m, 1H), 2.40-2.36 (m, 2H), 2.23-2.16 (m, 1H), 1.95 (dd, J=15.1, 7.5 Hz, 1H), 1.85 (dd, J=15.1, 3.4 Hz, 1H), 1.48 (d, J=7.0 Hz, 3H), 0.95 (d, J=6.4 Hz, 3H).

Example 138

(S)-3-((S)-1-(2',4'-difluorobiphenyl-4-yl)ethyl)-6-(4-fluorophenyl)-6-(2-oxopropyl)-1,3-oxazinan-2-one

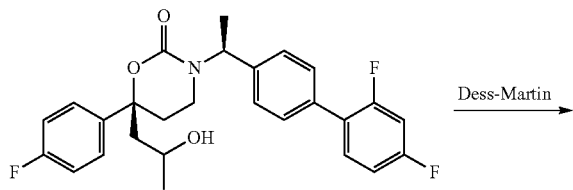

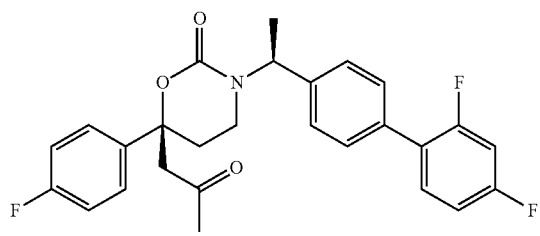

A mixture of the above alcohol (0.1830 g, 0.39 mmol) and Dess-Martin periodinane (0.1760 g, 0.41 mmol) in CH$_2$Cl$_2$ was stirred at rt for 2 h. The mixture was treated with satd aq NaHCO$_3$, diluted with EtOAc, and dried over Na$_2$SO$_4$. After the solvent was evaporated under reduced pressure, the residue was purified by preparative HPLC (SunFire™ Prep C$_{18}$ OBD™ 5 μm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford (S)-3-((S)-1-(2',4'-difluorobiphenyl-4-yl)ethyl)-6-(4-fluorophenyl)-6-(2-oxopropyl)-1,3-oxazinan-2-one. LC-MS Method 1 $t_R$=1.94 min, m/z 468 (MH$^+$); $^1$H NMR (400 MHz, CD$_3$OD) δ 7.34-7.27 (m, 3H), 7.19 (d, J=7.6 Hz, 2H), 7.01-6.90 (m, 6H), 5.49 (q, J=7.0 Hz, 1H), 3.06-3.02 (m, 1H), 2.99 (s, 2H), 2.54-2.49 (m, 1H), 2.38-2.24 (m, 2H), 1.97 (s, 3H), 1.46 (d, J=7.3 Hz, 3H); $^{19}$F NMR (376 MHz, CD$_3$OD) δ -113.66 (m), -115.74 (m), -116.72 (m).

Example 139

(S)-3-((S)-1-(2',4'-difluorobiphenyl-4-yl)ethyl)-6-(4-fluorophenyl)-6-(2-hydroxy-2-methylpropyl)-1,3-oxazinan-2-one

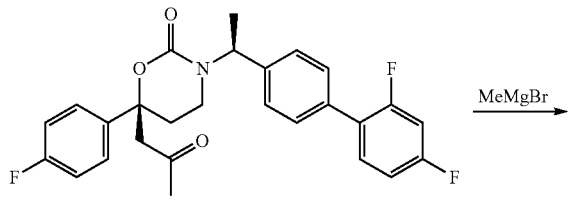

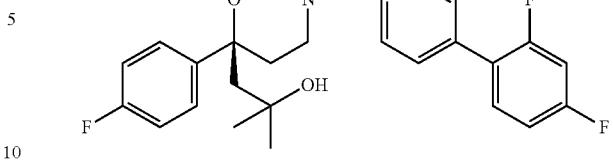

To a stirred solution of (S)-3-((S)-1-(2',4'-difluorobiphenyl-4-yl)ethyl)-6-(4-fluorophenyl)-6-(2-oxopropyl)-1,3-oxazinan-2-one (0.0303 g, 0.0648 mmol) in THF (5 mL) was added MeMgBr (1.4 M in toluene/THF, 1 mL, 1.4 mmol) at 0° C. The mixture was warmed to it and stirred for 1 h before quenching with satd aq NH$_4$Cl (1 mL). The mixture was diluted with CH$_2$Cl$_2$ and dried over Na$_2$SO$_4$. After the solvent was evaporated under reduced pressure, the residue was purified by preparative HPLC (SunFire™ Prep C$_{18}$ OBD™ 5 μm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford (S)-3-((S)-1-(2',4'-difluorobiphenyl-4-yl)ethyl)-6-(4-fluorophenyl)-6-(2-hydroxy-2-methylpropyl)-1,3-oxazinan-2-one. LC-MS Method 1 $t_R$=1.91 min, m/z 484 (MH$^+$), 426; $^1$H NMR (400 MHz, CD$_3$OD) δ 7.36-7.20 (m, 5H), 7.02-6.92 (m, 6H), 5.52 (q, J=7.0 Hz, 1H), 3.05-3.00 (m, 1H), 2.49-2.35 (m, 2H), 2.22-2.15 (m, 1H), 2.06 (s, 2H), 1.48 (d, J=7.0 Hz, 3H), 1.19 (s, 3H), 0.90 (s, 3H); $^{19}$F NMR (376 MHz, CD$_3$OD) δ -113.78 (m), -115.82 (m), -117.50 (m).

Example 140

(S)-3-((S)-1-(2',4'-difluorobiphenyl-4-yl)ethyl)-6-(4-fluorophenyl)-6-(2-methoxyethyl)-1,3-oxazinan-2-one

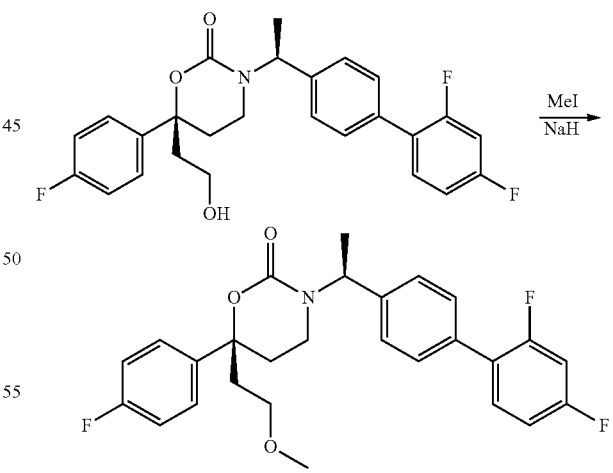

A mixture of NaH 6 mg, 0.21 mmol in THF (2 mL) was added dropwise to a mixture of (S)-3-((S)-1-(2',4'-difluorobiphenyl-4-yl)ethyl)-6-(4-fluorophenyl)-6-(2-hydroxyethyl)-1,3-oxazinan-2-one (80 mg, 0.196 mmol) in THF (5 mL) at -20° C. The mixture was stirred at -20° C. for 1 h, then iodomethane (30 mg, 0.21 mmol) was added dropwise. The mixture was refluxed overnight. The reaction was quenched with water and the mixture was extracted with EtOAc (3×10 mL). The organic layer was washed with brine, dried over sodium sulfate, filtered and concentrated to give the residue, which was purified by preparative TLC to give (S)-3-((S)-1-(2',4'-difluorobiphenyl-4-yl)ethyl)-6-(4-fluorophenyl)-6-(2-hydroxyethyl)-1,3-oxazinan-2-one (30 mg, 37%. $^1$H NMR (400 MHz, CD$_3$OD): δ=1.5 (m, 3H), 2.1 (m, 2H), 2.3 (m, 2H), 2.5 (m, 1H), 3.1 (m, 2H), 3.2 (s, 3H), 3.53 (m, 1H), 5.5 (m, 1H), 7.0 (m, 4H), 7.15 (m, 2H), 7.30 (m, 2H), 7.42 (m, 2H), 7.50 (m, 1H); LC-MS Method 3, $t_R$=1.393 min, m/z=470.2.

Example 141

1-(2-((R)-3-((S)-1-(2',4'-difluorobiphenyl-4-yl)ethyl)-6-(4-fluorophenyl)-2-oxo-1,3-oxazinan-6-yl)ethyl)-3-methylurea

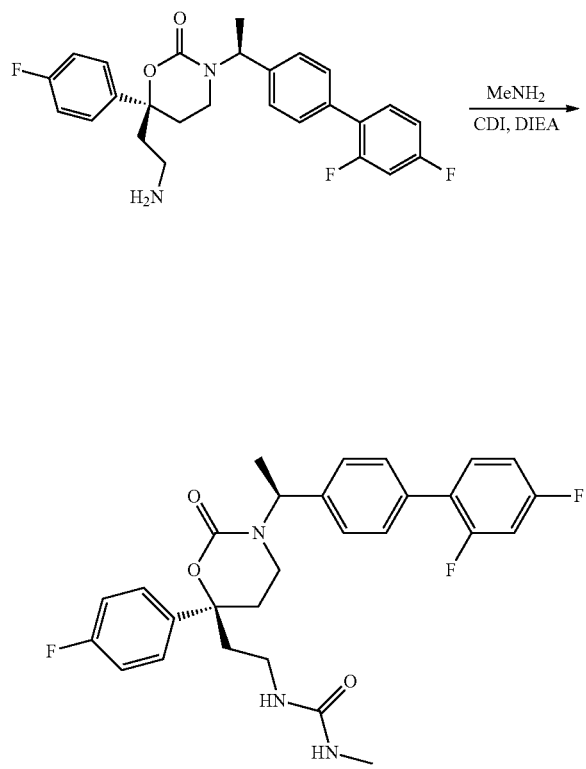

To a solution of methylamine (11 mg, 0.11 mmol) and CDI (20 mg, 0.13 mmol) in anhydrous CH$_2$Cl$_2$ (3 mL) was added DIEA (130 mg, 1.00 mmol) at 0° C. under nitrogen. The resulting mixture was stirred at ambient temperature for 1 h. (R)-6-(2-aminoethyl)-3-((S)-1-(2',4'-difluorobiphenyl-4-yl)ethyl)-6-(4-fluorophenyl)-1,3-oxazinan-2-one (40 mg, 0.088 mmol) was added to the above mixture, and the mixture was stirred at rt overnight. The mixture was concentrated in vacuo to give a residue, which was purified by preparative HPLC to afford 1-(2-((R)-3-((S)-1-(2',4'-difluorobiphenyl-4-yl)ethyl)-6-(4-fluorophenyl)-2-oxo-1,3-oxazinan-6-yl)ethyl)-3-methylurea (5 mg, 12%). $^1$H NMR (CDCl$_3$): 1.56 (m, 3H), 2.10-2.30 (m, 4H), 2.35 (m, 1H), 2.75 (s, 3H), 3.01 (m, 1H), 3.09 (m, 1H), 3.30 (m, 1H), 5.69 (m, 1H), 6.86-6.96 (m, 2H), 7.08 (m, 4H), 7.25 (m, 2H), 7.30 (m, 3H).

Example 142

4-((S)-1-((R)-6-(4-fluorophenyl)-6-(3-hydroxypropyl)-2-oxo-1,3-oxazinan-3-yl)ethyl)benzoic acid

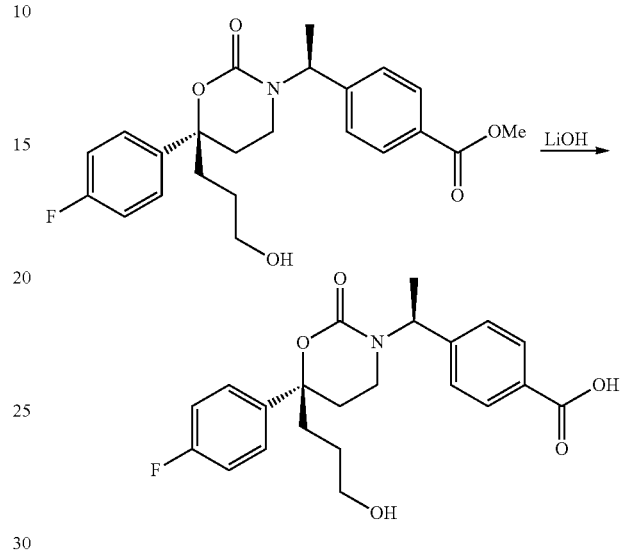

The title compound was prepared following a procedure analogous to that described in Example 94 Step 1. LC-MS Method 1 $t_R$=1.18 min, m/z=424 (M+Na); $^1$H NMR (CD$_3$OD) 7.79 (d, 2H), 7.32 (m, 2H), 7.13-6.97 (m, 4H), 5.57 (q, 1H), 3.47 (t, 2H), 3.14 (m, 2H), 2.48 (d, 1H), 2.34 (td, 1H), 2.23 (m, 1H), 1.55 (d, 3H).

Example 143

3-((S)-1-(4-bromophenyl)propyl)-6-(4-fluorophenyl)-6-(2-hydroxyethyl)-1,3-oxazinan-2-one

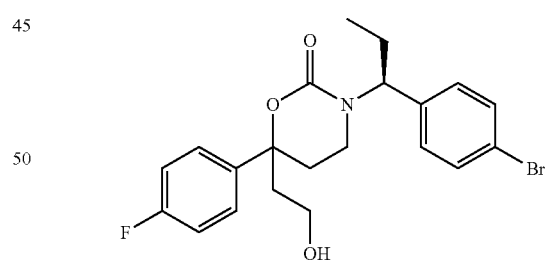

The title compound was prepared from 6-allyl-3-((S)-1-(4-bromophenyl)propyl)-6-(4-fluorophenyl)-1,3-oxazinan-2-one following a procedure analogous to that described in Example 74. The isomers were separated to afford:
Isomer 1: (R)-3-((S)-1-(4-bromophenyl)propyl)-6-(4-fluorophenyl)-6-(2-hydroxyethyl)-1,3-oxazinan-2-one.
LC-MS Method 3 $t_R$=1.206 min, m/z=435.9; $^1$H NMR (CD$_3$OD) 0.58 (m, 3H), 1.67-1.87 (m, 2H), 2.08 (m, 3H), 2.56 (m, 1H), 2.71-2.89 (m, 2H), 3.69 (m, 1H), 5.30 (m, 1H), 7.15-7.25 (m, 2H), 7.28 (m, 2H), 7.43 (m, 2H), 7.50 (m, 2H).
Isomer 2: (S)-3-((S)-1-(4-bromophenyl)propyl)-6-(4-fluorophenyl)-6-(2-hydroxyethyl)-1,3-oxazinan-2-one. LC-MS Method 3 $t_R$=1.287 min, m/z=460.1; $^1$H NMR (CD$_3$OD) 0.97 (m, 3H), 1.94-2.04 (m, 2H), 2.12 (m, 2H), 2.30 (m, 2H), 2.49 (m, 1H), 3.09 (m, 1H), 3.66 (m, 1H), 5.28 (m, 1H), 6.94 (m, 2H), 7.05 (m, 2H), 7.28 (m, 4H).

Example 144

(6S)-3-((S)-1-(4-bromophenyl)ethyl)-6-(2,3-dihydroxypropyl)-6-(4-fluorophenyl)-1,3-oxazinan-2-one

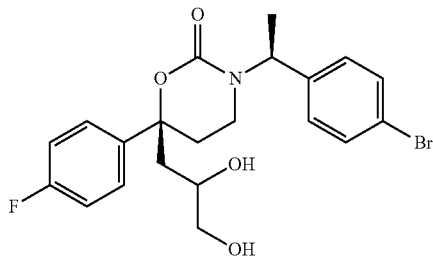 [SMILES: C[C@@H](c1ccc(Br)cc1)N1CC[C@](CC(O)CO)(c2ccc(F)cc2)OC1=O]

The title compound was prepared from (R)-6-allyl-3-((S)-1-(4-bromophenyl)ethyl)-6-(4-fluorophenyl)-1,3-oxazinan-2-one following a procedure analogous to that described in Example 77. The two isomers were separated by chromatography.

Isomer 1: LC-MS Method 1 $t_R$=1.55 min, m/z=452, 454; $^1$H NMR (CD$_3$OD) 7.27-7.24 (m, 2H), 7.21 (d, J=8.2 Hz, 2H), 7.04 (t, J=8.8 Hz, 2H), 6.80 (d, J=8.5 Hz, 2H), 5.42 (q, J=7.0 Hz, 1H), 3.75-3.71 (m, 1H), 3.22 (m, 2H), 3.04-2.99 (m, 1H), 2.44-2.39 (m, 2H), 2.21-2.14 (m, 1H), 2.00-1.95 (m, 1H), 1.87-1.81 (m, 1H), 1.44 (d, J=7.0 Hz, 3H).

Isomer 2: LC-MS Method 1 $t_R$=1.52 min, m/z=452, 454; $^1$H NMR (CD$_3$OD) 7.34-7.30 (m, 2H), 7.19 (d, J=8.5 Hz, 2H), 7.04 (t, J=8.6 Hz, 2H), 6.75 (d, J=8.8 Hz, 2H), 5.40 (q, J=7.0 Hz, 1H), 3.38-3.27 (m, 3H), 3.08-3.04 (m, 1H), 2.67-2.61 (m, 1H), 2.34-2.27 (m, 1H), 2.23-2.15 (m, 1H), 2.03-1.91 (m, 1H), 1.43 (d, J=7.0 Hz, 3H).

Example 145

3-((R)-3-((S)-1-(2',4'-difluorobiphenyl-4-yl)ethyl)-6-(4-fluorophenyl)-2-oxo-1,3-oxazinan-6-yl)propanamide

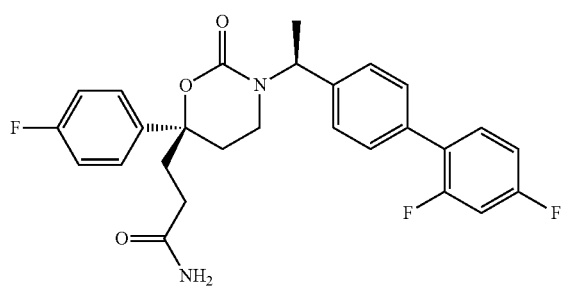 [SMILES: C[C@@H](c1ccc(-c2ccc(F)cc2F)cc1)N1CC[C@](CCC(N)=O)(c2ccc(F)cc2)OC1=O]

The title compound was prepared from 3-((R)-3-((S)-1-(2',4'-difluorobiphenyl-4-yl)ethyl)-6-(4-fluorophenyl)-2-oxo-1,3-oxazinan-6-yl)propanoic acid following a procedure analogous to that described in Example 76. LC-MS Method 3 $t_R$=1.212 min, m/z=483.1; $^1$H NMR (CD$_3$OD) 1.50 (m, 3H), 1.92-2.08 (m, 1H), 2.10-2.39 (m, 5H), 2.43 (m, 1H), 5.63 (m, 1H), 5.85 (s, 1H), 6.02 (s, 1H), 6.84 (m, 2H), 6.98 (m, 4H), 7.20 (m, 2H), 7.26 (m, 3H).

Example 146

3-((R)-3-((S)-1-(2',4'-difluorobiphenyl-4-yl)ethyl)-6-(4-fluorophenyl)-2-oxo-1,3-oxazinan-6-yl)-N-methylpropanamide

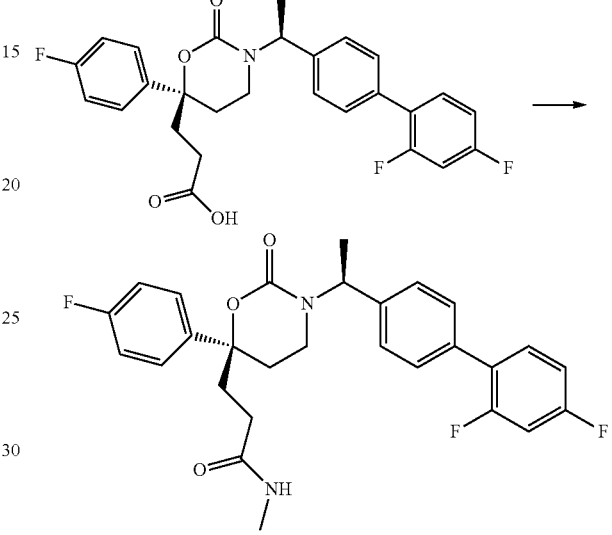

The title compound was prepared from 3-((R)-3-((S)-1-(2',4'-difluorobiphenyl-4-yl)ethyl)-6-(4-fluorophenyl)-2-oxo-1,3-oxazinan-6-yl)propanoic acid following a procedure analogous to that described in Example 76 using methylamine in place of ammonia. LC-MS Method 3 $t_R$=1.249 min, m/z=497.2; $^1$H NMR (CD$_3$OD) 1.51 (m, 3H), 1.97 (s, 1H), 2.07-2.31 (m, 6H), 2.64-2.74 (s, 3H), 2.94 (d, 1H), 5.62 (m, 1H), 6.13 (s, 1H), 6.79-6.89 (m, 2H), 6.97 (m, 4H), 7.15 (s, 2H), 7.23 (m, 3H).

Example 147

N-(2-((R)-3-((S)-1-(2',4'-difluorobiphenyl-4-yl)ethyl)-6-(4-fluorophenyl)-2-oxo-1,3-oxazinan-6-yl)ethyl)acetamide

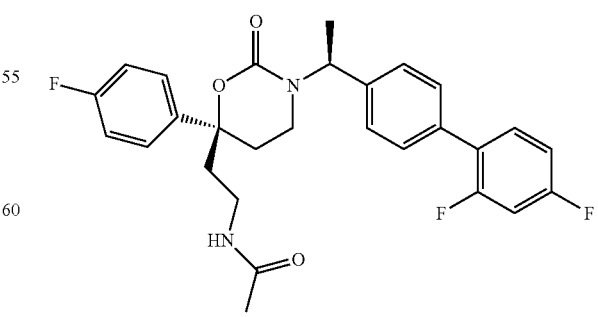

The title compound was prepared from (R)-6-(2-aminoethyl)-3-((S)-1-(2',4'-difluorobiphenyl-4-yl)ethyl)-6-(4-fluorophenyl)-1,3-oxazinan-2-one following a procedure analogous to that described in Example 98. LC-MS Method 3 $t_R$=1.252 min, m/z=497.1; $^1$H NMR (CD$_3$OD) 1.57 (m, 3H), 1.80-1.96 (s, 3H), 2.13 (m, 2H), 2.23 (s, 2H), 2.35 (m, 1H), 2.99 (m, 1H), 3.08 (m, 1H), 3.40 (m, 1H), 5.68 (m, 1H), 6.26 (s, 1H), 6.90 (m, 2H), 7.04 (m, 4H), 7.22-7.33 (m, 6H).

Example 148

2-((S)-3-((S)-1-(2',4'-difluorobiphenyl-4-yl)ethyl)-6-(4-fluorophenyl)-2-oxo-1,3-oxazinan-6-yl)ethyl methylcarbamate

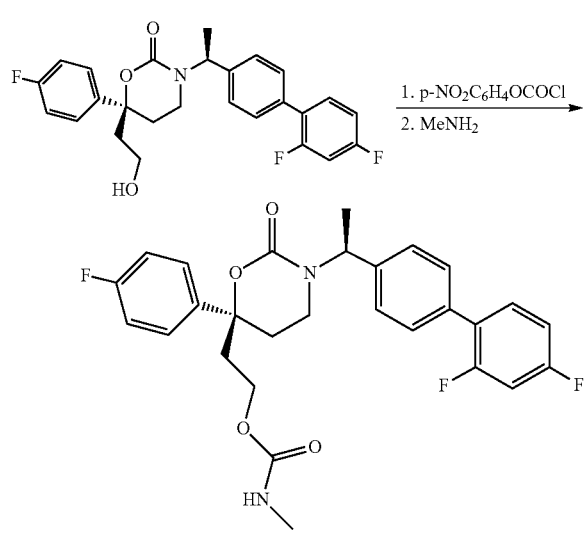

Step 1

A solution of 4-nitrophenyl chloroformate (133 mg, 0.66 mmol) in dichloromethane (1 mL) was added to a solution of (S)-3-((S)-1-(2',4'-difluorobiphenyl-4-yl)ethyl)-6-(4-fluorophenyl)-6-(2-hydroxyethyl)-1,3-oxazinan-2-one (100 mg, 0.22 mmol) and pyridine (608 mg, 7.7 mmol) in dichloromethane (2.8 mL). The mixture was stirred at it overnight. The reaction was quenched with 1 N HCl (7 mL), and the mixture was extracted with EtOAc (3×10 mL). The combined organic layer was washed with brine, dried and concentrated to give 2-((S)-3-((S)-1-(2',4'-difluorobiphenyl-4-yl)ethyl)-6-(4-fluorophenyl)-2-oxo-1,3-oxazinan-6-yl)ethyl 4-nitrophenyl carbonate (70 mg, crude), which was used for the next step without purification.

Step 2

Methylamine (15 mg, 0.22 mmol) and TEA (2 mL) was added to a solution of 2-((S)-3-((S)-1-(2',4'-difluorobiphenyl-4-yl)ethyl)-6-(4-fluorophenyl)-2-oxo-1,3-oxazinan-6-yl) ethyl 4-nitrophenyl carbonate (70 mg, crude) in 8 mL of THF. The mixture was stirred at rt overnight. The reaction was quenched with saturated NH$_4$Cl. The mixture was extracted with EtOAc for 3 times, washed with brine, dried over anhydrous Na$_2$SO$_4$ and concentrated to give the residue, which was purified by preparative HPLC to give 2-((S)-3-((S)-1-(2', 4'-difluorobiphenyl-4-yl)ethyl)-6-(4-fluorophenyl)-2-oxo-1, 3-oxazinan-6-yl)ethyl methylcarbamate (5 mg, 9%). $^1$H NMR (CDCl$_3$): 1.55 (m, 3H), 2.36 (m, 5H), 2.74 (m, 3H), 2.99 (m, 1H), 4.09 (m, 2H), 5.71 (m, 1H), 6.92 (m, 2H), 7.04 (m, 4H), 7.33 (m, 5H). LC-MS Method 3 $t_R$=1.32 min, m/z=513, 535.

Example 149

(6S)-6-(2-(aminosulfonylamino)ethyl)-3-((S)-1-(2', 4'-difluorobiphenyl-4-yl)ethyl)-6-(4-fluorophenyl)-1, 3-oxazinan-2-one

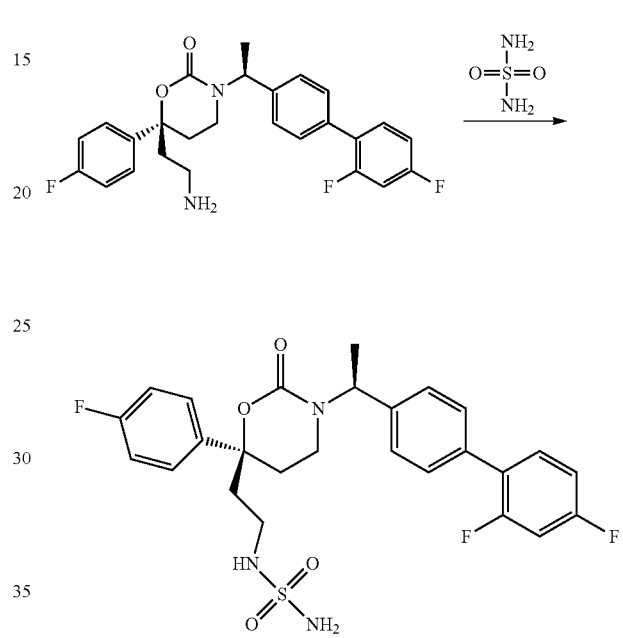

A mixture of (R)-6-(2-aminoethyl)-3-((S)-1-(2',4'-difluorobiphenyl-4-yl)ethyl)-6-(4-fluoro phenyl)-1,3-oxazinan-2-one (40 mg, 0.09 mmol) and sulfamide (44 mg, 0.45 mmol) in 1,4-dioxane (10 mL) was heated to reflux overnight. When the reaction was over, the solvent was removed to give the residue, which was purified by preparative HPLC to give the desired product (12 mg, 25%). $^1$H NMR (CDCl$_3$): 1.54 (m, 3H), 2.26 (m, 5H), 3.08 (m, 3H), 4.56 (s, 2H), 5.67 (m, 1H), 6.89 (m, 2H), 7.05 (m, 4H), 7.28 (m, 5H). LC-MS Method 3 $t_R$=1.24 min, m/z=534.

Example 150

2-((S)-3-((S)-1-(2',4'-difluorobiphenyl-4-yl)ethyl)-6-(4-fluorophenyl)-2-oxo-1,3-oxazinan-6-yl)ethyl sulfamate

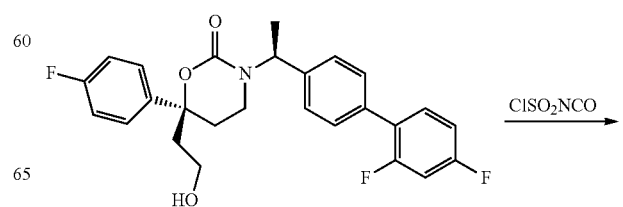

195

-continued

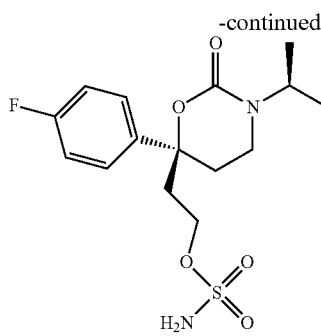

To a solution of chlorosulfonyl isocyanate (64 mg, 0.45 mmol) in MeCN (2 mL) was added dropwise a solution of formic acid (20 mg, 0.45 mmol) in MeCN (1 mL) at 0° C. After stirring at rt for 3 h, the reaction mixture was cooled to 0° C. A solution of (S)-3-((S)-1-(2',4'-difluorobiphenyl-4-yl)ethyl)-6-(4-fluorophenyl)-6-(2-hydroxy ethyl)-1,3-oxazinan-2-one (40 mg, 0.09 mmol) and DIEA (58 mg, 0.45 mmol) in MeCN (1 mL) was added, and the mixture was stirred at rt overnight. The mixture was concentrated, and the residue was dissolved in EtOAc (50 mL). The mixture was washed with water, 2 N aq HCl and brine, dried over anhydrous sodium sulfate and concentrated to give the residue, which was purified by preparative HPLC to give 2-((S)-3-((S)-1-(2',4'-difluorobiphenyl-4-yl)ethyl)-6-(4-fluorophenyl)-2-oxo-1,3-oxazinan-6-yl)ethylsulfamate (6 mg, 12%). $^1$H NMR (CDCl$_3$): 1.49 (m, 3H), 2.35 (m, 5H), 2.92 (m, 1H), 4.02 (m, 1H), 4.29 (m, 1H), 5.16 (s, 2H), 5.61 (m, 1H), 6.82 (m, 2H), 7.01 (m, 4H), 7.22 (m, 5H). LC-MS Method 3 $t_R$=1.28 min, 535, 557.

Example 151

2-((S)-3-((S)-1-(2',4'-difluorobiphenyl-4-yl)ethyl)-6-(4-fluorophenyl)-2-oxo-1,3-oxazinan-6-yl)ethyl dihydrogen phosphate

196

-continued

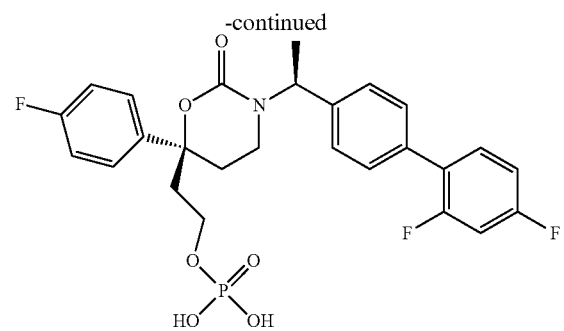

To a solution of (S)-3-((S)-1-(2',4'-difluorobiphenyl-4-yl)ethyl)-6-(4-fluorophenyl)-6-2-hydroxyethyl)-1,3-oxazinan-2-one (500 mg, 1.1 mmol) and Et$_3$N (222 mg, 2.2 mmol) in THF (20 mL) was added POCl$_3$ (340 mg, 2.2 mmol) in THF at 0° C. The mixture was quenched with NaHCO$_3$ and treated with 1 N HCl. The organic phase was separated, and concentrated to give the crude product, which was purified by preparative HPLC to give 2-((S)-3-((S)-1-(2',4'-difluorobiphenyl-4-yl)ethyl)-6-(4-fluorophenyl)-2-oxo-1,3-oxazinan-6-yl)ethyl dihydrogen phosphate (120 mg, 20%). $^1$H NMR: (400 MHz, CD$_3$OD): δ=1.55 (d, 3H), 2.30 (m, 4H), 2.55 (m, 1H), 3.10 (m, 1H), 3.75 (m, 1H), 4.10 (m, 1H), 5.50 (m, 1H), 7.00 (m, 4H), 7.10 (m, 2H), 7.25 (m, 2H), 7.35 (m, 2H), 7.40 (m, 1H).

Example 152

2-amino-N-(2-((R)-3-((S)-1-(2',4'-difluorobiphenyl-4-yl)ethyl)-6-(4-fluorophenyl)-2-oxo-1,3-oxazinan-6-yl)ethyl)acetamide

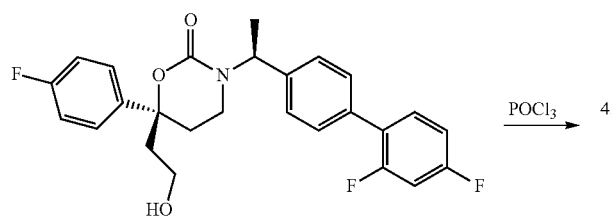

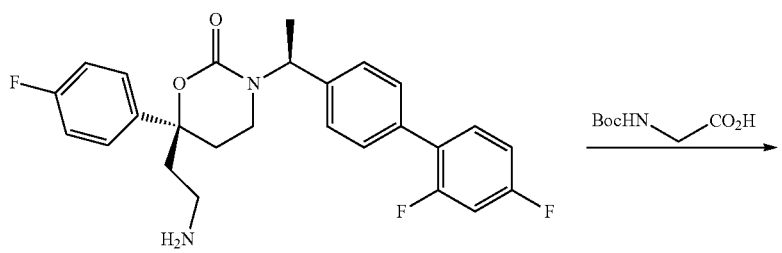

-continued

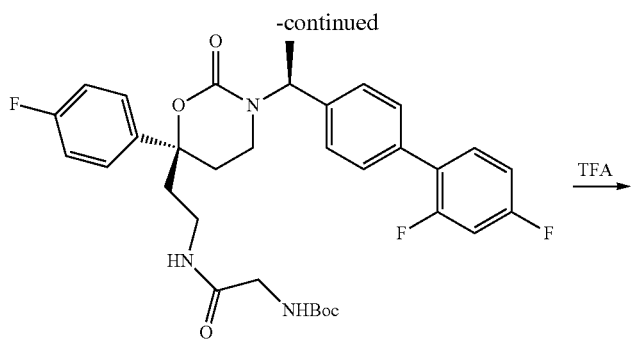

TFA →

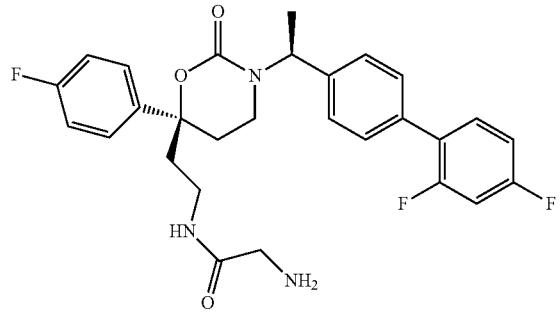

Step 1

A solution of (R)-6-(2-aminoethyl)-3-((S)-1-(2',4'-difluorobiphenyl-4-yl)ethyl)-6-(4-fluorophenyl)-1,3-oxazinan-2-one (100 mg, 0.22 mmol), 2-(tert-butoxy-carbonyl-amino)acetic acid (58 mg, 0.33 mmol), HOBt (60 mg, 0.44 mmol), EDC (87 mg, 0.44 mmol) and i-Pr$_2$NEt (142 mg, 1.1 mmol) in CH$_2$Cl$_2$ (5 mL) was stirred at rt overnight. After the solvents were evaporated, the crude product was purified by preparative TLC to give tert-butyl 2-(2-((R)-3-((S)-1-(2',4'-difluorobiphenyl-4-yl)ethyl)-6-(4-fluorophenyl)-2-oxo-1,3-oxazinan-6-yl)ethylamino)-2-oxoethylcarbamate (98 mg, 74%).

Step 2

A solution of tert-butyl 2-(2-((R)-3-((S)-1-(2',4'-difluorobiphenyl-4-yl)ethyl)-6-(4-fluorophenyl)-2-oxo-1,3-oxazinan-6-yl)ethylamino)-2-oxoethylcarbamate (98 mg, 0.16 mmol) in TFA/CH$_2$Cl$_2$ (20%, 5 mL) was stirred at 0° C. for 2 h. The solvent was evaporated to give the crude product, which was purified by preparative HPLC to afford 2-amino-N-(2-((R)-3-((S)-1-(2',4'-difluorobiphenyl-4-yl)ethyl)-6-(4-fluorophenyl)-2-oxo-1,3-oxazinan-6-yl)ethyl)acetamide (50 mg, 60%). $^1$H NMR (CDCl$_3$): 1.41-1.49 (d, 3H), 2.15-2.29 (m, 5H), 2.80-2.94 (m, 2H), 3.25-3.36 (m, 1H), 3.70-3.85 (m, 2H), 5.50 (m, 1H), 6.75-6.97 (m, 7H), 7.00-7.14 (m, 3H), 7.26-7.29 (m, 1H).

Example 153

4-((S)-1-((R)-6-allyl-6-(4-fluorophenyl)-2-oxo-1,3-oxazinan-3-yl)ethyl)benzamide

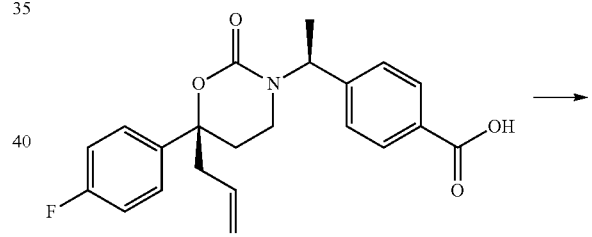

→

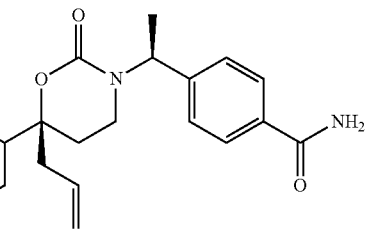

4-((S)-1-((R)-6-allyl-6-(4-fluorophenyl)-2-oxo-1,3-oxazinan-3-yl)ethyl)benzoic acid (12 mg, 0.03 mmol), ammonia in methanol (c.a. 7N, 1 mL, excess), HATU (12 mg, 1.1 equiv.), and DIEPA (11 µL, 2 equiv.) were mixed in 4:1 CH$_2$Cl$_2$ and DMF (2 mL). The mixture was stirred overnight at rt, diluted with EtOAc (5 mL), washed with 5% aq HCl (2×2 mL). The organic layer was concentrated and purified by prep HPLC to afford 4-((S)-1-((R)-6-allyl-6-(4-fluorophenyl)-2-oxo-1,3-oxazinan-3-yl)ethyl)benzamide (2 mg, 17.5%) product. LC-MS Method 1 t$_R$=1.4 min, m/z=383

(M+1); ¹H NMR (CDCl₃) 7.55 (d, 2H), 7.25 (t, 2H), 7.03 (t, 2H), 6.94 (d, 2H), 6.03 (br d, 2H), 5.68 (m, 2H), 5.05 (dd, 2H), 2.95 (m, 1H), 1.54 (d, 3H).

Example 154

(R)-6-(4-fluorophenyl)-3-((S)-1-(4-(hydroxymethyl)phenyl)ethyl)-6-(3-hydroxypropyl)-1,3-oxazinan-2-one

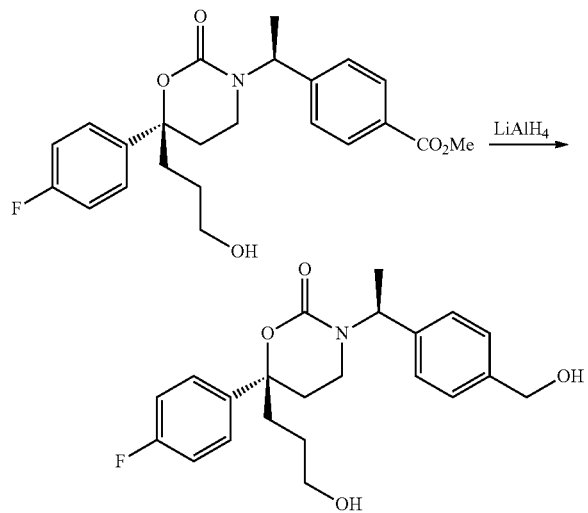

Methyl 4-((S)-1-((R)-6-(4-fluorophenyl)-6-(3-hydroxypropyl)-2-oxo-1,3-oxazinan-3-yl)ethyl)benzoate (10 mg, 0.024 mmol) was dissolved in dry THF (4 mL) and cooled to 0° C. LiAlH₄ (2 mg, excess) was added slowly. After 10 min, the mixture was warmed to rt and stirred for 2 h. LC-MS found reaction completed. The mixture was quenched with water, diluted with EtOAc (5 mL), washed with 1% aq HCl (2 mL). After concentration, the residue was purified by prep HPLC to afford (R)-6-(4-fluorophenyl)-3-((S)-1-(4-(hydroxymethyl)phenyl)ethyl)-6-(3-hydroxypropyl)-1,3-oxazinan-2-one (3.0 mg, 32%). LC-MS Method 1 $t_R$=1.2 min, m/z=410 (M+Na); ¹H NMR (CDCl₃) 7.23 (m, 2H), 7.14 (d, 2H), 7.03 (q, 2H), 6.95 (t, 2H), 5.66 (m, 1H), 4.61 (s, 2H), 3.59 (t, 2H), 1.53 (d, 3H).

Example 155

4-((S)-1-((R)-6-allyl-6-(4-fluorophenyl)-2-oxo-1,3-oxazinan-3-yl)ethyl)-N-methylbenzamide

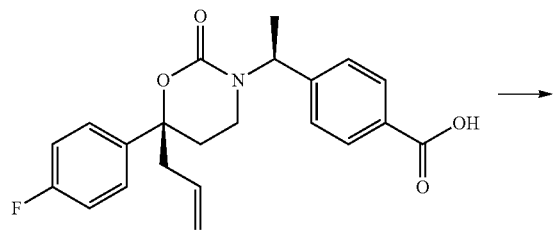

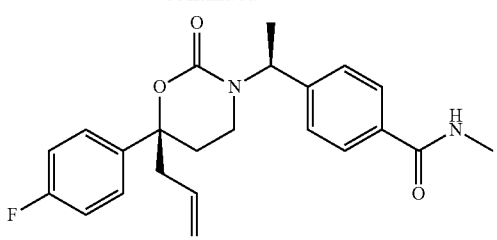

The title compound was prepared following a procedure analogous to that described in Example 153, using methylamine in place of ammonia. LC-MS Method 1 $t_R$=1.47 min, m/z=397 (M+1); ¹H NMR (CDCl₃) 7.49 (d, 2H), 7.24 (dd, 2H), 7.04 (t, 2H), 6.92 (d, 2H), 6.29 (br s, 1H), 5.65 (m, 2H), 5.06 (dd, 2H), 3.03 (s, 3H), 2.59 (m, 2H), 1.53 (d, 3H).

Example 156

(R)-6-allyl-6-(4-fluorophenyl)-3-((S)-1-(4-(2-hydroxypropan-2-yl)phenyl)ethyl)-1,3-oxazinan-2-one

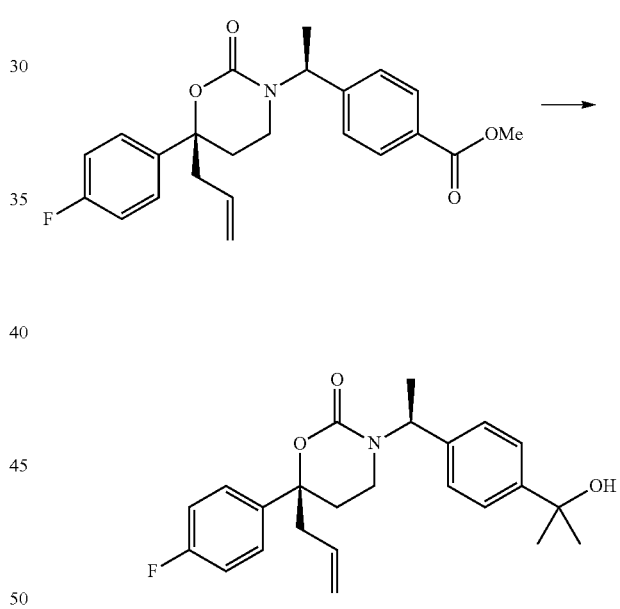

Methyl 4-((S)-1-((R)-6-allyl-6-(4-fluorophenyl)-2-oxo-1,3-oxazinan-3-yl)ethyl)benzoate (34.5 mg, 0.087 mmol) and CuI (2 mg, cat. amount) were mixed with dry THF (3 mL). The mixture was degassed and refilled with N₂ gas for 3 times. The mixture was then cooled to −78° C. A solution of methyl lithium (1.0M in diethyl ether, 500 μL, excess) was added slowly. After 15 min, the mixture was warmed up to rt slowly and stirred overnight at rt. The mixture was quenched with satd aq NH₄Cl (5 mL), diluted with EtOAc (8 mL), washed with 1% aq HCl (3 mL), brine (2 mL), and dried over Na₂SO₄. After filtration and concentration, the residue was purified by prep HPLC to afford (R)-6-allyl-6-(4-fluorophenyl)-3-((S)-1-(4-(2-hydroxypropan-2-yl)phenyl)ethyl)-1,3-oxazinan-2-one (7.1 mg, 21% yield). LC-MS Method 1 $t_R$=1.65 min, m/z=398 (M+1); ¹H NMR (CDCl₃) 7.24-7.18 (m, 4H), 7.00

(q, 2H), 6.83 (dd, 2H), 5.63 (m, 2H), 5.03 (dd, 2H), 2.92 (m, 1H), 2.57 (m, 2H), 1.50 (d, 9H).

Example 157

6-allyl-3-((S)-1-(4-bromophenyl)ethyl)-6-(thiophen-2-yl)-1,3-oxazinan-2-one

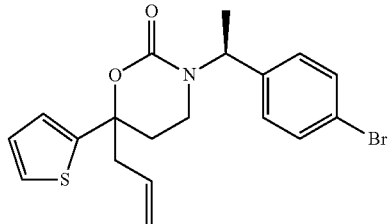 [SMILES: C=CCC1(c2cccs2)CCN([C@@H](C)c2ccc(Br)cc2)C(=O)O1]

The title compound was prepared following a procedure analogous to that described in Example 95 using 3-chloro-1-(thiophen-2-yl)propan-1-one in place of 3-chloro-1-(4-fluorophenyl)propan-1-one. The diastereomers were separated by chromatography on silica gel.

Isomer 1: (R)-6-allyl-3-((S)-1-(4-bromophenyl)ethyl)-6-(thiophen-2-yl)-1,3-oxazinan-2-one (10 g, 32.6%). $^1$H NMR (CD$_3$OD): 1.52 (t, 3H), 2.25 (m, 1H), 240 (m, 1H), 2.58 (m, 1H), 2.68 (t, 2H), 3.14 (m, 1H), 5.19 (t, 2H), 5.48 (m, 1H), 5.70 (m, 1H), 6.86 (d, 3H), 6.98 (t, 1H), 7.28 (d, 2H), 741 (d, 1H). LC-MS Method 3 $t_R$=1.33 min, m/z=406, 408.

Isomer 2: (S)-6-Allyl-3-((S)-1-(4-bromophenyl)ethyl)-6-(thiophen-2-yl)-1,3-oxazinan-2-one (10 g, 32.6%). $^1$H NMR (CD$_3$OD): 1.38 (t, 3H), 2.10 (m, 1H), 2.38 (m, 1H), 2.68 (m, 2H), 2.75 (m, 1H), 3.04 (m, 1H), 5.19 (t, 2H), 5.50 (m, 1H), 5.70 (m, 1H), 6.96 (d, 1H), 7.08 (t, 1H), 7.22 (d, 2H), 738 (d, 1H), 7.48 (d, 2H). LC-MS Method 3 $t_R$=1.35 min, m/z=406, 408.

Example 158

6-allyl-6-(4-fluorophenyl)-3-((1-phenylpiperidin-4-yl)methyl)-1,3-oxazinan-2-one

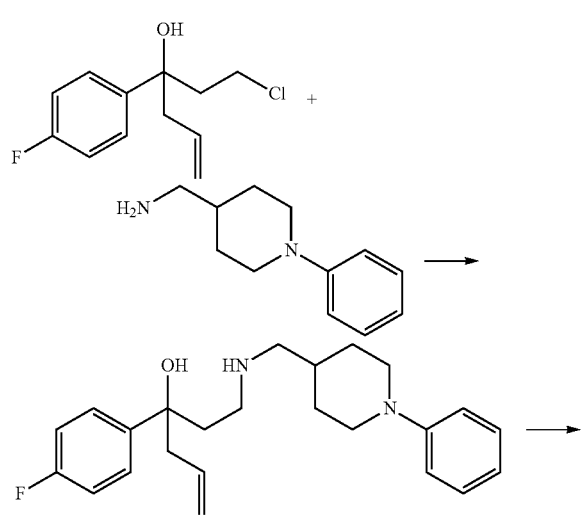

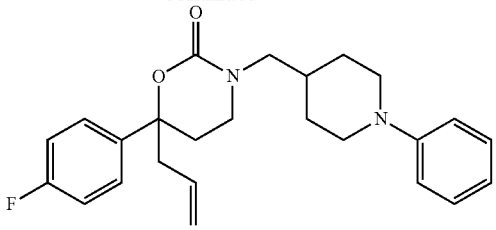

Step 1

1-Chloro-3-(4-fluorophenyl)hex-5-en-3-ol (223 mg, 0.97 mmol), (1-phenylpiperidin-4-yl)methanamine (295 mg, 1.6 equiv.), potassium iodide (178 mg, 1.1 equiv.) and DIEPA (186 μL, 1.1 equiv.) were mixed with DMF (5 mL) and heated at 80° C. for overnight. The mixture was diluted with EtOAc (50 mL), washed by water (2×15 mL), brine (2×10 mL), and dried over Na$_2$SO$_4$. After filtration and concentration, the residue was purified by chromatography on a 12-g silica gel cartridge eluted with a 0~20% methanol in CH$_2$Cl$_2$ gradient to afford 3-(4-fluorophenyl)-1-((1-phenylpiperidin-4-yl)methylamino)hex-5-en-3-ol (245 mg. 66%).

Step 2

3-(4-fluorophenyl)-1-((1-phenylpiperidin-4-yl)methylamino)hex-5-en-3-ol (120 mg, 0.314 mmol) was dissolved in THF (30 mL) and pyridine (c.a. 500 μL, excess). A solution of triphosgene (60 mg, excess) in THF (5 mL) was added slowly in 4 batches. After stirring 4 h at rt, DBU (94 μL, 2 equiv.) was added and the mixture was heated to reflux for overnight. There was still a lot of starting material on LC-MS spectra. The mixture was concentrated, redissolved in EtOAc (40 mL), washed with 5% aq HCl (2×8 mL), brine (8 mL), and dried over Na$_2$SO$_4$. After filtration and concentration, the residue was purified by prep HPLC to afford 6-allyl-6-(4-fluorophenyl)-3-((1-phenylpiperidin-4-yl)methyl)-1,3-oxazinan-2-one (17 mg, 13%). LC-MS Method 1 $t_R$=1.32 min, m/z=409 (M+1); $^1$H NMR (CD$_3$OD) 7.62-7.53 (m, 4H), 7.39 (m, 2H), 7.13 (t, 2H), 5.67 (m, 1H), 5.04 (dd, 2H), 3.05 (m, 2H), 2.63 (d, 2H), 2.57 (d, 1H), 2.32 (m, 1H), 2.06 (m, 1H).

Example 159

(S)-3-((S)-1-(4'-fluorobiphenyl-4-yl)ethyl)-6-(2-hydroxyethyl)-6-phenyl-1,3-oxazinan-2-one

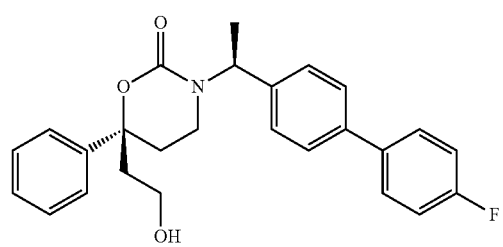 [SMILES: C[C@@H](c1ccc(-c2ccc(F)cc2)cc1)N1CC[C@](CCO)(c2ccccc2)OC1=O]

The title compound was prepared following a procedure analogous to that described in Example 74. $^1$H NMR (CDCl$_3$): 1.53 (m, 3H), 2.29 (m, 5H), 2.91 (m, 1H), 3.56 (m, 1H), 3.75 (m, 1H), 6.56 (m, 1H), 6.93 (m, 2H), 7.06 (m, 2H), 7.35 (m, 7H), 7.43 (m, 2H). LC-MS Method 3 $t_R$=1.23 min, m/z=420, 442.

Example 160

6-allyl-3-((S)-1-(4'-fluorobiphenyl-4-yl)ethyl)-6-(thiophen-2-yl)-1,3-oxazinan-2-one

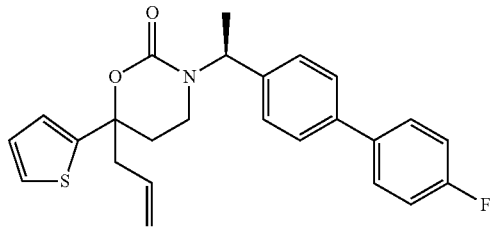 [SMILES: C=CCC1(c2cccs2)CCN([C@@H](C)c2ccc(-c3ccc(F)cc3)cc2)C(=O)O1]

The two diastereomers of the title compound were prepared separately from the diastereomers of 6-allyl-3-((S)-1-(4-bromophenyl)ethyl)-6-(thiophen-2-yl)-1,3-oxazinan-2-one following a procedure analogous to that described in Example 111 using 4-fluorophenylboronic acid. The diastereomers were separated.

Isomer 1: $^1$H NMR (CD$_3$OD): 1.38 (t, 3H), 2.10 (m, 1H), 238 (m, 1H), 2.68 (m, 2H), 2.85 (m, 1H), 3.04 (m, 1H), 5.09 (t, 2H), 5.55-5.80 (m, 2H), 6.98 (d, 2H), 7.15 (t, 2H), 7.22-7.42 (m, 4H), 758 (m, 3H).

Isomer 2: $^1$H NMR (CD$_3$OD): 1.52-1.60 (d, 3H), 2.20-2.26 (m, 2H), 2.58-2.62 (m, 3H), 2.95-3.04 (m, 1H), 5.05-5.47 (m, 2H), 5.68-5.80 (m, 2H), 6.90 (m, 1H), 6.94 (m, 1H), 7.00-7.05 (m, 2H), 7.05-7.14 (m, 2H), 7.23 (m, 1H), 7.29-7.34 (m, 2H), 7.42-7.54 (m, 2H).

Example 161

6-allyl-3-((S)-1-(4-bromophenyl)ethyl)-6-(4-fluorophenyl)-4-methyl-1,3-oxazinan-2-one

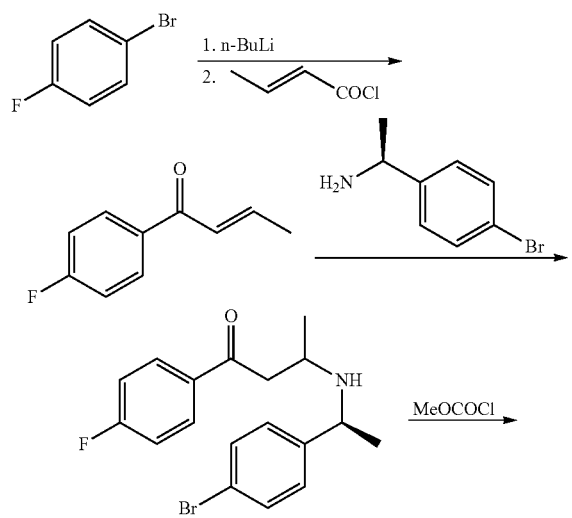

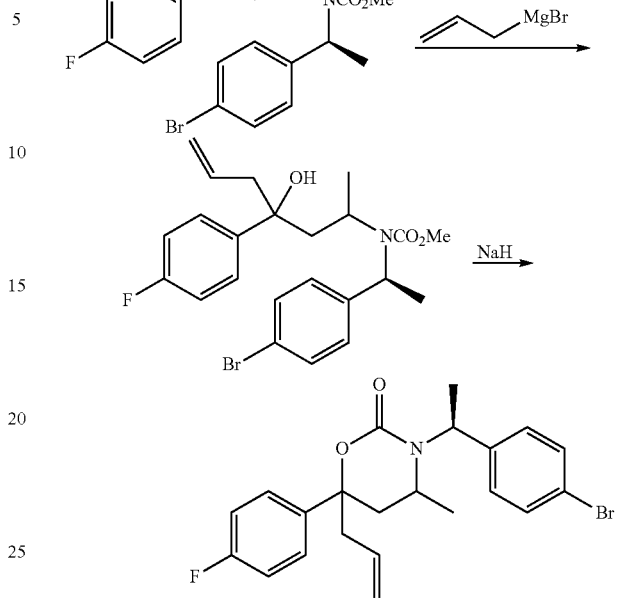

Step 1

To a solution of 1-bromo-4-fluorobenzene (28 g, 0.162 mol) in THF (90 mL) was added n-BuLi (70 mL, 2.5 M) at −78° C. and stirred for 1 h under nitrogen. Then to a premixed solution of CuCl (18 g, 0.16 mol) and LiCl (15 g, 0.354 mol) in THF (160 mL) at −78° C. was added the above solution quickly. The formed solution was stirred for 20 minutes, and was treated with crotonyl chloride (21 g, 0.176 mol). The resulting solution was stirred for 30 minutes. The mixture was quenched with aq NH$_4$Cl, the organic phase was separated, concentrated to give the crude product which was purified by column chromatography to afford 1-(4-fluorophenyl)but-2-en-1-one (2.6 g, 10%). $^1$H NMR (400 MHz, CDCl$_3$): δ=2.02 (d, 3H), 6.88 (m, 1H), 7.10 (m, 3H), 7.98 (m, 2H).

Step 2

A solution of 1-(4-fluorophenyl)but-2-en-1-one (13 g, 79.2 mmol) in EtOH (150 mL) was added (S)-1-(4-bromophenyl)ethanamine (32 g, 158 mmol), and the resulting mixture was stirred overnight. The solvent was removed in vacuo to give the crude 3-((S)-1-(4-bromophenyl)ethylamino)-1-(4-fluorophenyl)butan-1-one which was used for the next step without purification.

Step 3

A solution of 3-((S)-1-(4-bromophenyl)ethylamino)-1-(4-fluorophenyl)butan-1-one (28.8 g, 79.2 mmol) and K$_2$CO$_3$ (100 g, 0.79 mol) in methylene chloride (1000 mL) was added methyl carbonochloridate (100 g, 0.72 mol) at 0° C. The formed mixture was stirred at rt overnight. The mixture was filtered and concentrated to give the crude product, which was purified by preparative HPLC to give methyl (S)-1-(4-bromophenyl)ethyl(4-(4-fluorophenyl)-4-oxobutan-2-yl)carbamate (7.5 g, 23%). $^1$H NMR (400 MHz, CDCl$_3$): δ=1.28 (d, 3H), 1.52 (d, 3H), 2.59 (m, 1H), 3.72 (m, 5H), 5.43 (m, 1H), 6.98 (m, 3H), 7.16 (m, 2H), 7.31 (m, 2H), 7.60 (m, 2H).

Step 4

To a solution of methyl (S)-1-(4-bromophenyl)ethyl((S)-4-(4-fluorophenyl)-4-oxobutan-yl)carbamate (0.5 g, 1.18 mmol) in THF (10 mL) was added allylmagnesium bromide (3 mL, 1 M) under nitrogen at −78° C. The mixture was stirred overnight at rt. The mixture was quenched by water and extracted with EtOAc, the combined organic phase was concentrated to give the crude methyl (S)-1-(4-bromophenyl)ethyl(4-(4-fluorophenyl)-4-hydroxyhept-6-en-2-yl)carbamate, which was used for the next step without purification.

Step 5

To a solution of methyl (S)-1-(4-bromophenyl)ethyl(4-(4-fluorophenyl)-4-hydroxyhept-6-en-2-yl)carbamate (20 mg, 0.043 mmol) was added NaH at 0° C. The mixture was stirred and heated to reflux for 1 h. The mixture was cooled to rt and quenched with water. The organic phase was extracted by EtOAc and concentrated to give the crude product which was purified by preparative TLC to give three isomers of 6-allyl-3-((S)-1-(4-bromophenyl)ethyl)-6-(4-fluorophenyl)-4-methyl-1,3-oxazinan-2-one.

Isomer 1: $^1$H NMR (400 MHz, CDCl$_3$): δ=0.78 (d, 3H), 1.56 (d, 3H), 2.04 (m, 1H), 2.13 (m, 1H), 2.50 (m, 2H), 3.25 (m, 1H), 4.94 (m, 1H), 5.03 (m, 1H), 5.38 (m, 1H), 5.60 (m, 1H), 6.96 (m, 2H), 7.18 (m, 2H), 7.30 (m, 2H), 7.43 (m, 2H).

Isomer 2: $^1$H NMR (400 MHz, CDCl$_3$): δ=1.02 (d, 3H), 1.43 (d, 3H), 2.00 (m, 1H), 2.50 (m, 3H), 3.32 (m, 1H), 4.76 (m, 1H), 4.95-5.08 (m, 2H), 5.68 (m, 1H), 6.88 (m, 1H), 7.00 (m, 2H), 7.18 (m, 2H), 7.28 (m, 2H).

Isomer 3: $^1$H NMR (400 MHz, CDCl$_3$): δ=0.52 (d, 3H), 1.62 (d, 3H), 2.08 (m, 1H), 2.36 (m, 1H), 2.52 (d, 2H), 3.65 (m, 1H), 4.90 (m, 1H), 5.00 (m, 1H), 5.29 (m, 1H), 5.53 (m, 1H), 6.96 (m, 2H), 7.20 (m, 2H), 7.30 (m, 2H), 7.35 (m, 2H).

Example 162

(R)-3-((S)-1-(4'-fluorobiphenyl-4-yl)ethyl)-6-(3-hydroxypropyl)-6-phenyl-1,3-oxazinan-2-one

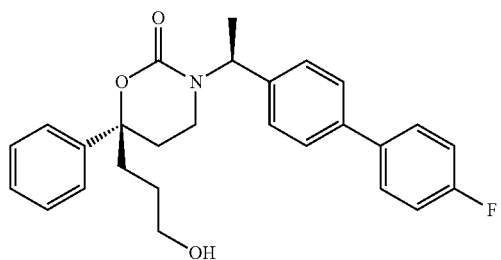 [SMILES: C[C@@H](c1ccc(-c2ccc(F)cc2)cc1)N1CC[C@](CCCO)(c2ccccc2)OC1=O]

The title compound was prepared following a procedure analogous to that described in Example 78 starting with (R)-6-allyl-3-((S)-1-(4'-fluorobiphenyl-4-yl)ethyl)-6-phenyl-1,3-oxazinan-2-one. $^1$H NMR (CDCl$_3$): δ=1.34 (m, 1H), 1.48 (m, 3H), 1.63 (m, 1H), 1.91 (m, 2H), 2.12 (m, 1H), 2.22 (m, 2H), 2.83 (m, 1H), 3.50 (m, 2H), 5.61 (m, 1H), 6.87 (m, 2H), 7.02 (m, 2H), 7.25 (m, 5H), 7.29 (m, 2H), 7.37 (m, 2H). LC-MS Method 3 tR=1.28 min, m/z=434, 456.

Example 163

3-((S)-1-(4-bromophenyl)ethyl)-6-(4-fluorophenyl)-6-(2-hydroxyethyl)-4-methyl-1,3-oxazinan-2-one

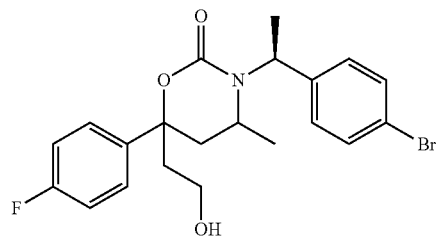 [SMILES: CC1CC(CCO)(c2ccc(F)cc2)OC(=O)N1[C@@H](C)c1ccc(Br)cc1]

Isomer 1 of the title compound was prepared from 6-allyl-3-((S)-1-(4-bromophenyl)ethyl)-6-(4-fluorophenyl)-4-methyl-1,3-oxazinan-2-one isomer 1 following a procedure analogous to that described in Example 74. $^1$H NMR (400 MHz, DCCl$_3$): δ=0.78 (d, 3H), 1.59 (d, 3H), 2.00-2.06 (m, 4H), 3.30 (m, 1H), 3.40 (m, 1H), 3.61 (m, 1H), 5.40 (m, 1H), 7.00 (m, 2H), 7.18 (m, 2H), 7.28 (m, 2H), 7.42 (m, 2H).

Isomer 2 of the title compound was prepared from 6-allyl-3-((S)-1-(4-bromophenyl)ethyl)-6-(4-fluorophenyl)-4-methyl-1,3-oxazinan-2-one isomer 2 following a procedure analogous to that described in Example 74.

Isomer 3 of the title compound was prepared from 6-allyl-3-((S)-1-(4-bromophenyl)ethyl)-6-(4-fluorophenyl)-4-methyl-1,3-oxazinan-2-one isomer 3 following a procedure analogous to that described in Example 74.

Example 164

(S)-3-((S)-1-(2',4'-difluorobiphenyl-4-yl)ethyl)-6-(2-hydroxyethyl)-6-phenyl-1,3-oxazinan-2-one

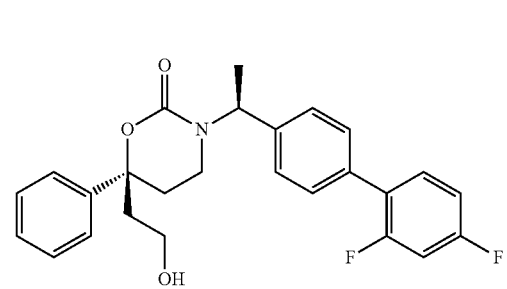 [SMILES: C[C@@H](c1ccc(-c2ccc(F)cc2F)cc1)N1CC[C@](CCO)(c2ccccc2)OC1=O]

The title compound was prepared following a procedure analogous to that described in Example 74. $^1$H NMR (CDCl$_3$): 1.49 (m, 3H), 2.14-2.32 (m, 2H), 2.28 (m, 3H), 2.89 (m, 1H), 3.50 (m, 0.6H), 3.70 (m, 0.6H), 4.18 (m, 0.4H), 4.44

(m, 0.4H), 5.61 (m, 1H), 6.76-6.89 (m, 4H), 7.18 (m, 2H), 7.20-7.30 (m, 6H). LC-MS Method 3 $t_R$=1.25 min, m/z=438, 460.

Example 165

(S)-6-allyl-3-((S)-1-(2',4'-difluorobiphenyl-4-yl)ethyl)-6-(thiophen-2-yl)-1,3-oxazinan-2-one

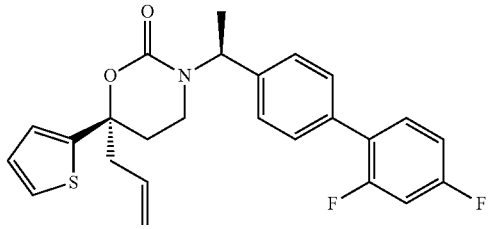 [SMILES: C=CC[C@@]1(c2cccs2)CCN([C@@H](C)c2ccc(-c3ccc(F)cc3F)cc2)C(=O)O1]

The title compound was prepared following a procedure analogous to that described in Example 111. $^1$H NMR (CD$_3$OD): 1.42 (t, 3H), 2.16 (m, 1H), 238 (m, 1H), 2.68 (m, 2H), 2.80 (m, 1H), 3.04 (m, 1H), 5.09 (t, 2H), 5.58-5.70 (m, 2H), 6.98 (d, 2H), 7.15 (t, 2H), 7.30 (m, 1H), 7.42 (m, 3H), 748 (m, 3H). LC-MS Method 4 tR=1.1 min, m/z=440, 462.

Example 166

(S)-3-((S)-1-(4'-fluorobiphenyl-4-yl)ethyl)-6-(3-hydroxypropyl)-6-(thiophen-2-yl)-1,3-oxazinan-2-one

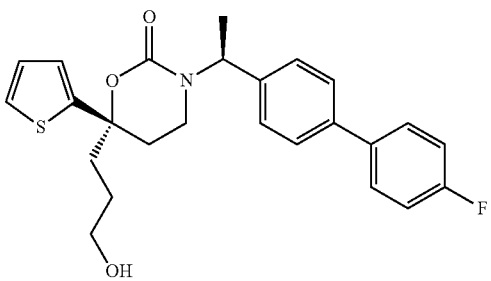 [SMILES: C[C@@H](c1ccc(-c2ccc(F)cc2)cc1)N1CC[C@@](CCCO)(c2cccs2)OC1=O]

The title compound was prepared following a procedure analogous to that described in Example 78 starting with (S)-6-allyl-3-((S)-1-(4'-fluorobiphenyl-4-yl)ethyl)-6-(thiophen-2-yl)-1,3-oxazinan-2-one. $^1$H NMR (CDCl$_3$): 1.32 (m, 3H), 1.45 (m, 1H), 1.73 (m, 2H), 1.89-2.18 (m, 4H), 2.72 (m, 1H), 2.86 (m, 1H), 3.52 (m, 2H), 5.75 (m, 1H), 6.90 (m, 2H), 7.15 (m, 2H), 7.25 (m, 4H), 748 (m, 3H).

Example 167

(6R)-3-((S)-1-(4'-fluorobiphenyl-4-yl)ethyl)-6-(2-hydroxypropyl)-6-(thiophen-2-yl)-1,3-oxazinan-2-one

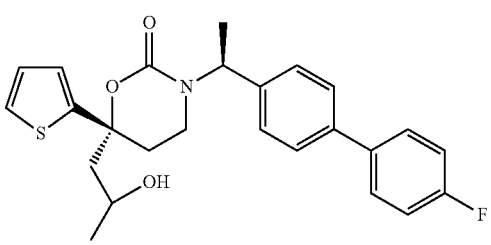 [SMILES: CC(O)C[C@@]1(c2cccs2)CCN([C@@H](C)c2ccc(-c3ccc(F)cc3)cc2)C(=O)O1]

The title compound was isolated as a byproduct following a procedure analogous to that described in Example 78 starting with (S)-6-allyl-3-((S)-1-(4'-fluorobiphenyl-4-yl)ethyl)-6-(thiophen-2-yl)-1,3-oxazinan-2-one. The alcohol epimers were separated by preparative TLC.

Isomer 1: $^1$H NMR (CDCl$_3$): 1.18 (m, 3H), 1.30 (m, 3H), 1.90-2.18 (m, 3H), 2.28 (m, 1H), 2.63-2.96 (m, 2H), 4.04 (m, 1H), 4.56 (m, 1H), 5.72 (m, 1H), 6.90 (m, 2H), 7.05 (m, 2H), 7.25 (m, 4H), 748 (m, 3H).

Isomer 2: $^1$H NMR (CDCl$_3$): 1.14 (m, 3H), 1.34 (m, 3H), 1.96 (m, 1H), 2.05-2.20 (m, 3H), 2.68-2.96 (m, 2H), 3.86-4.02 (m, 1H), 4.60 (s, 1H), 5.74 (m, 1H), 6.90 (m, 2H), 7.05 (m, 2H), 7.25 (m, 3H), 748 (m, 4H).

Example 168

(6S)-6-(2,3-dihydroxypropyl)-3-((S)-1-(4'-fluorobiphenyl-4-yl)ethyl)-6-phenyl-1,3-oxazinan-2-one

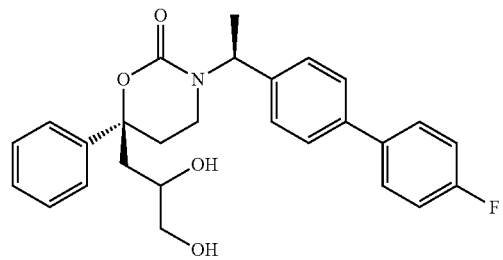 [SMILES: C[C@@H](c1ccc(-c2ccc(F)cc2)cc1)N1CC[C@](CC(O)CO)(c2ccccc2)OC1=O]

The title compound was prepared following a procedure analogous to that described in Example 52 starting with (S)-6-allyl-3-((S)-1-(4'-fluorobiphenyl-4-yl)ethyl)-6-(thiophen-2-yl)-1,3-oxazinan-2-one. The secondary alcohol epimers were separated.

Isomer 1: $^1$H NMR (CDCl$_3$): 1.48 (m, 3H), 1.95 (m, 1H), 2.09 (m, 1H), 2.35 (m, 5H), 2.87 (m, 1H), 3.41 (m, 1H), 3.52 (m, 1H), 3.73 (m, 1H), 5.61 (m, 1H), 6.84 (m, 2H), 7.03 (m, 2H), 7.19 (m, 3H), 7.29 (m, 5H), 7.37 (m, 2H).

Isomer 2: $^1$H NMR (CDCl$_3$): 1.49 (m, 3H), 1.89 (m, 1H), 2.08 (m, 1H), 2.25 (m, 3H), 2.82 (m, 1H), 3.27 (m, 1H), 3.38 (m, 1H), 3.77 (m, 1H), 5.61 (m, 1H), 6.89 (m, 2H), 7.03 (m, 2H), 7.19 (m, 1H), 7.25 (m, 6H), 7.43 (m, 2H).

Example 169

(R)-3-((S)-1-(2',4'-difluorobiphenyl-4-yl)ethyl)-6-(3-hydroxypropyl)-6-phenyl-1,3-oxazinan-2-one

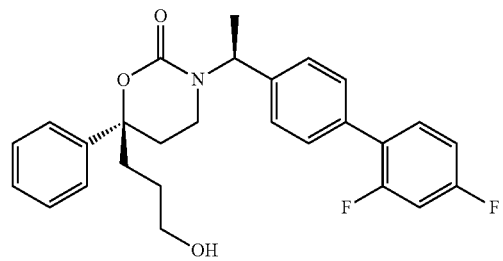 [SMILES: C[C@@H](c1ccc(-c2ccc(F)cc2F)cc1)N1CC[C@](CCCO)(c2ccccc2)OC1=O]

The title compound was prepared from (R)-6-allyl-3-((S)-1-(2',4'-difluorobiphenyl-4-yl)ethyl)-6-phenyl-1,3-oxazinan-2-one following a procedure analogous to that described in Example 78. $^1$H NMR (CDCl$_3$): 1.32 (m, 1H), 1.49 (m, 3H), 1.68 (m, 1H), 1.90 (m, 2H), 2.14 (m, 1H), 2.28 (m, 2H), 2.88 (m, 1H), 3.50 (m, 2H), 5.53 (m, 1H), 6.77-6.90 (m, 4H), 7.15 (m, 2H), 7.26 (m, 6H).

Example 170

(6S)-3-((S)-1-(2',4'-difluorobiphenyl-4-yl)ethyl)-6-(2-hydroxypropyl)-6-phenyl-1,3-oxazinan-2-one

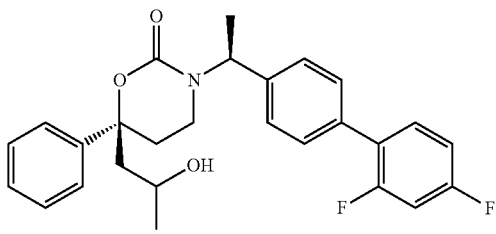 [SMILES: CC(O)C[C@]1(c2ccccc2)CCN([C@@H](C)c2ccc(-c3ccc(F)cc3F)cc2)C(=O)O1]

The title compound was isolated as a byproduct following a procedure analogous to that described in Example 78. $^1$H NMR (CDCl$_3$): 0.97-1.13 (m, 3H), 1.49 (m, 3H), 1.85-1.96 (m, 1H), 2.04 (m, 1H), 2.17-2.94 (m, 3H), 2.86 (m, 1H), 3.79-4.00 (m, 1H), 5.52 (m, 1H), 6.79-6.92 (m, 4H), 7.16 (m, 2H), 7.21-7.35 (m, 5H).

Example 171

3-((S)-1-(2',4'-difluorobiphenyl-4-yl)ethyl)-6-(3-hydroxypropyl)-6-(thiophen-2-yl)-1,3-oxazinan-2-one

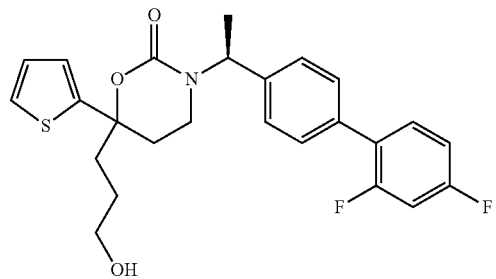 [SMILES: C[C@@H](c1ccc(-c2ccc(F)cc2F)cc1)N1CCC(CCCO)(c2cccs2)OC1=O]

Isomer 1: (R)-3-((S)-1-(2',4'-difluorobiphenyl-4-yl)ethyl)-6-(3-hydroxypropyl)-6-(thiophen-2-yl)-1,3-oxazinan-2-one was prepared following a procedure analogous to that described in Example 78. $^1$H NMR (CD$_3$OD): 1.40 (m, 1H), 1.50 (m, 3H), 1.65 (m, 1H), 2.00 (m, 2H), 2.35 (m, 1H), 2.40 (m, 1H), 2.60 (m, 1H), 3.15 (m, 1H), 3.50 (m, 2H), 5.60 (m, 1H), 6.90 (m, 1H), 7.00 (m, 3H), 7.10 (m, 2H), 7.40 (m, 4H). LC-MS Method 3 t$_R$=1.42 min, m/z=458, 480.

Isomer 2: (S)-3-((S)-1-(2',4'-difluorobiphenyl-4-yl)ethyl)-6-(3-hydroxypropyl)-6-(thiophen-2-yl)-1,3-oxazinan-2-one was prepared following a procedure analogous to that described in Example 78. $^1$H NMR (CDCl$_3$) 1.38 (m, 4H), 1.64 (m, 1H), 1.98 (m, 2H), 2.13 (m, 1H), 2.35 (m, 1H), 2.86 (m, 1H), 3.02 (m, 1H), 3.45 (m, 2H), 5.62 (m, 1H), 6.98 (m, 4H), 7.34 (m, 3H), 7.42 (m, 3H).

Example 172

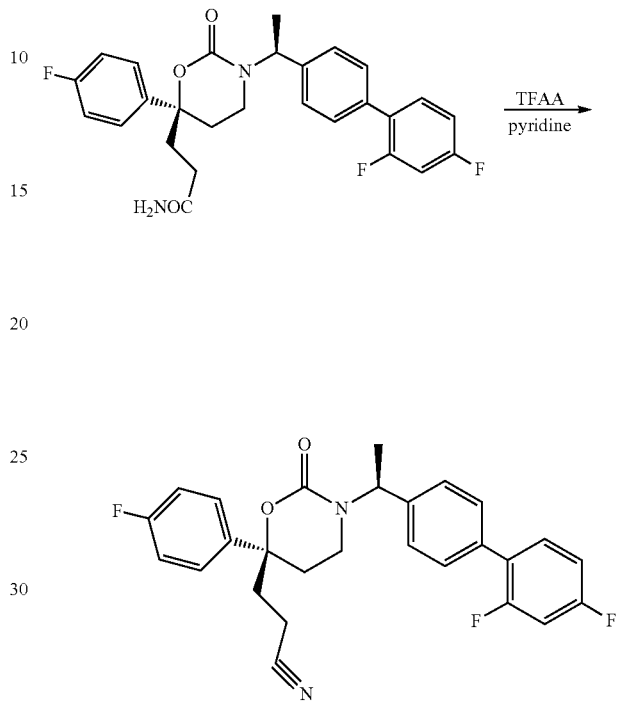

To a solution of 3-((R)-3-((S)-1-(2',4'-difluorobiphenyl-4-yl)ethyl)-6-(4-fluorophenyl)-2-oxo-1,3-oxazinan-6-yl) propanamide (80 mg, 0.166 mmol) in anhydrous CH$_2$Cl$_2$ (5 mL) and DIEA (0.5 mL) was added TFAA (72 mg, 0.332 mmol) at 0° C. The mixture was stirred for 2 h. The solvent was removed under reduced pressure, and the residue was purified by preparative HPLC to afford 3-((R)-3-((S)-1-(2',4'-difluorobiphenyl-4-yl)ethyl)-6-(4-fluorophenyl)-2-oxo-1,3-oxazinan-6-yl) propanenitrile (40 mg, yield 54%). $^1$H NMR (CDCl$_3$): 1.98-2.18 (m, 1H), 2.11-2.40 (m, 4H), 2.51-2.60 (m, 1H), 2.92 (m, 1H), 5.53 (m, 1H), 6.80-6.90 (m, 2H), 6.94 (m, 2H), 7.01 (m, 2H), 7.19 (m, 2H), 7.21 (m, 2H). LC-MS Method 3 t$_R$=1.22 min, m/z=488.

Example 173

(6S)-3-((S)-1-(2',4'-difluorobiphenyl-4-yl)ethyl)-6-(2,3-dihydroxypropyl)-6-phenyl-1,3-oxazinan-2-one

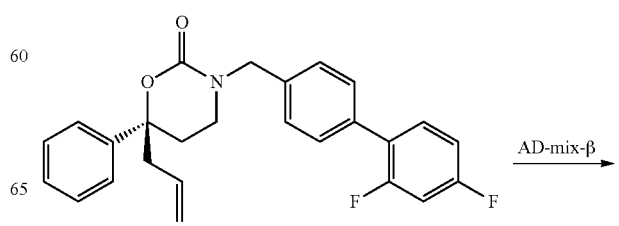

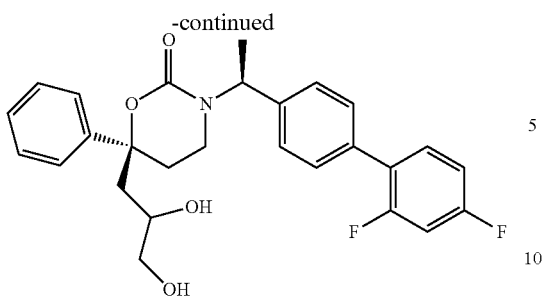

A solution of (R)-6-allyl-3-((S)-1-(2',4'-difluorobiphenyl-4-yl)ethyl)-6-phenyl-1,3-oxazinan-2-one (200 mg, 0.46 mmol) in tert-BuOH (7 mL) was added dropwise to an ice-cooled solution of AD-mix-β (800 mg) in H$_2$O (7 mL). The reaction mixture was stirred for 3 days. Na$_2$SO$_3$ was added, and the mixture was stirred at rt for 1 h. The mixture was extracted with EtOAc. The organic phase was dried over Na$_2$SO$_4$, filtered and concentrated to give the residue, which was purified by preparative HPLC to afford two isomers.

Isomer 1: (20 mg, 9%). $^1$H NMR (CDCl$_3$): 1.48 (m, 3H), 1.96 (m, 1H), 2.08 (m, 1H), 2.15-2.42 (m, 5H), 2.89 (m, 1H), 3.41 (m, 1H), 3.55 (m, 1H), 3.74 (m, 1H), 5.60 (m, 1H), 6.79-6.90 (m, 4H), 7.17 (m, 2H), 7.20-7.35 (m, 6H).

Isomer 2: (13 mg, 7%). $^1$H NMR (CDCl$_3$): 1.49 (m, 3H), 1.85-1.95 (m, 1H), 2.10 (m, 2H), 2.30 (m, 2H), 2.71-2.96 (m, 1H), 3.21-3.45 (m, 2H), 3.79 (m, 1H), 5.61 (m, 1H), 6.78-6.94 (m, 4H), 7.19 (m, 2H), 7.20-7.48 (m, 6H).

Example 174

2-((S)-3-((S)-1-(2',4'-difluorobiphenyl-4-yl)ethyl)-6-(4-fluorophenyl)-2-oxo-1,3-oxazinan-6-yl)acetic acid

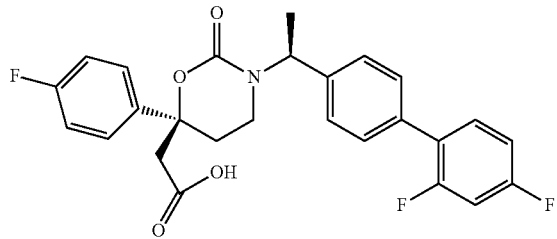 [SMILES: C[C@@H](c1ccc(-c2ccc(F)cc2F)cc1)N1CC[C@](CC(=O)O)(c2ccc(F)cc2)OC1=O]

The title compound was prepared following a procedure analogous to that described in Example 70. $^1$H NMR (CDCl$_3$): 1.56 (m, 3H), 2.39 (m, 1H), 2.55 (m, 1H), 2.69 (m, 1H), 2.82-2.94 (m, 2H), 3.14 (m, 1H), 5.06 (m, 1H), 6.93-7.11 (m, 6H), 7.26 (m, 2H), 7.50 (m, 3H). LC-MS

Example 175

3-((S)-1-(2',4'-difluorobiphenyl-4-yl)propyl)-6-(4-fluorophenyl)-6-(2-hydroxyethyl)-1,3-oxazinan-2-one

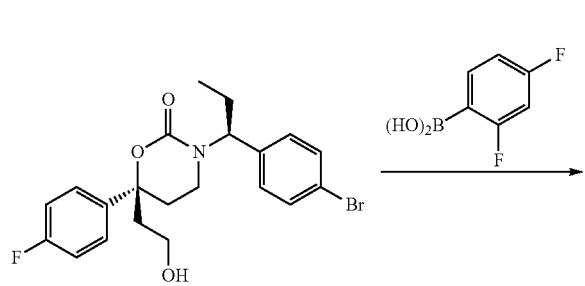

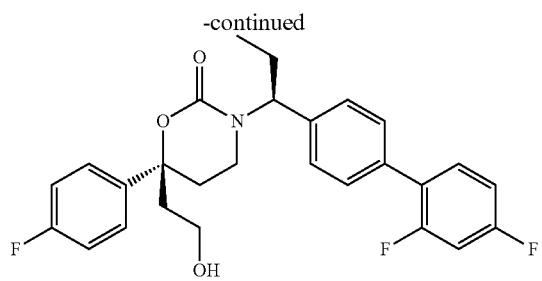

To a solution of (S)-3-((S)-1-(4-bromophenyl)propyl)-6-(4-fluorophenyl)-6-(2-hydroxy ethyl)-1,3-oxazinan-2-one (60 mg, 0.14 mmol), 2,4-difluorophenylboronic acid (26 mg, 0.17 mmol) and Pd(PPh$_3$)$_4$ (16 mg, 0.01 mmol) in dioxane (5 mL) was added a solution of CsCO$_3$ (2 M, 1 mL) at 0° C. Then the reaction mixture was refluxed overnight under nitrogen. The reaction mixture was washed with water and then extract with CH$_2$Cl$_2$ twice. The combined organic phases were dried over Na$_2$SO$_4$, filtered and concentrated to give the residue, which was purified by preparative HPLC to afford (S)-3-((S)-1-(2',4'-difluorobiphenyl-4-yl)propyl)-6-(4-fluorophenyl)-6-(2-hydroxyethyl)-1,3-oxazinan-2-one (17 mg, 26%). $^1$H NMR (CD$_3$OD): 0.96 (m, 3H), 2.01 (m, 2H), 2.12 (m, 2H), 2.30 (m, 2H), 2.48 (m, 1H), 3.10 (m, 1H), 3.33 (m, 1H), 3.65 (m, 1H), 5.38 (m, 1H), 7.02 (m, 4H), 7.08 (m, 2H), 7.28 (m, 4H), 7.42 (m, 1H). 443-114-3.

(R)-3-((S)-1-(2',4'-difluorobiphenyl-4-yl)propyl)-6-(4-fluorophenyl)-6-(2-hydroxyethyl)-1,3-oxazinan-2-one was prepared from (R)-3-((S)-1-(4-bromophenyl)propyl)-6-(4-fluorophenyl)-6-(2-hydroxy ethyl)-1,3-oxazinan-2-one following a procedure analogous to that described immediately above. $^1$H NMR (CD$_3$OD): 0.62 (m, 3H), 1.76 (m, 1H), 1.92 (m, 1H), 2.12 (m, 3H), 2.56 (m, 1H), 2.78 (m, 1H), 2.89 (m, 1H), 3.33 (m, 1H), 3.71 (m, 1H), 5.38 (m, 1H), 7.05 (m, 2H), 7.16 (m, 2H), 7.44 (m, 7H).

Example 176

(R)-3-((S)-1-(2',4'-difluorobiphenyl-4-yl)ethyl)-6-(2-(dimethylamino)ethyl)-6-(4-fluorophenyl)-1,3-oxazinan-2-one

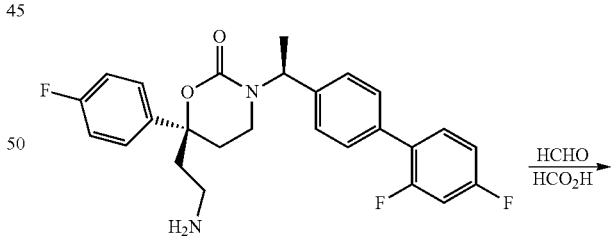

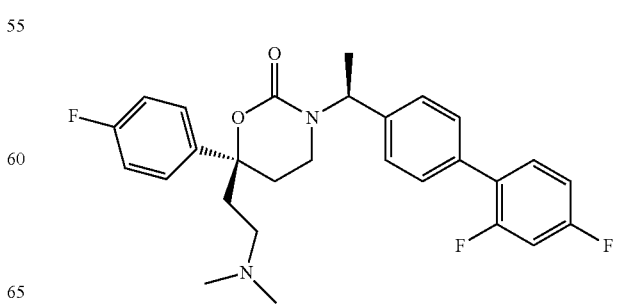

(R)-6-(2-aminoethyl)-3-((S)-1-(2',4'-difluorobiphenyl-4-yl)ethyl)-6-(4-fluorophenyl)-1,3-oxazinan-2-one (50 mg, 0.11 mmol) was added to form acid, followed by the addition of 30% aqueous solution of formaldehyde at 0° C. The solution was then heated to 90° C. and stirred for 24 h. After leaving to cool, 0.1 mol of 1 M HCl was added and the mixture was extracted with dichloromethane for 3 times. Aqueous NaOH solution (20%) was then added to the thus purified aqueous phase until the pH was basic. The alkaline water was extracted with dichloromethane. The organic solution was dried over $Na_2SO_4$, filtered off and evaporated under reduced pressure to give the crude product, which was purified by preparative TLC and separated by preparative HPLC to give (R)-3-((S)-1-(2',4'-difluorobiphenyl-4-yl)ethyl)-6-(2-(dimethylamino)ethyl)-6-(4-fluorophenyl)-1,3-oxazinan-2-one (2.78 mg, 5%). $^1$H NMR (CDCl$_3$): 6.60 (s, 1H), 7.35 (d, 1H), 7.70 (m, 1H), 7.82 (m, 1H), 7.95 (d, 1H), 8.60 (d, 1H).

Example 177

3-((R)-3-((S)-1-(2',4'-difluorobiphenyl-4-yl)ethyl)-6-(4-fluorophenyl)-2-oxo-1,3-oxazinan-6-yl)propanoic acid The title compound was prepared following a procedure analogous to that described in Example 70. $^1$H NMR (CDCl$_3$): 1.56 (m, 3H), 2.05 (m, 1H), 2.10-2.28 (m, 3H), 2.29-2.50 (m, 3H), 3.12 (m, 1H), 5.09 (m, 1H), 6.98-7.10 (m, 6H), 7.29 (m, 4H), 7.39 (m, 1H). LC-MS Method 3 $t_R$=1.27 min, m/z=484, 506.

Example 178

(R)-3-((S)-1-(2',4'-difluorobiphenyl-4-yl)ethyl)-6-(4-fluorophenyl)-6-(2-(2-hydroxyethylamino)ethyl)-1,3-oxazinan-2-one Step 1

To a solution of (S)-3-((S)-1-(2',4'-difluorobiphenyl-4-yl)ethyl)-6-(4-fluorophenyl)-6-(2-hydroxyethyl)-1,3-oxazinan-2-one (50 mg, 0.11 mmol) in dry CH$_2$Cl$_2$ (2 mL) was added Et$_3$N (33 mg, 0.33 mmol) at 0~−5° C. Then a solution of MsCl (12 mg, 0.13 mmol) in dry CH$_2$Cl$_2$ (1 mL) was added dropwise at the same temperature. After addition, the mixture was allowed to warm to rt gradually. When the reaction was over, water (10 mL) was added. The layers were separated, and the aqueous layer was extracted with CH$_2$Cl$_2$ (3×10 mL). The combined organic layers was washed with 10% citric acid, aqueous NaHCO$_3$ and brine respectively, dried over Na$_2$SO$_4$, filtered and concentrated to give 2-((S)-3-((S)-1-(2',4'-difluorobi-phenyl-4-yl)ethyl)-6-(4-fluorophenyl)-2-oxo-1,3-oxazinan-6-yl)ethyl methanesulfonate (58 mg, crude), which was used for the next step without purification.

Step 2

To a solution of 2-((S)-3-((S)-1-(2',4'-difluorobi-phenyl-4-yl)ethyl)-6-(4-fluorophenyl)2-oxo 1,3-oxazinan-6-yl)ethyl methanesulfonate (58 mg, 0.11 mmol) in anhydrous MeOH was added 2-amino-ethanol (54 mg, 0.88 mmol). Then the reaction mixture was refluxed overnight. When the reaction was over, solvent was removed in vacuo. The residue was purified by preparative HPLC to give (R)-3-((S)-1-(2',4'-difluorobiphenyl-4-yl)ethyl)-6-(4-fluorophenyl)-6-(2-(2-hydroxyethylamino)ethyl)-1,3-oxazinan-2-one (2 mg, 3%). $^1$H NMR (CDCl$_3$): 1.53 (m, 3H), 2.25-2.36 (m, 4H), 2.51 (m, 1H), 2.87-3.24 (m, 5H), 3.75-4.02 (m, 2H), 5.60 (m, 1H), 6.85-6.96 (m, 2H), 6.96-7.10 (m, 4H), 7.22 (m, 2H), 7.38 (m, 4H).

Example 179

N-(2-((R)-3-((S)-1-(2',4'-difluorobiphenyl-4-yl)ethyl)-6-(4-fluorophenyl)-2-oxo-1,3-oxazinan-6-yl)ethyl)-2-hydroxyacetamide

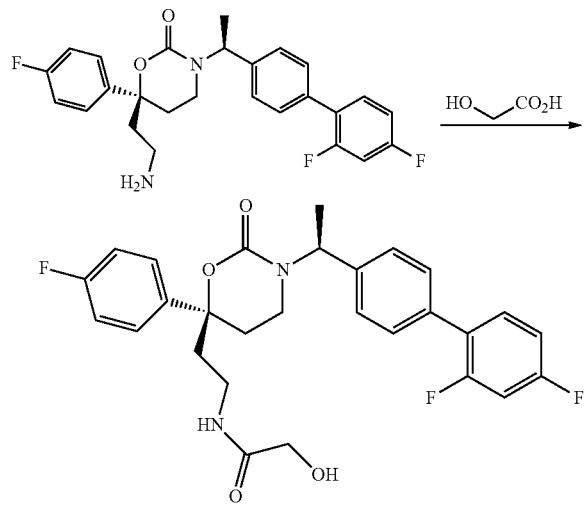

To a solution of (R)-6-(2-aminoethyl)-3-((S)-1-(2',4'-difluorobiphenyl-4-yl)ethyl)-6-(4-fluoro-phenyl)-1,3-oxazinan-2-one stirred in anhydrous CH₂Cl₂ (5 ml) was added HOBT (36 mg, 0.264 mmol), EDCl (52 mg, 0.264 mmol), DIEA (0.5 ml) and hydroxy-acetic acid (50.1 mg, 0.66 mmol) at 0° C. under N₂ atmosphere. The solution was stirred at rt overnight. Then the solvent was removed under reduced pressure to give the residue, which was purified by preparative HPLC to afford N-(2-((R)-3-((S)-1-(2',4'-difluorobiphenyl-4-yl)ethyl)-6-(4-fluorophenyl)-2-oxo-1,3-oxazinan-6-yl)ethyl)-2-hydroxyacetamide (19.2 mg, 28.6%). ¹H NMR (CDCl₃): 1.49-1.50 (d, 3H), 2.01-2.13 (m, 1H), 2.14-2.15 (m, 3H), 2.17 (m, 1H), 2.97-2.98 (m, 2H), 3.46-3.52 (m, 4H), 4.01-4.02 (m, 2H), 5.60-5.61 (m, 1H), 6.82-6.88 (m, 2H), 6.98-7.04 (m, 3H), 7.17 (s, 1H), 7.19-7.22 (m, 3H), 7.25-7.27 (m, 3H).

Example 180

Methyl 2-((R)-3-((S)-1-(2',4'-difluorobiphenyl-4-yl)ethyl)-6-(4-fluorophenyl)-2-oxo-1,3-oxazinan-6-yl)ethylcarbamate

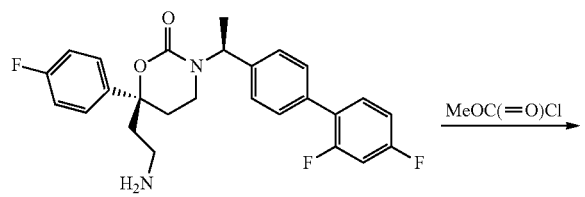

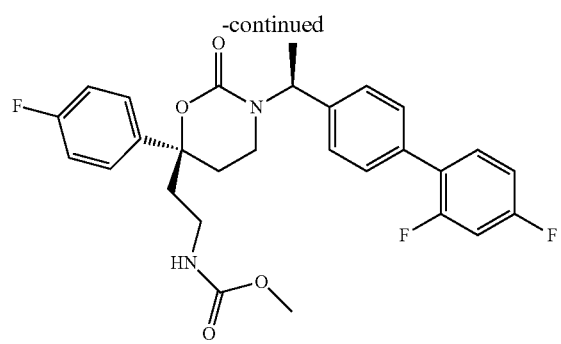

To a solution of (R)-6-(2-aminoethyl)-3-((S)-1-(2',4'-difluorobiphenyl-4-yl)ethyl)-6-(4-fluorophenyl)-1,3-oxazinan-2-one (40 mg, 0.088 mmol) and DMAP (4 mg, 10%) in dry CH₂Cl₂ (3 mL), was added Et₃N (27 mg, 0.264 mmol). The resulting mixture was cooled to 0-5° C. under ice-water bath, and a solution of methyl chloroformate (41 mg, 0.44 mmol) in dry CH₂Cl₂ (1 mL) was added dropwise. After addition, the reaction mixture was stirred for 1-2 h at 0~5° C. After the starting material was disappeared, water (5 mL) was added. The layers were separated, and the aqueous layer was extracted with CH₂Cl₂ (3×5 mL). The combined organic layers were washed with 10% citric acid (2×10 mL) and brine, dried over Na₂SO₄, filtered and concentrated to give the residue, which was purified by preparative HPLC to afford methyl 2-((R)-3-((S)-1-(2',4'-difluorobiphenyl-4-yl)ethyl)-6-(4-fluorophenyl)-2-oxo-1,3-oxazinan-6-yl)ethylcarbamate (10 mg, 22%). ¹H NMR (CDCl₃): 1.50 (m, 3H), 2.06 (m, 2H), 2.10-2.32 (m, 4H), 3.10 (m, 1H), 3.05-3.20 (m, 2H), 3.55 (s, 3H), 4.88 (s, 1H), 5.63 (m, 1H), 6.80-6.90 (m, 2H), 6.92-7.01 (m, 4H), 7.21 (m, 1H), 7.25 (m, 4H).

Example 181

(R)-3-((S)-1-(2',4'-difluorobiphenyl-4-yl)ethyl)-6-(4-fluorophenyl)-6-(2-morpholinoethyl)-1,3-oxazinan-2-one

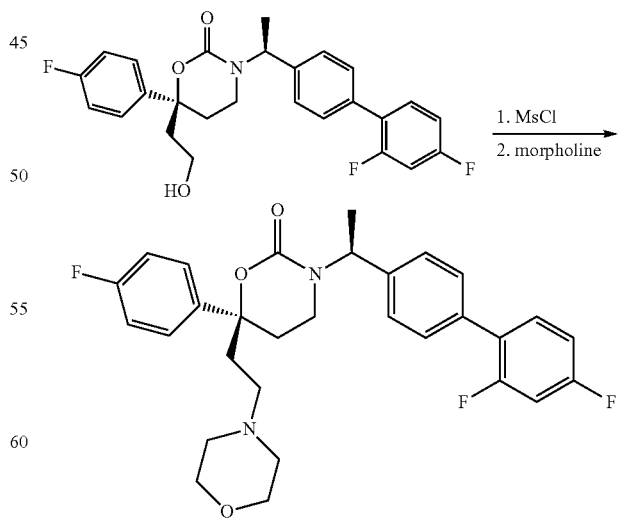

The title compound was prepared following a procedure analogous to that described in Example 178 using morpholine in place of ethanolamine. ¹H NMR (CDCl₃): 1.50 (m, 3H), 2.06-2.29 (m, 3H), 2.30-2.51 (m, 3H), 2.61-2.82 (m, 3H), 2.90 (m, 1H), 3.10-3.29 (m, 2H), 3.49 (m, 1H), 3.79-3.98 (m, 4H), 5.62 (m, 2H), 6.80-6.89 (m, 2H), 7.00 (m, 4H), 7.16 (m, 2H), 7.23 (m, 3H).

Example 182

1-(2-((R)-3-((S)-1-(2',4'-difluorobiphenyl-4-yl)ethyl)-6-(4-fluorophenyl)-2-oxo-1,3-oxazinan-6-yl)ethyl)-3-ethylurea

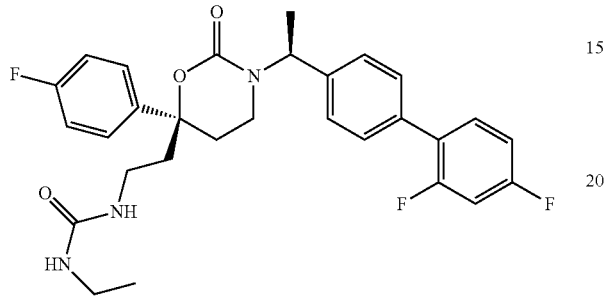

The title compound was prepared following a procedure analogous to that described in Example 141. $^1$H NMR (400 MHz, CDCl$_3$): 1.46 (t, 3H), 1.56 (m, 3H), 2.14 (m, 2H), 2.25 (m, 2H), 2.37 (m, 1H), 2.98 (m, 3H), 3.14 (q, 2H), 3.30 (m, 2H), 5.67 (m, 1H), 6.87 (m, 2H), 7.04 (m, 4H), 7.21 (m, 2H), 7.30 (m, 3H).

Example 183

2-cyano-1-(2-((R)-3-((S)-1-(2',4'-difluorobiphenyl-4-yl)ethyl)-6-(4-fluorophenyl)-2-oxo-1,3-oxazinan-6-yl)ethyl)-3-methylguanidine

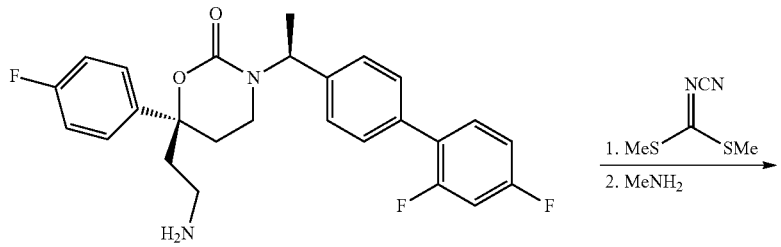

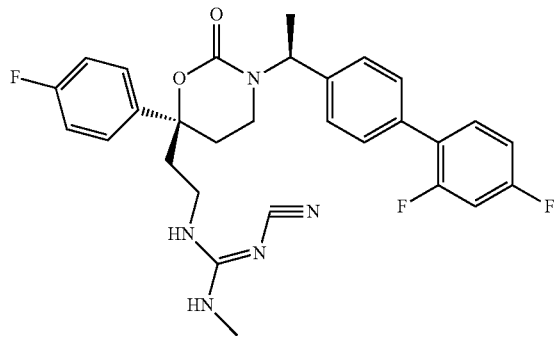

Step 1

A mixture of (R)-6-(2-aminoethyl)-3-((S)-1-(2',4'-difluorobiphenyl-4-yl)ethyl)-6-(4-fluoro phenyl)-1,3-oxazinan-2-one (40 mg, 0.09 mmol) and dimethyl cyanocarbonimidodithioate (40 mg, 0.27 mmol) in acetonitrile (4 mL) was heated to reflux overnight. The solvent was removed to give methyl N'-cyano-N-(2-((R)-3-((S)-1-(2',4'-difluorobiphenyl-4-yl)ethyl)-6-(4-fluorophenyl)-2-oxo-1,3-oxazinan-6-yl)ethyl)carbamimidothioate (50 mg, crude), which was used for the next step without purification.

Step 2

A mixture of (Z)-methyl N'-cyano-N-(2-((R)-3-((S)-1-(2',4'-difluorobiphenyl-4-yl)ethyl)-6-(4-luorophenyl)-2-oxo-1,3-oxazinan-6-yl)ethyl)carbamimidothioate (50 mg, crude) in the solution of methylamine in ethanol (10 mL) was heated to reflux overnight. The solvent was removed under reduced pressure, and the residue was purified by preparative HPLC to give 2-cyano-1-(2-((R)-3-((S)-1-(2',4'-difluorobiphenyl-4-yl)ethyl)-6-(4-fluorophenyl)-2-oxo-1,3-oxazinan-6-yl)ethyl)-3-methylguanidine (10 mg, 21%). $^1$H NMR (CDCl$_3$): 1.49 (m, 3H), 2.15 (m, 4H), 2.26 (m, 2H), 2.71 (s, 3H), 2.95 (m, 1H), 3.08 (s, 1H), 3.28 (s, 1H), 5.60 (m, 2H), 6.85 (m, 2H), 7.01 (m, 4H), 7.19 (m, 2H), 7.23 (m, 3H). LC-MS Method 3 $t_R$=1.28 min, m/z=536.

Example 184

3-((R)-3-((S)-1-(2',4'-difluorobiphenyl-4-yl)ethyl)-6-(4-fluorophenyl)-2-oxo-1,3-oxazinan-6-yl)-N-(methylsulfonyl)propanamide

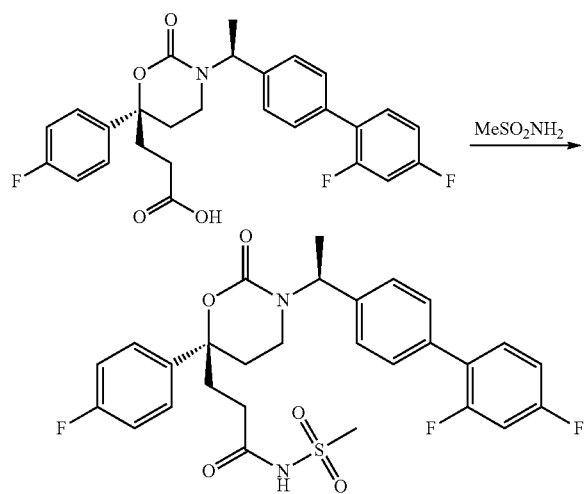

A mixture of 3-((R)-3-((S)-1-(2',4'-difluorobiphenyl-4-yl)ethyl)-6-(4-fluorophenyl)-2-oxo-1,3-oxazinan-6-yl)propanoic acid (60 mg, 0.13 mmol), methanesulfonamide (24 mg, 0.26 mmol), HOBt (53 mg, 0.39 mmol), EDCl (75 mg, 0.39 mmol) and DIEA (1 mL) in CH$_2$Cl$_2$ was stirred at rt overnight. The solvent was removed to give the crude product. It was purified by preparative HPLC to give 3-((R)-3-((S)-1-(2',4'-difluorobiphenyl-4-yl)ethyl)-6-(4-fluorophenyl)-2-oxo-1,3-oxazinan-6-yl)-N-(methylsulfonyl)propanamide (7 mg, 10%). $^1$H NMR (CDCl$_3$): 1.50 (m, 3H), 2.21 (m, 6H), 2.54 (m, 1H), 2.93 (m, 1H), 3.15 (s, 3H), 5.59 (m, 1H), 6.83 (m, 2H), 6.98 (m, 4H), 7.18 (m, 2H), 7.24 (m, 3H), 9.58 (s, 1H). LC-MS Method 3, $t_R$=1.26 min, m/z=561.

Example 185

N-(3-((R)-3-((S)-1-(2',4'-difluorobiphenyl-4-yl)ethyl)-6-(4-fluorophenyl)-2-oxo-1,3-oxazinan-6-yl)propyl)methanesulfonamide

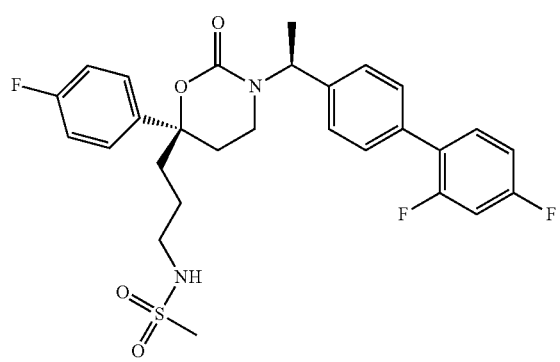 [SMILES: C[C@@H](c1ccc(-c2ccc(F)cc2F)cc1)N1CC[C@](CCCNS(C)(=O)=O)(c2ccc(F)cc2)OC1=O]

The title compound was prepared from (R)-6-(3-aminopropyl)-3-((S)-1-(2',4'-difluorobiphenyl-4-yl)ethyl)-6-(4-fluorophenyl)-1,3-oxazinan-2-one following a procedure analogous to that described in Example 99. LC-MS Method 3 $t_R$=1.47 min, m/z=547; $^1$H NMR (CDCl$_3$) 1.44-1.53 (d, 3H), 1.59-1.68 (m, 1H), 2.17-2.20 (m, 1H), 2.22-2.33 (m, 2H), 2.76 (s, 3H), 2.89-2.97 (m, 1H), 2.09-3.05 (m, 2H), 4.18-4.32 (m, 1H), 5.58-5.67 (m, 1H), 6.76-6.89 (m, 2H), 6.91-7.03 (m, 4H), 7.13-7.18 (m, 2H), 7.22-7.27 (m, 3H).

Example 186

6-(3-hydroxypropyl)-3-phenethyl-6-phenyl-1,3-oxazinan-2-one

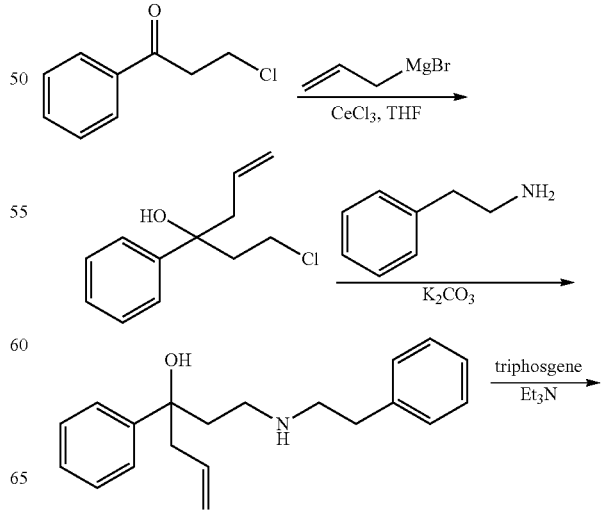

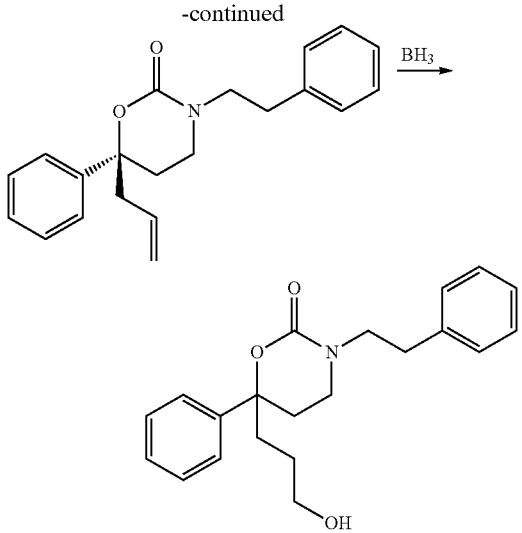

Step 1

A 1000-mL flask was charged with anhydrous CeCl₃ (50 g, 0.2 mol) and THF (360 mL). The mixture was vigorously stirred for 3.5 h at rt. The suspension was then cooled to −78° C., and a solution of allylmagnesium bromide (1.0 M in THF, 200 mL) was added. After stirring for 2 h at −78° C., a solution of 3-chloro-1-phenyl-propan-1-one (25 g, 149 mmol) in THF (269 mL) was added dropwise. The reaction mixture was allowed to slowly warm to rt while stirring overnight. The reaction was then quenched with satd aq NaHCO₃, extracted with EtOAc, and dried over Na₂SO₄. After the solvents were evaporated, the residue was purified by chromatography on silica gel eluted with hexanes/EtOAc to afford of 1-chloro-3-phenyl-hex-5-en-3-ol (25 g, 82%) as an oil. ¹H NMR (CDCl₃): 2.30 (m, 2H), 2.51 (m, 1H), 2.72 (m, 1H), 3.20 (m, 1H), 3.54 (m, 1H), 5.16 (m, 2H), 5.51 (m, 1H), 7.24 (m, 1H), 7.35 (m, 4H).

Step 2

A mixture of 1-chloro-3-phenyl-hex-5-en-3-ol (500 mg, 2.38 mmol), phenethylamine (348 mg, 2.862.24 mmol), and K₂CO₃ (643 mg, 4.76 mmol) in anhydrous CH₃CN (10 mL) were stirred at rt under N₂. Then the solution was refluxing at 80-90° C. overnight. The solid was filtered, and the filtrate was condensed under reduced pressure to give the residue, which was purified by preparative TLC to afford 1-phenethylamino-3-phenyl-hex-5-en-3-ol (320 mg, 45%). ¹H NMR (CDCl₃): 2.07-2.15 (m, 1H), 2.28-2.39 (m, 1H), 2.51-2.69 (m, 3H), 2.81 (m, 1H), 2.90-3.01 (m, 3H), 3.09 (m, 1H), 5.04 (m, 2H), 5.47-5.58 (m, 1H), 7.17-7.38 (m, 11H).

Step 3

To a solution of 1-phenethylamino-3-phenyl-hex-5-en-3-ol (120 mg, 0.41 mmol) and Et₃N (0.5 mL) in anhydrous CH₂Cl₂ (5 mL) was added triphosgene (40 mg, 0.134 mmol) in portions at 0° C. under N₂. Then the solution was refluxing at 80-90° C. overnight. The solvent was removed under reduced pressure, and the residue was purified by preparative TLC to afford 6-allyl-3-phenethyl-6-phenyl-[1,3]oxazinan-2-one (234 mg, yield: 19%). ¹H NMR (CDCl₃): 2.07-2.17 (m, 2H), 2.44-2.60 (m, 2H), 2.62-2.84 (m, 4H), 3.25 (m, 1H), 3.52 (m, 1H), 3.09 (m, 1H), 5.04 (m, 2H), 5.47-5.58 (m, 1H), 6.94 (m, 2H), 7.10 (m, 3H), 7.27 (m, 3H), 7.31 (m, 2H).

Step 4

To a solution of 6-allyl-3-phenethyl-6-phenyl-[1,3]oxazinan-2-one (100 mg, 0.31 mmol) in dry THF (4 mL) was added dropwise BH₃.THF (0.6 mL, 0.62 mmol, 1 M) at 0° C. After 2 h at rt, the reaction mixture was cooled to 0° C., and water (1 mL), aqueous NaOH (1 mL, 3 M) and H₂O₂ (0.5 mL, 30%) were successively added. The mixture was stirred for 2-3 h at rt, and then diluted with water (8 mL). The pH of the mixture was adjusted to 6-7 with 0.5 N HCl. The layers were separated, and the aqueous phase was extracted with EtOAc (3×6 mL). The combined organic layers were washed with a saturated aqueous NaHCO₃ solution (10 mL) and brine (10 mL), dried over Na₂SO₄, and concentrated in vacuo to give the crude product, which was purified by preparative TLC to afford two isomers of 6-(3-hydroxypropyl)-3-phenethyl-6-phenyl-1,3-oxazinan-2-one.

Isomer 1 (12 mg, 11%). LC-MS Method 3 t_R=1.13, min, m/z=340, 362; ¹H NMR (CDCl₃): 1.21-1.33 (m, 1H), 1.64 (m, 1H), 1.81-1.98 (m, 2H), 2.06 (m, 2H), 2.15 (m, 1H), 2.61-2.83 (m, 4H), 3.29 (m, 1H), 3.51 (m, 3H), 6.99 (m, 2H), 7.12 (m, 3H), 7.21 (m, 1H), 7.25 (m, 1H), 7.28 (m, 1H), 7.30 (m, 2H).

Isomer 2: (12 mg, 17%). LC-MS Method 3 t_R=1.13, min, m/z=340, 362; ¹H NMR (CDCl₃): 1.20-1.38 (m, 2H), 1.67 (m, 2H), 1.86-2.00 (m, 2H), 2.02-2.34 (m, 2H), 2.64-2.88 (m, 4H), 3.31 (m, 1H), 3.50-3.62 (m, 3H), 7.02 (m, 2H), 7.15 (m, 3H), 7.21 (m, 1H), 7.28 (m, 2H), 7.33 (m, 2H).

Example 187

3-((S)-1-(4-chlorophenyl)ethyl)-6-(3-hydroxypropyl)-6-isopropyl-1,3-oxazinan-2-one

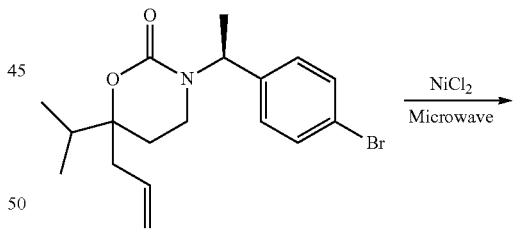

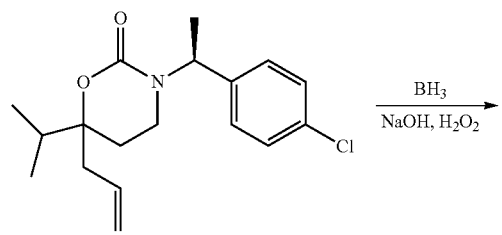

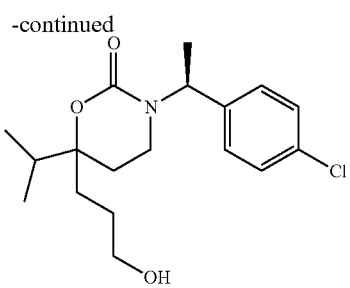

1.62 (m, 5H), 1.87 (m, 1H), 2.07 (m, 1H), 2.68 (m, 1H), 3.03 (m, 1H), 3.59 (m, 2H), 5.74 (m, 1H), 7.22 (m, 2H), 7.29 (m, 2H).

Example 188

6-(3-hydroxypropyl)-6-phenyl-3-(2-phenylcyclopropyl)-1,3-oxazinan-2-one

Step 1

In a 10 mL glass tube was placed 6-allyl-3-((S)-1-(4-bromophenyl)ethyl)-6-isopropyl-1,3-oxazinan-2-one (50 mg, 0.14 mmol), nickel(II) chloride (18 mg, 0.14 mmol) and DMF (0.5 mL). The vessel was sealed with a spectrum and placed into the microwave cavity. Microwave irradiation of 100 W was used, the temperature being ramped from rt to 170° C. Once this temperature was reached, the reaction mixture was held at this temperature for 8 minutes. After the mixture cooled to rt, the reaction vessel was opened and the contents were poured into a separating funnel, and the tube was washed with water and then EtOAc, these washings being added to the separatory funnel. The mixture was partitioned. The aqueous layer was extracted with EtOAc for 3 times, the combined organic layer was washed with brine, dried over $Na_2SO_4$, and concentrated to give 6-allyl-3-((S)-1-(4-chlorophenyl)ethyl)-6-isopropyl-1,3-oxazinan-2-one (45 mg, crude).

Step 2

To a solution of 6-allyl-3-((S)-1-(4-chlorophenyl)ethyl)-6-isopropyl-1,3-oxazinan-2-one (45 mg, 0.14 mmol) in dry THF (5 mL) was added dropwise 1 M $BH_3$·THF (0.28 mL, 0.28 mmol) at 0° C. After 2 h at rt, the reaction mixture was cooled to 0° C., and water (1 mL), 3 M aqueous NaOH (1 mL, 3 M) and 30% $H_2O_2$ (0.5 mL) were successively added. The mixture was stirred for 2-3 h at rt and was then diluted with water (6 mL). The pH of the mixture was adjusted to 6-7 with 0.5 N HCl. The layers were separated, and the aqueous phase was extracted with EtOAc (3×5 mL). The combined organic layers were washed with a saturated aqueous $NaHCO_3$ solution (8 mL) and brine (8 mL), dried over $Na_2SO_4$, and concentrated in vacuo to give the crude product, which was purified by preparative TLC followed by preparative HPLC to afford two isomers.

Isomer 1: (5 mg, 10%) LC-MS Method 3 $t_R$=1.22, min, m/z=340, 362; $^1$H NMR (CDCl$_3$) 0.86 (m, 6H), 1.46 (m, 3H), 1.58-1.74 (m, 6H), 1.94 (m, 1H), 2.66 (m, 1H), 3.08 (m, 1H), 3.61 (m, 2H), 5.70 (m, 1H), 7.19 (m, 2H), 7.27 (m, 2H).

Isomer 2 (5 mg, 10%): LC-MS Method 3 $t_R$=1.19, min, m/z=340, 362; $^1$H NMR (CDCl$_3$) 0.91 (m, 6H), 1.49 (m, 3H), Step 1

To a solution of 2-phenylcyclopropanecarboxylic acid (1.0 g, 6.17 mmol) in dry toluene (20 mL) was added triethylamine (934 mg, 9.26 mmol) and DPPA (2.0 g, 7.41 mmol) under $N_2$, and the reaction mixture was refluxed for 3 h. The solution was concentrated to give (2-isocyanatocyclopropyl)benzene (800 mg), which was used for the next step without further purification.

Step 2

To a solution of (2-isocyanatocyclopropyl)benzene (800 mg, 5.03 mmol) in THF (15 mL) was added DBU (1.61 g, 10.48 mmol) and 1-chloro-3-phenylhex-5-en-3-ol (880 mg, 4.19 mmol), and the mixture was refluxed overnight. The solution was diluted with EtOAc, and washed with 1 N HCl (2×15 mL). The aqueous phase was extracted with EtOAc. The combined organic layers were washed with brine, dried over $Na_2SO_4$, filtered and concentrated to give crude product, which was purified by preparative TLC to afford 6-allyl-6-phenyl-3-(2-phenylcyclopropyl)-1,3-oxazinan-2-one (100 mg, 6%). ¹H NMR (CDCl₃): 1.05-1.21 (m, 3H), 1.36-1.42 (m, 1H), 2.13-2.34 (m, 1H), 2.39-2.61 (m, 2H), 2.92-3.15 (m, 1H), 3.76-4.01 (m, 1H), 4.95-5.10 (m, 2H), 5.42-5.73 (m, 1H), 6.95-6.99 (m, 1H), 7.10-7.24 (m, 10H).

Step 3

To a solution of 6-allyl-6-phenyl-3-(2-phenylcyclopropyl)-1,3-oxazinan-2-one (200 mg, 0.60 mmol) in dry THF (5 mL) was added dropwise 1 M of BH₃/THF (1.8 mL, 1.8 mmol) at 0° C. under N₂. After stirring at rt for 2 h, the reaction mixture was cooled to 0° C. again, and water (0.1 mL), 3 M of aqueous NaOH solution (0.1 mL), and 30% H₂O₂ (0.3 mL) were added sequentially. After the mixture was stirred at rt for another 2 h, 1 N aqueous HCl (0.5 mL) was added. The mixture was extracted with EtOAc. The organic layer was washed with brine, dried over Na₂SO₄, filtered and concentrated to give the crude product, which was purified by preparative TLC followed by preparative HPLC to afford two isomers.

Isomer 1 (20 mg, 9%): LC-MS Method 3 $t_R$=1.151, min, m/z=352.2; ¹H NMR (CDCl₃) 0.83 (m, 2H), 1.12 (m, 1H), 1.23 (m, 4H), 1.68 (m, 1H), 1.97 (m, 2H), 2.16 (m, 1H), 2.21 (m, 1H), 2.84 (m, 1H), 3.13 (m, 1H), 3.52 (m, 2H), 4.14 (m, 1H), 7.03 (m, 2H), 7.11 (m, 1H), 7.17 (m, 2H), 7.29 (m, 4H), 7.46-7.63 (m, 1H).

Isomer 2 (15 mg, 7%): LC-MS Method 3 $t_R$=1.149, min, m/z=352.2; ¹H NMR (CDCl₃) 0.85 (m, 2H), 1.11 (m, 1H), 1.26 (m, 3H), 1.67 (m, 2H), 1.96 (m, 2H), 2.18 (m, 1H), 2.27 (m, 1H), 2.83 (m, 1H), 3.13 (m, 1H), 3.52 (m, 2H), 4.15 (m, 1H), 7.02 (m, 2H), 7.11 (m, 1H), 7.15 (m, 2H), 7.26 (m, 3H), 7.29 (m, 2H), 7.46-7.63 (m, 1H).

Example 189

6-allyl-6-(4-fluorophenyl)-3-((S)-1-p-tolylethyl)-1,3-oxazinan-2-one

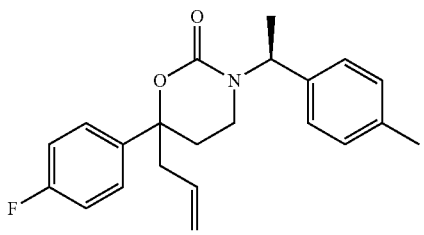 [SMILES: C=CCC1(c2ccc(F)cc2)CCN([C@@H](C)c2ccc(C)cc2)C(=O)O1]

The title compound was prepared following a procedure analogous to that described in Example 110 Step 2 using (S)-1-(1-isocyanatoethyl)-4-methylbenzene. Two isomers were isolated.

Isomer 1: LC-MS Method 1 $t_R$=1.94, min, m/z=354; ¹H NMR (CDCl₃) 7.31-7.27 (m, 2H), 7.19-7.13 (m, 4H), 7.10-7.05 (m, 2H), 5.75-5.63 (m, 2H), 5.09-4.97 (m, 2H), 2.73-2.52 (m, 4H), 2.34 (s, 3H), 2.22-2.16 (dt, 1H), 2.07-1.99 (m, 1H), 1.25 (d, 3H).

Isomer 2: LC-MS Method 1 $t_R$=1.99, min, m/z=354; ¹H NMR (CDCl₃) 7.26-7.22, 7.03-6.95, 5.75-5.57, 5.08-4.98, 2.3, 1.47.

Example 190

(R)-6-allyl-6-(4-fluorophenyl)-3-((S)-1-(4-hydroxyphenyl)ethyl)-1,3-oxazinan-2-one

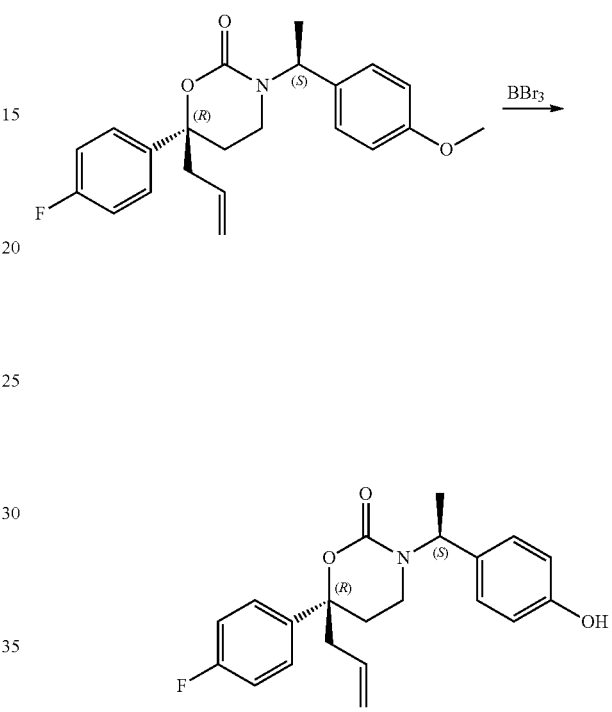

A solution of (R)-6-allyl-6-(4-fluorophenyl)-3-((S)-1-(4-methoxyphenyl)ethyl)-1,3-oxazinan-2-one (0.1094 g, 0.30 mmol, 1.0 equiv) in 6 mL of dry CH₂Cl₂ was cooled to −78° C. At this temperature, BBr₃ (1.0 M solution in CH₂Cl₂, 0.6 mL, 0.60 mmol, 2.0 equiv) was added under N₂ atmosphere. After 1 h, the reaction mixture was stirred at an ice bath for further 3 h. After the reaction mixture was cooled with a dry ice—acetone bath, surplus of BBr₃ was hydrolyzed with methanol (3 mL). The mixture was then treated with brine, diluted with CH₂Cl₂, and dried over Na₂SO₄. After the solvent was evaporated under reduced pressure, the residue was purified by reversed-phase HPLC (SunFire™ Prep C₁₈ OBD™ 5 μm 19×50 mm column, 10%→90% CH₃CN/H₂O, 0.1% CF₃COOH over 8 min and then 90% CH₃CN/H₂O, 0.1% CF₃COOH over 2 min, flow rate 20 ml/min) to afford 0.0669 g (64%) of (R)-6-allyl-6-(4-fluorophenyl)-3-((S)-1-(4-hydroxyphenyl)ethyl)-1,3-oxazinan-2-one. LC-MS Method 1 $t_R$=1.57 min, m/z 356 (MH⁺); ¹H NMR (400 MHz, CD₃OD) δ 7.23-7.18 (m, 2H), 7.00-6.96 (m, 2H), 6.63 (d, J=8.8 Hz, 2H), 6.43 (d, J=8.2 Hz, 2H), 5.64-5.54 (m, 1H), 5.34 (q, J=7.0 Hz, 1H), 4.96-4.89 (m, 2H), 2.93-2.88 (m, 1H), 2.50 (d, J=7.0 Hz, 2H), 2.34-2.29 (m, 1H), 2.18-2.03 (m, 2H), 1.36 (d, J=7.0 Hz, 3H); $^{19}$F NMR (376 MHz, CD$_3$OD) δ −117.48 (m).

Example 191

(S)-6-(2-hydroxyethyl)-3-((S)-1-(4-methoxyphenyl)ethyl)-6-phenyl-1,3-oxazinan-2-one

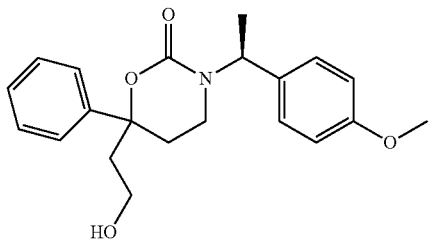 [SMILES: COc1ccc([C@H](C)N2CCC(CCO)(c3ccccc3)OC2=O)cc1]

The title compound was prepared from (R)-6-allyl-6-(4-fluorophenyl)-3-((S)-1-(4-methoxyphenyl)ethyl)-1,3-oxazinan-2-one following a procedure analogous to that described in Example 74. LC-MS Method 3 t$_R$=0.893, min, m/z=355.9; $^1$H NMR (CDCl$_3$) 1.43 (d, 3H), 2.02-2.23 (m, 5H), 2.73 (m, 1H), 3.51 (m, 1H), 3.68 (s, 3H), 3.72 (m, 1H), 5.53 (m, 1H), 6.57 (d, 1H), 6.76 (d, 1H), 7.19-7.33 (m, 5H).

Example 192

4-((S)-1-((R)-6-allyl-6-(4-fluorophenyl)-2-oxo-1,3-oxazinan-3-yl)ethyl)benzonitrile

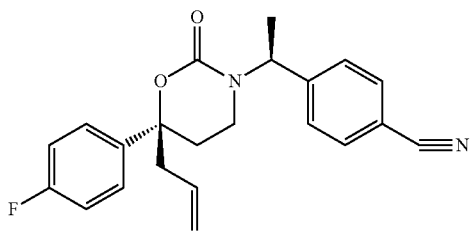 [SMILES: C=CC[C@]1(c2ccc(F)cc2)CCN([C@@H](C)c2ccc(C#N)cc2)C(=O)O1]

The title compound was prepared from 4-((S)-1-((R)-6-allyl-6-(4-fluorophenyl)-2-oxo-1,3-oxazinan-3-yl)ethyl)benzamide using a procedure analogous to that described in Example 172. LC-MS Method 1 t$_R$=1.74, min, m/z=365; $^1$H NMR (CDCl$_3$) 7.39 (d, 2H), 7.26 (t, 2H), 7.05 (t, 2H), 6.93 (d, 2H), 5.74-5.62 (m, 2H), 5.06 (dd, 2H), 2.99 (m, 2H), 2.59 (m, 2H), 1.53 (d, 3H).

Example 193

6-allyl-6-(4-fluorophenyl)-3-((1S)-1-(4-methoxyphenyl)ethyl)-1,3-oxazinan-2-one

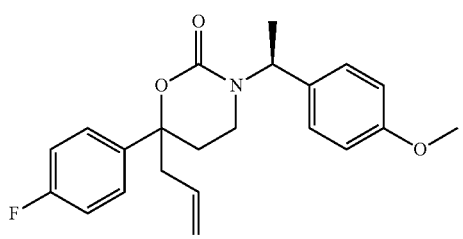 [SMILES: C=CCC1(c2ccc(F)cc2)CCN([C@@H](C)c2ccc(OC)cc2)C(=O)O1]

The title compound was prepared following a procedure analogous to that described in Example 110 Step 2 using (S)-1-(1-isocyanatoethyl)-4-methoxybenzene. Two isomers were isolated.

Isomer 1: LC-MS Method 1 t$_R$=1.82, min, m/z=370; $^1$H NMR (CDCl$_3$) 7.28-7.23 (m, 2H), 7.04-7.00 (m, 2H), 6.79 (d, J=8.8 Hz, 2H), 6.64 (d, J=8.8 Hz, 2H), 5.77-5.66 (m, 1H), 5.60 (q, J=7.0 Hz, 1H), 5.10-5.00 (m, 2H), 3.74 (s, 3H), 2.90-2.85 (m, 1H), 2.64-2.52 (m, 2H), 2.30-2.13 (m, 3H), 1.48 (d, J=7.0 Hz, 3H).

Isomer 2: LC-MS Method 1 t$_R$=1.88, min, m/z=370; $^1$H NMR (CDCl$_3$) 7.32-7.27 (m, 2H), 7.22 (d, J=8.5 Hz, 2H), 7.09-7.05 (m, 2H), 6.86 (d, J=8.5 Hz, 2H), 5.77-5.66 (m, 2H), 5.08-4.98 (m, 2H), 3.80 (s, 3H), 2.70-2.66 (m, 2H), 2.63-2.52 (m, 2H), 2.20-2.15 (m, 1H), 2.06-1.98 (m, 1H), 1.23 (d, J=7.0 Hz, 3H).

Example 194

(R)-3-((S)-1-(4-(hydroxymethyl)phenyl)ethyl)-6-(3-hydroxypropyl)-6-phenyl-1,3-oxazinan-2-one

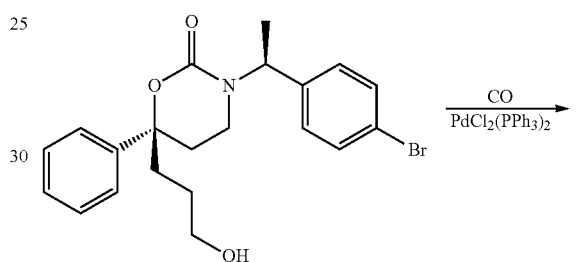

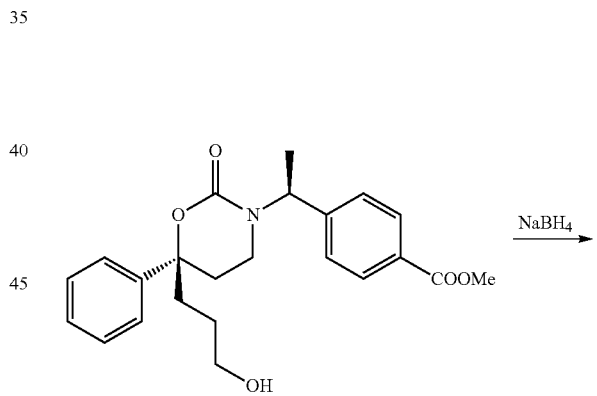

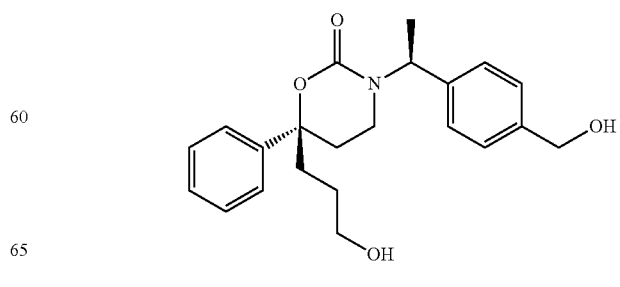

Step 1

A mixture of (R)-3-((S)-1-(4-bromophenyl)ethyl)-6-(3-hydroxypropyl)-6-phenyl-1,3-oxazinan-2-one (80 mg, 0.19 mmol), Pd(PPh$_3$)$_2$Cl$_2$ (14 mg, 0.02 mmol) and TEA (38 mg, 0.38 mmol) in methanol (10 mL) was stirred in a sealed tube under 50 Psi carbon monoxide atmosphere at 80° C. overnight. The mixture was filtered, and the filtrate was concentrated to give the crude product, which was purified by preparative TLC to give methyl 4-((S)-1-((R)-6-(3-hydroxypropyl)-2-oxo-6-phenyl-1,3-oxazinan-3-yl)ethyl)benzoate (60 mg, crude).

Step 2

To a solution of methyl 4-((S)-1-((R)-6-(3-hydroxypropyl)-2-oxo-6-phenyl-1,3-oxazinan-3-yl)ethyl)benzoate (60 mg, 0.25 mmol) in THF (5 mL) was added NaBH$_4$ (48 mg, 1.25 mmol). The mixture was heated to reflux for 15 minutes. Then methanol (3 mL) was added. The mixture was heated to reflux overnight. The reaction was quenched with water, and the solvent was removed. The aqueous layer was extracted with EtOAc for 3 times. The combined organic layer was washed with brine, dried over Na$_2$SO$_4$, and concentrated to give the crude product, which was purified by preparative TLC to give (R)-3-((S)-1-(4-(hydroxymethyl)phenyl)ethyl)-6-(3-hydroxypropyl)-6-phenyl-1,3-oxazinan-2-one (5 mg, 5%). LC-MS Method 2 t$_R$=1.29, min, m/z=370, 392; $^1$H NMR (CDCl$_3$): 1.33 (m, 1H), 1.45 (m, 3H), 1.64 (m, 1H), 1.90 (m, 2H), 2.11-2.24 (m, 2H), 2.81 (m, 1H), 3.50 (m, 2H), 4.52 (s, 2H), 5.58 (m, 1H), 6.82 (m, 2H), 7.03 (m, 2H), 7.25 (m, 5H).

Example 195

(S)-6-(4-fluorophenyl)-6-(2-hydroxyethyl)-3-((S)-1-(4-methoxyphenyl)ethyl)-1,3-oxazinan-2-one

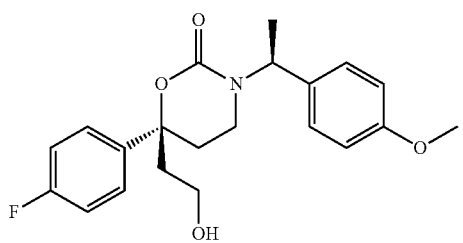 [SMILES: COc1ccc([C@H](C)N2CC[C@](CCO)(c3ccc(F)cc3)OC2=O)cc1]

The title compound was prepared from (R)-6-allyl-6-(4-fluorophenyl)-3-((S)-1-(4-methoxyphenyl)ethyl)-1,3-oxazinan-2-one following a procedure analogous to that described in Example 97. LC-MS Method 1 t$_R$=1.45, min, m/z=374; $^1$H NMR (CD$_3$OD) 7.28-7.24 (m, 2H), 7.06-7.02 (m, 2H), 6.82 (d, J=8.5 Hz, 2H), 6.62 (d, J=8.5 Hz, 2H), 5.44 (q, J=7.0 Hz, 1H), 3.67 (s, 3H), 3.66-3.60 (m, 1H), 3.31-3.25 (m, 1H), 3.02-2.95 (m, 1H), 2.44-2.38 (m, 1H), 2.24-2.10 (m, 2H), 2.07 (t, J=7.3 Hz, 2H), 1.44 (d, J=7.0 Hz, 3H).

Example 196

6-allyl-3-((1S)-1-(4-chlorophenyl)ethyl)-6-(4-fluorophenyl)-1,3-oxazinan-2-one

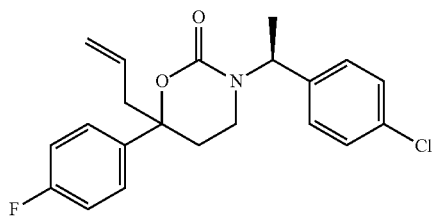 [SMILES: C=CCC1(c2ccc(F)cc2)CCN([C@@H](C)c2ccc(Cl)cc2)C(=O)O1]

The title compound was prepared following a procedure analogous to that described in Example 110 Step 2 using (S)-1-chloro-4-(1-isocyanatoethyl)benzene. Two isomers were isolated.

Isomer 1: (R)-6-allyl-3-((S)-1-(4-chlorophenyl)ethyl)-6-(4-fluorophenyl)-1,3-oxazinan-2-one: LC-MS Method 1 tR=1.97, min, m/z=374; 1H NMR (CDCl3) 7.28-7.24 (m, 2H), 7.09-7.02 (m, 4H), 6.78 (d, 2H), 5.75-5.64 (m, 1H), 5.64-5.59 (q, 1H), 5.11-5.00 (m, 2H), 2.94-2.89 (m, 1H), 2.64-2.52 (m, 2H), 2.34-2.15 (m, 3H), 1.49 (d, 3H).

Isomer 2: (S)-6-allyl-3-((S)-1-(4-chlorophenyl)ethyl)-6-(4-fluorophenyl)-1,3-oxazinan-2-one: LC-MS Method 1 tR=2.01, m/z=374 (M+1); 1H NMR (CDCl3) 7.32-7.21 (m, 6H), 7.10-7.04 (t, 2H, J=9.0 Hz), 5.75-5.65 (m, 2H), 5.09-4.98 (m, 2H), 2.75-2.64 (m, 2H), 2.62-2.52 (m, 2H), 2.24-2.19 (m, 1H), 2.08-2.00 (m, 1H), 1.24 (d, 3H, J=7.3 Hz).

Example 197

(6S)-3-((1S)-1-cyclohexylethyl)-6-(2,3-dihydroxypropyl)-6-(4-fluorophenyl)-1,3-oxazinan-2-one

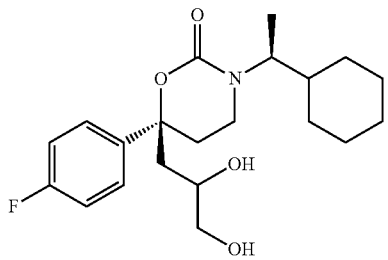 [SMILES: C[C@@H](C1CCCCC1)N1CC[C@](CC(O)CO)(c2ccc(F)cc2)OC1=O]

The title compound was prepared from (R)-6-allyl-3-((S)-1-cyclohexylethyl)-6-(4-fluorophenyl)-1,3-oxazinan-2-one using AD-mix-β following a procedure analogous to that described in Example 173. Two isomers were isolated.

Isomer 1: LC-MS Method 2 t$_R$=2.183, min, m/z=402.2; $^1$H NMR (CDCl$_3$) 1.01-1.13 (m, 6H), 1.42-1.71 (m, 5H), 1.92-2.43 (m, 8H), 2.51-2.71 (m, 2H), 3.08 (m, 1H), 3.47 (m, 1H), 3.61 (m, 1H), 3.75 (m, 1H), 3.97 (m, 1H), 7.02-7.09 (m, 2H), 7.22-7.39 (m, 2H).

Isomer 2: LC-MS Method 2 t$_R$=2.215, min, m/z=402.2; $^1$H NMR (CDCl$_3$) 0.96-1.03 (m, 6H), 1.38-1.71 (m, 8H), 1.73 (m, 1H), 2.01-2.09 (m, 1H), 2.29 (m, 3H), 2.53 (m, 1H), 3.01

(m, 1H), 3.22 (m, 1H), 3.48 (m, 1H), 3.73 (m, 1H), 3.89 (m, 1H), 7.03 (m, 2H), 7.22 (m, 2H).

Example 198

(R)-3-((S)-1-(4-(2-hydroxyethyl)phenyl)ethyl)-6-(3-hydroxypropyl)-6-phenyl-1,3-oxazinan-2-one

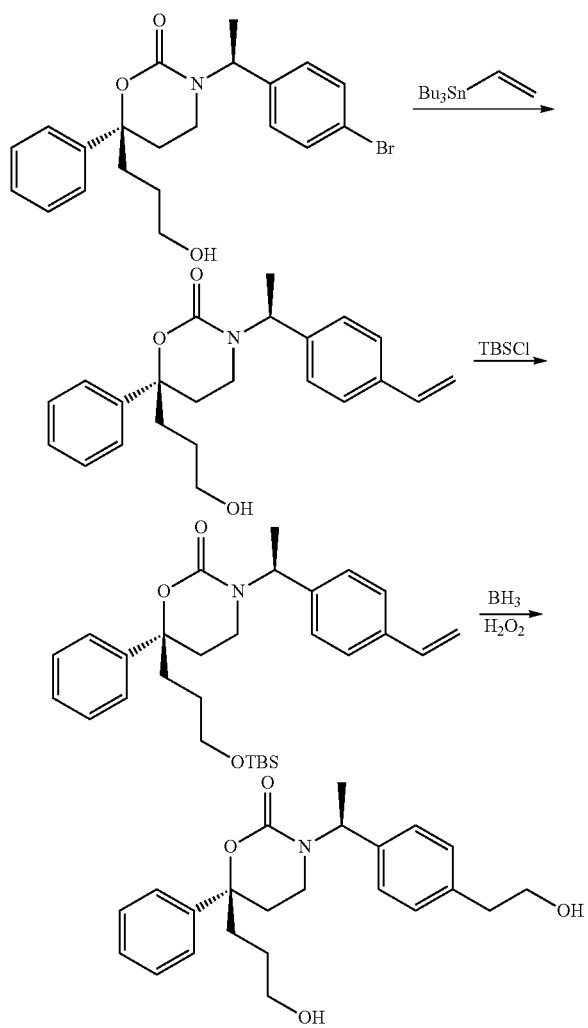

Step 1

A solution of (R)-3-((S)-1-(4-bromophenyl)ethyl)-6-(3-hydroxypropyl)-6-phenyl-1,3-oxazinan-2-one (200 mg, 0.462 mmol), tributyl-vinyl-stannane (198 mg, 0.624 mmol), $Pd_2(dba)_3$ (23 mg, 0.005 mmol) and BINAP (6.84 mg, 0.011 mmol) in toluene (20 mL) was heated to reflux overnight. The reaction mixture was filtered, and the filtrate was concentrated to give the crude product, which was purified by preparative TLC to give (R)-6-(3-hydroxypropyl)-6-phenyl-3-((S)-1-(4-vinylphenyl)ethyl)-1,3-oxazinan-2-one (50 mg, 30%). $^1$H NMR ($CDCl_3$): 0.81 (m, 2H), 1.07-1.28 (m, 5H), 1.53 (d, 3H), 1.83-1.97 (m, 4H), 2.22 (m, 3H), 2.83 (m, 1H), 3.55 (m, 2H), 5.09 (m, 1H), 5.21 (m, 1H), 5.58 (m, 1H), 6.63-6.77 (m, 2H), 7.04-28 (m, 13H), 7.43 (m, 2H), 7.68 (m, 1H).

Step 2

To a solution of (R)-6-(3-hydroxypropyl)-6-phenyl-3-((S)-1-(4-vinylphenyl)ethyl)-1,3-oxazinan-2-one (50 mg, 0.137 mmol) and imidazole (11.2 mg 0.165 mmol) in $CH_2Cl_2$ (10 mL) was added a solution of TBSCl (24.6 mg, 0.164 mmol) in $CH_2Cl_2$ (15 mL) dropwise at 0° C. The mixture was stirred overnight at rt. The mixture was filtered, and the solvent was evaporated to give (R)-6-(3-(tert-butyldimethylsilyloxy)propyl)-6-phenyl-3-((S)-1-(4-vinylphenyl)ethyl)-1,3-oxazinan-2-one (40 mg, 60%). $^1$H NMR ($CDCl_3$): 0.02 (s, 6H), 0.87 (m, 9H), 1.23 (m, 1H), 1.52 (d, 3H), 1.62 (m, 1H), 1.98 (m, 2H), 2.14-2.38 (m, 3H), 2.97 (m, 1H), 3.58 (m, 2H), 5.28 (m, 1H), 5.71 (m, 1H), 6.68 (m, 1H), 6.88 (m, 1H), 7.16 (m, 1H), 7.22-7.38 (m, 7H).

Step 3

To a solution of (R)-6-(3-(tert-butyldimethylsilyloxy)propyl)-6-phenyl-3-((S)-1-(4-vinylphenyl)ethyl)-1,3-oxazinan-2-one (20 mg, 0.042 mmol) in dry THF (10 mL) was added $BH_3$ THF (0.5 ml, 0.5 mmol) dropwise at 0° C. After stirring for 2 h at rt, the mixture was cooled to 0° C., and $H_2O$ (0.5 mL), 3 M aqueous NaOH (0.5 mL) and 30% $H_2O_2$ (0.5 mL) were added successively added. The mixture was stirred overnight at rt. The mixture was diluted with 1 M HCl, and the pH of the mixture was adjusted to 6-7 with 1 M HCl. The layers were separated, and the aqueous phase was extracted with EtOAc (3×5 mL). The combined organic layer was washed with a saturated aqueous $NaHCO_3$ solution (5 mL) and brine (5 mL), dried over $Na_2SO_4$, and concentrated in vacuo to give the crude product, which was purified by TLC and preparative HPLC to afford (R)-3-((S)-1-(4-(2-hydroxyethyl)phenyl)ethyl)-6-(3-hydroxy propyl)-6-phenyl-1,3-oxazinan-2-one (7.02 mg, 20%). LC-MS Method 2 $t_R$=1.757, min, m/z=406.2; $^1$H NMR ($CDCl_3$): 1.31 (m, 1H), 1.47 (d, 3H), 1.68 (m, 1H), 1.89 (m, 2H), 2.18 (m, 2H), 2.70 (m, 1H), 2.83 (m, 1H), 3.49 (m, 2H), 3.71 (m, 2H), 5.58 (m, 1H), 6.75 (m, 2H), 6.88 (m, 2H), 7.23 (m, 5H).

Example 199

(R)-6-(3-hydroxypropyl)-3-((S)-1-(4-(methoxymethyl)phenyl)ethyl)-6-phenyl-1,3-oxazinan-2-one

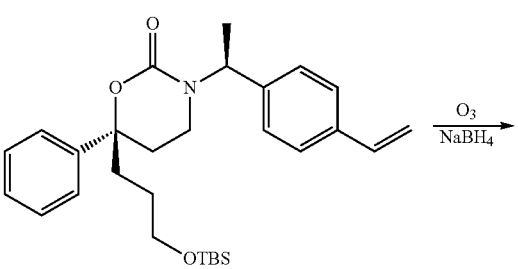

233

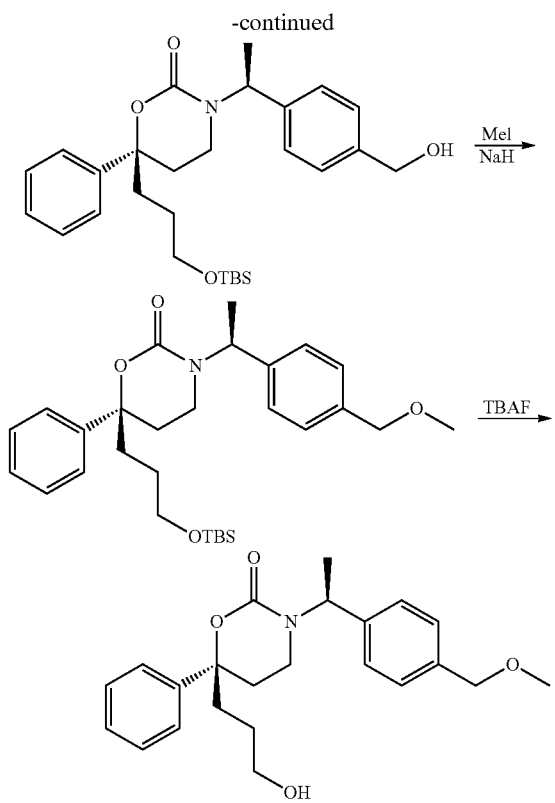

Step 1

To a solution of (R)-6-(3-(tert-butyldimethylsilyloxy)propyl)-6-phenyl-3-((S)-1-(4-vinylphenyl)ethyl)-1,3-oxazinan-2-one (40 mg, 0.08 mmol) in CH$_2$Cl$_2$ (15 mL) was treated with ozone at −78° C. until the mixture turned blue. The system was then flushed with oxygen to move excess ozone. NaBH$_4$ (12.2 mg, 0.32 mmol) was added to the mixture in portions at rt, and the mixture was stirred overnight at rt. The reaction was quenched by water, and the layers were separated. The aqueous layer was extracted with CH$_2$Cl$_2$ (2×). The organic layer was combined, washed with brine, dried over anhydrous Na$_2$SO$_4$ and concentrated to give the crude product, which was purified by preparative TLC to give (R)-6-(3-(tert-butyldimethylsilyloxy)propyl)-3-((S)-1-(4-(hydroxylmethyl)phenyl)ethyl)-6-phenyl-1,3-oxazinan-2-one (10 mg, 25%). $^1$H NMR (CDCl$_3$): 0.00 (s, 4H), 0.09 (s, 2H), 0.87 (s, 8H), 1.28 (s, 4H), 1.53 (d, 3H), 1.98 (d, 2H), 3.53 (m, 2H), 4.25 (m, 1H), 4.98 (m, 1H), 4.61 (m, 1H), 5.71 (m, 1H), 6.90 (m, 1H), 7.12-7.38 (m, 10H).

Step 2

To a solution of (R)-6-(3-(tert-butyldimethylsilyloxy)propyl)-3-((S)-1-(4-(hydroxymethyl)phenyl)ethyl)-6-phenyl-1,3-oxazinan-2-one (10 mg, 0.02 mmol) in THF (5 mL) was added NaH (1.4 mg) at 0° C. After stirring for 1 h at rt, the mixture was cooled to 0° C., and CH$_3$I (90 mg 0.78 mmol) was added. The mixture was stirred overnight at rt. The reaction was quenched with H$_2$O, and the layers were separated. The aqueous layer was extracted with CH$_2$Cl$_2$ for two times. The organic layer was combined, washed with brine, dried over Na$_2$SO$_4$ and concentrated to give the crude product, which was purified by preparative TLC to give (R)-6-(3-(tert-butyldimethylsilyloxy)propyl)-3-((S)-1-(4-(methoxymethyl)phenyl)ethyl)-6-phenyl-1,3-oxazinan-2-one (10 mg, 71%).

Step 3

To a solution of (R)-6-(3-(tert-butyldimethylsilyloxy)propyl)-3-((S)-1-(4-(methoxymethyl)phenyl)ethyl)-6-phenyl-1,3-oxazinan-2-one (7 mg, 0.02 mmol) in EtOAc (5 mL) was added TBAF (26.1 mg, 0.10 mmol) at rt, and the mixture was stirred at rt overnight. The mixture was concentrated in vacuo to give the crude product, which was purified by preparative TLC followed by preparative HPLC to afford (R)-6-(3-hydroxypropyl)-3-((S)-1-(4-(methoxymethyl)phenyl)ethyl)-6-phenyl-1,3-oxazinan-2-one (1.63 mg). LC-MS Method 3 $t_R$=0.96, min, m/z=406; $^1$H NMR (CDCl$_3$): 1.39 (m, 1H), 1.49 (m, 3H), 1.71 (m, 1H), 1.89 (m, 3H), 2.01 (m, 1H), 2.18 (m, 2H), 2.75-2.88 (m, 3H), 3.23 (m, 1H), 3.48 (m, 1H), 3.70 (m, 1H) □4.19 (m, 1H), 5.58 (m, 1H), 6.73-6.86 (m, 2H), 7.08-7.29 (m, 6H).

Example 200

3-((S)-1-(4-bromophenyl)ethyl)-6-(3-hydroxypropyl)-6-isopropyl-1,3-oxazinan-2-one

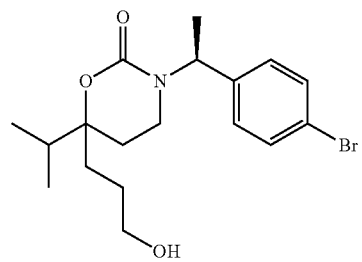 [SMILES: CC(C)C1(CCCO)CCN([C@@H](C)c2ccc(Br)cc2)C(=O)O1]

The title compound was prepared from 6-allyl-3-((S)-1-(4-bromophenyl)ethyl)-6-isopropyl-1,3-oxazinan-2-one following a procedure analogous to that described in Example 78. Two isomers were isolated.

Isomer 1: LC-MS Method 3 $t_R$=1.28, min, m/z=384, 386; $^1$H NMR (CDCl$_3$) 0.90 (m, 6H), 1.51 (m, 3H), 1.62-1.94 (m, 6H), 2.02 (m, 1H), 2.73 (m, 1H), 3.15 (m, 1H), 3.66 (m, 2H), 5.73 (m, 1H), 7.18 (m, 2H), 7.46 (m, 2H).

LC-MS Method 3 $t_R$=1.24, min, m/z=384, 386; $^1$H NMR (CDCl$_3$) 0.92 (m, 6H), 1.51 (m, 3H), 1.62 (m, 5H), 1.87 (m, 1H), 2.05 (m, 1H), 2.69 (m, 1H), 3.04 (m, 1H), 3.61 (m, 2H), 5.73 (m, 1H), 7.18 (m, 2H), 7.46 (m, 2H).

Example 201

6-(4-fluorophenyl)-6-(3-hydroxypropyl)-3-((1S)-1-(4-methoxyphenyl)ethyl)-1,3-oxazinan-2-one

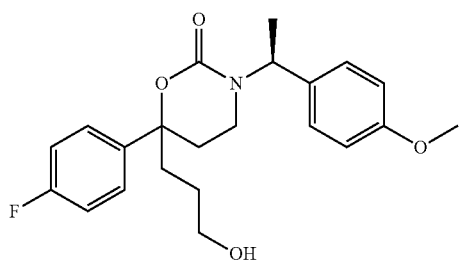 [SMILES: COc1ccc([C@H](C)N2CCC(CCCO)(c3ccc(F)cc3)OC2=O)cc1]

The title compound was prepared from 6-allyl-6-(4-fluorophenyl)-3-((S)-1-(4-methoxyphenyl)ethyl)-1,3-oxazinan-2-one following a procedure analogous to that described in Example 78. Two isomers were isolated.

Isomer 1: (R)-6-(4-fluorophenyl)-6-(3-hydroxypropyl)-3-((S)-1-(4-methoxyphenyl)ethyl)-1,3-oxazinan-2-one.
LC-MS Method 1 $t_R$=1.49, min, m/z=388; $^1$H NMR (CD$_3$OD) 7.24-7.21 (m, 2H), 7.03-6.99 (m, 2H), 6.80 (d, J=8.8 Hz, 2H), 6.60 (d, J=8.5 Hz, 2H), 5.42 (q, J=7.0 Hz, 1H), 3.64 (s, 3H), 3.39 (t, J=6.2 Hz, 2H), 2.98-2.94 (m, 1H), 2.39-2.31 (m, 1H), 2.19-2.06 (m, 2H), 1.88-1.81 (m, 2H), 1.57-1.49 (m, 1H), 1.42 (d, J=7.0 Hz, 3H), 1.27-1.18 (m, 1H).

Isomer 2: (S)-6-(4-fluorophenyl)-6-(3-hydroxypropyl)-3-((S)-1-(4-methoxyphenyl)ethyl)-1,3-oxazinan-2-one.
LC-MS Method 1 $t_R$=1.55, min, m/z=388; $^1$H NMR (CD$_3$OD) 7.31-7.27 (m, 2H), 7.15 (d, J=8.8 Hz, 2H), 7.10-7.06 (m, 2H), 6.83 (d, J=8.5 Hz, 2H), 5.49 (q, J=7.0 Hz, 1H), 3.71 (s, 3H), 3.40-3.36 (m, 2H), 2.74-2.63 (m, 3H), 2.35-2.30 (m, 1H), 2.04-1.91 (m, 1H), 1.89-1.83 (m, 2H), 1.59-1.50 (m, 1H), 1.20 (d, J=7.0 Hz, 3H).

Example 202

(R)-3-((1S)-1-(4-chlorophenyl)ethyl)-6-(4-fluorophenyl)-6-(3-hydroxypropyl)-1,3-oxazinan-2-one

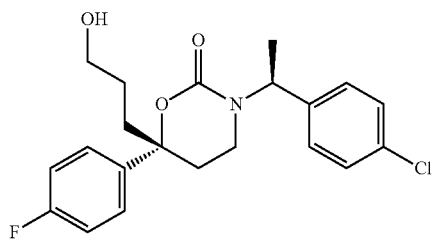 [SMILES: C[C@@H](c1ccc(Cl)cc1)N1CC[C@](CCCO)(c2ccc(F)cc2)OC1=O]

The title compound was prepared from (R)-6-allyl-3-((S)-1-(4-chlorophenyl)ethyl)-6-(4-fluorophenyl)-1,3-oxazinan-2-one following a procedure analogous to that described in Example 78. LC-MS Method 1 $t_R$=1.64, min, m/z=414; $^1$H NMR (CDCl$_3$) 7.25-7.22 (m, 2H), 7.12-7.02 (m, 4H), 6.86-6.84 (d, 2H), 5.65-5.59 (m, 1H), 3.58 (t, 2H), 2.95-2.89 (m, 1H), 2.31-2.17 (m, 3H), 2.01-1.91 (m, 2H), 1.77-1.63 (m, 1H), 1.50 (d, 3H), 1.42-1.31 (m, 1H).

Example 203

(6S)-3-((S)-1-(4-chlorophenyl)ethyl)-6-(4-fluorophenyl)-6-(2-hydroxypropyl)-1,3-oxazinan-2-one

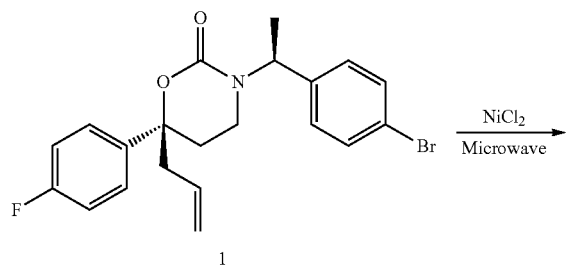

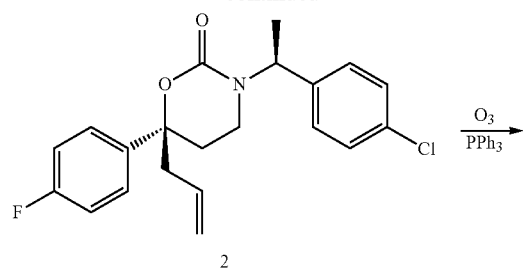

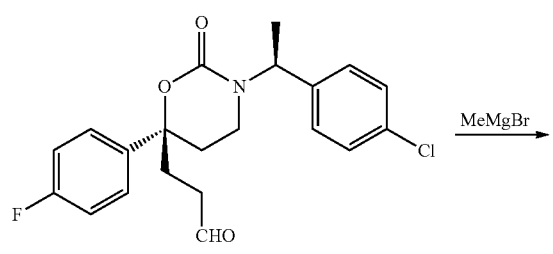

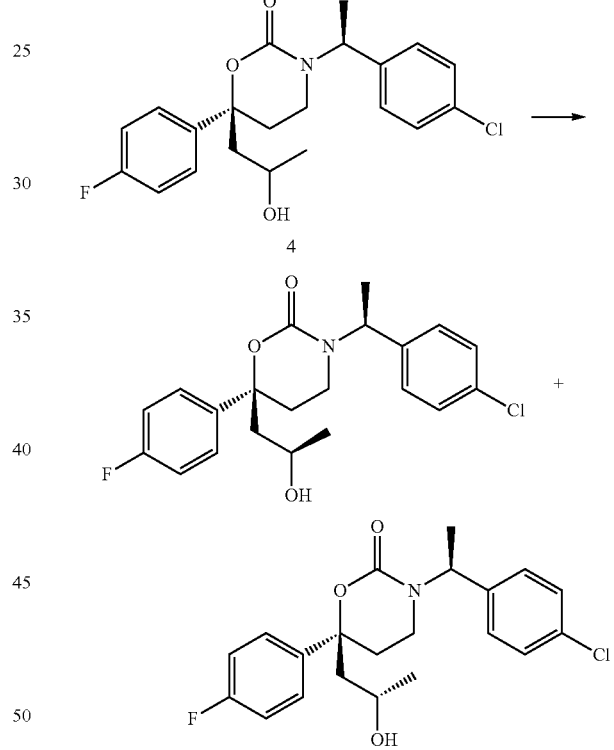

The title compound was prepared from (R)-6-allyl-3-((S)-1-(4-bromophenyl)ethyl)-6-(4-fluorophenyl)-1,3-oxazinan-2-one using a procedure analogous to that described in Example 187 Step 1, followed by a procedure analogous to that described in Example 408 Step 1, followed by a procedure analogous to that described in Example 372 Step 3. Two isomers were isolated.

Isomer 1: LC-MS Method 1 $t_R$=1.69, m/z=414.

Isomer 2: LC-MS Method 2 $t_R$=1.337 min, m/z=391.14; $^1$H NMR (CDCl$_3$) 1.05 (d, 3H), 1.48 (d, 3H), 1.55-1.71 (s, 1H), 1.84 (d, 1H), 2.00 (m, 1H), 2.15 (m, 2H) 2.30 (m, 1H) 2.83 (m, 1H), 3.85 (m, 1H), 5.56 (m, 1H), 6.79 (d, 2H), 7.03 (m, 2H) 7.21 (m, 2H).

The title compound was also isolated as a byproduct from the procedure used to prepare Example 202. LC-MS Method 1 $t_R$=1.7, min, m/z=392.

Example 204

6-allyl-3-((1S)-1-(4-bromophenyl)ethyl)-6-phenyl-1,3-oxazinan-2-one

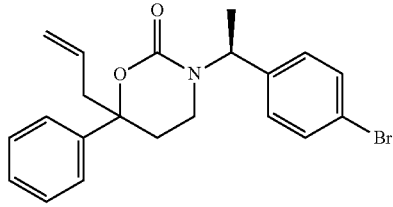 [SMILES: C=CCC1(c2ccccc2)CCN([C@@H](C)c2ccc(Br)cc2)C(=O)O1]

The title compound was prepared from 3-chloro-1-phenyl-propan-1-one following a procedure analogous to that described in Example 110. Two isomers were isolated.

Isomer 1: (R)-6-allyl-3-((S)-1-(4-bromophenyl)ethyl)-6-phenyl-1,3-oxazinan-2-one LC-MS Method 3 $t_R$=1.55, min, m/z=400, 402; $^1$H NMR (CDCl$_3$) 1.41 (m, 3H), 2.09-2.29 (m, 3H), 2.48-2.59 (m, 2H), 2.80 (m, 1H), 5.02 (m, 2H), 5.49 (m, 1H), 5.69 (m, 1H), 6.57 (m, 2H), 7.08 (m, 2H), 7.20-7.30 (m, 6H).

Isomer 2: (S)-6-allyl-3-((S)-1-(4-bromophenyl)ethyl)-6-phenyl-1,3-oxazinan-2-one LC-MS Method 2 $t_R$=1.56 min, m/z=401.9; $^1$H NMR (CDCl$_3$) 1.18-1.26 (d, 3H), 1.99-2.12 (m, 1H), 2.24 (m, 1H), 2.52-2.79 (m, 4H), 4.97-5.13 (m, 2H), 5.62-5.86 (m, 2H), 7.18 (d, 2H), 7.31 (m, 3H), 7.38 (m, 2H), 7.43 (d, 2H).

Example 205

(S)-6-(2-hydroxyethyl)-6-phenyl-3-((S)-1-(4-(pyridin-3-yl)phenyl)ethyl)-1,3-oxazinan-2-one

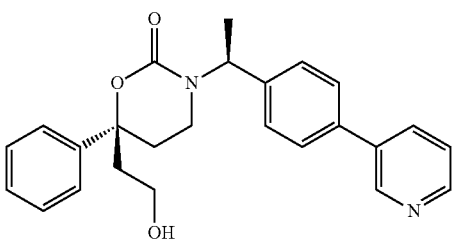 [SMILES: C[C@@H](c1ccc(-c2cccnc2)cc1)N1CC[C@](CCO)(c2ccccc2)OC1=O]

The title compound was prepared from (R)-6-allyl-3-((S)-1-(4-bromophenyl)ethyl)-6-phenyl-1,3-oxazinan-2-one and pyridine-3-boronic acid using a procedure analogous to that described in Example 64 followed by a procedure analogous to that described in Example 74. LC-MS Method 2 $t_R$=1.44, min, m/z=403; $^1$H NMR (CDCl$_3$) 1.50 (t, 3H), 1.68 (m, 2H), 1.91 (m, 2H), 2.05 (m, 1H), 2.26 (m, 2H), 2.83 (m, 1H), 3.53 (m, 2H), 5.62 (q, 1H), 6.93 (d, 2H), 7.20-7.32 (m, 8H), 7.73 (m, 1H), 8.51 (s, 1H), 8.72 (s, 1H).

Example 206

(6S)-6-(2,3-dihydroxypropyl)-6-(4-fluorophenyl)-3-((1S)-1-(4-methoxyphenyl)ethyl)-1,3-oxazinan-2-one

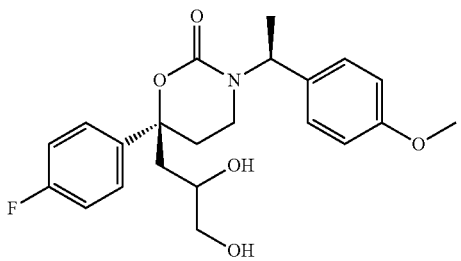 [SMILES: COc1ccc([C@H](C)N2CC[C@](CC(O)CO)(c3ccc(F)cc3)OC2=O)cc1]

The title compound was prepared from (R)-6-allyl-6-(4-fluorophenyl)-3-((S)-1-(4-methoxyphenyl)ethyl)-1,3-oxazinan-2-one following a procedure analogous to that described in Example 77. Two isomers were isolated.

Isomer 1: LC-MS Method 1 $t_R$=1.34, min, m/z=404; $^1$H NMR (CD$_3$OD) 7.30-7.27 (m, 2H), 7.03-6.99 (m, 2H), 6.74 (d, J=8.8 Hz, 2H), 6.58 (d, J=8.8 Hz, 2H), 5.39 (q, J=7.0 Hz, 1H), 3.63 (s, 3H), 3.35-3.28 (m, 3H), 3.00-2.95 (m, 1H), 2.60-2.56 (m, 1H), 2.25-2.10 (m, 2H), 2.00-1.86 (m, 2H), 1.40 (d, J=7.0 Hz, 3H).

Isomer 2: LC-MS Method 1 $t_R$=1.37, min, m/z=404; $^1$H NMR (CD$_3$OD) 7.25-7.21 (m, 2H), 7.02-6.98 (m, 2H), 6.79 (d, J=8.8 Hz, 2H), 6.59 (d, J=8.5 Hz, 2H), 5.40 (q, J=7.0 Hz, 1H), 3.74-3.68 (m, 1H), 3.63 (s, 3H), 3.23-3.16 (m, 2H), 2.95-2.90 (m, 1H), 2.39-2.32 (m, 2H), 2.11-2.04 (m, 1H), 1.95 (dd, J=14.9, 2.6 Hz, 1H), 1.82 (dd, J=15.2, 7.9 Hz, 1H), 1.40 (d, J=7.0 Hz, 3H).

Example 207

3-((S)-1-(2',4'-difluorobiphenyl-4-yl)ethyl)-6-(2-hydroxyethyl)-6-isopropyl-1,3-oxazinan-2-one

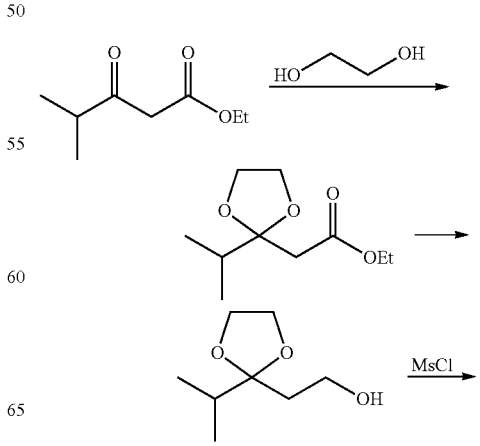

239
-continued

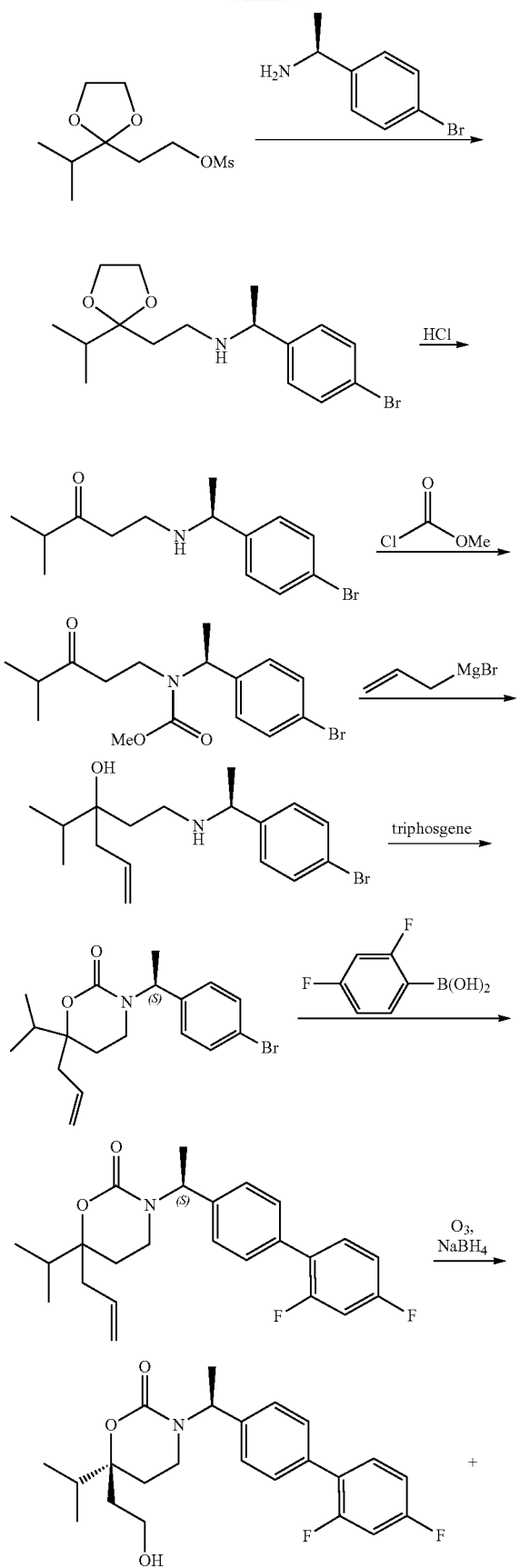

240
-continued

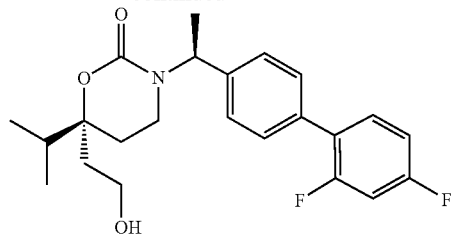

Step 1

To a solution of 4-methyl-3-oxo-pentanoic acid ethyl ester (79 g, 0.5 mol) and ethane-1,2-diol (62 g, 1 mol) in toluene (1600 mL) was added TsOH (1.9 g, 0.1 mol). The mixture was refluxed till the reaction was over. The mixture was concentrated in vacuum to give the crude (2-isopropyl-[1,3]dioxolan-2-yl)-acetic acid ethyl ester (83 g, crude), which was used for the next step without further purification.

Step 2

To a solution of (2-isopropyl-[1,3]dioxolan-2-yl)-acetic acid ethyl ester (83 g, 0.41 mol) in MeOH (1600 mL) was added $NaBH_4$ (78 g, 2.05 mol) and $ZnCl_2$ (8.3 g). The mixture was stirred overnight. The mixture was concentrated, and the residue was dissolved in the mixture of EtOAc and water. The layers were separated, and the aqueous layer was extracted with EtOAc. The combined organic phase was dried over $Na_2SO_4$, and concentrated to give the crude product, which was purified by column to give 2-(2-isopropyl-[1,3]dioxolan-2-yl)-ethanol (30 g, crude).

Step 3

To a solution of 2-(2-isopropyl-[1,3]dioxolan-2-yl)-ethanol (11 g, 0.069 mol) and TEA (20.91 g, 0.207 mol) in dried $CH_2Cl_2$ (110 mL) was added MsCl (15.8 g, 0.138 mol) dropwise at 0° C. The mixture was stirred till the reaction was over. The reaction was quenched with water. The layers were separated, and the aqueous layer was extracted with $CH_2Cl_2$. The combined organic phase was dried over $Na_2SO_4$, and concentrated to give the crude methanesulfonic acid 2-(2-isopropyl-[1,3]dioxolan-2-yl)-ethyl ester (19 g, crude), which was used for the next step without further purification.

Step 4

To a solution of methanesulfonic acid 2-(2-isopropyl-[1,3]dioxolan-2-yl)-ethyl ester (19 g, 0.08 mol) was added 1-(4-bromo-phenyl)-ethylamine (48 g, 0.24 mol). The mixture was refluxed overnight. The mixture was condensed to give the crude product, which was purified by column to give [1-(4-bromo-phenyl)-ethyl]-[2-(2-isopropyl-[1,3]dioxolan-2-yl)-ethyl]-amine (22 g, crude). $^1H$ NMR ($CDCl_3$): 0.88 (m, 6H), 1.32 (m, 3H), 1.83 (m, 3H), 2.51 (m, 2H), 3.69 (m, 1H), 3.87 (m, 4H), 7.18 (m, 2H), 7.43 (m, 2H).

Step 5

To a solution of [1-(4-bromo-phenyl)-ethyl]-[2-(2-isopropyl-[1,3]dioxolan-2-yl)-ethyl]-amine (14.5 g, 0.042 mol) in MeOH (70 mol) was added HCl (36%, 70 mol). The mixture was stirred at 65° C. till the reaction was over. The mixture was cooled to 0° C. The pH of the mixture was adjusted to 7.

The mixture was condensed, and the residue was extracted with EtOAc. The organic phase was dried over $Na_2SO_4$, and concentrated to give the crude 1-[1-(4-bromo-phenyl)-ethylamino]-4-methyl-pentan-3-one (10.3 g, crude), which was used for the next step without further purification. $^1$H NMR ($CDCl_3$): 1.08 (m, 6H), 1.35 (m, 3H), 2.51-2.70 (m, 6H), 3.72 (m, 1H), 7.19 (m, 2H), 7.42 (m, 2H).

Step 6

To a solution of 1-[1-(4-bromo-phenyl)-ethylamino]-4-methyl-pentan-3-one (3.42 g, 0.01 mol) and $K_2CO_3$ (6.9 g, 0.05 mol) in dried $CH_2Cl_2$ (50 mL) was added chloroformate (1.41 g, 0.015 mol). The mixture was refluxed overnight. The solvent was removed to give the crude product, which was purified by column to give [1-(4-bromo-phenyl)-ethyl]-(4-methyl-3-oxo-pentyl)-carbamic acid methyl ester (2.8 g, 79%). $^1$H NMR ($CDCl_3$): 1.01 (m, 6H), 1.48 (m, 3H), 2.25-2.47 (m, 2H), 2.62 (m, 1H), 3.24 (m, 2H), 5.46 (s, 1H), 7.17 (m, 2H), 7.45 (m, 2H).

Step 7

To a solution of [1-(4-bromo-phenyl)-ethyl]-(4-methyl-3-oxo-pentyl)-carbamic acid methyl ester (1.78 g, 5 mmol) in dried THF (20 mL) was added allymagnesium bromide (1 M, 25 mL, 25 mmol) dropwise at −78° C. The mixture was stirred overnight. The reaction was quenched with aqueous sat. $NH_4Cl$. The mixture was extracted with EtOAc. The organic phase was dried over $Na_2SO_4$, and condensed to give 3-{2-[1-(4-bromo-phenyl)-ethylamino]-ethyl}-2-methyl-hex-5-en-3-ol (2.2 g, crude).

Step 8

To a solution of 3-{2-[1-(4-bromo-phenyl)-ethylamino]-ethyl}-2-methyl-hex-5-en-3-ol (2.2 g, crude) and TEA (4 eq) in dried $CH_2Cl_2$ (60 mL) at 0° C. was added triphosgene (2.12 g, 7.12 mmol). The mixture was stirred at rt till the reaction was over. Water was added, and the layers were separated. The aqueous layer was extracted with $CH_2Cl_2$. The combined organic phase was washed with water, dried over $Na_2SO_4$, and condensed to give the crude product, which was purified by column to give 6-allyl-3-[1-(4-bromo-phenyl)-ethyl]-6-isopropyl-[1,3]oxazinan-2-one (500 mg, crude).

Step 9

A mixture of 6-allyl-3-[1-(4-bromo-phenyl)-ethyl]-6-isopropyl-[1,3]oxazinan-2-one (200 mg, 0.55 mmol), 2,4-difluorophenylboronic acid (104 mg, 0.66 mmol), $PdCl_2(PPh_3)_2$ (20 mg), aqueous $Cs_2CO_3$ solution (2 M, 2 mL) in 1,4-dioxane (8 mL) was heated to reflux for 2 h. The mixture was filtered, and the filtrate was extracted with EtOAc for 3 times. The combined organic layer was washed with brine, dried over $Na_2SO_4$ and concentrated to give the crude product, which was purified by preparative TLC to give 6-allyl-3-((S)-1-(2',4'-difluorobiphenyl-4-yl)ethyl)-6-isopropyl-1,3-oxazinan-2-one (160 mg, 73%). $^1$H NMR ($CDCl_3$): 0.96 (m, 6H), 1.61 (m, 3H), 1.68-2.09 (m, 3H), 2.32-2.47 (m, 2H), 2.84 (m, 1H), 3.18 (m, 1H), 5.02-5.19 (m, 2H), 5.84 (m, 2H), 6.93 (m, 2H), 7.41 (m, 3H), 7.50 (m, 2H).

Step 10

A solution of 6-allyl-3-((S)-1-(2',4'-difluorobiphenyl-4-yl)ethyl)-6-isopropyl-1,3-oxazinan-2-one (60 mg, crude) in dry $CH_2Cl_2$ (10 mL) was treated with ozone at −78° C. until the mixture turned blue. The system was then flushed with oxygen to remove excess ozone. $NaBH_4$ (29 mg, 0.75 mmol) was added to the mixture in portions at rt. The mixture was stirred overnight at rt. The mixture was quenched with water, and the layers were separated. The aqueous layer was extracted with $CH_2Cl_2$ (2×). The organic layers were combined, washed with brine, dried over anhydrous $Na_2SO_4$ and concentrated to give the crude product, which was purified by preparative TLC to give two isomers.

Isomer 1 (30 mg, 49%): LC-MS Method 3 $t_R$=1.37, min, m/z=404, 426; 1H NMR ($CDCl_3$) 0.89 (m, 6H), 1.53 (d, 3H), 1.74 (m, 4H), 2.11 (m, 1H), 2.81 (m, 1H), 3.15 (m, 1H), 3.76-4.02 (m, 2H), 5.78 (m, 1H), 6.88 (m, 2H), 7.33 (m, 3H), 7.45 (m, 2H).

Isomer 2 (10 mg, 17%): LC-MS Method 3 $t_R$=1.38, min, m/z=404, 426; $^1$H NMR ($CDCl_3$) 0.95 (m, 6H), 1.52 (d, 3H), 1.72 (m, 2H), 1.84 (m, 2H), 2.05 (m, 1H), 2.79 (m, 1H), 3.08 (m, 1H), 3.77 (m, 2H), 5.76 (m, 1H), 6.86 (m, 2H), 7.35 (m, 3H), 7.42 (m, 2H).

Example 208 tert-butyl 3-(6-(3-hydroxypropyl)-2-oxo-6-phenyl-1,3-oxazinan-3-yl)pyrrolidine-1-carboxylate

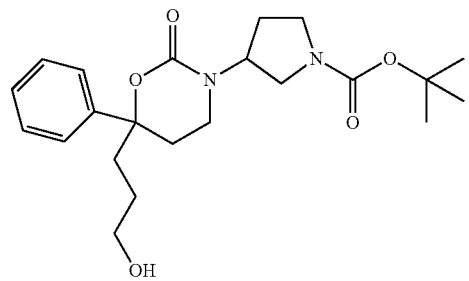 [SMILES: CC(C)(C)OC(=O)N1CCC(N2CCC(CCCO)(c3ccccc3)OC2=O)C1]

(3S)-tert-butyl 3-(6-(3-hydroxypropyl)-2-oxo-6-phenyl-1,3-oxazinan-3-yl)pyrrolidine-1-carboxylate was prepared using a procedure analogous to that described in Example 110 using 3-chloro-1-phenylpropan-1-one in Step 1 and (S)-tert-butyl 3-isocyanatopyrrolidine-1-carboxylate in Step 2 followed by a procedure analogous to that described in Example 78. Two isomers were isolated.

Isomer 1: LC-MS Method 2 $t_R$=2.033, min, m/z=305.2; $^1$H NMR ($CDCl_3$) 1.18 (m, 1H), 1.33 (s, 9H), 1.64 (m, 1H), 1.81-2.09 (m, 4H), 2.16 (m, 1H), 2.29 (m, 1H), 2.73 (m, 1H), 2.80-2.97 (m, 1H), 3.04 (m, 1H), 3.22 (m, 1H), 3.35 (m, 2H), 3.51 (t, 2H), 4.78 (m, 1H), 7.20 (m, 3H), 7.31 (m, 2H).

Isomer 2: LC-MS Method 2 $t_R$=1.244, min, m/z=304.9; $^1$H NMR ($CDCl_3$) 1.28 (m, 1H), 1.46 (s, 9H), 1.39 (m, 1H), 1.63 (m, 2H), 1.81 (m, 1H), 1.92 (m, 2H), 2.14 (m, 1H), 2.31 (m, 1H), 2.71 (m, 1H), 3.03 (m, 1H), 3.16 (m, 2H), 3.48-3.58 (m, 3H), 4.78 (m, 1H), 7.20-7.27 (m, 3H), 7.29-7.36 (m, 2H).

(3R)-tert-butyl 3-(6-(3-hydroxypropyl)-2-oxo-6-phenyl-1,3-oxazinan-3-yl)pyrrolidine-1-carboxylate was prepared as described immediately above using (R)-tert-butyl 3-isocyanatopyrrolidine-1-carboxylate to afford two isomers.

Isomer 3: LC-MS Method 3 tR=1.09, min, m/z=305, 427; 1H NMR (CDCl3) 1.38 (s, 9H), 1.63-1.70 (m, 2H), 1.80 (m, 1H), 1.95 (m, 2H), 2.16 (m, 1H), 2.30 (m, 1H), 2.71 (m, 1H), 3.0-3.30 (m, 3H), 3.52 (m, 3H), 4.82 (m, 1H), 7.20-7.27 (m, 3H), 7.28-7.39 (m, 2H).

Isomer 4: LC-MS Method 2 tR=2.03, min, m/z=405, 427; 1H NMR (CDCl3) 1.29 (m, 1H), 1.33 (s, 9H), 1.68 (m, 1H), 1.81-2.09 (m, 4H), 2.10-2.22 (m, 1H), 2.31 (m, 1H), 2.72 (m, 1H), 2.78-2.99 (m, 1H), 2.99-3.12 (m, 1H), 3.21 (m, 1H), 3.30-3.48 (m, 2H), 3.50 (m, 2H), 4.79 (m, 1H), 7.22 (m, 3H), 7.32 (m, 2H).

Example 209

N-(2-((S)-3-((S)-1-(2',4'-difluorobiphenyl-4-yl)ethyl)-6-(4-fluorophenyl)-2-oxo-1,3-oxazinan-6-yl)ethyl)methanesulfonamide

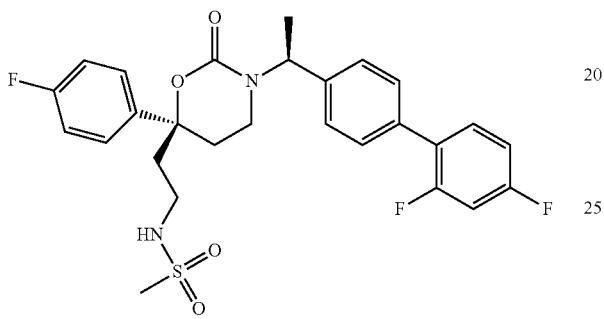

The title compound was prepared from (R)-6-(2-aminoethyl)-3-((S)-1-(2',4'-difluorobiphenyl-4-yl)ethyl)-6-(4-fluorophenyl)-1,3-oxazinan-2-one following a procedure analogous to that described in Example 99. LC-MS Method 3 $t_R$=1.45, min, m/z=533; $^1$H NMR (CDCl$_3$) 1.52-1.57 (d, 3H), 2.10-2.34 (m, 5H), 2.86 (s, 3H), 2.92-2.99 (m, 1H), 3.00-3.08 (m, 1H), 3.11-3.21 (m, 1H), 4.48-4.57 (s, 1H), 5.63-5.71 (m, 1H), 6.83-6.94 (m, 2H), 6.98-7.09 (m, 4H), 7.17-7.21 (m, 1H), 7.24-7.32 (m, 3H).

Example 210

(R)-6-(3-hydroxypropyl)-6-phenyl-3-((S)-1-(4-(pyridin-4-yl)phenyl)ethyl)-1,3-oxazinan-2-one

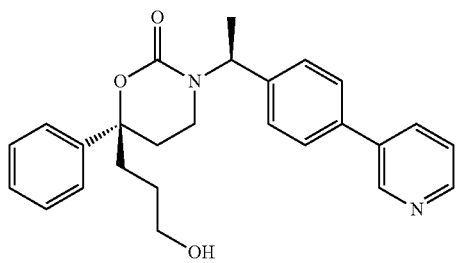 [SMILES: C[C@@H](c1ccc(-c2cccnc2)cc1)N1CC[C@](CCCO)(c2ccccc2)OC1=O]

The title compound was prepared from (R)-6-allyl-3-((S)-1-(4-bromophenyl)ethyl)-6-phenyl-1,3-oxazinan-2-one and pyridine-4-boronic acid using a procedure analogous to that described in Example 64 followed by a procedure analogous to that described in Example 74. LC-MS Method 2 $t_R$=2.2, min, m/z=417; $^1$H NMR (CDCl$_3$) 1.48 (m, 2H), 1.50 (t, 2H), 1.92 (m, 2H), 2.28 (m, 3H), 2.89 (m, 1H), 3.53 (m, 3H), 5.66 (m, 1H), 6.99 (m, 2H), 7.28 (q, 8H), 7.52 (d, 2H), 8.51 (m, 1H), 8.63 (m, 1H).

Example 211

(R)-6-(3-hydroxypropyl)-6-phenyl-3-((S)-1-(4-(pyridin-3-yl)phenyl)ethyl)-1,3-oxazinan-2-one

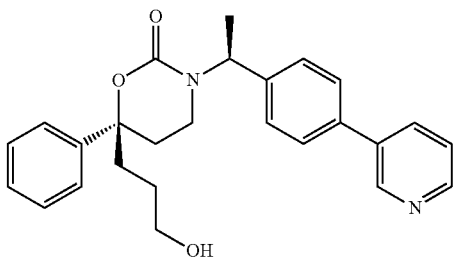

The title compound was prepared from (R)-6-allyl-3-((S)-1-(4-bromophenyl)ethyl)-6-phenyl-1,3-oxazinan-2-one and pyridine-3-boronic acid using a procedure analogous to that described in Example 64 followed by a procedure analogous to that described in Example 78. LC-MS Method 2 $t_R$=1.5, min, m/z=417; $^1$H NMR (CDCl$_3$) 1.32 (m, 2H), 1.50 (t, 3H), 1.68 (m, 2H), 1.91 (m, 2H), 2.15 (m, 1H), 2.26 (m, 2H), 2.83 (m, 1H), 3.51 (m, 2H), 5.62 (q, 1H), 6.93 (d, 2H), 7.20-7.32 (m, 8H), 7.73 (m, 1H), 8.51 (s, 1H), 8.72 (s, 1H).

Example 212

3-((1S)-1-(2',4'-difluorobiphenyl-4-yl)ethyl)-6-(3-hydroxypropyl)-6-isopropyl-1,3-oxazinan-2-one

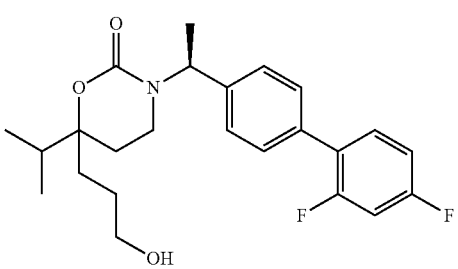 [SMILES: CC(C)C1(CCCO)CCN([C@@H](C)c2ccc(-c3ccc(F)cc3F)cc2)C(=O)O1]

The title compound was prepared from 6-allyl-3-((S)-1-(2',4'-difluorobiphenyl-4-yl)ethyl)-6-isopropyl-1,3-oxazinan-2-one following a procedure analogous to that described in Example 211. Two isomers were isolated.

Isomer 1: LC-MS Method 3 $t_R$=1.42, min, m/z=418; $^1$H NMR (CDCl$_3$) 0.91 (m, 6H), 1.58 (m, 3H), 1.62-1.95 (m, 6H), 2.03 (m, 1H), 2.82 (m, 1H), 3.19 (m, 1H), 3.67 (m, 2H), 5.82 (m, 1H), 6.93 (m, 2H), 7.39 (m, 3H), 7.47 (m, 2H).

Isomer 2: LC-MS Method 3 tR=1.42, min, m/z=418; 1H NMR (CDCl3) 0.89 (m, 6H), 1.52 (m, 3H), 1.62 (m, 5H), 1.84

(m, 1H), 2.03 (m, 1H), 2.72 (m, 1H), 3.03 (m, 1H), 3.57 (m, 2H), 5.79 (m, 1H), 6.86 (m, 2H), 7.32 (m, 3H), 7.43 (m, 2H).

Example 213

3-((1S)-1-(2',4'-difluorobiphenyl-4-yl)ethyl)-6-(2-hydroxypropyl)-6-isopropyl-1,3-oxazinan-2-one

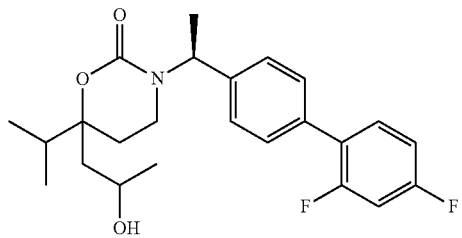 [SMILES: CC(O)CC1(C(C)C)CCN([C@@H](C)c2ccc(-c3ccc(F)cc3F)cc2)C(=O)O1]

The title compound was isolated as a byproduct from the procedure described in Example 212. LC-MS Method 3 $t_R$=1.48, min, m/z=418; $^1$H NMR (CDCl$_3$) 0.83-0.97 (m, 6H), 1.13 (m, 3H), 1.33-1.46 (m, 1H), 1.52 (m, 3H), 1.56 (m, 1H), 1.73-1.94 (m, 3H), 2.09 (m, 1H), 2.81 (m, 1H), 3.02-3.14 (m, 1H), 3.98-4.15 (m, 1H), 5.76 (m, 1H), 6.88 (m, 2H), 7.35 (m, 3H), 7.44 (m, 2H).

Example 214

(S)-6-(4-fluorophenyl)-6-(2-hydroxyethyl)-3-((S)-1-(4-(pyridin-3-yl)phenyl)ethyl)-1,3-oxazinan-2-one

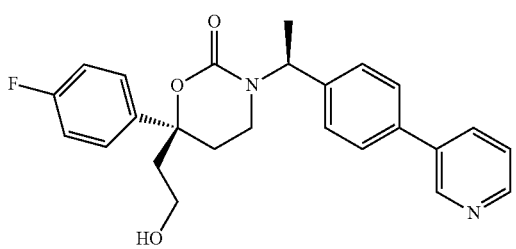 [SMILES: C[C@@H](c1ccc(-c2cccnc2)cc1)N1CC[C@](CCO)(c2ccc(F)cc2)OC1=O]

The title compound was prepared from (R)-6-allyl-3-((S)-1-(4-bromophenyl)ethyl)-6-(4-fluorophenyl)-1,3-oxazinan-2-one and pyridine-3-boronic acid using a procedure analogous to that described in Example 64 followed by a procedure analogous to that described in Example 74. LC-MS Method 2 $t_R$=1.412, min, m/z=421.2; $^1$H NMR (CDCl$_3$) 1.52 (d, 3H), 2.03-2.17 (m, 3H), 2.22-2.32 (m, 3H), 2.81 (m, 1H), 3.47-3.52 (m, 1H), 3.72 (m, 1H), 5.63 (m, 1H), 6.93-7.01 (m, 4H), 7.21-7.26 (m, 2H), 7.28-7.33 (m, 3H), 7.73 (m, 1H), 8.51 (m, 1H), 8.68 (m, 1H).

Example 215

(R)-6-allyl-6-(4-fluorophenyl)-3-((S)-1-(4-(5-methyl-1,3,4-oxadiazol-2-yl)phenyl)ethyl)-1,3-oxazinan-2-one

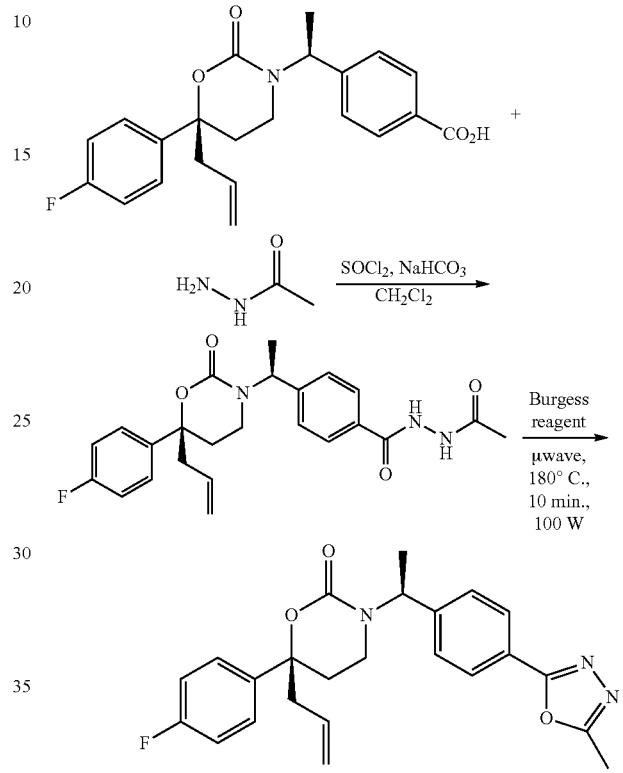

Step 1

4-((S)-1-((R)-6-allyl-6-(4-fluorophenyl)-2-oxo-1,3-oxazinan-3-yl)ethyl)benzoic acid (40 mg, 0.104 mmol) was dissolved in CH$_2$Cl$_2$ (6 mL). At 0° C., thionyl chloride (1 mL, excess) was added slowly. After 10 min., the mixture was warmed up to rt and stirred 1 h at rt The mixture was concentrated and redissolved in CH$_2$Cl$_2$ (6 mL). NaHCO$_3$ (22 mg, 2.5 equiv.) and acetohydrazide (12 mg, 1.5 equiv.) were added slowly. After stirring 1 h at rt, LC-MS found reaction completed. The mixture was diluted with CH$_2$Cl$_2$ (10 mL), filtered NaHCO$_3$ and washed by water (5 mL), 5% aq HCl (2×5 mL), satd aq NaHCO$_3$ (4 mL), brine (4 mL) and dried over Na$_2$SO$_4$. After filtration and concentration, the crude N'-acetyl-4-((S)-1-((R)-6-allyl-6-(4-fluorophenyl)-2-oxo-1,3-oxazinan-3-yl)ethyl)benzohydrazide (34 mg, 74%) was used for next step without further purification.

Step 2

Crude N'-acetyl-4-((S)-1-((R)-6-allyl-6-(4-fluorophenyl)-2-oxo-1,3-oxazinan-3-yl)ethyl)benzohydrazide (5 mg, 0.0114 mmol) was mixed with Burgess reagent (~4 mg, excess), dry THF (1 mL) and put into Microwave Oven, heated to 180° C. for 10 min. at 100 W. LC-MS found reaction completed. The mixture was diluted with EtOAc (8 mL), washed with water (2×3 mL), concentrated and purified by prep HPLC to afford (R)-6-allyl-6-(4-fluorophenyl)-3-((S)-1-(4-(5-methyl-1,3,4-oxadiazol-2-yl)phenyl)ethyl)-1,3-oxazinan-2-one (1.4 mg, 29%). LC-MS Method 1 $t_R$=1.61, min, m/z=422; $^1$H NMR (CDCl$_3$) 7.77 (d, 2H), 7.26 (m, 3H), 7.01 (m, 3H), 5.70 (m, 2H), 5.07 (dd, 2H), 2.98 (m, 1H), 2.62 (s, 3H), 1.55 (d, 3H).

Example 216

(R)-6-(3-hydroxypropyl)-6-phenyl-3-((S)-1-(4-(thiophen-2-yl)phenyl)ethyl)-1,3-oxazinan-2-one

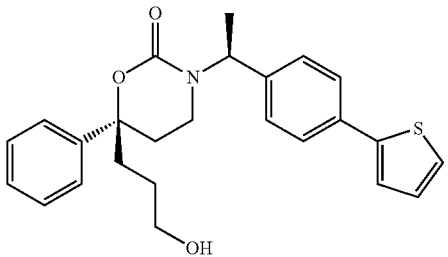 [SMILES: C[C@@H](c1ccc(-c2cccs2)cc1)N1CC[C@](CCCO)(c2ccccc2)OC1=O]

The title compound was prepared from (R)-6-allyl-6-phenyl-3-((S)-1-(4-(thiophen-2-yl)phenyl)ethyl)-1,3-oxazinan-2-one and thiophene-2-boronic acid using a procedure analogous to that described in Example 64 followed by a procedure analogous to that described in Example 78. LC-MS Method 2 $t_R$=2.47, min, m/z=422; $^1$H NMR (CDCl$_3$) 1.49 (d, 3H), 1.84-1.92 (m, 2H), 2.0-2.15 (m, 4H), 2.25 (m, 2H), 2.84 (m, 1H), 3.52 (m, 1H), 4.20 (m, 1H), 5.60 (m, 1H), 6.82 (dd, 2H), 7.0 (m, 1H), 7.15-7.38 (m, 9H).

Example 217

(R)-6-allyl-6-(4-fluorophenyl)-3-((S)-1-(4-morpholinophenyl)ethyl)-1,3-oxazinan-2-one

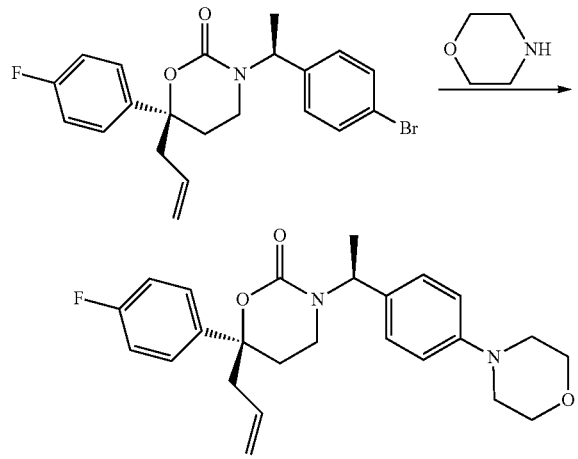

A flask was charged with (R)-6-allyl-3-((S)-1-(4-bromophenyl)ethyl)-6-(4-fluorophenyl)-1,3-oxazinan-2-one (400 mg, 0.96 mmol), morpholine (100 mg, 1.15 mmol) and t-BuONa (129 mg, 1.34 mmol) and Pd$_2$(dba)$_3$ (9 mg, 0.01 mmol) and BINAP (6 mg, 0.01 mmol) and toluene. The flask was heated to 80° C. and stirred overnight. The reaction mixture was concentrated to leave a residue, which was purified by preparative TLC to give (R)-6-allyl-6-(4-fluorophenyl)-3-((S)-1-(4-morpholinophenyl)ethyl)-1,3-oxazinan-2-one (162 mg, 0.4 mmol). LC-MS Method 3 $t_R$=1.29, min, m/z=425; $^1$H NMR (CD$_3$OD): 1.50 (m, 3H), 2.20 (m, 2H), 2.40 (m, 1H), 2.60 (m, 2H), 3.00 (m, 5H), 3.85 (m, 4H), 5.00 (m, 2H), 5.45 (m, 1H), 5.65 (m, 1H), 6.70 (m, 2H), 6.90 (m, 2H), 7.05 (m, 2H), 7.30 (m, 2H).

Example 218

(S)-3-((S)-1-(4'-fluorobiphenyl-4-yl)ethyl)-6-(2-hydroxyethyl)-6-(thiophen-2-yl)-1,3-oxazinan-2-one

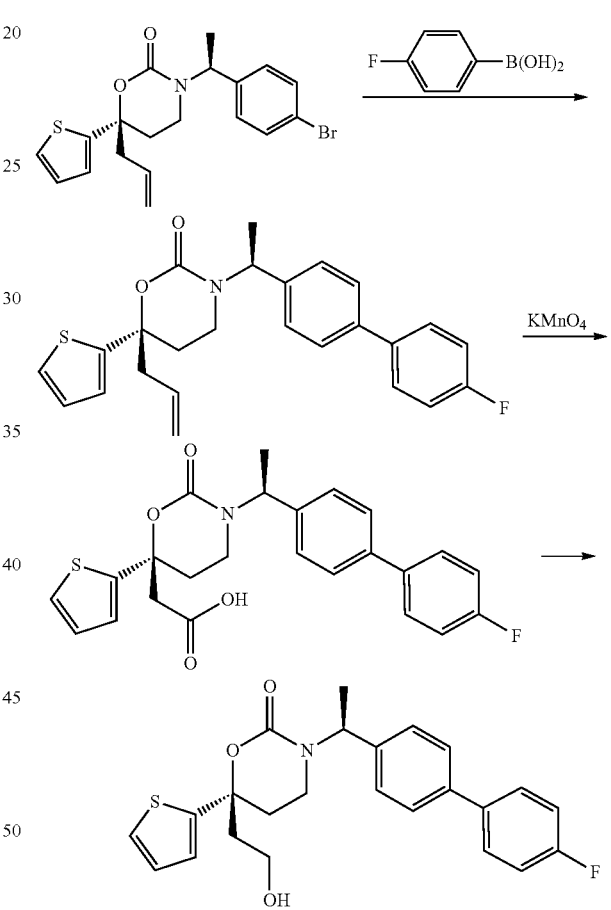

Step 1

Pd(PPh$_3$)$_2$Cl$_2$ (100 mg) was added to the solution of (R)-6-allyl-3-((S)-1-(4-bromophenyl)ethyl)-6-(thiophen-2-yl)-1,3-oxazinan-2-one (1.0 g, 2.5 mmol), 4-fluorophenylboronic acid (420 mg, 3.0 mmol) in 1,4-dioxane. Cs$_2$CO$_3$ (5 mL) was slowly added. The mixture was heated to reflux for 2 h. The mixture was quenched with water and separated, extracted with EtOAc twice, dried over anhydrous Na$_2$SO$_4$ and concentrated to afford the residue, which was purified by TLC to give (R)-6-allyl-3-((S)-1-(4'-fluorobiphenyl-4-yl)ethyl)-6-(thiophen-2-yl)-1,3-oxazinan-2-one (768 mg, 73%).

Step 2

To a solution of (R)-6-allyl-3-((S)-1-(4'-fluorobiphenyl-4-yl)ethyl)-6-(thiophen-2-yl)-1,3-oxazinan-2-one (300 mg, 0.71 mmol) was added aqueous solution of KMnO₄ (66 mg, 0.42 mmol) and NaIO₄ (537 mg, 2.52 mmol). The reaction mixture was stirred at rt overnight. The reaction mixture was filtered and concentrated, then extracted with CH₂Cl₂. The organic phases was dried over Na₂SO₄, filtered and concentrated to afford 2-((S)-3-((S)-1-(4'-fluorobiphenyl-4-yl)ethyl)-2-oxo-6-(thiophen-2-yl)-1,3-oxazinan-6-yl)acetic acid (218 mg, 70%).

Step 3

A solution of 2-((S)-3-((S)-1-(4'-fluorobiphenyl-4-yl)ethyl)-2-oxo-6-(thiophen-2-yl)-1,3-oxazinan-6-yl)acetic acid (218 mg, 0.5 mmol) in THF anhydrous (10 mL) was added BH₃ (3.0 mL) at 0□ and then stirred at reflux for 2 h. Then the reaction mixture quenched by water and separated, extracted with EtOAc twice. The organic phases was dried over Na₂SO₄, filtered and concentrated to afford the residue, which was purified by TLC to give (S)-3-((S)-1-(4'-fluorobiphenyl-4-yl)ethyl)-6-(2-hydroxyethyl)-6-(thiophen-2-yl)-1,3-oxazinan-2-one (85 mg, 40%). LC-MS Method 3 $t_R$=1.35, min, m/z=426, 448; ¹H NMR (CD₃OD): 1.50 (m, 3H), 2.15 (m, 2H), 2.30 (m, 1H), 2.40 (m, 1H), 2.60 (m, 1H), 3.15 (m, 1H), 3.45 (m, 1H), 3.70 (m, 1H), 5.60 (m, 1H), 6.90 (m, 1H), 7.00 (m, 1H), 7.10 (m, 4H), 7.35 (m, 3H), 7.55 (m, 2H).

(R)-3-((S)-1-(4'-fluorobiphenyl-4-yl)ethyl)-6-(2-hydroxyethyl)-6-(thiophen-2-yl)-1,3-oxazinan-2-one was prepared following a procedure analogous to that described immediately above. LC-MS Method 3 $t_R$=1.4, min, m/z=426, 448; ¹H NMR (CD₃OD) 1.38 (d, 3H), 2.01 (m, 1H), 2.18 (m, 3H), 2.41 (m, 1H), 2.86 (m, 1H), 3.02 (m, 1H), 3.41 (m, 1H), 3.72 (m, 1H), 5.62 (m, 1H), 6.98 (m, 1H), 7.03 (m, 1H), 7.15 (m, 1H), 7.36 (m, 3H), 7.58 (m, 4H).

Example 219

3-((R)-3-((S)-1-(4'-fluorobiphenyl-4-yl)ethyl)-2-oxo-6-phenyl-1,3-oxazinan-6-yl)propanenitrile

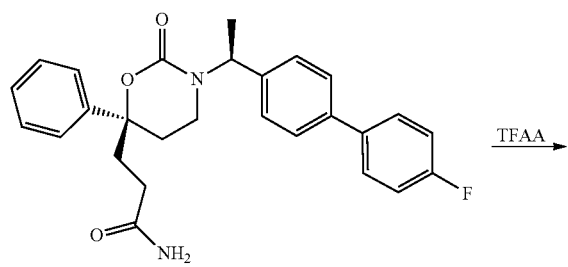

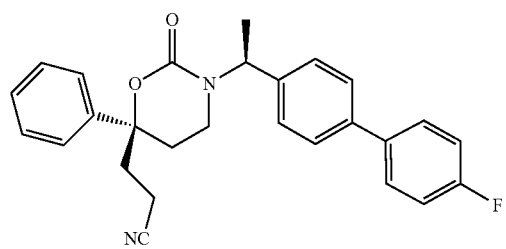

To a solution of 3-((R)-3-((S)-1-(4'-fluorobiphenyl-4-yl)ethyl)-2-oxo-6-phenyl-1,3-oxazinan-6-yl)propanamide (110 mg, 0.25 mmol) and DIEA (170 mg, 1.05 mmol) in anhydrous CH₂Cl₂ (5 mL) was added TFAA (158 mg, 0.75 mmol) at 0° C. The mixture was stirred for 2 h. The solvent was removed under reduced pressure, and the residue was purified by preparative HPLC to afford 3-((R)-3-((S)-1-(4'-fluorobiphenyl-4-yl)ethyl)-2-oxo-6-phenyl-1,3-oxazinan-6-yl)propanenitrile (8 mg, yield 10%). LC-MS Method 3 $t_R$=1.458, min, m/z=429.2; ¹H NMR (CDCl₃): 1.52 (d, 3H), 2.01 (m, 1H), 2.14 (m, 2H), 2.29 (m, 3H), 2.53 (m, 2H), 2.90 (m, 1H), 5.62 (m, 1H), 6.93 (m, 2H), 7.04 (m, 2H), 7.16-7.25 (m, 2H), 7.30-7.47 (m, 5H).

Example 220

(R)-3-((S)-1-(4-bromophenyl)propyl)-6-(3-hydroxypropyl)-6-phenyl-1,3-oxazinan-2-one

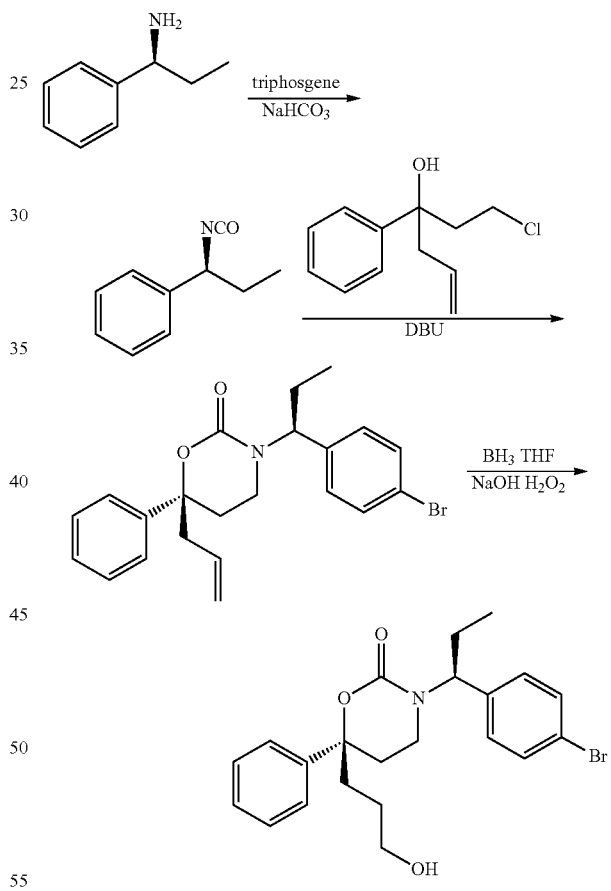

Step 1

To a solution of (S)-1-phenylpropan-1-amine (3.00 g, 14 mmol) in the mixture of methylene chloride (50 mL) and saturated NaHCO₃ (50 mL) was added triphosgene (1.40 g, 4.60 mmol) at 0° C. The mixture was stirred for 15 minutes. The organic phase was separated, dried and concentrated to give (S)-(1-isocyanatopropyl)benzene (3.0 g, 88%). ¹H NMR (CDCl₃): δ=0.93 (q, 3H), 1.81 (m, 2H), 4.50 (m, 1H), 7.13 (m, 2H), 7.22 (m, 1H), 7.50 (m, 2H).

Step 2

A mixture of (S)-(1-isocyanatopropyl)benzene (3.0 g, 12.5 mmol), 1-chloro-3-phenylhex-5-en-3-ol (3.6 g, 12.5 mmol) and DBU (3.80 g, 25 mmol) in tetrahydrofuran (20 mL) was heated to reflux overnight. The mixture was washed by 1 N HCl and extracted with EtOAc. The organic phase was concentrated to give the crude product which was purified by column chromatography to give (R)-6-allyl-3-((S)-1-(4-bromophenyl)propyl)-6-phenyl-1,3-oxazinan-2-one (1.0 g, 20%). $^1$H NMR (400 MHz, CDCl$_3$): δ=0.92 (t, 3H), 1.72-2.00 (m, 4H), 2.06-2.31 (m, 4H), 2.53 (m, 2H), 2.82 (m, 1H), 4.99 (m, 2H), 5.32 (m, 1H), 5.69 (m, 1H), 6.72 (m, 1H), 7.12 (m, 4H), 7.25 (m, 4H).

Step 3

To a solution of (R)-6-allyl-3-((S)-1-(4-bromophenyl)propyl)-6-phenyl-1,3-oxazinan-2-one (100 mg, 0.242 mmol) in tetrahydrofuran (10 mL) was added BH$_3$ THF (3 mL, 1 mol/L) at 0° C. under nitrogen. The formed mixture was stirred for 2 h. Then the reaction was quenched by water, followed by 3 mol/L NaOH and H$_2$O$_2$ (3 mL). The PH of the mixture was adjusted to <7 with 5% HCl. The organic phase was separated, extracted by EtOAc, and concentrated to give the crude product, which was purified by preparative HPLC to give (R)-3-((S)-1-(4-bromophenyl)propyl)-6-(3-hydroxypropyl)-6-phenyl-1,3-oxazinan-2-one (15 mg, 15%). LC-MS Method 3 t$_R$=1.36, min, m/z=432, 434; $^1$H NMR (CDCl$_3$): δ=0.99 (t, 3H), 1.29 (m, 1H), 1.63 (m, 1H), 1.98 (m, 4H), 2.20-2.42 (m, 2H), 2.48 (m, 1H), 3.08 (m, 1H), 3.49 (m, 1H), 5.30 (m, 1H), 6.92 (m, 2H), 7.26 (m, 4H), 7.35 (m, 2H).

Example 221

(R)-6-(3-hydroxypropyl)-3-((S)-1-(4-(6-oxo-1,6-dihydropyridin-3-yl)phenyl)ethyl)-6-phenyl-1,3-oxazinan-2-one

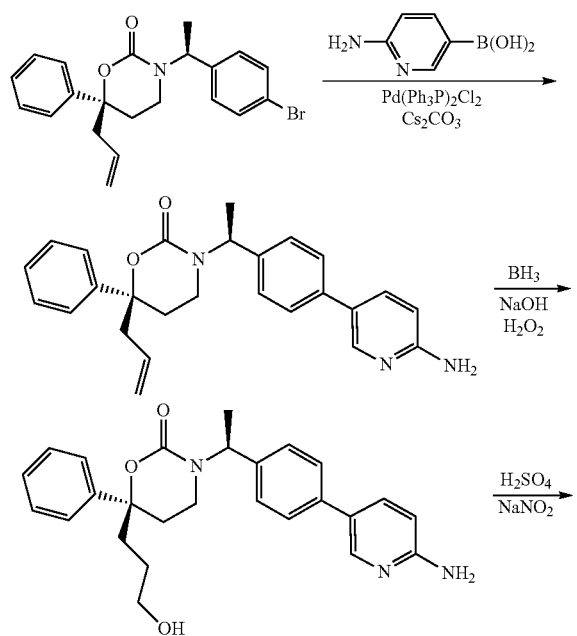

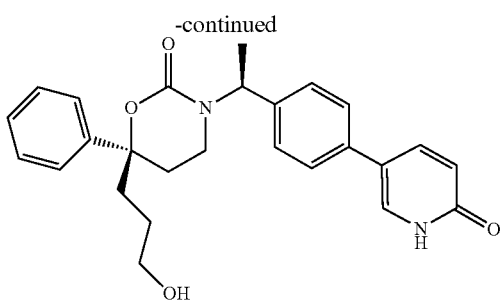

Step 1

A mixture of (R)-6-allyl-3-((S)-1-(4-bromophenyl)ethyl)-6-phenyl-1,3-oxazinan-2-one (150 mg, 0.375 mmol) and 6-aminopyridin-3-ylboronic acid (56 mg, 0.45 mmol), Pd(Ph$_3$P)$_2$Cl$_2$ (15 mg), and aqueous Cs$_2$CO$_3$ solution (0.5 mL, 2 M) in 1,4-dioxane (10 mL) was stirred and heated to reflux for 2 h. The organic phase was separated, and concentrated to give the crude product, which was purified by preparative HPLC to give (R)-6-allyl-3-((S)-1-(4-(6-aminopyridin-3-yl)phenyl)ethyl)-6-phenyl-1,3-oxazinan-2-one (90 mg, 60%).

Step 2

To a solution of (R)-6-allyl-3-((S)-1-(4-(6-aminopyridin-3-yl)phenyl)ethyl)-6-phenyl-1,3-oxazinan-2-one (90 mg, 0.23 mmol) in tetrahydrofuran (10 mL) was added BH$_3$ THF (3.0 mL, 1 mol/L, 4 mmol) at 0° C. under nitrogen atmosphere. The formed mixture was stirred for 2 h. The reaction was quenched by water. Then NaOH (2 mL, 3 mol/L) and H$_2$O$_2$ (1 mL) was added to the above mixture. When the reaction was over, the mixture was extracted with EtOAc. The combined organic phase was concentrated to give the crude product, which was purified by preparative HPLC to give (R)-3-((S)-1-(4-(6-aminopyridin-3-yl)phenyl)ethyl)-6-3-hydroxypropyl)-6-phenyl-1,3-oxazinan-2-one (40 mg, 41%).

Step 3

(R)-3-((S)-1-(4-(6-aminopyridin-3-yl)phenyl)ethyl)-6-(3-hydroxypropyl)-6-phenyl-1,3-oxazinan-2-one (40 mg, 0.09 mmoL) was dissolved in 3.5 M H$_2$SO$_4$ (10 mL), and 2 M NaNO$_2$ (10 mL) was added at 0° C. The reaction mixture was stirred at rt for 2 h and treated with NaOH solution. The mixture was extracted with EtOAc. The combined organic layer was washed with brine, dried over anhydrous Na$_2$SO$_4$, and concentrated to afford the residue, which was purified by preparative HPLC to give (R)-6-(3-hydroxypropyl)-3-((S)-1-(4-(6-oxo-1,6-dihydropyridin-3-yl)phenyl)ethyl)-6-phenyl-1,3-oxazinan-2-one (10 mg, 20%). LC-MS Method 2 t$_R$=1.66, min, m/z=433, 455; $^1$H NMR (CDCl$_3$): 1.36 (m, 2H), 1.50 (m, 3H), 1.68 (m, 2H), 1.92 (m, 2H), 2.10-2.30 (m, 3H), 2.84 (m, 1H), 3.50 (m, 2H), 5.12 (m, 1H), 6.62 (m, 1H), 6.86 (m, 2H), 7.08 (m, 2H), 7.18-7.32 (m, 5H), 7.46 (m, 1H), 7.62 (m, 1H).

Example 222

3-(4-((S)-1-((R)-6-(3-hydroxypropyl)-2-oxo-6-phenyl-1,3-oxazinan-3-yl)ethyl)phenyl)pyridine 1-oxide

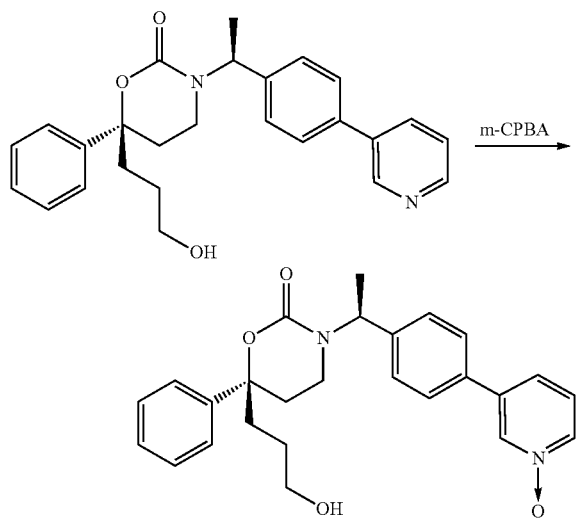

A mixture of (R)-1-((S)-1-(4'-fluorobiphenyl-4-yl)ethyl)-4-(4-fluorophenyl)-4-(3-hydroxypropyl)tetra-hydropyrimidin-2(1H)-one (30 mg, 0.07 mmol) and 3-chloro-perbenzoic acid (84 mg, 0.49 mmol) in THF (1.5 mL) was stirred at rt for 3 h. Satd aq NaHCO₃ was added to the reaction mixture, and the organic layer was separated. The organic layer was washed with brine, dried over Na₂SO₄ and concentrated to give the crude product, which was purified by preparative HPLC to give 3-(4-((S)-1-((R)-6-(3-hydroxypropyl)-2-oxo-6-phenyl-1,3-oxazinan-3-yl)ethyl)phenyl)pyridine 1-oxide (2.83 mg, 9%). LC-MS Method 2 $t_R$=1.623, min, m/z=433.2; ¹H NMR (400 MHz, CDCl₃): δ=1.54 (t, 3H), 1.94 (m, 2H), 2.21-2.24 (m, 2H), 2.35-2.39 (m, 2H), 2.49 (m, 1H), 3.1 (m, 1H), 3.44 (m, 1H), 5.57 (m, 1H), 7.07 (m, 2H), 7.28-7.42 (m, 6H), 7.58 (m, 1H), 7.77 (m, 1H), 8.19 (m, 1H), 8.28 (m, 1H), 8.49 (m, 1H).

Example 223

3-((1S)-1-(2',4'-difluorobiphenyl-4-yl)ethyl)-6-(2,3-dihydroxypropyl)-6-isopropyl-1,3-oxazinan-2-one

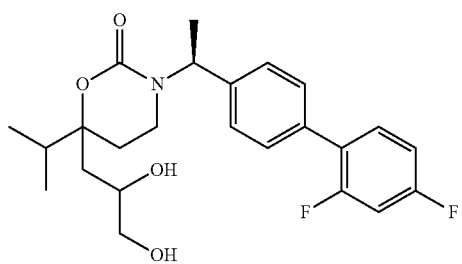 [SMILES: CC(C)C1(CC(O)CO)CCN([C@@H](C)c2ccc(-c3ccc(F)cc3F)cc2)C(=O)O1]

The title compound was prepared from 6-allyl-3-((S)-1-(2',4'-difluorobiphenyl-4-yl)ethyl)-6-isopropyl-1,3-oxazinan-2-one following a procedure analogous to that described in Example 173. Four isomers were isolated.

Isomer 1: LC-MS Method 2 $t_R$=1.34 min, m/z=456; ¹H NMR (CDCl₃) 0.87 (m, 6H), 1.53 (m, 3H), 1.65 (m, 2H), 1.82 (m, 2H), 2.05 (m, 1H), 2.75 (m, 1H), 3.13 (m, 1H), 3.39 (m, 1H), 3.59 (m, 1H), 4.03 (m, 1H), 5.74 (m, 1H), 6.88 (m, 2H), 7.34 (m, 3H), 7.43 (m, 2H).

Isomer 2: LC-MS Method 2 $t_R$=1.336 min, m/z=456.1; ¹H NMR (CDCl₃) 0.83 (m, 3H), 0.95 (m, 3H), 1.52 (m, 3H), 1.64 (m, 1H), 1.76-1.87 (m, 3H), 2.05 (m, 1H), 2.75 (m, 1H), 3.13 (m, 1H), 3.45 (m, 1H), 3.58 (m, 1H), 3.95 (m, 1H), 5.74 (m, 1H), 6.88 (m, 2H), 7.34 (m, 3H), 7.43 (m, 2H).

Isomer 3: LC-MS Method 2 $t_R$=1.335, min, m/z=456.1; ¹H NMR (CDCl₃) 0.89-0.96 (m, 6H), 1.51 (d, 3H), 1.57 (m, 2H), 1.81-1.94 (m, 2H), 2.13 (m, 1H), 2.73 (m, 1H), 3.07 (m, 1H), 3.36 (m, 1H), 3.57 (m, 1H), 3.98 (m, 1H), 5.76 (m, 1H), 6.81-6.92 (m, 2H), 7.28-7.37 (m, 3H), 7.43 (m, 2H).

Isomer 4: LC-MS Method 2 $t_R$=2.328 min, m/z=456.2; ¹H NMR (CDCl₃) 0.87 (m, 3H), 0.94 (m, 3H), 1.57 (m, 3H), 1.79-1.94 (m, 3H), 2.11 (m, 1H), 2.41 (m, 1H), 2.79 (m, 1H), 3.11 (m, 1H), 3.45 (m, 1H), 3.54 (m, 1H), 4.23 (m, 1H), 5.75 (m, 1H), 6.82-6.93 (m, 2H), 7.33 (m, 3H), 7.43 (m, 2H).

Example 224

(6S)-3-((1S)-1-(4'-fluorobiphenyl-4-yl)ethyl)-6-(2-hydroxypropyl)-6-phenyl-1,3-oxazinan-2-one

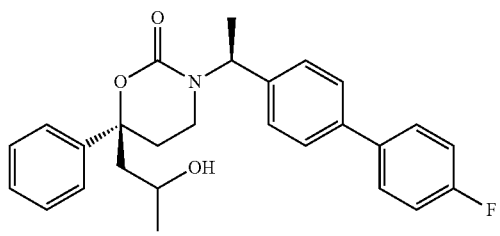 [SMILES: CC(O)C[C@]1(c2ccccc2)CCN([C@@H](C)c2ccc(-c3ccc(F)cc3)cc2)C(=O)O1]

The title compound was isolated as a byproduct of hydroboration of (R)-6-allyl-3-((S)-1-(4'-fluorobiphenyl-4-yl)ethyl)-6-phenyl-1,3-oxazinan-2-one following a procedure analogous to that described in Example 78. LC-MS Method 3 $t_R$=1.47, min, m/z=434; ¹H NMR (CDCl₃) 1.06 (m, 3H), 1.19 (s, 1H), 1.48 (m, 3H), 1.82-2.11 (m, 2H), 2.14-2.45 (m, 3H), 2.84 (m, 1H), 3.72-3.96 (m, 1H), 5.58 (m, 1H), 6.81 (m, 1H), 6.90 (m, 1H), 7.03 (m, 2H), 7.15-7.38 (m, 9H).

Two isomers were separated by preparative HPLC.

Isomer 1: LC-MS Method 1 $t_R$=1.84, min, m/z=434; ¹H NMR (CD₃OD) 7.45-7.41 (m, 2H), 7.33-7.24 (m, 5H), 7.22 (d, J=8.5 Hz, 2H), 7.08-7.03 (m, 2H), 6.84 (d, J=8.2 Hz, 2H), 5.46 (q, J=7.0 Hz, 1H), 3.49-3.45 (m, 1H), 3.03-2.98 (m, 1H), 2.64-2.59 (m, 1H), 2.34-2.27 (m, 1H), 2.19-2.12 (m, 1H), 2.04 (dd, J=14.3, 7.3 Hz, 1H), 1.88 (dd, J=14.3, 4.7 Hz, 1H), 1.46 (d, J=7.0 Hz, 3H), 1.06 (d, J=6.2 Hz, 3H).

Isomer 2: LC-MS Method 1 $t_R$=1.88, min, m/z=434; ¹H NMR (CD₃OD) 7.45-7.41 (m, 2H), 7.32-7.22 (m, 7H), 7.08-7.03 (m, 2H), 6.90 (d, J=8.2 Hz, 2H), 5.48 (q, J=7.1 Hz, 1H), 3.91-3.86 (m, 1H), 2.99-2.94 (m, 1H), 2.39-2.35 (m, 2H), 2.20-2.13 (m, 1H), 1.97 (dd, J=14.9, 7.3 Hz, 1H), 1.87 (dd, J=14.9, 3.5 Hz, 1H), 1.47 (d, J=7.3 Hz, 3H), 0.93 (d, J=6.2 Hz, 3H).

Example 225

(R)-6-(4-fluorophenyl)-6-(3-hydroxypropyl)-3-((S)-1-(4-(pyridin-3-yl)phenyl)ethyl)-1,3-oxazinan-2-one

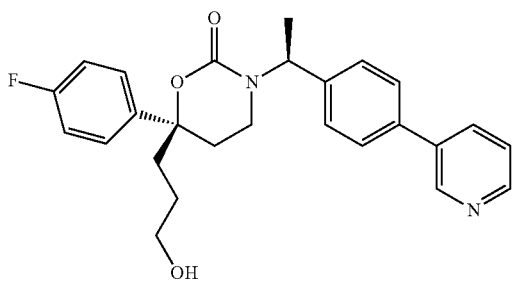 [SMILES: C[C@@H](c1ccc(-c2cccnc2)cc1)N1CC[C@](CCCO)(c2ccc(F)cc2)OC1=O]

The title compound was prepared from (R)-6-allyl-6-(4-fluorophenyl)-3-((S)-1-(4-(pyridin-3-yl)phenyl)ethyl)-1,3-oxazinan-2-one following a procedure analogous to that described in Example 78. LC-MS Method 2 $t_R$=1.463, min, m/z=435.2; $^1$H NMR (CDCl$_3$) 1.51 (d, 3H), 1.82-1.98 (m, 3H), 2.11-2.21 (m, 2H), 2.22-2.32 (m, 2H), 2.93 (m, 1H), 3.53 (m, 2H), 5.66 (m, 1H), 6.93-7.01 (m, 4H), 7.22 (m, 1H), 7.28 (m, 2H), 7.33 (m, 1H), 7.79 (m, 1H), 8.52 (m, 1H), 8.68 (m, 1H).

Example 226

(R)-3-((S)-1-(2',4'-difluorobiphenyl-4-yl)ethyl)-6-phenyl-6-propyl-1,3-oxazinan-2-one

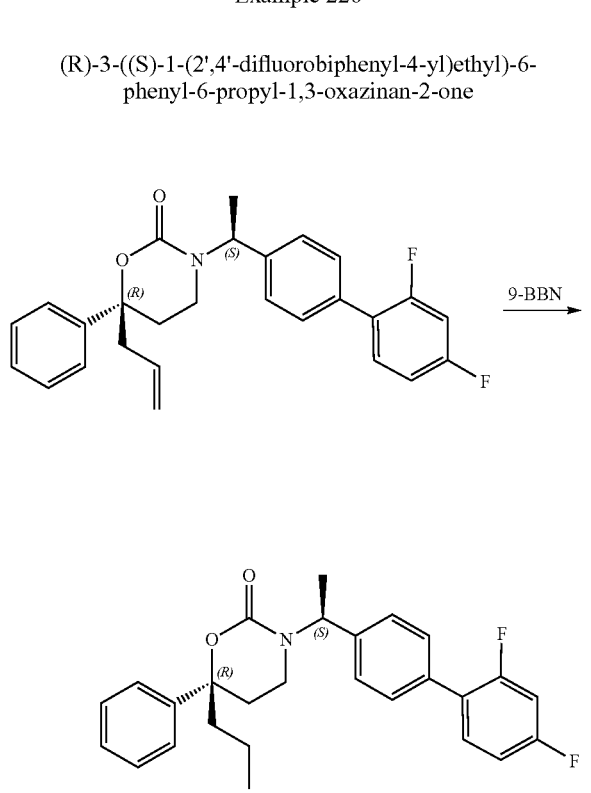

To a solution of (R)-6-allyl-3-((S)-1-(2',4'-difluorobiphenyl-4-yl)ethyl)-6-phenyl-1,3-oxazinan-2-one (0.2475 g, 0.57 mmol, 1.0 equiv) in 6 mL of dry THF was added 9-BBN (0.5 M solution in THF, 2.3 mL, 1.15 mmol, 2.0 equiv). The mixture was stirred for 3 h at rt. It was then subjected to oxidative workup by adding 3 N aqueous NaOH (6 mL) followed by careful and dropwise addition of 50% aq H$_2$O$_2$ (4 mL) with vigorous stirring. The reaction mixture was stirred for 1 h, extracted with CH$_2$Cl$_2$, and dried over Na$_2$SO$_4$. Surprisingly, the reductive product was observed instead of hydroboration-oxidation. After the solvent was evaporated under reduced pressure, the residue was purified by reversed-phase HPLC (SunFire™ Prep C$_{18}$ OBD™ 5 μm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford 0.0902 g of (R)-3-((S)-1-(2',4'-difluorobiphenyl-4-yl)ethyl)-6-phenyl-6-propyl-1,3-oxazinan-2-one LC-MS Method 1 tR=2.22, min, m/z=436; $^1$H NMR (400 MHz, CD$_3$OD) δ 7.33-7.14 (m, 8H), 6.96-6.87 (m, 4H), 5.48 (q, J=7.0 Hz, 1H), 3.01-2.96 (m, 1H), 2.41-2.36 (m, 1H), 2.29-2.21 (m, 1H), 2.14-2.07 (m, 1H), 1.81-1.72 (m, 2H), 1.46 (d, J=7.0 Hz, 3H), 1.39-1.29 (m, 1H), 1.08-0.98 (m, 1H), 0.76 (t, J=7.5 Hz, 3H); $^{19}$F NMR (376 MHz, CD$_3$OD) δ −113.79 (m), −115.77 (m).

Example 227

3-((S)-1-(4-bromophenyl)ethyl)-6-(4-fluorophenyl)-6-(3-hydroxypropyl)-1,3-oxazinan-2-one

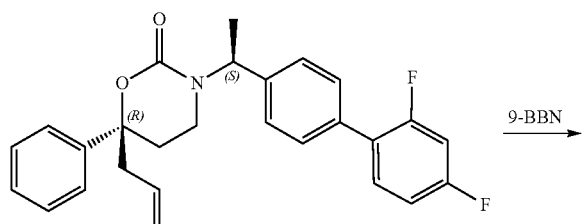

(R)-3-((S)-1-(4-bromophenyl)ethyl)-6-(4-fluorophenyl)-6-(3-hydroxypropyl)-1,3-oxazinan-2-one was prepared from (R)-6-allyl-3-((S)-1-(4-bromophenyl)ethyl)-6-(4-fluorophenyl)-1,3-oxazinan-2-one following a procedure analogous to that described in Example 78. LC-MS Method 3 $t_R$=1.287, min, m/z=458.1; $^1$H NMR (CDCl$_3$) 1.43 (d, 3H), 1.58-1.69 (m, 2H), 1.81-1.97 (m, 2H), 2.11-2.24 (m, 3H), 2.82 (m, 1H), 3.51 (m, 2H), 5.52 (m, 1H), 6.71 (d, 2H), 6.98 (m, 2H), 7.22 (m, 4H).

(S)-3-((S)-1-(4-bromophenyl)ethyl)-6-(4-fluorophenyl)-6-(3-hydroxypropyl)-1,3-oxazinan-2-one was prepared from (S)-6-allyl-3-((S)-1-(4-bromophenyl)ethyl)-6-(4-fluorophenyl)-1,3-oxazinan-2-one following a procedure analogous to that described in Example 78. LC-MS Method 3 $t_R$=1.27, min, m/z=436, 458; $^1$H NMR (CDCl$_3$) 1.48 (d, 3H), 1.55-1.65

(m, 2H), 1.82-1.94 (m, 2H), 2.08-2.24 (m, 3H), 2.84 (m, 1H), 3.50 (m, 2H), 5.53 (m, 1H), 6.72 (d, 2H), 6.96 (m, 2H), 7.19 (m, 4H).

Example 228

N-(4-((S)-1-((S)-6-(4-fluorophenyl)-6-(2-hydroxyethyl)-2-oxo-1,3-oxazinan-3-yl)ethyl)phenyl)methanesulfonamide

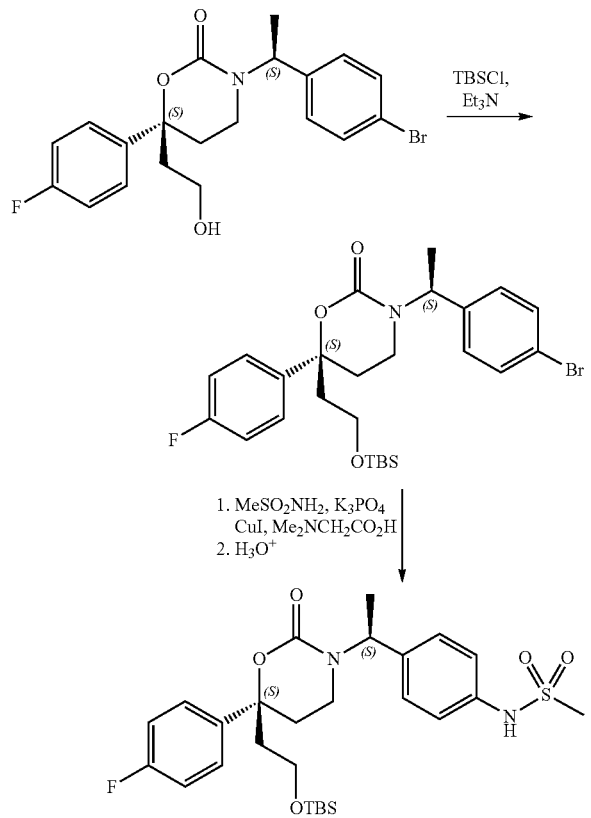

Step 1. (S)-3-((S)-1-(4-bromophenyl)ethyl)-6-(2-(tert-butyldimethylsilyloxy)ethyl)-6-(4-fluorophenyl)-1,3-oxazinan-2-one A mixture of (S)-3-((S)-1-(4-bromophenyl)ethyl)-6-(4-fluorophenyl)-6-(2-hydroxyethyl)-1,3-oxazinan-2-one (0.4300 g, 1.02 mmol), 4-dimethylaminopyridine (0.0783 g, 0.64 mmol), triethylamine (0.8 mL, 5.74 mmol), and tert-butyldimethylsilyl chloride (0.2870 g, 1.90 mmol) in $CH_2Cl_2$ was stirred for 16 h at rt. After the solvents were removed in vacuo, the residue was purified by chromatography on silica gel eluted with hexanes/EtOAc to give 0.2856 g of (S)-3-((S)-1-(4-bromophenyl)ethyl)-6-(2-(tert-butyldimethylsilyloxy)ethyl)-6-(4-fluorophenyl)-1,3-oxazinan-2-one as a solid. LC-MS Method 1 $t_R$=2.49 min, m/z 560, 558 ($MNa^+$), 538, 536 ($MH^+$), 494, 492; $^1H$ NMR (400 MHz, $CDCl_3$) δ 7.34-7.25 (m, 4H), 7.10-7.05 (m, 2H), 6.78 (d, J=8.5 Hz, 2H), 5.63 (q, J=7.0 Hz, 1H), 3.84-3.78 (m, 1H), 3.44-3.38 (m, 1H), 2.96-2.90 (m, 1H), 2.78-2.27 (m, 3H), 2.18-2.04 (m, 2H), 1.52 (d, J=7.3 Hz, 3H), 0.87 (s, 9H), 0.02 (s, 3H), 0.00 (s, 3H); $^{19}F$ NMR (376 MHz, $CDCl_3$) δ −114.99 (m).

Step 2. N-(4-((S)-1-((S)-6-(2-(tert-butyldimethylsilyloxy)ethyl)-6-(4-fluorophenyl)-2-oxo-1,3-oxazinan-3-yl)ethyl)phenyl)methanesulfonamide A mixture of (S)-3-((S)-1-(4-bromophenyl)ethyl)-6-(2-(tert-butyldimethylsilyloxy)ethyl)-6-(4-fluorophenyl)-1,3-oxazinan-2-one (0.0465 g, 0.0866 mmol), methanesulfonamide (0.0945 g), $K_3PO_4$ (0.2753 g), N,N-dimethylglycine (0.0686 g), and CuI (0.0687 g) in DMF (2 mL) was heated at 120° C. for 17 h. The mixture was diluted with EtOAc, filtered, washed with $CH_2Cl_2$. After the solvent was evaporated under reduced pressure, the residue was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford N-(4-((S)-1-((S)-6-(2-(tert-butyldimethylsilyloxy)ethyl)-6-(4-fluorophenyl)-2-oxo-1,3-oxazinan-3-yl)ethyl)phenyl)methanesulfonamide. LC-MS $t_R$=2.10 min in 3 min chromatography, m/z 551 ($MH^+$), 507.

Step 3. N-(4-((S)-1-((S)-6-(4-fluorophenyl)-6-(2-hydroxyethyl)-2-oxo-1,3-oxazinan-3-yl)ethyl)phenyl)methanesulfonamide To a solution of N-(4-((S)-1-((S)-6-(2-(tert-butyldimethylsilyloxy)ethyl)-6-(4-fluorophenyl)-2-oxo-1,3-oxazinan-3-yl)ethyl)phenyl)methanesulfonamide in acetonitrile—water, obtained as described above, was added 15 mL of 2 N HCl. The mixture was vigorously stirred at rt for 20 h. After the solvents were removed in vacuo, the residue was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford N-(4-((S)-1-((S)-6-(4-fluorophenyl)-6-(2-hydroxyethyl)-2-oxo-1,3-oxazinan-3-yl)ethyl)phenyl)methanesulfonamide. LC-MS Method 1 tR=1.17, min, m/z=437; $^1H$ NMR (400 MHz, $CD_3OD$) δ 7.25-7.22 (m, 2H), 7.03-6.99 (m, 2H), 6.94 (d, J=8.5 Hz, 2H), 6.84 (d, J=8.5 Hz, 2H), 5.43 (q, J=7.0 Hz, 1H), 3.63-3.56 (m, 1H), 3.27-3.21 (m, 1H), 3.03-2.96 (m, 1H), 2.79 (s, 3H), 2.44-2.37 (m, 1H), 2.22-2.12 (m, 2H), 2.03 (t, J=7.2 Hz, 2H), 1.42 (d, J=7.0 Hz, 3H); $^{19}F$ NMR (376 MHz, $CD_3OD$) δ −117.03 (m).

Example 229

(S)-3-((S)-1-(2',4'-difluorobiphenyl-4-yl)ethyl)-6-(4-fluorophenyl)-6-(2-(methylsulfonyl)ethyl)-1,3-oxazinan-2-one

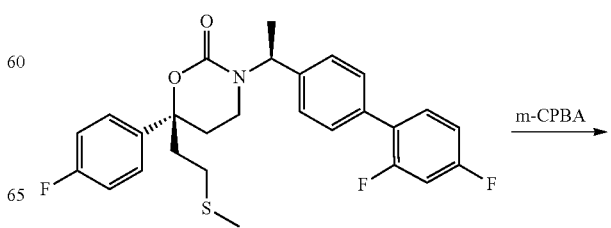

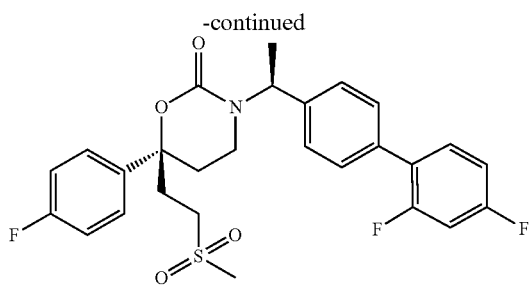

To a solution of (S)-3-((S)-1-(2',4'-difluorobiphenyl-4-yl)ethyl)-6-(4-fluorophenyl)-6-(2-(methylthio)ethyl)-1,3-oxazinan-2-one (30 mg, 0.062 mmol) in methylene chloride (5 mL) was added m-CPBA (25 mg, 0.12 mmol). The formed mixture was stirred for 1 h and then washed with saturated Na$_2$CO$_3$. The organic phase was separated, and concentrated to give the crude product which was purified by preparative HPLC to afford (S)-3-((S)-1-(2',4'-difluorobiphenyl-4-yl)ethyl)-6-(4-fluorophenyl)-6-(2-(methylsulfonyl)ethyl)-1,3-oxazinan-2-one (6 mg, 18%). LC-MS Method 3 $t_R$=1.44, min, m/z=518; $^1$H NMR (400 MHz, CDCl$_3$): δ=1.52 (d, 3H), 2.13-2.36 (m, 4H), 2.42 (m, 1H), 2.58 (m, 1H), 3.01 (m, 1H), 3.29 (m, 1H), 5.63 (m, 1H), 6.35 (m, 2H), 7.00 (m, 4H), 7.18 (m, 2H), 7.22 (m, 3H).

Example 230

(R)-6-allyl-6-(4-fluorophenyl)-3-((S)-1-(4-(5-methyl-1,3,4-thiadiazol-2-yl)phenyl)ethyl)-1,3-oxazinan-2-one

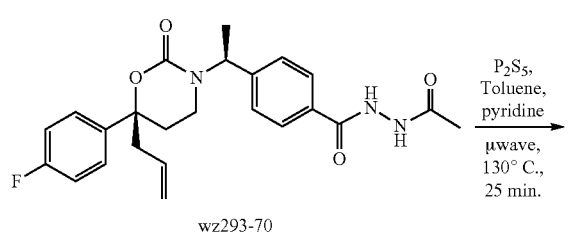

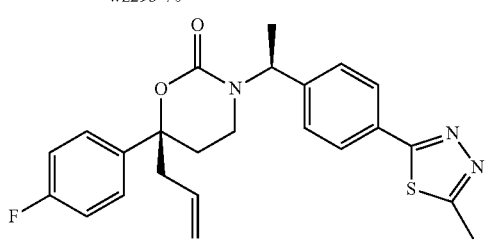

N'-acetyl-4-((S)-1-((R)-6-allyl-6-(4-fluorophenyl)-2-oxo-1,3-oxazinan-3-yl)ethyl)benzohydrazide (4 mg, 0.009 mmol) was dissolved in 5:1 toluene/pyridine (1.5 mL). Phosphorous pentasulfide (8.1 mg, 2 equiv.) was added and the mixture was heated in Microwave Oven for 25 min at 130° C. LC-MS found reaction completed. The mixture was diluted with EtOAc (8 mL), washed with 5% HCl (2×5 mL), satd aq NaHCO$_3$ solution (4 mL), brine (4 mL) and dried over Na$_2$SO$_4$. After filtration and concentration, the residue was purified by prep HPLC to afford 2.43 mg (61% yield). LC-MS Method 1 $t_R$=1.7, min, m/z=438; $^1$H NMR (CDCl$_3$) 7.66 (d, 2H), 7.26 (t, 2H), 7.02 (t, 2H), 6.97 (d, 2H), 5.69 (m, 2H), 5.07 (dd, 2H), 2.98 (m, 1H), 2.83 (s, 3H), 1.56 (d, 3H).

Example 231

(R)-6-allyl-6-(4-fluorophenyl)-3-((S)-1-(4-(4-methylpiperazin-1-yl)phenyl)ethyl)-1,3-oxazinan-2-one

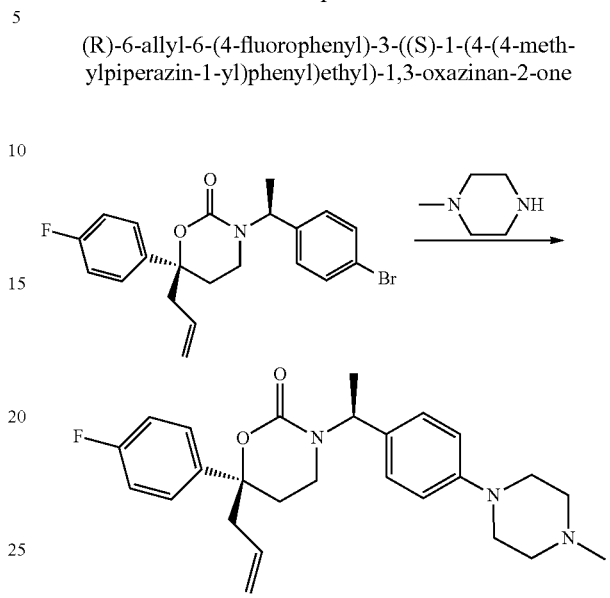

A mixture of (R)-6-allyl-3-((S)-1-(4-bromophenyl)ethyl)-6-(4-fluorophenyl)-1,3-oxazinan-2-one (400 mg, 0.96 mmol), 1-methylpiperazine (100 mg, 1.0 mmol), t-BuONa (129 mg, 1.34 mmol), Pd$_2$(dba)$_3$ (9 mg, 0.01 mmol), BINAP (6 mg, 0.01 mmol) in toluene. was heated to 80° C. and stirred overnight. Then the reaction mixture was concentrated to afford the residue, which was purified by preparative TLC to give (R)-6-allyl-6-(4-fluorophenyl)-3-((S)-1-(4-(4-methylpiperazin-1-yl)phenyl)ethyl)-1,3-oxazinan-2-one (162 mg, 0.4 mmol). LC-MS Method 2 $t_R$=1.77, min, m/z=438; $^1$H NMR (CD$_3$OD) 1.50 (m, 3H), 2.20 (m, 2H), 2.30 (m, 3H), 2.35 (m, 1H), 2.60 (m, 6H), 3.00 (m, 1H), 3.10 (m, 4H), 5.00 (m, 2H), 5.45 (m, 1H), 5.65 (m, 1H), 6.70 (m, 2H), 6.80 (m, 2H), 7.05 (m, 2H), 7.25 (m, 2H).

Example 232

(R)-3-((S)-1-(4'-fluorobiphenyl-4-yl)ethyl)-6-(3-hydroxypropyl)-6-(thiophen-2-yl)-1,3-oxazinan-2-one

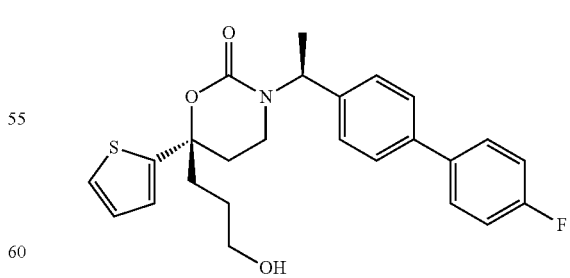

The title compound was prepared from (R)-6-allyl-3-((S)-1-(4'-fluorobiphenyl-4-yl)ethyl)-6-(thiophen-2-yl)-1,3-oxazinan-2-one following a procedure analogous to that described in Example 78. LC-MS Method 3 $t_R$=1.39, min, m/z=440; $^1$H NMR (CD$_3$OD) 1.40 (m, 1H), 1.50 (m, 3H), 1.65 (m, 1H), 2.00 (m, 2H), 2.35 (m, 1H), 2.40 (m, 1H), 2.60 (m, 1H), 3.15 (m, 1H), 3.45 (m, 2H), 5.60 (m, 1H), 6.90 (m, 1H), 7.00 (m, 1H), 7.10 (m, 4H), 7.35 (m, 3H), 7.55 (m, 2H).

Example 233

3-((S)-1-(2',4'-difluorobiphenyl-4-yl)ethyl)-6-(2-hydroxyethyl)-6-(thiophen-2-yl)-1,3-oxazinan-2-one

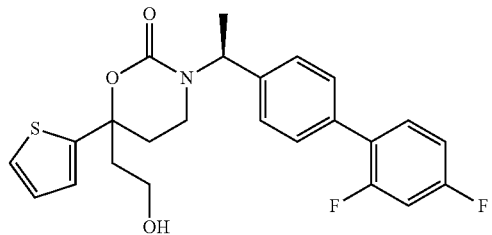 [SMILES: C[C@@H](c1ccc(-c2ccc(F)cc2F)cc1)N1CCC(CCO)(c2cccs2)OC1=O]

(S)-3-((S)-1-(2',4'-difluorobiphenyl-4-yl)ethyl)-6-(2-hydroxyethyl)-6-(thiophen-2-yl)-1,3-oxazinan-2-one was prepared from (R)-6-allyl-3-((S)-1-(2',4'-difluorobiphenyl-4-yl)ethyl)-6-(thiophen-2-yl)-1,3-oxazinan-2-one following a procedure analogous to that described in Example 218. LC-MS Method 3 $t_R$=1.38, min, m/z=444, 466; $^1$H NMR (CD$_3$OD) 1.55 (m, 3H), 2.18 (m, 2H), 2.30 (m, 1H), 2.45 (m, 1H), 2.60 (m, 1H), 3.15 (m, 1H), 3.45 (m, 1H), 3.70 (m, 1H), 5.60 (m, 1H), 6.90 (m, 1H), 7.00 (m, 5H), 7.30 (m, 2H), 7.40 (m, 2H).

(R)-3-((S)-1-(2',4'-difluorobiphenyl-4-yl)ethyl)-6-(2-hydroxyethyl)-6-(thiophen-2-yl)-1,3-oxazinan-2-one was prepared from (S)-6-allyl-3-((S)-1-(2',4'-difluorobiphenyl-4-yl)ethyl)-6-(thiophen-2-yl)-1,3-oxazinan-2-one following a procedure analogous to that described in Example 218. LC-MS Method 3 $t_R$=1.26, min, m/z=444, 466; $^1$H NMR (CD$_3$OD) 1.38 (d, 3H), 2.17 (m, 2H), 2.21 (m, 1H), 2.41 (m, 1H), 2.86 (m, 1H), 3.02 (m, 1H), 3.45 (m, 1H), 3.71 (m, 1H), 5.62 (m, 1H), 6.98 (m, 4H), 7.36 (m, 3H), 7.45 (m, 3H).

Example 234

3-((R)-3-((S)-1-(4'-fluorobiphenyl-4-yl)ethyl)-2-oxo-6-phenyl-1,3-oxazinan-6-yl)propanamide

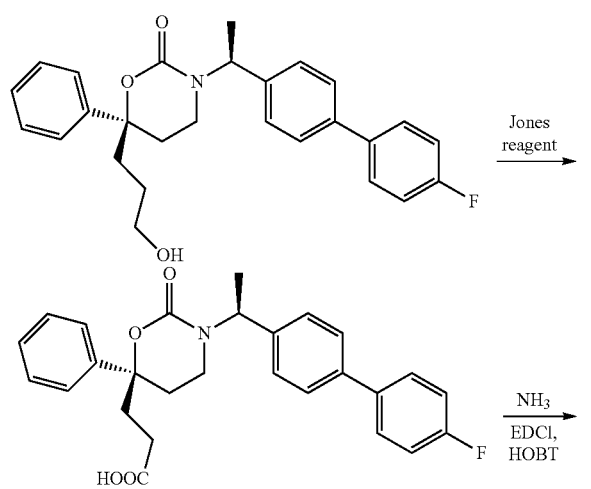

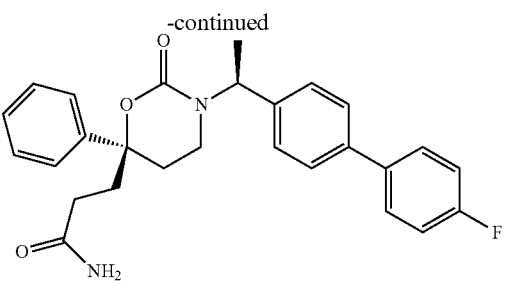

Step 1

CrO$_3$ (1 g) was added to H$_2$SO$_4$ (1 mL) and water was added to bring the total volume to 4 mL. (R)-3-((S)-1-(4'-fluorobiphenyl-4-yl)ethyl)-6-(3-hydroxypropyl)-6-phenyl-1,3-oxazinan-2-one (600 mg, 1.4 mmol) was dissolved in 10 mL acetone, and cooled in an ice bath. The Jones reagent (0.5 mL) was slowly added to the mixture and stirred overnight. Solvent was removed in vacuo, the residue was dissolved in CH$_2$Cl$_2$ (10 mL) and water (10 mL). The layers were separated, and the aq layer was extracted with CH$_2$Cl$_2$ (3×10 mL). The combined organic layers were washed with brine, dried over Na$_2$SO$_4$, filtered and concentrated to give 3-((R)-3-((S)-1-(4'-fluorobiphenyl-4-yl)ethyl)-2-oxo-6-phenyl-1,3-oxazinan-6-yl)propanoic acid (500 mg, crude), which was not purified.

Step 2

A mixture of 3-((R)-3-((S)-1-(4'-fluorobiphenyl-4-yl)ethyl)-2-oxo-6-phenyl-1,3-oxazinan-6-yl)propanoic acid (500 mg, 1.12 mmol), HOBT (302 mg, 2.24 mmol), EDCl (440 mg, 2.24 mmol) and DIEA (1 mL) in anhydrous CH$_2$Cl$_2$ (10 mL) were stirred at 0□ under NH$_3$. Then the solution was stirred at rt overnight. The solvent was removed under reduced pressure, and the residue was purified by preparative HPLC to afford 3-((R)-3-((S)-1-(4'-fluorobiphenyl-4-yl)ethyl)-2-oxo-6-phenyl-1,3-oxazinan-6-yl)propanamide (234 mg, yield 48%). $^1$H NMR (CDCl$_3$): 1.49 (m, 3H), 1.91-2.02 (m, 1H), 1.87-1.98 (m, 1), 2.10-2.31 (m, 5H), 2.39-2.5 (m, 1H), 2.87 (m, 1H), 5.27 (s, 1H), 5.51 (s, 1H), 5.64 (m, 1H), 6.94 (m, 2H), 7.04 (m, 2H), 7.21-7.35 (m, 6H), 7.39 (m, 2H). LC-MS Method 3 $t_R$=1.3, min, m/z=447, 469; $^1$H NMR (CDCl$_3$) 1.49 (m, 3H), 1.91-2.02 (m, 1H), 1.87-1.98 (m, 1), 2.10-2.31 (m, 5H), 2.39-2.5 (m, 1H), 2.87 (m, 1H), 5.27 (s, 1H), 5.51 (s, 1H), 5.64 (m, 1H), 6.94 (m, 2H), 7.04 (m, 2H), 7.21-7.35 (m, 6H), 7.39 (m, 2H).

Example 235

(R)-6-(3-hydroxypropyl)-3-((S)-1-(4-(6-methoxypyridin-3-yl)phenyl)ethyl)-6-phenyl-1,3-oxazinan-2-one

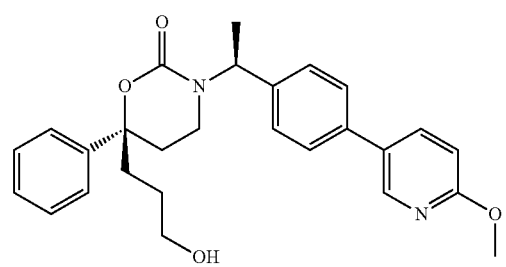 [SMILES: COc1ccc(-c2ccc([C@H](C)N3CC[C@](CCCO)(c4ccccc4)OC3=O)cc2)cn1]

The title compound was prepared from (R)-6-allyl-3-((S)-1-(4-bromophenyl)ethyl)-6-phenyl-1,3-oxazinan-2-one and 2-methoxypyridine-5-boronic acid using a procedure analogous to that described in Example 64 followed by a procedure analogous to that described in Example 78. LC-MS Method 3 $t_R$=1.22, min, m/z=447; $^1$H NMR (CDCl$_3$) 1.01 (d, 1H), 1.10 (d, 1H), 1.49 (s, 3H), 1.85-1.95 (m, 1H), 2.00-2.07 (m, 1H), 2.21-2.30 (m, 2H), 2.40 (m, 1H), 2.35 (m, 1H), 3.87 (m, 1H), 3.90 (s, 3H), 3.95 (m, 1H), 5.61 (m, 1H), 6.71 (d, 1H), 6.83 (d, 1H), 6.91 (m, 1H), 7.16 (m, 2H), 7.25 (m, 2H), 7.31 (m, 3H), 7.61 (d, 1H), 8.22 (s, 1H).

Example 236

3-((R)-6-(4-fluorophenyl)-2-oxo-3-((S)-1-(4-(pyridin-3-yl)phenyl)ethyl)-1,3-oxazinan-6-yl)propanamide

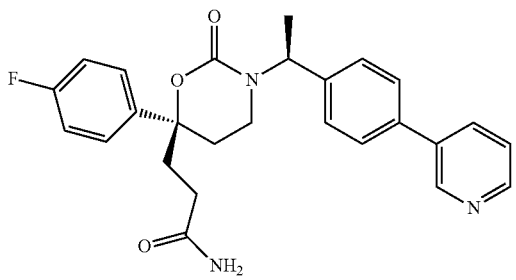 [SMILES: C[C@@H](c1ccc(-c2cccnc2)cc1)N1CC[C@](CCC(N)=O)(c2ccc(F)cc2)OC1=O]

The title compound was prepared from (R)-6-(4-fluorophenyl)-6-(3-hydroxypropyl)-3-((S)-1-(4-(pyridin-3-yl)phenyl)ethyl)-1,3-oxazinan-2-one following a procedure analogous to that described in Example 234. LC-MS Method 2 $t_R$=1.372, min, m/z=448.3; $^1$H NMR (CDCl$_3$) 1.52 (d, 3H), 1.97 (m, 2H), 2.27-2.33 (m, 4H), 2.43 (m, 1H), 2.97 (m, 1H), 5.13 (s, 1H), 5.24 (s, 1H), 5.66 (m, 1H), 6.92-7.08 (m, 4H), 7.22 (m, 2H), 7.31 (m, 2H), 7.48 (m, 1H), 7.97 (m, 1H), 8.57 (m, 1H), 8.74 (m, 1H).

Example 237

(R)-3-((S)-1-(4'-fluorobiphenyl-4-yl)propyl)-6-(3-hydroxypropyl)-6-phenyl-1,3-oxazinan-2-one

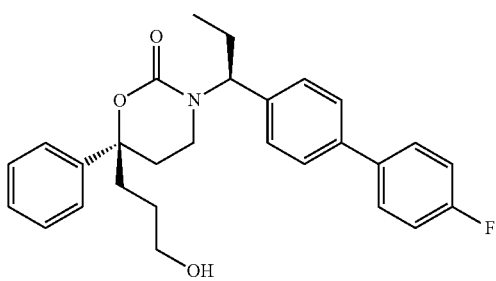 [SMILES: CC[C@@H](c1ccc(-c2ccc(F)cc2)cc1)N1CC[C@](CCCO)(c2ccccc2)OC1=O]

The title compound was prepared from (R)-6-allyl-3-((S)-1-(4-bromophenyl)propyl)-6-phenyl-1,3-oxazinan-2-one and 4-fluorobenzeneboronic acid using a procedure analogous to that described in Example 64 followed by a procedure analogous to that described in Example 78. LC-MS Method 3 tR=1.48, min, m/z=448; 1H NMR (CDCl3) 0.99 (t, 3H), 1.28 (m, 1H), 1.62 (m, 1H), 1.91-2.08 (m, 4H), 2.25 (m, 1H), 2.34 (m, 1H), 2.42 (m, 1H), 3.08 (m, 1H), 3.46 (m, 2H), 5.39 (m, 1H), 7.02-7.16 (m, 4H), 7.22-7.42 (m, 7H), 7.51 (m, 2H).

Example 238

(S)-3-((S)-1-(4'-fluorobiphenyl-4-yl)ethyl)-6-(2-hydroxy-2-methylpropyl)-6-phenyl-1,3-oxazinan-2-one

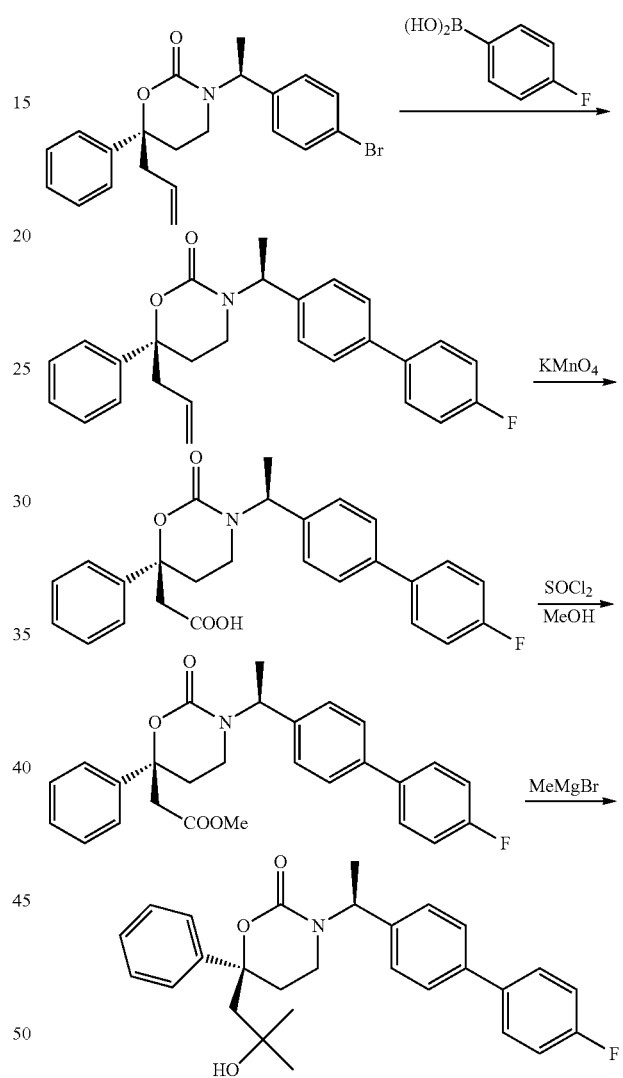

Step 1

A mixture of (R)-6-allyl-3-((S)-1-(4-bromophenyl)ethyl)-6-phenyl-1,3-oxazinan-2-one (5.83 g, 15 mmol), 4-fluorophenylboronic acid (3 g, 22 mmol), PdCl$_2$(PPh$_3$)$_2$ (1 g, 1.4 mmol), and aqueous Cs$_2$CO$_3$ solution (2 M, 8.0 mL) in 1,4-dioxane (50 mL) was heated to reflux for 2 h. The mixture was filtered, and the filtrate was extracted with EtOAc (3×). The combined organic layer was washed with brine, dried over Na$_2$SO$_4$ and concentrated to give the crude product, which was purified by preparative TLC to give (R)-6-allyl-3-((S)-1-(4'-fluorobiphenyl-4-yl)ethyl)-6-phenyl-1,3-oxazinan-2-one (5.3 g, 88%).

Step 2

To a solution of (R)-6-allyl-3-((S)-1-(4'-fluorobiphenyl-4-yl)ethyl)-6-phenyl-1,3-oxazinan-2-one (3 g, 7.23 mmol) in acetone (20 mL) was added a solution of $KMnO_4$ (685 mg, 4.34 mmol) and $NaIO_4$ (5.6 g, 26 mmol) in $H_2O$ (15 mL) dropwise at 0° C. The mixture was stirred for 4 h. When TLC showed that the starting material had disappeared, the precipitate was removed by filtration, and the acetone was removed under reduced pressure. The resulting mixture was basified to pH=13 by the addition of 1 M aq NaOH, and then washed with ether (3×50 mL). The aqueous phase was acidified to pH=1 by addition of 1 N aq HCl, and extracted with $CH_2Cl_2$ (3×15 mL). The organic layers were combined, washed with brine, dried over $Na_2SO_4$ and concentrated in vacuo to give 2-((S)-3-((S)-1-(4'-fluorobiphenyl-4-yl)ethyl)-2-oxo-6-phenyl-1,3-oxazinan-6-yl)acetic acid (2.8 g, 90%).

Step 3

To a solution of 2-((S)-3-((S)-1-(4'-fluorobiphenyl-4-yl)ethyl)-2-oxo-6-phenyl-1,3-oxazinan-6-yl)acetic acid (1 g, 2.3 mmol) in MeOH (15 mL) was added thionyl chloride (408 mg, 3.5 mmol) dropwise at 0° C. under $N_2$ atmosphere. After refluxing overnight, the mixture was concentrated to give the crude product, which was purified by chromatography to give methyl 2-((S)-3-((S)-1-(4'-fluorobiphenyl-4-yl)ethyl)-2-oxo-6-phenyl-1,3-oxazinan-6-yl)acetate (680 mg, 68%).

Step 4

To a solution of methyl 2-((S)-3-((S)-1-(4'-fluorobiphenyl-4-yl)ethyl)-2-oxo-6-phenyl-1,3-oxazinan-6-yl)acetate (180 mg, 0.4 mmol) in dry THF (5 mL) under $N_2$ at −78° C. was added methylmagnesium bromide (1.5 mL, 3 M, 4.5 mmol) dropwise at −78° C. After addition, the mixture was stirred for 1 h at rt. Then the reaction was quenched with water and the mixture was extracted with ethyl acetate for three times (3×5 mL). The organic layers were combined, washed with brine, dried over $Na_2SO_4$, filtered and concentrated. The residue was purified by preparative HPLC to give (S)-3-((S)-1-(4'-fluorobiphenyl-4-yl)ethyl)-6-(2-hydroxy-2-methylpropyl)-6-phenyl-1,3-oxazinan-2-one (2.48 mg, 1%). $^1H$ NMR ($CDCl_3$): 1.05 (s, 1H), 1.13 (s, 3H), 1.50 (d, 3H), 2.14-2.23 (m, 2H), 2.25-2.40 (m, 1H), 2.80 (m, 1H), 5.63 (m, 1H), 6.94 (m, 2H), 7.02 (m, 2H), 7.18-7.30 (m, 7H), 7.38 (m, 2H). LC-MS Method 3 $t_R$=1.51, min, m/z=448, 470.

Example 239

(6S)-3-((1S)-1-(4-bromophenyl)propyl)-6-(2,3-dihydroxypropyl)-6-phenyl-1,3-oxazinan-2-one

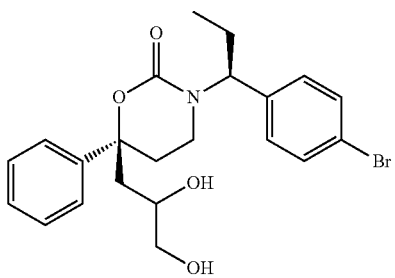 [SMILES: CC[C@@H](c1ccc(Br)cc1)N1CC[C@](CC(O)CO)(c2ccccc2)OC1=O]

The title compound was prepared from (R)-6-allyl-3-((S)-1-(4-bromophenyl)propyl)-6-phenyl-1,3-oxazinan-2-one using AD-mix-beta following a procedure analogous to that described in Example 173. Two isomers were isolated.

Isomer 1: LC-MS Method 3 $t_R$=1.2, min, m/z=448, 472; $^1H$ NMR ($CDCl_3$) 0.96 (d, 3H), 1.93 (m, 2H), 2.04 (m, 2H), 2.22-2.41 (m, 2H), 2.50 (m, 2H), 3.04 (m, 1H), 3.38 (m, 1H), 3.42 (m, 2H), 5.28 (m, 1H), 6.85 (m, 2H), 7.24 (m, 2H), 7.35 (m, 5H).

Isomer 2: LC-MS Method 3 tR=1.18, min, m/z=448, 472; 1H NMR (CDCl3) 0.99 (d, 3H), 1.93 (m, 2H), 2.04 (m, 2H), 2.22-2.41 (m, 2H), 2.70 (m, 1H), 3.04 (m, 1H), 3.32 (m, 1H), 3.42 (m, 2H), 5.27 (m, 1H), 6.85 (m, 2H), 7.24 (m, 2H), 7.35 (m, 5H).

Example 240

3-((R)-3-((S)-1-(4-bromophenyl)ethyl)-6-(4-fluorophenyl)-2-oxo-1,3-oxazinan-6-yl)propanamide

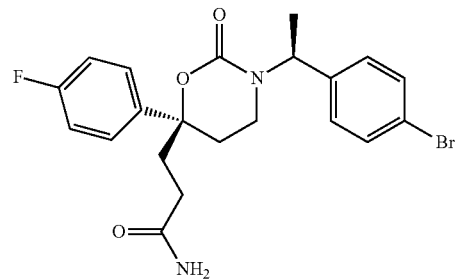 [SMILES: C[C@@H](c1ccc(Br)cc1)N1CC[C@](CCC(N)=O)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one following a procedure analogous to that described in Example 234. LC-MS Method 3 $t_R$=1.18, min, m/z=449, 451; $^1H$ NMR ($CDCl_3$) 1.49 (m, 3H), 1.91-2.00 (m, 1H), 2.11-2.32 (m, 5H), 2.46 (m, 1H), 2.90 (m, 1H), 5.31-5.55 (s, 2H), 5.61 (m, 1H), 6.81 (m, 2H), 7.02 (m, 2H), 7.22 (m, 2H), 7.28 (m, 2H).

Example 241

(R)-3-((S)-1-(4-bromophenyl)propyl)-6-(4-fluorophenyl)-6-(3-hydroxypropyl)-1,3-oxazinan-2-one

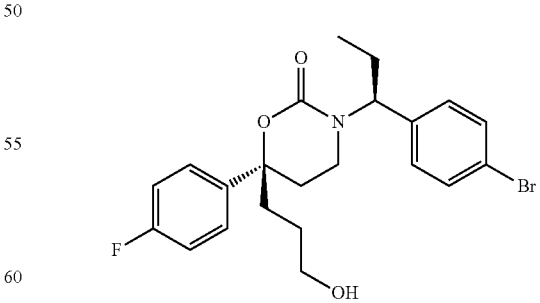

The title compound was prepared from (R)-6-allyl-3-((S)-1-(4-bromophenyl)propyl)-6-(4-fluorophenyl)-1,3-oxazinan-2-one following a procedure analogous to that described in Example 78. LC-MS Method 3 $t_R$=1.37, min, m/z=450, 452, 472, 474; $^1H$ NMR ($CDCl_3$) 0.99 (t, 3H), 1.34 (m, 1H), 1.67 (m, 1H), 1.81-2.02 (m, 4H), 2.21 (m, 1H), 2.32 (m, 1H), 2.92 (m, 1H), 3.56 (t, 2H), 5.39 (m, 1H), 6.87 (d, 2H), 6.98 (m, 2H), 7.19 (m, 2H), 7.25 (d, 2H).

Example 242

2-((S)-3-((S)-1-(2',4'-difluorobiphenyl-4-yl)ethyl)-6-(4-fluorophenyl)-2-oxo-1,3-oxazinan-6-yl)acetonitrile

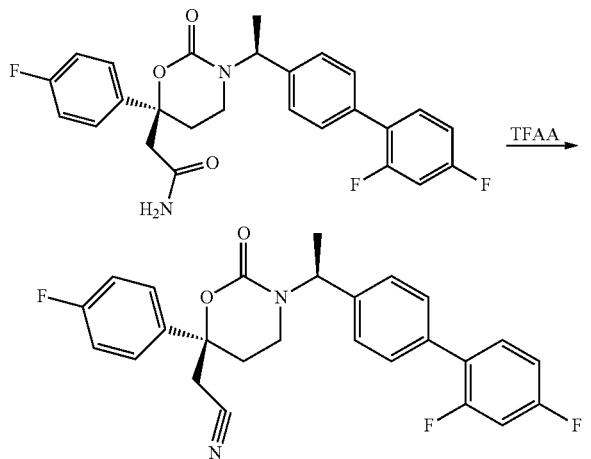

To a solution of 2-((S)-3-((S)-1-(2',4'-difluorobiphenyl-4-yl)ethyl)-6-(4-fluorophenyl)-2-oxo-1,3-oxazinan-6-yl)acetamide (60 mg, 0.128 mmol) in anhydrous $CH_2Cl_2$ (4 mL) and DIEA (0.3 mL) was added TFAA (55 mg, 0.256 mmol) at 0□. The mixture was stirred for 2 h. The solvent was removed under reduced pressure, and the residue was purified by preparative TLC to afford 2-((S)-3-((S)-1-(2',4'-difluorobiphenyl-4-yl)ethyl)-6-(4-fluorophenyl)-2-oxo-1,3-oxazinan-6-yl)acetonitrile (40 mg, 82%). LC-MS Method 3 tR=1.52, min, m/z=451, 473; $^1$H NMR (CDCl$_3$): 1.56 (m, 3H), 2.40 (m, 2H), 2.54 (m, 1H), 2.82-2.98 (m, 2H), 3.04 (m, 1H), 5.64 (m, 1H), 6.83-6.94 (m, 5H), 7.09 (m, 2H), 7.21 (m, 1H), 7.28 (m, 1H), 7.37 (m, 2H).

Example 243

(R)-6-allyl-6-(4-fluorophenyl)-3-((S)-1-(4-(piperidine-1-carbonyl)phenyl)ethyl)-1,3-oxazinan-2-one

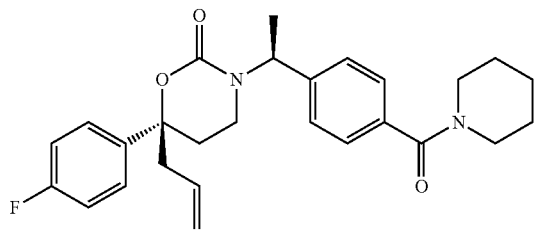 [SMILES: C=CC[C@]1(c2ccc(F)cc2)CCN([C@@H](C)c2ccc(C(=O)N3CCCCC3)cc2)C(=O)O1]

The title compound was prepared from 4-((S)-1-((R)-6-allyl-6-(4-fluorophenyl)-2-oxo-1,3-oxazinan-3-yl)ethyl) benzoic acid following a procedure analogous to that described in Example 153. LC-MS Method 1 $t_R$=1.72, min, m/z=451; $^1$H NMR (CDCl$_3$) 7.26 (t, 2H), 7.13 (d, 2H), 7.04 (t, 2H), 5.73-5.60 (m, 2H), 5.07 (dd, 2H), 3.71 (br s, 2H), 3.26 (br s, 2H), 2.91 (m, 1H), 2.59 (m, 2H), 1.52 (d, 5H).

Example 244

(R)-6-allyl-3-((S)-1-(4-(2,4-dimethylthiazol-5-yl)phenyl)ethyl)-6-(4-fluorophenyl)-1,3-oxazinan-2-one

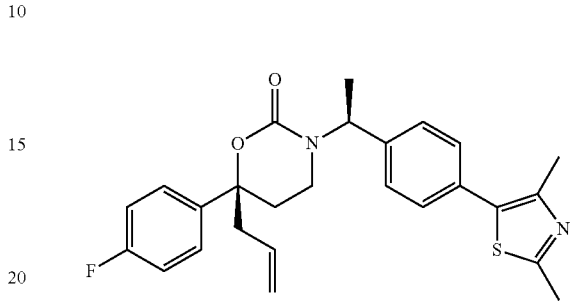

The title compound was prepared from (R)-6-allyl-3-((S)-1-(4-bromophenyl)ethyl)-6-(4-fluorophenyl)-1,3-oxazinan-2-one and 2,4-dimethylthiazole-5-boronic acid following a procedure analogous to that described in Example 64. LC-MS Method 1 $t_R$=1.82, min, m/z=451; $^1$H NMR (CDCl$_3$) 7.26 (t, 2H), 7.13 (d, 2H), 7.03 (t, 2H), 6.91 (d, 2H), 5.76-5.64 (m, 2H), 5.06 (dd, 2H), 2.98 (m, 1H), 2.74 (s, 3H), 2.42 (s, 3H), 1.53 (d, 3H).

Example 245

(R)-3-((S)-1-(4'-fluorobiphenyl-4-yl)ethyl)-6-(4-fluorophenyl)-6-(3-hydroxypropyl)-1,3-oxazinan-2-one

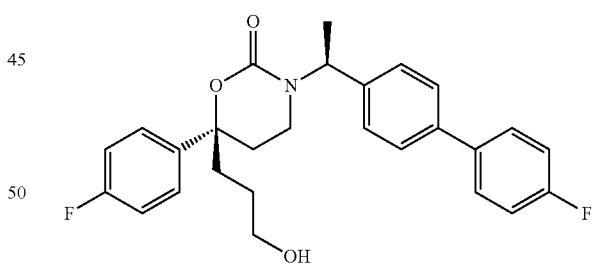

The title compound was prepared from (R)-6-allyl-3-((S)-1-(4'-fluorobiphenyl-4-yl)ethyl)-6-(4-fluorophenyl)-1,3-oxazinan-2-one following a procedure analogous to that described in Example 78. LC-MS Method 3 $t_R$=1.45, min, m/z=452, 474; $^1$H NMR (CDCl$_3$) 1.30 (m, 1H), 1.50 (m, 3H), 1.66 (m, 1H), 1.91 (m, 2H), 2.20 (m, 3H), 2.88 (m, 1H), 3.50 (m, 2H), 5.63 (m, 1H), 6.90-7.09 (m, 6H), 7.18 (m, 1H), 7.23 (m, 3H), 7.40 (m, 2H).

Example 246

(R)-3-((S)-1-(4'-fluorobiphenyl-4-yl)ethyl)-6-(2-fluorophenyl)-6-(3-hydroxypropyl)-1,3-oxazinan-2-one

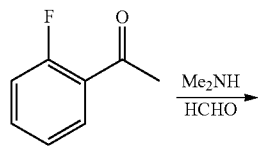

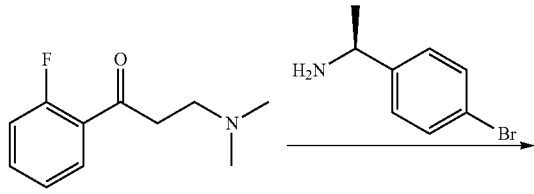

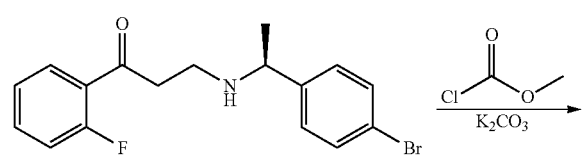

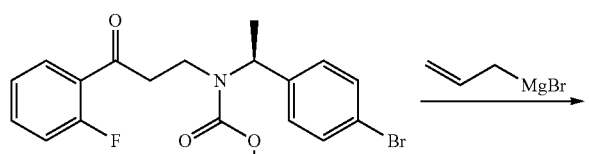

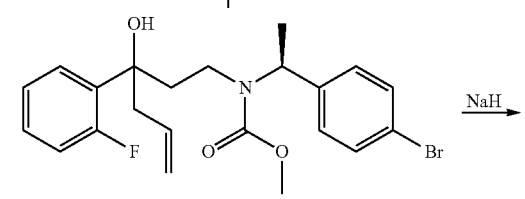

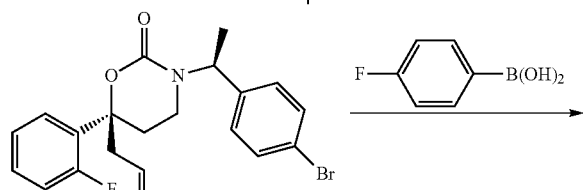

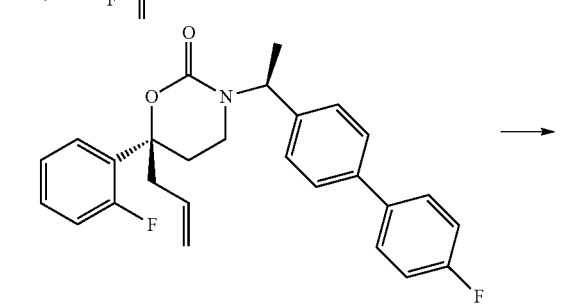

-continued

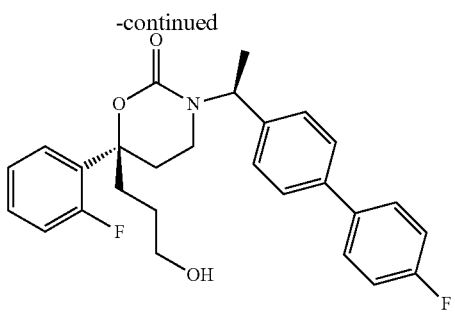

Step 1

1-(2-Fluorophenyl)ethanone (170 g, 1.23 mol), dimethylamine (137 g, 1.72 mol), and paraformaldehyde (55 g, 1.85 mol) were suspended in ethanol (500 mL), then concentrated HCl (3 mL) was added, and the mixture was heated to reflux overnight. The solvent was removed under vacuum. The residue was washed with EtOAc for 3 times to give 3-(dimethylamino)-1-(2-fluorophenyl)propan-1-one (207 g, 88%), which was used for the next step without purification. $^1$H NMR (CDCl$_3$): δ=2.69 (s, 6H), 2.52 (m, 4H), 7.30 (m, 2H), 7.66 (m, 1H), 7.96 (m, 1H).

Step 2

A solution of 3-dimethylamino-1-(2-fluoro-phenyl)-propan-1-one (17 g, 0.087 mol) and (S)-1-(4-bromophenyl)ethanamine (17 g, 0.087 mol) in EtOH (50 mL)/H$_2$O (50 mL) was refluxed at 80° C. over night. The solvent was removed under vacuum. The residue was purified by column chromatography to afford (S)-3-(1-(4-bromophenyl)ethylamino)-1-(2-fluorophenyl)propan-1-one (1 g, 3%).

Step 3

To a solution of (S)-3-(1-(4-bromophenyl)ethylamino)-1-(2-fluorophenyl)propan-1-one (500 mg, 1.43 mmol) in anhydrous CH$_3$CN (15 mL) was added K$_2$CO$_3$ and methyl carbonochloridate (403 mg, 4.29 mmol), and the mixture was stirred at rt for 2 h. The solution was concentrate, and the residue was purified by preparative TLC to afford (S)-methyl 1-(4-bromophenyl)ethyl(3-(2-fluorophenyl)-3-oxopropyl)carbamate (400 mg, 70%). $^1$H NMR (CDCl$_3$): δ=1.50 (m, 3H), 3.00 (m, 2H), 3.36 (m, 2H), 3.78 (m, 3H), 5.40 (m, 1H), 7.11 (m, 4H), 7.28-7.50 (m, 3H), 7.71 (m, 1H).

Step 4

To a solution of (S)-methyl-1-(4-bromophenyl)ethyl(3-(2-fluorophenyl)-3-oxopropyl)carbamate (400 mg, 1 mmol) in dry THF (10 mL) was added dropwise 1 M allylmagnesium bromide (20 mL)-78° C. After addition completely, the mixture was allowed to stir at rt for 3 h. The reaction was quenched with saturated aq NH$_4$Cl solution, and the solution was extract with EtOAc. The combined organic layer was washed with brine, dried over anhydrous Na$_2$SO$_4$ and concentrated to give methyl (S)-1-(4-bromophenyl)ethyl (3-(2-fluorophenyl)-3-hydroxyhex-5-enyl)carbamate (300 mg, 67%).

Step 5

To a suspension of NaH (55 g, 1.4 mmol) in THF (10 mL) at 0° C. was added a solution of methyl (S)-1-(4-bromophenyl)ethyl(3-(2-fluorophenyl)-3-hydroxyhex-5-enyl)carbamate (300 mg, 0.68 mmol) in THF (10 mL). The resulting mixture was stirred for 10 minutes, and then was refluxed for 1 h. The reaction was quenched with saturated aq NH$_4$Cl solution, and the solution was extract with EtOAc. The combine organic layer washed with brine, dried over anhydrous Na$_2$SO$_4$ and concentrated. The residue was purified by preparative TLC to afford (R)-6-allyl-3-((S)-1-(4-bromophenyl)ethyl)-6-(2-fluorophenyl)-1,3-oxazinan-2-one (100 mg, 35%) and (S)-6-allyl-3-((S)-1-(4-bromophenyl)ethyl)-6-(2-fluorophenyl)-1,3-oxazinan-2-one (100 mg, 35%).

Step 6

A mixture of (R)-6-allyl-3-((S)-1-(4-bromophenyl)ethyl)-6-(2-fluorophenyl)-1,3-oxazinan-2-one (100 mg, 0.24 mmol) and 4-fluorophenylboronic acid (55 mg, 0.36 mmol), Pd(Ph$_3$P)$_2$Cl$_2$ (20 mg), and aq Cs$_2$CO$_3$ solution (0.5 mL, 2 M) in 1,4-dioxane (10 mL) was stirred and heated to reflux for 2 h. The organic phase was separated, and concentrated to give the crude product, which was purified by preparative TLC to give (R)-6-allyl-3-((S)-1-(4'-fluorobiphenyl-4-yl)ethyl)-6-(2-fluorophenyl)-1,3-oxazinan-2-one (80 mg, 80%). $^1$H NMR (CDCl$_3$): δ=1.49 (m, 3H), 2.13 (m, 1H), 2.32 (m, 1H), 2.50 (m, 1H), 2.69 (m, 2H), 2.89 (m, 1H), 5.00 (m, 2H), 5.75 (m, 2H), 6.91-7.10 (m, 6H), 7.15 (m, 1H), 7.22 (m, 2H), 7.38 (m, 2H), 7.48 (m, 1H).

Step 7

To a solution of (R)-6-allyl-3-((S)-1-(4'-fluorobiphenyl-4-yl)ethyl)-6-(2-fluorophenyl)-1,3-oxazinan-2-one (80 mg, 0.18 mmol) in THF (10 mL) was added BH$_3$ THF (1.5 mL, 1 mol/L) at 0° C. under nitrogen. The formed mixture was stirred for 2 h. The reaction was quenched by water. Then aq NaOH (0.3 mL, 3 mol/L) solution and H$_2$O$_2$ (3 mL) was added to the above mixture. The resulting mixture was stirred for 1.5 h. The mixture was extracted with EtOAc, and the combined organic phase was concentrated to give the crude product, which was purified by preparative HPLC to give (R)-3-((S)-1-(4'-fluorobiphenyl-4-yl)ethyl)-6-(2-fluorophenyl)-6-(3-hydroxypropyl)-1,3-oxazinan-2-one (15 mg, 17%). LC-MS Method 2 t$_R$=1.48, min, m/z=452.2; $^1$H NMR (CD$_3$OD) 1.22-1.34 (m, 2H), 1.53 (d, 3H), 1.62-1.73 (m, 1H), 1.98-2.33 (m, 4H), 2.61 (d, 1H), 3.13 (m, 1H), 3.51 (m, 2H), 5.61 (m, 1H), 7.01-7.19 (m, 5H), 7.23 (m, 1H), 7.31-7.43 (m, 4H), 7.53 (m, 2H).

(S)-3-((S)-1-(4'-fluorobiphenyl-4-yl)ethyl)-6-(2-fluorophenyl)-6-(3-hydroxypropyl)-1,3-oxazinan-2-one was prepared from (S)-6-allyl-3-((S)-1-(4-bromophenyl)ethyl)-6-(2-fluorophenyl)-1,3-oxazinan-2-one following procedures analogous to those described in Steps 6 and 7 immediately above. LC-MS Method 3 t$_R$=1.531, min, m/z=452.2; $^1$H NMR (CD$_3$OD) 1.18-1.30 (m, 2H), 1.33 (d, 3H), 1.62-1.73 (m, 1H), 1.97-2.21 (m, 3H), 2.57-2.62 (d, 1H), 2.73-2.92 (m, 2H), 3.42-3.52 (m, 2H), 5.63 (m, 1H), 7.04-7.18 (m, 3H), 7.26 (m, 1H), 7.32-7.46 (m, 4H), 7.56-7.63 (m, 4H).

Example 247

(R)-3-((S)-1-(4'-fluorobiphenyl-4-yl)ethyl)-6-(3-fluorophenyl)-6-(3-hydroxypropy-1)-1,3-oxazinan-2-one

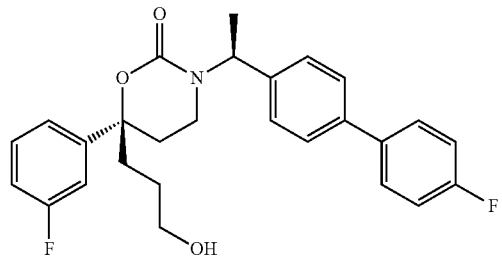 [SMILES: C[C@@H](c1ccc(-c2ccc(F)cc2)cc1)N1CC[C@](CCCO)(c2cccc(F)c2)OC1=O]

The title compound was prepared from 3-chloro-1-(3-fluorophenyl)propan-1-one using a procedure analogous to that described in Example 95 followed by a procedure analogous to that described in Example 78. LC-MS Method 3 t$_R$=1.214, min, m/z=452.1; $^1$H NMR (CDCl$_3$) 1.36-1.42 (m, 1H), 1.53 (d, 3H), 1.92-2.08 (m, 2H), 2.17-2.38 (m, 3H), 2.96 (m, 1H), 3.58 (m, 1H), 3.78-3.93 (m, 2H), 4.23 (m, 1H), 5.69 (m, 1H), 6.92-7.13 (m, 7H), 7.21-7.37 (m, 4H), 7.41-7.47 (m, 2H).

Example 248

(R)-3-((S)-1-(4'-fluorobiphenyl-4-yl)ethyl)-6-(3-hydroxy-3-methylbutyl)-6-phenyl-1,3-oxazinan-2-one

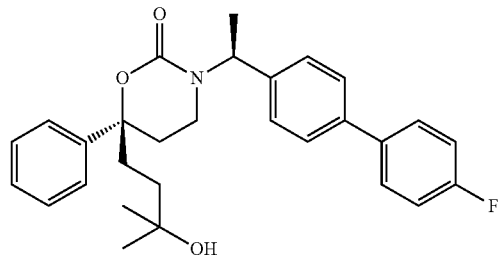 [SMILES: C[C@@H](c1ccc(-c2ccc(F)cc2)cc1)N1CC[C@](CCC(C)(C)O)(c2ccccc2)OC1=O]

The title compound was prepared from (R)-3-((S)-1-(4'-fluorobiphenyl-4-yl)ethyl)-6-(3-hydroxypropyl)-6-phenyl-1,3-oxazinan-2-one using a procedure analogous to that described in Example 117. LC-MS Method 3 t$_R$=1.284, min, m/z=484.1; $^1$H NMR (CDCl$_3$) 1.03 (s, 3H), 1.04 (s, 3H), 1.11-1.21 (m, 1H), 1.46 (d, 3H), 1.58-1.67 (m, 1H), 1.84-2.02 (m, 2H), 2.09-2.31 (m, 3H), 2.84 (m, 1H), 5.61-5.68 (m, 1H), 6.84-6.89 (m, 2H), 7.01-7.08 (m, 2H), 7.21 (m, 1H), 7.23 (m, 3H), 7.29 (m, 2H), 7.38 (m, 2H).

Example 249

(R)-3-((S)-1-(4-(5-acetylthiophen-2-yl)phenyl)ethyl)-6-(3-hydroxypropyl)-6-phenyl-1,3-oxazinan-2-one

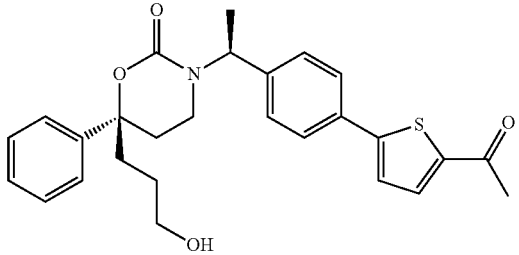 [SMILES: CC(=O)c1ccc(-c2ccc([C@H](C)N3CC[C@](CCCO)(c4ccccc4)OC3=O)cc2)s1]

The title compound was prepared from (R)-6-allyl-3-((S)-1-(4-bromophenyl)ethyl)-6-phenyl-1,3-oxazinan-2-one and 5-acetylthiophene-2-boronic acid using a procedure analogous to that described in Example 64 followed by a procedure analogous to that described in Example 78. LC-MS Method 3 $t_R$=1.26, min, m/z=464, 486; $^1$H NMR (CDCl$_3$) 1.46 (d, 3H), 1.63 (m, 2H), 1.92 (m, 2H), 2.12 (m, 1H), 2.26 (t, 2H), 2.49 (s, 3H), 2.85 (m, 1H), 3.50 (t, 2H), 5.60 (q, 1H), 6.85 (d, 2H), 7.20 (m, 8H), 7.56 (d, 1H).

Example 250

3-((R)-3-((S)-1-(2',4'-difluorobiphenyl-4-yl)ethyl)-2-oxo-6-phenyl-1,3-oxazinan-6-yl)propanamide

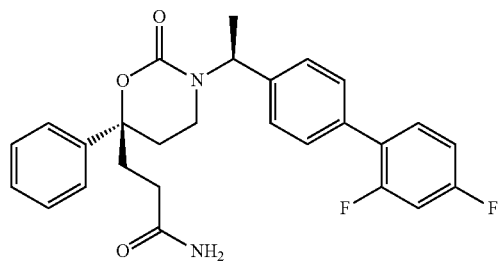 [SMILES: C[C@@H](c1ccc(-c2ccc(F)cc2F)cc1)N1CC[C@](CCC(N)=O)(c2ccccc2)OC1=O]

The title compound was prepared from (R)-3-((S)-1-(2',4'-difluorobiphenyl-4-yl)ethyl)-6-(3-hydroxypropyl)-6-phenyl-1,3-oxazinan-2-one using a procedure analogous to that described in Example 234. LC-MS Method 3 $t_R$=1.3, min, m/z=465; $^1$H NMR (CDCl$_3$): 1.51-1.60 (d, 3H), 1.91-2.03 (m, 1H), 2.12-2.38 (m, 5H), 2.46-2.57 (m, 1H), 2.88-2.97 (m, 1H), 5.32-5.54 (d, 2H), 5.63-5.74 (m, 1H), 6.82-6.93 (m, 2H), 6.94-7.02 (m, 2H), 7.19-7.22 (m, 1H), 7.27-7.38 (m, 6H).

Example 251

(6R)-3-((1S)-1-(4-(5-(1-aminoethyl)thiophen-2-yl)phenyl)ethyl)-6-(3-hydroxypropyl)-6-phenyl-1,3-oxazinan-2-one

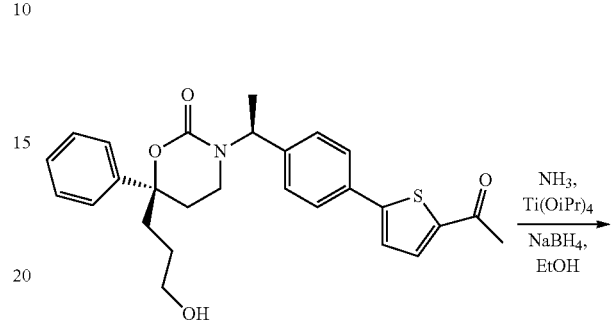

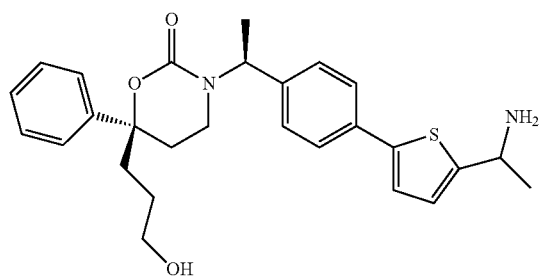

(R)-3-((S)-1-(4-(5-acetylthiophen-2-yl)phenyl)ethyl)-6-(3-hydroxypropyl)-6-phenyl-1,3-oxa-zinan-2-one (40 mg, 0.086 mmol) and tetraisopropoxytitanium (49 mg, 0.17 mmol) are stirred overnight in the solution of NH$_3$ in EtOH. To this solution/paste was added NaBH$_4$ and stirring another 24 h. The reaction was diluted with NH$_4$OH and stirred for 1 h. The mixture was filtered through celite and rinsed with EtOAc. Water and EtOAc were added and the organic layer was separated. The aq layer is extracted with EtOAc for three times. The combined organic layer was dried over Na$_2$SO$_4$, filtered and concentrated to afford (6R)-3-((1S)-1-(4-(5-(1-aminoethyl)thiophen-2-yl)phenyl)ethyl)-6-(3-hydroxypropyl)-6-phenyl-1,3-oxazinan-2-one (1.26 mg, 3%). LC-MS Method 2 $t_R$=1.014, min, m/z=448.1; $^1$H NMR (CDCl$_3$, 400 MHz): 1.33 (m, 1H), 1.47 (q, 6H), 1.90 (m, 2H), 2.13 (m, 1H), 2.22 (m, 2H), 2.82 (m, 1H), 3.50 (m, 2H), 4.33 (q, 1H), 5.58 (q, 1H), 6.81 (m, 3H), 6.98 (d, 1H), 7.25 (m, 7H).

Example 252

(R)-3-((S)-1-(4'-fluorobiphenyl-4-yl)propyl)-6-(4-fluorophenyl)-6-(3-hydroxypropyl)-1,3-oxazinan-2-one

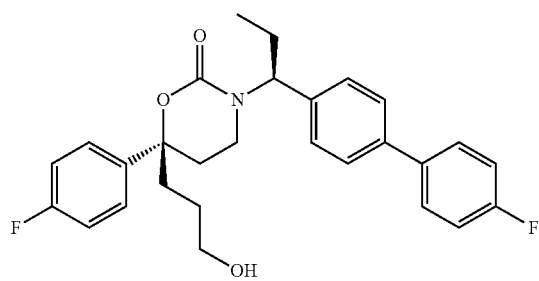 [SMILES: CC[C@@H](c1ccc(-c2ccc(F)cc2)cc1)N1CC[C@](CCCO)(c2ccc(F)cc2)OC1=O]

The title compound was prepared from (R)-6-allyl-3-((S)-1-(4'-fluorobiphenyl-4-yl)propyl)-6-(4-fluorophenyl)-1,3-oxazinan-2-one using a procedure analogous to that in Example 78. LC-MS Method 3 $t_R$=1.48, min, m/z=466, 488; $^1$H NMR (CDCl$_3$) 1.02 (t, 3H), 1.44 (m, 1H), 1.68 (m, 2H), 1.90-2.06 (m, 4H), 2.23 (m, 2H), 2.34 (m, 1H), 2.98 (m, 1H), 3.58 (t, 2H), 5.5-48 (m, 1H), 6.97 (m, 2H), 7.02-7.12 (m, 4H), 7.18-7.23 (m, 2H), 7.31 (d, 2H), 7.46 (m, 2H).

Example 253

(R)-3-((S)-1-(2',4'-difluorobiphenyl-4-yl)propyl)-6-(3-hydroxypropyl)-6-phenyl-1,3-oxazinan-2-one

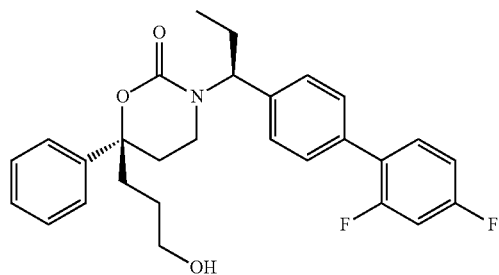 [SMILES: CC[C@@H](c1ccc(-c2ccc(F)cc2F)cc1)N1CC[C@](CCCO)(c2ccccc2)OC1=O]

The title compound was prepared from (R)-6-allyl-3-((S)-1-(2',4'-difluorobiphenyl-4-yl)propyl)-6-phenyl-1,3-oxazinan-2-one using a procedure analogous to that in Example 78. LC-MS Method 3 tR=1.5, min, m/z=466; 1H NMR (CDCl3) 1.02 (t, 3H), 1.31 (m, 1H), 1.63 (m, 1H), 1.96-2.11 (m, 4H), 2.25 (m, 1H), 2.36 (m, 1H), 2.48 (m, 1H), 3.12 (m, 1H), 3.49 (m, 2H), 5.39 (m, 1H), 7.00-7.11 (m, 4H), 7.22-7.36 (m, 7H), 7.42 (m, 1H).

Example 254

(6R)-3-((1S)-1-(4-(5-(1-hydroxyethyl)thiophen-2-yl)phenyl)ethyl)-6-(3-hydroxypropyl)-6-phenyl-1,3-oxazinan-2-one

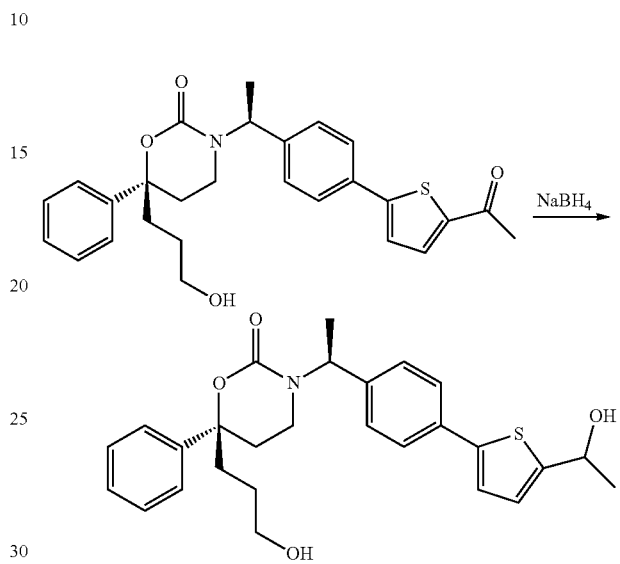

LC-MS Method 2 $t_R$=2.13, min, m/z=466, 488; $^1$H NMR (CDCl$_3$) 1.45 (d, 2H), 1.56 (d, 2H), 1.64 (m, 2H), 1.90 (m, 2H), 2.11 (m, 1H), 2.21 (m, 2H), 2.31 (s, 1H), 2.80 (m, 1H), 3.49 (t, 2H), 5.03 (q, 1H), 5.57 (q, 1H), 6.80 (d, 2H), 6.84, (d, 1H), 6.98 (d, 1H), 7.24 (m, 7H).

Example 255

(6S)-3-((1S)-1-(4-bromophenyl)propyl)-6-(2,3-dihydroxypropyl)-6-(4-fluorophenyl)-1,3-oxazinan-2-one

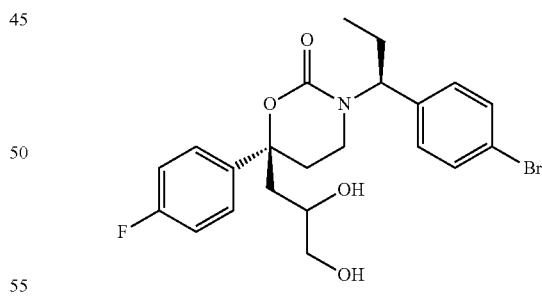

The title compound was prepared from (R)-6-allyl-3-((S)-1-(4-bromophenyl)propyl)-6-(4-fluorophenyl)-1,3-oxazinan-2-one using a procedure analogous to that described in Example 173. Two isomers were isolated.

Isomer 1: LC-MS Method 3 $t_R$=1.175, min, m/z=488.1; $^1$H NMR (CDCl$_3$) 0.99 (t, 3H), 1.82-2.01 (m, 3H), 2.22-2.31 (m, 3H), 2.33-2.43 (m, 1H), 2.96 (m, 1H), 3.33 (m, 1H), 3.48 (m, 1H), 3.79 (m, 1H), 5.38 (m, 1H), 6.88 (m, 2H), 7.03 (m, 2H), 7.19 (m, 2H), 7.28 (m, 2H).

Isomer 2: LC-MS Method 3 tR=1.186, min, m/z=490.1; 1H NMR (CDCl3) 0.97-1.02 (m, 3H), 1.82-1.98 (m, 3H), 2.21-2.32 (m, 3H), 2.33-2.45 (m, 1H), 2.89-2.94 (m, 1H), 3.32 (m, 1H), 3.48 (m, 1H), 3.78 (m, 1H), 5.88 (m, 1H), 6.89 (m, 2H), 7.02 (m, 2H), 7.18 (m, 2H), 7.27 (m, 2H).

Example 256

(R)-6-(3-aminopropyl)-3-((S)-1-(2',4'-difluorobiphenyl-4-yl)ethyl)-6-(4-fluorophenyl)-1,3-oxazinan-2-one

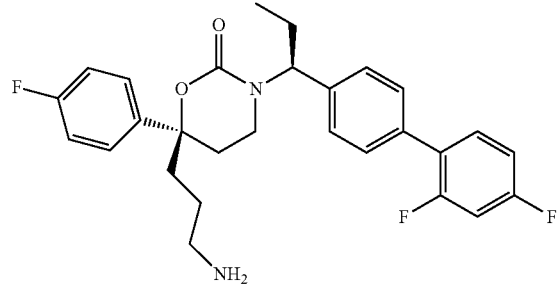 [SMILES: CC[C@@H](c1ccc(-c2ccc(F)cc2F)cc1)N1CC[C@](CCCN)(c2ccc(F)cc2)OC1=O]

The title compound was prepared from (R)-3-((S)-1-(2',4'-difluorobiphenyl-4-yl)ethyl)-6-(4-fluorophenyl)-6-(3-hydroxypropyl)-1,3-oxazinan-2-one using procedures analogous to those described in Example 75 Steps 2 to 4. LC-MS Method 2 $t_R$=2.15, min, m/z=469; $^1$H NMR (CDCl$_3$) 1.42-1.51 (d, 3H), 1.51-1.54 (m, 1H), 1.73-1.82 (m, 1H), 1.96-2.06 (m, 2H), 2.13-2.26 (m, 3H), 2.82-2.96 (m, 3H), 5.46-5.53 (m, 1H), 6.79-6.98 (m, 6H), 7.10-7.14 (m, 2H), 7.22-7.27 (m, 2H), 8.13-8.29 (m, 2H).

Example 257

(R)-3-((S)-1-(2',4'-difluorobiphenyl-4-yl)ethyl)-6-(4-fluorophenyl)-6-(2-(methylamino)ethyl)-1,3-oxazinan-2-one

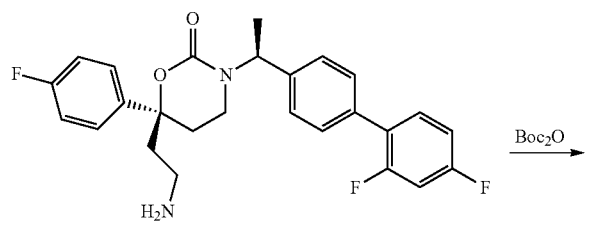

Boc$_2$O →

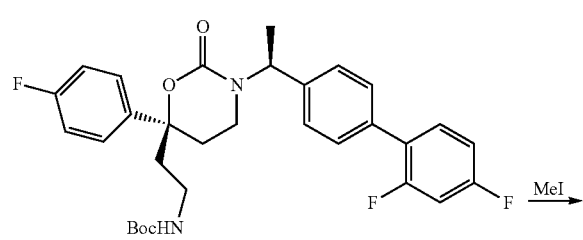

MeI →

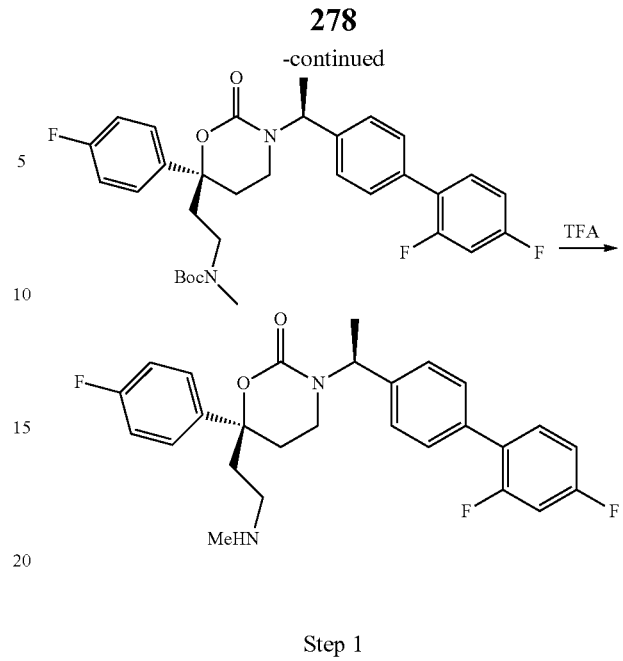

TFA →

Step 1

To a solution of (R)-6-(2-aminoethyl)-3-((S)-1-(2',4'-difluorobiphenyl-4-yl)ethyl)-6-(4-fluorophenyl)-1,3-oxazinan-2-one (150 mg, 0.33 mmol) and Et$_3$N (83.3 mg, 0.825 mmol) in dichloromethane (5 mL) was added di-tert-butyl dicarbonate (85.5 mg, 0.4 mmol) at 0-5° C. The resulting mixture was stirred at rt overnight. The solid was filtered and the resulting filtrate was washed with 5% HCl, extracted with CH$_2$Cl$_2$ give the organic layer which was concentrated to give tert-butyl 2-((R)-3-((S)-1-(2',4'-difluorobiphenyl-4-yl)ethyl)-6-(4-fluorophenyl)-2-oxo-1,3-oxazinan-6-yl)ethylcarbamate (53 mg, 29%).

Step 2

To a solution of tert-butyl 2-((R)-3-((S)-1-(2',4'-difluorobiphenyl-4-yl)ethyl)-6-(4-fluorophenyl)-2-oxo-1,3-oxazinan-6-yl)ethylcarbamate (53 mg, 0.1 mmol) in tetrahydrofuran was added NaH (300 mg, 12.5 mmol) at 0° C. The mixture was stirred at 0° C. for 1 h. Then iodomethane (1.3 g, 9.15 mmol) was added to the above mixture and the mixture was stirred for 2 h. The reaction was quenched with H$_2$O and extracted with EtOAc to give the organic layer which was washed with brine, dried over Na$_2$SO$_4$ and filtered. The filtrate was concentrated to give tert-butyl 2-((R)-3-((S)-1-(2',4'-difluorobiphenyl-4-yl)ethyl)-6-(4-fluorophenyl)-2-oxo-1,3-oxazinan-6-yl)ethyl(methyl)carbamate (36 mg, 66%).

Step 3

A solution of tert-butyl 2-((R)-3-((S)-1-(2',4'-difluorobiphenyl-4-yl)ethyl)-6-(4-fluorophenyl)-2-oxo-1,3-oxazinan-6-yl)ethyl(methyl)carbamate (73 mg, 0.13 mmol) in TFA/CH$_2$Cl$_2$ (20%, 6 mL) was stirred at 0° C. for 1 h. After the material was consumed, the solution was concentrated to give residue, which was purified by preparative TLC followed by preparative HPLC to give (R)-3-((S)-1-(2',4'-difluorobiphenyl-4-yl)ethyl)-6-(4-fluorophenyl)-6-(2-(methylamino)ethyl)-1,3-oxazinan-2-one (13 mg, 21%). LC-MS Method 3 $t_R$=1.10, min, m/z=469; $^1$H NMR (CDCl$_3$): 1.50 (d, 3H), 2.25

(m, 4H), 2.37 (m, 1H), 2.60 (m, 3H), 2.81 (m, 1H), 2.98 (m, 2H) 6.85 (m, 2H), 7.00 (m, 4H), 7.18 (m, 2H), 7.28 (m, 3H).

Example 258

(R)-6-allyl-6-(4-fluorophenyl)-3-((S)-1-(4-(3-(trifluoromethyl)-1H-pyrazol-1-yl)phenyl)ethyl)-1,3-oxazinan-2-one

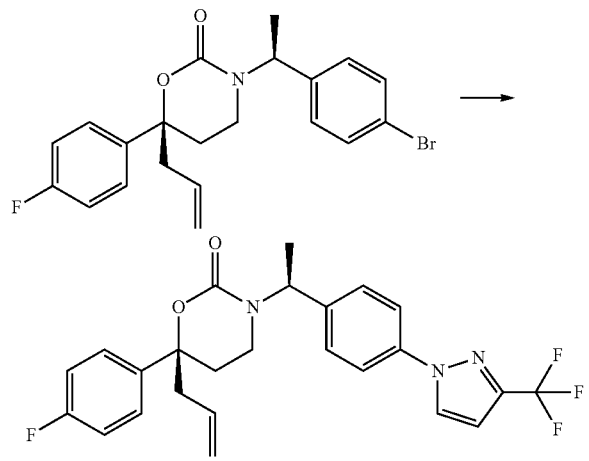

(R)-6-Allyl-3-((S)-1-(4-bromophenyl)ethyl)-6-(4-fluorophenyl)-1,3-oxazinan-2-one (20 mg, 0.048 mmol), 3-(trifluoromethyl)-1H-pyrazole (20 mg, 3 equiv.), CuI (1.4 mg, 15% mol), (1R,2R)-(–)-1,2-transcyclohexanediamine (2 mg, 30% mol), K$_3$PO$_4$ (20 mg, 2 equiv.) were mixed with dry toluene (2 mL) and heated in Microwave Oven for 1 h at 130° C. LC-MS found product peak. The mixture was diluted with EtOAc (8 mL), washed by water (2 mL), brine (3 mL) and dried over Na$_2$SO$_4$. After filtration and concentration, the residue was purified chromatography on a 4-g silica gel cartridge eluted with a gradient from 5 to 55% EtOAc in gexanes to afford (R)-6-allyl-6-(4-fluorophenyl)-3-((S)-1-(4-(3-(trifluoromethyl)-1H-pyrazol-1-yl)phenyl)ethyl)-1,3-oxazinan-2-one (9.7 mg, 43%) product. LC-MS Method 1 $t_R$=2.05, min, m/z=474; $^1$H NMR (CDCl$_3$) 7.86 (s, 1H), 7.43 (d, 2H), 7.26 (t, 2H), 7.01 (dd, 2H), 6.69 (d, 1H), 5.76-5.64 (m, 2H), 5.05 (dd, 2H), 2.95 (m, 1H), 2.65-2.51 (m, 2H), 1.54 (d, 3H).

Example 259

(S)-6-(4-fluorophenyl)-6-(2-hydroxyethyl)-3-((S)-1-(4-(1,1-dioxo-hexahydro-1,2-thiazin-2-yl)phenyl)ethyl)-1,3-oxazinan-2-one

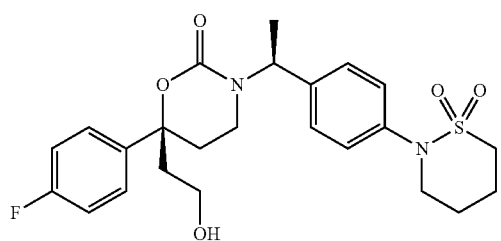 [SMILES: C[C@@H](c1ccc(N2CCCCS2(=O)=O)cc1)N1CC[C@](CCO)(c2ccc(F)cc2)OC1=O]

The title compound was prepared from (S)-3-((S)-1-(4-bromophenyl)ethyl)-6-(4-fluorophenyl)-6-(2-hydroxyethyl)-1,3-oxazinan-2-one and 1,1-dioxo-hexahydro-1,2-thiazine following a procedure analogous to that described in Example 228. LC-MS Method 1 $t_R$=1.35, min, m/z=477; $^1$H NMR (CD$_3$OD) 7.26-7.22 (m, 2H), 7.05-7.01 (m, 4H), 6.87 (d, J=8.5 Hz, 2H), 5.45 (q, J=7.0 Hz, 1H), 3.61-3.55 (m, 4H), 3.15-3.12 (m, 2H), 3.05-3.01 (m, 1H), 2.44-2.40 (m, 1H), 2.24-2.17 (m, 4H), 2.04 (t, J=72 Hz, 2H), 1.83-1.77 (m, 2H), 1.44 (d, J=7.0 Hz, 3H).

Example 260

(R)-3-((S)-1-(2',4'-difluorobiphenyl-4-yl)ethyl)-6-(3-hydroxy-3-methylbutyl)-6-phenyl-1,3-oxazinan-2-one

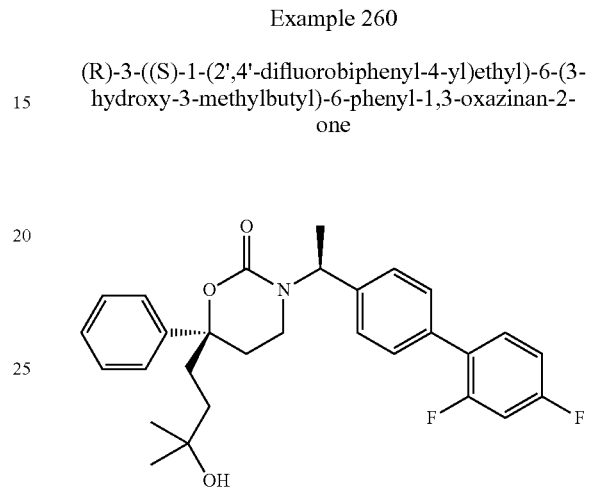

The title compound was prepared from (R)-3-((S)-1-(2',4'-difluorobiphenyl-4-yl)ethyl)-6-(3-hydroxypropyl)-6-phenyl-1,3-oxazinan-2-one following a procedure analogous to that described in Example 117. LC-MS Method 3 $t_R$=1.561, min, m/z=436.3; $^1$H NMR (CDCl3) 1.11 (s, 3H), 1.13 (s, 3H), 1.18-1.27 (m, 1H), 1.53 (d, 3H), 1.61-1.72 (m, 1H), 1.91-2.06 (m, 2H), 2.16-2.24 (m, 1H), 2.27-2.38 (m, 2H), 2.91 (m, 1H), 5.68-5.72 (m, 1H), 6.82-6.97 (m, 4H), 7.19 (m, 2H), 7.23-7.36 (m, 6H).

Example 261

(R)-3-((S)-1-(2',4'-difluorobiphenyl-4-yl)propyl)-6-(4-fluorophenyl)-6-(3-hydroxypropyl)-1,3-oxazinan-2-one

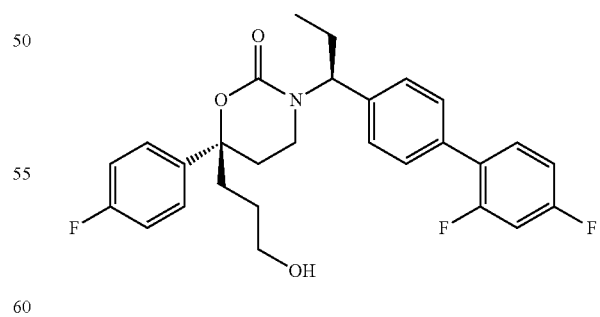

The title compound was prepared from (R)-6-allyl-3-((S)-1-(4-bromophenyl)propyl)-6-(4-fluorophenyl)-1,3-oxazinan-2-one and 2,4-difluorobenzeneboronic acid using a procedure analogous to that described in Example 64 followed by a procedure analogous to that described in Example 78. LC-MS Method 3 $t_R$=1.49, min, m/z=484; $^1$H NMR (CDCl$_3$) 1.01 (t, 3H), 1.34 (m, 1H), 1.68 (m, 2H), 1.89-2.04 (m, 4H), 2.23 (m, 2H), 2.34 (m, 1H), 2.98 (m, 1H), 3.58 (t, 2H), 5.49 (t, 1H), 6.85-6.98 (m, 4H), 7.09 (d, 2H), 7.21 (m, 2H), 7.25-7.31 (m, 3H).

Example 262

(S)-3-((S)-1-(2',4'-difluorobiphenyl-4-yl)ethyl)-6-(4-fluorophenyl)-6-(2-(methylthio)ethyl)-1,3-oxazinan-2-one

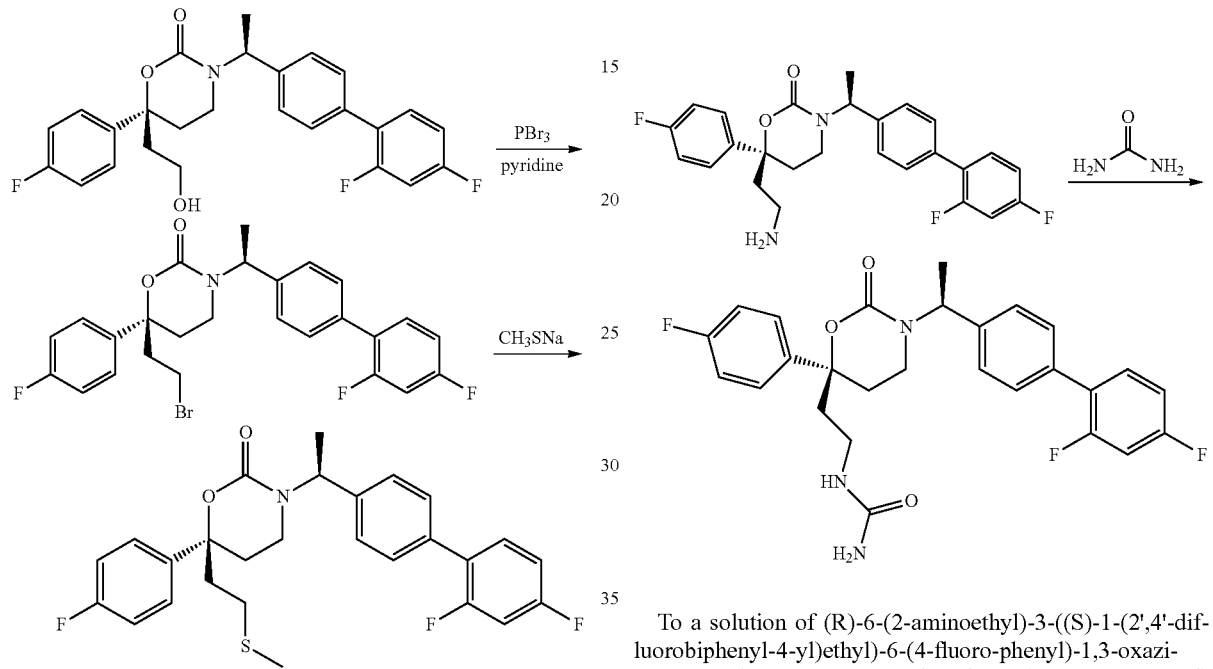

Step 1

To a solution of (S)-3-((S)-1-(2',4'-difluorobiphenyl-4-yl)ethyl)-6-(4-fluorophenyl)-6-(2-hydroxyethyl)-1,3-oxazinan-2-one (250 mg, 0.55 mmol) in methylene chloride (10 mL) was added pyridine (0.5 mL) and PBr$_3$ (75 mg). The formed mixture was stirred for 2 h. The mixture was washed with water. The organic phase was separated, and concentrated to give the crude product, which was purified by preparative TLC to afford (S)-6-(2-bromoethyl)-3-((S)-1-(2',4'-difluorobiphenyl-4-yl)ethyl)-6-(4-fluorophenyl)-1,3-oxazinan-2-one (60 mg, 23%). $^1$H NMR: (400 MHz, CDCl$_3$): δ=1.45 (d, 3H), 2.12-2.38 (d, 4H), 2.43 (m, 1H), 2.94 (m, 3H), 3.49 (m, 1H), 5.22 (m, 1H), 6.83 (m, 2H), 6.95 (m, 4H), 7.19 (m, 1H), 7.22 (m, 2H).

Step 2

To a solution of (S)-6-(2-bromoethyl)-3-((S)-1-(2',4'-difluorobiphenyl-4-yl)ethyl)-6-(4-fluorophenyl)-1,3-oxazinan-2-one (30 mg, 0.058 mmol) in tetrahydrofuran (10 mL) was added CH$_3$SNa (0.5 mL). The formed mixture was stirred overnight. The mixture was washed with water. The organic phase was separated, and concentrated to give the crude product, which was purified by preparative TLC to afford (S)-3-((S)-1-(2',4'-difluorobiphenyl-4-yl)ethyl)-6-(4-fluorophenyl)-6-(2-(methylthio)ethyl)-1,3-oxazinan-2-one (20 mg, 71%). LC-MS Method 3 t$_R$=1.74, min, m/z=486, 508; $^1$H NMR: (400 MHz, CDCl$_3$): δ=1.48 (d, 3H), 1.96 (m, 2H), 2.02 (m, 1H), 2.11-2.31 (m, 6H), 2.61 (m, 1H), 2.90 (m, 1H), 5.64 (q, 1H), 6.80-6.90 (m, 2H), 6.92-6.98 (m, 4H), 7.18 (m, 2H), 7.26 (m, 2H).

Example 263

1-(2-((R)-3-((S)-1-(2',4'-difluorobiphenyl-4-yl)ethyl)-6-(4-fluorophenyl)-2-oxo-1,3-oxazinan-6-yl)ethyl)urea

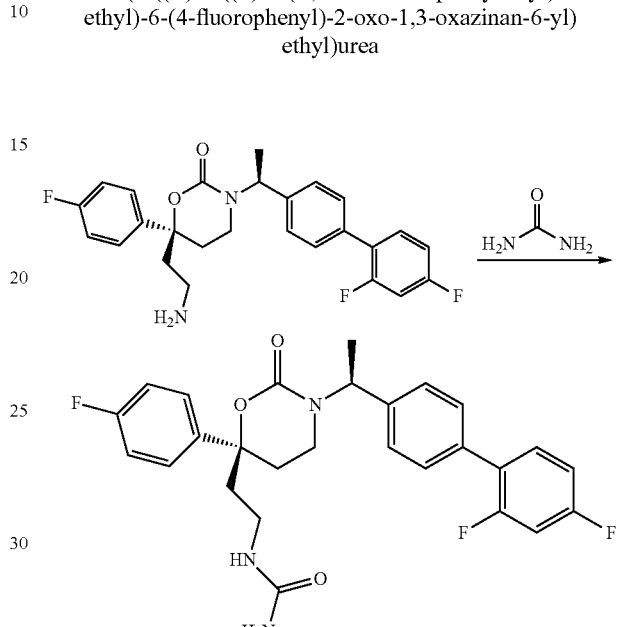

To a solution of (R)-6-(2-aminoethyl)-3-((S)-1-(2',4'-difluorobiphenyl-4-yl)ethyl)-6-(4-fluoro-phenyl)-1,3-oxazinan-2-one (30 mg, 0.065 mmol) and urea (16 mg, 0.26 mmol) in H$_2$O (3 mL) was added concentrated HCl (0.05 mL), and the mixture was refluxed overnight. The reaction mixture was crystallized by standing at rt. The precipitate was filtered and rinsed well with water to give 1-(2-((R)-3-((S)-1-(2',4'-difluorobiphenyl-4-yl)ethyl)-6-(4-fluorophenyl)-2-oxo-1,3-oxazinan-6-yl)ethyl)urea (20 mg, 68%). LC-MS Method 3 tR=1.3, min, m/z=498; $^1$H NMR (CDCl$_3$): 1.54-1.60 (d, 3H), 2.01-2.09 (m, 1H), 2.22-2.41 (m, 4H), 2.91-3.14 (m, 2H), 3.35-3.44 (m, 1H), 5.56-5.62 (s, 1H), 5.63-5.71 (m, 1H), 6.87-6.99 (m, 2H), 7.01-7.12 (m, 3H), 7.22-7.31 (m, 2H), 7.32-7.48 (m, 3H).

Example 264

2-((S)-3-((S)-1-(2',4'-difluorobiphenyl-4-yl)ethyl)-6-(4-fluorophenyl)-2-oxo-1,3-oxazinan-6-yl)ethyl carbamate

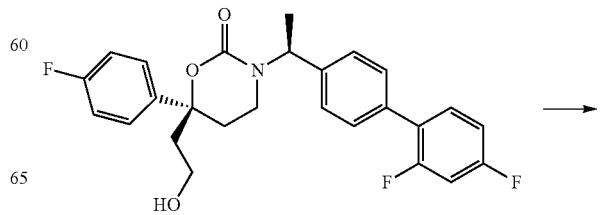

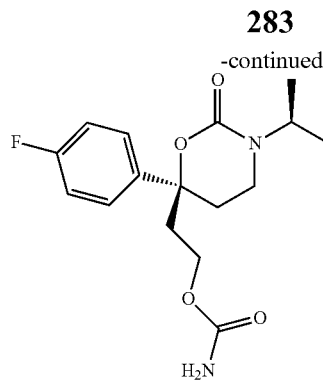

(S)-3-((S)-1-(2',4'-difluorobiphenyl-4-yl)ethyl)-6-(4-fluorophenyl)-6-(2-hydroxyethyl)-1,3-oxazinan-2-one (50 mg, 0.11 mmol) was dissolved in CH$_2$Cl$_2$ (3 mL), followed by the addition of TEA (1 mL) and 4-nitrophenyl carbonochloridate (88 mg, 0.44 mmol). The mixture was stirred at rt overnight. Aqueous ammonia (2 mL) was added and the mixture was stirred at rt for 3 h. After separation of the water layer, the organic layer was washed with brine, dried over Na$_2$SO$_4$, and concentrated in vacuo to give the crude product, which was purified by preparative TLC to afford 2-((S)-3-((S)-1-(2',4'-difluorobiphenyl-4-yl)ethyl)-6-(4-fluorophenyl)-2-oxo-1,3-oxazinan-6-yl)ethyl carbamate (20 mg, 35%). LC-MS Method 3 t$_R$=1.36, min, m/z=499; $^1$H NMR (CDCl$_3$): 1.48 (m, 3H), 2.14-2.33 (m, 5H), 2.91 (m, 1H), 3.42 (s, 1H), 3.95 (m, 1H), 4.07 (m, 1H), 4.62 (s, 2H), 5.61 (m, 1H), 6.79-7.01 (m, 6H), 7.23 (m, 5H).

Example 265

(6S)-3-((S)-1-(2',4'-difluorobiphenyl-4-yl)ethyl)-6-(4-fluorophenyl)-6-(2-hydroxy-3-(methylamino)propyl)-1,3-oxazinan-2-one

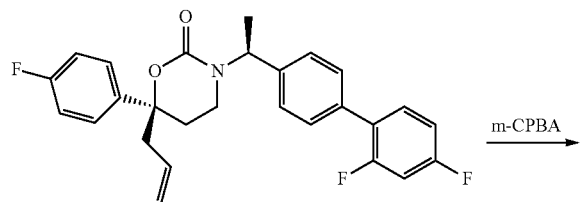

Step 1

To a solution of (R)-6-allyl-3-((S)-1-(2',4'-difluorobiphenyl-4-yl)ethyl)-6-(4-fluorophenyl)-1,3-oxazinan-2-one (900 mg, 2.0 mmol) in dry CH$_2$Cl$_2$ (30 mL) was added dropwise 3-chlorobenzoperoxoic acid (690 mg, 4.0 mmol) by portion at 0° C. Then the reaction mixture was stirred overnight at ambient temperature. The reaction mixture was quenched by 10% Na$_2$SO$_3$ solution. The organic phase was dried over Na$_2$SO$_4$, filtered and concentrated to afford the residue, which was purified by TLC to give (6S)-3-((S)-1-(2',4'-difluorobiphenyl-4-yl)ethyl)-6-(4-fluorophenyl)-6-(oxiran-2-ylmethyl)-1,3-oxazinan-2-one (470 mg, 50%). $^1$H NMR (CDCl$_3$): 1.54 (m, 3H), 1.71 (m, 3H), 2.01 (m, 2H), 2.15 (m, 3H), 2.48 (m, 2H), 2.67 (m, 1H), 3.00 (m, 1H), 5.67 (m, 1H), 6.84 (m, 4H), 7.02 (m, 2H), 7.21 (m, 4H), 7.31 (m, 1H).

Step 2

To a solution of (6S)-3-((S)-1-(2',4'-difluorobiphenyl-4-yl)ethyl)-6-(4-fluorophenyl)-6-(oxiran-2-ylmethyl)-1,3-oxazinan-2-one (135 mg, 0.289 mmol) in MeOH (2 mL) was added methylamine alcohol solution (2 mL, 25 mmol) at 0□. Then the mixture was stirred overnight at ambient temperature. The reaction mixture was concentrated to give the residue, which was purified by preparative HPLC to give (6S)-3-((S)-1-(2',4'-difluorobiphenyl-4-yl)ethyl)-6-(4-fluorophenyl)-6-(2-hydroxy-3-(methylamino)propyl)-1,3-oxazinan-2-one (23 mg, 16%). $^1$H NMR (CDCl$_3$): 1.52 (m, 3H), 1.81 (m, 2H), 2.03 (m, 6H), 2.28 (m, 2H), 2.63 (m, 3H), 2.51 (m, 2H), 2.95 (m, 1H), 3.46 (m, 1H), 5.64 (m, 1H), 6.85 (m, 4H), 7.01 (m, 2H), 7.22 (m, 4H), 7.32 (m, 1H).

Example 266

(S)-3-((S)-1-(2',4'-difluorobiphenyl-4-yl)ethyl)-6-(4-fluorophenyl)-6-(2-(2-hydroxyethoxy)ethyl)-1,3-oxazinan-2-one

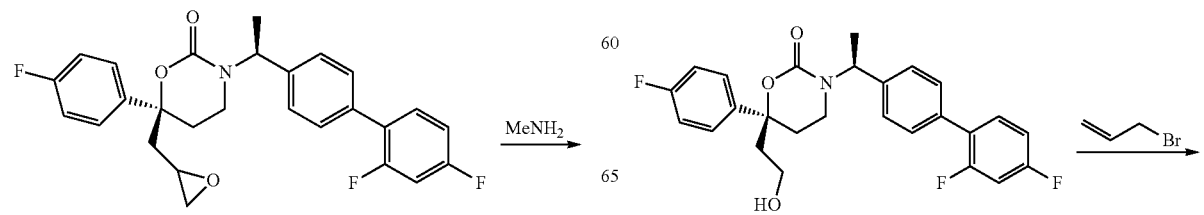

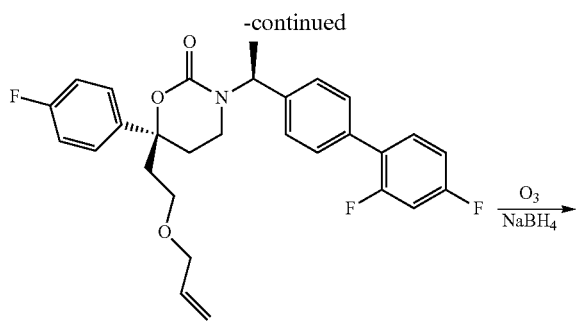

Step 1

To a solution of (S)-3-((S)-1-(2',4'-difluorobiphenyl-4-yl)ethyl)-6-(4-fluorophenyl)-6-(2-hydro-xyethyl)-1,3-oxazinan-2-one (100 mg, 0.22 mmol) in THF (5 mL) was added NaH (30 mg, 1.10 mmol) at 0° C. After stirring for 1 h, allyl bromide (79 mg, 0.66 mmol) was added, and the mixture was stirred at rt overnight. The reaction was quenched with water, and extracted with EtOAc. The combined organic layers were washed with brine, dried over Na$_2$SO$_4$, filtered and concentrated. The residue was purified by preparative TLC to give (S)-6-(2-(allyloxy)ethyl)-3-((S)-1-(2',4'-difluorobiphenyl-4-yl)ethyl)-6-(4-fluorophenyl)-1,3-oxazinan-2-one (100 mg, 92%) $^1$H NMR (CDCl$_3$): 1.47-1.59 (d, 3H), 2.05-2.15 (m, 2H), 2.21-2.38 (m, 3H), 2.88-2.93 (m, 1H), 3.12-3.19 (m, 1H), 3.52-3.59 (m, 1H). 3.62-3.85 (m, 2H), 5.03-5.18 (m, 2H), 5.61-5.69 (m, 1H), 5.71-5.81 (m, 1H), 6.81-6.92 (m, 3H), 6.92-7.01 (m, 2H), 7.13-7.20 (m, 4H), 7.21-7.26 (m, 3H).

Step 2

A solution of (S)-6-(2-(allyloxy)ethyl)-3-((S)-1-(2',4'-difluorobiphenyl-4-yl)ethyl)-6-(4-fluorophenyl)-1,3-oxazinan-2-one (100 mg, 0.20 mmol) in CH$_2$Cl$_2$ (10 mL) was treated with O$_3$ at −78° C. till the mixture was turned blue. Then NaBH$_4$ (50 mg, 1.0 mmol) was added, and the mixture was stirred at rt overnight. The solution was concentrated and the residue was purified by preparative HPLC to give (S)-3-((S)-1-(2',4'-difluorobiphenyl-4-yl)ethyl)-6-(4-fluorophenyl)-6-(2-(2-hydroxyethoxy)ethyl)-1,3-oxazinan-2-one (40 mg, 30%). LC-MS Method 3 tR=1.41, min, m/z=500, 522; $^1$H NMR (CDCl$_3$): 1.48-1.61 (d, 3H), 1.92-2.05 (m, 2H), 2.09-2.41 (m, 5H), 2.88-3.02 (m, 1H), 3.27-3.56 (m, 2H), 3.58-3.69 (m, 2H), 5.63-5.72 (m, 1H), 6.82-7.08 (m, 6H), 7.17-7.34 (m, 5H).

Example 267

(S)-6-(2-(1H-imidazol-1-yl)ethyl)-3-((S)-1-(2',4'-difluorobiphenyl-4-yl)ethyl)-6-(4-fluorophenyl)-1,3-oxazinan-2-one

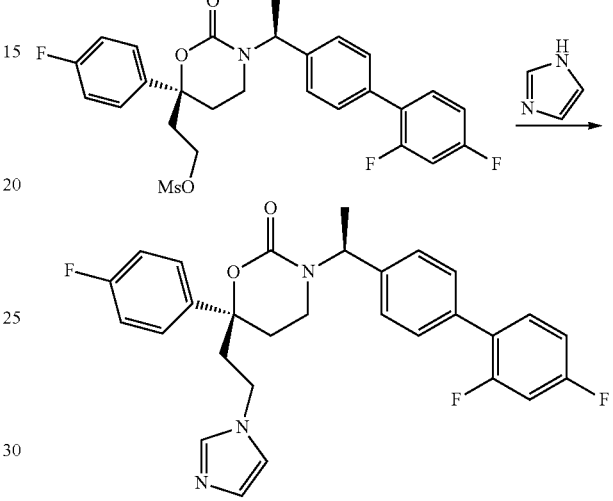

A mixture of 2-((S)-3-((S)-1-(2',4'-difluorobiphenyl-4-yl)ethyl)-6-(4-fluorophenyl)-2-oxo-1,3-oxazinan-6-yl)ethyl methanesulfonate (230 mg, 0.43 mmol), imidazole (44 mg, 0.65 mmol), K$_2$CO$_3$ (178.7 mg, 1.29 mmol) in acetonitrile (4 mL) was heated to reflux overnight. The solvent was removed and the residue was partitioned between EtOAc and water. The aqueous layer was extracted with EtOAc and the combined organic layer was washed with brine, dried over Na$_2$SO$_4$, filtered and concentrated to give the crude product, which was purified by preparative HPLC to give (R)-3-[(S)-1-(2',4'-difluoro-biphenyl-4-yl)-ethyl]-6-(4-fluoro-phenyl)-6-(2-imidazol-1-yl-ethyl)-[1,3]oxazinan-2-one (2.5 mg, 1.2%). LC-MS Method 2 t$_R$=2.14, min, m/z=506; $^1$H NMR (CDCl$_3$): 1.51 (d, 3H), 2.16-2.63 (m, 7H), 2.94 (m, 2H), 3.91 (m, 1H), 4.32 (m, 1H), 5.66 (m, 1H), 6.25 (m, 1H), 6.81-6.90 (m, 2H), 6.94-7.08 (m, 5H), 7.14-7.26 (m, 6H).

Example 268

(R)-6-(2-(2H-tetrazol-5-yl)ethyl)-3-((S)-1-(2',4'-difluorobiphenyl-4-yl)ethyl)-6-(4-fluorophenyl)-1,3-oxazinan-2-one

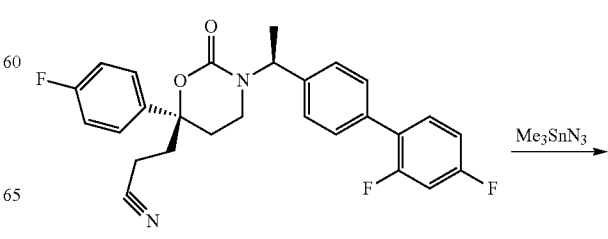

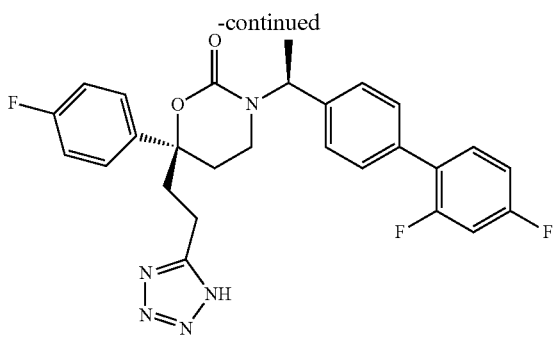

To a solution of 3-((R)-3-((S)-1-(2',4'-difluorobiphenyl-4-yl)ethyl)-6-(4-fluorophenyl)-2-oxo-1,3-oxazinan-6-yl)propanenitrile (40 mg, 0.086 mmol) in anhydrous toluene (3 mL) was added Me₃SnN₃ (89 mg, 0.43 mmol) at 0° C. The mixture was refluxed overnight. The solvent was removed under reduced pressure and the residue was purified by preparative TLC to afford (R)-6-(2-(1H-tetrazol-5-yl)ethyl)-3-((S)-1-(2',4'-difluorobiphenyl-4-yl)ethyl)-6-(4-fluorophenyl)-1,3-oxazinan-2-one (10 mg, yield: 22%). ¹H NMR (CDCl₃): 1.20 (m, 3H), 1.73-1.88 (m, 1H), 1.91-2.07 (m, 4H), 2.20-2.31 (m, 1H), 2.58-2.77 (m, 2H), 5.43 (m, 1H), 6.67-6.90 (m, 7H), 7.01 (m, 2H), 7.11 (m, 2H), 7.18 (m, 1H).

Example 269

N-(2-((R)-3-((S)-1-(2',4'-difluorobiphenyl-4-yl)ethyl)-6-(4-fluorophenyl)-2-oxo-1,3-oxazinan-6-yl)ethyl)-N-methylacetamide

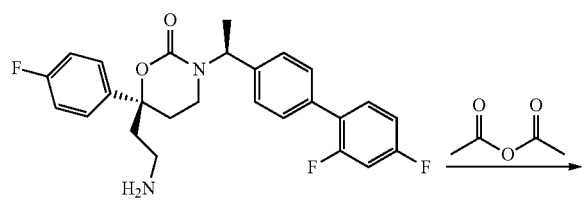

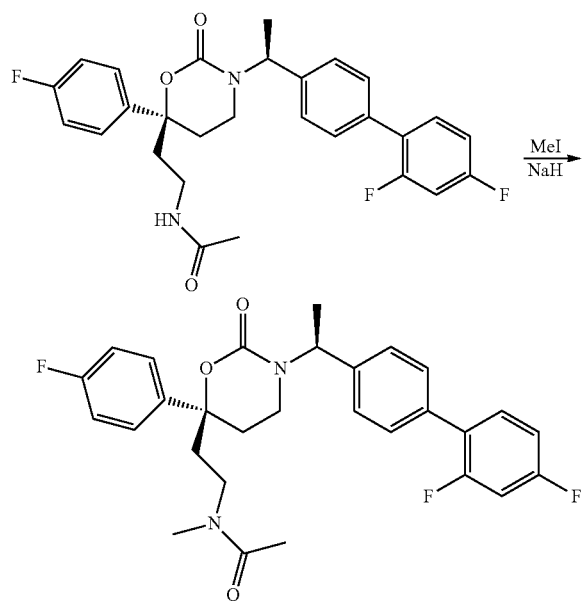

Step 1

To a solution of (R)-6-(2-aminoethyl)-3-((S)-1-(2',4'-difluorobiphenyl-4-yl)ethyl)-6-(4-fluorophenyl)-1,3-oxazinan-2-one (120 mg, 0.264 mmol) and pyridine (41 mg, 0.528 mmol) in anhydrous CH₂Cl₂ (5 mL) was dropwise added acetic anhydride (30 mg, 0.291 mmol) in anhydrous CH₂Cl₂ (5 mL) at 0° C. under nitrogen. The above mixture was allowed to stir for overnight at ambient temperature. The mixture was diluted with CH₂Cl₂ and washed with water. The organic layer was dried over Na₂SO₄ and concentrate to give the crude product, which was purified by preparative TLC to give N-(2-((R)-3-((S)-1-(2',4'-difluorobiphenyl-4-yl)ethyl)-6-(4-fluorophenyl)-2-oxo-1,3-oxazinan-6-yl)ethyl)acetamide (60 mg, 46%).

Step 2

A solution of N-(2-((R)-3-((S)-1-(2',4'-difluorobiphenyl-4-yl)ethyl)-6-(4-fluorophenyl)-2-oxo-1,3-oxazinan-6-yl)ethyl)acetamide (60 mg, 0.121 mmol) in tetrahydrofuran anhydrous (5 mL) was added sodium hydride (15 mg, 0.605 mmol) at 0° C. and then stirred for 30 minutes at the same temperature. Iodomethane (86 mg, 0.605 mmol) was then added to the above mixture. The reaction mixture was stirred at rt for a further 8 h. The reaction mixture was poured into ice/water and extracted with EtOAc. The combined organic phases were dried over Na₂SO₄, filtered and concentrated to afford the residue, which was purified by TLC and separated by preparative HPLC to give N-(2-((R)-3-((S)-1-(2',4'-difluorobiphenyl-4-yl)ethyl)-6-(4-fluorophenyl)-2-oxo-1,3-oxazinan-6-yl)ethyl)-N-methylacetamide (9 mg, 15%). LC-MS Method 3 $t_R$=1.43, min, m/z=511; ¹H NMR (CDCl₃): 1.26 (m, 1H), 1.56 (m, 3H), 1.96 (m, 1H), 2.04 (m, 3H), 2.22 (m, 4H), 2.83 (m, 1H), 2.94 (m, 3H), 3.36 (m, 1H), 5.69 (m, 1H), 6.87 (m, 2H), 7.04 (m, 4H), 7.26 (m, 5H).

Example 270

N-(3-((R)-3-((S)-1-(4'-fluorobiphenyl-4-yl)ethyl)-2-oxo-6-phenyl-1,3-oxazinan-6-yl)propyl)methanesulfonamide

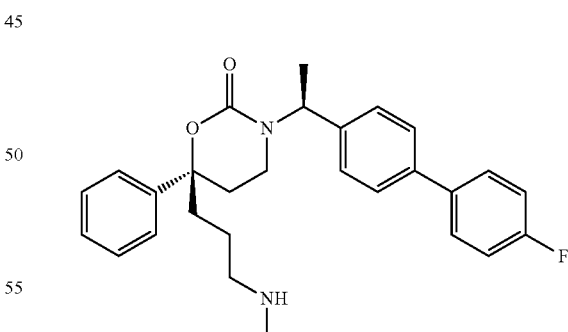

The title compound was prepared from (R)-6-(3-aminopropyl)-3-((S)-1-(4'-fluorobiphenyl-4-yl)ethyl)-6-phenyl-1,3-oxazinan-2-one following a procedure analogous to that described in Example 99. LC-MS Method 3 $t_R$=1.396, min, m/z=511.3; ¹H NMR (CDCl₃) 1.23-1.34 (m, 1H), 1.51 (d, 3H), 1.61-1.68 (m, 1H), 1.89-1.93 (m, 3H), 2.19-2.32 (m, 3H), 2.82 (s, 3H), 2.83-2.92 (m, 1H), 3.03 (m, 2H), 4.22 (s, 1H), 5.63 (m, 1H), 6.93 (m, 2H), 7.01-7.08 (m, 2H), 7.20-7.23 (m, 5H), 7.31 (m, 2H), 7.33 (m, 2H).

Example 271

1-(3-((R)-3-((S)-1-(2',4'-difluorobiphenyl-4-yl)ethyl)-6-(4-fluorophenyl)-2-oxo-1,3-oxazinan-6-yl)propyl)urea

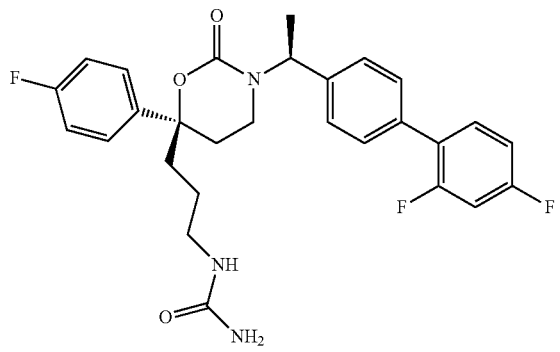 [SMILES: C[C@@H](c1ccc(-c2ccc(F)cc2F)cc1)N1CC[C@](CCCNC(N)=O)(c2ccc(F)cc2)OC1=O]

The title compound was prepared from (R)-6-(3-aminopropyl)-3-((S)-1-(2',4'-difluorobiphenyl-4-yl)ethyl)-6-(4-fluorophenyl)-1,3-oxazinan-2-one following a procedure analogous to that described in Example 263. LC-MS Method 3 $t_R$=1.32, min, m/z=512; $^1$H NMR (CD$_3$OD) 1.44-1.53 (m, 1H), 1.62-1.73 (d, 3H), 1.97-2.09 (m, 2H), 2.31-2.38 (m, 1H), 2.43-2.52 (m, 1H), 2.54-2.63 (m, 1H), 3.13-3.18 (m, 2H), 3.13-3.28 (m, 1H), 4.71 (s, 1H), 5.68-5.76 (m, 1H), 7.12-7.24 (m, 5H), 7.36-7.49 (m, 4H), 7.49-7.58 (m, 1H).

Example 272

3-((R)-3-((S)-1-(2',4'-difluorobiphenyl-4-yl)ethyl)-6-(4-fluorophenyl)-2-oxo-1,3-oxazinan-6-yl)propyl carbamate

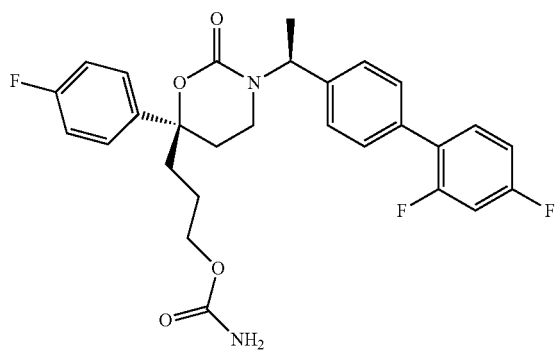

The title compound was prepared from (R)-3-((S)-1-(2',4'-difluorobiphenyl-4-yl)ethyl)-6-(4-fluorophenyl)-6-(3-hydroxypropyl)-1,3-oxazinan-2-one following a procedure analogous to that described in Example 264. $^1$H NMR (CD$_3$OD) 1.31 (m, 1H), 1.46 (m, 3H), 1.62 (m, 1H), 1.86 (m, 2H), 2.13 (m, 1H), 2.24 (m, 1H), 2.39 (m, 1H), 3.02 (m, 1H), 3.21 (m, 1H), 3.83 (m, 2H), 5.49 (m, 1H), 6.98 (m, 6H), 7.21 (m, 4H), 7.31 (m, 1H).

Example 273

(6S)-3-((1S)-1-(2',4'-difluorobiphenyl-4-yl)ethyl)-6-(3-(dimethylamino)-2-hydroxypropyl)-6-(4-fluorophenyl)-1,3-oxazinan-2-one

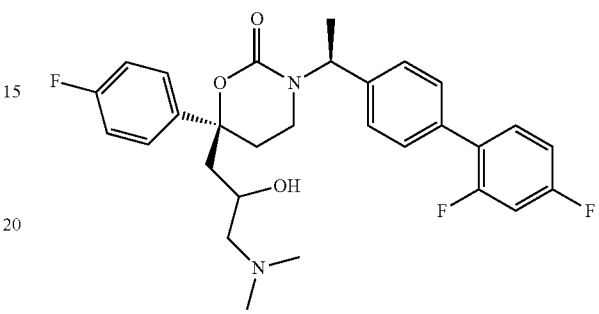

The title compound was prepared from (6S)-3-((S)-1-(2',4'-difluorobiphenyl-4-yl)ethyl)-6-(4-fluorophenyl)-6-(oxiran-2-ylmethyl)-1,3-oxazinan-2-one and dimethylamine following a procedure analogous to that described in Example 265 Step 2. Two isomers were isolated.

Isomer 1: LC-MS Method 3 $t_R$=1.1, min, m/z=513; $^1$H NMR (CD$_3$OD) 1.46 (m, 3H), 1.81 (m, 1H), 2.95 (m, 2H), 2.08 (m, 6H), 2.22 (m, 2H), 2.38 (m, 1H), 3.01 (m, 1H), 3.83 (m, 1H), 5.49 (m, 1H), 6.91 (m, 4H), 7.01 (m, 2H), 7.24 (m, 2H), 7.30 (m, 3H).

Isomer 2: LC-MS Method 3 $t_R$=1.09, min, m/z=513; 1H NMR (CD3OD) 1.46 (m, 3H), 1.95 (m, 2H), 2.19 (m, 6H), 2.22 (m, 3H), 2.33 (m, 1H), 2.60 (m, 1H), 3.05 (m, 1H), 3.43 (m, 1H), 5.48 (m, 1H), 6.89 (m, 4H), 7.00 (m, 2H), 7.17 (m, 2H), 7.30 (m, 3H).

Example 274

(S)-6-(2-(2-amino-1H-imidazol-1-yl)ethyl)-3-((S)-1-(2',4'-difluorobiphenyl-4-yl)ethyl)-6-(4-fluorophenyl)-1,3-oxazinan-2-one

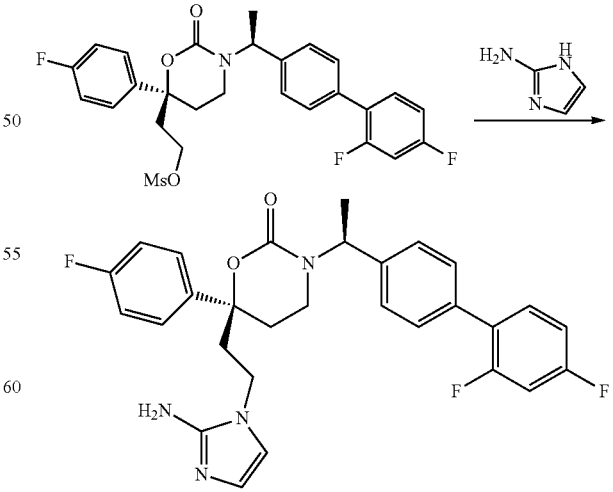

A mixture of 2-((S)-3-((S)-1-(2',4'-difluorobiphenyl-4-yl)ethyl)-6-(4-fluorophenyl)-2-oxo-1,3-oxazinan-6-yl)ethyl methanesulfonate (40 mg, 0.07 mmol), 1H-imidazol-2-amine (18 mg, 0.21 mmol), K$_2$CO$_3$ (29 mg, 0.21 mmol) in acetonitrile (4 mL) was heated to reflux overnight. The solvent was removed and the residue was partitioned between EtOAc and water. The aqueous layer was extracted with EtOAc and the combined organic layer was washed with brine, dried over Na$_2$SO$_4$, filtered and concentrated to give the crude product. It was purified by preparative HPLC to give (R)-6-(2-(1H-imidazol-2-ylamino)ethyl)-3-((S)-1-(2',4'-difluorobiphenyl-4-yl)ethyl)-6-(4-fluorophenyl)-1,3-oxazinan-2-one (7 mg, 17%). LC-MS Method 3 tR=1.15, min, m/z=521; $^1$H NMR (CDCl$_3$): 1.55 (m, 3H), 2.16-2.33 (m, 7H), 2.94 (m, 1H), 3.56 (m, 1H), 4.02 (m, 1H), 5.66 (m, 1H), 6.25 (m, 1H), 6.52 (m, 1H), 6.90 (m, 2H), 7.04 (m, 4H), 7.18 (m, 2H), 7.26 (m, 3H).

Example 275

1-(3-((R)-3-((S)-1-(2',4'-difluorobiphenyl-4-yl)ethyl)-6-(4-fluorophenyl)-2-oxo-1,3-oxazinan-6-yl)propyl)-3-methyl urea

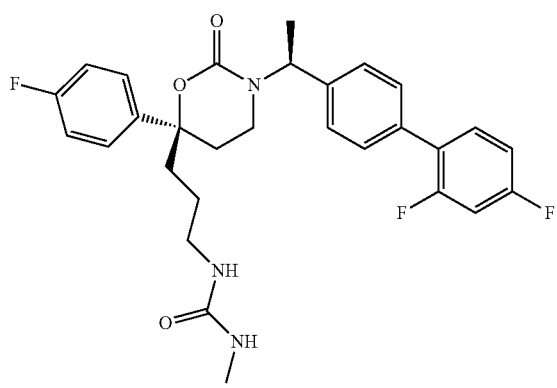 [SMILES: CNC(=O)NCCC[C@]1(c2ccc(F)cc2)CCN([C@@H](C)c2ccc(-c3ccc(F)cc3F)cc2)C(=O)O1]

The title compound was prepared from (R)-6-(3-aminopropyl)-3-((S)-1-(2',4'-difluorobiphenyl-4-yl)ethyl)-6-(4-fluorophenyl)-1,3-oxazinan-2-one following a procedure analogous to that described in Example 141. LC-MS Method 3 t$_R$=1.38, min, m/z=526; $^1$H NMR (CDCl$_3$) 1.28-1.41 (m, 1H), 1.42-1.53 (d, 3H), 1.81-1.92 (m, 2H), 2.09-2.31 (m, 4H), 2.72 (s, 3H), 2.84-2.93 (m, 1H), 3.04-3.12 (m, 2H), 5.56-5.65 (m, 1H), 6.80-6.91 (m, 2H), 6.92-6.99 (m, 3H), 7.12-7.19 (m, 2H), 7.21-7.29 (m, 3H).

Example 276

1-(3-((S)-3-((S)-1-(2',4'-difluorobiphenyl-4-yl)ethyl)-6-(4-fluorophenyl)-2-oxo-1,3-oxazinan-6-yl)-2-hydroxypropyl)urea

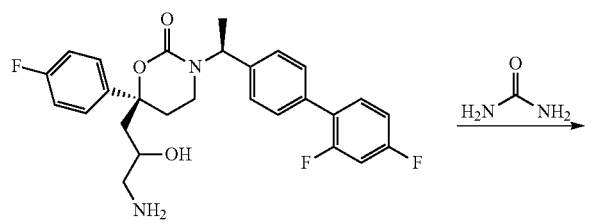

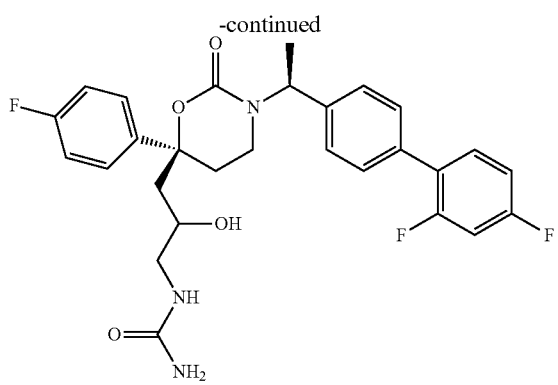

To a solution of (6S)-6-(3-amino-2-hydroxypropyl)-3-((S)-1-(2',4'-difluorobiphenyl-4-yl)ethyl)-6-(4-fluorophenyl)-1,3-oxazinan-2-one (300 mg, 0.62 mmol) in H$_2$O (10 mL) was added HCl (12 N, 0.05 mL), urea (372 mg, 6.2 mmol) and EtOH (2 mL). Then the mixture was heated to reflux overnight. The reaction mixture was cooled to rt and adjusted pH to 9~10 by saturated NaHCO$_3$ solution. The mixture was concentrated and extracted by CH$_2$Cl$_2$. The combined organic layer was dried and concentrated to give the residue, which was purified by preparative HPLC followed by chiral preparative HPLC to give two isomers.

Isomer 1 (51 mg, 16%): $^1$H NMR (CD$_3$OD): 1.59 (d, 3H), 2.02 (m, 2H), 2.31 (m, 1H), 2.49 (m, 2H), 2.93 (m, 1H), 3.14 (m, 2H), 3.81 (m, 1H), 4.62 (s, 3H), 5.59 (q, 1H), 7.00~7.14 (m, 6H), 7.29~7.46 (m, 5H). 445~018-1P.

Isomer 2 (23 mg, 7%): LC-MS Method 3 t$_R$=1.28, min, m/z=528; $^1$H NMR (CD$_3$OD): 1.59 (d, 3H), 2.06 (m, 2H), 2.31 (m, 1H), 2.45 (m, 1H), 2.72 (m, 1H), 3.09 (m, 1H), 3.15 (m, 2H), 3.49 (m, 1H), 4.62 (s, 3H), 5.59 (q, 1H), 6.98-7.14 (m, 6H), 7.29 (m, 2H), 7.45 (m, 3H).

Example 277

N-(3-((S)-3-((S)-1-(4'-fluorobiphenyl-4-yl)ethyl)-6-(4-fluorophenyl)-2-oxo-1,3-oxazinan-6-yl)-2-hydroxypropyl)methanesulfonamide

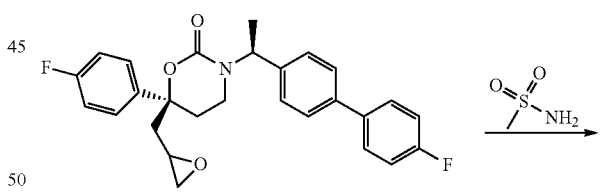

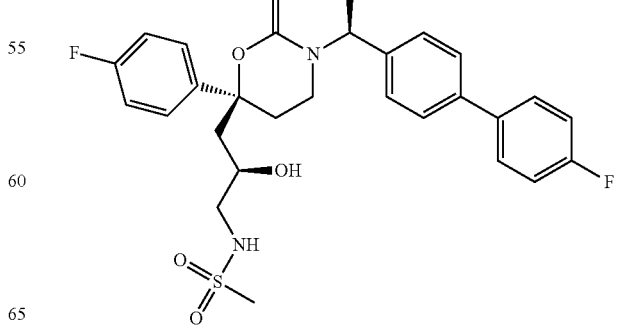

Methanesulfonamide (57 mg, 0.60 mmol), K₂CO₃ (41 mg, 0.30 mmol) and (C₄H₉)₄NHSO₄ (101 mg, 0.30 mmol) were added into a solution of 3-[1-4-fluoro-biphenyl-4-yl]-ethyl]-6-(4-fluoro-phenyl)-6-oxiranylmethyl-[1,3]oxazinan-2-one (70 mg, 0.15 mmol) with 1,4-dioxane (10 mL) as solvents. Then the reaction mixture was refluxed for 6 h. After the solvents were evaporated, the crude product was purified by preparation HPLC to give two isomers.

Isomer 1: (3.4 mg, 4%): LC-MS Method 3 $t_R$=1.156, min, m/z=545.1; ¹H NMR (CDCl₃): 1.48 (m, 3H), 1.86-1.91 (m, 2H), 2.18 (m, 1H), 2.22 (m, 2H), 2.86 (m, 3H), 2.91 (m, 2H), 3.06 (m, 1H), 3.71 (m, 2H), 4.72 (m, 1H), 5.61 (m, 1H), 6.94-7.08 (m, 6H), 7.23 (m, 2H), 7.25 (m, 2H), 7.38 (m, 2H).

Isomer 2: (12.3 mg, 16%). LC-MS Method 3 $t_R$=1.152, min, m/z=545.1; ¹H NMR (CDCl₃): 1.49 (m, 3H), 2.02-1.11 (m, 2H), 2.21-2.29 (m, 3H), 2.91 (m, 3H), 3.07 (m, 1H), 3.23 (m, 1H), 3.75 (m, 2H), 5.08 (m, 1H), 5.61 (m, 1H), 6.94 (m, 2H), 7.08 (m, 4H), 7.26 (m, 2H), 7.41 (m, 2H).

Example 278

N-(3-((S)-3-((1S)-1-(4'-fluorobiphenyl-4-yl)ethyl)-6-(4-fluorophenyl)-2-oxo-1,3-oxazinan-6-yl)-2-hydroxypropyl)-N-methylmethanesulfonamide

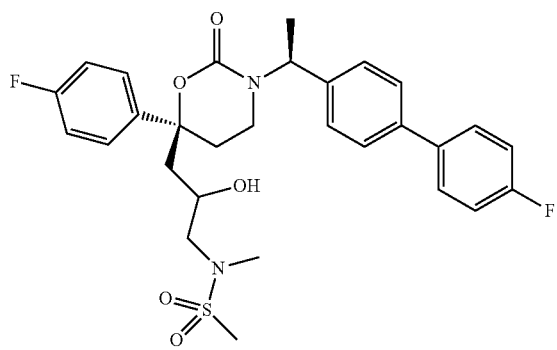 [SMILES: C[C@@H](c1ccc(-c2ccc(F)cc2)cc1)N1CC[C@](CC(O)CN(C)S(C)(=O)=O)(c2ccc(F)cc2)OC1=O]

The title compound was prepared from 3-[1-4-fluoro-biphenyl-4-yl]-ethyl]-6-(4-fluoro-phenyl)-6-oxiranylmethyl-[1,3]oxazinan-2-one and N-methyl methanesulfonamide using a procedure analogous to that described in Example 277. Two isomers were isolated.

Isomer 1: LC-MS Method 3 $t_R$=1.409, min, m/z=559.1; ¹H NMR (CDCl₃) 1.49 (d, 3H), 1.96-2.08 (m, 3H), 2.17-2.38 (m, 3H), 2.69 (m, 5H), 2.68-3.04 (m, 3H), 3.12 (s, 1H), 3.68 (m, 1H), 5.62 (m, 1H), 6.92-7.07 (m, 5H), 7.22 (m, 5H), 7.39 (m, 2H).

Isomer 2: LC-MS Method 2 $t_R$=1.397, m/z=559.1; ¹H NMR (CDCl₃) 1.49 (d, 3H), 2.07 (m, 2H), 2.15-2.35 (m, 2H), 2.41 (m, 1H), 2.78 (d, 6H), 2.91-3.31 (m, 3H), 3.73 (m, 1H), 5.60 (m, 1H), 6.91 (m, 2H), 7.06 (m, 4H), 7.28 (m, 4H), 7.33 (m, 2H).

Example 279

(R)-3-((R)-1-(2',4'-difluorobiphenyl-4-yl)ethyl)-6-(4-fluorophenyl)-6-(2-hydroxyethyl)-1,3-oxazinan-2-one

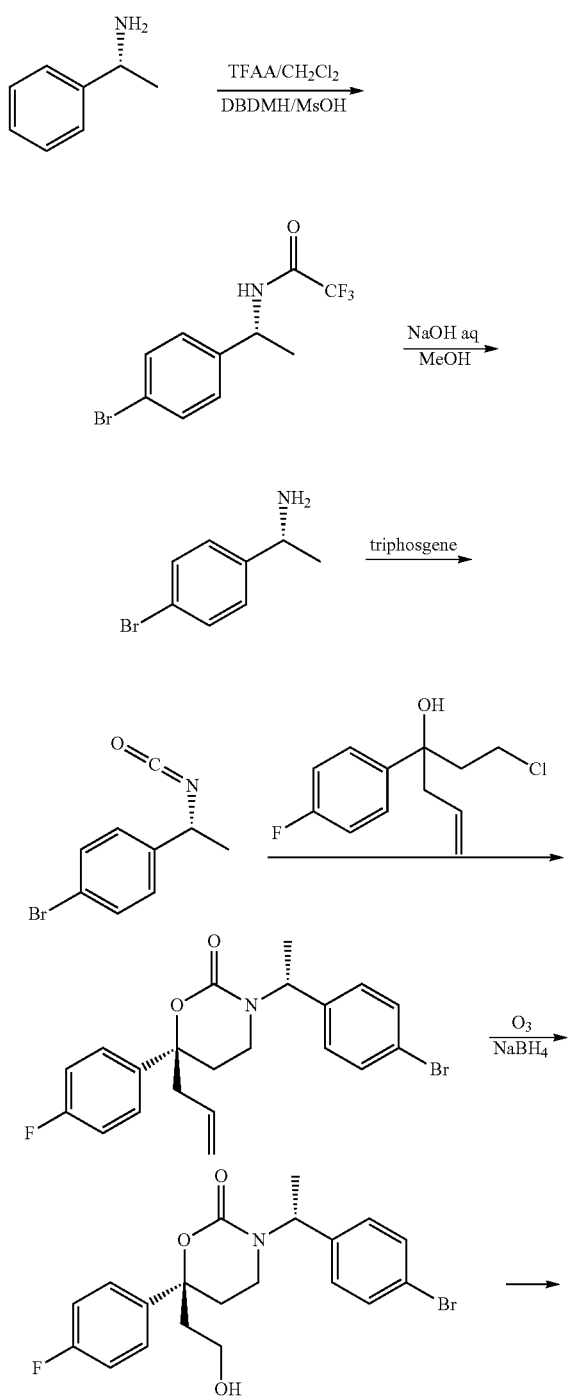

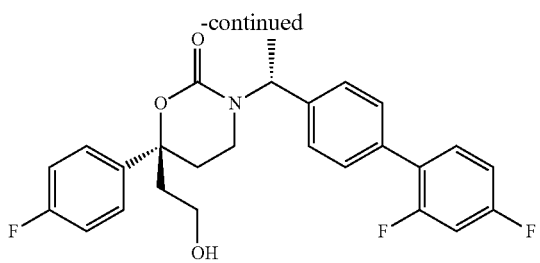

Step 1

TFAA (134 mL, 948 mmol) was dissolved in CH$_2$Cl$_2$ (600 mL) and cooled in an ice water bath. A solution of (S)-1-phenylpropan-1-amine (112.8 g, 930 mmol) in CH$_2$Cl$_2$ (200 mL) was added dropwise and then the ice bath was removed. The reaction mixture was stirred for 3 hrs at ambient temperature. Then the above mixture was cooled in an ice bath and MsOH (160 mL, 2.5 mol) was added dropwise followed by DBDMH (130 g, 454 mmol). The reaction mixture was left stirring overnight at it and then quenched with water and brine. The combined organic phases were dried over NaSO$_4$, filtered and concentrated to give (R)—N-(1-(4-bromophenyl)ethyl)-2,2,2-trifluoroacetamide (120 g, 44%) as a off-white solid. $^1$H NMR (CDCl$_3$): 1.56 (m, 3H), 1.86 (m, 2H), 5.11 (m, 1H), 6.63 (m, 1H), 7.18 (m, 2H), 7.50 (m, 2H).

Step 2

(R)—N-(1-(4-bromophenyl)ethyl)-2,2,2-trifluoroacetamide (20 g, 68 mmol) was dissolved in methanol (200 mL) and cooled in an ice-water bath. Then aqueous NaOH (2 M, 100 mL) was added to the above mixture. The reaction mixture was stirred overnight at ambient temperature. The reaction mixture was concentrated and then partitioned between CH$_2$Cl$_2$ and water. The aqueous layer was extracted with addition CH$_2$Cl$_2$ and the combined organic phases were dried over Na$_2$SO$_4$, filtered and concentrated to give (R)-1-(4-bromophenyl)ethan amine (9.8 g, 73%). $^1$H NMR (DMSO): 1.19 (m, 3H), 3.92 (m, 1H), 7.28 (m, 2H), 7.42 (m, 2H).

Step 3

To a solution of (S)-1-(4-bromophenyl)propan-1-amine (5 g, 25 mmol) in CH$_2$Cl$_2$ (10 mL) was added saturated aqueous NaHCO$_3$ (10 mL) and then triphosgene (2.45 g, 8 mmol) at 0 μl. Then the reaction mixture was stirred for 15 minutes at 0° C. under nitrogen. The reaction mixture was extracted with CH$_2$Cl$_2$ twice. The combined organic phases were dried over Na$_2$SO$_4$, filtered and concentrated to afford (R)-1-bromo-4-(1-isocyanatoethyl)benzene (2.5 g, 44%), which was used for the next step without purification.

Step 4

To a solution of (R)-1-bromo-4-(1-isocyanatoethyl)benzene (2.5 g, 11 mmol) in THF anhydrous (40 mL) was added 1-chloro-3-(4-fluorophenyl)hex-5-en-3-ol (1.69 g, 7 mmol) and DBU (5.68 g, 33 mmol) at ambient temperature and the reaction mixture was refluxed overnight. The reaction mixture was extracted with 1 N aq HCl and EtOAc. The combined organic phases were dried over Na$_2$SO$_4$, filtered and concentrated to afford the residue, which was purified by column chromatography to give two isomers.

Isomer 1: (R)-6-allyl-3-((R)-1-(4-bromophenyl)ethyl)-6-(4-fluorophenyl)-1,3-oxazinan-2-one (334 mg, 7%). $^1$H NMR (CD$_3$OD): 1.50 (m, 3H), 2.16-2.38 (m, 2H), 2.46 (m, 1H), 2.60 (m, 2H), 3.10 (m, 1H), 5.05 (m, 2H), 5.48 (m, 1H), 5.66 (m, 1H), 6.82 (m, 2H), 7.08 (m, 2H), 7.26 (m, 4H).

Isomer 2: (S)-6-allyl-3-((R)-1-(4-bromophenyl)ethyl)-6-(4-fluorophenyl)-1,3-oxazinan-2-one.

Step 5

A solution of (R)-6-allyl-3-((R)-1-(4-bromophenyl)ethyl)-6-(4-fluorophenyl)-1,3-oxazinan-2-one (334 mg, 0.80 mmol) in dry CH$_2$Cl$_2$ (20 mL) was treated with ozone at –78° C. until the reaction mixture became blue. Then the mixture was flushed with oxygen to remove excess ozone. To the above mixture was added NaBH$_4$ (273 mg, 7 mmol) at 0° C. and the reaction mixture was stirred for 4 hrs at ambient temperature under nitrogen. The reaction mixture was washed with water and then extract with CH$_2$Cl$_2$ twice. The combined organic phases were dried over NaSO$_4$, filtered and concentrated to give the residue, which was purified by preparative HPLC to afford (S)-3-((R)-1-(4-bromophenyl)ethyl)-6-(4-fluorophenyl)-6-(2-hydroxyethyl)-1,3-oxazinan-2-one (118 mg, 35%). $^1$H NMR (CD3OD): 1.50 (m, 3H), 2.12 (m, 2H), 2.29 (m, 2H), 2.50 (m, 1H), 3.10 (m, 1H), 3.33 (m, 1H), 3.68 (m, 1H), 4.56 (m, 1H), 5.50 (m, 1H), 6.86 (m, 2H), 7.10 (m, 2H), 7.30 (m, 4H).

Step 6

To a solution of (S)-3-((R)-1-(4-bromophenyl)ethyl)-6-(4-fluorophenyl)-6-(2-hydroxyethyl)-1,3-oxazinan-2-one (109 mg, 0.26 mmol), 2,4-difluorophenylboronic acid (49 mg, 0.31 mmol) and Pd(PPh$_3$)$_4$ (30 mg, 0.03 mmol) in dioxane (8 mL) was added a solution of CsCO$_3$ (2 M, 1 mL) at 0□. Then the reaction mixture was refluxed overnight under nitrogen. The reaction mixture was washed with water and then extract with CH$_2$Cl$_2$ twice. The combined organic phases were dried over Na$_2$SO$_4$, filtered and concentrated to give the residue, which was purified by preparative HPLC to afford (S)-3-((R)-1-(2',4'-difluorobiphenyl-4-yl)ethyl)-6-(4-fluorophenyl)-6-(2-hydroxyethyl)-1,3-oxazinan-2-one (49 mg, 42%). LC-MS Method 3 tR=1.41, min, m/z=456; $^1$H NMR (CD$_3$OD): 1.55 (m, 3H), 2.12 (m, 2H), 2.22-2.46 (m, 3H), 2.52 (m, 1H), 3.12 (m, 1H), 3.33 (m, 1H), 3.68 (m, 1H), 5.56 (m, 1H), 7.08 (m, 6H), 7.08 (m, 2H), 7.35 (m, 5H). 443-155-3.

(R)-3-((R)-1-(2',4'-difluorobiphenyl-4-yl)ethyl)-6-(4-fluorophenyl)-6-(2-hydroxyethyl)-1,3-oxazinan-2-one was prepared from (S)-6-allyl-3-((R)-1-(4-bromophenyl)ethyl)-6-(4-fluorophenyl)-1,3-oxazinan-2-one following procedures analogous to those described in Steps 5 and 6 immediately above. LC-MS Method 3 $t_R$=1.47, min, m/z=456; $^1$H NMR (CD$_3$OD) 1.35 (m, 3H), 2.18 (m, 2H), 2.40 (m, 1H), 2.51 (m, 1H), 2.82 (m, 1H), 3.33 (m, 1H), 3.71 (m, 1H), 4.22-4.48 (m, 1H), 5.62 (m, 1H), 7.03 (m, 2H), 7.18 (m, 2H), 7.38 (m, 4H), 7.50 (m, 3H).

Example 280

(R)-3-((S)-1-(4-(2-hydroxypropan-2-yl)phenyl)ethyl)-6-(3-hydroxypropyl)-6-phenyl-1,3-oxazinan-2-one

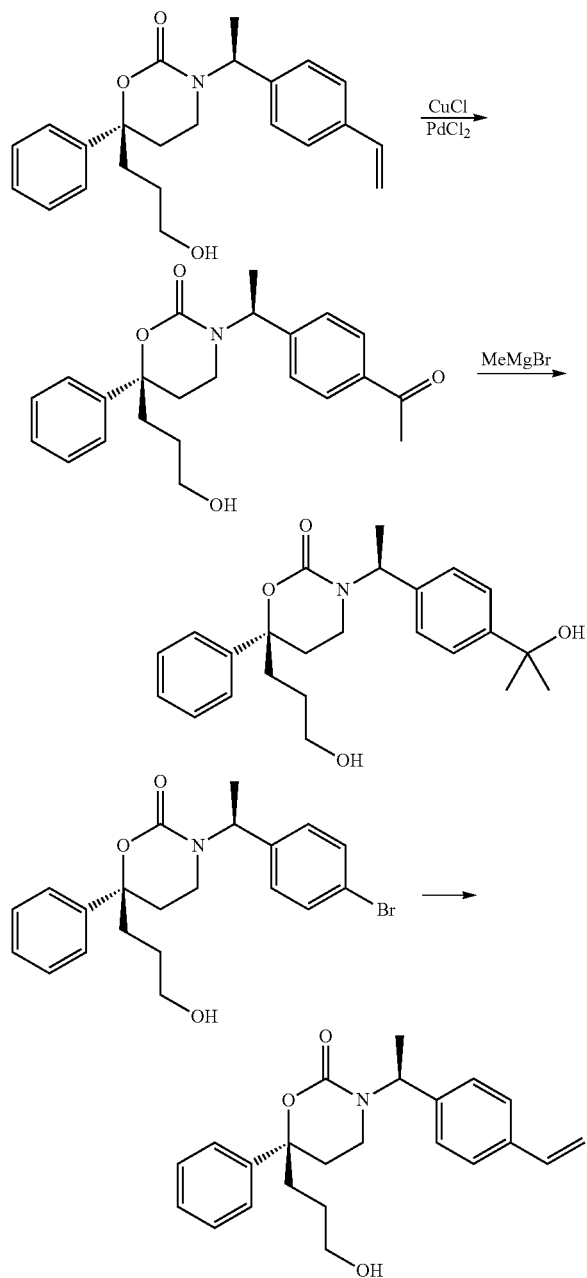

Step 1

A mixture of (R)-3-((S)-1-(4-bromophenyl)ethyl)-6-(3-hydroxypropyl)-6-phenyl-1,3-oxazinan-2-one (3 g, 7.2 mmol), tributyl(vinyl)stannane (2.73 g, 8.64 mmol) and Pd(PPh$_3$)$_4$ (1 g, 0.87 mmol) in toluene (100 mL) was heated to reflux for 3 h. The reaction mixture was filtered, and the filtrate was concentrated to give the crude product, which was purified by column chromatography to afford (R)-6-(3-hydroxypropyl)-6-phenyl-3-((S)-1-(4-vinylphenyl)ethyl)-1,3-oxazinan-2-one (1.8 g, 68%). $^1$H NMR (CDCl$_3$): 1.32 (m, 1H), 1.46 (m, 3H), 1.65 (m, 1H), 1.84-2.22 (m, 5H), 2.78 (m, 1H), 3.51 (m, 2H), 5.12 (m, 1H), 5.59 (m, 2H), 6.54 (m, 1H), 6.78 (m, 1H), 7.07 (m, 1H), 7.16 (m, 1H), 7.18-7.32 (m, 6H).

Step 2

A round-bottom flask was charged with copper(I) chloride (49 mg, 0.5 mmol), and a solution of (R)-6-(3-hydroxypropyl)-6-phenyl-3-((S)-1-(4-vinylphenyl)ethyl)-1,3-oxazinan-2-one (80 mg, 0.2 mmol) in DMF (3 mL) was added, followed by H$_2$O (0.5 mL) and palladium(II) chloride (18 mg, 0.1 mmol). The reaction mixture was vigorously stirred under a balloon of oxygen at rt overnight. The reaction was diluted with EtOAc (5 mL), and filtered. The filtrate was separated, and the aqueous layer was extracted with EtOAc (3×). The combined organic layer was washed with brine, dried over Na$_2$SO$_4$ and concentrated to give the crude product, which was purified by preparative TLC to afford (R)-3-((S)-1-(4-acetylphenyl)ethyl)-6-(3-hydroxypropyl)-6-phenyl-1,3-oxazinan-2-one (40 mg, 52%). $^1$H NMR (CDCl$_3$): 1.34 (m, 1H), 1.49 (m, 3H), 1.68 (m, 1H), 1.92 (m, 2H), 2.11-2.27 (m, 3H), 2.46 (s, 3H), 2.84 (m, 2H), 3.51 (m, 2H), 5.64 (m, 1H), 6.86 (m, 2H), 7.26 (m, 6H), 7.51 (m, 2H).

Step 3

To a solution of (R)-3-((S)-1-(4-acetylphenyl)ethyl)-6-(3-hydroxypropyl)-6-phenyl-1,3-oxazinan-2-one (40 mg, 0.1 mmol) in THF (10 mL) was added dropwise methylmagnesium bromide (3 M, 1 mL, 1 mmol) at −78° C. under N$_2$. The mixture was stirred at rt for 2 days. The reaction was quenched with water, and the layers were separated. The aqueous layer was extracted with EtOAc (3×). The combined organic layer was washed with brine, dried over Na$_2$SO$_4$ and concentrated to give the crude product, which was purified by preparative HPLC to give (R)-3-((S)-1-(4-(2-hydroxypropan-2-yl)phenyl)ethyl)-6-(3-hydroxypropyl)-6-phenyl-1,3-oxazinan-2-one (5 mg, 13%). $^1$H NMR (CDCl$_3$): 1.31 (m, 1H), 1.44 (m, 3H), 1.64 (m, 1H), 1.93 (m, 2H), 2.11-2.25 (m, 3H), 2.82 (m, 1H), 3.51 (m, 2H), 5.58 (m, 1H), 6.81 (m, 2H), 7.14 (m, 2H), 7.27 (m, 5H). LC-MS Method 2 t$_R$=1.141, min, m/z=420.

Example 281

(R)-6-(4-fluorophenyl)-6-(3-hydroxypropyl)-3-((S)-1-(4-(6-(trifluoromethyl)pyridin-3-yl)phenyl)ethyl)-1,3-oxazinan-2-one

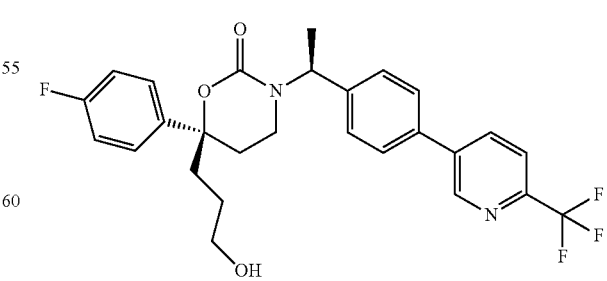

The title compound was prepared from (R)-3-((S)-1-(4-bromophenyl)ethyl)-6-(4-fluorophenyl)-6-(3-hydroxypropyl)-1,3-oxazinan-2-one and 2-trifluoromethylpyridine-3- boronic acid following a procedure analogous to that described in Example 64. LC-MS Method 3 $t_R$=1.36 min, m/z=459.3; $^1$H NMR (CDCl$_3$) 1.40 (m, 1H), 1.51 (m, 3H), 1.63 (m, 1H), 1.70-1.98 (m, 3H), 2.11-2.33 (m, 3H), 2.95 (m, 1H), 3.50-3.63 (m, 2H), 5.66 (m, 1H), 6.97 (m, 4H), 7.20 (m, 2H), 7.29 (m, 2H), 7.67 (m, 1H), 7.87-7.90 (m, 1H), 8.78 (m, 1H).

Example 282

6-(3-hydroxypropyl)-3-((S)-1-(4-methoxyphenyl)ethyl)-6-phenyl-1,3-oxazinan-2-one

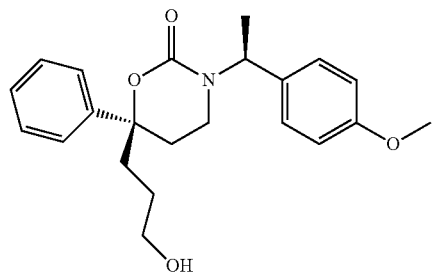 [SMILES: COc1ccc([C@H](C)N2CC[C@](CCCO)(c3ccccc3)OC2=O)cc1]

(R)-6-(3-hydroxypropyl)-3-((S)-1-(4-methoxyphenyl)ethyl)-6-phenyl-1,3-oxazinan-2-one was prepared from (R)-6-allyl-3-((S)-1-(4-methoxyphenyl)ethyl)-6-phenyl-1,3-oxazinan-2-one following a procedure analogous to that described in Example 78. LC-MS Method 3 $t_R$=1.092 min, m/z=761.3; $^1$H NMR (CDCl$_3$) 1.26-1.49 (m, 2H), 1.55 (m, 3H), 1.98 (m, 2H), 2.23 (m, 3H), 2.85 (m, 1H), 3.59 (m, 2H), 3.73 (s, 3H), 5.63 (m, 1H), 6.63 (m, 2H), 6.83 (m, 2H), 7.31 (m, 5H).

(S)-6-(3-hydroxypropyl)-3-((S)-1-(4-methoxyphenyl)ethyl)-6-phenyl-1,3-oxazinan-2-one was prepared from (S)-6-allyl-3-((S)-1-(4-methoxyphenyl)ethyl)-6-phenyl-1,3-oxazinan-2-one following a procedure analogous to that described in Example 78. LC-MS Method 2 $t_R$=2.149 min, m/z=761.3; $^1$H NMR (CDCl$_3$) 0.93 (m, 1H), 1.17 (m, 3H), 1.25 (m, 1H), 1.56 (m, 1H), 1.91 (m, 3H), 2.15 (m, 1H), 2.58 (m, 1H), 3.49 (m, 2H), 3.73 (s, 3H), 5.67 (m, 1H), 6.79 (m, 2H), 7.17 (m, 2H), 7.23 (m, 3H), 7.31 (m, 2H).

Example 283

(R)-6-(4-fluorophenyl)-3-((S)-1-(3-fluorophenyl)ethyl)-6-(3-hydroxypropyl)-1,3-oxazinan-2-one

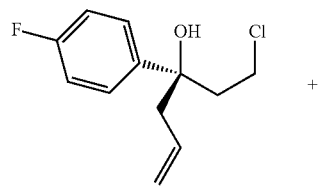

+

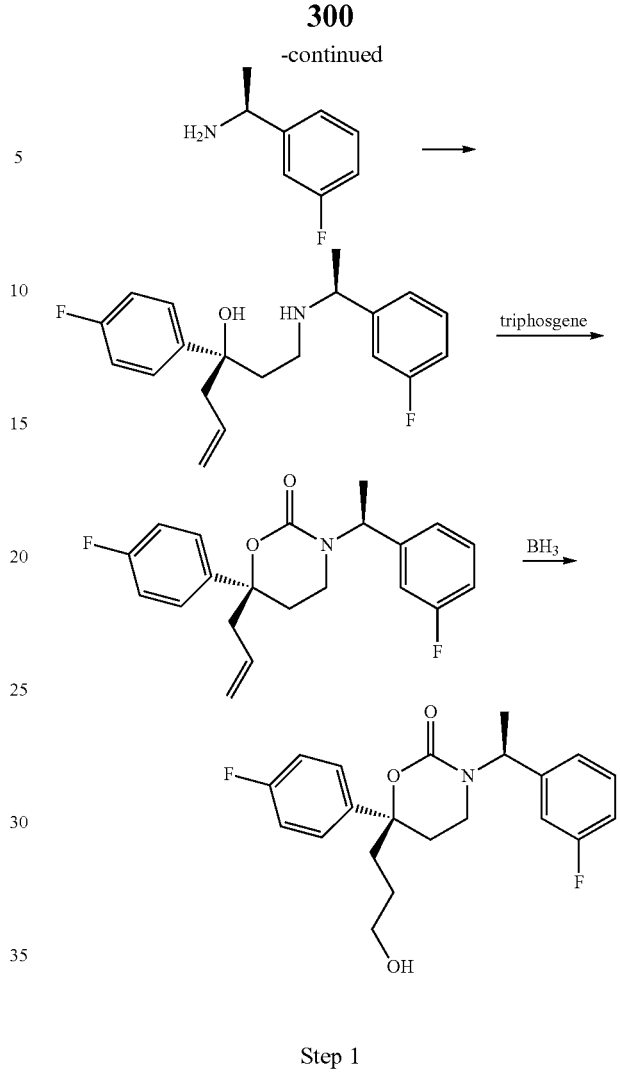

Step 1

A mixture of 1-chloro-3-(4-fluorophenyl)hex-5-en-3-ol (547 mg, 2.4 mmol), (S)-1-(3-fluorophenyl)ethanamine (500 mg, 3.6 mmol), K$_2$CO$_3$ (662 mg, 4.8 mmol), and KI (797 mg, 4.8 mmol) in anhydrous CH$_3$CN (15 mL) was stirred at rt under N$_2$. Then the solution was refluxed overnight. The solid was filtered off, and the solvent was removed under reduced pressure. The residue was purified by preparative TLC to afford 3-(4-fluorophenyl)-1-((S)-1-(3-fluorophenyl)ethylamino)hex-5-en-3-ol (350 mg, 44%).

Step 2

To a solution of 3-(4-fluorophenyl)-1-((S)-1-(3-fluorophenyl)ethylamino)hex-5-en-3-ol (350 mg, 1.1 mmol) and Et$_3$N (333 mg, 3.3 mmol) in anhydrous CH$_2$Cl$_2$ (6 mL) was added triphosgene (155 mg, 0.52 mmol) in portions at 0° C. under N$_2$. Then the solution was refluxed overnight. After the solvent was removed under reduced pressure, the residue was purified by preparative TLC to afford (R)-6-allyl-6-(4-fluorophenyl)-3-((S)-1-(3-fluorophenyl)ethyl)-1,3-oxazinan-2-one (80 mg, 21%).

Step 3

To a solution of (R)-6-allyl-6-(4-fluorophenyl)-3-((S)-1-(3-fluorophenyl)ethyl)-1,3-oxazinan-2-one (80 mg, 0.392 mmol) in dry THF (4 mL) was added dropwise BH$_3$.THF (0.2 mL, 0.2 mmol, 1 M) at 0° C. After stirring for 2 h at rt, the reaction mixture was cooled to 0° C. and water (1 mL), aqueous NaOH (0.5 mL, 3 M) and $H_2O_2$ (0.3 mL, 30%) were added successively. The mixture was stirred for 2-3 h at rt and diluted with water (8 mL). The pH was adjusted to 6-7 with 0.5 N aq HCl. The layers were separated, and the aqueous phase was extracted with EtOAc (3×6 mL). The combined organic layers were washed with a satd aq $NaHCO_3$ (10 mL) and brine (10 mL), dried over $Na_2SO_4$, and concentrated in vacuo to give the crude product, which was purified by preparative TLC to afford (R)-6-(4-fluorophenyl)-3-((S)-1-(3-fluorophenyl)ethyl)-6-(3-hydroxypropyl)-1,3-oxazinan-2-one (40 mg, 48%). LC-MS Method 2 $t_R$=2.151 min, m/z=332.1; $^1H$ NMR ($CDCl_3$): 1.31 (m, 1H) 1.49 (m, 3H), 1.64 (m, 1H), 1.81-1.93 (m, 2H), 2.14-2.26 (m, 3H), 2.88 (m, 1H), 3.51 (m, 2H), 5.68 (m, 1H), 6.96 (m, 2H), 7.13 (m, 1H), 7.19 (m, 4H), 7.37 (m, 1H).

Example 284

(R)-6-(4-fluorophenyl)-3-((S)-1-(2-fluorophenyl)ethyl)-6-(3-hydroxypropyl)-1,3-oxazinan-2-one

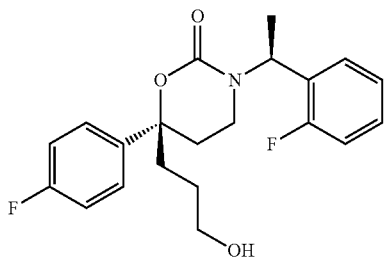 [SMILES: C[C@@H](c1ccccc1F)N1CC[C@](CCCO)(c2ccc(F)cc2)OC1=O]

The title compound was prepared following a procedure analogous to that described in Example 283 using (S)-1-(2-fluorophenyl)ethanamine in Step 1. LC-MS Method 3 $t_R$=1.12 min, m/z=332.1; $^1H$ NMR ($CDCl_3$) 1.24-1.41 (m, 1H), 1.52 (d, 3H), 1.61-1.72 (m, 1H), 2.03-2.38 (m, 2H), 2.10-2.28 (m, 3H), 2.98 (m, 1H), 3.53 (t, 2H), 4.22 (t, 1H), 5.70 (q, 1H), 6.84 (t, 1H), 6.99 (m, 3H), 7.16 (m, 4H).

Example 285

(R)-6-(4-fluorophenyl)-3-((S)-1-(4-fluorophenyl)ethyl)-6-(3-hydroxypropyl)-1,3-oxazinan-2-one

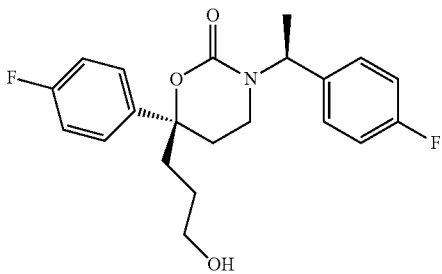 [SMILES: C[C@@H](c1ccc(F)cc1)N1CC[C@](CCCO)(c2ccc(F)cc2)OC1=O]

The title compound was prepared following a procedure analogous to that described in Example 283 using (S)-1-(4-fluorophenyl)ethanamine in Step 1. LC-MS Method 3 $t_R$=1.155 min, m/z=332.1; $^1H$ NMR ($CDCl_3$) 1.25-1.38 (m, 1H), 1.46 (d, 3H), 1.67 (m, 1H), 1.81-1.98 (m, 2H), 2.11-2.23 (m, 3H), 2.84 (m, 1H), 3.51 (t, 2H), 5.58 (t, 1H), 6.75 (t, 2H), 6.84 (m, 2H), 6.98 (t, 2H), 7.18 (t, 2H)

Example 286

6-(2,3-dihydroxypropyl)-3-((1S)-1-(4-methoxyphenyl)ethyl)-6-phenyl-1,3-oxazinan-2-one

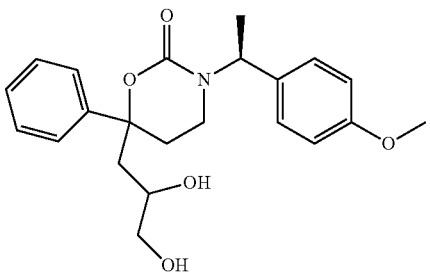 [SMILES: COc1ccc([C@H](C)N2CCC(CC(O)CO)(c3ccccc3)OC2=O)cc1]

(6S)-6-(2,3-dihydroxypropyl)-3-((1S)-1-(4-methoxyphenyl)ethyl)-6-phenyl-1,3-oxazinan-2-one was prepared from (R)-6-allyl-3-((S)-1-(4-methoxyphenyl)ethyl)-6-phenyl-1,3-oxazinan-2-one following a procedure analogous to that described in Example 173. Two isomers were isolated.

Isomer 1: LC-MS Method 2 $t_R$=1.156 min, m/z=386; $^1H$ NMR ($CDCl_3$) 1.41 (d, 3H), 1.98 (dd, 1H), 2.6 (m, 1H), 2.16 (m, 2H), 2.25 (m, 3H), 2.79 (m, 1H), 3.41 (m, 1H), 3.53 (m, 1H), 3.63 (s, 3H), 3.73 (m, 1H), 5.51 (q, 1H), 6.54 (d, 2H), 6.72 (d, 2H), 7.21-7.32 (m, 5H).

Isomer 2: LC-MS Method 2 $t_R$=1.166 min, m/z=386.1; $^1H$ NMR ($CDCl_3$) 1.41 (d, 3H), 1.89 (dd, 1H), 2.02-2.14 (m, 1H), 2.8 (m, 2H), 2.25-2.38 (m, 3H), 2.71-2.82 (m, 1H), 3.24 (m, 1H), 3.339 (m, 1H), 3.65 (s, 3H), 3.77 (m, 1H), 5.51 (q, 1H), 6.58 (d, 2H), 6.78 (d, 2H), 7.19-7.31 (m, 5H).

(6R)-6-(2,3-dihydroxypropyl)-3-((1S)-1-(4-methoxyphenyl)ethyl)-6-phenyl-1,3-oxazinan-2-one was prepared from (S)-6-allyl-3-((S)-1-(4-methoxyphenyl)ethyl)-6-phenyl-1,3-oxazinan-2-one following a procedure analogous to that described in Example 173. Two isomers were isolated.

Isomer 3: LC-MS Method 2 $t_R$=1.964 min, m/z=386.2; $^1H$ NMR ($CDCl_3$) 1.18 (d, 3H), 1.35 (m, 1H), 1.90 (d, 1H), 2.02-2.12 (m, 2H), 2.18 (d, 1H), 2.48-2.67 (m, 2H), 3.26 (m, 1H), 3.32-3.42 (m, 1H), 3.75 (s, 3H), 5.68 (q, 1H), 6.79 (d, 2H), 7.14 (d, 2H), 7.21-7.42 (m, 3H), 7.35 (m, 2H).

Isomer 4: LC-MS Method 2 $t_R$=1.937 min, m/z=386.2; $^1H$ NMR ($CDCl_3$) 1.18 (d, 3H), 1.92-2.12 (m, 4H), 2.25 (d, 1H), 2.54-2.65 (m, 2H), 3.41 (m, 1H), 3.50 (m, 1H), 3.74 (s, 3H), 5.63 (q, 1H), 6.78 (d, 2H), 7.14 (d, 2H), 7.27 (m, 3H), 7.34 (m, 2H).

Example 287

3-((R)-3-((S)-1-(4-chlorophenyl)ethyl)-2-oxo-6-phenyl-1,3-oxazinan-6-yl)propanamide

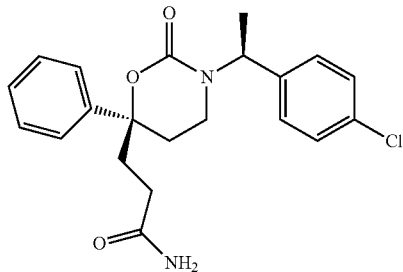 [SMILES: C[C@@H](c1ccc(Cl)cc1)N1CC[C@](CCC(N)=O)(c2ccccc2)OC1=O]

The title compound was prepared from (R)-3-((S)-1-(4-chlorophenyl)ethyl)-6-(3-hydroxypropyl)-6-phenyl-1,3-oxazinan-2-one following a procedure analogous to that described in Example 234. LC-MS Method 2 $t_R$=2.118 min, m/z=343.1; $^1$H NMR (CDCl$_3$) 1.45 (d, 3H), 1.91 (m, 1H), 2.01-2.28 (m, 5H), 2.38-2.48 (m, 1H), 2.84 (m, 1H), 5.54 (q, 1H), 6.78 (d, 2H), 7.01 (d, 2H), 7.21-7.33 (m, 4H).

Example 288

3-((R)-6-(4-fluorophenyl)-3-((S)-1-(3-fluorophenyl)ethyl)-2-oxo-1,3-oxazinan-6-yl)propanamide

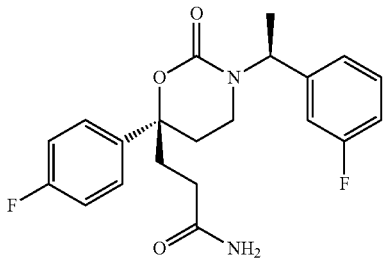 [SMILES: C[C@@H](c1cccc(F)c1)N1CC[C@](CCC(N)=O)(c2ccc(F)cc2)OC1=O]

The title compound was prepared from (R)-6-(4-fluorophenyl)-3-((S)-1-(3-fluorophenyl)ethyl)-6-(3-hydroxypropyl)-1,3-oxazinan-2-one following a procedure analogous to that described in Example 234. LC-MS Method 2 $t_R$=1.998 min, m/z=345.1; $^1$H NMR (CDCl$_3$) 1.39 (d, 3H), 1.86-1.98 (m, 2H), 2.12 (m, 2H), 2.22 (m, 2H), 2.38-2.49 (m, 1H), 2.87 (m, 1H), 2.98-3.10 (m, 1H), 3.60 (m, 1H), 5.23 (s, 1H), 5.48 (s, 1H), 5.52 (q, 1H), 6.58 (d, 1H), 6.68 (d, 1H), 6.79 (t, 1H), 6.98 (m, 2H), 7.05 (t, 1H), 7.18 (t, 2H).

Example 289

3-((R)-6-(4-fluorophenyl)-3-((S)-1-(4-methoxyphenyl)ethyl)-2-oxo-1,3-oxazinan-6-yl)propanamide

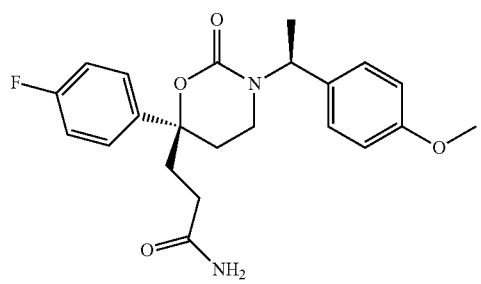 [SMILES: COc1ccc([C@H](C)N2CC[C@](CCC(N)=O)(c3ccc(F)cc3)OC2=O)cc1]

The title compound was prepared from (R)-6-(4-fluorophenyl)-6-(3-hydroxypropyl)-3-((S)-1-(4-methoxyphenyl)ethyl)-1,3-oxazinan-2-one following a procedure analogous to that described in Example 234. LC-MS Method 2 $t_R$=1.953 min, m/z=401.2; $^1$H NMR (CDCl$_3$) 1.42 (d, 3H), 1.35-1.98 (m, 1H), 2.05-2.22 (m, 5H), 2.36-2.48 (m, 1H), 2.82 (m, 1H), 3.67 (s, 3H), 5.13 (m, 1H), 5.32 (m, 1H), 5.55 (q, 1H), 6.61 (d, 2H), 6.81 (d, 2H), 6.97 (t, 2H), 7.17 (m, 2H).

Example 290

(R)-6-allyl-3-((S)-1-(4-(difluoromethoxy)phenyl)ethyl)-6-(4-fluorophenyl)-1,3-oxazinan-2-one

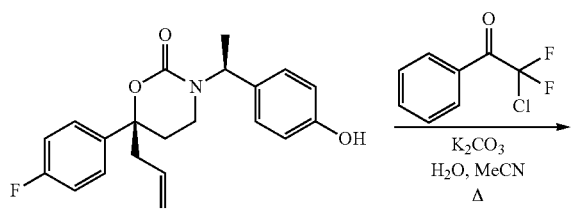

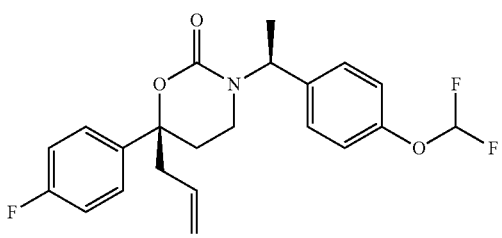

To a mixture of (R)-6-allyl-6-(4-fluorophenyl)-3-((S)-1-(4-hydroxyphenyl)ethyl)-1,3-oxazinan-2-one (0.5227 g, 1.47 mmol), K$_2$CO$_3$ (7.7665 g, 56.2 mmol), CH$_3$CN (6 mL) and H$_2$O (6 mL) at room temperature was added 2-chloro-2,2-difluoroacetophene (1.6500 g, 8.66 mmol). The reaction flask was sealed, and the mixture was heated at 80° C. and stirred for 4 h. Then the mixture was diluted with CH$_2$Cl$_2$, quenched with 6 N HCl (17.5 mL), extracted with CH$_2$Cl$_2$, and dried over Na$_2$SO$_4$. After the solvents were evaporated, the residue was purified by reversed-phase HPLC (SunFire™ Prep C$_{18}$ OBD™ 5 µm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford 0.2780 g (47%) of (R)-6-allyl-3-((S)-1-(4-(difluoromethoxy)phenyl)ethyl)-6-(4-fluorophenyl)-1,3-oxazinan-2-one. LC-MS Method 1 $t_R$=1.90 min, m/z=406 (M+1); $^1$H NMR (CD$_3$OD) 7.25-7.21 (m, 2H), 7.01 (t, J=8.6 Hz, 2H), 6.88 (d, J=8.8 Hz, 2H), 6.82 (d, J=8.8 Hz, 2H), 6.65 (t, J=74.1 Hz, 1H), 5.66-5.56 (m, 1H), 5.44 (q, J=7.1 Hz, 1H), 4.99-4.92 (m, 2H), 3.05-3.01 (m, 1H), 2.53 (d, J=7.3 Hz, 2H), 2.40-2.35 (m, 1H), 2.26-2.08 (m, 2H), 1.44 (d, J=7.3 Hz, 3H).

Example 291

(R)-3-((S)-1-(4-(1H-pyrazol-3-yl)phenyl)ethyl)-6-(3-hydroxypropyl)-6-phenyl-1,3-oxazinan-2-one

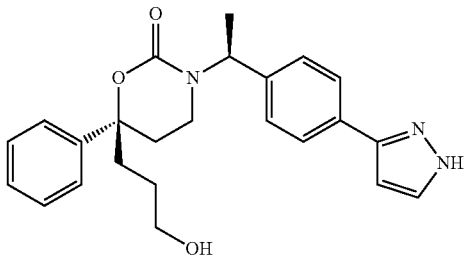 [SMILES: C[C@@H](c1ccc(-c2cc[nH]n2)cc1)N1CC[C@](CCCO)(c2ccccc2)OC1=O]

The title compound was prepared from (R)-6-allyl-3-((S)-1-(4-bromophenyl)ethyl)-6-phenyl-1,3-oxazinan-2-one and pyrazole-3-boronic acid using a procedure analogous to that described in Example 64 followed by a procedure analogous to that described in Example 78. LC-MS Method 2 $t_R$=1.808 min, m/z=362.2; $^1$H NMR (CDCl$_3$) 1.48 (d, 3H), 1.60-1.72 (m, 2H), 1.90 (m, 2H), 2.22 (m, 3H), 2.84 (m, 1H), 3.46-3.54 (m, 2H), 5.61 (q, 1H), 6.48 (s, 1H), 6.89 (d, 2H), 7.19-7.30 (m, 6H), 7.43 (d, 2H), 7.52 (s, 1H).

Example 292

(R)-6-allyl-3-((S)-1-(4-(5-fluoropyridin-3-yl)phenyl)ethyl)-6-phenyl-1,3-oxazinan-2-one

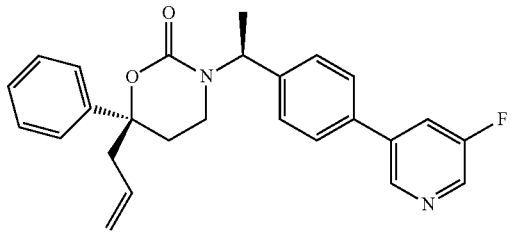 [SMILES: C=CC[C@]1(c2ccccc2)CCN([C@@H](C)c2ccc(-c3cncc(F)c3)cc2)C(=O)O1]

The title compound was prepared from (R)-6-allyl-3-((S)-1-(4-bromophenyl)ethyl)-6-phenyl-1,3-oxazinan-2-one and 5-fluoropyridine-3-boronic acid using a procedure analogous to that described in Example 64. LC-MS Method 1 $t_R$=1.84 min, m/z=417 (M+1); $^1$H NMR (CDCl$_3$) 8.58 (s, 1H), 8.45 (d, 1H, J=3 Hz), 7.57-7.54 (m, 1H), 7.39-7.30 (m, 5H), 7.27-7.25 (m, 2H), 6.93 (d, 2H, J=8 Hz), 5.80-5.68 (m, 2H), 5.11-5.03 (m, 2H), 2.97-2.91 (m, 1H), 2.69-2.55 (m, 2H), 2.41-2.21 (m, 3H), 1.55 (d, 3H, J=7 Hz).

Example 293

(R)-6-(4-fluorophenyl)-6-(3-hydroxypropyl)-3-((S)-1-(3-(trifluoromethyl)phenyl)ethyl)-1,3-oxazinan-2-one

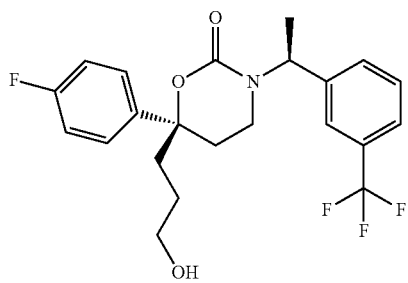 [SMILES: C[C@@H](c1cccc(C(F)(F)F)c1)N1CC[C@](CCCO)(c2ccc(F)cc2)OC1=O]

The title compound was prepared from (R)-6-allyl-6-(4-fluorophenyl)-3-((S)-1-(3-(trifluoromethyl)phenyl)ethyl)-1,3-oxazinan-2-one following a procedure analogous to that described in Example 78. LC-MS Method 3 $t_R$=1.103 min, m/z=382; $^1$H NMR (CDCl$_3$) 1.32-1.45 (m, 1H), 1.51 (m, 3H), 1.65 (m, 1H), 1.82-1.96 (m, 2H), 2.03-2.22 (m, 3H), 2.86 (m, 1H), 3.42-3.53 (m, 2H), 5.68 (m, 1H), 6.96 (m, 2H), 7.03 (m, 1H), 7.17 (m, 4H), 7.36 (m, 1H).

Example 294

(R)-6-(4-fluorophenyl)-6-(3-hydroxypropyl)-3-((S)-1-(4-(trifluoromethyl)phenyl)ethyl)-1,3-oxazinan-2-one

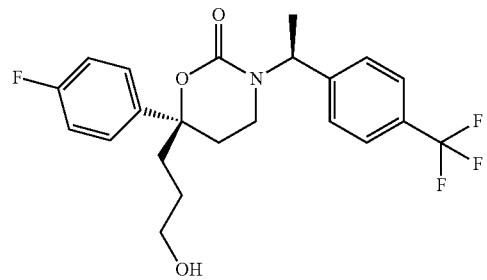 [SMILES: C[C@@H](c1ccc(C(F)(F)F)cc1)N1CC[C@](CCCO)(c2ccc(F)cc2)OC1=O]

The title compound was prepared from (R)-6-allyl-6-(4-fluorophenyl)-3-((S)-1-(4-(trifluoromethyl)phenyl)ethyl)-1,3-oxazinan-2-one following a procedure analogous to that described in Example 78. LC-MS Method 3 $t_R$=1.112 min, m/z=382; $^1$H NMR (CDCl$_3$) 1.23-1.48 (m, 1H), 1.48 (d, 3H), 1.58-1.71 (m, 1H), 1.81-1.98 (m, 2H), 2.15 (m, 1H), 2.19-2.30 (m, 2H), 2.89 (m, 1H), 3.51 (t, 2H), 5.63 (q, 1H), 6.97 (m, 4H), 7.16-7.31 (m, 2H), 7.33 (d, 2H).

Example 295

3-((R)-2-oxo-6-phenyl-3-((S)-1-(4-(pyridin-3-yl)phenyl)ethyl)-1,3-oxazinan-6-yl)propanamide

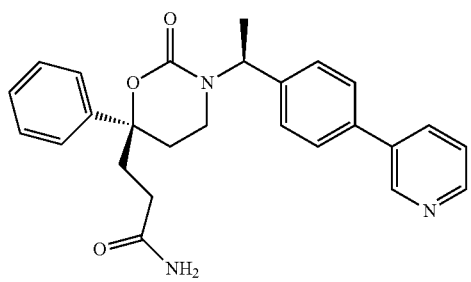 [SMILES: C[C@@H](c1ccc(-c2cccnc2)cc1)N1CC[C@](CCC(N)=O)(c2ccccc2)OC1=O]

The title compound was prepared from (R)-6-(3-hydroxypropyl)-6-phenyl-3-((S)-1-(4-(pyridin-3-yl)phenyl)ethyl)-1,3-oxazinan-2-one following a procedure analogous to that described in Example 234. LC-MS Method 2 $t_R$=1.381 min, m/z=430.2; $^1$H NMR (CDCl$_3$) 1.56 (m, 3H), 1.92-2.03 (m, 3H), 2.18-2.37 (m, 5H), 2.51 (m, 1H), 2.94 (m, 1H), 5.29-5.61 (m, 2H), 5.71 (m, 1H), 7.03 (m, 2H), 7.21-7.38 (m, 8H), 7.77 (m, 1H), 8.53 (m, 1H), 8.72 (s, 1H).

Example 296

3-((R)-2-oxo-6-phenyl-3-((S)-1-(4-(pyridin-4-yl)phenyl)ethyl)-1,3-oxazinan-6-yl)propanamide

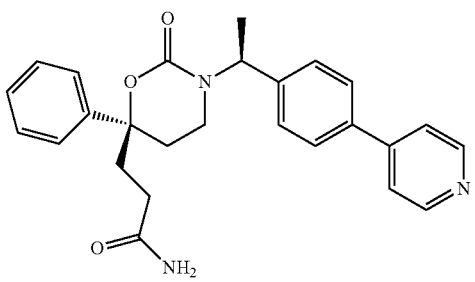 [SMILES: C[C@@H](c1ccc(-c2ccncc2)cc1)N1CC[C@](CCC(N)=O)(c2ccccc2)OC1=O]

The title compound was prepared from (R)-6-(3-hydroxypropyl)-6-phenyl-3-((S)-1-(4-(pyridin-4-yl)phenyl)-1,3-oxazinan-2-one following a procedure analogous to that described in Example 234. LC-MS Method 2 $t_R$=1.327 min, m/z=430.2; $^1$H NMR (CDCl$_3$) 1.49 (m, 3H), 1.93 (m, 1H), 2.12-2.34 (m, 5H), 2.44 (m, 1H), 2.94 (m, 1H), 5.46 (m, 2H), 5.67 (m, 1H), 7.08 (m, 2H), 7.19-7.42 (m, 5H), 7.45 (m, 2H), 7.80 (m, 2H), 8.76 (m, 2H).

Example 297

(S)-3-((S)-1-(4'-fluorobiphenyl-4-yl)ethyl)-6-(3-hydroxypropyl)-6-phenyl-1,3-oxazinan-2-one

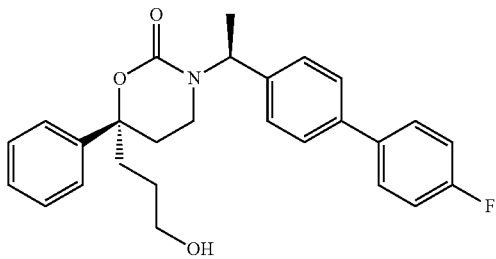 [SMILES: C[C@@H](c1ccc(-c2ccc(F)cc2)cc1)N1CC[C@@](CCCO)(c2ccccc2)OC1=O]

The title compound was prepared from (S)-6-allyl-3-((S)-1-(4'-fluorobiphenyl-4-yl)ethyl)-6-phenyl-1,3-oxazinan-2-one following a procedure analogous to that described in Example 78. LC-MS Method 3 $t_R$=1.463 min, m/z=433.21; $^1$H NMR (CDCl$_3$) 1.28 (d, 3H), 1.35 (m, 1H), 1.74 (m, 1H), 1.96 (m, 3H), 2.24 (m, 1H), 2.69 (m, 2H), 3.56 (m, 2H), 5.80 (q, 1H), 7.12 (t, 2H), 7.28-7.42 (m, 7H), 7.49 (m, 4H)

Example 298

(R)-3-((S)-1-(4-(5-fluoropyridin-3-yl)phenyl)ethyl)-6-(3-hydroxypropyl)-6-phenyl-1,3-oxazinan-2-one

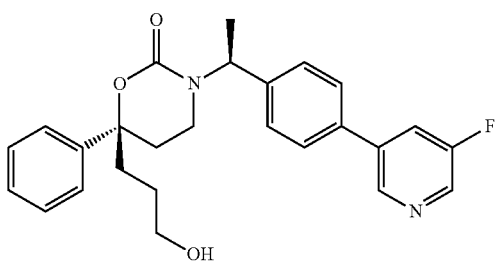 [SMILES: C[C@@H](c1ccc(-c2cncc(F)c2)cc1)N1CC[C@](CCCO)(c2ccccc2)OC1=O]

The title compound was prepared from (R)-6-allyl-3-((S)-1-(4-(5-fluoropyridin-3-yl)phenyl)ethyl)-6-phenyl-1,3-oxazinan-2-one following a procedure analogous to that described in Example 78. LC-MS Method 1 $t_R$=1.5 min, m/z=457 (M+Na); $^1$H NMR (CDCl$_3$) 8.64 (s, 1H), 8.50 (s, 1H), 7.74-7.71 (dd, 1H, J=2, 9 Hz), 7.41-7.27 (m, 7H), 7.05 (dd, 2H, J=3, 8 Hz), 5.74-5.68 (m, 1H), 4.27-4.24 (t, 1H, J=6, 6 Hz), 3.60-3.57 (t, 1H, J=6, 6 Hz), 2.98-2.93 (m, 1H), 2.38-2.20 (m, 3H), 2.10-1.93 (m, 3H), 1.73-1.70 (1H, m), 1.57 (d, 3H, J=7 Hz), 1.41-1.37 (m, 1H).

Example 299

3-((R)-6-(4-fluorophenyl)-2-oxo-3-((S)-1-(3-(trifluoromethyl)phenyl)ethyl)-1,3-oxazinan-6-yl)propanamide

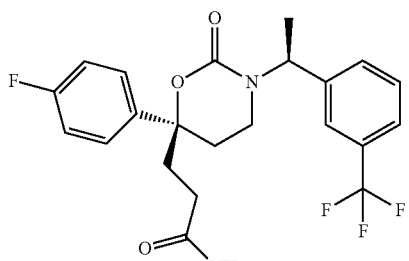

The title compound was prepared from (R)-6-(4-fluorophenyl)-6-(3-hydroxypropyl)-3-((S)-1-(3-(trifluoromethyl)phenyl)ethyl)-1,3-oxazinan-2-one following a procedure analogous to that described in Example 234. LC-MS Method 2 $t_R$=2.194 min, m/z=439.2; $^1$H NMR (CDCl$_3$) 1.49 (m, 3H), 1.89 (m, 1H), 2.10-2.22 (m, 5H), 2.41 (m, 1H), 2.87 (m, 1H), 5.30 (s, 1H), 5.45 (s, 1H), 5.66 (m, 1H), 6.97 (m, 2H), 7.08 (m, 1H), 7.19 (m, 4H), 7.36 (m, 1H).

Example 300

3-(4-((S)-1-((R)-6-(3-amino-3-oxopropyl)-2-oxo-6-phenyl-1,3-oxazinan-3-yl)ethyl)phenyl)pyridine 1-oxide

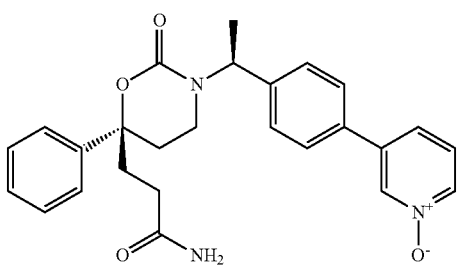

The title compound was prepared from 3-((R)-2-oxo-6-phenyl-3-((S)-1-(4-(pyridin-3-yl)phenyl)ethyl)-1,3-oxazinan-6-yl)propanamide following a procedure analogous to that described Example 222. LC-MS Method 2 $t_R$=1.476 min, m/z=445.2; $^1$H NMR (CDCl$_3$) 1.56 (d, 3H), 1.98-2.15 (m, 1H), 2.18-2.37 (m, 5H), 2.47-2.58 (m, 1H), 2.96 (m, 1H), 5.51 (s, 1H), 5.57 (s, 1H), 5.70 (q, 1H), 7.03 (q, 2H), 7.26-7.38 (m, 9H), 8.20 (d, 1H), 8.49 (s, 1H).

Example 301

N-(2-((S)-6-(4-fluorophenyl)-3-((S)-1-(4-methoxyphenyl)ethyl)-2-oxo-1,3-oxazinan-6-yl)ethyl)methanesulfonamide

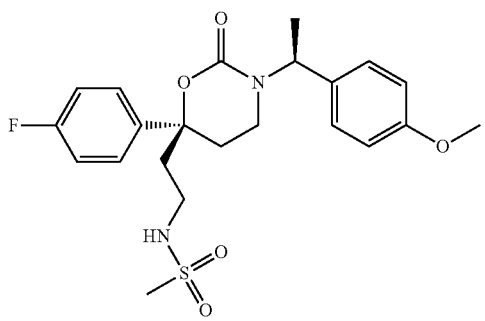 [SMILES: COc1ccc([C@H](C)N2CC[C@](CCNS(C)(=O)=O)(c3ccc(F)cc3)OC2=O)cc1]

The title compound was prepared from (R)-6-(2-aminoethyl)-6-(4-fluorophenyl)-3-((S)-1-(4-methoxyphenyl)ethyl)-1,3-oxazinan-2-one following a procedure analogous to that described Example 99. LC-MS Method 3 $t_R$=1.017 min, m/z=451; $^1$H NMR (CDCl$_3$) 1.48 (d, 3H), 2.06-2.22 (m, 5H), 2.82 (s, 4H), 2.92-3.02 (m, 1H), 3.08-3.19 (m, 1H), 3.67 (s, 3H), 5.55 (q, 1H), 6.59 (d, 2H), 6.82 (d, 2H), 7.01 (t, 2H), 7.18 (t, 2H).

Example 302

(R)-6-allyl-6-(4-fluorophenyl)-3-((S)-1-(4-(5-fluoropyridin-3-yl)phenyl)ethyl)-1,3-oxazinan-2-one

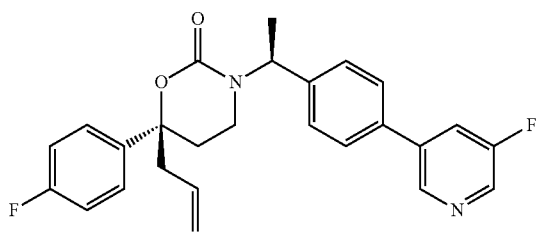 [SMILES: C=CC[C@]1(c2ccc(F)cc2)CCN([C@@H](C)c2ccc(-c3cncc(F)c3)cc2)C(=O)O1]

The title compound was prepared from (R)-6-allyl-6-(4-fluorophenyl)-3-((S)-1-(4-(5-fluoropyridin-3-yl)phenyl)ethyl)-1,3-oxazinan-2-one following a procedure analogous to that described in Example 78. LC-MS Method 1 $t_R$=1.84 min, m/z=435 (M+1); $^1$H NMR (CDCl$_3$) 8.58 (t, 1H, J=1.5, 1.5 Hz), 8.44 (d, 1H, J=3 Hz), 7.51-7.48 (ddd, 1H, J=9, 4, 2 Hz), 7.33-7.262 (m, 4H), 7.04 (at, J=9, 9 Hz), 6.98 (d, 2H, 8 Hz), 5.76-5.66 (m, 2H), 5.11-5.00 (m, 2H), 3.00-2.95 (m, 1H), 2.65-2.5 (m, 2H), 2.41-2.33 (m, 1H) 2.31-2.18 (m, 2H), 1.55 (d, 3H, J=7 Hz).

Example 303

3-((R)-3-((S)-1-(4'-fluorobiphenyl-4-yl)ethyl)-2-oxo-6-phenyl-1,3-oxazinan-6-yl)-2,2-dimethylpropanenitrile

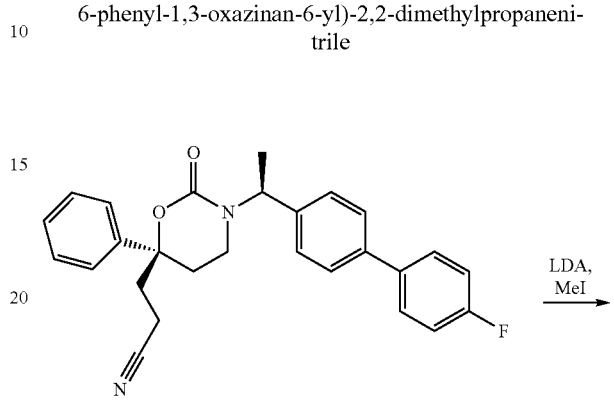

To a solution of 3-((R)-3-((S)-1-(4'-fluorobiphenyl-4-yl)ethyl)-2-oxo-6-phenyl-1,3-oxazinan-6-yl)propanenitrile (35 mg, 0.08 mmol) in dry THF (15 mL) in ice-bath under N$_2$ protection was added LiHMDS (1 mL/1M) dropwise slowly. After addition, HMPA (31 mg, 0.16 mmol) was added, and the mixture was stirred for 1 hour at 0° C. Then MeI (114 mg, 0.8 mmol) was added dropwise slowly. The mixture was stirred for 4 h and cooled to 0° C. To the above solution was added LiHMDS (1 mL/1M) and HMPA (31 mg, 0.16 mmol). The mixture was stirred for 1 h, and MeI (114 mg, 0.8 mmol) was added. Then the mixture was stirred overnight. The reaction was quenched with satd aq NH$_4$Cl (5 mL), and the mixture was extracted with EtOAc (3×10 mL). The combined organic phase was washed with brine, dried over Na$_2$SO$_4$, filtered and concentrated. The residue was purified by chromatography to give 3-{(R)-3-(S)-[1-(4'-fluoro-biphenyl-4-yl)-ethyl]-2-oxo-6-phenyl-[1,3]oxazinan-6-yl}-2,2-dimethyl-propionitrile (10 mg, 27%).

LC-MS Method 3 $t_R$=1.323 min, m/z=479.1; $^1$H NMR (CDCl$_3$) 1.18 (s, 6H), 1.28 (s, 3H), 1.37 (t, 2H), 1.42 (s, 3H), 1.48 (d, 3H), 1.79 (m, 1H), 2.10 (s, 2H), 2.19-2.30 (m, 1H), 2.45 (m, 2H), 2.81-2.91 (m, 1H), 3.06 (m, 1H), 3.68 (m, 1H), 5.61 (q, 1H), 6.83 (d, 2H), 7.02 (t, 2H), 7.18 (m, 2H), 7.30 (m, 4H), 7.37 (m, 2H)

Example 304

3-((R)-3-((S)-1-(4-(6-methoxypyridin-3-yl)phenyl)ethyl)-2-oxo-6-phenyl-1,3-oxazinan-6-yl)propanamide

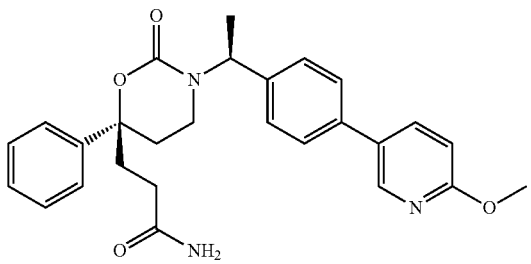 [SMILES: COc1ccc(-c2ccc([C@H](C)N3CC[C@](CCC(N)=O)(c4ccccc4)OC3=O)cc2)cn1]

The title compound was prepared from 3-((R)-3-((S)-1-(4-bromophenyl)ethyl)-2-oxo-6-phenyl-1,3-oxazinan-6-yl)propanamide and 6-methoxypyridine-3-boronic acid following a procedure analogous to that described in Example 64. LC-MS Method 3 $t_R$=1.106 min, m/z=460.2; $^1$H NMR (CD$_3$OD) 1.54 (m, 3H), 1.95 (m, 1H), 2.16-2.29 (m, 4H), 2.40 (m, 2H), 2.44 (m, 1H), 3.10 (m, 1H), 3.99 (s, 3H), 5.56 (m, 1H), 6.94 (m, 1H), 7.03 (m, 2H), 7.28-7.39 (m, 8H), 7.93 (m, 1H), 8.28 (m, 1H).

Example 305

(R)-6-(4-fluorophenyl)-6-(3-hydroxypropyl)-3-((S)-1-(4-(5-methoxypyridin-3-yl)phenyl)ethyl)-1,3-oxazinan-2-one

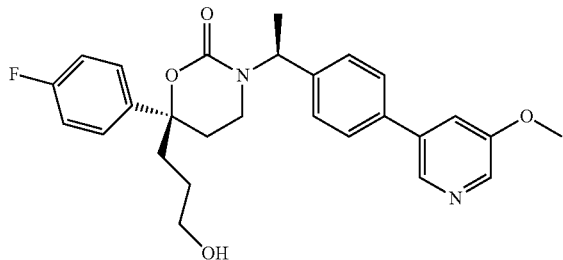 [SMILES: COc1cncc(-c2ccc([C@H](C)N3CC[C@](CCCO)(c4ccc(F)cc4)OC3=O)cc2)c1]

The title compound was prepared from (R)-3-((S)-1-(4-bromophenyl)ethyl)-6-(4-fluorophenyl)-6-(3-hydroxypropyl)-1,3-oxazinan-2-one and 5-methoxypyridine-3-boronic acid following a procedure analogous to that described in Example 64. LC-MS Method 2 $t_R$=1.694 min, m/z=465.2; $^1$H NMR (CDCl$_3$) 1.34 (m, 1H), 1.53 (m, 3H), 1.68 (m, 1H), 1.94 (m, 3H), 2.18-2.32 (m, 3H), 2.95 (m, 1H), 3.56 (m, 2H), 3.88 (s, 3H), 5.69 (m, 1H), 7.01 (m, 4H), 7.24 (m, 3H), 7.31 (m, 2H), 8.25 (m, 1H), 8.34 (m, 1H).

Example 306

(R)-6-allyl-3-((S)-1-(4-(5-chloropyridin-3-yl)phenyl)ethyl)-6-(4-fluorophenyl)-1,3-oxazinan-2-one

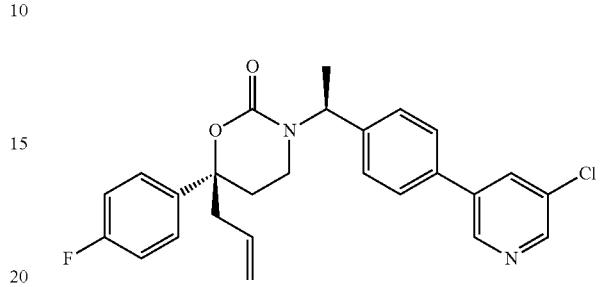

The title compound was prepared from (R)-3-((S)-1-(4-bromophenyl)ethyl)-6-(4-fluorophenyl)-6-(3-hydroxypropyl)-1,3-oxazinan-2-one and 5-chloropyridine-3-boronic acid following a procedure analogous to that described in Example 64. LC-MS Method 1 $t_R$=1.97 min, m/z=451 (M+1); $^1$H NMR (CDCl$_3$) 8.68 (d, 1H, J=2 Hz), 8.59 (d, 1H, J=2 Hz), 7.94 (t, 1H, J=2.2 Hz), 7.33-7.27 (m, 4H), 7.04 (ap q, 2H, J=9, 17 Hz), 5.75-5.65 (m, 2H), 5.12-5.02 (m, 2H), 3.03-2.98 (m, 1H), 2.66-2.54 (m, 2H), 2.41-2.17 (m, 3H), 1.56 (d, 3H, J=7 Hz).

Example 307

N-(2-((S)-2-oxo-6-phenyl-3-((S)-1-(4-(pyridin-3-yl)phenyl)ethyl)-1,3-oxazinan-6-yl)ethyl)methanesulfonamide

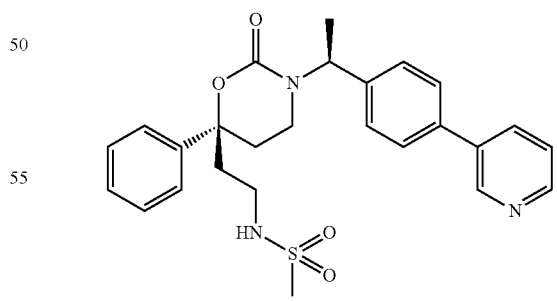

The title compound was prepared from (R)-6-(2-aminoethyl)-6-phenyl-3-((S)-1-(4-(pyridin-3-yl)phenyl)ethyl)-1,3-oxazinan-2-one following a procedure analogous to that described in Example 99. LC-MS Method 2 $t_R$=1.525 min, m/z=480.2; $^1$H NMR (CDCl$_3$) 1.52 (d, 3H), 2.05-2.32 (m, 6H), 2.81 (s, 3H), 2.86 (m, 1H), 2.93-3.04 (m, 1H), 3.06-3.20

(m, 1H), 4.73 (s, 1H), 5.63 (q, 1H), 6.95 (d, 2H), 7.05-7.22 (m, 2H), 7.23-7.40 (m, 6H), 7.71 (d, 1H), 8.50 (d, 1H), 8.66 (s, 1H).

Example 308

(S)-6-(4-fluorophenyl)-6-(2-hydroxyethyl)-3-((S)-1-(4-(methylsulfonyl)phenyl)ethyl)-1,3-oxazinan-2-one

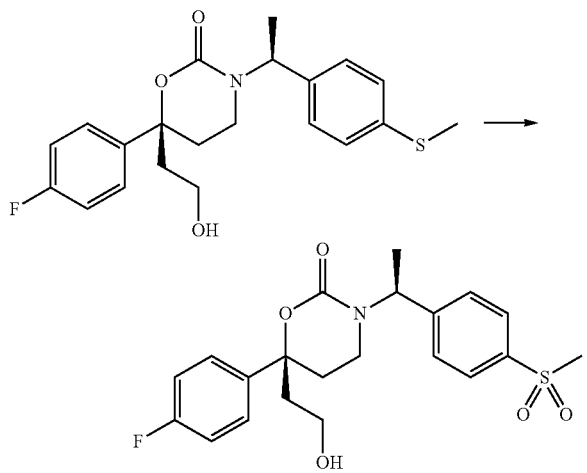

The title compound was prepared using conditions analogous to those described in Example 229. LC-MS Method 1 $t_R$=1.18 min, m/z=422 (M+1); $^1$H NMR (CD$_3$OD) 7.66 (d, J=7.9 Hz, 2H), 7.28-7.24 (m, 2H), 7.15 (d, J=8.2 Hz, 2H), 7.04 (t, J=8.5 Hz, 2H), 5.51 (q, J=7.0 Hz, 1H), 3.64-3.57 (m, 1H), 3.29-3.23 (m, 1H), 3.15-3.11 (m, 1H), 2.98 (s, 3H), 2.49-2.43 (m, 1H), 2.33-2.20 (m, 2H), 2.05 (t, J=7.2 Hz, 2H), 1.50 (d, J=7.0 Hz, 3H).

Example 309

(R)-3-((S)-1-(4-(difluoromethoxy)phenyl)ethyl)-6-(4-fluorophenyl)-6-(3-hydroxypropyl)-1,3-oxazinan-2-one

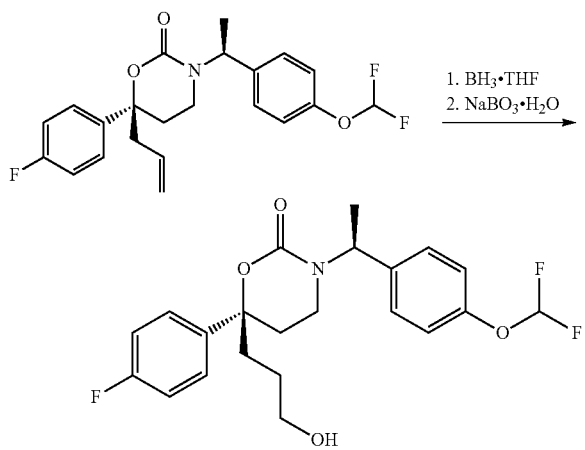

A solution of (R)-6-allyl-3-((S)-1-(4-(difluoromethoxy)phenyl)ethyl)-6-(4-fluorophenyl)-1,3-oxazinan-2-one (0.2780 g, 0.686 mmol, 1.0 equiv) in THF (20 mL) was degassed and then cooled with an ice-salt bath (−9° C.). To this solution was added a solution of 1.0 M BH$_3$.THF complex in THF (1.5 mL, 1.5 mmol, 2.2 equiv). The resulting mixture was allowed to slowly warm to rt while stirring overnight (21 h) and then quenched with H$_2$O (3 mL) and NaBO$_3$.H$_2$O (0.680 g, 6.8 mmol, 10 equiv). The mixture was vigorously stirred at rt overnight and then diluted with CH$_2$Cl$_2$, and dried over Na$_2$SO$_4$. After the solvents were evaporated, the residue was purified by chromatography on silica gel eluted with hexanes/ethyl acetate to give 0.2337 g (80%) of (R)-3-((S)-1-(4-(difluoromethoxy)phenyl)ethyl)-6-(4-fluorophenyl)-6-(3-hydroxypropyl)-1,3-oxazinan-2-one. LC-MS Method 1 $t_R$=1.59 min, m/z 446 (MNa$^+$), 380, 210, 171; $^1$H NMR (400 MHz, CD$_3$OD) δ 7.27-7.23 (m, 2H), 7.04 (t, J=8.8 Hz, 2H), 6.94 (d, J=8.5 Hz, 2H), 6.85 (d, J=8.8 Hz, 2H), 6.67 (t, J=74.1 Hz, 1H), 5.48 (q, J=7.1 Hz, 1H), 3.43-3.39 (m, 2H), 3.07-3.02 (m, 1H), 2.42-2.37 (m, 1H), 2.26-2.10 (m, 2H), 1.91-1.85 (m, 2H), 1.58-1.50 (m, 1H), 1.46 (d, J=7.0 Hz, 3H), 1.29-1.20 (m, 1H); $^{19}$F NMR (376 MHz, CD$_3$OD) δ −83.95 (d, J=73.8 Hz), −117.51 (m).

Example 310

3-((R)-3-((S)-1-(4'-fluorobiphenyl-4-yl)ethyl)-2-oxo-6-phenyl-1,3-oxazinan-6-yl)propyl dihydrogen phosphate

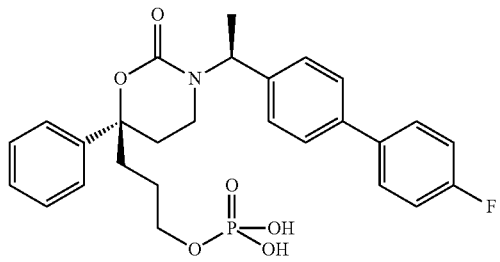 [SMILES: C[C@@H](c1ccc(-c2ccc(F)cc2)cc1)N1CC[C@](CCCOP(=O)(O)O)(c2ccccc2)OC1=O]

The title compound was prepared from (R)-3-((S)-1-(4'-fluorobiphenyl-4-yl)ethyl)-6-(3-hydroxypropyl)-6-phenyl-1,3-oxazinan-2-one following a procedure analogous to that described in Example 151. LC-MS Method 1 $t_R$=1.63 min, m/z=514 (M+1); $^1$H NMR (CD$_3$OD) 7.48-7.44 (m, 2H), 7.34-7.24 (m, 7H), 7.07 (t, J=8.5 Hz, 2H), 6.94 (d, J=7.9 Hz, 2H), 5.51 (q, J=7.0 Hz, 1H), 3.84 (q, J=6.4 Hz, 2H), 3.05-3.00 (m, 1H), 2.44-2.39 (m, 1H), 2.29-2.12 (m, 2H), 1.98-1.93 (m, 2H), 1.76-1.68 (m, 1H), 1.49 (d, J=7.0 Hz, 3H), 1.44-1.35 (m, 1H).

Example 311

(R)-6-(4-fluorophenyl)-6-(3-hydroxypropyl)-3-((S)-1-(4-(2-methylpyridin-4-yl)phenyl)ethyl)-1,3-oxazinan-2-one

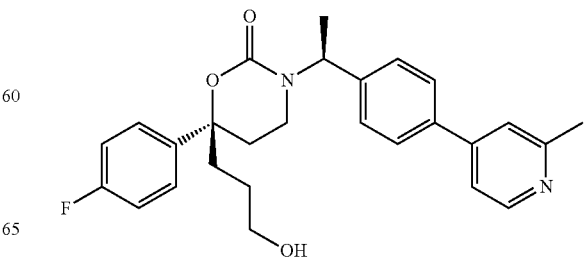

The title compound was prepared from (R)-3-((S)-1-(4-bromophenyl)ethyl)-6-(4-fluorophenyl)-6-(3-hydroxypropyl)-1,3-oxazinan-2-one and 2-methylpyridine-4-boronic acid following a procedure analogous to that described in Example 64. LC-MS Method 1 $t_R$=1.29 min, m/z=431 (M+1); $^1$H NMR (CDCl$_3$) 8.71 (d, 1H, J=6 Hz), 7.78 (d, 1H, J=6 Hz), 7.7 (s, 1H), 7.49 (t, 2H, J=7, 7 Hz), 7.27-7.24 (m, 2H), 7.17 (m, 2H), 7.09-7.02 (aq, 2H, J=9, 17 Hz), 5.73 (q, 1H, J=7, 14 Hz), 4.27 (t, 1H, J=6, 6 Hz), 3.60 (t, 1H, J=6, 6 Hz), 3.09-3.03 (m, 1H), 2.95 (s, 3H), 2.41-2.25 (m, 3H), 2.06-1.90 (m, 2H) 1.73-1.64 (m, 1H), 1.58 (d, 3H, J=7 Hz), 1.40-1.33 (m, 1H).

Example 312

(R)-3-((S)-1-(4-(2-hydroxy-2-methylpropyl)phenyl)ethyl)-6-(3-hydroxypropyl)-6-phenyl-1,3-oxazinan-2-one

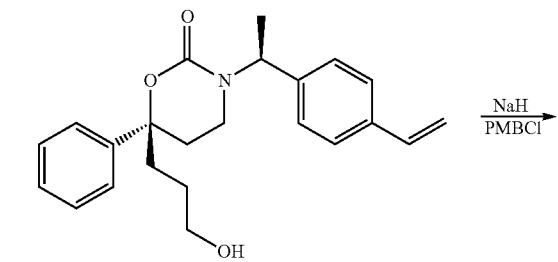

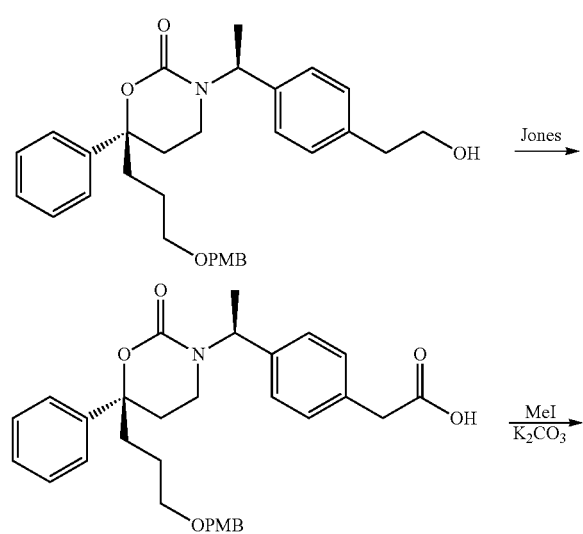

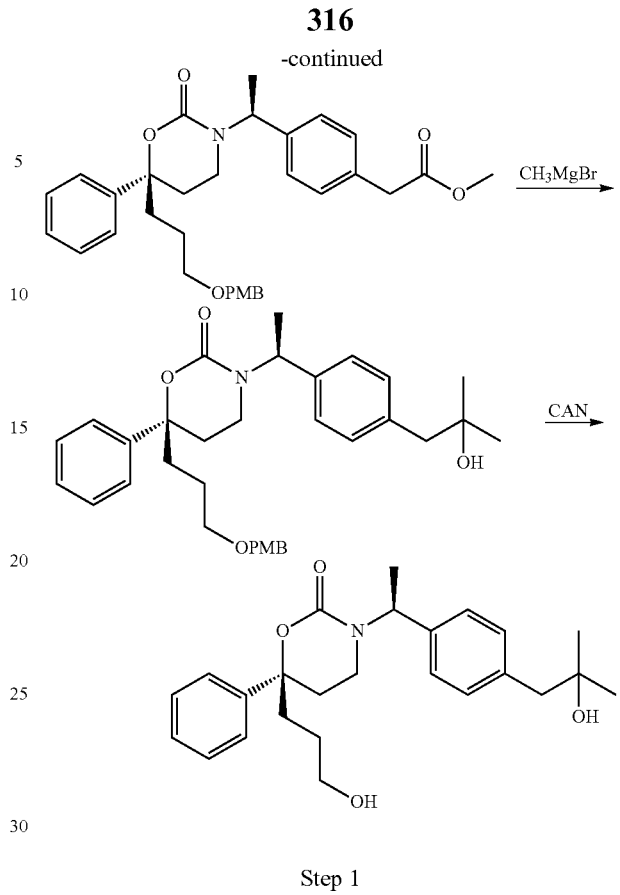

Step 1

To a suspension of NaH (180 mg, 4.4 mmol) in THF (5 mL) was added a solution of (R)-6-(3-hydroxypropyl)-6-phenyl-3-((S)-1-(4-vinylphenyl)ethyl)-1,3-oxazinan-2-one (800 mg, 2.2 mmol) in THF (10 mL) at 0° C. The resulting mixture was stirred for 30 min. Then PMBCl (520 mg, 3.3 mmol) was added to the above mixture. The mixture was stirred for 3 h. The reaction was quenched with aqueous NH$_4$Cl solution. The organic phase was separated, and concentrated to give the crude (R)-6-(3-(4-methoxybenzyloxy)propyl)-6-phenyl-3-((S)-1-(4-vinylphenyl)ethyl)-1,3-oxazinan-2-one, which was used for the next step without purification (460 mg, 46%).

Step 2

To a solution of (R)-6-(3-(4-methoxybenzyloxy)propyl)-6-phenyl-3-((S)-1-(4-vinylphenyl)ethyl)-1,3-oxazinan-2-one (260 mg, 0.536 mmol) in THF (3 mL) was added BH$_3$·THF (1.6 mL, 1 mol/L) at 0° C. under nitrogen atmosphere. The formed mixture was stirred for 2 h. The reaction was quenched with water. Then aqueous NaOH solution (1 mol/L, 2 mL) and H$_2$O$_2$ (1 mL) were added to the above mixture. The resulting mixture was stirred for 1.5 h. The mixture was extracted with EtOAc and the combined organic phase was concentrated to give crude (R)-3-((S)-1-(4-(2-hydroxyethyl)phenyl)ethyl)-6-(3-(4-methoxybenzyloxy)propyl)-6-phenyl-1,3-oxazinan-2-one (260 mg, 96%), which was used for the next step without purification. $^1$H NMR (CDCl$_3$): δ=1.32 (m, 2H), 1.41 (d, 3H), 1.89 (m, 2H), 2.12 (m, 1H), 2.22 (m, 2H), 2.68 (m, 1H), 2.81 (m, 1H), 3.27 (m, 2H), 3.72 (s, 3H), 4.26 (s, 2H), 5.53 (q, 1H), 6.71-6.88 (m, 5H), 7.13 (m, 2H), 7.26 (m, 4H).

Step 3

To a solution of (R)-3-((S)-1-(4-(2-hydroxyethyl)phenyl)ethyl)-6-(3-(4-methoxybenzyloxy)propyl)-6-phenyl-1,3-oxazinan-2-one (260 mg, 0.517 mmol) in acetone (2 mL) was added Jones reagent (0.25 mL, 2.5 mol/L), and the formed mixture was stirred for 30 min. The mixture was extracted with EtOAc. The combined organic layer was concentrated to give crude 2-(4-((S)-1-((R)-6-(3-(4-methoxybenzyloxy)propyl)-2-oxo-6-phenyl-1,3-oxazinan-3-yl)ethyl)phenyl)acetic acid (260 mg, 97%), which was used for the next step without purification.

Step 4

To a mixture of 2-(4-((S)-1-((R)-6-(3-(4-methoxybenzyloxy)propyl)-2-oxo-6-phenyl-1,3-oxazinan-3-yl)ethyl)phenyl)acetic acid (260 mg, 0.50 mmol) and K₂CO₃ in DMF (2 mL) was added CH₃I (0.2 g, 1 mmol). The resulting mixture was stirred overnight. The solid was filtered, and the filtrate was concentrated to give the crude product, which was purification by TLC to afford methyl 2-(4-((S)-1-((R)-6-(3-(4-methoxybenzyloxy)propyl)-2-oxo-6-phenyl-1,3-oxazinan-3-yl)ethyl)phenyl)acetate (100 mg, 37%). ¹H NMR (CDCl₃): δ=1.42 (d, 3H), 1.68 (m, 1H), 1.88 (m, 2H), 2.12 (m, 1H), 2.23 (m, 2H), 2.78 (m, 1H), 3.29 (m, 2H), 3.44 (s, 2H), 3.64 (s, 3H), 3.75 (s, 3H), 4.28 (s, 2H), 5.56 (q, 1H), 6.73 (m, 4H), 6.92 (m, 2H), 7.14 (m, 2H), 7.25 (m, 5H).

Step 5

To a solution of methyl 2-(4-((S)-1-((R)-6-(3-(4-methoxybenzyloxy)propyl)-2-oxo-6-phenyl-1,3-oxazinan-3-yl)ethyl)phenyl)acetate (100 mg, 0.188 mmol) in THF (2 mL) was added methylmagnesium bromide (0.3 mL, 3 mol/L) at −78° C. The formed mixture was stirred for 3 h. The reaction was quenched by aqueous solution of NH₄Cl. The organic phase was separated and concentrated to provide the crude product, which was purified by TLC to give (R)-3-((S)-1-(4-(2-hydroxy-2-methylpropyl)phenyl)ethyl)-6-(3-hydroxypropyl)-6-phenyl-1,3-oxazinan-2-one (10 mg, 10%). ¹H NMR (CDCl₃): δ=1.08 (d, 6H), 1.19 (m, 2H), 1.42 (d, 3H), 1.64 (m, 2H), 1.84 (m, 2H), 2.04-2.19 (m, 4H), 2.53 (s, 2H), 2.80 (m, 1H), 3.29 (t, 2H), 3.72 (s, 3H), 4.25 (s, 2H), 5.54 (q, 1H), 6.74 (m, 5H), 6.82 (m, 2H), 7.10 (m, 3H), 7.23 (m, 4H).

Step 6

To a solution of methyl (R)-3-((S)-1-(4-(2-hydroxy-2-methylpropyl)phenyl)ethyl)-6-(3-(4-methoxybenzyloxy)propyl)-6-phenyl-1,3-oxazinan-2-one (10 mg, 0.188 mmol) in DCM/H₂O (10:1, 2 mL) was added CAN (100 mg). The formed mixture was stirred for 3 h. The reaction was washed with water and extracted with CH₂Cl₂. The combined organic phase was concentrated to provide the crude product, which was purified by preparative HPLC to give (R)-3-((S)-1-(4-(2-hydroxy-2-methylpropyl)phenyl)ethyl)-6-(3-(4-methoxybenzyloxy)propyl)-6-phenyl-1,3-oxazinan-2-one (0.8 mg, 10%). LC-MS Method 2 t_R=1.191 min, m/z=411.24; ¹H NMR (CDCl₃): δ=0.81 (m, 4H), 1.09 (d, 6H), 1.43 (d, 3H), 1.64 (m, 3H), 1.92 (m, 3H), 2.16-2.26 (m, 4H), 2.59 (s, 2H), 2.83 (m, 1H), 3.52 (t, 2H), 5.62 (q, 1H), 6.78 (m, 2H), 6.86 (m, 2H), 6.94 (m, 1H), 7.26 (m, 4H).

Example 313

(R)-6-(3-hydroxypropyl)-3-((S)-1-(4-(1-methyl-6-oxo-1,6-dihydropyridin-3-yl)phenyl)ethyl)-6-phenyl-1,3-oxazinan-2-one

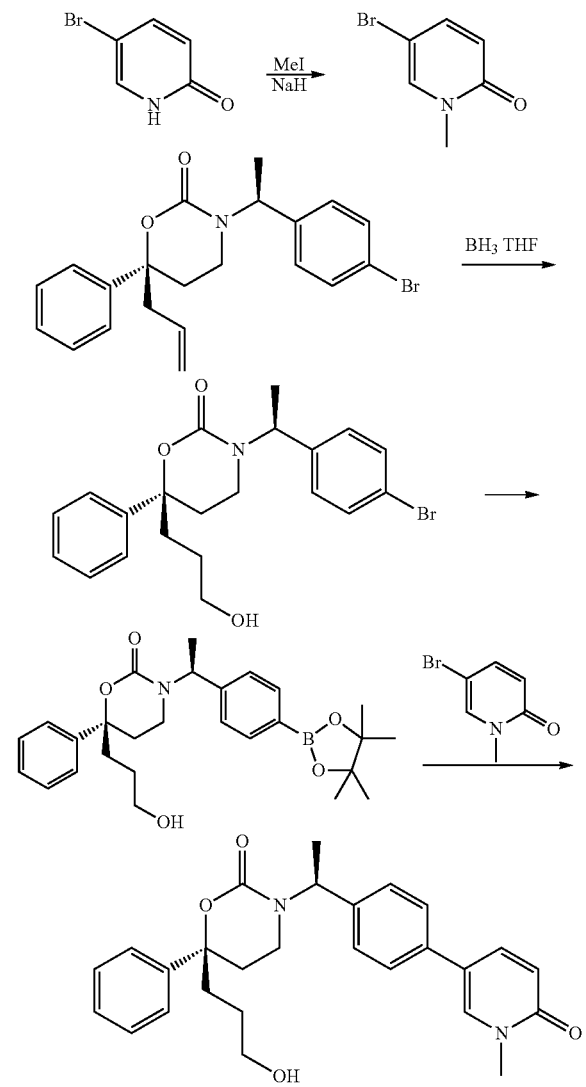

Step 1

To a suspension of NaH (4.8 g, 0.2 mol) in THF (10 mL) was added a solution of 5-bromopyridin-2(1H)-one (8.6 g, 0.05 mol) in THF (120 mL) at 0° C. The resulting mixture was stirred for 1 h and CH₃I (35.5 g, 0.25 mol) was added. The mixture was stirred for 3 h. The reaction was quenched with aqueous NH₄Cl solution. The organic phase was concentrated to give the crude product, which was purified by column chromatography to give 5-bromo-1-methylpyridin-2(1H)-one (8.9 g, 96.78%). ¹H NMR (CDCl₃): δ=3.5 (S, 3H), 6.52 (m, 1H), 7.32 (m, 1H), 7.45 (m, 1H).

Step 2

To a solution of (R)-6-allyl-3-((S)-1-(4-bromophenyl)ethyl)-6-phenyl-1,3-oxazinan-2-one (5 g, 12.5 mmol) in tetrahydrofuran (60 mL) was added BH₃ THF (25 mL, 1 mol/L, 25 mmol) at 0° C. under nitrogen atmosphere. The formed mixture was stirred for 2 h. The reaction was quenched with water. Then NaOH (3 mol/L, 10 mL) and $H_2O_2$ (15 mL) were added to the above mixture. When the reaction was over, the mixture was extracted with EtOAc. The combined organic phase was concentrated to give the crude product, which was purified by column chromatography to give (R)-3-((S)-1-(4-bromophenyl)ethyl)-6-(3-hydroxypropyl)-6-phenyl-1,3-oxazinan-2-one (2.5 g, 40%). ¹H NMR: (400 MHz, CDCl₃): δ=1.48 (t, 3H), 1.53 (m, 1H), 1.73 (m, 1H), 1.93-1.98 (m, 2H), 2.17-2.28 (m, 3H), 3.57 (t, 2H), 5.59 (m, 1H), 6.72 (m, 2H), 7.20 (m, 2H), 7.25-7.37 (m, 5H).

Step 3

To a solution of ((R)-3-((S)-1-(4-bromophenyl)ethyl)-6-(3-hydroxypropyl)-6-phenyl-1,3-oxazinan-2-one (2 g, 4.8 mmol) in DMSO (30 mL) were added bis(pinacolato)diboron (1.58 g, 6.3 mmol), KOAc (1.51 g, 15.4 mmol) and PdCl₂ (130 mg, 0.16 mmol) under nitrogen atmosphere. The formed mixture was stirred at 90° C. for 20 h. The reaction was quenched with water and extracted with EtOAc. The combined organic phase was concentrated to give the crude product, which was purified by column chromatography to give (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one (1.7 g, 77%). ¹H NMR: (400 MHz, CDCl₃): δ=1.18 (t, 1H), 1.33 (S, 11H), 1.43 (m, 2H), 1.48 (m, 3H), 1.71 (m, 1H), 1.88 (m, 2H), 2.1-2.3 (t, 3H), 2.7 (m, 1H) □3.5 (m, 2H), 5.5 (m, 1H), 6.72 (m, 2H), 7.25-7.37 (m, 5H), 7.48 (m, 2H).

Step 4

A mixture of (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one (1.7 g, 3.7 mmol) and 5-bromo-1-methylpyridin-2(1H)-one (816 mg, 4.4 mmol), Pd(Ph₃P)₂Cl₂ (200 mg), and aq Cs₂CO₃ solution (4 mL, 2M) in 1,4-dioxane (30 mL) was stirred and heated to reflux for 2 h. When the reaction was over, the mixture was washed with water and extracted with EtOAc, and the organic phase was washed with brine, dried over Na₂SO₄, filtered and concentrated to give crude product, which was purified by preparative TLC to give (R)-6-(3-hydroxypropyl)-3-((S)-1-(4-(1-methyl-6-oxo-1,6-dihydropyridin-3-yl)phenyl)ethyl)-6-phenyl-1,3-oxazinan-2-one (614 mg, 37%). LC-MS Method 2 $t_R$=1.075 min, m/z=447.1; ¹H NMR (CDCl₃): δ=1.38 (m, 1H), 1.47 (d, 3H), 1.73 (m, 2H), 1.98 (m, 2H), 2.20 (m, 1H), 2.31 (m, 2H), 2.94 (m, 1H), 3.51 (m, 2H), 3.56 (s, 3H), 5.63 (m, 1H), 6.67 (m, 1H), 6.87 (m, 2H), 7.05 (m, 2H), 7.31-7.41 (m, 6H), 7.48 (m, 1H).

Example 314

N-(3-((R)-6-(4-fluorophenyl)-3-((S)-1-(4-methoxyphenyl)ethyl)-2-oxo-1,3-oxazinan-6-yl)propyl)methanesulfonamide

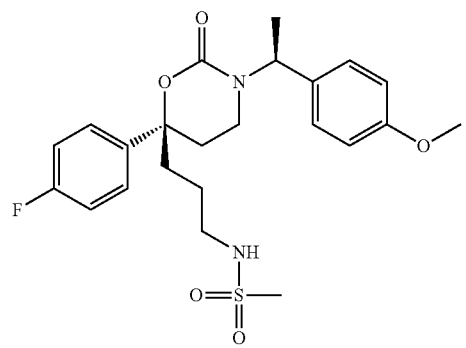 [SMILES: COc1ccc([C@H](C)N2CC[C@](CCCNS(C)(=O)=O)(c3ccc(F)cc3)OC2=O)cc1]

The title compound was prepared from (R)-6-(3-aminopropyl)-6-(4-fluorophenyl)-3-((S)-1-(4-methoxyphenyl)ethyl)-1,3-oxazinan-2-one following procedures analogous to those described in Example 319. LC-MS Method 3 $t_R$=1.032 min, m/z=465.1; ¹H NMR (CDCl₃) 1.28-1.40 (m, 1H), 1.48 (d, 3H), 1.66 (m, 1H), 1.82-1.92 (m, 1H), 1.93-2.08 (m, 1H), 2.21 (m, 2H), 2.83-2.93 (m, 4H), 3.06 (t, 2H), 3.71 (s, 3H), 4.42 (s, 1H), 5.58 (q, 1H), 6.66 (d, 2H), 6.86 (d, 2H), 7.02 (t, 2H), 7.18 (m, 2H).

Example 315

3-((R)-3-((S)-1-(4-methoxyphenyl)ethyl)-2-oxo-6-phenyl-1,3-oxazinan-6-yl)propanamide

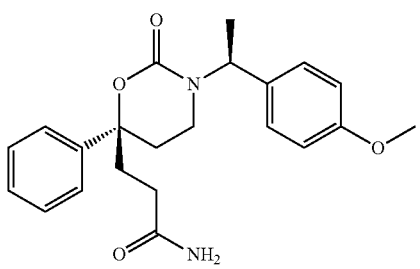 [SMILES: COc1ccc([C@H](C)N2CC[C@](CCC(N)=O)(c3ccccc3)OC2=O)cc1]

The title compound was prepared from (R)-6-(3-hydroxypropyl)-3-((S)-1-(4-methoxyphenyl)ethyl)-6-phenyl-1,3-oxazinan-2-one one following a procedure analogous to that described Example 234. LC-MS Method 2 $t_R$=1.166 min, m/z=383.1; ¹H NMR (CDCl₃) 1.43 (d, 3H), 1.86 (m, 1H), 2.09 (m, 2H), 2.12-2.14 (m, 1H), 2.19 (m, 2H), 2.60 (m, 1H), 2.78 (m, 1H), 3.66 (s, 3H), 5.42 (s, 1H), 5.55 (q, 1H), 6.58 (d, 2H), 6.80 (d, 2H), 7.15 (m, 1H), 7.26 (m, 3H).

Example 316

3-((R)-6-(4-fluorophenyl)-3-((S)-1-(4-fluorophenyl)ethyl)-2-oxo-1,3-oxazinan-6-yl)propanamide

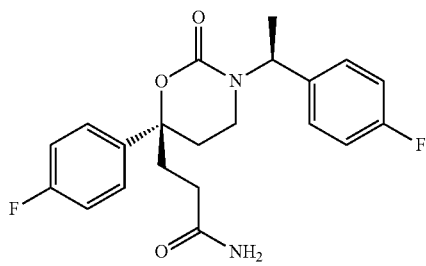 [SMILES: C[C@@H](c1ccc(F)cc1)N1CC[C@](CCC(N)=O)(c2ccc(F)cc2)OC1=O]

The title compound was prepared from (R)-6-(4-fluorophenyl)-3-((S)-1-(4-fluorophenyl)ethyl)-6-(3-hydroxypropyl)-1,3-oxazinan-2-one following a procedure analogous to that described Example 234. LC-MS Method 2 $t_R$=1.212 min, m/z=410.9; $^1$H NMR (CDCl$_3$) 1.48 (d, 3H), 1.83-1.98 (m, 1H), 2.06-2.22 (m, 5H), 2.38-2.49 (m, 1H), 2.85 (m, 1H), 5.28 (s, 1H), 5.42 (s, 1H), 5.58 (q, 1H), 6.77 (m, 2H), 6.87 (m, 2H), 6.92-7.02 (m, 2H), 7.18 (m, 2H).

Example 317

3-((R)-3-((S)-1-cyclohexylethyl)-6-(4-fluorophenyl)-2-oxo-1,3-oxazinan-6-yl)propanamide

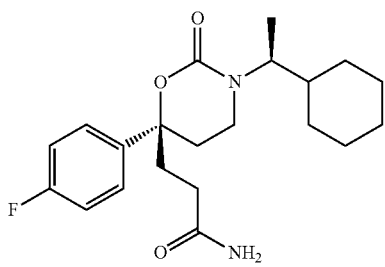 [SMILES: C[C@@H](C1CCCCC1)N1CC[C@](CCC(N)=O)(c2ccc(F)cc2)OC1=O]

The title compound was prepared from (R)-3-((S)-1-cyclohexylethyl)-6-(4-fluorophenyl)-6-(3-hydroxypropyl)-1,3-oxazinan-2-one following a procedure analogous to that described Example 234. LC-MS Method 2 $t_R$=1.304 min, m/z=398.9; 1H NMR (CDCl$_3$) 1.13 (d, 6H), 1.20 (s, 2H), 1.37-1.71 (m, 6H), 1.83-1.95 (m, 1H), 2.04-2.20 (m, 3H), 2.30 (d, 1H), 2.36-2.48 (m, 1H), 2.48-2.58 (m, 1H), 3.00 (m, 1H), 3.88-3.98 (m, 1H), 5.35 (s, 2H), 7.01 (t, 2H), 7.22 (m, 2H).

Example 318

N-(2-((S)-3-((S)-1-cyclohexylethyl)-6-(4-fluorophenyl)-2-oxo-1,3-oxazinan-6-yl)ethyl)methanesulfonamide

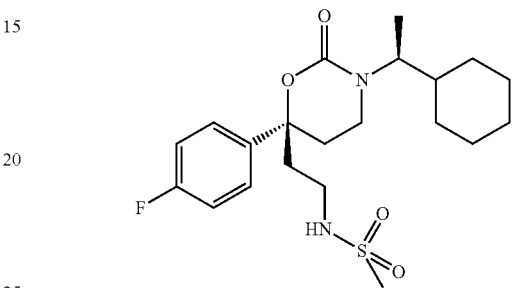

The title compound was prepared from (R)-6-(2-aminoethyl)-3-((S)-1-cyclohexylethyl)-6-(4-fluorophenyl)-1,3-oxazinan-2-one following a procedure analogous to that described Example 99. LC-MS Method 2 $t_R$=1.373 min, m/z=427; $^1$H NMR (CDCl$_3$) 1.04 (d, 6H), 1.20 (s, 1H), 1.38-1.54 (m, 3H), 1.55-1.68 (m, 4H), 2.02-2.21 (m, 3H), 2.30 (d, 1H), 2.48-2.58 (m, 1H), 2.80 (s, 3H), 2.91-3.02 (m, 2H), 3.05-3.18 (m, 1H), 4.54 (m, 1H), 7.04 (t, 2H), 7.23 (m, 2H).

Example 319

N-(3-((R)-3-((S)-1-cyclohexylethyl)-6-(4-fluorophenyl)-2-oxo-1,3-oxazinan-6-yl)propyl)methanesulfonamide

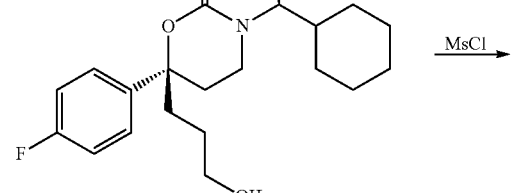

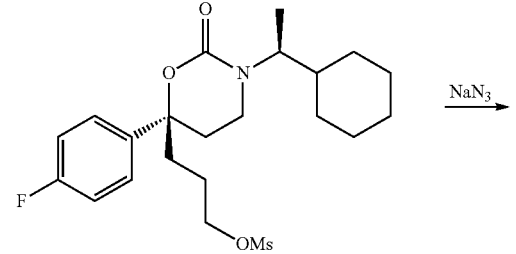

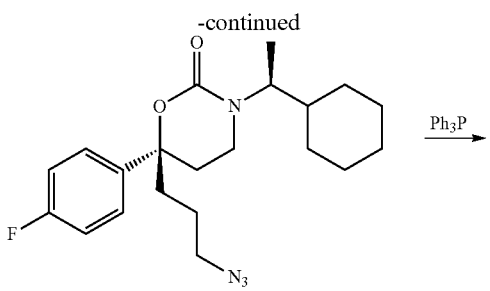

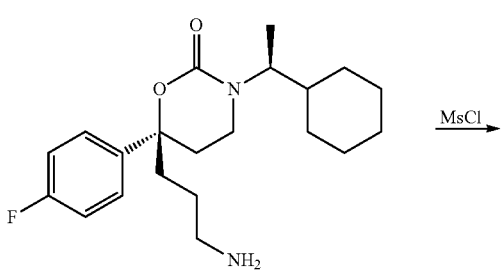

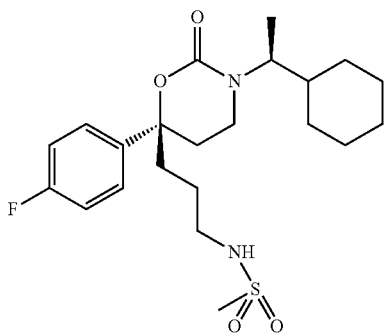

Step 1

To a solution of (R)-3-((S)-1-cyclohexylethyl)-6-(4-fluorophenyl)-6-(3-hydroxy propyl)-1,3-oxazinan-2-one (200 mg, 0.55 mmol) in CH$_2$Cl$_2$ (10 mL) was added Et$_3$N (290 mg, 2.87 mmol) and MsCl (196 mg, 1.72 mmol) at 0° C. The reaction solution was stirred at rt for 2 h. The reaction was quenched by H$_2$O and extracted with CH$_2$Cl$_2$. The organic phase was concentrated to give the 3-((R)-3-((S)-1-cyclohexylethyl)-6-(4-fluorophen-yl)-2-oxo-1,3-oxazinan-6-yl) propyl methanesulfonate (240 mg, 92%).

Step 2

To a solution of 3-((R)-3-((S)-1-cyclohexylethyl)-6-(4-fluorophenyl)-2-oxo-1,3-oxazinan-6-yl)propyl methanesulfonate (240 mg, 0.54 mmol) in DMF (10 mL) was added NaN$_3$ (112 mg, 1.72 mmol). After stirring at 100° C. for 3 h, the reaction was quenched by H$_2$O, and the mixture was extracted with EtOAc. The organic phase was washed with brine and concentrated to give (R)-6-(3-azidopropyl)-3-((S)-1-cyclohexylethyl)-6-(4-fluorophenyl)-1,3-oxazinan-2-one (180 mg, 88%). $^1$H NMR (CDCl$_3$): δ=1.04 (m, 6H), 1.21 (m, 1H), 1.41 (m, 1H), 1.5 (m, 2H), 1.7 (m, 1H), 1.8 (m, 7H), 2.12 (m, 1H), 2.3 (m, 1H), 2.6 (m, 1H), 3.01 (m, 2H), 3.22 (m, 2H), 3.92 (m, 1H), 7.02 (m, 2H), 7.3 (m, 2H).

Step 3

To a solution of (R)-6-(3-azidopropyl)-3-((S)-1-cyclohexylethyl)-6-(4-fluorophenyl)-1,3-oxazinan-2-one (210 mg, 0.54 mmol) in THF (5 mL) and H$_2$O (0.25 mL) was added Ph$_3$P (420 mg, 1.60 mmol). After refluxing for 3 h, the mixture was concentrated to give the crude product, which was purified by preparative TLC to give (R)-6-(3-aminopropyl)-3-((S)-1-cyclohexyle-thyl)-6-(4-fluorophenyl)-1,3-oxazinan-2-one (50 mg, 25%).

Step 4

To a solution of (R)-6-(3-aminopropyl)-3-((S)-1-cyclohexylethyl)-6-(4-fluorophenyl)-1,3-oxazinan-2-one (30 mg, 0.10 mmol) was added Et$_3$N (40 mg, 0.4 mmol) and MsCl (30 mg, 0.24 mmol) at 0° C. The reaction solution was stirred at rt for 2 h. The reaction was quenched by H$_2$O and the mixture was extracted with CH$_2$Cl$_2$. The organic phase was concentrated to give the crude product, which was purified by preparative TLC to give N-(3-((R)-3-((S)-1-cyclohexylethyl)-6-(4-fluorophenyl)-2-oxo-1,3-oxazinan-6-yl)propyl) methanesulfonamide (11.5 mg, 33%). LC-MS Method 2 $t_R$=1.397 min, m/z=440.9; $^1$H NMR (CDCl$_3$) 1.04 (d, 6H), 1.13-1.34 (m, 2H), 1.43-1.68 (m, 6H), 1.73-1.98 (m, 3H), 2.03-2.14 (m, 1H), 2.29 (d, 1H), 2.52 (tt, 1H), 2.85 (s, 3H), 2.92-3.08 (m, 3H), 3.68 (m, 1H), 3.88-3.98 (m, 1H), 4.33 (t, 1H), 7.01 (t, 2H), 7.22 (m, 2H).

Example 320

(S)-3-((S)-1-(4-(difluoromethoxy)phenyl)ethyl)-6-(4-fluorophenyl)-6-(2-hydroxyethyl)-1,3-oxazinan-2-one

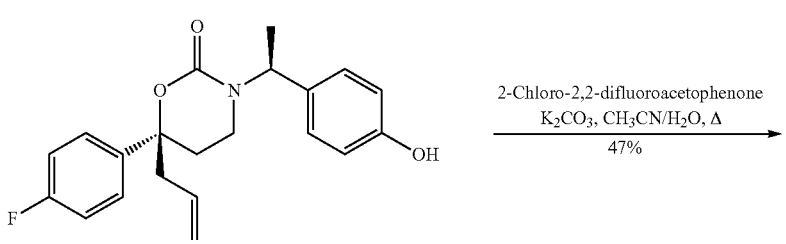

2-Chloro-2,2-difluoroacetophenone
K$_2$CO$_3$, CH$_3$CN/H$_2$O, Δ
47%

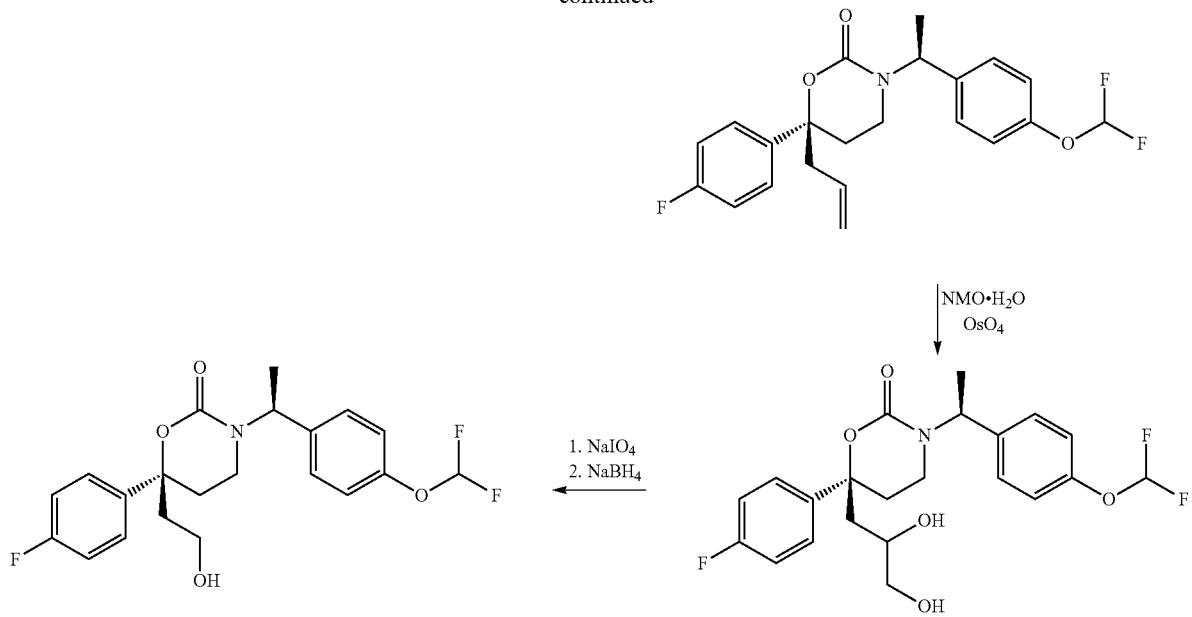

Step 1

To a mixture of (R)-6-allyl-6-(4-fluorophenyl)-3-((S)-1-(4-hydroxyphenyl)ethyl)-1,3-oxazinan-2-one (0.5227 g, 1.47 mmol), $K_2CO_3$ (7.7665 g, 56.2 mmol), $CH_3CN$ (6 mL) and $H_2O$ (6 mL) at room temperature was added 2-chloro-2,2-difluoroacetophene (1.6500 g, 8.66 mmol). The reaction flask was sealed, and the mixture was heated at 80° C. and stirred for 4 h. Then the mixture was diluted with $CH_2Cl_2$, quenched with 6 N HCl (17.5 mL), extracted with $CH_2Cl_2$, and dried over $Na_2SO_4$. After the solvents were evaporated, the residue was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford 0.2780 g (47%) of (R)-6-allyl-3-((S)-1-(4-(difluoromethoxy)phenyl)ethyl)-6-(4-fluorophenyl)-1,3-oxazinan-2-one. LC-MS Method 1 $t_R$=1.90 min, m/z 406 (MH$^+$), 171; $^1$H NMR (400 MHz, $CD_3OD$) δ 7.25-7.21 (m, 2H), 7.01 (t, J=8.6 Hz, 2H), 6.88 (d, J=8.8 Hz, 2H), 6.82 (d, J=8.8 Hz, 2H), 6.65 (t, J=74.1 Hz, 1H), 5.66-5.56 (m, 1H), 5.44 (q, J=7.1 Hz, 1H), 4.99-4.92 (m, 2H), 3.05-3.01 (m, 1H), 2.53 (d, J=7.3 Hz, 2H), 2.40-2.35 (m, 1H), 2.26-2.08 (m, 2H), 1.44 (d, J=7.3 Hz, 3H); $^{19}$F NMR (376 MHz, $CD_3OD$) δ −83.96 (d, J=73.7 Hz), −117.39 (m).

Step 2

A mixture of (R)-6-allyl-3-((S)-1-(4-(difluoromethoxy)phenyl)ethyl)-6-(4-fluorophenyl)-1,3-oxazinan-2-one (0.0320 g, 0.0789 mmol, 1.0 equiv), $NMO·H_2O$ (0.0587 g, 0.434 mmol, 5.5 equiv), and $OsO_4$ (2.5 wt. % in t-BuOH, 0.0450 g, 0.0044 mmol, 0.056 equiv) in $CH_2Cl_2$ (5 mL) was stirred at rt for 17 h. The mixture was diluted with $CH_2Cl_2$, washed with 1 N aq HCl, and dried over $Na_2SO_4$. After the solvents were evaporated, the residue was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford 0.0340 g (98%) of (6S)-3-((S)-1-(4-(difluoromethoxy)phenyl)ethyl)-6-(2,3-dihydroxypropyl)-6-(4-fluorophenyl)-1,3-oxazinan-2-one. LC-MS $t_R$=1.46 min in 3 min chromatography, m/z 440 (MH$^+$), 396, 270, 226, 171.

Step 3

To a solution of (6S)-3-((S)-1-(4-(difluoromethoxy)phenyl)ethyl)-6-(2,3-dihydroxypropyl)-6-(4-fluorophenyl)-1,3-oxazinan-2-one (0.0340 g, 0.0773 mmol, 1.0 equiv) in acetone (2 mL) and $H_2O$ (0.5 mL) was added $NaIO_4$ (0.0545 g, 0.255 mmol, 3.3 equiv). The mixture was stirred at room temperature for 2 h and then diluted with EtOAc, dried over $Na_2SO_4$. LC-MS $t_R$=1.67 min in 3 min chromatography, m/z 408 (MH$^+$), 238, 171.

After the solvents were evaporated, the crude aldehyde was dissolved into MeOH. To this solution was added $NaBH_4$ (0.100 g). The resulting mixture was stirred at rt for 20 min and then quenched with acetone and stirred overnight. After the solvent was evaporated, the residue was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford 0.0165 g (52%) of (S)-3-((S)-1-(4-(difluoromethoxy)phenyl)ethyl)-6-(4-fluorophenyl)-6-(2-hydroxyethyl)-1,3-oxazinan-2-one. LC-MS Method 1 $t_R$=1.53 min, m/z 410 (MH$^+$), 171; $^1$H NMR (400 MHz, $CDCl_3$) δ 7.27-7.24 (m, 2H), 7.04 (t, J=8.5 Hz, 2H), 6.92-6.86 (m, 4H), 6.43 (t, J=73.8 Hz, 1H), 5.63 (q, J=6.7 Hz, 1H), 3.76 (m, 1H), 3.55 (m, 1H), 2.98 (br s, 1H), 2.97-2.91 (m, 1H), 2.32-2.08 (m, 5H), 1.50 (d, J=6.7 Hz, 3H); ¹⁹F NMR (376 MHz, CDCl₃) δ −81.50 (d, J=73.7 Hz), −114.70 (m).

Example 321

(S)-3-((S)-1-(4-(difluoromethoxy)phenyl)ethyl)-6-(4-fluorophenyl)-6-(2-oxopropyl)-1,3-oxazinan-2-one

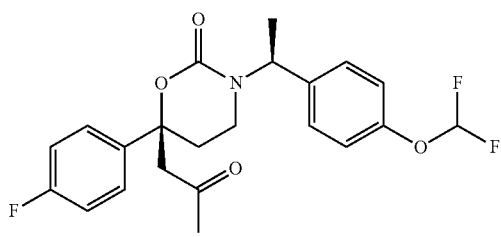 [SMILES: CC(=O)C[C@]1(c2ccc(F)cc2)CCN([C@@H](C)c2ccc(OC(F)F)cc2)C(=O)O1]

The title compound was prepared following a procedure analogous to that described in Example 328 Step 1. LC-MS Method 1 tR=1.69 min, m/z=444 (M+23); 1H NMR (CDCl3) 7.34-7.30 (m, 2H), 7.02 (t, J=8.5 Hz, 2H), 6.87-6.82 (m, 4H), 6.43 (t, J=73.8 Hz, 1H), 5.60 (q, J=7.0 Hz, 1H), 3.01-2.92 (m, 3H), 2.63-2.55 (m, 1H), 2.41-2.28 (m, 2H), 2.07 (s, 3H), 1.49 (d, J=7.0 Hz, 3H).

Example 322

(S)-3-((S)-1-(4-(difluoromethoxy)phenyl)ethyl)-6-(4-fluorophenyl)-6-(2-hydroxy-2-methylpropyl)-1,3-oxazinan-2-one

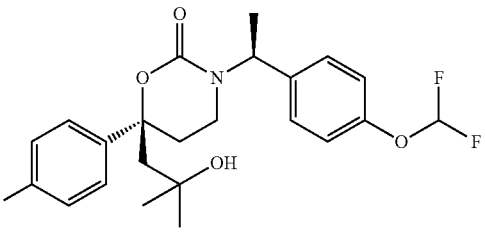

The title compound was prepared following a procedure analogous to that described in Example 328 Step 2. LC-MS Method 1 tR=1.66 min, m/z=460 (M+23); 1H NMR (CD3OD) 7.25-7.21 (m, 2H), 7.01-6.97 (m, 2H), 6.92 (d, J=8.8 Hz, 2H), 6.83 (d, J=8.5 Hz, 2H), 6.64 (t, J=73.8 Hz, 1H), 5.45 (q, J=7.0 Hz, 1H), 2.99-2.96 (m, 1H), 2.45-2.32 (m, 2H), 2.14-2.06 (m, 1H), 2.04 (s, 2H), 1.43 (d, J=7.0 Hz, 3H), 1.17 (s, 3H), 0.88 (s, 3H).

Example 323

(S)-6-(but-3-enyl)-3-((S)-1-(4-(difluoromethoxy)phenyl)ethyl)-6-(4-fluorophenyl)-1,3-oxazinan-2-one

A)

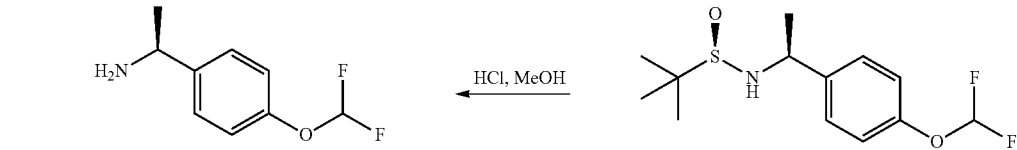

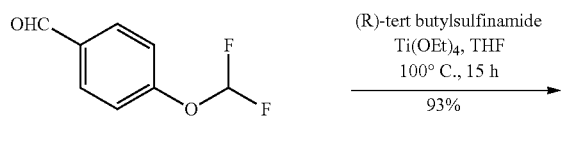

B)

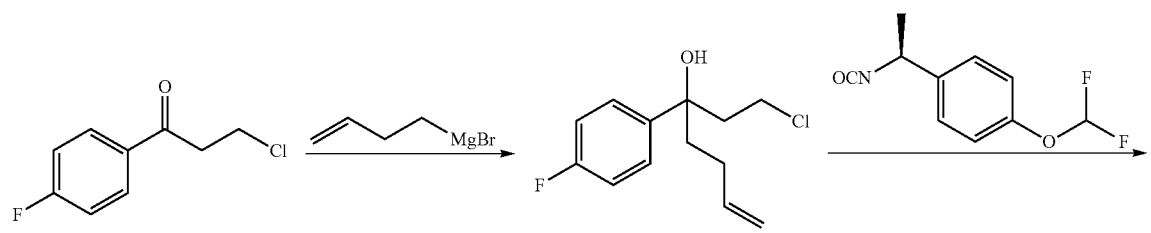

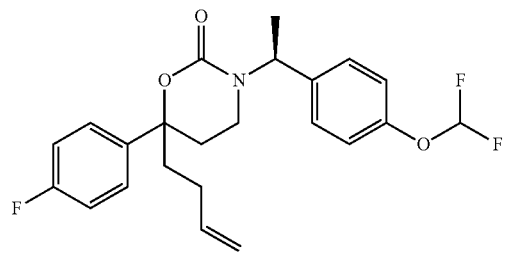

Step 1

A solution of 4-(difluoromethoxy)benzaldehyde (3.1060 g, 18.04 mmol, 1.08 equiv), (R)-(+)-2-methyl-2-propanesulfinamide (2.0210 g, 16.67 mmol, 1.0 equiv), and Ti(OEt)$_4$ (8.080 g, 35.4 mmol, 2.1 equiv) in THF (25 mL) was heated at 100° C. for 15 h. After cooling, the reaction mixture was quenched with saturated brine (7 mL), with vigorous stirring. The mixture was diluted with CH$_2$Cl$_2$ and dried over Na$_2$SO$_4$. After the solvents were evaporated, the residue was purified by chromatography on silica gel eluted with hexanes/ethyl acetate to give 4.2666 g (93%) of [N(E),S(R)]-N-(4-(difluoromethoxy)benzylidene)-2-methylpropane-2-sulfinamide as a solid. LC-MS Method 1 $t_R$=1.78 min, m/z 276 (MH$^+$), 220; $^1$H NMR (400 MHz, CDCl$_3$) δ 8.56 (s, 1H), 7.87 (d, J=8.2 Hz, 2H), 7.21 (d, J=8.5 Hz, 2H), 6.59 (t, J=73.0 Hz, 1H), 1.26 (s, 9H); $^{19}$F NMR (376 MHz, CDCl$_3$) δ −82.04 (d, J=72.4 Hz); $^{13}$C NMR (100 MHz, CDCl$_3$) δ 161.32, 154.08 (t, J=2.7 Hz), 131.18, 131.12, 119.44, 115.36 (t, J=261.5 Hz), 57.83, 22.57.

Step 2

Methylmagnesium bromide (1.4 M solution in toluene/THF, 120 mL, 168 mmol, 11 equiv) was added dropwise to a solution of [N(E),S(R)]-N-(4-(difluoromethoxy)benzylidene)-2-methylpropane-2-sulfinamide (4.2263 g, 15.35 mmol, 1.0 equiv) in THF (30 mL) at −78° C. under N$_2$. The reaction mixture was stirred at −78° C. and gradually warmed to 18° C. over 24 h. The reaction mixture was cooled to −78° C. and quenched with saturated NH$_4$Cl (30 mL), with vigorous stirring. The mixture was extracted with CH$_2$Cl$_2$ and dried over Na$_2$SO$_4$. After the solvents were evaporated, the residue was purified by chromatography on silica gel eluted with hexanes/ethyl acetate to give 4.2086 g (94%) of [S(R)]-N-((1S)-1-(4-(difluoromethoxy)phenyl)ethyl)-2-methylpropane-2-sulfinamide as a solid. LC-MS Method 1 $t_R$=1.57 min, m/z 292 (MH$^+$), 218, 171; $^1$H NMR (400 MHz, CDCl$_3$) δ 7.33 (d, J=8.5 Hz, 2H), 7.09 (d, J=8.5 Hz, 2H), 6.51 (t, J=73.9 Hz, 1H), 4.60-4.54 (m, 1H), 3.31 (m, 1H), 1.52 (d, J=6.7 Hz, 3H), 1.20 (s, 9H); $^{19}$F NMR (376 MHz, CDCl$_3$) δ −81.14 (d, J=73.7 Hz); $^{13}$C NMR (100 MHz, CDCl$_3$) δ 140.57, 128.37, 119.53, 115.89 (t, J=260 Hz), 55.57, 53.87, 25.15, 22.53.

Step 3

A solution of [S(R)]-N-((1S)-1-(4-(difluoromethoxy)phenyl)ethyl)-2-methylpropane-2-sulfinamide (2.1356 g, 7.33 mmol) in a mixture of 4 M HCl in dioxane (15 mL) and MeOH (15 mL) was stirred at room temperature for 24 h. After the solvents were removed in vacuo, the residue was treated with 3 N NaOH (15 mL), extracted with CH$_2$Cl$_2$, dried over K$_2$CO$_3$. After the solvents were evaporated, the crude product was directly used in the next step without further purification. LC-MS Method 1 $t_R$=0.83 min, m/z 171 (M$^+$−NH$_2$); $^1$H NMR (400 MHz, CDCl$_3$) δ 7.34 (d, J=8.5 Hz, 2H), 7.07 (d, J=8.5 Hz, 2H), 6.48 (t, J=73.9 Hz, 1H), 4.13 (q, J=6.7 Hz, 1H), 1.36 (d, J=6.7 Hz, 3H), 1.18 (s, 9H); $^{19}$F NMR (376 MHz, CDCl$_3$) δ −80.99 (d, J=73.7 Hz).

Step 4

(S)-1-(difluoromethoxy)-4-(1-isocyanatoethyl)benzene was prepared from (S)-1-(4-(difluoromethoxy)phenyl)ethanamine.

Step 5

1-chloro-3-(4-fluorophenyl)hept-6-en-3-ol was prepared from 3-chloro-1-(4-fluorophenyl)propan-1-one and 3-butenylmagnesium bromide following a procedure analogous to that described in Example 110 Step 1.

Step 6

6-(but-3-enyl)-3-((S)-1-(4-(difluoromethoxy)phenyl)ethyl)-6-(4-fluorophenyl)-1,3-oxazinan-2-one was prepared from 1-chloro-3-(4-fluorophenyl)hept-6-en-3-ol and (S)-1-(difluoromethoxy)-4-(1-isocyanatoethyl)benzene following a procedure analogous to that described in Example 110 Step 2. Two isomers were isolated.

Isomer 1: LC-MS Method 1 $t_R$=2.02 min, m/z=420 (M+1); $^1$H NMR (CDCl$_3$) 7.29-7.24 (m, 4H), 7.08-7.03 (m, 4H), 6.49 (t, J=73.8 Hz, 1H), 5.75-5.61 (m, 2H), 4.93-4.86 (m, 2H), 2.68-2.63 (m, 2H), 2.26-2.17 (m, 2H), 2.06-1.71 (m, 4H), 1.24 (d, J=7.3 Hz, 3H).

Isomer 2: LC-MS Method 1 $t_R$=1.96 min, m/z=420 (M+1); $^1$H NMR (CDCl$_3$) 7.25-7.20 (m, 2H), 7.04-6.99 (m, 2H), 6.90-6.86 (m, 4H), 6.42 (t, J=73.8 Hz, 1H), 5.73-5.61 (m, 2H), 4.95-4.87 (m, 2H), 2.92-2.88 (m, 1H), 2.28-2.16 (m, 4H), 1.99-1.77 (m, 3H), 1.49 (d, J=7.3 Hz, 3H).

Example 324

3-((R)-3-((S)-1-(4-(difluoromethoxy)phenyl)ethyl)-6-(4-fluorophenyl)-2-oxo-1,3-oxazinan-6-yl)propanamide

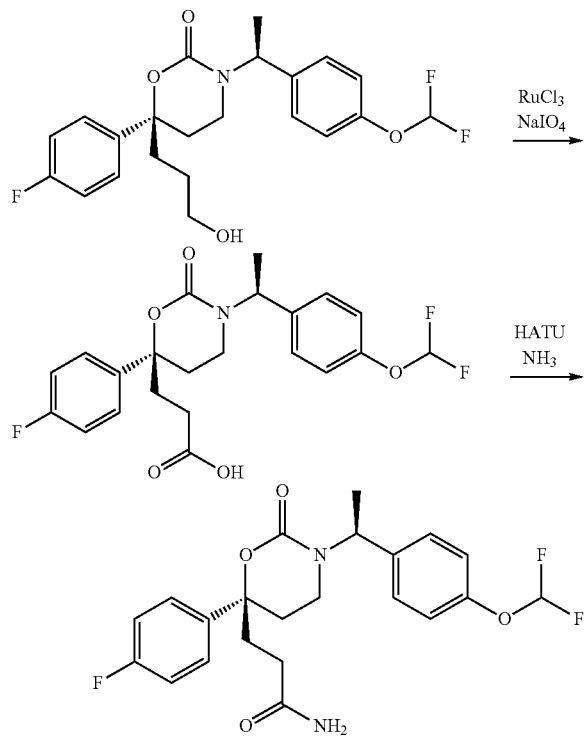

Step 1

A mixture of (R)-3-((S)-1-(4-(difluoromethoxy)phenyl)ethyl)-6-(4-fluorophenyl)-6-(3-hydroxypropyl)-1,3-oxazinan-2-one (0.1608 g, 0.38 mmol, 1.0 equiv), RuCl$_3$.xH$_2$O (0.0490 g, 0.24 mmol, 0.6 equiv), and NaIO$_4$ (0.5990 g, 2.8 mmol, 7.4 equiv) in 14 mL of solvent (1:1:1.5 CCl$_4$:CH$_3$CN:H$_2$O) was stirred at 0° C. for 3 h. The reaction mixture was then quenched with 1 N HCl (1 mL), extracted with CH$_2$Cl$_2$ and dried over Na$_2$SO$_4$. After the solvents were evaporated, the residue was purified by reversed-phase HPLC (SunFire™ Prep C$_{18}$ OBD™ 5 μm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford 0.0920 g (55%) of 3-((R)-3-((S)-1-(4-(difluoromethoxy)phenyl)ethyl)-6-(4-fluorophenyl)-2-oxo-1,3-oxazinan-6-yl)propanoic acid. LC-MS Method 1 $t_R$=1.59 min, m/z=460 (MNa$^+$), 438 (MH$^+$), 171; $^1$H NMR (400 MHz, CDCl$_3$) δ 9.31 (br s, 1H), 7.22-7.19 (m, 2H), 7.01 (t, J=8.5 Hz, 2H), 6.94 (d, J=8.8 Hz, 2H), 6.88 (d, J=8.8 Hz, 2H), 6.43 (t, J=73.8 Hz, 1H), 5.61 (q, J=6.9 Hz, 1H), 2.97-2.94 (m, 1H), 2.53-2.44 (m, 1H), 2.30-2.07 (m, 6H), 1.49 (d, J=7.0 Hz, 3H); $^{19}$F NMR (376 MHz, CDCl$_3$) δ −81.54 (d, J=73.7 Hz), −114.53 (m).

Step 2

To a solution of 3-((R)-3-((S)-1-(4-(difluoromethoxy)phenyl)ethyl)-6-(4-fluorophenyl)-2-oxo-1,3-oxazinan-6-yl)propanoic acid (0.0485 g, 0.11 mmol) in DMF (2 mL) was added HATU (0.2603 g, 0.68 mmol), DIPEA (0.5 mL), and 0.8 M NH$_3$ in THF (3 mL). The mixture was stirred at rt for 22 h. After the solvents were removed in vacuo, the residue was purified by reversed-phase HPLC (SunFire™ Prep C$_{18}$ OBD™ 5 μm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford 0.0235 g (49%) of 3-((R)-3-((S)-1-(4-(difluoromethoxy)phenyl)ethyl)-6-(4-fluorophenyl)-2-oxo-1,3-oxazinan-6-yl)propanamide. LC-MS Method 1 $t_R$=1.48 min, m/z 459 (MNa$^+$), 393; $^1$H NMR (400 MHz, CDCl$_3$) δ 7.23-7.20 (m, 2H), 7.04-6.99 (m, 2H), 6.95 (d, J=8.2 Hz, 2H), 6.89 (d, J=8.5 Hz, 2H), 6.43 (t, J=73.8 Hz, 1H), 5.83-5.78 (m, 2H), 5.62 (q, J=7.0 Hz, 1H), 2.95-2.91 (m, 1H), 2.45 (m, 1H), 2.27-2.15 (m, 5H), 1.98 (m, 1H), 1.49 (d, J=7.0 Hz, 3H); $^{19}$F NMR (376 MHz, CDCl$_3$) δ −81.51 (d, J=73.7 Hz), −114.66 (m).

Example 325

N-(3-((R)-3-((S)-1-(4-(difluoromethoxy)phenyl)ethyl)-6-(4-fluorophenyl)-2-oxo-1,3-oxazinan-6-yl)propyl)methanesulfonamide

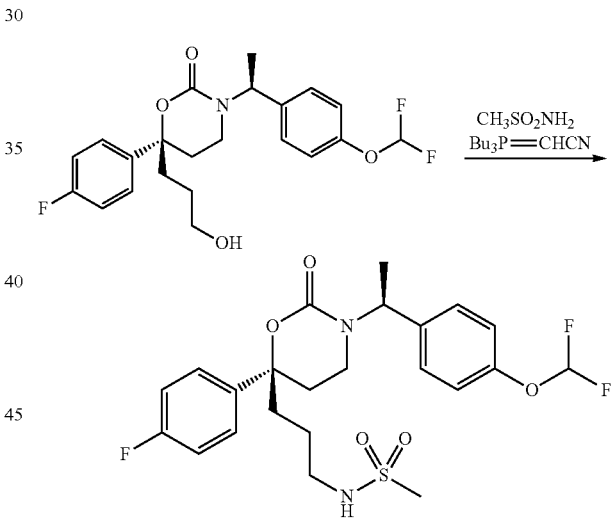

To a solution of (R)-3-((S)-1-(4-(difluoromethoxy)phenyl)ethyl)-6-(4-fluorophenyl)-6-(3-hydroxypropyl)-1,3-oxazinan-2-one (0.0332 g, 0.0784 mmol) and methanesulfonamide (0.0549 g, 0.577 mmol) in dry toluene (2 mL) was added (cyanomethene)tributylphosphorane (CMBP, 0.1720 g, 0.713 mmol) at rt under N$_2$. The mixture was stirred for 19 h at rt. After the solvents were removed in vacuo, the residue was purified by reversed-phase HPLC (SunFire™ Prep C$_{18}$ OBD™ 5 μm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford 0.0137 g (35%) of N-(3-((R)-3-((S)-1-(4-(difluoromethoxy)phenyl)ethyl)-6-(4-fluorophenyl)-2-oxo-1,3-oxazinan-6-yl)propyl)methanesulfonamide. LC-MS Method 1 $t_R$=1.64 min, m/z=523 (MNa$^+$), 501 (MH$^+$), 171; $^1$H NMR (400 MHz, CD$_3$OD) δ 7.24-7.21 (m, 2H), 7.01 (t, J=8.6 Hz, 2H), 6.92 (d, J=8.8 Hz, 2H), 6.83 (d, J=8.5 Hz, 2H), 6.65 (t, J=73.8 Hz, 1H), 5.45 (q, J=7.0 Hz, 1H), 3.04-3.00 (m, 1H), 2.93-2.86 (m, 2H), 2.77 (s, 3H), 2.38-2.34 (m, 1H), 2.22-2.09 (m, 2H), 1.92-1.82 (m, 2H), 1.58-1.50 (m, 1H), 1.44 (d, J=7.0 Hz, 3H), 1.26-1.18 (m, 1H); $^{19}$F NMR (376 MHz, CD$_3$OD) δ −83.93 (d, J=75.0 Hz), −117.33 (m).

Example 326

3-((R)-3-((S)-1-(4-(difluoromethoxy)phenyl)propyl)-6-(4-fluorophenyl)-2-oxo-1,3-oxazinan-6-yl)propanamide

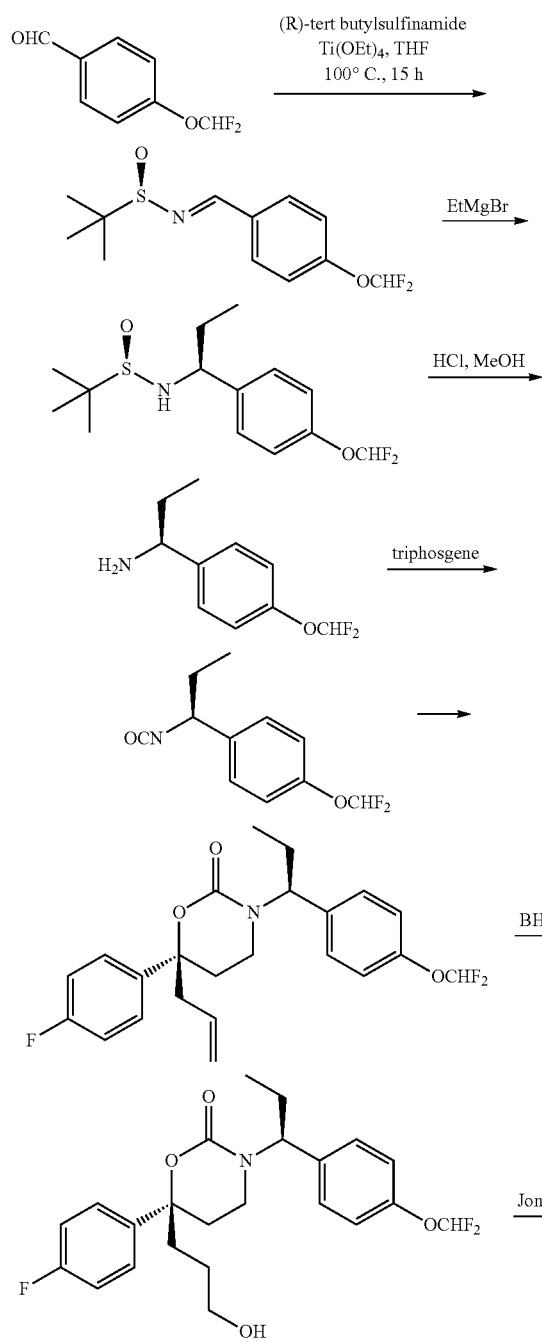

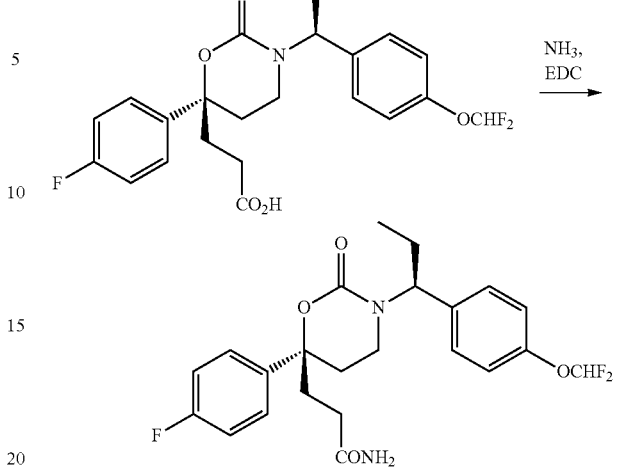

(S)-1-(difluoromethoxy)-4-(1-isocyanatopropyl)benzene was prepared following conditions analogous to those described in Example 323 Steps 1 to 4 using EtMgBr in Step 2. 6-allyl-3-((S)-1-(4-(difluoromethoxy)phenyl)propyl)-6-(4-fluorophenyl)-1,3-oxazinan-2-one was prepared following a procedure analogous to that described in Example 110 Step 2 using (S)-1-(difluoromethoxy)-4-(1-isocyanatopropyl)benzene and 1-chloro-3-(4-fluorophenyl)hex-5-en-3-ol. (R)-6-allyl-3-((S)-1-(4-(difluoromethoxy)phenyl)propyl)-6-(4-fluorophenyl)-1,3-oxazinan-2-one was separated chromatographically. (R)-3-((S)-1-(4-(difluoromethoxy)phenyl)propyl)-6-(4-fluorophenyl)-6-(3-hydroxypropyl)-1,3-oxazinan-2-one was prepared following a procedure analogous to that described in Example 78. 3-((R)-3-((S)-1-(4-(difluoromethoxy)phenyl)propyl)-6-(4-fluorophenyl)-2-oxo-1,3-oxazinan-6-yl)propanamide was prepared following a procedure analogous to that described in Example 234. LC-MS Method 2 $t_R$=1.251 min, m/z=451.4; $^1$H NMR (CDCl$_3$) 0.92 (t, 3H), 1.78-1.92 (m, 3H), 2.10-2.23 (m, 5H), 2.43 (m, 1H), 2.90 (m, 1H), 5.34 (t, 1H), 5.40-5.63 (d, 2H), 6.18-6.56 (m, 1H), 6.89 (m, 4H), 6.99 (d, 2H), 7.11 (m, 2H).

Example 327

(S)-3-((S)-1-(4-(difluoromethoxy)phenyl)ethyl)-6-(2-hydroxyethyl)-6-phenyl-1,3-oxazinan-2-one

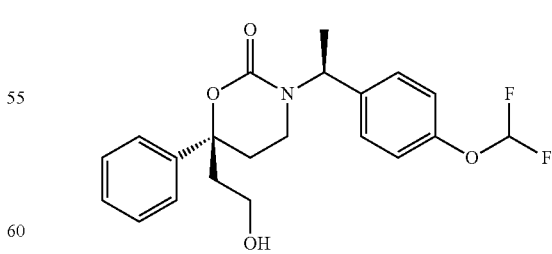

The title compound was prepared from (R)-6-allyl-3-((S)-1-(4-(difluoromethoxy)phenyl)ethyl)-6-phenyl-1,3-oxazinan-2-one following procedures analogous to those described in Example 320. LC-MS Method 2 $t_R$=1.248 min, m/z=319.16; $^1$H NMR (CDCl$_3$) 1.48 (d, 3H), 2.02-2.33 (m, 5H), 2.82 (m, 1H), 3.51 (m, 1H), 3.72 (m, 1H) 5.55 (m, 1H) 6.16-6.54 (m, 1H), 6.76 (m, 4H), 7.18-7.31 (m, 5H).

Example 328

(S)-3-((S)-1-(4-(difluoromethoxy)phenyl)ethyl)-6-(2-hydroxy-2-methylpropyl)-6-phenyl-1,3-oxazinan-2-one

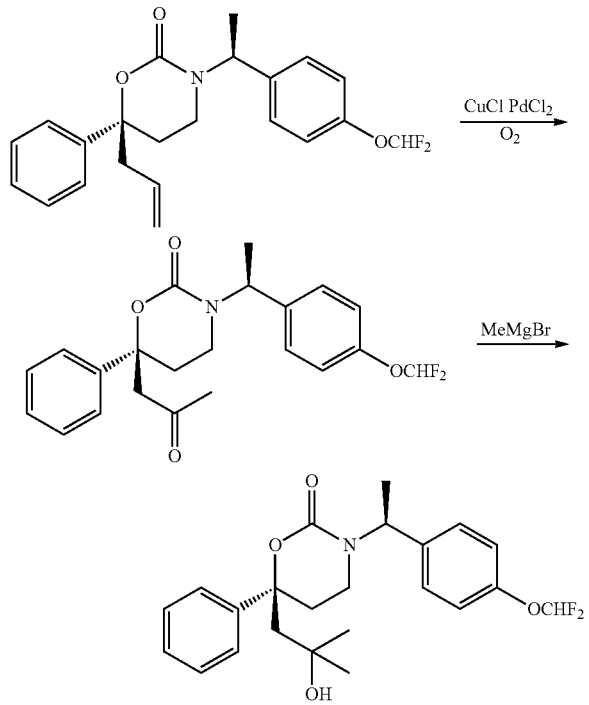

Step 1

To a solution of (R)-6-allyl-3-((S)-1-(4-(difluoromethoxy)phenyl)ethyl)-6-phenyl-1,3-oxazinan-2-one (379 mg, 1 mmol) in DMF were added CuCl (227 mg, 2.3 mmol) and PdCl$_2$ (53 mg, 0.3 mmol) at 0° C. under O$_2$, and the mixture was stirred overnight at 30° C. The mixture was washed with water and extracted with EtOAc. The organic layer was separated, and concentrated to give the crude product, which was purified by preparative TLC to afford (S)-3-((S)-1-(4-(difluoromethoxy)phenyl)ethyl)-6-(2-oxopropyl)-6-phenyl-1,3-oxazinan-2-one (180 mg, 50%).

Step 2

To a solution of (S)-3-((S)-1-(4-(difluoromethoxy)phenyl)ethyl)-6-(2-oxopropyl)-6-phenyl-1,3-oxazinan-2-one (150 mg, 0.39 mmol) in THF (10 mL) was added methylmagnesium bromide (1 M, 2.5 mL) under nitrogen at −78° C. The mixture was stirred at rt until the reaction was over. The reaction was quenched with satd aq NH$_4$Cl. The organic phase was separated and concentrated to give crude product, which was purified by preparative HPLC to give (S)-3-((S)- 1-(4-(difluoromethoxy)phenyl)ethyl)-6-(2-hydroxy-2-methylpropyl)-6-phenyl-1,3-oxazinan-2-one (15 mg, 10%). $^1$H NMR (CDCl$_3$): 1.05 (s, 3H), 1.10 (s, 3H), 1.45 (s, 3H), 2.10 (m, 1H), 2.16 (m, 2H), 2.20 (m, 1H), 2.33 (m, 1H), 2.76 (m, 1H), 5.60 (m, 1H), 6.16-6.58 (m, 1H), 6.78 (m, 2H), 6.86 (m, 2H), 7.26 (m, 5H).

Example 329

(R)-3-((S)-1-(4-(difluoromethoxy)phenyl)ethyl)-6-(3-hydroxypropyl)-6-phenyl-1,3-oxazinan-2-one

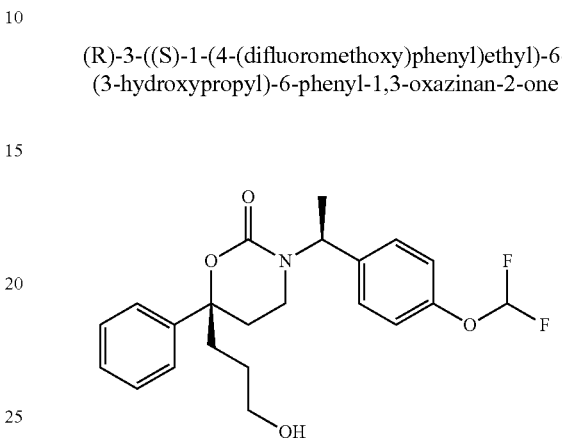

The title compound was prepared following procedures analogous to those described in Example 78 starting with (R)-6-allyl-3-((S)-1-(4-(difluoromethoxy)phenyl)ethyl)-6-phenyl-1,3-oxazinan-2-one. LC-MS Method 2 $t_R$=1.868 min, m/z=428.1; $^1$H NMR (CDCl$_3$) 1.35 (m, 1H), 1.49 (d, 3H), 1.65 (m, 1H), 1.85-1.99 (m, 2H), 2.83 (m, 1H), 3.50 (m, 2H), 5.57 (m, 1H), 6.16-6.54 (t, 1H), 6.77 (dd, 4H), 7.25 (m, 4H).

Example 330

3-((R)-3-((S)-1-(4-(difluoromethoxy)phenyl)ethyl)-2-oxo-6-phenyl-1,3-oxazinan-6-yl)propanamide

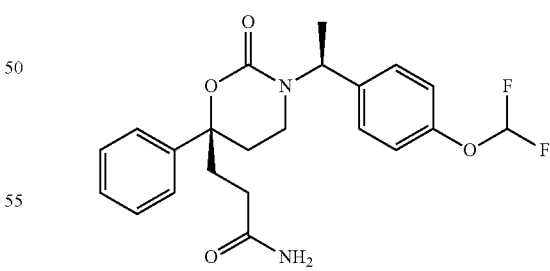

The title compound was prepared following procedures analogous to those described in Example 234 starting with (R)-3-((S)-1-(4-(difluoromethoxy)phenyl)ethyl)-6-(3-hydroxypropyl)-6-phenyl-1,3-oxazinan-2-one. LC-MS Method 2 $t_R$=1.769 min, m/z=464.1; $^1$H NMR (CDCl$_3$) 1.49 (d, 3H), 2.91 (m, 1H), 2.11-2.30 (m, 5H), 2.45 (m, 1H), 2.83 (m, 1H), 5.21 (s, 1H), 5.35 (d, 1H), 5.60 (m, 1H), 6.16-6.54 (t, 1H), 6.74 (m, 2H), 6.85 (m, 2H), 7.18-7.30 (m, 5H).

Example 331

N-(3-((R)-3-((S)-1-(4-(difluoromethoxy)phenyl)ethyl)-2-oxo-6-phenyl-1,3-oxazinan-6-yl)propyl)methanesulfonamide

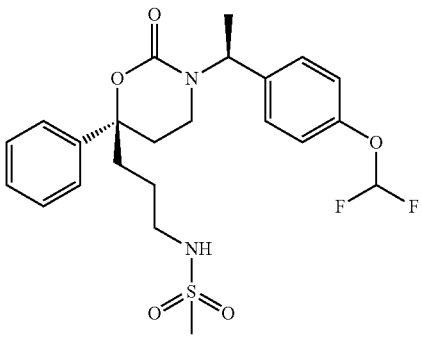 [SMILES: C[C@@H](c1ccc(OC(F)F)cc1)N1CC[C@](CCCNS(C)(=O)=O)(c2ccccc2)OC1=O]

The title compound was prepared following procedures analogous to those described in Example 359 starting with (R)-3-((S)-1-(4-(difluoromethoxy)phenyl)ethyl)-6-(3-hydroxypropyl)-6-phenyl-1,3-oxazinan-2-one. LC-MS Method 2 $t_R$=1.3 min, m/z=483; $^1$H NMR (CDCl$_3$) 1.34 (m, 1H), 1.51 (d, 3H), 1.65 (m, 1H), 1.95 (m, 1H), 2.05 (m, 1H), 2.10-2.34 (m, 3H), 2.39 (s, 3H), 2.91 (m, 1H), 3.06 (m, 2H), 4.30 (m, 1H), 5.62 (m, 1H), 6.20-6.62 (m, 1H), 6.90 (dd, 4H), 7.20 (m, 2H), 7.34 (m, 3H).

Example 332

6-(3-hydroxypropyl)-6-isopropyl-3-((1S)-1-(4-methoxyphenyl)ethyl)-1,3-oxazinan-2-one

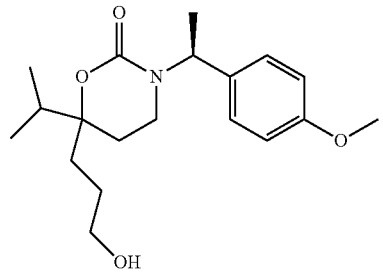 [SMILES: COc1ccc([C@H](C)N2CCC(CCCO)(C(C)C)OC2=O)cc1]

The title compound was prepared following procedures analogous to those described in Example 207 using (S)-1-(4-methoxyphenyl)ethanamine in Step 4. Two isomers were isolated.

Isomer 1: LC-MS Method 3 $t_R$=0.91 min, m/z=693.3; $^1$H NMR (CDCl$_3$) 1.26 (m, 6H), 1.25 (s, 1H), 1.45 (d, 3H), 1.58-1.66 (m, 6H), 1.95 (m, 1H), 2.66 (m, 3H), 3.05 (m, 1H), 3.60 (m, 2H), 3.74 (s, 3H), 5.70 (m, 1H), 6.83 (m, 2H), 7.18 (m, 2H).

Isomer 2:

Example 333

3-(6-isopropyl-3-((1S)-1-(4-methoxyphenyl)ethyl)-2-oxo-1,3-oxazinan-6-yl)propanamide

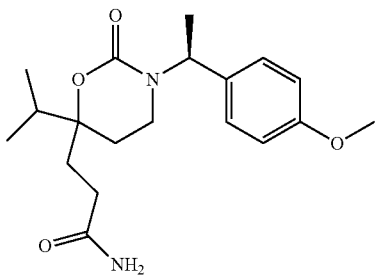 [SMILES: COc1ccc([C@H](C)N2CCC(CCC(N)=O)(C(C)C)OC2=O)cc1]

The title compound was prepared following procedures analogous to those described in Example 234 starting with 6-(3-hydroxypropyl)-6-isopropyl-3-((S)-1-(4-methoxyphenyl)ethyl)-1,3-oxazinan-2-one. Two isomers were isolated.

Isomer 1: LC-MS Method 2 $t_R$=1.133 min, m/z=349.1; $^1$H NMR (CDCl$_3$) 0.84 (m, 6H), 1.43 (d, 3H), 1.58 (m, 1H), 1.67 (m, 1H), 1.92 (m, 3H), 2.33 (m, 2H), 2.65 (m, 1H), 3.02 (m, 1H), 3.76 (s, 3H), 5.31 (m, 1H), 5.54 (m, 1H), 5.67 (m, 1H), 6.89 (m, 2H), 7.18 (m, 2H).

Isomer 2: LC-MS Method 2 $t_R$=1.169 min, m/z=371; $^1$H NMR (CDCl$_3$) 0.89 (d, 6H), 1.42 (d, 3H), 1.50-1.69 (m, 1H), 1.77-1.91 (m, 3H), 1.99 (m, 1H), 2.29 (m, 2H), 2.70 (m, 2H), 3.00 (m, 1H), 3.72 (s, 3H), 5.66 (m, 1H), 5.78-5.89 (s, 1H), 5.90-6.02 (s, 1H), 6.81 (d, 2H), 7.18 (d, 2H).

Example 334

3-(3-((S)-1-(4-chlorophenyl)ethyl)-6-isopropyl-2-oxo-1,3-oxazinan-6-yl)propanamide

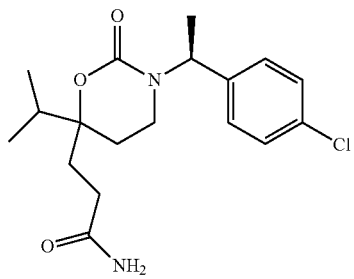 [SMILES: CC(C)C1(CCC(N)=O)CCN([C@@H](C)c2ccc(Cl)cc2)C(=O)O1]

The title compound was prepared from 6-allyl-3-((S)-1-(4-bromophenyl)ethyl)-6-isopropyl-1,3-oxazinan-2-one isomer 1 following procedures analogous to those described in Example 187 Steps 1 and 2 followed by procedures analogous to those described in Example 234. Two isomers were isolated.

Isomer 1: LC-MS Method 3 $t_R$=1.409 min, m/z=353; $^1$H NMR (CDCl$_3$) 0.87 (m, 6H), 1.19 (m, 1H), 1.50 (d, 3H), 1.55 (m, 1H), 1.73 (m, 1H), 1.87-2.00 (m, 3H), 2.68 (m, 1H), 3.11 (m, 1H), 5.50 (m, 1H), 5.65 (m, 1H), 5.78 (m, 1H), 7.14-7.45 (m, 4H).

Isomer 2: LC-MS Method 2 $t_R$=0.917 min, m/z=353; $^1$H NMR (CDCl$_3$) 0.89 (m, 6H), 1.47 (d, 3H), 1.51-1.62 (m, 1H), 2.01 (m, 1H), 2.29 (m, 2H), 2.70 (m, 1H), 3.01 (m, 1H), 5.28-5.41 (s, 1H), 5.56-5.65 (s, 1H), 5.69 (m, 1H), 7.21 (d, 2H), 7.28 (d, 2H).

Example 335

3-((1S)-1-(4-bromophenyl)ethyl)-6-tert-butyl-6-(3-hydroxypropyl)-1,3-oxazinan-2-one

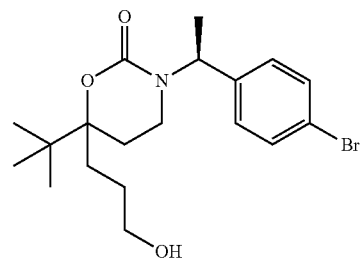 [SMILES: C[C@@H](c1ccc(Br)cc1)N1CCC(CCCO)(C(C)(C)C)OC1=O]

6-allyl-3-((S)-1-(4-bromophenyl)ethyl)-6-tert-butyl-1,3-oxazinan-2-one was prepared from ethyl 4,4-dimethyl-3-oxopentanoate following procedures analogous to those described in Example 207 Steps 1 to 8. The title compound was prepared from 6-allyl-3-((S)-1-(4-bromophenyl)ethyl)-6-tert-butyl-1,3-oxazinan-2-one following procedures analogous to those described in Example 78. Two isomers were isolated.

Isomer 1: LC-MS Method 2 $t_R$=1.349 min, m/z=397.13; $^1$H NMR (CDCl$_3$) 0.94 (s, 9H), 1.44 (d, 3H), 1.54 (m, 3H), 1.58 (m, 1H), 1.65 (m, 2H), 1.97 (m, 1H), 2.66 (m, 1H), 2.93 (m, 1H), 3.48 (m, 1H), 5.67 (m, 1H), 7.16 (d, 2H), 7.40 (d, 2H).

LC-MS Method 2 $t_R$=1.383 min, m/z=397.13; $^1$H NMR (CDCl$_3$) 0.93 (s, 9H), 1.44 (d, 3H), 1.58-1.68 (m, 4H), 1.80 (m, 2H), 2.68 (m, 1H), 3.10 (m, 1H), 3.58 (m, 2H), 5.67 (m, 1H), 7.16 (d, 2H), 7.40 (d, 2H).

Example 336

6-tert-butyl-3-((1S)-1-(2',4'-difluorobiphenyl-4-yl)ethyl)-6-(2-hydroxyethyl)-1,3-oxazinan-2-one

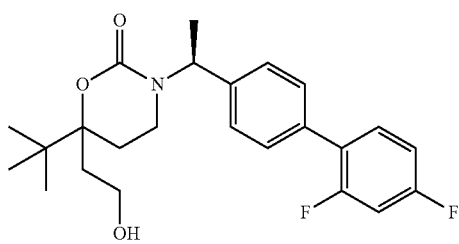 [SMILES: C[C@@H](c1ccc(-c2ccc(F)cc2F)cc1)N1CCC(CCO)(C(C)(C)C)OC1=O]

The title compound was prepared from ethyl 4,4-dimethyl-3-oxopentanoate following procedures analogous to those described in Example 207. Two isomers were isolated.

Isomer 1: LC-MS Method 3 $t_R$=1.207 min, m/z=431.23; $^1$H NMR (CD$_3$OD) 1.01 (S, 9H), 1.50 (m, 2H), 1.57 (d, 3H), 1.59-1.90 (m, 4H), 2.14 (m, 1H), 2.84 (m, 1H), 3.17 (m, 1H), 3.44 (m, 2H), 5.66 (m, 1H), 7.04 (m, 2H), 7.43-7.53 (m, 5H).

Isomer 2: LC-MS Method 3 $t_R$=1.219 min, m/z=431.23; $^1$H NMR (CD$_3$OD) 1.02 (S, 9H), 1.59 (d, 3H), 1.63 (m, 2H), 1.81-1.94 (m, 4H), 2.98 (m, 1H), 3.31 (m, 1H), 3.56 (m, 2H), 5.68 (m, 1H), 7.04 (m, 2H), 7.42-7.53 (m, 5H).

Example 337

6-allyl-6-(4-fluorophenyl)-3-(2-((4-methylpiperazin-1-yl)methyl)benzyl)-1,3-oxazinan-2-one

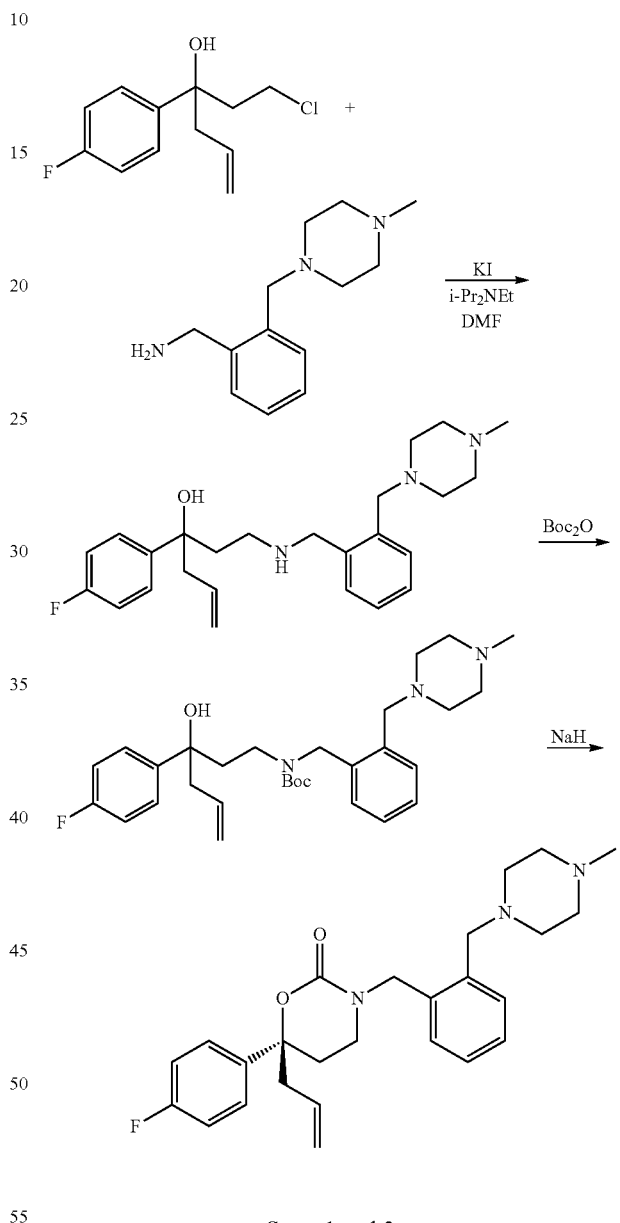

Steps 1 and 2

A heavy walled glass tube was charged with 1-chloro-3-(4-fluorophenyl)hex-5-en-3-ol (250 mg, 1.1 mmol), (2-((4-methylpiperazin-1-yl)methyl)phenyl)methanamine (239 mg, 1.1 mmol), KI (200 mg, 1.2 mmol), i-Pr$_2$NEt (0.22 mL, 1.2 mmol) and DMF (2 mL). The mixture was sealed, heated and stirred at 80° C. for 16 h. The mixture was cooled to rt, diluted with EtOAc (80 mL) and extracted with water (2×25 mL). The combined water layer was diluted with THF (50 mL) and solid K$_2$CO$_3$ (5 g) was added, followed by Boc$_2$O (357 mg, 1.64 mmol). The mixture was stirred at rt for 3 h, diluted with brine (50 mL) and extracted with EtOAc (2×75 mL). These EtOAc extracts were combined dried over Na₂SO₄ and concentrated to afford crude tert-butyl 3-(4-fluorophenyl)-3-hydroxyhex-5-enyl(2-((4-methylpiperazin-1-yl)methyl)benzyl)carbamate (323 mg, 72%) which was used without further purification. LC-MS Method 1 $t_R$=0.95 min, m/z=412.

Step 3 tert-Butyl 3-(4-fluorophenyl)-3-hydroxyhex-5-enyl(2-((4-methylpiperazin-1-yl)methyl)benzyl)carbamate (17 mg, 34 μmol) was dissolved in dry THF (1 mL) and 60% NaH in oil (7 mg, 0.17 mmol) was added. The mixture was heated and stirred at 50° C. for 24 h. Water (0.5 mL) was added, followed by hexanes (1 mL) and MeOH (1.5 mL). The aqueous MeOH layer was separated and submitted to preparative HPLC to afford 6-allyl-6-(4-fluorophenyl)-3-(2-((4-methylpiperazin-1-yl)methyl)benzyl)-1,3-oxazinan-2-one as its TFA salt (1.1 mg, 8%). LC-MS Method 1 $t_R$=1.35 min, m/z=438.

Example 338

(S)-tert-butyl 3-((R)-6-(4-fluorophenyl)-6-(3-hydroxypropyl)-2-oxo-1,3-oxazinan-3-yl)piperidine-1-carboxylate

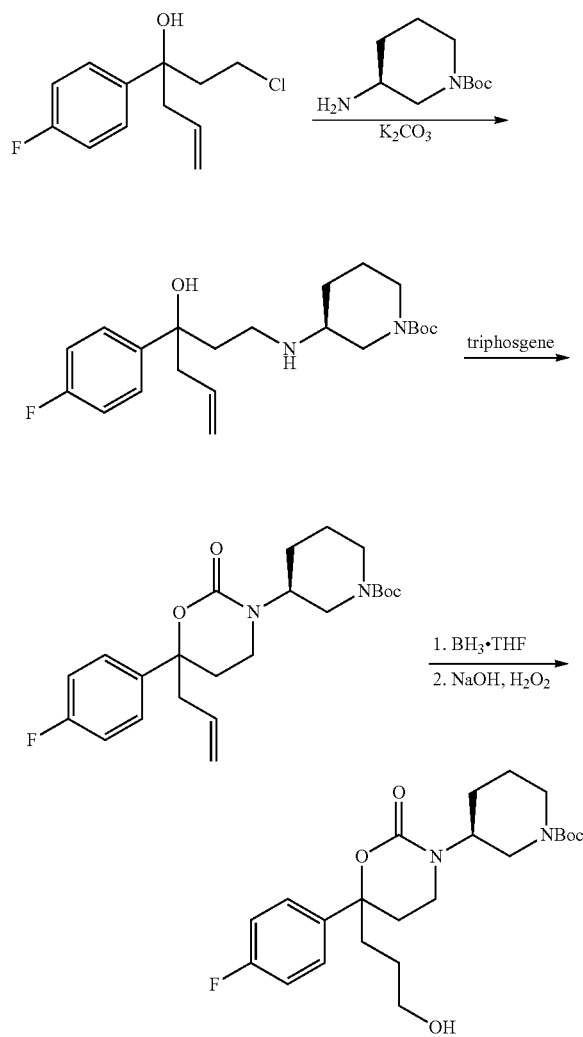

Step 1

A mixture of 1-chloro-3-(4-fluorophenyl)hex-5-en-3-ol (760 mg, 3.3 mmol), (S)-tert-butyl 3-aminopiperidine-1-carboxylate (1.0 g, 5 mmol), KI (1.1 g, 6.7 mmol) and K₂CO₃ (920 mg, 6.7 mmol) in acetonitrile (33 mL) was heated to reflux overnight. The reaction mixture was filtered. The filtrate was condensed to give the crude product, which was purified by preparative TLC to afford (3S)-tert-butyl-3-(3-(4-fluorophenyl)-3-hydroxyhex-5-enylamino)piperidine-1-carboxylate (500 mg, 38%). ¹H NMR: (CDCl₃): 1.23 (m, 1H), 1.38 (d, 9H), 1.57 (m, 1H), 1.75 (broad, 1H), 1.94 (m, 2H), 2.37 (m, 1H), 2.43 (m, 2H), 2.56 (m, 1H), 2.80 (broad, 3H), 3.49 (broad, 1H), 3.71 (broad, 3H), 4.95 (d, 2H), 5.56 (m, 1H), 6.95 (t, 2H), 7.32 (m, 2H).

Step 2

To a solution of (3S)-tert-butyl 3-(3-(4-fluorophenyl)-3-hydroxyhex-5-enylamino)-piperidine-1-carboxylate (500 mg, 1.27 mmol) and triethylamine (515 mg, 5.1 mmol) in dried methylene chloride (13 mL) at 0° C. was added triphosgene (126 mg, 0.42 mmol). The mixture was stirred at room temperature till the reaction was over. Water was added, and the layers were separated. The aqueous layer was extracted with methylene chloride. The combined organic layer was washed with water, dried over Na₂SO₄, and condensed to give the crude product, which was purified by column chromatography on silica gel to afford (3S)-tert-butyl 3-(6-allyl-6-(4-fluorophenyl)-2-oxo-1,3-oxazinan-3-yl)piperidine-1-carboxylate (70 mg, 13%). ¹H NMR: (CDCl₃): 1.37 (d, 9H), 1.43 (m, 1H), 1.64 (m, 1H), 2.22 (m, 2H), 2.64 (m, 5H), 3.11 (m, 1H), 3.91 (broad, 3H), 5.00 (q, 2H), 5.65 (m, 1H), 6.99 (t, 3H), 7.20 (m, 2H).

Step 3

The title compound was prepared from (3S)-tert-butyl 3-(6-allyl-6-(4-fluorophenyl)-2-oxo-1,3-oxazinan-3-yl)piperidine-1-carboxylate following a procedure analogous to that described in Example 78. Two isomers were isolated.

Isomer 1: LC-MS Method 2 $t_R$=1.308 min, m/z=459; ¹H NMR (CDCl₃) 1.24 (m, 1H), 1.34 (s, 9H), 1.42 (m, 2H), 1.62 (m, 3H), 1.80-1.97 (m, 2H), 2.10 (m, 1H), 2.24 (m, 1H), 2.34-2.48 (m, 1H), 2.57 (m, 1H), 2.67 (m, 1H), 3.10 (m, 1H), 3.48 (t, 2H), 3.55-4.06 (m, 3H), 6.98 (t, 2H), 7.18 (m, 2H).

Isomer 2: LC-MS Method 2 $t_R$=1.313 min, m/z=337; ¹H NMR (CDCl₃) 1.27 (m, 1H), 1.39 (s, 9H), 1.41-1.52 (m, 4H), 1.56 (m, 2H), 1.59-1.61 (m, 1H), 1.83-2.00 (m, 2H), 2.09-2.20 (m, 1H), 2.25 (m, 1H), 2.39-2.57 (m, 1H), 2.69-2.83 (m, 2H), 3.01 (m, 1H), 3.50 (t, 2H), 3.70-3.88 (s, 1H), 3.89-4.00 (m, 2H), 6.94-7.03 (t, 2H), 7.18-7.29 (m, 2H).

Example 339

(S)-tert-butyl 3-((R)-6-(3-amino-3-oxopropyl)-6-(4-fluorophenyl)-2-oxo-1,3-oxazinan-3-yl)piperidine-1-carboxylate

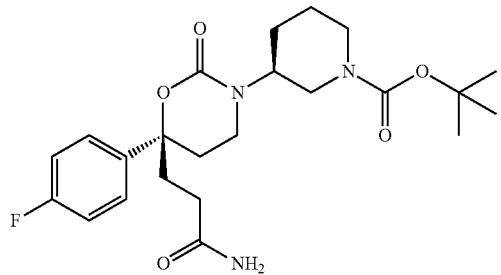 [SMILES: CC(C)(C)OC(=O)N1CCC[C@H](N2CC[C@](CCC(N)=O)(c3ccc(F)cc3)OC2=O)C1]

The title compound was prepared following procedures analogous to those described in Example 234 using PDC in place of Jones reagent. LC-MS Method 2 $t_R$=1.207 min, m/z=350.4; $^1$H NMR (CDCl$_3$) 1.36 (s, 9H), 1.46 (m, 1H), 1.62 (m, 2H), 1.71 (m, 1H), 1.86 (m, 1H), 2.10 (m, 1H), 2.18 (m, 2H), 2.23 (m, 1H), 2.42 (m, 2H), 2.66 (m, 2H), 3.12 (m, 1H), 3.70-3.98 (d, 2H), 5.29 (s, 1H), 5.43 (s, 1H), 7.01 (t, 2H), 7.18 (m, 2H).

Example 340

(S)-benzyl 3-((R)-6-(4-fluorophenyl)-6-(3-hydroxypropyl)-2-oxo-1,3-oxazinan-3-yl)piperidine-1-carboxylate

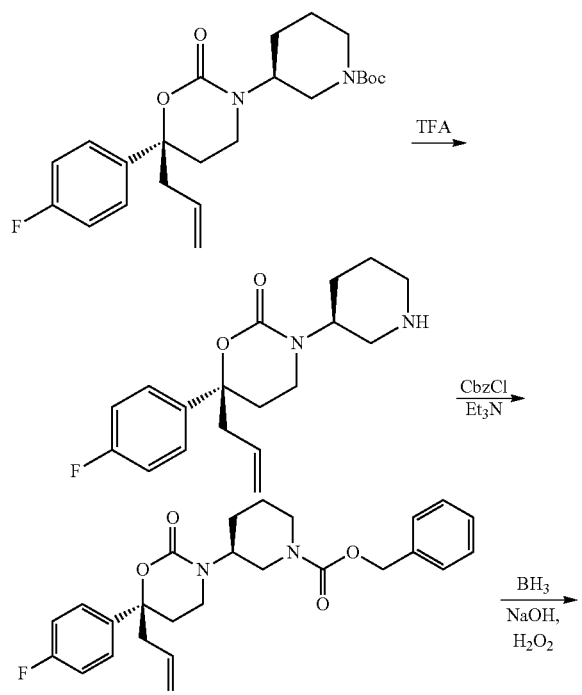

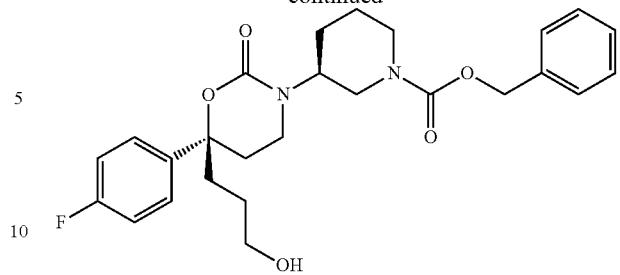

Step 1

A solution of (S)-tert-butyl 3-((R)-6-allyl-6-(4-fluorophenyl)-2-oxo-1,3-oxazinan-3-yl)piperidine-1-carboxylate (150 mg, 0.359 mmol) in 20% TFA/CH$_2$Cl$_2$ (5 mL) was stirred at 0° C. for 2 h. The mixture was concentrated to give (R)-6-allyl-6-(4-fluorophenyl)-3-((S)-piperidin-3-yl)-1,3-oxazinan-2-one (112 mg, crude), which was used for the next without further purification.

Step 2

To a solution of (R)-6-allyl-6-(4-fluorophenyl)-3-((S)-piperidin-3-yl)-1,3-oxazinan-2-one (112 mg, 0.35 mmol) and Et$_3$N (71 mg, 0.70 mmol) in CH$_2$Cl$_2$ (10 mL) was added CbzCl (71 mg, 0.7 mmol) at 0° C. Then the mixture was stirred at rt till the reaction was over. The reaction was quenched with H$_2$O. The mixture was extracted with EtOAc, and the organic phase was washed with brine, dried over Na$_2$SO$_4$, filtered and concentrated to give the crude product, which was purified by preparative TLC to afford (S)-benzyl 3-((R)-6-allyl-6-(4-fluorophenyl)-2-oxo-1,3-oxazinan-3-yl)piperidine-1-carboxylate (78 mg, 49%). $^1$H NMR (CDCl$_3$): 1.63 (m, 3H), 2.07-2.26 (m, 2H), 2.54 (m, 3H), 2.21 (m, 2H), 3.09 (m, 1H), 3.68 (m, 1H), 3.99 (m, 1H), 4.93-5.09 (m, 4H), 5.09-5.18 (m, 1H), 6.87-7.03 (m, 2H), 7.14 (m, 1H), 7.31 (m, 6H).

Step 3

To a solution of (S)-benzyl 3-((R)-6-allyl-6-(4-fluorophenyl)-2-oxo-1,3-oxazinan-3-yl)piperidine-1-carboxylate (78 mg, 0.17 mmol) in THF (3 mL) was added BH$_3$.THF (0.5 mL, 1 mol/L) at 0° C. under nitrogen atmosphere. The formed mixture was stirred for 2 h. The reaction was quenched with water. Then aqueous NaOH solution (3 mol/L, 0.2 mL) and H$_2$O$_2$ (30%, 0.4 mL) was added to the above mixture. The resulting mixture was stirred for 1.5 h. The mixture was extracted with EtOAc, and the combined organic phase was concentrated to give the crude product, which was purified by preparative TLC to give (S)-benzyl 3-((R)-6-(4-fluorophenyl)-6-(3-hydroxypropyl)-2-oxo-1,3-oxazinan-3-yl)piperidine-1-carboxylate (15 mg, 20%). LC-MS Method 2 $t_R$=1.299 min, m/z=493.1; $^1$H NMR (CDCl$_3$): 1.12-1.35 (m, 2H), 1.46 (m, 1H), 1.57-1.28 (m, 4H), 1.82-1.98 (m, 2H), 2.11 (m, 1H), 2.23 (m, 1H), 2.46-2.73 (m, 3H), 3.11 (m, 1H), 3.50

(m, 2H), 3.86-4.03 (m, 1H), 5.06 (m, 2H), 6.89-7.01 (m, 2H), 7.16 (m, 2H), 7.23-7.33 (m, 4H).

Example 341

(R)-3-((S)-1-benzylpiperidin-3-yl)-6-(4-fluorophenyl)-6-(3-hydroxypropyl)-1,3-oxazinan-2-one

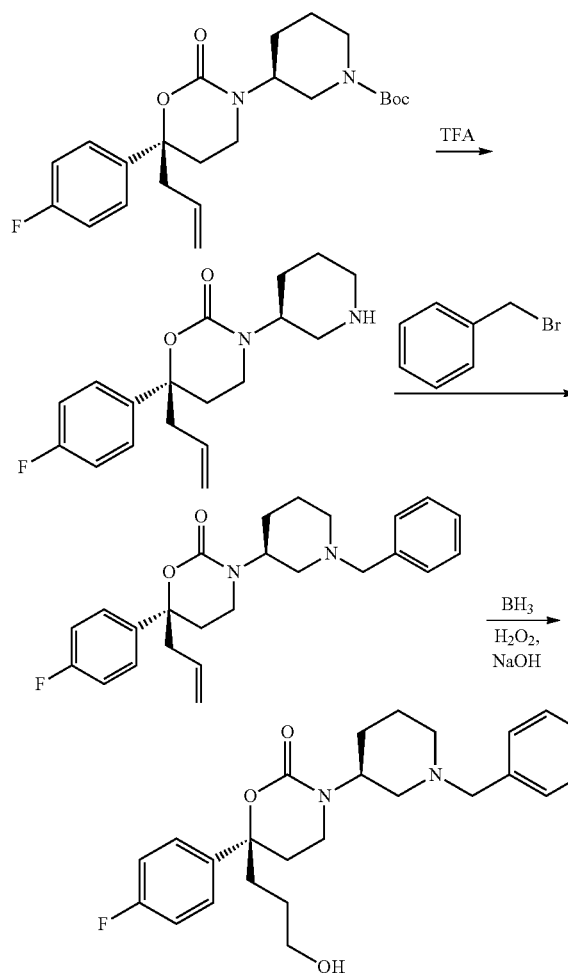

Step 1

To a solution of (S)-tert-butyl 3-((R)-6-allyl-6-(4-fluorophenyl)-2-oxo-1,3-oxazinan-3-yl)piperidine-1-carboxylate (700 mg, 1.67 mmol) in CH$_2$Cl$_2$ (16 mL) was added TFA (3.2 mL) at 0° C. The mixture was stirred at rt for 2 h. Then aqueous solution of NaHCO$_3$ was added, and the mixture was extracted with CH$_2$Cl$_2$. The organic layer was dried over Na$_2$SO$_4$ and concentrated. The residue was purified by preparative TLC to give (R)-6-allyl-6-(4-fluorophenyl)-3-((S)-piperidin-3-yl)-1,3-oxazinan-2-one (530 mg, 100%).

Step 2

To a solution of (R)-6-allyl-6-(4-fluorophenyl)-3-((S)-piperidin-3-yl)-1,3-oxazinan-2-one (530 mg, 1.67 mmol) in DMF (10 mL) was added benzyl bromide (573 mg, 3.35 mmol) and K$_2$CO$_3$ (924 mg, 6.7 mmol), and the mixture was heated to 80° C. for 5 hours. The reaction was quenched by H$_2$O. The layers were separated, and the aqueous phase was extracted with CH$_2$Cl$_2$. The combined organic layer was dried over Na$_2$SO$_4$ and concentrated. The residue was purified by preparative TLC to give (R)-6-allyl-3-((S)-1-benzylpiperidin-3-yl)-6-(4-fluorophenyl)-1,3-oxazinan-2-one (90 mg, 13%).

Step 3

To a solution of (R)-6-allyl-3-((S)-1-benzylpiperidin-3-yl)-6-(4-fluorophenyl)-1,3-oxazinan-2-one (90 mg, 0.22 mmol) in THF (3 mL) was added BH$_3$/THF (1 M, 0.44 mL) at 0° C. and the mixture was stirred at rt for 2 h. Then the mixture was cooled at 0° C., and H$_2$O (0.2 ml), NaOH (3 M, 0.15 mL), 30% H$_2$O$_2$ (0.4 mL) were added. After the solution was stirred at rt for another 2 h, 1N aq HCl was added, and the mixture was extracted with EtOAc. The combined organic layer was dried over Na$_2$SO$_4$ and concentrated. The residue was purified by preparative TLC to give (R)-3-((S)-1-benzylpiperidin-3-yl)-6-(4-fluorophenyl)-6-(3-hydroxypropyl)-1,3-oxazinan-2-one (30 mg, 30%). LC-MS Method 2 t$_R$=0.976 min, m/z=427.7; $^1$H NMR (CDCl$_3$): 1.28 (m, 2H), 1.36-1.45 (m, 1H), 1.58-1.67 (m, 6H), 1.88 (m, 2H), 2.10 (m, 1H), 2.17 (m, 1H), 2.48 (m, 1H), 2.64 (m, 2H), 3.12 (m, 1H), 3.34 (s, 2H), 3.48 (m, 2H), 4.05-4.15 (m, 1H), 6.94 (m, 2H), 7.15 (m, 5H), 7.22 (m, 2H).

Example 342

6-allyl-3-(2,4-dichlorobenzyl)-6-(4-fluorophenyl)-1,3-oxazinan-2-one

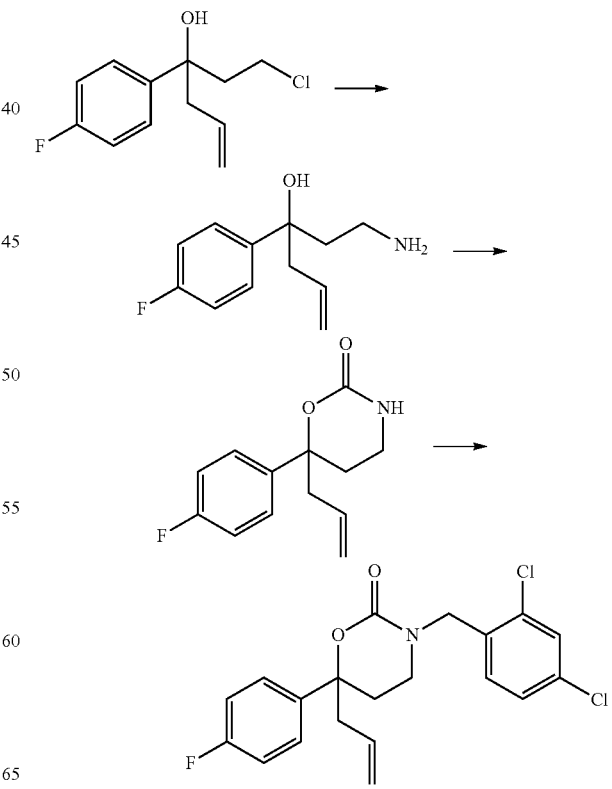

Step 1

A mixture of 1-chloro-3-(4-fluorophenyl)hex-5-en-3-ol (100 mg), EtOH (4 mL) and conc NH₄OH (2 mL) was heated at 120° C. for 30 min in the microwave. The mixture was concentrated and the residue was partitioned between 5% aq HCl (2×40 mL) and ether (70 mL). The combined aq HCl layers were basified by addition of solid K₂CO₃ and extracted with CH₂Cl₂ (2×45 mL). The combined CH₂Cl₂ extracts were washed with brine (10 mL) and dried over Na₂SO₄. Removal of the solvent left 1-amino-3-(4-fluorophenyl)hex-5-en-3-ol (53 mg) as an oil. LC-MS Method 1 $t_R$=0.90 min, m/z=210, 192.

Step 2

A stirred solution of 1-amino-3-(4-fluorophenyl)hex-5-en-3-ol (53 mg, 0.25 mmol) and i-Pr₂NEt (0.091 mL, 0.50 mmol) in CH₂Cl₂ (10 mL) was cooled in an ice bath and solid triphosgene (25 mg, 0.08 mmol) was added. The ice bath was allowed to melt and the mixture was stirred at rt for 6 h. The mixture was diluted with ether (80 mL), washed with 5% aq HCl (20 mL) and satd aq NaHCO₃ (20 mL), and dried over MgSO₄. Removal of the solvent afforded 6-allyl-6-(4-fluorophenyl)-1,3-oxazinan-2-one (50 mg, 84%) as an oil, which was used without further purification. LC-MS Method 1 $t_R$=1.32 min, m/z=236.

Step 3

To a stirred solution of 6-allyl-6-(4-fluorophenyl)-1,3-oxazinan-2-one (15 mg, 0.064 mmol) and 2,4-dichlorobenzyl chloride (25 mg, 0.13 mmol) in dry DMF (0.5 mL) under N₂ was added 60% NaH in oil in small portions until gas evolution ceased. The mixture was stirred overnight at rt and quenched with water (0.5 mL). The mixture was applied to a 10-mL Chem-Elut cartridge and eluted with ether (50 mL). The eluate was evaporated to dryness and the residue was purified by preparative HPLC to afford 6-allyl-3-(2,4-dichlorobenzyl)-6-(4-fluorophenyl)-1,3-oxazinan-2-one (5.5 mg, 22%). LC-MS Method 1 $t_R$=2.1 min, m/z=394; ¹H NMR (CDCl₃) 2.30 (2H), 2.60 (m, 2H), 2.96 (m, 1H), 3.08 (m, 1H), 4.44 (d, 1H), 4.65 (d, 1H), 4.75 (1H), 5.06 (m, 2H), 5.67 (m, 1H), 6.86 (d, 1H), 7.08 (3H), 7.30 (3H).

Example 343

3-(2,4-dichlorobenzyl)-6-(4-fluorophenyl)-6-(3-hydroxypropyl)-1,3-oxazinan-2-one

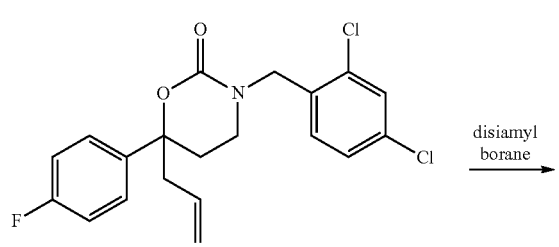

disiamyl borane
→

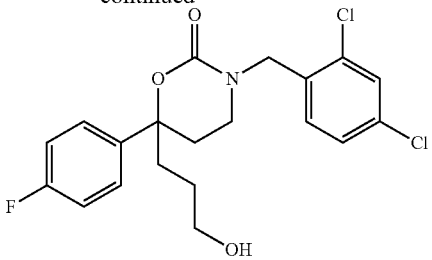

A stirred solution of BH₃.Me₂S (0.7 mL, 7.0 mmol) in dry THF (7 mL) was cooled in an ice bath and 2 M 2-methylbutene in THF (7 mL, 14 mmol) was added dropwise over 3 min. The mixture was stirred in the ice bath for 1.5 h. An aliquot of this solution (0.25 mL, 0.12 mmol) was added to an ice-cold solution of 6-allyl-3-(2,4-dichlorobenzyl)-6-(4-fluorophenyl)-1,3-oxazinan-2-one (3.2 mg, 8.0 µmol) in dry THF (0.5 mL). The mixture was stirred overnight at rt. Water (2 mL) was added and the mixture was stirred for 3 h. Solid NaBO₃.H₂O (10 mg) was added. The mixture was stirred overnight, applied to a 10-mL ChemElut cartridge and eluted with CH₂Cl₂ (20 mL). The eluate was concentrated and the residue was purified by prep HPLC to afford 3-(2,4-dichlorobenzyl)-6-(4-fluorophenyl)-6-(3-hydroxypropyl)-1,3-oxazinan-2-one (1.3 mg, 39%). LC-MS Method 1 $t_R$=1.78 min, m/z=368; ¹H NMR (CDCl₃) 1.37 (m, 1H), 1.66 (m, 1H), 1.99 (m, 2H), 2.30 (m, 2H), 2.92 (m, 1H), 3.10 (m, 1H), 3.58 (t, 2H), 4.50 (d, 1H), 4.63 (d, 1H), 6.90-7.35 (7H).

Example 344

6-allyl-3-(2,5-dichlorobenzyl)-6-(4-fluorophenyl)-1,3-oxazinan-2-one

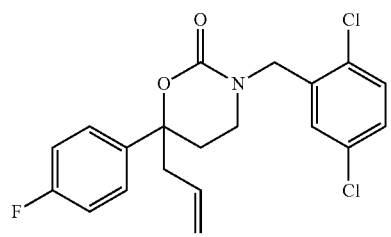 [SMILES: C=CCC1(c2ccc(F)cc2)CCN(Cc2cc(Cl)ccc2Cl)C(=O)O1]

The title compound was prepared following procedures analogous to those described in Example 342 using 2,5-dichlorobenzyl bromide. LC-MS Method 1 $t_R$=2.07 min, m/z=394; ¹H NMR (CDCl₃) 2.32 (m, 2H), 2.60 (m, 2H), 2.99 (m, 1H), 3.08 (m, 1H), 4.39 (d, 1H), 4.79 (d, 1H), 5.06 (m, 2H), 5.72 (m, 1H), 6.77 (s, 1H), 7.05-7.40 (6H).

Example 345

3-(2,5-dichlorobenzyl)-6-(4-fluorophenyl)-6-(3-hydroxypropyl)-1,3-oxazinan-2-one

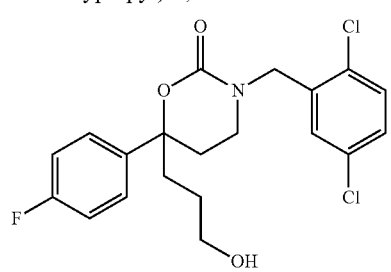

The title compound was prepared following procedures analogous to those described in Example 343. LC-MS Method 1 $t_R$=1.72 min, m/z=368; $^1$H NMR (CDCl$_3$) 1.39 (m, 1H), 1.74 (m, 1H), 1.99 (m, 2H), 2.35 (m, 2H), 2.94 (m, 1H), 3.08 (m, 1H), 3.59 (t, 2H), 4.41 (d, 1H), 4.78 (d, 1H), 6.88 (s, 1H), 7.05-7.35 (6H).

Example 346

6-allyl-3-(2,6-dichlorobenzyl)-6-(4-fluorophenyl)-1,3-oxazinan-2-one

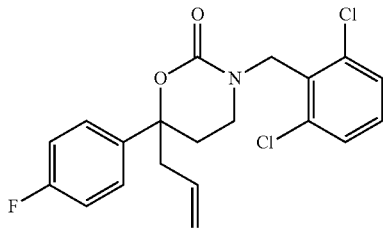 [SMILES: C=CCC1(c2ccc(F)cc2)CCN(Cc2c(Cl)cccc2Cl)C(=O)O1]

The title compound was prepared following procedures analogous to those described in Example 342 using 2,6-dichlorobenzyl bromide. LC-MS Method 1 $t_R$=1.98 min, m/z=418, 416, 396, 394; $^1$H NMR (CDCl$_3$) 2.19 (m, 2H0, 2.57 (3H), 2.95 (m, 2H), 4.79 (d, 1H), 4.95 (d, 1H), 6.02 (m, 2H), 5.64 (m, 1H), 6.99 (m, 2H), 7.12 (m, 1H), 7.20 (4H).

Example 347

3-(2,6-dichlorobenzyl)-6-(4-fluorophenyl)-6-(3-hydroxypropyl)-1,3-oxazinan-2-one

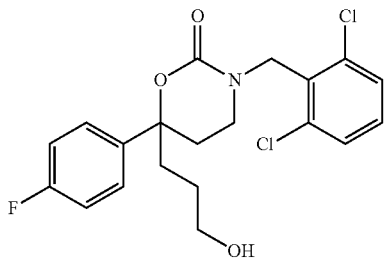

The title compound was prepared from 6-allyl-3-(2,6-dichlorobenzyl)-6-(4-fluorophenyl)-1,3-oxazinan-2-one following procedures analogous to those described in Example 343. LC-MS Method 1 $t_R$=1.65 min, m/z=368; $^1$H NMR (CDCl$_3$) 1.26 (m, 1H), 1.62 (m, 1H), 1.90 (m, 2H), 2.17 (m, 2H), 2.54 (m, 1H), 2.92 (m, 1H), 3.48 (t, 2H), 4.78 (d, 1H), 4.93 (d, 1H), 6.90-7.20 (7H).

Example 348

3-(2,6-difluorobenzyl)-6-(4-fluorophenyl)-6-(3-hydroxypropyl)-1,3-oxazinan-2-one

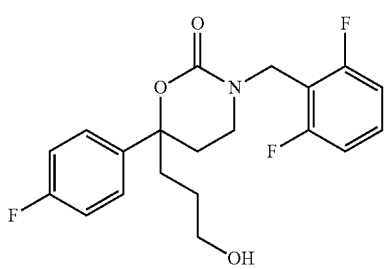 [SMILES: O=C1OC(CCCO)(c2ccc(F)cc2)CCN1Cc1c(F)cccc1F]

The title compound was prepared following a procedures analogous to that described in Example 342 using 2,6-difluorobenzyl bromide, followed by a procedure analogous to that described in Example 343. LC-MS Method 1 $t_R$=1.5 min, m/z=336; $^1$H NMR (CDCl$_3$) 1.34 (m, 1H), 1.70 (m, 1H), 1.97 (m, 2H), 2.24 (m, 2H), 2.77 (m, 1H), 3.10 (m, 1H), 3.58 (t, 2H), 4.48 (d, 1H), 4.80 (d, 1H), 6.81 (t, 2H), 7.00 (m, 2H), 7.20 (3H).

Example 349

3-(2-chloro-6-fluorobenzyl)-6-(4-fluorophenyl)-6-(3-hydroxypropyl)-1,3-oxazinan-2-one

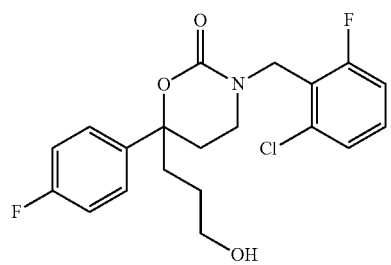 [SMILES: O=C1OC(CCCO)(c2ccc(F)cc2)CCN1Cc1c(F)cccc1Cl]

The title compound was prepared following a procedures analogous to that described in Example 342 using 2-chloro-6-fluorobenzyl bromide, followed by a procedure analogous to that described in Example 343. LC-MS Method 1 $t_R$=1.58 min, m/z=352; $^1$H NMR (CDCl$_3$) 1.33 (m, 1H), 1.68 (m, 1H), 1.95 (m, 2H), 2.21 (m, 2H), 2.63 (m, 1H), 3.02 (m, 1H), 3.57 (t, 2H), 4.64 (d, 1H), 4.91 (d, 1H), 6.90-7.30 (7H).

Example 350

6-allyl-3-(2-bromobenzyl)-6-(4-fluorophenyl)-1,3-oxazinan-2-one

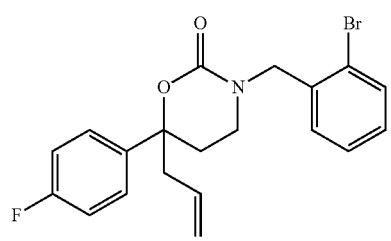 [SMILES: C=CCC1(c2ccc(F)cc2)CCN(Cc2ccccc2Br)C(=O)O1]

The title compound was prepared following procedures analogous to those described in Example 342 using 2-bromobenzyl bromide. LC-MS Method 1 $t_R$=1.94 min, m/z=406, 404; 1H NMR (CDCl3) 2.30 (m, 2H), 2.61 (m, 2H), 2.94 (m, 1H), 3.08 (m, 1H), 4.48 (d, 1H), 4.68 (d, 1H), 5.08 (m, 2H), 5.72 (m, 1H), 6.83 (m, 1H), 7.10 (4H), 7.37 (m, 2H), 7.46 (m, 1H).

Example 351

3-(2-bromobenzyl)-6-(4-fluorophenyl)-6-(3-hydroxypropyl)-1,3-oxazinan-2-one

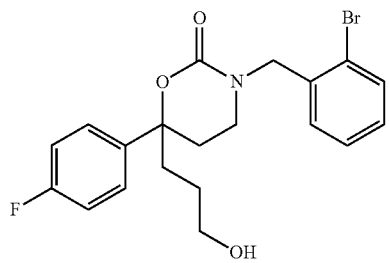 [SMILES: O=C1OC(CCCO)(c2ccc(F)cc2)CCN1Cc1ccccc1Br]

The title compound was prepared from 6-allyl-3-(2-bromobenzyl)-6-(4-fluorophenyl)-1,3-oxazinan-2-one following procedures analogous to those described in Example 343. LC-MS Method 1 $t_R$=1.67 min, m/z=380, 378; $^1$H NMR (CDCl$_3$) 1.38 (m, 1H), 1.69 (m, 1H), 1.90 (1H), 1.98 (m, 2H), 2.30 (m, 2H), 2.90 (m, 1H), 3.08 (m, 1H), 3.58 (m, 2H), 5.56 (d, 1H), 5.67 (d, 1H), 6.88 (m, 1H), 7.05-7.20 (4H), 7.34 (m, 2H), 7.48 (d, 1H).

Example 352

(R)-methyl 2-((6-(4-fluorophenyl)-6-(3-hydroxypropyl)-2-oxo-1,3-oxazinan-3-yl)methyl)benzoate

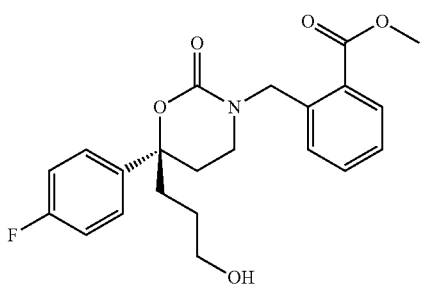 [SMILES: COC(=O)c1ccccc1CN1CC[C@](CCCO)(c2ccc(F)cc2)OC1=O]

The title compound was prepared from (R)-6-allyl-3-(2-bromobenzyl)-6-(4-fluorophenyl)-1,3-oxazinan-2-one following a procedure analogous to that described in Example 124, followed by a procedure analogous to that described in Example 78. LC-MS Method 1 $t_R$=1.48 min, m/z=424 (M+Na); $^1$H NMR (CDCl$_3$) 7.90 (d, 1H), 7.30 (m, 4H), 7.10 (q, 2H), 7.00 (t, 1H), 4.92 (d, 2H), 4.26 (t, 1H), 3.85 (s, 3H), 3.13 (m, 1H), 2.92 (m, 1H), 2.33 (m, 2H), 2.10-1.91 (m, 3H).

Example 353

(R)-6-allyl-3-((S)-1-(3-bromophenyl)ethyl)-6-(4-fluorophenyl)-1,3-oxazinan-2-one

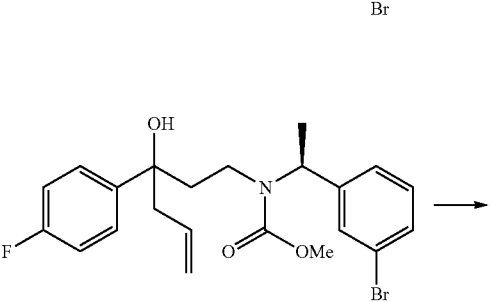

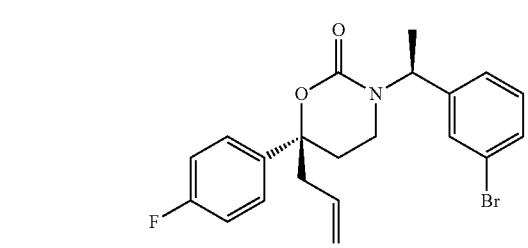

The title compound was prepared following procedures analogous to those described in Example 337 except that methyl chloroformate was used in place of Boc2O in Step 2. LC-MS Method 1 $t_R$=1.99 min, m/z=418 (M+1); $^1$H NMR (CDCl$_3$) 7.25 (m, 3H), 7.06-6.94 (m, 4H), 6.77 (d, 1H), 5.76-

5.59 (m, 2H), 5.10-5.00 (dd, 2H), 2.90 (m, 1H), 2.56 (m, 2H), 2.34-2.14 (m, 3H), 1.49 (d, 3H).

Example 354

(R)-3-((S)-1-(3-bromophenyl)ethyl)-6-(4-fluorophenyl)-6-(3-hydroxypropyl)-1,3-oxazinan-2-one

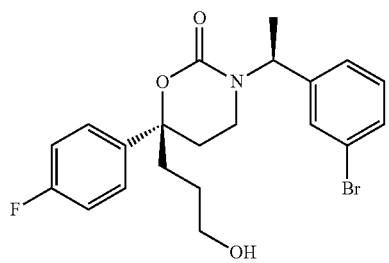 [SMILES: C[C@@H](c1cccc(Br)c1)N1CC[C@](CCCO)(c2ccc(F)cc2)OC1=O]

The title compound was prepared from (R)-6-allyl-3-((S)-1-(3-bromophenyl)ethyl)-6-(4-fluorophenyl)-1,3-oxazinan-2-one following procedures analogous to those described in Example 343. LC-MS Method 1 $t_R$=1.67 min, m/z=458 (M+Na); ¹H NMR (CDCl₃) 7.26 (m, 3H), 7.10-6.97 (m, 4H), 6.84 (t, 1H), 5.64 (q, 1H), 4.26 (t, 1H), 3.57 (t, 1H), 3.14 (m, 1H), 2.31-2.16 (m, 3H), 1.49 (d, 3H), 1.32 (t, 2H).

Example 355

(6S)-3-((S)-1-(3-bromophenyl)ethyl)-6-(4-fluorophenyl)-6-(2-hydroxypropyl)-1,3-oxazinan-2-one

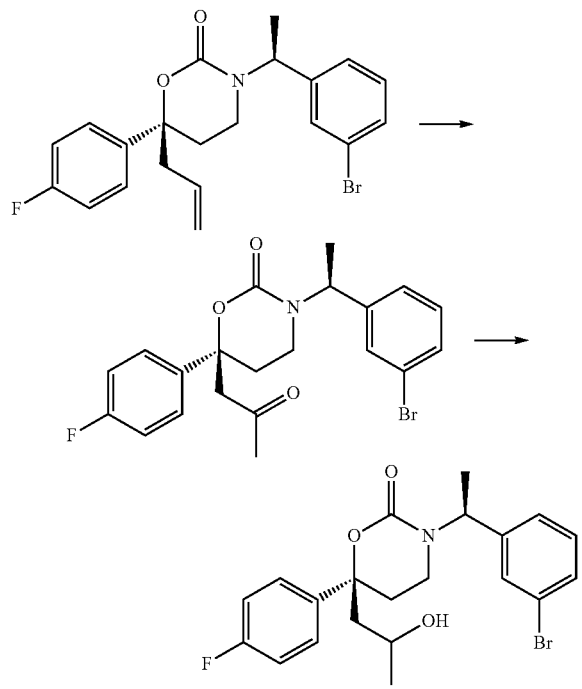

Step 1

(R)-6-allyl-3-((S)-1-(3-bromophenyl)ethyl)-6-(4-fluorophenyl)-1,3-oxazinan-2-one (55 mg, 0.13 mmol), PdCl₂ (6 mg, 0.3 equiv.), and CuCl (26 mg, 2.3 equiv.) were mixed with DMF (2 mL) and water (~250 µL). A balloon of oxygen was attached to the flask and the mixture was stirred vigorously overnight. LC-MS found the reaction completed. The mixture was quenched by satd aq NH₄Cl solution (2 mL), diluted with EtOAc (20 mL), washed by brine (7 mL), dried over Na₂SO₄. After filtration and concentration, the residue was purified by preparative HPLC to afford (S)-3-((S)-1-(3-bromophenyl)ethyl)-6-(4-fluorophenyl)-6-(2-oxopropyl)-1,3-oxazinan-2-one (49 mg, 86% yield). LC-MS (3 min) $t_R$=1.76 min, m/z=434, 436 (M+1).

Step 2

A solution of (S)-3-((S)-1-(3-bromophenyl)ethyl)-6-(4-fluorophenyl)-6-(2-oxopropyl)-1,3-oxazinan-2-one (12 mg, 0.028 mmol) in 3:1 THF/MeOH (4 mL) was cooled to 0° C. NaBH₄ (2.1 mg, 2 equiv) was added. After 15 min, the mixture was warmed to rt slowly. After stirring 1.5 h, LC-MS found the reaction completed. The mixture was quenched by water (2 mL), concentrated, and purified by preparative HPLC to afford (6S)-3-((S)-1-(3-bromophenyl)ethyl)-6-(4-fluorophenyl)-6-(2-hydroxypropyl)-1,3-oxazinan-2-one (4.4 mg, 36%). LC-MS (3 min) $t_R$=1.68 min, m/z=458, 460 (M+Na). ¹H NMR (CDCl₃) 7.36-7.21 (m, 3H), 7.12-6.96 (m, 4H), 6.83 (m, 1H), 5.63 (m, 1H), 2.93 (m, 1H), 1.51 (d, 3H), 1.17 (d, 3H).

Example 356

(S)-3-((S)-1-(3-bromophenyl)ethyl)-6-(4-fluorophenyl)-6-(2-hydroxy-2-methylpropyl)-1,3-oxazinan-2-one

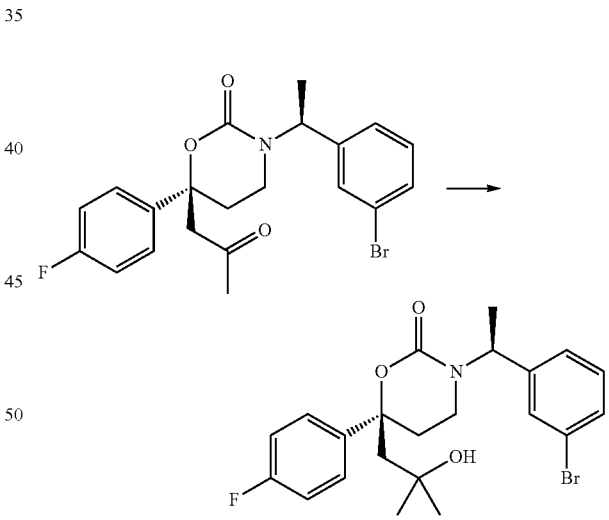

A solution of (S)-3-((S)-1-(3-bromophenyl)ethyl)-6-(4-fluorophenyl)-6-(2-oxopropyl)-1,3-oxazinan-2-one (18.5 mg, 0.043 mmol) in dry toluene (3 mL) was cooled to 0° C. A solution of MeMgBr (3.0M in THF, 45 µL, 3 equiv) was added. After 15 min, the mixture was warmed to rt slowly and stirred 2 h. LC-MS found reaction completed. The reaction was quenched by satd aq NH₄Cl solution (2 mL), diluted with EtOAc (10 mL), washed with 1% aq HCl (3 mL), brine (3 mL), and dried over Na₂SO₄. After filtration and concentration, the residue was purified by preparative HPLC to afford (S)-3-((S)-1-(3-bromophenyl)ethyl)-6-(4-fluorophenyl)-6-(2-hydroxy-2-methylpropyl)-1,3-oxazinan-2-one (8.0 mg, 42%). LC-MS (3 min) $t_R$=1.75 min, m/z=472, 474 (M+Na); $^1$H NMR (CDCl$_3$) 7.32-7.21 (m, 3H), 7.12-6.98 (m, 4H), 6.89 (m, 1H), 5.65 (q, 1H), 2.89 (m, 1H), 1.50 (d, 3H), 1.15 (d, 6H).

Example 357

(R)-3-((S)-1-(3-bromophenyl)ethyl)-6-(4-fluorophenyl)-6-(3-hydroxy-3-methylbutyl)-1,3-oxazinan-2-one

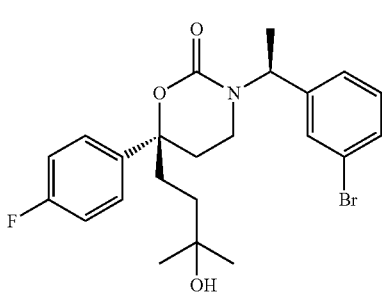 [SMILES: C[C@@H](c1cccc(Br)c1)N1CC[C@](CCC(C)(C)O)(c2ccc(F)cc2)OC1=O]

The title compound was prepared from methyl 3-((R)-3-((S)-1-(3-bromophenyl)ethyl)-6-(4-fluorophenyl)-2-oxo-1,3-oxazinan-6-yl)propanoate following procedures analogous to those described in Example 117. LC-MS Method 1 $t_R$=1.79 min, m/z=464, 466 (M+1); $^1$H NMR (CDCl$_3$) 7.30 (d, 1H), 7.23 (m, 2H), 7.10-6.99 (m, 4H), 6.87 (d, 1H), 6.65 (q, 1H), 2.92 (m, 1H), 2.32-2.18 (m, 3H), 2.08-1.88 (m, 2H), 1.63 (td, 1H), 1.51 (d, 3H), 1.15 (d, 6H).

Example 358

3-((R)-3-((S)-1-(3-bromophenyl)ethyl)-6-(4-fluorophenyl)-2-oxo-1,3-oxazinan-6-yl)propanamide

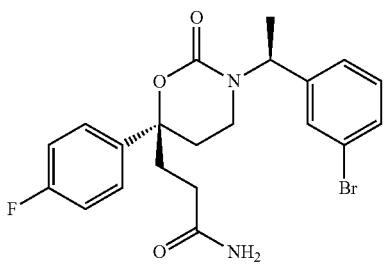

The title compound was prepared from (R)-3-((S)-1-(3-bromophenyl)ethyl)-6-(4-fluorophenyl)-6-(3-hydroxypropyl)-1,3-oxazinan-2-one following procedures analogous to those described in Example 234. LC-MS Method 1 $t_R$=1.55 min, m/z=449, 451 (M+1); $^1$H NMR (CDCl$_3$) 7.32 (d, 1H), 7.22 (m, 2H), 7.12-7.02 (m, 4H), 6.90 (m, 2H), 6.33 (br s, 1H), 5.62 (q, 1H), 2.96 (m, 1H), 2.50 (m, 1H), 2.34-2.17 (m, 5H), 2.10 (m, 1H), 1.52 (d, 3H).

Example 359

N-(3-((R)-3-((S)-1-(3-bromophenyl)ethyl)-6-(4-fluorophenyl)-2-oxo-1,3-oxazinan-6-yl)propyl)methanesulfonamide

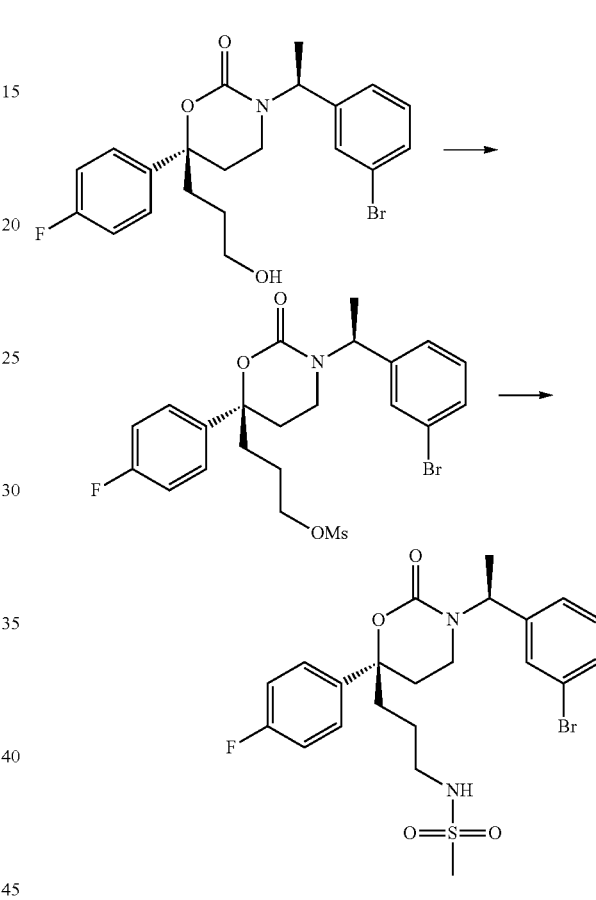

Step 1

To a solution of (R)-3-((S)-1-(3-bromophenyl)ethyl)-6-(4-fluorophenyl)-6-(3-hydroxypropyl)-1,3-oxazinan-2-one (20 mg, 0.046 mmol) in CH$_2$Cl$_2$ (2 mL) was added Et$_3$N (13 μL, 2 equiv) and MsCl (6 μL, 1.55 equiv) at 0° C. After 5 min, the mixture was warmed to rt and stirred for 1 h. The mixture was concentrated, acidified with 5% aq HCl to pH=~6 and purified by preparative HPLC to afford 3-((R)-3-((S)-1-(3-bromophenyl)ethyl)-6-(4-fluorophenyl)-2-oxo-1,3-oxazinan-6-yl)propyl methanesulfonate (6.8 mg, 29%). LC-MS (3 min) $t_R$=1.83 min., m/z 514, 516 (M+1).

Step 2

3-((R)-3-((S)-1-(3-bromophenyl)ethyl)-6-(4-fluorophenyl)-2-oxo-1,3-oxazinan-6-yl)propyl methanesulfonate (6.8 mg, 0.013 mmol) was diluted with acetonitrile (2 mL), added K$_2$CO$_3$ (10 mg, excess) and methanesulfonamide (2.5 mg, 2 equiv.). The mixture was stirred overnight at rt. After filtration and concentration, the residue was purified by preparative HPLC to afford N-(3-((R)-3-((S)-1-(3-bromophenyl)ethyl)-6-(4-fluorophenyl)-2-oxo-1,3-oxazinan-6-yl)propyl)methanesulfonamide (2.5 mg, 37%). LC-MS (3 min) $t_R$=1.87 min, m/z=514, 516 (M+1). $^1$H NMR (CDCl$_3$) 7.31 (m, 1H), 7.23 (m, 2H), 7.14-7.05 (m, 3H), 7.02 (t, 1H), 6.87 (d, 1H), 5.64 (q, 1H), 4.17 (m, 2H), 2.97 (s, 3H), 2.33-2.11 (m, 3H), 1.52 (d, 3H).

Example 360

(R)-3-((S)-1-(3-chlorophenyl)ethyl)-6-(4-fluorophenyl)-6-(3-hydroxypropyl)-1,3-oxazinan-2-one

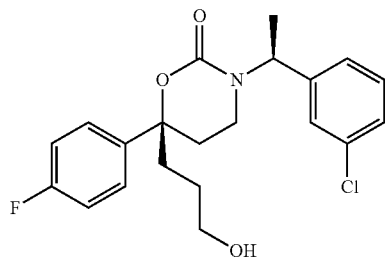 [SMILES: C[C@@H](c1cccc(Cl)c1)N1CC[C@](CCCO)(c2ccc(F)cc2)OC1=O]

The title compound was prepared from (R)-6-allyl-3-((S)-1-(3-bromophenyl)ethyl)-6-(4-fluorophenyl)-1,3-oxazinan-2-one following procedures analogous to those described in Example 187. LC-MS Method 1 $t_R$=1.66 min, m/z=392 (M+1); $^1$H NMR (CDCl$_3$) 7.34-7.20 (m, 2H), 7.15-7.02 (m, 4H), 6.89 (s, 1H), 6.81 (m, 1H), 5.64 (m, 1H), 3.58 (t, 2H), 2.93 (m, 1H), 1.50 (d, 3H).

Example 361

3-((R)-3-((S)-1-(3-cyanophenyl)ethyl)-6-(4-fluorophenyl)-2-oxo-1,3-oxazinan-6-yl)propyl 2,2,2-trifluoroacetate

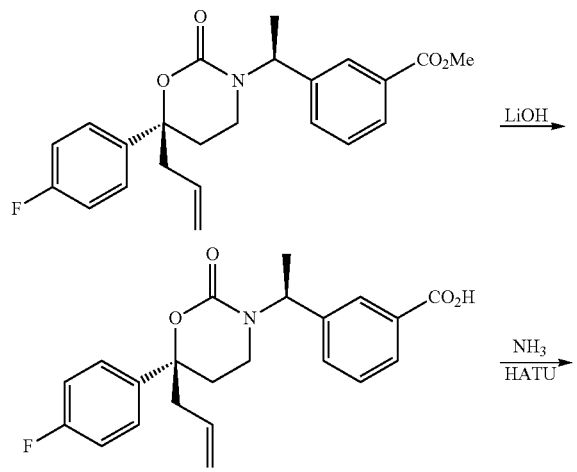

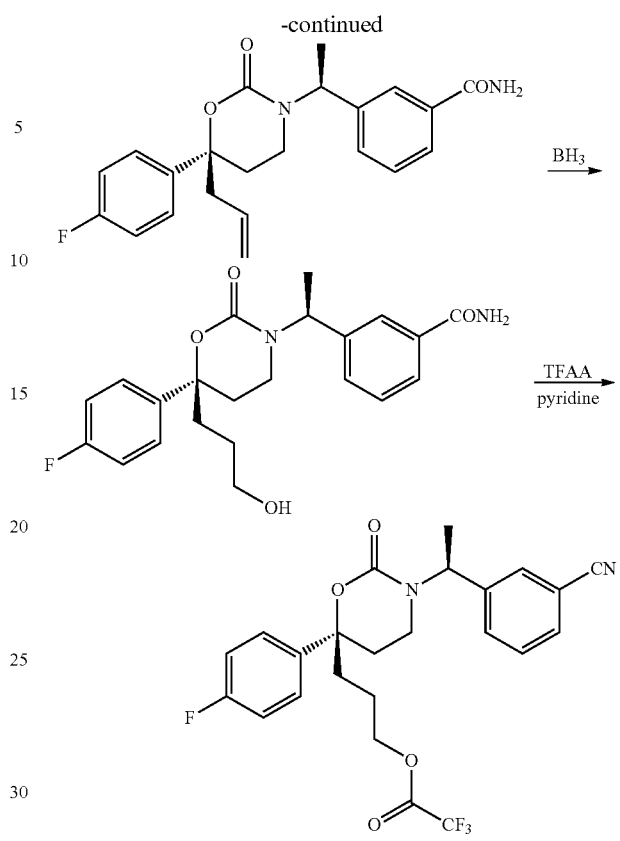

The title compound was prepared from methyl 3-((S)-1-((R)-6-allyl-6-(4-fluorophenyl)-2-oxo-1,3-oxazinan-3-yl)ethyl)benzoate by treatment with LiOH in aq THF, followed by a procedure analogous to that described in Example 153, followed by a procedure analogous to that described in Example 78, followed by a procedure analogous to that described in Example 172. LC-MS Method 1 $t_R$=1.9 min, m/z=479 (M+1); $^1$H NMR (CDCl$_3$) 8.89 (d, 1H), 7.85 (t, 1H), 7.47 (d, 1H), 7.24 (m, 2H), 7.08 (m, 3H), 5.68 (m, 1H), 4.27 (t, 1H), 1.53 (d, 3H).

Example 362

Methyl 3-((S)-1-((R)-6-allyl-6-(4-fluorophenyl)-2-oxo-1,3-oxazinan-3-yl)ethyl)benzoate

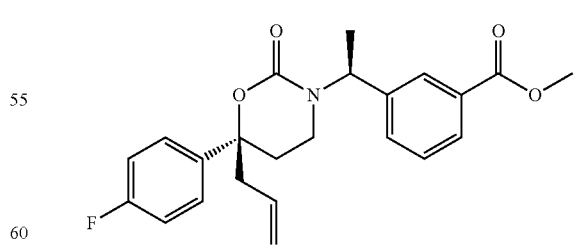

The title compound was prepared from (R)-6-allyl-3-((S)-1-(3-bromophenyl)ethyl)-6-(4-fluorophenyl)-1,3-oxazinan-2-one following procedures analogous to those described in Example 124. LC-MS Method 1 $t_R$=1.82 min, m/z=420 (M+Na); $^1$H NMR (CDCl$_3$) 7.82 (d, 1H), 7.67 (s, 1H), 7.22

(m, 2H), 7.16 (t, 1H), 6.99 (m, 3H), 5.67 (m, 2H), 5.05 (dd, 2H), 3.88 (s, 3H), 2.93 (m, 1H), 2.57 (m, 2H), 2.22 (m, 3H), 1.55 (d, 3H).

Example 363

(R)-6-(4-fluorophenyl)-3-((S)-1-(3-(hydroxymethyl)phenyl)ethyl)-6-(3-hydroxypropyl)-1,3-oxazinan-2-one

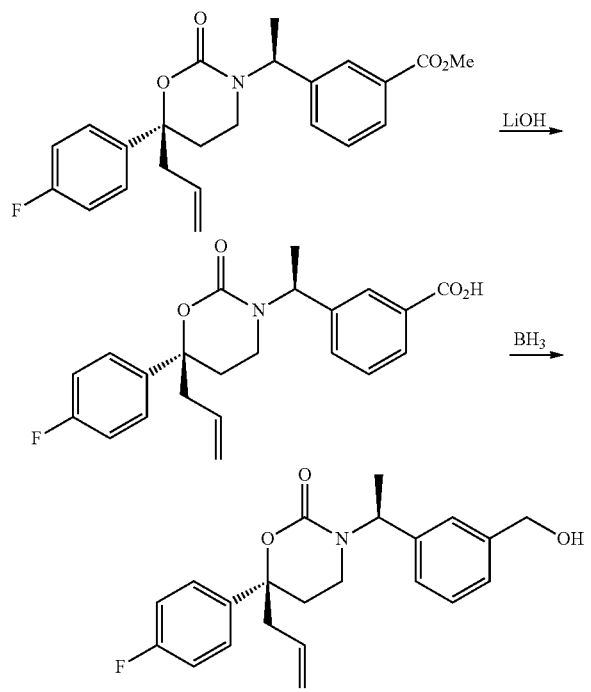

LC-MS Method 1 $t_R$=1.24 min, m/z=410 (M+Na); $^1$H NMR (CDCl$_3$) 7.23 (m, 2H), 7.15 (m, 2H), 7.04 (q, 2H), 6.94 (s, 1H), 6.86 (m, 1H), 5.63 (m, 1H), 4.52 (s, 2H), 3.57 (t, 1H), 1.52 (d, 3H).

Example 364

(R)-6-allyl-6-(4-fluorophenyl)-3-((S)-1-(3-(2-hydroxypropan-2-yl)phenyl)ethyl)-1,3-oxazinan-2-one

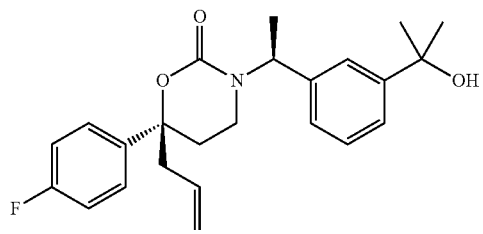 [SMILES: C=CC[C@]1(c2ccc(F)cc2)CCN([C@@H](C)c2cccc(C(C)(C)O)c2)C(=O)O1]

The title compound was prepared from methyl 3-((S)-1-((R)-6-allyl-6-(4-fluorophenyl)-2-oxo-1,3-oxazinan-3-yl)ethyl)benzoate following procedures analogous to those described in Example 238 Step 3. LC-MS Method 1 $t_R$=1.68 min, m/z=420 (M+Na); $^1$H NMR (CDCl$_3$) 7.26 (m, 3H), 7.12 (m, 2H), 7.01 (t, 2H), 6.81 (d, 1H), 5.65 (m, 2H), 5.15 (dd, 2H), 2.89 (m, 1H), 2.58 (m, 2H), 1.54 (d, 3H), 1.42 (d, 6H).

Example 365

3-((1S)-1-(4-bromophenyl)ethyl)-6-(2,4-difluorophenyl)-6-(2-hydroxyethyl)-1,3-oxazinan-2-one

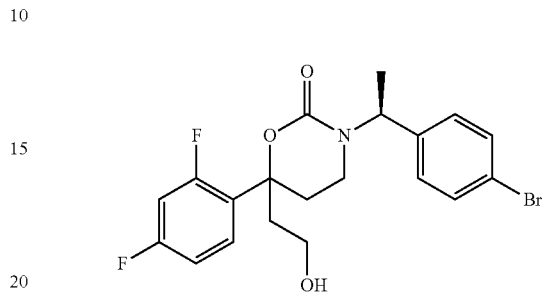

The title compound was prepared from 3-chloro-1-(2,4-difluorophenyl)propan-1-one using a procedure analogous to that described in Example 110 followed by a procedure analogous to that described in Example 97. 3-chloro-1-(2,4-difluorophenyl)propan-1-one was prepared by treatment of 1,3-difluorobenzene with 3-chloropropanoyl chloride and AlCl$_3$. Two isomers were isolated.

Isomer 1: (S)-3-((S)-1-(4-bromophenyl)ethyl)-6-(2,4-difluorophenyl)-6-(2-hydroxyethyl)-1,3-oxazinan-2-one
LC-MS Method 1 $t_R$=1.71 min, m/z=442, 440 (M+1); $^1$H NMR (CD$_3$OD) 7.28-7.21 (m, 3H), 6.94-6.84 (m, 4H), 5.44 (q, J=7.0 Hz, 1H), 3.65-3.59 (m, 1H), 3.32-3.26 (m, 1H), 3.11-3.03 (m, 1H), 2.52-2.43 (m, 1H), 2.23-2.07 (m, 4H), 1.43 (d, J=7.3 Hz, 3H).

Isomer 2: (R)-3-((S)-1-(4-bromophenyl)ethyl)-6-(2,4-difluorophenyl)-6-(2-hydroxyethyl)-1,3-oxazinan-2-one
LC-MS Method 1 $t_R$=1.75 min, m/z=442, 440 (M+1); $^1$H NMR (CD$_3$OD) 7.43-7.14 (m, 5H), 6.99-6.93 (m, 2H), 5.45 (q, J=7.3 Hz, 1H), 3.65-3.59 (m, 1H), 3.31-3.24 (m, 1H), 2.79-2.66 (m, 2H), 2.49-2.45 (m, 1H), 2.22-2.01 (m, 3H), 1.25 (d, J=7.3 Hz, 3H).

Example 366

(R)-3-((S)-1-(4-bromophenyl)ethyl)-6-(2,4-difluorophenyl)-6-(3-hydroxypropyl)-1,3-oxazinan-2-one

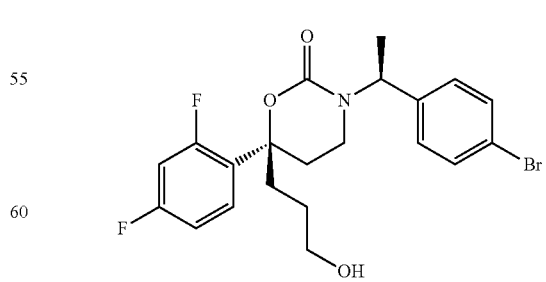

The title compound was prepared from (R)-6-allyl-3-((S)-1-(4-bromophenyl)ethyl)-6-(2,4-difluorophenyl)-1,3-oxazinan-2-one following procedures analogous to those described in Example 78. LC-MS Method 1 $t_R$=1.76 min, m/z=456, 454 (M+1); $^1$H NMR (CD$_3$OD) 7.30-7.24 (m, 3H), 6.95-6.85 (m, 4H), 5.44 (q, J=7.0 Hz, 1H), 3.42-3.37 (m, 2H), 3.11-3.06 (m, 1H), 2.52-2.45 (m, 1H), 2.24-2.09 (m, 2H), 2.05-1.87 (m, 2H), 1.62-1.53 (m, 1H), 1.44 (d, J=7.0 Hz, 3H), 1.22-1.13 (m, 1H).

Example 367

(R)-6-(4-fluorophenyl)-6-(3-hydroxypropyl)-3-((S)-1-(6-methylpyridin-3-yl)ethyl)-1,3-oxazinan-2-one

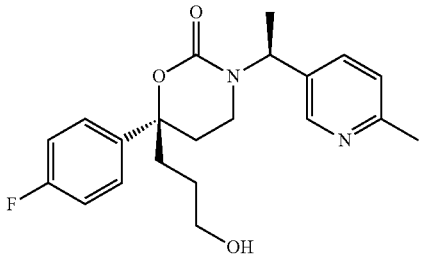

The title compound was prepared following procedures analogous to those described in Example 283 using (S)-1-(6-methylpyridin-3-yl)ethanamine in Step 1. LC-MS Method 2 $t_R$=1.198 min, m/z=372.18; $^1$H NMR (CD$_3$OD) 1.18 (m, 1H), 1.47 (d, 3H), 1.52 (m, 1H), 1.84 (m, 2H), 2.17 (m, 1H), 2.37-2.42 (m, 3H), 2.56 (s, 3H), 3.36 (m, 2H), 5.48 (m, 1H), 6.96 (m, 2H), 7.26 (m, 3H), 7.46 (m, 1H), 8.40 (s, 1H).

Example 368

3-((R)-3-((S)-1-(4-bromophenyl)propyl)-6-(4-fluorophenyl)-2-oxo-1,3-oxazinan-6-yl)propanamide

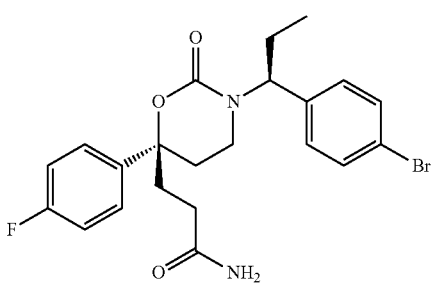 [SMILES: CC[C@@H](c1ccc(Br)cc1)N1CC[C@](CCC(N)=O)(c2ccc(F)cc2)OC1=O]

The title compound was prepared from (R)-3-((S)-1-(4-bromophenyl)propyl)-6-(4-fluorophenyl)-6-(3-hydroxypropyl)-1,3-oxazinan-2-one following procedures analogous to those described in Example 234. LC-MS Method 3 $t_R$=1.092 min, m/z=464.9; $^1$H NMR (CDCl$_3$) 0.91 (t, 3H), 1.90 (m, 2H), 2.12-2.22 (m, 5H), 2.23-2.39 (m, 1H), 2.89 (m, 1H), 5.34 (m, 1H), 5.41-5.59 (m, 2H), 6.86-6.95 (m, 4H), 7.11 (m, 2H), 7.21 (m, 2H).

Example 369

N-(3-((R)-3-((S)-1-(4-bromophenyl)ethyl)-6-(4-fluorophenyl)-2-oxo-1,3-oxazinan-6-yl)propyl)methanesulfonamide

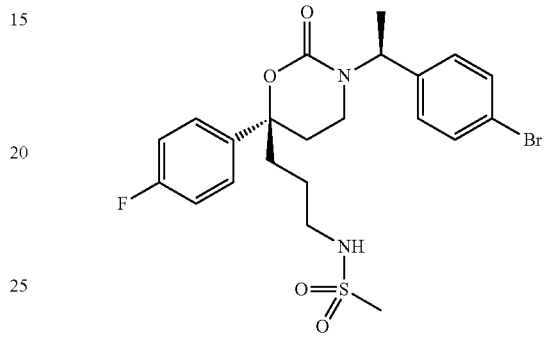

The title compound was prepared from (R)-3-((S)-1-(4-bromophenyl)ethyl)-6-(4-fluorophenyl)-6-(3-hydroxypropyl)-1,3-oxazinan-2-one following procedures analogous to those described in Example 359. LC-MS Method 3 $t_R$=1.168 min, m/z=512.08; $^1$H NMR (CDCl$_3$) 1.28 (m, 1H), 1.44 (d, 3H), 1.60 (m, 1H), 1.80-1.95 (m, 2H), 2.10-2.21 (m, 2H), 2.84 (s, 3H), 3.00 (m, 2H), 4.21 (m, 1H), 5.52 (m, 1H), 6.75 (d, 2H), 6.99 (t, 2H), 7.12-7.22 (m, 4H).

Example 370

(S)-3-((S)-1-(4-bromophenyl)ethyl)-6-(4-fluorophenyl)-6-(2-hydroxy-2-methylpropyl)-1,3-oxazinan-2-one

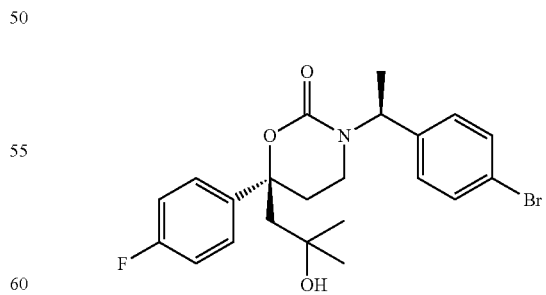

The title compound was prepared from (R)-6-allyl-3-((S)-1-(4-bromophenyl)ethyl)-6-(4-fluorophenyl)-1,3-oxazinan-2-one following procedures analogous to those described in Example 356. LC-MS Method 3 $t_R$=1.168 min, m/z=472; $^1$H NMR (CDCl$_3$) 1.06 (d, 6H), 1.18 (s, 1H), 1.43 (d, 3H), 2.10

(m, 4H), 2.33 (m, 1H), 2.79 (m, 1H), 5.54 (m, 1H), 6.77 (d, 2H), 6.98 (t, 2H), 7.19 (m, 2H), 7.22 (m, 2H).

Example 371

(6S)-3-((1S)-1-(4-bromophenyl)ethyl)-6-(4-fluorophenyl)-6-(2-hydroxypropyl)-1,3-oxazinan-2-one

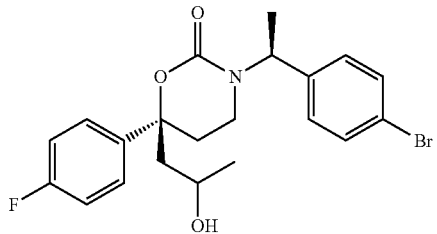 [SMILES: CC(O)C[C@]1(c2ccc(F)cc2)CCN([C@@H](C)c2ccc(Br)cc2)C(=O)O1]

The title compound was prepared from (S)-3-((S)-1-(4-bromophenyl)ethyl)-6-(4-fluorophenyl)-6-(2-oxopropyl)-1,3-oxazinan-2-one following procedures analogous to those described in Example 355. Two isomers were isolated.

Isomer 1: LC-MS Method 2 $t_R$=1.368 min, m/z=460.1; $^1$H NMR (CDCl$_3$) 1.20 (d, 3H), 1.42 (d, 3H), 1.88 (m, 1H), 2.01 (m, 1H), 2.18-2.30 (m, 2H), 2.35-2.54 (m, 1H), 2.80-2.90 (m, 1H), 3.78-3.90 (m, 1H), 5.52 (m, 1H), 6.65 (d, 2H), 6.94-7.03 (m, 2H), 7.17-7.45 (m, 4H).

Isomer 2: LC-MS Method 2 $t_R$=1.399 min, m/z=459.9; $^1$H NMR (CDCl$_3$) 1.01 (d, 3H), 1.43 (d, 3H), 1.85 (d, 1H), 2.03 (m, 1H), 2.19 (m, 2H), 2.28 (m, 1H), 2.83 (m, 1H), 3.82 (m, 1H), 5.52 (m, 1H), 6.74 (d, 2H), 7.01 (t, 2H), 7.19 (m, 5H).

Example 372

(6R)-3-((S)-1-(4-bromophenyl)ethyl)-6-(4-fluorophenyl)-6-(3-hydroxybutyl)-1,3-oxazinan-2-one

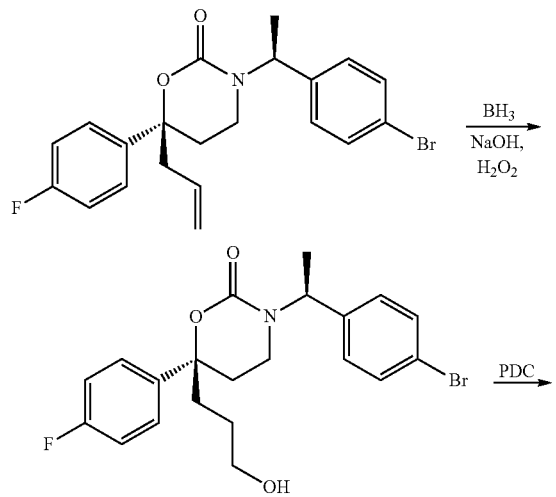

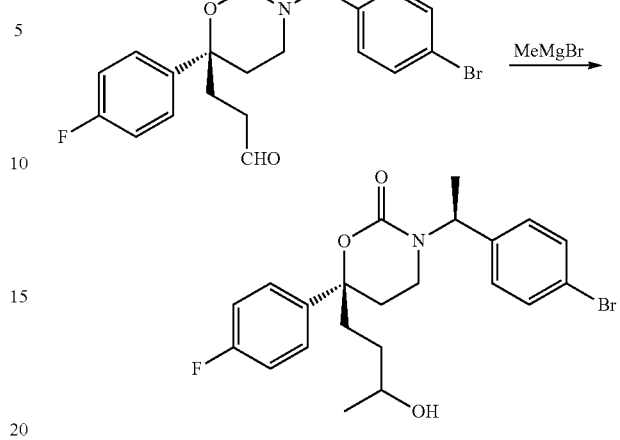

Step 1

To a solution of (R)-6-allyl-3-((S)-1-(4-bromophenyl)ethyl)-6-(4-fluorophenyl)-1,3-oxazinan-2-one (2.0 g, 4.8 mmol) in THF (48 ml) was added BH$_3$.THF (5.7 ml, 1 mol/L) at 0° C. under nitrogen atmosphere, and the resulting solution was stirred for 2 h at rt. The reaction was quenched with water. Then aqueous NaOH solution (2.0 ml, 3 mol/L) and H$_2$O$_2$ (2 mL, 30%) were added to the mixture. The resulting mixture was stirred for 2 h at rt. The mixture was diluted with EtOAc, and the pH was adjusted to 6-7 with 1M aq HCl. The aqueous phase was extracted with EtOAc, and the combined organic phase was washed with satd aq NaHCO$_3$ and brine, dried over Na$_2$SO$_4$, concentrated to give the crude product, which was purified on silica gel to give (R)-3-((S)-1-(4-bromophenyl)ethyl)-6-(4-fluorophenyl)-6-(3-hydroxypropyl)-1,3-oxazinan-2-one (1.13 g, 54%). $^1$H NMR: (400 MHz, CDCl$_3$): 1.32 (m, 1H), 1.43 (d, 3H), 1.63 (m, 1H), 1.90 (m, 2H), 2.21 (m, 3H), 2.84 (m, 1H), 3.51 (t, 2H), 5.54 (q, 1H), 6.72 (d, 2H), 6.98 (t, 2H), 7.18 (m, 4H).

Step 2

A mixture of (R)-3-((S)-1-(4-bromophenyl)ethyl)-6-(4-fluorophenyl)-6-(3-hydroxy-propyl)-1,3-oxazinan-2-one (500 mg, 1.15 mmol), PDC (870 mg, 2.30 mmol) and 3 Å molecular sieves (1.3 g) in methylene chloride was stirred at room temperature for 3 hours. The reaction mixture was chromatographed on silica gel directly to give 3-((R)-3-((S)-1-(4-bromophenyl)ethyl)-6-(4-fluorophenyl)-2-oxo-1,3-oxazinan-6-yl)propanal (300 mg, 60%). $^1$H NMR: (400 MHz, CDCl$_3$): 1.43 (d, 2H), 2.10 (m, 2H), 2.19 (m, 3H), 2.67 (m, 1H), 2.86 (m, 1H), 5.54 (q, 1H), 6.75 (d, 2H), 7.00 (t, 2H), 7.17 (m, 4H), 9.60 (s, 1H).

Step 3

To a solution of 3-((R)-3-((S)-1-(4-bromophenyl)ethyl)-6-(4-fluorophenyl)-2-oxo-1,3-oxazinan-6-yl)propanal (300 mg, 0.69 mmol) in THF (4 ml) was added dropwise MeMgBr (0.7 ml, 3 mol/L) at −78° C. The mixture was stirred for 2 h and the temperature was allowed to be warm to rt at this stage. The reaction was quenched with aqueous NH$_4$Cl. The organic layer was separated, and the aqueous layer was extracted with EtOAc. The combined organic layer was washed with brine, dried over Na$_2$SO$_4$ and concentrated to give the crude product, which was purified by HPLC and chiral HPLC to give two isomers.

Isomer 1: (30.76 mg, 10%). LC-MS Method 2 t$_R$=1.389 min, m/z=474; $^1$H NMR (CDCl$_3$) 1.05 (d, 4H), 1.42 (d, 4H), 1.49-1.50 (m, 1H), 1.81-1.91 (m, 1H), 1.92-2.01 (m, 1H), 2.07-2.18 (m, 1H), 2.19-2.36 (m, 2H), 2.79-2.91 (m, 1H), 3.65 (m, 1H), 5.54 (m, 1H), 6.73 (d, 2H), 6.94 (m, 2H), 7.17 (m, 4H).

Isomer 2: LC-MS Method 2 t$_R$=1.417 min, m/z=473.8; $^1$H NMR (CDCl$_3$) 1.07 (d, 3H), 1.18-1.30 (m, 1H), 1.44 (d, 4H), 1.47-1.57 (m, 1H), 1.71-1.82 (m, 1H), 1.94-2.09 (m, 1H), 2.11-2.29 (m, 3H), 2.83 (m, 1H), 3.60 (m, 1H), 5.54 (m, 1H), 6.70 (d, 2H), 6.96-6.99 (t, 2H), 7.16-7.19 (m, 5H).

Example 373

(R)-3-((S)-1-(4-bromophenyl)ethyl)-6-(4-fluorophenyl)-6-(3-hydroxy-3-methylbutyl)-1,3-oxazinan-2-one

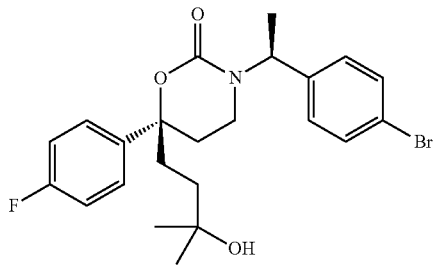 [SMILES: C[C@@H](c1ccc(Br)cc1)N1CC[C@](CCC(C)(C)O)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one following procedures analogous to those described in Example 117. LC-MS Method 2 t$_R$=1.434 min, m/z=487.8; $^1$H NMR (CDCl$_3$) 1.07 (d, 6H), 1.12-1.20 (m, 1H), 1.45 (d, 3H), 1.54-1.64 (m, 1H), 1.80-2.01 (m, 2H), 2.10-2.23 (m, 3H), 2.84 (m, 1H), 5.54 (m, 1H), 6.72 (d, 2H), 6.97 (t, 2H), 7.15-7.20 (m, 4H).

Example 374

(R)-6-(2-(azetidin-1-yl)ethyl)-3-((S)-1-(4-bromophenyl)ethyl)-6-(4-fluorophenyl)-1,3-oxazinan-2-one

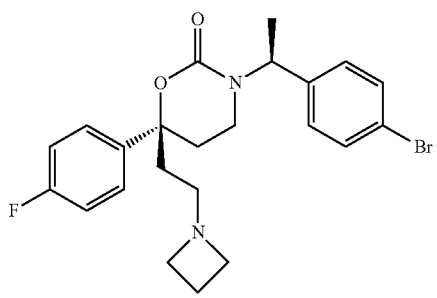 [SMILES: C[C@@H](c1ccc(Br)cc1)N1CC[C@](CCN2CCC2)(c2ccc(F)cc2)OC1=O]

The title compound was prepared from (S)-3-((S)-1-(4-bromophenyl)ethyl)-6-(4-fluorophenyl)-6-(2-hydroxyethyl)-1,3-oxazinan-2-one and azetidine following procedures analogous to those described in Example 178. LC-MS Method 2 t$_R$=1.15 min, m/z=463; $^1$H NMR (CDCl$_3$) 1.43 (d, 4H), 2.05-2.27 (m, 7H), 2.56-2.74 (m, 2H), 2.86 (m, 1H), 3.20 (m, 1H), 3.50 (m, 1H), 3.71 (m, 1H), 4.17-4.39 (d, 2H), 5.52 (m, 1H), 6.80 (d, 2H), 6.95-7.02 (m, 2H), 7.13-7.24 (m, 4H).

Example 375

(R)-3-((S)-1-(4-bromophenyl)ethyl)-6-(2-(2-fluoroethylamino)ethyl)-6-(4-fluorophenyl)-1,3-oxazinan-2-one

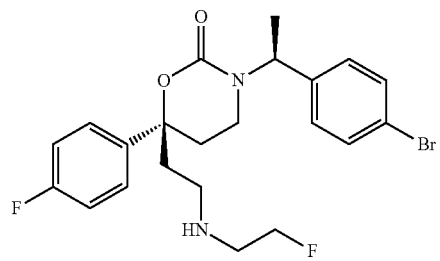 [SMILES: C[C@@H](c1ccc(Br)cc1)N1CC[C@](CCNCCF)(c2ccc(F)cc2)OC1=O]

The title compound was prepared from (S)-3-((S)-1-(4-bromophenyl)ethyl)-6-(4-fluorophenyl)-6-(2-hydroxyethyl)-1,3-oxazinan-2-one and 2-fluoroethylamine following procedures analogous to those described in Example 178. LC-MS Method 2 t$_R$=1.1 min, m/z=489; $^1$H NMR (CDCl$_3$) 1.50 (d, 3H), 1.97-2.38 (m, 7H), 2.41-2.56 (m, 1H), 2.79-2.98 (m, 3H), 4.45 (m, 1H), 4.54 (m, 1H), 5.61 (m, 1H), 6.80 (d, 2H), 7.03-7.14 (t, 2H), 7.21-7.31 (m, 6H).

Example 376

(R)-3-((S)-1-(4-bromophenyl)ethyl)-6-(4-fluorophenyl)-6-(2-(pyrrolidin-1-yl)ethyl)-1,3-oxazinan-2-one

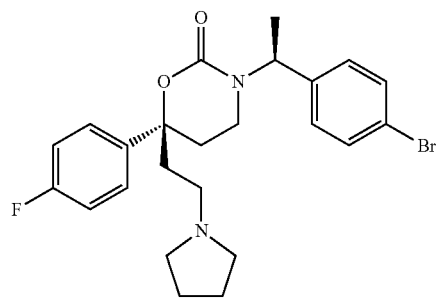 [SMILES: C[C@@H](c1ccc(Br)cc1)N1CC[C@](CCN2CCCC2)(c2ccc(F)cc2)OC1=O]

The title compound was prepared from (S)-3-((S)-1-(4-bromophenyl)ethyl)-6-(4-fluorophenyl)-6-(2-hydroxyethyl)-1,3-oxazinan-2-one and pyrrolidine following procedures analogous to those described in Example 178. LC-MS Method 2 t$_R$=1.167 min, m/z=475.1; $^1$H NMR (CDCl$_3$) 1.48 (d, 3H), 2.00 (m, 2H), 2.13 (m, 2H), 2.22 (m, 1H), 2.32 (m, 1H), 2.43 (m, 1H), 2.58 (m, 1H), 2.76 (m, 2H), 2.88 (m, 1H), 3.18 (m, 1H), 3.61 (m, 1H), 3.75 (m, 1H), 4.41 (s, 2H), 5.52 (m, 1H), 6.80 (d, 2H), 7.02 (t, 2H), 7.13 (m, 2H), 7.24 (m, 2H).

Example 377

(R)-3-((S)-1-(4-bromophenyl)ethyl)-6-(4-fluorophenyl)-6-(2-((S)-3-fluoropyrrolidin-1-yl)ethyl)-1,3-oxazinan-2-one

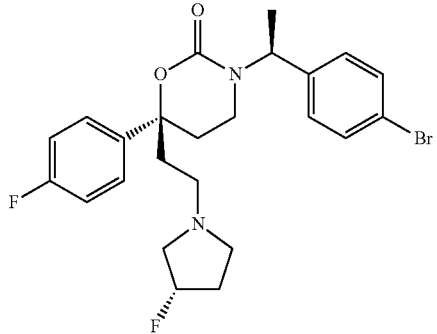 [SMILES: C[C@@H](c1ccc(Br)cc1)N1CC[C@](CCN2CC[C@H](F)C2)(c2ccc(F)cc2)OC1=O]

The title compound was prepared from (S)-3-((S)-1-(4-bromophenyl)ethyl)-6-(4-fluorophenyl)-6-(2-hydroxyethyl)-1,3-oxazinan-2-one and (S)-3-fluoropyrrolidine following procedures analogous to those described in Example 178. LC-MS Method 2 $t_R$=0.984 min, m/z=517; $^1$H NMR (CDCl$_3$) 1.43 (d, 3H), 1.84-2.09 (m, 4H), 2.11-2.29 (m, 5H), 2.61 (m, 1H), 2.71-2.87 (m, 3H), 4.96 (s, 1H), 5.13 (s, 1H), 5.53 (m, 1H), 6.71 (d, 2H), 6.98 (t, 2H), 7.18 (m, 3H), 7.20 (m, 1H).

Example 378

(R)-3-((S)-1-(4-bromophenyl)ethyl)-6-(4-fluorophenyl)-6-(2-((R)-3-fluoropyrrolidin-1-yl)ethyl)-1,3-oxazinan-2-one

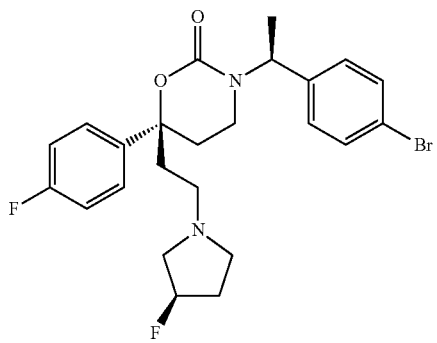 [SMILES: C[C@@H](c1ccc(Br)cc1)N1CC[C@](CCN2CC[C@@H](F)C2)(c2ccc(F)cc2)OC1=O]

The title compound was prepared from (S)-3-((S)-1-(4-bromophenyl)ethyl)-6-(4-fluorophenyl)-6-(2-hydroxyethyl)-1,3-oxazinan-2-one and (R)-3-fluoropyrrolidine following procedures analogous to those described in Example 178. LC-MS Method 2 $t_R$=1.682 min, m/z=516.9; $^1$H NMR (CDCl$_3$) 1.42 (d, 3H), 1.82-2.30 (m, 9H), 2.52-2.64 (m, 1H), 2.67-2.88 (m, 3H), 4.93-5.13 (m, 1H), 5.53 (m, 1H), 6.71 (d, 2H), 6.98 (m, 2H), 7.18 (m, 2H), 7.19 (m, 1H).

Example 379

(R)-3-((S)-1-(4-bromophenyl)ethyl)-6-(4-fluorophenyl)-6-(2-(3-oxopiperazin-1-yl)ethyl)-1,3-oxazinan-2-one

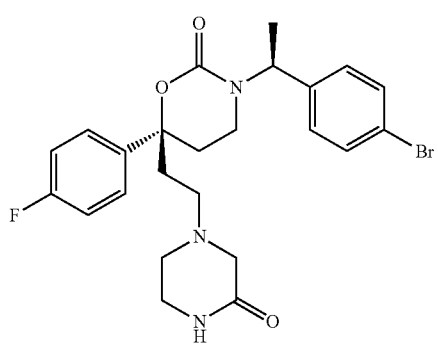 [SMILES: C[C@@H](c1ccc(Br)cc1)N1CC[C@](CCN2CCNC(=O)C2)(c2ccc(F)cc2)OC1=O]

The title compound was prepared from (S)-3-((S)-1-(4-bromophenyl)ethyl)-6-(4-fluorophenyl)-6-(2-hydroxyethyl)-1,3-oxazinan-2-one and piperazin-2-one following procedures analogous to those described in Example 178. LC-MS Method 2 $t_R$=1.117 min, m/z=506; $^1$H NMR (CDCl$_3$) 1.42 (d, 3H), 2.16-2.35 (m, 5H), 2.75-2.88 (m, 2H), 3.17-3.40 (m, 3H), 3.56-3.80 (m, 4H), 5.45 (m, 1H), 5.61-6.52 (s, 2H), 6.78 (d, 2H), 7.01-7.24 (m, 6H).

Example 380

(S)-3-((S)-1-(4-chlorophenyl)ethyl)-6-(4-fluorophenyl)-6-(2-hydroxyethyl)-1,3-oxazinan-2-one

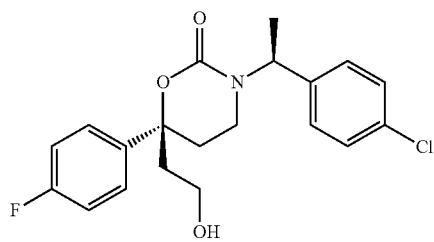 [SMILES: C[C@@H](c1ccc(Cl)cc1)N1CC[C@](CCO)(c2ccc(F)cc2)OC1=O]

The title compound was prepared from (S)-3-((S)-1-(4-bromophenyl)ethyl)-6-(4-fluorophenyl)-6-(2-hydroxyethyl)-1,3-oxazinan-2-one following procedures analogous to those described in Example 187 Step 1. LC-MS Method 3 $t_R$=1.077 min, m/z=377.12; $^1$H NMR (CDCl$_3$) 1.19 (m, 1H), 1.44 (d, 3H), 1.97-2.25 (m, 5H), 2.84 (m, 1H), 3.49 (m, 1H), 3.68 (m, 1H), 5.54 (m, 1H), 6.76 (d, 2H), 7.02 (m, 4H), 7.21 (m, 2H).

Example 381

(S)-3-((S)-1-(4-chlorophenyl)ethyl)-6-(4-fluorophenyl)-6-(2-hydroxy-2-methylpropyl)-1,3-oxazinan-2-one

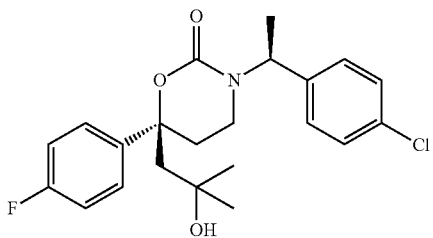

The title compound was prepared from (S)-3-((S)-1-(4-bromophenyl)ethyl)-6-(4-fluorophenyl)-6-(2-hydroxy-2-methylpropyl)-1,3-oxazinan-2-one following procedures analogous to those described in Example 187 Step 1. LC-MS Method 3 $t_R$=1.106 min, m/z=428; $^1$H NMR (CDCl$_3$) 1.08 (d, 6H), 1.19 (s, 1H), 1.43 (d, 3H), 2.04-2.22 (m, 4H), 2.28-2.40 (m, 1H), 2.80 (m, 1H), 5.56 (m, 1H), 6.83 (d, 2H), 6.95 (m, 2H), 7.15 (m, 2H), 7.22 (m, 2H).

Example 382

(R)-3-((S)-1-(4-chlorophenyl)ethyl)-6-(4-fluorophenyl)-6-(3-hydroxy-3-methylbutyl)-1,3-oxazinan-2-one

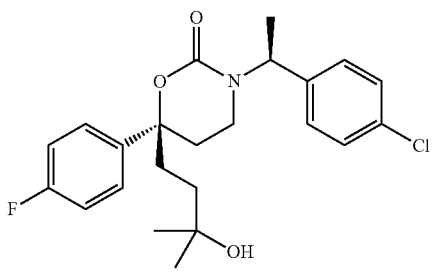

The title compound was prepared from (R)-3-((S)-1-(4-bromophenyl)ethyl)-6-(4-fluorophenyl)-6-(3-hydroxy-3-methylbutyl)-1,3-oxazinan-2-one following procedures analogous to those described in Example 187 Step 1. LC-MS Method 2 $t_R$=1.391 min, m/z=442; $^1$H NMR (CDCl$_3$) 1.02-1.19 (m, 6H), 1.48 (s, 3H), 1.57 (m, 1H), 1.81-1.99 (m, 2H), 2.08-2.23 (m, 3H), 2.83 (m, 1H), 3.42 (s, 1H), 5.55 (m, 1H), 6.77 (d, 2H), 6.96-7.05 (m, 4H), 7.17 (m, 2H).

Example 383

(6R)-3-((1S)-1-(4-chlorophenyl)ethyl)-6-(4-fluorophenyl)-6-(3-hydroxybutyl)-1,3-oxazinan-2-one

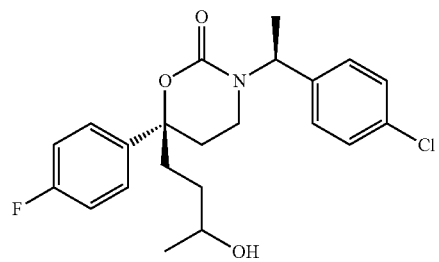 [SMILES: CC(O)CC[C@]1(c2ccc(F)cc2)CCN([C@@H](C)c2ccc(Cl)cc2)C(=O)O1]

The title compound was prepared from (6R)-3-((S)-1-(4-bromophenyl)ethyl)-6-(4-fluorophenyl)-6-(3-hydroxybutyl)-1,3-oxazinan-2-one following procedures analogous to those described in Example 187 Step 1. Two isomers were isolated.

Isomer 1: LC-MS Method 2 $t_R$=1.203 min, m/z=362.25; $^1$H NMR (CDCl$_3$) 1.05 (m, 4H), 1.42 (d, 3H), 1.53 (m, 1H), 1.86 (m, 1H), 1.93 (m, 1H), 2.05-2.26 (m, 3H), 2.84 (m, 1H), 3.67 (m, 1H), 5.56 (m, 1H), 6.78 (d, 2H), 6.97 (t, 2H), 7.04 (d, 2H), 7.17 (m, 2H).

Isomer 2: LC-MS Method 2 $t_R$=1.353 min, m/z=405.15; $^1$H NMR (CDCl$_3$) 1.05 (d, 3H), 1.24 (m, 1H), 1.48 (d, 3H), 1.76 (m, 1H), 2.01 (m, 1H), 2.10-2.28 (m, 3H), 2.73 (m, 1H) 3.61 (m, 1H), 5.57 (m, 1H), 6.77 (d, 2H), 6.95-7.08 (m, 4H), 7.15 (m, 2H).

Example 384

N-(3-((R)-3-((S)-1-(4-chlorophenyl)ethyl)-6-(4-fluorophenyl)-2-oxo-1,3-oxazinan-6-yl)propyl)methanesulfonamide

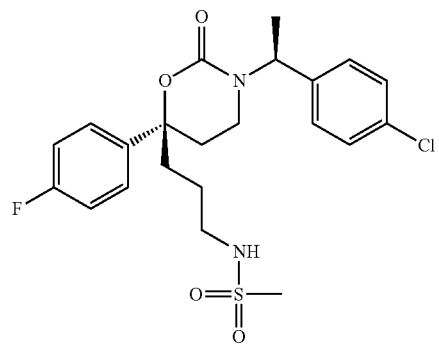 [SMILES: C[C@@H](c1ccc(Cl)cc1)N1CC[C@](CCCNS(C)(=O)=O)(c2ccc(F)cc2)OC1=O]

The title compound was prepared from N-(3-((R)-3-((S)-1-(4-bromophenyl)ethyl)-6-(4-fluorophenyl)-2-oxo-1,3-oxazinan-6-yl)propyl)methanesulfonamide following procedures analogous to those described in Example 187 Step 1. LC-MS Method 3 $t_R$=2.026 min, m/z=468.13; $^1$H NMR (CDCl$_3$) 1.28 (m, 1H), 1.45 (d, 3H), 1.61 (m, 1H), 1.83-1.95

(m, 2H), 2.10-2.21 (m, 4H), 2.84 (s, 3H), 2.90 (m, 2H), 4.20 (m, 1H), 5.55 (m, 1H), 6.82 (d, 2H), 6.98 (t, 2H), 7.06 (d, 2H), 7.16 (m, 2H).

Example 385

3-((R)-3-((S)-1-(4-chlorophenyl)ethyl)-6-(4-fluorophenyl)-2-oxo-1,3-oxazinan-6-yl)propanamide

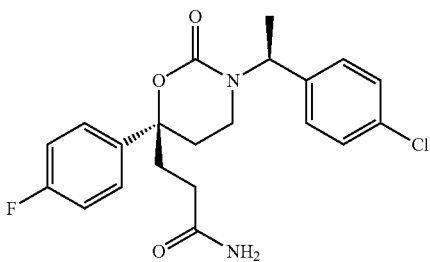

The title compound was prepared from 3-((R)-3-((S)-1-(4-bromophenyl)ethyl)-6-(4-fluorophenyl)-2-oxo-1,3-oxazinan-6-yl)propanamide following procedures analogous to those described in Example 187 Step 1. LC-MS Method 3 $t_R$=1.491 min, m/z=427.1; $^1$H NMR (CDCl$_3$) 1.50 (d, 3H), 2.01 (m, 1H), 2.14 (m, 2H), 2.46 (m, 2H), 2.89 (s, 2H), 2.90 (m, 1H), 5.63 (m, 2H), 5.72 (s, 1H), 6.89 (d, 2H), 7.03 (t, 2H), 7.12 (d, 2H), 7.4 (m, 2H).

Example 386

2'((6-(4-fluorophenyl)-6-(3-hydroxypropyl)-2-oxo-1,3-oxazinan-3-yl)methyl)biphenyl-4-carboxamide

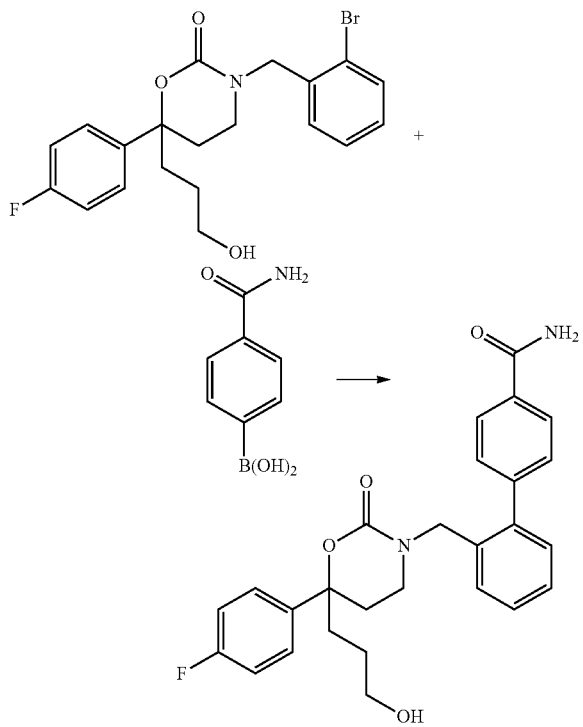

A thick-walled vial was charged with 3-(2-bromobenzyl)-6-(4-fluorophenyl)-6-(3-hydroxypropyl)-1,3-oxazinan-2-one (9.1 mg, 22 µmol), PdCl$_2$(PPh$_3$)$_2$ (4 mg, 5 µmol), Cs$_2$CO$_3$ (56 mg, 0.17 mmol), H$_2$O (0.5 mL) and dioxane (2 mL). The vial was capped and N2 was bubbled through the mixture for 15 min. The mixture was heated at 120 C for 30 min in a microwave. The mixture was applied to a 10-mL ChemElut cartridge prewetted with water and eluted with CH$_2$Cl$_2$ (50 mL). The eluate was concentrated and the residue was purified by prep HPLC to afford 2'-((6-(4-fluorophenyl)-6-(3-hydroxypropyl)-2-oxo-1,3-oxazinan-3-yl)methyl)biphenyl-4-carboxamide (2.8 mg, 28%) as an oil. LC-MS Method 1 $t_R$=1.37 min, m/z=419; $^1$H NMR (CDCl$_3$) 1.35 (m, 1H), 1.63 (m, 1H), 1.90 (m, 2H), 2.10 (m, 1H), 2.19 (m, 1H), 2.63 (m, 1H), 2.78 (m, 1H), 3.57 (t, 2H), 4.42 (d, 1H), 4.59 (d, 1H), 7.00-7.40 (10H), 7.83 (d, 2H).

Example 387

(S)-6-(4-fluorophenyl)-6-(2-hydroxyethyl)-3-((S)-1-(4-(trifluoromethyl)phenyl)ethyl)-1,3-oxazinan-2-one

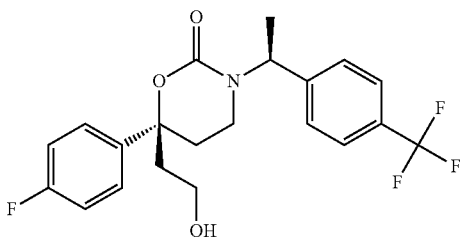 [SMILES: C[C@@H](c1ccc(C(F)(F)F)cc1)N1CC[C@](CCO)(c2ccc(F)cc2)OC1=O]

The title compound was prepared from (R)-6-allyl-6-(4-fluorophenyl)-3-((S)-1-(4-(trifluoromethyl)phenyl)ethyl)-1,3-oxazinan-2-one following procedures analogous to those described in Example 65. LC-MS Method 2 $t_R$=1.082 min, m/z=475; $^1$H NMR (CDCl$_3$) 1.47 (d, 3H), 2.01-2.17 (m, 2H), 2.25 (m, 3H), 2.89 (m, 1H), 3.49 (m, 1H), 3.70 (m, 1H), 5.63 (m, 1H), 6.98 (m, 4H), 7.21 (m, 2H), 7.30 (m, 2H).

Example 388

(6S)-6-(4-fluorophenyl)-6-(2-hydroxypropyl)-3-((1S)-1-(4-(trifluoromethyl)phenyl)ethyl)-1,3-oxazinan-2-one

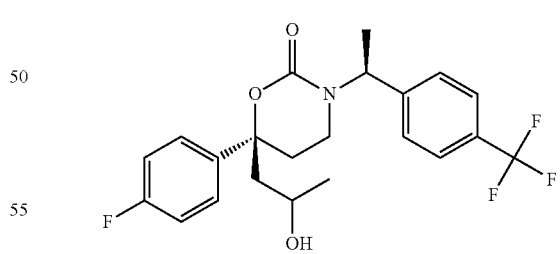

The title compound was prepared from (R)-6-allyl-6-(4-fluorophenyl)-3-((S)-1-(4-(trifluoromethyl)phenyl)ethyl)-1,3-oxazinan-2-one following a procedure analogous to that described in Example 355. Two isomers were isolated.

Isomer 1: LC-MS Method 2 $t_R$=1.362 min, m/z=425.16; $^1$H NMR (CDCl$_3$) 1.04 (d, 3H), 1.48 (d, 3H), 1.85 (d, 1H), 2.01 (m, 1H), 2.21 (m, 2H), 2.33 (m, 1H), 2.50 (s, 1H), 2.89 (m, 1H), 3.83 (m, 1H), 5.60 (m, 1H), 6.94 (m, 4H), 7.18 (m, 3H), 7.43 (d, 2H).

Isomer 2: LC-MS Method 2 $t_R$=1.344 min, m/z=448; $^1$H NMR (CDCl$_3$) 1.09 (d, 3H), 1.46 (d, 2H), 1.86 (d, 1H), 2.01 (m, 1H), 2.20-2.31 (m, 2H), 2.44 (m, 2H), 2.92 (m, 1H), 3.79 (s, 1H), 5.62 (m, 1H), 6.91 (d, 2H), 6.99 (t, 2H), 7.24-7.35 (m, 4H).

Example 389

N-(3-((R)-6-(4-fluorophenyl)-2-oxo-3-((S)-1-(4-(trifluoromethyl)phenyl)ethyl)-1,3-oxazinan-6-yl)propyl)methanesulfonamide

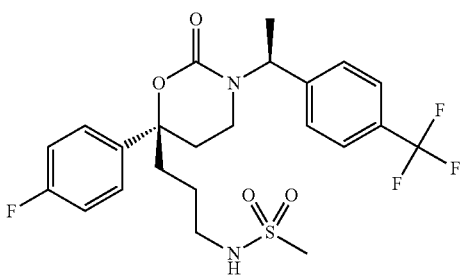 [SMILES: C[C@@H](c1ccc(C(F)(F)F)cc1)N1CC[C@](CCCNS(C)(=O)=O)(c2ccc(F)cc2)OC1=O]

The title compound was prepared from (R)-6-(4-fluorophenyl)-6-(3-hydroxypropyl)-3-((S)-1-(4-(trifluoromethyl)phenyl)ethyl)-1,3-oxazinan-2-one following procedures analogous to those described in Example 359. LC-MS Method 3 $t_R$=1.143 min, m/z=502.15; $^1$H NMR (CDCl$_3$) 1.48 (d, 3H), 1.63 (m, 2H), 1.85 (m, 2H), 1.94 (m, 1H), 2.11-2.33 (m, 3H), 2.86 (s, 3H) 2.95 (m, 1H), 3.04 (m, 2H), 4.15 (s, 1H), 5.62 (m, 1H), 6.97 (m, 4H), 7.15 (m, 2H), 7.35 (m, 2H).

Example 390

(S)-6-(4-fluorophenyl)-6-(2-hydroxy-2-methylpropyl)-3-((S)-1-(4-(trifluoromethyl)phenyl)ethyl)-1,3-oxazinan-2-one

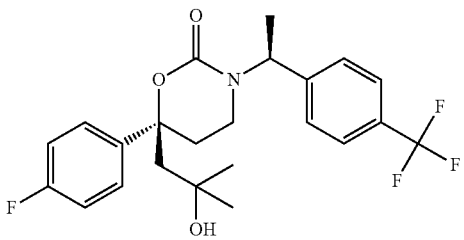 [SMILES: C[C@@H](c1ccc(C(F)(F)F)cc1)N1CC[C@](CC(C)(C)O)(c2ccc(F)cc2)OC1=O]

The title compound was prepared from (R)-6-allyl-6-(4-fluorophenyl)-3-((S)-1-(4-(trifluoromethyl)phenyl)ethyl)-1,3-oxazinan-2-one following procedures analogous to those described in Example 280. LC-MS Method 2 $t_R$=1.374 min, m/z=439.18; $^1$H NMR (CDCl$_3$) 1.06 (d, 6H), 1.48 (d, 3H), 2.10-2.25 (m, 4H), 2.45 (m, 1H), 2.85 (m, 1H), 5.63 (m, 1H), 6.99 (m, 4H), 7.22 (m, 2H), 7.35 (d, 2H).

Example 391

3-((R)-6-(4-fluorophenyl)-2-oxo-3-((S)-1-(4-(trifluoromethyl)phenyl)ethyl)-1,3-oxazinan-6-yl)propanamide

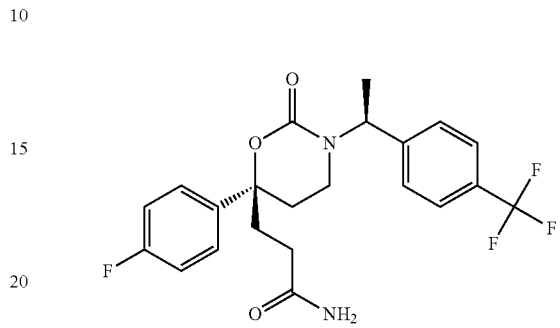

The title compound was prepared from (R)-6-(4-fluorophenyl)-6-(3-hydroxypropyl)-3-((S)-1-(4-(trifluoromethyl)phenyl)ethyl)-1,3-oxazinan-2-one following procedures analogous to those described in Example 234. LC-MS Method 3 $t_R$=1.051 min, m/z=461.1; $^1$H NMR (CDCl$_3$) 1.50 (d, 3H), 1.98 (m, 1H), 2.21 (m, 4H), 2.27 (m, 1H), 2.42 (m, 1H), 2.94 (m, 1H), 5.63 (m, 1H), 5.74 (s, 1H), 6.13 (s, 1H), 7.03 (m, 4H), 7.16 (m, 2H), 7.36 (d, 2H).

Example 392

(R)-3-((S)-1-(4-bromophenyl)ethyl)-6-(3-hydroxypropyl)-6-phenyl-1,3-oxazinan-2-one

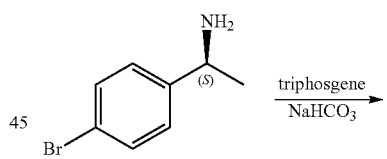

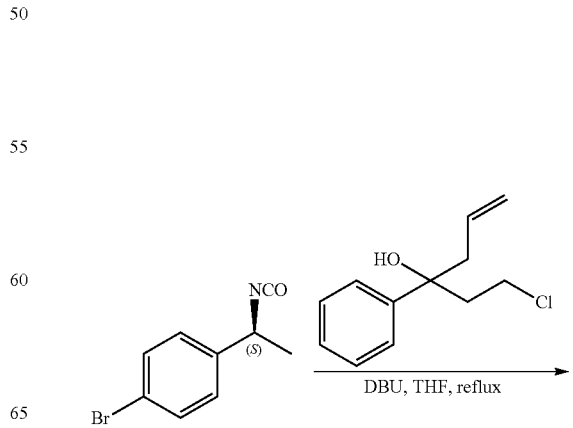

-continued

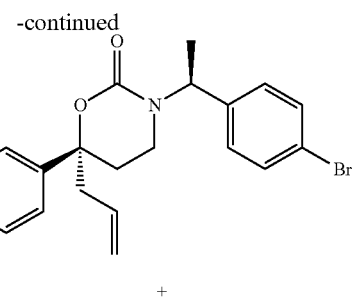

+

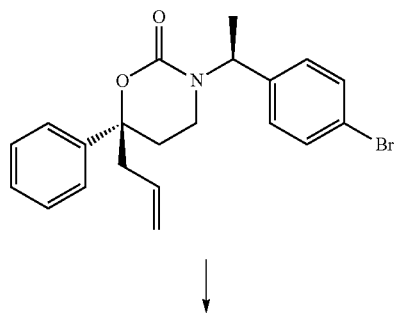

↓

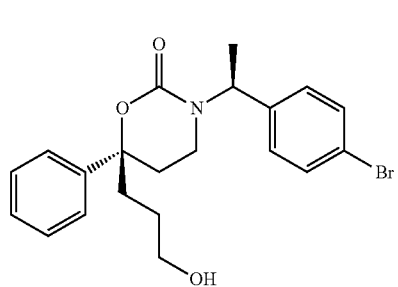

Step 1

To a solution of (S)-1-(4-bromophenyl)ethanamine (40 g, 0.2 mol) in methylene chloride (600 mL) and satd aq NaHCO₃ (600 mL) was added triphosgene (27 g, 0.025 mol) at 0° C. The mixture was stirred for 15 min. The organic phase was separated, dried and concentrated to give 1-bromo-4-(1-isocyanato-ethyl)-benzene (35 g, crude).

Step 2

A mixture of 1-chloro-3-phenyl-hex-5-en-3-ol (27.5 g, 130 mmol), (S)-(−)-1-(-bromophenyl)ethyl isocyanate (35 g, 160 mmol), and DBU (80 g, 325 mmol) in THF (400 mL) was heated to reflux for 25 h. The mixture was diluted with EtOAc and washed with 1 N aq HCl. The aqueous phase was extracted with EtOAc (3×). The combined organic phase was dried over Na₂SO₄. After the solvents were evaporated, the crude product was purified by column chromatography to give (R)-6-allyl-3-((S)-1-(4-bromophenyl)ethyl)-6-phenyl-1,3-oxazinan-2-one (30 g, yield 45%).

Step 3

The title compound was prepared from (R)-6-allyl-3-((S)-1-(4-bromophenyl)ethyl)-6-phenyl-1,3-oxazinan-2-one following a procedure analogous to that described in Example 78. LC-MS Method 2 $t_R$=1.36 min, m/z=440.1; ¹H NMR (CDCl₃) 1.26-1.39 (m, 1H), 1.42 (d, 3H), 1.58-1.71 (m, 1H), 1.85-1.95 (m, 2H), 2.11-2.45 (m, 3H), 2.79 (m, 1H), 3.52 (m, 2H), 5.54 (m, 1H), 6.67 (d, 2H), 7.12-7.31 (m, 7H).

Example 393

3-((R)-3-((S)-1-(4-bromophenyl)ethyl)-2-oxo-6-phenyl-1,3-oxazinan-6-yl)propanamide

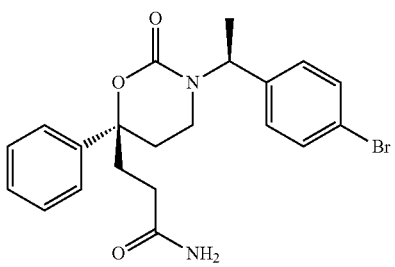 [SMILES: C[C@@H](c1ccc(Br)cc1)N1CC[C@](CCC(N)=O)(c2ccccc2)OC1=O]

The title compound was prepared from (R)-3-((S)-1-(4-bromophenyl)ethyl)-6-(3-hydroxypropyl)-6-phenyl-1,3-oxazinan-2-one following procedures analogous to those described in Example 234. LC-MS Method 2 $t_R$=1.288 min, m/z=431.2; ¹H NMR (CDCl₃) 1.48 (m, 3H), 1.91 (m, 1H), 2.08-2.3 (m, 5H), 2.45 (m, 1H), 2.81 (m, 1H), 5.32-5.51 (m, 2H), 5.60 (m, 1H), 6.72 (d, 2H), 7.02 (m, 4H), 7.32 (m, 3H).

Example 394

N-(3-((R)-3-((S)-1-(4-bromophenyl)ethyl)-2-oxo-6-phenyl-1,3-oxazinan-6-yl)propyl)methanesulfonamide

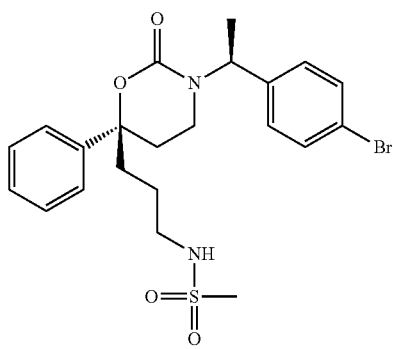 [SMILES: C[C@@H](c1ccc(Br)cc1)N1CC[C@](CCCNS(C)(=O)=O)(c2ccccc2)OC1=O]

The title compound was prepared from (R)-3-((S)-1-(4-bromophenyl)ethyl)-6-(3-hydroxypropyl)-6-phenyl-1,3-oxazinan-2-one following procedures analogous to those described in Example 359. LC-MS Method 2 $t_R$=1.458 min, m/z=494.09; $^1$H NMR (CDCl$_3$) 1.48 (d, 3H), 1.54 (m, 1H), 1.89-2.09 (m, 3H), 2.12-2.31 (m, 3H), 2.54 (s, 1H), 2.88 (m, 1H), 2.94 (s, 3H), 4.14 (m, 2H), 5.59 (m, 1H), 6.74 (d, 6H), 7.22 (m, 4H), 7.34 (m, 3H).

Example 395

(S)-3-((S)-1-(4-bromophenyl)ethyl)-6-(2-hydroxy-2-methylpropyl)-6-phenyl-1,3-oxazinan-2-one

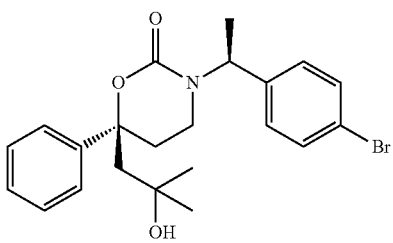 [SMILES: C[C@@H](c1ccc(Br)cc1)N1CC[C@](CC(C)(C)O)(c2ccccc2)OC1=O]

Method 1

The title compound was prepared from (R)-6-allyl-3-((S)-1-(4-bromophenyl)ethyl)-6-phenyl-1,3-oxazinan-2-one following procedures analogous to those described in Example 280. LC-MS Method 2 $t_R$=1.387 min, m/z=455.8; $^1$H NMR (CDCl$_3$) 1.10 (s, 3H), 1.16 (s, 3H), 1.49 (d, 3H), 2.13 (m, 1H), 2.19 (m, 2H), 2.26 (m, 1H), 2.37 (m, 1H), 2.82 (m, 1H), 5.61 (m, 1H), 6.77 (d, 2H), 7.24 (m, 1H), 7.32 (m, 5H).

Method 2

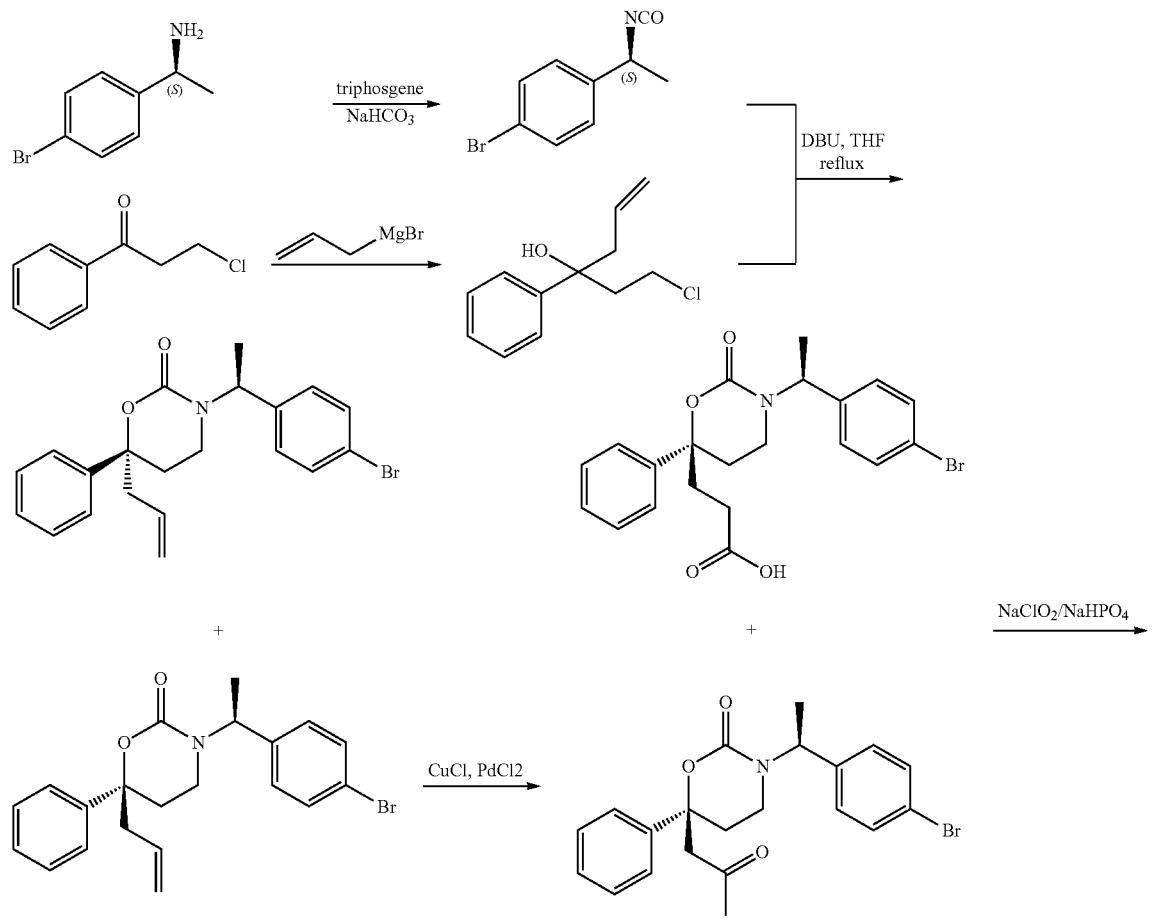

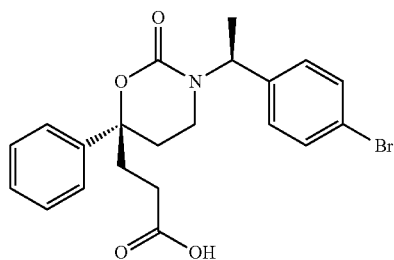

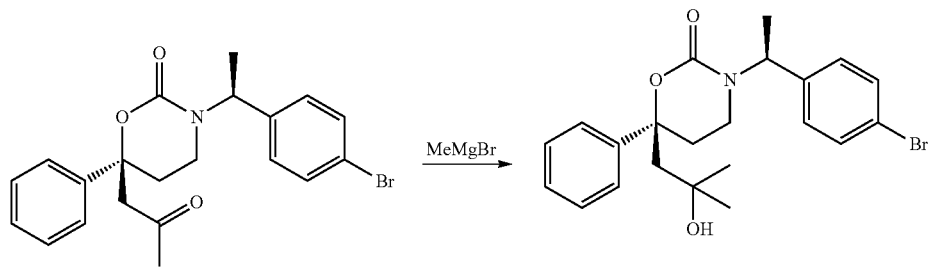

Step 1: (S)-1-bromo-4-(1-isocyanatoethyl)benzene

To a solution of (S)-1-(4-bromophenyl)ethanamine (240 g, 1.2 mol) in methylene chloride (3 L) and satd aq NaHCO$_3$ (3 L) solution was added triphosgene (118 g, 0.396 mol) at 0° C. The mixture was stirred for 15 min. The organic phase was separated, dried over Na$_2$SO$_4$ and concentrated to give 1-bromo-4-(1-isocyanato-ethyl)-benzene (170 g, 63%).

Step 2: 1-chloro-3-phenylhex-5-en-3-ol

To a solution of 3-chloro-1-phenylpropan-1-one (170 g, 1.01 mol) in anhydrous THF (1200 mL) was added allylmagnesium bromide (1.2 L, 1 mol/L) at −78° C. under nitrogen. The formed mixture was stirred for 30 min at −78° C. The reaction was quenched with aqueous NaHCO$_3$ solution. The organic phase was separated, dried over Na$_2$SO$_4$ and concentrated to give the crude product, which was purified by column chromatography (petroleum ether/EtOAc=100:1) to afford 1-chloro-3-phenylhex-5-en-3-ol (180 g, 86%). $^1$H NMR (CDCl$_3$): 2.27 (m, 2H), 2.51 (m, 1H), 2.74 (m, 1H), 3.22 (m, 1H), 3.58 (m, 1H), 5.16 (m, 2H), 5.53 (m, 1H), 7.23 (m, 1H), 7.39 (m, 4H).

Step 3: (R)-6-allyl-3-((S)-1-(4-bromophenyl)ethyl)-6-phenyl-1,3-oxazinan-2-one

A mixture of 1-chloro-3-phenyl-hex-5-en-3-ol (105 g, 0.050 mmol), (S)-(−)-1-(-bromophenyl)ethyl isocyanate (170 g, 0.752 mol), and DBU (228 g, 1.5 mol) in THF (1700 mL) was heated to reflux overnight. The mixture was diluted with EtOAc and washed with 1N aq HCl. The aqueous phase was extracted with EtOAc (3×). The combined organic phase was dried over Na$_2$SO$_4$. After the solvents were evaporated, the crude product was purified by column chromatography (petroleum ether/EtOAc=20:1 to 5:1) to give (R)-6-allyl-3-((S)-1-(4-bromophenyl)ethyl)-6-phenyl-1,3-oxazinan-2-one (100 g, 34%). $^1$H NMR (CDCl$_3$): 1.39 (d, 3H), 2.14 (m, 1H), 2.24 (m, 2H), 2.48-2.61 (m, 3H), 2.82 (m, 2H), 5.01 (m, 2H), 5.52 (q, 1H), 5.73 (m, 1H), 6.62 (d, 2H), 7.12 (m, 2H), 7.28 (m, 2H).

Step 4: (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal To a solution of (R)-6-allyl-3-((S)-1-(4-bromophenyl)ethyl)-6-phenyl-1,3-oxazinan-2-one (31 g, 78 mmol) and CuCl (19.3 g, 195 mmol) in dry DMF (150 mL) was added H$_2$O (50 mL) and PdCl$_2$ (4.10 g, 23 mmol) at rt. After addition, the mixture was stirred overnight under oxygen. After TLC showed the starting material had disappeared, the solid was filtered off. Water (200 mL) and EtOAc (200 mL) was added, the organic layers were separated and the aqueous layer was extracted with EtOAc (3×40 mL). The combined organic layer was washed with brine, dried over Na$_2$SO$_4$, filtered and concentrated to give a residue which was purified by column chromatography (petroleum ether/EtOAc=5:1 to 1:1) to give a mixture of (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal, (26 g, 81%).

Step 5: (S)-3-((S)-1-(4-bromophenyl)ethyl)-6-(2-oxopropyl)-6-phenyl-1,3-oxazinan-2-one To a mixture of (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal (20 g, 48.2 mmol) in t-BuOH (250 mL) and 2-methyl-2-butene (50 mL) was added a solution of NaClO$_2$ (19.3 g, 0.213 mol) and NaH$_2$PO$_4$ (28 g, 0.179 mol) in H$_2$O (300 mL) at 0° C. The formed mixture was stirred for 1 h at 0° C. The mixture was treated with water (100 mL) and extracted with CH$_2$Cl$_2$. The combined organic layer was dried over Na$_2$SO$_4$, filtered and concentrated to leave a residue, which was purified by column chromatography (petroleum ether/EtOAc=5:1 to 2.5:1) to afford (S)-3-((S)-1-(4-bromophenyl)ethyl)-6-(2-oxopropyl)-6-phenyl-1,3-oxazinan-2-one (10.0 g, 83%). $^1$H NMR (CDCl$_3$): 1.49 (d, 3H), 2.12 (s, 3H), 2.33 (m, 2H), 2.63 (m, 1H), 2.86-3.08 (m, 3H), 5.57 (q, 1H), 6.66 (d, 2H), 7.19 (m, 2H), 7.33 (m, 5H).

Step 6: (S)-3-((S)-1-(4-bromophenyl)ethyl)-6-(2-hydroxy-2-methylpropyl)-6-phenyl-1,3-oxazinan-2-one To a solution of (S)-3-((S)-1-(4-bromophenyl)ethyl)-6-(2-oxopropyl)-6-phenyl-1,3-oxazinan-2-one (20 g, 46.4 mmol) in anhydrous THF (200 mL) was added dropwise methylmagnesium bromide (31 mL, 144 mmol) at −78° C. under nitrogen. Then the mixture was stirred at rt for 1 h. The reaction mixture was quenched with aq NaHCO$_3$ (50 mL) under ice water bath. The organic layers were separated. The aqueous layer was extracted with EtOAc (150 mL). The combined organic layers were washed with brine, dried over Na$_2$SO$_4$ and concentrated in vacuo to give the crude product, which was purified column chromatography (petroleum ether/EtOAc=5:1 to 2:1) to afford (S)-3-((S)-1-(4-bromophenyl)ethyl)-6-(2-hydroxy-2-methylpropyl)-6-phenyl-1,3-oxazinan-2-one (13 g, 65%). After re-crystallization from EtOH, 4 g of the pure compound was obtained. $^1$H NMR (CDCl$_3$): 1.06 (s, 3H), 1.12 (s, 3H), 1.44 (d, 3H), 2.14 (m, 3H), 2.21 (m, 1H), 2.33 (m, 1H), 2.76 (m, 1H), 5.54 (q, 1H), 6.74 (d, 2H), 7.16 (d, 2H), 7.28 (m, 5H).

Alternative Procedure for Method 2 Step 2

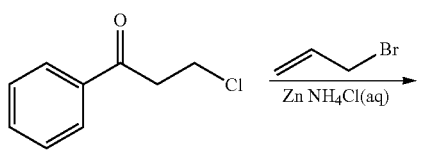

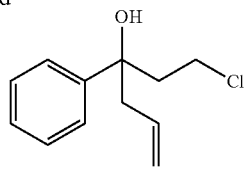

A solution of 3-chloro-1-phenylpropan-1-one (100 g, 0.595 mol) in THF (280 ml) was added dropwise to a well-stirred mixture of zinc powder (need not be activated) (40 g, 1.231 mol, satd aq NH$_4$Cl solution (1500 ml) and THF (400 ml). Allyl bromide (143 g, 1.19 mol) was dissolved in THF (200 ml) was slowly added to the reaction mixture. The reaction was mildly exothermic, and the mixture began to reflux spontaneously. After refluxing had ceased, the mixture was stirred for 1 h. The mixture was extracted with EtOAc, dried over anhydrous Na$_2$SO$_4$, and concentrated to give 1-chloro-3-phenylhex-5-en-3-ol (122 g, 97%). $^1$H NMR: (400 MHz, CDCl$_3$): δ=2.24 (s, 1H), 2.34 (m, 2H), 2.53 (m, 1H), 2.75 (m, 1H), 3.20 (m, 1H), 3.58 (m, 1H), 5.18 (t, 1H), 5.51 (m, 1H), 7.26 (m, 1H), 7.26-7.39 (m, 3H).

Method 3

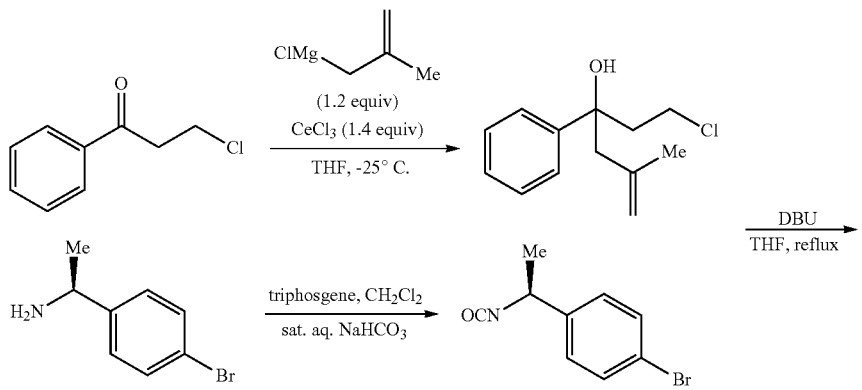

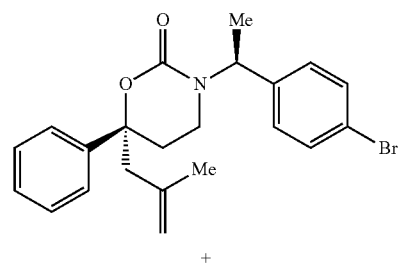

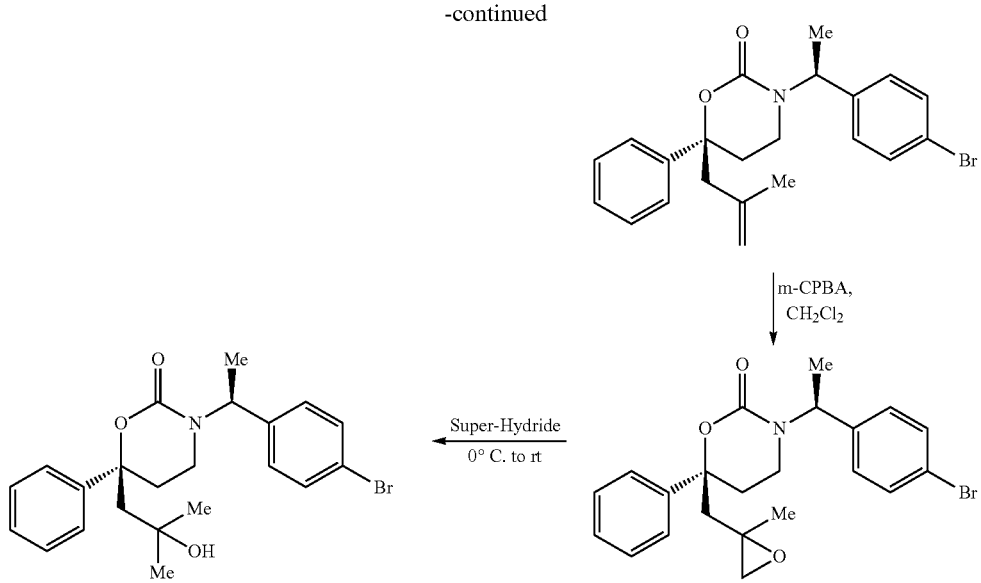

Step 1. 1-Chloro-5-methyl-3-phenyl-hex-5-en-3-ol

To a stirred suspension of magnesium turnings (46.7 g, 1.94 mol) in 1500 mL of THF ($H_2O$<100 ppm based on Karl Fischer titration) was charged 53.0 mL of 1 M DIBAL-H in hexane under nitrogen at rt. Then 3-chloro-2-methylprop-1-ene (160 g, 1.77 mol) was introduced while maintaining the internal temperature below 30° C. The resulting solution was agitated for 2 h at rt. The solution was titrated in the presence of 1.1'-bipyridine to indicate 0.8 M of the corresponding Grignard reagent. To a dry flask containing 307.0 g of anhydrous $CeCl_3$ (1.25 mol) at rt under nitrogen was added 1556.8 mL of the Grignard reagent (0.8 M, 1.25 mol). The resulting slurry was cooled to −10° C. and agitated for 0.5 h. To the slurry was added 200 g of 3-chloro-1-phenylpropan-1-one (1.19 mol) in 200 mL of THF while maintaining the internal temperature below 0° C. After the mixture was stirred for 0.5 h, 1200 mL of 1 M aq HCl was added to obtain a clear solution while maintaining the internal temperature below 30° C. After the phase cut, the aqueous layer was extracted with EtOAc (500 mL). The combined organic layers were washed with brine and dried over sodium sulfate. Removal of the solvent under vacuum produced crude 1-chloro-5-methyl-3-phenyl-hex-5-en-3-ol, which was chased with THF to achieve $H_2O$<500 ppm based on Karl Fischer titration. The crude product (306 g, 83 wt %, 95% yield) was used directly in Step 3. $^1$H-NMR spectroscopy (500 MHz, $CDCl_3$) δ 7.38-7.37 (d, J=7.8 Hz, 2H), 7.33 (t, J=7.9 Hz, 2H), 7.24 (t, J=7.4 Hz, 1H), 4.91 (s, 1H), 4.76 (s, 1H), 3.57 (ddd, J=5.6, 10.7, and 10.7, 1H), 3.13 (ddd, J=4.7, 10.7 and 10.7 Hz, 1H), 2.66 (d, J=13.3 Hz, 1H), 2.54 (d, J=11.3 Hz, 1H), 2.53 (s, 1H), 2.36 (ddd, J=5.4, 10.6 and 13.9 Hz. 1H), 2.29 (ddd, J=5.6, 11.3 and 13.3 Hz, 1H), 1.29 (s, 3H). $^{13}$C-NMR spectroscopy (125 MHz, $CDCl_3$) δ 144.3, 141.4, 128.0, 126.6, 124.8, 116.1, 74.2, 51.2, 46.0, 39.9, 23.9.

Step 2. 1-Bromo-4-((S)-1-isocyanato-ethyl)-benzene

To a 10 L jacketed reactor was charged 241 g of sodium bicarbonate (2.87 mol, 2.30 equiv) and 5 L of deionized water. The resulting solution was agitated for 10-20 min, until the solids dissolved (homogeneous). To the clear solution was charged 250 g (1.25 mol, 1.00 equiv) of (S)-(−)-1-(4-bromophenyl)ethylamine as a solution in 1.00 L of dichloromethane. An additional 4 L of dichloromethane was charged to the reactor. The biphasic solution was agitated and cooled to $T_{int}$=2-3° C. Triphosgene (126 g, 424 mmol, 0.340 equiv) was charged to the reactor in approximately two equal portions ~6 min apart. It should be noted that a slight exotherm was noted upon the addition of triphosgene. The resulting murky solution was agitated at $T_{int}$=2-5° C. for 30 min, at which point HPLC analysis indicates >99 A % conversion (220 nm). The dichloromethane layer was cut and dried with anhydrous sulfate. The resulting solution was passed through a celite plug and concentrated to ~1.5 L which fine particles of a white solid developed. The solution was filtered and concentrated to a thick oil via reduced pressure to produce 239 g of 1-bromo-4-((S)-1-isocyanato-ethyl)-benzene (93.7 wt %, 79.4% yield). $^1$H-NMR spectroscopy (400 MHz, $CD_2Cl_2$) δ 7.53 (d, J=11.4 Hz, 2H), 7.26 (d, J=8.2 Hz, 2H), 4.80 (q, J=6.7 Hz, 1H), 1.59 (d, J=6.7 Hz, 3H). The material was used in Step 3 without further purification.

Step 3. (R)-3-((S)-1-(4-bromophenyl)ethyl)-6-(2-methylallyl)-6-phenyl-1,3-oxazinan-2-one To a dried 10 L jacketed reactor under a nitrogen atmosphere was charged 1-chloro-5-methyl-3-phenyl-hex-5-en-3-ol (167 g, 81.7 wt %, 610 mmol, 1.00 equiv), 1-bromo-4-((S)-1-isocyanato-ethyl)-benzene (219 g, 93.7 wt %, 911 mmol, 1.50 equiv), anhydrous tetrahydrofuran (3.00 L), and then 1,8-diazabicyclo[5.4.0]undec-7-ene (DBU, 409 mL, 2.73 mol, 4.50 equiv). The resulting solution was agitated and refluxed ($T_{int}$=67-69° C., $T_{ext}$=75° C.) for 19 h, at which point HPLC analysis indicated ~1 A % (220 nm) of the 1-chloro-5-methyl-3-phenyl-hex-5-en-3-ol remained. The dark solution was cooled to $T_{int}$=20-25° C. Two liters of tetrahydrofuran were removed by distillation under reduced pressure. The remaining dark solution was diluted with 4.0 L of ethyl acetate and 1.0 L of hexanes. The resulting solution was washed with 4.0 L of a 1.0 M aqueous solution of hydrogen chloride (note: the wash is slightly exothermic). The aqueous solution was cut and the remaining organic solution was dried with anhydrous sodium sulfate, filtered and then concentrated to an oil via reduced pressure. The resulting material was subjected to flash silica chromatography (5-30% ethyl acetate/hexanes, 1.74 kg of silica) to produce 137.8 g of material (59 wt %, 3.1:1 diastereomeric ratio favoring the desired diastereomer (R)-3-(S)-1-(4-bromophenyl)ethyl)-6-(2-methylallyl)-6-phenyl-1,3-oxazinan-2-one, 32.3% yield). The material was used in Step 4 without further purification.

Analytical data for (R)-3-((S)-1-(4-bromophenyl)ethyl)-6-(2-methylallyl)-6-phenyl-1,3-oxazinan-2-one: $^1$H-NMR spectroscopy (500 MHz, CD$_2$Cl$_2$) δ 7.42-7.35 (m, 3H), 7.33-7.31 (m, 2H), 7.25-7.23 (m, 2H), 6.80-6.74 (m, 2), 5.55 (q, J=7.1 Hz, 1H), 5.37-5.36 (m, 1H), 4.89 (s, 1H), 4.69 (s, 1H), 2.96-2.93 (m, 1H), 2.61 (dd, J=13.8 and 26.4 Hz, 2H), 2.37-2.25 (m, 3H), 1.68 (s, 3H), 1.50 (d, J=7.1 Hz, 3H). $^{13}$C-NMR spectroscopy (125 MHz, CD$_2$Cl$_2$) δ 152.5, 141.5, 140.1, 138.3, 130.6, 128.1, 128.0, 126.9, 124.4, 120.2, 115.3, 82.4, 52.1, 50.1, 35.6, 29.8, 23.4, 14.5.

Analytical data for (S)-3-((S)-1-(4-bromophenyl)ethyl)-6-(2-methylallyl)-6-phenyl-1,3-oxazinan-2-one: $^1$H-NMR spectroscopy (400 MHz, CD$_2$Cl$_2$) δ 7.50-7.48 (m, 2H), 7.43-7.39 (m, 2H), 7.35-7.32 (m, 3H), 7.20-7.18 (m, 2H), 5.60 (q, J=7.1 Hz, 1H), 4.85 (s, 1H), 4.66 (s, 1H), 2.73-2.67 (m, 2H), 2.60 (dd, J=13.9 and 19.4 Hz, 2H), 2.28 (dt, J=3.3 and 13.7 Hz, 1H), 2.14-2.05 (m, 1H), 1.66 (s, 3H), 1.24 (d, J=7.2 Hz, 3H). $^{13}$C-NMR spectroscopy (100 MHz, CD$_2$Cl$_2$) δ 153.4, 142.5, 141.0, 140.1, 131.8, 129.3, 128.9, 127.8, 125.3, 121.5, 116.3, 83.9, 53.2, 51.0, 36.6, 31.3, 24.3, 15.4.

Step 4. (6S)-3-((S)-1-(4-bromophenyl)ethyl)-6-((2-methyloxiran-2-yl)methyl)-6-phenyl-1,3-oxazinan-2-one To a 1.0 L 2-neck RBF was charged (R)-3-((S)-1-(4-bromophenyl)ethyl)-6-(2-methylallyl)-6-phenyl-1,3-oxazinan-2-one (135.8 g, 59 wt %, 3.1:1 dr, 193 mmol, 1.00 equiv), dichloromethane (700 mL), and then 3-chloroperbenzoic acid (m-CPBA, 70%, 95.3 g, 386 mmol, 2.0 equiv). The resulting solution was agitated at rt (T$_{int}$=20-25° C.) for 1 h, which HPLC analysis indicates >99 A % (220 nm) conversion. The resulting solution was diluted with 700 mL of methyl tert-butyl ether (MTBE) and washed with 1×500 mL of 30 wt % solution of sodium thiosulfate and 1×500 mL of saturated aqueous solution of sodium bicarbonate. The wash sequence was repeated until the peak on an HPLC trace of the organic solution that corresponds to a HPLC sample peak of m-CPBA is <2.5 A % (220 nm), which in this example the wash sequence was repeated 3 times. The resulting organic layer was dried with anhydrous sodium sulfate, filtered and then concentrated to an oil via reduced pressure. The resulting material was diluted with 200 mL of anhydrous tetrahydrofuran and then concentrated to a thick oil via reduced pressure to provide (6S)-3-((S)-1-(4-bromophenyl)ethyl)-6-((2-methyloxiran-2-yl)methyl)-6-phenyl-1,3-oxazinan-2-one which was used directly in Step 5.

Step 5. (S)-3-((S)-1-(4-bromophenyl)ethyl)-6-(2-hydroxy-2-methylpropyl)-6-phenyl-1,3-oxazinan-2-one To a 2.0 L 3-neck oven-dried RBF was charged the crude (6S)-3-((S)-1-(4-bromophenyl)ethyl)-6-((2-methyloxiran-2-yl)methyl)-6-phenyl-1,3-oxazinan-2-one and 750 mL of anhydrous THF. The resulting solution was agitated and cooled to T$_{int}$=2-3° C. To the agitated clear solution was charged 1.0 M lithium triethylborohydride in tetrahydrofuran (Super Hydride, 348 mL, 348 mmol, 1.8 equiv). The addition is exothermic and addition was controlled to maintain T$_{int}$=<8° C. The resulting solution was agitated at T$_{int}$=2-3° C. for 1.5 h and then allowed to warm to T$_{int}$=10-13° C. over a 2.5 h, which HPLC analysis indicates ~94 A % (220 nm) conversion. To the agitated solution was charged a solution of hydrogen peroxide (95.7 mL of a 35 wt % aqueous solution diluted with 400 mL of water, 1.08 mol, 5.60 equiv). The addition is highly exothermic and addition was controlled to maintain T$_{int}$=<25° C. The resulting solution was diluted with 1.00 L of methyl tert-butyl ether (MTBE) and washed with 1.00 L of water followed by 500 mL of a ~30 wt % solution of sodium thiosulfate. The organic solution was dried with anhydrous sodium sulfate, filtered, and then concentrated via reduced pressure. The resulting material was subjected to flash silica chromatography (10-60% ethyl acetate, 600 g of silica) to produce 68 g of material consisting of both diastereomers (1.98:1 dr) and 41 g of the desired diastereomer, (>99:1 dr). The material consisting of the mixed fractions was recrystallized from 250 mL of isopropyl acetate (IPAC) and 200 mL of heptane (anti-solvent) to produce upon filtration 31.3 g of product (95.7 A % at 220 nm, 74:1 dr). The two samples were combined to produce 72.3 g of (S)-3-((S)-1-(4-bromophenyl)ethyl)-6-(2-hydroxy-2-methylpropyl)-6-phenyl-1,3-oxazinan-2-one (83.6% yield for the two step operation). $^1$H-NMR spectroscopy (400 MHz, CDCl$_3$) δ 7.37-7.29 (m, 5H), 7.25-7.21 (m, 2H), 6.82-6.79 (m, 2H), 5.61 (q, J=6.9 Hz, 1H), 2.83 (ddd, J=2.5, 5.4 and 11.6 Hz, 1H), 2.39 (ddd, J=5.7, 12.0 and 14.1 Hz, 1H), 2.27 (ddd, J=2.6, 4.8 and 14.0 Hz, 1H), 2.21-2.14 (m, 3H), 2.08 (s, 1H), 1.49 (d, J=7.0 Hz, 3H), 1.18 (s, 3H), 1.13 (s, 3H). $^{13}$C-NMR spectroscopy (100 MHz, CDCl$_3$) δ 153.2, 142.6, 138.5, 131.6, 129.13, 129.10, 128.0, 125.3, 121.6, 84.2, 71.4, 54.1, 53.3, 36.4, 33.6, 32.1, 30.8, 15.6.

Example 396

(S)-3-((S)-1-(4-bromophenyl)ethyl)-6-(2-hydroxyethyl)-6-phenyl-1,3-oxazinan-2-one

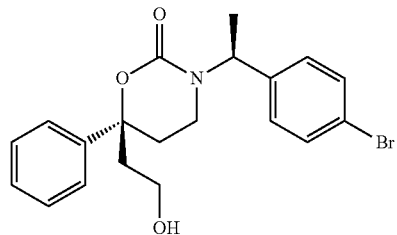 [SMILES: C[C@@H](c1ccc(Br)cc1)N1CC[C@](CCO)(c2ccccc2)OC1=O]

The title compound was prepared from (R)-6-allyl-3-((S)-1-(4-bromophenyl)ethyl)-6-phenyl-1,3-oxazinan-2-one following procedures analogous to those described in Example 74. LC-MS Method 2 t$_R$=1.332 min, m/z=425.9; $^1$H NMR (CDCl₃) 1.42 (d, 3H), 2.04-2.33 (m, 5H), 2.81 (m, 1H), 3.51 (m, 1H), 3.21 (m, 1H), 5.53 (m, 1H), 6.65 (d, 2H), 7.12 (m, 2H), 7.22-7.31 (m, 5H).

Example 397

(R)-3-((S)-1-(4-bromophenyl)ethyl)-6-(2-morpholinoethyl)-6-phenyl-1,3-oxazinan-2-one

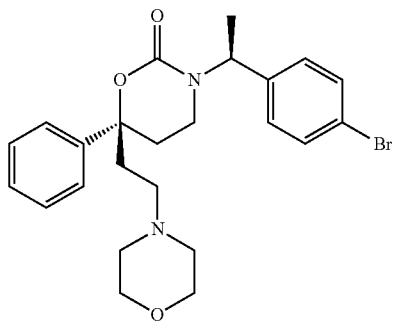 [SMILES: C[C@@H](c1ccc(Br)cc1)N1CC[C@](CCN2CCOCC2)(c2ccccc2)OC1=O]

The title compound was prepared from (S)-3-((S)-1-(4-bromophenyl)ethyl)-6-(2-hydroxyethyl)-6-phenyl-1,3-oxazinan-2-one following procedures analogous to those described in Example 178. LC-MS Method 2 $t_R$=1.645 min, m/z=472.14; ¹H NMR (CDCl₃) 1.52 (d, 3H), 1.65 (s, 2H), 2.14 (m, 3H), 2.20-2.42 (m, 7H), 2.58 (m, 1H), 2.89 (m, 1H), 3.67 (m, 4H), 5.64 (m, 1H), 6.75 (d, 2H), 7.23 (d, 2H), 7.30 (m, 2H), 7.37 (m, 3H).

Example 398

3-((R)-3-((S)-1-(4-bromophenyl)propyl)-2-oxo-6-phenyl-1,3-oxazinan-6-yl)propanamide

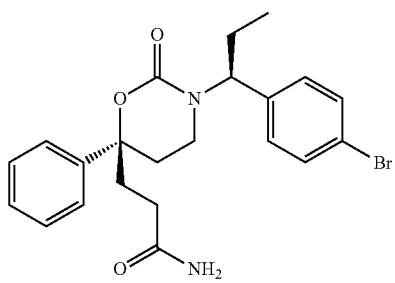 [SMILES: CC[C@@H](c1ccc(Br)cc1)N1CC[C@](CCC(N)=O)(c2ccccc2)OC1=O]

The title compound was prepared from (R)-3-((S)-1-(4-bromophenyl)propyl)-6-(3-hydroxypropyl)-6-phenyl-1,3-oxazinan-2-one following procedures analogous to those described in Example 234. LC-MS Method 2 $t_R$=1.328 min, m/z=469; ¹H NMR (CDCl₃) 0.91 (t, 3H), 1.75-1.93 (m, 3H), 2.11-2.26 (m, 5H), 2.37-2.47 (m, 1H), 2.86 (m, 1H), 5.22 (m, 1H), 5.35 (m, 2H), 6.82 (d, 2H), 7.12-7.25 (m, 7H).

Example 399

(S)-6-(2-hydroxyethyl)-6-phenyl-3-((S)-1-(4-(trifluoromethyl)phenyl)ethyl)-1,3-oxazinan-2-one

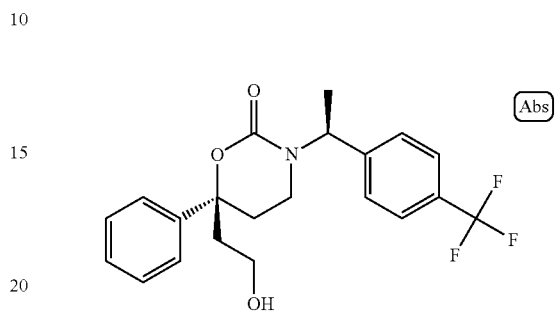

The title compound was prepared from (R)-6-allyl-6-phenyl-3-((S)-1-(4-(trifluoromethyl)phenyl)ethyl)-1,3-oxazinan-2-one following procedures analogous to those described in Example 74. LC-MS Method 3 $t_R$=1.074 min, m/z=394; ¹H NMR (CDCl₃) 1.47 (d, 3H), 2.03-2.19 (m, 2H), 2.20-2.37 (m, 3H), 2.87 (m, 1H), 3.53 (m, 1H), 3.72 (m, 1H), 5.62 (m, 1H), 6.89 (d, 2H), 7.20-7.34 (m, 7H).

Example 400

(S)-6-(2-hydroxy-2-methylpropyl)-6-phenyl-3-((S)-1-(4-(trifluoromethyl)phenyl)ethyl)-1,3-oxazinan-2-one

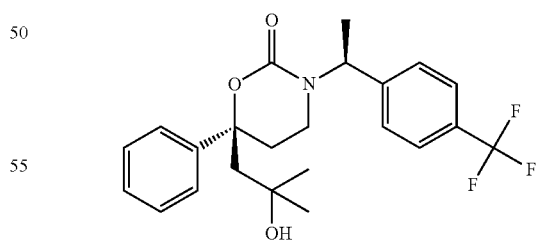

The title compound was prepared from (R)-6-allyl-6-phenyl-3-((S)-1-(4-(trifluoromethyl)phenyl)ethyl)-1,3-oxazinan-2-one following procedures analogous to those described in Example 280. LC-MS Method 3 $t_R$=1.17 min, m/z=444; ¹H NMR (CDCl₃) 1.06 (s, 3H), 1.11 (s, 3H), 1.48 (d, 3H), 2.09-

2.17 (m, 3H), 2.24 (m, 1H), 2.37 (m, 1H), 2.81 (m, 1H), 5.63 (m, 1H), 6.97 (d, 2H), 7.21-7.73 (m, 7H).

Example 401

(S)-3-((S)-1-(4-chlorophenyl)ethyl)-6-(2-hydroxyethyl)-6-phenyl-1,3-oxazinan-2-one

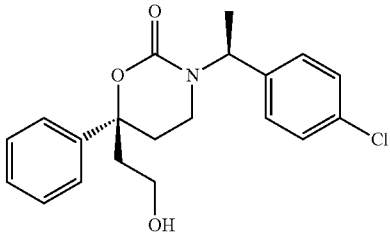 [SMILES: C[C@@H](c1ccc(Cl)cc1)N1CC[C@](CCO)(c2ccccc2)OC1=O]

The title compound was prepared from (S)-3-((S)-1-(4-bromophenyl)ethyl)-6-(2-hydroxyethyl)-6-phenyl-1,3-oxazinan-2-one following procedures analogous to those described in Example 187 Step 1. LC-MS Method 2 $t_R$=1.95 min, m/z=359.9; $^1$H NMR (CDCl$_3$) 1.49 (d, 3H), 2.09-2.40 (m, 5H), 2.89 (m, 1H), 3.56 (m, 1H), 3.74 (m, 1H), 5.61 (m, 1H), 6.79 (d, 2H), 7.06 (d, 2H), 7.28 (m, 2H), 7.37 (m, 3H).

Example 402

(S)-3-((S)-1-(4-chlorophenyl)ethyl)-6-(2-hydroxy-2-methylpropyl)-6-phenyl-1,3-oxazinan-2-one

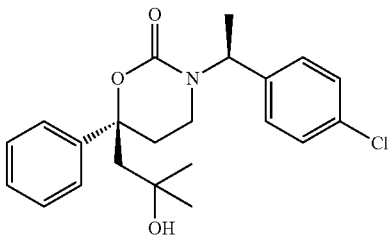 [SMILES: C[C@@H](c1ccc(Cl)cc1)N1CC[C@](CC(C)(C)O)(c2ccccc2)OC1=O]

The title compound was prepared from (R)-6-allyl-3-((S)-1-(4-chlorophenyl)ethyl)-6-phenyl-1,3-oxazinan-2-one following procedures analogous to those described in Example 328. LC-MS Method 2 $t_R$=1.35 min, m/z=409.95; $^1$H NMR (CDCl$_3$) 1.08 (s, 3H), 1.21 (s, 3H), 1.43 (d, 3H), 2.12 (m, 1H), 2.17 (m, 2H), 2.18 (m, 1H), 2.32 (m, 1H), 2.77 (m, 1H), 5.54 (m, 1H), 6.81 (d, 2H), 7.02 (d, 2H), 7.23-7.31 (m, 5H).

Example 403

(R)-3-((S)-1-(4-chlorophenyl)ethyl)-6-(3-hydroxypropyl)-6-phenyl-1,3-oxazinan-2-one

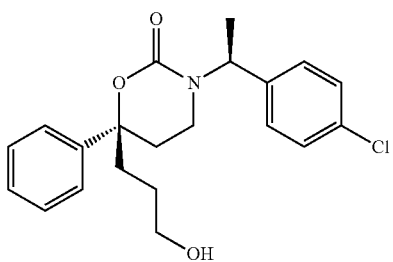 [SMILES: C[C@@H](c1ccc(Cl)cc1)N1CC[C@](CCCO)(c2ccccc2)OC1=O]

The title compound was prepared from (R)-3-((S)-1-(4-bromophenyl)ethyl)-6-(3-hydroxypropyl)-6-phenyl-1,3-oxazinan-2-one following a procedure analogous to that described in Example 187 Step 1. LC-MS Method 2 $t_R$=1.334 min, m/z=396; $^1$H NMR (CDCl$_3$) 1.40 (m, 1H), 1.53 (d, 3H), 1.73 (m, 1H), 2.00 (m, 2H), 2.12-2.35 (m, 3H), 2.86 (m, 1H), 3.59 (m, 2H), 5.63 (m, 1H), 6.79 (d, 2H), 7.06 (d, 2H), 7.28 (m, 2H), 7.37 (m, 3H).

Example 404

N-(3-((R)-3-((S)-1-(4-chlorophenyl)ethyl)-2-oxo-6-phenyl-1,3-oxazinan-6-yl)propyl)methanesulfonamide

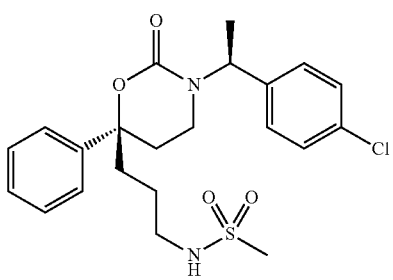 [SMILES: C[C@@H](c1ccc(Cl)cc1)N1CC[C@](CCCNS(C)(=O)=O)(c2ccccc2)OC1=O]

The title compound was prepared from N-(3-((R)-3-((S)-1-(4-bromophenyl)ethyl)-2-oxo-6-phenyl-1,3-oxazinan-6-yl)propyl)methanesulfonamide following a procedure analogous to that described in Example 187 Step 1. LC-MS Method 2 $t_R$=1.449 min, m/z=452.1; $^1$H NMR (CDCl$_3$) 1.41 (d, 3H), 1.50 (m, 2H), 1.88-1.98 (m, 3H), 2.08-2.26 (m, 3H), 2.79 (m, 1H), 2.91 (s, 3H), 4.07-(m, 2H), 5.56 (m, 1H), 6.73 (s, 2H), 6.98 (s, 2H), 7.18 (m, 2H), 7.26 (m, 3H).

Example 405

3-((R)-3-((S)-1-(4-cyanophenyl)ethyl)-6-(4-fluorophenyl)-2-oxo-1,3-oxazinan-6-yl)propanamide

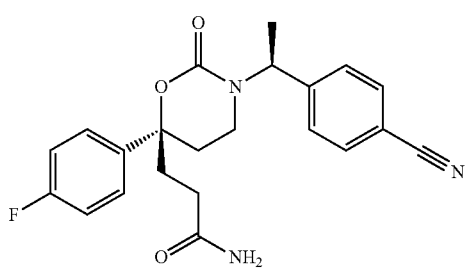 [SMILES: C[C@@H](c1ccc(C#N)cc1)N1CC[C@](CCC(N)=O)(c2ccc(F)cc2)OC1=O]

The title compound was prepared by treatment of (R)-6-allyl-3-((S)-1-(4-bromophenyl)ethyl)-6-(4-fluorophenyl)-1,3-oxazinan-2-one with Zn(CN)$_2$ followed by a procedure analogous to that described in Example 78 followed by a procedure analogous to that described in Example 243. LC-MS Method 3 $t_R$=0.697 min, m/z=418; $^1$H NMR (CDCl$_3$) 1.55 (d, 3H), 2.21 (m, 1H), 2.23-2.34 (m, 4H), 2.52 (m, 1H), 3.03 (m, 1H), 5.44 (m, 2H), 5.70 (m, 1H), 7.08 (m, 4H), 7.26 (m, 2H), 7.48 (d, 2H).

Example 406

(S)-6-(4-fluorophenyl)-3-((S)-1-(4-fluorophenyl)ethyl)-6-(2-hydroxyethyl)-1,3-oxazinan-2-one

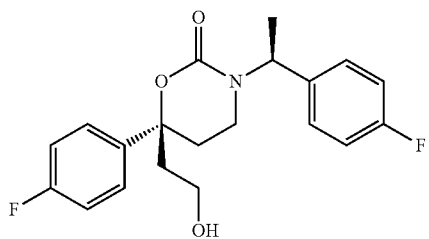 [SMILES: C[C@@H](c1ccc(F)cc1)N1CC[C@](CCO)(c2ccc(F)cc2)OC1=O]

The title compound was prepared from (R)-6-allyl-6-(4-fluorophenyl)-3-((S)-1-(4-fluorophenyl)ethyl)-1,3-oxazinan-2-one following procedures analogous to those described in Example 74. LC-MS Method 2 $t_R$=1.251 min, m/z=361.38; $^1$H NMR (CD$_3$OD) 1.51 (m, 3H), 2.11 (t, 2H), 2.25 (m, 2H), 2.47 (m, 1H), 3.08 (m, 1H), 3.34 (m, 1H), 3.68 (m, 1H), 5.51 (m, 1H), 6.85 (m, 2H), 6.97 (m, 2H), 7.10 (m, 2H), 7.231 (m, 3H).

Example 407

(S)-6-(4-fluorophenyl)-3-((S)-1-(4-fluorophenyl)ethyl)-6-(2-hydroxy-2-methylpropyl)-1,3-oxazinan-2-one

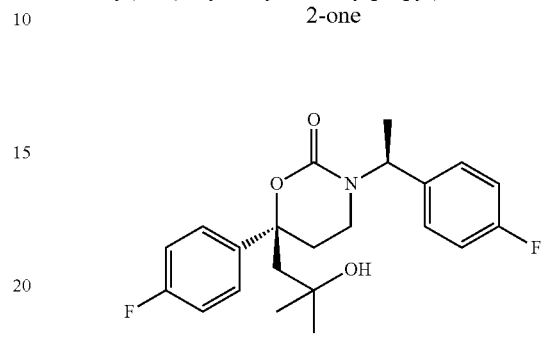

The title compound was prepared from (R)-6-allyl-6-(4-fluorophenyl)-3-((S)-1-(4-fluorophenyl)ethyl)-1,3-oxazinan-2-one following procedures analogous to those described in Example 328. LC-MS Method 2 $t_R$=1.939 min, m/z=412; $^1$H NMR (CDCl$_3$) 1.15 (d, 6H), 1.48 (d, 3H), 2.09-2.26 (m, 4H), 2.40 (m, 1H), 2.87 (m, 1H), 5.64 (m, 1H), 6.80 (t, 2H), 6.90 (t, 2H), 7.02 (t, 2H), 7.27 (m, 2H).

Example 408

(6S)-6-(4-fluorophenyl)-3-((S)-1-(4-fluorophenyl)ethyl)-6-(2-hydroxypropyl)-1,3-oxazinan-2-one

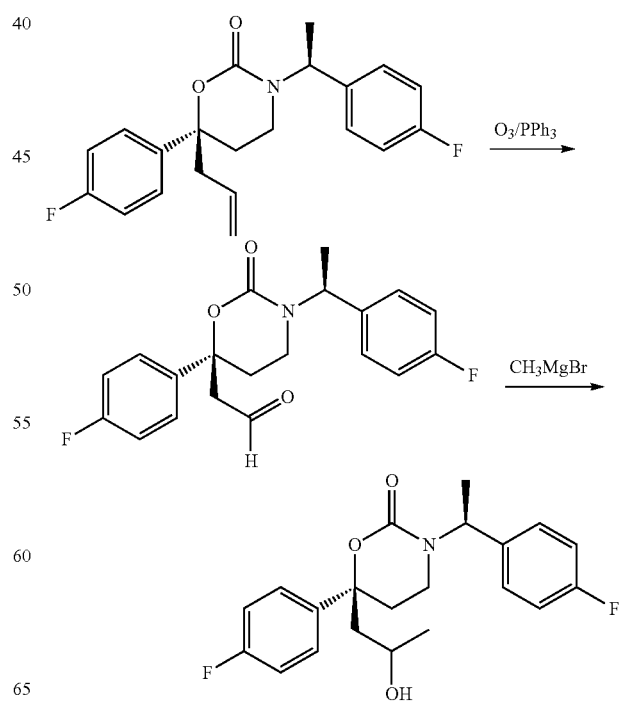

Step 1

Ozone was passed into a solution of (R)-6-allyl-6-(4-fluorophenyl)-3-((S)-1-(4-fluorophenyl)ethyl)-1,3-oxazinan-2-one (500 mg, 1.40 mmol) in anhydrous CH$_2$Cl$_2$ (20 mL) at −78° C. until a blue color appeared. Then Ph$_3$P (920 mg, 3.5 mmol) was added at −78° C. The formed mixture was stirred overnight. The mixture was concentrated to give crude 2-((S)-6-(4-fluorophenyl)-3-((S)-1-(4-fluorophenyl)ethyl)-2-oxo-1,3-oxazinan-6-yl)acetaldehyde, which was used for the next step without purification.

Step 2

To a solution of 2-((S)-6-(4-fluorophenyl)-3-((S)-1-(4-fluorophenyl)ethyl)-2-oxo-1,3-oxazinan-6-yl)acetaldehyde (500 mg, 1.40 mmol) in anhydrous THF (100 mL) was added CH$_3$MgBr (5 mL, 3 mol/L) at −78° C. under nitrogen. The formed mixture was stirred for 3 h at −78° C. The reaction was quenched by water. The organic phase was separated and concentrated to give the crude product, which was purified by TLC and chiral preparative HPLC to afford (6S)-6-(4-fluorophenyl)-3-((S)-1-(4-fluorophenyl)ethyl)-6-(2-hydroxypropyl)-1,3-oxazinan-2-one (19 mg, 4%). LC-MS Method 2 t$_R$=1.92 min, m/z=398; $^1$H NMR: (400 MHz, CDCl$_3$): δ=1.02 (d, 3H), 1.48 (d, 3H), 1.84 (m, 4H), 2.01 (m, 1H), 2.14 (m, 1H), 2.29 (m, 1H), 2.84 (m, 1H), 3.83 (m, 1H), 5.54 (q, 1H), 6.74 (m, 2H), 6.82 (m, 2H), 6.99 (m, 2H), 7.21 (m, 1H).

Example 409

N-(3-((R)-6-(4-fluorophenyl)-3-((S)-1-(4-fluorophenyl)ethyl)-2-oxo-1,3-oxazinan-6-yl)propyl)methanesulfonamide

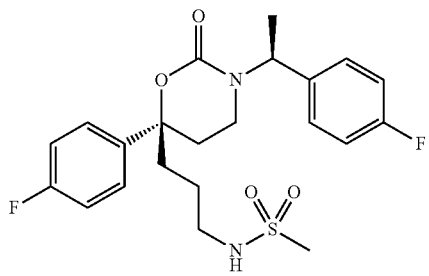 [SMILES: C[C@@H](c1ccc(F)cc1)N1CC[C@](CCCNS(C)(=O)=O)(c2ccc(F)cc2)OC1=O]

The title compound was prepared from (R)-6-(4-fluorophenyl)-3-((S)-1-(4-fluorophenyl)ethyl)-6-(3-hydroxypropyl)-1,3-oxazinan-2-one following procedures analogous to those described in Example 359. LC-MS Method 3 t$_R$=1.071 min, m/z=452.16; $^1$H NMR (CDCl$_3$) 1.27 (m, 1H), 1.48 (d, 3H), 1.54-1.67 (m, 1H), 1.85 (m, 1H), 1.94 (m, 1H), 2.09-2.21 (m, 3H), 2.78 (m, 4H), 3.01 (t, 2H), 4.39 (s, 1H), 5.55 (m, 1H), 6.77 (m, 2H), 6.86 (m, 2H), 6.98 (m, 2H), 7.15 (m, 2H).

Example 410

(R)-6-(4-fluorophenyl)-3-((S)-1-(4-fluorophenyl)ethyl)-6-(3-hydroxy-3-methylbutyl)-1,3-oxazinan-2-one

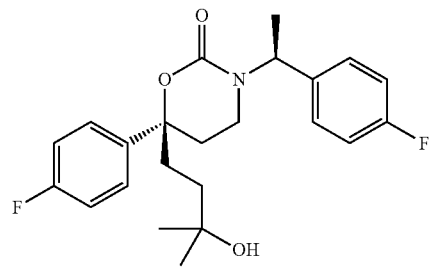 [SMILES: C[C@@H](c1ccc(F)cc1)N1CC[C@](CCC(C)(C)O)(c2ccc(F)cc2)OC1=O]

The title compound was prepared from (R)-6-(4-fluorophenyl)-3-((S)-1-(4-fluorophenyl)ethyl)-6-(3-hydroxypropyl)-1,3-oxazinan-2-one following procedures analogous to those described in Example 117. LC-MS Method 2 t$_R$=1.331 min, m/z=426; $^1$H NMR (CDCl$_3$) 1.08-1.19 (m, 7H), 1.49 (d, 3H), 1.51 (m, 1H), 1.87-2.06 (m, 2H), 2.21 (m, 3H), 2.90 (m, 1H), 5.63 (m, 1H), 6.82 (m, 2H), 6.89 (m, 2H), 7.04 (m, 2H), 7.10 (m, 2H).

Example 411

(R)-6-(4-fluorophenyl)-3-((1S)-1-(4-fluorophenyl)ethyl)-6-(3-hydroxybutyl)-1,3-oxazinan-2-one

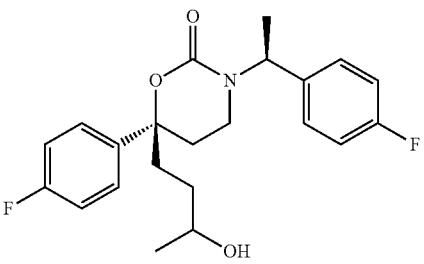 [SMILES: CC(O)CC[C@]1(c2ccc(F)cc2)CCN([C@@H](C)c2ccc(F)cc2)C(=O)O1]

The title compound was prepared from (R)-6-allyl-6-(4-fluorophenyl)-3-((S)-1-(4-fluorophenyl)ethyl)-1,3-oxazinan-2-one following procedures analogous to those described in Example 372. Two isomers were isolated.

Isomer 1: LC-MS Method 2 t$_R$=1.296 min, m/z=412; $^1$H NMR (CDCl$_3$) 1.04 (d, 3H), 1.43 (d, 3H), 1.50-1.60 (m, 1H), 1.79-2.00 (m, 2H), 2.05-2.15 (m, 3H), 2.84 (m, 1H), 3.65 (m, 1H), 5.58 (m, 1H), 6.75 (t, 2H), 6.84 (m, 2H), 6.96 (t, 2H), 7.18 (m, 2H).

Isomer 2: LC-MS Method 2 t$_R$=1.307 min, m/z=389.18; $^1$H NMR (CDCl$_3$) 1.01 (d, 3H), 1.21 (m, 1H), 1.48 (d, 3H), 1.50

(m, 1H), 1.72 (m, 1H), 1.94 (m, 1H), 2.11 (m, 3H), 2.78 (m, 1H), 3.55 (m, 1H), 5.52 (m, 1H), 6.66-6.80 (m, 4H), 6.91 (m, 2H), 7.14 (m, 2H).

Example 412

(S)-3-((S)-1-(4-fluorophenyl)ethyl)-6-(2-hydroxyethyl)-6-phenyl-1,3-oxazinan-2-one

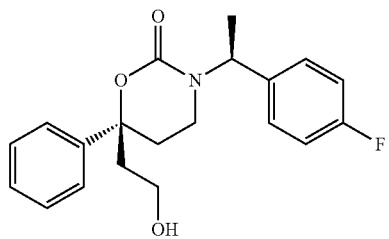 [SMILES: C[C@@H](c1ccc(F)cc1)N1CC[C@](CCO)(c2ccccc2)OC1=O]

The title compound was prepared from (R)-6-allyl-3-((S)-1-(4-fluorophenyl)ethyl)-6-phenyl-1,3-oxazinan-2-one following procedures analogous to those described in Example 74. LC-MS Method 3 $t_R$=0.921 min, m/z=343.9; $^1$H NMR (CDCl$_3$) 1.19 (m, 1H), 1.43 (d, 3H), 2.03-2.34 (m, 4H), 2.82 (m, 1H), 3.51 (m, 1H), 3.69 (m, 1H), 5.56 (m, 1H), 6.71 (m, 2H), 6.78 (m, 2H), 7.18-7.32 (m, 4H).

Example 413

(S)-3-((S)-1-(4-fluorophenyl)ethyl)-6-(2-hydroxy-2-methylpropyl)-6-phenyl-1,3-oxazinan-2-one

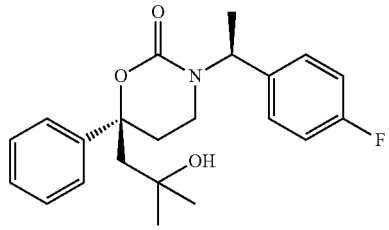 [SMILES: C[C@@H](c1ccc(F)cc1)N1CC[C@](CC(C)(C)O)(c2ccccc2)OC1=O]

The title compound was prepared from (R)-6-allyl-3-((S)-1-(4-fluorophenyl)ethyl)-6-phenyl-1,3-oxazinan-2-one following procedures analogous to those described in Example 280. LC-MS Method 3 $t_R$=1.059 min, m/z=394; $^1$H NMR (CDCl$_3$) 1.05 (s, 3H), 1.11 (s, 3H), 1.43 (d, 3H), 2.05 (m, 1H), 2.18 (s, 2H), 2.21 (m, 1H), 2.33 (m, 1H), 2.76 (m, 1H), 5.59 (m, 1H), 6.75 (m, 2H), 6.86 (m, 2H), 7.21-7.30 (m, 5H).

Example 414

(R)-3-((S)-1-(4-fluorophenyl)ethyl)-6-(3-hydroxypropyl)-6-phenyl-1,3-oxazinan-2-one

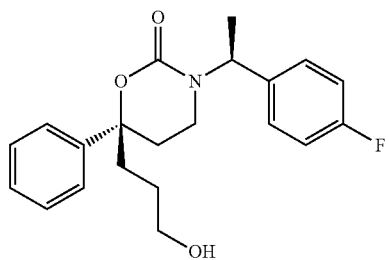 [SMILES: C[C@@H](c1ccc(F)cc1)N1CC[C@](CCCO)(c2ccccc2)OC1=O]

The title compound was prepared from (R)-6-allyl-3-((S)-1-(4-fluorophenyl)ethyl)-6-phenyl-1,3-oxazinan-2-one following procedures analogous to those described in Example 78. LC-MS Method 2 $t_R$=1.105 min, m/z=314.1; $^1$H NMR (CDCl3) 1.26-1.39 (m, 1H), 1.33 (m, 3H), 1.59-1.72 (m, 1H), 1.79-2.09 (m, 2H), 2.09-2.29 (m, 3H), 2.80 (m, 1H), 3.51 (m, 2H), 5.57 (m, 1H), 6.68 (m, 2H), 6.79 (m, 2H), 7.28 (m, 4H).

Example 415

3-((R)-3-((S)-1-(4-fluorophenyl)ethyl)-2-oxo-6-phenyl-1,3-oxazinan-6-yl)propanamide

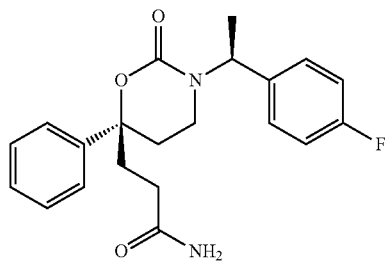 [SMILES: C[C@@H](c1ccc(F)cc1)N1CC[C@](CCC(N)=O)(c2ccccc2)OC1=O]

The title compound was prepared from (R)-3-((S)-1-(4-fluorophenyl)ethyl)-6-(3-hydroxypropyl)-6-phenyl-1,3-oxazinan-2-one following procedures analogous to those described in Example 234. LC-MS Method 2 $t_R$=1.037 min, m/z=371.1; $^1$H NMR (CDCl$_3$) 1.42 (m, 3H), 1.88-2.02 (m, 1H), 2.04-2.28 (m, 5H), 2.38-2.51 (m, 1H), 2.82 (m, 1H), 5.56 (m, 1H), 5.88 (m, 1H), 6.06 (m, 1H), 6.71 (m, 2H), 6.86 (m, 2H), 7.19 (m, 2H), 7.20-7.34 (m, 3H).

Example 416

(R)-3-((S)-1-(4-fluorophenyl)ethyl)-6-(3-hydroxy-3-methylbutyl)-6-phenyl-1,3-oxazinan-2-one

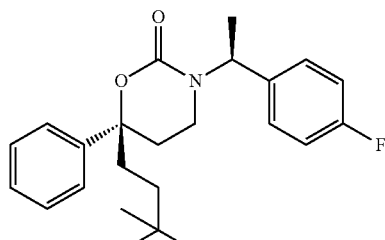

The title compound was prepared from (R)-3-((S)-1-(4-fluorophenyl)ethyl)-6-(3-hydroxypropyl)-6-phenyl-1,3-oxazinan-2-one following procedures analogous to those described in Example 117. LC-MS Method 3 $t_R$=1.073 min, m/z=408.1; $^1$H NMR (CDCl$_3$) 1.05-1.17 (m, 7H), 1.46 (d, 3H), 1.63 (m, 1H), 1.88-2.05 (m, 2H), 2.14-2.26 (m, 3H), 2.83 (m, 1H), 5.56 (m, 1H), 6.72 (m, 2H), 6.85 (m, 2H), 7.15-7.31 (m, 5H).

Example 417

(S)-6-(4-fluorophenyl)-6-(2-hydroxy-2-methylpropyl)-3-((S)-1-p-tolylethyl)-1,3-oxazinan-2-one

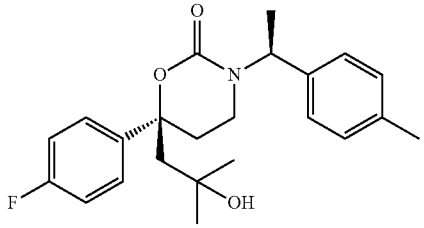 [SMILES: Cc1ccc([C@H](C)N2CC[C@](CC(C)(C)O)(c3ccc(F)cc3)OC2=O)cc1]

The title compound was prepared from (R)-6-allyl-6-(4-fluorophenyl)-3-((S)-1-p-tolylethyl)-1,3-oxazinan-2-one following procedures analogous to those described in Example 280. LC-MS Method 1 $t_R$=1.71, m/z=386 (M+1); $^1$H NMR (CDCl$_3$) 7.29-7.25 (m, 2H), 7.02 (t, 2H, J=9.0 Hz), 6.95 (d, 2H, J=8.0 Hz), 6.85 (d, 2H, J=8.0 Hz), 5.63 (q, 1H, J=7 Hz), 2.86-2.80 (m, 1H), 2.40-2.32 (m, 1H), 2.25 (s, 3H), 2.21-2.10 (m, 4H), 1.49 (d, 3H, J=7.0 Hz), 1.16 (s, 3H), 1.11 (s, 3H).

Example 418

(R)-6-(4-fluorophenyl)-6-(3-hydroxypropyl)-3-((S)-1-p-tolylethyl)-1,3-oxazinan-2-one

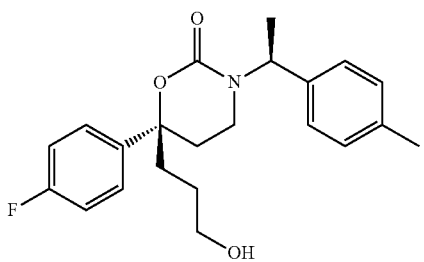 [SMILES: Cc1ccc([C@H](C)N2CC[C@](CCCO)(c3ccc(F)cc3)OC2=O)cc1]

The title compound was prepared from (R)-6-allyl-6-(4-fluorophenyl)-3-((S)-1-p-tolylethyl)-1,3-oxazinan-2-one following a procedure analogous to that described in Example 343.

Example 419

3-((R)-6-(4-fluorophenyl)-2-oxo-3-((S)-1-p-tolylethyl)-1,3-oxazinan-6-yl)propanamide

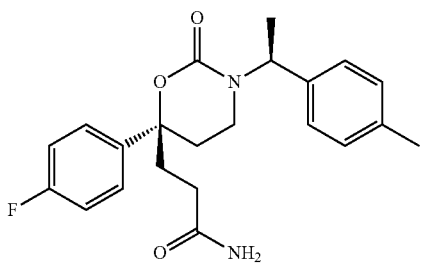 [SMILES: Cc1ccc([C@H](C)N2CC[C@](CCC(N)=O)(c3ccc(F)cc3)OC2=O)cc1]

The title compound was prepared from (R)-6-(4-fluorophenyl)-6-(3-hydroxypropyl)-3-((S)-1-p-tolylethyl)-1,3-oxazinan-2-one following procedures analogous to those described in Example 234.

Example 420

N-(3-((R)-6-(4-fluorophenyl)-2-oxo-3-((S)-1-p-tolylethyl)-1,3-oxazinan-6-yl)propyl)methanesulfonamide

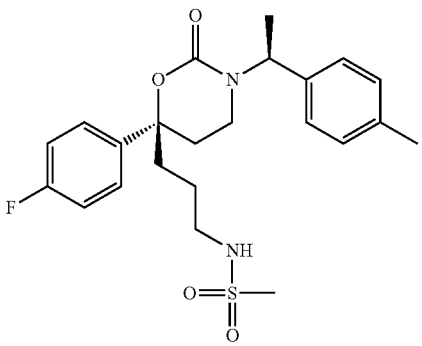 [SMILES: Cc1ccc([C@H](C)N2CC[C@](CCCNS(C)(=O)=O)(c3ccc(F)cc3)OC2=O)cc1]

The title compound was prepared from (R)-6-(4-fluorophenyl)-6-(3-hydroxypropyl)-3-((S)-1-p-tolylethyl)-1,3-oxazinan-2-one following procedures analogous to those described in Example 359.

Example 421

(S)-6-(4-fluorophenyl)-6-(2-hydroxyethyl)-3-((S)-1-p-tolylethyl)-1,3-oxazinan-2-one

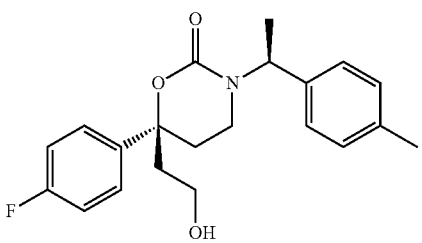 [SMILES: Cc1ccc([C@H](C)N2CC[C@](CCO)(c3ccc(F)cc3)OC2=O)cc1]

The title compound was prepared from (R)-6-allyl-6-(4-fluorophenyl)-3-((S)-1-p-tolylethyl)-1,3-oxazinan-2-one following procedures analogous to those described in Example 74.

Example 422

(S)-6-(2-hydroxy-2-methylpropyl)-6-phenyl-3-((S)-1-p-tolylethyl)-1,3-oxazinan-2-one

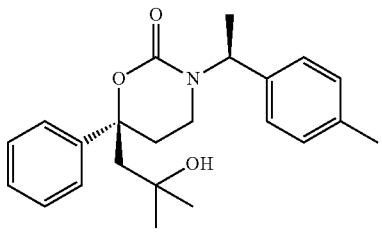 [SMILES: Cc1ccc([C@H](C)N2CC[C@](CC(C)(C)O)(c3ccccc3)OC2=O)cc1]

The title compound was prepared from (R)-6-allyl-6-phenyl-3-((S)-1-p-tolylethyl)-1,3-oxazinan-2-one following procedures analogous to those described in Example 328. LC-MS Method 1 $t_R$=1.7 min, m/z=368 (M+1); $^1$H NMR (CDCl₃) 7.32 (m, 5H), 6.88 (dd, 4H), 5.62 (q, 1H), 2.81 (m, 1H), 2.23 (s, 3H), 1.50 (d, 3H), 1.14 (d, 6H).

Example 423

(R)-6-(3-hydroxypropyl)-6-phenyl-3-((S)-1-p-tolyl-ethyl)-1,3-oxazinan-2-one

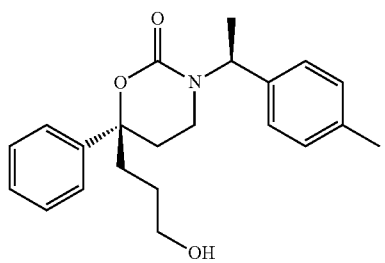 [SMILES: Cc1ccc([C@H](C)N2CC[C@](CCCO)(c3ccccc3)OC2=O)cc1]

The title compound was prepared from (R)-6-allyl-6-phenyl-3-((S)-1-p-tolylethyl)-1,3-oxazinan-2-one following a procedure analogous to that described in Example 343. LC-MS Method 1 $t_R$=1.62 min, m/z=354 (M+1); ¹H NMR (CDCl₃) 7.40-7.18 (m, 5H), 6.91 (d, 2H), 6.79 (d, 2H), 5.59 (m, 1H), 3.60 (m, 1H), 2.87 (m, 1H), 2.26 (s, 3H), 1.51 (d, 3H).

Example 424

3-((R)-2-oxo-6-phenyl-3-((S)-1-p-tolylethyl)-1,3-oxazinan-6-yl)propanamide

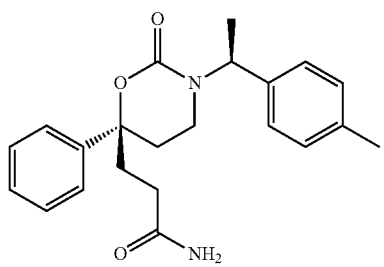 [SMILES: Cc1ccc([C@H](C)N2CC[C@](CCC(N)=O)(c3ccccc3)OC2=O)cc1]

The title compound was prepared from (R)-6-(3-hydroxypropyl)-6-phenyl-3-((S)-1-p-tolylethyl)-1,3-oxazinan-2-one following procedures analogous to those described in Example 234. ¹H NMR (CDCl₃) 1.50 (d, 3H), 1.98 (m, 1H), 2.10-2.30 (8H), 2.52 (m, 1H), 2.83 (m, 1H), 5.59 (q, 1H), 6.03 (2H), 6.80 (d, 2H), 6.93 (d, 2H), 7.20-7.40 (4H).

Example 425

(S)-6-(4-fluorophenyl)-6-(2-hydroxy-2-methylpropyl)-3-((S)-1-(4-methoxyphenyl)ethyl)-1,3-oxazinan-2-one

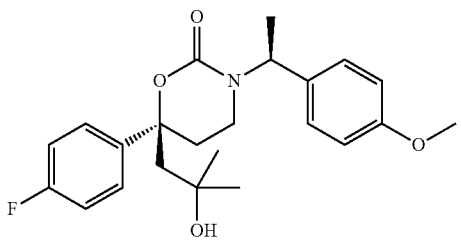 [SMILES: COc1ccc([C@H](C)N2CC[C@](CC(C)(C)O)(c3ccc(F)cc3)OC2=O)cc1]

The title compound was prepared from (R)-6-allyl-6-(4-fluorophenyl)-3-((S)-1-(4-methoxyphenyl)ethyl)-1,3-oxazinan-2-one following procedures analogous to those described in Example 328. LC-MS Method 2 $t_R$=1.129 min, m/z=447.3; ¹H NMR (CDCl₃) 1.05 (s, 3H), 1.09 (s, 3H), 1.42 (s, 3H), 2.08 (m, 4H), 2.29 (m, 1H), 2.79 (m, 1H), 3.67 (s, 3H), 5.55 (m, 1H), 6.61 (d, 2H), 6.85 (d, 2H), 6.96 (t, 2H), 7.21 (d, 2H).

Example 426

(R)-6-(4-fluorophenyl)-6-(3-hydroxy-3-methylbutyl)-3-((S)-1-(4-methoxyphenyl)ethyl)-1,3-oxazinan-2-one

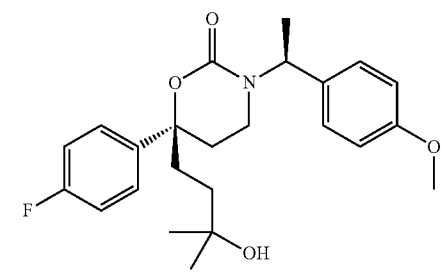 [SMILES: COc1ccc([C@H](C)N2CC[C@](CCC(C)(C)O)(c3ccc(F)cc3)OC2=O)cc1]

The title compound was prepared from (R)-6-(4-fluorophenyl)-6-(3-hydroxypropyl)-3-((S)-1-(4-methoxyphenyl)ethyl)-1,3-oxazinan-2-one following procedures analogous to those described in Example 117. LC-MS Method 2 $t_R$=1.306 min, m/z=438.1; ¹H NMR (CDCl₃) 1.06 (s, 3H), 1.09 (s, 3H), 1.16 (m, 1H), 1.48 (d, 3H), 1.58 (m, 1H), 1.79-

1.98 (m, 3H), 2.06-2.19 (m, 3H), 2.79 (m, 1H), 3.67 (s, 1H), 5.56 (m, 1H), 6.59 (d, 2H), 6.79 (d, 2H), 6.94 (t, 2H), 7.16 (m, 2H).

Example 427

(S)-6-(2-hydroxy-2-methylpropyl)-3-((S)-1-(4-methoxyphenyl)ethyl)-6-phenyl-1,3-oxazinan-2-one

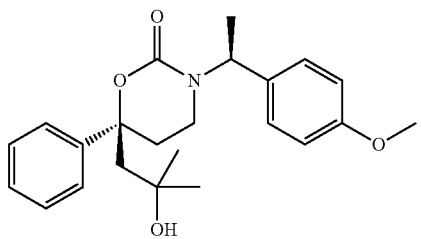 [SMILES: COc1ccc([C@H](C)N2CC[C@](CC(C)(C)O)(c3ccccc3)OC2=O)cc1]

The title compound was prepared from (R)-6-allyl-3-((S)-1-(4-methoxyphenyl)ethyl)-6-phenyl-1,3-oxazinan-2-one following procedures analogous to those described in Example 328. LC-MS Method 3 $t_R$=1.498 min, m/z=789.3; $^1$H NMR (CDCl$_3$) 1.10 (s, 3H), 1.18 (s, 3H), 1.49 (d, 3H), 1.77 (s, 2H), 2.04-2.50 (m, 5H), 2.80 (m, 1H), 3.73 (s, 3H), 5.60 (m, 1H), 6.63 (d, 2H), 6.89 (d, 2H), 7.25-7.52 (m, 5H).

Example 428

(R)-6-(3-hydroxy-3-methylbutyl)-3-((S)-1-(4-methoxyphenyl)ethyl)-6-phenyl-1,3-oxazinan-2-one

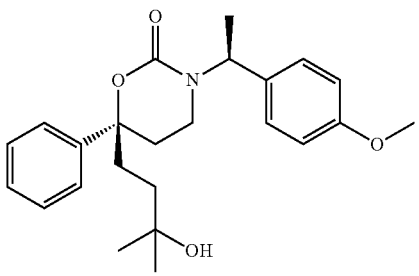 [SMILES: COc1ccc([C@H](C)N2CC[C@](CCC(C)(C)O)(c3ccccc3)OC2=O)cc1]

The title compound was prepared from (R)-6-(3-hydroxypropyl)-3-((S)-1-(4-methoxyphenyl)ethyl)-6-phenyl-1,3-oxazinan-2-one following procedures analogous to those described in Example 117. LC-MS Method 2 $t_R$=1.291 min, m/z=420.1; $^1$H NMR (CDCl$_3$) 1.12 (m, 6H), 1.25 (m, 1H), 1.48 (d, 3H), 1.66 (m, 1H), 1.89-2.05 (m, 2H), 2.14-2.28 (m, 3H), 2.84 (m, 1H), 3.70 (s, 3H), 5.62 (m, 1H), 6.62 (d, 2H), 6.80 (d, 2H), 7.21-7.38 (m, 5H).

Example 429

6-(4-(hydroxymethyl)phenyl)-3-((1S)-1-(4-methoxyphenyl)ethyl)-6-methyl-1,3-oxazinan-2-one

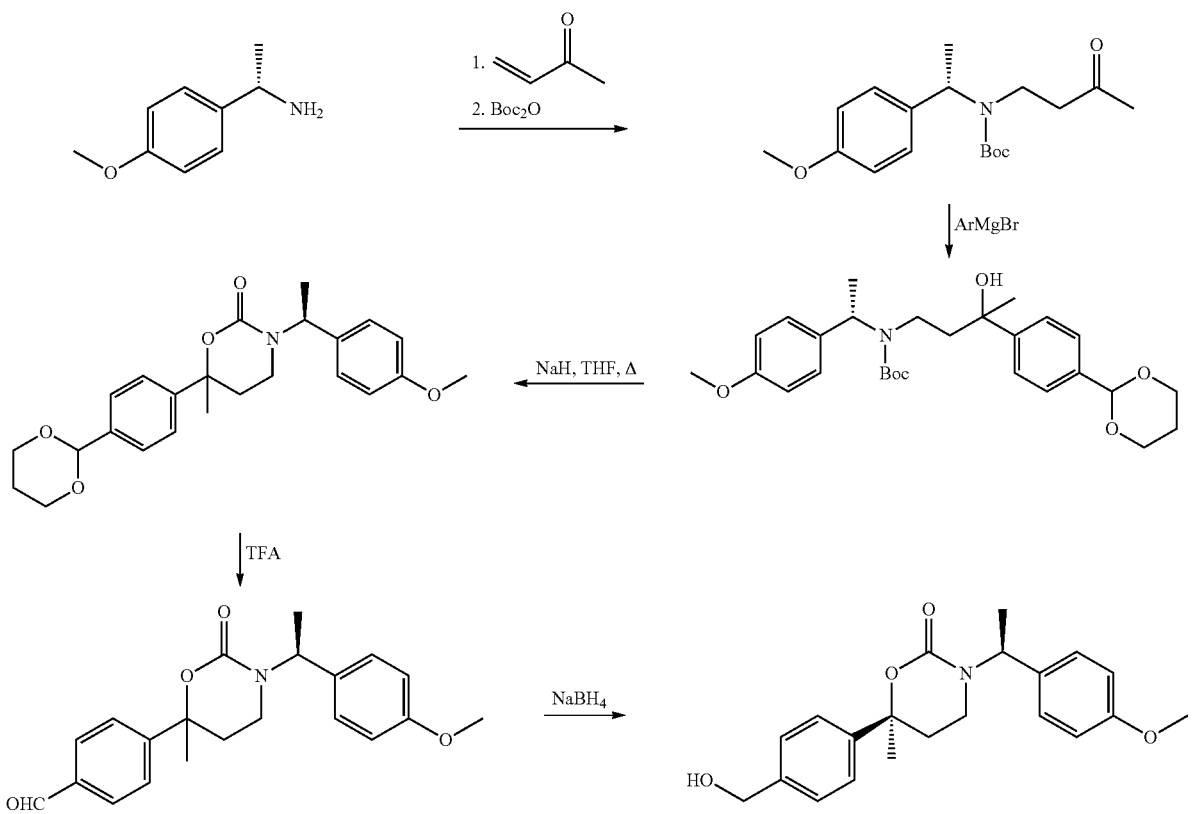

Step 1

A solution of (S)-1-(4-methoxyphenyl)ethanamine (1.1570 g, 7.65 mmol, 1.0 equiv) and methyl vinyl ketone (0.5900 g, 8.42 mmol, 1.1 equiv) in THF (18 mL) was allowed to stand in a refrigerator (ca. 3.3° C.) for 3 d. $Boc_2O$ (2.6800 g, 12.28 mmol, 1.6 equiv) was added to the mixture at room temperature. After stirring for 2 h, the solvent was removed under reduced pressure. The residue was purified by chromatography on silica gel eluted with hexanes/ethyl acetate to give 2.2074 g (90% in two steps) of (S)-tert-butyl 1-(4-methoxyphenyl)ethyl(3-oxobutyl)carbamate as an oil. LC-MS Method 1 $t_R$=1.82 min, m/z 344 ($MNa^+$).

Step 2

A solution of (4-(1,3-dioxan-2-yl)phenyl)magnesium bromide (0.25 M in THF, 34 mL, 8.5 mmol) was added dropwise to a solution of (S)-tert-butyl 1-(4-methoxyphenyl)ethyl(3-oxobutyl)carbamate (0.4222 g, 1.31 mmol) in THF (5 mL) under $N_2$ at 0° C. After stirring for 24 h at rt, the mixture was quenched with 1 mL of satd aq $NH_4Cl$ and diluted with $CH_2Cl_2$, dried over $K_2CO_3$. After the solvents were evaporated, the crude product was directly used in the next step without further purification. LC-MS Method 1 $t_R$=2.02 min, m/z=508 ($MNa^+$), 412.

Step 3

A mixture of tert-butyl 3-(4-(1,3-dioxan-2-yl)phenyl)-3-hydroxybutyl((S)-1-(4-methoxyphenyl)ethyl)carbamate, obtained as described above, and 1.340 g of 60% NaH in THF (10 mL) was heated to reflux for 24 h. The reaction was then quenched with 1.5 mL of $H_2O$, diluted with $CH_2Cl_2$, dried over $Na_2SO_4$. Removal of the solvent afforded crude 6-(4-(1,3-dioxan-2-yl)phenyl)-3-((S)-1-(4-methoxyphenyl)ethyl)-6-methyl-1,3-oxazinan-2-one. LC-MS Method 1 $t_R$=1.65, 1.69 min, m/z=412 ($MH^+$).

The crude product was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford two isomers of 4-(3-((S)-1-(4-methoxyphenyl)ethyl)-6-methyl-2-oxo-1,3-oxazinan-6-yl) benzaldehyde.

Isomer 1: 0.0145 g LC-MS Method 1 $t_R$=1.53 min, m/z=354 ($MH^+$).
Isomer 2: 0.0163 g LC-MS Method 1 $t_R$=1.59 min, m/z=354 ($MH^+$).

Step 4

A mixture of 0.0163 g of 4-(3-((S)-1-(4-methoxyphenyl) ethyl)-6-methyl-2-oxo-1,3-oxazinan-6-yl)benzaldehyde isomer 2, obtained as described above, and 0.100 g of $NaBH_4$ in MeOH (3 mL) was stirred at room temperature for 24 h. After the solvent was evaporated, the residue was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford (S)-6-(4-(hydroxymethyl)phenyl)-3-((S)-1-(4-methoxyphenyl) ethyl)-6-methyl-1,3-oxazinan-2-one. LC-MS Method 1 $t_R$=1.43 min, m/z 356 ($MH^+$); $^1$H NMR (400 MHz, $CD_3OD$) δ 7.42-7.25 (m, 4H), 7.14 (d, J=8.8 Hz, 2H), 6.81 (d, J=8.8 Hz, 2H), 5.50 (q, J=7.3 Hz, 1H), 4.53 (s, 2H), 3.69 (s, 3H), 2.70-2.65 (m, 2H), 2.36-2.30 (m, 1H), 1.98-1.87 (m, 1H), 1.50 (s, 3H), 1.19 (d, J=7.3 Hz, 3H).

Reaction of 4-(3-((S)-1-(4-methoxyphenyl)ethyl)-6-methyl-2-oxo-1,3-oxazinan-6-yl)benzaldehyde isomer 1 with $NaBH_4$, under conditions analogous to those described above for isomer 2, afforded (R)-6-(4-(hydroxymethyl)phenyl)-3-((S)-1-(4-methoxyphenyl)ethyl)-6-methyl-1,3-oxazinan-2-one. LC-MS Method 1 $t_R$=1.39 min, m/z=356 (M+1); $^1$H NMR ($CD_3OD$) 7.27 (d, J=8.5 Hz, 2H), 7.21 (d, J=8.5 Hz, 2H), 6.78 (d, J=8.8 Hz, 2H), 6.59 (d, J=8.8 Hz, 2H), 5.41 (q, J=7.0 Hz, 1H), 4.53 (s, 2H), 3.62 (s, 3H), 2.96-2.91 (m, 1H), 2.37-2.32 (m, 1H), 2.22-2.15 (m, 1H), 2.10-2.02 (m, 1H), 1.51 (s, 3H), 1.41 (d, J=7.0 Hz, 3H).

Example 430

(S)-6-(4-fluorophenyl)-6-(2-hydroxyethyl)-3-((S)-1-(4-(pyridin-2-yl)phenyl)ethyl)-1,3-oxazinan-2-one

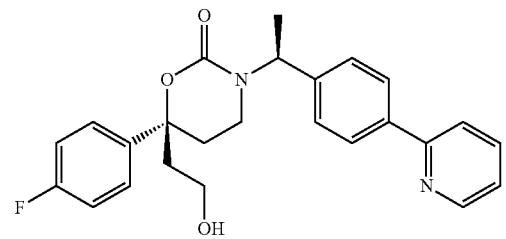 [SMILES: C[C@@H](c1ccc(-c2ccccn2)cc1)N1CC[C@](CCO)(c2ccc(F)cc2)OC1=O]

The title compound was prepared from (S)-3-((S)-1-(4-bromophenyl)ethyl)-6-(4-fluorophenyl)-6-(2-hydroxyethyl)-1,3-oxazinan-2-one and pyridine-2-boronic acid following a procedure analogous to that described in Example 75 Step 1. LC-MS Method 2 $t_R$=1.462 min, m/z=420.18; $^1$H NMR ($CDCl_3$) 1.48 (d, 3H), 2.03-2.30 (m, 5H), 2.85 (m, 1H), 3.50 (m, 1H), 3.72 (m, 1H), 5.65 (m, 1H), 6.98 (m, 4H), 7.24 (m, 2H), 7.60 (m, 1H), 7.74 (m, 3H), 8.62 (m, 1H).

Example 431

(S)-6-(4-fluorophenyl)-6-(2-hydroxy-2-methylpropyl)-3-((S)-1-(4-(pyridin-2-yl)phenyl)ethyl)-1,3-oxazinan-2-one

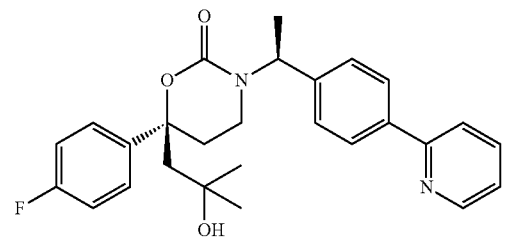 [SMILES: C[C@@H](c1ccc(-c2ccccn2)cc1)N1CC[C@](CC(C)(C)O)(c2ccc(F)cc2)OC1=O]

The title compound was prepared from (S)-3-((S)-1-(4-bromophenyl)ethyl)-6-(4-fluorophenyl)-6-(2-hydroxy-2-methylpropyl)-1,3-oxazinan-2-one and pyridine-2-boronic acid following a procedure analogous to that described in Example 75 Step 1. LC-MS Method 2 t<sub>R</sub>=1.049 min, m/z=391; $^1$H NMR (CDCl$_3$) 1.06-1.19 (d, 6H), 1.50 (s, 3H), 2.11-2.38 (m, 6H), 2.80 (m, 1H), 5.66 (m, 1H), 6.97 (m, 2H), 7.04 (d, 2H), 7.18 (m, 1H), 7.23 (m, 2H), 7.58 (m, 1H), 7.73 (m, 3H), 8.60 (d, 1H).

Example 432

(R)-6-(4-fluorophenyl)-6-(3-hydroxypropyl)-3-((S)-1-(4-(pyridin-2-yl)phenyl)ethyl)-1,3-oxazinan-2-one

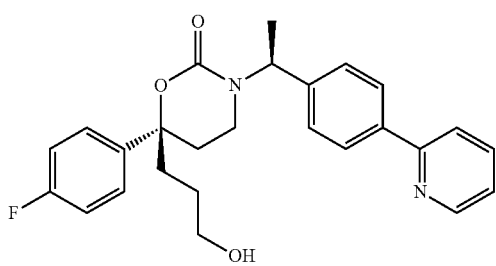 [SMILES: C[C@@H](c1ccc(-c2ccccn2)cc1)N1CC[C@](CCCO)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one and pyridine-2-boronic acid following a procedure analogous to that described in Example 75 Step 1. LC-MS Method 2 t$_R$=0.905 min, m/z=435.2; $^1$H NMR (CDCl$_3$) 1.22-1.37 (m, 1H), 1.49 (d, 3H), 1.60-1.70 (m, 2H), 1.80-1.97 (m, 2H), 2.07-2.31 (m, 3H), 2.85 (m, 1H), 3.50 (m, 2H), 5.65 (m, 1H), 6.97 (m, 4H), 7.20 (m, 3H), 7.57-7.70 (m, 4H), 8.60 (m, 1H).

Example 433

3-((R)-6-(4-fluorophenyl)-2-oxo-3-((S)-1-(4-(pyridin-2-yl)phenyl)ethyl)-1,3-oxazinan-6-yl)propanamide

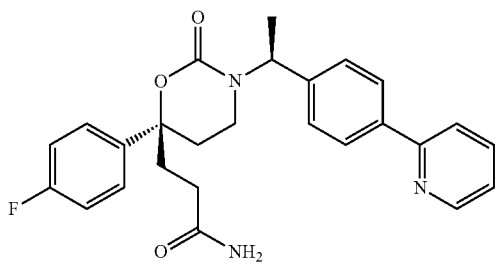 [SMILES: C[C@@H](c1ccc(-c2ccccn2)cc1)N1CC[C@](CCC(N)=O)(c2ccc(F)cc2)OC1=O]

The title compound was prepared from 3-((R)-3-((S)-1-(4-bromophenyl)ethyl)-6-(4-fluorophenyl)-2-oxo-1,3-oxazinan-6-yl)propanamide and pyridine-2-boronic acid following a procedure analogous to that described in Example 75 Step 1. LC-MS Method 2 t$_R$=0.976 min, m/z=448; $^1$H NMR (CDCl$_3$) 1.50 (d, 3H), 1.91 (m, 1H), 2.17-2.23 (m, 5H), 2.41 (m, 1H), 2.86 (m, 1H), 5.18 (m, 1H), 5.32 (m, 1H), 5.66 (m, 1H), 7.00 (m, 4H), 7.18 (m, 3H), 7.57 (d, 1H), 7.69 (m, 3H), 8.58 (d, 1H).

Example 434

N-(3-((R)-6-(4-fluorophenyl)-2-oxo-3-((S)-1-(4-(pyridin-2-yl)phenyl)ethyl)-1,3-oxazinan-6-yl)propyl)methanesulfonamide

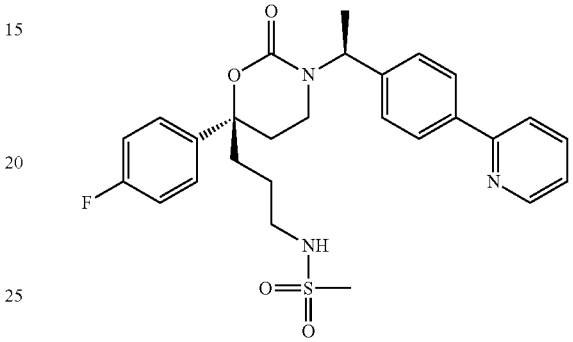

The title compound was prepared from N-(3-((R)-3-((S)-1-(4-bromophenyl)ethyl)-6-(4-fluorophenyl)-2-oxo-1,3-oxazinan-6-yl)propyl)methanesulfonamide and pyridine-2-boronic acid following a procedure analogous to that described in Example 75 Step 1. LC-MS Method 2 t$_R$=1.036 min, m/z=512.1; $^1$H NMR (CDCl$_3$) 1.49 (d, 3H), 1.60-1.70 (m, 1H), 1.84 (m, 1H), 1.89-1.99 (m, 2H), 2.10-2.20 (m, 2H), 2.25 (m, 1H), 2.74 (s, 3H), 3.01 (m, 2H), 4.22 (m, 1H), 5.64 (m, 1H), 6.97 (m, 4H), 7.16 (m, 3H), 7.58 (d, 1H), 7.70 (m, 3H), 8.60 (m, 1H).

Example 435

(R)-6-(4-fluorophenyl)-6-(3-hydroxypropyl)-3-((S)-1-(4-(6-methylpyridin-2-yl)phenyl)ethyl)-1,3-oxazinan-2-one

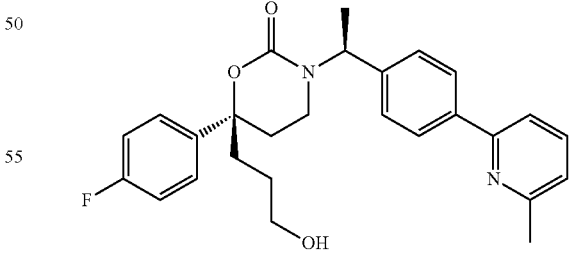

The title compound was prepared from (R)-3-((S)-1-(4-bromophenyl)ethyl)-6-(4-fluorophenyl)-6-(3-hydroxypropyl)-1,3-oxazinan-2-one and 6-methylpyridine-2-boronic acid following a procedure analogous to that described in Example 75 Step 1. LC-MS Method 2 t$_R$=0.868 min, m/z=449.2; $^1$H NMR (CD$_3$OD) 1.28 (m, 1H), 1.56 (d, 3H), 1.61 (m, 1H), 1.95 (m, 2H), 2.23 (m, 1H), 2.34 (m, 1H), 2.46

(m, 1H), 2.55 (s, 3H), 3.11 (m, 1H), 3.46 (m, 2H), 5.50 (m, 1H), 7.06 (m, 4H), 7.19 (d, 1H), 7.31 (m, 2H), 7.51 (d, 1H), 7.73 (m, 3H).

Example 436

(S)-6-(4-fluorophenyl)-6-(2-hydroxyethyl)-3-((S)-1-(4-(6-methoxypyridin-3-yl)phenyl)ethyl)-1,3-oxazinan-2-one

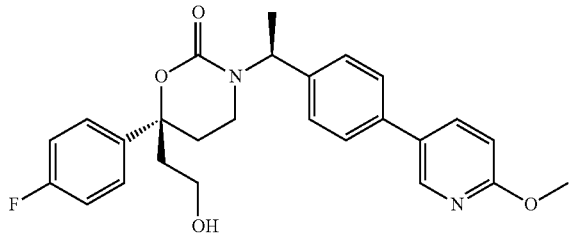 [SMILES: COc1ccc(-c2ccc([C@H](C)N3CC[C@](CCO)(c4ccc(F)cc4)OC3=O)cc2)cn1]

The title compound was prepared from (S)-3-((S)-1-(4-bromophenyl)ethyl)-6-(4-fluorophenyl)-6-(2-hydroxyethyl)-1,3-oxazinan-2-one and 6-methoxypyridine-3-boronic acid following a procedure analogous to that described in Example 75 Step 1. LC-MS Method 2 $t_R$=1.887 min, m/z=450.2; $^1$H NMR (CDCl$_3$) 1.54 (d, 3H), 2.07-2.29 (m, 2H), 2.34 (m, 3H), 2.97 (m, 1H), 3.55 (m, 1H), 3.74 (m, 1H), 4.06 (d, 3H), 5.64 (m, 1H), 6.93 (m, 1H), 6.95-7.11 (m, 2H), 7.26-7.37 (m, 2H), 7.90 (m, 1H), 8.38 (m, 1H).

Example 437

(S)-6-(4-fluorophenyl)-6-(2-hydroxy-2-methylpropyl)-3-((S)-1-(4-(6-methoxypyridin-3-yl)phenyl)ethyl)-1,3-oxazinan-2-one

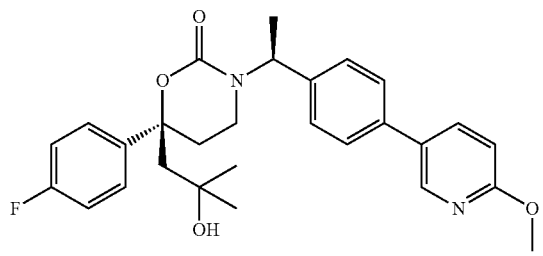

The title compound was prepared from (S)-3-((S)-1-(4-bromophenyl)ethyl)-6-(4-fluorophenyl)-6-(2-hydroxy-2-methylpropyl)-1,3-oxazinan-2-one and 6-methoxypyridine-3-boronic acid following a procedure analogous to that described in Example 75. Step 1. LC-MS Method 3 $t_R$=1.111 min, m/z=478.23; $^1$H NMR (CDCl$_3$) 1.15 (d, 6H), 1.55 (d, 3H), 2.17-2.29 (m, 4H), 2.42 (m, 1H), 2.91 (m, 1H), 3.95 (s, 3H), 5.70 (m, 1H) 6.80 (d, 1H), 7.03 (m, 4H), 7.30 (m, 4H), 7.71 (m, 1H), 8.30 (s, 1H).

Example 438

(R)-6-(4-fluorophenyl)-6-(3-hydroxypropyl)-3-((S)-1-(4-(6-methoxypyridin-3-yl)phenyl)ethyl)-1,3-oxazinan-2-one

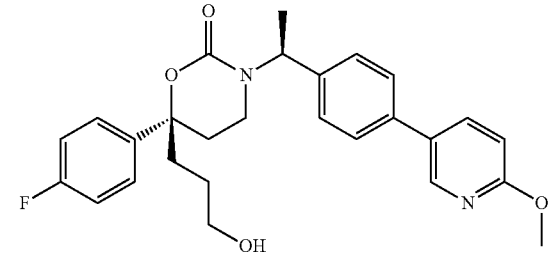 [SMILES: COc1ccc(-c2ccc([C@H](C)N3CC[C@](CCCO)(c4ccc(F)cc4)OC3=O)cc2)cn1]

The title compound was prepared from (R)-3-((S)-1-(4-bromophenyl)ethyl)-6-(4-fluorophenyl)-6-(3-hydroxypropyl)-1,3-oxazinan-2-one and 6-methoxypyridine-3-boronic acid following a procedure analogous to that described in Example 75 Step 1. LC-MS Method 2 $t_R$=1.3 min, m/z=487.1; $^1$H NMR (CD$_3$OD) 1.25-1.37 (m, 1H), 1.55 (d, 3H), 1.61 (m, 1H), 1.95 (m, 2H), 2.17-2.28 (m, 1H), 2.36 (m, 1H), 2.48 (m, 1H), 3.12 (m, 1H), 3.48 (m, 2H), 3.94 (s, 3H), 5.58 (m, 1H), 6.86 (d, 1H), 7.07 (m, 4H), 7.35 (m, 4H), 7.86 (dd, 1H), 8.28 (s, 1H).

Example 439

3-((R)-6-(4-fluorophenyl)-3-((S)-1-(4-(6-methoxypyridin-3-yl)phenyl)ethyl)-2-oxo-1,3-oxazinan-6-yl)propanamide

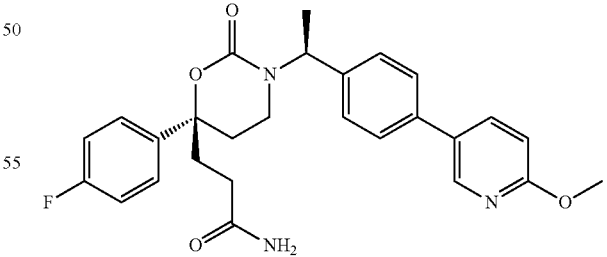

The title compound was prepared from 3-((R)-3-((S)-1-(4-bromophenyl)ethyl)-6-(4-fluorophenyl)-2-oxo-1,3-oxazinan-6-yl)propanamide and 6-methoxypyridine-3-boronic acid following a procedure analogous to that described in Example 75 Step 1. LC-MS Method 2 $t_R$=1.254 min, m/z=477.21; $^1$H NMR (CDCl$_3$) 1.55 (d, 3H), 2.01 (m, 1H), 2.15-2.34 (m, 5H), 2.46 (m, 1H), 2.96 (m, 1H), 4.00 (s, 3H), 5.66 (m, 1H), 5.80 (s, 1H), 6.19 (s, 1H), 6.86 (d, 1H), 7.03 (m, 4H), 7.23 (m, 2H), 7.79 (dd, 1H), 8.36 (s, 1H).

Example 440

N-(3-((R)-6-(4-fluorophenyl)-3-((S)-1-(4-(6-methoxypyridin-3-yl)phenyl)ethyl)-2-oxo-1,3-oxazinan-6-yl)propyl)methanesulfonamide

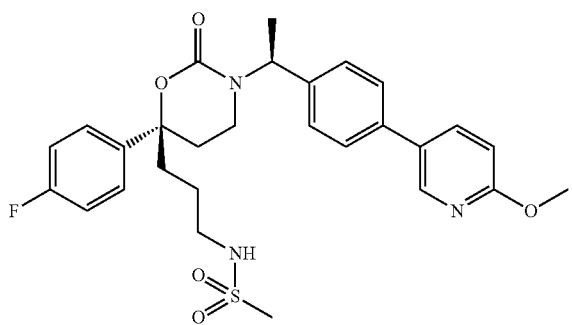 [SMILES: COc1ccc(-c2ccc([C@H](C)N3CC[C@](CCCNS(C)(=O)=O)(c4ccc(F)cc4)OC3=O)cc2)cn1]

The title compound was prepared from N-(3-((R)-3-((S)-1-(4-bromophenyl)ethyl)-6-(4-fluorophenyl)-2-oxo-1,3-oxazinan-6-yl)propyl)methanesulfonamide and 6-methoxypyridine-3-boronic acid following a procedure analogous to that described in Example 75 Step 1. LC-MS Method 2 $t_R$=1.327 min, m/z=542.1; $^1$H NMR (CD$_3$OD) 1.33 (m, 1H), 1.58 (d, 3H), 1.66 (m, 1H), 1.98 (m, 2H), 2.20-2.39 (m, 2H), 2.47 (m, 1H), 2.87 (s, 3H), 2.99 (m, 2H), 3.15 (m, 1H), 3.96 (s, 3H), 5.60 (m, 1H), 6.87 (d, 1H), 7.12 (m, 4H), 7.36 (m, 4H), 7.87 (d, 1H), 8.29 (s, 1H).

Example 441

3-(4-((S)-1-((R)-6-(3-amino-3-oxopropyl)-6-(4-fluorophenyl)-2-oxo-1,3-oxazinan-3-yl)ethyl)phenyl) pyridine 1-oxide

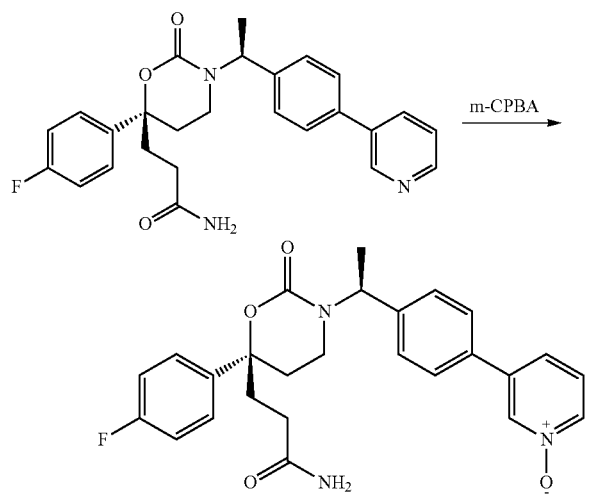

To a solution of 3-((R)-6-(4-fluorophenyl)-2-oxo-3-((S)-1-(4-(pyridin-3-yl)phenyl)ethyl)-1,3-oxazinan-6-yl)propanamide (70 mg, 0.16 mmol) in CH$_2$Cl$_2$ (10 mL), was added m-CPBA (135 mg, 0.79 mmol), and the reaction mixture was stirred at it for 3 h. After the solvent was removed under reduced pressure, the residue was purified by preparative TLC to afford 3-((R)-6-(4-fluorophenyl)-2-oxo-3-((S)-1-(4-(pyridin-3-yl)phenyl)ethyl)-1,3-oxazinan-6-yl)propanoic acid (10 mg, 15%). LC-MS Method 2 $t_R$=0.987 min, m/z=464.17; $^1$H NMR (CDCl$_3$): 1.51 (m, 3H), 1.92 (m, 1H), 2.12-2.28 (m, 5H), 2.43 (m, 1H), 2.95 (m, 1H), 5.56 (m, 1H), 5.65 (m, 1H), 5.31 (m, 1H), 6.95 (m, 2H), 7.08 (m, 2H), 7.15 (m, 1H), 7.20 (m, 1H), 7.25 (m, 2H), 7.56 (m, 1H), 7.24 (m, 1H), 8.35 (m, 1H), 8.65 (m, 1H).

Example 442

(R)-3-((S)-1-(4-(5-chloropyridin-3-yl)phenyl)ethyl)-6-(4-fluorophenyl)-6-(3-hydroxypropyl)-1,3-oxazinan-2-one

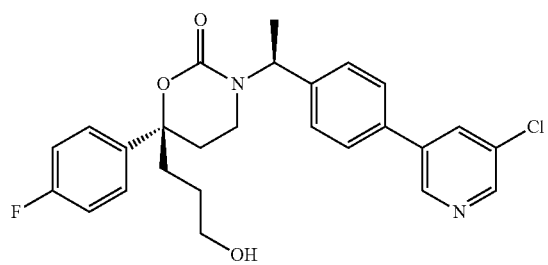 [SMILES: C[C@@H](c1ccc(-c2cncc(Cl)c2)cc1)N1CC[C@](CCCO)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one and 5-chloropyridine-3-boronic acid following a procedure analogous to that described in Example 75 Step 1.

Example 443

3-((R)-6-(4-fluorophenyl)-3-((S)-1-(4-(5-fluoropyridin-3-yl)phenyl)ethyl)-2-oxo-1,3-oxazinan-6-yl) propanoic acid

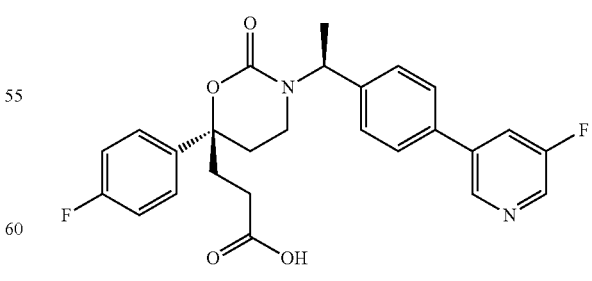

The title compound was prepared from (R)-6-(4-fluorophenyl)-3-((S)-1-(4-(5-fluoropyridin-3-yl)phenyl)ethyl)-6-(3-hydroxypropyl)-1,3-oxazinan-2-one following a procedure analogous to that described in Example 234 Step 1.

Example 444

5-(4-((S)-1-((R)-6-(4-fluorophenyl)-6-(3-hydroxypropyl)-2-oxo-1,3-oxazinan-3-yl)ethyl)phenyl)nicotinamide

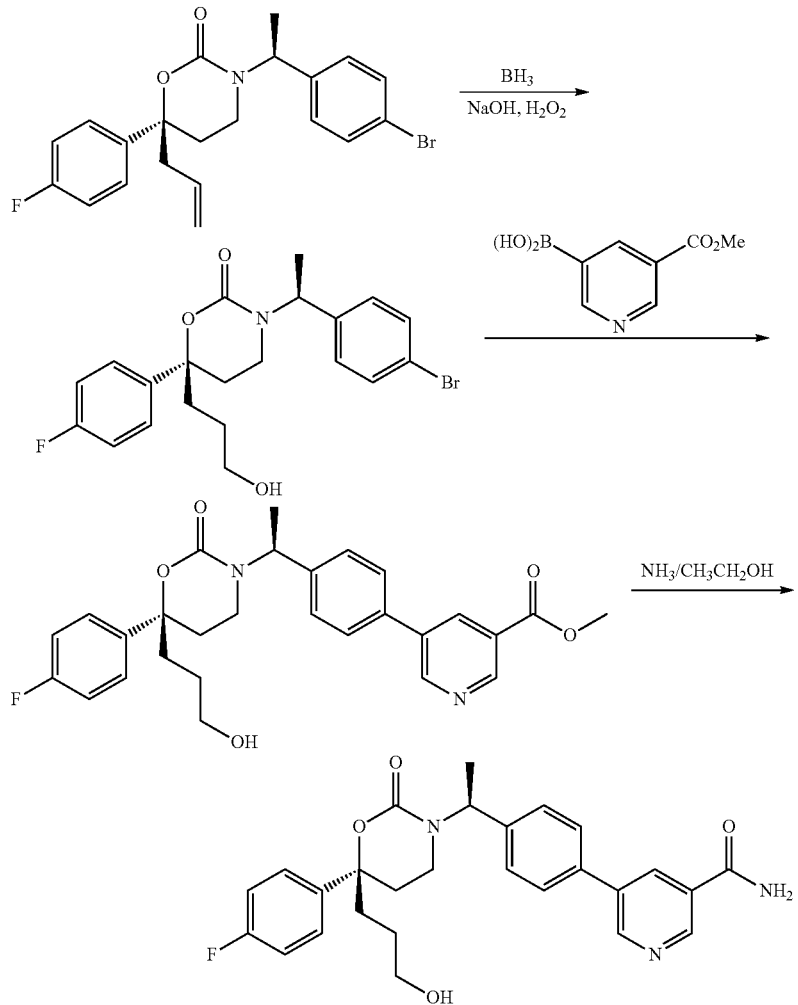

Step 1

To a solution of (R)-6-allyl-3-((S)-1-(4-bromophenyl)ethyl)-6-(4-fluorophenyl)-1,3-oxazinan-2-one (1 g, 2.4 mmol) in dry THF (15 mL) was added dropwise BH$_3$.THF (5 mL, 1 M) at 0° C. After stirring for 2 h at rt, the reaction mixture was cooled to 0° C. and water (1 mL), aqueous NaOH (0.5 mL, 3 M) and H$_2$O$_2$ (0.5 mL, 30%) were successively added. The mixture was stirred for 2-3 h at rt and diluted with water (8 mL). The pH was adjusted to 6-7 with 0.5 N HCl. The layers were separated, and the aqueous phase was extracted with EtOAc (3×10 mL). The combined organic layers were washed with a satd aq NaHCO$_3$ (20 mL) and brine (20 mL), dried over Na$_2$SO$_4$, and concentrated in vacuo to give the crude product, which was purified by preparative TLC to afford (R)-3-((S)-1-(4-bromophenyl)ethyl)-6-(4-fluorophenyl)-6-(3-hydroxypropyl)-1,3-oxazinan-2-one (400 mg, 38%).

Step 2

A mixture of (R)-3-((S)-1-(4-bromophenyl)ethyl)-6-(4-fluorophenyl)-6-(3-hydroxypropyl)-1,3-oxazinan-2-one (250 mg, 0.6 mmol), 5-(methoxycarbonyl)pyridin-3-ylboronic acid (163 mg, 0.9 mmol), PdCl$_2$(PPh$_3$)$_2$ (50 mg, 20%) and aqueous Cs$_2$CO$_3$ solution (2 M, 2 mL) in 1,4-dioxane (6 mL) was heated to reflux at 100° C. overnight under N$_2$. The mixture was filtered, and the filtrate was extracted with EtOAc for 3 times. The combined organic layer was washed with brine, dried over Na$_2$SO$_4$ and concentrated to the crude product, which was purified by preparative HPLC to give methyl 5-(4-((S)-1-((R)-6-(4-fluorophenyl)-6-(3-hydroxypropyl)-2-oxo-1,3-oxazinan-3-yl)ethyl)phenyl)nicotinate (220 mg, crude).

Step 3

Methyl 5-(4-((S)-1-((R)-6-(4-fluorophenyl)-6-(3-hydroxypropyl)-2-oxo-1,3-oxazinan-3-yl)ethyl)phenyl)nicotinate (30 mg, 0.1 mmol) was dissolved in anhydrous NH$_3$ in EtOH (5 mL). Then the mixture was stirred at rt overnight. The solvent was removed in vacuo to give the crude product, which was purified by preparative HPLC to provide 5-(4-((S)-1-((R)-6-(4-luorophenyl)-6-(3-hydroxypropyl)-2-oxo- 1,3-oxazinan-3-yl)ethyl)phenyl)nicotinamide (10 mg, 34%). LC-MS Method 2 t_R=1.022 min, m/z=478; $^1$H NMR (CD$_3$OD): 1.31 (m, 1H), 1.56 (m, 3H), 1.59 (m, 1H), 1.91 (m, 2H), 2.17-2.28 (m, 1H), 2.33 (m, 1H), 2.44 (m, 1H), 3.14 (m, 1H), 3.44 (m, 2H), 5.60 (m, 1H), 7.04-7.17 (m, 4H), 7.29 (m, 2H), 7.49 (m, 2H), 8.41 (m, 1H), 8.86 (m, 1H), 8.97 (m, 1H).

Example 445

5-(4-((S)-1-((R)-6-(4-fluorophenyl)-6-(3-hydroxypropyl)-2-oxo-1,3-oxazinan-3-yl)ethyl)phenyl)-N,N-dimethylnicotinamide

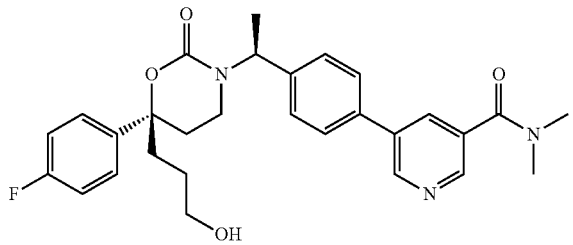 [SMILES: C[C@@H](c1ccc(-c2cncc(C(=O)N(C)C)c2)cc1)N1CC[C@](CCCO)(c2ccc(F)cc2)OC1=O]

The title compound was prepared methyl 5-(4-((S)-1-((R)-6-(4-fluorophenyl)-6-(3-hydroxypropyl)-2-oxo-1,3-oxazinan-3-yl)ethyl)phenyl)nicotinate following a procedure analogous to that described in Example 444 Step 3 using dimethylamine in place of ammonia. LC-MS Method 2 t_R=1.086 min, m/z=506.3; $^1$H NMR (CDCl$_3$) 0.87 (m, 1H), 1.21-1.37 (m, 4H), 1.64 (m, 1H), 1.98 (m, 2H), 2.22 (m, 1H), 2.35 (m, 1H), 2.54 (m, 1H), 2.65 (m, 1H), 3.05 (m, 3H), 3.15 (m, 4H), 3.45 (m, 2H), 5.63 (m, 1H), 7.03-7.18 (m, 4H), 7.34 (m, 2H), 7.49 (m, 2H), 8.06 (m, 1H), 8.58 (m, 1H), 8.81 (m, 1H).

Example 446

5-(4-((S)-1-((R)-6-(4-fluorophenyl)-6-(3-hydroxypropyl)-2-oxo-1,3-oxazinan-3-yl)ethyl)phenyl)-N-methylnicotinamide

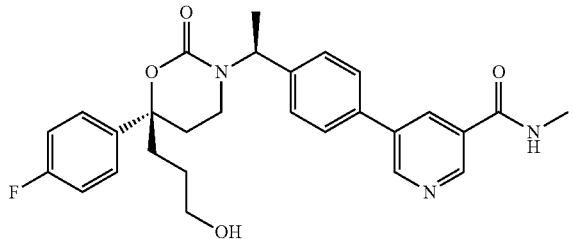 [SMILES: CNC(=O)c1cncc(-c2ccc([C@H](C)N3CC[C@](CCCO)(c4ccc(F)cc4)OC3=O)cc2)c1]

The title compound was prepared methyl 5-(4-((S)-1-((R)-6-(4-fluorophenyl)-6-(3-hydroxypropyl)-2-oxo-1,3-oxazinan-3-yl)ethyl)phenyl)nicotinate following a procedure analogous to that described in Example 444 Step 3 using methylamine in place of ammonia. LC-MS Method 2 t_R=1.055 min, m/z=491.12; $^1$H NMR (CD$_3$OD) 1.18 (m, 1H), 1.48 (d, 3H), 1.51 (m, 1H), 1.85 (m, 2H), 2.13 (m, 1H), 2.25 (m, 1H), 2.48 (m, 1H), 2.88 (s, 3H), 3.09 (m, 1H), 3.38 (m, 2H), 5.51 (m, 1H), 6.98-7.07 (m, 4H), 7.22 (m, 2H), 7.42 (m, 2H), 8.28 (m, 1H), 8.75 (s, 1H), 8.82 (s, 1H).

Example 447

3-((R)-6-(4-fluorophenyl)-2-oxo-3-((S)-1-(4-(pyridin-4-yl)phenyl)ethyl)-1,3-oxazinan-6-yl)propanamide

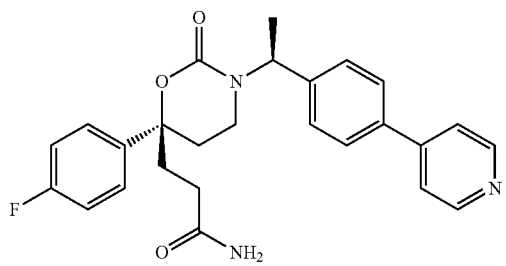 [SMILES: C[C@@H](c1ccc(-c2ccncc2)cc1)N1CC[C@](CCC(N)=O)(c2ccc(F)cc2)OC1=O]

The title compound was prepared from 3-((R)-3-((S)-1-(4-bromophenyl)ethyl)-6-(4-fluorophenyl)-2-oxo-1,3-oxazinan-6-yl)propanamide and pyridine-4-boronic acid following a procedure analogous to that described in Example 75 Step 1. LC-MS Method 2 t_R=0.906 min, m/z=448.1; $^1$H NMR (CDCl$_3$) 1.59 (d, 3H), 2.15 (m, 1H), 2.24-2.32 (m, 4H), 2.45 (m, 1H), 3.07 (m, 2H), 5.66 (m, 1H), 5.71 (m, 1H), 5.84 (m, 1H), 7.03 (m, 2H), 7.05 (m, 2H), 7.22 (m, 1H), 7.25 (m, 1H), 7.50 (d, 2H), 7.93 (d, 2H), 8.84 (d, 2H).

Example 448

(S)-6-(4-fluorophenyl)-6-(2-hydroxyethyl)-3-((S)-1-(4-(2-methylpyridin-4-yl)phenyl)ethyl)-1,3-oxazinan-2-one

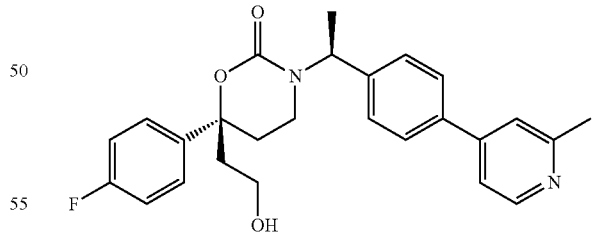

The title compound was prepared from (S)-3-((S)-1-(4-bromophenyl)ethyl)-6-(4-fluorophenyl)-6-(2-hydroxyethyl)-1,3-oxazinan-2-one and 2-methylpyridine-4-boronic acid following a procedure analogous to that described in Example 75 Step 1. LC-MS Method 2 t_R=0.945 min, m/z=435.5; $^1$H NMR (CD$_3$OD) 1.56 (d, 3H), 1.92 (m, 1H), 2.01 (m, 1H), 2.17 (m, 2H), 2.36 (m, 2H), 2.48 (m, 1H), 2.56

(m, 3H), 3.12 (m, 1H), 3.62 (m, 1H), 5.62 (m, 1H), 7.05 (m, 4H), 7.30 (m, 2H), 7.44 (m, 1H), 7.54 (m, 3H), 8.39 (s, 2H).

Example 449

(S)-6-(4-fluorophenyl)-6-(2-hydroxy-2-methylpropyl)-3-((S)-1-(4-(2-methylpyridin-4-yl)phenyl)ethyl)-1,3-oxazinan-2-one

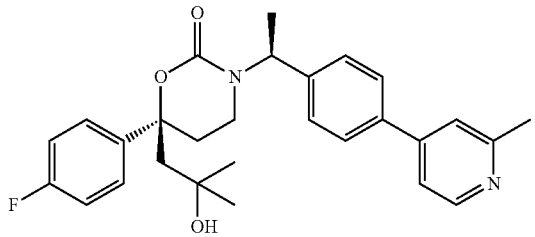 [SMILES: Cc1cc(-c2ccc([C@H](C)N3CC[C@](CC(C)(C)O)(c4ccc(F)cc4)OC3=O)cc2)ccn1]

The title compound was prepared from (S)-3-((S)-1-(4-bromophenyl)ethyl)-6-(4-fluorophenyl)-6-(2-hydroxy-2-methylpropyl)-1,3-oxazinan-2-one and 2-methylpyridine-4-boronic acid following a procedure analogous to that described in Example 75. Step 1. LC-MS Method 2 $t_R$=0.976 min, m/z=463.8; $^1$H NMR (CDCl$_3$) 1.09 (d, 6H), 1.49 (d, 3H), 2.16 (m, 4H), 2.35 (m, 1H), 2.56 (d, 3H), 2.85 (m, 1H), 5.65 (m, 1H), 6.94-7.05 (m, 4H), 7.17-7.26 (m, 4H), 7.34 (d, 2H), 8.47 (d, 1H).

Example 450

3-((R)-6-(4-fluorophenyl)-3-((S)-1-(4-(2-methylpyridin-4-yl)phenyl)ethyl)-2-oxo-1,3-oxazinan-6-yl)propanoic acid

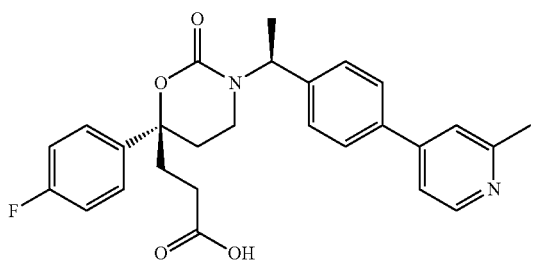 [SMILES: Cc1cc(-c2ccc([C@H](C)N3CC[C@](CCC(=O)O)(c4ccc(F)cc4)OC3=O)cc2)ccn1]

The title compound was prepared from (R)-6-(4-fluorophenyl)-6-(3-hydroxypropyl)-3-((S)-1-(4-(2-methylpyridin-4-yl)phenyl)ethyl)-1,3-oxazinan-2-one following procedures analogous to those described in Example 234 Step 1.

Example 451

3-((R)-6-(4-fluorophenyl)-3-((S)-1-(4-(2-methylpyridin-4-yl)phenyl)ethyl)-2-oxo-1,3-oxazinan-6-yl)propanamide

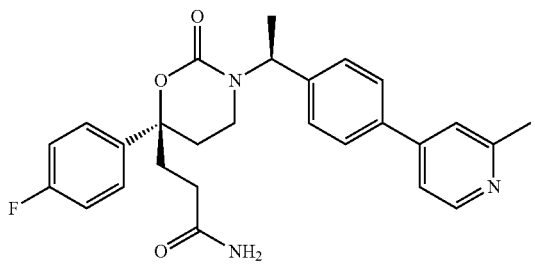 [SMILES: Cc1cc(-c2ccc([C@H](C)N3CC[C@](CCC(N)=O)(c4ccc(F)cc4)OC3=O)cc2)ccn1]

The title compound was prepared from 3-((R)-6-(4-fluorophenyl)-3-((S)-1-(4-(2-methylpyridin-4-yl)phenyl)ethyl)-2-oxo-1,3-oxazinan-6-yl)propanoic acid following procedures analogous to those described in Example 234 Step 2. LC-MS Method 2 $t_R$=0.793 min, m/z=462.2; $^1$H NMR (CDCl$_3$) 1.51 (d, 3H), 2.12-2.38 (m, 6H), 2.43 (m, 1H), 2.61 (s, 3H), 2.89 (m, 1H), 5.10-5.34 (d, 2H), 5.66 (m, 1H), 6.99 (m, 4H), 7.17-7.27 (m, 4H), 7.36 (d, 2H), 8.46 (d, 1H).

Example 452

(R)-6-(4-fluorophenyl)-6-(3-hydroxy-3-methylbutyl)-3-((S)-1-(4-(2-methylpyridin-4-yl)phenyl)ethyl)-1,3-oxazinan-2-one

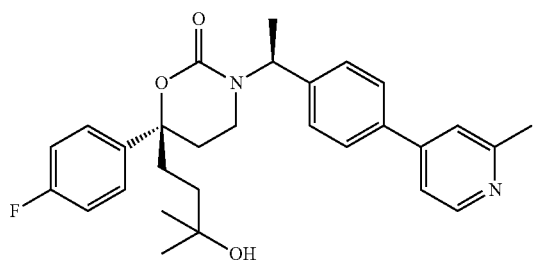 [SMILES: Cc1cc(-c2ccc([C@H](C)N3CC[C@](CCC(C)(C)O)(c4ccc(F)cc4)OC3=O)cc2)ccn1]

The title compound was prepared from (R)-6-(4-fluorophenyl)-6-(3-hydroxypropyl)-3-((S)-1-(4-(2-methylpyridin-4-yl)phenyl)ethyl)-1,3-oxazinan-2-one following procedures analogous to those described in Example 117. LC-MS Method 2 $t_R$=0.992 min, m/z=477.5; $^1$H NMR (CDCl$_3$) 1.08 (d, 6H), 1.15 (m, 1H), 1.52 (d, 3H), 1.59 (m, 1H), 1.84-2.01 (m, 2H), 2.15-2.34 (m, 3H), 2.83 (s, 3H), 2.98 (m, 1H), 5.67 (m, 1H), 6.96 (t, 2H), 7.09 (d, 2H), 7.20 (m, 2H), 7.41 (d, 2H), 7.65 (d, 2H), 8.75 (s, 1H).

Example 453

N-(3-((R)-6-(4-fluorophenyl)-3-((S)-1-(4-(2-methylpyridin-4-yl)phenyl)ethyl)-2-oxo-1,3-oxazinan-6-yl)propyl)methanesulfonamide

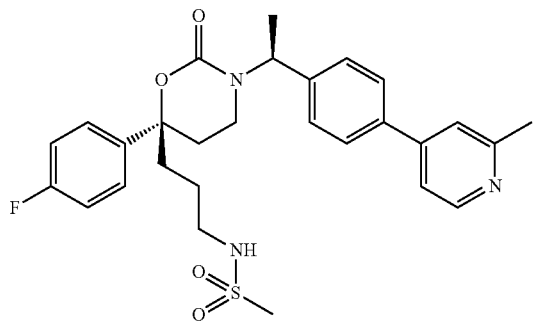 [SMILES: Cc1cc(-c2ccc([C@H](C)N3CC[C@](CCCNS(C)(=O)=O)(c4ccc(F)cc4)OC3=O)cc2)ccn1]

The title compound was prepared from N-(3-((R)-3-((S)-1-(4-bromophenyl)ethyl)-6-(4-fluorophenyl)-2-oxo-1,3-oxazinan-6-yl)propyl)methanesulfonamide and 2-methylpyridine-4-boronic acid following procedures analogous to those described in Example 75 Step 1. LC-MS Method 2 $t_R$=0.964 min, m/z=525.21; $^1$H NMR (CDCl$_3$) 1.31-1.43 (m, 1H), 1.50 (d, 3H), 1.62 (m, 2H), 1.07-2.09 (m, 2H), 2.13-2.47 (m, 3H), 2.83 (d, 6H), 3.01 (m, 3H), 4.35 (s, 1H), 5.66 (m, 1H) 7.07 (m, 2H), 7.14 (m, 2H), 7.29 (m, 5H), 7.44 (m, 2H), 7.65 (m, 1H), 7.73 (d, 1H), 8.78 (d, 1H).

Example 454

(R)-3-((S)-1-(4-(2,6-dimethylpyridin-4-yl)phenyl)ethyl)-6-(4-fluorophenyl)-6-(3-hydroxypropyl)-1,3-oxazinan-2-one

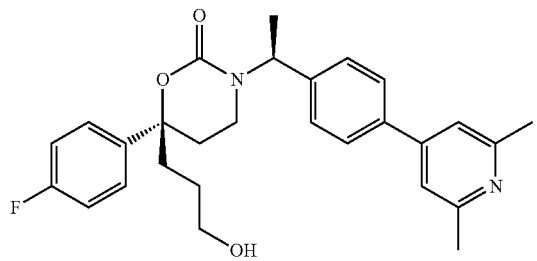 [SMILES: Cc1cc(-c2ccc([C@H](C)N3CC[C@](CCCO)(c4ccc(F)cc4)OC3=O)cc2)cc(C)n1]

The title compound was prepared from (R)-6-allyl-3-((S)-1-(4-bromophenyl)ethyl)-6-(4-fluorophenyl)-1,3-oxazinan-2-one following a procedure analogous to that described in Example 455 Steps 1 and 2, using 4-bromo-2,6-dimethylpyridine-N-oxide in step 2, followed by a procedure analogous to that described in Example 343. LC-MS Method 1 $t_R$=1.1 min, m/z=463 (M+1); $^1$H NMR (CDCl$_3$) 7.50 (s, 2H), 7.45 (d, 1H), 7.25 (m, 3H), 7.17-6.99 (m, 4H), 5.73 (q, 1H), 4.28 (t, 1H), 3.04 (m, 1H), 2.82 (s, 6H), 2.31 (m, 3H), 1.91 (m, 3H), 1.58 (d, 3H).

Example 455

(R)-6-(4-fluorophenyl)-6-(3-hydroxypropyl)-3-((S)-1-(4-(thiazol-2-yl)phenyl)ethyl)-1,3-oxazinan-2-one

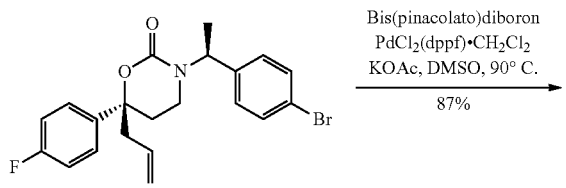

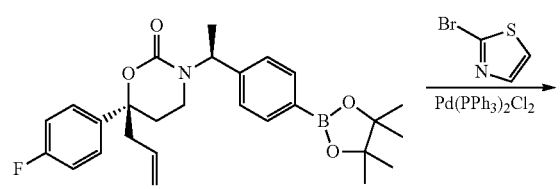

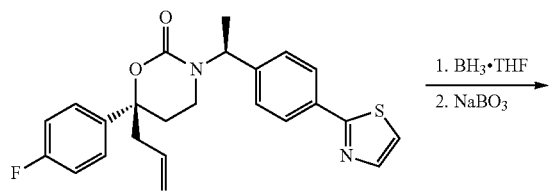

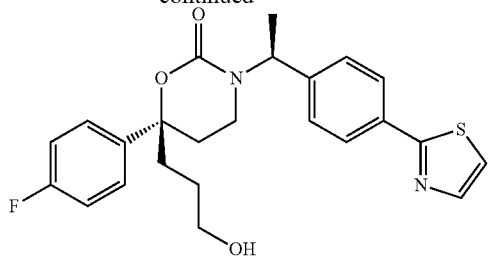

Step 1

A mixture of (R)-6-allyl-3-((S)-1-(4-bromophenyl)ethyl)-6-(4-fluorophenyl)-1,3-oxazinan-2-one (0.4910 g, 1.17 mmol, 1.0 equiv), bis(pinacolato)diboron (0.3925 g, 1.55 mmol, 1.3 equiv), KOAc (0.3696 g, 3.76 mmol, 3.2 equiv), and PdCl$_2$(dppf)·CH$_2$Cl$_2$ (0.0316 g, 0.0386 mmol, 0.033 equiv) in DMSO (6 mL) was heated at 90° C. under N$_2$ for 20 h. After cooling, the reaction mixture was partitioned between EtOAc and water. The organic phase was washed with brine, and dried over Na$_2$SO$_4$. After the solvents were evaporated, the residue was purified by chromatography on silica gel eluted with hexanes/ethyl acetate to give 0.4776 g (87%) of (R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one as a white solid.

Step 2

(R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one (20 mg, 0.043 mmol), 2-bromothiazole (14 mg, 2 equiv), 2M aq Na$_2$SO$_4$ solution (0.5 mL) and Pd(PPh$_3$)$_2$Cl$_2$ were mixed with THF (0.6 mL) and heated in a microwave oven for 2 h at 140° C. LC-MS found reaction completed. The mixture was diluted with EtOAc (8 mL), washed with water (2 mL), 1% aq HCl (2 mL) and brine (1.5 mL). After concentration, the residue was purified by preparative HPLC to afford (R)-6-allyl-6-(4-fluorophenyl)-3-((S)-1-(4-(thiazol-2-yl)phenyl)ethyl)-1,3-oxazinan-2-one (6.0 mg, 33%). LC-MS (3 min) $t_R$=1.86 min, m/z=423 (M+1).

Step 3

(R)-6-allyl-6-(4-fluorophenyl)-3-((S)-1-(4-(thiazol-2-yl)phenyl)ethyl)-1,3-oxazinan-2-one (6.0 mg, 0.014 mmol) was dissolved in dry THF (2 mL) and cooled to 0° C. BH$_3$-THF (1.0M, 100 μL, excess) was added slowly. After 10 min, the mixture was warmed to it and stirred for 3 h. LC-MS found reaction completed. The mixture was quenched with water (1 mL). NaBO$_3$ (ca 4 mg) was added. The mixture was stirred 40 min, filtered, concentrated and purified by preparative HPLC to afford (R)-3-((S)-1-(4-(2,6-dimethylpyridin-4-yl)phenyl)ethyl)-6-(4-fluorophenyl)-6-(3-hydroxypropyl)-1,3-oxazinan-2-one (3.4 mg, 54%), LC-MS (3 min) $t_R$=1.86 min, m/z=423 (M+1). LC-MS Method 1 $t_R$=1.86 min, m/z=423

(M+1); NMR (CDCl$_3$) 7.71 (m, 2H), 7.40-7.22 (m, 4H), 7.16-7.03 (m, 3H), 6.96 (m, 1H), 5.66 (m, 1H), 2.96 (m, 1H), 1.54 (d, 3H).

Example 456

(R)-3-((S)-1-(4-(2,4-dimethylthiazol-5-yl)phenyl)ethyl)-6-(4-fluorophenyl)-6-(3-hydroxypropyl)-1,3-oxazinan-2-one

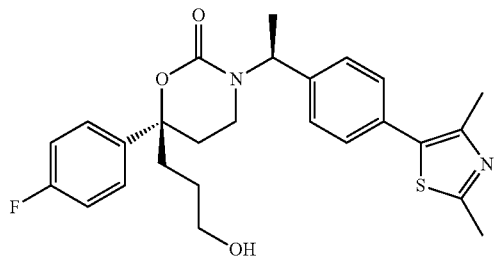 [SMILES: Cc1nc(C)c(-c2ccc([C@H](C)N3CC[C@](CCCO)(c4ccc(F)cc4)OC3=O)cc2)s1]

The title compound was prepared from (R)-6-allyl-3-((S)-1-(4-bromophenyl)ethyl)-6-(4-fluorophenyl)-1,3-oxazinan-2-one and 2,4-dimethylthiazole-5-boronic acid following a procedure analogous to that described in Example 111, followed by a procedure analogous to that described in Example 78. LC-MS Method 1 t$_R$=1.49 min, m/z=469; $^1$H NMR (CDCl$_3$) 7.28 (m, 2H), 7.15 (d, 2H), 7.03 (q, 4H), 5.68 (q, 1H), 3.59 (t, 1H), 3.02 (m, 1H), 2.91 (s, 3H), 2.48 (s, 3H), 1.55 (d, 3H).

Example 457

3-((R)-3-((S)-1-(4-(2,4-dimethylthiazol-5-yl)phenyl)ethyl)-6-(4-fluorophenyl)-2-oxo-1,3-oxazinan-6-yl)propanamide

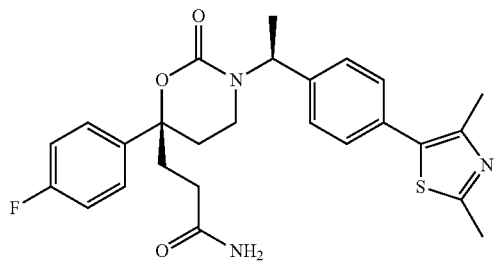 [SMILES: Cc1nc(C)c(-c2ccc([C@H](C)N3CC[C@](CCC(N)=O)(c4ccc(F)cc4)OC3=O)cc2)s1]

The title compound was prepared from (R)-3-((S)-1-(4-(2,4-dimethylthiazol-5-yl)phenyl)ethyl)-6-(4-fluorophenyl)-6-(3-hydroxypropyl)-1,3-oxazinan-2-one following procedures analogous to those described in Example 234. LC-MS Method 1 t$_R$=1.38 min, m/z=482 (M+1); $^1$H NMR (CDCl$_3$) 7.32 (m, 5H), 7.18 (d, 2H), 7.04 (m, 4H), 5.69 (q, 1H), 2.84 (s, 3H), 2.45 (s, 3H), 2.02 (m, 1H), 1.55 (d, 3H).

Example 458

(S)-6-(4-fluorophenyl)-6-(2-hydroxyethyl)-3-((S)-1-(4-(1-methyl-6-oxo-1,6-dihydropyridin-3-yl)phenyl)ethyl)-1,3-oxazinan-2-one

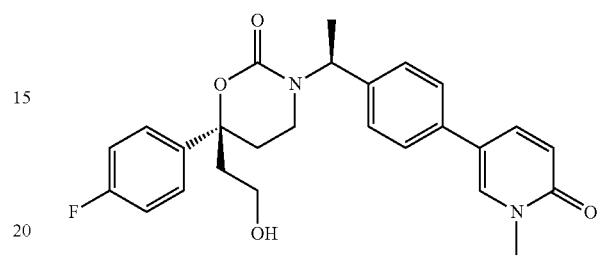

The title compound was prepared from (R)-6-allyl-3-((S)-1-(4-bromophenyl)ethyl)-6-(4-fluorophenyl)-1,3-oxazinan-2-one following a procedure analogous to that described in Example 455 Steps 1 and 2, using 5-bromo-1-methylpyridin-2(1H)-one in Step 2, followed by a procedure analogous to that described in Example 97. LC-MS Method 1 t$_R$=1.21 min, m/z=451 (M+1); $^1$H NMR (CD$_3$OD) 7.80 (m, 1H), 7.69 (d, J=9.4 Hz, 1H), 7.22-7.19 (m, 4H), 7.00-6.92 (m, 4H), 6.52 (d, J=9.4 Hz, 1H), 5.45 (q, J=7.0 Hz, 1H), 3.60-3.52 (m, 1H), 3.52 (s, 3H), 3.24-3.18 (m, 1H), 3.02-2.98 (m, 1H), 2.39-2.35 (m, 1H), 2.23-2.12 (m, 2H), 2.01 (t, J=7.3 Hz, 2H), 1.43 (d, J=7.0 Hz, 3H).

Example 459

(S)-6-(4-fluorophenyl)-6-(2-hydroxy-2-methylpropyl)-3-((S)-1-(4-(1-methyl-6-oxo-1,6-dihydropyridin-3-yl)phenyl)ethyl)-1,3-oxazinan-2-one Method 1

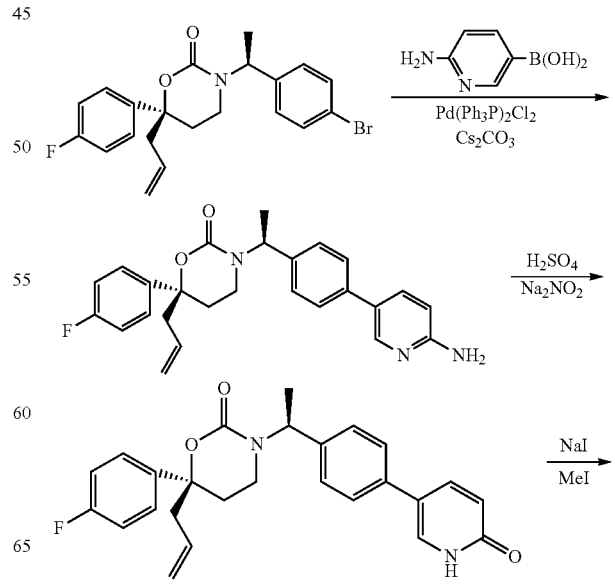

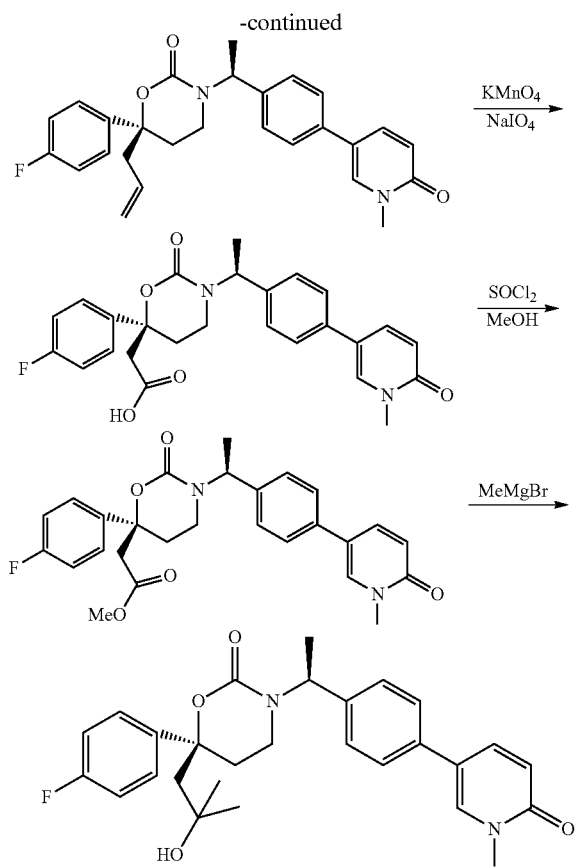

Step 1

A mixture of (R)-6-allyl-3-((S)-1-(4-bromophenyl)ethyl)-6-(4-fluorophenyl)-1,3-oxa zinan-2-one (1.6 g, 3.84 mmol) and 6-aminopyridin-3-ylboronic acid (1.0 g, 4.61 mmol), Pd(Ph$_3$P)$_2$Cl$_2$ (150 mg), and aq Cs$_2$CO$_3$ solution (3.84 mL, 2 M) in 1,4-dioxane (150 mL) was stirred and heated to reflux for 2 h. The mixture was filtered and the filtrate was extracted with EtOAc. The combined organic phase was washed with brine, dried over anhydrous Na$_2$SO$_4$, and concentrated to give (R)-6-allyl-3-((S)-1-(4-(6-aminopyridin-3-yl)phenyl)ethyl)-6-(4-fluorophenyl)-1,3-oxazinan-2-one (1.5 g, 90%), which was used for the next step without purification. $^1$H NMR (CDCl$_3$): δ=1.51 (d, 3H), 2.17-2.31 (m, 3H), 2.54-2.60 (m, 2H), 2.90 (m, 1H), 4.46 (s, 2H), 4.99-5.09 (m, 2H), 5.65-5.71 (m, 2H), 6.54 (m, 2H), 6.88 (d, 2H), 7.03 (t, 2H), 7.21-7.27 (m, 3H), 7.58 (d, 1H), 8.22 (d, 1H).

Step 2

To a solution of (R)-6-allyl-3-((S)-1-(4-(6-aminopyridin-3-yl)phenyl)ethyl)-6-(4-fluorophenyl)-1,3-oxazinan-2-one (1.5 g, 3.47 mmoL) in 3.5 M H$_2$SO$_4$ (25 mL) was added 2 M NaNO$_2$ (15 mL) at 0° C. The reaction mixture was stirred at rt overnight. The reaction was treated with aqueous NaOH solution (8%), and the mixture was extracted with CH$_2$Cl$_2$. The combined organic layer was washed with brine, dried over anhydrous Na$_2$SO$_4$ and concentrated to give crude product, which was purified by preparative TLC to give (R)-6-allyl-6-(4-fluorophenyl)-3-((S)-1-(4-(6-oxo-1,6-dihydropyridin-3-yl)phenyl)ethyl)-1,3-oxazinan-2-one (891 mg, 59%). $^1$H NMR (CDCl$_3$): δ=1.52 (d, 3H), 2.15-2.38 (m, 3H), 2.51-2.60 (m, 2H), 2.94 (m, 1H), 4.99-5.11 (m, 2H), 5.65-5.74 (m, 2H), 6.67 (m, 1H), 6.89 (d, 2H), 7.00 (t, 2H), 7.13-7.20 (m, 2H), 7.20-7.27 (d, 2H), 7.33 (m, 1H), 7.46 (m, 1H), 7.77 (m, 1H).

Step 3

To a suspension of NaH (330 mg, 8.24 mmol) in THF (20 mL) was added a solution of (R)-6-allyl-6-(4-fluorophenyl)-3-((S)-1-(4-(6-oxo-1,6-dihydropyridin-3-yl)phenyl)ethyl)-1,3-oxazinan-2-one (891 mg, 0.174 mmol) in THF (30 mL) at 0° C., and the resulting mixture was stirred for 1 h. CH$_3$I (2 ml) was added and the mixture was stirred overnight. The reaction was quenched by aqueous NH$_4$Cl solution. The organic phase was separated, and concentrated to give the crude product, which was purified by preparative TLC to give (R)-6-allyl-6-(4-fluorophenyl)-3-((S)-1-(4-(1-methyl-6-oxo-1,6-dihydropyridin-3-yl)phenyl)ethyl)-1,3-oxazinan-2-one (634 mg, 69%). $^1$H NMR (CDCl$_3$): δ=1.52 (d, 3H), 2.16-2.35 (m, 3H), 2.52-2.64 (m, 2H), 2.94 (m, 1H), 3.61 (s, 3H), 5.00-5.11 (m, 2H), 5.66-5.74 (m, 2H), 6.64 (d, 1H), 6.90 (d, 2H), 7.02 (t, 2H), 7.11-7.14 (d, 2H), 7.25-7.28 (m, 2H), 7.41 (m, 1H), 7.53 (m, 1H).

Step 4

To a solution of (R)-6-allyl-6-(4-fluorophenyl)-3-((S)-1-(4-(1-methyl-6-oxo-1,6-dihydropyridin-3-yl)phenyl)ethyl)-1,3-oxazinan-2-one (320 mg, 0.717 mmol) in acetone (20 mL) was added aqueous KMnO$_4$ and NaIO$_4$ solution (15 mL). Then the formed mixture was stirred for 30 min at 0° C. The mixture was filtered, and the filtrate was adjusted to pH=5-6 with 1 N aq HCl solution. The mixture was extracted with EtOAc, and the combined organic phase was washed with brine, dried over anhydrous Na$_2$SO$_4$ and concentrated to give 2-((S)-6-(4-fluorophenyl)-3-((S)-1-(4-(1-methyl-6-oxo-1,6-dihydropyridin-3-yl)phenyl)ethyl)-2-oxo-1,3-oxazinan-6-yl)acetic acid.

Step 5

To a solution of 2-((S)-6-(4-fluorophenyl)-3-((S)-1-(4-(1-methyl-6-oxo-1,6-dihydropyridin-3-yl)phenyl)ethyl)-2-oxo-1,3-oxazinan-6-yl)acetic acid (290 mg, 0.625 mol) in MeOH (20 mL) was added SOCl$_2$ (2 mL) at 0° C., and the reaction mixture was stirred at rt for 2 h. The reaction mixture was concentrated to give the residue, which was purified by preparative TLC to give methyl 2-((S)-6-(4-fluorophenyl)-3-((S)-1-(4-(1-methyl-6-oxo-1,6-dihydropyridin-3-yl)phenyl)ethyl)-2-oxo-1,3-oxazinan-6-yl)acetate (130 mg, 43.5%). $^1$H NMR (CDCl$_3$): δ=1.52 (d, 3H), 2.36-2.55 (m, 3H), 2.67-2.71 (m, 2H), 2.90-3.04 (m, 3H), 3.68 (s, 3H), 3.71 (s, 3H), 5.66 (m, 2H), 6.66 (d, 1H), 6.90 (d, 2H), 7.03 (t, 2H), 7.13-7.15 (d, 2H), 7.23-7.29 (m, 2H), 7.42 (m, 1H), 7.56 (m, 1H).

Step 6

To a solution of methyl 2-((S)-6-(4-fluorophenyl)-3-((S)-1-(4-(1-methyl-6-oxo-1,6-dihydropyridin-3-yl)phenyl)ethyl)-2-oxo-1,3-oxazinan-6-yl)acetate (130 mg, 0.22 mmol) in dry THF (20 mL) was added MeMgBr (2 mL) at −78° C., and the mixture was stirred under N$_2$ at rt overnight. The reaction was quenched with water, and the mixture was extracted with EtOAc. The combined organic phase was dried over Na$_2$SO$_4$, and concentrated to give the residue, which was purified by preparative HPLC to give (S)-6-(4-fluorophenyl)-6-(2-hydroxy-2-methylpropyl)-3-((S)-1-(4-(1-methyl-6-oxo-1,6-dihydropyridin-3-yl)phenyl)ethyl)-1,3-oxazinan-2- one (24 mg, 30%). LC-MS Method 2 $t_R$=1.116 min, m/z=479.1; ¹H NMR (CDCl₃): 1.1 (m, 6H), 1.18 (m, 1H), 1.48 (d, 3H), 1.58 (m, 1H), 1.80-2.00 (m, 2H), 2.21 (m, 3H), 2.86 (m, 1H), 5.55 (m, 1H), 7.72 (m, 2H), 7.00 (m, 2H), 7.18 (m, 4H).

Method 2

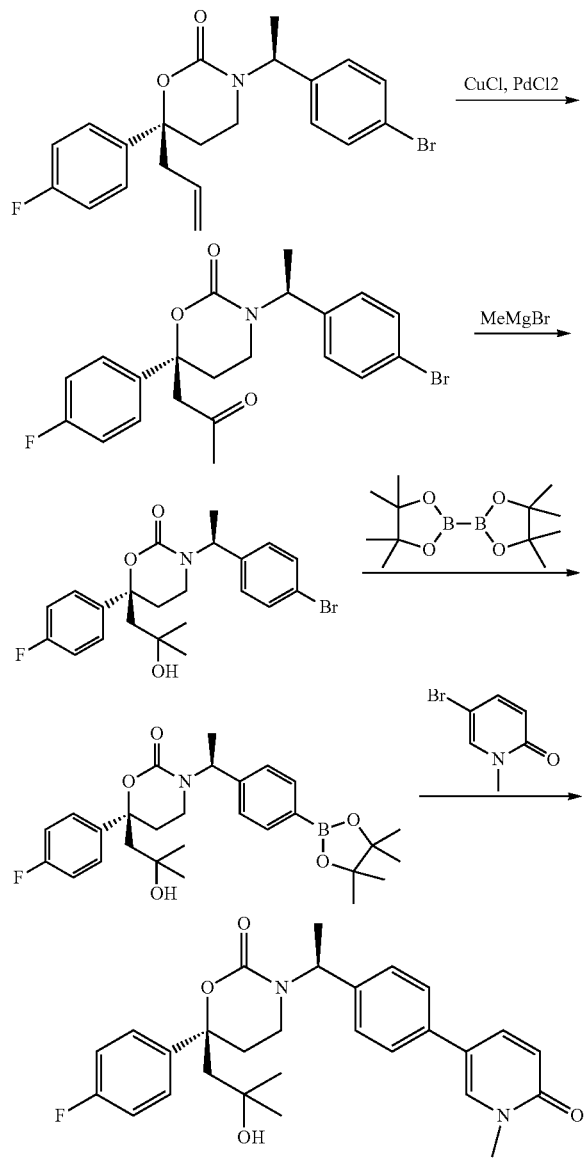

Step 1

To a solution of (R)-6-allyl-3-((S)-1-(4-bromophenyl) ethyl)-6-(4-fluorophenyl)-1,3-oxazinan-2-one (5 g, 12 mmol) and CuCl (2.75 g, 27.8 mmol) in dry DMF (50 mL) was added H₂O (20 mL) and PdCl₂ (950 mg, 3.2 mmol) at room temperature. The mixture was vigorously stirred under a balloon of oxygen for 24 h. After TLC showed the starting material had disappeared, the solid was filtered off. Water (200 mL) and EtOAc (50 mL) was added, the layers were separated and the aqueous layer was extracted with EtOAc (3×40 mL). The combined organic layer was washed with brine, dried over Na₂SO₄, filtered and concentrated to give (S)-3-((S)-1-(4-bromophenyl)ethyl)-6-(4-fluorophenyl)-6-(2-oxopropyl)-1,3-oxazinan-2-one (5.25 g, 92%), which was purified by column chromatography. ¹H NMR (CDCl₃): 1.47 (s, 3H), 2.06 (s, 3H), 2.10-2.36 (m, 3H), 2.58 (m, 1H), 2.90 (m, 2H), 5.58 (m, 1H), 6.69 (m, 1H), 6.79 (m, 1H), 7.02 (m, 2H), 7.19-7.33 (m, 4H).

Step 2

To a solution of (S)-3-((S)-1-(4-bromophenyl)ethyl)-6-(4-fluorophenyl)-6-(2-oxopropyl)-1,3-oxazinan-2-one (5.25 g, 12.1 mmol) in anhydrous THF (100 mL) was added dropwise methylmagnesium bromide (20 mL, 60 mmol) at −78° C. under nitrogen. Then the mixture was stirred at rt for 2 h. The reaction mixture was cooled in an ice bath and quenched with aqueous NH₄Cl. The layers were separated. The aqueous layer was extracted with EtOAc (15 mL), washed with a brine (30 mL), dried over Na₂SO₄ and concentrated in vacuo to give the crude product, which was purified by preparative HPLC and chiral HPLC to afford (S)-3-((S)-1-(4-bromophenyl) ethyl)-6-(4-fluorophenyl)-6-(2-hydroxy-2-methylpropyl)-1, 3-oxazinan-2-one (2.5 mg, 46%). ¹H NMR (CDCl₃): 1.08 (s, 3H), 1.12 (s, 3H), 1.48 (m, 3H), 1.99 (m, 1H), 2.10-2.24 (m, 4H), 2.35 (m, 1H), 2.85 (m, 1H), 5.61 (m, 1H), 6.80 (m, 2H), 6.99 (m, 2H), 7.15-7.28 (m, 5H).

Step 3

A mixture of (S)-3-((S)-1-(4-bromophenyl)ethyl)-6-(4-fluorophenyl)-6-(2-hydroxy-2-methylpropyl)-1,3-oxazinan-2-one (640 mg, 1.42 mmol), 4,4,4',4',5,5,5',5'-octamethyl-2, 2'-bi(1,3,2-dioxaborolane) (470 mg, 1.85 mmol), PdCl₂dppf (40 mg, 0.047 mmol☐KOAc (490 mg, 4.97 mmol) in DMSO (8 mL) was heated at 90° C. for 20 h. The mixture was diluted with EtOAc, and washed with water. The organic phase was separated, and concentrated to give the crude product, which was purified by preparative TLC to afford (S)-6-(4-fluorophenyl)-6-(2-hydroxy-2-methylpropyl)-3-((S)-1-(4-(4,4, 5,5-tetramethyl-1,3,2-dioxaborolan-2-yl)phenyl)ethyl)-1,3-oxazinan-2-one (700 mg, 99%). ¹H NMR (CDCl₃): δ=1.08 (s, 3H), 1.13 (s, 3H), 1.32 (s, 12H), 1.51 (t, 3H), 1.94 (m, 2H), 2.16 (m, 5H), 2.33 (m, 1H), 2.83 (m, 1H), 5.69 (m, 1H), 6.99 (m, 4H), 7.25 (m, 2H), 7.61 (m, 2H).

Step 4

A mixture of (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one (700 mg, 1.41 mmol), 5-bromo-1-methylpyridin-2(1H)-one (398 mg, 2.12 mmol), PdCl₂(Ph₃P)₂ (70 mg), Cs₂CO₃ (1.5 mL, 3.0 mmol) in 1,4-dioxane (15 mL) was heated under reflux for 2 h. The mixture was diluted with EtOAc, and washed with water. The organic phase was separated, and concentrated to give the crude product, which was purified by preparative TLC to afford (S)-6-(4-fluorophenyl)-6-(2-hydroxy-2-methylpropyl)-3-((S)-1-(4-(1-methyl-6-oxo-1,6-dihydropyridin-3-yl)phenyl)ethyl)-1,3-oxazinan-2-one (150 mg, 22%). ¹H NMR (CDCl₃): δ=1.12 (s, 3H), 1.13 (s, 3H), 1.51 (t, 3H), 2.16 (m, 2H), 2.21 (m, 2H), 2.41 (m, 1H), 2.92 (m, 1H), 3.63 (s, 3H), 5.69 (q, 1H), 6.69 (m, 1H), 6.99 (m, 4H), 7.18 (m, 2H) δ7.27 (m, 2H) δ 7.42 (m, 1H), 7.52 (m, 1H).

Example 460

(R)-6-(4-fluorophenyl)-6-(3-hydroxypropyl)-3-((S)-1-(4-(1-methyl-6-oxo-1,6-dihydropyridin-3-yl)phenyl)ethyl)-1,3-oxazinan-2-one

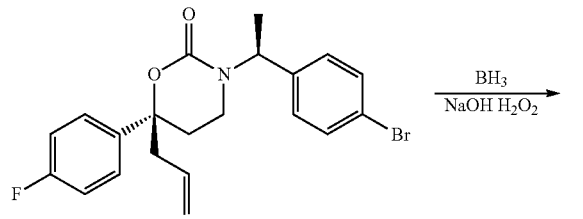

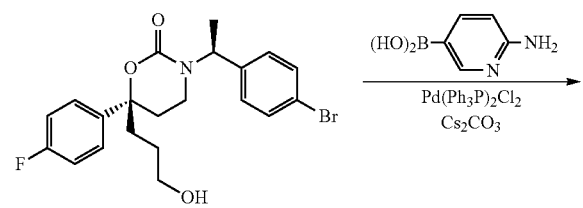

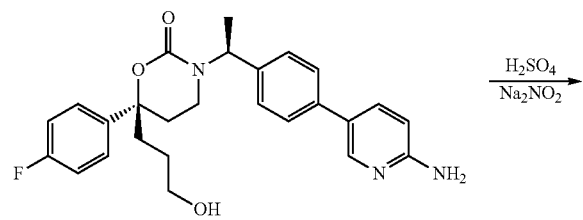

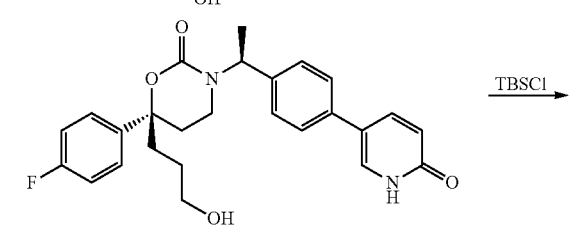

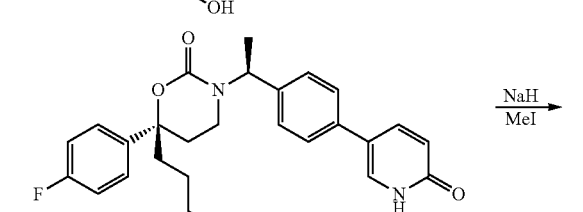

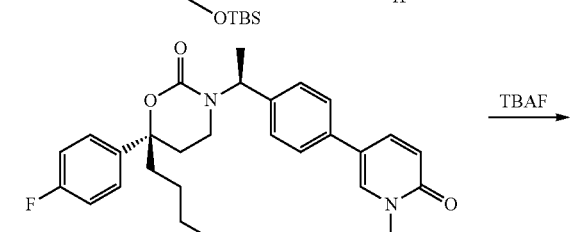

-continued

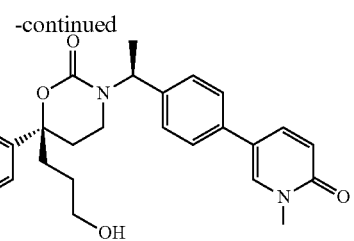

Step 1

To a solution of (R)-6-allyl-3-((S)-1-(4-bromophenyl)ethyl)-6-(4-fluorophenyl)-1,3-oxazinan-2-one (1.19 g, 2.8 mmol) in THF (30 mL) was added BH$_3$ THF (8.5 mL, 1 mol/L, 8.5 mmol) at 0° C. under nitrogen atmosphere. The formed mixture was stirred for 2 h. The reaction was quenched with water. Then NaOH (1 mol/L, 6 mL) and H$_2$O$_2$ (5 mL) were added to the above mixture. When the reaction was over, the mixture was extracted with EtOAc. The combined organic phase was concentrated to give the crude product, which was purified by preparative TLC to give (R)-3-((S)-1-(4-bromophenyl)ethyl)-6-(4-fluorophenyl)-6-(3-hydroxypropyl)-1,3-oxazinan-2-one (1.13 g, 92%).

Step 2

A mixture of (R)-3-((S)-1-(4-bromophenyl)ethyl)-6-(4-fluorophenyl)-6-(3-hydroxypropyl)-1,3-oxazinan-2-one (520 mg, 1.2 mmol) and 6-aminopyridin-3-ylboronic acid (280 mg, 1.44 mmol), Pd(Ph$_3$P)$_2$Cl$_2$ (100 mg), and aq Cs$_2$CO$_3$ solution (3 mL, 2M) in 1,4-dioxane (20 mL) was stirred and heated to reflux for 2 h. The organic phase was separated, and concentrated to give crude product, which was purified by preparative TLC to give (R)-3-((S)-1-(4-(6-aminopyridin-3-yl)phenyl)ethyl)-6-(4-fluoophenyl)-6-(3-hydroxy propyl)-1,3-oxazinan-2-one. (400 mg, 74%).

Step 3

(R)-3-((S)-1-(4-(6-aminopyridin-3-yl)phenyl)ethyl)-6-(4-fluorophenyl)-6-(3-hydroxypropyl)-1,3-oxazinan-2-one (400 mg, 0.88 mmoL) was dissolved in 3.5 M H$_2$SO$_4$ (10 mL), and 2 M NaNO$_2$ (6 mL) was added at 0° C. The reaction mixture was stirred at rt for 20 min. The reaction mixture was then treated with aqueous NaOH solution (8%), and extracted with CH$_2$Cl$_2$. The combined organic layer was washed with brine, dried over anhydrous Na$_2$SO$_4$, and concentrated to give crude product, which was purified by preparative TLC to give (R)-6-(4-fluorophenyl)-6-(3-hydroxypropyl)-3-((S)-1-(4-(6-oxo-1,6-dihydropyridin-3-yl)phenyl)ethyl)-1,3-oxazinan-2-one (350 mg, 0.78 mmol). $^1$H NMR (CDCl$_3$): δ=1.10-1.25 (m, 8H), 1.37 (m, 1H), 1.42-1.55 (m, 2H), 1.78-1.93 (m, 2H), 2.10-2.38 (m, 2H), 2.87 (m, 2H), 3.52-3.58 (m, 1H), 3.31-3.97 (m, 1H), 4.12-4.19 (m, 1H), 5.53-5.63 (m, 1H), 6.85-7.15 (m, 3H), 7.35-7.55 (m, 1H), 7.75-7.89 (m, 1H), 8.10-8.12 (m, 1H).

Step 4

A mixture of (R)-6-(4-fluorophenyl)-6-(3-hydroxypropyl)-3-((S)-1-(4-(6-oxo-1,6-dihydropyridin-3-yl)phenyl)ethyl)-1,3-oxazinan-2-one (100 mg, 0.78 mmol), imidazole (142.8 mg, 2.1 mmol), and tert-butylchlorodimethylsilane (350 mg, 2.34 mmol) in CH$_2$Cl$_2$ (20 mL) was stirred overnight. The mixture was washed with water and extracted with EtOAc. The combined organic phase was washed with brine, dried over Na$_2$SO$_4$, filtered and concentrated to give crude (R)-6-(3-(tert-butyldimethylsilyloxy)propyl)-6-(4-fluorophenyl)-3-((S)-1-(4-(6-oxo-1,6-dihydropyridin-3-yl)phenyl)ethyl)-1,3-oxazinan-2-one (120 mg), which was used for the next step without further purification.

Step 5

To a suspension of NaH (18 mg, 0.72 mmol) in THF (0.5 mL) was added a solution of (R)-6-(3-(tert-butyldimethylsilyloxy)propyl)-6-(4-fluorophenyl)-3-((S)-1-(4-(6-oxo-1,6-dihydropyridin-3-yl)phenyl)ethyl)-1,3-oxazinan-2-one (100 mg, 0.18 mmol) in THF (10 mL) at 0° C. The resulting mixture was stirred for 1 h. Then CH$_3$I (613 mg, 43.2 mmol) was added, and the mixture was stirred for 3 h. The reaction was quenched with aq NH$_4$Cl solution. The organic phase was separated, and concentrated to give (R)-6-(3-(tert-butyldimethylsilyloxy)propyl)-6-(4-fluorophenyl)-3-((S)-1-(4-(1-methyl-6-oxo-1,6-dihydropyridin-3-yl)phenyl)ethyl)-1,3-oxazinan-2-one (104 mg, 100%), which was used for the next step without further purification.

Step 6

A mixture of (R)-6-(3-(tert-butyldimethylsilyloxy)propyl)-6-(4-fluorophenyl)-3-((S)-1-(4-(1-methyl-6-oxo-1,6-dihydropyridin-3-yl)phenyl)ethyl)-1,3-oxazinan-2-one (200 mg, 0.35 mmol) and TBAF (182 mg, 0.7 mmol) in CH$_3$CN was stirred and heated to reflux for 15 min. When the reaction was over, the mixture was washed with water and extracted with EtOAc. The combined organic phase was washed with brine, dried over Na$_2$SO$_4$, filtered and concentrated to give crude product, which was purified by preparative HPLC to give (R)-6-(4-fluorophenyl)-6-(3-hydroxypropyl)-3-((S)-1-(4-(1-methyl-6-oxo-1,6-dihydropyridin-3-yl)phenyl)ethyl)-1,3-oxazinan-2-one (5.01 mg, 4%). LC-MS Method 2 $t_R$=1.065 min, m/z=464.21; $^1$H NMR (CDCl$_3$): δ=1.38 (m, 1H), 1.47 (d, 3H), 1.63 (m, 2H), 1.91 (m, 2H), 2.10-2.30 (m, 3H), 2.87 (m, 1H), 2.84 (m, 1H), 3.51 (m, 2H), 3.56 (s, 3H), 5.63 (m, 1H), 6.67 (m, 1H), 6.87-6.98 (m, 4H), 7.15 (m, 2H), 7.27 (m, 1H), 7.29 (m, 1H), 7.32 (m, 1H), 7.55 (m, 1H).

Example 461

N-(3-((R)-6-(4-fluorophenyl)-3-((S)-1-(4-(1-methyl-6-oxo-1,6-dihydropyridin-3-yl)phenyl)ethyl)-2-oxo-1,3-oxazinan-6-yl)propyl)methanesulfonamide

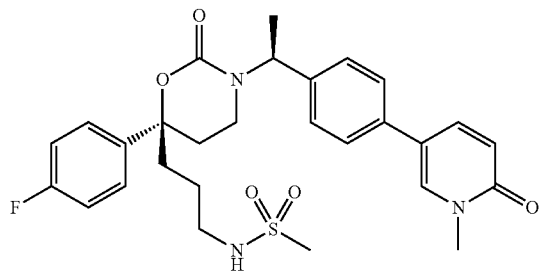 [SMILES: C[C@@H](c1ccc(-c2ccc(=O)n(C)c2)cc1)N1CC[C@](CCCNS(C)(=O)=O)(c2ccc(F)cc2)OC1=O]

The title compound was prepared from (R)-6-(4-fluorophenyl)-6-(3-hydroxypropyl)-3-((S)-1-(4-(1-methyl-6-oxo-1,6-dihydropyridin-3-yl)phenyl)ethyl)-1,3-oxazinan-2-one following procedures analogous to those described in Example 359. LC-MS Method 2 $t_R$=1.02 min, m/z=542.3; $^1$H NMR (CDCl$_3$) 1.35 (m, 1H), 1.53 (d, 3H), 1.69 (m, 1H), 1.89 (m, 1H), 2.00 (m, 1H), 2.17-2.33 (m, 3H), 2.89 (s, 3H), 2.97 (m, 1H), 3.06 (m, 2H), 3.66 (s, 3H), 4.38 (s, 1H), 5.67 (m, 1H), 6.82 (d, 1H), 6.99 (m, 4H), 7.15 (m, 2H), 7.22 (m, 2H), 7.47 (s, 1H), 7.63 (d, 1H).

Example 462

(R)-6-(2-(azetidin-1-yl)ethyl)-3-((S)-1-(4'-fluorobiphenyl-4-yl)ethyl)-6-(4-fluorophenyl)-1,3-oxazinan-2-one

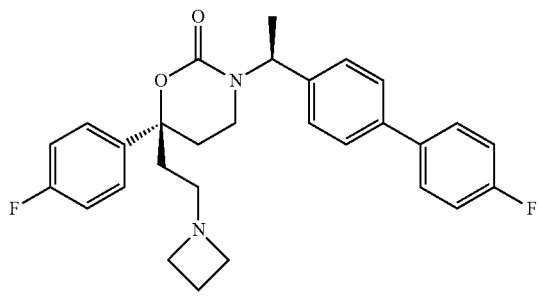 [SMILES: C[C@@H](c1ccc(-c2ccc(F)cc2)cc1)N1CC[C@](CCN2CCC2)(c2ccc(F)cc2)OC1=O]

The title compound was prepared from (S)-3-((S)-1-(4'-fluorobiphenyl-4-yl)ethyl)-6-(4-fluorophenyl)-6-(2-hydroxyethyl)-1,3-oxazinan-2-one following procedures analogous to those described in Example 178 using azetidine in Step 2. LC-MS Method 2 $t_R$=1.193 min, m/z=477.2; $^1$H NMR (CD$_3$OD) 1.57 (d, 3H), 2.16 (m, 2H), 2.26 (m, 2H), 2.48 (m, 1H), 2.50 (m, 2H), 3.01 (m, 1H), 3.11 (m, 1H), 3.25 (m, 1H), 3.40 (m, 2H), 4.20 (m, 2H), 5.59 (m, 1H), 7.08 (d, 2H), 7.14 (m, 4H), 7.33 (m, 2H), 7.37 (m, 2H), 7.54 (m, 2H).

Example 463

(R)-3-((S)-1-(4'-fluorobiphenyl-4-yl)ethyl)-6-(2-(2-fluoroethylamino)ethyl)-6-(4-fluorophenyl)-1,3-oxazinan-2-one

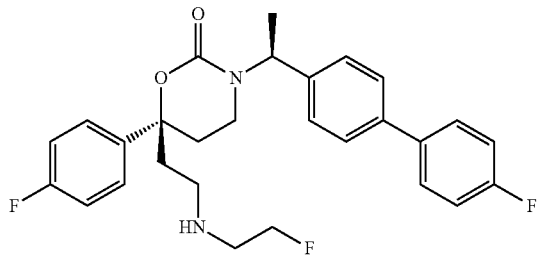 [SMILES: C[C@@H](c1ccc(-c2ccc(F)cc2)cc1)N1CC[C@](CCNCCF)(c2ccc(F)cc2)OC1=O]

The title compound was prepared from (S)-3-((S)-1-(4'-fluorobiphenyl-4-yl)ethyl)-6-(4-fluorophenyl)-6-(2-hydroxyethyl)-1,3-oxazinan-2-one following procedures analogous to those described in Example 178 using 2-fluoroethylamine in Step 2. LC-MS Method 2 $t_R$=1.183 min, m/z=505.1; $^1$H NMR (CDCl$_3$) 1.48 (d, 3H), 1.94-2.32

(m, 5H), 2.40 (m, 1H), 2.67-2.85 (m, 3H), 2.86 (m, 1H), 4.34 (t, 1H), 4.45 (t, 1H), 5.62 (m, 1H), 6.88-7.19 (m, 6H), 7.20 (m, 4H), 7.40 (m, 2H).

Example 464

(R)-3-((S)-1-(4'-fluorobiphenyl-4-yl)ethyl)-6-(4-fluorophenyl)-6-(2-(pyrrolidin-1-yl)ethyl)-1,3-oxazinan-2-one

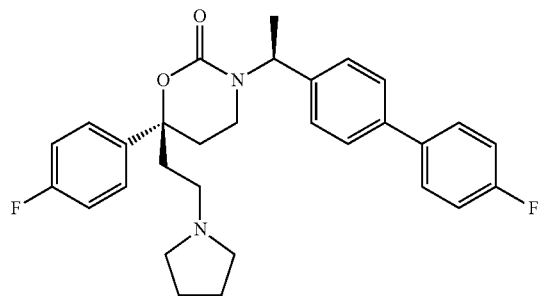 [SMILES: C[C@@H](c1ccc(-c2ccc(F)cc2)cc1)N1CC[C@](CCN2CCCC2)(c2ccc(F)cc2)OC1=O]

The title compound was prepared from (S)-3-((S)-1-(4'-fluorobiphenyl-4-yl)ethyl)-6-(4-fluorophenyl)-6-(2-hydroxyethyl)-1,3-oxazinan-2-one following procedures analogous to those described in Example 178 using pyrrolidine in Step 2. LC-MS Method 2 $t_R$=1.225 min, m/z=491.1; $^1$H NMR (CD$_3$OD) 1.62 (d, 3H), 2.01 (m, 2H), 2.14 (m, 2H), 2.22-2.49 (m, 4H), 2.56 (m, 1H), 2.92-3.13 (m, 3H), 3.19 (m, 1H), 3.41 (m, 1H), 3.69 (m, 2H), 5.64 (m, 1H), 7.12 (d, 2H), 7.21 (m, 3H), 7.43 (m, 4H), 7.57 (m, 2H).

Example 465

(R)-3-((S)-1-(4'-fluorobiphenyl-4-yl)ethyl)-6-(4-fluorophenyl)-6-(2-((S)-3-fluoropyrrolidin-1-yl)ethyl)-1,3-oxazinan-2-one

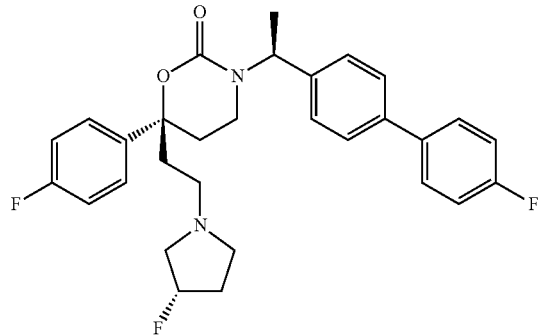 [SMILES: C[C@@H](c1ccc(-c2ccc(F)cc2)cc1)N1CC[C@](CCN2CC[C@H](F)C2)(c2ccc(F)cc2)OC1=O]

The title compound was prepared from (S)-3-((S)-1-(4'-fluorobiphenyl-4-yl)ethyl)-6-(4-fluorophenyl)-6-(2-hydroxyethyl)-1,3-oxazinan-2-one following procedures analogous to those described in Example 178 using (S)-3-fluoropyrrolidine in Step 2. LC-MS Method 3 $t_R$=0.962 min, m/z=531.1; $^1$H NMR (CDCl$_3$) 0.80-0.92 (m, 1H), 1.46-1.57 (m, 4H), 1.59 (s, 3H), 2.16-2.40 (m, 6H), 2.75-3.09 (m, 3H), 5.10-5.38 (m, 1H), 5.70 (m, 1H), 7.01-7.13 (m, 6H), 7.30-7.49 (m, 4H), 7.46 (m, 2H).

Example 466

(R)-3-((S)-1-(4'-fluorobiphenyl-4-yl)ethyl)-6-(4-fluorophenyl)-6-(2-((R)-3-fluoropyrrolidin-1-yl)ethyl)-1,3-oxazinan-2-one

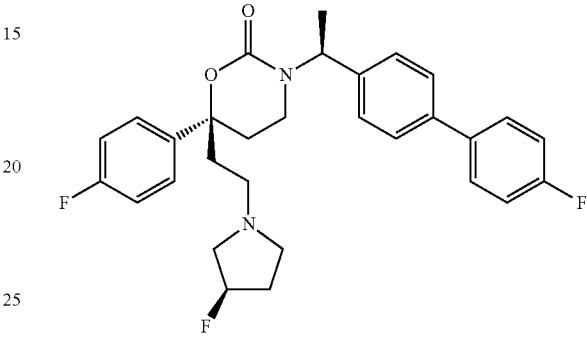

The title compound was prepared from (S)-3-((S)-1-(4'-fluorobiphenyl-4-yl)ethyl)-6-(4-fluorophenyl)-6-(2-hydroxyethyl)-1,3-oxazinan-2-one following procedures analogous to those described in Example 178 using (R)-3-fluoropyrrolidine in Step 2. LC-MS Method 2 $t_R$=1.2 min, m/z=509.1; $^1$H NMR (CDCl$_3$) 0.67-0.86 (m, 1H), 1.47 (d, 6H), 1.87-2.34 (m, 7H), 2.70-2.91 (m, 3H), 5.00-5.23 (d, 2H), 5.63 (m, 1H), 6.92-7.06 (m, 6H), 7.25 (m, 4H), 7.39 (m, 2H).

Example 467

(R)-3-((S)-1-(4'-fluorobiphenyl-4-yl)ethyl)-6-(4-fluorophenyl)-6-(2-(3-oxopiperazin-1-yl)ethyl)-1,3-oxazinan-2-one

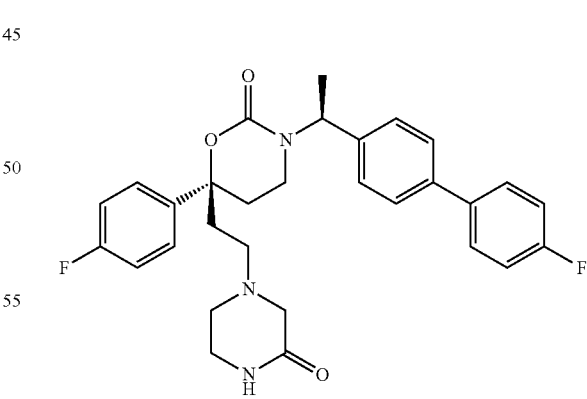

The title compound was prepared from (S)-3-((S)-1-(4'-fluorobiphenyl-4-yl)ethyl)-6-(4-fluorophenyl)-6-(2-hydroxyethyl)-1,3-oxazinan-2-one following procedures analogous to those described in Example 178 using piperazin-2-one in Step 2. LC-MS Method 2 $t_R$=1.213 min, m/z=519.23; $^1$H NMR (CDCl$_3$) 1.46 (d, 3H), 2.13-2.27 (m, 3H), 2.35 (m, 2H), 2.75 (m, 1H), 2.88 (m, 1H), 3.20-3.39 (m, 3H), 3.51 (s, 2H), 3.66 (s, 2H), 5.54 (m, 1H), 6.94-7.05 (m, 6H), 7.14 (m, 2H), 7.25 (d, 2H), 7.37 (m, 2H), 7.85 (m, 1H).

Example 468

(S)-6-(2-hydroxyethyl)-6-phenyl-3-((S)-1-(4-(pyridin-2-yl)phenyl)ethyl)-1,3-oxazinan-2-one

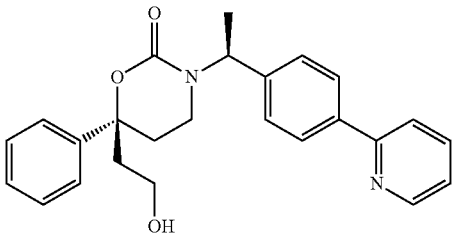 [SMILES: C[C@@H](c1ccc(-c2ccccn2)cc1)N1CC[C@](CCO)(c2ccccc2)OC1=O]

The title compound was prepared from (S)-3-((S)-1-(4-bromophenyl)ethyl)-6-(2-hydroxyethyl)-6-phenyl-1,3-oxazinan-2-one and pyridine-2-boronic acid following procedures analogous to those described in Example 75 Step 1. LC-MS Method 2 $t_R$=0.976 min, m/z=805.3; $^1$H NMR (CDCl$_3$) 1.50 (d, 2H), 2.06-2.19 (m, 2H), 2.26 (m, 3H), 2.83 (m, 1H), 3.53 (m, 1H), 3.71 (m, 1H), 5.64 (m, 1H), 6.94 (d, 2H), 7.14 (m, 1H), 7.24 (m, 3H), 7.28 (m, 2H), 7.56 (d, 2H), 7.67 (m, 3H), 8.59 (d, 1H).

Example 469

(S)-6-(2-hydroxy-2-methylpropyl)-6-phenyl-3-((S)-1-(4-(pyridin-2-yl)phenyl)ethyl)-1,3-oxazinan-2-one

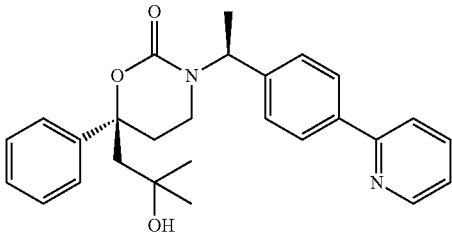 [SMILES: C[C@@H](c1ccc(-c2ccccn2)cc1)N1CC[C@](CC(C)(C)O)(c2ccccc2)OC1=O]

The title compound was prepared from (S)-3-((S)-1-(4-bromophenyl)ethyl)-6-(2-hydroxy-2-methylpropyl)-6-phenyl-1,3-oxazinan-2-one and pyridine-2-boronic acid following procedures analogous to those described in Example 75 Step 1. LC-MS Method 2 $t_R$=1.542 min, m/z=430.23; $^1$H NMR (CDCl$_3$) 1.02-1.15 (d, 6H), 1.50 (d, 3H), 2.09-2.21 (m, 6H), 2.32 (m, 1H), 2.78 (m, 1H), 5.65 (m, 1H), 6.98 (d, 2H), 7.15-7.30 (m, 6H), 7.55 (m, 1H), 7.70 (d, 1H), 8.60 (d, 1H).

Example 470

(R)-6-(3-hydroxypropyl)-6-phenyl-3-((S)-1-(4-(pyridin-2-yl)phenyl)ethyl)-1,3-oxazinan-2-one

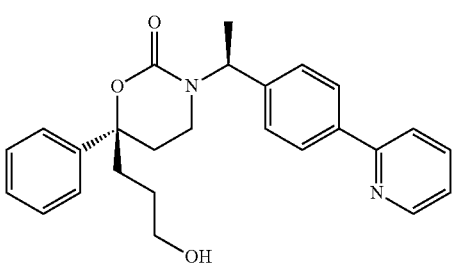

The title compound was prepared from (R)-3-((S)-1-(4-bromophenyl)ethyl)-6-(3-hydroxypropyl)-6-phenyl-1,3-oxazinan-2-one and pyridine-2-boronic acid following procedures analogous to those described in Example 75 Step 1. LC-MS Method 2 $t_R$=1.01 min, m/z=416.21; $^1$H NMR (CD$_3$OD) 1.30 (m, 1H), 1.55 (d, 3H), 1.62 (m, 1H), 1.94 (m, 2H), 2.20 (m, 1H), 2.32 (m, 1H), 2.48 (m, 1H), 3.09 (m, 1H), 3.44 (m, 2H), 5.57 (m, 1H), 7.03 (d, 2H), 7.29-7.40 (m, 6H), 7.67 (d, 2H), 7.73 (d, 1H), 7.84 (t, 1H), 8.55 (d, 1H).

Example 471

3-((R)-2-oxo-6-phenyl-3-((S)-1-(4-(pyridin-2-yl)phenyl)ethyl)-1,3-oxazinan-6-yl)propanamide

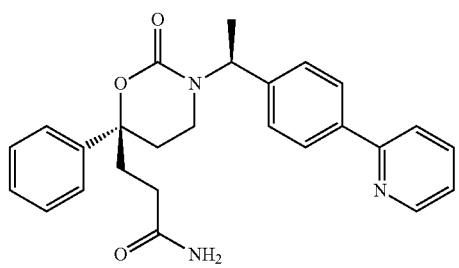 [SMILES: C[C@@H](c1ccc(-c2ccccn2)cc1)N1CC[C@](CCC(N)=O)(c2ccccc2)OC1=O]

The title compound was prepared from 3-((R)-3-((S)-1-(4-bromophenyl)ethyl)-2-oxo-6-phenyl-1,3-oxazinan-6-yl)propanamide and pyridine-2-boronic acid following procedures analogous to those described in Example 75 Step 1. LC-MS Method 2 $t_R$=0.932 min, m/z=430.1; $^1$H NMR (CDCl$_3$) 1.52 (d, 3H), 1.90 (m, 1H), 2.13 (m, 1H), 2.21 (m, 4H), 2.45 (m, 1H), 2.82 (m, 1H), 5.15 (s, 1H), 5.35 (s, 1H), 5.65 (m, 1H), 6.98 (d, 2H), 7.13-7.32 (m, 6H), 7.56 (m, 1H), 7.65 (m, 3H), 8.57 (d, 1H).

Example 472

N-(3-((R)-2-oxo-6-phenyl-3-((S)-1-(4-(pyridin-2-yl)phenyl)ethyl)-1,3-oxazinan-6-yl)propyl)methanesulfonamide

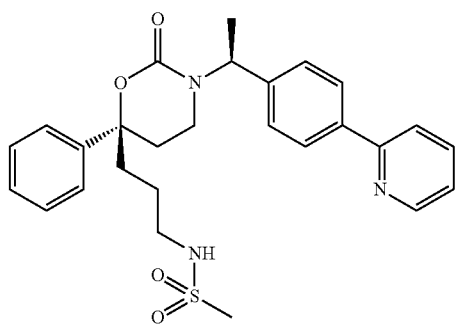 [SMILES: C[C@@H](c1ccc(-c2ccccn2)cc1)N1CC[C@](CCCNS(C)(=O)=O)(c2ccccc2)OC1=O]

The title compound was prepared from N-(3-((R)-3-((S)-1-(4-bromophenyl)ethyl)-2-oxo-6-phenyl-1,3-oxazinan-6-yl)propyl)methanesulfonamide and pyridine-2-boronic acid following procedures analogous to those described in Example 75 Step 1. LC-MS Method 2 $t_R$=1.017 min, m/z=494.1; $^1$H NMR (CDCl$_3$) 1.37-1.48 (m, 1H), 1.49 (d, 3H), 1.67 (m, 1H), 1.82-1.99 (m, 2H), 2.05-2.18 (m, 1H), 2.12-2.23 (m, 2H), 2.82 (m, 4H), 3.00 (m, 2H), 4.25 (m, 1H), 5.65 (m, 1H), 6.96 (d, 2H), 7.14-7.29 (m, 6H), 7.55 (d, 1H), 7.65 (m, 3H), 8.58 (d, 1H).

Example 473

(R)-6-(3-hydroxypropyl)-3-((S)-1-(4-(6-methylpyridin-2-yl)phenyl)ethyl)-6-phenyl-1,3-oxazinan-2-one

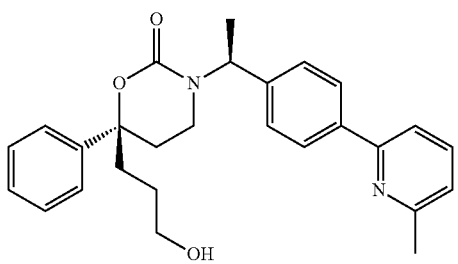 [SMILES: Cc1cccc(-c2ccc([C@H](C)N3CC[C@](CCCO)(c4ccccc4)OC3=O)cc2)n1]

The title compound was prepared from (R)-3-((S)-1-(4-bromophenyl)ethyl)-6-(3-hydroxypropyl)-6-phenyl-1,3-oxazinan-2-one and 6-methylpyridine-2-boronic acid following procedures analogous to those described in Example 75 Step 1. LC-MS Method 2 $t_R$=0.986 min, m/z=431.1; $^1$H NMR (CDCl$_3$) 1.33 (m, 2H), 1.52 (d, 3H), 1.69 (m, 1H), 1.97 (m, 2H), 2.12-2.30 (m, 3H), 2.56 (s, 3H), 2.85 (m, 1H), 3.52 (t, 2H), 5.67 (m, 1H), 6.95 (d, 2H), 7.03 (d, 1H), 7.22-7.37 (m, 6H), 7.55 (t, 1H), 7.64 (d, 2H).

Example 474

N-(3-((R)-2-oxo-6-phenyl-3-((S)-1-(4-(pyridin-3-yl)phenyl)ethyl)-1,3-oxazinan-6-yl)propyl)methanesulfonamide

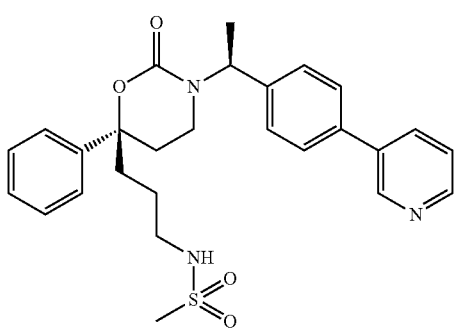 [SMILES: C[C@@H](c1ccc(-c2cccnc2)cc1)N1CC[C@](CCCNS(C)(=O)=O)(c2ccccc2)OC1=O]

The title compound was prepared from N-(3-((R)-3-((S)-1-(4-bromophenyl)ethyl)-2-oxo-6-phenyl-1,3-oxazinan-6-yl)propyl)methanesulfonamide and pyridine-3-boronic acid following procedures analogous to those described in Example 75 Step 1. LC-MS Method 2 $t_R$=1.466 min, m/z=497.3; $^1$H NMR (CDCl$_3$) 1.33 (m, 1H), 1.53 (d, 3H), 1.63 (m, 1H), 1.84-2.03 (m, 2H), 2.18 (m, 1H), 2.30 (m, 2H), 2.84 (s, 3H), 2.93 (m, 1H), 3.02 (t, 2H), 4.30 (s, 1H), 5.64 (m, 1H), 7.02 (d, 2H), 7.22 (m, 2H), 7.31 (m, 5H), 7.77 (m, 1H), 7.80 (d, 1H), 8.71 (d, 1H), 8.93 (s, 1H).

Example 475

(S)-6-(2-hydroxyethyl)-3-((S)-1-(4-(6-methoxypyridin-3-yl)phenyl)ethyl)-6-phenyl-1,3-oxazinan-2-one

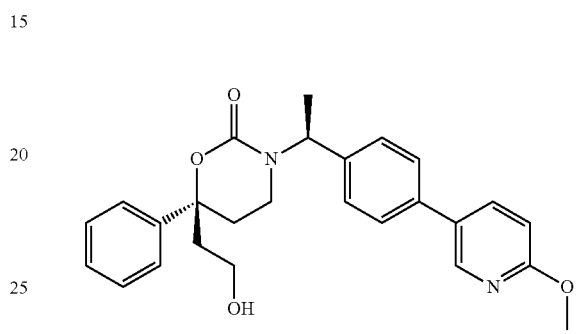

The title compound was prepared from (S)-3-((S)-1-(4-bromophenyl)ethyl)-6-(2-hydroxyethyl)-6-phenyl-1,3-oxazinan-2-one and 6-methoxypyridine-3-boronic acid following procedures analogous to those described in Example 75 Step 1. LC-MS Method 2 $t_R$=1.269 min, m/z=432.2; $^1$H NMR (CDCl$_3$) 1.50 (d, 3H), 2.05-2.35 (m, 5H), 2.90 (m, 1H), 3.51 (m, 1H), 3.70 (m, 1H), 3.97 (s, 3H), 5.63 (m, 1H), 6.85 (d, 1H), 6.92 (m, 2H), 7.17-7.35 (m, 6H), 7.81 (d, 1H), 8.32 (s, 1H).

Example 476

(S)-6-(2-hydroxy-2-methylpropyl)-3-((S)-1-(4-(6-methoxypyridin-3-yl)phenyl)ethyl)-6-phenyl-1,3-oxazinan-2-one

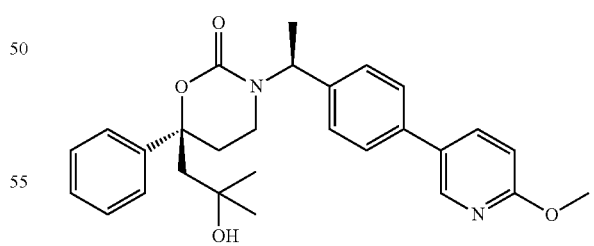

The title compound was prepared from (S)-3-((S)-1-(4-bromophenyl)ethyl)-6-(2-hydroxy-2-methylpropyl)-6-phenyl-1,3-oxazinan-2-one and 6-methoxypyridine-3-boronic acid following procedures analogous to those described in Example 75 Step 1. LC-MS Method 2 $t_R$=1.989 min, m/z=403.1; $^1$H NMR (CDCl$_3$) 1.10 (s, 3H), 1.17 (s, 3H), 1.52 (d, 3H), 2.13-2.28 (m, 6H), 2.47 (m, 1H), 2.87 (m, 1H), 3.95

(s, 3H), 5.70 (m, 1H), 6.79 (d, 1H), 7.02 (d, 2H), 7.21-7.38 (m, 6H), 7.58 (d, 1H), 8.27 (d, 1H).

Example 477

N-(3-((R)-3-((S)-1-(4-(6-methoxypyridin-3-yl)phenyl)ethyl)-2-oxo-6-phenyl-1,3-oxazinan-6-yl)propyl)methanesulfonamide

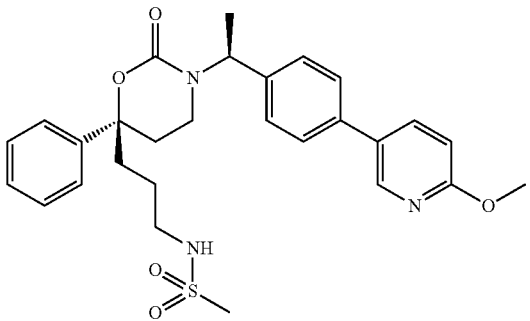 [SMILES: COc1ccc(-c2ccc([C@H](C)N3CC[C@](CCCNS(C)(=O)=O)(c4ccccc4)OC3=O)cc2)cn1]

The title compound was prepared from N-(3-((R)-3-((S)-1-(4-bromophenyl)ethyl)-2-oxo-6-phenyl-1,3-oxazinan-6-yl)propyl)methanesulfonamide and 6-methoxypyridine-3-boronic acid following procedures analogous to those described in Example 75 Step 1. LC-MS Method 2 $t_R$=1.316 min, m/z=524.1; $^1$H NMR (CDCl$_3$) 1.28-1.38 (m, 1H), 1.48 (d, 3H), 1.67 (m, 1H), 1.81-1.98 (m, 2H), 2.13 (m, 1H), 2.24 (m, 2H), 2.83 (m, 4H), 3.01 (m, 2H), 3.91 (s, 3H), 4.15 (m, 1H), 5.62 (m, 1H), 6.73 (d, 1H), 6.91 (d, 2H), 7.18-7.32 (m, 7H), 7.62 (dd, 1H), 8.21 (s, 1H).

Example 478

(R)-3-((S)-1-(4-(6-aminopyridin-3-yl)phenyl)ethyl)-6-(3-hydroxypropyl)-6-phenyl-1,3-oxazinan-2-one

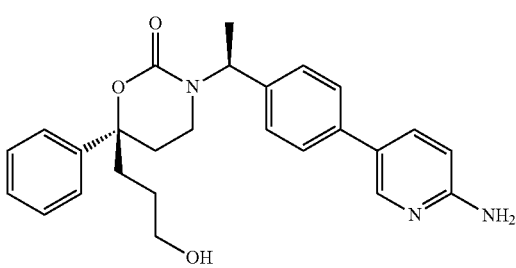 [SMILES: C[C@@H](c1ccc(-c2ccc(N)nc2)cc1)N1CC[C@](CCCO)(c2ccccc2)OC1=O]

The title compound was prepared from (R)-3-((S)-1-(4-bromophenyl)ethyl)-6-(3-hydroxypropyl)-6-phenyl-1,3-oxazinan-2-one and 6-aminopyridine-3-boronic acid following procedures analogous to those described in Example 75 Step 1. LC-MS Method 2 $t_R$=0.963 min, m/z=431.8; $^1$H NMR (CDCl$_3$) 1.36 (d, 3H), 1.75 (m, 1H), 1.98 (m, 3H), 2.21 (m, 1H), 2.38 (m, 2H), 2.89 (m, 1H), 3.56 (m, 2H), 5.05 (s, 1H), 5.65 (m, 1H), 6.62 (d, 1H), 6.97 (d, 2H), 7.17 (d, 2H), 7.20-7.39 (m, 5H), 7.63 (d, 1H), 8.12 (s, 1H).

Example 479

(S)-6-(2-hydroxyethyl)-3-((S)-1-(4-(2-methylpyridin-4-yl)phenyl)ethyl)-6-phenyl-1,3-oxazinan-2-one

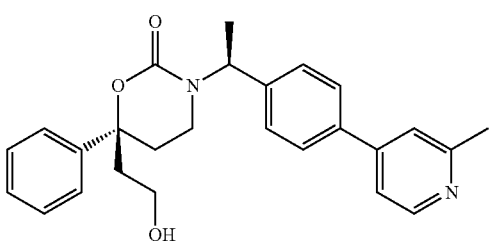 [SMILES: Cc1cc(-c2ccc([C@H](C)N3CC[C@](CCO)(c4ccccc4)OC3=O)cc2)ccn1]

The title compound was prepared from (S)-3-((S)-1-(4-bromophenyl)ethyl)-6-(2-hydroxyethyl)-6-phenyl-1,3-oxazinan-2-one and 2-methylpyridine-4-boronic acid following procedures analogous to those described in Example 75 Step 1. LC-MS Method 2 $t_R$=0.928 min, m/z=444.4; $^1$H NMR (CDCl$_3$) 1.50 (d, 3H), 2.05-2.18 (m, 2H), 2.26-2.39 (m, 6H), 2.82 (s, 3H), 2.94 (m, 1H), 3.51 (m, 1H), 3.72 (m, 1H), 5.54 (m, 1H), 7.00 (d, 2H), 7.24-7.38 (m, 7H), 7.57 (s, 1H), 7.64 (d, 1H), 8.75 (d, 1H).

Example 480

(S)-6-(2-hydroxy-2-methylpropyl)-3-((S)-1-(4-(2-methylpyridin-4-yl)phenyl)ethyl)-6-phenyl-1,3-oxazinan-2-one

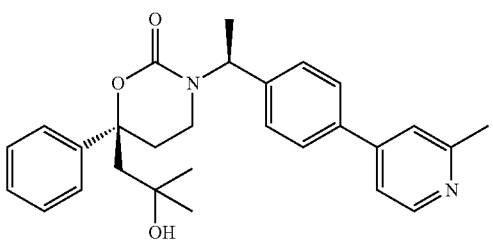 [SMILES: Cc1cc(-c2ccc([C@H](C)N3CC[C@](CC(C)(C)O)(c4ccccc4)OC3=O)cc2)ccn1]

The title compound was prepared from (S)-3-((S)-1-(4-bromophenyl)ethyl)-6-(2-hydroxy-2-methylpropyl)-6-phenyl-1,3-oxazinan-2-one and 2-methylpyridine-4-boronic acid following procedures analogous to those described in Example 75 Step 1. LC-MS Method 2 $t_R$=0.866 min, m/z=444.2; $^1$H NMR (CDCl$_3$) 1.04-1.16 (d, 6H), 1.50 (d, 3H), 2.14-2.25 (m, 4H), 2.45 (m, 1H), 2.57 (s, 3H), 2.83 (m, 1H), 5.65 (m, 1H), 7.04 (d, 2H), 7.20-7.33 (m, 9H), 8.45 (d, 1H).

Example 481

3-((R)-3-((S)-1-(4-(2-methylpyridin-4-yl)phenyl)ethyl)-2-oxo-6-phenyl-1,3-oxazinan-6-yl)propanamide

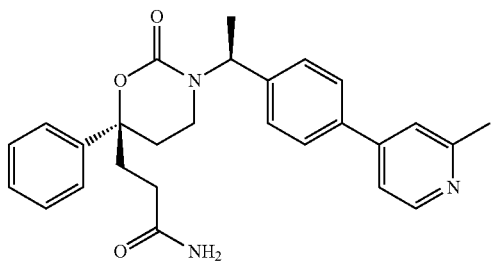 [SMILES: Cc1cc(-c2ccc([C@H](C)N3CC[C@](CCC(N)=O)(c4ccccc4)OC3=O)cc2)ccn1]

The title compound was prepared from 3-((R)-3-((S)-1-(4-bromophenyl)ethyl)-2-oxo-6-phenyl-1,3-oxazinan-6-yl)propanamide and 2-methylpyridine-4-boronic acid following procedures analogous to those described in Example 75 Step 1. LC-MS Method 2 $t_R$=0.917 min, m/z=444.4; $^1$H NMR (CDCl$_3$) 1.51 (d, 3H), 1.92 (m, 1H), 2.13-2.32 (m, 5H), 2.44 (m, 1H), 2.82 (s, 3H), 2.93 (m, 1H), 5.50-5.68 (m, 3H), 7.06 (d, 2H), 7.19-7.35 (m, 5H), 7.39 (d, 2H), 7.58 (s, 1H), 7.65 (d, 1H), 8.74 (d, 1H).

Example 482

N-(3-((R)-3-((S)-1-(4-(2-methylpyridin-4-yl)phenyl)ethyl)-2-oxo-6-phenyl-1,3-oxazinan-6-yl)propyl)methanesulfonamide

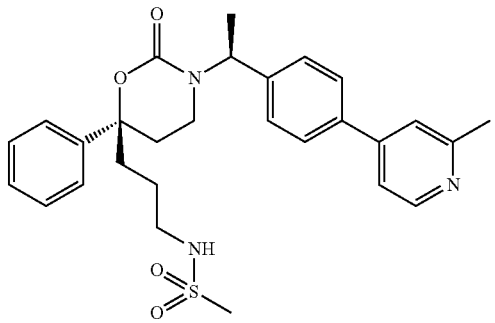 [SMILES: Cc1cc(-c2ccc([C@H](C)N3CC[C@](CCCNS(C)(=O)=O)(c4ccccc4)OC3=O)cc2)ccn1]

The title compound was prepared from N-(3-((R)-3-((S)-1-(4-bromophenyl)ethyl)-2-oxo-6-phenyl-1,3-oxazinan-6-yl)propyl)methanesulfonamide and 2-methylpyridine-4-boronic acid following procedures analogous to those described in Example 75 Step 1. LC-MS Method 2 $t_R$=0.988 min, m/z=508.2; $^1$H NMR (CDCl$_3$) 1.36 (m, 1H), 1.51 (d, 3H), 1.70 (m, 1H), 1.96 (m, 2H), 2.17 (m, 1H), 2.26 (m, 2H), 2.59 (s, 3H), 2.86 (m, 4H), 3.02 (m, 2H), 4.19 (m, 1H), 5.62 (m, 1H), 6.96 (d, 2H), 7.19 (m, 3H), 7.26 (d, 2H), 7.29 (m, 4H), 8.47 (d, 1H).

Example 483

(R)-6-(3-hydroxypropyl)-3-((S)-1-(4-(1-methyl-1H-pyrazol-3-yl)phenyl)ethyl)-6-phenyl-1,3-oxazinan-2-one

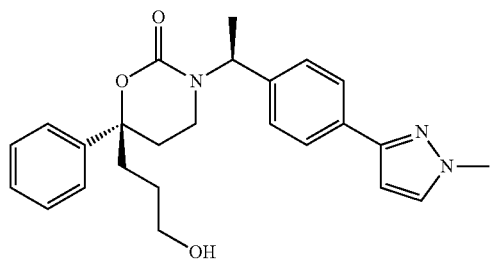 [SMILES: C[C@@H](c1ccc(-c2ccn(C)n2)cc1)N1CC[C@](CCCO)(c2ccccc2)OC1=O]

The title compound was prepared from (R)-6-allyl-3-((S)-1-(4-bromophenyl)ethyl)-6-phenyl-1,3-oxazinan-2-one and pyrazole-3-boronic acid following a procedure analogous to that described in Example 64, followed by treatment with NaH and MeI, using a procedure analogous to that described in Example 199 Step 2, and hydroboration using a procedure analogous to that described in Example 78. LC-MS Method 3 $t_R$=1.18 min, m/z=442.1; $^1$H NMR (CDCl$_3$) 1.29 (m, 1H), 1.47 (d, 3H), 1.65 (m, 1H), 1.83-2.03 (m, 3H), 2.11 (m, 1H), 2.18-2.37 (m, 3H), 2.75-2.96 (m, 1H), 3.52 (m, 2H), 3.78 (m, 1H), 3.91 (s, 1H), 5.63 (m, 1H), 6.41 (s, 1H), 6.87 (d, 2H), 6.94 (d, 1H), 7.08 (d, 1H), 7.19-7.37 (m, 7H), 7.43 (d, 2H).

Example 484

3-((R)-2-oxo-3-((S)-1-(4-(6-oxo-1,6-dihydropyridin-3-yl)phenyl)ethyl)-6-phenyl-1,3-oxazinan-6-yl)propanamide

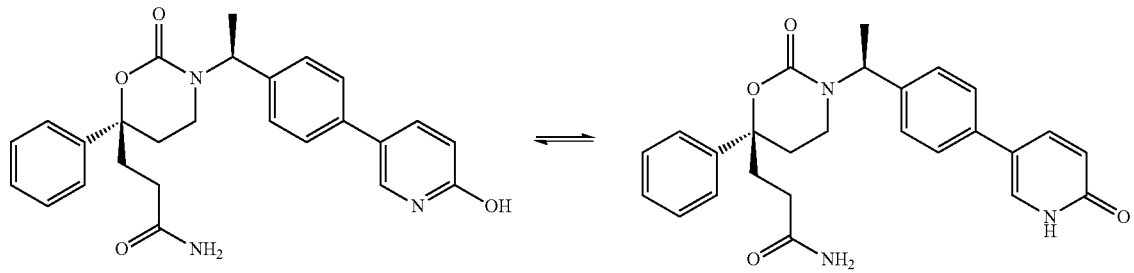 [SMILES: C[C@@H](c1ccc(-c2ccc(O)nc2)cc1)N1CC[C@](CCC(N)=O)(c2ccccc2)OC1=O ; C[C@@H](c1ccc(-c2ccc(=O)[nH]c2)cc1)N1CC[C@](CCC(N)=O)(c2ccccc2)OC1=O]

The title compound was prepared from (R)-6-(3-hydroxypropyl)-3-((S)-1-(4-(6-oxo-1,6-dihydropyridin-3-yl)phenyl)ethyl)-6-phenyl-1,3-oxazinan-2-one following procedures analogous to those described in Example 234. LC-MS Method 2 $t_R$=0.999 min, m/z=446.1; $^1$H NMR (CD$_3$OD) 1.53 (d, 3H), 1.91-2.01 (m, 1H), 2.18-2.34 (m, 4H), 2.35-2.51 (m, 2H), 3.03-3.12 (m, 1H), 5.56 (m, 1H), 6.62 (d, 2H), 7.03 (d, 2H), 7.24-7.44 (m, 7H), 7.59 (m, 1H), 7.87 (m, 1H).

Example 485

(S)-6-(2-hydroxyethyl)-3-((S)-1-(4-(1-methyl-6-oxo-1,6-dihydropyridin-3-yl)phenyl)ethyl)-6-phenyl-1,3-oxazinan-2-one

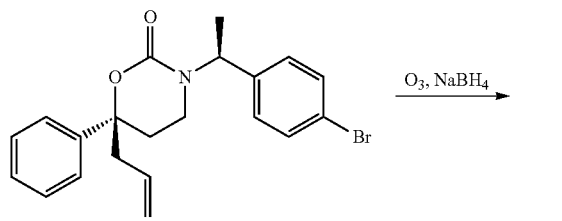

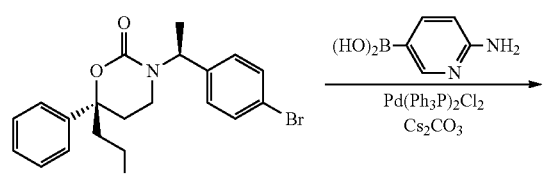

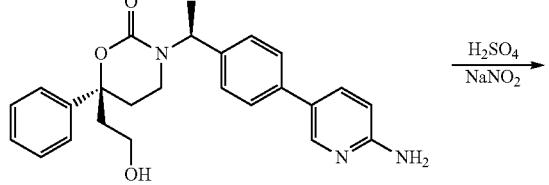

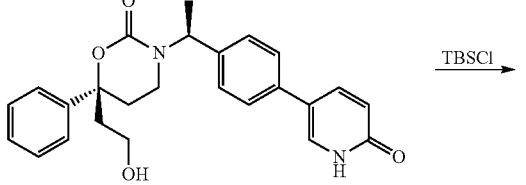

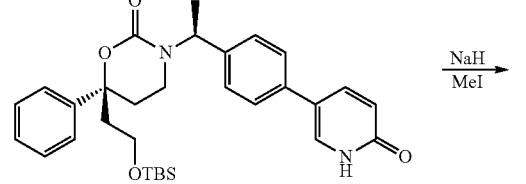

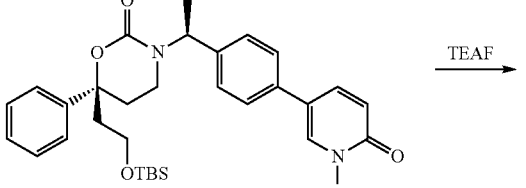

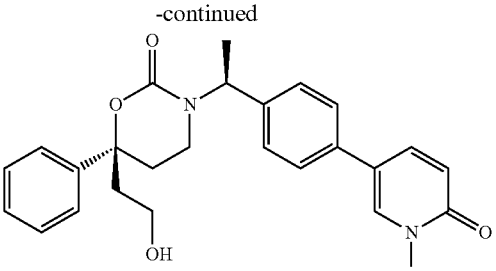

The title compound was prepared from (R)-6-allyl-3-((S)-1-(4-bromophenyl)ethyl)-6-phenyl-1,3-oxazinan-2-one using a procedure analogous to that described in Example 74, followed by procedures analogous to those described in Example 458 Steps 2 to 6. LC-MS Method 2 $t_R$=1.038 min, m/z=433.1; $^1$H NMR (CDCl$_3$) 1.48 (d, 3H), 2.06-2.19 (m, 2H), 2.11-2.31 (m, 3H), 2.84 (m, 1H), 3.50 (m, 1H), 3.54 (s, 3H), 3.72 (m, 1H), 5.62 (m, 1H), 6.60 (d, 1H), 6.86 (d, 2H), 7.06 (d, 2H), 7.26 (m, 3H), 7.32 (m, 3H), 7.47 (d, 1H).

Example 486

(S)-6-(2-hydroxy-2-methylpropyl)-3-((S)-1-(4-(1-methyl-6-oxo-1,6-dihydropyridin-3-yl)phenyl)ethyl)-6-phenyl-1,3-oxazinan-2-one Method 1

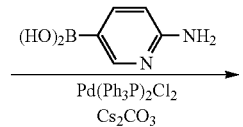

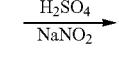

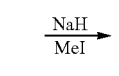

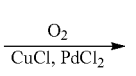

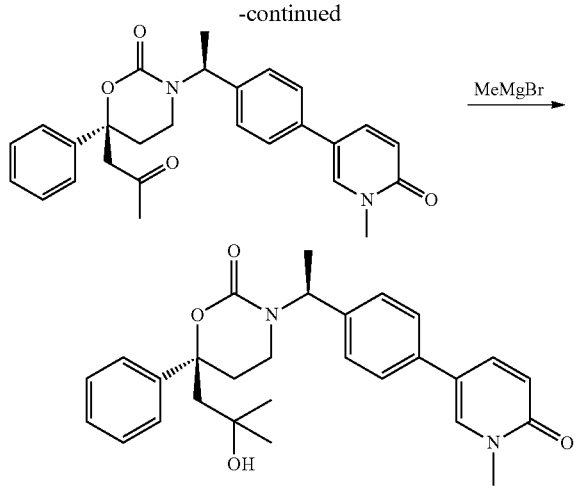

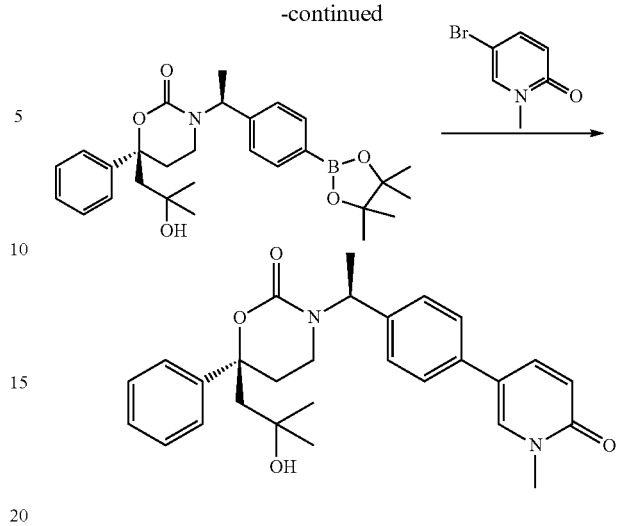

The title compound was prepared from (R)-6-allyl-3-((S)-1-(4-bromophenyl)ethyl)-6-phenyl-1,3-oxazinan-2-one using procedures analogous to those described in Example 458 Steps 2, 3 and 5, followed by procedures analogous to those described in Example 328. LC-MS Method 2 $t_R$=1.116 min, m/z=461.1; $^1$H NMR (CDCl$_3$) 1.09 (s, 3H), 1.16 (s, 3H), 1.51 (m, 3H), 2.05-2.20 (4H), 2.40 (m, 1H), 2.84 (m, 1H), 3.59 (s, 3H), 5.64 (m, 1H), 6.62 (m, 1H), 6.96 (m, 2H), 7.14 (m, 2H), 7.28-7.39 (m, 5H), 7.48 (m, 1H), 7.50 (m, 1H).

Method 2

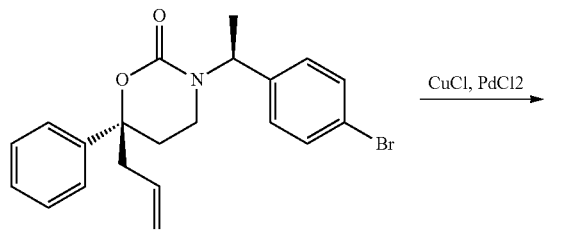

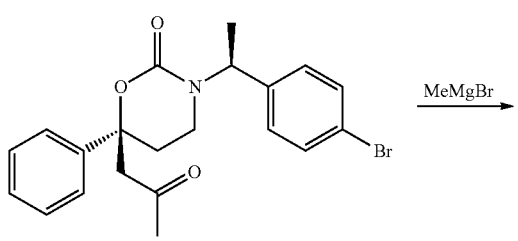

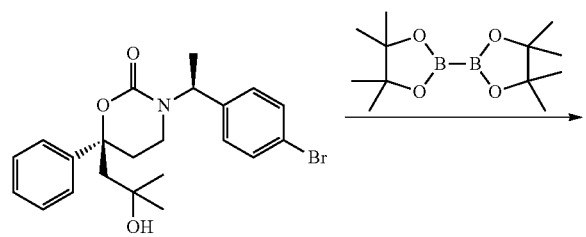

Step 1

To a solution of (R)-6-allyl-3-((S)-1-(4-bromophenyl)ethyl)-6-phenyl-1,3-oxazinan-2-one (20 g, 50 mmol) and CuCl (12.4 g, 125 mmol) in dry DMF (50 mL) was added H$_2$O (12 mL) and PdCl$_2$ (2.66 g, 15 mmol) at 0~−5° C. After addition, the mixture was allowed to warm to rt gradually for 48 h under O$_2$. After TLC showing the stating material had disappeared, the solid was filtered off. Water (200 mL) and EtOAc (50 mL) were added. The layers were separated and the aqueous layer was extracted with EtOAc (3×40 mL). The combined organic layer was washed with brine, dried over Na$_2$SO$_4$, filtered and concentrated to give a residue, which was purified by column chromatography to give (S)-3-((S)-1-(4-bromo-phenyl)ethyl)-6-(2-oxopropyl)-6-phenyl-1,3-oxazinan-2-one (12 g, 58%).

Step 2

To a solution of (S)-3-((S)-1-(4-bromophenyl)ethyl)-6-(2-oxopropyl)-6-phenyl-1,3-oxazinan-2-one (12 g, 28.8 mmol) in anhydrous THF (100 mL) was added dropwise methylmagnesium bromide (48 mL, 144 mmol) at −78° C. under nitrogen. The mixture was stirred at rt for 1 h. The reaction mixture was quenched with aqueous NH$_4$Cl solution (50 mL) in ice water bath. The layers were separated and the aqueous layer was extracted with EtOAc (150 mL). The combined organic phases were washed with brine (30 mL), dried over Na$_2$SO$_4$ and concentrated in vacuo to give the crude product, which was purified by preparative HPLC and chiral HPLC to afford (S)-3-((S)-1-(4-bromophenyl)ethyl)-6-(2-hydroxy-2-methylpropyl)-6-phenyl-1,3-oxazinan-2-one (6.6 g, 53%).

Step 3

To a solution of (S)-3-((S)-1-(4-bromophenyl)ethyl)-6-(2-hydroxy-2-methylpropyl)-6-phenyl-1,3-oxazinan-2-one (6.6 g, 15.2 mmol) and 4,4,4',4',5,5,5',5'-octamethyl-2,2'-bi(1,3,2-dioxaborolane) (6.1 g, 24.3 mmol) in dry DMSO (20 mL) was added KOAc (4.8 g, 48.6 mmol) and Pd(dppf)cl$_2$ (372 mg, 0.46 mmol). After addition, the mixture was allowed to warm to 100° C. for 20 h. After TLC showed the starting material had disappeared, the solid was filtered off. Water (60 mL) and EtOAc (20 mL) were added. The layers were separated and the aqueous layer was extracted with EtOAc (3×15 mL). The combined organic layer was washed with brine, dried over Na₂SO₄, filtered and concentrated to give a residue, which was purified by column chromatography to give (S)-6-(2-hydroxy-2-methylpropyl)-6-phenyl-3-((S)-1-(4-(4,4,5,5-tetramethyl-1,3,2-dioxaborol-an-2-yl)phenyl)ethyl)-1,3-oxazinan-2-one (4.4 g, 60%).

Step 4

To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (2.2 g, 4.58 mmol) and 5-bromo-1-methylpyridin-2(1H)-one (1.37 g, 7.33 mmol) in dry 1,4-dioxane (4 mL) was added aqueous CsCO₃ solution (10 mL, 10 mmol) and Pd(PPh₃)₂Cl₂ (967 mg, 1.38 mmol). After addition, the mixture was heated at 110° C. for 30 min in a microwave. After TLC showed the stating material had disappeared, the solid was filtered off. Water (20 mL) and EtOAc (10 mL) were added. The layers were separated and the aqueous layer was extracted with EtOAc (3×10 mL). The combined organic layer was washed with brine, dried over Na₂SO₄, filtered and concentrated to give a residue, which was purified by preparative HPLC to give (S)-6-(2-hydroxy-2-methylpropyl)-3-((S)-1-(4-(1-methyl-6-oxo-1,6-dihydropyridin-3-yl)phenyl)ethyl)-6-phenyl-1,3-oxazinan-2-one (730 mg, 35%). ¹H NMR (CDCl₃): 1.09 (s, 3H), 1.16 (s, 3H), 1.51 (m, 3H), 2.05-2.20 (4H), 2.40 (m, 1H), 2.84 (m, 1H), 3.59 (s, 3H), 5.64 (m, 1H), 6.62 (m, 1H), 6.96 (m, 2H), 7.14 (m, 2H), 7.28-7.39 (m, 5H), 7.48 (m, 1H), 7.50 (m, 1H).

Example 487

3-((R)-3-((S)-1-(4-(1-methyl-6-oxo-1,6-dihydropyridin-3-yl)phenyl)ethyl)-2-oxo-6-phenyl-1,3-oxazinan-6-yl)propanamide

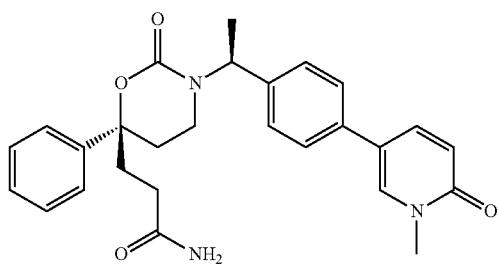 [SMILES: C[C@@H](c1ccc(-c2ccc(=O)n(C)c2)cc1)N1CC[C@](CCC(N)=O)(c2ccccc2)OC1=O]

The title compound was prepared from (R)-6-allyl-3-((S)-1-(4-(1-methyl-6-oxo-1,6-dihydropyridin-3-yl)phenyl) ethyl)-6-phenyl-1,3-oxazinan-2-one using a procedure analogous to that described in Example 78 followed by procedures analogous to those described in Example 234. LC-MS Method 2 $t_R$=1.028 min, m/z=460.2; ¹H NMR (CDCl₃) 1.53 (d, 3H), 1.91-2.01 (m, 1H), 2.11-2.42 (m, 5H), 2.46-2.54 (m, 1H), 2.88-2.96 (m, 1H), 3.60 (s, 3H), 5.26 (s, 1H), 5.42 (s, 1H), 5.66 (m, 1H), 6.69 (d, 1H), 6.95-7.03 (d, 2H), 7.12-7.20 (m, 2H), 7.24-7.41 (m, 5H), 7.52 (m, 1H).

Example 488

N-(3-((R)-3-((S)-1-(4-(1-methyl-6-oxo-1,6-dihydropyridin-3-yl)phenyl)ethyl)-2-oxo-6-phenyl-1,3-oxazinan-6-yl)propyl)methanesulfonamide

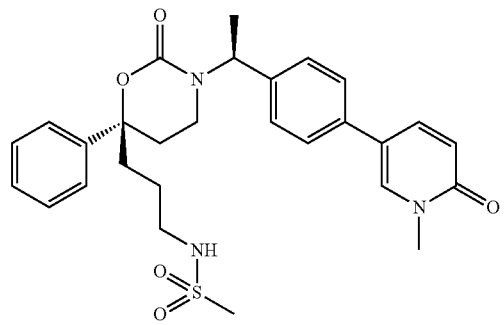 [SMILES: C[C@@H](c1ccc(-c2ccc(=O)n(C)c2)cc1)N1CC[C@](CCCNS(C)(=O)=O)(c2ccccc2)OC1=O]

The title compound was prepared from (R)-6-(3-hydroxypropyl)-3-((S)-1-(4-(1-methyl-6-oxo-1,6-dihydropyridin-3-yl)phenyl)ethyl)-6-phenyl-1,3-oxazinan-2-one following procedures analogous to those described in Example 359. LC-MS Method 2 $t_R$=1.095 min, m/z=524.1; ¹H NMR (CDCl₃) 1.30-1.41 (m, 1H), 1.52 (d, 3H), 1.71 (m, 1H), 1.87-2.07 (m, 3H), 2.09-2.20 (m, 3H), 2.22-2.32 (m, 2H), 2.88 (s, 3H), 3.06 (m, 2H), 3.60 (s, 3H), 4.32 (s, 1H), 5.65 (m, 1H), 6.67 (d, 1H), 6.94 (m, 2H), 7.11 (d, 2H), 7.25 (m, 1H), 7.27-7.40 (m, 4H), 7.53 (dd, 1H).

Example 489

(S)-3-((S)-1-(biphenyl-4-yl)ethyl)-6-(2-hydroxyethyl)-6-phenyl-1,3-oxazinan-2-one

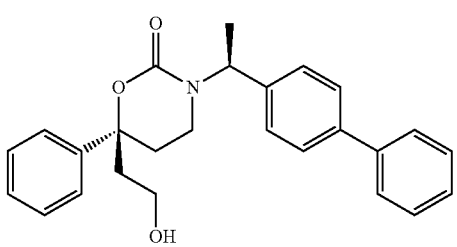

The title compound was prepared from (R)-6-allyl-3-((S)-1-(4-bromophenyl)ethyl)-6-phenyl-1,3-oxazinan-2-one and phenylboronic acid using a procedure analogous to that described in Example 64 followed by a procedure analogous to that described in Example 65. LC-MS Method 2 $t_R$=1.412 min, m/z=825.3; ¹H NMR (CDCl₃) 1.55 (d, 3H), 2.11-2.39

(m, 5H), 2.92 (m, 1H), 3.57 (m, 1H), 3.76 (m, 1H), 5.66 (m, 1H), 6.93 (d, 1H), 7.21-7.48 (m, 10H), 7.48 (m, 2H).

Example 490

(R)-3-((S)-1-(biphenyl-4-yl)ethyl)-6-(3-hydroxypropyl)-6-phenyl-1,3-oxazinan-2-one

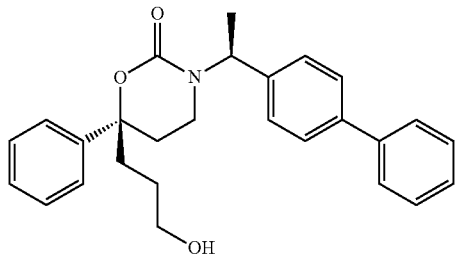 [SMILES: C[C@@H](c1ccc(-c2ccccc2)cc1)N1CC[C@](CCCO)(c2ccccc2)OC1=O]

The title compound was prepared from (R)-6-allyl-3-((S)-1-(4-bromophenyl)ethyl)-6-phenyl-1,3-oxazinan-2-one and phenylboronic acid using a procedure analogous to that described in Example 64 followed by a procedure analogous to that described in Example 78. LC-MS Method 2 $t_R$=1.408 min, m/z=415.52; $^1$H NMR (CD$_3$OD) 1.25-1.36 (m, 2H), 1.53 (d, 3H), 1.61 (m, 1H), 1.93 (m, 2H), 2.20 (m, 1H), 2.30 (m, 1H), 2.46 (m, 1H), 3.7 (m, 1H), 3.44 (t, 2H), 5.46 (m, 1H), 6.96 (d, 2H), 7.28-7.40 (m, 10H), 7.48 (m, 2H).

Example 491

(R)-3-((S)-1-(4'-fluorobiphenyl-4-yl)ethyl)-6-(2-morpholinoethyl)-6-phenyl-1,3-oxazinan-2-one

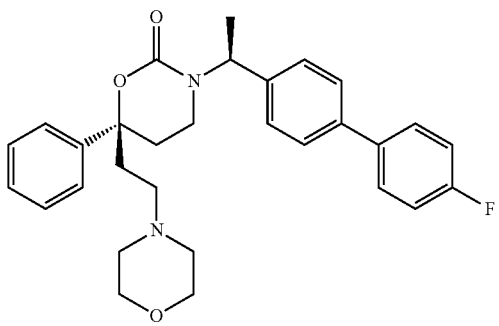 [SMILES: C[C@@H](c1ccc(-c2ccc(F)cc2)cc1)N1CC[C@](CCN2CCOCC2)(c2ccccc2)OC1=O]

The title compound was prepared from (S)-3-((S)-1-(4'-fluorobiphenyl-4-yl)ethyl)-6-(2-hydroxyethyl)-6-phenyl-1,3-oxazinan-2-one and morpholine following procedures analogous to those described in Example 178. LC-MS Method 2 $t_R$=1.19 min, m/z=511.2; $^1$H NMR (CDCl$_3$) 1.49 (t, 3H), 2.05-2.11 (m, 3H), 2.16 (m, 1H), 2.23-2.41 (m, 5H), 2.51 (m, 1H), 2.71 (m, 1H), 3.61 (m, 4H), 5.61 (m, 1H), 6.83 (d, 2H), 7.20-7.32 (m, 4H), 7.31 (m, 5H), 7.43 (m, 2H).

Example 492

3-((R)-3-((S)-1-(2',4'-difluorobiphenyl-4-yl)ethyl)-2-oxo-6-phenyl-1,3-oxazinan-6-yl)propyl dihydrogen phosphate

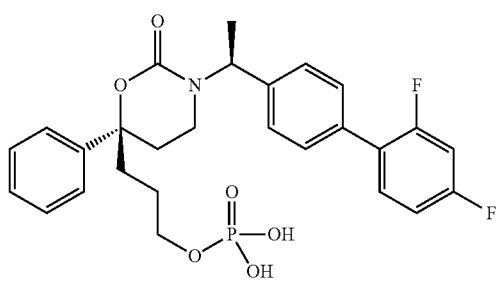 [SMILES: C[C@@H](c1ccc(-c2ccc(F)cc2F)cc1)N1CC[C@](CCCOP(=O)(O)O)(c2ccccc2)OC1=O]

The title compound was prepared from (R)-3-((S)-1-(2',4'-difluorobiphenyl-4-yl)ethyl)-6-(3-hydroxypropyl)-6-phenyl-1,3-oxazinan-2-one following procedures analogous to those described in Example 151. LC-MS Method 1 $t_R$=1.64 min, m/z=532 (M+1); $^1$H NMR (CD$_3$OD) 7.21-7.03 (m, 8H), 6.83-6.78 (m, 4H), 5.38 (q, J=7.0 Hz, 1H), 3.71 (q, J=6.4 Hz, 2H), 2.91-2.86 (m, 1H), 2.31-2.26 (m, 1H), 2.17-2.10 (m, 1H), 2.06-1.98 (m, 1H), 1.85-1.80 (m, 2H), 1.64-1.55 (m, 1H), 1.35 (d, J=7.0 Hz, 3H), 1.31-1.22 (m, 1H).

Example 493

(R)-3-((S)-1-(3'-(aminomethyl)biphenyl-4-yl)ethyl)-6-(3-hydroxypropyl)-6-phenyl-1,3-oxazinan-2-one

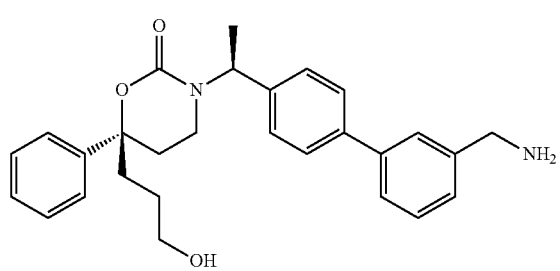 [SMILES: C[C@@H](c1ccc(-c2cccc(CN)c2)cc1)N1CC[C@](CCCO)(c2ccccc2)OC1=O]

The title compound was prepared from (R)-6-allyl-3-((S)-1-(4-bromophenyl)ethyl)-6-phenyl-1,3-oxazinan-2-one and 3-(aminomethyl)phenylboronic acid following a procedure analogous to that described in Example 64 followed by a procedure analogous to that described in Example 78. LC-MS Method 2 $t_R$=1.008 min, m/z=889.5; $^1$H NMR (CDCl$_3$) 1.25 (m, 1H), 1.56 (m, 3H), 1.62 (d, 1H), 1.92 (m, 2H), 2.22 (m, 1H), 2.33 (m, 1H), 2.46 (m, 1H), 3.15 (m, 1H), 3.48 (m, 2H), 5.56 (m, 1H), 7.12 (m, 2H), 7.31 (m, 3H), 7.35 (m, 2H), 7.47 (m, 3H), 7.56 (m, 1H), 7.61 (m, 2H).

Example 494

(R)-3-((S)-1-(4'-(hydroxymethyl)biphenyl-4-yl)ethyl)-6-(3-hydroxypropyl)-6-phenyl-1,3-oxazinan-2-one

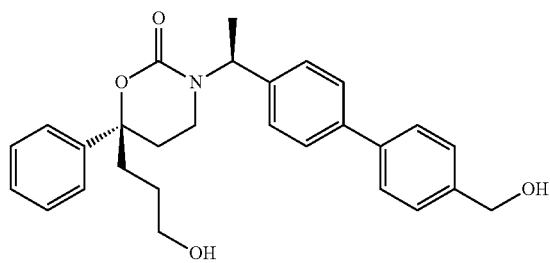 [SMILES: C[C@@H](c1ccc(-c2ccc(CO)cc2)cc1)N1CC[C@](CCCO)(c2ccccc2)OC1=O]

The title compound was prepared from (R)-3-((S)-1-(4-bromophenyl)ethyl)-6-(3-hydroxypropyl)-6-phenyl-1,3-oxazinan-2-one following procedures analogous to those described in Example 75 Step 1. LC-MS Method 2 $t_R$=0.983 min, m/z=444.57; $^1$H NMR (CD$_3$OD) 1.35 (m, 1H), 1.52 (d, 3H), 1.65 (m, 1H), 1.92 (m, 2H), 2.20 (m, 1H), 2.30 (m, 1H), 2.45 (m, 1H), 3.09 (m, 1H), 3.45 (m, 2H), 4.61 (s, 2H), 5.54 (m, 1H), 6.99 (d, 2H), 7.28-7.41 (m, 9H), 7.50 (m, 2H).

Example 495

(R)-3-((S)-1-(4'-(aminomethyl)biphenyl-4-yl)ethyl)-6-(3-hydroxypropyl)-6-phenyl-1,3-oxazinan-2-one

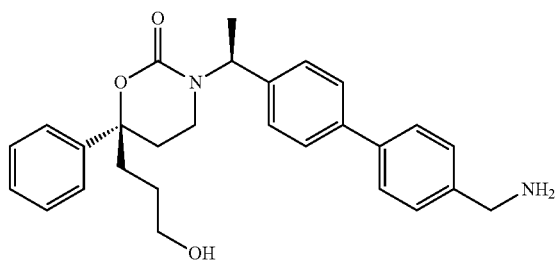 [SMILES: C[C@@H](c1ccc(-c2ccc(CN)cc2)cc1)N1CC[C@](CCCO)(c2ccccc2)OC1=O]

The title compound was prepared from (R)-6-allyl-3-((S)-1-(4-bromophenyl)ethyl)-6-phenyl-1,3-oxazinan-2-one and 4-carbamoylphenylboronic acid following procedures analogous to those described in Example 131 followed by a procedure analogous to that described in Example 78. LC-MS Method 2 $t_R$=1.008 min, m/z=424.18; $^1$H NMR (CD$_3$OD) 1.28 (m, 1H), 1.56 (d, 3H), 1.60 (m, 1H), 1.92 (m, 2H), 2.15 (m, 2H), 3.28 (m, 1H), 3.45 (m, 2H), 4.17 (m, 2H), 5.54 (m, 1H), 7.13 (m, 2H), 7.32 (m, 3H), 7.39 (m, 2H), 7.41 (m, 3H), 7.58 (m, 2H), 7.63 (m, 2H).

Example 496

(S)-3-((S)-1-(2',4'-difluorobiphenyl-4-yl)ethyl)-6-(3-hydroxypropyl)-6-phenyl-1,3-oxazinan-2-one

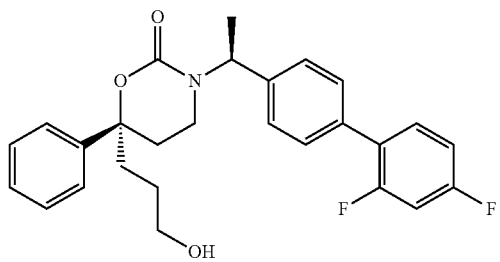 [SMILES: C[C@@H](c1ccc(-c2ccc(F)cc2F)cc1)N1CC[C@@](CCCO)(c2ccccc2)OC1=O]

The title compound was prepared from (S)-6-allyl-3-((S)-1-(2',4'-difluorobiphenyl-4-yl)ethyl)-6-phenyl-1,3-oxazinan-2-one following a procedure analogous to that described in Example 78. LC-MS Method 3 $t_R$=1.273 min, m/z=474.1; $^1$H NMR (CDCl$_3$) 1.29 (d, 3H), 1.34 (m, 1H), 1.76 (m, 1H), 1.99 (m, 2H), 2.06 (m, 1H), 2.25 (m, 1H), 2.72 (m, 2H), 3.56 (m, 2H), 5.81 (m, 1H), 6.96 (m, 2H), 7.29 (m, 3H), 7.36 (m, 5H), 7.43 (m, 2H).

Example 497

6-allyl-3-(1-(4-chloro-3-fluorophenyl)ethyl)-6-(4-fluorophenyl)-1,3-oxazinan-2-one

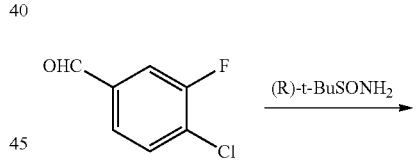

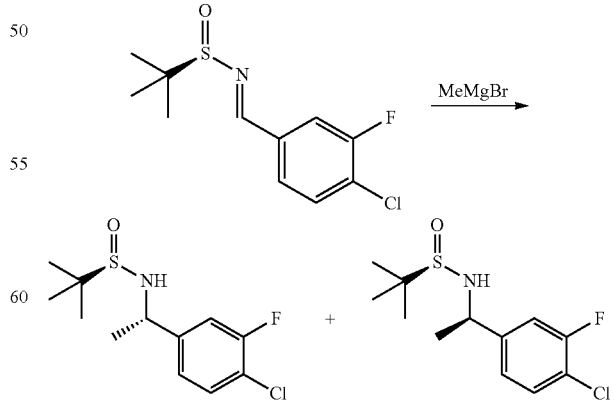

(R)-N-((R)-1-(4-chloro-3-fluorophenyl)ethyl-2-methylpropane-2-sulfinamide

-continued

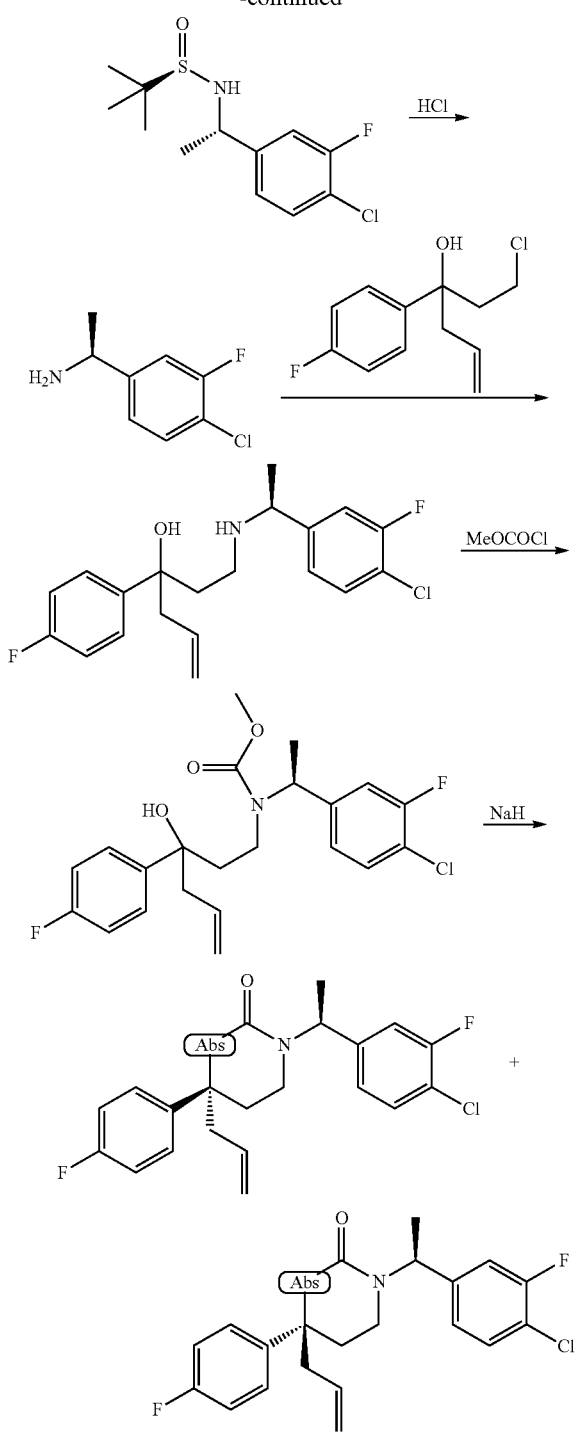

A mixture of (R)—N-((S)-1-(4-chloro-3-fluorophenyl)ethyl)-2-methylpropane-2-sulfinamide and (R)—N-((R)-1-(4-chloro-3-fluorophenyl)ethyl)-2-methylpropane-2-sulfinamide was prepared following procedures analogous to those described in Example 326 Steps 1 and 2. The two diastereomers were separated by chromatography on silica gel. The t-butylsifinyl group was removed from (R)—N-((S)-1-(4-chloro-3-fluorophenyl)ethyl)-2-methylpropane-2-sulfinamide by treatment with HCl and the resulting (S)-1-(4-chloro-3-fluorophenyl)ethanamine was reacted with 1-chloro-3-(4-fluorophenyl)hex-5-en-3-ol following procedures analogous to those described in Example 353 to afford isomers 1 and 2 of the title compound.

Isomer 1: (S)-6-allyl-3-((S)-1-(4-chloro-3-fluorophenyl)ethyl)-6-(4-fluorophenyl)-1,3-oxazinan-2-one LC-MS Method 1 $t_R$=2.03, m/z=392 (M+1); $^1$H NMR (CDCl$_3$) 7.36-7.24 (m, 3H), 7.11-7.00 (m, 4H), 5.76-5.65 (m, 2H), 5.10-4.98 (m, 2H), 2.78-2.65 (m, 2H), 2.64-2.52 (m, 2H), 2.27-2.22 (m, 1H), 2.10-2.02 (m, 1H), 1.23 (d, 3H, J=7.3 Hz).

Isomer 2: (R)-6-allyl-3-((S)-1-(4-chloro-3-fluorophenyl)ethyl)-6-(4-fluorophenyl)-1,3-oxazinan-2-one LC-MS Method 1 $t_R$=1.99, m/z=392 (M+1); $^1$H NMR (CDCl$_3$) 7.28-7.23 (m, 2H), 7.13-7.09 (t, 1H, J=8.0 Hz), 7.08-7.01 (m, 2H), 6.60-6.55 (m, 2H), 5.75-5.64 (m, 1H), 5.62-5.71 (q, 1H, J=7.0 Hz), 5.1-5.0 (m, 2H), 2.97-2.91 (m, 1H), 2.64-2.51 (m, 2H), 2.38-2.16 (m, 3H), 1.47 (d, 3H, J=7 Hz).

The t-butylsifinyl group was removed from (R)—N-((R)-1-(4-chloro-3-fluorophenyl)ethyl)-2-methylpropane-2-sulfinamide by treatment with HCl and the resulting (R)-1-(4-chloro-3-fluorophenyl)ethanamine was reacted with 1-chloro-3-(4-fluorophenyl)hex-5-en-3-ol following procedures analogous to those described in Example 353 to afford isomers 3 and 4 of the title compound.

Isomer 3: (S)-6-allyl-3-((R)-1-(4-chloro-3-fluorophenyl)ethyl)-6-(4-fluorophenyl)-1,3-oxazinan-2-one LC-MS Method 1 $t_R$=2.03, m/z=392 (M+1); $^1$H NMR (CDCl$_3$) 7.36-7.26 (m, 3H), 7.10-7.01 (m, 4H), 5.76-5.64 (m, 2H), 5.10-4.99 (m, 2H), 2.77-2.65 (m, 2H), 2.64-2.53 (m, 2H), 2.27-2.22 (m, 1H), 2.10-2.02 (m, 1H), 1.23 (d, 3H, J=7.0 Hz).

Isomer 4: (R)-6-allyl-3-((R)-1-(4-chloro-3-fluorophenyl)ethyl)-6-(4-fluorophenyl)-1,3-oxazinan-2-one LC-MS Method 1 $t_R$=1.99, m/z=392 (M+1); $^1$H NMR (CDCl$_3$) 7.28-7.24 (m, 2H), 7.13-7.09 (t, 1H, J=8 Hz), 7.08-7.03 (m, 2H), 6.60-6.55 (m, 2H), 5.75-5.64 (m, 1H), 5.63-5.57 (q, 1H, J=7.0 Hz), 5.10-5.00 (m, 2H), 2.97-2.92 (m, 1H), 2.64-2.52 (m, 2H), 2.38-2.17 (m, 3H), 1.47 (d, 3H, J=7 Hz).

Example 498

(R)-3-((S)-1-(4-chloro-3-fluorophenyl)ethyl)-6-(4-fluorophenyl)-6-(3-hydroxypropyl)-1,3-oxazinan-2-one

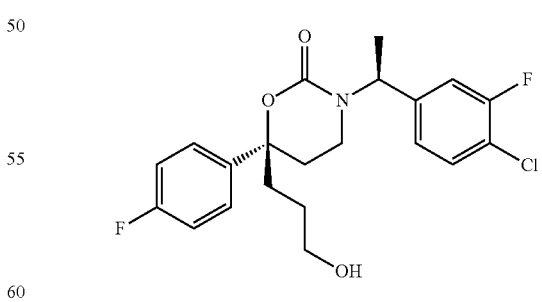

The title compound was prepared from (R)-6-allyl-3-((S)-1-(4-chloro-3-fluorophenyl)ethyl)-6-(4-fluorophenyl)-1,3-oxazinan-2-one following a procedure analogous to that described in Example 343. LC-MS Method 1 $t_R$=1.67, m/z=410 (M+1); $^1$H NMR (CDCl$_3$) 7.25-7.22 (m, 2H), 7.15 (t, 1H, 8 Hz), 7.06 (t, 2H, J=8.6 Hz), 6.70-6.63 (m, 2H), 5.62

(q, 1H, J=7.0 Hz), 3.59 (m, 1H), 2.98-2.93 (m, 1H), 2.54-2.17 (m, 4H), 2.04-1.89 (m, 2H), 1.74-1.63 (m, 1H), 1.49 (d, 3H, J=7 Hz), 1.42-1.32 (m, 2H).

Example 499

(S)-6-(2-hydroxyethyl)-3-((S)-1-(4-(1-methyl-6-oxo-1,6-dihydropyridin-3-yl)phenyl)propyl)-6-phenyl-1,3-oxazinan-2-one The title compound was prepared from (S)-3-((S)-1-(4-bromophenyl)propyl)-6-(2-hydroxyethyl)-6-phenyl-1,3-oxazinan-2-one following procedures analogous to those described in Example 313 Steps 3 and 4. (S)-3-((S)-1-(4-bromophenyl)propyl)-6-(2-hydroxyethyl)-6-phenyl-1,3-oxazinan-2-one was prepared from (R)-6-allyl-3-((S)-1-(4-bromophenyl)propyl)-6-phenyl-1,3-oxazinan-2-one following a procedure analogous to that described in Example 74. (R)-6-allyl-3-((S)-1-(4-bromophenyl)propyl)-6-phenyl-1,3-oxazinan-2-one was prepared from (R)-6-allyl-3-((S)-1-(4-bromophenyl)propyl)-6-phenyl-1,3-oxazinan-2-one and (S)-1-bromo-4-(1-isocyanatopropyl)benzene following procedures analogous to those described in Example 95. (S)-1-bromo-4-(1-isocyanatopropyl)benzene was prepared from (S)-1-(4-bromophenyl)propan-1-amine which was prepared by bromination of (S)-1-phenylpropan-1-amine with 1,3-dibromo-5,5-dimethylimidazolidine-2,4-dione and TFAA. LC-MS Method 2 $t_R$=1.627, m/z=447.1; $^1$H NMR (CDCl$_3$) 1.06 (m, 3H), 1.87-2.06 (m, 2H), 2.11-2.28 (m, 2H), 2.33 (m, 3H), 2.96 (m, 1H), 3.53 (m, 1H), 3.62 (s, 3H), 3.78 (m, 1H), 5.48 (m, 1H), 6.69 (m, 1H), 7.03 (m, 2H), 7.14 (m, 2H), 7.21-7.38 (m, 4H), 7.41 (s, 1H), 7.56 (m, 1H).

Example 500

(S)-3-((S)-1-(4-bromophenyl)ethyl)-6-(4-fluorophenyl)-6-((1-hydroxycyclopropyl)methyl)-1,3-oxazinan-2-one

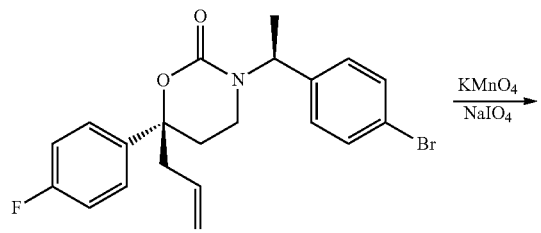

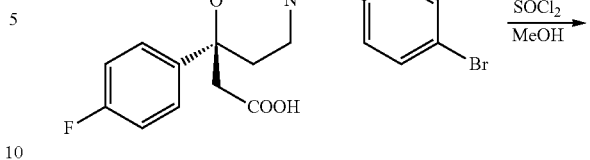

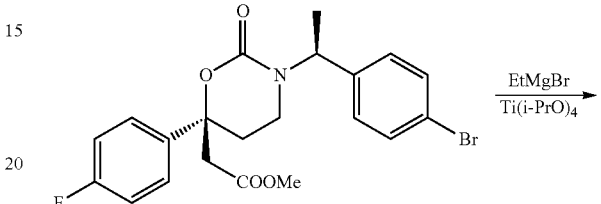

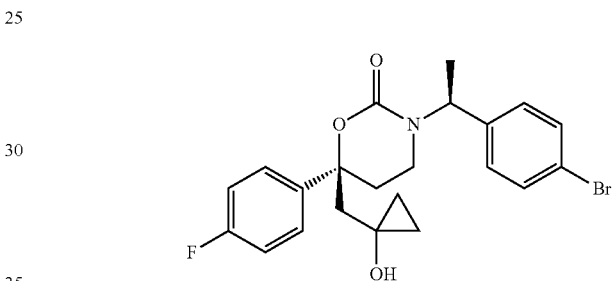

Step 1

To a solution of (R)-6-allyl-3-((S)-1-(4-bromophenyl)ethyl)-6-(4-fluorophenyl)-1,3-oxazinan-2-one (450 mg, 1.01 mmol) in acetone (10 mL) was added a solution of KMnO$_4$ (190 mg, 1.2 mmol) and NaIO$_4$ (1.5 g, 7.2 mmol) in water (10 mL). The mixture was stirred for 2 h at 0° C. The mixture was filtered and the filtrate was adjusted to pH 5-6 with aqueous 1 N aq HCl solution. The mixture was extracted with EtOAc. The organic phase washed with brine, dried over anhydrous Na$_2$SO$_4$ and concentrated to give 2-((S)-3-((S)-1-(4-bromophen-yl)ethyl)-6-(4-fluorophenyl)-2-oxo-1,3-oxazinan-6-yl)acetic acid (540 mg, crude), which was used for the next step without purification.

Step 2

To a solution of 2-((S)-3-((S)-1-(4-bromophen-yl)ethyl)-6-(4-fluorophenyl)-2-oxo-1,3-oxazinan-6-yl)acetic acid (540 mg, 1.24 mol) in MeOH (20 mL) was added SOCl$_2$ (5 mL) at 0° C., and the reaction mixture was stirred at rt for 2 h. The reaction mixture was concentrated and the residue was purified by preparative TLC to give methyl 2-((S)-6-(4-fluorophenyl)-3-((S)-1-(4-(1-methyl-6-oxo-1,6-dihydropyridin-3-yl)phenyl)-ethyl)-2-oxo-1,3-oxazinan-6-yl)acetate (150 mg, 27%). $^1$H NMR (CDCl$_3$): δ=1.49 (d, 3H), 2.19 (m, 1H), 2.44 (m, 1H), 2.60 (m, 1H), 2.77-3.08 (m, 3H), 3.51 (s, 3H), 5.52 (m, 2H), 6.62 (d, 2H), 6.98 (t, 2H), 7.23 (t, 2H), 7.28 (m, 2H).

Step 3

To a solution of methyl 2-((S)-6-(4-fluorophenyl)-3-((S)-1-(4-(1-methyl-6-oxo-1,6-dihydropyridin-3-yl)phenyl)-ethyl)-2-oxo-1,3-oxazinan-6-yl)acetate (150 mg, 0.33 mmol), and tetraisopropoxytitanium (189 mg, 0.66 mmol) in THF (20 mL) was added 3.0 M ethylmagnesium bromide (4 mL, 12 mmol) at rt under nitrogen. Then the mixture was stirred for 2 h. The reaction was quenched with aqueous $NH_4Cl$ solution, and the mixture was filtered. The filtrate was extracted with EtOAc. The combined organic phase was washed with brine, dried over anhydrous $Na_2SO_4$, and concentrated to give the crude product, which was purified by preparative HPLC to give (S)-3-((S)-1-(4-bromophenyl)ethyl)-6-(4-fluorophenyl)-6-((1-hydroxycyclopropyl)methyl)-1,3-oxazinan-2-one (2.51 mg, 2%). $^1$H NMR ($CDCl_3$): 0.03 (m, 1H), 0.18 (m, 1H), 0.49 (m, 1H), 0.60 (m, 1H), 1.43 (m, 3H), 2.08 (s, 2H), 2.26 (m, 1H), 2.37 (m, 2H), 2.88 (m, 1H), 5.53 (m, 1H), 6.66 (d, 2H), 6.97 (t, 2H), 7.16 (m, 2H), 7.26 (m, 2H).

Example 501

(R)-6-(4-fluorophenyl)-6-(3-hydroxypropyl)-3-((S)-1-(4-(2-oxo-1,2-dihydropyridin-3-yl)phenyl)ethyl)-1,3-oxazinan-2-one 7.42 (dd, 2H), 7.24 (m, 2H), 7.08-7.00 (m, 4H), 6.75 (t, 1H), 5.70 (m, 1H), 3.58 (t, 1H), 2.94 (m, 1H), 1.54 (d, 3H).

Example 502

6-(4-((S)-1-((R)-6-(4-fluorophenyl)-6-(3-hydroxypropyl)-2-oxo-1,3-oxazinan-3-yl)ethyl)phenyl)nicotinonitrile

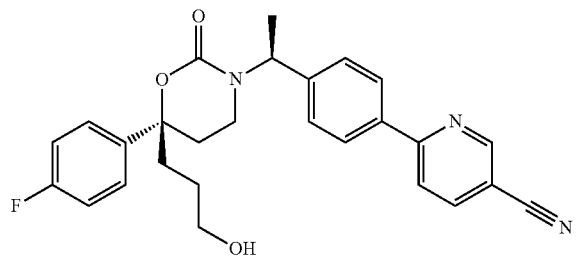

The title compound was prepared from (R)-6-allyl-6-(4-fluorophenyl)-3-((S)-1-(4-(4,4,5,5-tetramethyl-1,3,2-diox-

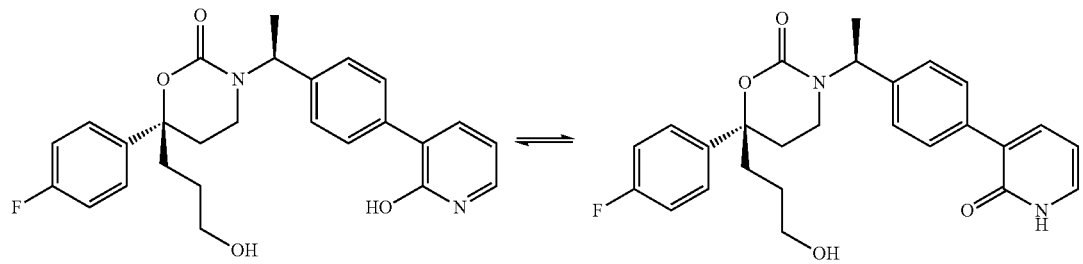 [SMILES: C[C@@H](c1ccc(-c2cccnc2O)cc1)N1CC[C@](CCCO)(c2ccc(F)cc2)OC1=O ; C[C@@H](c1ccc(-c2ccc[nH]c2=O)cc1)N1CC[C@](CCCO)(c2ccc(F)cc2)OC1=O]

The title compound was prepared from (R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one following a procedure analogous to that described in Example 313 Step 4 using 3-bromopyridin-2(1H)-one. LC-MS Method 1 $t_R$=1.24, m/z=452(M+1); $^1$H NMR ($CDCl_3$) 7.76 (d, 1H), 7.52 (d, 1H), aborolan-2-yl)phenyl)ethyl)-1,3-oxazinan-2-one following a procedure analogous to that described in Example 313 Step 4 using 2-bromo-5-cyanopyridine. LC-MS Method 1 tR=1.58, m/z=482(M+Na); 1H NMR (CDCl3) 8.93 (d, 1H), 8.01 (dt, 1H), 7.79 (m, 3H), 7.25 (m, 1H), 7.07 (m, 5H), 5.74 (q, 1H), 4.28 (t, 1H), 3.59 (t, 1H), 2.98 (m, 1H), 1.58 (d, 3H), 1.53 (m, 1H).

Example 503

3-((R)-3-((S)-1-(2',4'-difluorobiphenyl-4-yl)ethyl)-2-oxo-6-phenyl-1,3-oxazinan-6-yl)propanoic acid

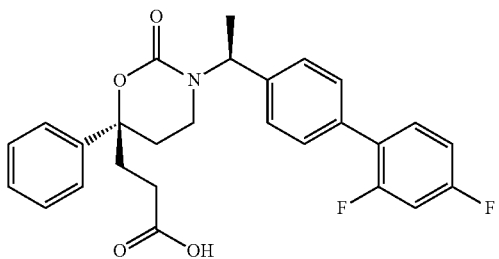 [SMILES: C[C@@H](c1ccc(-c2ccc(F)cc2F)cc1)N1CC[C@](CCC(=O)O)(c2ccccc2)OC1=O]

The title compound was prepared from (R)-3-((S)-1-(2',4'-difluorobiphenyl-4-yl)ethyl)-6-(3-hydroxypropyl)-6-phenyl-1,3-oxazinan-2-one as described in Example 234 Step 1. LC-MS Method 2 tR=1.421, m/z=466; 1H NMR (CDCl3) 1.52 (d, 3H), 2.08-2.21 (m, 3H), 2.23-2.38 (m, 3H), 2.56 (m, 1H), 2.92 (m, 1H), 5.68 (m, 1H), 6.89 (m, 2H), 6.93 (m, 2H), 7.22 (m, 2H), 7.23-7.38 (m, 5H).

Example 504

3-(3-((1S)-1-(4-bromophenyl)ethyl)-6-(2,4-difluorophenyl)-2-oxo-1,3-oxazinan-6-yl)propanamide

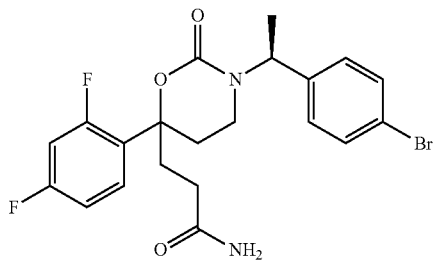 [SMILES: C[C@@H](c1ccc(Br)cc1)N1CCC(CCC(N)=O)(c2ccc(F)cc2F)OC1=O]

The title compound was prepared from 3-(3-((S)-1-(4-bromophenyl)ethyl)-6-(2,4-difluorophenyl)-2-oxo-1,3-oxazinan-6-yl)propanamide following procedures analogous to those described in Example 234. Two isomers were isolated.

Isomer 1: 3-((S)-3-((S)-1-(4-bromophenyl)ethyl)-6-(2,4-difluorophenyl)-2-oxo-1,3-oxazinan-6-yl)propanamide
LC-MS Method 1 $t_R$=1.66, m/z=467, 469 (M+1); $^1$H NMR (CD$_3$OD) 7.40 (d, J=8.2 Hz, 2H), 7.29-7.22 (m, 1H), 7.14 (d, J=8.8 Hz, 2H), 6.97-6.88 (m, 2H), 5.43 (q, J=7.0 Hz, 1H), 2.78-2.66 (m, 2H), 2.49-2.45 (m, 1H), 2.30-2.23 (m, 2H), 2.17-2.09 (m, 1H), 2.03-1.94 (m, 1H), 1.88-1.83 (m, 1H), 1.24 (d, J=7.0 Hz, 3H).

Isomer 2: 3-((R)-3-((S)-1-(4-bromophenyl)ethyl)-6-(2,4-difluorophenyl)-2-oxo-1,3-oxazinan-6-yl)propanamide
LC-MS Method 1 $t_R$=1.62, m/z=467, 469 (M+1); $^1$H NMR (CD$_3$OD) 7.29-7.23 (m, 3H), 6.95-6.86 (m, 4H), 5.45 (q, J=7.0 Hz, 1H), 3.12-3.08 (m, 1H), 2.51-2.47 (m, 1H), 2.33-2.10 (m, 5H), 1.94-1.88 (m, 1H), 1.45 (d, J=7.0 Hz, 3H).

Example 505

3-((R)-6-(4-fluorophenyl)-2-oxo-3-((S)-1-(4-(2,2,2-trifluoroethoxy)phenyl)ethyl)-1,3-oxazinan-6-yl)propanamide

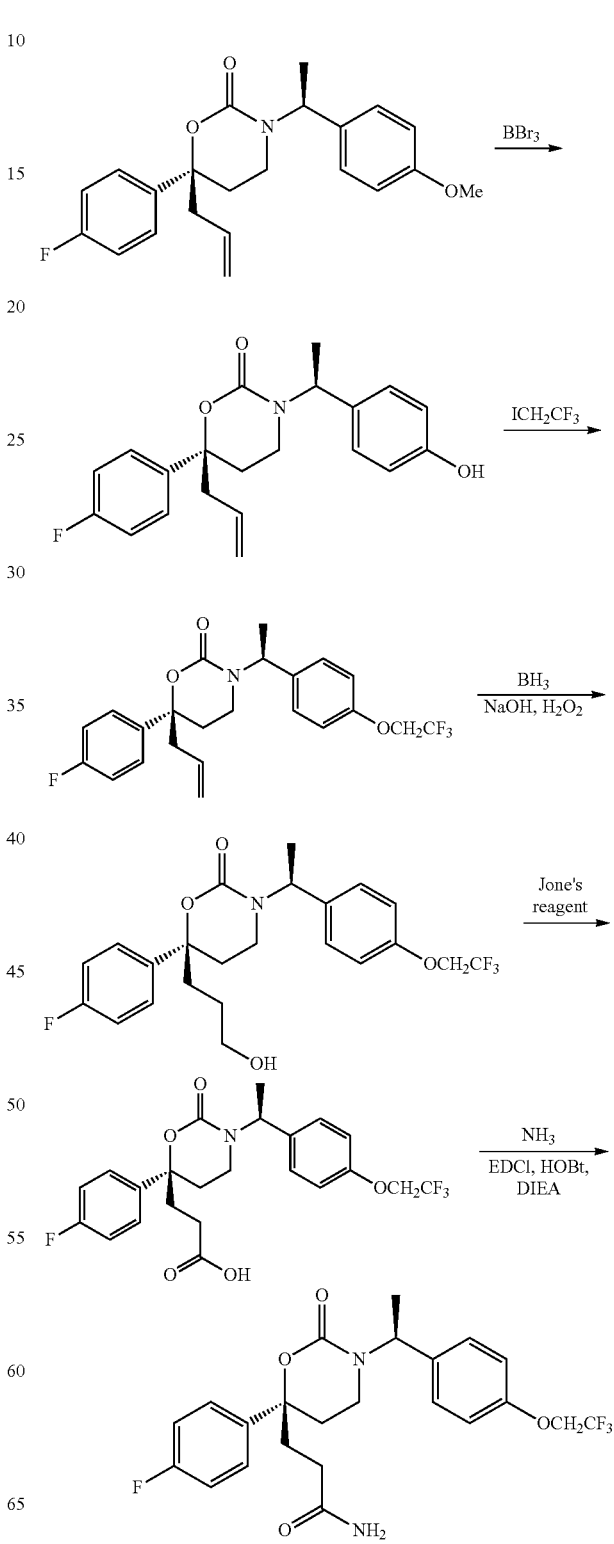

Step 1

To a solution of (R)-6-allyl-6-(4-fluorophenyl)-3-((S)-1-(4-methoxyphenyl)ethyl)-1,3-oxazinan-2-one (1.5 g, 4.07 mmol) in CH$_2$Cl$_2$ (40 mL) was added BBr$_3$ (3 g, 12.2 mmol) at −78° C. The mixture was stirred at this temperature for 2 h. The solution was washed with satd aq NaHCO$_3$ and the aqueous layer was extracted with CH$_2$Cl$_2$. The organic layer was dried over Na$_2$SO$_4$ and concentrated to give (R)-6-allyl-6-(4-fluorophenyl)-3-((S)-1-(4-hydroxyphenyl)ethyl)-1,3-oxazinan-2-one (1.2 g, 83%), which was used for the next step without further purification.

Step 2

A mixture of (R)-6-allyl-6-(4-fluorophenyl)-3-((S)-1-(4-hydroxyphenyl)ethyl)-1,3-oxazinan-2-one (700 mg, 1.97 mmol), CF$_3$CH$_2$I (621 mg, 2.96 mmol) and CsF (360 mg, 2.37 mmol) in DMSO (10 mL) was heated under 120° C. overnight. The mixture was poured into water and extracted with EtOAc. The organic layer was dried over Na$_2$SO$_4$ and concentrated. The residue was purified by preparative TLC to give (R)-6-allyl-6-(4-fluorophenyl)-3-((S)-1-(4-(2,2,2-trifluoroethoxy)phenyl)ethyl)-1,3-oxazinan-2-one (500 mg, 58%).

Step 3

To a solution of (R)-6-allyl-6-(4-fluorophenyl)-3-((S)-1-(4-(2,2,2-trifluoroethoxy)phenyl)ethyl)-1,3-oxazinan-2-one (500 mg, 1.6 mmol) in THF (20 mL) was added BH$_3$/THF (1 M, 3.2 mL) at 0° C. The mixture was stirred at rt for 2 h. The mixture was quenched with H$_2$O (2.5 mL) at 0° C., then NaOH (3 M, 1.1 mL) and 30% H$_2$O$_2$ (2.5 mL) were added. After stirring at rt for another 2 h, 1N HCl was added to the mixture. The mixture was extracted with EtOAc. The combined organic layer was dried over Na$_2$SO$_4$ and concentrated. The residue was purified by preparative TLC to give (R)-6-(4-fluorophenyl)-6-(3-hydroxypropyl)-3-((S)-1-(4-(2,2,2-trifluoroethoxy)phenyl)ethyl)-1,3-oxazinan-2-one (320 mg, 62%).

Step 4

To a solution of (R)-6-(4-fluorophenyl)-6-(3-hydroxypropyl)-3-((S)-1-(4-(2,2,2-trifluoroethoxy)phenyl)ethyl)-1,3-oxazinan-2-one (320 mg, 0.7 mmol) in acetone (7 mL) was added Jones reagent (2.5 M☐1.05 mL) at 0° C. The mixture was stirred at this temperature for 30 min. The formed mixture was filtered and the filtrate was concentrated. The residue was treated with H$_2$O (10 mL) and CH$_2$Cl$_2$ (10 mL). The mixture was separated, and the organic layer was washed with brine and concentrated. The residue was purified by preparative TLC to give 3-((R)-6-(4-fluorophenyl)-2-oxo-3-((S)-1-(4-(2,2,2-trifluoroethoxy)phenyl)ethyl)-1,3-oxazinan-6-yl) propanoic acid (290 mg, 88%).

Step 5

To a solution of 3-((R)-6-(4-fluorophenyl)-2-oxo-3-((S)-1-(4-(2,2,2-trifluoroethoxy)phenyl)ethyl)-1,3-oxazinan-6-yl) propanoic acid (145 mg, 1.37 mmol) in CH$_2$Cl$_2$ (5 mL) was added HOBt (167 mg, 1.24 mmol), EDCI (243 mg, 1.24 mmol) and DIEA (194 mg, 1.55 mmol) under NH$_3$ at 0° C. The mixture was stirred at rt overnight. 1N HCl was added and the mixture was extracted with CH$_2$Cl$_2$. The organic layer was dried and concentrated to give the residue, which was purified by preparative HPLC to give 3-((R)-6-(4-fluorophenyl)-2-oxo-3-((S)-1-(4-(2,2,2-trifluoroethoxy)phenyl) ethyl)-1,3-oxazinan-6-yl)propanamide (21 mg, 15%). LC-MS Method 2 t$_R$=1.16 min, m/z=491, 469, 425. $^1$H NMR (CDCl$_3$, 400 MHz): 1.43 (d, 3H), 1.88-1.95 (m, 1H), 2.07-2.19 (m, 5H), 2.40 (m, 1H), 2.83 (m, 1H), 4.21 (m, 1H), 5.18 (s, 1H), 5.33 (s, 1H), 5.56 (m, 1H), 6.64 (d, 2H), 6.85 (d, 2H), 6.97 (t, 2H), 7.17 (m, 2H).

Example 506

N-(3-((R)-3-((S)-1-(4-bromophenyl)ethyl)-2-oxo-6-phenyl-1,3-oxazinan-6-yl)propyl)-N-methylacetamide

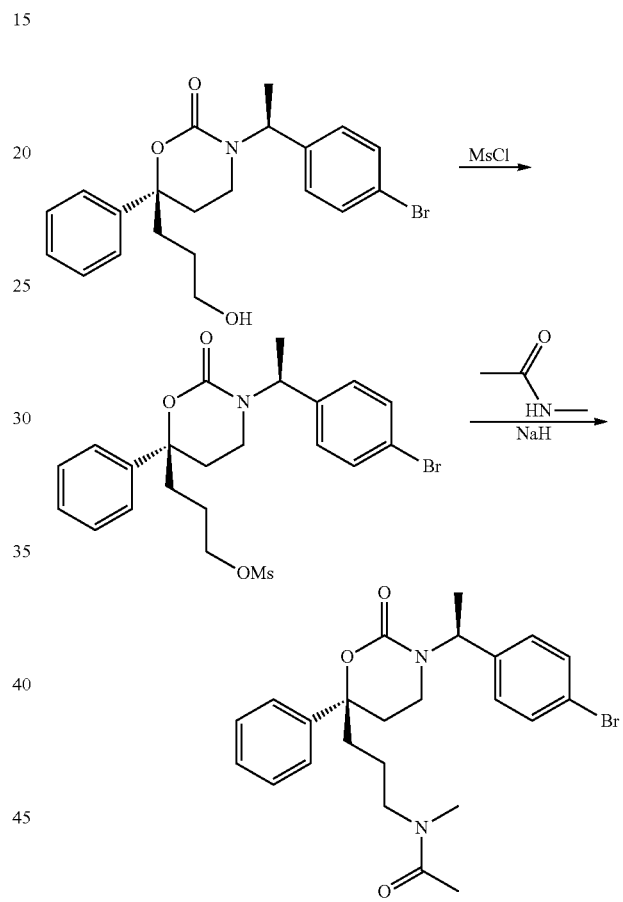

Step 1

To a solution of (R)-3-((S)-1-(4-bromophenyl)ethyl)-6-(3-hydroxypropyl)-6-phenyl-1,3-oxazinan-2-one (200 mg, 0.48 mmol) in CH$_2$Cl$_2$ (5 mL) was added Et$_3$N (240 mg, 2.4 mmol) and methanesulfonyl chloride (164 mg, 1.4 mmol) at 0° C. The reaction solution was stirred at rt for 1 h. The reaction was quenched with H$_2$O and the mixture was extracted with CH$_2$Cl$_2$. The organic phase was concentrated to give 3-((R)-3-((S)-1-(4-bromophenyl)ethyl)-2-oxo-6-phenyl-1,3-oxazinan-6-yl)propyl methanesulfonate (234 mg, 98%), which was used for the next step without further purification.

Step 2

To a solution of 3-((R)-3-((S)-1-(4-bromophenyl)ethyl)-2-oxo-6-phenyl-1,3-oxazinan-6-yl)propyl methanesulfonate (234 mg, 0.24 mmol) in CH$_2$Cl$_2$ (3 mL) was added NaH (82 mg, 3.4 mmol) at 0° C. The mixture was stirred at rt for 30 min. Then N-methylacetamide (204 mg, 2.8 mmol) was added the above mixture. The formed mixture was stirred at 80° C. for 5 h. After the reaction was over, the reaction was quenched with water and the mixture was extracted with EtOAc. The combined organic phase was concentrated to give the crude product, which was purified by preparative TLC to give N-(3-((R)-3-((S)-1-(4-bromophenyl)ethyl)-2-oxo-6-phenyl-1,3-oxazinan-6-yl)propyl)-N-methylacetamide (150 mg, 68%). LC-MS Method 2 tR=1.50 min, m/z=497, 495, 475, 473. $^1$H NMR (400 MHz, CDCl$_3$): δ=1.41 (m, 1H), 1.48 (t, 3H), 1.73 (m, 1H), 1.83-1.95 (m, 2H), 2.01 (m, 3H), 2.1-2.3 (m, 3H), 2.71 (m, 1H), 2.81 (s, 3H), 3.1 (m, 1H), 3.2 (m, 1H), 5.5 (m, 1H), 6.72 (m, 2H), 7.10 (m, 2H), 7.20 (m, 2H), 7.37 (m, 3H).

Example 507

N-(2-((S)-3-((S)-1-(4-bromophenyl)ethyl)-2-oxo-6-phenyl-1,3-oxazinan-6-yl)ethyl)methanesulfonamide

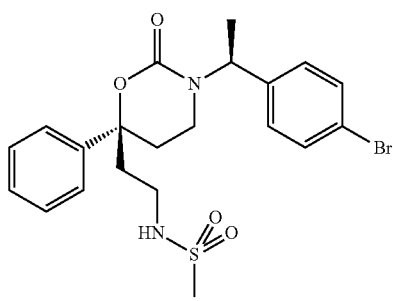 [SMILES: C[C@@H](c1ccc(Br)cc1)N1CC[C@](CCNS(C)(=O)=O)(c2ccccc2)OC1=O]

The title compound was prepared from (S)-3-((S)-1-(4-bromophenyl)ethyl)-6-(2-hydroxyethyl)-6-phenyl-1,3-oxazinan-2-one following a procedures analogous to those described in Example 359. LC-MS Method 2 t$_R$=1.336, m/z=482.7; $^1$H NMR (CDCl$_3$) 1.48 (d, 3H), 2.11-2.23 (m, 2H), 2.26-2.34 (m, 4H), 2.81 (s, 3H), 2.84 (m, 2H), 3.05 (m, 1H), 3.21 (m, 1H), 4.48 (s, 1H), 5.59 (m, 1H), 6.76 (d, 2H), 7.21 (m, 2H), 7.23 (m, 1H), 7.28 (m, 1H), 7.39 (m, 3H).

Example 508

(R)-6-(4-fluorophenyl)-6-(3-hydroxypropyl)-3-((S)-1-(5-(trifluoromethyl)pyridin-2-yl)piperidin-3-yl)-1,3-oxazinan-2-one

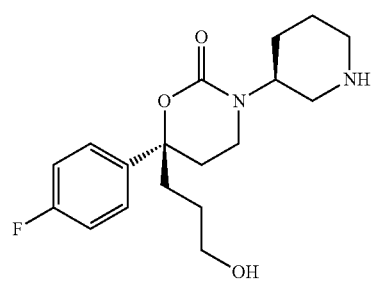

+

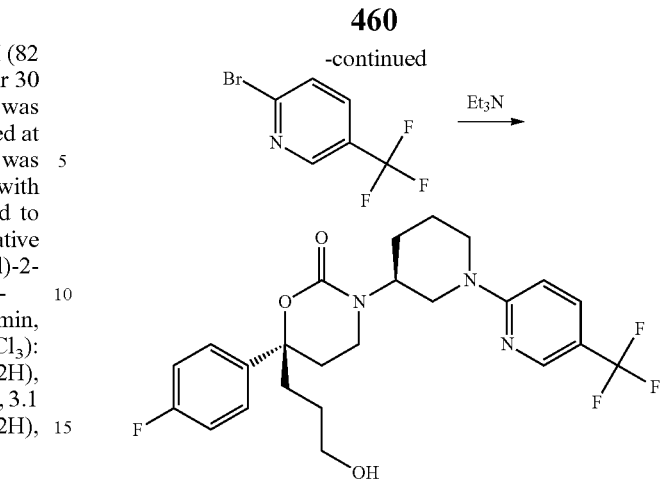

A mixture of (R)-6-(4-fluorophenyl)-6-(3-hydroxypropyl)-3-((S)-piperidin-3-yl)-1,3-oxazinan-2-one (100 mg, 0.30 mmol), 2-bromo-5-(trifluoromethyl)pyridine (67 mg, 0.36 mmol), and triethylamine (91 mg, 0.90 mmol) in acetonitrile was heated to reflux for 3 h. The reaction mixture was concentrated. The residue was purified by preparative TLC and preparative HPLC to afford (R)-6-(4-fluorophenyl)-6-(3-hydroxypropyl)-3-((S)-1-(5-(trifluoromethyl)pyridin-2-yl)piperidin-3-yl)-1,3-oxazinan-2-one (10.09 mg, 7%). LC-MS Method 2 t$_R$=1.34 min, m/z=482. $^1$H NMR (400 MHz, CDCl$_3$): 1.28 (m, 1H), 1.64 (m, 2H), 1.76 (m, 3H), 1.92 (m, 2H), 2.18 (m, 1H), 2.27 (m, 1H), 2.77 (m, 3H), 3.21 (m, 1H), 3.52 (t, 2H), 3.83 (broad, 1H), 4.11 (d, 1H), 4.25 (d, 1H), 6.57 (d, 1H), 7.03 (t, 2H), 7.23 (m, 2H), 7.54 (d, 1H), 8.29 (s, 1H).

Example 509

(R)-3-((S)-1-(4-bromophenyl)ethyl)-6-(3-(2-oxopyrrolidin-1-yl)propyl)-6-phenyl-1,3-oxazinan-2-one

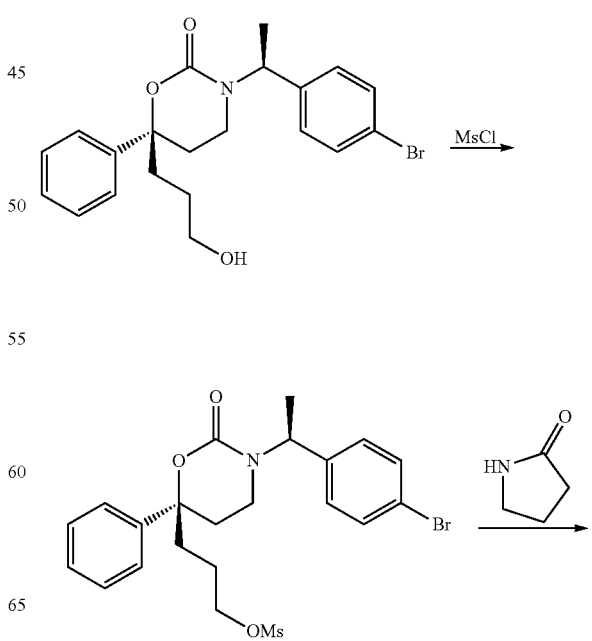

-continued

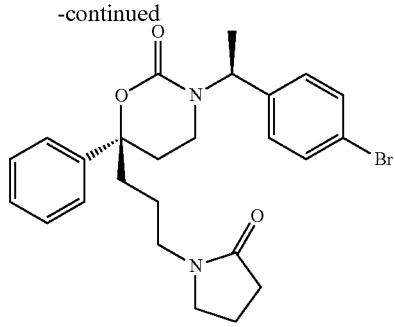

The title compound was prepared from (R)-3-((S)-1-(4-bromophenyl)ethyl)-6-(3-hydroxypropyl)-6-phenyl-1,3-oxazinan-2-one following procedures analogous to those described in Example 506. LC-MS Method 3 $t_R$=1.26, m/z=486.9; $^1$H NMR (CDCl$_3$) 1.26 (m, 1H), 1.42 (d, 3H), 1.63-1.96 (m, 5H), 2.05-2.24 (m, 3H), 2.29 (m, 2H), 2.74 (m, 1H), 3.11 (m, 3H), 3.21 (m, 1H), 5.56 (m, 1H), 6.68 (d, 2H), 7.13-7.21 (m, 4H), 7.23-7.34 (m, 3H).

Example 510

N-methyl-N-(3-((R)-3-((S)-1-(4-(2-methylpyridin-4-yl)phenyl)ethyl)-2-oxo-6-phenyl-1,3-oxazinan-6-yl)propyl)acetamide

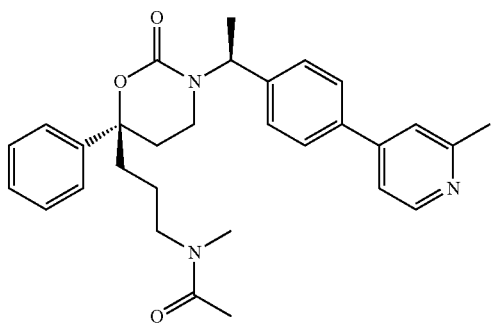 [SMILES: CC(=O)N(C)CCC[C@]1(c2ccccc2)CCN([C@@H](C)c2ccc(-c3ccnc(C)c3)cc2)C(=O)O1]

The title compound was prepared from N-(3-((R)-3-((S)-1-(4-bromophenyl)ethyl)-2-oxo-6-phenyl-1,3-oxazinan-6-yl)propyl)-N-methylacetamide and 2-methylpyridine-4-boronic acid following a procedure analogous to that described in Example 459 Step 1. LC-MS Method 2 $t_R$=0.98, m/z=486.2; $^1$H NMR (CDCl$_3$) 1.21-1.38 (m, 1H), 1.52 (d, 3H), 1.61-1.90 (m, 3H), 2.05 (d, 3H), 2.17 (m, 1H), 2.42 (m, 2H), 2.78 (s, 1H), 2.83 (s, 3H), 2.85 (s, 2H), 2.92 (m, 1H), 3.11-3.33 (m, 2H), 5.65 (m, 1H), 7.05 (d, 2H), 7.21 (m, 2H), 7.30 (m, 3H), 7.38 (d, 2H), 7.60 (s, 1H), 7.71 (d, 1H), 8.72 (d, 1H).

Example 511

N-(2-((S)-3-((S)-1-(4-(2-methylpyridin-4-yl)phenyl)ethyl)-2-oxo-6-phenyl-1,3-oxazinan-6-yl)ethyl)methanesulfonamide

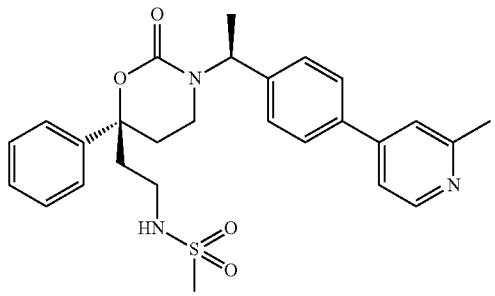 [SMILES: Cc1cc(-c2ccc([C@H](C)N3CC[C@](CCNS(C)(=O)=O)(c4ccccc4)OC3=O)cc2)ccn1]

The title compound was prepared from N-(2-((S)-3-((S)-1-(4-bromophenyl)ethyl)-2-oxo-6-phenyl-1,3-oxazinan-6-yl)ethyl)methanesulfonamide and 2-methylpyridine-4-boronic acid following a procedure analogous to that described in Example 459 Step 1. LC-MS Method 2 $t_R$=1.12, m/z=494; $^1$H NMR (CDCl$_3$) 1.48 (d, 3H), 2.10 (m, 2H), 2.20-2.41 (m, 2H), 2.43 (m, 1H), 2.71 (s, 3H), 2.73 (s, 3H), 3.11 (m, 2H), 5.52 (m, 1H), 7.13 (d, 2H), 7.25 (m, 3H), 7.34 (m, 2H), 7.62 (d, 2H), 7.91 (m, 1H), 8.08 (s, 1H), 8.56 (d, 1H).

Example 512

(R)-3-((S)-1-(4-(2-methylpyridin-4-yl)phenyl)ethyl)-6-(3-(2-oxopyrrolidin-1-yl)propyl)-6-phenyl-1,3-oxazinan-2-one

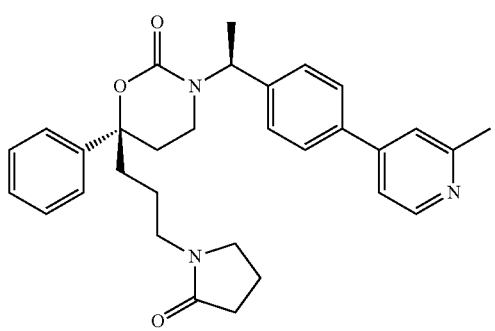 [SMILES: Cc1cc(-c2ccc([C@H](C)N3CC[C@](CCCN4CCCC4=O)(c4ccccc4)OC3=O)cc2)ccn1]

The title compound was prepared from (R)-3-((S)-1-(4-bromophenyl)ethyl)-6-(3-(2-oxopyrrolidin-1-yl)propyl)-6-phenyl-1,3-oxazinan-2-one and 2-methylpyridine-4-boronic acid following a procedure analogous to that described in Example 459 Step 1. LC-MS Method 2 $t_R$=0.992, m/z=498.1; $^1$H NMR (CDCl$_3$) 1.21 (m, 3H), 1.48 (d, 3H), 1.61-1.95 (m, 5H), 2.12 (m, 1H), 2.26 (m, 4H), 2.52 (s, 3H), 2.83 (m, 1H), 3.11 (m, 3H), 3.22 (m, 1H), 5.67 (m, 1H), 6.95 (d, 2H), 7.18 (m, 1H), 7.21 (m, 1H), 7.23 (m, 2H), 7.29 (m, 3H), 7.30 (m, 2H), 8.41 (d, 1H).

Example 513

(S)-3-((S)-1-(4-bromophenyl)ethyl)-6-(2-(1-dioxo-isothiazolidin-2-yl)ethyl)-6-phenyl-1,3-oxazinan-2-one

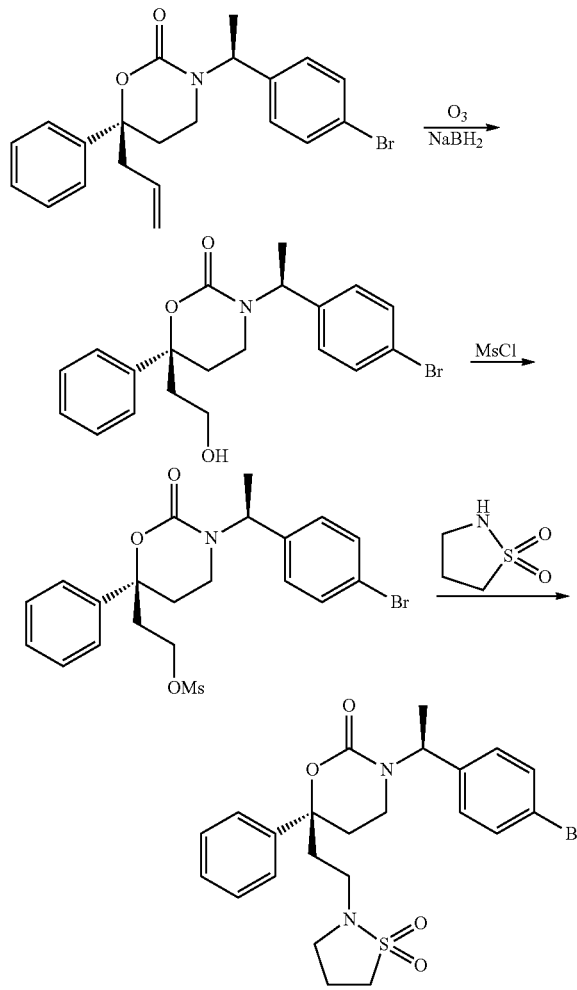

Step 1

To a solution of (R)-6-allyl-3-((S)-1-(4-bromophenyl) ethyl)-6-phenyl-1,3-oxazinan-2-one (3 g, 7.5 mmol) in $CH_2Cl_2$ (50 mL) was treated with $O_3$ at −78° C. till the mixture turned blue. Then $NaBH_4$ (285 mg, 75 mmol) was added to the solution at 0° C., and the reaction solution was stirred at room temperature for 3 hours. The reaction was quenched by $H_2O$, and the mixture was extracted with EtOAc. The combined organic phase was concentrated to give the crude product, which was purified by preparative TLC to give (S)-3-((S)-1-(4-bromo-phenyl)ethyl)-6-(2-hydroxyethyl)-6-phenyl-1,3-oxazinan-2-one (2.5 g, 84%). $^1$H NMR ($CDCl_3$): 1.48 (t, 3H), 2.05-2.41 (m, 4H), 2.71-2.92 (m, 2H), 3.51 (m, 1H), 3.71 (m, 1H), 5.58 (m, 1H), 6.73 (d, 2H), 7.12 (m, 2H), 7.23-7.45 (m, 6H).

Step 2

To a solution of (S)-3-((S)-1-(4-bromophenyl)ethyl)-6-(2-hydroxyethyl)-6-phenyl-1,3-oxazinan-2-one (300 mg, 0.75 mmol) in dichloromethane (20 mL) were added $Et_3N$ (390 mg, 3.75 mmol) and methanesulfonyl chloride (256 mg, 2.25 mmol) at 0° C. The reaction solution was stirred at rt for 1 h. The reaction was quenched with $H_2O$ and the mixture was extracted with dichloromethane. The organic phase was concentrated to give 2-((S)-3-((S)-1-(4-bromophenyl)ethyl)-2-oxo-6-phenyl-1,3-oxazinan-6-yl)ethyl-methane sulfonate (352.8 mg, 98%), which was used for the next step without further purification.

Step 3

To a solution of 2-((S)-3-((S)-1-(4-bromophenyl)ethyl)-2-oxo-6-phenyl-1,3-oxazinan-6-yl)ethyl-methanesulfonate (360 mg, 0.75 mmol) and $K_2CO_3$ (207 mg, 1.5 mmol) in acetonitrile (10 mL) was added isothiazolidine 1,1-dioxide (121 mg, 4.6 mmol), and the mixture was refluxed overnight. The mixture was filtered and the filtrate was concentrated to give the crude product, which was purified by preparative HPLC to afford compound (S)-3-((S)-1-(4-bromophenyl) ethyl)-6-(2-(1-dioxo-isothiazolidin-2-yl)ethyl)-6-phenyl-1, 3-oxazinan-2-one (2.43 mg, 1%). LC-MS Method 2 $t_R$=1.37 min, m/z=509, 507. $^1$H NMR ($CDCl_3$): 1.48 (t, 3H), 2.05-2.41 (m, 7H), 2.71-2.92 (m, 2H), 3.11 (m, 3H), 3.21 (m, 2H), 5.58 (m, 1H), 6.73 (d, 2H), 7.18 (m, 1H), 7.23 (m, 3H); 7.35 (m, 3H).

Example 514

N-(3-((R)-3-((S)-1-(4-bromophenyl)ethyl)-2-oxo-6-phenyl-1,3-oxazinan-6-yl)propyl)-N-methylmethane-sulfonamide

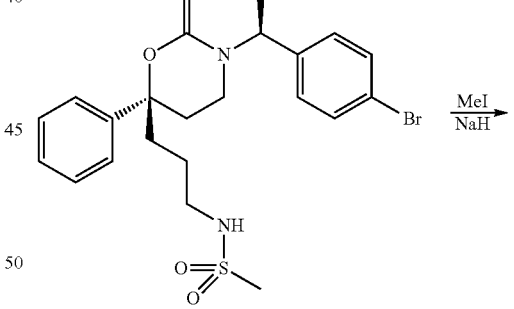

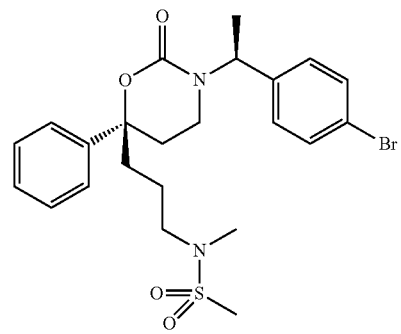

To a solution of 3-((R)-3-((S)-1-(4-bromophenyl)ethyl)-2-oxo-6-phenyl-1,3-oxazinan-6-yl)propyl methanesulfonate (180 mg, 0.36 mmol) in DMF (5 mL) was added NaH (14.6 mg, 0.36 mmol) at 0° C. The mixture was stirred at rt for 30 min. Then iodomethane (153 mg, 1.1 mmol) was added to the above mixture. The formed mixture was stirred at 40° C. for 3 h. After the reaction was over, the reaction was quenched with NH$_4$Cl solution and the mixture was extracted with EtOAc. The combined organic phase was concentrated to give the crude product, which was purified by preparative TLC to give N-(3-((R)-3-((S)-1-(4-bromophenyl)ethyl)-2-oxo-6-phenyl-1,3-oxazinan-6-yl)propyl)-N-methylmethanesulfonamide (100 mg, 55%). LC-MS Method 2 $t_R$=1.41 min, m/z=511, 509. $^1$H NMR (400 MHz, CDCl$_3$): δ=1.45 (m, 1H), 1.48 (t, 3H), 1.83-1.97 (m, 3H), 2.1-2.2 (m, 3H), 2.61 (s, 3H), 2.71 (s, 3H), 2.91 (m, 1H), 3.0 (m, 2H), 5.5 (m, 1H), 6.72 (m, 2H), 7.10 (m, 2H), 7.20 (m, 2H), 7.37 (m, 3H).

Example 515

(S)-6-(2-(1,1-dioxo-isothiazolidin-2-yl)ethyl)-3-((S)-1-(4-(2-methylpyridin-4-yl)phenyl)ethyl)-6-phenyl-1,3-oxazinan-2-one

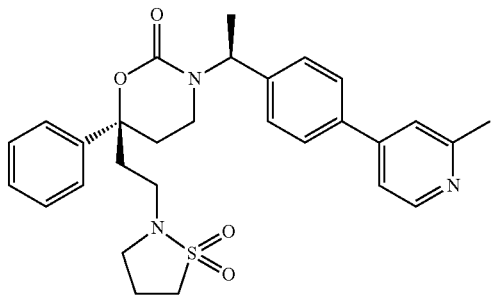 [SMILES: Cc1cc(-c2ccc([C@H](C)N3CC[C@](CCN4CCCS4(=O)=O)(c4ccccc4)OC3=O)cc2)ccn1]

The title compound was prepared from (S)-3-((S)-1-(4-bromophenyl)ethyl)-6-(2-(1-dioxo-isothiazolidin-2-yl)ethyl)-6-phenyl-1,3-oxazinan-2-one and 2-methylpyridine-4-boronic acid following a procedure analogous to that described in Example 459 Step 1. LC-MS Method 2 $t_R$=0.984, m/z=520.1; $^1$H NMR (CDCl$_3$) 1.52 (d, 3H), 2.11-2.29 (m, 5H), 2.32 (m, 2H), 2.81 (s, 3H), 2.83-2.96 (m, 2H), 2.98-3.08 (m, 3H), 3.11-3.22 (m, 2H), 5.67 (m, 1H), 7.06 (d, 2H), 7.24-7.36 (m, 5H), 7.38 (d, 2H), 7.61 (s, 1H), 7.69 (m, 1H), 8.73 (d, 1H).

Example 516

(R)-3-((S)-1-(4-bromophenyl)ethyl)-6-(3-(1,1-dioxo-isothiazolidin-2-yl)propyl)-6-phenyl-1,3-oxazinan-2-one

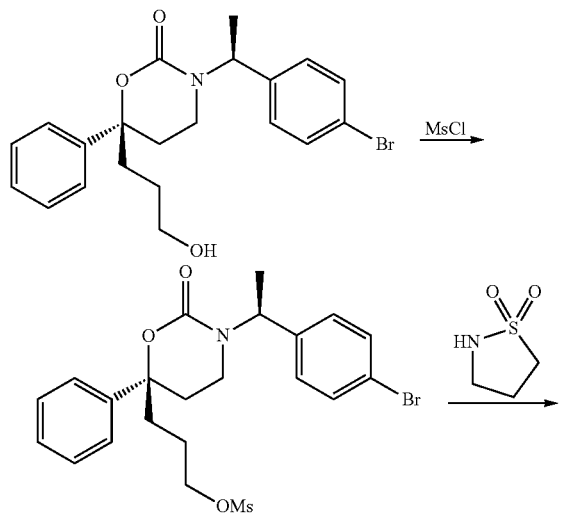

The title compound was prepared from (R)-3-((S)-1-(4-bromophenyl)ethyl)-6-(3-hydroxypropyl)-6-phenyl-1,3-oxazinan-2-one following a procedure analogous to that described in Example 513. LC-MS Method 2 tR=1.277, m/z=524.5; 1H NMR (CDCl3) 1.31 (m, 1H), 1.42 (d, 3H), 1.64 (m, 1H), 1.81-1.94 (m, 2H), 2.11-2.28 (m, 5H), 2.43 (m, 1H), 2.82 (m, 2H), 2.93-3.14 (m, 5H), 3.36 (m, 1H), 5.56 (m, 1H), 6.72 (d, 2H), 7.16 (m, 2H), 7.21 (m, 2H), 7.33 (m, 3H).

Example 517

(R)-6-(3-(1,1-dioxo-isothiazolidin-2-yl)propyl)-3-((S)-1-(4-(2-methylpyridin-4-yl)phenyl)ethyl)-6-phenyl-1,3-oxazinan-2-one

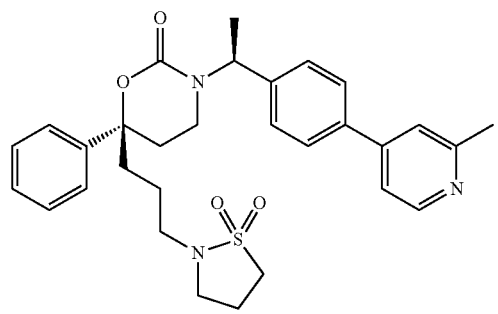 [SMILES: Cc1cc(-c2ccc([C@H](C)N3CC[C@](CCCN4CCCS4(=O)=O)(c4ccccc4)OC3=O)cc2)ccn1]

The title compound was prepared from (R)-3-((S)-1-(4-bromophenyl)ethyl)-6-(3-(1,1-dioxo-isothiazolidin-2-yl)propyl)-6-phenyl-1,3-oxazinan-2-one and 2-methylpyridine-4-boronic acid following a procedure analogous to that described in Example 459 Step 1. LC-MS Method 2 $t_R$=1.001, m/z=534.1; $^1$H NMR (CDCl$_3$) 1.22-1.33 (m, 1H), 1.52 (d, 3H), 1.68-1.81 (m, 1H), 1.83-2.03 (m, 2H), 2.12-2.38 (m, 5H), 2.83-2.91 (m, 5H), 2.93-3.13 (m, 5H), 5.68 (m, 1H), 7.09 (d, 2H), 7.18-7.32 (m, 5H), 7.36 (d, 2H), 7.61 (s, 1H), 7.68 (s, 1H), 8.24 (s, 1H).

Example 518

3-((1S)-1-(4-bromophenyl)ethyl)-6-(4-fluorophenyl)-6-methyl-1,3-oxazinan-2-one

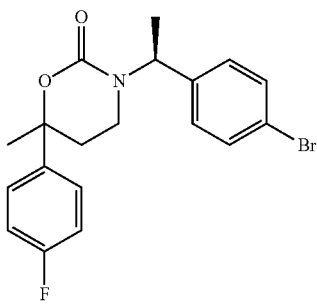 [SMILES: C[C@@H](c1ccc(Br)cc1)N1CCC(C)(c2ccc(F)cc2)OC1=O]

The title compound was prepared following procedures analogous to those described in Example 353 using 4-chloro-2-phenylbutan-2-ol in Step 1. Two isomers were isolated.

Isomer 1: (S)-3-((S)-1-(4-bromophenyl)ethyl)-6-(4-fluorophenyl)-6-methyl-1,3-oxazinan-2-one LC-MS Method 1 $t_R$=1.93, m/z=392 (M+); $^1$H NMR (CDCl$_3$) 7.47 (ap d, 2H, J=8.5 Hz), 7.33-7.29 (m, 2H), 7.19 (d, 2H, J=8.5 Hz), 7.07 (ap t, 2H, J=8.7 Hz), 5.74 (q, 1H, J=7.3 Hz), 2.74-2.63 (m, 2H), 2.27-2.22 (dt, 1H, J=13.8 Hz, 4 Hz), 2.03-1.97 (m, 1H), 1.61 (s, 3H), 1.29 (d, 3H, J=7 Hz).

Isomer 2: (R)-3-((S)-1-(4-bromophenyl)ethyl)-6-(4-fluorophenyl)-6-methyl-1,3-oxazinan-2-one LC-MS Method 1 $t_R$=1.89, m/z=392 (M+); $^1$H NMR (CDCl$_3$) 7.31-7.27 (m, 4H), 7.04 (t, 2H, J=8.8 Hz), 6.83 (d, 2H, J=8.8 Hz), 5.64 (q, 1H, J=5.7 Hz), 2.97-2.92 (m, 1H), 2.37-2.25 (m, 2H), 2.19-2.11 (m, 1H), 1.62 (s, 3H), 1.50 (d, 3H, J=7.2 Hz).

Example 519

(S)-6-(4-fluorophenyl)-6-methyl-3-((S)-1-(4-(2-methylpyridin-4-yl)phenyl)ethyl)-1,3-oxazinan-2-one

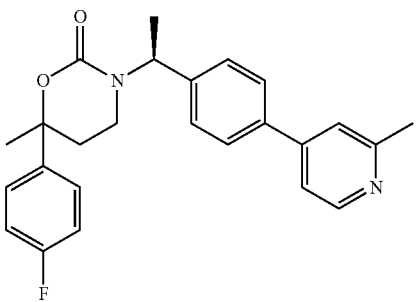

Isomer 1 of the title compound, (S)-6-(4-fluorophenyl)-6-methyl-3-((S)-1-(4-(2-methylpyridin-4-yl)phenyl)ethyl)-1,3-oxazinan-2-one, was prepared from (S)-3-((S)-1-(4-bromophenyl)ethyl)-6-(4-fluorophenyl)-6-methyl-1,3-oxazinan-2-one and 2-methylpyridine-4-boronic acid following a procedure analogous to that described in Example 64. LC-MS Method 1 $t_R$=1.28, m/z=405 (M+1); $^1$H NMR (CDCl$_3$) 8.84 (d, 1H, J=6.1 Hz), 7.81 (d, 1H, J=5.9 Hz), 7.75 (s, 1H), 7.70 (d, 2H, J=8.2 Hz), 7.52 (d, 2H, J=8.20 Hz), 7.34-7.31 (m, 2H), 7.09 (t, 2H, J=8.6 Hz), 5.81 (q, 1H, J=7.2 Hz), 2.89 (s, 3H), 2.84-2.72 (m, 2H), 2.31 (dt, 1H, J=13.9, 3.7 Hz), 2.11-2.03 (m, 1H), 1.64 (s, 3H), 1.38 (d, 3H, J=7 Hz).

Isomer 2 of the title compound, (R)-6-(4-fluorophenyl)-6-methyl-3-((S)-1-(4-(2-methylpyridin-4-yl)phenyl)ethyl)-1,3-oxazinan-2-one, was prepared from (R)-3-((S)-1-(4-bromophenyl)ethyl)-6-(4-fluorophenyl)-6-methyl-1,3-oxazinan-2-one and 2-methylpyridine-4-boronic acid following a procedure analogous to that described in Example 64. LC-MS Method 1 $t_R$=1.18, m/z=405 (M+1); $^1$H NMR (CDCl$_3$) 8.83 (s, 1H), 7.72 (s, 1H), 7.66 (s, 1H), 7.48 (d, 2H, J=7.3 Hz), 7.32 (br m, 2H), 7.16 (d, 2H, J=6.7), 7.04 (t, 2H, J=7.6 Hz), 5.77 (q, 1H, J=6.7 Hz), 3.05 (br m, 1H), 2.89 (s, 3H, 2.42-2.32 (m, 2H), 2.23 (br m, 1H), 1.64 (s, 3H), 1.59 (d, 3H, J=6.7 Hz).

Example 520

3-((R)-3-((S)-1-(4-bromophenyl)ethyl)-6-(4-fluorophenyl)-2-oxo-1,3-oxazinan-6-yl)-2-methylpropanenitrile

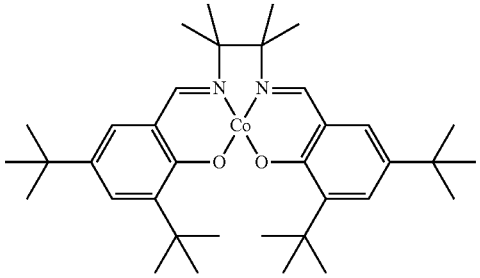

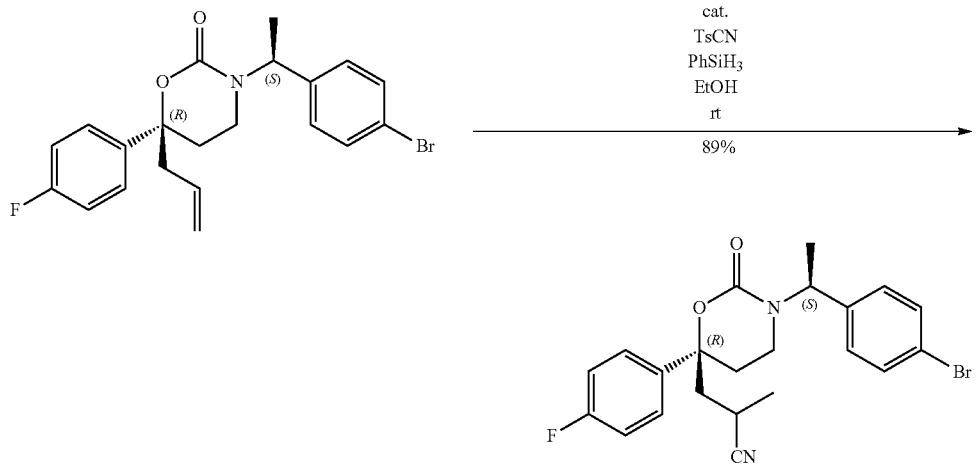

Step 1

A 50 mL flask was charged with N,N'-bis(3,5-di-tert-butylsalicylidene)-1,1,2,2-tetramethylethenediamine (0.4302 g, 0.78 mmol, 1.0 equiv), EtOH (17 mL), and Co(OAc)$_2$ (0.1385 g, 0.78 mmol, 1.0 equiv). The mixture was degassed and then heated to reflux under nitrogen for 3 h, cooled to room temperature. The precipitate was filtered and the purple solid was washed with EtOH (10 mL) and dried under high vacuum to give 0.3533 g (75%) of the cobalt(II) complex.

Step 2

A mixture of (R)-6-allyl-3-((S)-1-(4-bromophenyl)ethyl)-6-(4-fluorophenyl)-1,3-oxazinan-2-one (1.0668 g, 2.55 mmol, 1.0 equiv), the cobalt(II) catalyst (0.0160 g, 0.0264 mmol, 0.010 equiv), TsCN (0.5546 g, 3.06 mmol, 1.2 equiv), and PhSiH$_3$ (0.2944 g, 2.72 mmol, 1.07 equiv) in EtOH (5 mL) was stirred at room temperature for 4 h. After the solvent was removed under reduced pressure, the residue was purified by chromatography on silica gel eluted with hexanes/ethyl acetate to afford 1.0130 g (89%) of 3-((R)-3-((S)-1-(4-bromophenyl)ethyl)-6-(4-fluorophenyl)-2-oxo-1,3-oxazinan-6-yl)-2-methylpropanenitrile as a solid. LC-MS $t_R$=1.83, 1.86 min in 3 min chromatography, m/z 445, 447 (MH$^+$); $^1$H NMR (400 MHz, CDCl$_3$) δ 7.32-7.22 (m, 4H), 7.13-7.05 (m, 2H), 6.80-6.73 (m, 2H), 5.60-5.56 (m, 1H), 3.00-1.94 (m, 7H), 1.51-1.49 (m, 3H), 1.35-1.32 (m, 1.5H), 1.27-1.24 (m, 1.5H); $^{19}$F NMR (376 MHz, CDCl$_3$) δ -113.08 (m), -113.69 (m).

Example 521

3-((R)-3-((S)-1-(4-bromophenyl)ethyl)-6-(4-fluorophenyl)-2-oxo-1,3-oxazinan-6-yl)-2,2-dimethylpropanenitrile

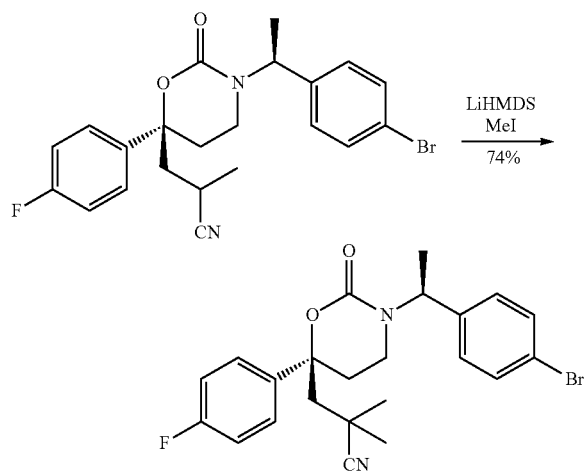

To a solution of 3-((R)-3-((S)-1-(4-bromophenyl)ethyl)-6-(4-fluorophenyl)-2-oxo-1,3-oxazinan-6-yl)-2-methylpropanenitrile (0.3322 g, 0.746 mmol) and MeI (1.40 g, 13 equiv) in THF (12 mL) at -78° C. was added 2.4 mL (2.4 mmol, 3.2 equiv) of a 1.0 M LiHMDS solution in THF. The resulting mixture was stirred overnight, with the temperature slowly rising to ambient. The reaction mixture was quenched with brine (1 mL), diluted with CH$_2$Cl$_2$, and dried over Na$_2$SO$_4$. After the solvents were evaporated, the residue was purified by reversed-phase HPLC (SunFire™ Prep C$_{18}$ OBD™ 5 μm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford 0.2547 g (74%) of 3-((R)-3-((S)-1-(4-bromophenyl)ethyl)-6-(4-fluorophenyl)-2-oxo-1,3-oxazinan-6-yl)-2,2-dimethylpropanenitrile. LC-MS Method 1 $t_R$=1.89 min, m/z 459, 461 (MH$^+$); $^1$H NMR (400 MHz, CD$_3$OD) δ 7.31-7.27 (m, 2H), 7.22-7.18 (m, 2H), 7.04-6.99 (m, 2H), 6.83 (d, J=8.2 Hz, 2H), 5.41 (q, J=7.0 Hz, 1H), 3.02-2.97 (m, 1H), 2.42-2.36 (m, 1H), 2.29-2.08 (m, 4H), 1.42 (d, J=7.0 Hz, 3H), 1.30 (s, 3H), 1.22 (s, 3H); $^{19}$F NMR (376 MHz, CD$_3$OD) δ -116.50 (m).

Example 522

3-((R)-3-((S)-1-(4-bromophenyl)ethyl)-6-(4-fluorophenyl)-2-oxo-1,3-oxazinan-6-yl)-2,2-dimethylpropanamide

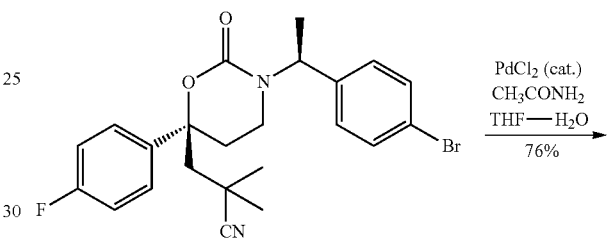

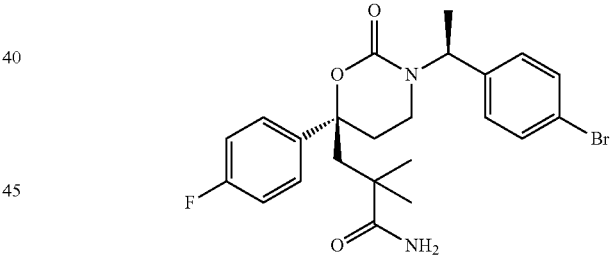

A mixture of 3-((R)-3-((S)-1-(4-bromophenyl)ethyl)-6-(4-fluorophenyl)-2-oxo-1,3-oxazinan-6-yl)-2,2-dimethylpropanenitrile (0.1232 g, 2.68 mmol, 1.0 equiv), acetamide (0.5723 g, 9.7 mmol, 36 equiv), and PdCl$_2$ (0.0273 g, 0.154 mmol, 0.57 equiv) in THF-H$_2$O (3:1, 6 mL) was stirred at room temperature for 24 h. The reaction mixture was purified by reversed-phase HPLC (SunFire™ Prep C$_{18}$ OBD™ 5 μm 19×50 mm column, 10%→90% CH$_3$CN/H$_2$O, 0.1% CF$_3$COOH over 8 min and then 90% CH$_3$CN/H$_2$O, 0.1% CF$_3$COOH over 2 min, flow rate 20 mL/min) to afford 0.1250 g of product, which was further purified by chromatography on silica gel eluted with CH$_2$Cl$_2$/MeOH to give 0.0972 g (76%) of 3-((R)-3-((S)-1-(4-bromophenyl)ethyl)-6-(4-fluorophenyl)-2-oxo-1,3-oxazinan-6-yl)-2,2-dimethylpropanamide. LC-MS Method 1 $t_R$=1.64 min, m/z 477, 479 (MH$^+$); $^1$H NMR (400 MHz, CD$_3$OD) δ 7.25-7.20 (m, 4H), 6.98 (t, J=8.8 Hz, 2H), 6.83 (d, J=8.5 Hz, 2H), 5.42 (q, J=7.0 Hz, 1H), 3.01-2.97 (m, 1H), 2.33 (d, J=15 Hz, 1H), 2.27-2.10 (m, 3H), 2.05 (d, J=15 Hz, 1H), 1.42 (d, J=7.0 Hz, 3H), 1.10 (s, 3H), 1.07 (s, 3H); ¹⁹F NMR (376 MHz, CD₃OD) δ −117.39 (m).

Example 523

3-((R)-3-((S)-1-(4-bromophenyl)ethyl)-6-(4-fluorophenyl)-2-oxo-1,3-oxazinan-6-yl)-2-methylpropanamide

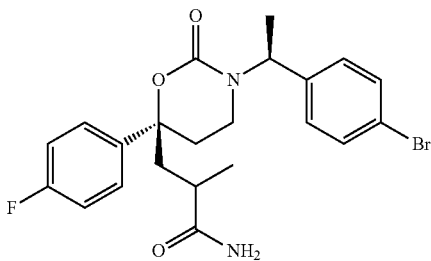 [SMILES: CC(C[C@]1(c2ccc(F)cc2)CCN([C@@H](C)c2ccc(Br)cc2)C(=O)O1)C(N)=O]

The title compound was prepared from 3-((R)-3-((S)-1-(4-bromophenyl)ethyl)-6-(4-fluorophenyl)-2-oxo-1,3-oxazinan-6-yl)-2-methylpropanenitrile following a procedure analogous to that described in Example 522. Two isomers were isolated.

Isomer 1: LC-MS Method 1 $t_R$=1.56, m/z=463, 465 (M+1); ¹H NMR (CD₃OD) 7.18-7.14 (m, 4H), 6.96-6.91 (m, 2H), 6.77 (d, J=8.5 Hz, 2H), 5.37 (q, J=7.0 Hz, 1H), 2.98-2.94 (m, 1H), 2.38-2.27 (m, 3H), 2.15-2.07 (m, 2H), 1.74-1.70 (m, 1H), 1.38 (d, J=7.0 Hz, 3H), 1.00 (d, J=6.5 Hz, 3H).

Isomer 2: LC-MS Method 1 $t_R$=1.63, m/z=463, 465 (M+1); ¹H NMR (CD₃OD) 7.27-7.18 (m, 4H), 7.04-7.00 (m, 2H), 6.80 (d, J=8.5 Hz, 2H), 5.40 (q, J=7.0 Hz, 1H), 3.04-3.00 (m, 1H), 2.47-2.36 (m, 2H), 2.28-2.08 (m, 3H), 1.68-1.64 (m, 1H), 1.41 (d, J=7.0 Hz, 3H), 0.88 (d, J=6.7 Hz, 3H).

Example 524

3-((R)-3-((S)-1-(4-bromophenyl)ethyl)-6-(4-fluorophenyl)-2-oxo-1,3-oxazinan-6-yl)propanenitrile

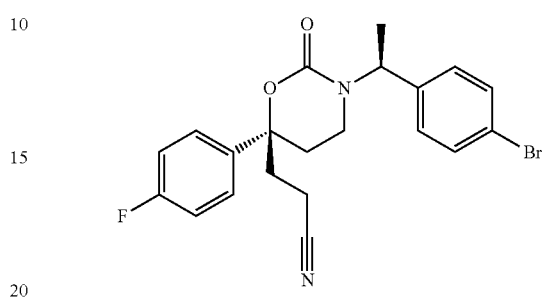

The title compound was prepared from 3-((R)-3-((S)-1-(4-bromophenyl)ethyl)-6-(4-fluorophenyl)-2-oxo-1,3-oxazinan-6-yl)propanamide following a procedure analogous to that described in Example 172. LC-MS Method 1 $t_R$=1.79, m/z=431, 433 (M+1); ¹H NMR (CD₃OD) 7.22-7.15 (m, 4H), 7.01 (t, J=8.8 Hz, 2H), 6.78 (d, J=8.5 Hz, 2H), 5.37 (q, J=7.0 Hz, 1H), 2.99-2.97 (m, 1H), 2.46-2.32 (m, 2H), 2.21-2.04 (m, 5H), 1.38 (d, J=7.0 Hz, 3H).

Example 525

2-((S)-3-((S)-1-(4-bromophenyl)ethyl)-6-(4-fluorophenyl)-2-oxo-1,3-oxazinan-6-yl)acetamide

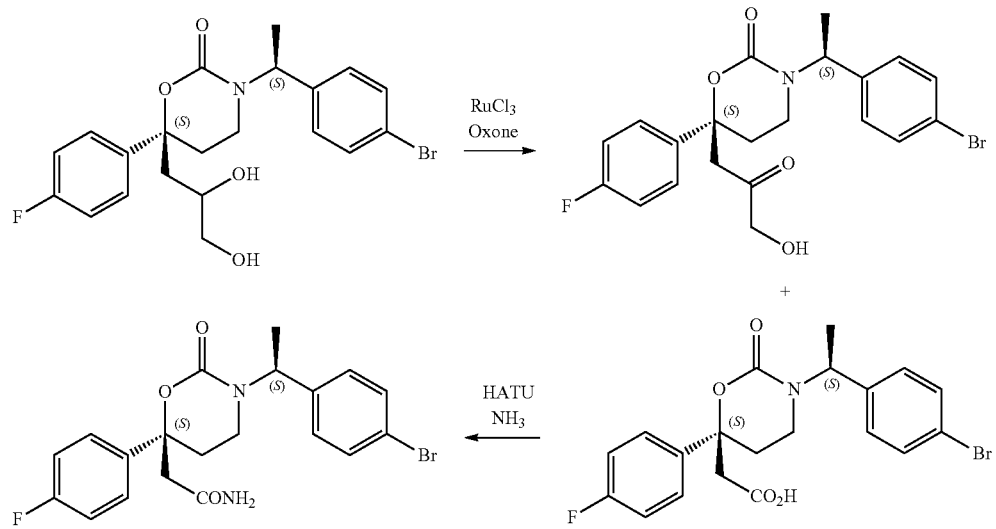

Step 1

To a solution of NaHCO₃ (0.0475 g, 0.56 mmol) in H₂O (0.2 mL)/CH₃CN (1.5 mL)/EtOAc (1.5 mL) were added 20 μL (2 μmol) of a 0.1 M RuCl₃.xH₂O solution in H₂O and 0.6804 g (1.1 mmol) of Oxone®. After the resulting mixture was stirred at room temperature to yield the bright yellow color, (6S)-3-((S)-1-(4-bromophenyl)ethyl)-6-(2,3-dihydroxypropyl)-6-(4-fluorophenyl)-1,3-oxazinan-2-one (0.1000 g, 0.22 mmol) was added in one portion. After 1 h, the reaction mixture was quenched with satd aq NaHCO₃ (3 mL) and saturated Na₂SO₃ (3 mL), diluted with CH₂Cl₂, and dried over Na₂SO₄. After the solvents were evaporated, the residue was purified by reversed-phase HPLC (SunFire™ Prep C₁₈ OBD™ 5 μm 19×50 mm column, 10%→90% CH₃CN/H₂O, 0.1% CF₃COOH over 8 min and then 90% CH₃CN/H₂O, 0.1% CF₃COOH over 2 min, flow rate 20 mL/min) to afford 0.0030 g of (S)-3-((S)-1-(4-bromophenyl)ethyl)-6-(4-fluorophenyl)-6-(3-hydroxy-2-oxopropyl)-1,3-oxazinan-2-one: LC-MS Method 1 $t_R$=1.62 min, m/z 450, 452 (MH⁺); ¹H NMR (400 MHz, CD₃OD) δ 7.30-7.27 (m, 2H), 7.21 (d, J=8.8 Hz, 2H), 7.03 (t, J=8.8 Hz, 2H), 6.79 (d, J=8.8 Hz, 2H), 5.41 (q, J=7.0 Hz, 1H), 4.08 (d, J=19.0 Hz, 1H), 3.96 (d, J=19.0 Hz, 1H), 3.06-3.02 (m, 1H), 2.93 (s, 2H), 2.58-2.54 (m, 1H), 2.44-2.36 (m, 1H), 2.28-2.22 (m, 1H), 1.43 (d, J=7.0 Hz, 3H); ¹⁹F NMR (376 MHz, CD₃OD) δ −116.60 (m) and 0.0260 g of 2-((S)-3-((S)-1-(4-bromophenyl)ethyl)-6-(4-fluorophenyl)-2-oxo-1,3-oxazinan-6-yl)acetic acid: LC-MS Method 1 $t_R$=1.66 min, m/z 436, 438 (MH⁺).

Step 2

To a solution of 2-((S)-3-((S)-1-(4-bromophenyl)ethyl)-6-(4-fluorophenyl)-2-oxo-1,3-oxazinan-6-yl)acetic acid (0.0259 g, 0.059 mmol) in DMF (2 mL) was added HATU (0.2298 g, 0.60 mmol), DIPEA (0.5 mL), and 0.8 M NH₃ in THF (4 mL). The mixture was stirred at rt for 2 d. After the solvents were removed in vacuo, the residue was purified by reversed-phase HPLC (SunFire™ Prep C₁₈ OBD™ 5 μm 19×50 mm column, 10%→90% CH₃CN/H₂O, 0.1% CF₃COOH over 8 min and then 90% CH₃CN/H₂O, 0.1% CF₃COOH over 2 min, flow rate 20 mL/min) to afford 0.0146 g (57%) of 2-((S)-3-((S)-1-(4-bromophenyl)ethyl)-6-(4-fluorophenyl)-2-oxo-1,3-oxazinan-6-yl)acetamide. LC-MS Method 1 $t_R$=1.55 min, m/z 435, 437 (MH⁺), 391, 393; ¹H NMR (400 MHz, CD₃OD) δ 7.30-7.26 (m, 2H), 7.19-7.16 (m, 2H), 7.04-6.99 (m, 2H), 6.74 (d, J=8.5 Hz, 2H), 5.39 (q, J=7.0 Hz, 1H), 3.06-3.01 (m, 1H), 2.72-2.58 (m, 3H), 2.42-2.34 (m, 1H), 2.26-2.19 (m, 1H), 1.41 (d, J=7.0 Hz, 3H); ¹⁹F NMR (376 MHz, CD₃OD) δ −116.70 (m).

Example 526

3-((R)-3-((S)-1-(4-bromophenyl)ethyl)-6-(4-fluorophenyl)-2-oxo-1,3-oxazinan-6-yl)propanoic acid

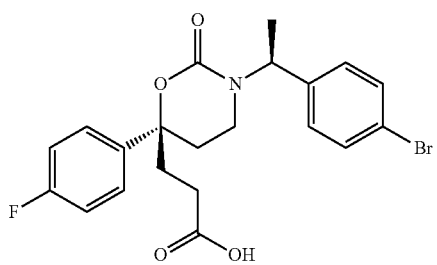 [SMILES: C[C@@H](c1ccc(Br)cc1)N1CC[C@](CCC(=O)O)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one following a procedure analogous to that described in Example 324 Step 1. LC-MS Method 2 $t_R$=1.487, m/z=449.9; ¹H NMR (CDCl₃) 1.52 (d, 3H), 2.11-2.22 (m, 3H), 2.23-2.35 (m, 3H), 2.54 (m, 1H), 2.96 (m, 1H), 5.61 (m, 1H), 6.82 (d, 2H), 7.08 (t, 2H), 7.11-7.32 (m, 4H).

Example 527

(S)-3-((S)-1-(4-bromophenyl)ethyl)-6-(4-fluorophenyl)-6-(3-hydroxy-2-oxopropyl)-1,3-oxazinan-2-one

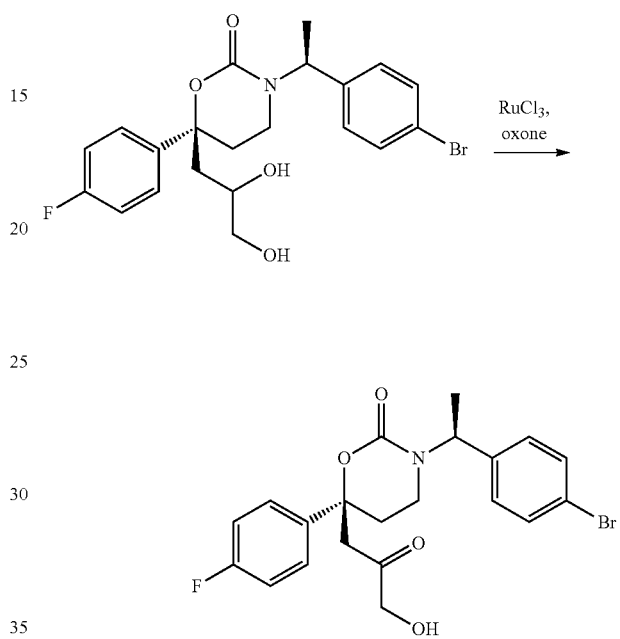

The title compound was isolated as a minor product from the oxidation of (6S)-3-((S)-1-(4-bromophenyl)ethyl)-6-(2,3-dihydroxypropyl)-6-(4-fluorophenyl)-1,3-oxazinan-2-one with RuCl₃/oxone described in Example 525 Step 1. LC-MS Method 1 $t_R$=1.62, m/z=450, 452 (M+1); 1H NMR (CD₃OD) 7.30-7.27 (m, 2H), 7.21 (d, J=8.8 Hz, 2H), 7.03 (t, J=8.8 Hz, 2H), 6.79 (d, J=8.8 Hz, 2H), 5.41 (q, J=7.0 Hz, 1H), 4.08 (d, J=19.0 Hz, 1H), 3.96 (d, J=19.0 Hz, 1H), 3.06-3.02 (m, 1H), 2.93 (s, 2H), 2.58-2.54 (m, 1H), 2.44-2.36 (m, 1H), 2.28-2.22 (m, 1H), 1.43 (d, J=7.0 Hz, 3H).

Example 528

(R)-3-((S)-1-(4-bromophenyl)ethyl)-6-(4-fluorophenyl)-6-(3-hydroxy-2,2-dimethylpropyl)-1,3-oxazinan-2-one

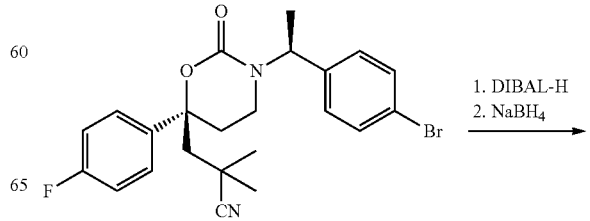

-continued

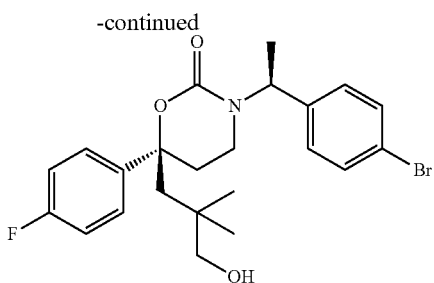

Step 1

To a stirred solution of 3-((R)-3-((S)-1-(4-bromophenyl)ethyl)-6-(4-fluorophenyl)-2-oxo-1,3-oxazinan-6-yl)-2,2-dimethylpropanenitrile (0.0640 g, 0.14 mmol) in $CH_2Cl_2$ (4 mL) at –78° C. under a nitrogen atmosphere was added DIBAL-H/heptane (1.0 M, 0.6 mL, 0.6 mmol). After 2 h, the reaction mixture was quenched with 0.1 M aqueous L-tartaric acid (2 mL) and allowed to warm to room temperature. The mixture was diluted with $CH_2Cl_2$, dried over $Na_2SO_4$. After the solvent was removed in vacuo, the crude aldehyde was directly used in the next step without further purification. LC-MS Method 1 $t_R$=1.93 min, m/z 462, 464 (MH$^+$).

Step 2

To a stirred solution of the aldehyde, obtained as described above, in MeOH (5 mL) at 0° C. was added $NaBH_4$ (0.170 g, 4.5 mmol). After 1.5 h, the reaction mixture was purified by reversed-phase HPLC (SunFire™ Prep $C_{18}$ OBD™ 5 μm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford 0.0125 g of (R)-3-((S)-1-(4-bromophenyl)ethyl)-6-(4-fluorophenyl)-6-(3-hydroxy-2,2-dimethylpropyl)-1,3-oxazinan-2-one. LC-MS Method 1 $t_R$=1.85 min, m/z 464, 466 (MH$^+$), 420, 422; $^1$H NMR (400 MHz, $CD_3OD$) δ 7.26-7.21 (m, 4H), 6.99 (t, J=8.8 Hz, 2H), 6.88 (d, J=8.2 Hz, 2H), 5.43 (q, J=7.0 Hz, 1H), 3.12 (d, J=11 Hz, 1H), 2.99-2.95 (m, 2H), 2.27-2.04 (m, 3H), 1.95-1.93 (m, 2H), 1.42 (d, J=7.0 Hz, 3H), 0.69 (s, 3H), 0.59 (s, 3H); $^{19}$F NMR (376 MHz, $CD_3OD$) δ –117.52 (m).

Example 529

N-(2-((S)-3-((S)-1-(4-bromophenyl)ethyl)-2-oxo-6-phenyl-1,3-oxazinan-6-yl)ethyl)-N-methylmethanesulfonamide

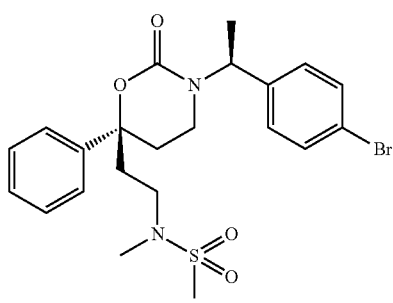 [SMILES: C[C@@H](c1ccc(Br)cc1)N1CC[C@](CCN(C)S(C)(=O)=O)(c2ccccc2)OC1=O]

The title compound was prepared from 2-((S)-3-((S)-1-(4-bromophenyl)ethyl)-2-oxo-6-phenyl-1,3-oxazinan-6-yl)ethyl methanesulfonate following a procedure analogous to that described in Example 514. LC-MS Method 3 $t_R$=1.281, m/z=494.9; $^1$H NMR ($CDCl_3$) 1.48 (d, 3H), 2.15-2.33 (m, 5H), 2.68 (s, 3H), 2.72 (s, 1H), 2.81-2.96 (m, 2H), 3.35 (m, 1H), 5.61 (m, 1H), 6.73 (d, 2H), 7.21 (m, 4H), 7.38 (m, 3H).

Example 530

(S)-3-((S)-1-(4-bromophenyl)ethyl)-6-((5-methyl-1,3,4-oxadiazol-2-yl)methyl)-6-phenyl-1,3-oxazinan-2-one

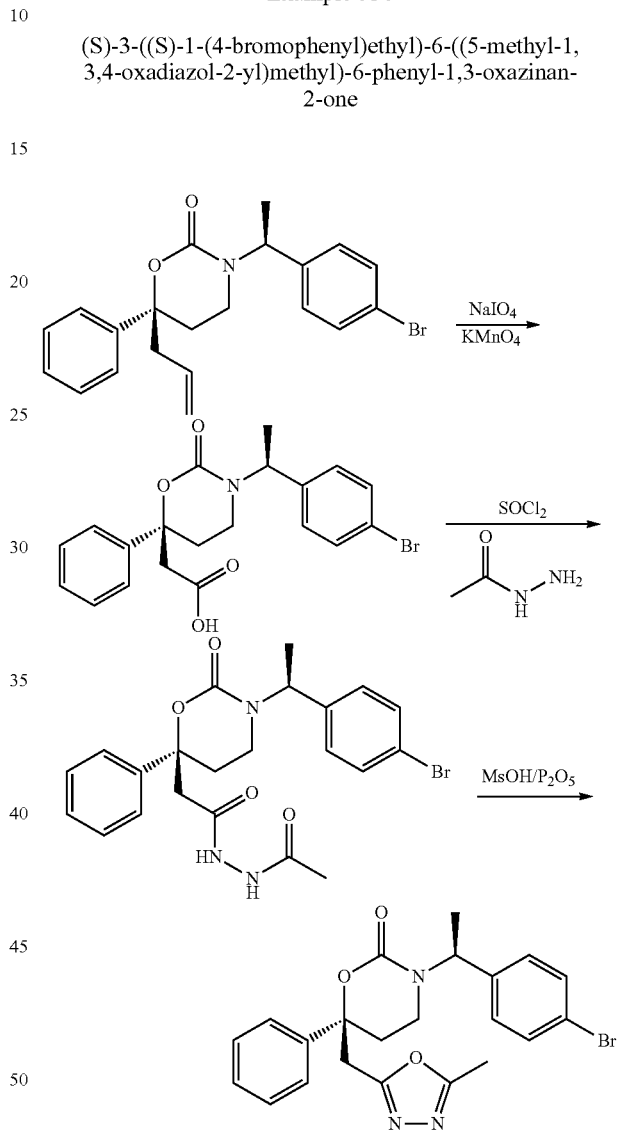

Step 1

To a solution of (R)-6-allyl-3-((S)-1-(4-bromophenyl)ethyl)-6-phenyl-1,3-oxazinan-2-one (4.0 g, 0.01 mol) in acetone (50 mL) was added a solution of $NaIO_4$ (10.6 g, 0.048 mol) and $KMnO_4$ (1.26 g, 8 mmol) in water (50 mL). The formed mixture was stirred for 1 h. The mixture was filtered, and the filtrate was concentrated to give a residue, which was acidified to pH<7 with 1 N aq HCl. The mixture was extracted with EtOAc, and the organic phase was concentrated to give crude 2-((S)-3-((S)-1-(4-bromophenyl)ethyl)-2-oxo-6-phenyl-1,3-oxazinan-6-yl)acetic acid (3.5 g, 84%), which was used for the next step without purification. $^1$H NMR (400

MHz, CDCl$_3$): δ=1.61 (d, 3H), 2.41 (m, 1H), 2.62 (m, 1H), 2.79 (m, 1H), 2.98 (m, 2H), 3.18 (m, 1H), 5.52 (q, 1H), 6.88 (m, 2H), 7.29 (m, 2H), 7.46 (m, 5H).

Step 2

To a solution of 2-((S)-3-((S)-1-(4-bromophenyl)ethyl)-2-oxo-6-phenyl-1,3-oxazinan-6-yl)acetic acid (200 mg, 0.47 mmol) in CH$_2$Cl$_2$ (2 mL) was added SOCl$_2$ (290 mg, 2.39 mmol) at room temperature. The mixture was stirred for 2 h. The reaction was concentrated to give a residue, which was dissolved in 1,4-dioxane (2 mL). Acethylhydrazide was added to the above solution. The resulting mixture was stirred for 10 min. The mixture was diluted with EtOAc, and washed with water. The organic layer was concentrated to give crude N'-acetyl-2-((S)-3-((S)-1-(4-bromophenyl)ethyl)-2-oxo-6-phenyl-1,3-oxazinan-6-yl)acetohydrazide, which was used for the next step without purification (200 mg, 88%). $^1$H NMR (400 MHz, CDCl$_3$): δ=1.42 (d, 3H), 1.98 (s, 3H), 2.21 (m, 2H), 2.41 (m, 1H), 2.54 (m, 1H), 2.71 (m, 1H), 2.86 (m, 2H), 5.49 (q, 1H), 6.64 (m, 2H), 7.12 (m, 2H), 7.22 (m, 2H), 7.31 (m, 3H), 7.94 (br, 1H), 8.51 (br, 1H).

Step 3

A suspension of P$_2$O$_5$ (73 mg, 0.52 mmol) and methanesulfonic acid (500 mg, 5.25 mmol) was stirred for 1 hour at room temperature. Then N'-acetyl-2-((S)-3-((S)-1-(4-bromophenyl)ethyl)-2-oxo-6-phenyl-1,3-oxazinan-6-yl)acetohydrazide (50 mg, 0.105 mmol) was added. After heating at 70-80° C. for 4 h, the mixture was neutralized with aqueous sodium carbonate. The resulting mixture was extracted with EtOAc, and the combined organic layer was concentrated to give the crude product, which was purified by preparative HPLC to afford (S)-3-((S)-1-(4-bromophenyl)ethyl)-6-((5-methyl-1,3,4-oxadiazol-2-yl)methyl)-6-phenyl-1,3-oxazinan-2-one (2.5 mg, 5%). $^1$H NMR (400 MHz, CDCl$_3$): δ=1.51 (d, 3H), 2.32-2.41 (m, 2H), 2.48 (s, 3H), 2.73 (m, 2H), 3.16 (m, 2H), 5.49 (m, 1H), 6.78 (m, 2H), 7.24 (m, 2H), 7.32 (m, 2H), 7.41 (m, 3H).

Alternative Procedure for Step 3

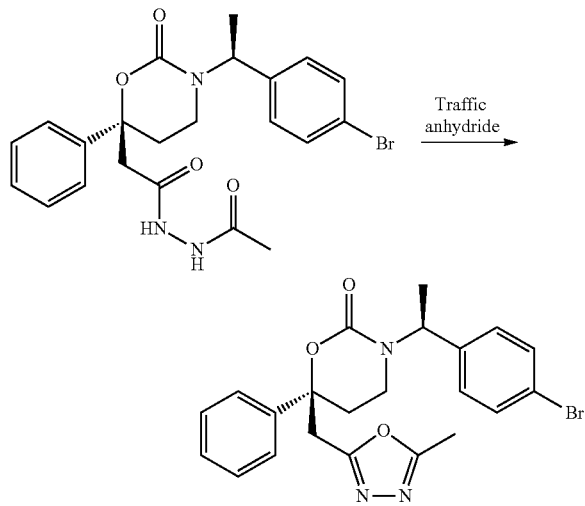

To a solution of N'-acetyl-2-((S)-3-((S)-1-(4-bromophenyl)ethyl)-2-oxo-6-phenyl-1,3-oxazinan-6-yl)acetohydrazide (100 mg, 0.21 mmol) in CH$_2$Cl$_2$ (2 mL) was added pyridine (37 mg, 0.46 mmol). The reaction mixture was cooled to −10° C. and triflic anhydride (125 mg, 0.44 mmol) was added. The reaction mixture was stirred at −10° C. for 1 h and at 0° C. for 1 h. The mixture was warmed to rt and quenched by addition of satd aq NaHCO$_3$. The aqueous layer was washed with CH$_2$Cl$_2$ and the combined organic phase was concentrated to give the crude product, which was purified by preparative TLC to afford (S)-3-((S)-1-(4-bromophenyl)ethyl)-6-((5-methyl-1,3,4-oxadiazol-2-yl)methyl)-6-phenyl-1,3-oxazinan-2-one (56 mg, 58%). $^1$H NMR (400 MHz, CDCl$_3$): δ=1.51 (d, 3H), 2.32-2.41 (m, 2H), 2.48 (s, 3H), 2.73 (m, 2H), 3.16 (m, 2H), 5.49 (m, 1H), 6.78 (d, 2H), 7.24 (m, 2H), 7.32 (m, 2H), 7.41 (m, 3H).

Example 531

(S)-3-((S)-1-(4-bromophenyl)ethyl)-6-((5-methyl-1,3,4-thiadiazol-2-yl)methyl)-6-phenyl-1,3-oxazinan-2-one

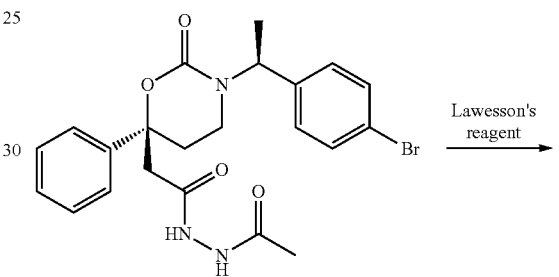

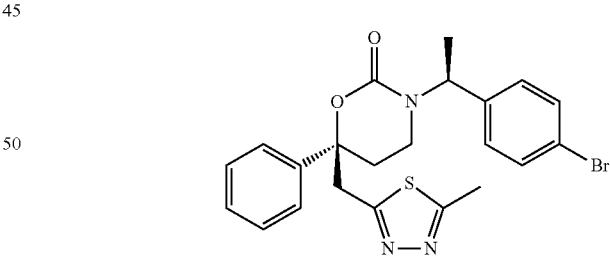

To a solution of N'-acetyl-2-((S)-3-((S)-1-(4-bromophenyl)ethyl)-2-oxo-6-phenyl-1,3-oxazinan-6-yl)acetohydrazide (50 mg, 0.105 mmol) in anhydrous THF (2 mL) was added Lawesson's Reagent (50 mg, 0.126 mmol) at rt. The mixture was heated to reflux for 3 h. The mixture was concentrated to give the crude product, which was purified by preparative TLC to give (S)-3-((S)-1-(4-bromophenyl)ethyl)-6-((5-methyl-1,3,4-thiadiazol-2-yl)methyl)-6-phenyl-1,3-oxazinan-2-one (10 mg, 20%). $^1$H NMR (400 MHz, CDCl$_3$): δ=1.39 (d, 3H), 2.02 (m, 1H), 2.22 (m, 1H), 2.39 (m, 1H), 2.69

(s, 3H), 2.81 (m, 1H), 3.58 (m, 1H), 5.52 (q, 1H), 6.66 (m, 2H), 7.16 (m, 2H), 7.21 (m, 2H), 7.32 (m, 3H).

Example 532

(R)-6-(3-hydroxypropyl)-6-phenyl-3-((S)-1-(4-(trifluoromethyl)phenyl)ethyl)-1,3-oxazinan-2-one

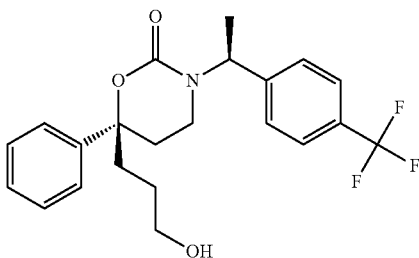 [SMILES: C[C@@H](c1ccc(C(F)(F)F)cc1)N1CC[C@](CCCO)(c2ccccc2)OC1=O]

The title compound was prepared from (R)-6-allyl-6-phenyl-3-((S)-1-(4-(trifluoromethyl)phenyl)ethyl)-1,3-oxazinan-2-one following a procedure analogous to that described in Example 78. LC-MS Method 3 $t_R$=1.108, m/z=408; $^1$H NMR (CDCl$_3$) 1.32 (m, 1H), 1.48 (m, 3H), 1.66 (m, 1H), 1.92 (m, 2H), 2.05-2.29 (m, 3H), 2.85 (m, 1H), 3.51 (t, 2H), 5.67 (m, 1H), 6.92 (d, 2H), 7.18 (m, 2H), 7.27 (m, 5H).

Example 533

(S)-3-((S)-1-(4-chloro-3-fluorophenyl)ethyl)-6-(4-fluorophenyl)-6-(2-hydroxyethyl)-1,3-oxazinan-2-one

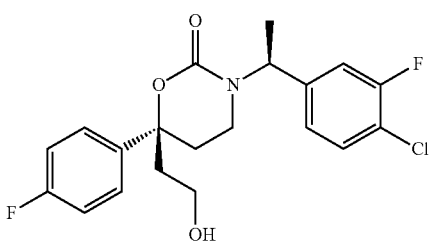 [SMILES: C[C@@H](c1ccc(Cl)c(F)c1)N1CC[C@](CCO)(c2ccc(F)cc2)OC1=O]

The title compound was prepared from (R)-6-allyl-3-((S)-1-(4-chloro-3-fluorophenyl)ethyl)-6-(4-fluorophenyl)-1,3-oxazinan-2-one following a procedure analogous to that described in Example 97. LC-MS Method 1 $t_R$=1.63, m/z=396 (M+); $^1$H NMR (CDCl$_3$) 7.3-7.28 (m, 2H), 7.15 (t, 1H, J=7.6 Hz), 7.05 (apt, 2H, J=8.6 Hz), 6.67-6.62 (m, 2H), 5.61 (q, 1H, J=7 Hz), 3.81-3.75 (m, 1H), 3.59-3.53 (m, 1H), 2.99-2.91 (m, 1H), 2.39-2.29 (m, 3H), 2.22-2.08 (m, 2H), 1.49 (d, 3H, J=7.2 Hz).

Example 534

(R)-3-((S)-1-(4-chloro-2-fluorophenyl)ethyl)-6-(4-fluorophenyl)-6-(3-hydroxypropyl)-1,3-oxazinan-2-one

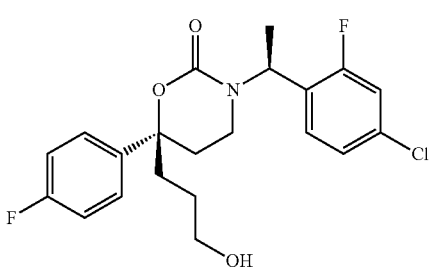

The title compound was prepared from (R)-6-allyl-3-((S)-1-(4-chloro-2-fluorophenyl)ethyl)-6-(4-fluorophenyl)-1,3-oxazinan-2-one following a procedure analogous to that described in Example 343. LC-MS Method 1 tR=1.64, m/z=432 (M+Na).

Example 535

N-(3-((R)-3-((S)-1-(4-chloro-3-fluorophenyl)ethyl)-6-(4-fluorophenyl)-2-oxo-1,3-oxazinan-6-yl)propyl)methanesulfonamide

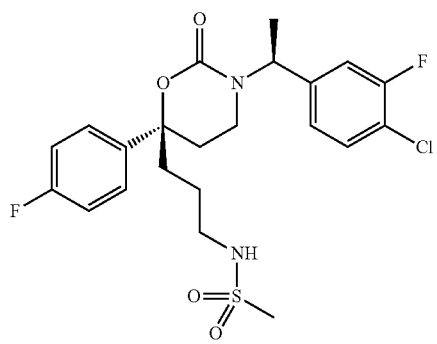 [SMILES: C[C@@H](c1ccc(Cl)c(F)c1)N1CC[C@](CCCNS(C)(=O)=O)(c2ccc(F)cc2)OC1=O]

The title compound was prepared from (R)-3-((S)-1-(4-chloro-3-fluorophenyl)ethyl)-6-(4-fluorophenyl)-6-(3-hydroxypropyl)-1,3-oxazinan-2-one following a procedure analogous to that described in Example 359. LC-MS Method 1 $t_R$=1.72, m/z=487 (M+1); $^1$H NMR (CDCl$_3$) 7.25-7.22 (m, 2H), 7.16 (t, 1H, J=8 Hz), 7.07 (t, 2H, J=8.6 Hz), 6.71-6.64 (m, 2H), 5.61 (q, 1H, J=7 Hz), 3.87 (q, 2H, J=7 Hz), 2.97-2.94 (m, 1H), 2.91 (s, 3H), 2.34-2.15 (m, 4 Hz), 2.04-1.86 (m, 2H), 1.77-1.66 (m, 1H), 1.49 (d, 3H, J=7 Hz).

Example 536

3-((R)-6-(4-fluorophenyl)-2-oxo-3-((S)-1-(4-(trifluoromethoxy)phenyl)ethyl)-1,3-oxazinan-6-yl)propanamide

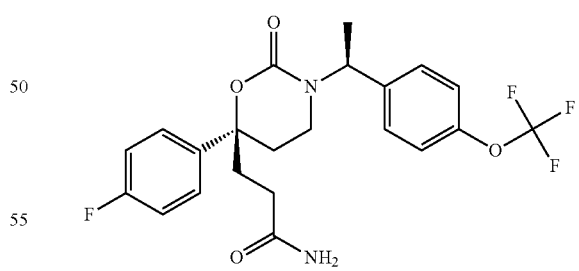

The title compound was prepared from (R)-6-allyl-6-(4-fluorophenyl)-3-((S)-1-(4-(trifluoromethoxy)phenyl)ethyl)-1,3-oxazinan-2-one using a procedure analogous to that described in Example 78 followed by procedures analogous to those described in Example 234. LC-MS Method 2 $t_R$=1.299, m/z=477; $^1$H NMR (CDCl$_3$) 1.46 (d, 3H), 1.91 (m, 1H), 2.10-2.23 (m, 5H), 2.48 (m, 1H), 2.91 (m, 1H), 5.22 (s, 1H), 5.39 (s, 1H), 5.61 (m, 1H), 6.91-7.01 (m, 6H), 7.18 (m, 2H).

Example 537

3-((R)-3-((S)-1-(4-(difluoromethoxy)phenyl)propyl)-2-oxo-6-phenyl-1,3-oxazinan-6-yl)propanamide

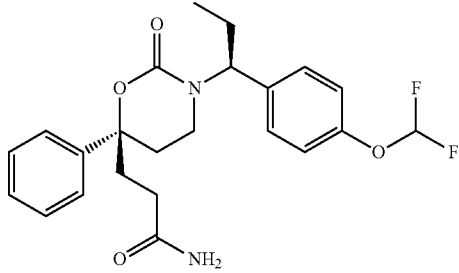 [SMILES: CC[C@@H](c1ccc(OC(F)F)cc1)N1CC[C@](CCC(N)=O)(c2ccccc2)OC1=O]

The title compound was prepared from (R)-6-allyl-3-((S)-1-(4-(difluoromethoxy)phenyl)propyl)-6-phenyl-1,3-oxazinan-2-one using a procedure analogous to that described in Example 78 followed by procedures analogous to those described in Example 234. LC-MS Method 3 $t_R$=0.975, m/z=433.4; $^1$H NMR (CDCl$_3$) 0.98 (t, 3H), 1.71-1.92 (m, 3H), 2.05-2.28 (m, 5H), 2.38-2.49 (m, 1H), 2.81 (m, 1H), 5.41 (m, 1H), 5.55 (s, 1H), 5.78 (s, 1H), 6.16-6.55 (t, 1H), 6.81 (d, 2H), 6.92 (d, 2H), 7.14 (d, 2H), 7.18-7.27 (m, 3H).

Example 538

6-(4-Fluoro-phenyl)-6-(3-hydroxy-propyl)-3-{1-[4-(1-methyl-2-oxo-1,2-dihydro-pyridin-3-yl)-phenyl]-ethyl}-[1,3]oxazinan-2-one

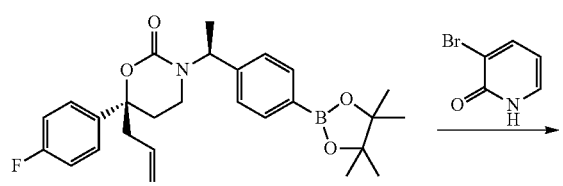

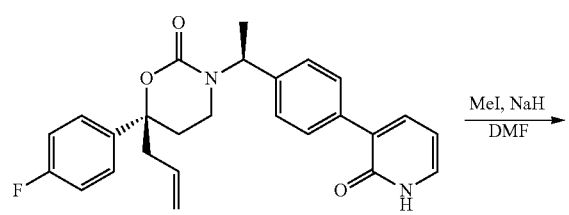

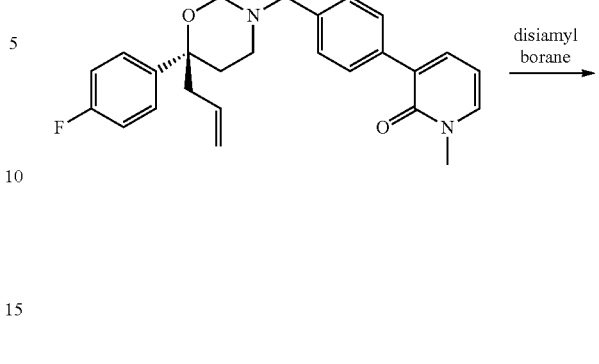

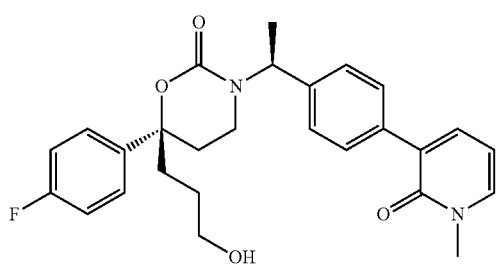

The title compound was prepared from (R)-6-allyl-6-(4-fluorophenyl)-3-((S)-1-(4-(4,4,5,5-tetramethyl-1,3,2-dioxaborolan-2-yl)phenyl)ethyl)-1,3-oxazinan-2-one. First a procedure analogous to that described in Example 313 Step 4 was followed using 3-bromopyridin-2(1H)-one. Second a procedure analogous to that described in Example 313 Step 1 was used. Third a procedure analogous to that described in Example 343 was used. LC-MS Method 1 $t_R$=1.33, m/z=487 (M+1); $^1$H NMR (CDCl$_3$) 7.47 (dd, 1H), 7.41 (d, 2H), 7.37 (dd, 1H), 7.25 (m, 2H), 7.07 (t, 2H), 6.96 (d, 2H), 6.39 (t, 1H), 5.66 (m, 1H), 4.26 (t, 1H), 3.66 (s, 3H), 2.91 (m, 1H), 1.54 (d, 3H).

Example 539

(R)-6-(4-fluorophenyl)-6-(3-hydroxypropyl)-3-((S)-1-(4-(6-oxo-1,6-dihydropyridazin-3-yl)phenyl)ethyl)-1,3-oxazinan-2-one

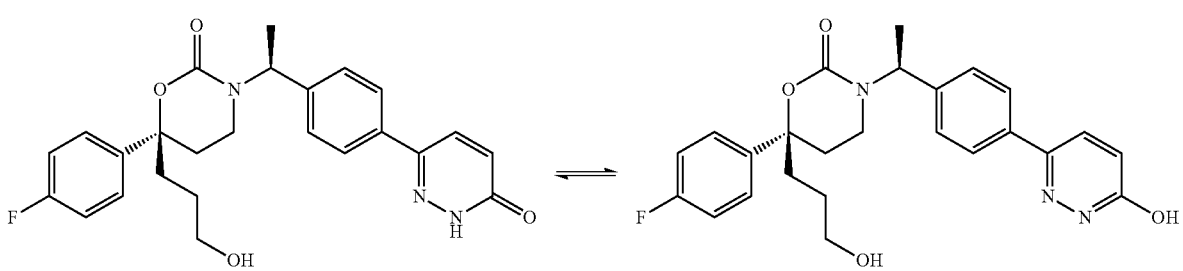 [SMILES: C[C@@H](c1ccc(-c2ccc(=O)[nH]n2)cc1)N1CC[C@](CCCO)(c2ccc(F)cc2)OC1=O ; C[C@@H](c1ccc(-c2ccc(O)nn2)cc1)N1CC[C@](CCCO)(c2ccc(F)cc2)OC1=O]

The title compound was prepared from (R)-6-allyl-3-((S)-1-(4-bromophenyl)ethyl)-6-(4-fluorophenyl)-1,3-oxazinan-2-one following procedures analogous to those described in Example using and 6-chloropyridazin-3(2H)-one in Step 4. LC-MS Method 2 $t_R$=1.231, m/z=490; $^1$H NMR (CD$_3$OD) 1.33 (m, 1H), 1.56 (d, 3H), 1.61 (m, 1H), 1.98 (m, 2H), 2.21 (m, 1H), 2.31 (m, 1H), 2.43 (m, 2H), 3.13 (m, 1H), 3.48 (m, 2H), 5.53 (m, 1H), 6.69 (d, 1H), 7.07-7.13 (m, 4H), 7.32 (m, 2H), 7.63 (m, 3H).

Example 540

(R)-3-((S)-1-(4-(1-ethyl-6-oxo-1,6-dihydropyridin-3-yl)phenyl)ethyl)-6-(3-hydroxypropyl)-6-phenyl-1,3-oxazinan-2-one

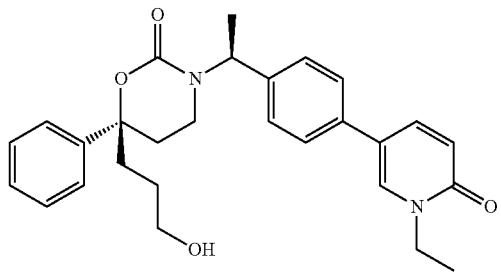 [SMILES: CCn1cc(-c2ccc([C@H](C)N3CC[C@](CCCO)(c4ccccc4)OC3=O)cc2)ccc1=O]

The title compound was prepared following procedures analogous to those described in Example 313 using 5-bromo-1-ethylpyridin-2(1H)-one in Step 4. LC-MS Method 2 $t_R$=1.297, m/z=461.1; $^1$H NMR (CDCl$_3$) 1.31 (m, 1H), 1.36 (t, 3H), 1.51 (d, 3H), 1.68 (m, 1H), 1.86-2.01 (m, 2H), 2.18 (m, 1H), 2.27 (m, 2H), 2.91 (m, 1H), 3.52 (m, 2H), 4.18 (m, 2H), 5.13 (m, 1H), 5.62 (m, 1H), 6.91 (m, 3H), 7.08 (m, 2H), 7.18-7.33 (m, 5H), 7.41 (s, 1H), 7.61 (d, 1H).

Example 541

(R)-6-(3-hydroxypropyl)-3-((S)-1-(4-(1-methyl-6-oxo-1,6-dihydropyridin-3-yl)phenyl)propyl)-6-phenyl-1,3-oxazinan-2-one

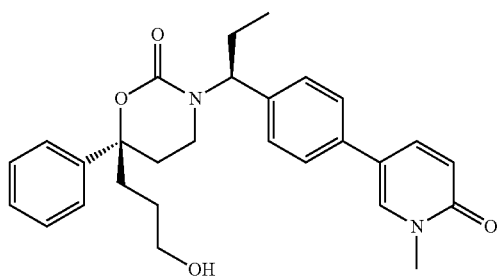 [SMILES: CC[C@@H](c1ccc(-c2ccc(=O)n(C)c2)cc1)N1CC[C@](CCCO)(c2ccccc2)OC1=O]

The title compound was prepared from (R)-6-allyl-3-((S)-1-(4-bromophenyl)propyl)-6-phenyl-1,3-oxazinan-2-one following procedures analogous to those described in Example 313. LC-MS Method 2 $t_R$=1.113, m/z=461.1; $^1$H NMR (CDCl$_3$) 0.95 (t, 3H), 1.30 (m, 1H), 1.68 (m, 1H), 1.81-1.99 (m, 2H), 2.11-2.32 (m, 3H), 2.88 (m, 1H), 3.50 (m, 2H), 3.58 (m, 2H), 5.43 (m, 1H), 6.49 (d, 1H), 6.98 (d, 2H), 7.08 (d, 2H), 7.19 (m, 1H), 7.25 (m, 4H), 7.32 (s, 1H), 7.47 (m, 1H).

Example 542

(R)-6-(4-fluorophenyl)-6-(3-hydroxypropyl)-3-((S)-1-(4-(pyrazin-2-yl)phenyl)ethyl)-1,3-oxazinan-2-one

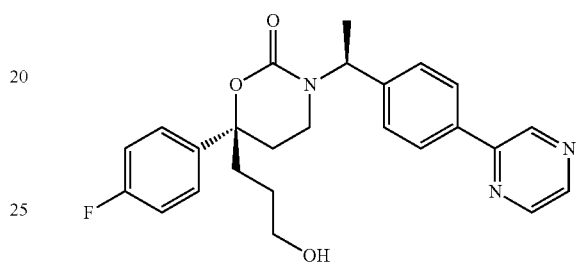

The title compound was prepared from (R)-6-allyl-3-((S)-1-(4-bromophenyl)ethyl)-6-(4-fluorophenyl)-1,3-oxazinan-2-one following procedures analogous to those described in Example 313 using 2-bromopyrazine in Step 4. LC-MS Method 2 $t_R$=1.157, m/z=458; $^1$H NMR (CDCl$_3$) 1.31 (m, 1H), 1.52 (d, 3H), 1.63 (m, 1H), 1.81-1.95 (m, 2H), 2.09-2.32 (m, 3H), 2.91 (m, 1H), 3.68 (t, 2H), 5.69 (m, 1H), 6.91 (m, 4H), 7.21 (m, 2H), 7.73 (m, 2H), 8.43 (s, 1H), 8.56 (s, 1H), 8.89 (s, 1H).

Example 543

(R)-6-(4-fluorophenyl)-6-(3-hydroxypropyl)-3-((S)-1-(4-(5-(trifluoromethyl)pyridin-2-yl)phenyl)ethyl)-1,3-oxazinan-2-one

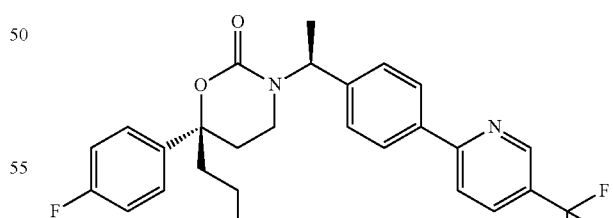

The title compound was prepared from (R)-6-allyl-3-((S)-1-(4-bromophenyl)ethyl)-6-(4-fluorophenyl)-1,3-oxazinan-2-one following procedures analogous to those described in Example 313 using 2-bromo-5-(trifluoromethyl)pyridine in Step 4. LC-MS Method 1 $t_R$=1.86, m/z=503 (M+1); $^1$H NMR (CDCl$_3$) 8.87 (s, 1H), 7.93 (dd, 1H), 7.72 (t, 3H), 7.18 (m, 2H), 6.98 (m, 4H), 5.67 (m, 1H), 3.52 (t, 1H), 2.89 (m, 1H), 1.49 (d, 3H).

Example 544

6-(4-((S)-1-((R)-6-(3-hydroxypropyl)-2-oxo-6-phenyl-1,3-oxazinan-3-yl)ethyl)phenyl)nicotinonitrile

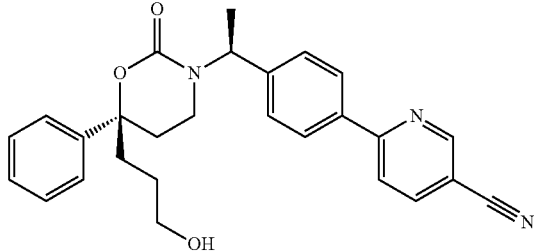 [SMILES: C[C@@H](c1ccc(-c2ccc(C#N)cn2)cc1)N1CC[C@](CCCO)(c2ccccc2)OC1=O]

The title compound was prepared from (R)-6-allyl-3-((S)-1-(4-bromophenyl)propyl)-6-phenyl-1,3-oxazinan-2-one following procedures analogous to those described in Example 313 using 2-bromo-5-cyanopyridine in Step 4. LC-MS Method 2 $t_R$=1.159, m/z=442.4; $^1$H NMR (CD$_3$OD) 1.21 (m, 1H), 1.48 (d, 3H), 1.53 (m, 1H), 1.85 (m, 2H), 2.15 (m, 1H), 2.22 (m, 1H), 2.42 (m, 1H), 3.05 (m, 1H), 3.38 (m, 2H), 5.50 (m, 1H), 6.98 (d, 2H), 7.25 (m, 3H), 7.28 (m, 2H), 7.79 (d, 2H), 7.89 (d, 1H), 8.08 (m, 1H), 8.82 (s, 1H).

Example 545

6-(4-((S)-1-((S)-6-(4-fluorophenyl)-6-(2-hydroxy-2-methylpropyl)-2-oxo-1,3-oxazinan-3-yl)ethyl)phenyl)nicotinonitrile

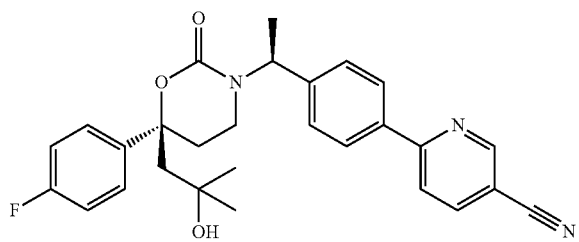 [SMILES: C[C@@H](c1ccc(-c2ccc(C#N)cn2)cc1)N1CC[C@](CC(C)(C)O)(c2ccc(F)cc2)OC1=O]

The title compound was prepared from (S)-3-((S)-1-(4-bromophenyl)ethyl)-6-(4-fluorophenyl)-6-(2-hydroxy-2-methylpropyl)-1,3-oxazinan-2-one following procedures analogous to those described in Example 313 Steps 3 and 4 using 2-bromo-5-cyanopyridine in Step 4. LC-MS Method 2 $t_R$=1.301, m/z=416; $^1$H NMR (CDCl$_3$) 1.09 (d, 6H), 1.49 (d, 3H), 2.09-2.22 (m, 4H), 2.37 (m, 1H), 2.87 (m, 1H), 5.68 (m, 1H), 6.92-7.01 (t, 2H), 7.06 (m, 2H), 7.23 (m, 2H), 7.71 (d, 1H), 7.78 (d, 2H), 7.91 (d, 1H), 8.88 (s, 1H).

Example 546

(R)-3-((S)-1-(4-(5-fluoropyridin-2-yl)phenyl)ethyl)-6-(3-hydroxypropyl)-6-phenyl-1,3-oxazinan-2-one

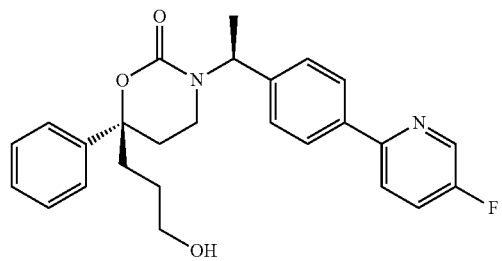

The title compound was prepared from (R)-3-((S)-1-(4-bromophenyl)ethyl)-6-(3-hydroxypropyl)-6-phenyl-1,3-oxazinan-2-one following procedures analogous to those described in Example 313 Steps 3 and 4 using 2-bromo-5-fluoropyridine in Step 4. LC-MS Method 2 $t_R$=1.197, m/z=435.1; $^1$H NMR (CDCl$_3$) 1.21-1.37 (m, 2H), 1.48 (d, 3H), 1.81-1.95 (m, 2H), 2.18 (m, 1H), 2.20-2.31 (m, 2H), 2.85 (m, 1H), 3.52 (t, 2H), 5.65 (m, 1H), 6.95 (d, 2H), 7.22 (m, 3H), 7.28 (m, 2H), 7.40 (m, 1H), 7.58 (m, 3H), 8.42 (d, 1H).

Example 547

(R)-6-(4-fluorophenyl)-6-(3-hydroxypropyl)-3-((S)-1-(4-(pyrimidin-2-yl)phenyl)ethyl)-1,3-oxazinan-2-one

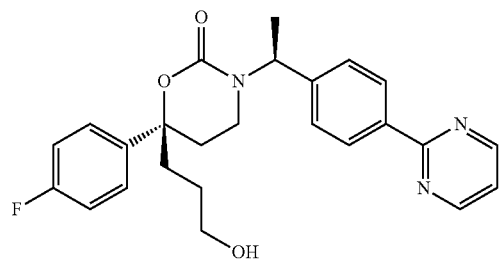 [SMILES: C[C@@H](c1ccc(-c2ncccn2)cc1)N1CC[C@](CCCO)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one following procedures analogous to those described in Example 313 Steps 3 and 4 using 2-chloropyrimidine in Step 4. LC-MS Method 2 $t_R$=1.401, m/z=436.1; $^1$H NMR (CDCl$_3$) 1.53 (d, 3H), 1.62 (m, 1H), 1.81-1.98 (m, 3H), 2.15 (m, 2H), 2.31 (m, 1H), 2.76 (m, 1H), 3.51 (t, 2H), 5.67 (m, 1H), 6.92 (m, 4H), 7.11 (m, 1H), 7.19 (m, 1H), 8.15 (d, 2H), 8.71 (d, 2H).

Example 548

(R)-6-(4-fluorophenyl)-6-(3-hydroxypropyl)-3-((S)-1-(4-(6-methylpyridazin-3-yl)phenyl)ethyl)-1,3-oxazinan-2-one

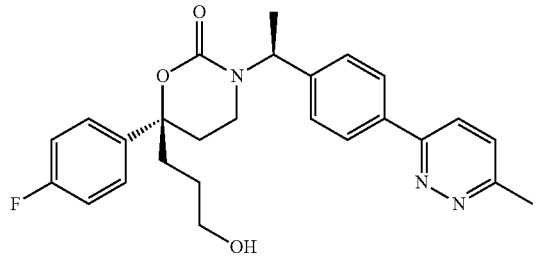 [SMILES: Cc1ccc(-c2ccc([C@H](C)N3CC[C@](CCCO)(c4ccc(F)cc4)OC3=O)cc2)nn1]

The title compound was prepared from (R)-3-((S)-1-(4-bromophenyl)ethyl)-6-(4-fluorophenyl)-6-(3-hydroxypropyl)-1,3-oxazinan-2-one following procedures analogous to those described in Example 313 Steps 3 and 4 using 3-chloro-6-methylpyridazine in Step 4. LC-MS Method 2 $t_R$=1.09, m/z=450; $^1$H NMR (CDCl$_3$) 1.26-1.39 (m, 1H), 1.50 (d, 3H), 1.59-1.70 (m, 1H), 1.81-1.99 (m, 3H), 2.09-2.20 (m, 2H), 2.22-2.34 (m, 1H), 2.71 (s, 3H), 2.90 (m, 1H), 3.50 (t, 2H), 5.67 (m, 1H), 6.90-7.08 (m, 4H), 7.19 (m, 1H), 7.21 (m, 1H), 7.33 (d, 1H), 7.62 (d, 1H), 7.77 (d, 2H).

Example 549

(S)-6-(4-fluorophenyl)-6-((1-hydroxycyclopropyl)methyl)-3-((S)-1-(4-(2-methylpyridin-4-yl)phenyl)ethyl)-1,3-oxazinan-2-one

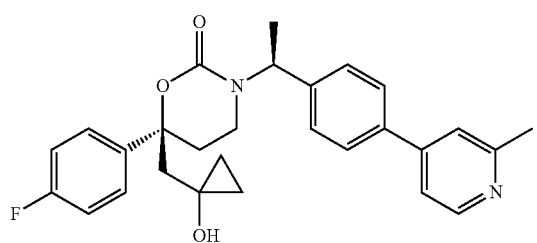 [SMILES: Cc1cc(-c2ccc([C@H](C)N3CC[C@](CC4(O)CC4)(c4ccc(F)cc4)OC3=O)cc2)ccn1]

The title compound was prepared from (S)-3-((S)-1-(4-bromophenyl)ethyl)-6-(4-fluorophenyl)-6-((1-hydroxycyclopropyl)methyl)-1,3-oxazinan-2-one and 2-methylpyridine-4-boronic acid following a procedure analogous to that described in Example 459 Step 1. LC-MS Method 2 $t_R$=0.996, m/z=461.1; $^1$H NMR (CDCl$_3$) 0.35 (m, 1H), 0.17 (m, 3H), 0.51 (m, 1H), 0.61 (m, 1H), 1.48 (d, 3H), 2.11 (s, 2H), 2.28 (m, 1H), 2.42 (m, 2H), 2.56 (s, 3H), 2.71 (s, 1H), 2.95 (m, 1H), 5.63 (m, 1H), 6.91 (m, 2H), 6.98 (m, 2H), 7.19 (m, 1H), 7.26-7.38 (m, 5H), 8.49 (d, 1H).

Example 550

3-((R)-6-(4-fluorophenyl)-3-((S)-1-(4-(2-methylpyridin-4-yl)phenyl)ethyl)-2-oxo-1,3-oxazinan-6-yl)-2,2-dimethylpropanenitrile

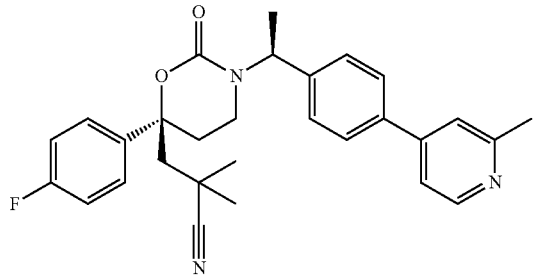 [SMILES: Cc1cc(-c2ccc([C@H](C)N3CC[C@](CC(C)(C)C#N)(c4ccc(F)cc4)OC3=O)cc2)ccn1]

The title compound was prepared from 3-((R)-3-((S)-1-(4-bromophenyl)ethyl)-6-(4-fluorophenyl)-2-oxo-1,3-oxazinan-6-yl)-2,2-dimethylpropanenitrile and 2-methylpyridine-4-boronic acid following a procedure analogous to that described in Example 459 Step 1. LC-MS Method 2 $t_R$=0.926, m/z=472.2; $^1$H NMR (CD$_3$OD) 1.31 (s, 3H), 1.41 (s, 1H), 1.58 (d, 3H), 2.30 (m, 2H), 2.34 (m, 1H), 2.43 (m, 1H), 2.61 (d, 2H), 2.81 (s, 3H), 3.21 (m, 1H), 5.62 (m, 1H), 7.08 (m, 2H), 7.29 (d, 2H), 7.41 (m, 2H), 7.79 (d, 2H), 8.09 (m, 1H), 8.19 (s, 1H), 8.68 (d, 1H).

Example 551

N-methyl-N-(2-((S)-3-((S)-1-(4-(2-methylpyridin-4-yl)phenyl)ethyl)-2-oxo-6-phenyl-1,3-oxazinan-6-yl)ethyl)methanesulfonamide

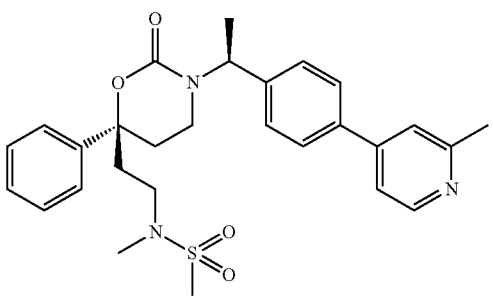 [SMILES: Cc1cc(-c2ccc([C@H](C)N3CC[C@](CCN(C)S(C)(=O)=O)(c4ccccc4)OC3=O)cc2)ccn1]

The title compound was prepared from N-(2-((S)-3-((S)-1-(4-bromophenyl)ethyl)-2-oxo-6-phenyl-1,3-oxazinan-6-yl)ethyl)-N-methylmethanesulfonamide and 2-methylpyridine-4-boronic acid following a procedure analogous to that described in Example 459 Step 1. LC-MS Method 2 $t_R$=0.989, m/z=508.1; $^1$H NMR (CDCl$_3$) 1.53 (d, 3H), 2.17-2.32 (m, 5H), 2.63 (s, 3H), 2.71 (s, 3H), 2.81 (s, 3H), 2.93 (m, 2H), 3.22 (m, 1H), 5.67 (m, 1H), 7.08 (m, 2H), 7.21 (s, 2H), 7.25 (m, 3H), 7.33 (m, 2H), 7.61 (s, 1H), 7.71 (d, 1H), 8.72 (d, 1H).

Example 552

(R)-3-((S)-1-(4-(2-methylpyridin-4-yl)phenyl)ethyl)-6-phenyl-6-(2-(1,1-dioxoisothiazolidin-2-yl)ethyl)-1,3-oxazinan-2-one

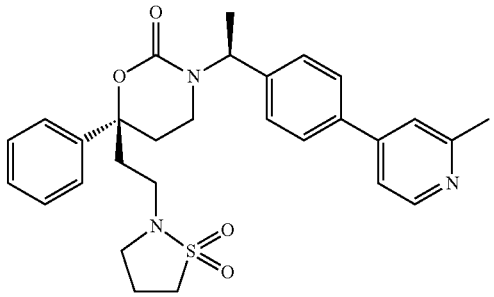 [SMILES: Cc1cc(-c2ccc([C@H](C)N3CC[C@](CCN4CCCS4(=O)=O)(c4ccccc4)OC3=O)cc2)ccn1]

The title compound was prepared from (S)-3-((S)-1-(4-bromophenyl)ethyl)-6-(2-(1,1-dioxo-isothiazolidin-2-yl)ethyl)-6-phenyl-1,3-oxazinan-2-one and 2-methylpyridine-4-boronic acid following a procedure analogous to that described in Example 459 Step 1.

Example 553

N-methyl-N-(3-((R)-3-((S)-1-(4-(2-methylpyridin-4-yl)phenyl)ethyl)-2-oxo-6-phenyl-1,3-oxazinan-6-yl)propyl)methanesulfonamide

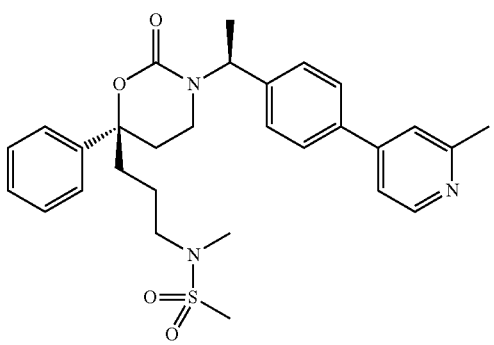 [SMILES: Cc1cc(-c2ccc([C@H](C)N3CC[C@](CCCN(C)S(C)(=O)=O)(c4ccccc4)OC3=O)cc2)ccn1]

The title compound was prepared from N-(3-((R)-3-((S)-1-(4-bromophenyl)ethyl)-2-oxo-6-phenyl-1,3-oxazinan-6-yl)propyl)-N-methylmethanesulfonamide and 2-methylpyridine-4-boronic acid following a procedure analogous to that described in Example 459 Step 1. LC-MS Method 2 $t_R$=1, m/z=522.1; $^1$H NMR (CDCl$_3$) 1.23 (m, 1H), 1.48 (d, 3H), 1.68-1.99 (m, 3H), 2.11-2.31 (m, 3H), 2.56 (s, 3H), 2.66 (s, 3H), 2.68 (s, 3H), 2.84-3.08 (m, 3H), 5.68 (m, 1H), 6.92 (d, 1H), 7.15 (d, 1H), 7.25 (m, 4H), 7.31 (m, 4H), 8.43 (d, 1H).

Example 554

4-(4-((S)-1-((R)-6-(3-hydroxypropyl)-2-oxo-6-phenyl-1,3-oxazinan-3-yl)ethyl)phenyl)-2,6-dimethylpyridine 1-oxide

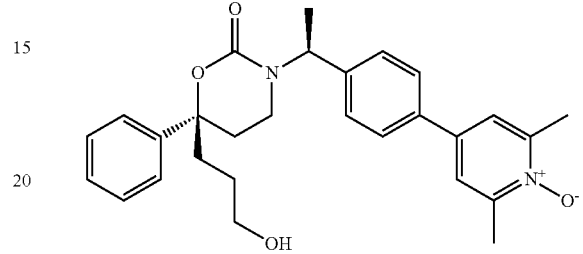

The title compound was prepared from (R)-3-((S)-1-(4-bromophenyl)ethyl)-6-(3-hydroxypropyl)-6-phenyl-1,3-oxazinan-2-one following procedures analogous to those described in Example 313 Steps 3 and 4 using 4-bromo-2,6-dimethylpyridine-N-oxide in Step 4. LC-MS Method 2 $t_R$=1.086, m/z=461.1; $^1$H NMR (CDCl$_3$) 1.34 (m, 1H), 1.50 (d, 3H), 1.61-1.72 (m, 2H), 1.88-2.00 (m, 2H), 2.18 (m, 1H), 2.22-2.34 (m, 2H), 2.62 (s, 6H), 2.88 (m, 1H), 3.51 (t, 2H), 5.65 (m, 1H), 6.93 (d, 2H), 7.21 (m, 1H), 7.26 (m, 4H), 7.29-7.38 (m, 4H).

Example 555

4-(4-((S)-1-((S)-6-(2-hydroxy-2-methylpropyl)-2-oxo-6-phenyl-1,3-oxazinan-3-yl)ethyl)phenyl)-2,6-dimethylpyridine 1-oxide

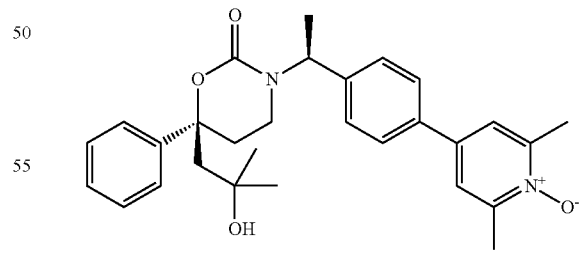

The title compound was prepared from (S)-3-((S)-1-(4-bromophenyl)ethyl)-6-(2-hydroxy-2-methylpropyl)-6-phenyl-1,3-oxazinan-2-one following procedures analogous to those described in Example 313 Steps 3 and 4 using 4-bromo-2,6-dimethylpyridine-N-oxide in Step 4. LC-MS Method 2 $t_R$=1.185, m/z=459.1; $^1$H NMR (CDCl$_3$) 1.11 (s, 3H), 1.18 (s, 3H), 1.57 (d, 3H), 2.20 (s, 2H), 2.22-2.35 (m, 2H), 2.38-2.49

(m, 1H), 2.72 (s, 6H), 2.91 (m, 1H), 5.70 (m, 1H), 7.08 (d, 2H), 7.31 (m, 3H), 7.37 (m, 4H), 7.43 (s, 2H).

Example 556

4-(4-((S)-1-((R)-6-(4-fluorophenyl)-6-(3-hydroxypropyl)-2-oxo-1,3-oxazinan-3-yl)ethyl)phenyl)-2,6-dimethylpyridine 1-oxide

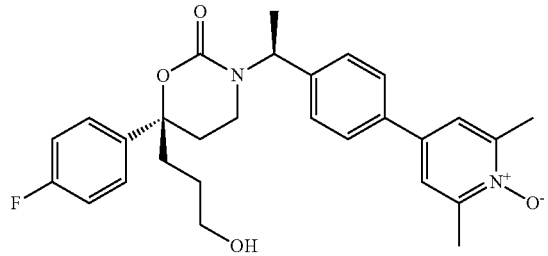 [SMILES: Cc1cc(-c2ccc([C@H](C)N3CC[C@](CCCO)(c4ccc(F)cc4)OC3=O)cc2)cc(C)[n+]1[O-]]

The title compound was prepared from (R)-3-((S)-1-(4-bromophenyl)ethyl)-6-(4-fluorophenyl)-6-(3-hydroxypropyl)-1,3-oxazinan-2-one following procedures analogous to those described in Example 313 Steps 3 and 4 using 4-bromo-2,6-dimethylpyridine-N-oxide in Step 4. LC-MS Method 2 $t_R$=1.092, m/z=479.1; $^1$H NMR (CDCl$_3$) 1.38 (m, 1H), 1.56 (d, 3H), 1.71 (m, 1H), 1.95 (m, 2H), 2.19-2.31 (m, 3H), 2.58 (s, 3H), 2.61 (s, 3H), 2.95 (m, 1H), 3.58 (m, 1H), 5.71 (m, 1H), 7.05 (m, 4H), 7.21-7.32 (m, 4H), 7.38 (m, 2H).

Example 557

4-(4-((S)-1-((S)-6-(4-fluorophenyl)-6-(2-hydroxy-2-methylpropyl)-2-oxo-1,3-oxazinan-3-yl)ethyl)phenyl)-2,6-dimethylpyridine 1-oxide

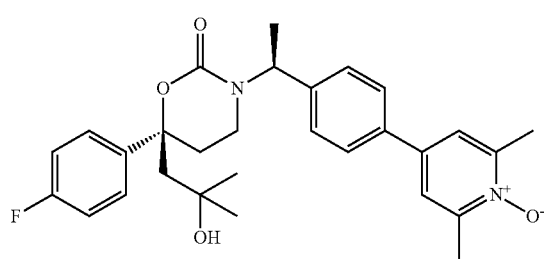 [SMILES: Cc1cc(-c2ccc([C@H](C)N3CC[C@](CC(C)(C)O)(c4ccc(F)cc4)OC3=O)cc2)cc(C)[n+]1[O-]]

The title compound was prepared from (S)-3-((S)-1-(4-bromophenyl)ethyl)-6-(4-fluorophenyl)-6-(2-hydroxy-2-methylpropyl)-1,3-oxazinan-2-one following procedures analogous to those described in Example 313 Steps 3 and 4 using 4-bromo-2,6-dimethylpyridine-N-oxide in Step 4. LC-MS Method 2 $t_R$=1.354, m/z=493; $^1$H NMR (CDCl$_3$) 1.18 (d, 6H), 1.48 (d, 3H), 2.08-2.21 (m, 5H), 2.36 (m, 1H), 2.53 (s, 6H), 2.82 (m, 1H), 5.65 (m, 1H), 6.98 (m, 4H), 7.18 (m, 4H), 7.28 (m, 2H).

Example 558

4-(4-((S)-1-((S)-6-(4-fluorophenyl)-6-(2-hydroxy-2-methylpropyl)-2-oxo-1,3-oxazinan-3-yl)ethyl)phenyl)-2-methylpyridine 1-oxide

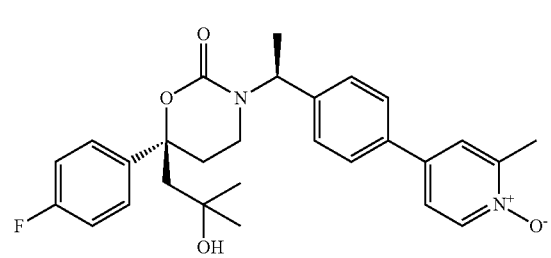 [SMILES: Cc1cc(-c2ccc([C@H](C)N3CC[C@](CC(C)(C)O)(c4ccc(F)cc4)OC3=O)cc2)cc[n+]1[O-]]

The title compound was prepared from (S)-6-(4-fluorophenyl)-6-(2-hydroxy-2-methylpropyl)-3-((S)-1-(4-(2-methylpyridin-4-yl)phenyl)ethyl)-1,3-oxazinan-2-one following a procedure analogous to that described in Example 441. LC-MS Method 1 $t_R$=1.28, m/z=479 (M+1); $^1$H NMR (CDCl$_3$) 8.52 (d, J=6.2 Hz, 1H), 7.56-7.27 (m, 6H), 7.11-7.00 (m, 4H), 5.70 (q, J=7.0 Hz, 1H), 2.97-2.93 (m, 1H), 2.69 (s, 3H), 2.50-2.42 (m, 1H), 2.31-2.16 (m, 4H), 1.55 (d, J=7.0 Hz, 3H), 1.14 (s, 6H).

Example 559

(R)-3-((S)-1-(4-(2-aminopyridin-4-yl)phenyl)ethyl)-6-(3-hydroxypropyl)-6-phenyl-1,3-oxazinan-2-one

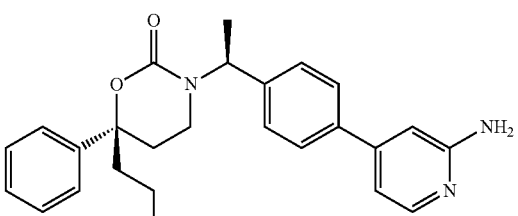

The title compound was prepared from (R)-3-((S)-1-(4-bromophenyl)ethyl)-6-(3-hydroxypropyl)-6-phenyl-1,3-oxazinan-2-one following procedures analogous to those described in Example 313 Steps 3 and 4 using 2-amino-4-bromopyridine in Step 4. LC-MS Method 2 $t_R$=0.951, m/z=432; $^1$H NMR (CDCl$_3$) 1.26-1.40 (m, 1H), 1.48 (d, 3H), 1.59-1.63 (m, 1H), 1.83-1.95 (m, 2H), 2.09-2.20 (m, 1H), 2.21-2.37 (m, 2H), 2.86 (m, 1H), 3.50 (m, 2H), 4.54-4.75 (s, 2H), 5.62 (m, 1H), 6.56 (s, 1H), 6.71 (d, 1H), 6.90 (d, 2H), 7.21-7.33 (m, 7H), 8.00 (m, 1H).

Example 560

(R)-6-(3-hydroxypropyl)-3-((S)-1-(4-(2-hydroxypyridin-4-yl)phenyl)ethyl)-6-phenyl-1,3-oxazinan-2-one

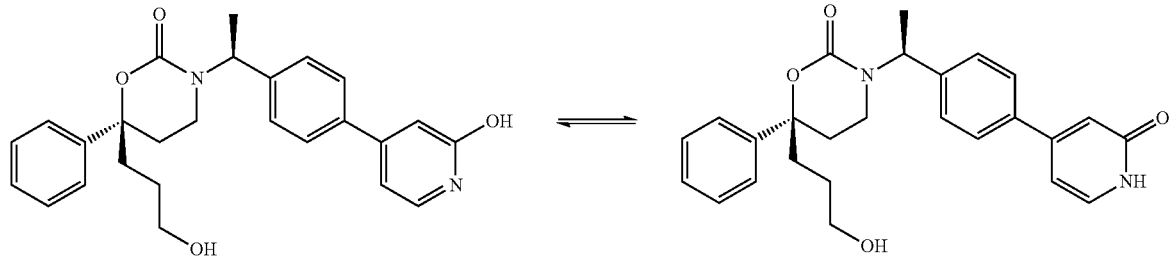 [SMILES: C[C@@H](c1ccc(-c2ccnc(O)c2)cc1)N1CC[C@](CCCO)(c2ccccc2)OC1=O ; C[C@@H](c1ccc(-c2cc[nH]c(=O)c2)cc1)N1CC[C@](CCCO)(c2ccccc2)OC1=O]

The title compound was prepared from (R)-3-((S)-1-(4-bromophenyl)ethyl)-6-(3-hydroxypropyl)-6-phenyl-1,3-oxazinan-2-one following procedures analogous to those described in Example 313 Steps 3 and 4 using 4-bromo-2-hydroxypyridine in Step 4. LC-MS Method 2 $t_R$=1.019, m/z=865.4; $^1$H NMR (CDCl$_3$) 1.29-1.40 (m, 1H), 1.49 (d, 3H), 1.60-1.72 (m, 1H), 1.83-2.01 (m, 3H), 2.18 (m, 1H), 2.21-2.37 (m, 2H), 2.88 (m, 1H), 3.51 (m, 2H), 5.63 (m, 1H), 6.41 (d, 1H), 6.68 (s, 1H), 6.90 (d, 2H), 7.21-7.33 (m, 7H), 7.39 (d, 1H).

Example 561

(R)-6-(4-fluorophenyl)-6-(3-hydroxypropyl)-3-((S)-1-(4-(2-methylpyrimidin-4-yl)phenyl)ethyl)-1,3-oxazinan-2-one

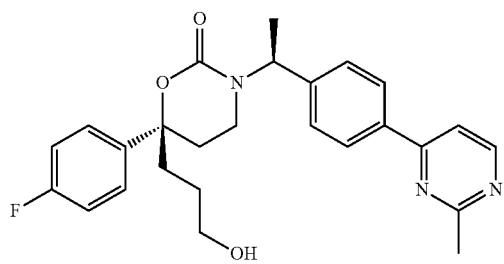 [SMILES: Cc1nccc(-c2ccc([C@H](C)N3CC[C@](CCCO)(c4ccc(F)cc4)OC3=O)cc2)n1]

The title compound was prepared from (R)-3-((S)-1-(4-bromophenyl)ethyl)-6-(4-fluorophenyl)-6-(3-hydroxypropyl)-1,3-oxazinan-2-one following procedures analogous to those described in Example 313 Steps 3 and 4 using 4-bromo-2-methylpyrimidine in Step 4. LC-MS Method 2 $t_R$=1.159, m/z=450; $^1$H NMR (CDCl$_3$) 1.33 (m, 3H), 1.52 (m, 3H), 1.63 (m, 3H), 1.80-1.95 (m, 2H), 2.15-2.30 (m, 3H), 2.75 (s, 3H), 2.90 (m, 1H), 3.51 (m, 2H), 5.68 (m, 1H), 6.99 (m, 4H), 7.20 (m, 2H), 7.41 (m, 1H), 7.79 (d, 2H), 8.60 (m, 1H).

Example 562

(R)-3-((S)-1-(4-(2,6-dimethylpyrimidin-4-yl)phenyl)ethyl)-6-(4-fluorophenyl)-6-(3-hydroxypropyl)-1,3-oxazinan-2-one

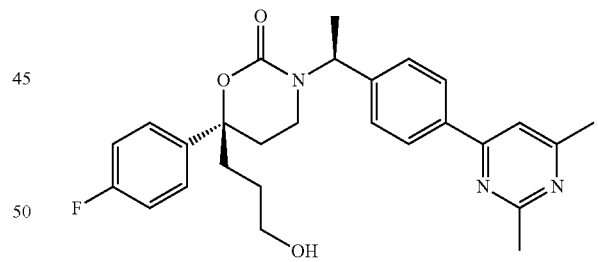

The title compound was prepared from (R)-3-((S)-1-(4-bromophenyl)ethyl)-6-(4-fluorophenyl)-6-(3-hydroxypropyl)-1,3-oxazinan-2-one following procedures analogous to those described in Example 313 Steps 3 and 4 using 4-bromo-2,6-dimethylpyrimidine in Step 4. LC-MS Method 2 tR=1.073, m/z=464.1; $^1$H NMR (CD$_3$OD) 1.21 (m, 1H), 1.48 (d, 3H), 1.82 (m, 2H), 2.15 (m, 1H), 2.23 (m, 2H), 2.38 (m, 1H), 2.46 (s, 3H), 2.62 (s, 3H), 3.08 (m, 1H), 3.39 (m, 2H), 5.51 (m, 1H), 6.95-7.08 (m, 4H), 7.21 (m, 2H), 7.51 (s, 1H), 7.83 (d, 2H).

5.52 (m, 1H), 6.99 (t, 2H), 7.08 (d, 2H), 7.23 (m, 2H), 7.42 (d, 2H), 8.91 (s, 2H), 9.06 (s, 1H).

Example 563

(R)-6-(4-fluorophenyl)-6-(3-hydroxypropyl)-3-((S)-1-(4-(pyrimidin-4-yl)phenyl)ethyl)-1,3-oxazinan-2-one

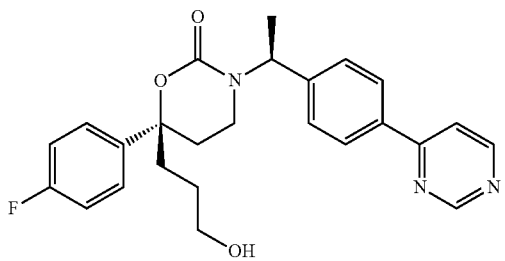 [SMILES: C[C@@H](c1ccc(-c2ccncn2)cc1)N1CC[C@](CCCO)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one following procedures analogous to those described in Example 313 Steps 3 and 4 using 4-chloropyrimidine in Step 4. LC-MS Method 2 tR=1.172, m/z=392.1; 1H NMR (CDCl3) 1.28-1.40 (m, 1H), 1.52 (m, 3H), 1.64 (m, 2H), 1.81-1.99 (m, 2H), 2.09-2.37 (m, 3H), 2.90 (m, 1H), 3.51 (t, 2H), 5.68 (m, 1H), 6.88-7.07 (m, 3H), 7.16-7.28 (m, 3H), 7.58 (m, 1H), 7.79 (d, 2H), 8.61-8.80 (d, 1H), 9.18 (s, 1H).

Example 564

(R)-6-(4-fluorophenyl)-6-(3-hydroxypropyl)-3-((S)-1-(4-(pyrimidin-5-yl)phenyl)ethyl)-1,3-oxazinan-2-one

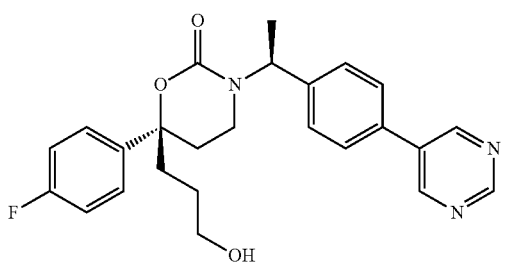 [SMILES: C[C@@H](c1ccc(-c2cncnc2)cc1)N1CC[C@](CCCO)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one following procedures analogous to those described in Example 313 Steps 3 and 4 using 5-bromopyrimidine in Step 4. LC-MS Method 2 tR=1.332, m/z=436.1; 1H NMR (CD3OD) 1.49 (d, 3H), 1.83 (m, 2H), 2.14-2.28 (m, 4H), 2.42 (m, 1H), 3.08 (m, 1H), 3.49 (m, 2H), Example 565

(R)-6-(3-hydroxypropyl)-3-((S)-1-(4-(1-methyl-6-oxo-1,6-dihydropyridin-2-yl)phenyl)ethyl)-6-phenyl-1,3-oxazinan-2-one

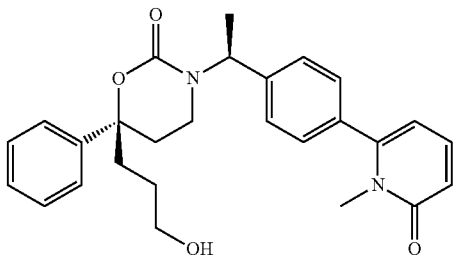 [SMILES: C[C@@H](c1ccc(-c2cccc(=O)n2C)cc1)N1CC[C@](CCCO)(c2ccccc2)OC1=O]

The title compound was prepared from (R)-3-((S)-1-(4-bromophenyl)ethyl)-6-(3-hydroxypropyl)-6-phenyl-1,3-oxazinan-2-one following procedures analogous to those described in Example 313 Steps 3 and 4 using 6-bromo-1-methylpyridin-2(1H)-one in Step 4. LC-MS Method 2 $t_R$=1.088, m/z=447; 1H NMR (CDCl3) 1.38 (m, 1H), 1.56 (d, 3H), 1.70 (m, 1H), 1.95-2.08 (m, 2H), 2.23 (m, 1H), 2.37 (s, 2H), 3.05 (m, 1H), 3.33 (s, 3H), 3.58 (m, 2H), 5.73 (m, 1H), 6.29 (d, 1H), 6.89 (d, 1H), 7.01-7.09 (m, 4H), 7.21-7.39 (m, 5H), 7.53 (t, 1H).

6-Bromo-1-methylpyridin-2(1H)-one was prepared from 6-bromopyridin-2(1H)-one following a procedure analogous to that described in Example 313 Step 1.

Example 566

(R)-6-(3-hydroxypropyl)-3-((S)-1-(4-(1-methyl-2-oxo-1,2-dihydropyridin-4-yl)phenyl)ethyl)-6-phenyl-1,3-oxazinan-2-one

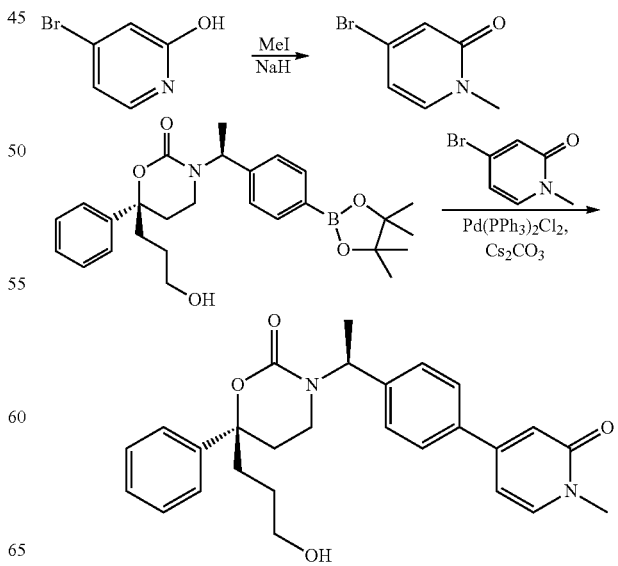

Step 1

To a suspension of NaH (80 mg, 2 mmol) in THF (10 mL) was added 4-bromopyridin-2-ol (80 mg, 0.46 mmol) at 0° C. The resulting mixture was stirred for 1 h. Then CH$_3$I (355 mg, 2.5 mmol) was added to the above mixture, and the mixture was stirred overnight. The reaction was quenched with aqueous NH$_4$Cl solution. The organic phase was concentrated to give the crude product, which was purified by column to give 4-bromo-1-methylpyridin-2(1H)-one (42.3 mg, 50%).

Step 2

A mixture of (R)-6-(3-hydroxypropyl)-6-phenyl-3-((S)-1-(4-(4,4,5,5-tetramethyl-1,3,2-dioxaborolan-2-yl)phenyl)ethyl)-1,3-oxazinan-2-one (50 mg, 0.11 mmol) and 4-bromo-1-methylpyridin-2(1H)-one (30 mg, 0.16 mmol), Pd(Ph$_3$P)$_2$Cl$_2$ (10 mg), and aq. Cs$_2$CO$_3$ solution (4 mL, 2 M) in 1,4-dioxane (10 mL) was stirred and heated to reflux for 2 h. When the reaction was over, the mixture was washed with water and extracted with EtOAc. The organic phase was washed with brine, dried over Na$_2$SO$_4$, filtered and concentrated to give the crude product, which was purified by preparative TLC to give (R)-6-(3-hydroxypropyl)-3-((S)-1-(4-(1-methyl-2-oxo-1,2-dihydropyridin-4-yl)phenyl)ethyl)-6-phenyl-1,3-oxazinan-2-one (25 mg, 51%). $^1$H NMR (CDCl$_3$): δ=1.35 (m, 1H), 1.47 (d, 3H), 1.63 (m, 2H), 1.94 (m, 2H), 2.18 (m, 1H), 2.39 (m, 2H), 2.86 (m, 1H), 3.51 (m, 5H), 5.63 (m, 1H), 6.31 (m, 1H), 6.70 (m, 1H), 6.91 (m, 2H), 7.20-7.32 (m, 8H).

Example 567

3-((R)-3-((S)-1-(4'-fluorobiphenyl-4-yl)ethyl)-2-oxo-6-phenyl-1,3-oxazinan-6-yl)propanoic acid

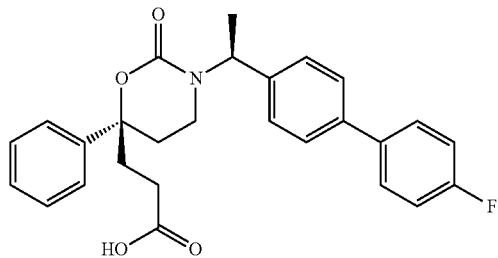 [SMILES: C[C@@H](c1ccc(-c2ccc(F)cc2)cc1)N1CC[C@](CCC(=O)O)(c2ccccc2)OC1=O]

The title compound was prepared from (R)-3-((S)-1-(4'-fluorobiphenyl-4-yl)ethyl)-6-(3-hydroxypropyl)-6-phenyl-1,3-oxazinan-2-one as described in Example 234 Step 1. LC-MS Method 2 t$_R$=1.397, m/z=448; $^1$H NMR (CDCl$_3$) 1.53 (d, 3H), 2.08-2.21 (m, 3H), 2.24-2.35 (m, 3H), 2.61 (m, 1H), 2.89 (m, 1H), 5.68 (m, 1H), 6.95 (d, 2H), 7.08 (m, 2H), 7.26 (m, 5H), 7.34 (m, 2H), 7.42 (m, 2H).

Example 568

3-((R)-3-((S)-1-(4'-fluorobiphenyl-4-yl)ethyl)-2-oxo-6-phenyl-1,3-oxazinan-6-yl)-2,2-dimethylpropanamide

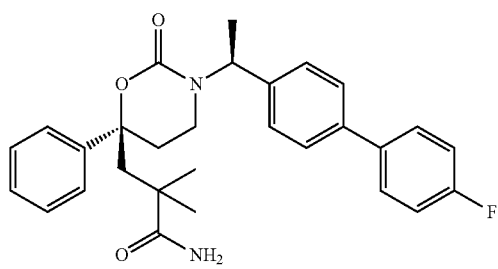 [SMILES: C[C@@H](c1ccc(-c2ccc(F)cc2)cc1)N1CC[C@](CC(C)(C)C(N)=O)(c2ccccc2)OC1=O]

The title compound was prepared from 3-((R)-3-((S)-1-(4'-fluorobiphenyl-4-yl)ethyl)-2-oxo-6-phenyl-1,3-oxazinan-6-yl)-2,2-dimethylpropanenitrile following a procedure analogous to that described in Example 522. LC-MS Method 1 t$_R$=1.79, m/z=475 (M+1); $^1$H NMR (CDCl$_3$) 7.45-7.42 (m, 2H), 7.31-7.27 (m, 7H), 7.10 (t, J=8.5 Hz, 2H), 7.03 (d, J=8.2 Hz, 2H), 5.70 (m, 1H), 2.96-2.93 (m, 1H), 2.66 (m, 2H), 2.49-2.45 (m, 1H), 2.30-2.23 (m, 2H), 1.56 (d, J=5.9 Hz, 3H), 1.26 (s, 3H), 1.20 (s, 3H).

Example 569

(S)-6-(2-hydroxy-2-methylpropyl)-6-phenyl-3-((S)-1-(4-(pyrazin-2-yl)phenyl)ethyl)-1,3-oxazinan-2-one

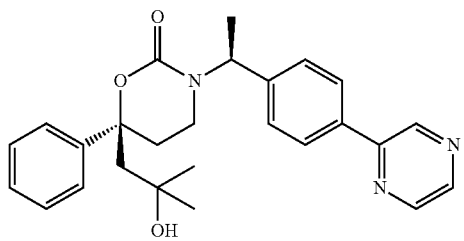 [SMILES: C[C@@H](c1ccc(-c2cnccn2)cc1)N1CC[C@](CC(C)(C)O)(c2ccccc2)OC1=O]

The title compound was prepared from (S)-3-((S)-1-(4-bromophenyl)ethyl)-6-(2-hydroxy-2-methylpropyl)-6-phenyl-1,3-oxazinan-2-one following procedures analogous to those described in Example 313 Steps 3 and 4 using 2-bromopyrazine. LC-MS Method 2 t$_R$=1.249, m/z=374; $^1$H NMR (CDCl$_3$) 1.12 (s, 3H), 1.28 (s, 3H), 1.58 (m, 3H), 2.19-2.20 (m, 4H), 2.39 (m, 1H), 2.89 (m, 1H), 5.74 (m, 1H), 7.09 (m, 2H), 7.28-7.40 (m, 5H), 7.78 (m, 2H), 8.48 (m, 1H), 8.59 (m, 1H), 8.94 (m, 1H).

Example 570

(S)-6-(2-hydroxy-2-methylpropyl)-6-phenyl-3-((S)-1-(4-(pyrimidin-4-yl)phenyl)ethyl)-1,3-oxazinan-2-one

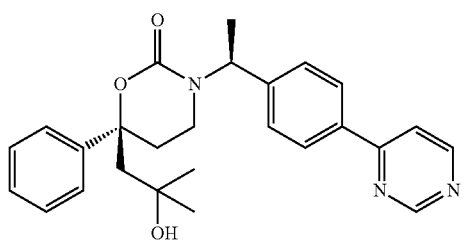 [SMILES: C[C@@H](c1ccc(-c2ccncn2)cc1)N1CC[C@](CC(C)(C)O)(c2ccccc2)OC1=O]

The title compound was prepared from (S)-3-((S)-1-(4-bromophenyl)ethyl)-6-(2-hydroxy-2-methylpropyl)-6-phenyl-1,3-oxazinan-2-one following procedures analogous to those described in Example 313 Steps 3 and 4 using 4-chloropyrimidine in Step 4. LC-MS Method 2 t$_R$=1.167, m/z=374; $^1$H NMR (CDCl$_3$) 1.06 (s, 3H), 1.11 (s, 3H), 1.49 (d, 3H), 2.11 (s, 1H), 2.17 (s, 2H), 2.21 (m, 1H), 2.35 (m, 1H), 2.80 (m, 1H), 5.66 (m, 1H), 7.02 (d, 2H), 7.21-7.36 (m, 5H), 7.54 (d, 1H), 7.78 (d, 2H), 8.68 (d, 1H), 9.16 (s, 1H).

Example 571

(R)-6-(4-fluorophenyl)-6-(3-hydroxypropyl)-3-((S)-1-(4-(pyridazin-3-yl)phenyl)ethyl)-1,3-oxazinan-2-one

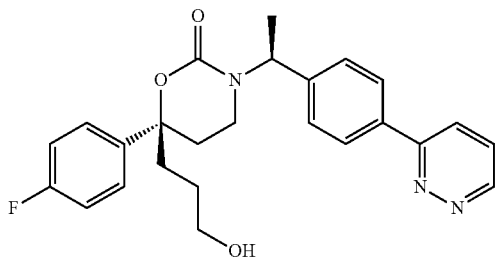 [SMILES: C[C@@H](c1ccc(-c2cccnn2)cc1)N1CC[C@](CCCO)(c2ccc(F)cc2)OC1=O]

The title compound was prepared from (R)-3-((S)-1-(4-bromophenyl)ethyl)-6-(4-fluorophenyl)-6-(3-hydroxypropyl)-1,3-oxazinan-2-one following procedures analogous to those described in Example 313 Steps 3 and 4 using 3-chloropyridazine in Step 4. LC-MS Method 2 $t_R$=1.067, m/z=436.1; $^1$H NMR (CDCl$_3$) 0.82 (m, 3H), 1.52 (d, 3H), 1.65 (m, 1H), 1.80-1.98 (m, 2H), 2.11-2.28 (m, 3H), 2.91 (m, 1H), 3.51 (t, 3H), 5.68 (m, 1H), 6.94-7.04 (m, 4H), 7.18 (m, 2H), 7.47 (m, 1H), 7.71 (d, 1H), 7.78 (d, 2H), 9.08 (d, 1H).

Example 572

(R)-3-((S)-1-(4-(2,6-dimethylpyridin-4-yl)phenyl)ethyl)-6-(3-hydroxypropyl)-6-phenyl-1,3-oxazinan-2-one

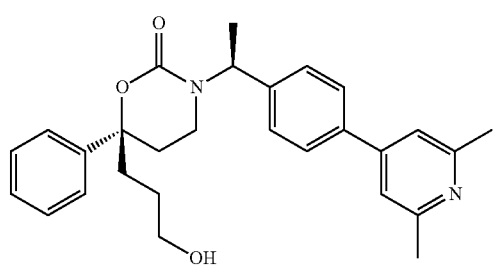 [SMILES: Cc1cc(-c2ccc([C@H](C)N3CC[C@](CCCO)(c4ccccc4)OC3=O)cc2)cc(C)n1]

The title compound was prepared from (R)-3-((S)-1-(4-bromophenyl)ethyl)-6-(3-hydroxypropyl)-6-phenyl-1,3-oxazinan-2-one following procedures analogous to those described in Example 313 Steps 3 and 4 using 4-bromo-2,6-dimethylpyridine in Step 4. LC-MS Method $t_R$=1.228, m/z=445; $^1$H NMR (CDCl$_3$) 1.32 (m, 1H) 1.51 (d, 3H), 1.60-1.72 (m, 1H), 1.86-2.02 (m, 2H), 2.19 (m, 1H), 2.25-2.39 (m, 2H), 2.79 (s, 6H), 2.93 (m, 1H), 3.50 (t, 2H), 5.64 (m, 1H), 7.00 (d, 2H), 7.21 (m, 2H), 7.29 (m, 2H), 7.32 (m, 3H), 7.40 (m, 2H).

Example 573

(S)-6-(2-hydroxy-2-methylpropyl)-3-((S)-1-(4-(6-methylpyridazin-3-yl)phenyl)ethyl)-6-phenyl-1,3-oxazinan-2-one

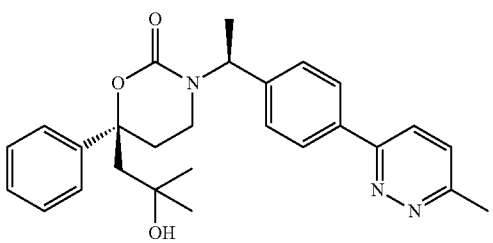 [SMILES: Cc1ccc(-c2ccc([C@H](C)N3CC[C@](CC(C)(C)O)(c4ccccc4)OC3=O)cc2)nn1]

The title compound was prepared from (S)-3-((S)-1-(4-bromophenyl)ethyl)-6-(2-hydroxy-2-methylpropyl)-6-phenyl-1,3-oxazinan-2-one following procedures analogous to those described in Example 313 Steps 3 and 4 using 3-chloro-6-methylpyridazine in Step 4. LC-MS Method 2 $t_R$=1.118, m/z=446; $^1$H NMR (CD$_3$OD) 0.96 (s, 3H), 1.26 (s, 3H), 1.58 (d, 3H), 2.17 (s, 2H), 2.26 (m, 1H), 2.50 (m, 2H), 2.69 (s, 3H), 3.08 (m, 1H), 5.59 (m, 1H), 7.11 (m, 2H), 7.25-7.40 (5H), 7.63 (m, 1H), 7.82 (m, 2H), 7.98 (d, 1H).

Method 2

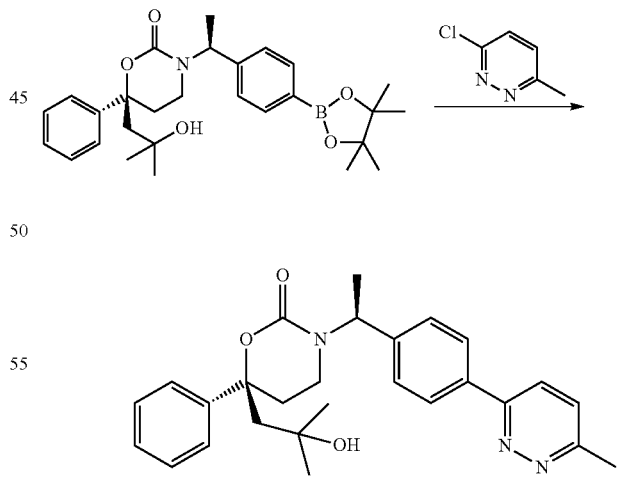

(S)-6-(2-Hydroxy-2-methyl-propyl)-3-{(S)-1-[4-(6-methyl-pyridazin-3-yl)-phenyl]-ethyl}-6-phenyl-[1,3]oxazinan-2-one was prepared from (S)-6-(2-hydroxy-2-methyl-propyl)-6-phenyl-3-[(S)-1-(4-(4,4,5,5-tetramethyl-1,3,2-dioxaborolan-2-yl)phenyl)ethyl]-1,3-oxazinan-2-one and 3-chloro-6-methyl-pyridazine following a procedure analogous to that described in Example 583 Method 2. Yield: 3.09 g (62% of theory). Mass spectrum (ESI⁺): m/z=446 [M+H]⁺

Example 574

(S)-6-(2-hydroxy-2-methylpropyl)-3-((S)-1-(4-(2-methylpyrimidin-4-yl)phenyl)ethyl)-6-phenyl-1,3-oxazinan-2-one

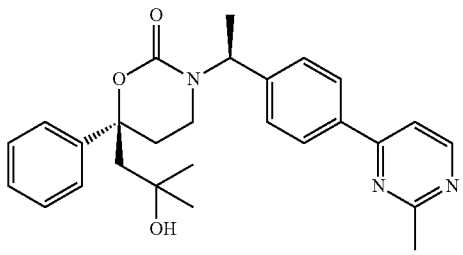 [SMILES: Cc1nccc(-c2ccc([C@H](C)N3CC[C@](CC(C)(C)O)(c4ccccc4)OC3=O)cc2)n1]

The title compound was prepared from (S)-3-((S)-1-(4-bromophenyl)ethyl)-6-(2-hydroxy-2-methylpropyl)-6-phenyl-1,3-oxazinan-2-one following procedures analogous to those described in Example 313 Steps 3 and 4 using 4-chloro-2-methylpyrimidine in Step 4. LC-MS Method 2 $t_R$=1.196, m/z=446; ¹H NMR (CD₃OD) 0.92 (s, 3H), 1.27 (s, 3H), 1.58 (d, 3H), 2.12 (s, 2H), 2.23 (m, 1H), 2.51-2.66 (m, 2H), 2.70 (s, 3H), 3.07 (m, 1H), 5.59 (m, 1H), 7.09 (d, 2H), 7.16-7.42 (m, 5H), 7.65 (d, 1H), 7.89 (d, 2H), 8.61 (d, 1H).

Example 575

(S)-3-((S)-1-(4-(5-fluoropyridin-2-yl)phenyl)ethyl)-6-(2-hydroxy-2-methylpropyl)-6-phenyl-1,3-oxazinan-2-one

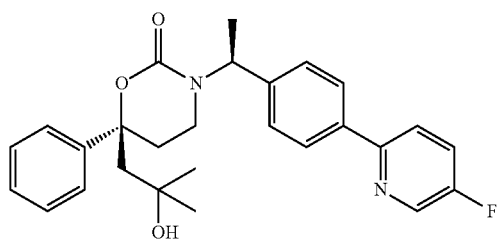 [SMILES: C[C@@H](c1ccc(-c2ccc(F)cn2)cc1)N1CC[C@](CC(C)(C)O)(c2ccccc2)OC1=O]

The title compound was prepared from (S)-3-((S)-1-(4-bromophenyl)ethyl)-6-(2-hydroxy-2-methylpropyl)-6-phenyl-1,3-oxazinan-2-one following procedures analogous to those described in Example 313 Steps 3 and 4 using 2-bromo-5-fluoropyridine in Step 4. LC-MS Method 2 $t_R$=1.363, m/z=390.9; ¹H NMR (CDCl₃) 1.11 (s, 3H), 1.19 (s, 3H), 1.53 (d, 3H), 2.16-2.30 (m, 4H), 2.32-2.43 (m, 1H), 2.86 (m, 1H), 5.71 (m, 1H), 7.03 (d, 2H), 7.30 (m, 1H), 7.36 (m, 4H), 7.44 (m, 1H), 7.69 (dd, 1H), 7.68 (d, 2H), 8.43 (d, 1H).

Example 576

(R)-6-(4-fluorophenyl)-6-(3-hydroxypropyl)-3-((S)-1-(4-(2-methylpyrimidin-5-yl)phenyl)ethyl)-1,3-oxazinan-2-one

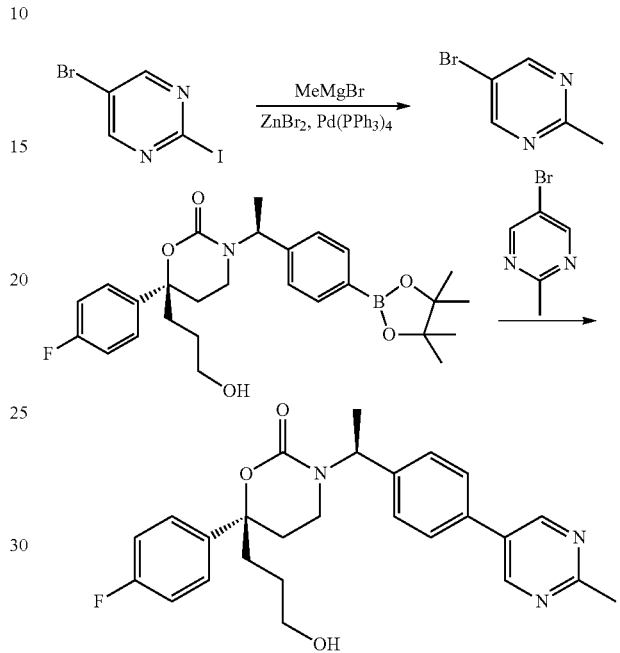

Step 1

To a solution of ZnBr₂ (1.33 g, 6 mmol) in THF (15 mL) was added MeMgBr (0.69 g, 6 mmol) under N₂ at −78° C. The mixture was stirred for 1 h and used for next step. To a solution of 5-bromo-2-iodo-pyrimidine (1.42 g, 5 mmol) in THF (15 mL) was added Pd(PPh₃)₄ (0.366 g, 0.33 mmol) and the prepared MeZnBr solution (10 mL) under N₂ at 0° C. The mixture was heated to 60° C. for 5 h during which time a second portion of MeZnBr solution (5 mL) was added. After cooling to room temperature, the reaction was poured into aqueous NH₄Cl solution. The mixture was extracted with EtOAc. The organic phase was separated and dried over Na₂SO₄, concentrated to give 5-bromo-2-methylpyrimidine (60 mg, 7%). ¹H NMR (CDCl₃): 1.63 (s, 3H), 8.82 (s, 2H).

Step 2

To a solution of (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one (61 mg, 0.13 mmol), 5-bromo-2-methylpyrimidine (18 mg, 0.11 mmol), PdCl₂(PPh₃)₂ (6 mg, 10%) and aqueous solution of Cs₂CO₃ (2 mol/L, 0.13 mL) in 1,4-dioxane (1 mL) was heated to reflux overnight. The reaction was quenched with water. The organic layer was separated, dried and concentrated to give the residue, which was purified by column chromatography to give (R)-6-(4-fluorophenyl)-6-(3-hydroxypropyl)-3-((S)-1-(4-(2-methylpyrimidin-5-yl)phenyl)ethyl)-1,3-oxazinan-2-one (22 mg, 39%). ¹H NMR (CDCl₃): 1.42 (m, 1H), 1.48 (d, 3H), 1.67 (m, 1H), 1.71-1.99 (m, 4H), 2.11-2.41 (m, 3H), 2.52

(s, 3H), 2.72 (m, 1H), 3.53 (m, 2H), 5.62 (m, 1H), 6.89-7.04 (m, 4H), 7.15-7.33 (m, 4H), 8.70 (s, 2H). LC-MS Method 2 $t_R$=1.184, m/z=450; $^1$H NMR (CDCl$_3$) 1.20 (d, 1H), 1.27-1.40 (m, 1H), 1.49 (d, 3H), 1.59-1.70 (m, 1H), 1.71-2.07 (m, 4H), 2.11-2.33 (m, 3H), 2.70 (s, 3H), 2.90 (m, 1H), 3.46-3.61 (t, 2H), 5.67 (m, 1H), 6.90-7.11 (m, 4H), 7.26 (m, 4H), 8.57-8.83 (s, 2H).

Example 577

(R)-3-((1S)-1-(4-bromophenyl)ethyl)-6-(4-fluorophenyl)-6-((R)-3-hydroxy-2-methylpropyl)-1,3-oxazinan-2-one

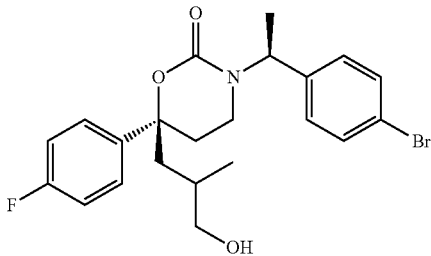 [SMILES: CC(CO)C[C@]1(c2ccc(F)cc2)CCN([C@@H](C)c2ccc(Br)cc2)C(=O)O1]

The title compound was prepared from 3-((R)-3-((S)-1-(4-bromophenyl)ethyl)-6-(4-fluorophenyl)-2-oxo-1,3-oxazinan-6-yl)-2-methylpropanenitrile following a procedure analogous to that described in Example 522. Two isomers were isolated by chromatography on a chiral column.

Isomer 1: LC-MS Method 1 $t_R$=1.78, m/z=450, 452 (M+1); $^1$H NMR (CD$_3$OD) 7.24-7.17 (m, 4H), 7.03-6.98 (m, 2H), 6.79 (d, J=8.5 Hz, 2H), 5.40 (q, J=7.0 Hz, 1H), 3.33-3.29 (m, 1H), 3.00-2.96 (m, 1H), 2.34-2.28 (m, 1H), 2.18-2.07 (m, 2H), 1.95-1.90 (m, 1H), 1.62-1.54 (m, 2H), 1.40 (d, J=7.0 Hz, 3H), 1.23-1.18 (m, 1H), 0.59 (d, J=6.5 Hz, 3H).

Isomer 2: LC-MS Method 1 $t_R$=1.75, m/z=450, 452 (M+1); $^1$H NMR (CD$_3$OD) 7.25-7.19 (m, 4H), 7.01 (t, J=8.8 Hz, 2H), 6.82 (d, J=8.5 Hz, 2H), 5.41 (q, J=7.0 Hz, 1H), 3.05-3.00 (m, 3H), 2.33-2.29 (m, 1H), 2.22-2.09 (m, 2H), 1.98-1.94 (m, 1H), 1.61-1.55 (m, 1H), 1.42 (d, J=7.0 Hz, 3H), 1.24-1.19 (m, 1H), 0.83 (d, J=6.7 Hz, 3H).

Example 578

3-((R)-3-((S)-1-(4-chloro-2-fluorophenyl)ethyl)-6-(4-fluorophenyl)-2-oxo-1,3-oxazinan-6-yl)-2,2-dimethylpropanamide

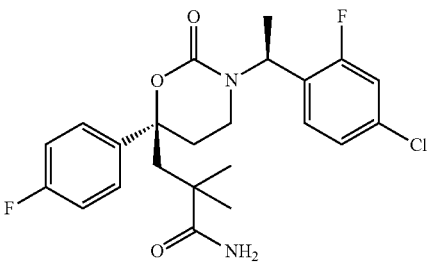 [SMILES: C[C@@H](c1ccc(Cl)cc1F)N1CC[C@](CC(C)(C)C(N)=O)(c2ccc(F)cc2)OC1=O]

The title compound was prepared from (R)-6-allyl-3-((S)-1-(4-chloro-2-fluorophenyl)ethyl)-6-(4-fluorophenyl)-1,3-oxazinan-2-one by sequentially following procedures analogous to those described in Examples 520, 521 and 522. LC-MS Method 1 $t_R$=1.62, m/z=451 (M+1).

Example 579

(R)-6-(4-fluorophenyl)-6-(3-hydroxypropyl)-3-((S)-1-(4-(2-hydroxypyrimidin-4-yl)phenyl)ethyl)-1,3-oxazinan-2-one

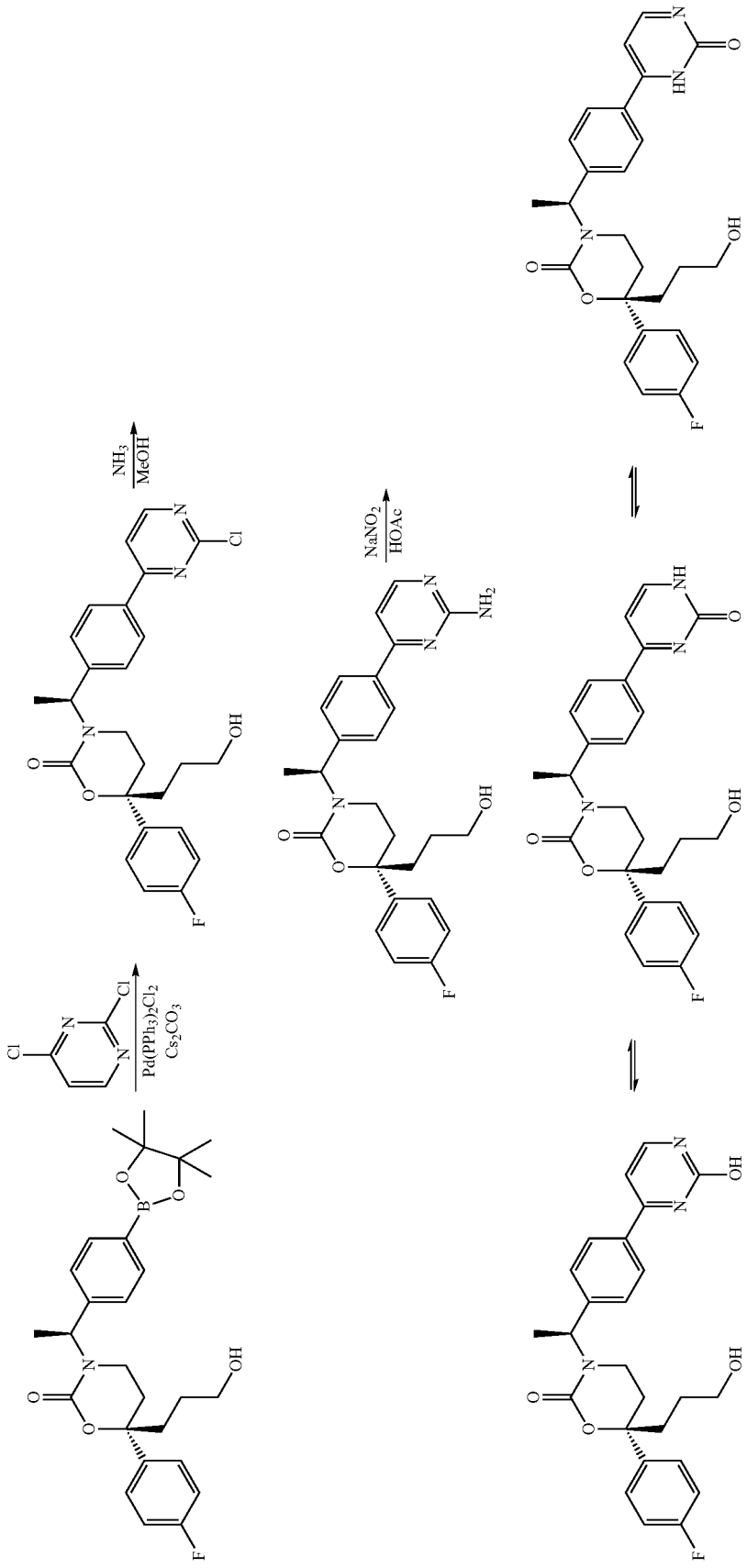

Step 1

A mixture of (R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one (500 mg, 1.03 mmol), 2,4-dichloropyrimidine (183.7 mg, 1.24 mmol), $PdCl_2(PPh_3)_2$ (41.2 mg, 5.9%) and aqueous solution of $Cs_2CO_3$ (2 mol/L, 2 mL) in 1,4-dioxane (5 mL) was heated to reflux overnight. The reaction was quenched with water. The organic layer was separated, dried, and concentrated to give the residue, which was purified by column chromatography to give (R)-3-((S)-1-(4-(2-chloropyrimidin-4-yl)phenyl)ethyl)-6-(4-fluorophenyl)-6-(3-hydroxypropyl)-1,3-oxazinan-2-one (300 mg, 62%).

Step 2

(R)-3-((S)-1-(4-(2-chloropyrimidin-4-yl)phenyl)ethyl)-6-(4-fluorophenyl)-6-(3-hydroxypropyl)-1,3-oxazinan-2-one (300 mg, 0.6 mmol) was dissolved in $MeOH/NH_3$ (10 mL). The resulting mixture was heated to 90° C. for 24 h. The mixture was concentrated to give the crude product, which was purified by preparative TLC to give (R)-3-((S)-1-(4-(2-aminopyrimidin-4-yl)phenyl)ethyl)-6-(4-fluorophenyl)-6-(3-hydroxypropyl)-1,3-oxazinan-2-one (270 mg, 90%).

Step 3

To a solution of (R)-3-((S)-1-(4-(2-aminopyrimidin-4-yl)phenyl)ethyl)-6-(4-fluorophenyl)-6-(3-hydroxypropyl)-1,3-oxazinan-2-one (40 mg, 0.089 mmol) in $CH_3COOH$ (0.3 mL) and $H_2O$ (0.13 mL) was added an aqueous solution of $NaNO_2$ (2 mol/L, 0.5 mL) dropwise at 0° C. The reaction was stirred for 10 min at this temperature before heating at 60° C. for 3 h. After the mixture was evaporated to dryness, the mixture was adjusted pH 9 with aqueous $NaHCO_3$ solution. The mixture was extracted with EtOAc, and the organic layer was dried and concentrated to give the residue, which was purified by preparative TLC to give (R)-6-(4-fluorophenyl)-6-(3-hydroxypropyl)-3-((S)-1-(4-(2-hydroxypyrimidin-4-yl)phenyl)ethyl)-1,3-oxazinan-2-one (3.18 mg, 8%). LC-MS Method 2 $t_R$=0.87 min, m/z=452. $^1$H NMR ($CD_3OD$): 1.19-1.23 (m, 2H), 1.48 (d, 3H), 1.82-1.86 (m, 2H), 2.05-2.41 (m, 3H), 3.01-3.10 (m, 1H), 3.37 (t, 2H), 5.50 (q, 1H), 6.90 (d, 1H), 6.95-7.02 (m, 4H), 7.18-7.22 (m, 2H), 7.00-7.05 (m, 3H), 7.21-7.24 (m, 2H), 7.80 (d, 2H).

Example 580

(R)-6-(4-fluorophenyl)-6-(3-hydroxypropyl)-3-((S)-1-(4-(6-hydroxypyrimidin-4-yl)phenyl)ethyl)-1,3-oxazinan-2-one

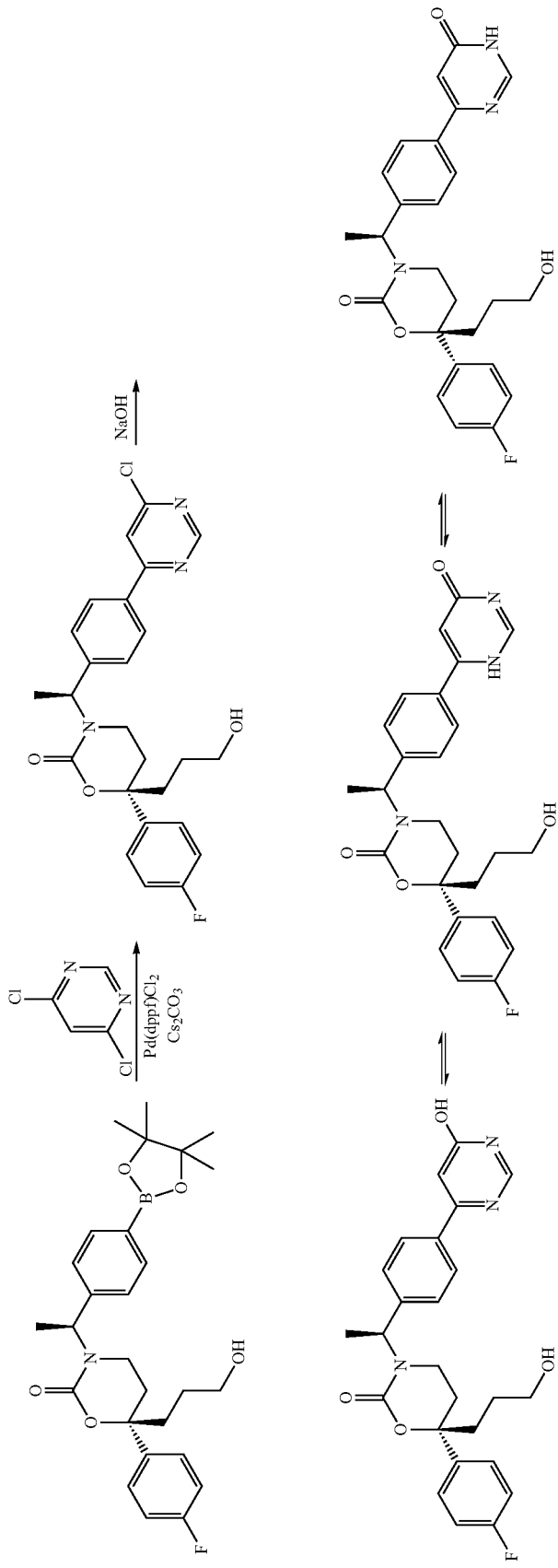

Step 1

To a mixture of ((R)-6-(4-fluorophenyl)-6-(3-hydroxypropyl)-3-((S)-1-(4-(4,4,5,5-tetramethyl-1,3,2-dioxaborolan-2-yl)phenyl)ethyl)-1,3-oxazinan-2-one (30 mg, 0.062 mmol), 4,6-dichloropyrimidine (12 mg, 0.081 mmol), and 2 M aqueous $Cs_2CO_3$ (1.0 mL) in dry THF (2 mL) was added Pd(dppf)$Cl_2$ (6 mg, 0.00621 mmol) under $N_2$ atmosphere. The mixture was heated to reflux for 2 hours. Then the solvent was evaporated, and the residue was purified by preparative TLC to afford (R)-3-((S)-1-(4-(6-chloropyrimidin-4-yl)phenyl)ethyl)-6-(4-fluorophenyl)-6-(3-hydroxypropyl)-1,3-oxazinan-2-one (20 mg, yield 68%).

Step 2

A mixture of (R)-3-((S)-1-(4-(6-chloropyrimidin-4-yl)phenyl)ethyl)-6-(4-fluorophenyl)-6-(3-hydroxypropyl)-1,3-oxazinan-2-one (20 mg, 0.0426 mmol) in 15% aq NaOH (5 mL) was heated to 110° C. overnight. Then the solvent was evaporated, and the residue was washed with EtOAc. The solid was filted off and the filtrate was dried, and condensed in vacuum to give the crude product, which was purified by preparative HPLC to afford (R)-6-(4-fluorophenyl)-6-(3-hydroxypropyl)-3-((S)-1-(4-(6-hydroxypyrimidin-4-yl)phenyl)ethyl)-1,3-oxazinan-2-one (15 mg, 78%). LC-MS Method 2 $t_R$=0.91 min, m/z=452, 408. $^1$H NMR (CD$_3$OD): δ=1.31 (m, 1H), 1.59 (m, 3H), 1.95 (m, 2H), 2.25 (m, 1H), 2.35 (m, 1H), 2.46 (m, 1H), 3.15 (m, 1H), 3.48 (m, 2H), 5.59 (m, 1H), 6.81 (s, 1H), 7.12 (m, 4H), 7.33 (m, 2H), 7.79 (m, 2H), 8.25 (s, 1H).

Example 581

(R)-3-((S)-1-(4-bromo-2-fluorophenyl)ethyl)-6-(4-fluorophenyl)-6-(3-hydroxypropyl)-1,3-oxazinan-2-one The title compound was prepared from (R)-6-allyl-3-((S)-1-(4-bromo-2-fluorophenyl)ethyl)-6-(4-fluorophenyl)-1,3-oxazinan-2-one following a procedure analogous to that described in Example 343.

Example 582

(S)-3-((S)-1-(4-bromophenyl)ethyl)-6-((5-methyl-1H-imidazol-2-yl)methyl)-6-phenyl-1,3-oxazinan-2-one

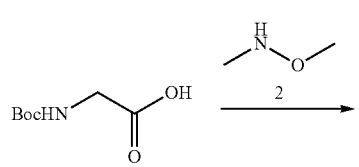

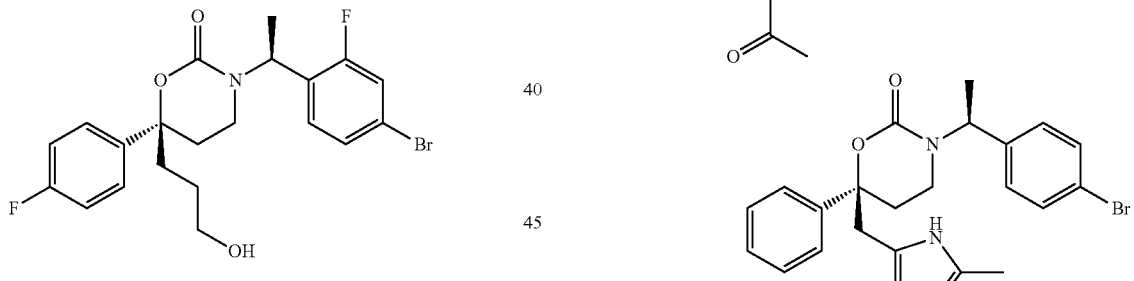

Step 1. tert-butyl 2-(methoxy(methyl)amino)-2-oxoethylcarbamate

To a solution of 2-(tert-butoxycarbonylamino)acetic acid (8.75 g, 0.05 mol) in tetrahydrofuran (150 mL) was added CDI (11.34 g, 0.07 mmol) at 0° C. The formed mixture was stirred for 1 h. Then N,O-dimethylhydroxylamine (6.8 g, 0.07 mol) and TEA (8 mL) were added to the above mixture. The mixture was stirred at rt overnight. When the reaction was over, the mixture was concentrated. The residue was washed with 1 N aq HCl and aq. NaHCO$_3$ (3×). The combined organic phase was concentrated to give crude product, which was used for next step without purification. $^1$H NMR (400 MHz, CDCl$_3$): δ=1.42 (s, 9H), 3.16 (s, 3H), 3.66 (s, 3H), 4.04 (s, 2H), 5.22 (s, 1H).

Step 2. tert-butyl 2-oxopropylcarbamate

To a solution of tert-butyl 2-(methoxy(methyl)amino)-2-oxoethylcarbamate (4.36 g, 0.02 mol) in THF (50 mL) added MeMgBr (40 ml, 0.08 ol) at −78° C. The formed mixture was stirred overnight. The mixture was quenched with NH$_4$Cl and extracted with EtOAc. The organic phase was separated, dried over anhydrous Na$_2$SO$_4$, concentrated and purified by column chromatography to give tert-butyl 2-oxopropylcarbamate (2.5 g, 72%). $^1$H NMR (400 MHz, CDCl$_3$): δ=1.42 (s, 9H), 2.18 (s, 3H), 4.01 (s, 2H), 5.22 (s, 1H).

Step 3. 1-aminopropan-2-one tert-Butyl 2-oxopropylcarbamate (2.5 g, 0.014 mol) was dissolved in a solution of 20% (V/V) TFA/CH$_2$Cl$_2$ (50 mL). The reaction mixture was stirred at rt for 1 h, and concentrated in vacuo to afford 1-aminopropan-2-one (1.03 g, 99%), which was used for next step directly without purification.

Step 4. 2-((S)-3-((S)-1-(4-bromophenyl)ethyl)-2-oxo-6-phenyl-1,3-oxazinan-6-yl)acetic acid To a solution of (R)-6-allyl-3-((S)-1-(4-bromophenyl)ethyl)-6-phenyl-1,3-oxazinan-2-one (3.0 g, 7.52 mmol) in acetone (50 mL) was added a solution of NaIO$_4$ (7.95 g, 30.8 mmol) and KMnO$_4$ (0.95 g, 4.51 mmol) in water (30 mL). The formed mixture was stirred for 1 h. The solid was filtered, and the filtrate was concentrated to give the residue, which was acidified to pH<7 with 1 N aq HCl. The mixture was extracted with EtOAc, and the organic phase was concentrated to give crude 2-((S)-3-((S)-1-(4-bromophenyl)ethyl)-2-oxo-6-phenyl-1,3-oxazinan-6-yl)acetic acid (2.6 g, 84%), which was used for the next step without purification.

Step 5. 2-((S)-3-((S)-1-(4-bromophenyl)ethyl)-2-oxo-6-phenyl-1,3-oxazinan-6-yl)-N-(2-oxopropyl)acetamide To a solution of 2-((S)-3-((S)-1-(4-bromophenyl)ethyl)-2-oxo-6-phenyl-1,3-oxazinan-6-yl)acetic acid (200 mg, 0.5 mmol) in anhydrous CH$_2$Cl$_2$ (10 mL) was added 1-aminopropan-2-one (119 mg, 0.7 mmol), HOBt (195 mg, 1.44 mmol), EDCl (283 mg, 1.44 mmol) and DIEA (620 mg, 4.8 mol) at 0° C. The formed mixture was stirred overnight at ambient temperature under nitrogen. Then the reaction mixture was washed with 1N aq HCl and water. The organic phase was dried over Na$_2$SO$_4$, filtered and concentrated to afford the residue, which was purified by prep TLC to give 2-((S)-3-((S)-1-(4-bromophenyl)ethyl)-2-oxo-6-phenyl-1,3-oxazinan-6-yl)-N-(2-oxopropyl)acetamide (118 mg, 50%). $^1$H NMR (400 MHz, CDCl$_3$): δ=1.43 (d, 3H), 2.06 (s, 3H), 2.20 (m, 1H), 2.43 (m, 2H), 2.68 (m, 1H), 2.86 (m, 2H), 3.90 (m, 1H), 4.12 (m, 1H), 5.51 (m, 1H), 6.53 (m, 1H), 6.78 (m, 2H), 7.14 (m, 2H), 7.30 (m, 5H).

Step 6. (S)-3-((S)-1-(4-bromophenyl)ethyl)-6-((5-methyl-1H-imidazol-2-yl)methyl)-6-phenyl-1,3-oxazinan-2-one To a solution of 2-((S)-3-((S)-1-(4-bromophenyl)ethyl)-2-oxo-6-phenyl-1,3-oxazinan-6-yl)-N-(2-oxopropyl)acetamide (50 mg, 0.11 mmol) in toluene (30 mL) was added CH$_3$COOH (2 mL) and NH$_4$OAc (500 mg) at room temperature. The formed mixture was heated to reflux for 4 hours. The mixture was concentrated to give the crude product, which was purified by preparative TLC and preparative HPLC to give (S)-3-((S)-1-(4-bromophenyl)ethyl)-6-((5-methyl-1H-imidazol-2-yl)methyl)-6-phenyl-1,3-oxazinan-2-one (1.86 mg, 4%). LC-MS Method 2, t$_R$=1.18 min, m/z=454. $^1$H NMR (400 MHz, CDCl$_3$): δ=1.51 (d, 3H), 2.23 (s, 3H), 2.25 (m, 1H), 2.68 (m, 1H), 3.11 (m, 1H), 3.50 (m, 2H), 5.46 (m, 1H), 6.78 (m, 2H), 7.04 (m, 1H), 7.18 (m, 2H), 7.23 (m, 2H), 7.36 (m, 3H).

Example 583

6-(4-((S)-1-((S)-6-(2-hydroxy-2-methylpropyl)-2-oxo-6-phenyl-1,3-oxazinan-3-yl)ethyl)phenyl)nicotinonitrile

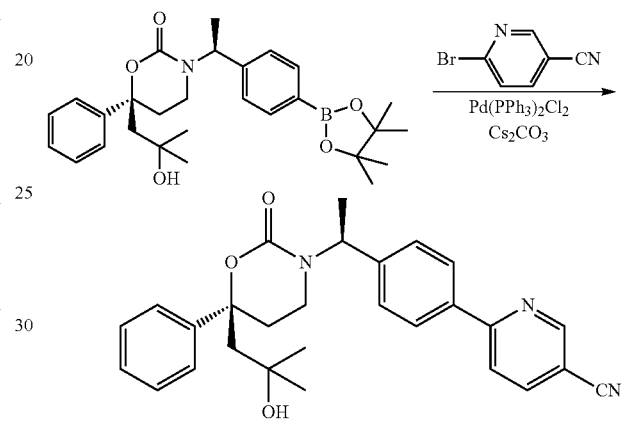

To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (200 mg, 0.42 mmol) in 1,4-dioxane (1.5 mL) was added 6-bromonicotinonitrile (123 mg, 0.67 mmol), Pd(PPh$_3$)$_2$Cl$_2$ (30 mg, 0.042 mmol), and Cs$_2$CO$_3$ (1 mL, 2 M) were added. The vessel was sealed with a septum and placed into the microwave cavity. Microwave irradiation of 100 W was used, and the temperature being ramped from rt to 120° C. Once this temperature was reached, the reaction mixture was held at this temperature for 30 min. After the mixture was cooled to rt, the mixture was filtered. The filtrate was extracted with EtOAc (4×20 mL). The organic layer was washed with brine, dried over Na$_2$SO$_4$ and concentrated to give the crude product, which was purified by preparative TLC to give 6-(4-((S)-1-((S)-6-(2-hydroxy-2-methylpropyl)-2-oxo-6-phenyl-1,3-oxazinan-3-yl)ethyl)phenyl)nicotinonitrile (120 mg, 62%). LC-MS Method 2 t$_R$=1.33, m/z=398; $^1$H NMR (CDCl$_3$): 1.13 (s, 3H), 1.19 (s, 3H), 1.58 (d, 3H), 2.22 (m, 2H), 2.27 (m, 2H), 2.40 (m, 1H), 2.89 (m, 1H), 3.49 (s, 1H), 5.73 (m, 1H), 7.11 (d, 2H), 7.28-7.38 (m, 5H), 7.80 (m, 3H), 8.00 (d, 1H), 8.93 (s, 1H).

Method 2

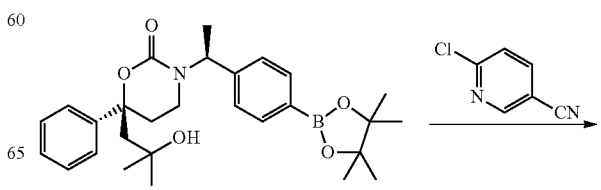

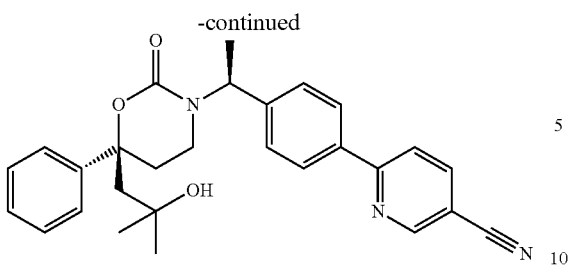

2 M aqueous Na₂CO₃ solution (1.04 mL) was added to a solution of (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.50 g) and 6-chloro-nicotinonitrile (0.22 g) in dimethylformamide (3 mL). The resulting mixture was sparged with argon for 5 min, before [1,1'-bis(diphenylphosphino)ferrocene]-dichloropalladium (II) dichloromethane complex (51 mg) is added. The mixture was heated to 100° C. and stirred at this temperature overnight. After cooling to ambient temperature, water was added and the resulting mixture was extracted with ethyl acetate. The combined organic extracts were washed with brine, dried (MgSO₄), and concentrated. The residue was purified by chromatography on silica gel (CH₂Cl₂/MeOH 98:2→80:20) to afford (S)-6-(4-{(S)-1-[6-(2-Hydroxy-2-methyl-propyl)-2-oxo-6-phenyl-[1,3]oxazinan-3-yl]-ethyl}-phenyl)-nicotinonitrile as an oil (0.50 g) which is crystallized from a mixture of ethyl acetate (15 mL) and iPr₂O (5 mL). Yield: 0.32 g (67% of theory). Mass spectrum (ESI⁺): m/z=456 [M+H]⁺. mp=160-162° C.

Example 584

6-((S)-3-((R)-6-(4-fluorophenyl)-6-(3-hydroxypropyl)-2-oxo-1,3-oxazinan-3-yl)piperidin-1-yl)nicotinamide

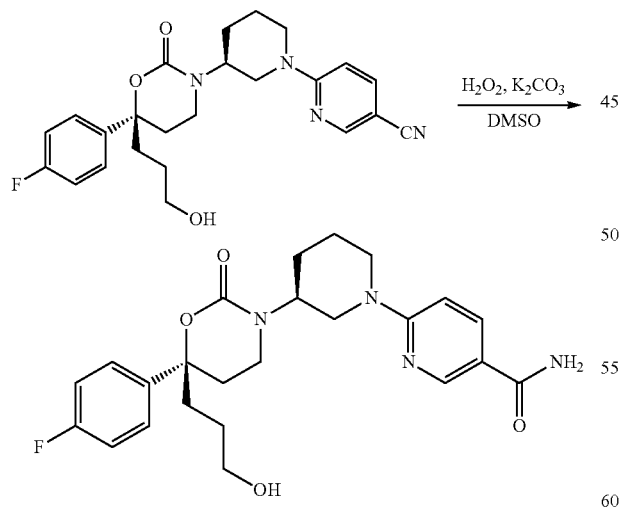

To a solution of 6-((S)-3-((R)-6-(4-fluorophenyl)-6-(3-hydroxypropyl)-2-oxo-1,3-oxazinan-3-yl)piperidin-1-yl)nicotinonitrile (520 mg, 1.19 mmol) in DMSO (10 mL) was added H₂O₂ (30%, 1 mL) and K₂CO₃ (82 mg, 0.59 mmol). The mixture was stirred at rt for 1 d. After water and EtOAc were added, the mixture was extracted with EtOAc. The organic layers were dried and concentrated to give 6-((S)-3-((R)-6-(4-fluorophenyl)-6-(3-hydroxypropyl)-2-oxo-1,3-oxazinan-3-yl)piperidin-1-yl)nicotinamide (430 mg, 79%). LC-MS Method 2 $t_R$=0.99 min, m/z=457. ¹H NMR (400 MHz, CDCl₃): 1.29-1.30 (m, 1H), 1.58-1.63 (m, 2H), 1.82-1.86 (m, 2H), 1.91-2.00 (m, 3H), 2.21-2.32 (m, 1H), 2.49-2.52 (m, 1H), 2.65-2.71 (m, 1H), 2.81-2.96 (m, 3H), 3.39 (m, 1H), 3.42-4.48 (m, 2H), 3.87 (m, 1H), 4.21-4.24 (m, 1H), 4.30 (s, 1H), 6.75-6.78 (d, 1H), 7.39-7.72 (t, 2H), 7.94-7.97 (m, 1H), 8.59-8.60 (s, 1H). LC-MS Method 2 tR=0.99 min, m/z=457.

Example 585

(S)-3-((S)-1-(4-(2,6-dimethylpyridin-4-yl)phenyl)ethyl)-6-(2-hydroxy-2-methylpropyl)-6-phenyl-1,3-oxazinan-2-one

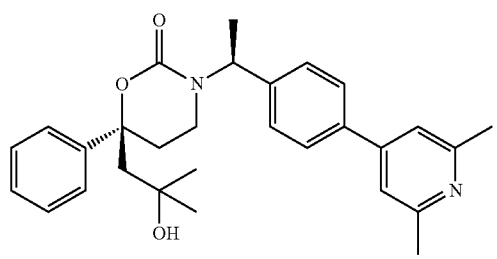 [SMILES: Cc1cc(-c2ccc([C@H](C)N3CC[C@](CC(C)(C)O)(c4ccccc4)OC3=O)cc2)cc(C)n1]

The title compound was prepared from (S)-3-((S)-1-(4-bromophenyl)ethyl)-6-(2-hydroxy-2-methylpropyl)-6-phenyl-1,3-oxazinan-2-one following procedures analogous to those described in Example 313 Steps 3 and 4 using 4-bromo-2,6-dimethylpyridine in Step 4. LC-MS Method 2 $t_R$=1.049, m/z=459.1; ¹H NMR (CD₃OD) 0.94 (s, 3H), 1.24 (s, 3H), 1.55 (d, 3H), 2.15 (s, 2H), 2.23 (m, 1H), 2.45 (m, 1H), 2.51 (s, 6H), 3.05 (m, 1H), 5.57 (m, 1H), 7.04 (d, 2H), 7.24 (s, 2H), 7.26-7.38 (m, 5H), 7.45 (m, 1H).

Example 586

N-(2-((R)-3-((S)-1-(4-bromophenyl)ethyl)-2-oxo-6-phenyl-1,3-oxazinan-6-yl)ethyl)-N-methylacetamide

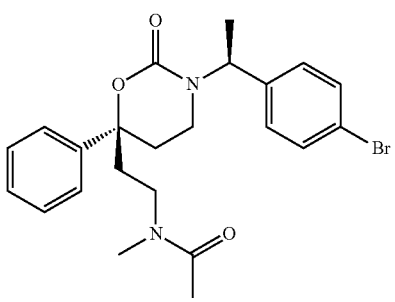 [SMILES: CC(=O)N(C)CC[C@]1(c2ccccc2)CCN([C@@H](C)c2ccc(Br)cc2)C(=O)O1]

The title compound was prepared from (S)-3-((S)-1-(4-bromophenyl)ethyl)-6-(2-hydroxyethyl)-6-phenyl-1,3-oxazinan-2-one by sequntial application of procedures analogous to those described in Examples 75 Steps 2, 3 and 4, Example 98 and Example 313 Step 1. LC-MS Method 2 $t_R$=1.359, m/z=460.9; ¹H NMR (CD₃OD) 1.49 (d, 3H), 1.84-1.96 (d, 3H), 2.08-2.31 (m, 4H), 2.38-2.52 (m, 1H), 2.75-2.92

(d, 3H), 3.03 (m, 1H), 3.22 (m, 1H), 3.36-3.52 (m, 1H), 5.49 (m, 1H), 6.88 (m, 2H), 7.21-7.57 (m, 7H).

Example 587

6-(4-((S)-1-((R)-6-(3-hydroxypropyl)-2-oxo-6-phenyl-1,3-oxazinan-3-yl)ethyl)phenyl)nicotinamide

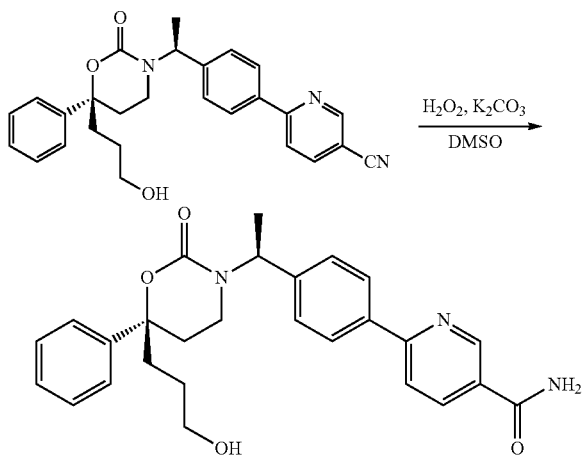

6-(4-((S)-1-((R)-6-(3-hydroxypropyl)-2-oxo-6-phenyl-1,3-oxazinan-3-yl)ethyl)phenyl)nicotinonitrile (50 mg, 0.11 mmol) and H₂O₂ (0.04 mL, 30%), K₂CO₃ (6.27 mg, 0.046 mmol) in DMSO (0.39 mL) was stirred overnight at room temperature. The reaction was added water and EtOAc. The layer was separated. The organic phase was washed with brine and dried, concentrated to give the product (9.95 mg, 19%) LC-MS Method 2 $t_R$=1.083, m/z=460.1; ¹H NMR (CD₃OD) 1.21 (m, 1H), 1.51 (d, 3H), 1.53-1.64 (m, 1H), 1.85-1.94 (m, 2H), 2.10-2.21 (m, 1H), 2.29 (m, 1H), 2.42 (m, 1H), 3.03 (m, 1H), 3.39 (t, 2H), 5.52 (m, 1H), 6.99 (d, 2H), 7.21-7.34 (m, 5H), 7.22 (d, 2H), 7.31 (d, 1H), 8.22 (d, 1H), 8.98 (s, 1H).

Example 588

(S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one

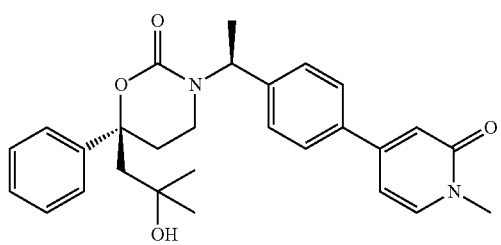 [SMILES: C[C@@H](c1ccc(-c2ccn(C)c(=O)c2)cc1)N1CC[C@](CC(C)(C)O)(c2ccccc2)OC1=O]

The title compound was prepared from (S)-3-((S)-1-(4-bromophenyl)ethyl)-6-(2-hydroxy-2-methylpropyl)-6-phenyl-1,3-oxazinan-2-one following procedures analogous to those described in Example 313 Steps 3 and 4 using 4-bromo-1-methylpyridin-2(1H)-one in Step 4. LC-MS Method 2 $t_R$=1.16, m/z=921.5; ¹H NMR (CDCl₃) 1.11 (s, 3H), 1.18 (s, 3H), 1.22 (t, 1H), 1.52 (m, 3H), 2.21 (s, 2H), 2.22-2.34 (m, 2H), 2.34-2.46 (m, 1H), 2.85 (m, 1H), 3.57 (s, 3H), 5.59 (m, 1H), 6.33 (d, 1H), 6.68 (s, 1H), 7.01 (d, 2H), 7.29-7.41 (m, 8H); ¹H NMR (CD₃OD) 0.98 (s, 3H), 1.29 (s, 3H), 1.58 (d, 3H), 2.17 (s, 2H), 2.22 (m, 1H), 2.50 (m, 2H), 3.08 (m, 1H), 3.59 (s, 3H), 5.59 (m, 1H), 6.61 (d, 1H), 6.66 (s, 1H), 7.08 (m, 2H), 7.30-7.40 (5H), 7.42 (d, 2H), 7.70 (d, 1H).

4-bromo-1-methylpyridin-2(1H)-one was prepared from 4-bromo-2-hydroxypyridine following a procedure analogous to that described in Example 313 Step 1.

Example 589

(R)-3-((S)-1-(4-(2,6-dimethylpyridin-3-yl)phenyl)ethyl)-6-(4-fluorophenyl)-6-(3-hydroxypropyl)-1,3-oxazinan-2-one

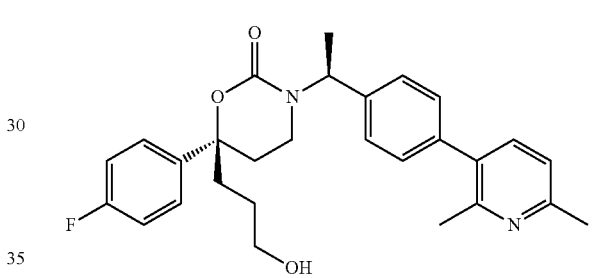

The title compound was prepared from (R)-3-((S)-1-(4-bromophenyl)ethyl)-6-(4-fluorophenyl)-6-(3-hydroxypropyl)-1,3-oxazinan-2-one following procedures analogous to those described in Example 313 Steps 3 and 4 using 3-bromo-2,6-dimethylpyridine in Step 4. LC-MS Method 2 $t_R$=1.012, m/z=463.1; ¹H NMR (CDCl₃) 1.32 (m, 2H), 1.49 (d, 3H), 1.62 (m, 2H), 1.86-1.96 (m, 2H), 2.17-2.29 (m, 3H), 2.31 (s, 3H), 2.49 (s, 3H), 2.93 (m, 1H), 3.51 (m, 2H), 5.68 (m, 1H), 6.88-7.03 (m, 7H), 7.25 (m, 3H).

Example 590

(R)-6-(3-amino-2,2-dimethylpropyl)-3-((S)-1-(4-bromophenyl)ethyl)-6-(4-fluorophenyl)-1,3-oxazinan-2-one

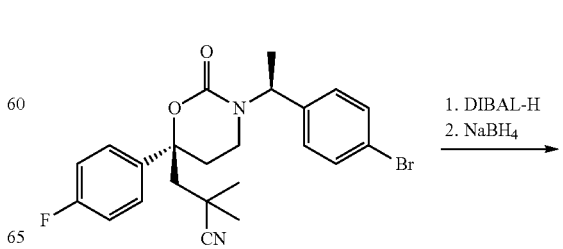

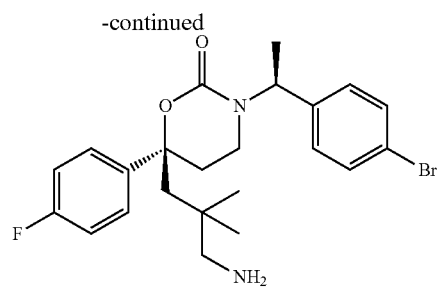

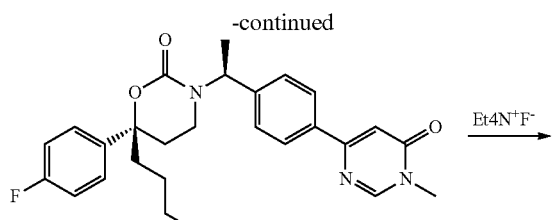

To a stirred solution of 3-((R)-3-((S)-1-(4-bromophenyl)ethyl)-6-(4-fluorophenyl)-2-oxo-1,3-oxazinan-6-yl)-2,2-dimethylpropanenitrile (0.0665 g, 0.14 mmol) in $CH_2Cl_2$ (4 mL) at 0° C. under a nitrogen atmosphere was added DIBAL-H/heptane (1.0 M, 0.9 mL, 0.9 mmol). The reaction mixture was allowed to slowly warm to rt while stirring overnight. After 25 h, the solvent was evaporated under reduced pressure. The residue was dissolved into EtOH (5 mL) and then $NaBH_4$ (0.3370 g) was added. After stirring at 0° C. for 2 h, the reaction mixture was purified by reversed-phase HPLC (SunFire™ Prep $C_{18}$ OBD™ 5 µm 19×50 mm column, 10%→90% $CH_3CN/H_2O$, 0.1% $CF_3COOH$ over 8 min and then 90% $CH_3CN/H_2O$, 0.1% $CF_3COOH$ over 2 min, flow rate 20 mL/min) to afford 0.0210 g of TFA salt of (R)-6-(3-amino-2,2-dimethylpropyl)-3-((S)-1-(4-bromophenyl)ethyl)-6-(4-fluorophenyl)-1,3-oxazinan-2-one. LC-MS Method 1 $t_R$=1.45 min, m/z 463, 465 (MH$^+$); $^1$H NMR (400 MHz, $CD_3OD$) δ 7.23-7.21 (m, 4H), 7.04-7.00 (m, 2H), 6.89 (d, J=7 Hz, 2H), 5.41 (q, J=6 Hz, 1H), 2.98-2.91 (m, 2H), 2.61-2.57 (m, 1H), 2.31-2.27 (m, 1H), 2.11-1.94 (m, 4H), 1.41 (d, J=6 Hz, 3H), 0.85 (s, 3H), 0.43 (s, 3H); $^{19}$F NMR (376 MHz, $CD_3OD$) δ −116.58 (m).

Example 591

(R)-6-(4-fluorophenyl)-6-(3-hydroxypropyl)-3-((S)-1-(4-(1-methyl-6-oxo-1,6-dihydropyrimidin-4-yl)phenyl)ethyl)-1,3-oxazinan-2-one

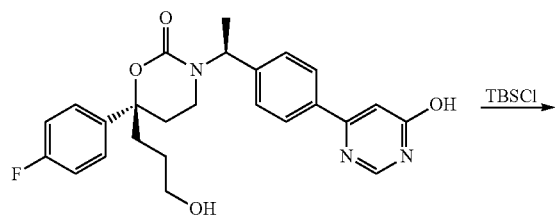

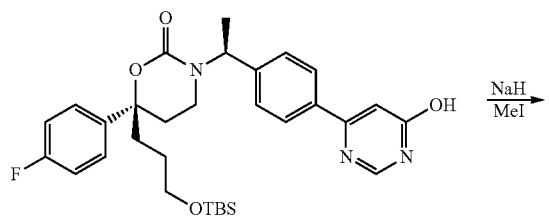

The title compound was prepared from (R)-6-(4-fluorophenyl)-6-(3-hydroxypropyl)-3-((S)-1-(4-(6-hydroxypyrimidin-4-yl)phenyl)ethyl)-1,3-oxazinan-2-one using a procedure analogous to that described in Example 198 Step 2, followed by procedures analogous to those described in Example 199 Steps 2 and 3. LC-MS Method 2 $t_R$=0.87, m/z=452.15; $^1$H NMR ($CD_3OD$) 1.20 (m, 2H), 1.49 (d, 3H), 1.83 (m, 2H), 2.15 (m, 1H), 2.22-2.41 (m, 2H), 3.07 (m, 1H), 3.38 (t, 2H), 5.50 (m, 1H), 6.88 (d, 1H), 7.01 (m, 4H), 7.21 (m, 2H), 7.79 (m, 2H), 7.90 (s, 1H).

Example 592

(R)-6-(4-fluorophenyl)-6-(3-hydroxypropyl)-3-((S)-1-(4-(1-methyl-6-oxo-1,6-dihydropyridazin-3-yl)phenyl)ethyl)-1,3-oxazinan-2-one The title compound was prepared from (R)-6-(4-fluorophenyl)-6-(3-hydroxypropyl)-3-((S)-1-(4-(6-oxo-1,6-dihydropyridazin-3-yl)phenyl)ethyl)-1,3-oxazinan-2-one using a procedure analogous to that described in Example 198 Step 2, followed by procedures analogous to those described in Example 199 Steps 2 and 3. LC-MS Method 2 $t_R$=1.111, m/z=488; $^1$H NMR ($CDCl_3$) 1.27-1.40 (m, 1H), 1.49 (d, 3H), 1.64 (m, 1H), 1.85-1.99 (m, 3H), 2.10-2.33 (m, 4H), 2.89 (m, 1H), 3.51 (t, 2H), 3.80 (s, 3H), 5.68 (m, 1H), 6.90-7.02 (m, 5H), 7.18 (m, 2H), 7.21 (m, 1H), 7.48 (d, 2H), 7.52 (d, 1H).

Example 593

2,2-dimethyl-3-((R)-3-((S)-1-(4-(1-methyl-6-oxo-1,6-dihydropyridin-3-yl)phenyl)ethyl)-2-oxo-6-phenyl-1,3-oxazinan-6-yl)propanenitrile

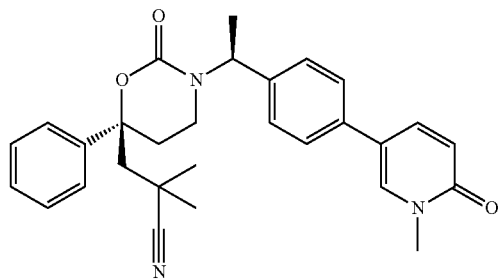 [SMILES: C[C@@H](c1ccc(-c2ccc(=O)n(C)c2)cc1)N1CC[C@](CC(C)(C)C#N)(c2ccccc2)OC1=O]

Method 1

The title compound was prepared from 3-((R)-3-((S)-1-(4-bromophenyl)ethyl)-2-oxo-6-phenyl-1,3-oxazinan-6-yl)-2,2-dimethylpropanenitrile following procedures analogous to those described in Example 313 Steps 3 and 4. LC-MS Method 2 $t_R$=1.231, m/z=470.1; $^1$H NMR (CDCl$_3$) 1.28 (s, 3H), 1.40 (s, 3H), 1.47 (d, 3H), 2.09 (s, 2H), 2.21 (m, 1H), 2.41 (m, 2H), 2.83 (m, 1H), 3.52 (s, 3H), 5.56 (m, 1H), 6.58 (d, 1H), 6.82 (d, 2H), 7.02 (d, 2H), 7.30 (m, 6H), 7.43 (m, 1H).

3-((R)-3-((S)-1-(4-bromophenyl)ethyl)-2-oxo-6-phenyl-1,3-oxazinan-6-yl)-2,2-dimethylpropanenitrile was prepared from (R)-6-allyl-3-((S)-1-(4-bromophenyl)ethyl)-6-phenyl-1,3-oxazinan-2-one by sequential application of procedures analogous to those described in Examples 520 and 521.

Method 2

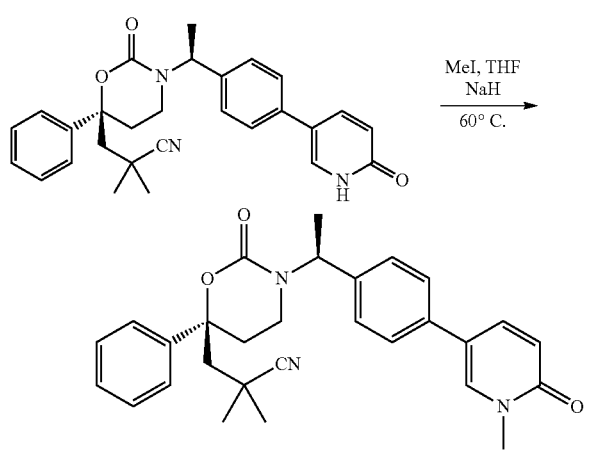

A solution of 2,2-dimethyl-3-((R)-2-oxo-3-((S)-1-(4-(6-oxo-1,6-dihydropyridin-3-yl)phenyl)ethyl)-6-phenyl-1,3-oxazinan-6-yl)propanenitrile (202 mg, 0.444 mmol) and MeI (110 μL, 4 equiv) in dry THF (5 mL) was cooled to 0° C. NaH (60% in mineral oil, 36 mg, 2 equiv) was added. After 10 min, the mixture was warmed to rt slowly and stirred for 3 h. LC-MS showed about 50% conversion. The mixture was heated for 1 h at 60° C. LC-MS found the reaction completed.

After cooling to rt, the mixture was cooled to 0° C. and quenched with satd aq NH$_4$Cl (3 mL). The mixture was then diluted with CH$_2$Cl$_2$ (20 mL), washed with 1% aq HCl (5 mL) and brine (4 mL), and dried over Na$_2$SO$_4$. After filtration and concentration, the residue was purified by prep HPLC to afford 2,2-dimethyl-3-((R)-3-((S)-1-(4-(1-methyl-6-oxo-1,6-dihydropyridin-3-yl)phenyl)ethyl)-2-oxo-6-phenyl-1,3-oxazinan-6-yl)propanenitrile (177.4 mg, 85% yield) product as a light brown oil.

Method 3

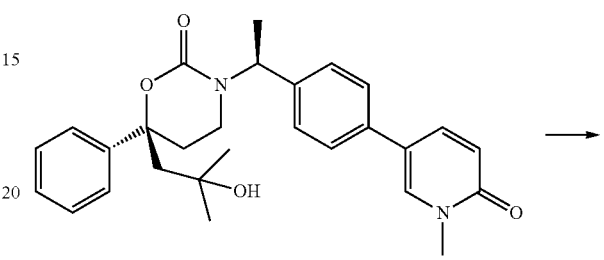

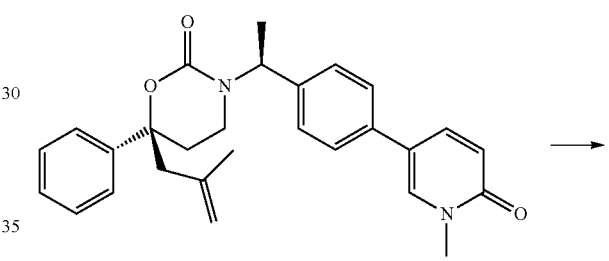

Mass spectrum (ESI+): m/z = 443 [M + H]+

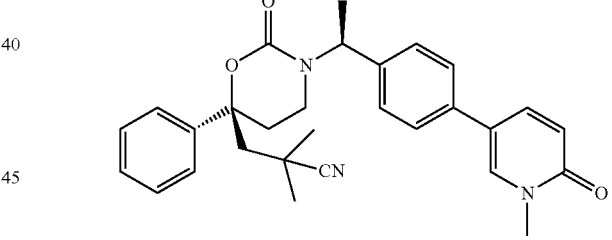

Mass spectrum (ESI+): m/z = 470 [M + H]+

2,2-Dimethyl-3-(3-{(S)-1-[4-(1-methyl-6-oxo-1,6-dihydro-pyridin-3-yl)-phenyl]-ethyl}-2-oxo-(S)-6-phenyl-[1,3]oxazinan-6-yl)-propionitrile was prepared from (S)-6-(2-hydroxy-2-methylpropyl)-3-((S)-1-(4-(1-methyl-6-oxo-1,6-dihydropyridin-3-yl)phenyl)ethyl)-6-phenyl-1,3-oxazinan-2-one following procedures analogous to those described in Example 658 in the Alternative Method to Prepare 3-((R)-3-((S)-1-(4-bromophenyl)ethyl)-2-oxo-6-phenyl-1,3-oxazinan-6-yl)-2,2-dimethylpropanenitrile. (S)-6-(2-hydroxy-2-methyl-propyl)-3-{(S)-1-[4-(1-methyl-6-oxo-1,6-dihydro-pyridin-3-yl)-phenyl]-ethyl}-6-phenyl-[1,3]oxazinan-2-one, is obtained from coupling (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one with 5-iodo-1-methyl-1H-pyridin-2-one by the action of Pd(PPh$_3$)$_4$ and 2 M aqueous Na$_2$CO$_3$ solution in a mixture of methanol and dioxane (1:3) at 80° C.

Example 594

2,2-dimethyl-3-((R)-3-((S)-1-(4-(1-methyl-2-oxo-1,2-dihydropyridin-4-yl)phenyl)ethyl)-2-oxo-6-phenyl-1,3-oxazinan-6-yl)propanenitrile

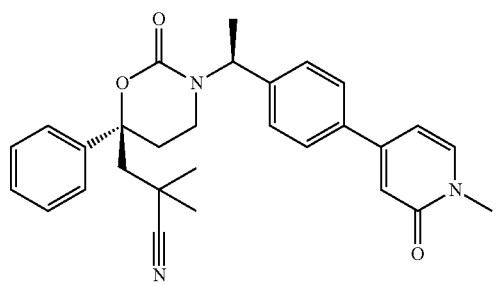 [SMILES: C[C@@H](c1ccc(-c2ccn(C)c(=O)c2)cc1)N1CC[C@](CC(C)(C)C#N)(c2ccccc2)OC1=O]

The title compound was prepared from 3-((R)-3-((S)-1-(4-bromophenyl)ethyl)-2-oxo-6-phenyl-1,3-oxazinan-6-yl)-2,2-dimethylpropanenitrile following procedures analogous to those described in Example 313 Steps 3 and 4 using 4-bromo-1-methylpyridin-2(1H)-one in Step 4. LC-MS Method 2 t$_R$=1.103, m/z=470.4; $^1$H NMR (CDCl$_3$) 1.26 (s, 3H), 1.41 (s, 3H), 1.49 (d, 3H), 2.09 (s, 2H), 2.24 (m, 1H), 2.53 (m, 2H), 2.88 (m, 1H), 3.56 (s, 3H), 5.59 (m, 1H), 6.38 (d, 1H), 6.78 (s, 1H), 6.84 (d, 2H), 7.19 (m, 2H), 7.31 (m, 6H).
Method 2

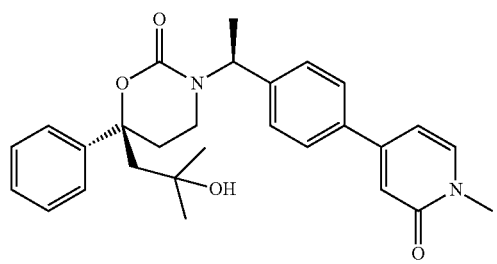

Mass spectrum (ESI+): m/z = 443 [M + H]+

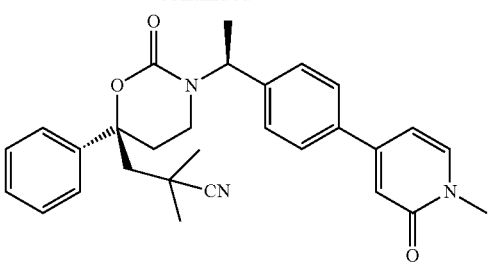

Mass spectrum (ESI+): m/z = 470 [M + H]+

(S)-2,2-Dimethyl-3-(3-{1-[(S)-4-(1-methyl-2-oxo-1,2-dihydro-pyridin-4-yl)-phenyl]-ethyl}-2-oxo-6-phenyl-[1,3] oxazinan-6-yl)-propionitrile was prepared from (S)-6-(2-hydroxy-2-methylpropyl)-3-((S)-1-(4-(1-methyl-2-oxo-1,2-dihydropyridin-4-yl)phenyl)ethyl)-6-phenyl-1,3-oxazinan-2-one following procedures analogous to those described in Example 658 Alternative Method to Prepare 3-((R)-3-((S)-1-(4-bromophenyl)ethyl)-2-oxo-6-phenyl-1,3-oxazinan-6-yl)-2,2-dimethylpropanenitrile. The starting compound, (S)-6-(2-hydroxy-2-methyl-propyl)-3-{(S)-1-[4-(1-methyl-2-oxo-1,2-dihydro-pyridin-4-yl)-phenyl]-ethyl}-6-phenyl-[1,3] oxazinan-2-one, is obtained from coupling (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one with trifluoro-methanesulfonic acid 1-methyl-2-oxo-1,2-dihydro-pyridin-4-yl ester employing the standard conditions, Pd(dppf)Cl$_2$*CH$_2$Cl$_2$, 2 M aqueous Na$_2$CO$_3$ solution, DMF, 90° C., 2 h.

Example 595

(R)-3-((S)-1-(4-bromophenyl)ethyl)-6-(2-(5-methyl-1,3,4-oxadiazol-2-yl)ethyl)-6-phenyl-1,3-oxazinan-2-one

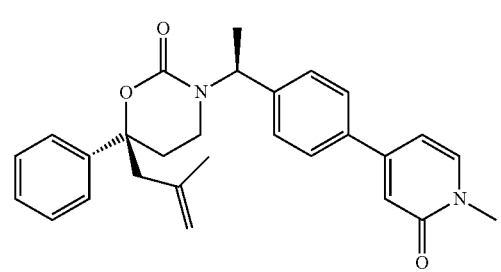

The title compound was prepared from (R)-3-((S)-1-(4-bromophenyl)ethyl)-6-(3-hydroxypropyl)-6-phenyl-1,3-oxazinan-2-one by sequential application of procedures analogous to those described in Example 234 Step 1 and Example 530 Steps 1, 2 and alternative Step 3. LC-MS Method 2 t$_R$=1.379, m/z=471.9; $^1$H NMR (CDCl$_3$) 1.43 (d, 3H), 2.11-

2.39 (m, 5H), 2.41 (s, 3H), 2.52 (m, 2H), 2.87 (m, 1H), 3.01 (m, 1H), 5.56 (m, 1H), 6.71 (d, 2H), 7.19 (m, 2H), 7.21 (m, 2H), 7.29-7.38 (m, 3H).

Example 596

6-((S)-3-((R)-6-(4-fluorophenyl)-6-(3-hydroxypropyl)-2-oxo-1,3-oxazinan-3-yl)piperidin-1-yl)-N-methylnicotinamide

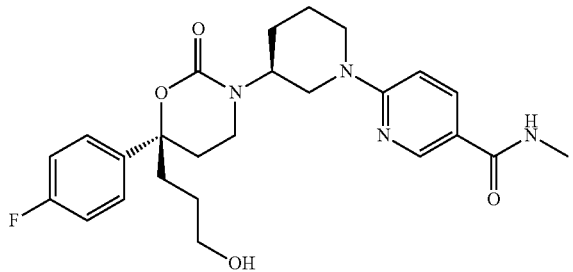

The title compound was prepared from 6-((S)-3-((R)-6-(4-fluorophenyl)-6-(3-hydroxypropyl)-2-oxo-1,3-oxazinan-3-yl)piperidin-1-yl)nicotinamide using a procedure analogous to that described in Example 198 Step 2, followed by procedures analogous to those described in Example 199 Steps 2 and 3. LC-MS Method 2 $t_R$=0.96, m/z=471.1; $^1$H NMR (CDCl$_3$) 0.83 (m, 1H), 1.20-1.33 (m, 2H), 1.58 (m, 1H), 1.70-1.81 (m, 3H), 1.83-2.00 (m, 2H), 2.18 (m, 1H), 2.28 (m, 1H), 2.68 (m, 1H), 2.79 (m, 2H), 2.91 (d, 3H), 3.20 (m, 1H), 3.51 (t, 2H), 3.84 (m, 1H), 4.12 (m, 1H), 4.24 (m, 1H), 6.00 (m, 1H), 6.52 (d, 1H), 7.02 (t, 2H), 7.25 (m, 2H), 7.80 (dd, 1H), 8.42 (d, 1H).

Example 597

3-((R)-6-(4-fluorophenyl)-3-((S)-1-(4-(2-methylpyrimidin-4-yl)phenyl)ethyl)-2-oxo-1,3-oxazinan-6-yl)-2,2-dimethylpropanenitrile

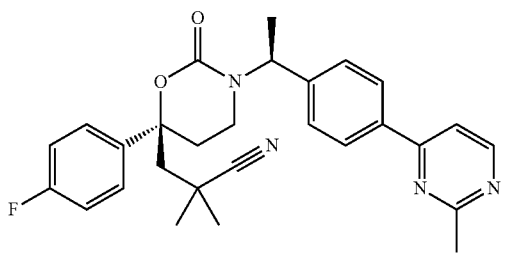 [SMILES: Cc1nccc(-c2ccc([C@H](C)N3CC[C@](CC(C)(C)C#N)(c4ccc(F)cc4)OC3=O)cc2)n1]

The title compound was prepared from 3-((R)-3-((S)-1-(4-bromophenyl)ethyl)-2-oxo-6-phenyl-1,3-oxazinan-6-yl)-2,2-dimethylpropanenitrile following procedures analogous to those described in Example 313 Steps 3 and 4 using 4-chloro-2-methylpyrimidine in Step 4. LC-MS Method 1 $t_R$=1.55, m/z=473 (M+1); $^1$H NMR (CDCl$_3$) 8.96 (s, 1H), 7.98 (d, 2H), 7.84 (s, 1H), 7.29 (m, 2H), 7.10 (m, 4H), 5.72 (d, 1H), 3.05 (d, 1H), 2.97 (s, 3H), 2.91 (m, 1H), 2.51 (d, 1H), 1.61 (d, 3H), 1.38 (d, 3H), 1.27 (d, 3H).

Example 598

6-(4-((S)-1-((S)-6-(2-hydroxy-2-methylpropyl)-2-oxo-6-phenyl-1,3-oxazinan-3-yl)ethyl)phenyl)nicotinamide

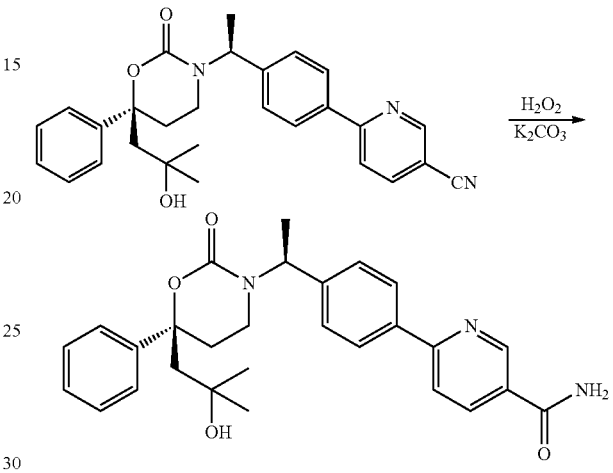

To a solution of 6-(4-((S)-1-((S)-6-(2-hydroxy-2-methylpropyl)-2-oxo-6-phenyl-1,3-oxazinan-3-yl)ethyl)phenyl)nicotinonitrile (120 mg, 0.26 mmol) in DMSO (8 mL) were added H$_2$O$_2$ (0.5 mL, 30%) and K$_2$CO$_3$ (35 mg, 0.26 mmol), and the mixture was stirred at rt for 3 h. The reaction was quenched with H$_2$O (10 mL) and the mixture was extracted with EtOAc (4×20 mL). The organic layer was washed with brine, dried over Na$_2$SO$_4$ and concentrated to give the crude product, which was purified by preparative HPLC to give 6-(4-((S)-1-((S)-6-(2-hydroxy-2-methylpropyl)-2-oxo-6-phenyl-1,3-oxazinan-3-yl)ethyl)phenyl)nicotinamide (55.46 mg, 45%). LC-MS Method 2 $t_R$=1.12 min, m/z=474, 416. $^1$H NMR (CDCl$_3$): 1.03 (s, 3H), 1.09 (s, 3H), 1.46 (d, 3H), 2.13-2.26 (m, 5H), 2.30 (m, 1H), 2.44 (s, 1H), 2.79 (d, 1H), 5.61 (m, 1H), 6.15-6.38 (s, 1H), 6.97 (d, 2H), 7.13-7.29 (m, 5H), 7.60 (d, 2H), 7.70 (d, 2H), 8.15 (d, 1H), 9.05 (s, 1H).

Example 599

(S)-3-((S)-1-(4-(2,6-dimethylpyridin-4-yl)phenyl)ethyl)-6-(4-fluorophenyl)-6-(2-hydroxy-2-methylpropyl)-1,3-oxazinan-2-one

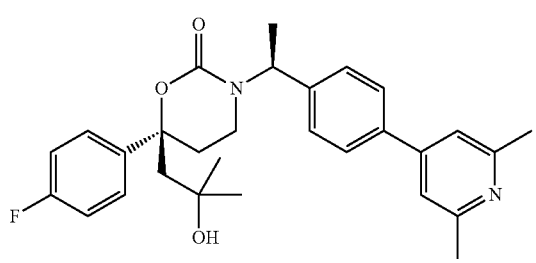 [SMILES: Cc1cc(-c2ccc([C@H](C)N3CC[C@](CC(C)(C)O)(c4ccc(F)cc4)OC3=O)cc2)cc(C)n1]

The title compound was prepared from (S)-3-((S)-1-(4-bromophenyl)ethyl)-6-(4-fluorophenyl)-6-(2-hydroxy-2-methylpropyl)-1,3-oxazinan-2-one following procedures analogous to those described in Example 313 Steps 3 and 4 using 4-bromo-2,6-dimethylpyridine in Step 4. LC-MS Method 2 $t_R$=1.001, m/z=477.1; $^1$H NMR (CDCl$_3$) 1.05-1.23 (d, 6H), 1.49 (d, 3H), 2.10-2.23 (m, 4H), 2.31-2.42 (m, 1H), 2.56 (s, 6H), 2.89 (m, 1H), 5.67 (m, 1H), 6.92-7.07 (m, 4H), 7.08 (s, 2H), 7.22 (m, 2H), 7.33 (d, 2H).

Example 600

6-((S)-3-((R)-6-(4-fluorophenyl)-6-(3-hydroxypropyl)-2-oxo-1,3-oxazinan-3-yl)piperidin-1-yl)-N,N-dimethylnicotinamide

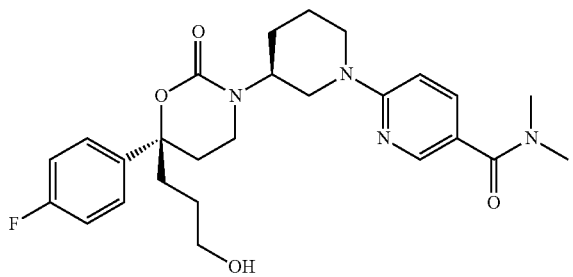 [SMILES: CN(C)C(=O)c1ccc(N2CCC[C@H](N3CC[C@](CCCO)(c4ccc(F)cc4)OC3=O)C2)nc1]

The title compound was prepared from 6-((S)-3-((R)-6-(4-fluorophenyl)-6-(3-hydroxypropyl)-2-oxo-1,3-oxazinan-3-yl)piperidin-1-yl)nicotinamide using a procedure analogous to that described in Example 198 Step 2, followed by procedures analogous to those described in Example 199 Steps 2 and 3. LC-MS Method 2 $t_R$=1.012, m/z=485.1; $^1$H NMR (CDCl$_3$) 0.79 (m, 1H), 1.19 (m, 2H), 1.76 (m, 3H), 1.92 (m, 2H), 2.17 (m, 1H), 2.28 (m, 1H), 2.68 (m, 1H), 2.79 (m, 2H), 3.00 (s, 6H), 3.20 (m, 1H), 3.51 (t, 2H), 3.84 (m, 1H), 4.12 (dd, 1H), 4.24 (m, 1H), 6.52 (d, 1H), 7.02 (t, 2H), 7.22 (m, 2H), 7.53 (dd, 1H), 8.19 (d, 1H).

Example 601

(R)-3-((S)-1-(4-bromophenyl)ethyl)-6-(2-(5-methyl-1,3,4-thiadiazol-2-yl)ethyl)-6-phenyl-1,3-oxazinan-2-one

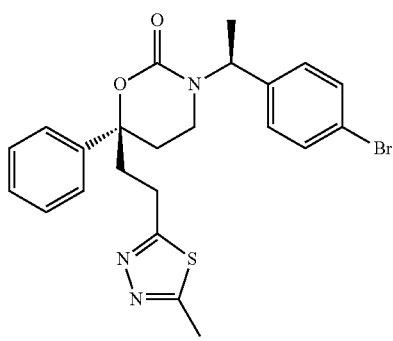 [SMILES: Cc1nnc(CC[C@]2(c3ccccc3)CCN([C@@H](C)c3ccc(Br)cc3)C(=O)O2)s1]

The title compound was prepared from N'-acetyl-3-((R)-3-((S)-1-(4-bromophenyl)ethyl)-2-oxo-6-phenyl-1,3-oxazinan-6-yl)propanehydrazide following procedures analogous to those described in Example 531. LC-MS Method 2 $t_R$=1.403, m/z=487.9; $^1$H NMR (CD$_3$OD) 1.49 (d, 3H), 2.20-2.31 (m, 2H), 2.33-2.44 (m, 2H), 2.52 (m, 1H), 2.63 (s, 3H), 2.81 (m, 1H), 3.06 (m, 1H), 3.20 (m, 1H), 3.81 (s, 1H), 5.47 (m, 1H), 6.82 (d, 2H), 7.21 (m, 2H), 7.30 (m, 2H), 7.34-7.46 (m, 3H).

Example 602

N-(3-((R)-3-((S)-1-(4-chloro-2-fluorophenyl)ethyl)-6-(4-fluorophenyl)-2-oxo-1,3-oxazinan-6-yl)propyl)methanesulfonamide

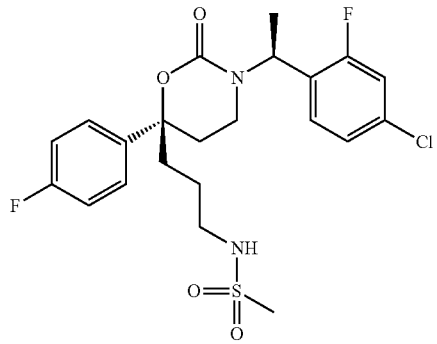 [SMILES: C[C@@H](c1ccc(Cl)cc1F)N1CC[C@](CCCNS(C)(=O)=O)(c2ccc(F)cc2)OC1=O]

The title compound was prepared from (R)-3-((S)-1-(4-chloro-2-fluorophenyl)ethyl)-6-(4-fluorophenyl)-6-(3-hydroxypropyl)-1,3-oxazinan-2-one following procedures analogous to those described in Example 359. LC-MS Method 1 $t_R$=1.7, m/z=487 (M+1); $^1$H NMR (CDCl$_3$) 7.12-7.09 (m, 2H), 7.03 (t, 1H, J=8.1 Hz), 6.97-6.93 (m, 3H), 684 (dd, 1H, J=10.0, 2.1 Hz), 5.56 (q, 1H, J=7.1 Hz), 4.33 (br m, 1H), 2.99 (q, 2H, J=6.4 Hz), 2.94-2.88 (m, 1H), 2.84 (s, 3H), 2.24-2.02 (m, 3H), 1.98-1.81 (m, 2H), 1.68-1.58 (m, 1H), 1.44 (d, 3H, J=7.3 Hz), 1.31-1.19 (m, 1H).

Example 603

2,2-dimethyl-3-((R)-3-((S)-1-(4-(1-methyl-2-oxo-1,2-dihydropyridin-4-yl)phenyl)ethyl)-2-oxo-6-phenyl-1,3-oxazinan-6-yl)propanamide

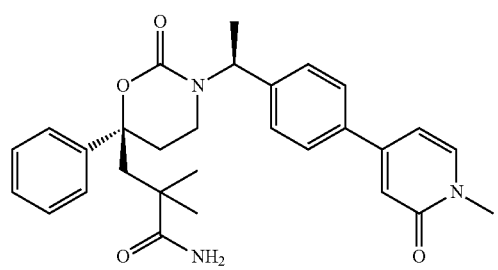 [SMILES: C[C@@H](c1ccc(-c2ccn(C)c(=O)c2)cc1)N1CC[C@](CC(C)(C)C(N)=O)(c2ccccc2)OC1=O]

The title compound was prepared from 3-((R)-3-((S)-1-(4-bromophenyl)ethyl)-2-oxo-6-phenyl-1,3-oxazinan-6-yl)-2,2-dimethylpropanenitrile following procedures analogous to those described in Example 313 Steps 3 and 4 using 4-bromo-1-methylpyridin-2(1H)-one in Step 4, followed by a procedure analogous to that described in Example 598. LC-MS Method 2 $t_R$=1.133, m/z=488.1; $^1$H NMR (CDCl$_3$) 1.12 (s, 3H), 1.19 (s, 3H), 1.49 (d, 3H), 2.09-2.28 (m, 3H), 2.32-2.58 (m, 2H), 2.89 (m, 1H), 3.59 (s, 3H), 5.61 (m, 1H), 6.54 (m, 1H), 6.88 (m, 1H), 6.97-7.10 (m, 2H), 7.28 (m, 6H), 7.42 (m, 1H), 7.53 (m, 1H).

Example 604

6-(4-*(S)-1-((R)-6-(2-(5-methyl-1,3,4-oxadiazol-2-yl)ethyl)-2-oxo-6-phenyl-1,3-oxazinan-3-yl)ethyl)phenyl)nicotinonitrile

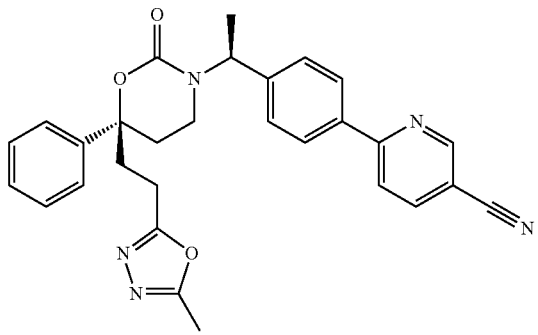

The title compound was prepared from N'-acetyl-3-((R)-3-((S)-1-(4-(5-cyanopyridin-2-yl)phenyl)ethyl)-2-oxo-6-phenyl-1,3-oxazinan-6-yl)propanehydrazide following a procedure analogous to that described in Example 530 Alternative Step 3. LC-MS Method 2 tR=1.265, m/z=494.1; 1H NMR (CDCl3) 1.59 (d, 3H), 2.06 (m, 1H), 2.33 (m, 5H), 2.48 (s, 2H), 2.52-2.71 (m, 2H), 2.97 (m, 1H), 3.09 (m, 1H), 5.72 (m, 1H), 7.08 (d, 2H), 7.29 (m, 2H), 7.32 (m, 2H), 7.34-7.58 (m, 2H), 7.77 (m, 2H), 7.99 (d, 1H), 8.89 (s, 1H).

Example 605

N-(3-((R)-3-((S)-1-(4-bromophenyl)ethyl)-6-(4-fluorophenyl)-2-oxo-1,3-oxazinan-6-yl)-2,2-dimethylpropyl)acetamide

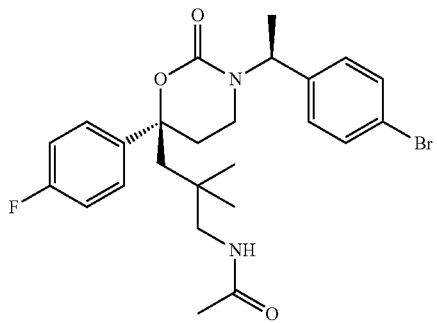 [SMILES: CC(=O)NCC(C)(C)C[C@]1(c2ccc(F)cc2)CCN([C@@H](C)c2ccc(Br)cc2)C(=O)O1]

The title compound was prepared from (R)-6-(3-amino-2,2-dimethylpropyl)-3-((S)-1-(4-bromophenyl)ethyl)-6-(4-fluorophenyl)-1,3-oxazinan-2-one following a procedure analogous to that described in Example 98. LC-MS Method 1 $t_R$=1.78, m/z=505, 507 (M+1); 1H NMR (CD3OD) 7.26-7.23 (m, 4H), 7.01 (t, J=8.8 Hz, 2H), 6.89 (d, J=8.2 Hz, 2H), 5.44 (q, J=7.0 Hz, 1H), 2.98-2.94 (m, 1H), 2.90 (s, 2H), 2.30-2.25 (m, 1H), 2.20-2.12 (m, 1H), 2.10-2.03 (m, 1H), 1.94 (d, J=15 Hz, 1H), 1.88 (d, J=15 Hz, 1H), 1.88 (s, 3H), 1.43 (d, J=7.0 Hz, 3H), 0.69 (s, 3H), 0.59 (s, 3H).

Example 606 methyl 1-((S)-3-((S)-1-(4-bromophenyl)ethyl)-6-(4-fluorophenyl)-2-oxo-1,3-oxazinan-6-yl)-2-methylpropan-2-ylcarbamate

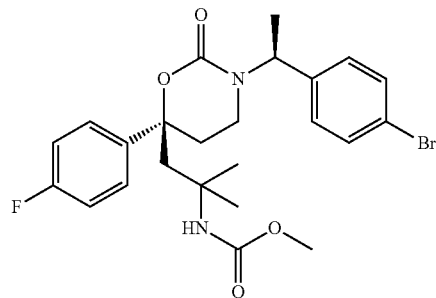 [SMILES: COC(=O)NC(C)(C)C[C@]1(c2ccc(F)cc2)CCN([C@@H](C)c2ccc(Br)cc2)C(=O)O1]

The title compound was prepared from (R)-6-(3-amino-2,2-dimethylpropyl)-3-((S)-1-(4-bromophenyl)ethyl)-6-(4-fluorophenyl)-1,3-oxazinan-2-one following a procedure analogous to that described in Example 180. LC-MS Method 1 $t_R$=1.87, m/z=507, 509 (M+1); 1H NMR (CD3OD) 7.23-7.19 (m, 4H), 6.98 (t, J=8.8 Hz, 2H), 6.83 (d, J=8.2 Hz, 2H), 5.41 (q, J=7.0 Hz, 1H), 3.33 (s, 3H), 2.98-2.93 (m, 1H), 2.45 (d, J=15 Hz, 1H), 2.28-2.16 (m, 3H), 2.13-2.06 (m, 1H), 1.42 (d, J=7.0 Hz, 3H), 1.17 (s, 3H), 1.14 (s, 3H).

Example 607

6-(4-((S)-1-((R)-6-(2-(5-methyl-1,3,4-thiadiazol-2-yl)ethyl)-2-oxo-6-phenyl-1,3-oxazinan-3-yl)ethyl)phenyl)nicotinonitrile

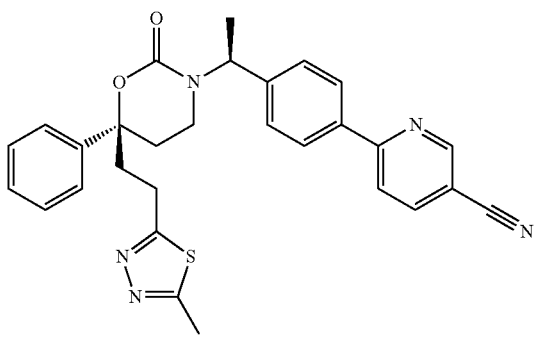

The title compound was prepared from N'-acetyl-3-((R)-3-((S)-1-(4-(5-cyanopyridin-2-yl)phenyl)ethyl)-2-oxo-6-phenyl-1,3-oxazinan-6-yl)propanehydrazide following a procedure analogous to that described in Example 531. LC-MS Method 2 $t_R$=1.306, m/z=511.1; 1H NMR (CDCl3) 1.59 (d, 3H), 2.25 (m, 1H), 2.43 (m, 2H), 2.49 (m, 2H), 2.74 (s, 3H), 2.82 (m, 1H), 2.99 (m, 1H), 3.31 (m, 1H), 5.72 (m, 1H), 7.09 (d, 2H), 7.31 (m, 3H), 7.40 (m, 2H), 7.72-7.87 (m, 3H), 8.00 (d, 1H), 8.91 (s, 1H).

Example 608

N-(3-((R)-3-((S)-1-(4-bromophenyl)ethyl)-6-(4-fluorophenyl)-2-oxo-1,3-oxazinan-6-yl)-2,2-dimethylpropyl)methanesulfonamide

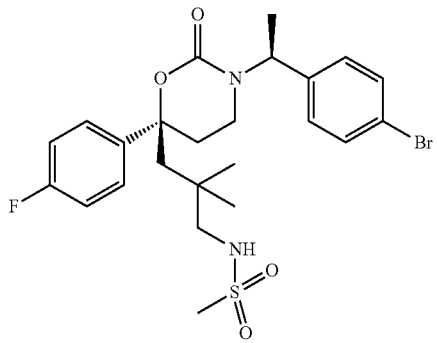 [SMILES: C[C@@H](c1ccc(Br)cc1)N1CC[C@](CC(C)(C)CNS(C)(=O)=O)(c2ccc(F)cc2)OC1=O]

The title compound was prepared from (R)-6-(3-amino-2,2-dimethylpropyl)-3-((S)-1-(4-bromophenyl)ethyl)-6-(4-fluorophenyl)-1,3-oxazinan-2-one following a procedure analogous to that described in Example 99. LC-MS Method 1 $t_R$=1.89, m/z=541, 543 (M+1); $^1$H NMR (CD$_3$OD) 7.28-7.24 (m, 4H), 7.03 (t, J=8.8 Hz, 2H), 6.92 (d, J=8.2 Hz, 2H), 5.45 (q, J=7.0 Hz, 1H), 3.01-2.96 (m, 1H), 2.85 (s, 3H), 2.84 (d, J=13 Hz, 1H), 2.67 (d, J=13 Hz, 1H), 2.30-2.25 (m, 1H), 2.21-2.13 (m, 1H), 2.11-2.04 (m, 1H), 2.02 (d, J=15 Hz, 1H), 1.93 (d, J=15 Hz, 1H), 1.45 (d, J=7.0 Hz, 3H), 0.68 (s, 3H), 0.66 (s, 3H).

Example 609

(R)-6-(4-fluorophenyl)-6-(3-hydroxypropyl)-3-((S)-1-(4-(2-methoxypyridin-4-yl)phenyl)ethyl)-1,3-oxazinan-2-one

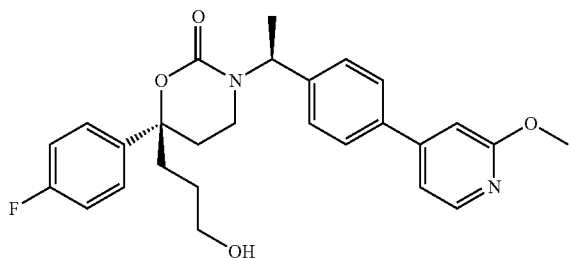 [SMILES: COc1cc(-c2ccc([C@H](C)N3CC[C@](CCCO)(c4ccc(F)cc4)OC3=O)cc2)ccn1]

The title compound was prepared from (R)-3-((S)-1-(4-bromophenyl)ethyl)-6-(4-fluorophenyl)-6-(3-hydroxypropyl)-1,3-oxazinan-2-one and 2-methoxypyridin-4-ylboronic acid following a procedure analogous to that described in Example 75 Step 1. LC-MS Method 1 $t_R$=1.9 min, m/z=447 (M+1); $^1$H NMR (CDCl$_3$) 8.29 (1H, d, J=5.5 Hz), 7.34 (2H, m), 7.21-7.15 (m, 3H), 7.02-6.93 (5H, m), 5.67-5.61 (1H, m), 4.05 (3H, s), 3.53 (1H, t, J=6.41 Hz), 2.97-2.93 (1H, m), 2.33-2.11 (3H, m), 2.06-1.83 (3H, m), 1.67-1.57 (1H, m), 1.50 (3H, d, J=7.03), 1.36-1.26 (1H, m).

Example 610

(R)-6-(4-fluorophenyl)-3-((S)-1-(4-(5-fluoropyridin-3-yl)phenyl)ethyl)-6-(3-hydroxypropyl)-1,3-oxazinan-2-one

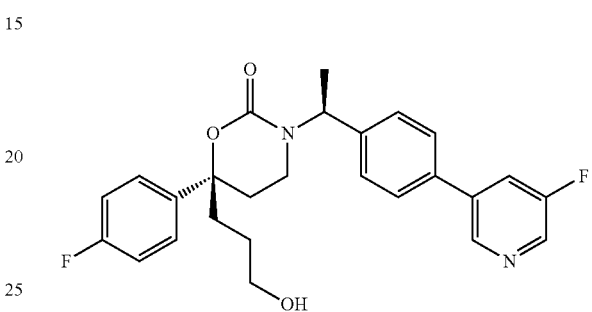

The title compound was prepared from (R)-3-((S)-1-(4-bromophenyl)ethyl)-6-(4-fluorophenyl)-6-(3-hydroxypropyl)-1,3-oxazinan-2-one and 5-fluoropyridin-3-ylboronic acid following a procedure analogous to that described in Example 75 Step 1. LC-MS Method 1 tR=1.5 min, m/z=453 (M+1).

Example 611

6-((S)-3-((R)-6-(4-fluorophenyl)-6-(3-hydroxypropyl)-2-oxo-1,3-oxazinan-3-yl)piperidin-1-yl)nicotinonitrile

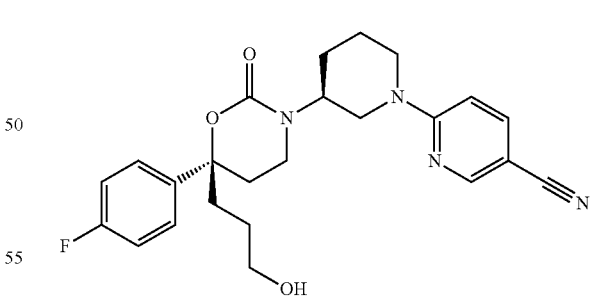

The title compound was prepared from (R)-6-(4-fluorophenyl)-6-(3-hydroxypropyl)-3-((S)-piperidin-3-yl)-1,3-oxazinan-2-one and 2-bromo-5-cyanopyridine following a procedure analogous to that described in Example 508. LC-MS Method 2 tR=1.218 min, m/z=439.1; $^1$H NMR (CDCl$_3$) 1.21-1.36 (m, 1H), 1.62 (m, 1H), 1.78 (m, 3H), 1.56 (m, 2H), 1.86-2.00 (m, 2H), 2.19 (m, 1H), 2.29 (m, 1H), 2.67-2.86 (m, 3H), 3.20 (m, 1H), 3.50 (t, 2H), 3.79 (m, 1H), 4.12 (m, 1H), 4.30 (d, 1H), 6.53 (m, 1H), 7.01 (t, 2H), 7.24 (m, 2H), 7.51 (d, 1H), 8.30 (s, 1H).

Example 612

Methyl 2-((R)-3-((S)-1-(4-bromophenyl)ethyl)-6-(4-fluorophenyl)-2-oxo-1,3-oxazinan-6-yl)ethylcarbamate

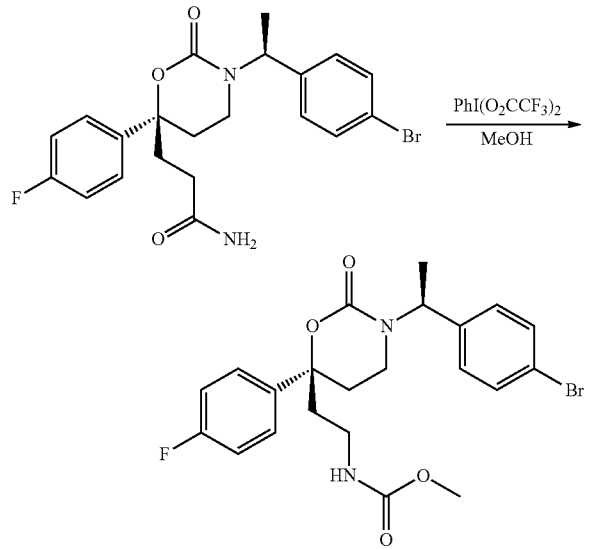

To a solution of 3-((R)-3-((S)-1-(4-bromophenyl)ethyl)-6-(4-fluorophenyl)-2-oxo-1,3-oxazinan-6-yl)propanamide (0.0135 g, 0.03 mmol, 1.0 equiv) in MeOH (10 mL) was added PhI(OCOCF$_3$)$_2$ (0.0649 g, 0.15 mmol, 5 equiv) at room temperature. The resulting mixture was stirred at room temperature for 24 h. The reaction mixture was purified by reversed-phase HPLC (SunFire™ Prep C$_{18}$ OBD™ 5 μm 19×250 mm column, 10%→90% CH$_3$CN/H$_2$O, 0.1% CF$_3$COOH over 13 min and then 90% CH$_3$CN/H$_2$O, 0.1% CF$_3$COOH over 4 min, flow rate 25 mL/min) to afford 0.0070 g (49%) of methyl 2-((R)-3-((S)-1-(4-bromophenyl)ethyl)-6-(4-fluorophenyl)-2-oxo-1,3-oxazinan-6-yl)ethylcarbamate. LC-MS Method 1 $t_R$=1.76 min, m/z=479, 481 (MH$^+$); $^1$H NMR (400 MHz, CD$_3$OD) δ 7.27-7.21 (m, 4H), 7.04 (t, J=8.8 Hz, 2H), 6.82 (d, J=8.2 Hz, 2H), 5.43 (q, J=7.0 Hz, 1H), 3.50 (s, 3H), 3.12-3.01 (m, 2H), 2.92-2.85 (m, 1H), 2.39-2.35 (m, 1H), 2.24-2.15 (m, 2H), 2.02 (t, J=7.6 Hz, 2H), 1.44 (d, J=7.0 Hz, 3H); $^{19}$F NMR (376 MHz, CD$_3$OD) δ −117.06 (m).

Example 613

(R)-6-(4-fluorophenyl)-6-(3-hydroxypropyl)-3-((S)-1-(4-(1-methyl-2-oxo-1,2-dihydropyrimidin-4-yl)phenyl)ethyl)-1,3-oxazinan-2-one

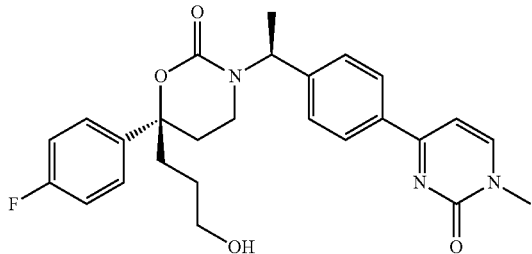 [SMILES: C[C@@H](c1ccc(-c2ccn(C)c(=O)n2)cc1)N1CC[C@](CCCO)(c2ccc(F)cc2)OC1=O]

The title compound was prepared from (R)-6-(4-fluorophenyl)-6-(3-hydroxypropyl)-3-((S)-1-(4-(2-hydroxypyrimidin-4-yl)phenyl)ethyl)-1,3-oxazinan-2-one using procedures analogous to those described in Example 460 Steps 4, 5 and 6. LC-MS Method 2 $t_R$=1.079 min, m/z=466.2; $^1$H NMR (CD$_3$OD) 1.20 (m, 3H), 1.49 (d, 3H), 1.78-1.91 (m, 2H), 2.08 (s, 1H), 2.14 (m, 1H), 2.28 (m, 1H), 2.39 (m, 1H), 3.07 (m, 1H), 3.36 (m, 3H), 3.50 (s, 3H), 4.50 (s, 2H), 5.49 (m, 1H), 6.90 (d, 1H), 6.95-7.08 (m, 4H), 7.21 (m, 2H), 7.80 (d, 2H), 8.06 (d, 1H).

Example 614

(S)-3-((S)-1-(4-(1-ethyl-6-oxo-1,6-dihydropyridin-3-yl)phenyl)propyl)-6-(2-hydroxy-2-methylpropyl)-6-phenyl-1,3-oxazinan-2-one

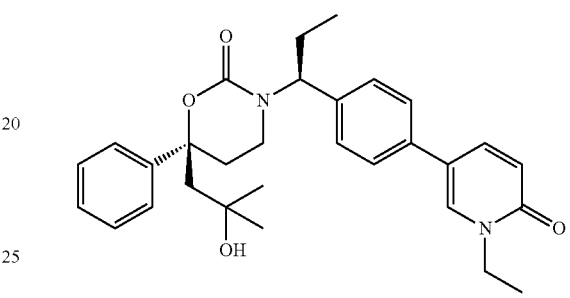

The title compound was prepared from (R)-6-allyl-3-((S)-1-(4-bromophenyl)propyl)-6-phenyl-1,3-oxazinan-2-one following a procedure analogous to that described in Example 459 Method 2 using 5-bromo-1-ethylpyridin-2(1H)-one in Step 4. LC-MS Method 2 $t_R$=1.732 min, m/z=475.1; $^1$H NMR (CDCl$_3$) 0.95 (s, 3H), 1.01 (t, 3H), 1.26 (s, 3H), 1.38 (t, 3H), 2.06 (m, 2H), 2.18-2.31 (m, 3H), 2.36 (m, 1H), 2.55 (m, 1H), 3.04 (m, 1H), 4.11 (m, 2H), 5.37 (m, 1H), 6.66 (d, 1H), 7.11 (m, 2H), 7.20-7.33 (m, 7H), 7.76 (d, 1H), 7.88 (s, 1H).

Example 615

(S)-3-((S)-1-(4-(1-ethyl-6-oxo-1,6-dihydropyridin-3-yl)phenyl)ethyl)-6-(2-hydroxy-2-methylpropyl)-6-phenyl-1,3-oxazinan-2-one

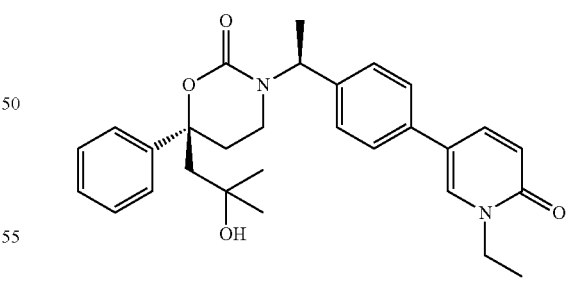

The title compound was prepared from (R)-6-allyl-3-((S)-1-(4-bromophenyl)ethyl)-6-phenyl-1,3-oxazinan-2-one following a procedure analogous to that described in Example 459 Method 2 using 5-bromo-1-ethylpyridin-2(1H)-one in Step 4. LC-MS Method 2 $t_R$=1.224 min, m/z=475.1; $^1$H NMR (CDCl$_3$) 1.11 (s, 3H), 1.19 (s, 3H), 1.39 (t, 3H), 1.56 (d, 3H), 2.20 (s, 2H), 2.26 (m, 1H), 2.36-2.57 (m, 2H), 2.87 (m, 1H), 4.03 (m, 2H), 5.69 (m, 1H), 6.62 (d, 1H), 7.00 (d, 2H), 7.17 (d, 2H), 7.28-7.51 (m, 6H), 7.50 (d, 1H).

Example 616

(S)-6-(2-hydroxy-2-methylpropyl)-3-((S)-1-(4-(1-methyl-6-oxo-1,6-dihydropyridin-3-yl)phenyl)propyl)-6-phenyl-1,3-oxazinan-2-one

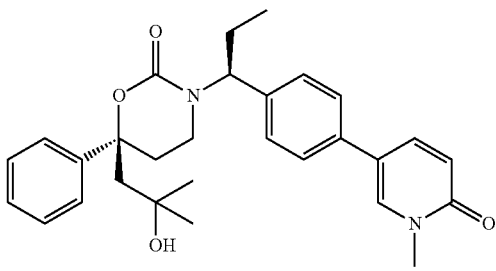 [SMILES: CC[C@@H](c1ccc(-c2ccc(=O)n(C)c2)cc1)N1CC[C@](CC(C)(C)O)(c2ccccc2)OC1=O]

The title compound was prepared from (R)-6-allyl-3-((S)-1-(4-bromophenyl)propyl)-6-phenyl-1,3-oxazinan-2-one following a procedure analogous to that described in Example 459 Method 2 using 5-bromo-1-methylpyridin-2(1H)-one in Step 4. LC-MS Method 2 $t_R$=1.746 min, m/z=475.2; $^1$H NMR (CD$_3$OD) 1.04 (t, 3H), 1.11 (s, 3H), 1.24 (s, 3H), 1.95-2.04 (m, 2H), 2.13-2.26 (m, 4H), 2.44 (m, 1H), 2.91 (m, 1H), 3.61 (s, 3H), 5.36 (m, 1H), 6.67 (d, 1H), 7.10-7.33 (m, 8H), 7.42 (s, 1H), 7.55 (d, 1H).

Example 617

(S)-6-(2-hydroxy-2-methylpropyl)-3-((S)-1-(4-(1-methyl-6-oxo-1,6-dihydropyridazin-3-yl)phenyl)ethyl)-6-phenyl-1,3-oxazinan-2-one

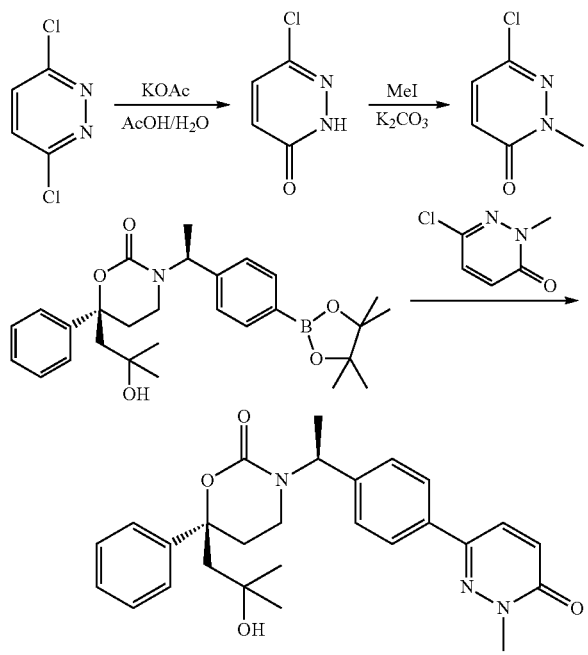

Step 1. 6-chloro-2H-pyridazin-3-one

To a solution of 3,6-dichloro-pyridazine (1 g, 0.006759 mol) in AcOH/H$_2$O (5/1) (20 mL) was added KOAc (0.662 g, 0.006759 moL), and the mixture was heated to 140° C. for 70 min under microwave conditions. The vial was cooled and the solvent was evaporated in vacuo. EtOAc and H$_2$O were added. The layers were separated, and the aqueous layer was extracted with EtOAc. The combined organic phase was washed brine, dried over Na$_2$SO$_4$, and concentrated to give 6-chloro-2H-pyridazin-3-one (0.813 g, 92.5%). $^1$H NMR (CDCl$_3$): 6.96 (d, 1H), 7.25 (d, 1H).

Step 2. 6-chloro-2-methylpyridazin-3(2H)-one

To a solution of 6-chloropyridazin-3(2H)-one (600 mg, 4.23 mmol) were added potassium carbonate (1.2 g, 8.46 mmol) and methyl iodide (1.2 g, 8.46 mmol) in DMF (3 mL). The resulting mixture was stirred at 25° C. for 4 h. After the reaction, water was added to the reaction solution, followed by extraction with EtOAc. The organic layer was washed with water and brine, dried over sodium sulfate and then filtered. The filtrate was concentrated under reduced pressure to give the residue which was purified by column chromatography to give 6-chloro-2-methylpyridazin-3(2H)-one (550 mg, 91%). $^1$H NMR (CDCl$_3$): 3.76 (s, 3H), 6.92 (d, 1H), 7.19 (d, 1H).

Step 3. (S)-6-(2-hydroxy-2-methylpropyl)-3-((S)-1-(4-(1-methyl-6-oxo-1,6-dihydro pyridazin-3-yl)phenyl)ethyl)-6-phenyl-1,3-oxazinan-2-one To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (774 mg, 1.62 mmol), 6-chloro-2-methylpyridazin-3(2H)-one (244.8 mg, 1.7 mmol), PdCl$_2$(PPh$_3$)$_2$ (77.4 mg, 10%) and aqueous solution of Cs$_2$CO$_3$ (2 mol/L, 1.6 mL) in 1,4-dioxane (15 mL) was heated to reflux overnight. The reaction was quenched with water. The organic layer was separated, dried, and concentrated to give the residue, which was purified by column chromatography to give (R)-6-(4-fluorophenyl)-6-(3-hydroxypropyl)-3-((S)-1-(4-(2-methylpyrimidin-5-yl)phenyl)ethyl)-1,3-oxazinan-2-one (321 mg, 43%). LC-MS Method 2 $t_R$=1.158 min, m/z=404; $^1$H NMR (CDCl$_3$): 1.12 (s, 3H), 1.18 (s, 3H), 1.54 (d, 3H), 2.18-2.27 (m, 4H), 2.33-2.48 (m, 1H), 2.82-2.92 (m, 1H), 3.86 (s, 3H), 5.70 (m, 1H), 6.99 (d, 2H), 7.05 (d, 2H), 7.26-7.50 (m, 5H), 7.51 (m, 2H), 7.57 (d, 1H).

Example 618

(S)-6-(2-hydroxy-2-methylpropyl)-3-((S)-1-(4-(1-methyl-2-oxo-1,2-dihydropyridin-4-yl)phenyl)propyl)-6-phenyl-1,3-oxazinan-2-one

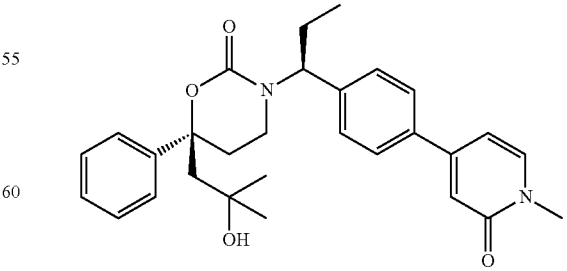

The title compound was prepared from (R)-6-allyl-3-((S)-1-(4-bromophenyl)propyl)-6-phenyl-1,3-oxazinan-2-one following a procedure analogous to that described in Example 459 Method 2 using 4-bromo-1-methylpyridin-2(1H)-one in Step 4. LC-MS Method 2 $t_R$=1.203 min, m/z=971.4; $^1$H NMR (CDCl$_3$) 0.97 (t, 3H), 1.12 (s, 3H), 1.19 (s, 3H), 1.79-2.02 (m, 2H), 2.11-2.24 (m, 4H), 2.29-2.42 (m, 1H), 2.81 (m, 1H), 3.50 (s, 3H), 5.40 (m, 1H), 6.28 (d, 1H), 6.64 (s, 1H), 7.02 (d, 2H), 7.18 (m, 3H), 7.20 (m, 2H), 7.28 (m, 3H).

Example 619

(S)-6-(2-hydroxy-2-methylpropyl)-3-((S)-1-(4-(2-methylpyrimidin-5-yl)phenyl)ethyl)-6-phenyl-1,3-oxazinan-2-one

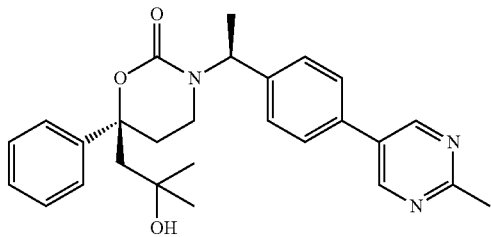 [SMILES: Cc1ncc(-c2ccc([C@H](C)N3CC[C@](CC(C)(C)O)(c4ccccc4)OC3=O)cc2)cn1]

The title compound was prepared from (S)-6-(2-hydroxy-2-methylpropyl)-6-phenyl-3-((S)-1-(4-(4, 4,5,5-tetramethyl-1,3,2-dioxaborolan-2-yl)phenyl)ethyl)-1,3-oxazinan-2-one and 2-methyl-5-bromopyrimidine following a procedure analogous to that described in Example 459 Step 4. LC-MS Method 2 $t_R$=1.221 min, m/z=468.2; $^1$H NMR (CDCl$_3$) 1.06 (s, 3H), 1.12 (s, 3H), 1.49 (d, 3H), 2.11-2.28 (m, 4H), 2.31-2.42 (m, 1H), 2.70 (s, 3H), 2.82 (m, 1H), 5.65 (m, 1H), 7.00 (d, 2H), 7.21-7.34 (m, 7H), 8.19 (s, 2H).
Method 2

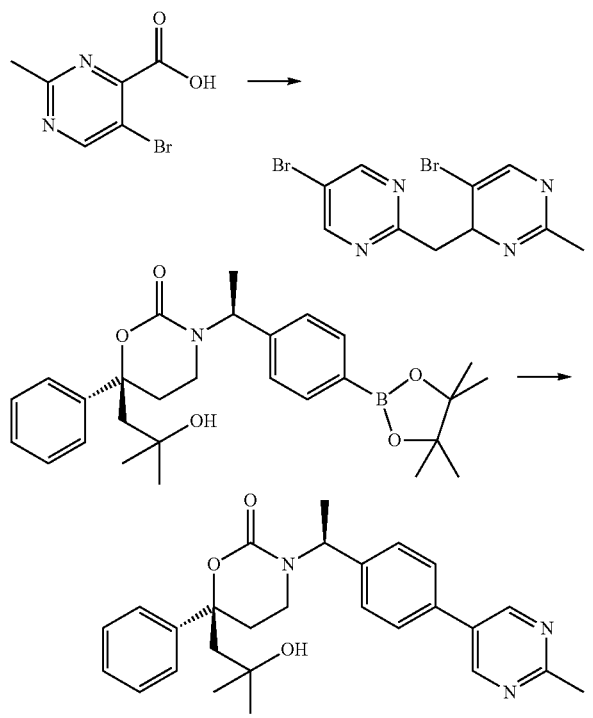

Step 1. 5-Bromo-2-(5-bromo-2-methyl-1,4-dihydro-pyrimidin-4-ylmethyl)-pyrimidine 5-Bromo-2-methyl-pyrimidine-4-carboxylic acid (5.0 g) was heated above its melting point (m$_p$ 176° C.) during which decarboxylation takes place. After cooling to ambient temperature, the tar-like substance was purified by chromatography on silica gel (CH$_2$Cl$_2$/MeOH 90:10→70:30) to afford the title compound as a black liquid. Yield: 0.45 g (6% of theory). Mass spectrum (ESI$^+$): m/z=345/347/349 (2 Br) [M+H]$^+$ Step 2. (S)-6-(2-Hydroxy-2-methyl-propyl)-3-{(S)-1-[4-(2-methyl-pyrimidin-5-yl)-phenyl]-ethyl}-6-phenyl-[1,3]oxazinan-2-one 2 M aqueous Na$_2$CO$_3$ solution (1.67 mL) was added to a solution of (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.80 g) and 5-bromo-2-(5-bromo-2-methyl-1,4-dihydro-pyrimidin-4-ylmethyl)-pyrimidine (0.40 g) in dimethylformamide (5 mL). The resulting mixture was sparged with argon for 5 min, before [1,1'-bis(diphenylphosphino)ferrocene]-dichloropalladium (II) dichloromethane complex (82 mg) was added. The mixture was heated to 100° C. and stirred at this temperature overnight. After cooling to ambient temperature, water was added, and the resulting mixture was extracted with ethyl acetate. The combined organic extracts were washed with brine, dried (MgSO$_4$), and concentrated. The residue was purified by chromatography on silica gel (CH$_2$Cl$_2$/MeOH 95:5→80:20) followed by HPLC (MeCN/H$_2$O/NH$_4$OH) to afford the title compound (340 mg) which was crystallized from iPr$_2$O. Yield: 0.25 g (34% of theory). Mass spectrum (ESI$^+$): m/z=446 [M+H]$^+$ Example 620 ethyl 2-((R)-3-((S)-1-(4-bromophenyl)ethyl)-6-(4-fluorophenyl)-2-oxo-1,3-oxazinan-6-yl)ethylcarbamate

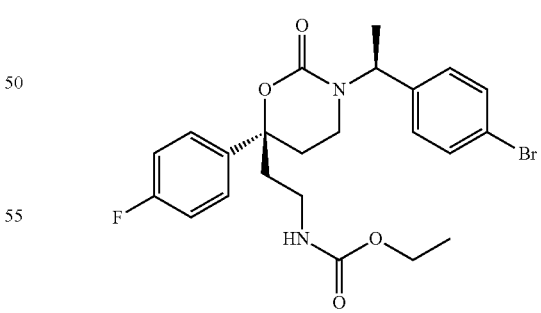

The title compound was prepared from 3-((R)-3-((S)-1-(4-bromophenyl)ethyl)-6-(4-fluorophenyl)-2-oxo-1,3-oxazinan-6-yl)propanamide following a procedure analogous to that described in Example 612 using ethanol as solvent. LC-MS Method 1 $t_R$=1.83 min, m/z=493, 495 (M+1); $^1$H NMR (CD$_3$OD) 7.25-7.20 (m, 4H), 7.03 (t, J=8.8 Hz, 2H), 6.81 (d, J=8.2 Hz, 2H), 5.41 (q, J=7.3 Hz, 1H), 3.91 (q, J=7.2 Hz, 2H), 3.10-3.00 (m, 2H), 2.90-2.85 (m, 1H), 2.38-2.34 (m, 1H), 2.22-2.14 (m, 2H), 2.01 (t, J=7.6 Hz, 2H), 1.42 (d, J=7.3 Hz, 3H), 1.10 (t, J=7.2 Hz, 3H).

Example 621

(S)-6-(2-amino-2-methylpropyl)-3-((S)-1-(4-bromophenyl)ethyl)-6-(4-fluorophenyl)-1,3-oxazinan-2-one

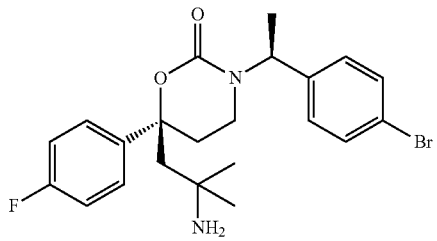 [SMILES: C[C@@H](c1ccc(Br)cc1)N1CC[C@](CC(C)(C)N)(c2ccc(F)cc2)OC1=O]

The title compound was prepared from 3-((R)-3-((S)-1-(4-bromophenyl)ethyl)-6-(4-fluorophenyl)-2-oxo-1,3-oxazinan-6-yl)propanamide following a procedure analogous to that described in Example 612 using t-butanol as solvent followed by treatment with 2 N aq HCl/CH$_3$CN at rt. LC-MS Method 1 t$_R$=1.41 min, m/z=449, 451 (M+1); $^1$H NMR (CD$_3$OD) 7.28-7.20 (m, 4H), 7.04 (t, J=8.6 Hz, 2H), 6.96 (d, J=8.2 Hz, 2H), 5.46 (q, J=7.0 Hz, 1H), 2.99-2.94 (m, 1H), 2.34-2.28 (m, 3H), 2.16-2.07 (m, 2H), 1.43 (d, J=7.0 Hz, 3H), 1.13 (s, 3H), 0.90 (s, 3H).

Example 622

(R)-6-ethyl-3-((S)-1-(4-(1-methyl-6-oxo-1,6-dihydropyridin-3-yl)phenyl)propyl)-6-phenyl-1,3-oxazinan-2-one

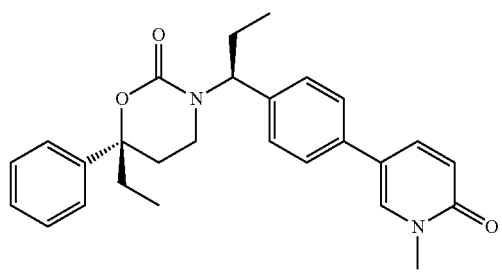 [SMILES: CC[C@@H](c1ccc(-c2ccc(=O)n(C)c2)cc1)N1CC[C@](CC)(c2ccccc2)OC1=O]

The title compound was prepared from (R)-3-((S)-1-(4-bromophenyl)propyl)-6-ethyl-6-phenyl-1,3-oxazinan-2-one following procedures analogous to those described in Example 459 Steps 3 and 4. LC-MS Method 1 t$_R$=1.6 min, m/z=431 (M+1).

(R)-3-((S)-1-(4-bromophenyl)propyl)-6-ethyl-6-phenyl-1,3-oxazinan-2-one was prepared from 1-chloro-3-phenylpentan-3-ol and (S)-1-(4-bromophenyl)propan-1-amine following procedures analogous to those described in Example 353.

1-chloro-3-phenylpentan-3-ol was prepared from 3-chloro-1-phenylpropan-1-one and ethylmagnesium bromide following a procedure analogous to that described in Example 110 Step 1.

Example 623

(R)-6-ethyl-3-((S)-1-(4-(1-ethyl-6-oxo-1,6-dihydropyridin-3-yl)phenyl)propyl)-6-phenyl-1,3-oxazinan-2-one

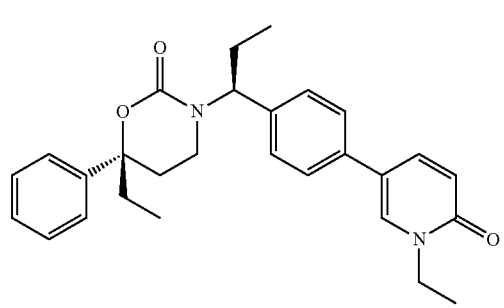 [SMILES: CC[C@@H](c1ccc(-c2ccc(=O)n(CC)c2)cc1)N1CC[C@](CC)(c2ccccc2)OC1=O]

The title compound was prepared from (R)-3-((S)-1-(4-bromophenyl)propyl)-6-ethyl-6-phenyl-1,3-oxazinan-2-one following procedures analogous to those described in Example 459 Steps 3 and 4 using 5-bromo-1-ethylpyridin-2 (1H)-one in Step 4. LC-MS Method 1 t$_R$=1.68 min, m/z=445 (M+1).

Example 624

(R)-6-ethyl-3-((S)-1-(4-(1-methyl-2-oxo-1,2-dihydropyridin-4-yl)phenyl)propyl)-6-phenyl-1,3-oxazinan-2-one

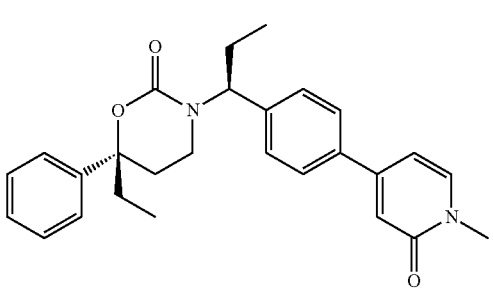 [SMILES: CC[C@@H](c1ccc(-c2ccn(C)c(=O)c2)cc1)N1CC[C@](CC)(c2ccccc2)OC1=O]

The title compound was prepared from (R)-3-((S)-1-(4-bromophenyl)propyl)-6-ethyl-6-phenyl-1,3-oxazinan-2-one following procedures analogous to those described in Example 459 Steps 3 and 4 using 4-iodo-1-methylpyridin-2 (1H)-one in Step 4. LC-MS Method 1 t$_R$=1.58 min, m/z=431 (M+1); $^1$H NMR (CDCl$_3$) 7.33 (1H, d, J=7.03 Hz), 7.29-7.21 (7H, m), 7.01 (2H, d, J=8.20 Hz), 6.75 (1H, d, J=2.05), 6.39 (1H, dd, J=2.05, 7.03), 5.48 (1H, ap dd, J=6.44, 9.66), 3.58

(3H, s), 2.95-2.87 (1H, m), 2.37-2.14 (3H, m), 2.06-1.81 (m, 4H), 1.00 (3H, t, J=7.32), 082 (3H, t, J=7.61).

Example 625

(S)-3-((S)-1-(4-bromophenyl)ethyl)-6-(2-fluoro-2-methylpropyl)-6-(4-fluorophenyl)-1,3-oxazinan-2-one

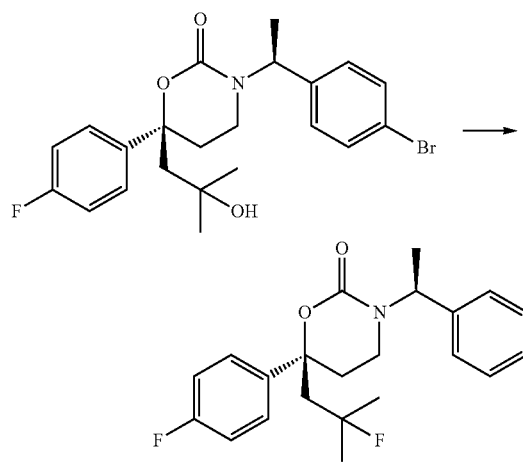

At −78° C., (CH$_3$OCH$_2$CH$_2$)$_2$NSF$_3$ (21 μL, 2 equiv.) was added to a solution of (S)-3-((S)-1-(4-bromophenyl)ethyl)-6-(4-fluorophenyl)-6-(2-hydroxy-2-methylpropyl)-1,3-oxazinan-2-one (26 mg, 0.0058 mmol) in dry CH$_2$Cl$_2$ (1.5 mL). After 20 min, the mixture was warmed to rt slowly. After stirring 2 h at rt LC-MS found the reaction was complete. The mixture was quenched with satd aq NaHCO$_3$ (2 mL), diluted with CH$_2$Cl$_2$ (20 mL). After separation, the aqueous layer was extracted with CH$_2$Cl$_2$ (6 mL). The combined organic layers were dried over Na$_2$SO$_4$. After concentration, the residue was purified by prep HPLC to afford (S)-3-((S)-1-(4-bromophenyl)ethyl)-6-(2-fluoro-2-methylpropyl)-6-(4-fluorophenyl)-1,3-oxazinan-2-one (9.8 mg, 26%). LC-MS Method 1 t$_R$=2.02 min., m/z 452, 454 (M+1); $^1$H NMR (CDCl$_3$) δ 7.25 (m, 4H), 7.05 (m, 2H), 6.77 (m, 2H), 5.59 (q, 1H), 2.89 (m, 1H), 2.50 (m, 1H), 2.34 (m, 1H), 2.28-2.17 (m, 3H), 1.50 (m, 6H), 1.19 (d, 3H); $^{19}$F NMR (CDCl$_3$) δ −114.5, −133.1.

Example 626

N-(1-((S)-3-((S)-1-(4-bromophenyl)ethyl)-6-(4-fluorophenyl)-2-oxo-1,3-oxazinan-6-yl)-2-methylpropan-2-yl)acetamide

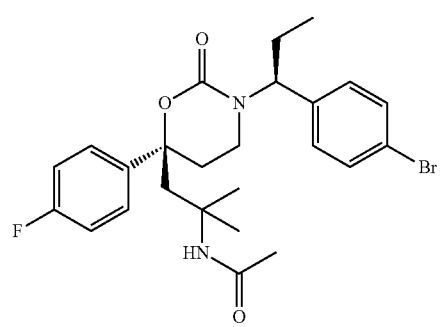 [SMILES: CC[C@@H](c1ccc(Br)cc1)N1CC[C@](CC(C)(C)NC(C)=O)(c2ccc(F)cc2)OC1=O]

The title compound was prepared from (S)-6-(2-amino-2-methylpropyl)-3-((S)-1-(4-bromophenyl)ethyl)-6-(4-fluorophenyl)-1,3-oxazinan-2-one following a procedure analogous to that described in Example 98. LC-MS Method 1 t$_R$=1.7 min, m/z=491, 493 (M+1); $^1$H NMR (CD$_3$OD) 7.25-7.21 (m, 4H), 7.01 (t, J=8.8 Hz, 2H), 6.87 (d, J=8.8 Hz, 2H), 5.43 (q, J=7.0 Hz, 1H), 3.00-2.96 (m, 1H), 2.62 (d, J=15.2 Hz, 1H), 2.33 (d, J=15.2 Hz, 1H), 2.24-2.08 (m, 3H), 1.48 (s, 3H), 1.44 (d, J=7.0 Hz, 3H), 1.24 (s, 3H), 1.16 (s, 3H).

Example 627

6-(4-{1-[6-(2-Hydroxy-2-methyl-propyl)-2-oxo-6-phenyl-[1,3]oxazinan-3-yl]-ethyl}-phenyl)-N-methyl-nicotinamide

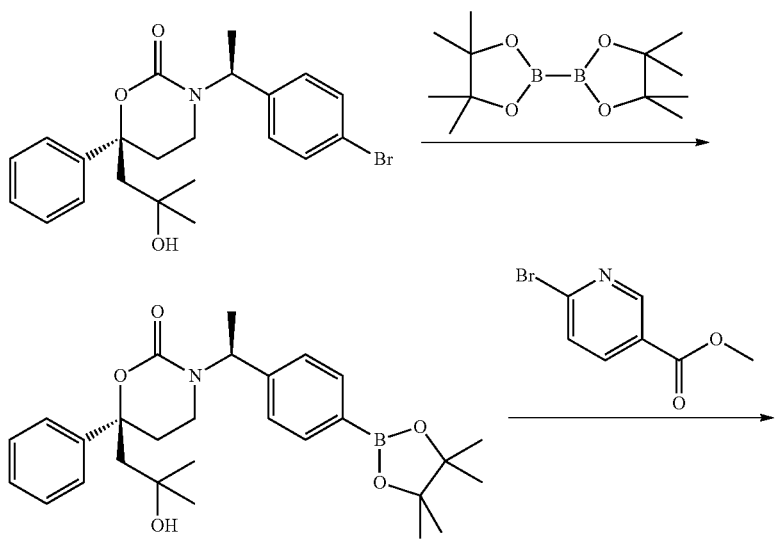

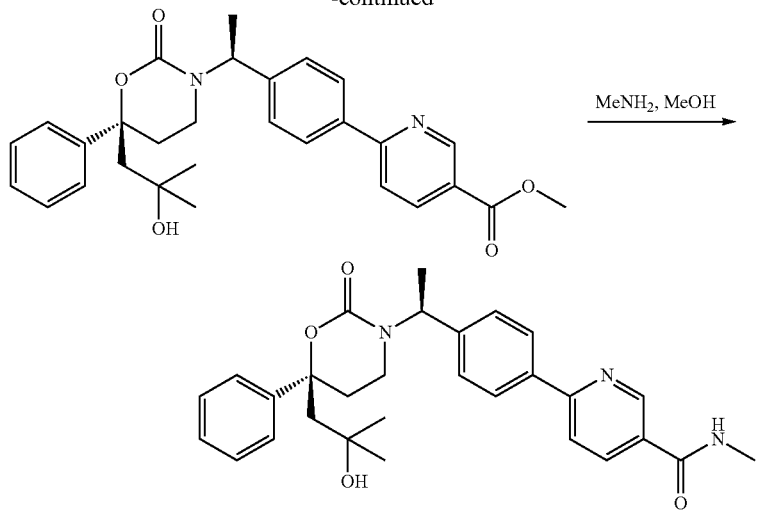

Step 1

To a solution of (S)-3-((S)-1-(4-bromophenyl)ethyl)-6-(2-hydroxy-2-methylpropyl)-6-phenyl-1,3-oxazinan-2-one (6.6 g, 15.2 mmol) and 4,4,4',4',5,5,5',5'-octamethyl-2,2'-bi(1,3,2-dioxaborolane) (6.1 g, 24.3 mmol) in dry DMSO (20 mL) was added KOAc (4.8 g, 48.6 mmol) and Pd(dppf)Cl$_2$ (372 mg, 0.46 mmol). After addition, the mixture was warmed to 100° C. for 20 h. After TLC showed the starting material had disappeared, the solid was filtered off. Water (60 mL) and EtOAc (20 mL) were added, the layers were separated and the aqueous layer was extracted with EtOAc (3×15 mL). The combined organic layer was washed with brine, dried over Na$_2$SO$_4$, filtered and concentrated to give (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (4.4 g, 60%), which was purified by column. $^1$H NMR (CDCl$_3$): 1.03 (s, 3H), 1.12 (s, 3H), 1.22 (s, 12H), 1.49 (d, 3H), 2.13 (m, 4H), 2.26 (m, 1H), 2.73 (m, 1H), 5.64 (q, 1H), 6.91 (d, 2H), 7.38 (m, 5H), 7.51 (d, 2H).

Step 2

To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (500 mg, 1.04 mmol) and methyl 6-bromonicotinate (292 mg, 1.35 mmol) in dry 1,4-dioxane (5 mL) was added CsCO$_3$ (1 mL, 2 mmol) and Pd(PPh$_3$)$_2$Cl$_2$ (50 mg). After addition, the mixture was warmed to 110° C. for 30 min under microwave. After TLC showed the starting material had disappeared, the solid was filtered off. Water (20 mL) and EtOAc (10 mL) was added, the layers were separated and the aqueous layer was extracted with EtOAc (3×10 mL). The combined organic layer was washed with brine, dried over Na$_2$SO$_4$, filtered and concentrated to give methyl 6-(4-((S)-1-((S)-6-(2-hydroxy-2-methylpropyl)-2-oxo-6-phenyl-1,3-oxazinan-3-yl)ethyl)phenyl)nicotinate (507 mg, 89%), which was purified by preparative TLC. $^1$H NMR (CDCl$_3$): 1.13 (s, 3H), 1.19 (s, 3H), 1.61 (d, 3H), 2.24 (m, 4H), 2.37 (m, 1H), 2.88 (m, 1H), 4.02 (s, 3H), 5.76 (q, 1H), 7.11 (d, 2H), 7.29-7.47 (m, 6H), 7.78 (m, 1H), 7.82 (m, 2H), 8.38 (d, 1H), 9.31 (s, 1H).

Step 3

Methyl 6-(4-((S)-1-((S)-6-(2-hydroxy-2-methylpropyl)-2-oxo-6-phenyl-1,3-oxazinan-3-yl)ethyl)phenyl)nicotinate (150 mg, 0.307 mmol) was dissolved in NH$_2$Me/MeOH (10 mL). The mixture was stirred at rt overnight. The solvent was removed in vacuo to give the crude product, which was purified by preparative HPLC and chiral HPLC to afford 6-(4-((S)-1-((S)-6-(2-hydroxy-2-methylpropyl)-2-oxo-6-phenyl-1,3-oxazinan-3-yl)ethyl)phenyl)-N-methylnicotinamide (54 mg, 36%). LC-MS Method 2 t$_R$=1.117 min, m/z=430.1; $^1$H NMR (CD$_3$OD) 0.93 (s, 3H), 1.27 (s, 3H), 1.59 (d, 3H), 2.16 (s, 2H), 2.22-2.37 (m, 1H), 2.41-2.60 (m, 2H), 2.99 (s, 3H), 3.11 (m, 1H), 5.60 (m, 1H), 7.12 (d, 1H), 7.29 (m, 5H), 7.80 (m, 2H), 8.01 (d, 1H), 8.41 (d, 1H), 9.03 (s, 1H).

Example 628

(S)-6-(2-hydroxy-2-methylpropyl)-3-((S)-1-(4-(1-isopropyl-6-oxo-1,6-dihydropyridin-3-yl)phenyl)ethyl)-6-phenyl-1,3-oxazinan-2-one

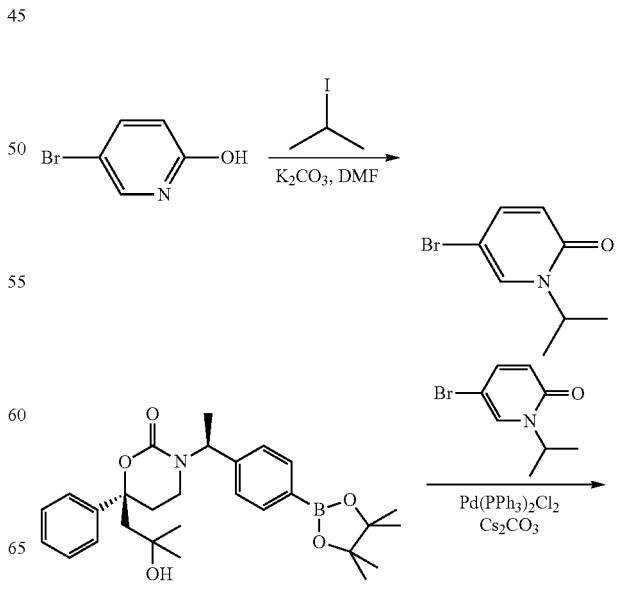

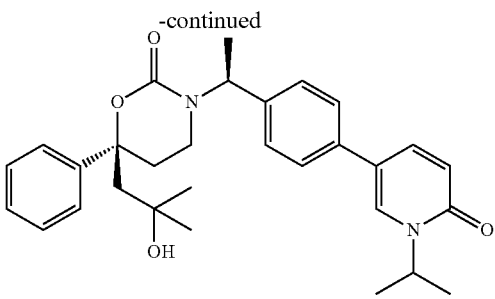

Step 1

To a solution of 5-bromopyridin-2-ol (1 g, 5.75 mmol) in DMF (10 mL) were added 2-iodopropane (4.9 g, 28.75 mmol) and $K_2CO_3$ (4 g, 28.75 mmol). The mixture was stirred at rt overnight. The mixture was diluted with water (20 mL) extracted with EtOAc (3×25 mL), the combined organic phase was washed with brine, dried over $Na_2SO_4$, concentrated and purified by prep TLC to give 5-bromo-1-isopropylpyridin-2(1H)-one (380 mg, 31%). $^1$H NMR (CDCl$_3$): 1.35 (d, 6H), 5.65-5.75 (m, 1H), 6.48 (d, 1H), 7.30 (m, 1H), 7.41 (d, 1H).

Step 2

To a solution of (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one (100 mg, 0.21 mmol) in 1,4-dioxane (2 mL) was added 5-bromo-1-isopropylpyridin-2(1H-one (54.2 mg, 0.25 mmol). Then catalysts of Pd(PPh$_3$)$_2$Cl$_2$ (14 mg, 0.02 mmol), Cs$_2$CO$_3$ (1 mL, 2 M) were added. The vessel was sealed with a septum and placed into the microwave cavity. Microwave irradiation of 100 W was used, the temperature being ramped from room temperature to 120° C. Once this temperature was reached, the reaction mixture was held at this temperature for 30 min. After the mixture cooled to rt, the mixture was filtered. The filtrate was extracted with EtOAc (20 mL×4), the organic layer was washed with brine, dried over Na$_2$SO$_4$ and concentrated to give the crude product which was purified by preparative HPLC to give (S)-6-(2-hydroxy-2-methylpropyl)-3-((S)-1-(4-(1-isopropyl-6-oxo-1,6-dihydropyridin-3-yl)phenyl)ethyl)-6-phenyl-1,3-oxazinan-2-one (22 mg, 21%). $^1$H NMR (CDCl$_3$): 1.13 (s, 3H), 1.19 (s, 3H), 1.40 (6H), 1.53 (d, 3H), 2.18-2.30 (m, 4H), 2.40 (m, 1H), 2.88 (m, 1H), 5.31 (m, 1H), 5.70 (m, 1H), 6.73 (d, 1H), 7.02 (d, 2H), 7.15 (d, 2H), 7.27-7.38 (m, 5H), 7.43 (d, 1H), 7.50 (d, 1H).

Example 629

(S)-6-(2-hydroxy-2-methylpropyl)-3-((S)-1-(4-(5-methylpyrazin-2-yl)phenyl)ethyl)-6-phenyl-1,3-oxazinan-2-one

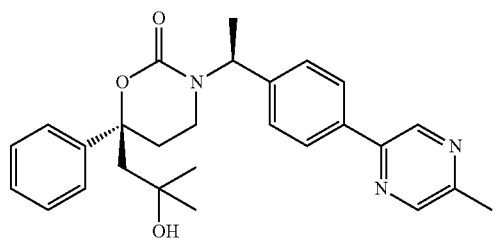 [SMILES: Cc1cnc(-c2ccc([C@H](C)N3CC[C@](CC(C)(C)O)(c4ccccc4)OC3=O)cc2)cn1]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromo-5-methylpyrazine following a procedure analogous to that described in Example 459 Step 4. LC-MS Method 2 $t_R$=1.257 min, m/z=388; $^1$H NMR (CDCl$_3$) 1.07 (s, 3H), 1.12 (s, 3H), 1.49 (d, 3H), 2.01-2.13 (m, 4H), 2.28-2.39 (m, 1H), 2.57 (s, 3H), 2.80 (m, 1H), 5.68 (m, 1H), 7.02 (d, 2H), 7.21-7.33 (m, 5H), 7.67 (d, 2H), 8.41 (s, 1H), 8.76 (s, 1H).

Example 630

(R)-6-ethyl-3-((S)-1-(4-(1-isopropyl-6-oxo-1,6-dihydropyridin-3-yl)phenyl)propyl)-6-phenyl-1,3-oxazinan-2-one

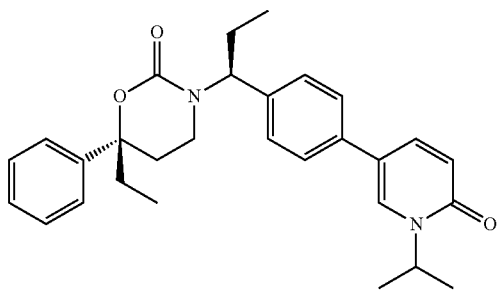 [SMILES: CC[C@@H](c1ccc(-c2ccc(=O)n(C(C)C)c2)cc1)N1CC[C@](CC)(c2ccccc2)OC1=O]

The title compound was prepared from (R)-3-((S)-1-(4-bromophenyl)propyl)-6-ethyl-6-phenyl-1,3-oxazinan-2-one following procedures analogous to those described in Example 459 Steps 3 and 4 using 5-bromo-1-isopropylpyridin-2(1H)-one in Step 4. LC-MS Method 1 $t_R$=1.75 min, m/z=459 (M+1); $^1$H NMR (CDCl$_3$) 7.49, (1H, dd, J=2.34, 9.37 Hz), 7.42 (1H, d, J=2.34 Hz), 7.32-7.24 (5H, m), 7.13 (1H, d, J=8.20), 7.04 (1H, d, J=8.49), 6.66 (1H, d, J=9.37), 5.49 (1H, aq q, J=6.44, 9.37), 5.33 (1H, m), 2.96-2.91 (1H, m), 2.39-2.32 (1H, m), 2.29-2.17 (2H, m), 2.05-1.85 (m, 4H), 1.41 (6H, dd, J=1.17, 6.73), 1.01 (3H, t, J=7.32 Hz), 0.832 (3H, t, J=7.32 Hz).

5-bromo-1-isopropylpyridin-2(1H)-one was prepared from 5-bromopyridin-2(1H)-one and isopropyl iodide following a procedure analogous to that described in Example 628 Step 1.

Example 631

5-fluoro-2-(4-((S)-1-((S)-6-(2-hydroxy-2-methylpropyl)-2-oxo-6-phenyl-1,3-oxazinan-3-yl)ethyl)phenyl)pyridine 1-oxide

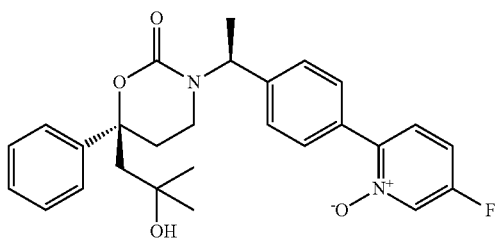

The title compound was prepared from (S)-3-((S)-1-(4-(5-fluoropyridin-2-yl)phenyl)ethyl)-6-(2-hydroxy-2-methylpropyl)-6-phenyl-1,3-oxazinan-2-one following a procedure analogous to that described in Example 441. LC-MS Method 1 $t_R$=1.29 min, m/z=465 (M+1), 407; $^1$H NMR (CD$_3$OD) 8.37 (m, 1H), 7.50-7.37 (m, 4H), 7.29-7.19 (m, 5H), 6.97 (d, J=7.9 Hz, 2H), 5.48 (q, J=7.0 Hz, 1H), 2.99-2.94 (m, 1H), 2.46-2.33 (m, 2H), 2.22-2.14 (m, 1H), 2.06 (s, 2H), 1.46 (d, J=7.0 Hz, 3H), 1.16 (s, 3H), 0.85 (s, 3H).

Example 632

5-(4-((S)-1-((S)-6-(4-fluorophenyl)-6-(2-hydroxy-2-methylpropyl)-2-oxo-1,3-oxazinan-3-yl)ethyl)phenyl)pyrazine-2-carbonitrile

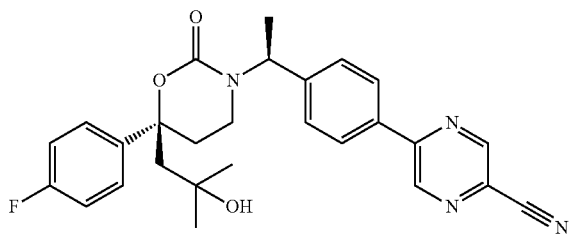 [SMILES: C[C@@H](c1ccc(-c2cnc(C#N)cn2)cc1)N1CC[C@](CC(C)(C)O)(c2ccc(F)cc2)OC1=O]

The title compound was prepared from (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 5-chloropyrazine-2-carbonitrile following a procedure analogous to that described in Example 459 Step 4. LC-MS Method 1 $t_R$=1.64 min, m/z=497 (M+Na); $^1$H NMR (CDCl$_3$) 8.98 (d, 2H), 7.89 (d, 2H), 7.27 (m, 1H), 7.17 (m, 2H), 7.04 (m, 3H), 5.72 (q, 1H), 4.40 (br s, 1H), 2.98 (m, 1H), 1.59 (d, 3H), 1.13 (d, 6H).

Example 633

4-(4-((S)-1-((S)-6-(2-hydroxy-2-methylpropyl)-2-oxo-6-phenyl-1,3-oxazinan-3-yl)propyl)phenyl)-2,6-dimethylpyridine 1-oxide

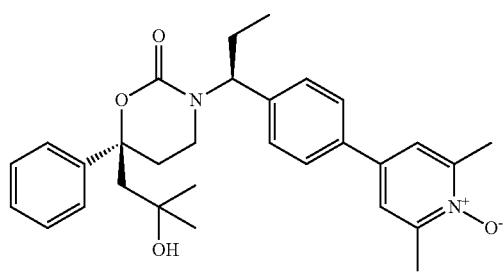 [SMILES: CC[C@@H](c1ccc(-c2cc(C)[n+]([O-])c(C)c2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 4-bromo-2,6-dimethylpyridine-N-oxide following a procedure analogous to that described in Example 459 Step 4. LC-MS Method 2 $t_R$=1.185 min, m/z=489.2; $^1$H NMR (CDCl$_3$) 0.96 (t, 3H), 1.03 (s, 3H), 1.12 (s, 3H), 1.81-2.00 (m, 4H), 2.11-2.22 (m, 5H), 2.30-2.42 (m, 1H), 2.57 (s, 6H), 2.87 (m, 1H), 5.43 (m, 1H), 7.09 (d, 2H), 7.18 (m, 1H), 7.22 (m, 4H), 7.26 (m, 2H), 7.31 (m, 2H).

Example 634

(S)-6-(4-fluorophenyl)-6-(2-hydroxy-2-methylpropyl)-3-((S)-1-(4-(6-methylpyridazin-3-yl)phenyl)ethyl)-1,3-oxazinan-2-one

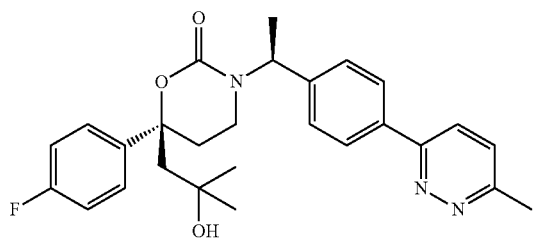 [SMILES: Cc1ccc(-c2ccc([C@H](C)N3CC[C@](CC(C)(C)O)(c4ccc(F)cc4)OC3=O)cc2)nn1]

The title compound was prepared from (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 3-chloro-6-methylpyridazine following a procedure analogous to that described in Example 459 Step 4. LC-MS Method 2 $t_R$=1.163 min, m/z=464; $^1$H NMR (CDCl$_3$) 1.12 (d, 6H), 1.55 (d, 3H), 2.18 (s, 2H), 2.19-2.28 (m, 2H), 2.40 (m, 1H), 2.74 (s, 3H), 2.90 (m, 1H), 5.71 (m, 1H), 6.96-7.05 (t, 2H), 7.10 (d, 2H), 7.29 (m, 2H), 7.38 (d, 2H), 7.69 (d, 1H), 7.82 (d, 2H).

Example 635

6-(4-((S)-1-((S)-6-(2-hydroxy-2-methylpropyl)-2-oxo-6-phenyl-1,3-oxazinan-3-yl)ethyl)phenyl)-N,N-dimethylnicotinamide

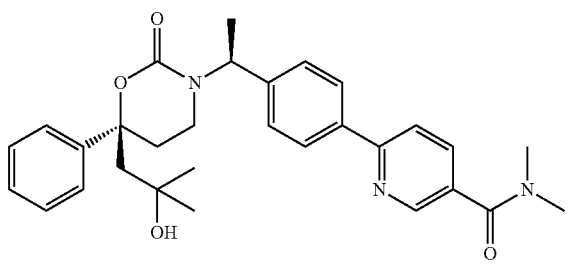 [SMILES: C[C@@H](c1ccc(-c2ccc(C(=O)N(C)C)cn2)cc1)N1CC[C@](CC(C)(C)O)(c2ccccc2)OC1=O]

The title compound was prepared from methyl 6-(4-((S)-1-((S)-6-(2-hydroxy-2-methylpropyl)-2-oxo-6-phenyl-1,3-oxazinan-3-yl)ethyl)phenyl)nicotinate and dimethylamine following a procedure analogous to that described in Example 627. LC-MS Method 2 $t_R$=1.708 min, m/z=444.1; $^1$H NMR (CDCl$_3$) 1.10 (s, 3H), 1.18 (s, 3H), 1.56 (d, 3H), 2.18-2.31 (m, 4H), 2.32-2.53 (m, 1H), 2.86 (m, 1H), 3.08 (s, 3H), 3.13 (s, 3H), 5.71 (m, 1H), 7.08 (d, 2H), 7.29-7.52 (m, 5H), 7.69 (d, 1H), 7.76 (d, 1H), 7.82 (d, 1H), 8.70 (s, 1H).

Example 636

(S)-6-(4-fluorophenyl)-6-(2-hydroxy-2-methylpropyl)-3-((S)-1-(4-(1-methyl-6-oxo-1,6-dihydropyridazin-3-yl)phenyl)ethyl)-1,3-oxazinan-2-one

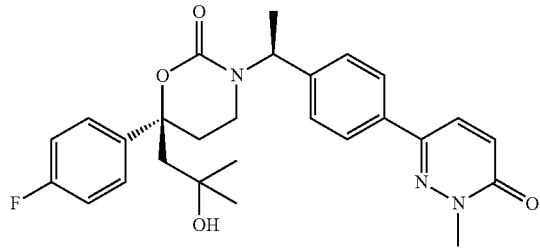

The title compound was prepared from (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 6-chloro-2-methylpyridazin-3(2H)-one following a procedure analogous to that described in Example 459 Step 4. LC-MS Method 2 $t_R$=1.179 min, m/z=422.1; $^1$H NMR (CDCl$_3$) 1.08 (d, 6H), 1.49 (d, 3H), 2.10 (s, 3H), 2.18 (m, 1H), 2.32-2.41 (m, 1H), 2.83 (m, 1H), 3.79 (s, 3H), 5.63 (m, 1H), 6.90-7.03 (m, 5H), 7.23 (m, 2H), 7.46-7.59 (m, 3H).

Example 637

(S)-3-((S)-1-(4-(1,5-dimethyl-6-oxo-1,6-dihydropyridin-3-yl)phenyl)ethyl)-6-(2-hydroxy-2-methylpropyl)-6-phenyl-1,3-oxazinan-2-one

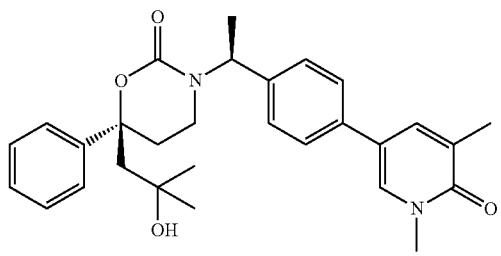 [SMILES: Cc1cc(-c2ccc([C@H](C)N3CC[C@](CC(C)(C)O)(c4ccccc4)OC3=O)cc2)cn(C)c1=O]

The title compound was prepared following a procedure analogous to that described in Example 628 using 1 5-bromo-3-methylpyridin-2(1H)-one and methyl iodide in Step 1. LC-MS Method 2 $t_R$=1.197 min, m/z=475.1; $^1$H NMR (CDCl$_3$) 1.04 (s, 3H), 1.11 (s, 3H), 1.46 (d, 3H), 2.18 (m, 5H), 2.21 (m, 1H), 2.29-2.40 (m, 1H), 2.80 (m, 1H), 3.41 (s, 3H), 3.56 (s, 3H), 5.60 (m, 1H), 6.91 (d, 2H), 7.07 (d, 2H), 7.21-7.40 (m, 7H).

Example 638

(S)-3-((S)-1-(4-(1-ethyl-6-oxo-1,6-dihydropyridin-3-yl)phenyl)ethyl)-6-(4-fluorophenyl)-6-(2-hydroxy-2-methylpropyl)-1,3-oxazinan-2-one

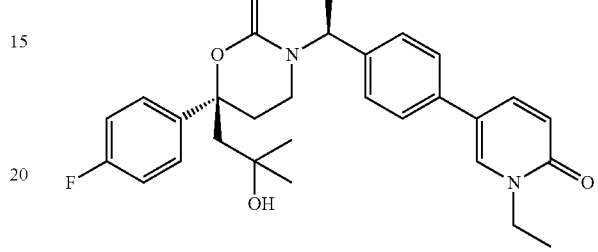

The title compound was prepared following a procedure analogous to that described in Example 628, using 5-bromopyridin-2(1H)-one and ethyl iodide in Step 1 and (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one in Step 2. LC-MS Method 2 $t_R$=1.205 min, m/z=493.2; $^1$H NMR (CDCl$_3$) 1.16 (d, 6H), 1.39 (t, 3H), 1.52 (d, 3H), 2.19 (s, 4H), 2.20-2.31 (m, 2H), 2.38-2.50 (m, 1H), 2.90 (m, 1H), 4.04 (m, 2H), 5.69 (m, 1H), 6.66 (d, 1H), 7.00 (m, 4H), 7.18 (d, 2H), 7.30 (m, 2H), 7.41 (s, 1H), 7.51 (d, 1H).

Example 639

(R)-6-methyl-3-((S)-1-(4-(1-methyl-2-oxo-1,2-dihydropyridin-4-yl)phenyl)propyl)-6-phenyl-1,3-oxazinan-2-one

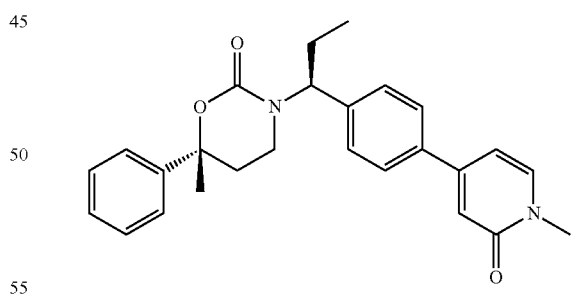

The title compound was prepared from (R)-3-((S)-1-(4-bromophenyl)propyl)-6-methyl-6-phenyl-1,3-oxazinan-2-one following procedures analogous to those described in Example 459 Steps 3 and 4 using 4-iodo-1-methylpyridin-2(1H)-one in Step 4. LC-MS Method 1 $t_R$=1.55 min, m/z=417 (M+1); $^1$H NMR (CDCl$_3$) 7.41 (1H, d, J=7.03 Hz), 7.33 (2H, d, J=8.20 Hz), 7.29-7.19 (5H, m), 7.10 (1H, d, J=8.20), 6.95 (1H, d=1.76), 6.55 (1H, dd, J=2, 7.03 Hz), 5.51 (1H, q, J=6.49, 9.66 Hz), 3.65 (3H, s), 3.00-2.95 (1H, m), 2.44-2.36 (1H, m), 2.33-2.15 (2H, m), 2.06-1.86 (2H, m), 1.64 (3H, s), 1.02 (3H, t, J=7.32 Hz).

(R)-3-((S)-1-(4-bromophenyl)propyl)-6-methyl-6-phenyl-1,3-oxazinan-2-one was prepared from 4-chloro-2-phenylbutan-2-ol and (S)-1-(4-bromophenyl)propan-1-amine following procedures analogous to those described in Example 353.

4-chloro-2-phenylbutan-2-ol was prepared from 3-chloro-1-phenylpropan-1-one and methylmagnesium bromide following a procedure analogous to that described in Example 110 Step 1.

Example 640

6-(4-((S)-1-((S)-6-(4-fluorophenyl)-6-(2-hydroxy-2-methylpropyl)-2-oxo-1,3-oxazinan-3-yl)ethyl)phenyl)pyrazine-2-carbonitrile

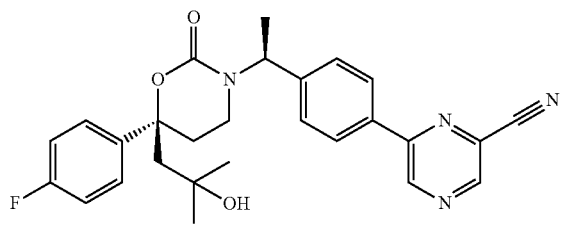 [SMILES: C[C@@H](c1ccc(-c2cncc(C#N)n2)cc1)N1CC[C@](CC(C)(C)O)(c2ccc(F)cc2)OC1=O]

The title compound was prepared from (S)-6-(4-fluorophenyl)-6-(2-hydroxy-2-methylpropyl)-3-((S)-1-(4-(4,4,5,5-tetramethyl-1,3,2-dioxaborolan-2-yl)phenyl)ethyl)-1,3-oxazinan-2-one and 6-chloropyrazine-2-carbonitrile following a procedure analogous to that described in Example 459 Step 4. LC-MS Method 1 $t_R$=1.61 min, m/z=497 (M+Na); $^1$H NMR (CDCl3) 8.98 (d, 2H), 7.87 (d, 2H), 7.26 (m, 1H), 7.18 (m, 3H), 7.04 (t, 2H), 5.72 (q, 1H), 2.99 (m, 1H), 1.59 (d, 3H), 1.14 (d, 6H).

Example 641

(S)-3-((S)-1-(4-(1,6-dimethyl-2-oxo-1,2-dihydropyridin-4-yl)phenyl)ethyl)-6-(2-hydroxy-2-methylpropyl)-6-phenyl-1,3-oxazinan-2-one

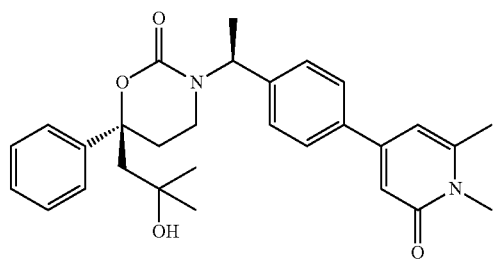 [SMILES: Cc1cc(-c2ccc([C@H](C)N3CC[C@](CC(C)(C)O)(c4ccccc4)OC3=O)cc2)cc(=O)n1C]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 4-bromo-1,6-dimethylpyridin-2(1H)-one following a procedure analogous to that described in Example 459 Step 4. LC-MS Method 2 $t_R$=1.173 min, m/z=475.2; $^1$H NMR (CDCl$_3$) 1.10 (s, 3H), 1.16 (s, 3H), 1.51 (d, 3H), 2.18 (m, 3H), 2.21 (m, 1H), 2.42 (m, 4H), 2.86 (m, 1H), 3.54 (s, 3H), 5.66 (m, 1H), 6.21 (s, 1H), 6.60 (s, 1H), 6.97 (m, 2H), 7.23-7.34 (m, 7H).

4-bromo-1,6-dimethylpyridin-2(1H)-one was prepared by methylation of 4-bromo-6-methylpyridin-2(1H)-one with methyl iodide using K$_2$CO$_3$ following a procedure analogous to that described in Example 628 Step 1.

Example 642

(S)-3-((S)-1-(4-(1-ethyl-2-oxo-1,2-dihydropyridin-4-yl)phenyl)ethyl)-6-(2-hydroxy-2-methylpropyl)-6-phenyl-1,3-oxazinan-2-one

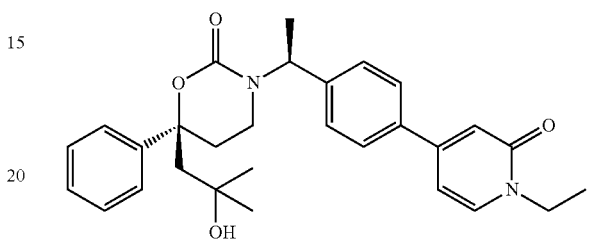

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 1-ethyl-4-iodopyridin-2(1H)-one following a procedure analogous to that described in Example 459 Step 4. LC-MS Method 2 $t_R$=1.228 min, m/z=971.4; $^1$H NMR (CDCl$_3$) 1.10 (s, 3H), 1.14 (s, 3H), 1.36 (m, 3H), 1.53 (d, 3H), 2.17 (s, 2H), 2.21-2.32 (m, 2H), 2.32-2.48 (m, 1H), 2.88 (m, 1H), 4.00 (m, 2H), 5.68 (m, 1H), 6.39 (d, 1H), 6.78 (s, 1H), 6.99 (d, 2H), 7.27-7.38 (m, 8H).

1-ethyl-4-iodopyridin-2(1H)-one was prepared from 4-iodopyridin-2(1H)-one and ethyl iodide following a procedure analogous to that described in Example 628 Step 1.

Example 643

(S)-6-(2-hydroxy-2-methylpropyl)-3-((S)-1-(4-(2-oxo-1-(2,2,2-trifluoroethyl)-1,2-dihydropyridin-4-yl)phenyl)ethyl)-6-phenyl-1,3-oxazinan-2-one

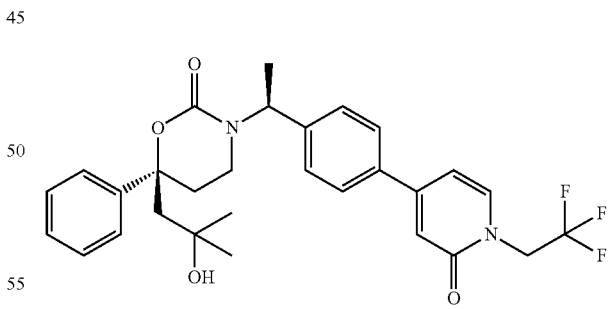

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 4-iodo-1-(2,2,2-trifluoroethyl)pyridin-2(1H)-one following a procedure analogous to that described in Example 459 Step 4. LC-MS Method 2 $t_R$=1.871 min, m/z=471.1; $^1$H NMR (CDCl$_3$) 1.11 (s, 3H), 1.17 (s, 3H), 1.53 (d, 3H), 2.16-2.33 (m, 4H), 2.35-2.47 (m, 1H), 2.89 (m, 1H), 4.58-4.70 (m, 2H), 5.69 (m, 1H), 6.71 (s, 1H), 7.00 (d, 2H), 7.19-7.38 (m, 8H).

4-iodo-1-(2,2,2-trifluoroethyl)pyridin-2(1H)-one was prepared from 4-iodopyridin-2(1H)-one and 2,2,2-trifluoroethyl trifluoromethanesulfonate following a procedure analogous to that described in Example 628 Step 1.

Example 644

2-(4-((S)-1-((S)-6-(2-hydroxy-2-methylpropyl)-2-oxo-6-phenyl-1,3-oxazinan-3-yl)ethyl)phenyl)-N,N-dimethylthiazole-5-carboxamide

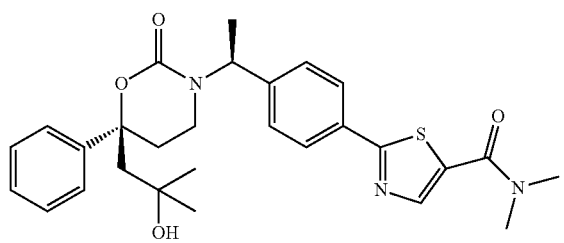 [SMILES: C[C@@H](c1ccc(-c2ncc(C(=O)N(C)C)s2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 2-bromo-N,N-dimethylthiazole-5-carboxamide following a procedure analogous to that described in Example 459 Step 4. LC-MS Method 2 $t_R$=1.215 min, m/z=450.1; $^1$H NMR (CD$_3$OD) 0.92 (s, 3H), 1.22 (s, 3H), 1.53 (d, 3H), 2.11 (s, 2H), 2.19-2.28 (m, 1H), 2.40-2.58 (m, 2H), 3.00-3.31 (m, 4H), 5.56 (m, 1H), 7.02 (d, 2H), 7.26-7.39 (m, 5H), 7.69 (d, 2H), 8.08 (s, 1H).

Example 645

6-(4-{1-[6-(4-Fluoro-phenyl)-6-(2-hydroxy-2-methyl-propyl)-2-oxo-[1,3]oxazinan-3-yl]-ethyl}-phenyl)-pyrazine-2-carboxylic acid amide

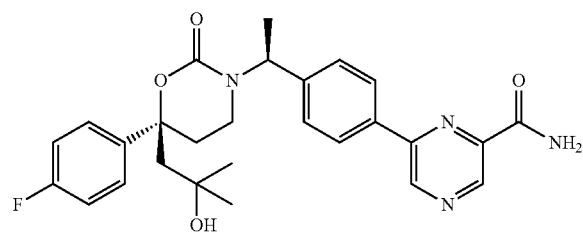 [SMILES: C[C@@H](c1ccc(-c2cncc(C(N)=O)n2)cc1)N1CC[C@](CC(C)(C)O)(c2ccc(F)cc2)OC1=O]

The title compound was prepared from 6-(4-((S)-1-((S)-6-(4-fluorophenyl)-6-(2-hydroxy-2-methylpropyl)-2-oxo-1,3-oxazinan-3-yl)ethyl)phenyl)pyrazine-2-carbonitrile following a procedure analogous to that described in Example 584. LC-MS Method 1 $t_R$=1.32 min, m/z=493; $^1$H NMR (CDCl$_3$) 9.24 (d, 2H), 7.88 (s, 1H), 7.83 (d, 2H), 4.29 (m, 2H), 7.16 (d, 2H), 7.06 (t, 2H), 6.62 (s, 1H), 5.74 (q, 1H), 3.00 (m, 1H), 2.48 (m, 1H), 1.60 (d, 3H), 1.17 (d, 6H).

Example 646

(S)-6-(2-hydroxy-2-methylpropyl)-3-((S)-1-(4-(6-oxo-1-(2,2,2-trifluoroethyl)-1,6-dihydropyridin-3-yl)phenyl)ethyl)-6-phenyl-1,3-oxazinan-2-one

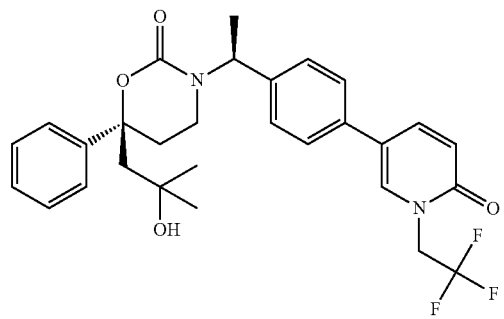 [SMILES: C[C@@H](c1ccc(-c2ccc(=O)n(CC(F)(F)F)c2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 5-bromo-1-(2,2,2-trifluoroethyl)pyridin-2(1H)-one following a procedure analogous to that described in Example 459 Step 4. LC-MS Method 2 $t_R$=1.323 min, m/z=471.1; $^1$H NMR (CDCl$_3$) 1.13 (s, 3H), 1.19 (s, 3H), 1.53 (d, 3H), 2.19-2.30 (m, 4H), 2.40 (m, 1H), 2.89 (m, 1H), 4.67 (m, 2H), 5.69 (m, 1H), 6.70 (d, 1H), 7.03 (d, 2H), 7.13 (d, 2H), 7.29-7.38 (m, 6H), 7.55 (d, 1H).

5-bromo-1-(2,2,2-trifluoroethyl)pyridin-2(1H)-one was prepared from 5-bromopyridin-2(1H)-one and 2,2,2-trifluoroethyl trifluoromethanesulfonate following a procedure analogous to that described in Example 628 Step 1.

Example 647

(S)-6-(2-hydroxy-2-methylpropyl)-3-((S)-1-(4-(1-isopropyl-2-oxo-1,2-dihydropyridin-4-yl)phenyl)ethyl)-6-phenyl-1,3-oxazinan-2-one

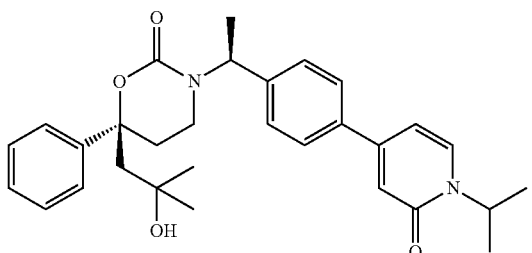

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)propyl)-1,3-oxazinan-2-one and 4-iodo-1-isopropylpyridin-2(1H)-one following a procedure analogous to that described in Example 459 Step 4. LC-MS Method 2 $t_R$=1.846 min, m/z=489.2; $^1$H NMR (CDCl$_3$) 1.10 (s, 3H), 1.24 (s, 3H), 1.39 (d, 6H), 1.52 (d, 3H), 2.17-2.31 (m, 4H), 2.35-2.46 (m, 1H), 2.88 (m, 1H), 5.27 (m, 1H), 5.69 (m, 1H), 6.49 (d, 1H), 6.88 (s, 1H), 7.00 (d, 2H), 7.29-7.38 (m, 7H), 7.40 (d, 1H).

4-iodo-1-isopropylpyridin-2(1H)-one was prepared from 4-iodopyridin-2(1H)-one and isopropyl iodide following a procedure analogous to that described in Example 628 Step 1.

Example 648

(R)-3-((S)-1-(4-bromophenyl)ethyl)-6-(2-hydroxy-2-methylpropyl)-6-phenyl-1,3-oxazinan-2-one

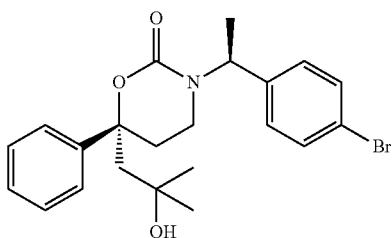 [SMILES: C[C@@H](c1ccc(Br)cc1)N1CC[C@@](CC(C)(C)O)(c2ccccc2)OC1=O]

The title compound was prepared from (S)-6-allyl-3-((S)-1-(4-bromophenyl)ethyl)-6-phenyl-1,3-oxazinan-2-one following a procedure analogous to that described in Example 280. LC-MS Method 2 $t_R$=2.119 min, m/z=375.8; $^1$H NMR (CDCl$_3$) 1.09 (s, 3H), 1.19 (m, 1H), 1.27 (d, 3H), 2.17-2.28 (m, 4H), 2.52-2.69 (m, 2H), 5.67-5.79 (m, 1H), 7.18 (d, 2H), 7.34 (m, 3H), 7.39 (m, 2H), 7.42 (d, 2H).

Example 649

6-allyl-3-((R)-1-(4-bromophenyl)ethyl)-6-phenyl-1,3-oxazinan-2-one

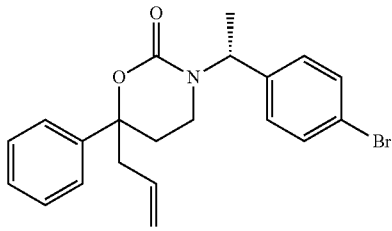 [SMILES: C=CCC1(c2ccccc2)CCN([C@H](C)c2ccc(Br)cc2)C(=O)O1]

The title compound was prepared following procedures analogous to those described in Example 395 using (R)-1-(4-bromophenyl)ethanamine in Step 1. Two isomers were isolated.

Isomer 1: LC-MS Method 2 $t_R$=1.552 min, m/z=401.8; $^1$H NMR (CDCl$_3$) 1.22 (d, 3H), 2.00-2.11 (m, 1H), 2.25 (m, 1H), 2.56-2.78 (m, 4H), 5.00-5.12 (m, 2H), 5.69-5.81 (m, 2H), 7.19 (d, 2H), 7.31 (m, 3H), 7.39 (m, 2H), 7.46 (m, 2H).

Isomer 2: LC-MS Method 2 $t_R$=1.493 min, m/z=400; $^1$H NMR (CD$_3$OD) 1.49 (d, 3H), 2.17-2.36 (m, 2H), 2.48 (m, 1H), 2.61 (m, 2H), 3.06 (m, 1H), 5.02 (m, 2H), 5.46 (m, 1H), 5.65-5.78 (m, 1H), 6.79 (d, 2H), 7.22 (m, 2H), 7.28-7.41 (m, 5H).

Example 650

(S)-3-((S)-1-(4-(1-ethyl-6-oxo-1,6-dihydropyridazin-3-yl)phenyl)ethyl)-6-(2-hydroxy-2-methylpropyl)-6-phenyl-1,3-oxazinan-2-one

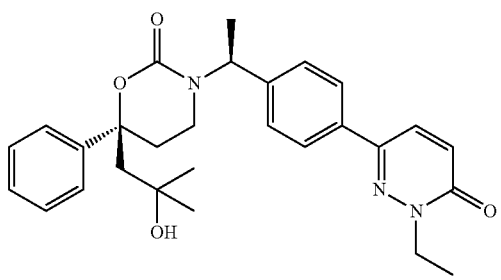

The title compound was prepared following a procedure analogous to that described in Example 617 using ethyl bromide in Step 2. LC-MS Method 2 $t_R$=1.297 min, m/z=418; $^1$H NMR (CDCl$_3$) 1.12 (s, 3H), 1.19 (s, 3H), 1.43 (t, 3H), 1.56 (d, 3H), 2.20-2.31 (m, 4H), 2.37-2.48 (m, 1H), 2.88 (m, 1H), 4.29 (m, 2H), 5.70 (m, 1H), 6.98 (d, 1H), 7.06 (d, 2H), 7.29-7.40 (m, 5H), 7.56 (m, 3H).

Example 651

3-((R)-6-(4-fluorophenyl)-3-((S)-1-(4-(1-methyl-6-oxo-1,6-dihydropyridin-3-yl)phenyl)ethyl)-2-oxo-1,3-oxazinan-6-yl)-2,2-dimethylpropanenitrile

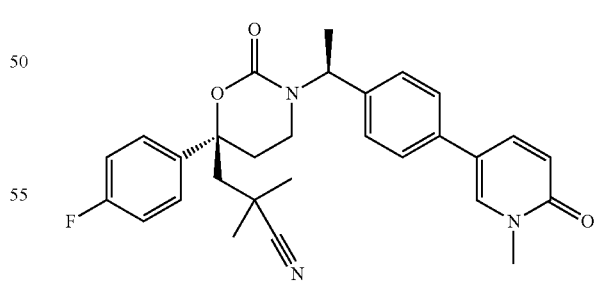

The title compound was prepared from 3-((R)-3-((S)-1-(4-bromophenyl)ethyl)-6-(4-fluorophenyl)-2-oxo-1,3-oxazinan-6-yl)-2,2-dimethylpropanenitrile following procedures analogous to those described in Example 313 Steps 3 and 4. LC-MS Method 1 $t_R$=1.45 min, m/z=488; $^1$H NMR (CDCl$_3$) 7.68 (dd, 1H), 7.52 (d, 1H), 7.32 (q, 2H), 7.17 (d, 2H), 7.06 (t, 2H), 6.97 (d, 2H), 6.91 (d, 1H), 5.66 (q, 1H), 3.72 (s, 3H), 2.99

(dt, 1H), 2.48 (dd, 2H), 2.27 (m, 1H), 2.11 (s, 2H), 1.55 (d, 3H), 1.44 (s, 3H), 1.34 (s, 3H).

Example 652

(S)-6-(2-hydroxy-2-methylpropyl)-3-((S)-1-(4-(1-isopropyl-6-oxo-1,6-dihydropyridazin-3-yl)phenyl)ethyl)-6-phenyl-1,3-oxazinan-2-one

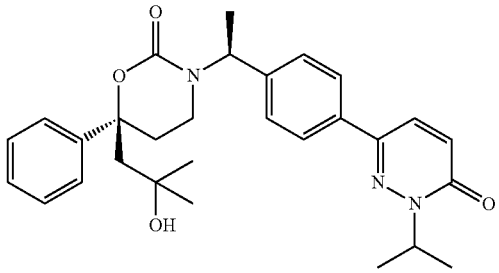 [SMILES: CC(C)n1nc(-c2ccc([C@H](C)N3CC[C@](CC(C)(C)O)(c4ccccc4)OC3=O)cc2)ccc1=O]

The title compound was prepared following a procedure analogous to that described in Example 617 using isopropyl iodide in Step 2. LC-MS Method 2 $t_R$=1.885 min, m/z=432.1; $^1$H NMR (CDCl$_3$) 1.10 (s, 3H), 1.18 (s, 3H), 1.39 (d, 6H), 1.53 (d, 3H), 2.18-2.29 (m, 4H), 2.31-2.47 (m, 1H), 2.88 (m, 1H), 5.32 (m, 1H), 5.69 (m, 1H), 6.92 (d, 1H), 7.03 (d, 2H), 7.27-7.38 (m, 5H), 7.52 (d, 3H).

Example 653

(S)-6-(2-hydroxy-2-methylpropyl)-3-((S)-1-(4-(6-oxo-1-(2,2,2-trifluoroethyl)-1,6-dihydropyridazin-3-yl)phenyl)ethyl)-6-phenyl-1,3-oxazinan-2-one

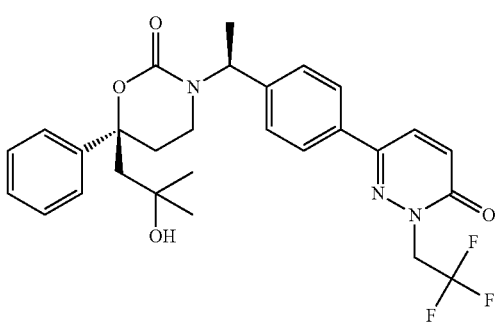 [SMILES: C[C@@H](c1ccc(-c2ccc(=O)n(CC(F)(F)F)n2)cc1)N1CC[C@](CC(C)(C)O)(c2ccccc2)OC1=O]

The title compound was prepared following a procedure analogous to that described in Example 617 using 2,2,2-trifluoroethyl trifluoromethanesulfonate in Step 2. LC-MS Method 2 $t_R$=1.172 min, m/z=472.1; $^1$H NMR (CD$_3$OD) 0.93 (s, 3H), 1.28 (s, 3H), 1.54 (d, 3H), 2.04 (s, 2H), 2.20-2.31 (m, 1H), 2.42-2.59 (m, 2H), 3.06 (m, 1H), 4.91-5.00 (m, 2H), 5.59 (m, 1H), 7.07 (d, 3H), 7.25-7.39 (m, 5H), 7.61 (d, 2H), 7.92 (d, 1H).

Example 654

3-((R)-1-(4-bromophenyl)ethyl)-6-(2-hydroxy-2-methylpropyl)-6-phenyl-1,3-oxazinan-2-one

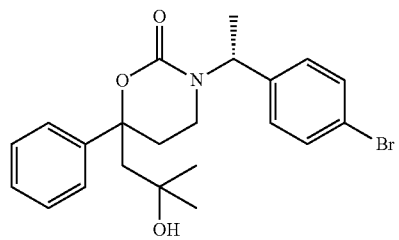 [SMILES: C[C@H](c1ccc(Br)cc1)N1CCC(CC(C)(C)O)(c2ccccc2)OC1=O]

Isomer 1 of the title compound was prepared from isomer 1 of 6-allyl-3-((1R)-1-(4-bromophenyl)ethyl)-6-phenyl-1,3-oxazinan-2-one following procedures analogous to those described in Example 395 Method 2 Steps 4, 5 and 6. LC-MS Method 2 $t_R$=1.362 min, m/z=374, 376; $^1$H NMR (CDCl$_3$) 1.12 (s, 3H), 1.17 (s, 3H), 1.48-1.49 (d, 3H), 2.14-2.20 (m, 4H), 2.24-2.29 (m, 1H), 2.35-2.43 (m, 1H), 2.80-2.85 (m, 1H), 5.58-5.64 (m, 1H), 6.79-6.81 (d, 2H), 7.21-7.24 (d, 2H), 7.29-7.37 (m, 5H).

Isomer 2 of the title compound was prepared following procedures analogous to those described in Example 395 Method 2 Steps 4, 5 and 6. LC-MS Method 2 $t_R$=1.509 min, m/z=374; $^1$H NMR (CDCl$_3$) 1.00 (s, 3H), 1.12 (s, 3H), 1.20 (d, 3H), 2.10-2.20 (m, 4H), 2.52 (m, 2H), 5.64 (m, 1H), 7.10 (d, 2H), 7.25 (m, 3H), 7.32 (m, 2H), 7.38 (m, 2H).

Example 655

(S)-3-((S)-1-(4-(1-ethyl-5-methyl-6-oxo-1,6-dihydropyridin-3-yl)phenyl)ethyl)-6-(2-hydroxy-2-methylpropyl)-6-phenyl-1,3-oxazinan-2-one

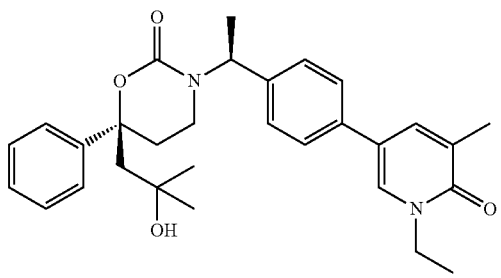

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 5-bromo-1-ethyl-3-methylpyridin-2(1H)-one following procedures analogous to those described in Example 486 Step 4. LC-MS Method 2 $t_R$=1.314 min, m/z=489; $^1$H NMR (CDCl$_3$) 1.09 (s, 3H), 1.15 (s, 3H), 1.35 (t, 3H), 1.50 (d, 3H), 2.15-2.25 (m, 7H), 2.35 (m, 1H), 2.86 (m, 1H), 4.03 (m, 2H), 5.66 (q, 1H), 6.96 (d, 2H), 7.13 (d, 2H), 7.25-7.36 (m, 7H).

5-Bromo-1-ethyl-3-methylpyridin-2(1H)-one was prepared by alkylation of 5-bromo-3-methylpyridin-2(1H)-one with ethyl iodide following a procedure analogous to that described in Example 628 Step 1.

Example 656

(S)-3-((S)-1-(4-(6-ethoxy-5-methylpyridin-3-yl)phenyl)ethyl)-6-(2-hydroxy-2-methylpropyl)-6-phenyl-1,3-oxazinan-2-one

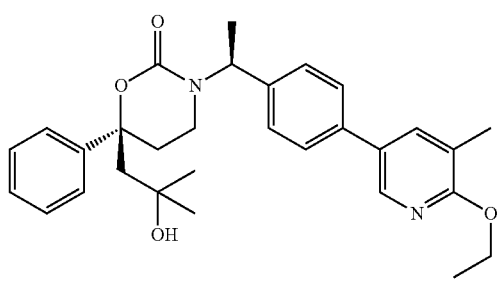 [SMILES: CCOc1ncc(-c2ccc([C@H](C)N3CC[C@](CC(C)(C)O)(c4ccccc4)OC3=O)cc2)cc1C]

The title compound was isolated as a byproduct from the preparation of Example 655. LC-MS Method $t_R$=1.314 min, m/z=489; $^1$H NMR (CDCl$_3$) 1.04 (s, 3H), 1.11 (s, 3H), 1.34 (t, 3H), 1.47 (d, 3H), 2.13-2.24 (m, 7H), 2.32 (m, 1H), 2.81 (m, 1H), 4.34 (q, 2H), 5.62 (q, 1H), 6.93 (d, 2H), 7.17-7.27 (m, 7H), 7.42 (s, 1H), 8.02 (s, 1H).

Example 657

N-cyclopropyl-6-(4-((S)-1-((S)-6-(2-hydroxy-2-methylpropyl)-2-oxo-6-phenyl-1,3-oxazinan-3-yl)ethyl)phenyl)nicotinamide

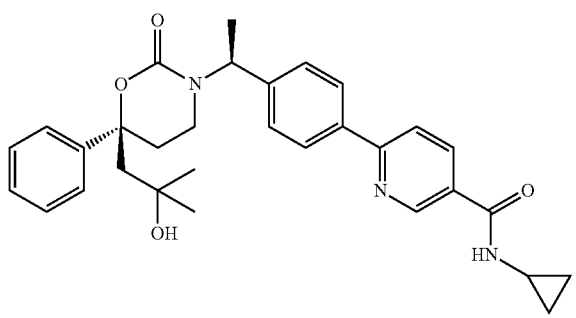 [SMILES: C[C@@H](c1ccc(-c2ccc(C(=O)NC3CC3)cn2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 6-bromo-N-cyclopropylnicotinamide following procedures analogous to those described in Example 486 Step 4. LC-MS Method $t_R$=1.74 min, m/z=456.1; $^1$H NMR (CDCl$_3$) 0.61 (m, 2H), 0.82 (m, 2H), 1.13 (s, 3H), 1.22 (s, 3H), 1.49 (d, 3H), 2.17 (m, 3H), 2.21 (m, 1H), 2.31 (m, 1H), 2.79 (m, 1H), 2.88 (m, 1H), 5.66 (m, 1H), 6.40 (s, 1H), 6.99 (d, 1H), 7.20-7.31 (m, 5H), 7.60 (d, 1H), 7.68 (d, 2H), 8.07 (d, 1H), 8.89 (s, 1H).

6-bromo-N-cyclopropylnicotinamide was prepared from 6-bromonicotinoyl chloride and cyclopropylamine.

Example 658

2,2-dimethyl-3-((R)-2-oxo-3-((S)-1-(4-(6-oxo-1,6-dihydropyridin-3-yl)phenyl)ethyl)-6-phenyl-1,3-oxazinan-6-yl)propanenitrile

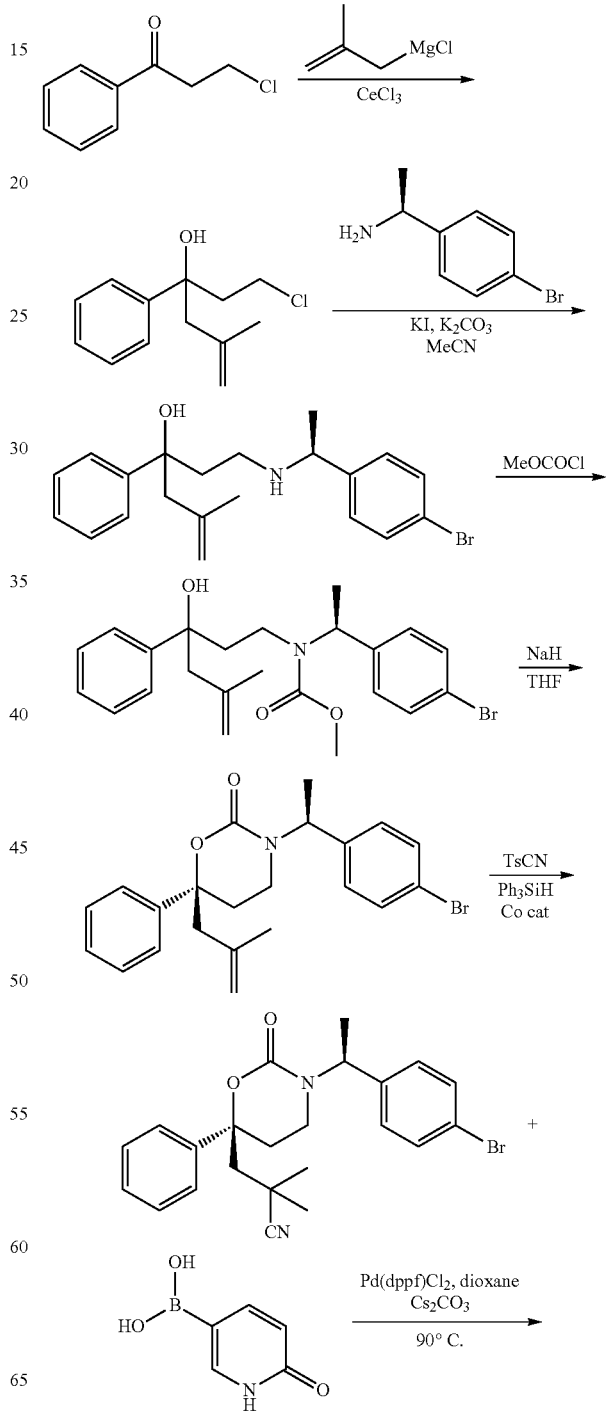

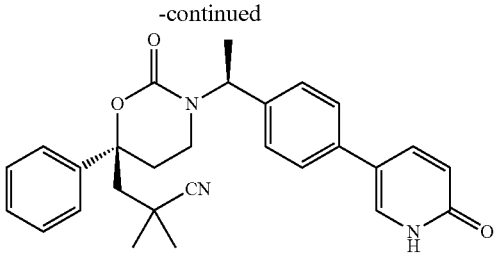

Step 1

A 250 mL flask was charged with anhydrous CeCl₃ (7.1890 g, 29.2 mmol) and THF (55 mL). The mixture was vigorously stirred for 2 h at rt. The suspension was then cooled to −78° C. and a solution of 2-methylallylmagnesium chloride (0.5 M in THF, 56 mL, 28.0 mmol) was added. After stirring for 2 h at −78° C., a solution of 3-chloropropiophenone (3.350 g, 19.8 mmol) in THF (30 mL) was added via cannula. The reaction mixture was allowed to slowly warm to 8° C. while stirring overnight (18 h). The reaction was then quenched with satd aq NaHCO₃, extracted with EtOAc, and dried over Na₂SO₄. After the solvents were evaporated, the crude 1-chloro-5-methyl-3-phenylhex-5-en-3-ol was directly used in the next step without further purification. LC-MS Method 1 $t_R$=1.91 min, m/z 248, 207 (M−OH)⁺; ¹H NMR (400 MHz, CDCl₃) δ 7.39-7.22 (m, 5H), 4.92 (m, 1H), 4.77 (m, 1H), 3.60-3.53 (m, 1H), 3.17-3.10 (m, 1H), 2.67 (d, J=13.2 Hz, 1H), 2.55 (d, J=13.2 Hz, 1H), 2.41-2.25 (m, 2H), 1.29 (s, 3H); ¹³C NMR (100 MHz, CDCl₃) δ 144.55, 141.72, 128.32, 126.88, 125.07, 116.50, 74.44, 51.46, 46.34, 40.19, 24.22.

Step 2

1-chloro-5-methyl-3-phenylhex-5-en-3-ol (1.28 g, 5.7 mmol), (S)-1-(4-bromophenyl)ethanamine (1.37 g, 1.2 equiv), KI (995 mg, 1.05 equiv), K₂CO₃ (1.57 g, 2 equiv) were mixed with acetonitrile (15 mL) and heated to reflux (oil bath 96° C.) for overnight. After being cooled to rt, the mixture was filtered, concentrated, and purified by chromatography on a 40-g silica gel column, eluted with 0-8% MeOH in CH₂Cl₂, to afford 1-((S)-1-(4-bromophenyl)ethylamino)-5-methyl-3-phenylhex-5-en-3-ol (1.33 g, 60%).

Step 3

To a solution of 1-((S)-1-(4-bromophenyl)ethylamino)-5-methyl-3-phenylhex-5-en-3-ol (1.33 g, 3.43 mmol) in CH₂Cl₂ (100 mL) was added pyridine (277 µL, 1 equiv) and triethylamine (717 µL, 1.5 equiv). The mixture was cooled to 0° C. Methyl chloroformate (397 µL, 1.5 equiv) was added slowly. After 15 min, the mixture was warmed to rt slowly and stirred for 3 h. The mixture was then diluted with ether (200 mL), washed with 5% aq HCl (2×25 mL), satd aq NaHCO₃ (25 mL) and brine (20 mL), and dried over Na₂SO₄. After filtration and concentration, the crude methyl (S)-1-(4-bromophenyl)ethyl(3-hydroxy-5-methyl-3-phenylhex-5-enyl)carbamate was used for next steps without further purification.

Step 4

The crude methyl (S)-1-(4-bromophenyl)ethyl(3-hydroxy-5-methyl-3-phenylhex-5-enyl)carbamate from above procedure was dissolved in dry THF (75 mL), NaH (60% in mineral oil, 274 mg, 2 equiv) was added slowly at rt. After 10 min, the mixture was heated to reflux for 2 h. LC-MS found reaction completed. The mixture was cooled to 0° C., quenched with satd aq NH₄Cl (10 mL), diluted with ether (100 mL), washed with 1% aq HCl (25 mL) and brine (15 mL), and dried over Na₂SO₄. After filtration and concentration, the crude product was purified by chromatography on a 40-g silica gel column, eluted with 10-35% EtOAc in hexanes. The second UV active peak was collected to afford (R)-3-((S)-1-(4-bromophenyl)ethyl)-6-(2-methylallyl)-6-phenyl-1,3-oxazinan-2-one (490 mg 34.5% overall yield for Steps 3 and 4).

Step 5

A mixture of (R)-3-((S)-1-(4-bromophenyl)ethyl)-6-(2-methylallyl)-6-phenyl-1,3-oxazinan-2-one (490 mg, 1.18 mmol), TsCN (257 mg, 1.2 equiv), PhSiH₃ (157 µL, 1.07 equiv) and the cobalt N,N'-bis(3,5-di-tert-butylsalicylidene)-1,1,2,2-tetramethylethenediamine catalyst prepared as described in Example 520 Step 1 (7.5 mg, 0.01 equiv) and ethanol (20 mL) was stirred 4 h at rt. LC-MS found the reaction completed. The mixture was concentrated and purified by ISCO (40 g column, 25~80% EtOAc in Hexanes) to afford 267 mg product (51% yield). LC-MS Method 1 $t_R$=1.89 min., m/z 441, 443 (M+1).

Step 6

To a solution of 3-((R)-3-((S)-1-(4-bromophenyl)ethyl)-2-oxo-6-phenyl-1,3-oxazinan-6-yl)-2,2-dimethylpropanenitrile (208 mg, 0.47 mmol) in 1,4-dioxane (5 mL) were added 6-oxo-1,6-dihydropyridin-3-ylboronic acid (98 mg, 1.5 equiv.), 2.0 M aq Cs₂CO₃ solution (500 µL), and Pd(dppf)Cl₂ (20 mg, 0.06 equiv.). The mixture was degassed and refilled with N₂ gas 3 times, before being heated to 90° C. (oil bath) for 3 h. LC-MS found the reaction was complete. The mixture was cooled to rt, diluted with EtOAc (25 mL), and washed with water (10 mL). The aqueous layer was extracted with EtOAc (2×10 mL). The combined organic layers were washed with water (10 mL) and brine (8 mL), and dried over Na₂SO₄. After filtration and concentration, the residue was purified by chromatography (12-g silica gel cartridge, 0~10% MeOH in CH₂Cl₂, major UV peak) to afford 2,2-dimethyl-3-((R)-2-oxo-3-((S)-1-(4-(6-oxo-1,6-dihydropyridin-3-yl)phenyl)ethyl)-6-phenyl-1,3-oxazinan-6-yl)propanenitrile (202 mg, 94%) as a brown oil. LC-MS Method 1 $t_R$=1.34 min, m/z=456 (M+1); ¹H NMR (CDCl₃) 8.01 (d, 1H), 7.80 (s, 1H), 7.36 (dt, 6H), 7.19 (d, 2H), 6.98 (m, 3H), 5.65 (d, 1H), 2.98 (d, 1H), 2.50 (m, 2H), 2.32 (m, 1H), 2.17 (s, 2H), 1.57 (d, 3H), 1.40 (s, 3H), 1.32 (s, 3H).

Alternative Method to Prepare 3-((R)-3-((S)-1-(4-bromophenyl)ethyl)-2-oxo-6-phenyl-1,3-oxazinan-6-yl)-2,2-dimethylpropanenitrile

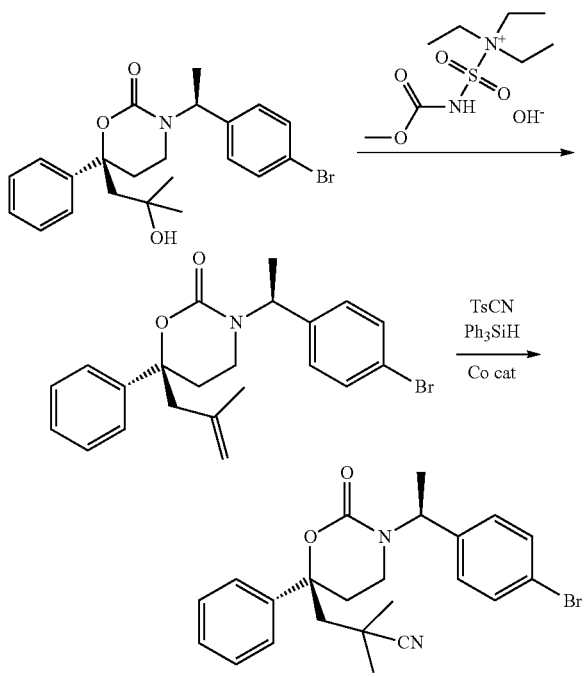

Step 1. 3-[(S)-1-(4-Bromo-phenyl)-ethyl]-(S)-6-(2-methyl-allyl)-6-phenyl-[1,3]oxazinan-2-one (Methoxycarbonylsulfamoyl)triethylammonium hydroxide (1.38 g) is added to 3-[(S)-1-(4-bromo-phenyl)-ethyl]-(S)-6-(2-hydroxy-2-methyl-propyl)-6-phenyl-[1,3]oxazinan-2-one (2.0 g) dissolved in tetrahydrofuran (30 mL) and toluene (15 mL). The resulting solution was stirred at room temperature for 0.5 h and at 75° C. for 1 h. After cooling to room temperature, the solution was concentrated and ethyl acetate was added to the residue. The resulting mixture was washed with aqueous NaHCO₃ solution and brine and dried (MgSO₄). The title compound was obtained after removal of the solvent. Yield: 1.9 g (quantitative). Mass spectrum (ESI⁺): m/z=414/416 (Br) [M+H]⁺

Step 2. 3-{3-[(S)-1-(4-Bromo-phenyl)-ethyl]-2-oxo-(S)-6-phenyl-[1,3]oxazinan-6-yl}-2,2-dimethyl-propionitrile 3-[(S)-1-(4-Bromo-phenyl)-ethyl]-(S)-6-(2-methyl-allyl)-6-phenyl-[1,3]oxazinan-2-one (0.21 g), p-toluenesulfonyl cyanide (143 mg), tert-BuOOH (5.5 M in decane, 27 µL), and phenylsilane (64 µL) were added in the given order to a flask charged with a stir bar, (1R,2R)-(−)-1,2-cyclohexanediamino-N,N'-bis(3,5-di-tert-butylsalicyliden)cobalt(II) (3 mg) and ethanol (15 mL) in argon atmosphere. The resulting solution was stirred at room temperature for 3 h and then concentrated under reduced pressure. The residue was purified by chromatography on silica gel (cyclohexane/ethyl acetate 60:40→0:100) to afford the title compound as a resin-like solid. Yield: 0.16 g (70% of theory). Mass spectrum (ESI⁺): m/z=441/443 (Br) [M+H]⁺

Example 659

(S)-3-((S)-1-(4-(1-ethyl-6-methyl-2-oxo-1,2-dihydropyridin-4-yl)phenyl)ethyl)-6-(2-hydroxy-2-methylpropyl)-6-phenyl-1,3-oxazinan-2-one

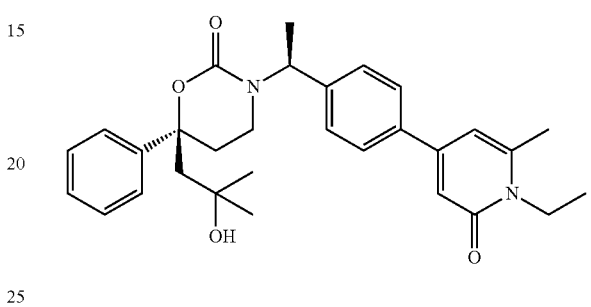

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 4-bromo-1-ethyl-6-methylpyridin-2(1H)-one following a procedure analogous to that described in Example 459 Step 4. LC-MS Method 2 t_R=1.211 min, m/z=489.2; ¹H NMR (CDCl₃) 1.10 (s, 3H), 1.17 (s, 3H), 1.49 (s, 9H), 1.57 (d, 3H), 2.22 (m, 4H), 2.37 (m, 1H), 2.84 (m, 1H), 5.60 (m, 1H), 5.91 (s, 1H), 7.06 (d, 2H), 7.27-7.40 (m, 5H), 7.68 (d, 1H), 7.24 (d, 2H), 8.09 (d, 1H), 8.90 (s, 1H).

4-bromo-1-ethyl-6-methylpyridin-2(1H)-one was prepared by alkylation of 4-bromo-6-methylpyridin-2(1H)-one with ethyl iodide using K₂CO₃ following a procedure analogous to that described in Example 628 Step 1.

Example 660

(S)-3-((S)-1-(4-(2-ethoxy-6-methylpyridin-4-yl)phenyl)ethyl)-6-(2-hydroxy-2-methylpropyl)-6-phenyl-1,3-oxazinan-2-one

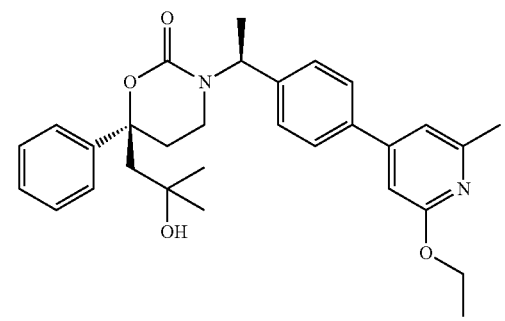 [SMILES: CCOc1cc(-c2ccc([C@H](C)N3CC[C@](CC(C)(C)O)(c4ccccc4)OC3=O)cc2)cc(C)n1]

The title compound was isolated as a byproduct from the preparation of Example 659. LC-MS Method 2 t_R=1.259 min, m/z=489.2; ¹H NMR (CDCl₃) 1.10 (s, 3H), 1.15 (s, 3H), 1.34 (m, 3H), 1.49 (m, 3H), 2.16 (m, 3H), 2.19 (m, 1H), 2.32 (m, 1H), 2.42 (m, 3H), 2.79 (m, 1H), 4.32 (m, 2H), 5.66 (m, 1H), 6.55 (s, 1H), 6.76 (s, 1H), 6.98 (m, 2H), 7.19-7.29 (m, 7H).

Example 661

N-tert-butyl-6-(4-((S)-1-((S)-6-(2-hydroxy-2-methyl-propyl)-2-oxo-6-phenyl-1,3-oxazinan-3-yl)ethyl)phenyl)nicotinamide

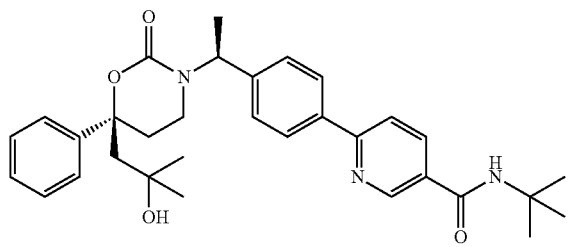 [SMILES: C[C@@H](c1ccc(-c2ccc(C(=O)NC(C)(C)C)cn2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 6-bromo-N-tert-butylnicotinamide following procedures analogous to those described in Example 486 Step 4. LC-MS Method 2 $t_R$=1.898 min, m/z=472.2; $^1$H NMR (CDCl$_3$) 1.08 (s, 3H), 1.15 (s, 3H), 1.34 (s, 9H), 1.49 (d, 3H), 2.16 (m, 3H), 2.19 (m, 1H), 2.32 (m, 1H), 2.42 (m, 3H), 2.79 (m, 1H), 4.32 (m, 2H), 5.66 (m, 1H), 6.55 (s, 1H), 6.76 (s, 1H), 6.98 (m, 2H), 7.19-7.29 (m, 7H).

6-bromo-N-tert-butylnicotinamide was prepared from 6-bromonicotinoyl chloride and tert-butylamine.

Example 662

2-(4-((S)-1-((S)-6-(2-hydroxy-2-methylpropyl)-2-oxo-6-phenyl-1,3-oxazinan-3-yl)ethyl)phenyl)isonicotinonitrile

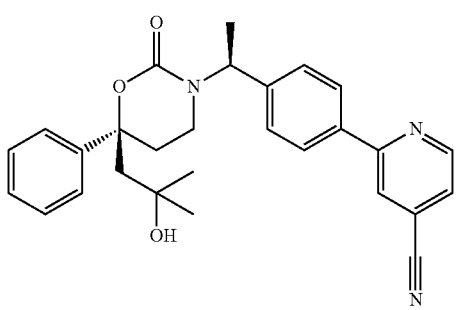 [SMILES: C[C@@H](c1ccc(-c2cc(C#N)ccn2)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromoisonicotinonitrile following a procedure analogous to that described in Example 583. LC-MS Method 2 $t_R$=1.419 min, m/z=478.1; $^1$H NMR (CD$_3$OD) 0.93 (s, 3H), 1.26 (s, 3H), 1.57 (d, 3H), 2.17 (s, 2H), 2.25 (m, 1H), 2.41-2.58 (m, 2H), 3.06 (m, 1H), 5.58 (m, 1H), 7.08 (d, 2H), 7.25-7.40 (m, 5H), 7.59 (d, 1H), 7.80 (d, 2H), 8.10 (s, 1H), 8.29 (d, 1H).

Example 663

2-(4-((S)-1-((S)-6-(2-hydroxy-2-methylpropyl)-2-oxo-6-phenyl-1,3-oxazinan-3-yl)ethyl)phenyl)nicotinonitrile

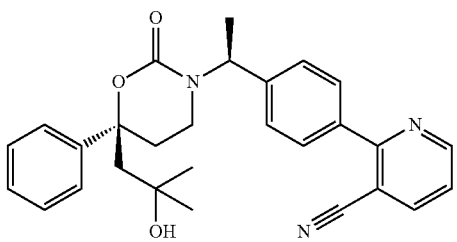 [SMILES: C[C@@H](c1ccc(-c2ncccc2C#N)cc1)N1CC[C@](CC(C)(C)O)(c2ccccc2)OC1=O]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 2-bromonicotinonitrile following a procedure analogous to that described in Example 583. LC-MS Method 2 $t_R$=1.23 min, m/z=398.1; $^1$H NMR (CD$_3$OD) 0.93 (s, 3H), 1.26 (s, 3H), 1.57 (d, 3H), 2.17 (s, 2H), 2.28 (m, 1H), 2.50 (m, 2H), 3.09 (m, 1H), 5.58 (m, 1H), 7.08 (d, 2H), 7.22-7.41 (m, 5H), 7.50 (m, 1H), 7.62 (d, 2H), 8.23 (d, 1H), 8.81 (m, 1H).

Example 664

(S)-6-(2-hydroxy-2-methylpropyl)-6-phenyl-3-((S)-1-(4-(1,5,6-trimethyl-2-oxo-1,2-dihydropyridin-4-yl)phenyl)ethyl)-1,3-oxazinan-2-one

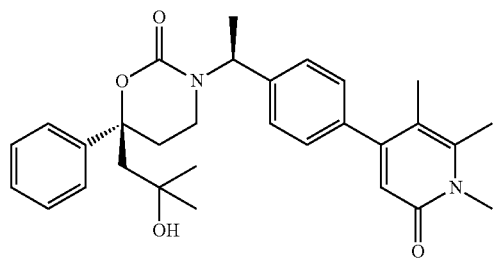 [SMILES: Cc1c(-c2ccc([C@H](C)N3CC[C@](CC(C)(C)O)(c4ccccc4)OC3=O)cc2)cc(=O)n(C)c1C]

The title compound was prepared from (S)-6-(2-hydroxy-2-methylpropyl)-6-phenyl-3-((S)-1-(4-(4,4,5,5-tetramethyl-1,3,2-dioxaborolan-2-yl)phenyl)ethyl)-1,3-oxazinan-2-one and 4-bromo-1,5,6-trimethylpyridin-2(1H)-one following a procedure analogous to that described in Example 459 Step 4. LC-MS Method 2 $t_R$=1.187 min, m/z=489.2; $^1$H NMR (CDCl$_3$) 1.10 (s, 3H), 1.15 (s, 3H), 1.32 (m, 3H), 1.52 (m, 3H), 1.72 (s, 1H), 2.18 (m, 3H), 2.19 (m, 1H), 2.42 (m, 4H), 2.86 (m, 1H), 4.12 (m, 2H), 5.66 (m, 1H), 6.16 (s, 1H), 6.53 (s, 1H), 6.98 (m, 2H), 7.23-7.34 (m, 7H).

4-bromo-1,5,6-trimethylpyridin-2(1H)-one was prepared by alkylation of 4-bromo-5,6-dimethylpyridin-2(1H)-one with methyl iodide using K$_2$CO$_3$ following a procedure analogous to that described in Example 628 Step 1. 4-bromo- 5,6-dimethylpyridin-2(1H)-one was prepared following the procedure described in McElroy, W. T. and DeShong, P. Org. Lett. 2003, 5, 4779.

Example 665

2,2-dimethyl-3-((R)-3-((S)-1-(4-(6-methylpyridazin-3-yl)phenyl)ethyl)-2-oxo-6-phenyl-1,3-oxazinan-6-yl)propanenitrile

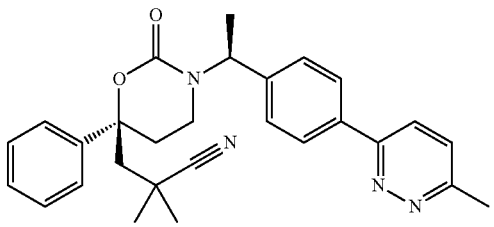 [SMILES: Cc1ccc(-c2ccc([C@H](C)N3CC[C@](CC(C)(C)C#N)(c4ccccc4)OC3=O)cc2)nn1]

The title compound was prepared from 2,2-dimethyl-3-((R)-2-oxo-6-phenyl-3-((S)-1-(4-(4, 4,5,5-tetramethyl-1,3,2-dioxaborolan-2-yl)phenyl)ethyl)-1,3-oxazinan-6-yl)propanenitrile and 3-chloro-6-methylpyridazine following a procedure analogous to that described in Example 459 Step 4. LC-MS Method 1 $t_R$=1.41 min, m/z=455; $^1$H NMR (CDCl$_3$) 8.20 (d, 1H), 7.92 (d, 1H), 7.74 (d, 2H), 7.37 (dt, 6H), 7.05 (d, 2H), 5.66 (q, 1H), 3.00 (dm, 1H), 2.93 (s, 3H), 2.49 (m, 2H), 2.34 (m, 1H), 2.17 (d, 2H), 1.58 (d, 3H), 1.39 (s, 3H), 1.33 (s, 3H).

Biological Test Example 1

The inhibition of a microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxyseroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 μl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 μL of the test compounds in DMSO previously diluted in half-log increments (8 points) starting at 0.1 mM. After a 10 minute pre-incubation, 50 μL of enzyme solution containing microsomes isolated from CHO cells overexpressing human 11β-HSD1 (10-20 μg/ml of total protein) was added, and the plates were incubated for 90 minutes at rt. The reaction was stopped by adding 50 μl of the SPA beads suspension containing 10 μM 18β-glycyrrhetinic acid, 5 mg/ml protein A coated YSi SPA beads (GE Healthcare) and 3.3 μg/ml of anti-cortisol antibody (East Coast Biologics) in Superblock buffer (Bio-Rad). The plates were shaken for 120 minutes at rt, and the SPA signal corresponding to [$^3$H]cortisol was measured on a Microbeta plate reader.

Biological Test Example 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% $CO_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% $CO_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 μL. The cells were pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) was added to achieve a final concentration of cortisone of 100 nM. The cells were incubated for 3-4 hrs at 37° C., 5% $CO_2$. Negative controls were incubated without radioactive substrate and received the same amount of [$^3$H] cortisone at the end of the incubation. Formation of [$^3$H] cortisol was monitored by analyzing 25 μL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

TABLE OF BIOLOGICAL ASSAY RESULTS

| | | Biological Test Example 1 | |
| --- | --- | --- | --- |
| Compound | IC$_{50}$ Range$^a$ | Average % inhibition at 100 nM | Average % inhibition at 111.1 nM |
| EXAMPLE 1 | ++ | | 62.7 |
| EXAMPLE 1 Isomer 1 | ++ | | 78.7 |
| EXAMPLE 1 Isomer 2 | + | | 32.6 |
| EXAMPLE 2 | + | | 28.8 |
| EXAMPLE 3 | ++ | | 74.3 |
| EXAMPLE 4 | + | | 56.2 |
| EXAMPLE 5 | + | | 34.4 |
| EXAMPLE 6 | ++ | | 78.1 |
| EXAMPLE 7 | + | | 37.3 |
| EXAMPLE 8 | + | | 6.4 |
| EXAMPLE 9 | ++ | | 93.8 |
| EXAMPLE 10 | ++ | | 90.5 |
| EXAMPLE 11 | + | | 28.4 |
| EXAMPLE 12 | ++ | | 86.4 |
| EXAMPLE 13 | + | | 19.2 |
| EXAMPLE 14 | + | | 21.9 |
| EXAMPLE 15 | + | | 38.5 |
| EXAMPLE 16 | + | | 35.7 |
| EXAMPLE 17 | ++ | | 58.8 |
| EXAMPLE 18 | + | | 7.2 |
| EXAMPLE 19 | + | | 24.0 |
| EXAMPLE 20 | ++ | | 54.8 |
| EXAMPLE 21 | ++ | | 76.7 |

TABLE OF BIOLOGICAL ASSAY RESULTS

| Compound | IC$_{50}$ Range$^a$ | Average % inhibition at 100 nM | Average % inhibition at 111.1 nM |
|---|---|---|---|
| EXAMPLE 22 | ++ | | 88.9 |
| EXAMPLE 23 | ++ | 94.0 | 88.3 |
| EXAMPLE 24 | ++ | 93.4 | 86.0 |
| EXAMPLE 25 | ++ | 91.7 | 84.2 |
| EXAMPLE 26 | ++ | 88.2 | 87.0 |
| EXAMPLE 27 | ++ | | 67.0 |
| EXAMPLE 28 | ++ | 93.6 | 82.3 |
| EXAMPLE 28 Isomer 1 | ++ | | 72.3 |
| EXAMPLE 28 Isomer 2 | ++ | | 96.6 |
| EXAMPLE 29 | + | | 29.8 |
| EXAMPLE 30 | + | | 23.1 |
| EXAMPLE 31 | + | | 27.5 |
| EXAMPLE 32 | + | | 46.0 |
| EXAMPLE 33 | + | | 37.1 |
| EXAMPLE 34 | ++ | | 72.0 |
| EXAMPLE 35 | + | | 26.7 |
| EXAMPLE 36 | ++ | | 63.3 |
| EXAMPLE 37 | ++ | | 81.0 |
| EXAMPLE 38 | + | | 17.8 |
| EXAMPLE 39 | + | | 24.8 |
| EXAMPLE 40 | + | | 28.8 |
| EXAMPLE 41 | + | | 19.9 |
| EXAMPLE 42 | + | | 36.7 |
| EXAMPLE 43 | ++ | | 77.7 |
| EXAMPLE 44 | + | | 35.0 |
| EXAMPLE 45 | + | | 31.2 |
| EXAMPLE 46 | + | | 46.4 |
| EXAMPLE 47 | + | | 36.3 |
| EXAMPLE 48 | + | | 37.0 |
| EXAMPLE 49 | + | | 15.4 |
| EXAMPLE 50 | ++ | | 96.3 |
| EXAMPLE 51 Isomer 1 | ++ | | 93.7 |
| EXAMPLE 51 Isomer 2 | + | | 38.6 |
| EXAMPLE 52 | ++ | 98.6 | |
| EXAMPLE 52 Isomer 1 | ++ | 92.8 | |
| EXAMPLE 52 Isomer 2 | ++ | 90.8 | 97.0 |
| EXAMPLE 53 | ++ | | 57.1 |
| EXAMPLE 54 | + | | 15.5 |
| EXAMPLE 55 | + | | 3.7 |
| EXAMPLE 56 | + | | 5.6 |
| EXAMPLE 57 | + | | 10.4 |
| EXAMPLE 58 | + | | 34.8 |
| EXAMPLE 59 | + | | 18.0 |
| EXAMPLE 60 | + | | 51.3 |
| EXAMPLE 61 | + | | 17.7 |
| EXAMPLE 62 | + | | 20.5 |
| EXAMPLE 63 | ++ | | 59.0 |
| EXAMPLE 64 | ++ | | 94.0 |
| EXAMPLE 65 | ++ | 95.9 | 98.4 |
| EXAMPLE 65 Isomer 1 | ++ | 94.8 | 97.6 |
| EXAMPLE 65 Isomer 2 | ++ | 48.8 | 57.1 |
| EXAMPLE 66 | ++ | 90.8 | 93.0 |
| EXAMPLE 67 | ++ | 93.1 | 96.6 |
| EXAMPLE 68 | ++ | 92.0 | 92.9 |
| EXAMPLE 69 | ++ | 94.7 | 94.8 |
| EXAMPLE 70 | + | | 9.3 |
| EXAMPLE 71 | + | | |
| EXAMPLE 72 | ++ | | 77.5 |
| EXAMPLE 73 | + | | 48.4 |
| EXAMPLE 74 | ++ | | 70.0 |
| EXAMPLE 75 | ++ | | 57.8 |
| EXAMPLE 76 | ++ | 81.0 | |
| EXAMPLE 77 | ++ | 88.7 | 89.2 |
| EXAMPLE 78 | ++ | | 93.8 |
| EXAMPLE 79 | ++ | | 75.3 |
| EXAMPLE 80 | ++ | | 77.8 |
| EXAMPLE 81 | ++ | | 72.2 |
| EXAMPLE 82 Isomer 1 | ++ | | 87.6 |
| EXAMPLE 82 Isomer 2 | ++ | | 89.2 |
| EXAMPLE 83 Isomer 1 | + | | 50.3 |
| EXAMPLE 83 Isomer 2 | + | | 45.8 |
| EXAMPLE 84 | ++ | | 94.6 |
| EXAMPLE 84 Isomer 1 | ++ | | 74.8 |
| EXAMPLE 85 | ++ | | 102.0 |
| EXAMPLE 85 Isomer 1 | ++ | | 93.1 |
| EXAMPLE 86 | ++ | | 85.7 |
| EXAMPLE 86 Isomer 1 | + | | 43.3 |
| EXAMPLE 87 | ++ | | |
| EXAMPLE 87 Isomer 1 | + | | 13.3 |
| EXAMPLE 88 | ++ | | 97.1 |
| EXAMPLE 88 Isomer 1 | + | | 74.4 |
| EXAMPLE 89 | ++ | | 71.4 |
| EXAMPLE 90 | ++ | | 83.1 |
| EXAMPLE 91 | + | | 39.8 |
| EXAMPLE 92 | + | | 35.0 |
| EXAMPLE 93 | + | | 45.3 |
| EXAMPLE 94 | + | | 16.2 |
| EXAMPLE 95 | ++ | | 97.3 |
| EXAMPLE 95 Isomer 1 | ++ | | 91.0 |
| EXAMPLE 96 | ++ | | 91.9 |
| EXAMPLE 96 Isomer 1 | ++ | 88.3 | 98.5 |
| EXAMPLE 96 Isomer 2 | − | | 9.7 |
| EXAMPLE 97 Isomer 1 | + | | 52.8 |
| EXAMPLE 97 Isomer 2 | ++ | | 88.2 |
| EXAMPLE 98 | ++ | | 73.4 |
| EXAMPLE 99 | ++ | | 75.3 |
| EXAMPLE 100 | ++ | | 93.7 |
| EXAMPLE 101 | ++ | | 84.4 |
| EXAMPLE 102 | ++ | | 91.7 |
| EXAMPLE 102 Isomer 1 | + | | 35.4 |
| EXAMPLE 102 Isomer 2 | ++ | 94.0 | 95.5 |
| EXAMPLE 103 | ++ | | 86.9 |
| EXAMPLE 104 | ++ | | 85.7 |
| EXAMPLE 104 Isomer 1 | + | | 44.3 |
| EXAMPLE 104 Isomer 2 | ++ | | 98.1 |
| EXAMPLE 105 | ++ | | 87.4 |
| EXAMPLE 106 | ++ | | 88.7 |
| EXAMPLE 107 | ++ | 90.9 | 97.0 |
| EXAMPLE 108 | ++ | | 55.4 |
| EXAMPLE 109 | ++ | 94.1 | 94.0 |
| EXAMPLE 109 Isomer 1 | ++ | | 67.0 |
| EXAMPLE 109 Isomer 2 | ++ | 98.4 | 93.7 |
| EXAMPLE 110 Isomer 1 | ++ | 90.5 | |
| EXAMPLE 110 Isomer 2 | ++ | 96.6 | 95.0 |
| EXAMPLE 111 Isomer 1 | ++ | | 90.9 |
| EXAMPLE 111 Isomer 2 | ++ | | 58.9 |
| EXAMPLE 112 Isomer 1 | ++ | | 34.7 |
| EXAMPLE 112 Isomer 2 | ++ | 95.2 | 99.9 |
| EXAMPLE 113 Isomer 1 | ++ | | 83.2 |
| EXAMPLE 113 Isomer 2 | ++ | | 82.6 |
| EXAMPLE 114 Isomer 1 | − | 17.4 | |
| EXAMPLE 114 Isomer 2 | ++ | 66.6 | |
| EXAMPLE 115 Isomer 1 | + | | 54.7 |
| EXAMPLE 115 Isomer 2 | ++ | 99.3 | 104.2 |
| EXAMPLE 116 | ++ | | 97.6 |
| EXAMPLE 117 | ++ | | 82.8 |
| EXAMPLE 118 | ++ | | 96.8 |
| EXAMPLE 119 Isomer 1 | ++ | 95.4 | |
| EXAMPLE 119 Isomer 2 | ++ | | 56.3 |
| EXAMPLE 120 Isomer 1 | ++ | 91.8 | 91.5 |
| EXAMPLE 120 Isomer 2 | ++ | 90.6 | |
| EXAMPLE 121 | + | | 34.2 |
| EXAMPLE 122 | ++ | 94.1 | 95.6 |
| EXAMPLE 123 | ++ | | 97.6 |
| EXAMPLE 124 | ++ | 95.2 | 96.8 |
| EXAMPLE 125 | ++ | 98.3 | 94.0 |
| EXAMPLE 126 | ++ | 79.0 | 80.7 |
| EXAMPLE 127 | ++ | 86.3 | |
| EXAMPLE 128 Isomer 1 | + | 26.1 | 27.5 |
| EXAMPLE 128 Isomer 2 | − | | 6.5 |
| EXAMPLE 129 | + | | 32.1 |
| EXAMPLE 129 Isomer 1 | + | | 29.2 |
| EXAMPLE 129 Isomer 2 | + | | 20.9 |
| EXAMPLE 130 Isomer 1 | ++ | 92.2 | |

TABLE OF BIOLOGICAL ASSAY RESULTS

Biological Test Example 1

| Compound | IC$_{50}$ Range$^a$ | Average % inhibition at 100 nM | Average % inhibition at 111.1 nM |
|---|---|---|---|
| EXAMPLE 130 Isomer 2 | ++ |  | 87.7 |
| EXAMPLE 131 | − | 6.6 | 11.3 |
| EXAMPLE 132 | + |  | 30.4 |
| EXAMPLE 133 | ++ | 85.8 | 95.4 |
| EXAMPLE 134 | ++ | 93.9 | 96.2 |
| EXAMPLE 135 | ++ | 88.9 | 93.8 |
| EXAMPLE 136 | ++ | 96.4 | 97.3 |
| EXAMPLE 137 Isomer 1 | ++ |  | 96.7 |
| EXAMPLE 137 Isomer 2 | ++ | 96.4 | 95.5 |
| EXAMPLE 138 | ++ | 95.9 | 95.4 |
| EXAMPLE 139 | ++ | 93.8 | 96.2 |
| EXAMPLE 140 | ++ | 95.6 | 97.1 |
| EXAMPLE 141 | ++ | 90.6 | 92.2 |
| EXAMPLE 142 | + | 34.4 | 27.4 |
| EXAMPLE 143 Isomer 1 | ++ |  | 54.4 |
| EXAMPLE 143 Isomer 2 | ++ | 95.4 |  |
| EXAMPLE 144 Isomer 1 | ++ |  | 90.6 |
| EXAMPLE 144 Isomer 2 | ++ | 95.3 | 96.6 |
| EXAMPLE 145 | ++ | 96.5 |  |
| EXAMPLE 146 | ++ |  | 79.9 |
| EXAMPLE 147 | ++ |  | 89.5 |
| EXAMPLE 148 | ++ |  | 85.0 |
| EXAMPLE 149 | ++ | 95.3 |  |
| EXAMPLE 150 | ++ |  | 92.9 |
| EXAMPLE 151 | ++ |  | 77.0 |
| EXAMPLE 152 | ++ |  | 79.0 |
| EXAMPLE 153 | + | 27.0 | 26.6 |
| EXAMPLE 154 | ++ |  | 79.0 |
| EXAMPLE 155 | + |  | 45.6 |
| EXAMPLE 156 | ++ |  | 93.8 |
| EXAMPLE 157 Isomer 1 | ++ | 97.4 |  |
| EXAMPLE 157 Isomer 2 | ++ | 92.9 | 90.7 |
| EXAMPLE 158 | + |  | 23.8 |
| EXAMPLE 159 | ++ | 98.6 |  |
| EXAMPLE 160 Isomer 1 | ++ |  | 93.5 |
| EXAMPLE 160 Isomer 2 | ++ | 95.9 | 95.2 |
| EXAMPLE 161 Isomer 1 | ++ |  | 81.7 |
| EXAMPLE 161 Isomer 2 | + |  | 60.5 |
| EXAMPLE 161 Isomer 3 | ++ | 93.2 | 89.8 |
| EXAMPLE 162 | ++ | 96.5 |  |
| EXAMPLE 163 Isomer 1 | ++ |  | 66.8 |
| EXAMPLE 163 Isomer 2 | ++ | 96.9 |  |
| EXAMPLE 163 Isomer 3 | # | 11.3 |  |
| EXAMPLE 164 | ++ | 95.9 |  |
| EXAMPLE 165 | ++ |  | 92.9 |
| EXAMPLE 166 | ++ |  | 81.8 |
| EXAMPLE 167 Isomer 1 | ++ | 73.7 | 79.0 |
| EXAMPLE 167 Isomer 2 | ++ |  | 77.2 |
| EXAMPLE 168 Isomer 1 | ++ | 97.2 |  |
| EXAMPLE 168 Isomer 2 | ++ | 95.6 |  |
| EXAMPLE 169 | ++ | 97.0 |  |
| EXAMPLE 170 | ++ | 97.0 |  |
| EXAMPLE 171 Isomer 1 | ++ | 95.7 |  |
| EXAMPLE 171 Isomer 2 | ++ | 68.6 |  |
| EXAMPLE 172 | ++ | 95.8 |  |
| EXAMPLE 173 Isomer 1 | ++ | 96.7 |  |
| EXAMPLE 173 Isomer 2 | ++ | 94.5 |  |
| EXAMPLE 174 | + |  | 48.0 |
| EXAMPLE 175 Isomer 1 | ++ | 94.3 | 93.7 |
| EXAMPLE 175 Isomer 2 | + |  | 25.8 |
| EXAMPLE 176 | + |  | 54.8 |
| EXAMPLE 177 | ++ |  | 77.4 |
| EXAMPLE 178 | ++ |  | 77.7 |
| EXAMPLE 179 | ++ |  | 79.4 |
| EXAMPLE 180 | ++ | 85.2 | 84.9 |
| EXAMPLE 181 | ++ | 101.0 | 90.7 |
| EXAMPLE 182 | ++ |  | 79.5 |
| EXAMPLE 183 | ++ |  | 88.6 |
| EXAMPLE 184 | + |  | 65.4 |
| EXAMPLE 185 | ++ | 98.4 |  |
| EXAMPLE 186 Isomer 1 | ++ | 64.5 |  |
| EXAMPLE 186 Isomer 2 | # | 33.5 |  |
| EXAMPLE 187 Isomer 1 | ++ | 98.7 |  |
| EXAMPLE 187 Isomer 2 | ++ | 46.4 |  |
| EXAMPLE 188 Isomer 1 | ++ | 77.0 |  |
| EXAMPLE 188 Isomer 2 | # | 31.7 |  |
| EXAMPLE 189 Isomer 1 | ++ | 95.2 |  |
| EXAMPLE 189 Isomer 2 | ++ | 90.1 |  |
| EXAMPLE 190 | ++ | 76.0 |  |
| EXAMPLE 191 Isomer 1 | ++ | 98.9 |  |
| EXAMPLE 191 Isomer 2 | ++ | 69.0 |  |
| EXAMPLE 192 | ++ | 70.7 |  |
| EXAMPLE 193 Isomer 1 | ++ | 95.6 |  |
| EXAMPLE 193 Isomer 2 | ++ | 94.3 |  |
| EXAMPLE 194 | ++ | 89.5 |  |
| EXAMPLE 195 | ++ | 96.8 |  |
| EXAMPLE 196 Isomer 1 | ++ | 101.1 |  |
| EXAMPLE 196 Isomer 2 | ++ | 98.9 |  |
| EXAMPLE 197 Isomer 1 | ++ | 90.4 |  |
| EXAMPLE 197 Isomer 2 | ++ | 82.1 |  |
| EXAMPLE 198 | ++ | 88.2 |  |
| EXAMPLE 199 | ++ | 90.3 |  |
| EXAMPLE 200 Isomer 1 | ++ | 96.4 |  |
| EXAMPLE 200 Isomer 2 | ++ | 73.1 |  |
| EXAMPLE 201 Isomer 1 | ++ | 93.2 |  |
| EXAMPLE 201 Isomer 2 | # | 27.0 |  |
| EXAMPLE 202 | ++ | 95.9 |  |
| EXAMPLE 203 Isomer 1 | ++ | 88.6 |  |
| EXAMPLE 203 Isomer 2 | ++ | 93.8 |  |
| EXAMPLE 204 Isomer 1 | ++ | 97.4 |  |
| EXAMPLE 204 Isomer 2 | ++ | 99.4 |  |
| EXAMPLE 205 | ++ | 98.0 |  |
| EXAMPLE 206 Isomer 1 | ++ | 90.3 |  |
| EXAMPLE 206 Isomer 2 | ++ | 85.9 |  |
| EXAMPLE 207 Isomer 1 | ++ | 89.9 |  |
| EXAMPLE 207 Isomer 2 | ++ | 89.3 |  |
| EXAMPLE 208 Isomer 1 | ++ | 76.6 |  |
| EXAMPLE 208 Isomer 2 | # | 38.5 |  |
| EXAMPLE 208 Isomer 3 | ++ | 64.6 |  |
| EXAMPLE 208 Isomer 4 | ++ | 29.3 |  |
| EXAMPLE 209 | ++ | 88.8 |  |
| EXAMPLE 210 | ++ | 96.3 |  |
| EXAMPLE 211 | ++ | 93.3 |  |
| EXAMPLE 212 Isomer 1 | ++ | 96.8 |  |
| EXAMPLE 212 Isomer 2 | ++ | 82.6 |  |
| EXAMPLE 213 | ++ | 79.1 |  |
| EXAMPLE 214 | ++ | 94.3 |  |
| EXAMPLE 215 | ++ | 72.1 |  |
| EXAMPLE 216 | ++ | 92.6 |  |
| EXAMPLE 217 | ++ | 88.0 |  |
| EXAMPLE 218 Isomer 1 | ++ | 97.4 |  |
| EXAMPLE 218 Isomer 2 | ++ | 60.3 |  |
| EXAMPLE 219 | ++ | 92.7 |  |
| EXAMPLE 220 | ++ | 85.5 |  |
| EXAMPLE 221 | ++ | 94.1 |  |
| EXAMPLE 222 | ++ | 87.3 |  |
| EXAMPLE 223 Isomer 1 | ++ | 94.2 |  |
| EXAMPLE 223 Isomer 2 | ++ | 97.1 |  |
| EXAMPLE 223 Isomer 3 | # | 27.8 |  |
| EXAMPLE 223 Isomer 4 | # | 52.5 |  |
| EXAMPLE 224 | ++ | 97.3 |  |
| EXAMPLE 224 Isomer 1 | ++ | 100.4 |  |
| EXAMPLE 224 Isomer 2 | ++ | 95.6 |  |
| EXAMPLE 225 | ++ | 96.5 |  |
| EXAMPLE 226 | ++ | 90.7 |  |
| EXAMPLE 227 Isomer 1 | ++ | 95.0 |  |
| EXAMPLE 227 Isomer 2 | ++ | 60.7 |  |
| EXAMPLE 228 | + | 30.6 | 19.6 |
| EXAMPLE 229 | ++ | 81.6 |  |
| EXAMPLE 230 | ++ | 73.6 |  |
| EXAMPLE 231 | ++ | 57.0 |  |
| EXAMPLE 232 | ++ | 96.9 |  |
| EXAMPLE 233 Isomer 1 | ++ | 98.9 |  |
| EXAMPLE 233 Isomer 2 | ++ | 64.1 |  |

TABLE OF BIOLOGICAL ASSAY RESULTS

Biological Test Example 1

| Compound | IC$_{50}$ Range$^a$ | Average % inhibition at 100 nM | Average % inhibition at 111.1 nM |
|---|---|---|---|
| EXAMPLE 234 | ++ | 93.4 | |
| EXAMPLE 235 | ++ | 93.4 | |
| EXAMPLE 236 | ++ | 96.8 | |
| EXAMPLE 237 | ++ | 92.6 | |
| EXAMPLE 238 | ++ | 98.0 | |
| EXAMPLE 239 Isomer 1 | ++ | 91.5 | |
| EXAMPLE 239 Isomer 2 | ++ | 89.5 | |
| EXAMPLE 240 | ++ | 94.6 | |
| EXAMPLE 241 | ++ | 96.7 | |
| EXAMPLE 242 | ++ | 91.4 | |
| EXAMPLE 243 | ++ | 38.9 | |
| EXAMPLE 244 | ++ | 90.9 | |
| EXAMPLE 245 | ++ | 92.6 | |
| EXAMPLE 246 Isomer 1 | ++ | 94.8 | |
| EXAMPLE 246 Isomer 2 | ++ | 92.9 | |
| EXAMPLE 247 | ++ | 96.8 | |
| EXAMPLE 248 | ++ | 96.7 | |
| EXAMPLE 249 | ++ | 96.3 | |
| EXAMPLE 250 | ++ | 97.1 | |
| EXAMPLE 251 | ++ | 90.9 | |
| EXAMPLE 252 | ++ | 99.0 | |
| EXAMPLE 253 | ++ | 93.3 | |
| EXAMPLE 254 | ++ | 96.0 | |
| EXAMPLE 255 Isomer 1 | ++ | 92.5 | |
| EXAMPLE 255 Isomer 2 | ++ | 89.3 | |
| EXAMPLE 256 | ++ | 93.1 | |
| EXAMPLE 257 | ++ | 78.5 | |
| EXAMPLE 258 | ++ | 86.2 | |
| EXAMPLE 259 | ++ | 43.1 | |
| EXAMPLE 260 | ++ | 94.1 | |
| EXAMPLE 261 | ++ | 96.2 | |
| EXAMPLE 262 | ++ | 86.5 | |
| EXAMPLE 263 | ++ | 92.3 | |
| EXAMPLE 264 | ++ | 99.9 | |
| EXAMPLE 265 | ++ | 56.8 | |
| EXAMPLE 266 | ++ | 93.5 | |
| EXAMPLE 267 | ++ | 88.0 | |
| EXAMPLE 268 | ++ | 50.8 | |
| EXAMPLE 269 | ++ | 92.8 | |
| EXAMPLE 270 | ++ | 96.1 | |
| EXAMPLE 271 | ++ | 94.6 | |
| EXAMPLE 272 | ++ | 93.8 | |
| EXAMPLE 273 Isomer 1 | ++ | 53.6 | |
| EXAMPLE 273 Isomer 2 | # | 17.9 | |
| EXAMPLE 274 | ++ | 96.2 | |
| EXAMPLE 275 | ++ | 91.5 | |
| EXAMPLE 276 Isomer 1 | ++ | 83.1 | |
| EXAMPLE 276 Isomer 2 | # | 35.4 | |
| EXAMPLE 277 Isomer 1 | ++ | 91.1 | |
| EXAMPLE 277 Isomer 2 | ++ | 65.6 | |
| EXAMPLE 278 Isomer 1 | ++ | 86.6 | |
| EXAMPLE 278 Isomer 2 | ++ | 65.5 | |
| EXAMPLE 279 Isomer 1 | # | 11.9 | |
| EXAMPLE 279 Isomer 2 | ++ | 42.5 | |
| EXAMPLE 280 | ++ | 82.4 | |
| EXAMPLE 281 | ++ | 100.1 | |
| EXAMPLE 282 Isomer 1 | ++ | 94.0 | |
| EXAMPLE 282 Isomer 2 | ++ | 77.8 | |
| EXAMPLE 283 | ++ | 92.6 | |
| EXAMPLE 284 | ++ | 97.7 | |
| EXAMPLE 285 | ++ | 96.2 | |
| EXAMPLE 286 Isomer 1 | ++ | 94.1 | |
| EXAMPLE 286 Isomer 2 | ++ | 94.5 | |
| EXAMPLE 286 Isomer 3 | ++ | 70.5 | |
| EXAMPLE 286 Isomer 4 | # | 29.3 | |
| EXAMPLE 287 | ++ | 89.8 | |
| EXAMPLE 288 | ++ | 72.4 | |
| EXAMPLE 289 | ++ | 94.1 | |
| EXAMPLE 290 | ++ | 91.8 | |
| EXAMPLE 291 | ++ | 96.7 | |
| EXAMPLE 292 | ++ | 93.4 | |
| EXAMPLE 293 | ++ | 94.0 | |
| EXAMPLE 294 | ++ | 97.2 | |
| EXAMPLE 295 | ++ | 91.0 | |
| EXAMPLE 296 | ++ | 94.3 | |
| EXAMPLE 297 | ++ | 86.6 | |
| EXAMPLE 298 | ++ | 96.7 | |
| EXAMPLE 299 | ++ | 71.7 | |
| EXAMPLE 300 | ++ | 81.2 | |
| EXAMPLE 301 | ++ | 86.7 | |
| EXAMPLE 302 | ++ | 96.1 | |
| EXAMPLE 303 | ++ | 98.4 | |
| EXAMPLE 304 | ++ | 94.5 | |
| EXAMPLE 305 | ++ | 98.7 | |
| EXAMPLE 306 | ++ | 97.1 | |
| EXAMPLE 307 | ++ | 96.5 | |
| EXAMPLE 308 | − | 25.0 | 8.6 |
| EXAMPLE 309 | ++ | 97.2 | |
| EXAMPLE 310 | ++ | 77.5 | |
| EXAMPLE 311 | ++ | 96.7 | |
| EXAMPLE 312 | ++ | 85.7 | |
| EXAMPLE 313 | ++ | 96.7 | |
| EXAMPLE 314 | ++ | 96.5 | |
| EXAMPLE 315 | ++ | 93.2 | |
| EXAMPLE 316 | ++ | 88.8 | |
| EXAMPLE 317 | ++ | 87.5 | |
| EXAMPLE 318 | ++ | 83.8 | |
| EXAMPLE 319 | ++ | 93.4 | |
| EXAMPLE 320 | ++ | 97.5 | |
| EXAMPLE 321 | ++ | 96.1 | |
| EXAMPLE 322 | ++ | 96.3 | |
| EXAMPLE 323 Isomer 1 | ++ | 85.9 | |
| EXAMPLE 323 Isomer 2 | ++ | 100.9 | |
| EXAMPLE 324 | ++ | 94.3 | |
| EXAMPLE 325 | ++ | 97.1 | |
| EXAMPLE 326 | ++ | 97.7 | |
| EXAMPLE 327 | ++ | 97.2 | |
| EXAMPLE 328 | ++ | 98.8 | |
| EXAMPLE 329 | ++ | 99.8 | |
| EXAMPLE 330 | ++ | 97.8 | |
| EXAMPLE 331 | ++ | 97.1 | |
| EXAMPLE 332 Isomer 1 | ++ | 97.8 | |
| EXAMPLE 332 Isomer 2 | # | 32.2 | |
| EXAMPLE 333 Isomer 1 | ++ | 96.2 | |
| EXAMPLE 333 Isomer 2 | # | 9.1 | |
| EXAMPLE 334 Isomer 1 | ++ | 96.6 | |
| EXAMPLE 334 Isomer 2 | # | 31.9 | |
| EXAMPLE 335 Isomer 1 | ++ | 48.2 | |
| EXAMPLE 335 Isomer 2 | ++ | 96.7 | |
| EXAMPLE 336 Isomer 1 | ++ | 50.8 | |
| EXAMPLE 336 Isomer 2 | ++ | 94.6 | |
| EXAMPLE 337 | ++ | 59.4 | |
| EXAMPLE 338 Isomer 1 | ++ | 89.1 | |
| EXAMPLE 338 Isomer 2 | # | 30.5 | |
| EXAMPLE 339 | ++ | 65.9 | |
| EXAMPLE 340 | ++ | 75.9 | |
| EXAMPLE 341 | ++ | 82.0 | |
| EXAMPLE 342 | ++ | 64.2 | |
| EXAMPLE 343 | ++ | 82.3 | |
| EXAMPLE 344 | ++ | 65.7 | |
| EXAMPLE 345 | ++ | 74.7 | |
| EXAMPLE 346 | ++ | 94.0 | |
| EXAMPLE 347 | ++ | 96.0 | |
| EXAMPLE 348 | ++ | 48.9 | |
| EXAMPLE 349 | ++ | 89.8 | |
| EXAMPLE 350 | ++ | 91.8 | |
| EXAMPLE 351 | ++ | 83.1 | |
| EXAMPLE 352 | ++ | 60.8 | |
| EXAMPLE 353 | ++ | 90.7 | |
| EXAMPLE 354 | ++ | 95.2 | |
| EXAMPLE 355 | ++ | 95.5 | |
| EXAMPLE 356 | ++ | 92.0 | |
| EXAMPLE 357 | ++ | 60.7 | |
| EXAMPLE 358 | ++ | 84.0 | |

TABLE OF BIOLOGICAL ASSAY RESULTS

Biological Test Example 1

| Compound | IC$_{50}$ Range$^a$ | Average % inhibition at 100 nM | Average % inhibition at 111.1 nM |
|---|---|---|---|
| EXAMPLE 359 | ++ | 67.5 | |
| EXAMPLE 360 | ++ | 97.0 | |
| EXAMPLE 361 | ++ | 67.4 | |
| EXAMPLE 362 | ++ | 93.4 | |
| EXAMPLE 363 | ++ | 74.5 | |
| EXAMPLE 364 | ++ | 66.3 | |
| EXAMPLE 365 Isomer 1 | ++ | 97.5 | |
| EXAMPLE 365 Isomer 2 | ++ | 61.1 | |
| EXAMPLE 366 | ++ | 95.1 | |
| EXAMPLE 367 | ++ | 44.8 | |
| EXAMPLE 368 | ++ | 96.9 | |
| EXAMPLE 369 | ++ | 100.1 | |
| EXAMPLE 370 | ++ | 97.0 | |
| EXAMPLE 371 Isomer 1 | ++ | 98.4 | |
| EXAMPLE 371 Isomer 2 | ++ | 97.4 | |
| EXAMPLE 372 Isomer 1 | ++ | 97.7 | |
| EXAMPLE 372 Isomer 2 | ++ | 98.8 | |
| EXAMPLE 373 | ++ | 89.1 | |
| EXAMPLE 374 | ++ | 52.2 | |
| EXAMPLE 375 | ++ | 70.9 | |
| EXAMPLE 376 | ++ | 50.3 | |
| EXAMPLE 377 | ++ | 72.0 | |
| EXAMPLE 378 | ++ | 70.0 | |
| EXAMPLE 379 | ++ | 57.7 | |
| EXAMPLE 380 | ++ | 97.2 | |
| EXAMPLE 381 | ++ | 97.2 | |
| EXAMPLE 382 | ++ | 81.3 | |
| EXAMPLE 383 Isomer 1 | ++ | 94.7 | |
| EXAMPLE 383 Isomer 2 | ++ | 95.3 | |
| EXAMPLE 384 | ++ | 89.2 | |
| EXAMPLE 385 | ++ | 95.3 | |
| EXAMPLE 386 | ++ | 52.5 | |
| EXAMPLE 387 | ++ | 95.8 | |
| EXAMPLE 388 Isomer 1 | ++ | 92.8 | |
| EXAMPLE 388 Isomer 2 | ++ | 94.7 | |
| EXAMPLE 389 | ++ | 96.4 | |
| EXAMPLE 390 | ++ | 96.3 | |
| EXAMPLE 391 | ++ | 94.5 | |
| EXAMPLE 392 | ++ | 97.9 | |
| EXAMPLE 393 | ++ | 99.2 | |
| EXAMPLE 394 | ++ | 99.1 | |
| EXAMPLE 395 | ++ | 98.8 | |
| EXAMPLE 396 | ++ | 98.6 | |
| EXAMPLE 397 | ++ | 94.7 | |
| EXAMPLE 398 | ++ | 97.7 | |
| EXAMPLE 399 | ++ | 97.9 | |
| EXAMPLE 400 | ++ | 96.8 | |
| EXAMPLE 401 | ++ | 98.6 | |
| EXAMPLE 402 | ++ | 96.8 | |
| EXAMPLE 403 | ++ | 99.5 | |
| EXAMPLE 404 | ++ | 91.2 | |
| EXAMPLE 405 | ++ | 55.7 | |
| EXAMPLE 406 | ++ | 86.4 | |
| EXAMPLE 407 | ++ | 94.7 | |
| EXAMPLE 408 | ++ | 90.2 | |
| EXAMPLE 409 | ++ | 91.6 | |
| EXAMPLE 410 | ++ | 52.0 | |
| EXAMPLE 411 Isomer 1 | ++ | 88.7 | |
| EXAMPLE 411 Isomer 2 | ++ | 93.1 | |
| EXAMPLE 412 | ++ | 94.7 | |
| EXAMPLE 413 | ++ | 95.3 | |
| EXAMPLE 414 | ++ | 94.4 | |
| EXAMPLE 415 | ++ | 87.6 | |
| EXAMPLE 416 | ++ | 55.1 | |
| EXAMPLE 417 | ++ | 97.1 | |
| EXAMPLE 418 | ++ | 99.2 | |
| EXAMPLE 419 | ++ | 96.9 | |
| EXAMPLE 420 | ++ | 97.3 | |
| EXAMPLE 421 | ++ | 96.1 | |
| EXAMPLE 422 | ++ | 100.3 | |
| EXAMPLE 423 | ++ | 97.6 | |
| EXAMPLE 424 | ++ | 97.0 | |
| EXAMPLE 425 | ++ | 96.2 | |
| EXAMPLE 426 | ++ | 82.5 | |
| EXAMPLE 427 | ++ | 97.8 | |
| EXAMPLE 428 | ++ | 82.0 | |
| EXAMPLE 429 Isomer 1 | ++ | 77.9 | |
| EXAMPLE 429 Isomer 2 | # | 23.0 | |
| EXAMPLE 430 | ++ | 99.4 | |
| EXAMPLE 431 | ++ | 97.4 | |
| EXAMPLE 432 | ++ | 100.5 | |
| EXAMPLE 433 | ++ | 91.9 | |
| EXAMPLE 434 | ++ | 96.2 | |
| EXAMPLE 435 | ++ | 97.9 | |
| EXAMPLE 436 | ++ | 101.1 | |
| EXAMPLE 437 | ++ | 99.6 | |
| EXAMPLE 438 | ++ | 99.0 | |
| EXAMPLE 439 | ++ | 95.6 | |
| EXAMPLE 440 | ++ | 100.9 | |
| EXAMPLE 441 | ++ | 50.0 | |
| EXAMPLE 442 | ++ | 98.3 | |
| EXAMPLE 443 | ++ | 49.7 | |
| EXAMPLE 444 | ++ | 68.7 | |
| EXAMPLE 445 | ++ | 64.8 | |
| EXAMPLE 446 | ++ | 65.3 | |
| EXAMPLE 447 | ++ | 95.7 | |
| EXAMPLE 448 | ++ | 97.7 | |
| EXAMPLE 449 | ++ | 98.7 | 99.4 |
| EXAMPLE 450 | ++ | 79.9 | |
| EXAMPLE 451 | ++ | 95.8 | |
| EXAMPLE 452 | ++ | 76.9 | |
| EXAMPLE 453 | ++ | 96.0 | |
| EXAMPLE 454 | ++ | 99.3 | |
| EXAMPLE 455 | ++ | 98.1 | |
| EXAMPLE 456 | ++ | 94.7 | |
| EXAMPLE 457 | ++ | 93.3 | |
| EXAMPLE 458 | ++ | 90.1 | |
| EXAMPLE 459 | ++ | 96.4 | |
| EXAMPLE 460 | ++ | 95.9 | |
| EXAMPLE 461 | ++ | 95.0 | |
| EXAMPLE 462 | ++ | 72.3 | |
| EXAMPLE 463 | ++ | 81.3 | |
| EXAMPLE 464 | ++ | 80.2 | |
| EXAMPLE 465 | ++ | 65.0 | |
| EXAMPLE 466 | ++ | 55.3 | |
| EXAMPLE 467 | ++ | 81.2 | |
| EXAMPLE 468 | ++ | 94.3 | |
| EXAMPLE 469 | ++ | 99.6 | |
| EXAMPLE 470 | ++ | 99.8 | |
| EXAMPLE 471 | ++ | 98.3 | |
| EXAMPLE 472 | ++ | 98.9 | |
| EXAMPLE 473 | ++ | 96.7 | |
| EXAMPLE 474 | ++ | 90.2 | |
| EXAMPLE 475 | ++ | 97.3 | |
| EXAMPLE 476 | ++ | 101.5 | |
| EXAMPLE 477 | ++ | 98.7 | |
| EXAMPLE 478 | ++ | 93.9 | |
| EXAMPLE 479 | ++ | 99.8 | |
| EXAMPLE 480 | ++ | 98.8 | |
| EXAMPLE 481 | ++ | 97.8 | |
| EXAMPLE 482 | ++ | 98.5 | |
| EXAMPLE 483 | ++ | 93.1 | |
| EXAMPLE 484 | ++ | 95.8 | |
| EXAMPLE 485 | ++ | 95.0 | |
| EXAMPLE 486 | ++ | 96.5 | |
| EXAMPLE 487 | ++ | 74.3 | |
| EXAMPLE 488 | ++ | 99.1 | |
| EXAMPLE 489 | ++ | 98.3 | |
| EXAMPLE 490 | ++ | 94.8 | |
| EXAMPLE 491 | ++ | 99.3 | |
| EXAMPLE 492 | ++ | 87.7 | |
| EXAMPLE 493 | ++ | 89.1 | |
| EXAMPLE 494 | ++ | 100.1 | |
| EXAMPLE 495 | ++ | 95.8 | |

TABLE OF BIOLOGICAL ASSAY RESULTS

| | Biological Test Example 1 | | |
|---|---|---|---|
| Compound | IC$_{50}$ Range$^a$ | Average % inhibition at 100 nM | Average % inhibition at 111.1 nM |
| EXAMPLE 496 | ++ | 87.7 | |
| EXAMPLE 497 Isomer 1 | ++ | | |
| EXAMPLE 497 Isomer 2 | ++ | | |
| EXAMPLE 497 Isomer 3 | # | | |
| EXAMPLE 497 Isomer 4 | ++ | | |
| EXAMPLE 498 | ++ | 97.8 | |
| EXAMPLE 499 | ++ | 95.9 | |
| EXAMPLE 500 | ++ | 98.2 | |
| EXAMPLE 501 | ++ | 88.7 | |
| EXAMPLE 502 | ++ | 100.4 | |
| EXAMPLE 503 | ++ | 90.1 | |
| EXAMPLE 504 Isomer 1 | ++ | 49.9 | |
| EXAMPLE 504 Isomer 2 | ++ | 94.4 | |
| EXAMPLE 505 | ++ | 96.3 | |
| EXAMPLE 506 | ++ | 97.7 | |
| EXAMPLE 507 | ++ | 96.1 | |
| EXAMPLE 508 | ++ | 94.9 | |
| EXAMPLE 509 | ++ | 83.1 | |
| EXAMPLE 510 | ++ | 94.3 | |
| EXAMPLE 511 | ++ | 98.5 | |
| EXAMPLE 512 | ++ | 88.0 | |
| EXAMPLE 513 | ++ | 84.4 | |
| EXAMPLE 514 | ++ | 93.1 | |
| EXAMPLE 515 | ++ | 86.3 | |
| EXAMPLE 516 | ++ | 91.3 | |
| EXAMPLE 517 | ++ | 79.6 | |
| EXAMPLE 518 Isomer 1 | ++ | 92.2 | |
| EXAMPLE 518 Isomer 2 | ++ | 98.0 | |
| EXAMPLE 519 Isomer 1 | ++ | 95.5 | |
| EXAMPLE 519 Isomer 2 | ++ | 93.6 | |
| EXAMPLE 520 | ++ | 98.0 | |
| EXAMPLE 521 | ++ | 98.1 | |
| EXAMPLE 522 | ++ | 97.5 | |
| EXAMPLE 523 Isomer 1 | ++ | 94.5 | |
| EXAMPLE 523 Isomer 2 | ++ | 85.4 | |
| EXAMPLE 524 | ++ | 97.9 | |
| EXAMPLE 525 | ++ | 86.0 | |
| EXAMPLE 526 | ++ | 54.6 | |
| EXAMPLE 527 | ++ | 89.7 | |
| EXAMPLE 528 | ++ | 98.6 | |
| EXAMPLE 529 | ++ | 93.7 | |
| EXAMPLE 530 | ++ | 73.3 | |
| EXAMPLE 531 | ++ | 73.5 | |
| EXAMPLE 532 | ++ | 96.3 | |
| EXAMPLE 533 | ++ | 94.5 | |
| EXAMPLE 534 | ++ | 98.5 | |
| EXAMPLE 535 | ++ | 96.8 | |
| EXAMPLE 536 | ++ | 95.7 | |
| EXAMPLE 537 | ++ | 94.7 | |
| EXAMPLE 538 | ++ | 88.4 | |
| EXAMPLE 539 | ++ | 73.4 | |
| EXAMPLE 540 | ++ | 96.6 | |
| EXAMPLE 541 | ++ | 102.0 | |
| EXAMPLE 542 | ++ | 98.1 | |
| EXAMPLE 543 | ++ | 91.5 | |
| EXAMPLE 544 | ++ | 93.9 | |
| EXAMPLE 545 | ++ | 97.6 | |
| EXAMPLE 546 | ++ | 95.2 | |
| EXAMPLE 547 | ++ | 92.4 | |
| EXAMPLE 548 | ++ | 98.9 | |
| EXAMPLE 549 | ++ | 95.1 | |
| EXAMPLE 550 | ++ | 99.6 | |
| EXAMPLE 551 | ++ | 93.9 | |
| EXAMPLE 552 | ++ | | |
| EXAMPLE 553 | ++ | 90.8 | |
| EXAMPLE 554 | ++ | 93.1 | |
| EXAMPLE 555 | ++ | 97.3 | |
| EXAMPLE 556 | ++ | 94.5 | |
| EXAMPLE 557 | ++ | 93.6 | 89.7 |
| EXAMPLE 558 | ++ | 88.1 | |
| EXAMPLE 559 | ++ | 98.6 | |
| EXAMPLE 560 | ++ | 97.9 | |
| EXAMPLE 561 | ++ | 96.7 | |
| EXAMPLE 562 | ++ | 93.7 | |
| EXAMPLE 563 | ++ | 96.5 | |
| EXAMPLE 564 | ++ | 93.9 | |
| EXAMPLE 565 | ++ | 94.8 | |
| EXAMPLE 566 | ++ | 100.1 | |
| EXAMPLE 567 | ++ | 78.3 | |
| EXAMPLE 568 | ++ | 97.7 | |
| EXAMPLE 569 | ++ | 97.9 | |
| EXAMPLE 570 | ++ | 98.5 | |
| EXAMPLE 571 | ++ | 95.2 | |
| EXAMPLE 572 | ++ | 99.2 | |
| EXAMPLE 573 | ++ | 97.6 | |
| EXAMPLE 574 | ++ | 97.3 | |
| EXAMPLE 575 | ++ | 97.8 | 99.9 |
| EXAMPLE 576 | ++ | 99.0 | |
| EXAMPLE 577 Isomer 1 | ++ | 99.5 | |
| EXAMPLE 577 Isomer 2 | ++ | 94.7 | |
| EXAMPLE 578 | ++ | 97.7 | |
| EXAMPLE 579 | ++ | 91.8 | |
| EXAMPLE 580 | ++ | 53.3 | |
| EXAMPLE 581 | ++ | 96.4 | |
| EXAMPLE 582 | ++ | 61.2 | |
| EXAMPLE 583 | ++ | 100.0 | |
| EXAMPLE 584 | ++ | 81.6 | 77.0 |
| EXAMPLE 585 | ++ | 97.6 | |
| EXAMPLE 586 | ++ | 98.0 | |
| EXAMPLE 587 | ++ | 98.7 | |
| EXAMPLE 588 | ++ | 95.0 | |
| EXAMPLE 589 | ++ | 101.9 | |
| EXAMPLE 590 | ++ | 92.3 | |
| EXAMPLE 591 | ++ | 89.0 | |
| EXAMPLE 592 | ++ | 96.5 | |
| EXAMPLE 593 | ++ | 97.4 | |
| EXAMPLE 594 | ++ | 97.1 | |
| EXAMPLE 595 | ++ | 90.6 | |
| EXAMPLE 596 | ++ | 55.2 | |
| EXAMPLE 597 | ++ | 96.4 | |
| EXAMPLE 598 | ++ | 97.6 | 98.3 |
| EXAMPLE 599 | ++ | 98.6 | |
| EXAMPLE 600 | ++ | 72.5 | |
| EXAMPLE 601 | ++ | 89.4 | |
| EXAMPLE 602 | ++ | 98.6 | |
| EXAMPLE 603 | ++ | 93.4 | |
| EXAMPLE 604 | ++ | 72.4 | |
| EXAMPLE 605 | ++ | 85.8 | |
| EXAMPLE 606 | ++ | 96.2 | |
| EXAMPLE 607 | ++ | 78.9 | |
| EXAMPLE 608 | ++ | 84.7 | |
| EXAMPLE 609 | ++ | 98.7 | |
| EXAMPLE 610 | ++ | 97.4 | |
| EXAMPLE 611 | ++ | 94.7 | |
| EXAMPLE 612 | ++ | 80.7 | |
| EXAMPLE 613 | ++ | 53.9 | |
| EXAMPLE 614 | ++ | 95.4 | |
| EXAMPLE 615 | ++ | 96.6 | |
| EXAMPLE 616 | ++ | 96.0 | |
| EXAMPLE 617 | ++ | 96.4 | |
| EXAMPLE 618 | ++ | 96.6 | |
| EXAMPLE 619 | ++ | 95.5 | |
| EXAMPLE 620 | ++ | 68.7 | |
| EXAMPLE 621 | ++ | 78.3 | |
| EXAMPLE 622 | ++ | 102.8 | |
| EXAMPLE 623 | ++ | 102.2 | |
| EXAMPLE 624 | ++ | 104.7 | |
| EXAMPLE 625 | ++ | 103.4 | |
| EXAMPLE 626 | ++ | 94.8 | |
| EXAMPLE 627 | ++ | 97.0 | |
| EXAMPLE 628 | ++ | 95.9 | |
| EXAMPLE 629 | ++ | 97.0 | |
| EXAMPLE 630 | ++ | 94.5 | |
| EXAMPLE 631 | ++ | 65.4 | |

TABLE OF BIOLOGICAL ASSAY RESULTS

| | | Biological Test Example 1 | |
|---|---|---|---|
| Compound | IC$_{50}$ Range[a] | Average % inhibition at 100 nM | Average % inhibition at 111.1 nM |
| EXAMPLE 632 | ++ | 94.7 | |
| EXAMPLE 633 | ++ | 90.7 | |
| EXAMPLE 634 | ++ | 94.7 | |
| EXAMPLE 635 | ++ | 96.4 | |
| EXAMPLE 636 | ++ | 93.9 | |
| EXAMPLE 637 | ++ | 96.2 | |
| EXAMPLE 638 | ++ | 96.9 | |
| EXAMPLE 639 | ++ | 96.2 | |
| EXAMPLE 640 | ++ | 96.3 | |
| EXAMPLE 641 | ++ | 94.9 | |
| EXAMPLE 642 | ++ | 96.1 | |
| EXAMPLE 643 | ++ | 96.0 | |
| EXAMPLE 644 | ++ | 95.7 | |
| EXAMPLE 645 | ++ | 94.6 | |
| EXAMPLE 646 | ++ | 97.7 | |
| EXAMPLE 647 | ++ | 95.6 | |
| EXAMPLE 648 | ++ | 69.8 | |
| EXAMPLE 649 Isomer 1 | ++ | 72.2 | |
| EXAMPLE 649 Isomer 2 | ++ | 56.5 | |
| EXAMPLE 650 | ++ | 94.5 | |
| EXAMPLE 651 | ++ | 98.1 | |
| EXAMPLE 652 | ++ | 94.7 | |
| EXAMPLE 653 | ++ | 95.5 | |
| EXAMPLE 654 Isomer 1 | # | 18.5 | |
| EXAMPLE 654 Isomer 2 | ++ | 81.5 | |
| EXAMPLE 655 | ++ | 96.5 | |
| EXAMPLE 656 | ++ | 95.0 | |
| EXAMPLE 657 | ++ | 95.1 | |
| EXAMPLE 658 | ++ | 92.2 | |
| EXAMPLE 659 | ++ | 95.6 | |
| EXAMPLE 660 | ++ | 87.2 | |
| EXAMPLE 661 | ++ | 90.3 | |
| EXAMPLE 662 | ++ | 99.4 | |
| EXAMPLE 663 | ++ | 94.5 | |
| EXAMPLE 664 | ++ | 99.2 | |
| EXAMPLE 665 | ++ | 96.5 | |

[a] ++ means IC$_{50}$ = <100 nM, + means IC$_{50}$ = 100-1000 nM, # means IC$_{50}$ > 100 nM, − means IC$_{50}$ > 1000 nM.

Intermediate I

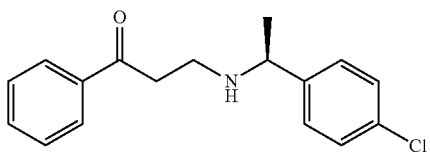 [SMILES: C[C@H](NCCC(=O)c1ccccc1)c1ccc(Cl)cc1]

3-[(S)-1-(4-Chloro-phenyl)-ethylamino]-1-phenyl-propan-1-one

NEt$_3$ (60 mL) followed by (S)-1-(4-chloro-phenyl)-ethylamine (20.5 g) was added to a solution of 3-chloro-1-phenyl-propan-1-one (23.2 g) in tetrahydrofuran (200 mL). The resulting mixture was stirred at room temperature overnight. Then, the solution was concentrated, water (100 mL) was added to the residue, and the resulting mixture was extracted with tert-butyl methyl ether. The combined organic extracts were washed with water and brine and dried (MgSO$_4$). The title compound was obtained after removal of the solvent.
Yield: 38.0 g (quantitative)
Mass spectrum (ESI$^+$): m/z=288/290 (Cl) [M+H]$^+$ The following compound was obtained in analogy to Intermediate I:

3-[(S)-1-(4-Bromo-phenyl)-ethylamino]-1-phenyl-propan-1-one

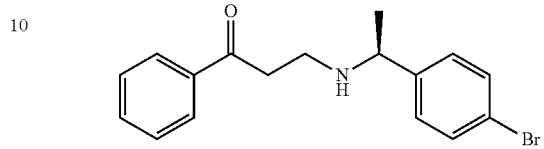

Mass spectrum (ESI$^+$): m/z=332/334 (Br) [M+H]$^+$

Intermediate II

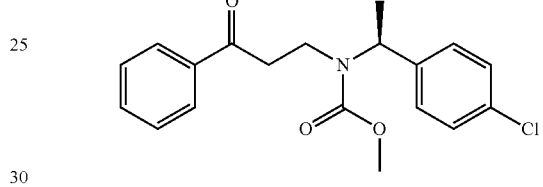

[(S)-1-(4-Chloro-phenyl)-ethyl]-(3-oxo-3-phenyl-propyl)-carbamic acid methyl ester Methyl chloroformate (15.5 mL) dissolved in dichloromethane (100 mL) was added to a mixture of 3-[(S)-1-(4-chloro-phenyl)-ethylamino]-1-phenyl-propan-1-one (38.0 g) and Na$_2$CO$_3$ (23.5 g) in a mixture of dichloromethane (100 mL) and water (100 mL) at such a rate that the solution temperature maintains between 20 and 26° C. After complete addition, the solution was stirred at ambient temperature for an additional 30 min. Then, the organic phase was separated and the aqueous phase was extracted once with dichloromethane. The combined organic phases were washed with brine and dried (MgSO$_4$). Then, silica gel (20 g) was added and the resulting mixture was stirred vigorously for 30 min. The silica gel was separated by filtration, washed with dichloromethane (200 mL), and the combined filtrate was concentrated under reduced pressure to give an oil. The oil was treated with iPr$_2$O (150 mL) to precipitate the title compound that was separated by filtration, washed with petroleum ether (30 mL), and dried. The filtrate was concentrated and the residue was taken up in petroleum ether (60 mL). The precipitate formed after a while of stirring was separated by filtration, washed with petroleum ether (20 mL), dried, and combined with the precipitate obtained before.
Yield: 38.2 g (82% of theory)
Mass spectrum (ESI$^+$): m/z=346/348 (Cl) [M+H]$^+$ The following compound was obtained in analogy to Intermediate II:

[(S)-1-(4-Bromo-phenyl)-ethyl]-(3-oxo-3-phenyl-propyl)-carbamic acid methyl ester

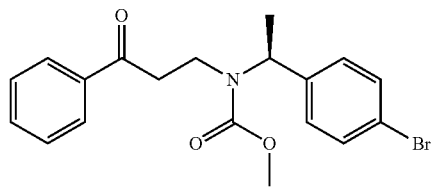 [SMILES: COC(=O)N(CCC(=O)c1ccccc1)[C@@H](C)c1ccc(Br)cc1]

Mass spectrum (ESI+): m/z=390/392 (Br) [M+H]+

Intermediate III

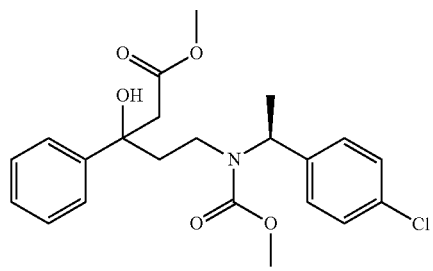 [SMILES: COC(=O)CC(O)(CCN(C(=O)OC)[C@@H](C)c1ccc(Cl)cc1)c1ccccc1]

5-{[(S)-1-(4-Chloro-phenyl)-ethyl]-methoxycarbonyl-amino}-3-hydroxy-3-phenyl-pentanoic acid methyl ester (mixture of two diastereomers)

Et$_2$Zn (1 M in hexane, 55 mL) was added dropwise to [(S)-1-(4-chloro-phenyl)-ethyl]-(3-oxo-3-phenyl-propyl)-carbamic acid methyl ester (3.80 g) dissolved in 1,2-dichloroethane (30 mL) and chilled to 0° C. under argon atmosphere. Then, (Ph$_3$P)$_3$RhCl (0.50 g) was added followed by the dropwise addition of methyl bromoacetate (1.0 mL) dissolved in 1,2-dichloroethane (10 mL). The resulting solution was stirred at 0-5° C. for 1 h and at ambient temperature for another 1.5 h. The solution was poured into ice-cold half-saturated aqueous NH$_4$Cl solution (150 mL). After addition of dichloromethane, the mixture was filtered through Celite that was extracted with an additional portion of dichloromethane. The organic phase was separated and washed with water and dried (MgSO$_4$). The solvent was removed and the residue was purified by chromatography on silica gel (cyclohexane/ethyl acetate 85:15→70:30) to give the title compound as a mixture of two diastereomers.

Yield: 4.6 g (quantitative)
Mass spectrum (ESI+): m/z=420/422 (Cl) [M+H]+

The following compound was obtained in analogy to Intermediate III:

5-{[(S)-1-(4-Bromo-phenyl)-ethyl]-methoxycarbonyl-amino}-3-hydroxy-3-phenyl-pentanoic acid methyl ester (mixture of two diastereomers)

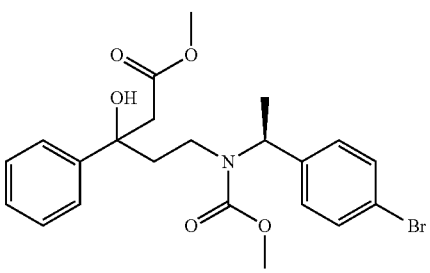 [SMILES: COC(=O)CC(O)(CCN(C(=O)OC)[C@@H](C)c1ccc(Br)cc1)c1ccccc1]

Mass spectrum (ESI+): m/z=464/466 (Br) [M+H]+

Intermediate IV

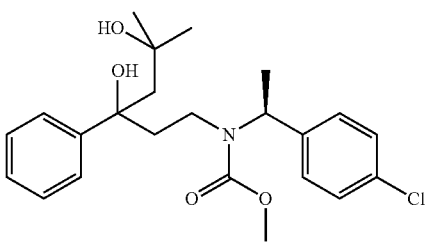 [SMILES: COC(=O)N(CCC(O)(CC(C)(C)O)c1ccccc1)[C@@H](C)c1ccc(Br)cc1]

[(S)-1-(4-Chloro-phenyl)-ethyl]-(3,5-dihydroxy-5-methyl-3-phenyl-hexyl)-carbamic acid methyl ester (mixture of two diastereomers)

MeLi (1.6 M in Et$_2$O, 5.1 mL) diluted with tetrahydrofuran (3 mL) was added to a solution of 5-{[(S)-1-(4-chloro-phenyl)-ethyl]-methoxycarbonyl-amino}-3-hydroxy-3-phenyl-pentanoic acid methyl ester (product from Intermediate III, 1.10 g) in tetrahydrofuran (8 mL) chilled to −75° C. under argon atmosphere. The solution was stirred at ca. −70° C. for 2.5 h and then poured into half-saturated aqueous NH$_4$Cl solution (150 mL). The resulting mixture was extracted with ethyl acetate and the combined extracts were washed with brine and dried (MgSO$_4$). The solvent was removed and the residue was purified by chromatography on silica gel (cyclohexane/ethyl acetate 85:15→70:30) to give the title compound as a mixture of two diastereomers.

Yield: 0.62 g (56% of theory)
Mass spectrum (ESI+): m/z=420/422 (Cl) [M+H]+

The reaction may also be conducted using MeMgCl instead of MeLi as described above.

The following compound was obtained in analogy to Intermediate IV:

[(S)-1-(4-Bromo-phenyl)-ethyl]-(3,5-dihydroxy-5-methyl-3-phenyl-hexyl)-carbamic acid methyl ester (mixture of two diastereomers)

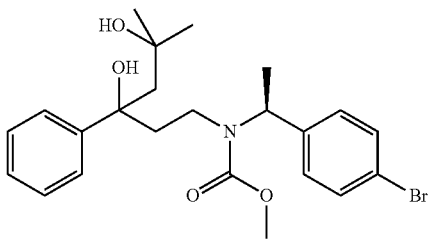

Mass spectrum (ESI⁺): m/z=464/466 (Br) [M+H]⁺

Intermediate V

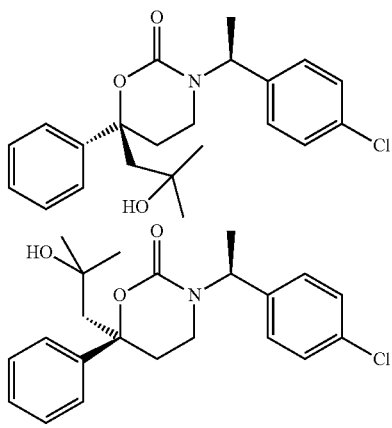

3-[(S)-1-(4-Chloro-phenyl)-ethyl]-(S)-6-(2-hydroxy-2-methyl-propyl)-6-phenyl-[1,3]oxazinan-2-one and
3-[(S)-1-(4-chloro-phenyl)-ethyl]-(R)-6-(2-hydroxy-2-methyl-propyl)-6-phenyl-[1,3]oxazinan-2-one NaH (60% in mineral oil, 0.15 g) was added to a solution of [(S)-1-(4-chloro-phenyl)-ethyl]-(3,5-dihydroxy-5-methyl-3-phenyl-hexyl)-carbamic acid methyl ester (product from Intermediate IV, 0.60 g) in tetrahydrofuran (10 mL) under argon atmosphere. The resulting mixture was stirred at reflux temperature for 2.5 h. Then, aqueous NH₄Cl solution was added and the resulting mixture was extracted with ethyl acetate. The combined organic extracts were washed with brine, dried (MgSO₄), and concentrated. The residue was purified by chromatography on silica gel (cyclohexane/ethyl acetate 60:40→0:100) to give the two title compounds separated. 3-[(S)-1-(4-Chloro-phenyl)-ethyl]-(S)-6-(2-hydroxy-2-methyl-propyl)-6-phenyl-[1,3]oxazinan-2-one: Yield: 40 mg (7% of theory)

Mass spectrum (ESI⁺): m/z=388/390 (Cl) [M+H]⁺

$^1$H NMR (400 MHz, DMSO-d$_6$) δ 0.80 (s, 3H), 1.18 (s, 3H), 1.41 (d, J=7.0 Hz, 3H), 2.01 (s, 2H), 2.08 (td, J=11.5, 5.4 Hz, 1H), 2.37-2.51 (m, 2H), 2.95-3.02 (m, 1H), 4.23 (s, 1H), 5.38 (q, J=7.0 Hz, 1H), 6.86 (d, J=8.4 Hz, 2H), 7.14 (d, J=8.4 Hz, 2H), 7.27-7.39 (m, 5H).

3-[(S)-1-(4-Chloro-phenyl)-ethyl]-(R)-6-(2-hydroxy-2-methyl-propyl)-6-phenyl-[1,3]oxazinan-2-one: Yield: 93 mg (17% of theory)

Mass spectrum (ESI⁺): m/z=388/390 (Cl) [M+H]⁺

$^1$H NMR (400 MHz, DMSO-d$_6$) δ 0.81 (s, 3H), 1.16 (s, 3H), 1.18 (d, J=7.3 Hz, 3H), 2.03 (s, 2H), 2.31-2.41 (m, 2H), 2.51-2.59 (m, 1H), 2.64-2.71 (m, 1H), 4.20 (s, 1H), 5.31 (q, J=7.1 Hz, 1H), 7.25 (d, J=8.4 Hz, 2H), 7.28-7.35 (m, 3H), 7.37-7.43 (m, 4H).

The following compound was obtained in analogy to Intermediate V:

3-[(S)-1-(4-Bromo-phenyl)-ethyl]-(S)-6-(2-hydroxy-2-methyl-propyl)-6-phenyl-[1,3]oxazinan-2-one

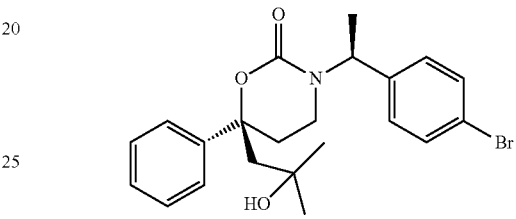

The compound was obtained from [(S)-1-(4-bromo-phenyl)-ethyl]-(3,5-dihydroxy-5-methyl-3-phenyl-hexyl)-carbamic acid methyl ester (mixture of two diastereomers) in a mixture with 3-[(S)-1-(4-bromo-phenyl)-ethyl]-(R)-6-(2-hydroxy-2-methyl-propyl)-6-phenyl-[1,3]oxazinan-2-one that was resolved into the pure diastereomers by chromatography as described above.

Intermediate VI

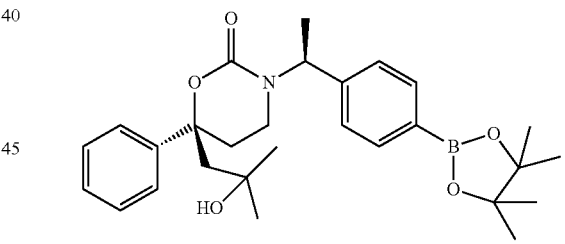

(S)-6-(2-Hydroxy-2-methyl-propyl)-6-phenyl-3-{(S)-1-[4-(4,4,5,5-tetramethyl-[1,3,2]dioxaborolan-2-yl)-phenyl]-ethyl}-[1,3]oxazinan-2-one A flask charged with a stir bar, 3-[(S)-1-(4-bromo-phenyl)-ethyl]-(S)-6-(2-hydroxy-2-methyl-propyl)-6-phenyl-[1,3]oxazinan-2-one (4.00 g), bis(pinacolato)diboron (3.05 g), 1,1'-bis(diphenylphosphino)ferrocene (0.25 g), KOAc (3.18 g), and dimethyl sulfoxide (30 mL) was sparged with argon for 15 min. Then, [1,1'-bis(diphenylphosphino)ferrocene]-dichloropalladium(II) dichloromethane complex (0.38 g) was added and the resulting mixture was heated to 90° C. and stirred at thwas temperature overnight. After cooling to ambient temperature, ethyl acetate (150 mL) was added and the mixture was washed with water (3×50 mL) and brine (50 mL) and dried (MgSO₄). The solvent was removed under reduced pressure and the residue was purified by chromatography on silica gel (cyclohexane/ethyl acetate 33:66→0:100) to give the title compound as a colorless solid.

Yield: 3.50 mg (79% of theory)

Mass spectrum (ESI$^+$): m/z=480 [M+H]$^+$

The following compound was obtained in analogy to Intermediate VI:

(1) (R)-6-Methoxymethyl-6-phenyl-3-{(S)-1-[4-(4,4,5,5-tetramethyl-[1,3,2]dioxaborolan-2-yl)-phenyl]-ethyl}-[1,3]oxazinan-2-one

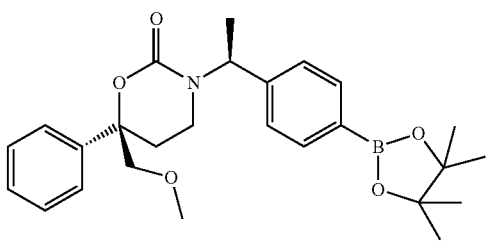

3-[1-(4-Bromo-phenyl)-ethyl]-6-methoxymethyl-6-phenyl-[1,3]oxazinan-2-one (Example 687) was used as starting compound Intermediate VII

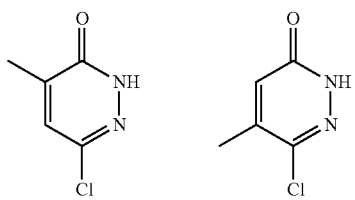

6-Chloro-4-methyl-2H-pyridazin-3-one and 6-chloro-5-methyl-2H-pyridazin-3-one

A suspension of 3,6-dichloro-4-methylpyridazine (6.60 g) in 3.3 M aqueous NaOH solution (66 mL) was stirred at reflux temperature for 2 h. The heating bath was removed and 50% aqueous acetic acid (25 mL) was added. The aqueous solution was adjusted to pH value 6 and the precipitate formed thereafter was separated by filtration and washed with little water. The precipitate was purified by chromatography on silica gel (cyclohexane/ethyl acetate 90:10→0:100) to afford the two title compounds separated.

6-Chloro-4-methyl-2H-pyridazin-3-one: Yield: 2.70 g (46% of theory)

Mass spectrum (ESI$^+$): m/z=145/147 (Cl) [M+H]$^+$ $^1$H NMR (400 MHz, DMSO-d$_6$) δ 2.06 (d, J=1.3 Hz, 3H), 7.44 (incompletely resolved q, J=1.3 Hz, 1H), 13.03 (broad s, 1H).

6-Chloro-5-methyl-2H-pyridazin-3-one: Yield: 1.90 g (32% of theory)

Mass spectrum (ESI$^+$): m/z=145/147 (Cl) [M+H]$^+$ $^1$H NMR (400 MHz, DMSO-d$_6$) δ 2.19 (d, J=1.3 Hz, 3H), 6.91 (incompletely resolved q, J=1.3 Hz, 1H), 13.02 (broad s, 1H).

The following compound was obtained in analogy to Intermediate VII:

6-Chloro-2H-pyridazin-3-one

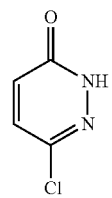

Mass spectrum (ESI$^+$): m/z=131/133 (Cl) [M+H]$^+$

Intermediate VIII

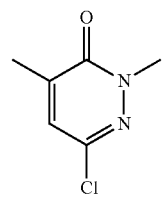

6-Chloro-2,4-dimethyl-2H-pyridazin-3-one

Methyl iodide (1.3 mL) was added to a mixture of 6-chloro-4-methyl-2H-pyridazin-3-one (2.70 g) and K$_2$CO$_3$ (3.40 g) in dimethylformamide (27 mL). The resulting mixture was stirred at ambient temperature overnight. Then, water was added and the mixture was extracted with ethyl acetate. The combined organic extracts were washed with water and brine and dried (MgSO$_4$). After removal of the solvent, the title compound was obtained as a solid.

Yield: 2.97 g (100% of theory)

Mass spectrum (ESI$^+$): m/z=159/161 (Cl) [M+H]$^+$

The following compound was obtained in analogy to Intermediate VIII:

6-Chloro-2,5-dimethyl-2H-pyridazin-3-one

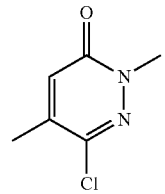

Mass spectrum (ESI$^+$): m/z=159/161 (Cl) [M+H]$^+$

Intermediate IX

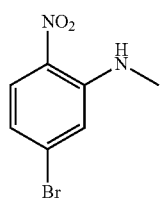

(5-Bromo-2-nitro-phenyl)-methyl-amine

Methylamine (2 M in tetrahydrofuran, 11.4 mL) was added to a mixture of 4-bromo-2-fluoro-1-nitro-benzene (2.50 g) and $K_2CO_3$ (1.90 g) in dimethylformamide (40 mL). The resulting mixture was stirred at ambient temperature overnight. Then, the mixture was concentrated under reduced pressure and dichloromethane was added. The resulting mixture was washed with 0.5 M aqueous HCl solution and brine and dried ($MgSO_4$). The solvent was removed to give the product as a solid.

Yield: 2.60 g (99% of theory)
Mass spectrum (ESI$^+$): m/z=231/233 (Br) [M+H]$^+$ The following compound was obtained in analogy to Intermediate IX:

(4-Bromo-2-nitro-phenyl)-methyl-amine

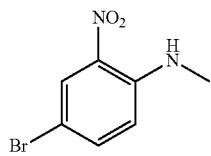

Mass spectrum (ESI$^+$): m/z=231/233 (Br) [M+H]$^+$

Intermediate X

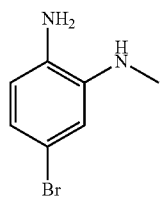

4-Bromo-2-methylamino-aniline

A mixture of (5-bromo-2-nitro-phenyl)-methyl-amine (2.60 g) and Raney nickel (0.25 g) in tetrahydrofuran (100 mL) was shaken under hydrogen atmosphere (50 psi) at room temperature overnight. Then, the catalyst was separated by filtration and the filtrate was concentrated under reduced pressure to give the crude title compound as a brown oil that was used without further purification.

Yield: 2.20 g (97% of theory)
Mass spectrum (ESI$^+$): m/z=201/203 (Br) [M+H]$^+$ The following compound was obtained in analogy to Intermediate X:

5-Bromo-2-methylamino-aniline

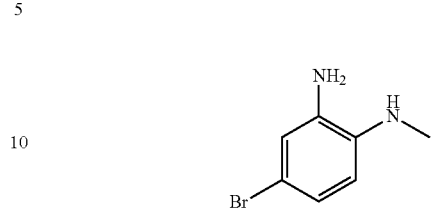

Mass spectrum (ESI$^+$): m/z=201/203 (Br) [M+H]$^+$

Intermediate XI

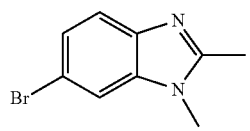

6-Bromo-1,2-dimethyl-1H-benzoimidazole

A solution of 4-bromo-2-methylamino-aniline (1.10 g) in acetic acid (15 mL) was stirred at 130° C. for 2 h. After cooling to ambient temperature, the solution was concentrated under reduced pressure and the residue was taken up in ethyl acetate. The resulting solution was washed with 10% aqueous $K_2CO_3$ solution and brine and dried ($MgSO_4$). The solvent was removed and the remainder was purified by chromatography on silica gel ($CH_2Cl_2$/MeOH/$NH_4OH$ 99:1:0.1→9:1:0.1) to give the title compound as a solid.

Yield: 0.58 g (47% of theory)
Mass spectrum (ESI$^+$): m/z=225/227 (Br) [M+H]$^+$ The following compound was obtained in analogy to Intermediate XI:

5-Bromo-1,2-dimethyl-1H-benzoimidazole

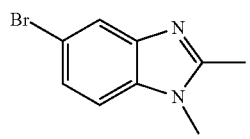

Mass spectrum (ESI$^+$): m/z=225/227 (Br) [M+H]$^+$

Intermediate XII

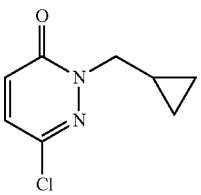 [SMILES: O=c1ccc(Cl)nn1CC1CC1]

6-Chloro-2-cyclopropylmethyl-2H-pyridazin-3-one

Cyclopropylmethyl bromide (0.82 mL) was added to a mixture of 6-chloro-2H-pyridazin-3-one (1.0 g) and K₂CO₃ (2.10 g) in dimethylformamide (10 mL). The resulting mixture was stirred at 60° C. overnight. Then, water was added and the mixture was extracted with ethyl acetate. The combined organic extracts were washed with water and brine and dried (MgSO₄). After removal of the solvent, the residue was purified by chromatography on silica gel (CH₂Cl₂/MeOH/NH₄OH 99:1:0.1) to afford the title compound as an oil.

Yield: 0.85 g (60% of theory)

Mass spectrum (ESI⁺): m/z=185/187 (Cl) [M+H]⁺

Intermediate XIII

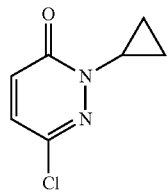

6-Chloro-2-cyclopropyl-2H-pyridazin-3-one

A microwave-suited vessel charged with a stir bar, 6-chloro-2H-pyridazin-3-one (0.15 g), cyclopropylboronic acid (0.30 g), pyridine (0.75 mL), triethylamine (0.8 mL), and tetrahydrofuran (5 mL) was sparged with argon for 5 min. Then, Cu(OAc)₂ (0.42 g) was added and the mixture was stirred in a microwave oven under microwave irradiation at 140° C. for 10 min. Then, the solvent was evaporated and water was added. The resultant mixture was extracted with ethyl acetate and the combined organic extracts were washed with water and aqueous NaHCO₃ solution. After drying (MgSO₄) and removing the solvent, the residue was purified by chromatography on silica gel (CH₂Cl₂/MeOH/NH₄OH 99:1:0.1→9:1:0.1) to afford the title compound.

Yield: 35 mg (18% of theory)

Mass spectrum (ESI⁺): m/z=171/173 (Cl) [M+H]⁺

The following compound was obtained in analogy to Intermediate XIII:

1-Cyclopropyl-4-(4-methoxy-benzyloxy)-1H-pyridin-2-one

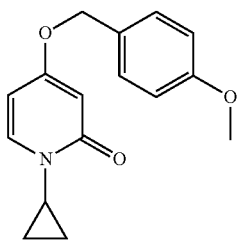 [SMILES: COc1ccc(COc2ccn(C3CC3)c(=O)c2)cc1]

Mass spectrum (ESI⁺): m/z=272 [M+H]⁺

Intermediate XIV

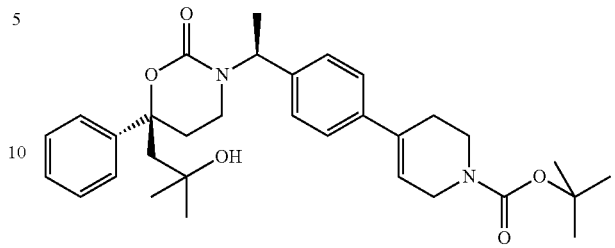

4-(4-{(S)-1-[(S)-6-(2-Hydroxy-2-methyl-propyl)-2-oxo-6-phenyl-[1,3]oxazinan-3-yl]-ethyl}-phenyl)-3,6-dihydro-2H-pyridine-1-carboxylic acid tert-butyl ester Dimethylformamide (5 mL) was added to a flask charged with a stir bar, 3-[(S)-1-(4-bromo-phenyl)-ethyl]-(S)-6-(2-hydroxy-2-methyl-propyl)-6-phenyl-[1,3]oxazinan-2-one (0.30 g), 4-(4,4,5,5-tetramethyl-[1,3,2]dioxaborolan-2-yl)-3,6-dihydro-2H-pyridine-1-carboxylic acid tert-butyl ester (0.22 g), K₂CO₃ (0.29 g), and [1,1'-bis(diphenylphosphino)ferrocene]-dichloropalladium(II) (57 mg) under argon atmosphere. The resulting mixture was stirred at 80° C. overnight. After cooling to ambient temperature, water was added and the resulting mixture was extracted with ethyl acetate. The combined organic extracts were washed with brine, dried (MgSO₄), and concentrated. The residue was purified by chromatography on silica gel (cyclohexane/ethyl acetate 40:60→0:100) to afford the title compound.

Yield: 0.35 g (93% of theory)

Mass spectrum (ESI⁺): m/z=535 [M+H]⁺

Intermediate XV

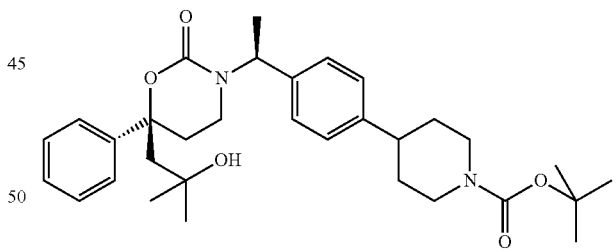

4-(4-{(S)-1-[(S)-6-(2-Hydroxy-2-methyl-propyl)-2-oxo-6-phenyl-[1,3]oxazinan-3-yl]-ethyl}-phenyl)-piperidine-1-carboxylic acid tert-butyl ester A mixture of 4-(4-{(S)-1-[(S)-6-(2-hydroxy-2-methyl-propyl)-2-oxo-6-phenyl-[1,3]oxazinan-3-yl]ethyl}-phenyl)-3,6-dihydro-2H-pyridine-1-carboxylic acid tert-butyl ester (0.34 g) and 10% palladium on carbon (60 mg) in methanol (10 mL) was shaken in hydrogen atmosphere (50 psi) for 4 h. Then, the catalyst was separated by filtration and the filtrate was concentrated to yield the title compound.

Yield: 0.30 g (88% of theory)

Mass spectrum (ESI⁺): m/z=537 [M+H]⁺

Intermediate XVI

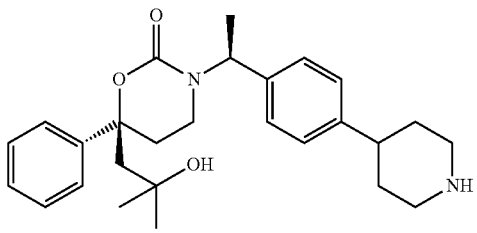

(S)-6-(2-Hydroxy-2-methyl-propyl)-6-phenyl-3-[(S)-1-(4-piperidin-4-yl-phenyl)-ethyl]-[1,3]oxazinan-2-one Trifluoroacetic acid (0.40 mL) was added to a solution of 4-(4-{(S)-1-[(S)-6-(2-hydroxy-2-methyl-propyl)-2-oxo-6-phenyl-[1,3]oxazinan-3-yl]-ethyl}-phenyl)-piperidine-1-carboxylic acid tert-butyl ester (0.29 g) in dichloromethane (10 mL). The resulting solution was stirred at room temperature overnight. Then, more dichloromethane was added and the solution was neutralized using aqueous saturated NaHCO$_3$ solution. The organic phase was separated, washed with water, and dried (MgSO$_4$). The solvent was removed under reduced pressure to give the title compound.
Yield: 0.22 g (93% of theory)

Intermediate XVII

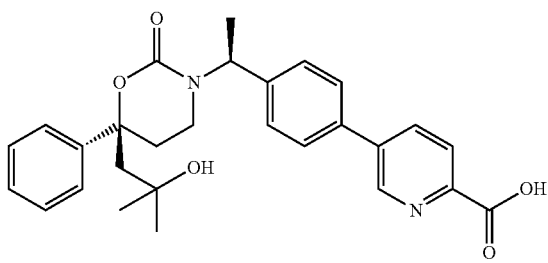

5-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid 2 M aqueous Na$_2$CO$_3$ solution (1.3 mL) was added to a solution of (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.60 g) and 5-bromo-pyridine-2-carboxylic acid methyl ester (0.41 g) in dimethylformamide (4 mL). The resulting mixture was sparged with argon for 10 min, before [1,1'-bis(diphenylphosphino)ferrocene]-dichloropalladium(II) dichloromethane complex (61 mg) was added. The mixture was heated to 100° C. and stirred at this temperature overnight. After cooling to ambient temperature, the mixture was diluted with ethyl acetate and extracted with water and brine. The aqueous extracts were combined, acidified (pH ca. 5-6) using citric acid, and extracted with CH$_2$Cl$_2$/MeOH (ca. 10:1). The combined organic extracts were washed with brine and dried (MgSO$_4$). The solvent was removed and the residue was purified by chromatography on silica gel (CH$_2$Cl$_2$/MeOH 98:2→50:50) to afford the title compound as a resin-like solid.
Yield: 0.44 g (73% of theory)
Mass spectrum (ESI$^+$): m/z=475 [M+H]$^+$ Intermediate XVIII

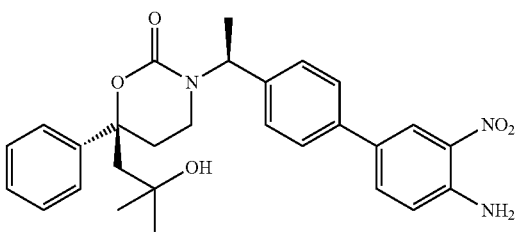

3-[(S)-1-(4'-Amino-3'-nitro-biphenyl-4-yl)-ethyl]-(S)-6-(2-hydroxy-2-methyl-propyl)-6-phenyl-[1,3]oxazinan-2-one A flask charged with a stir bar, 3-[(S)-1-(4-bromo-phenyl)-ethyl]-(S)-6-(2-hydroxy-2-methyl-propyl)-6-phenyl-[1,3]oxazinan-2-one (1.00 g), 2-nitro-4-(4,4,5,5-tetramethyl-[1,3,2]dioxaborolan-2-yl)-phenylamine (0.92 g), and 2 M aqueous Na$_2$CO$_3$ solution (2.3 mL) was sparged with argon for 15 min. Then, [1,1'-bis(diphenylphosphino)ferrocene]-dichloropalladium(II) dichloromethane complex (57 mg) was added and the mixture was stirred at 100° C. overnight. After cooling to ambient temperature, water was added and the resulting mixture was extracted with ethyl acetate. The combined organic extracts are washed with brine, dried (MgSO$_4$), and concentrated. The residue was purified by chromatography on silica gel (CH$_2$Cl$_2$/MeOH 98:2→80:20) to afford the title compound as an oil that was crystallized using a mixture of ethyl acetate and iPr$_2$O (ca. 10:1).
Yield: 0.53 g (93% of theory)
Mass spectrum (ESI$^+$): m/z=490 [M+H]$^+$ Intermediate XIX

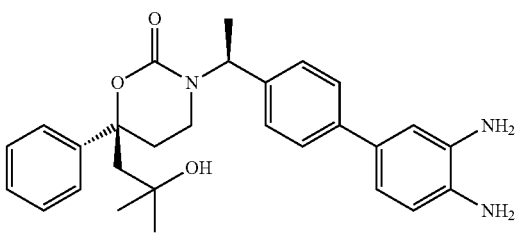

3-[(S)-1-(3',4'-Diamino-biphenyl-4-yl)-ethyl]-(S)-6-(2-hydroxy-2-methyl-propyl)-6-phenyl-[1,3]oxazinan-2-one A mixture of 3-[(S)-1-(4'-amino-3'-nitro-biphenyl-4-yl)-ethyl]-(S)-6-(2-hydroxy-2-methyl-propyl)-6-phenyl-[1,3]oxazinan-2-one (0.50 g) and 10% palladium on carbon (0.10 g) in a mixture of methanol (10 mL) and tetrahydrofuran (10 mL) was shaken in hydrogen atmosphere (3 bar) at room temperature for 3.5 h. Then, the catalyst was separated by filtration and the filtrate was concentrated under reduced pressure to afford the title compound as an oil.

Yield: 0.46 g (97% of theory)
Mass spectrum (ESI$^+$): m/z=460 [M+H]$^+$

Intermediate XX

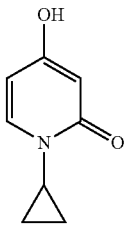 [SMILES: O=c1cc(O)ccn1C1CC1]

1-Cyclopropyl-4-hydroxy-1H-pyridin-2-one

Trifluoroacetic acid (1 mL) was added to a flask charged with a stir bar and 1-cyclopropyl-4-(4-methoxy-benzyloxy)-1H-pyridin-2-one (0.17 g) and chilled in an ice/EtOH bath. The resulting mixture was stirred with cooling for 1.5 h and at ambient temperature for another 4.5 h. Then, the solution was concentrated under reduced pressure and the residue was triturated with tert-butyl methyl ether and dried to give the title compound as a solid.

Yield: 0.10 g (quantitative)
Mass spectrum (ESI$^+$): m/z=152 [M+H]$^+$

Intermediate XXI

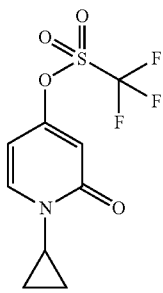 [SMILES: O=c1cc(OS(=O)(=O)C(F)(F)F)ccn1C1CC1]

Trifluoro-methanesulfonic acid
1-cyclopropyl-2-oxo-1,2-dihydro-pyridin-4-yl ester Trifluoromethanesulfonic anhydride (0.12 mL) was added to a flask charged with a stir bar, 1-cyclopropyl-4-hydroxy-1H-pyridin-2-one (0.10 g), NEt$_3$ (0.24 mL), and dichloromethane (8 mL) and chilled in an ice/EtOH bath. The resulting mixture was stirred with cooling for 2 h and at ambient temperature for another 2 h. Then, the solution was diluted with dichloromethane and washed in succession with water, aqueous NaHCO$_3$ solution, and water. The organic solution was dried (MgSO$_4$), the solvent was removed, and the residue was purified by chromatography on silica gel (dichloromethane/methanol 99:1→90:10) to afford the title compound as a resin-like solid.

Yield: 0.07 g (36% of theory)
Mass spectrum (ESI$^+$): m/z=284 [M+H]$^+$

The following compound was obtained in analogy to Intermediate XXI:

(1) Trifluoro-methanesulfonic acid 1-methyl-2-oxo-1,2-dihydro-pyridin-4-yl ester

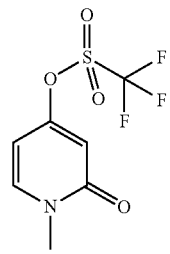 [SMILES: Cn1ccc(OS(=O)(=O)C(F)(F)F)cc1=O]

Mass spectrum (ESI$^+$): m/z=258 [M+H]$^+$

Intermediate XXII

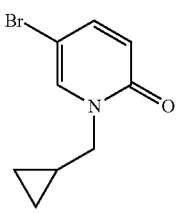 [SMILES: O=c1ccc(Br)cn1CC1CC1]

5-Bromo-1-cyclopropylmethyl-1H-pyridin-2-one

KO$^t$Bu (0.68 g) was added to a solution of 5-bromo-1H-pyridin-2-one (1.00 g) in tetrahydrofuran (20 mL) at room temperature. After stirring for 30 min, cyclopropylmethyl bromide (0.77 mL) and dimethylformamide (3 mL) were added to the suspension and the resulting mixture was warmed to 70° C. After stirring the mixture at 70° C. for 2 h, the reaction was complete. The mixture was cooled to room temperature, diluted with ethyl acetate (50 mL), and washed with water (2×20 mL) and brine (20 mL). Then, the solution was dried (MgSO$_4$) and the solvent was removed to give the title compound as a colorless oil.

Yield: 1.18 g (90% of theory)
Mass spectrum (ESI$^+$): m/z=228/230 (Br) [M+H]$^+$ Intermediate XXIII

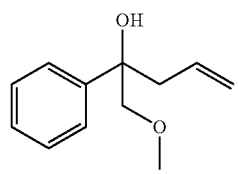

1-Methoxy-2-phenyl-pent-4-en-2-ol

2-Methoxy-1-phenyl-ethanone (5.00 g) dissolved in tetrahydrofuran (50 mL) was added to 2 M allylmagnesium chloride in tetrahydrofuran (21 mL) at room temperature. The solution was stirred at room temperature for 3 h and then 10% aqueous NH₄Cl solution (50 mL) was added. The resulting mixture was extracted with tert-butyl methyl ether (3×50 mL) and the combined extracts were washed with water (50 mL) and brine (50 mL). The solvent was evaporated to afford the title compound as a colorless oil.

Yield: 6.40 g (quantitative)
Mass spectrum (ESI⁺): m/z=175 [M+H−H₂O]⁺

Intermediate XXIV

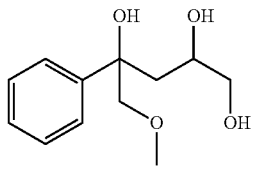 [SMILES: COCC(O)(CC(O)CO)c1ccccc1]

5-Methoxy-4-phenyl-pentane-1,2,4-triol

OsO₄ (4% in water, 2 mL; alternatively, K₂OsO₄ may be used) followed by N-methyl-morpholine-N-oxide (5.20 g) was added to a solution of 1-methoxy-2-phenyl-pent-4-en-2-ol (1.10 g) in tetrahydrofuran (10 mL) chilled in an ice bath. The cooling bath was removed and the solution was stirred at room temperature overnight. Then, 10% aqueous Na₂S₂O₅ solution (10 mL) was added and the resulting mixture was stirred at room temperature for another 1.5 h. After removal of the organic solvent under reduced pressure, the remaining mixture was extracted with ethyl acetate. The combined extracts were washed with brine and dried (MgSO₄). The solvent was evaporated to afford the title compound in good purity (ca. 95%).

Yield: 1.20 g (96% of theory)
Mass spectrum (ESI"): m/z=225 [M−H]⁻

Intermediate XXV

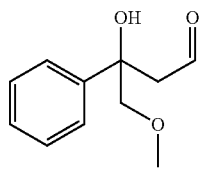

3-Hydroxy-4-methoxy-3-phenyl-butyraldehyde

NaIO₄ (5.20 g) was added to a mixture of 5-methoxy-4-phenyl-pentane-1,2,4-triol (1.10 g), dichloromethane (10 mL), and water (5 mL) chilled in an ice bath. The mixture was stirred vigorously while warming to ambient temperature in the cooling bath and further stirred at this temperature overnight. Then, water (20 mL) and dichloromethane (50 mL) were added, the organic layer was separated, and the aqueous layer was extracted with dichloromethane (2×25 mL). The combined organic phases were washed with water and dried (MgSO₄). After removal of the solvent, the title compound was yielded which was directly submitted to the next reaction step (glycol cleavage).

Yield: 0.94 g (quantitative)

Intermediate XXVI

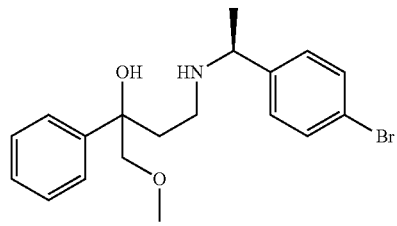 [SMILES: COCC(O)(CCN[C@@H](C)c1ccc(Br)cc1)c1ccccc1]

4-[(S)-1-(4-Bromo-phenyl)-ethylamino]-1-methoxy-2-phenyl-butan-2-ol (S)-1-(4-Bromo-phenyl)-ethylamine (0.93 g), NaB(OAc)₃ (0.98 g), and acetic acid (0.27 mL) were added in the given order to a solution of 3-hydroxy-4-methoxy-3-phenyl-butyraldehyde (0.90 g) in tetrahydrofuran (20 mL) at ca. 10-15° C. The cooling bath was removed and the mixture was stirred at room temperature for 2 h. Then, water (50 mL) and 1 M aqueous NaOH solution (20 mL) were added and the resulting mixture was stirred for another 30 min. The mixture was extracted with ethyl acetate and the combined extracts were washed with water and brine. After drying (MgSO₄), the solvent was removed to give the title compound which was submitted to the subsequent reaction step without further purification.

Yield: 1.80 g (quantitative)
Mass spectrum (ESI⁺): m/z=378/380 (Br) [M+H]⁺

Intermediate XXVII

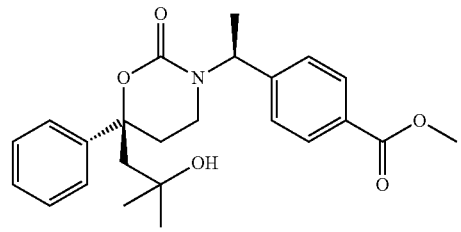

4-{(S)-1-[(S)-6-(2-Hydroxy-2-methyl-propyl)-2-oxo-6-phenyl-[1,3]oxazinan-3-yl]-ethyl}-benzoic acid methyl ester NEt₃ (0.47 mL) and [1,1'-bis(diphenylphosphino)ferrocene]-dichloropalladium(II) dichloromethane complex (0.15 g) were added to a solution of 3-[(S)-1-(4-bromo-phenyl)-ethyl]-(S)-6-(2-hydroxy-2-methyl-propyl)-6-phenyl-[1,3]oxazinan-2-one (1.04 g) in MeCN (2.5 mL), MeOH (20 mL), and dimethylformamide (5 mL). The resulting mixture was sparged with argon for 5 min and then transferred to a pressure-proved vessel that was filled with CO (5.5. bar). The mixture was heated to 70° C. and stirred at thwas temperature for 18 h before another portion of [1,1'-bis(diphenylphosphino)ferrocene]-dichloropalladium(II) dichloromethane complex (0.15 g) was added. After stirring at 70° C. for another 4 h, the mixture was cooled to ambient temperature, filtered, and concentrated under reduced pressure. The residue was taken up in ethyl acetate and the resulting mixture was washed with water and brine and dried (MgSO$_4$). The solvent was removed and the residue was purified by chromatography on silica gel (cyclohexane/ethyl acetate 40:60→0:100) to afford the title compound as an oil.

Yield: 0.73 g (55% of theory)
Mass spectrum (ESI$^-$): m/z=456 [M+HCOO]$^-$

Intermediate XXVIII

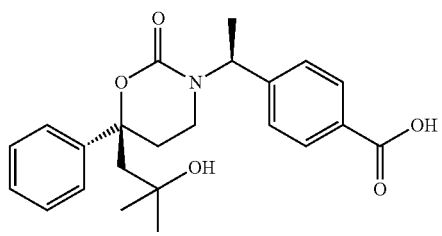

4-{(S)-1-[(S)-6-(2-Hydroxy-2-methyl-propyl)-2-oxo-6-phenyl-[1,3]oxazinan-3-yl]-ethyl}-benzoic acid 1 M aqueous NaOH solution (5 mL) was added to a solution of 4-{(S)-1-[(S)-6-(2-hydroxy-2-methyl-propyl)-2-oxo-6-phenyl-[1,3]oxazinan-3-yl]-ethyl}-benzoic acid methyl ester (0.73 g) in tetrahydrofuran (5 mL). The resulting solution was stirred at room temperature overnight. Then, the solution was concentrated and the residue was taken up in water and filtered. The aqueous filtrate was acidified with 1 M hydrochloric acid and the resulting mixture was extracted with ethyl acetate. The combined extracts were washed with brine and dried (MgSO$_4$). The solvent was removed to afford the title compound as a foam-like solid.

Yield: 0.38 g (72% of theory)
Mass spectrum (ESI$^+$): m/z=398 [M+H]$^+$

Intermediate XXIX

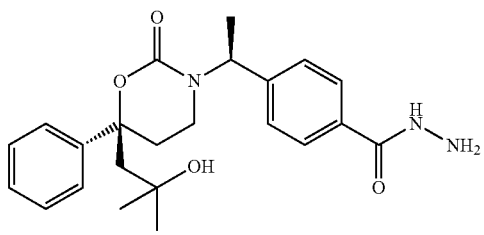

4-{(S)-1-[(S)-6-(2-Hydroxy-2-methyl-propyl)-2-oxo-6-phenyl-[1,3]oxazinan-3-yl]-ethyl}-benzoic acid hydrazide TBTU [2-(1H-benzotriazol-1-yl)-1,1,3,3-tetramethyluronium tetrafluoroborate, 0.33 g] was added to 4-{(S)-1-[(S)-6-(2-hydroxy-2-methyl-propyl)-2-oxo-6-phenyl-[1,3]oxazinan-3-yl]-ethyl}-benzoic acid (0.37 g) and EtNiPr$_2$ (0.41 mL) dissolved in dimethylformamide (5 mL). After stirring the solution at room temperature for 10 min, hydrazine hydrate (0.23 mL) was added. The solution was stirred at room temperature overnight and then diluted with water. The resulting mixture was extracted with ethyl acetate and the combined extracts were washed with brine and dried (MgSO$_4$). The solvent was removed and the residue was purified by chromatography on silica gel (CH$_2$Cl$_2$/MeOH 98:2→90:10) to afford the title compound as a colorless foam-like solid.

Yield: 0.19 g (50% of theory)
Mass spectrum (ESI$^-$): m/z=410 [M+H]$^-$

Example 666

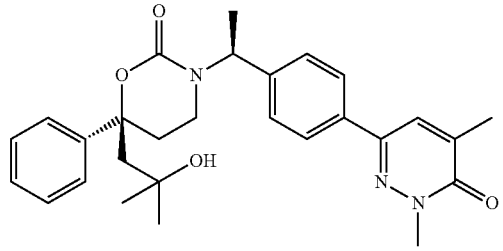

3-{(S)-1-[4-(1,5-Dimethyl-6-oxo-1,6-dihydro-pyridazin-3-yl)-phenyl]-ethyl}-(S)-6-(2-hydroxy-2-methyl-propyl)-6-phenyl-[1,3]oxazinan-2-one 2 M aqueous Na$_2$CO$_3$ solution (0.31 mL) was added to a solution of (S)-6-(2-hydroxy-2-methylpropyl)-6-phenyl-3-[(S)-1-(4-(4,4,5,5-tetramethyl-1,3,2-dioxaborolan-2-yl)phenyl)ethyl]-1,3-oxazinan-2-one (0.15 g) and 6-chloro-2,4-dimethyl-2H-pyridazin-3-one (75 mg) in dimethylformamide (1 mL). The resulting mixture was sparged with argon for 10 min, before [1,1-bis(diphenylphosphino)ferrocene]-dichloropalladium(II) dichloromethane complex (15 mg) was added. The mixture was heated to 100° C. and stirred at this temperature overnight. After cooling to ambient temperature, water was added, and the resulting mixture was extracted with ethyl acetate. The combined organic extracts were washed with brine, dried (MgSO$_4$), and concentrated. The residue was purified by chromatography on silica gel (CH$_2$Cl$_2$/MeOH 98:2→80:20) to afford the title compound.

Yield: 0.10 g (67% of theory)
Mass spectrum (ESI$^+$): m/z=476 [M+H]$^+$

The following compounds were obtained in analogy to Example 666:

The reactions were carried out using either the bromo, chloro or trifluoromethanesulfonyloxyl derivatized coupling partners (=electrophilic component)

Example 667

3-{(S)-1-[4-(1,4-Dimethyl-6-oxo-1,6-dihydro-pyridazin-3-yl)-phenyl]-ethyl}-(S)-6-(2-hydroxy-2-methyl-propyl)-6-phenyl-[1,3]oxazinan-2-one

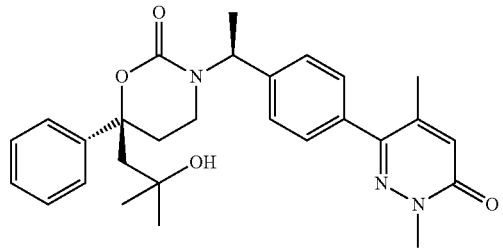

Mass spectrum (ESI$^+$): m/z=476 [M+H]$^+$

Example 668

3-{(S)-1-[4-(2,3-Dimethyl-3H-benzoimidazol-5-yl)-phenyl]-ethyl}-(S)-6-(2-hydroxy-2-methyl-propyl)-6-phenyl-[1,3]oxazinan-2-one

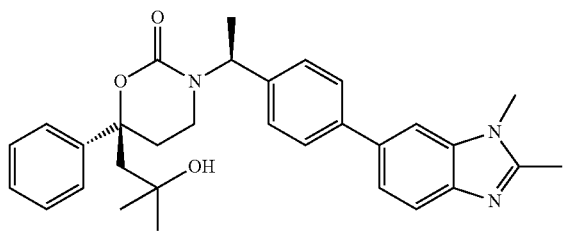

Mass spectrum (ESI+): m/z=498 [M+H]+

Example 669

(S)-6-(2-Hydroxy-2-methyl-propyl)-3-{(S)-1-[4-(3-methyl-3H-benzoimidazol-5-yl)-phenyl]-ethyl}-6-phenyl-[1,3]oxazinan-2-one

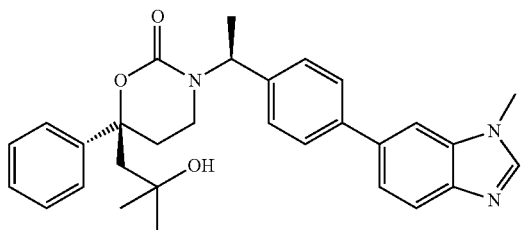

Mass spectrum (ESI+): m/z=484 [M+H]+

Example 670

(S)-6-(2-Hydroxy-2-methyl-propyl)-3-{(S)-1-[4-(1-methyl-1H-benzoimidazol-5-yl)-phenyl]-ethyl}-6-phenyl-[1,3]oxazinan-2-one

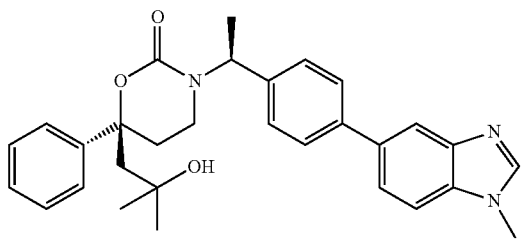

Mass spectrum (ESI+): m/z=484 [M+H]+

Example 671

3-{(S)-1-[4-(1,2-Dimethyl-1H-benzoimidazol-5-yl)-phenyl]-ethyl}-(S)-6-(2-hydroxy-2-methyl-propyl)-6-phenyl-[1,3]oxazinan-2-one

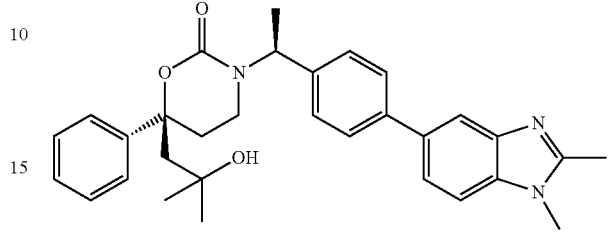

Mass spectrum (ESI+): m/z=498 [M+H]+

Example 672

3-{(S)-1-[4-(1-Cyclopropylmethyl-6-oxo-1,6-dihydro-pyridazin-3-yl)-phenyl]-ethyl}-(S)-6-(2-hydroxy-2-methyl-propyl)-6-phenyl-[1,3]oxazinan-2-one

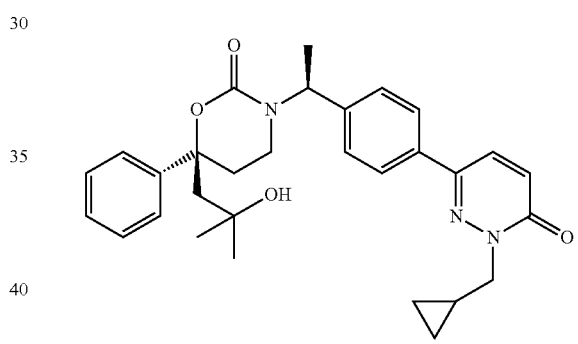

Mass spectrum (ESI+): m/z=502 [M+H]+

Example 673

3-{(S)-1-[4-(1-Cyclopropyl-6-oxo-1,6-dihydro-pyridazin-3-yl)-phenyl]-ethyl}-(S)-6-(2-hydroxy-2-methyl-propyl)-6-phenyl-[1,3]oxazinan-2-one

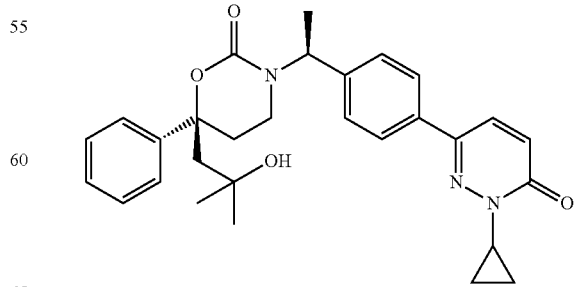

Mass spectrum (ESI+): m/z=488 [M+H]+

Example 674

3-{(S)-1-[4-(1-Cyclopropyl-2-oxo-1,2-dihydro-pyridin-4-yl)-phenyl]-ethyl}-(S)-6-(2-hydroxy-2-methyl-propyl)-6-phenyl-[1,3]oxazinan-2-one

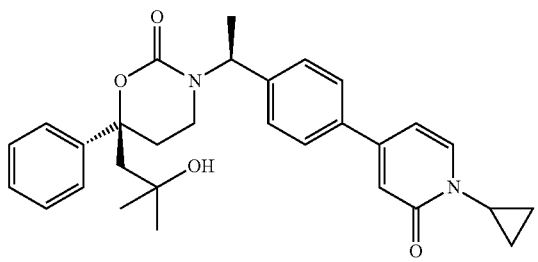

Mass spectrum (ESI⁺): m/z=487 [M+H]⁺
Trifluoro-methanesulfonic acid 1-cyclopropyl-2-oxo-1,2-dihydro-pyridin-4-yl ester was employed as the coupling partner under the conditions described above.

Example 675

2-(4-{(S)-1-[(S)-6-(2-Hydroxy-2-methyl-propyl)-2-oxo-6-phenyl-[1,3]oxazinan-3-yl]-ethyl}-phenyl)-nicotinonitrile

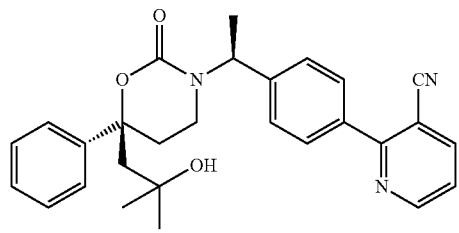

Mass spectrum (ESI⁻): m/z=500 [M+HCOO]⁻

Example 676

3-{(S)-1-[4-(1-Cyclopropylmethyl-6-oxo-1,6-dihydro-pyridin-3-yl)-phenyl]-ethyl}-(S)-6-(2-hydroxy-2-methyl-propyl)-6-phenyl-[1,3]oxazinan-2-one

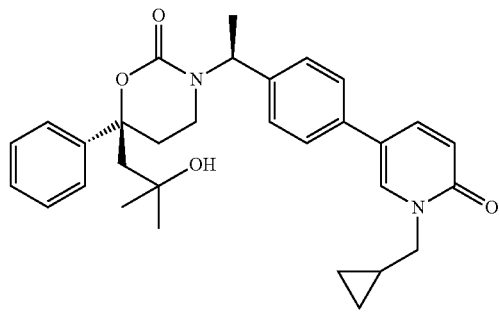

Mass spectrum (ESI⁺): m/z=501 [M+H]⁺

Example 677

(R)-6-Methoxymethyl-3-{(S)-1-[4-(6-methyl-pyridazin-3-yl)-phenyl]-ethyl}-6-phenyl-[1,3]oxazinan-2-one

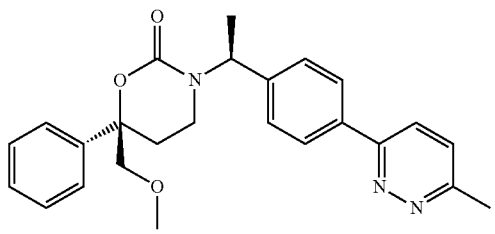

Mass spectrum (ESI⁺): m/z=418 [M+H]⁺

Example 678

(R)-6-Methoxymethyl-3-{(S)-1-[4-(1-methyl-6-oxo-1,6-dihydro-pyridin-3-yl)-phenyl]-ethyl}-6-phenyl-[1,3]oxazinan-2-one

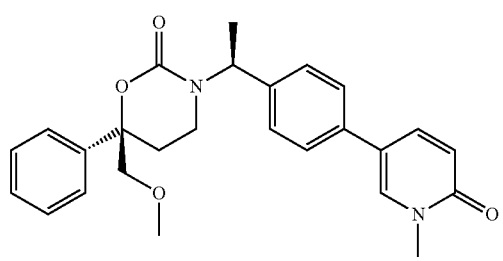

Mass spectrum (ESI⁺): m/z=433 [M+H]⁺

Example 679

(R)-6-Methoxymethyl-3-{(S)-1-[4-(1-methyl-2-oxo-1,2-dihydro-pyridin-4-yl)-phenyl]-ethyl}-6-phenyl-[1,3]oxazinan-2-one

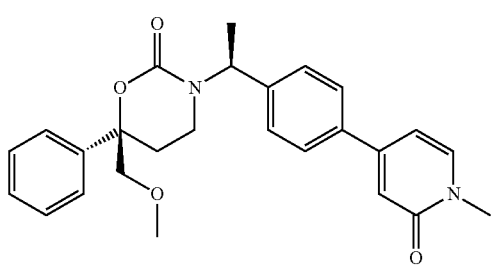

Mass spectrum (ESI⁺): m/z=433 [M+H]⁺

Trifluoro-methanesulfonic acid 1-methyl-2-oxo-1,2-dihydro-pyridin-4-yl ester was used as the coupling partner under the conditions described above.

Example 680

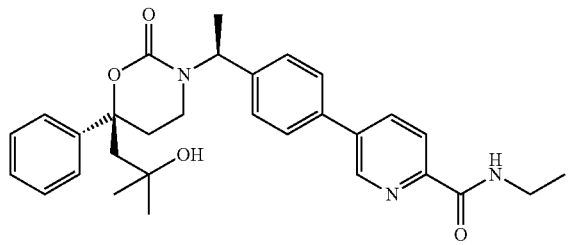

5-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid ethylamide 2-(1H-Benzotriazol-1-yl)-1,1,3,3-tetramethyluronium tetrafluoroborate (75 mg) was added to a solution of 5-(4-{(S)-1-[(S)-6-(2-hydroxy-2-methyl-propyl)-2-oxo-6-phenyl-[1,3]oxazinan-3-yl]-ethyl}-phenyl)-pyridine-2-carboxylic acid (0.10 g) and diisopropylethylamine (50 µL) in dimethylformamide (1 mL) at room temperature. The resulting solution was stirred for 25 min, before diethylamine (70% in water, 50 µL) was added. The solution was stirred at room temperature overnight and then concentrated under reduced pressure. The crude product was purified by HPLC on reversed phase (MeCN/H$_2$O) to afford the title compound as a foam-like solid.

Yield: 25 mg (24% of theory)

Mass spectrum (ESI$^+$): m/z=502 [M+H]$^+$

The following compounds were obtained in analogy to Example 680:

Example 681

5-(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid methylamide

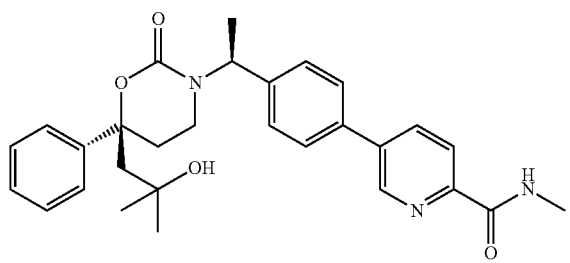

Mass spectrum (ESI$^+$): m/z=488 [M+H]$^+$

Example 682

(4-{(S)-1-[(S)-6-(2-Hydroxy-2-methyl-propyl)-2-oxo-6-phenyl-[1,3]oxazinan-3-yl]-ethyl}-phenyl)-pyridine-2-carboxylic acid dimethylamide

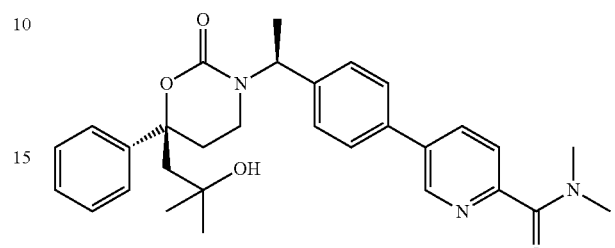

Mass spectrum (ESI$^+$): m/z=502 [M+H]$^+$

Example 683

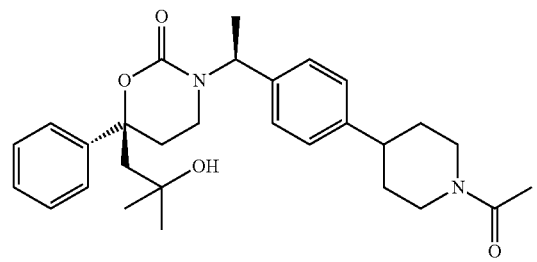

3-{(S)-1-[4-(1-Acetyl-piperidin-4-yl)-phenyl]-ethyl}-(S)-6-(2-hydroxy-2-methyl-propyl)-6-phenyl-[1,3]oxazinan-2-one Triethylamine (0.10 mL), acetic anhydride (50 µL), and 4-dimethylaminopyridine (5 mg) were added consecutively to (S)-6-(2-hydroxy-2-methyl-propyl)-6-phenyl-3-[(S)-1-(4-piperidin-4-yl-phenyl)-ethyl]-[1,3]oxazinan-2-one (0.12 g) dissolved in tetrahydrofuran (5 mL) at room temperature. The solution was stirred at room temperature for 4 h and then diluted with ethyl acetate. The resulting solution was washed with aqueous saturated NaHCO$_3$ solution and brine and dried (Na$_2$SO$_4$). After removal of the solvent, the residue was purified by chromatography on silica gel (CH$_2$Cl$_2$/MeOH 98:2→90:10) to afford the title compound as a colorless foam-like solid.

Yield: 80 mg (61% of theory)

Mass spectrum (ESI$^+$): m/z=479 [M+H]$^+$

Example 684

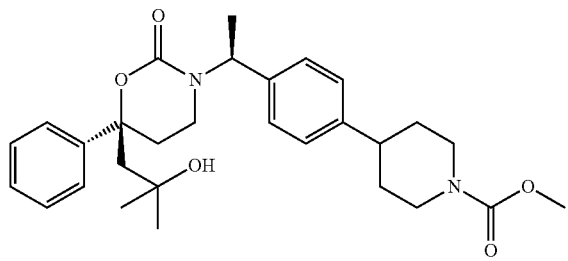

4-(4-{(S)-1-[(S)-6-(2-Hydroxy-2-methyl-propyl)-2-oxo-6-phenyl-[1,3]oxazinan-3-yl]-ethyl}-phenyl)-piperidine-1-carboxylic acid methyl ester Triethylamine (0.10 mL) and methyl chloroformate (24 µL) were added consecutively to (S)-6-(2-hydroxy-2-methyl-propyl)-6-phenyl-3-[(S)-1-(4-piperidin-4-yl-phenyl)-ethyl]-[1,3]oxazinan-2-one (0.12 g) dissolved in dichloromethane (5 mL) at room temperature. The resulting solution was stirred at room temperature overnight and then diluted with dichloromethane. The resulting solution was washed with water and brine and dried (Na$_2$SO$_4$). After removal of the solvent, the residue was purified by chromatography on silica gel (CH$_2$Cl$_2$/MeOH 99:1→90:10) to afford the title compound as a foam-like solid.
Yield: 100 mg (70% of theory)
Mass spectrum (ESI$^+$): m/z=495 [M+H]$^+$

Example 685

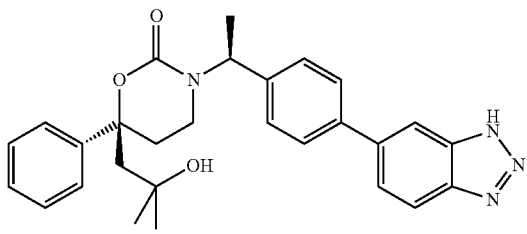

3-{(S)-1-[4-(3H-Benzotriazol-5-yl)-phenyl]-ethyl}-(S)-6-(2-hydroxy-2-methyl-propyl)-6-phenyl-[1,3]oxazinan-2-one A solution of NaNO$_2$ (0.16 g) in water (2 mL) was added dropwise to an ice-cold solution of 3-[(S)-1-(3',4'-diamino-biphenyl-4-yl)-ethyl]-(S)-6-(2-hydroxy-2-methyl-propyl)-6-phenyl-[1,3]oxazinan-2-one (0.43 g) in acetic acid (10 mL). The resulting mixture was stirred with cooling for 2 h and at room temperature for another 1 h. Then, water (100 mL) was added and the resulting mixture was extracted with ethyl acetate. The combined organic extracts were washed with saturated aqueous NaHCO$_3$ solution, water, and brine and dried (Na$_2$SO$_4$). The solvent was removed and the residue was purified by chromatography on silica gel (ethyl acetate/MeOH 98:2→80:20) to afford the title compound as a foam-like solid.
Yield: 0.30 g (69% of theory)
Mass spectrum (ESI$^+$): m/z=471 [M+H]$^+$

Example 686

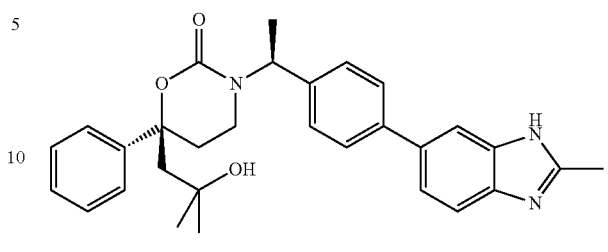

(S)-6-(2-Hydroxy-2-methyl-propyl)-3-{(S)-1-[4-(2-methyl-3H-benzoimidazol-5-yl)-phenyl]-ethyl}-6-phenyl-[1,3]oxazinan-2-one 3-[(S)-1-(3',4'-Diamino-biphenyl-4-yl)-ethyl]-(S)-6-(2-hydroxy-2-methyl-propyl)-6-phenyl-[1,3]oxazinan-2-one (120 mg) taken up in acetic acid (2 mL) was stirred under microwave irradiation at 150° C. for 30 min. After cooling to ambient temperature, the mixture was concentrated under reduced pressure and the residue was purified by HPLC on reversed phase (MeCN/H$_2$O) to afford the title compound.
Yield: 77 mg (61% of theory)
Mass spectrum (ESI$^+$): m/z=484 [M+H]$^+$

Examples 687 and 688

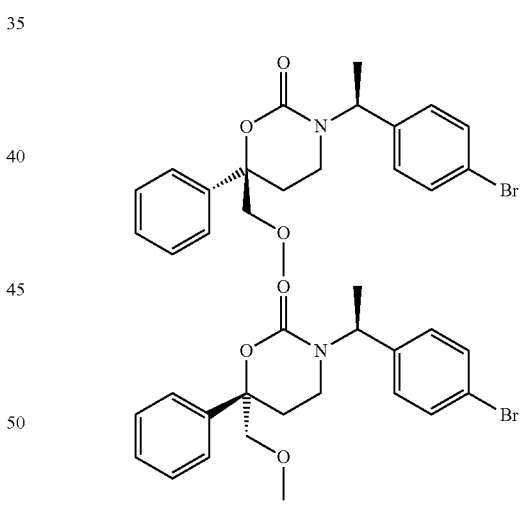

3-[(S)-1-(4-Bromo-phenyl)-ethyl]-(R)-6-methoxymethyl-6-phenyl-[1,3]oxazinan-2-one and 3-[(S)-1-(4-Bromo-phenyl)-ethyl]-(S)-6-methoxymethyl-6-phenyl-[1,3]oxazinan-2-one Triphosgene (157 mg) was added to an ice-cold solution of 4-[(S)-1-(4-bromo-phenyl)-ethylamino]-1-methoxy-2-phenyl-butan-2-ol (1:1 diastereomeric mixture, 200 mg) and EtNiPr$_2$ (91 µL) in dichloromethane (5 mL). The resulting solution was stirred with cooling for 2 h and at room temperature overnight. Then, the solution was concentrated under

Example 687

3-[(S)-1-(4-Bromo-phenyl)-ethyl]-(R)-6-methoxymethyl-6-phenyl-[1,3]oxazinan-2-one Yield: 45 mg (21% of theory)
Mass spectrum (ESI$^+$): m/z=404 [M+H]$^+$
$^1$H NMR (400 MHz, DMSO-d$_6$) δ 1.41 (d, J=7.1 Hz, 3H), 2.19 (td, J=11.2, 5.2 Hz, 1H), 2.24-2.34 (m, 1H), 2.34-2.41 (m, 1H), 3.02-3.09 (m, 1H), 3.27 (s, 3H), 3.49 (d, B part of an AB signal, J=10.6 Hz, 1H), 3.53 (d, A part of an AB signal, J=10.6 Hz, 1H), 5.34 (q, J=7.0 Hz, 1H), 6.80 (dm, J=8.4 Hz, 2H), 7.27 (dm, J=8.4 Hz, 2H), 7.32-7.42 (m, 5H).

Example 688

3-[(S)-1-(4-Bromo-phenyl)-ethyl]-(S)-6-methoxymethyl-6-phenyl-[1,3]oxazinan-2-one Yield: 45 mg (21% of theory)
Mass spectrum (ESI$^+$): m/z=404 [M+H]$^+$
$^1$H NMR (400 MHz, DMSO-d$_6$) δ 1.20 (d, J=7.2 Hz, 3H), 2.13-2.23 (m, 1H), 2.32-2.40 (m, 1H), 2.63-2.72 (m, 1H), 2.73-2.81 (m, 1H), 3.26 (s, 3H), 3.48 (d, B part of an AB signal, J=10.6 Hz, 1H), 3.55 (d, A part of an AB signal, J=10.6 Hz, 1H), 5.35 (q, J=7.2 Hz, 1H), 7.19 (dm, J=8.4 Hz, 2H), 7.32-7.45 (m, 5H), 7.53 (dm, J=8.4 Hz, 2H).

Example 689

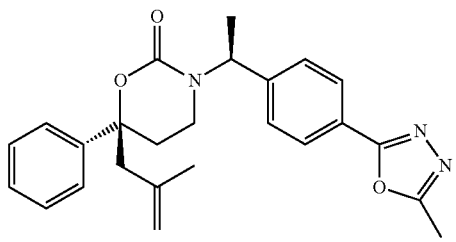

(S)-6-(2-Methyl-allyl)-3-{(S)-1-[4-(5-methyl-[1,3,4]oxadiazol-2-yl)-phenyl]-ethyl}-6-phenyl-[1,3]oxazinan-2-one A mixture of 4-{(S)-1-[(S)-6-(2-hydroxy-2-methyl-propyl)-2-oxo-6-phenyl-[1,3]oxazinan-3-yl]-ethyl}-benzoic acid hydrazide (90 mg), toluene-4-sulfonic acid monohydrate (10 mg), and 1,1,1-trimethoxy-ethane (1 ml) was stirred at room temperature for 1 h, at 80° C. for 2 h, and finally at reflux temperature for 1.5 h. After cooling to ambient temperature, ethyl acetate was added and the resulting mixture was washed with aqueous NaHCO$_3$ solution and brine. The solvent was removed under reduced pressure and the residue was purified by chromatography on silica gel (CH$_2$Cl$_2$/MeOH 99:1→95:5) to afford the title compound as a colorless resin-like solid.
Yield: 55 mg (60% of theory)
Mass spectrum (ESI$^+$): m/z=418 [M+H]$^+$

Biological Test Example 3

In vitro inhibition of 11 β-HSD1 by test compounds was determined with HTRF (Homogeneous Time-Resolved Fluorescence) technology (cisbio international, France) detecting cortisol generated from cortisterone by human liver microsomes. Briefly, compounds were incubated for 1 hour at 37° C. in Tris buffer (20 mM tris, 5 mM EDTA, pH 6.0) containing NADPH (200 NM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction was typically 2 hours. The amount of cortisol was determined by reading the time-resolved fluorescence of the wells (Ex 320/75 nm; Em 615/8.5 nm and 665/7.5 nm). The ratio of the two emission signals was then calculated (Em665*10000/Em615). Each assay contained incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contained a calibration curve with cortisol to transform the fluorescent data into cortisol concentrations. Percent inhibition of each compound was determined relative to the carbenoxolone signal.

In following table the 11β-HSD 1 inhibitory activities, determined as described above, wherein 100% indicates no inhibition and a value of zero or below zero indicates complete inhibition.

TABLE OF BIOLOGICAL ASSAY RESULTS FOR BIOLOGICAL TEST 3

| Example | Average % control inhibition at 100 nM |
|---|---|
| 666 | 14 |
| 667 | 63 |
| 668 | -3 |
| 669 | 3 |
| 670 | -5 |
| 671 | -19 |
| 672 | 10 |
| 673 | 9 |
| 674 | -14 |
| 676 | 17 |
| 677 | 43 |
| 678 | 59 |
| 679 | 58 |
| 680 | -32 |
| 681 | -19 |
| 682 | -8 |
| 683 | -1 |
| 684 | -13 |
| 685 | 34 |
| 686 | 23 |
| 687 | 28 |
| 688 | 88 |

Example 690

3-((R)-3-((S)-1-(4-(1-isopropyl-6-oxo-1,6-dihydro-pyridin-3-yl)phenyl)ethyl)-2-oxo-6-phenyl-1,3-oxazinan-6-yl)-2,2-dimethylpropanenitrile

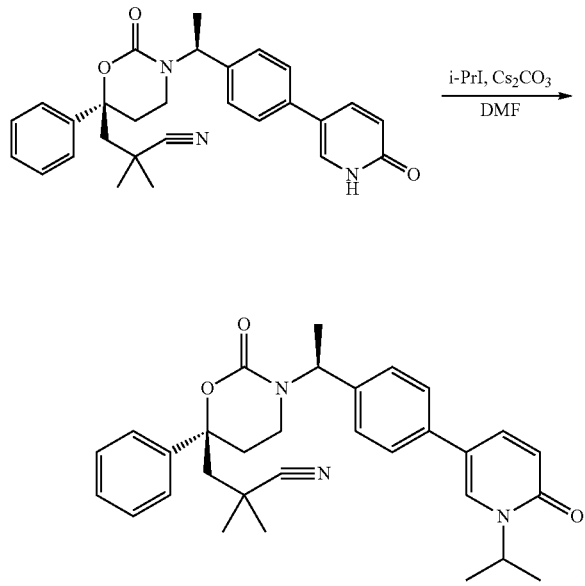

2,2-dimethyl-3-((R)-2-oxo-3-((S)-1-(4-(6-oxo-1,6-dihydropyridin-3-yl)phenyl)ethyl)-6-phenyl-1,3-oxazinan-6-yl)propanenitrile (6 mg, 0.013 mmol) was dissolved in DMF (2.5 mL). Cs$_2$CO$_3$ (c.a. 15 mg, excess) and i-PrI (100 µL, excess) were added. The mixture was stirred for 3 h at rt. LC-MS found the reaction was complete. The mixture was purified by prep HPLC to afford 3-((R)-3-((S)-1-(4-(1-isopropyl-6-oxo-1,6-dihydropyridin-3-yl)phenyl)ethyl)-2-oxo-6-phenyl-1,3-oxazinan-6-yl)-2,2-dimethylpropanenitrile (1.99 mg, 30%). LC-MS Method 1 $t_R$=2.03 min, m/z=498; $^1$H NMR (CDCl$_3$) 8.35 (d, 1H), 7.80 (dd, 1H), 7.37 (m, 5H), 7.22 (d, 2H), 6.92 (d, 2H), 6.83 (d, 1H), 5.66 (q, 1H), 5.22 (m, 1H), 2.93 (m, 1H), 2.16 (s, 2H), 1.55 (d, 3H), 1.46 (s, 3H), 1.40 (d, 6H), 1.33 (s, 3H).

Example 691

(S)-6-(2-amino-2-methylpropyl)-3-((S)-1-(4-bromophenyl)ethyl)-6-phenyl-1,3-oxazinan-2-one

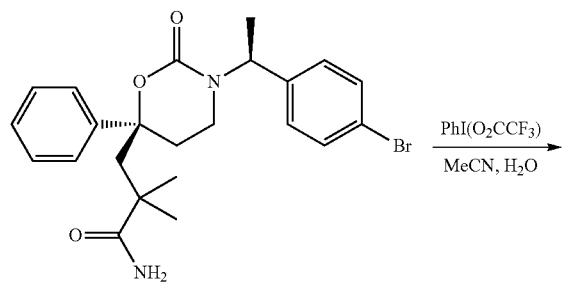

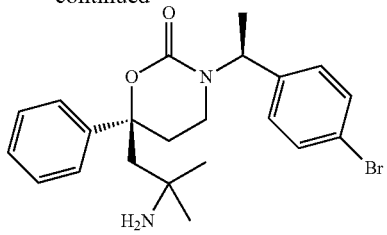

To a solution of 3-((R)-3-((S)-1-(4-bromophenyl)ethyl)-2-oxo-6-phenyl-1,3-oxazinan-6-yl)-2,2-dimethylpropanamide (41 mg, 0.090 mmol) in 1:1 acetonitrile:water [0.2M] was added [bis(trifluoroacetoxy)iodo]benzene (60 mg, 0.13 mmol). The reaction was allowed to stir overnight. The solvent was evaporated and purified via prep HPLC to afford the TFA salt of (S)-6-(2-amino-2-methylpropyl)-3-((S)-1-(4-bromophenyl)ethyl)-6-phenyl-1,3-oxazinan-2-one (49 mg). LC-MS Method 1 $t_R$=1.39 min, m/z=431; $^1$H NMR (CDCl$_3$) 7.39-7.22 (7H, m), 6.90 (2H, d, J=8.5 Hz), 5.54 (1H, q, J=6.4 Hz), 2.81 (1H, dd, J=12.3 2.9 Hz), 2.72 (1H, d, J=15 Hz), 2.33-2.16 (3H, m), 2.02 (1H, dt, J=12.2, 4.4 Hz), 1.47 (3H, d, J=6.7 Hz), 1.38 (3H, s), 0.94 (3H, s).

Example 692

N-(1-((S)-3-((S)-1-(4-bromophenyl)ethyl)-2-oxo-6-phenyl-1,3-oxazinan-6-yl)-2-methylpropan-2-yl)cyclopropanecarboxamide

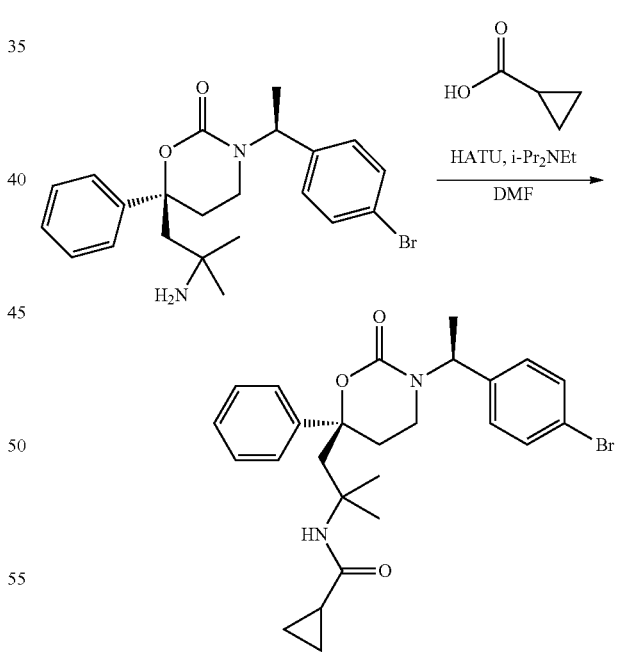

A solution of trifluoroacetic acid salt (S)-6-(2-amino-2-methylpropyl)-3-((S)-1-(4-bromophenyl)ethyl)-6-phenyl-1,3-oxazinan-2-one (10 mg, 0.02 mmol) in DMF (0.2 mL) was added to i-Pr$_2$NEt (5 drops), HATU (9 mg, 0.02 mmol), and cyclopropane carboxylic acid. The reaction mixture was diluted with acetonitrile and purified via prep HPLC to afford N-(1-((S)-3-((S)-1-(4-bromophenyl)ethyl)-2-oxo-6-phenyl-1,3-oxazinan-6-yl)-2-methylpropan-2-yl)cyclopropanecarboxamide (6 mg). LC-MS Method 1 $t_R$=1.83 min, m/z=499; $^1$H NMR (CDCl$_3$) 7.35-7.28 (5H, m), 7.23 (2H, d, J=8.5 Hz), 5.59 (1H, q, J=7.02 Hz), 5.41 (1H, s), 2.83 (1H, m), 2.68 (1H, d, J=15.2 Hz), 2.29 (1H, d, J=15.2 Hz), 2.17 (3H, s), 1.48 (3H, d, J=7.0 Hz), 1.37 (3H, s), 1.22 (3H, s), 0.88-0.84 (1H, m), 0.77-0.75 (2H, m), 0.61-0.51 (2H, m).

Example 693

N-(1-((S)-3-((S)-1-(4-bromophenyl)ethyl)-2-oxo-6-phenyl-1,3-oxazinan-6-yl)-2-methylpropan-2-yl) pivalamide

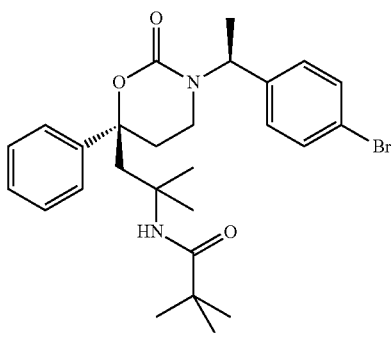 [SMILES: C[C@@H](c1ccc(Br)cc1)N1CC[C@](CC(C)(C)NC(=O)C(C)(C)C)(c2ccccc2)OC1=O]

The title compound was prepared (S)-6-(2-amino-2-methylpropyl)-3-((S)-1-(4-bromophenyl)ethyl)-6-phenyl-1,3-oxazinan-2-one following a procedure analogous to that described in Example 688 using pivalic acid. LC-MS Method 1 $t_R$=2.05 min, m/z=515; $^1$H NMR (CDCl$_3$) 7.36-7.27 (5H, m), 7.22 (2H, d, J=8.5 Hz), 6.79 (2H, d, J=8.2 Hz), 6.20 (1H, s), 5.58 (1H, q, J=7.0 Hz), 2.79 (1H, m), 2.44 (1H, d, J=15.5 Hz), 2.37 (1H, d, J=15.2 Hz), 2.24-2.06 (3H, m), 1.47 (3H, d, J=7.03 Hz), 1.37 (3H, s) 1.10 (9H, s), 1.05 (3H, s).

Example 694

N-(1-((S)-3-((S)-1-(4-bromophenyl)ethyl)-2-oxo-6-phenyl-1,3-oxazinan-6-yl)-2-methylpropan-2-yl) methanesulfonamide

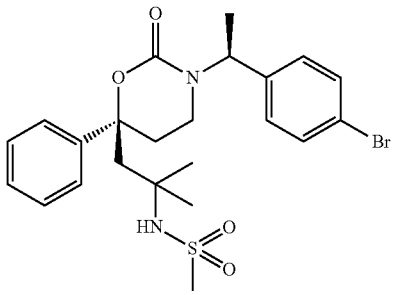 [SMILES: C[C@@H](c1ccc(Br)cc1)N1CC[C@](CC(C)(C)NS(C)(=O)=O)(c2ccccc2)OC1=O]

The title compound was prepared (S)-6-(2-amino-2-methylpropyl)-3-((S)-1-(4-bromophenyl)ethyl)-6-phenyl-1,3-oxazinan-2-one following a procedure analogous to that described in Example 99. LC-MS Method 1 $t_R$=1.8 min, m/z=509; $^1$H NMR (CDCl$_3$) 7.39-7.29 (5H, m), 7.23 (1H, d, J=8.5 Hz), 6.82 (1H, d, J=7.9 Hz), 5.59 (1H, q, J=7.0 Hz), 4.59 (1H, s), 2.92 (3H, s), 2.85 (1H, dt, J=11.3, 4.0 Hz), 2.45 (1H, d, J=15.2 Hz), 2.31 (1H, d, J=15.2 Hz), 2.28-2.24 (2H, m), 2.17-2.11 (1H, m), 1.48 (3H, d, J=7.0 Hz), 1.32 (3H, s), 1.26 (3H, s).

| TABLE OF BIOLOGICAL ASSAY RESULTS FOR EXAMPLES 690-694 | | | |
|---|---|---|---|
| | | Biological Test Example 1 | |
| Compound | IC$_{50}$ Range$^a$ | Average % inhibition at 100 nM | Average % inhibition at 111.1 nM |
| EXAMPLE 690 | ++ | | 94.9 |
| EXAMPLE 691 | ++ | | 90.1 |
| EXAMPLE 692 | ++ | | 80.65 |
| EXAMPLE 693 | # | | 17.65 |
| EXAMPLE 694 | ++ | | 91.5 |

$^a$++ means IC$_{50}$ = <100 nM, + means IC$_{50}$ = 100-1000 nM, # means IC$_{50}$ > 100 nM, – means IC$_{50}$ > 1000 nM.

Example 695

(S)-3-[(S)-1-(4-Bromo-phenyl)-ethyl]-6-(2-hydroxy-2-methyl-propyl)-6-phenyl-perhydro-1,3-oxazin-2-one

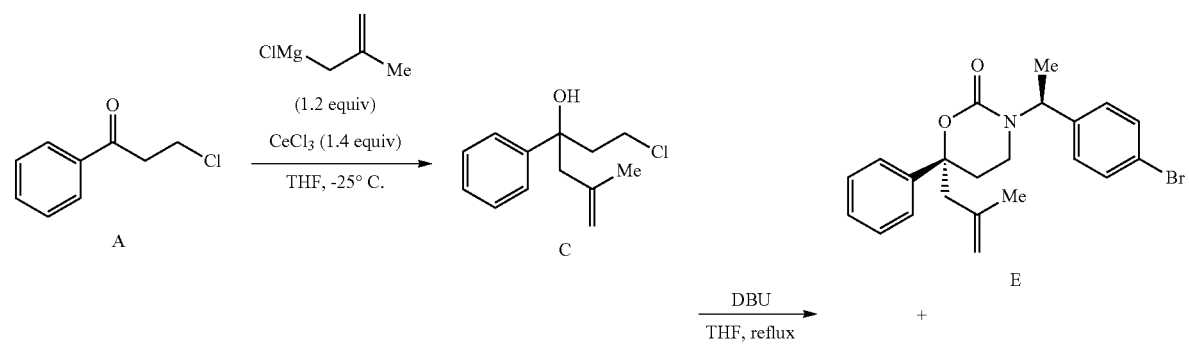

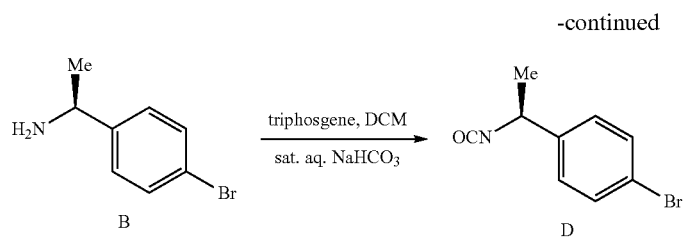

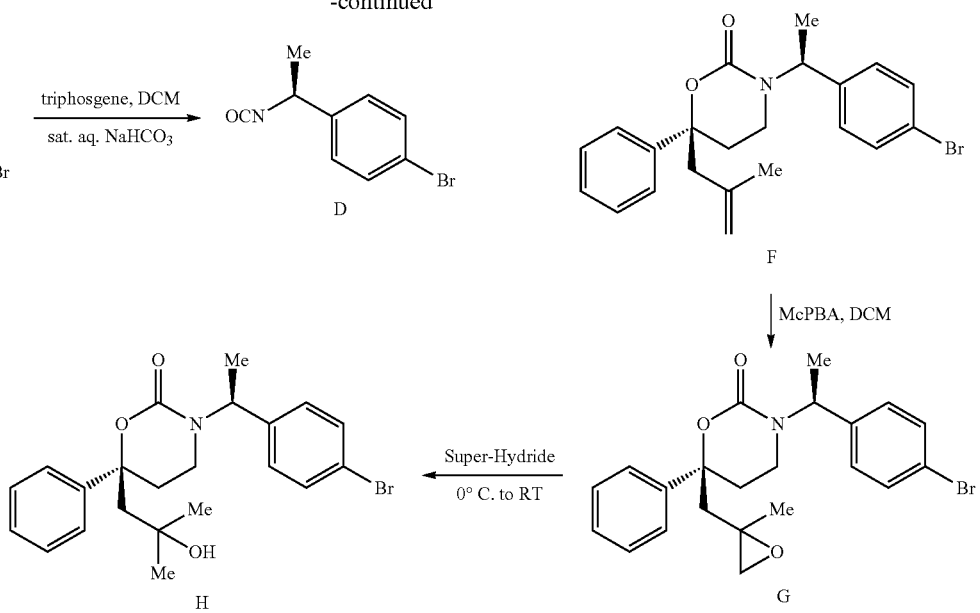

Step 1: 1-Chloro-5-methyl-3-phenyl-hex-5-en-3-ol (C)

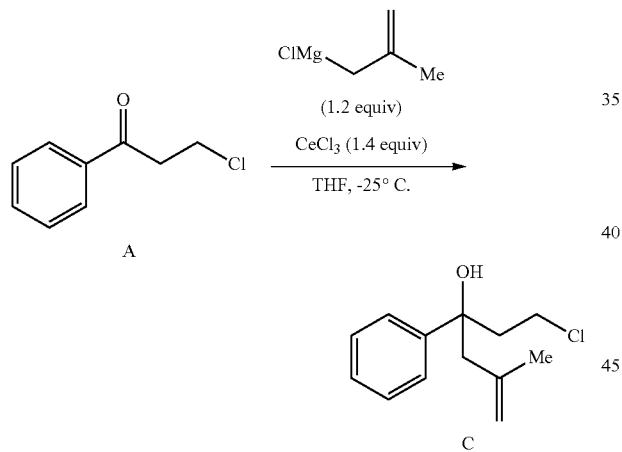

To a stirred suspension of magnesium turnings (46.7 g, 1.94 mol) in 1500 mL of THF (KF<100 ppm) was charged 53.0 mL of 1 M DIBAL-H in hexane under nitrogen at room temperature. Then beta-methylallylic chloride (160 g, 1.77 mol) was introduced while maintaining the internal temperature below 30° C. The resulting solution was agitated for 2 h at room temperature. The solution was titrated in the presence of 1,1'-bipyridine to indicate 0.8 M of the corresponding Grignard reagent. To a dry flask containing 307.0 g of anhydrous $CeCl_3$ (1.25 mol) at room temperature under nitrogen was added 1556.8 mL of the Grignard reagent (0.8 M, 1.25 mol). The resulting slurry was cooled to −10° C. and agitated for 0.5 h. To the slurry was added 200 g of the ketone (1.19 mol) in 200 mL of THF while maintaining the internal temperature below 0° C. After the mixture was stirred for 0.5 h, 1200 mL of 1 M HCl was added to obtain a clear solution while maintaining the internal temperature below 30° C.

After the phase cut, the aqueous layer was extracted with EtOAc (500 mL). The combined organic layers were washed with brine and dried over sodium sulfate. Removal of the solvent under vacuum produced the crude product, which was chased with THF to achieve KF<500 ppm. The crude product (306 g, 83 wt %, 95% yield) was used directly for subsequent coupling. Analytical data for C: $^1$H-NMR spectroscopy (500 MHz, $CDCl_3$) δ 7.38-7.37 (d. J=7.8 Hz, 2H), 7.33 (t, J=7.9 Hz, 2H), 7.24 (t, J=7.4 Hz, 1H), 4.91 (s, 1H), 4.76 (s, 1H), 3.57 (ddd, J=5.6, 10.7, and 10.7, 1H), 3.13 (ddd, J=4.7, 10.7 and 10.7 Hz, 1H), 2.66 (d, J=13.3 Hz, 1H), 2.54 (d, J=11.3 Hz, 1H), 2.53 (s, 1H), 2.36 (ddd, J=5.4, 10.6 and 13.9 Hz. 1H), 2.29 (ddd, J=5.6, 11.3 and 13.3 Hz, 1H), 1.29 (s, 3H). $^{13}$C-NMR spectroscopy (125 MHz, $CDCl_3$) δ 144.3, 141.4, 128.0, 126.6, 124.8, 116.1, 74.2, 51.2, 46.0, 39.9, 23.9.

Step 2: 1-Bromo-4-((S)-1-isocyanato-ethyl)-benzene (D)

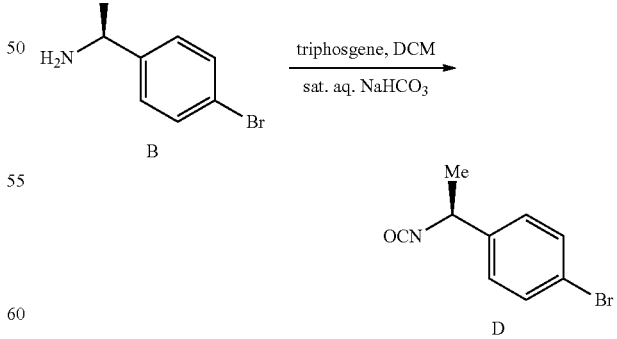

To a 10 L jacketed reactor was charged 241 g of sodium bicarbonate (2.87 mol, 2.30 equiv) and 5 L of deionized water. The resulting solution was agitated for 10-20 min, until the solids dissolved (homogeneous). To the clear solution was charged 250 g (1.25 mol, 1.00 equiv) of (S)-(−)-1-(4-bromophenyl)ethylamine as a solution in 1.00 L of dichloromethane. An additional 4 L of dichloromethane was charged to the reactor. The biphasic solution was agitated and cooled to Tint=2-3° C. Triphosgene (126 g, 424 mmol, 0.340 equiv) was charged to the reactor in approximately two equal portions ~6 min apart. It should be noted that a slight exotherm was noted upon the addition of triphosgene. The resulting murky solution was agitated at Tint=2-5° C. for 30 min, at which point HPLC analysis indicates >99 A % conversion (220 nm). The dichloromethane layer was cut and dried with anhydrous sulfate. The resulting solution was passed through a celite plug and concentrated to ~1.5 L which fine particles of a white solid developed. The solution was filtered and concentrated to a thick oil via reduced pressure to produce 239 g of product (93.7 wt %, 79.4% yield). The material was used in the following coupling without further purification. Analytical data for D: 1H-NMR spectroscopy (400 MHz, CD2Cl2) δ 7.53 (d, J=11.4 Hz, 2H), 7.26 (d, J=8.2 Hz, 2H), 4.80 (q, J=6.7 Hz, 1H), 1.59 (d, J=6.7 Hz, 3H).

Step 3: R)-3-[(S)-1-(4-Bromo-phenyl)-ethyl]-6-(2-methyl-allyl)-6-phenyl-perhydro-1,3-oxazin-2-one (F)

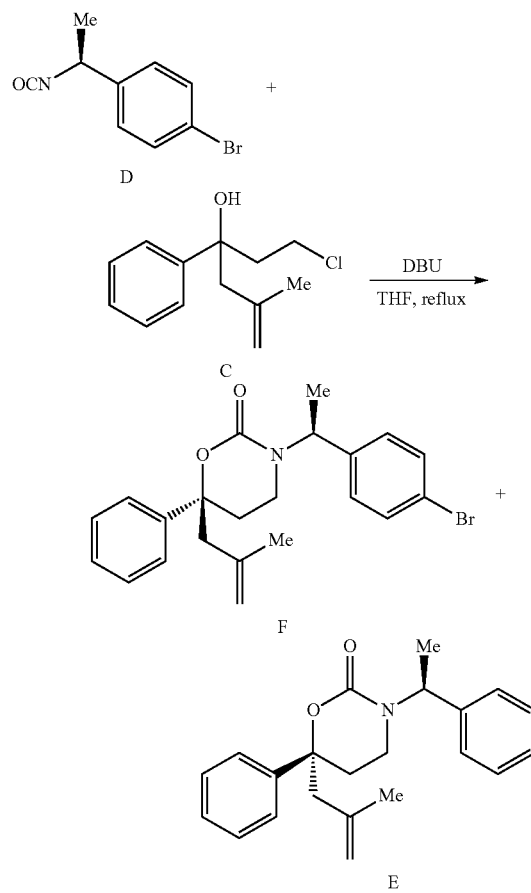

(To a dried 10 L jacketed reactor under a nitrogen atmosphere was charged 1-chloro-5-methyl-3-phenyl-hex-5-en-3-ol (C, 167 g, 81.7 wt %, 610 mmol, 1.00 equiv), 1-bromo-4-((S)-1-isocyanato-ethyl)-benzene (D, 219 g, 93.7 wt %, 911 mmol, 1.50 equiv), anhydrous tetrahydrofuran (3.00 L), and then 1,8-diazabicyclo[5.4.0]undec-7-ene (DBU, 409 mL, 2.73 mol, 4.50 equiv). The resulting solution was agitated and refluxed (Tint=67-69° C., Text=75° C.) for 19 h, at which point HPLC analysis indicates ~1 A % (220 nm) of the 1-chloro-5-methyl-3-phenyl-hex-5-en-3-ol (3) remains. The dark solution was cooled to Tint=20-25° C. Two liters of tetrahydrofuran were removed by distillation under reduced pressure. The remaining dark solution was diluted with 4.0 L of ethyl acetate and 1.0 L of hexanes. The resulting solution was washed with 4.0 L of a 1.0 M aqueous solution of hydrogen chloride (note: the wash is slightly exothermic). The aqueous solution was cut and the remaining organic solution was dried with anhydrous sodium sulfate, filtered and then concentrated to an oil via reduced pressure. The resulting material was subjected to flash silica chromatography (5-30% ethyl acetate/hexanes, 1.74 kg of silica) to produce 137.8 g of material (59 wt %, 3.1:1 diastereomeric ratio favoring the desired diastereomer 6, 32.3% yield). The material was used in the following epoxidation without further purification.

Analytical data for (R)-3-[(S)-1-(4-bromo-phenyl)-ethyl]-6-(2-methyl-allyl)-6-phenyl-perhydro-1,3-oxazin-2-one (F): 1H-NMR spectroscopy (500 MHz, CD2Cl2) δ 7.42-7.35 (m, 3H), 7.33-7.31 (m, 2H), 7.25-7.23 (m, 2H), 6.80-6.74 (m, 2), 5.55 (q, J=7.1 Hz, 1H), 5.37-5.36 (m, 1H), 4.89 (s, 1H), 4.69 (s, 1H), 2.96-2.93 (m, 1H), 2.61 (dd, J=13.8 and 26.4 Hz, 2H), 2.37-2.25 (m, 3H), 1.68 (s, 3H), 1.50 (d, J=7.1 Hz, 3H). 13C-NMR spectroscopy (125 MHz, CD2Cl2) δ 152.5, 141.5, 140.1, 138.3, 130.6, 128.1, 128.0, 126.9, 124.4, 120.2, 115.3, 82.4, 52.1, 50.1, 35.6, 29.8, 23.4, 14.5.

Analytical data for (S)-3-[(S)-1-(4-bromo-phenyl)-ethyl]-6-(2-methyl-allyl)-6-phenyl-perhydro-1,3-oxazin-2-one (E): 1H-NMR spectroscopy (400 MHz, CD2Cl2) δ 7.50-7.48 (m, 2H), 7.43-7.39 (m, 2H), 7.35-7.32 (m, 3H), 7.20-7.18 (m, 2H), 5.60 (q, J=7.1 Hz, 1H), 4.85 (s, 1H), 4.66 (s, 1H), 2.73-2.67 (m, 2H), 2.60 (dd, J=13.9 and 19.4 Hz, 2H), 2.28 (dt, J=3.3 and 13.7 Hz, 1H), 2.14-2.05 (m, 1H), 1.66 (s, 3H), 1.24 (d, J=7.2 Hz, 3H). 13C-NMR spectroscopy (100 MHz, CD2Cl2) δ 153.4, 142.5, 141.0, 140.1, 131.8, 129.3, 128.9, 127.8, 125.3, 121.5, 116.3, 83.9, 53.2, 51.0, 36.6, 31.3, 24.3, 15.4.

Step 4: (S)-3-[(S)-1-(4-Bromo-phenyl)-ethyl]-6-(2-hydroxy-2-methyl-propyl)-6-phenyl-perhydro-1,3-oxazin-2-one)

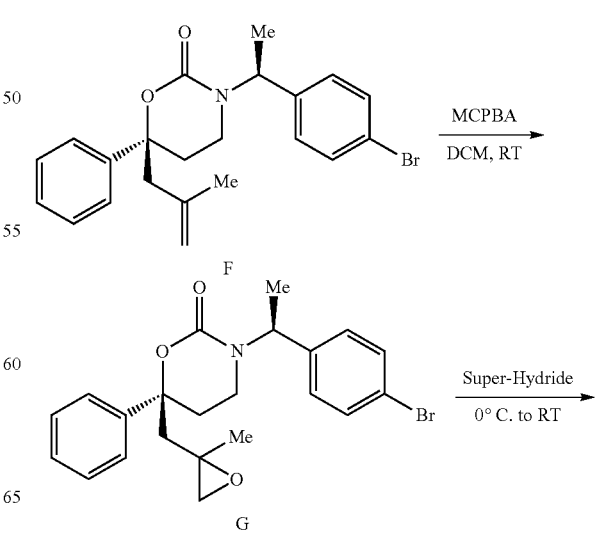

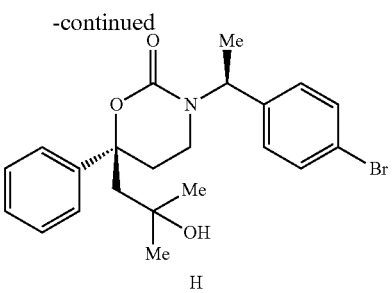

To a 1.0 L 2-neck RBF was charged (R)-3-[(S)-1-(4-bromo-phenyl)-ethyl]-6-(2-methyl-allyl)-6-phenyl-perhydro-1,3-oxazin-2-one (F, 135.8 g, 59 wt %, 3.1:1 dr, 193 mmol, 1.00 equiv), dichloromethane (700 mL), and then 3-chloroperbenzoic acid (MCPBA, 70%, 95.3 g, 386 mmol, 2.0 equiv). The resulting solution was agitated at RT (Tint=20-25° C.) for 1H, which HPLC analysis indicates >99 A % (220 nm) conversion. The resulting solution was diluted with 700 mL of methyl tert-butyl ether (MTBE) and washed with 1×500 mL of 30 wt % solution of sodium thiosulfate and 1×500 mL of saturated aqueous solution of sodium bicarbonate. The wash sequence were repeated until the peak on an HPLC trace of the organic solution that corresponds to a HPLC sample peak of MCPBA is <2.5 A % (220 nm), which in this example the wash sequence was repeated 3 times. The resulting organic layer was dried with anhydrous sodium sulfate, filtered and then concentrated to an oil via reduced pressure. The resulting material was diluted with 200 mL of anhydrous tetrahydrofuran and then concentrated to a thick oil via reduced pressure to provide (S)-3-[(S)-1-(4-bromo-phenyl)-ethyl]-6-(2-methyl-oxiranylmethyl)-6-phenyl-perhydro-1,3-oxazin-2-one (G) which was used directly in the following reduction.

To a 2.0 L 3-neck oven-dried RBF was charged the crude (S)-3-[(S)-1-(4-bromo-phenyl)-ethyl]-6-(2-methyl-oxiranylmethyl)-6-phenyl-perhydro-1,3-oxazin-2-one (G) and 750 mL of anhydrous tetrahydrofuran. The resulting solution was agitated and cooled to Tint=2-3° C. To the agitated clear solution was charged 1.0 M lithium triethylborohydride in tetrahydrofuran (Super Hydride, 348 mL, 348 mmol, 1.8 equiv). The addition is exothermic and addition controlled to maintain Tint=<8° C. The resulting solution was agitated at Tint=2-3° C. for 1.5 h and then allowed to warm to Tint=10-13° C. over a 2.5 h, which HPLC analysis indicates ~94 A % (220 nm) conversion. To the agitated solution was charged a solution of hydrogen peroxide (95.7 mL of a 35 wt % aqueous solution diluted with 400 mL of water, 1.08 mol, 5.60 equiv). The addition is highly exothermic and addition controlled to maintain Tint=<25° C. The resulting solution was diluted with 1.00 L of methyl tert-butyl ether (MTBE) and washed with 1.00 L of water followed by 500 mL of a ~30 wt % solution of sodium thiosulfate. The organic solution was dried with anhydrous sodium sulfate, filtered, and then concentrated via reduced pressure. The resulting material was subjected to flash silica chromatography (10-60% ethyl acetate, 600 g of silica) to produce 68 g of material consisting of both diastereomers (1.98:1 dr) and 41 g of the desired diastereomer (>99:1 dr). The material consisting of the mixed fractions was recrystallized from 250 mL of isopropyl acetate (IPAC) and 200 mL of heptane (anti-solvent) to produce upon filtration 31.3 g of product (95.7 A % at 220 nm, 74:1 dr). The two samples were combined to produce 72.3 g of product (83.6% yield for the two step operation). Analytical data for H: 1H-NMR spectroscopy (400 MHz, CDCl3) δ 7.37-7.29 (m, 5H), 7.25-7.21 (m, 2H), 6.82-6.79 (m, 2H), 5.61 (q, J=6.9 Hz, 1H), 2.83 (ddd, J=2.5, 5.4 and 11.6 Hz, 1H), 2.39 (ddd, J=5.7, 12.0 and 14.1 Hz, 1H), 2.27 (ddd, J=2.6, 4.8 and 14.0 Hz, 1H), 2.21-2.14 (m, 3H), 2.08 (s, 1H), 1.49 (d, J=7.0 Hz, 3H), 1.18 (s, 3H), 1.13 (s, 3H). $^{13}$C-NMR spectroscopy (100 MHz, CDCl3) δ 153.2, 142.6, 138.5, 131.6, 129.13, 129.10, 128.0, 125.3, 121.6, 84.2, 71.4, 54.1, 53.3, 36.4, 33.6, 32.1, 30.8, 15.6.

The compounds of the invention are useful for ameliorating or treating disorders or diseases in which decreasing the level of cortisol is effective in treating a disease state. Thus, the compounds of the invention can be used in the treatment or prevention of diabetes mellitus (e.g., type II diabetes), obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. The compounds of the invention can be used as therapeutic agents for pseudo Cushing's Syndrome associated with alcoholic liver disease. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypretriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease.

A pharmaceutical composition of the invention may, alternatively or in addition to a compound of Formula I, comprise a pharmaceutically acceptable salt of a compound of Formula I or a prodrug or pharmaceutically active metabolite of such a compound or salt and one or more pharmaceutically acceptable carriers therefore. Alternatively, a pharmaceutical composition of the invention may comprise a compound of Formula I, Ia-I or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant ($IC_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of a compound of Formula I, or an enantiomer, diastereomer, or pharmaceutically acceptable salt thereof or of composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of Formula I or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of Formula I or composition thereof in a combination therapy with one or more other 11β-HSD1 inhibitors (whether such inhibitors are also compounds of Formula I or are compounds of a different class/genus), or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

What is claimed is:
1. A compound of Formula (Ib), (Ic), (Id), (Ie) or (If):

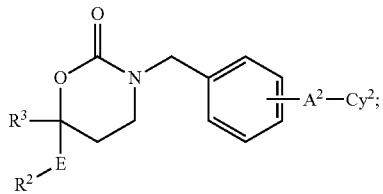
Ib

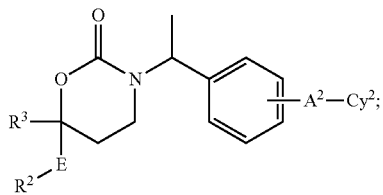
Ic

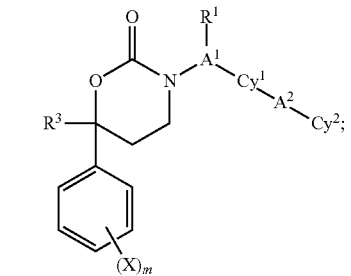
Id

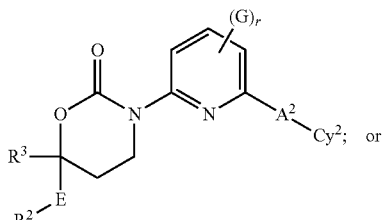
Ie

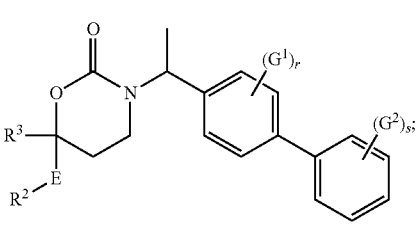
If wherein:
R$^1$ is absent or is selected from (C$_1$-C$_6$)alkyl, (C$_2$-C$_6$)alkenyl, (C$_2$-C$_6$)alkynyl and (C$_1$-C$_3$)alkoxy(C$_1$-C$_3$)alkoxy, each of which is optionally substituted with up to four groups independently selected from fluorine, cyano, oxo, R$^4$, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$ NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$ NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, heterocyclyl, heteroaryl, arylamino and heteroarylamino;

A$^1$ is (a) a bond, or (b) (C$_1$-C$_3$)alkylene, CH$_2$CH$_2$O, wherein the oxygen is attached to Cy$^1$, or CH$_2$C(=O), wherein the carbonyl carbon is attached to Cy$^1$;

Cy$^1$ is aryl, heteroaryl, monocyclic cycloalkyl or monocyclic heterocyclyl each of which is optionally substituted with 1 to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$) alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkythio, (C$_4$-C$_7$)cycloalkylalkylthio, halo(C$_1$-C$_6$) alkylthio, halo(C$_3$-C$_6$)cycloalkythio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$) alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$) alkylamino, (C$_1$-C$_6$)alkoxy(C$_1$-C$_6$)alkoxy, halo(C$_1$-C$_6$) alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclosulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, C$_1$-C$_6$)alkoxy (C$_1$-C$_6$)alkyl, halo(C$_1$-C$_6$)alkoxy(C$_1$-C$_6$)alkyl, hydroxy (C$_1$-C$_6$)alkoxy, heteroaryl and oxo;

A$^2$ is (a) a bond, O, S or NR$^4$; or (b) (C$_1$-C$_3$)alkylene or (C$_1$-C$_2$)alkyleneoxy, each of which is optionally substituted with 1 to 4 groups independently selected from methyl, ethyl, trifluoromethyl or oxo;

Cy$^2$ is aryl, heteroaryl, cycloalkyl or heterocyclyl, each of which is optionally substituted with 1 to 4 groups independently selected from fluorine, chlorine, bromine, iodine, cyano, nitro, amino, hydroxy, carboxy, (C$_1$-C$_6$) alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkynyl, (C$_3$-C$_6$)cycloalkyl(C$_2$-C$_4$)alkynyl, halo (C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$) cycloalkoxy, halo(C$_4$-C$_7$)cycloalkylalkoxy, (C$_1$-C$_6$) alkylthio, (C$_3$-C$_6$)cycloalkythio, (C$_4$-C$_7$) cycloalkylalkythio, halo(C$_1$-C$_6$)alkylthio, halo(C$_3$-C$_6$)

cycloalkythio, halo($C_4$-$C_7$)cycloalkylalkylthio, ($C_1$-$C_6$) alkanesulfinyl, ($C_3$-$C_6$)cycloalkanesulfinyl, ($C_4$-$C_7$) cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$N$SO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl and oxo;

Y is ($C_1$-$C_6$)alkyl, halo($C_1$-$C_6$)alkyl or oxo;

n is 0, 1 or 2;

E is (a) a bond or (b) ($C_1$-$C_3$)alkylene or ($C_1$-$C_2$)alkylenyloxy, wherein the O is attached to $R^2$, each of which is optionally substituted with 1 to 4 groups independently selected from methyl, ethyl, trifluoromethyl and oxo;

$R^2$ is ($C_1$-$C_6$)alkyl, aryl, heteroaryl, cycloalkyl or heterocyclyl, each of which is optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$N$SO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl or oxo;

$R^3$ is selected from ($C_1$-$C_6$)alkyl, ($C_2$-$C_6$)alkenyl, ($C_2$-$C_6$)alkynyl and ($C_1$-$C_3$)alkoxy($C_1$-$C_3$)alkoxy each of which is optionally substituted with up to four groups independently selected from fluorine, cyano, oxo, $R^4$, $R^4$O—, ($R^4$)$_2$N—$R^4$O$_2$C—, $R^4$S, $R^4$S(=O)—, $R^4$S(=O)$_2$—, $R^4$C(=O)N$R^4$—, ($R^4$)$_2$NC(=O)—, ($R^4$)$_2$NC(=O)O—, ($R^4$)$_2$NC(=O)N$R^4$—, $R^4$OC(=O)N$R^4$—, ($R^4$)$_2$NC(=NCN)N$R^4$—, ($R^4$O)$_2$P(=O)O—, ($R^4$O)$_2$P(=O)N$R^4$—, $R^4$OS(=O)$_2$N$R^4$—, ($R^4$)$_2$NS(=O)$_2$O—, ($R^4$)$_2$NS(=O)$_2$N$R^4$—, $R^4$S(=O)$_2$N$R^4$—, $R^4$S(=O)$_2$NHC(=O)—, $R^4$S(=O)$_2$NHC(=O)O—, $R^4$S(=O)$_2$NHC(=O)N$R^4$—, $R^4$OS(=O)$_2$NHC(=O)—, $R^4$OS(=O)$_2$NHC(=O)O—, $R^4$OS(=O)$_2$NHC(=O)N$R^4$—, ($R^4$)$_2$NS(=O)$_2$NHC(=O)—, ($R^4$)$_2$NS(=O)$_2$NHC(=O)O—, ($R^4$)$_2$NS(=O)$_2$NHC(=O)N$R^4$—, $R^4$C(=O)NHS(=O)$_2$—, $R^4$C(=O)NHS(=O)$_2$O—, $R^4$C(=O)NHS(=O)$_2$N$R^4$—, $R^4$OC(=O)NHS(=O)$_2$—, $R^4$OC(=O)NHS(=O)$_2$O—, $R^4$OC(=O)NHS(=O)$_2$N$R^4$—, ($R^4$)$_2$NC(=O)NHS(=O)$_2$—, ($R^4$)$_2$NC(=O)NHS(=O)$_2$O—, ($R^4$)$_2$NC(=O)NHS(=O)$_2$N$R^4$—, heterocyclyl (which in turn may be optionally substituted with alkyl, haloalkyl or oxo), heteroaryl which in turn may be optionally substituted with alkyl, haloalkyl, alkoxy, alkylthio, alkylsulfonyl, halogen, trifluoromethyl, dialkylamino, nitro, cyano, $CO_2$H, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2$H, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2$H $CONH_2$, N-monoalkyl-substituted amido, N,N-dialkyl-substituted amido, or oxo);

$R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl;

m is 0, 1, 2, 3 or 4;

X is independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$N$SO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy ($C_1$-$C_6$)alkoxy heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

r is 0, 1, 2, 3 or 4; and

G, $G^1$ and $G^2$ are each independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl;

or a pharmaceutically acceptable salt, enantiomer or diastereomer thereof.

2. A compound of Formula (Ik):

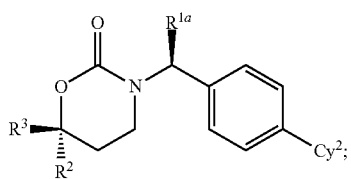

Ik wherein:

$R^{1a}$ is methyl or ethyl;

$Cy^2$ is aryl, heteroaryl, cycloalkyl or heterocyclyl, each of which is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclosulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl or oxo;

$R^3$ is selected from ($C_1$-$C_6$)alkyl, ($C_2$-$C_6$)alkenyl, ($C_2$-$C_6$)alkynyl and ($C_1$-$C_3$)alkoxy($C_1$-$C_3$)alkoxy each of which is optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2$ NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, heterocyclyl (which in turn may be optionally substituted with alkyl, haloalkyl or oxo), heteroaryl which in turn may be optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, CO$_2$H, CONH$_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo); and R$^4$ is independently selected from H, (C$_1$-C$_6$)alkyl, halo(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, hydroxy(C$_1$-C$_6$)alkyl and (C$_1$-C$_6$)alkoxy(C$_1$-C$_6$)alkyl;

or a pharmaceutically acceptable salt, enantiomer or diastereomer thereof.

3. A method of treating a subject with a disease or disorder associated with the activity or expression of 11β-HSD1, comprising the step of administering to the subject an effective amount of the compound in claim 1, wherein the disease or disorder is selected from diabetes mellitus, obesity, metabolic syndrome, prothrombotic state, proinflammatory state, glucose intolerance, hyperglycemia, hypertension, hyperlipidemia, insulin resistance, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, cognitive decline, polycystic ovarian syndrome, hypergonadism, tuberculosis, leprosy, psoriasis, to promote wound healing, hypertriglyceridemia, hypercholesterolemia, low HDL levels, high LDL levels, vascular restenosis, pancreatitis, abdominal obesity, coronary heart disease, peripheral vascular disease, hyperinsulinemia, viral diseases, and Syndrome X.

4. A pharmaceutical composition comprising: i) a pharmaceutically acceptable carrier or diluent; and ii) the compound in claim 1; or a pharmaceutically acceptable salt, enantiomer or diastereomer thereof.

5. The method of claim 3, wherein the disease is diabetes mellitus.

6. The compound of claim 1, wherein:

R$^1$ is absent or is methyl or ethyl;

A$^1$ is a bond or CH$_2$ or CH when R$^1$ is present;

Cy$^1$ is phenyl, cyclohexyl, pyridyl, N-oxo-pyridyl, thiazolyl or pyrimidinyl, each of which is optionally substituted with 1 to 4 groups independently selected from halo, methyl, trifluoromethyl, hydroxy, methoxy, methoxycarbonyl, carboxy, ethoxycarbonylmethoxy and 2-hydroxy-2-methylpropoxy;

A$^2$ is a bond, O or OCH$_2$CO;

Cy$^2$ is phenyl, thienyl, pyridyl, N-oxo-pyridyl, cyclopropyl, piperidinyl or piperazinyl, each of which is optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl and tetrazolyl;

E is a bond or CH$_2$;

R$^2$ is phenyl, thienyl or pyridyl, each of which is optionally substituted with halo, methyl, methylthio or (4-morpholino)methyl; and R$^3$ is methyl, ethyl, propyl, vinyl or allyl, each of which is optionally substituted with up to two groups independently selected from HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O— oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC=N)NH—, and oxo.

7. The compound of claim 1, wherein:

R$^1$ is absent or is methyl or ethyl;

A$^1$ is a bond, CH$_2$, CH$_2$CH$_2$, or CH when R$^1$ is present;

Cy$^1$ is phenyl, cyclopropyl, cyclohexyl, pyrrolidinyl, pyridyl, N-oxo-pyridyl, thiazolyl or pyrimidinyl, each of which is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl and methylsulfonylamino;

A$^2$ is a bond, O, OCH$_2$CO or C=O;

Cy$^2$ is phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl, each of which is optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;

E is a bond or CH$_2$;

R$^2$ is phenyl, thienyl, pyridyl or isopropyl, each of which is optionally substituted with halo, methyl, methylthio or (4-morpholino)methyl; and R$^3$ is methyl, ethyl, propyl, butyl, vinyl, allyl or ethoxyethyl, each of which is optionally substituted with up to two groups independently selected from Methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC=N)NH—, Me-, MeS—, MeSO$_2$— MeSO$_2$N(Me)—, MeS(=O)$_2$NHC(=O)—, imidazolylamino-, imidazolyl, tetrazolyl, H$_2$NCONH—, H$_2$NCO$_2$—, HOCH$_2$CH$_2$O—, MeNH—, Me$_2$N— and MeCONMe.

8. The compound of claim 1, wherein:

R$^1$ is absent or is methyl or ethyl;

A$^1$ is a bond, CH$_2$ or CH$_2$CH$_2$ or CH when R$^1$ is present;

Cy$^1$ is phenyl, cyclopropyl, cyclohexyl, pyrrolidinyl, pyridyl, N-oxo-pyridyl, thiazolyl, piperidinyl or pyrimidinyl, each of which is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl;

A$^2$ is a bond, CH$_2$, O, OCH$_2$CO or C=O;

Cy$^2$ is phenyl, thienyl, pyridyl, N-oxo-pyridyl, cyclopropyl, piperidinyl, piperazinyl, morpholinyl, thiazolyl, oxadiazolyl, thiadiazolyl, pyrazolyl, S,S-dioxothiazinyl, 2-oxo-1,2-dihydropyridyl, each of which is optionally substituted by 1 to 4 groups independently selected from halo, hydroxy, methoxy, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;

E is a bond or CH$_2$;

R$^2$ is phenyl, thienyl, pyridyl, t-butyl or isopropyl, each of which is optionally substituted with halo, methyl, methylthio, hydroxymethyl or (4-morpholino)methyl;

R$^3$ is methyl, ethyl, propyl, butyl, vinyl, allyl or ethoxyethyl, each of which is optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC=N)NH—, Me-, MeS—, MeSO$_2$— MeSO$_2$N(Me)—, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H$_2$NCONH—, H$_2$NCO$_2$—, HOCH$_2$CH$_2$O—, MeNH—, Me$_2$N— and MeCONMe;

G is alkyl, alkoxy, alkylthio, alkylsulfonyl, halogen, trifluoromethyl, dialkylamino, nitro, cyano, CO$_2$H, CONH$_2$, N-monoalkyl-substituted amido or N,N-dialkyl-substituted amido;

r is 0, 1 or 2;

G$^1$ and G$^2$ are each independently alkyl, alkoxy, alkylthio, alkylsulfonyl, halogen, trifluoromethyl, dialkylamino, nitro, cyano, CO$_2$H, CONH$_2$, N-monoalkyl-substituted amido or N,N-dialkyl-substituted amido; and s is 0, 1 or 2.

9. The compound of claim 2, wherein:

R$^{1a}$ is methyl or ethyl,

R$^2$ is phenyl optionally substituted with up to 2 groups selected from halogen, methyl, trifluoromethyl and cyano, R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl; and Cy$^2$ is 5-oxo-4,5-dihydro-1H-pyrazolyl, 3-oxo-2,3-dihydro-1H-pyrazolyl, 5-oxo-4,5-dihydro-1H-imidazolyl, 2-oxo-2,3-dihydro-1H-imidazolyl, 5-oxo-4,5-dihydro-1H-1,2,4-triazol-3-yl, 5-oxo-4,5-dihydro-1,3,4-thiadiazolyl, 1,2-dihydro-2-oxopyridyl, 2,3-dihydro-3-oxopyridazinyl, 1,2-dihydro-2-oxopyrimidinyl, 3,4-dihydro-4-oxopyrimidinyl or 1,2-dihydro-2-oxopyrazinyl optionally substituted with up to 3 groups independently selected from fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, and (C$_1$-C$_4$)alkylcarbonylamino.

10. The compound of claim 2, wherein:

R$^{1a}$ is methyl or ethyl,

R$^2$ is phenyl optionally substituted with up to 2 groups selected from halogen, methyl, trifluoromethyl and cyano, R$^3$ is 2-hydroxy-2-methylpropyl or 2-cyano-2-methylpropyl; and Cy$^2$ is heteroaryl optionally substituted with up 2 groups selected from (C$_1$-C$_4$)alkyl, halo(C$_1$-C$_4$)alkyl, halogen, cyano, CONH$_2$, (C$_1$-C$_4$)alkylaminocarbonyl, di(C$_1$-C$_4$)alkylaminocarbonyl and (C$_3$-C$_5$)cycloalkylaminocarbonyl.

11. A pharmaceutical composition comprising: i) a pharmaceutically acceptable carrier or diluent; and ii) the compound in claim 2; or a pharmaceutically acceptable salt, enantiomer or diastereomer thereof.

12. A method of treating a subject with a disease or disorder selected from diabetes mellitus, obesity, prothrombotic state, proinflammatory state, glucose intolerance, hyperglycemia, hypertension, hyperlipidemia, insulin resistance, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, cognitive decline, polycystic ovarian syndrome, hypergonadism, tuberculosis, leprosy, psoriasis, to promote wound healing, hypertriglyceridemia, hypercholesterolemia, low HDL levels, high LDL levels, vascular restenosis, pancreatitis, abdominal obesity, coronary heart disease, peripheral vascular disease, hyperinsulinemia, viral diseases, and Syndrome X, comprising the step of administering to the subject an effective amount of the compound in claim 2.

13. The method of claim 12, wherein the disease is diabetes mellitus.

14. A pharmaceutical composition comprising: i) a pharmaceutically acceptable carrier or diluent; and ii) a compound of Formula (I):

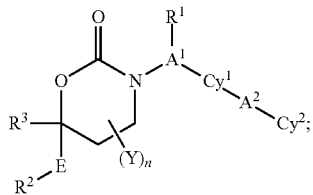

wherein:

R¹ is (a) absent or (b) is selected from (C₁-C₆)alkyl, (C₂-C₆)alkenyl, (C₂-C₆)alkynyl, (C₁-C₃)alkoxy(C₁-C₃)alkoxy, and (C₁-C₃)alkoxy(C₁-C₃)alkyl, each of which is optionally substituted with up to four groups independently selected from fluorine, cyano, oxo, R⁴, R⁴O—, (R⁴)₂N—, R⁴O₂C—, R⁴S, R⁴S(=O)—, R⁴S(=O)₂—, R⁴C(=O)NR⁴—, (R⁴)₂NC(=O)—, (R⁴)₂NC(=O)O—, (R⁴)₂NC(=O)NR⁴—, R⁴OC(=O)NR⁴—, (R⁴)₂NC(=NCN)NR⁴—, (R⁴O)₂P(=O)O—, (R⁴O)₂P(=O)NR⁴—, R⁴OS(=O)₂NR⁴—, (R⁴)₂NS(=O)₂O—, (R⁴)₂NS(=O)₂NR⁴—, R⁴S(=O)₂NR⁴—, R⁴S(=O)₂NHC(=O)—, R⁴S(=O)₂NHC(=O)O—, R⁴S(=O)₂NHC(=O)NR⁴—, R⁴OS(=O)₂NHC(=O)—, R⁴OS(=O)₂NHC(=O)O—, R⁴OS(=O)₂NHC(=O)NR⁴—, (R⁴)₂NS(=O)₂NHC(=O)—, (R⁴)₂NS(=O)₂NHC(=O)O—, (R⁴)₂NS(=O)₂NHC(=O)NR⁴—, R⁴C(=O)NHS(=O)₂—, R⁴C(=O)NHS(=O)₂O—, R⁴C(=O)NHS(=O)₂NR⁴—, R⁴OC(=O)NHS(=O)₂—, R⁴OC(=O)NHS(=O)₂O—, R⁴OC(=O)NHS(=O)₂NR⁴—, (R⁴)₂NC(=O)NHS(=O)₂—, (R⁴)₂NC(=O)NHS(=O)₂O—, (R⁴)₂NC(=O)NHS(=O)₂NR⁴—, heterocyclyl, heteroaryl, arylamino and heteroarylamino;

A¹ is (a) a bond, or (b) (C₁-C₃)alkylene, CH₂CH₂O, wherein the oxygen is attached to Cy¹, or CH₂C(=O), wherein the carbonyl carbon is attached to Cy¹;

Cy¹ is aryl, heteroaryl, monocyclic cycloalkyl or monocyclic heterocyclyl, each of which is optionally substituted with 1 to 4 groups independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkythio, (C₄-C₇)cycloalkylalkylthio, halo(C₁-C₆)alkylthio, halo(C₃-C₆)cycloalkythio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkanesulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclosulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl amino(C₂-C₆)alkoxy, (C₁-C₆)alkylamino(C₂-C₆)alkoxy, di(C₁-C₆)alkylamino(C₂-C₆)alkoxy, (C₁-C₆)alkylcarbonyl, (C₃-C₆)cycloalkylcarbonyl, (C₃-C₆)cycloalkylaminocarbonyl, {(C₃-C₆)cycloalkyl}{(C₁-C₆)alkyl}aminocarbonyl, di(C₃-C₆)cycloalkylaminocarbonyl, (C₃-C₆)cycloalkylaminosulfonyl, {(C₃-C₆)cycloalkyl}{(C₁-C₆)alkyl}aminosulfonyl, di(C₃-C₆)cycloalkylaminosulfonyl, cyano(C₁-C₆)alkyl, aminocarbonyl(C₁-C₆)alkyl, (C₁-C₆)alkylaminocarbonyl(C₁-C₆)alkyl, di(C₁-C₆)alkylaminocarbonyl(C₁-C₆)alkyl, (C₃-C₆)cycloalkylaminocarbonyl(C₁-C₆)alkyl, {(C₃-C₆)cycloalkyl}{(C₁-C₆)alkyl}aminocarbonyl(C₁-C₆)alkyl and di(C₃-C₆)cycloalkylaminocarbonyl(C₁-C₆)alkyl;

A² is (a) a bond, O, S or NR⁴; or (b) (C₁-C₃)alkylene or (C₁-C₂)alkyleneoxy, each of which is optionally substituted with 1 to 4 groups independently selected from methyl, ethyl, trifluoromethyl or oxo;

Cy² is aryl, heteroaryl, cycloalkyl or heterocyclyl, each of which is optionally substituted with 1 to 4 groups independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkythio, (C₄-C₇)cycloalkylalkylthio, halo(C₁-C₆)alkylthio, halo(C₃-C₆)cycloalkythio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkanesulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃)alkylaminocarbonyl, heterocyclylcarbonyl, (C₁-C₆)alkylaminosulfonyl, di(C₁-C₆)alkylaminosulfonyl, heterocyclosulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl amino(C₂-C₆)alkoxy, (C₁-C₆)alkylamino(C₂-C₆)alkoxy, di(C₁-C₆)alkylamino(C₂-C₆)alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl;

Y is $(C_1-C_6)$alkyl, halo$(C_1-C_6)$alkyl or oxo;

n is 0, 1 or 2;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl and oxo;

$R^2$ is $(C_1-C_6)$alkyl, aryl, heteroaryl, cycloalkyl or heterocyclyl, each of which is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl;

$R^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, and $(C_1-C_3)$alkoxy$(C_1-C_3)$alkyl, each of which is optionally substituted with up to four groups independently selected from fluorine, cyano, oxo, $R^4$, $R^4O-$, $(R^4)_2N-$, $R^4O_2C-$, $R^4C(=O)O-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

or a pharmaceutically acceptable salt, enantiomer or diastereomer thereof.

15. The pharmaceutical composition of claim 14, wherein:
$R^1$ is absent or is selected from $(C_1-C_6)$alkyl, $(C_2-C_6)$alkenyl, $(C_2-C_6)$alkynyl and $(C_1-C_3)$alkoxy$(C_1-C_3)$alkoxy, each of which is optionally substituted with up to four groups independently selected from fluorine, cyano, oxo, $R^4$, $R^4O-$, $(R^4)_2N-$, $R^4O_2C-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC$ (=O)NHS(=O)$_2$—, (R$^4$)$_2$NC(=O)NHS(=O)$_2$O—, (R$^4$)$_2$NC(=O)NHS(=O)$_2$NR$^4$—, heterocyclyl, heteroaryl, arylamino and heteroarylamino;

A$^1$ is (a) a bond, or (b) (C$_1$-C$_3$)alkylene, CH$_2$CH$_2$O, wherein the oxygen is attached to Cy$^1$, or CH$_2$C(=O), wherein the carbonyl carbon is attached to Cy$^1$;

Cy$^1$ is aryl, heteroaryl, monocyclic cycloalkyl or monocyclic heterocyclyl each of which is optionally substituted with 1 to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkythio, (C$_4$-C$_7$)cycloalkylalkylthio, halo(C$_1$-C$_6$)alkylthio, halo(C$_3$-C$_6$)cycloalkythio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclosulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl and oxo;

A$^2$ is (a) a bond, O, S or NR$^4$; or (b) (C$_1$-C$_3$)alkylene or (C$_1$-C$_2$)alkyleneoxy, each of which is optionally substituted with 1 to 4 groups independently selected from methyl, ethyl, trifluoromethyl or oxo;

Cy$^2$ is aryl, heteroaryl, cycloalkyl or heterocyclyl, each of which is optionally substituted with 1 to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkythio, (C$_4$-C$_7$)cycloalkylalkylthio, halo(C$_1$-C$_6$)alkylthio, halo(C$_3$-C$_6$)cycloalkythio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclosulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl and oxo;

Y is (C$_1$-C$_6$)alkyl, halo(C$_1$-C$_6$)alkyl or oxo;

n is 0, 1 or 2;

E is (a) a bond or (b) (C$_1$-C$_3$)alkylene or (C$_1$-C$_2$)alkylenyloxy, wherein the O is attached to R$^2$, each of which is optionally substituted with 1 to 4 groups independently selected from methyl, ethyl, trifluoromethyl and oxo;

R$^2$ is (C$_1$-C$_6$)alkyl, aryl, heteroaryl, cycloalkyl or heterocyclyl, each of which is optionally substituted with up to 4 groups independently selected from fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkythio, (C$_4$-C$_7$)cycloalkylalkylthio, halo(C$_1$-C$_6$)alkylthio, halo(C$_3$-C$_6$)cycloalkythio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo(C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclosulfonyl, (C$_1$-C$_6$)alkylcarbonylamino, (C$_1$-C$_6$)alkylcarbonylamino(C$_1$-C$_6$)alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, hydroxy(C$_1$-C$_6$)alkoxy, heteroaryl or oxo;

R$^3$ is selected from (C$_1$-C$_6$)alkyl, (C$_2$-C$_6$)alkenyl, (C$_2$-C$_6$)alkynyl and (C$_1$-C$_3$)alkoxy(C$_1$-C$_3$)alkoxy each of which is optionally substituted with up to four groups independently selected from fluorine, cyano, oxo, R$^4$, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, $R^4C(=O)NHS(=O)_2NR^4—$, $R^4OC(=O)NHS(=O)_2—$, $R^4OC(=O)NHS(=O)_2O—$, $R^4OC(=O)NHS(=O)_2NR^4—$, $(R^4)_2NC(=O)NHS(=O)_2—$, $(R^4)_2NC(=O)NHS(=O)_2O—$, $(R^4)_2NC(=O)NHS(=O)_2NR^4—$, heterocyclyl (which in turn may be optionally substituted with alkyl, haloalkyl or oxo), heteroaryl which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

or a pharmaceutically acceptable salt, enantiomer or diastereomer thereof.

16. The pharmaceutical composition of claim 15, wherein:

$R^1$ is absent or is methyl or ethyl;

$A^1$ is a bond or $CH_2$; or CH if $R^1$ is present;

$Cy^1$ is phenyl, cyclohexyl, pyridyl, N-oxo-pyridyl, thiazolyl or pyrimidinyl, each of which is optionally substituted with 1 to 4 groups independently selected from halo, methyl, trifluoromethyl, hydroxy, methoxy, methoxycarbonyl, carboxy, ethoxycarbonylmethoxy and 2-hydroxy-2-methylpropoxy;

$A^2$ is a bond, O or $OCH_2CO$;

$Cy^2$ is phenyl, thienyl, pyridyl, N-oxo-pyridyl, cyclopropyl, piperidinyl or piperazinyl, each of which is optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl and tetrazolyl;

n is 0;

E is a bond or $CH_2$;

$R^2$ is phenyl or pyridyl, each of which is optionally substituted with one group selected from halo, methyl, methylthio and (4-morpholino)methyl; and $R^3$ is methyl, ethyl, propyl, vinyl or allyl, each of which is optionally substituted with up to two groups independently selected from methyl, HO—, MeO—, $H_2N—$, $MeC(=O)NH—$, $MeS(=O)_2NH—$, $H_2NC(=O)—$, $MeNHC(=O)—$, $HO_2C—$, $(HO)_2P(=O)O—$, $H_2NS(=O)_2O—$, $H_2NS(=O)_2NH—$, $MeNHC(=O)NH—$, $MeNHC(=O)O—$, cyano, $HO_2C—$, $HOCH_2CH_2NH—$, 4-morpholino, $HOCH_2C(=O)NH—$, $H_2NCH_2C(=O)NH—$, $EtNHC(=O)NH$, $MeOC(=O)NH—$, $MeNHC(=NC=N)NH—$, or oxo;

or a pharmaceutically acceptable salt, enantiomer or diastereomer thereof.

17. The pharmaceutical composition of claim 15, wherein the compound is of Formula (Ia):

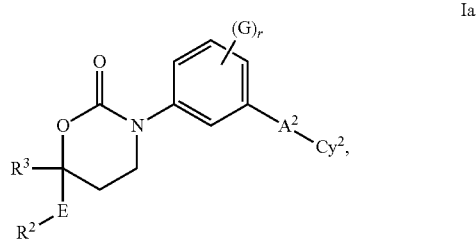

Ia wherein:
r is 0, 1, 2, 3 or 4; and
G is independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylamino-carbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclosulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy and heteroaryl;

or a pharmaceutically acceptable salt, enantiomer or diastereomer thereof.

18. The compound of claim 15, wherein the compound is of Formula (Ih):

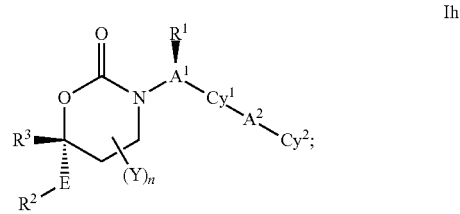

Ih or a pharmaceutically acceptable salt, enantiomer or diastereomer thereof.

19. A method of treating a subject with a disease or disorder selected from diabetes mellitus, obesity, prothrombotic state, proinflammatory state, glucose intolerance, hyperglycemia, metabolic syndrome, hypertension, hyperlipidemia, insulin resistance, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, cognitive decline, polycystic ovarian syndrome, hypergonadism, tuberculosis, leprosy, psoriasis, to promote wound healing, hypertriglyceridemia, hypercholesterolemia, low HDL levels, high LDL levels, vascular restenosis, pancreatitis, abdominal obesity, coronary heart disease, peripheral vascular disease, hyperinsulinemia, viral diseases, and Syndrome X, comprising the step of administering to the subject an effective amount of the pharmaceutical composition of claim 14.

20. The method of claim 19, wherein the disease is diabetes mellitus.

* * * * *

UNITED STATES PATENT AND TRADEMARK OFFICE
CERTIFICATE OF CORRECTION

PATENT NO. : 8,575,156 B2 Page 1 of 1
APPLICATION NO. : 12/670205
DATED : November 5, 2013
INVENTOR(S) : Claremon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 696 days.

Signed and Sealed this
Twenty-second Day of September, 2015

Michelle K. Lee
*Director of the United States Patent and Trademark Office*